US012649733B2

(12) United States Patent
Davidson et al.

(10) Patent No.: US 12,649,733 B2
(45) Date of Patent: Jun. 9, 2026

(54) 3,6-DIAMINO-PYRIDAZIN-3-YL DERIVATIVES, PHARMACEUTICAL COMPOSITIONS CONTAINING THEM AND THEIR USES AS PRO-APOPTOTIC AGENTS

(71) Applicants: LES LABORATOIRES SERVIER, Suresnes Cedex (FR); VERNALIS (R&D) LTD, Cambridge (GB)

(72) Inventors: James Edward Paul Davidson, Great Shelford (GB); Tibor Novak, Budapest (HU); Attila Paczal, Budapest (HU); András Kotschy, Törökbálint (HU); Jérôme-Benoît Starck, Rueil-Malmaison (FR); James Brooke Murray, Linton (GB); Simon Bedford, Harlow (GB); Maïa Chanrion, Issy les Moulineaux (FR); Frédéric Colland, Puiseux-en-France (FR); Patrice Desos, Bois-Colombes (FR); Mark Philip Dodsworth, Manchester (GB); Petra Dunkel, Budapest (HU); Andràs Herner, Tata (HU); Zoltán Madarász, Budapest (HU); Ana Leticia Maragno, Croissy-sur-Seine (FR); Márk Molnár, Vál (HU); Miklós Nyerges, Leányfalu (HU); Rachel Jane Parsons, Royston (GB); Monika Rudasová, Budapest (HU); Ágnes Strofek, Esztergom (HU); Marianna Szigeti, Èrd (HU); Mátyás Pál Timári, Budapest (HU); Paul Webb, Chatteris (GB)

(73) Assignees: LES LABORATOIRES SERVIER, Suresnes Cedex (FR); VERNALIS (R & D) LTD, Cambridge (GB)

( * ) Notice: Subject to any disclaimer, the term of this patent is extended or adjusted under 35 U.S.C. 154(b) by 958 days.

(21) Appl. No.: 17/630,655

(22) PCT Filed: Jul. 28, 2020

(86) PCT No.: PCT/EP2020/071179

§ 371 (c)(1),
(2) Date: Jan. 27, 2022

(87) PCT Pub. No.: WO2021/018857

PCT Pub. Date: Feb. 4, 2021

(65) Prior Publication Data

US 2022/0289734 A1 Sep. 15, 2022

(30) Foreign Application Priority Data

Jul. 29, 2019 (EP) .................................... 19188747

(51) Int. Cl.

| | |
|---|---|
| *C07D 417/14* | (2006.01) |
| *A61K 31/501* | (2006.01) |
| *A61K 45/06* | (2006.01) |
| *A61P 35/00* | (2006.01) |
| *C07D 417/12* | (2006.01) |

(52) U.S. Cl.

CPC .......... *C07D 417/14* (2013.01); *A61K 31/501* (2013.01); *A61K 45/06* (2013.01); *A61P 35/00* (2018.01); *C07D 417/12* (2013.01)

(58) Field of Classification Search

CPC .. C07D 417/14; C07D 417/12; A61K 31/501; A61K 45/06; A61P 35/00

See application file for complete search history.

(56) References Cited

FOREIGN PATENT DOCUMENTS

| | | | | |
|---|---|---|---|---|
| RU | 2017123942 | | 1/2019 | |
| WO | WO-03059354 A2 * | | 7/2003 | ......... A61K 31/5025 |
| WO | WO2003059354 | | 7/2003 | |
| WO | WO2009020603 | | 2/2009 | |
| WO | WO-2009020603 A2 * | | 2/2009 | ........... C07D 403/06 |
| WO | WO 2016/094505 | | 6/2016 | |
| WO | WO 2016/094509 | | 6/2016 | |
| WO | WO 2016/094517 | | 6/2016 | |
| WO | WO 2017/214233 | | 12/2017 | |

OTHER PUBLICATIONS

Elmeligie et al., Chem Pharm Bull, 2017, 65:236-247 (Year: 2017).*
International Search Report for PCT/EP2020/071179 dated Oct. 14, 2020.
Velentza, et al., Bioorganic & Medicinal Chemistry Letters, 2003, 13, 3465-3470.

* cited by examiner

*Primary Examiner* — Andrew D Kosar
*Assistant Examiner* — Jonathan D Mahlum
(74) *Attorney, Agent, or Firm* — HUESCHEN AND SAGE

(57) ABSTRACT

Compounds of formula (I):

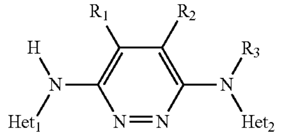

(I)

wherein $Het_1$, $Het_2$, $R_1$, $R_2$ and $R_3$ are as defined in the description.

52 Claims, No Drawings

Specification includes a Sequence Listing.

SEQUENCE LISTING

```
<160> NUMBER OF SEQ ID NOS: 5

<210> SEQ ID NO 1
<211> LENGTH: 19
<212> TYPE: PRT
<213> ORGANISM: Homo sapiens

<400> SEQUENCE: 1

Ala Arg Glu Ile Gly Ala Gln Leu Arg Arg Met Ala Asp Asp Leu Asn
1               5                   10                  15

Ala Gln Tyr


<210> SEQ ID NO 2
<211> LENGTH: 440
<212> TYPE: PRT
<213> ORGANISM: Homo sapiens

<400> SEQUENCE: 2

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30
```

-continued

```
Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
    210                 215                 220

Arg Gly Ile Pro Glu Phe Glu Phe Ser Gln Ser Asn Arg Glu Leu Val
225                 230                 235                 240

Val Asp Phe Leu Ser Tyr Lys Leu Ser Gln Lys Gly Tyr Ser Trp Ser
                245                 250                 255

Gln Phe Ser Asp Val Glu Glu Asn Arg Thr Glu Ala Pro Glu Gly Thr
            260                 265                 270

Glu Ser Glu Met Glu Thr Pro Ser Ala Ile Asn Gly Asn Pro Ser Trp
        275                 280                 285

His Leu Ala Asp Ser Pro Ala Val Asn Gly Ala Thr Gly His Ser Ser
    290                 295                 300

Ser Leu Asp Ala Arg Glu Val Ile Pro Met Ala Ala Val Lys Gln Ala
305                 310                 315                 320

Leu Arg Glu Ala Gly Asp Glu Phe Glu Leu Arg Tyr Arg Arg Ala Phe
                325                 330                 335

Ser Asp Leu Thr Ser Gln Leu His Ile Thr Pro Gly Thr Ala Tyr Gln
            340                 345                 350

Ser Phe Glu Gln Val Val Asn Glu Leu Phe Arg Asp Gly Val Asn Trp
        355                 360                 365

Gly Arg Ile Val Ala Phe Phe Ser Phe Gly Gly Ala Leu Cys Val Glu
    370                 375                 380

Ser Val Asp Lys Glu Met Gln Val Leu Val Ser Arg Ile Ala Ala Trp
385                 390                 395                 400

Met Ala Thr Tyr Leu Asn Asp His Leu Glu Pro Trp Ile Gln Glu Asn
                405                 410                 415

Gly Gly Trp Asp Thr Phe Val Glu Leu Tyr Gly Asn Asn Ala Ala Ala
            420                 425                 430

Glu Ser Arg Lys Gly Gln Glu Arg
        435                 440
```

-continued

<210> SEQ ID NO 3
<211> LENGTH: 249
<212> TYPE: PRT
<213> ORGANISM: Homo sapiens

<400> SEQUENCE: 3

Met His His His His His His His His Gly Ala Thr Gly Ser Thr Ala
1 5 10 15

Gly Ser Gly Thr Ala Gly Ser Thr Gly Ala Ser Gly Ala Ser Thr Gly
20 25 30

Gly Thr Gly Ala Thr His His His His His His His His Asp Asp Asp
35 40 45

Asp Lys Ser Pro Met Gly Ser Gln Ser Asn Arg Glu Leu Val Val Asp
50 55 60

Phe Leu Ser Tyr Lys Leu Ser Gln Lys Gly Tyr Ser Trp Ser Gln Phe
65 70 75 80

Ser Asp Val Glu Glu Asn Arg Thr Glu Ala Pro Glu Gly Thr Glu Ser
85 90 95

Glu Met Glu Thr Pro Ser Ala Ile Asn Gly Asn Pro Ser Trp His Leu
100 105 110

Ala Asp Ser Pro Ala Val Asn Gly Ala Thr Gly His Ser Ser Ser Leu
115 120 125

Asp Ala Arg Glu Val Ile Pro Met Ala Ala Val Lys Gln Ala Leu Arg
130 135 140

Glu Ala Gly Asp Glu Phe Glu Leu Arg Tyr Arg Arg Ala Phe Ser Asp
145 150 155 160

Leu Thr Ser Gln Leu His Ile Thr Pro Gly Thr Ala Tyr Gln Ser Phe
165 170 175

Glu Gln Val Val Asn Glu Leu Phe Arg Asp Gly Val Asn Trp Gly Arg
180 185 190

Ile Val Ala Phe Phe Ser Phe Gly Gly Ala Leu Cys Val Glu Ser Val
195 200 205

Asp Lys Glu Met Gln Val Leu Val Ser Arg Ile Ala Ala Trp Met Ala
210 215 220

Thr Tyr Leu Asn Asp His Leu Glu Pro Trp Ile Gln Glu Asn Gly Gly
225 230 235 240

Trp Asp Thr Phe Val Glu Leu Tyr Gly
245

<210> SEQ ID NO 4
<211> LENGTH: 21
<212> TYPE: PRT
<213> ORGANISM: Homo sapiens

<400> SEQUENCE: 4

Gln Trp Ala Arg Glu Ile Gly Ala Gln Leu Arg Arg Met Ala Asp Asp
1 5 10 15

Leu Asn Ala Gln Tyr
20

<210> SEQ ID NO 5
<211> LENGTH: 26
<212> TYPE: PRT
<213> ORGANISM: Homo sapiens

-continued

```
<400> SEQUENCE: 5

Asp Met Arg Pro Glu Ile Trp Ile Ala Gln Glu Leu Arg Arg Ile Gly
1               5                   10                  15

Asp Glu Ala Asn Ala Tyr Tyr Ala Arg Arg
            20                  25
```

3,6-DIAMINO-PYRIDAZIN-3-YL DERIVATIVES, PHARMACEUTICAL COMPOSITIONS CONTAINING THEM AND THEIR USES AS PRO-APOPTOTIC AGENTS

FIELD OF THE INVENTION

The present invention relates to 3,6-diamino-pyridazin-3-yl derivatives, to pharmaceutical compositions containing them and their uses as pro-apoptotic agents. The compounds of the present invention inhibit the activity of the Bcl-xL protein and may be of interest in the treatment of cancer, immune and autoimmune diseases.

BACKGROUND OF THE INVENTION

Apoptosis (programmed cell death) is an evolutionarily conserved pathway essential for tissue homeostasis, development and removal of damaged cells. Deregulation of apoptosis contributes to human diseases, including malignancies, neurodegenerative disorders, diseases of the immune system and autoimmune diseases (Hanahan and Weinberg, *Cell.* 2011 Mar. 4; 144(5):646-74; Marsden and Strasser, *Annu Rev Immunol.* 2003; 21:71-105; Vaux and Flavell, *Curr Opin Immunol.* 2000 December; 12(6):719-24). Evasion of apoptosis is recognized as a hallmark of cancer, participating in the development as well as the sustained expansion of tumors and the resistance to anticancer treatments (Hanahan and Weinberg, *Cell.* 2000 Jan. 7; 100(1):57-70).

The Bcl-2 protein family comprises key regulators of cell survival which can suppress (e.g., Bcl-2, Bcl-xL, Mcl-1) or promote (e.g., Bad, Bax) apoptosis (Gross et al., *Genes Dev.* 1999 Aug. 1; 13(15):1899-911, Youle and Strasser, *Nat. Rev. Mol. Cell Biol.* 2008 January; 9(1):47-59).

In the face of stress stimuli, whether a cell survives or undergoes apoptosis is dependent on the extent of pairing between the Bcl-2 family members that promote cell death with family members that promote cell survival. For the most part, these interactions involve the docking of the Bcl-2 homology 3 (BH3) domain or proapoptotic family members into a groove on the surface of pro-survival members. The presence of Bcl-2 homology (BH) domain defines the membership of the Bcl-2 family, which is divided into three main groups depending upon the particular BH domains present within the protein. The prosurvival members such as Bcl-2, Bcl-xL, and Mcl-1 contain BH domains 1-4, whereas Bax and Bak, the proapoptotic effectors of mitochondrial outer membrane permeabilization during apoptosis, contain BH domains 1-3 (Youle and Strasser, *Nat. Rev. Mol. Cell Biol.* 2008 January; 9(1):47-59).

Overexpression of the prosurvival members of the Bcl-2 family is a hallmark of cancer and it has been shown that these proteins play an important role in tumor development, maintenance and resistance to anticancer therapy (Czabotar et al., *Nat. Rev. Mol. Cell Biol.* 2014 January; 15(1):49-63). Bcl-xL (also named BCL2L1, from BCL2-like 1) is frequently amplified in cancer (Beroukhim et al., *Nature* 2010 Feb. 18; 463(7283):899-905) and it has been shown that its expression inversely correlates with sensitivity to more than 120 anti-cancer therapeutic molecules in a representative panel of cancer cell lines (NCI-60)(Amundson et al., *Cancer Res.* 2000 Nov. 1; 60(21):6101-10).

In addition, several studies using transgenic knockout mouse models and transgenic overexpression of Bcl-2 family members highlighted the importance of these proteins in the diseases of the immune system and autoimmune diseases (for a review, see Merino et al., *Apoptosis* 2009 April; 14(4):570-83. doi: 10.1007/s10495-008-0308-4.PMID: 19172396). Transgenic overexpression of Bcl-xL within the T-cell compartment resulted in resistance to apoptosis induced by glucocorticoid, g-radiation and CD3 crosslinking, suggesting that transgenic Bcl-xL overexpression can reduce apoptosis in resting and activated T-cells (Droin et al., *Biochim Biophys Acta* 2004 Mar. 1; 1644(2-3):179-88. doi: 10.1016/j.bbamer.2003.10.011.PMID: 14996502). In patient samples, persistent or high expression of antiapoptotic Bcl-2 family proteins has been observed (Pope et al., *Nat Rev Immunol.* 2002 July; 2(7):527-35. doi: 10.1038/nri846.PMID: 12094227). In particular, T-cells isolated from the joints of rheumatoid arthritis patients exhibited increased Bcl-xL expression and were resistant to spontaneous apoptosis (Salmon et al., *J Clin Invest.* 1997 Feb. 1; 99(3):439-46. doi: 10.1172/JCI119178.PMID: 9022077). The use of BH3 mimetics has also shown benefit in pre-clinical models of diseases of the immune system and autoimmune diseases. Treatment with ABT-737 (Bcl-2, Bcl-xL, and Bcl-w inhibitor) resulted in potent inhibition of lymphocyte proliferation in vitro. Importantly, mice treated with ABT-737 in animal models of arthritis and lupus showed a significant decrease in disease severity (Bardwell et al., *J Clin Invest.* 1997 Feb. 1; 99(3):439-46. doi: 10.1172/JCI119178.PMID: 9022077). In addition, it has been shown that ABT-737 prevented allogeneic T-cell activation, proliferation, and cytotoxicity in vitro and inhibited allogeneic T- and B-cell responses after skin transplantation with high selectivity for lymphoid cells (Cippa et al., Transpl Int. 2011 July; 24(7):722-32. doi: 10.1111/j.1432-2277.2011.01272.x. Epub 2011 May 25. PMID: 21615547).

The findings indicated above motivated the discovery and development of a new class of drugs named BH3 mimetics. These molecules are able to disrupt the interaction between the proapoptotic and antiapoptotic members of the Bcl-2 family and are potent inducers of apoptosis. This new class of drugs includes inhibitors of Bcl-2, Bcl-xL, Bcl-w and Mcl-1. The first BH3 mimetics described were ABT-737 and ABT-263, targeting Bcl-2, Bcl-xL and Bcl-w (Park et al., *J. Med. Chem.* 2008 Nov. 13; 51(21):6902-15; Roberts et al., *J. Clin. Oncol.* 2012 Feb. 10; 30(5):488-96). After that, selective inhibitors of Bcl-2 (ABT-199 and S55746—Souers et al., *Nat Med.* 2013 February; 19(2):202-8; Casara et al., *Oncotarget* 2018 Apr. 13; 9(28):20075-20088), Bcl-xL (A-1155463 and A-1331852—Tao et al., *ACS Med Chem Lett.* 2014 Aug. 26; 5(10):1088-93; Leverson et al., *Sci Transl Med.* 2015 Mar. 18; 7(279):279ra40) and Mcl-1 (A-1210477, S63845, S64315, AMG-176 and AZD-5991—Leverson et al., *Cell Death Dis.* 2015 Jan. 15; 6:e1590; Kotschy et al., *Nature* 2016, 538, 477-482; Maragno et al., *AACR* 2019, Poster #4482; Kotschy et al., WO 2015/097123; Caenepeel et al., *Cancer Discov.* 2018 December; 8(12):1582-1597; Tron et al., *Nat. Commun.* 2018 Dec. 17; 9(1):5341) were also discovered. The selective Bcl-2 inhibitor ABT-199 is now approved for the treatment of patients with CLL and AML in combination therapy, while the other inhibitors are still under pre-clinical or clinical development. In pre-clinical models, ABT-263 has shown activity in several hematological malignancies and solid tumors (Shoemaker et al., *Clin. Cancer Res.* 2008 Jun. 1; 14(11); 3268-77; Ackler et al., *Cancer Chemother. Pharmacol.* 2010 October; 66(5):869-80; Chen et al., *Mol Cancer Ther.* 2011 December; 10(12):2340-9). In clinical studies, ABT-263 exhibited objective antitumor activity in lymphoid malignancies (Wilson et al., *Lancet Oncol.* 2010 December; 11(12):1149-59; Roberts et al., *J. Clin. Oncol.* 2012 Feb. 10; 30(5):488-96)

and its activity is being investigated in combination with several therapies in solid tumors. The selective Bcl-xL inhibitors, A-1155463 or A-1331852, exhibited in vivo activity in pre-clinical models of T-ALL (T-cell Acute Lymphoblastic Leukemia) and different types of solid tumors (Tao et al., *ACS Med. Chem. Lett.* 2014 Aug. 26; 5(10): 1088-93; Leverson et al., *Sci. Transl. Med.* 2015 Mar. 18; 7(279):279ra40). The Mcl-1 selective inhibitors have shown promising in vivo activity in several types of hematological cell malignancies in preclinical models and three of them, S64315, AMG176 and AZD5991, are currently being investigated in clinical trials (Yang et al., *Eur. J. Med. Chem.* 2019 May 8; 177:63-75). Therefore, BH3 mimetics represent a highly attractive approach for the development of novel therapies in oncology and in the field of immune and autoimmune diseases. In particular, the need exists for small molecules that inhibit selectively the Bcl-xL protein. The present invention fulfills this need.

SUMMARY OF THE INVENTION

The present invention provides potent selective Bcl-xL inhibitors of formula (I) as defined below. We have shown that these compounds are able to induce apoptosis of cancer cells to vivo, triggering tumor regression in mice. Based on their pro-apoptotic properties, the compounds of the invention could be of interest for the treatment of pathologies involving a deregulation in apoptosis, such as, for example, cancer, auto-immune diseases and diseases of the immune system. In addition, these compounds were well tolerated in mice, with no clinically relevant body weight lass upon treatment with efficacious doses, indicating a possible therapeutic margin for the use of these Bcl-xL-targeting small molecules in cancer treatment. In agreement with the previously described role of Bcl-xL in the regulation of platelets life-span (Zhang et al., *Cell Death Differ.* 2007 May; 14(5): 943-51; Mason et al., *Cell.* 2007 Mar. 23; 128(6):1173-86), we observed a reduction in the number of circulating platelets after treatment of mice with these inhibitors, with recovery after treatment discontinuation. Considering this effect in platelet survival, the Bcl-xL inhibitors of the present invention could also be used for treating diseases or conditions characterized by an excess or a deregulated activity of platelets, such as, for example, pro-thrombotic conditions.

DETAILED DESCRIPTION OF THE INVENTION

In a First embodiment (E1), the present invention provides compounds of formula (I):

(I)

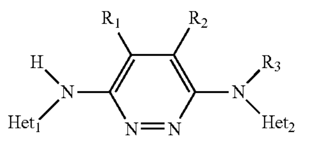

wherein:

$R_1$ and $R_2$ independently of one another represent a group selected from: hydrogen; linear or branched $C_1$-$C_6$alkyl optionally substituted by a hydroxyl or a $C_1$-$C_6$alkoxy group; $C_3$-$C_6$cycloalkyl; trifluoromethyl; linear or branched $C_1$-$C_6$alkylene-heterocycloalkyl wherein the heterocycloalkyl group is optionally substituted by a a linear or branched $C_1$-$C_6$alkyl group;

or $R_1$ and $R_2$ form with the carbon atoms carrying them a $C_1$-$C_6$cycloalkylene group.

$R_3$ represents a group selected from: hydrogen; $C_1$-$C_6$cycloalkyl; linear or branched $C_1$-$C_6$alkyl; $—X_1—NR_aR_b$; $—X_1—N'R_aR_bR_c$; $—X_1—O—R_c$; $—X_1—COOR_c$; $—X_1—PO(OH)_2$; $—X_1—SO_2(OH)$; $—X_1—N_3$ and:

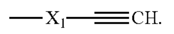

$R_a$ and $R_b$ independently of one another represent a group selected from: hydrogen; heterocycloalkyl; $—SO_2$-phenyl wherein the phenyl may be substituted by a linear or branched $C_1$-$C_6$alkyl; linear or branched $C_1$-$C_6$alkyl optionally substituted by one or two hydroxyl groups; $C_1$-$C_6$alkylene-$SO_2OH$; $C_1$-$C_6$alkylene-$SO_2O^-$; $C_1$-$C_6$alkylene-COOH; $C_1$-$C_6$alkylene-$PO(OH)_2$; $C_1$-$C_6$alkylene-$NR_dR_e$; $C_1$-$C_6$alkylene-$N'R_dR_eR_f$; $C_1$-$C_6$alkylene-phenyl wherein the phenyl may be substituted by a $C_1$-$C_6$alkoxy group;

the group:

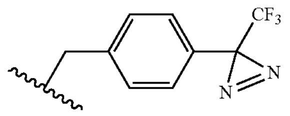 [SMILES: *Cc1ccc(C2(C(F)(F)F)N=N2)cc1]

or $R_a$ and $R_b$ form with the nitrogen atom carrying them a cycle $B_1$;

or $R_a$, $R_b$ and $R_c$ form with the nitrogen atom carrying them a bridged $C_3$-$C_8$heterocycloalkyl, $R_c$, $R_d$, $R_e$, $R_f$, independently of one another represents a hydrogen or a linear or branched $C_1$-$C_6$alkyl group, or $R_d$ and $R_e$ form with the nitrogen atom carrying them a a cycle $B_2$, or $R_d$, $R_e$ and $R_f$ form with the nitrogen atom carrying them bridged $C_3$-$C_8$heterocycloalkyl, $Het_1$ represents a group selected from:

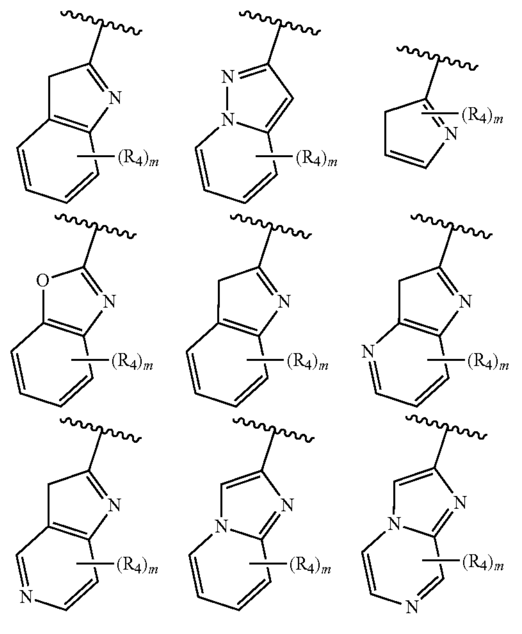

-continued

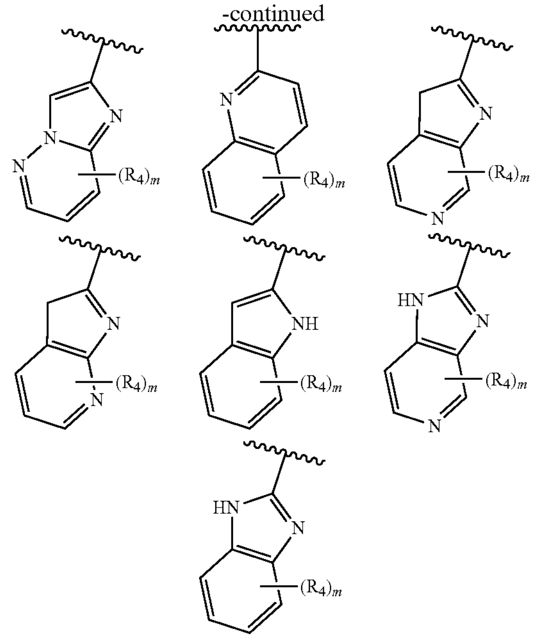

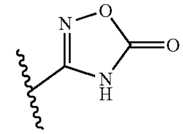, 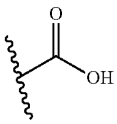, 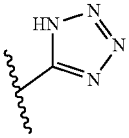,

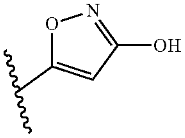, 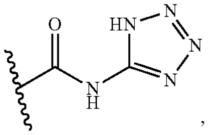,

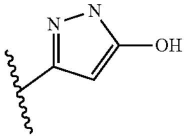, 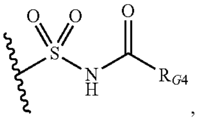,

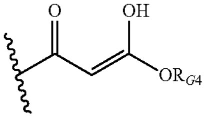, 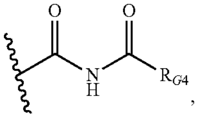,

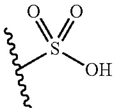, 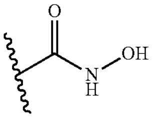, 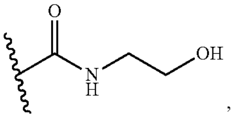,

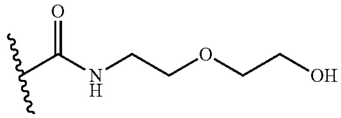, 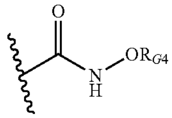,

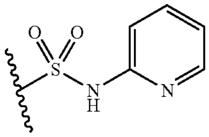, 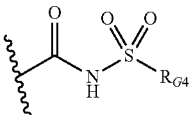 and

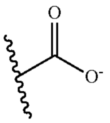

$Het_2$ represents a group selected from:

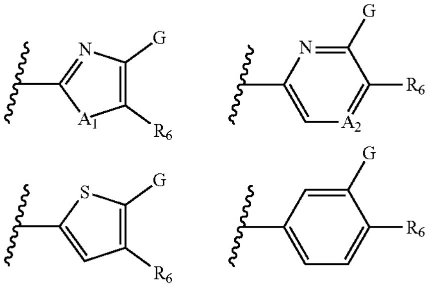

$A_1$ is —NH—, —N($C_1$-$C_3$alkyl), O, S or Se, $A_2$ is N, CH or C($R_5$),

G is selected from the group consisting of:

—C(O)O$R_{G3}$, —C(O)N$R_{G1}R_{G2}$, —C(O)$R_{G2}$, —N$R_{G1}$C(O)$R_{G2}$, —N$R_{G1}$C(O)N$R_{G1}R_{G2}$, —OC(O)N$R_{G1}R_{G2}$, —N$R_{G1}$C(O)O$R_{G3}$, —C(=NO$R_{G1}$)N$R_{G1}R_{G2}$, —N$R_{G1}$C(=NCN)N$R_{G1}R_{G2}$, —N$R_{G1}$(SO)$_2$N$R_{G1}R_{G2}$, —S(O)$_2$$R_{G3}$, —S(O)$_2$N$R_{G1}R_{G2}$, —N$R_{G1}$S(O)$_2$$R_{G2}$, —N$R_{G1}$C(=N$R_{G2}$)N$R_{G1}R_{G2}$, —C(=S)N$R_{G1}R_{G2}$, —C(=N$R_{G1}$)N$R_{G1}R_{G2}$, halogen, —$NO_2$, and —CN, in which:

$R_{G1}$ and $R_{G2}$ at each occurrence are each independently selected from the group consisting of hydrogen, $C_1$-$C_6$alkyl optionally substituted by 1 to 3 halogen atoms, $C_2$-$C_6$alkenyl, $C_2$-$C_6$-alkynyl, $C_3$-$C_6$cycloalkyl, phenyl and —$(CH_2)_{1-4}$-phenyl;

$R_{G3}$ is selected from the group consisting of $C_1$-$C_6$alkyl optionally substituted by 1 to 3 halogen atoms, $C_2$-$C_6$alkenyl, $C_2$-$C_6$alkynyl, $C_3$-$C_6$cycloalkyl, phenyl and —$(CH_2)_{1-4}$-phenyl; or $R_{G1}$ and $R_{G2}$, together with the atom to which each is attached are combined to form a $C_3$-$C_8$heterocycloalkyl; or in the alternative, G is selected from the group consisting of:

wherein $R_{G4}$ is selected from $C_1$-$C_6$alkyl optionally substituted by 1 to 3 halogen atoms, $C_2$-$C_6$alkenyl, $C_2$-$C_6$alkynyl and $C_3$-$C_6$cycloalkyl, $R_4$ represents a hydrogen, fluorine, chlorine or bromine atom, a methyl, a hydroxyl or a methoxy group, $R_5$ represents a group selected from: $C_1$-$C_6$alkyl optionally substituted by 1 to 3 halogen atoms; $C_2$-$C_6$alkenyl; $C_2$-$C_6$alkynyl; halogen or —CN, $R_6$ represents a group selected from:

hydrogen;

—$C_2$-$C_6$alkenyl;

—$X_2$—O—$R_7$;

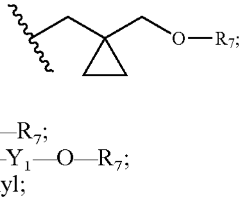

—$X_2$—$NSO_2$—$R_7$;

—C═C($R_9$)—$Y_1$—O—$R_7$;

$C_3$-$C_6$cycloalkyl;

$C_3$-$C^6$heterocycloalkyl optionally substituted by a hydroxyl group;

$C_3$-$C_6$cycloalkylene-$Y_2$—$R_7$;

$C_3$-$C_6$heterocycloalkylene-$Y_2$—$R_7$ group, an heteroarylene-$R_7$ group optionally substituted by a linear or branched $C_1$-$C_6$alkyl group, $R_7$ represents a group selected from: linear or branched $C_1$-$C_6$alkyl group; ($C_3$-$C_6$)cycloalkylene-$R_8$; or:

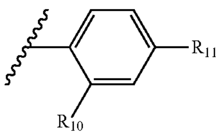

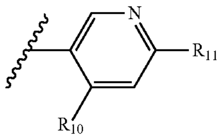

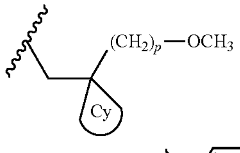

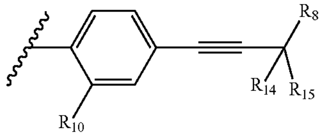

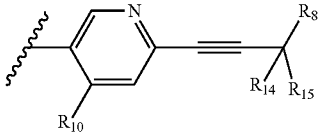

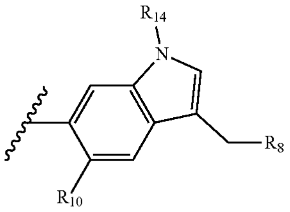

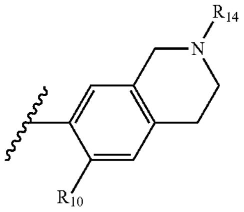

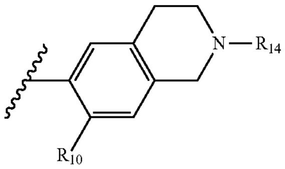

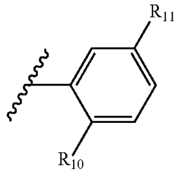

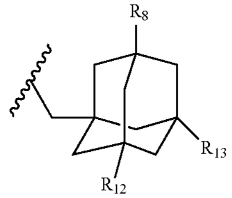

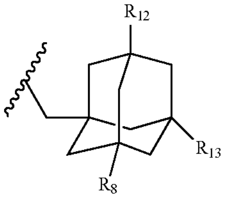

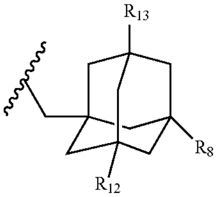

wherein Cy represents a $C_3$-$C_8$cycloalkyl, $R_8$ represents a group selected from: hydrogen; linear or branched $C_1$-$C_6$alkyl, —$NR'_aR'_b$; —$NR'_a$—CO—$OR'_c$; —$NR'_a$—CO—$R'_c$; —$N'R'_aR'_bR'_c$; —O—$R'_c$; —NH—$X'_2$—$N'R'_aR'_bR'_c$; —O—$X'_2$—$NR'_aR'_b$, —$X'_2$—$NR'_aR'_b$, —$NR'_c$—$X'_2$—$N_3$ and:

$$—NR'_c—X'_2—\equiv CH.$$

$R_9$ represents a group selected from linear or branched $C_1$-$C_6$alkyl, trifluoromethyl, hydroxyl, halogen, $C_1$-$C_6$alkoxy, $R_{10}$ represents a group selected from hydrogen, fluorine, chlorine, bromine, —$CF_3$ and methyl, $R_{11}$ represents a group selected from hydrogen, $C_1$-$C_3$alkylene-$R_8$, —O—$C_1$-$C_3$alkylene-$R_8$, —CO—$NR_hR_i$ and —CH═CH—$C_1$-$C_4$alkylene-$NR_hR_i$, —CH═CH—CHO, $C_3$-$C_8$cycloalkylene-$CH_2$—$R_8$, $C_3$-$C_8$heterocycloalkylene-$CH_2$—$R_8$, $R_{12}$ and $R_{13}$, independently of one another, represent a hydrogen atom or a methyl group, $R_{14}$ and $R_{15}$, independently of one another, represent a hydrogen or a methyl group, or $R_{14}$ and $R_{15}$ form with the carbon atom carrying them a a cyclohexyl, $R_h$ and $R_i$, independently of one another, represent a hydrogen or a linear or branched $C_1$-$C_6$alkyl group, $X_1$ and $X_2$ independently of one another, represent a linear or branched $C_1$-$C_6$alkylene group optionally substituted by one or two groups selected from trifluoromethyl, hydroxyl, halogen, $C_1$-$C_6$alkoxy, $X'_2$ represents a linear or branched $C_1$-$C_6$alkylene, $R'_a$ and $R'_b$ independently of one another, represent a group selected from: hydrogen; heterocycloalkyl; —$SO_2$-phenyl wherein the phenyl may be substituted by a linear or branched $C_1$-$C_6$alkyl; linear or branched $C_1$-$C_6$alkyl optionally substituted by one or two hydroxyl or $C_1$-$C_6$alkoxy groups; $C_1$-$C_6$alkylene-$SO_2OH$; $C_1$-$C_6$alkylene-$SO_2O^-$; $C_1$-$C_6$alkylene-COOH; $C_1$-$C_6$alkylene-$PO(OH)_2$; $C_1$-$C_6$alkylene-$NR'_dR'_e$; $C_1$-$C_6$alkylene-$N'R'_dR'_eR'_f$, $C_1$-$C_6$alkylene-O—$C_1$-$C_6$alkylene-OH; $C_1$-$C_6$alkylene-phenyl wherein the phenyl may be substituted by a hydroxyl or a $C_1$-$C_6$alkoxy group;

the group:

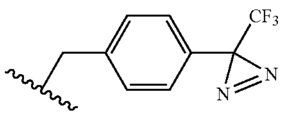 [SMILES: *Cc1ccc(C2(C(F)(F)F)N=N2)cc1]

or $R'_a$ and $R'_b$ form with the nitrogen atom carrying them a cycle $B_3$, or $R'_a$, $R'_b$ and $R'_c$ form with the nitrogen atom carrying them a bridged $C_3$-$C_8$heterocycloalkyl, $R'_c$, $R'_d$, $R'_e$, $R'_f$, independently of one another, represents a hydrogen or a linear or branched $C_1$-$C_6$alkyl group, or $R'_d$ and $R'_e$ form with the nitrogen atom carrying them a cycle $B_4$, or $R'_d$, $R'_e$ and $R'_f$ form with the nitrogen atom carrying them a bridged $C_3$-$C_8$heterocycloalkyl, $Y_1$ represents a linear or branched $C_1$-$C_4$alkylene, $Y_2$ represents a bond, —O—, —O—$CH_2$—, —O—CO—, —O—$SO_2$—, —$CH_2$—, —$CH_2$—O, —$CH_2$—CO—, —$CH_2$—$SO_2$—, —$C_2H_5$—, —CO—, —CO—O—, —CO—$CH_2$, —CO—NH—$CH_2$—, —$SO_2$—, —$SO_2$—$CH_2$—, —NH—CO—, —NH—$SO_2$—, m=0, 1 or 2, p=1, 2, 3 or 4, $B_1$, $B_2$, $B_3$ and $B_4$, independently of one another, represents a $C_3$-$C_8$heterocycloalkyl group, which group can: (i) be a mono- or bi-cyclic group, wherein bicyclic group includes fused, bridged or spiro ring system, (ii) can contain, in addition to the nitrogen atom, one or two hetero atoms selected independently from oxygen, sulphur and nitrogen, (iii) be substituted by one or two groups selected from: fluorine, bromine, chlorine, linear or branched $C_1$-$C_6$alkyl, hydroxyl, —$NH_2$, oxo or piperidinyl, it also being understood that:

"aryl" means a phenyl, naphthyl, biphenyl or indenyl group,

"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens), "cycloalkyl" means any mono- or bi-cyclic non-aromatic carbocyclic group containing from 3 to 10 ring members, which may include fused, bridged or spiro ring systems, "heterocycloalkyl" means any mono- or bi-cyclic non-aromatic carbocyclic group, composed of from 3 to 10 ring members, and containing from one to 3 hetero atoms selected from oxygen, sulphur, SO, $SO_2$ and nitrogen, it being understood that bicyclic group may be fused or spiro type, heteroarylene, cycloalkylene, heterocycloalkylene mean a divalent heteroaryl, cycloalkyl and heterocycloalkyl, its enantiomers and diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid and camphoric acid.

Among the pharmaceutically acceptable bases there may be mentioned, without implying any limitation, sodium hydroxide, potassium hydroxide, triethylamine and tert-butylamine.

Further enumerated embodiments (E) of the invention are described herein. It will be recognized that features specified in each embodiment may be combined with other specified features to provide further embodiments of the present invention.

E2. Compound according to E1 wherein $Het_1$ represents:

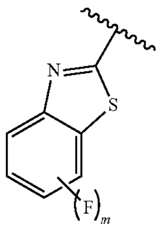

or

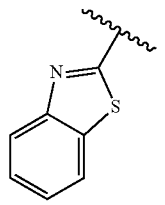

E3. Compound according to E1 or E2 wherein $R_1$ represents a methyl up and $R_2$ represents a hydrogen atom.

E4. Compound according to E1 or E2 wherein $R_1$ and $R_2$ represent each a methyl group or a hydrogen atom.

E5. Compound according to E1 or E2 wherein $R_1$ or $R_2$ represents a linear or branched $C_1$-$C_6$alkyl optionally substituted by a hydroxyl or a $C_1$-$C_6$alkoxy group, preferably a group selected from: methyl, methoxymethyl, hydroxymethyl, ethyl and prop-2-yl.

E6. Compound according to E1 or E2 wherein $R_1$ or $R_2$ represents a $C_3$-$C_6$cycloalkyl, preferably a cyclopropyl group.

E7. Compound according to E1 or E2 wherein $R_1$ represents a trifluoromethyl group.

E8. Compound according to E1 or E2 wherein $R_2$ represents a linear or branched $C_1$-$C_6$alkylene-heterocycloalkyl, preferably a (4-methyl-piperazin-1-yl)propyl group.

E9. Compound according to E1 or E2 wherein $R_1$ and $R_2$ form with the carbon atoms carrying them a cyclohexene or a cyclopentene group.

E10. Compound according to any of E1 to E9 wherein $R_3$ represents a hydrogen atom or a methyl group.

E11. Compound according to any of E1 to E9 wherein $R_3$ represents —$X_1$—$PO(OH)_2$, —$X_1$—$SO_2(OH)$, —$X_1$—$NR_aR_b$; —$X_1$—$N^+R_aR_bR_c$, wherein $R_a$ or $R_b$, or both of them, represent a group selected from $C_1$-$C_6$alkylene-$SO_2OH$, $C_1$-$C_6$alkylene-$SO_2O^-$ and $C_1$-$C_6$alkylene-$PO(OH)_2$.

E12. Compound according to any of E1 to E9 wherein $R_8$ represents —$NR'_aR'_b$, —$N^+R'_aR'_bR'_c$; —NH—$X'_2$—$N^+R'_aR'_bR'_c$, wherein $R'_a$ and $R'_b$, or both of them, represent a group selected from $C_1$-$C_6$alkylene-$SO_2OH$ and $C_1$-$C_6$alkylene-$PO(OH)_2$.

E13. Compound according to any of E1 to E9 wherein $R_3$ represents a group selected from: ethyl, propyl; 2-methoxy-ethyl, 2-(morpholin-4-yl)ethyl, 3-(morpholin-4-yl)propyl, 3-diethylamino-propyl, 3-methoxy-propyl, 3-hydroxy-propyl, 3,4-dihydroxy-butyl, 4-methoxy-3-hydroxy-butyl, 4-hydroxy-3-methoxy-butyl, 2,3-dihydroxy-propyl, 4,5-dihydroxy-pentyl, 4-hydroxy-butyl, 3-hydroxy-2-morpholino-propyl, 5-hydroxy-4-methoxy-pentyl, 5-morpholino-4-hydroxy-pentyl, 3-hydroxy-2-methoxy-propyl, 5-[2-(dimethylamino)ethyl-methyl-amino]-4-hydroxy-pentyl, 5-hydroxy-pentyl, 5-methoxy-4-hydroxy-pentyl, 5-(dimethylamino)-4-hydroxy-pentyl, 4-hydroxy-5-(trimethylammonio)pentyl, 5-[3-sulfonate-propyl-dimethyl-ammonio]-4-hydroxy-pentyl, 4-hydroxy-5-(methylamino)pentyl, 3-carboxy-propyl, 5-[methyl(4-piperidyl)amino]pentyl, 5-(2-morpholinoethylamino) pentyl, 5-[2-(4-methyl-piperazin-1-yl)ethylamino) pentyl, 4-[2-(4-methyl-piperazin-1-yl)ethylamino) butyl, 4-hydroxy-5-[methyl-[2-(methylamino)ethyl] amino]pentyl, 5-[2-(diethylamino)ethylamino]-4-hydroxy-pentyl, 5-(4-Amino-1-piperidyl)-4-hydroxy-pentyl, 4-hydroxy-5-piperazin-1-yl-pentyl, 5-[2-(1-piperidyl)ethylamino]pentyl, 4-(4-Amino-1-piperidyl) butyl, 4-[2-(diethylamino)ethylamino]butyl, 5-(4-Amino-1-piperidyl)pentyl, 4-[methyl-[2-(methylamino)ethyl]amino]butyl, 4-(2-morpholinoethylamino)butyl, 4-[2-(4-methyl-piperazin-1-yl)ethylamino)butyl, 4-[(1-methyl-4-piperidyl)amino]butyl, 5-[2-(diethylamino) ethylamino]pentyl, 4-piperazin-1-ylbutyl, 4-(methylamino)butyl, 5-piperazin-1-ylpentyl, 5-[methyl-[2-(methylamino)ethyl, 5-aminopentyl, 4-aminobutyl, 5-(methylamino)pentyl, 5-[3-(4-methylpiperazin-1-yl)propylamino]pentyl, 4-hydroxy-5-[methyl(2-phosphonoethyl)amino]pentyl, 6-(dimethylamino)hexyl, 3-(dimethylamino)propyl, 2-(trimethylammonio)ethyl, 3-(trimethylammonio)propyl, 2-(dimethylamino)ethyl, 4-(dimethylamino)butyl, 5-[3-sulfonate-propyl-dimethyl-ammonio]pentyl, 4-(trimethylammonio)butyl, 4-hydroxy-5-quinuclidin-1-ium-1-yl-pentyl, 4-hydroxy-5-(1-aza-4-azoniabicyclo[2.2.2]octan-4-yl)pentyl, 4-hydroxy-5-(4-methylmorpholin-4-ium-4-yl)pentyl, 5-(trimethylammonio) pentyl, 4-hydroxy-5-(1-methylpiperidin-1-ium-1-yl)

pentyl, 5-(1,4-dimethylpiperazin-1-ium-1-yl)-4-hydroxy-pentyl, 6-(trimethylammonio)hexyl, 5-[3-hydroxypropyl(dimethyl)ammonio]pentyl, 5-[2-hydroxyethyl(dimethyl)ammonio]pentyl, 5-[carboxymethyl(dimethyl)ammonio]pentyl, 5-[carboxymethyl(dimethyl)ammonio]pentyl, 3-phosphonopropyl, 3-[3-sulfonate-propyl-dimethyl-ammonio]propyl, 3-sulfopropyl, 4-sulfobutyl, 4-phosphonobutyl, 4-carboxybutyl, 3-aminopropyl, 3-azidopropyl, pent-4-yn-1-yl, 4-aminobutyl, 4-azidobutyl, hex-5-yn-1-yl, 5-azidopentyl.

E14. Compound according to any of E1 to E13 wherein $Het_2$ represents:

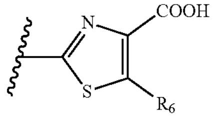

E15. Compound according to any of E1 to E13 wherein $Het_2$ represents:

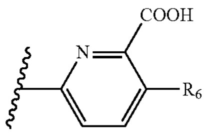

E16. Compound according to E14 or E15 wherein $R_6$ represents a hydrogen atom.

E17. Compound according to E14 wherein $R_6$ represents a —$X_2$—O—$R_7$ group wherein $X_2$ is a propylene group.

E18. Compound according to E17 wherein $R_7$ represents the following group:

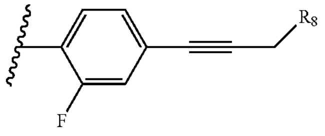

E19. Compound according to E17 wherein $R_7$ represents the following group:

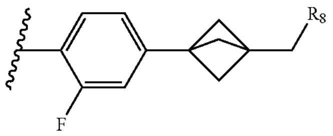

E20. Compound according to E17 wherein $R_7$ represents the following group:

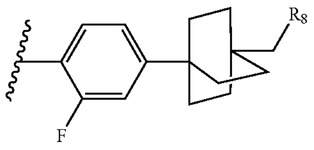

-continued

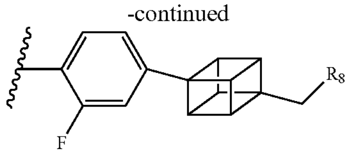

E21. The compound according to any of E18 to E20 wherein $R_8$ represents $NR'_aR'_b$.

E22. Compound according to any of E18 to E20 wherein $R_8$ represents a group selected from: dimethylamino, methylamino, methylethylamino, diethylamino, methyl [2-(methylamino)ethyl]amino, (2-hydroxyethyl)(methyl)amino, 4-morpholinyl, pyrrolidin-1-yl, 1-piperidyl, [(tert-butoxy)carbonyl](methyl)amino, hydroxyl, bis(3-sulfopropyl)amino, 3-sulfopropylamino, methyl(3-sulfopropyl)amino, methyl(p-tolylsulfonyl)amino, (4-methoxyphenyl)methyl-methyl-amino, 2-(dimethylamino)ethylamino and:

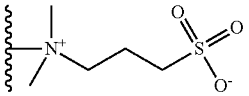
,
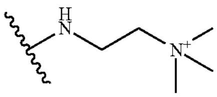
or
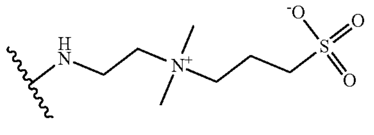

E23. Compound according to any of E18 to E20 wherein $R_8$ represents a group selected from: 3-piperazin-1-yl, 3-hydroxypropyl(methyl)amino, [(3S)-3,4-dihydroxy-butyl]-methyl-amino, 3-hydroxypropylamino, [(3S)-3,4-dihydroxybutyl]amino, 4-hydroxybutyl(methyl)amino, [(3R)-3,4-dihydroxybutyl]-methyl-amino, 4-hydroxybutylamino, [(3R)-3,4-dihydroxybutyl]amino.

E24. Compound according to E17 wherein $R_7$ represents:

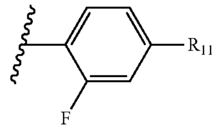

wherein $R_{11}$ is selected from dimethylcarbamoyl, 3-(dimethylamino)propyl, 3-(methylamino)propyl, 3-(methylamino)propyl.

wherein $R_{11}$ is selected from dimethylcarbamoyl, 3-(dimethylamino)propyl, 3-(methylamino)propyl, 3-(methylamino)propyl.

E25. Compound according to E14 wherein $R_6$ represents a $C_3$-$C_6$heterocycloalkylene-$Y_2$—$R_7$ group wherein the heterocycloalkylene group is selected from:

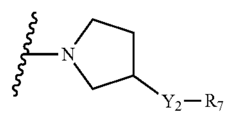
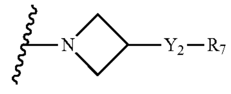
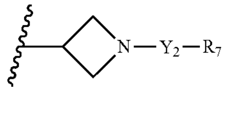
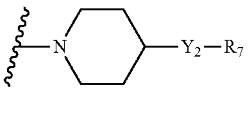

-continued

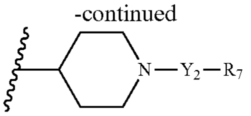

E26. Compound according to E25 wherein $R_7$ is selected from: methyl, methylethyl, tert-butyl, 2-methylpropyl and phenyl, preferably phenyl.

E27. Compound according to E14 or E15 wherein $R_6$ represents $—C{=}C(R_9)—Y_1—O—R_7$ wherein $Y_1$ is a methylene group.

E28. Compound according to E14 or E15 wherein $R_6$ represents:

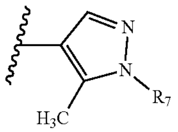

E29. Compound according to E28 wherein $R_7$ represents a group selected from:

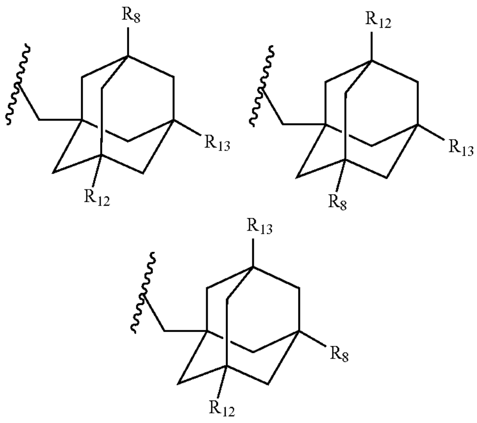

wherein $R_8$ represents $—O—X'_2—NR'_aR'_b$ or $—X'_2—NR'_aR'_b$, preferably $—O—X'_2—NR'_aR'_b$.

E30. Compound according to E28 wherein $R_7$ represents a group selected from:

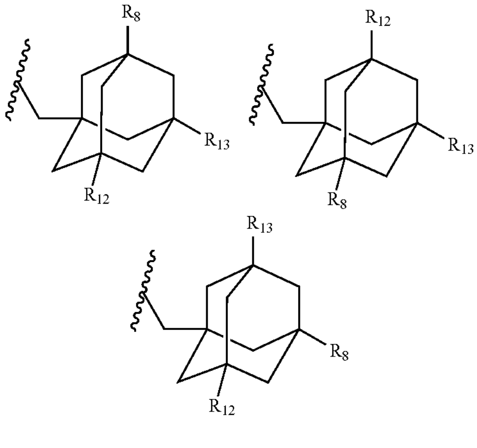

wherein $R_8$ represents a group selected from: hydrogen, 2-(methylamino)ethoxy and:

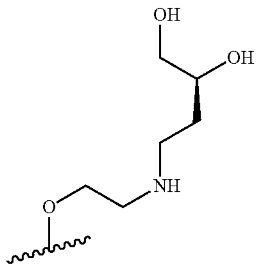

or

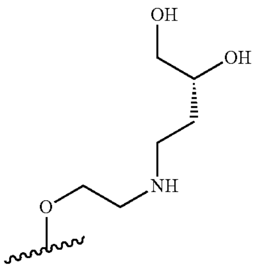

E31. The compound according to E28 wherein $R_7$ represents a group selected from:

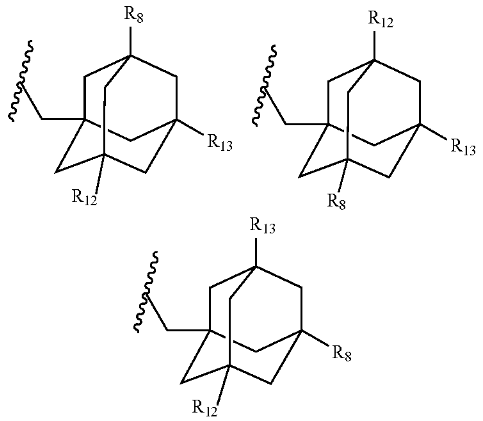

wherein $R_8$ represents a group selected from: 2-(dimethylamino)ethoxy, 2-[(2-sulfoethyl)amino]ethoxy, 2-[methyl(2-sulfoethyl)amino]ethoxy, 2-(3-hydroxypropylamino)ethoxy, 2-(3-methoxypropylamino)ethoxy, 2-morpholinoethoxy, 2-(2-carboxyethylamino)ethoxy, 2-[(3-hydroxyphenyl)methylamino]ethoxy, 2-(methylamino)ethoxy, 2-pyrrolidin-1-ylethoxy, 2-(4-methylpiperazin-1-yl)ethoxy, 2-(4-hydroxybutylamino)ethoxy, 2-piperazin-1-ylethoxy, 2-[3-hydroxypropyl(methyl)amino]ethoxy, 2-[4-hydroxybutyl(methyl)amino]ethoxy; 2-[[3-hydroxy-2-(hydroxymethyl)propyl]amino]ethoxy; 2-[bis(3-hydroxypropyl)amino]ethoxy.

E32. A compound according to E1 selected in the following group:

2-({6-[(1,3-Benzothiazol-2-yl)amino]-5-methylpyridazin-3-yl}(4-hydroxybutyl)amino)-5-(3-{2-fluoro-4-[3-(methylamino)prop-1-yn-1-yl]phenoxy}propyl)-1,3-thiazole-4-carboxylic acid, 2-[[6-(1,3-Benzothiazol-2-ylamino)-5-methyl-pyridazin-3-yl]-methyl-amino]-5-[3-[4-[3-(dimethylamino)prop-1-ynyl]-2-fluoro-phenoxy]propyl]thiazole-4-carboxylic acid, 2-({6-[(1,3-Benzothiazol-2-yl)amino]-5-methylpyridazin-3-yl}(methyl)amino)-5-(3-{2-fluoro-4-[3-(methylamino)prop-1-yn-1-yl]phenoxy}propyl)-1,3-thiazole-4-carboxylic acid, 2-[[6-(1,3-Benzothiazol-2-ylamino)-5-methyl-pyridazin-3-yl]-(3,4-dihydroxybutyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(3-hydroxy-4-methoxy-butyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(2,3-dihydroxypropyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(4,5-dihydroxypentyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(3,4-dihydroxybutyl)amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-(3-hydroxypropyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-[4-hydroxy-5-(trimethylammonio)pentyl]amino]-5-[3-[2-fluoro-4-[3-(methylamino)prop-1-ynyl]phenoxy]propyl]thiazole-4-carboxylate, 3-[[5-[[6-(1,3-Benzothiazol-2-ylamino)-5-methyl-pyridazin-3-yl]-[4-carboxy-5-[3-[2-fluoro-4-[3-(methylamino)prop-1-ynyl]phenoxy]propyl]thiazol-2-yl]amino]-2-hydroxy-pentyl]-dimethyl-ammonio]propane-1-sulfonate, 2-[[6-(1,3-Benzothiazol-2-ylamino)-5-methyl-pyridazin-3-yl]-(4-hydroxybutyl)amino]-5-[3-[2-fluoro-4-[3-[methyl(3-sulfopropyl)amino]prop-1-ynyl]phenoxy]propyl]thiazole-4-carboxylic acid, 5-{1-[(Adamantan-1-yl)methyl]-5-methyl-1H-pyrazol-4-yl}-2-({6-[(1,3-benzothiazol-2-yl)amino]-5-methylpyridazin-3-yl}(methyl)amino)-1,3-thiazole-4-carboxylic acid, 5-{1-[(Adamantan-1-yl)methyl]-5-methyl-1H-pyrazol-4-yl}-2-({6-[(1,3-benzothiazol-2-yl)amino]-5-cyclopropylpyridazin-3-yl}(methyl)amino)-1,3-thiazole-4-carboxylic acid, 2-[[6-(1,3-Benzothiazol-2-ylamino)-5-methyl-pyridazin-3-yl]-[5-[2-(diethylamino)ethylamino]-4-hydroxy-pentyl]amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-[5-[2-(4-methylpiperazin-1-yl)ethylamino]pentyl]amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-(4-hydroxy-5-piperazin-1-yl-pentyl)amino]-5-[3-[4-[3-(dimethylamino)prop-1-ynyl]-2-fluoro-phenoxy]propyl]thiazole-4-carboxylic acid, 2-({6-[(1,3-Benzothiazol-2-yl)amino]-5-methylpyridazin-3-yl}(methyl)amino)-5-[(2S)-3-{4-[3-(dimethylamino)prop-1-yn-1-yl]-2-fluorophenoxy}-2-methylpropyl]-1,3-thiazole-4-carboxylic acid, 2-[4-Aminobutyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid, 2-[5-Aminopentyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-[3-(dimethylamino)propyl]amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-methyl-amino]-5-[3-[4-[3-(dimethylamino)but-1-ynyl]-2-fluoro-phenoxy]propyl]thiazole-4-carboxylic acid, 2-[[6-(1,3-Benzothiazol-2-ylamino)-5-methyl-pyridazin-3-yl]-[4-hydroxy-5-(trimethylammonio)pentyl]amino]-5-[3-[4-[3-(dimethylamino)prop-1-ynyl]-2-fluoro-phenoxy]propyl]thiazole-4-carboxylate, 3-[2-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-dimethyl-ammonio]propane-1-sulfonate, 2-[[6-(1,3-Benzothiazol-2-ylamino)-5-methyl-pyridazin-3-yl]-[4-hydroxy-5-(4-methylmorpholin-4-ium-4-yl)pentyl]amino]-5-[3-[4-[3-(dimethylamino)prop-1-ynyl]-2-fluoro-phenoxy]propyl]thiazole-4-carboxylate, 2-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-trimethyl-ammonium, 2-[[6-(1,3-Benzothiazol-2-ylamino)-5-methyl-pyridazin-3-yl]-[6-(trimethylammonio)hexyl]amino]-5-[3-[2-fluoro-4-[3-(methylamino)prop-1-ynyl]phenoxy]propyl]thiazole-4-carboxylate, 2-[[6-(1,3-Benzothiazol-2-ylamino)-5-methyl-pyridazin-3-yl]-[5-[2-hydroxyethyl(dimethyl)ammonio]pentyl]amino]-5-[3-[4-[3-(dimethylamino)prop-1-ynyl]-2-fluoro-phenoxy]propyl]thiazole-4-carboxylate, 2-[[6-(1,3-Benzothiazol-2-ylamino)-5-methyl-pyridazin-3-yl]-[5-[carboxymethyl(dimethyl)ammonio]pentyl]amino]-5-[3-[4-[3-(dimethylamino)prop-1-ynyl]-2-fluoro-phenoxy]propyl]thiazole-4-carboxylate, 3-[[5-[[6-(1,3-Benzothiazol-2-ylamino)-5-methyl-pyridazin-3-yl]-[4-carboxy-5-[3-[2-fluoro-4-[(E)-3-oxo-prop-1-enyl]phenoxy]propyl]thiazol-2-yl]amino]-2-hydroxy-pentyl]-dimethyl-ammonio]propane-1-sulfonate, 2-[[6-(1,3-Benzothiazol-2-ylamino)-5-methyl-pyridazin-3-yl]-methyl-amino]-5-[3-[4-[3-(dimethylamino)prop-1-ynyl]phenoxy[propyl]thiazole-4-carboxylic acid, 2-[[6-(1,3-Benzothiazol-2-ylamino)-5-methyl-pyridazin-3-yl]-methyl-amino]-5-[3-[4-[1-[(dimethylamino)methyl]-3-bicyclo[1.1.1]pentanyl]phenoxy]propyl]thiazole-4-carboxylic acid, 2-[[6-(1,3-Benzothiazol-2-ylamino)-5-methyl-pyridazin-3-yl]-(3-phosphonopropyl)amino]-5-[3-[2-fluoro-4-[3-(methylamino)prop-1-ynyl]phenoxy]propyl]thiazole-4-carboxylic acid, 2-({6-[(1,3-Benzothiazol-2-yl)amino]-5-methylpyridazin-3-yl}(3-carboxypropyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(3-phosphonopropyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(3-sulfopropyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(4-sulfobutyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(4-phosphonobutyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(4-carboxybutyl)amino)-5-(3-{4-[3-(dimethylamino)prop-1-yn-1-yl]-2-fluorophenoxy}propyl)-1,3-thiazole-4-carboxylic acid, 2-[{6-[(1,3-benzothiazol-2-yl)amino]-5-methylpyridazin-3-yl}(pent-4-yn-1-yl)amino]-5-(3-{2-fluoro-4-[3-(methylamino)prop-1-yn-1-yl]phenoxy}propyl)-1,3-thiazole-4-carboxylic acid, 2-({6-[(1,3-Benzothiazol-2-yl)amino]-5-methylpyridazin-3-yl}(methyl)amino)-5-{3-[2-fluoro-4-(3-{methyl[2-(methylamino)ethyl]amino}prop-1-yn-1-yl)phenoxy]propyl}-1,3-thiazole-4-carboxylic acid, 2-({6-[(1,3-Benzothiazol-2-yl)amino]-5-methylpyridazin-3-yl}(methyl)amino)-5-{3-(2-fluoro-4-{3-[(2-hydroxyethyl)(methyl)amino]prop-1-yn-1-yl}phenoxy)propyl}-1,3-thiazole-4-carboxylic acid, 2-({6-[(1,3-Benzothiazol-2-yl)amino]-5-methylpyridazin-3-yl}(methyl)amino)-5-{3-[2-fluoro-4-(3-hydroxyprop-1-yn-1-yl)phenoxy]propyl}-1,3-thiazole-4-carboxylic acid, 2-[5-azidopentyl-[6-[(1,3-benzothiazol-2-yl)amino]-5-methyl-pyridazin-3-yl]amino]-5-[3-[2-fluoro-4-[3-(methylamino)prop-1-ynyl]phenoxy]propyl]-1,3-thiazole-4-carboxylic acid, its enantiomers and diastereoisomers, and addition salts thereof with a pharmaceutically acceptable acid or base.

E33. A compound according to E1 selected in the following group:

6-[{6-[(1,3-benzothiazol-2-yl)amino]-5-methylpyridazin-3-yl}(methyl)amino]-3-[1-({3-[2-(dimethylamino)ethoxy]-5,7-dimethyladamantan-1-yl}methyl)-5-methyl-1H-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-(3-hydroxypropylamino)ethoxy]-5,7-dimethyl-1-adamantyl]methyl]-5-methyl-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-(3-methoxypropylamino)ethoxy]-5,7-dimethyl-1-adamantyl]methyl]-5-methyl-pyrazol-4-yl]pyridine-2-carboxylic acid, 6-[{6-[(1,3-benzothiazol-2-yl)amino]-5-methylpyridazin-3-yl}(methyl)amino]-3-(1-{[3-(2-{[(3S)-3,4-dihydroxybutyl]amino}ethoxy)-5,7-dimethyladamantan-1-yl]methyl}-5-methyl-1H-pyrazol-4-yl)pyridine-2-carboxylic acid, 6-[[6-(1,3-benzothiazol-2-ylamino)-5-methyl-pyridazin-3-yl]-methyl-amino]-3-[1-[[3,5-dimethyl-7-(2-morpholinoethoxy)-1-adamantyl]methyl]-5-methyl-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-(2-carboxyethylamino)ethoxy]-5,7-dimethyl-1-adamantyl]methyl]-5-methyl-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-[(3-hydroxyphenyl)methylamino]ethoxy]-5,7-dimethyl-1-adamantyl]methyl]-5-methyl-pyrazol-4-yl]pyridine-2-carboxylic acid, 2-[[6-(1,3-benzothiazol-2-ylamino)-5-methyl-pyridazin-3-yl]-methyl-amino]-5-[3-[4-[3-(dimethylamino)prop-1-ynyl]-2-fluoro-phenoxy]propyl]thiazole-4-carboxylic acid, 2-[[6-(1,3-benzothiazol-2-ylamino)-5-methyl-pyridazin-3-yl]-(3-hydroxypropyl)amino]-5-[3-[2-fluoro-4-[3-(methylamino)prop-1-ynyl]phenoxy]propyl]thiazole-4-carboxylic acid, 2-[[6-(1,3-benzothiazol-2-ylamino)-5-methyl-pyridazin-3-yl]-methyl-amino]-5-[3-[2-fluoro-4-(3-pyrrolidin-1-yl-prop-1-ynyl)phenoxy]propyl]thiazole-4-carboxylic acid, its enantiomers and diastereoisomers, and addition salts thereof with a pharmaceutically acceptable acid or base.

E34. Process for the preparation of a compound of formula (I) according to any of E1 to E33, which process is characterized in that there is used as starting material the compound of formula (II):

(II)

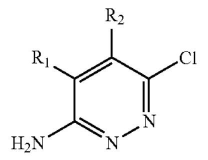

wherein $R_1$ and $R_2$ are as defined in formula (I), which compound of formula (II) is subjected to a Buchwald reaction, in an aqueous or organic medium, in the presence of a palladium catalyst (preferably $Pd_2(dba)_3$), of a base (preferably $Cs_2CO_3$ and DIPEA), of a phosphine (preferably Xantphos) and of the compound of formula (III):

(III)

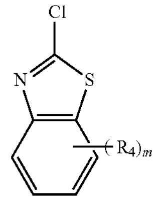

wherein $R_4$ and m are as defined in formula (I), to yield the compound of formula (IV):

(IV)

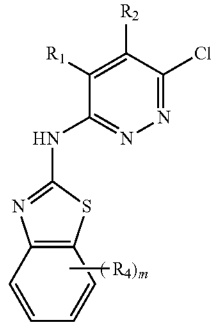

which amino function of compound of formula (IV) is further protected to yield the compound of formula (V):

(V)

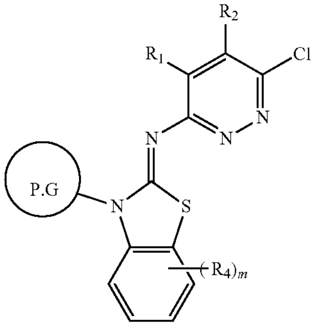

wherein

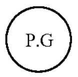

represents a protecting group (preferably a 2-trimethylsilylethoxymethyl group), which compound of formula (V) is further subjected to a Buchwald reaction, in an aqueous or organic medium, in the presence of a palladium catalyst (preferably $Pd_2(dba)_3$), of a base (preferably $Cs_2CO_3$ and DIPEA), of a phosphine (preferably Xantphos) and of the compound of formula (VI):

(VI-a)

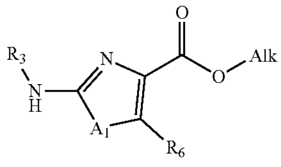

or (VI-b)

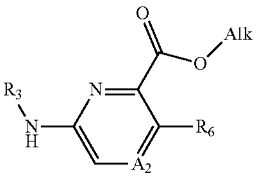

wherein $A_1$, $R_3$ and $R_6$ are as defined in formula (I) and Alk represents a $C_1$-$C_6$alkyl group, to yield the compound of formula (VII-a) or (VII-b):

(VII-a)

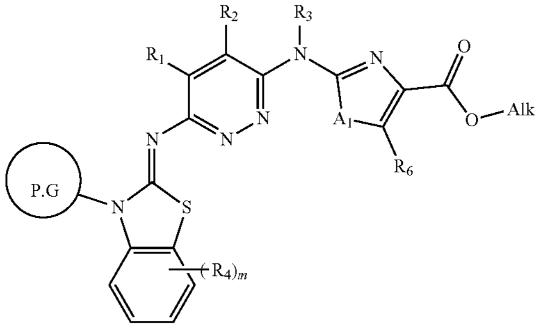

or (VII-b)

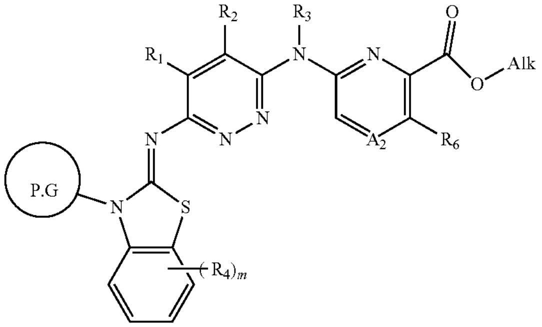

the benzothiazole group of which compound of formula (VII-a) or (VII-b) is deprotected (using preferably HF×Pyr) and the ester function is hydrolysed (using preferably $LiOH \times H_2O$) to yield the compound of formula (I), which compound of formula (I) may be purified according to a conventional separation technique, which may be converted into its addition salts with a pharmaceutically acceptable acid or base and which is optionally separated into its isomers according to a conventional separation technique, it being understood that, at any time considered appropriate in the course of the above-described process, hydroxy, amino, carboxylic and phosphono groups of the reagents or intermediates of synthesis may be protected and then deprotected according to the requirements of synthesis.

E35. Process according to E34 wherein the compound (VI-b) is:

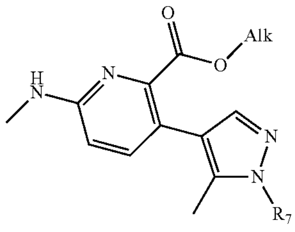

and wherein $R_7$ is selected from the group:

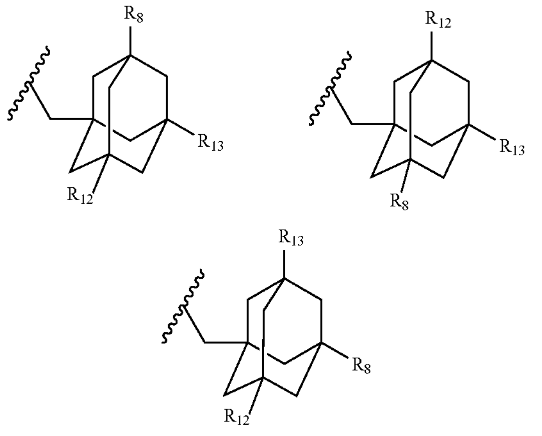

wherein $R_8$, $R_{12}$ and $R_{13}$ are as defined in formula (I).

E36. Process for the preparation of a compound of formula (I) according to E28 wherein $R_6$ represents:

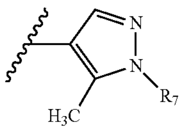

and $R_7$ is as defined in formula (I), which process is characterized in that there is used as starting material the compound of formula (II):

(II)

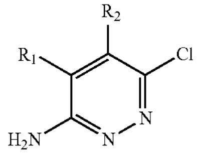

wherein $R_1$ and $R_2$ are as defined in formula (I), which compound of formula (II) is subjected to a Buchwald reaction, in an aqueous or organic medium, in the presence of a palladium catalyst (preferably $Pd_2(dba)_3$), of a base (preferably $Cs_2CO_3$ and DIPEA), of a phosphine (preferably Xantphos) and of the compound of formula (III):

(III)

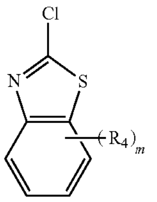

wherein $R_4$ and m are as defined in formula (I), to yield the compound of formula (IV):

(IV)

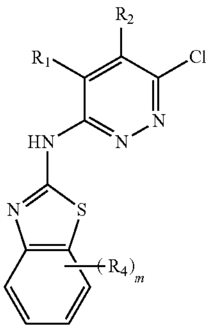

which amino function of compound of formula (IV) is further protected to yield the compound of formula (V):

(V)

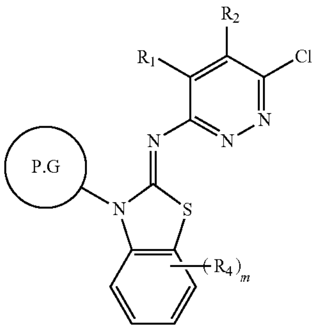

wherein

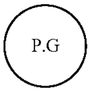

represents a protecting group (preferably a 2-trimethylsilylethoxymethyl group), which compound of formula (V) is further subjected to a Buchwald reaction, in an aqueous or organic medium, in the presence of a palladium catalyst (preferably $Pd_2(dba)_3$), of a base (preferably $Cs_2CO_3$ and DIPEA), of a phosphine (preferably Xantphos) and of the compound or formula (VI'):

(VI')

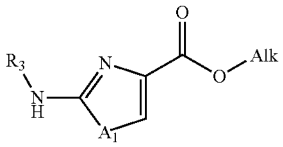

wherein $A_1$ and $R_3$ are as defined in formula (I) and Alk represents a $C_1$-$C_6$alkyl group, to yield the compound of formula (VIII):

(VIII)

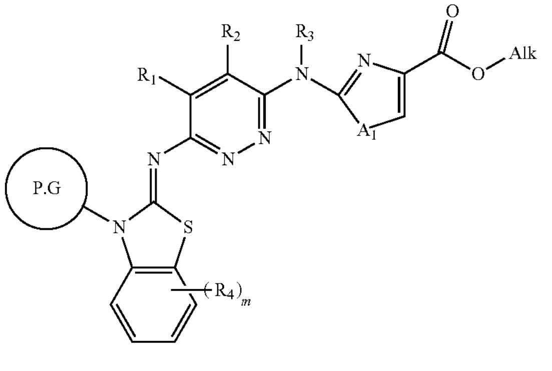

which compound of formula (VIII) is subjected to a halogenation (using preferably N-bromosuccinimide or N-iodosuccinimide) to yield the compound of formula (IX):

(IX)

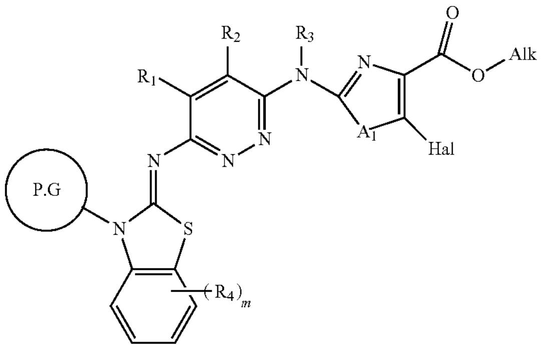

wherein Hal represents a halogen atom, which compound of formula (IX) is further subjected to a Suzuki coupling reaction, in an aqueous or organic medium, in the presence of a palladium catalyst (preferably Pd(dppf) $Cl_2$), of a base (preferably potassium carbonate), with a compound of formula (X):

(X)

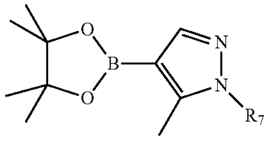

to yield the compound of formula (XI):

(XI)

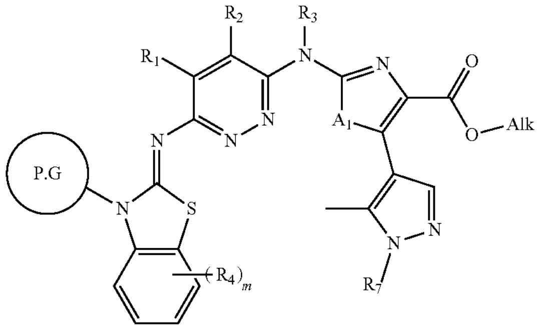

the benzothiazole group of which compound of formula (XI) is deprotected (using preferably HF×Pyr) and the ester function is hydrolysed (using preferably LiOH×$H_2O$) to yield the compound of formula (I), which compound of formula (I) may be purified according to a conventional separation technique, which may be converted into its addition salts with a pharmaceutically acceptable acid or base and which is optionally separated into its isomers according to a conventional separation technique, it being understood that, at any time considered appropriate in the course of the above-described process, hydroxy, amino, carboxylic and phosphono groups of the reagents or intermediates of synthesis may be protected and then deprotected according to the requirements of synthesis.

E37. Synthesis intermediate according to E34 or E36 which is:

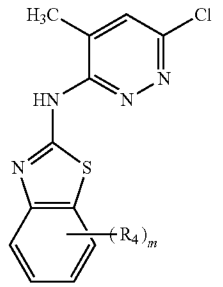

wherein $R_4$ and m are as defined in general formula (I), preferably $R_4$ represents a hydrogen atom.

E38. The compound according to E1 wherein $R_8$ represents a hydrogen, fluorine, chlorine or bromine atom, a methyl or a methoxy group.

E39. The compound according to E1 wherein $R_8$ represents a group selected from: hydrogen; linear or branched $C_1$-$C_6$alkyl, —NR'$_a$R'$_b$; —NR'$_a$—CO—OR'$_c$; —N'R'$_a$R'$_b$R'$_c$; —O—R'$_c$; —NH—X'$_2$—N'R'$_a$R'$_b$R'$_c$; —O—X'$_2$—NR'$_a$R'$_b$, —NR'$_c$—X'$_2$—$N_3$ and:

$$—NR'_c—X'_2—\equiv CH$$

E40. The compound according to E1 wherein R'$_a$ and R'$_b$ independently of one another, represent a group selected from: hydrogen; heterocycloalkyl; —$SO_2$-phenyl wherein the phenyl may be substituted by a linear or branched $C_1$-$C_6$alkyl; linear or branched $C_1$-$C_6$alkyl optionally substituted by one or two hydroxyl groups; $C_1$-$C_6$alkylene-$SO_2OH$; $C_1$-$C_6$alkylene-$SO_2O^-$; $C_1$-$C_6$alkylene-COOH; $C_1$-$C_6$alkylene-$PO(OH)_2$; $C_1$-$C_6$alkylene-$NR'_dR'_e$; $C_1$-$C_6$alkylene-$N^+R'_dR'_eR'_f$, $C_1$-$C_6$alkylene-O—$C_1$-$C_6$alkylene-OH; $C_1$-$C_6$alkylene-phenyl wherein the phenyl may be substituted by a $C_1$-$C_6$alkoxy group;

the group:

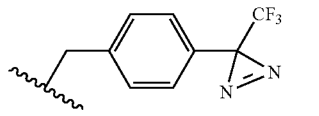 [SMILES: *Cc1ccc(C2(C(F)(F)F)N=N2)cc1]

or $R'_a$ and $R'_b$ form with the nitrogen atom carrying them a cycle $B_3$, or $R'_a$, $R'_b$ and $R'_c$ form with the nitrogen atom carrying them a bridged $C_3$-$C_8$heterocycloalkyl.

E41. Compound according to any of E1 to E31 wherein m=1.

Pharmacological study of the compounds of the invention has shown that they have pro-apoptotic properties. The ability to reactivate the apoptotic process in cells is of major therapeutic interest in the treatment of cancers and of immune and auto-immune diseases. In particular, the compounds according to the invention will be useful in the treatment or chemo- or radio-resistant cancers.

In another embodiment, the compounds of the invention could be used for treating diseases or conditions characterized by an excess or a deregulated activity of platelets, especially pro-thrombotic conditions.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

Among the cancer treatments envisaged there may be mentioned, without implying any limitation, the treatment of haematological malignancies and solid tumors. Haematological malignancies include myeloma, especially multiple myeloma, lymphoma, especially Non-Hodgkin Lymphoma (NHL) and more especially Diffuse Large B-cell Lymphoma (DLBCL), and leukemia, especially Chronic Lymphocytic Leukemia (CLL), T-cell Acute Lymphoblastic Leukemia (T-ALL), B-cell Acute Lymphoblastic Leukemia (B-ALL) and Acute Myelogenous Leukemia (AML). Solid tumors include the bladder, brain, breast, uterus, esophagus and liver cancers, colorectal cancer, renal cancer, melanoma, ovarian cancer, prostate cancer, pancreatic cancer and lung cancer, especially non-small-cell lung cancer and small-cell lung cancer.

In particular, T-ALL results from the leukemic transformation of thymic cell precursors and their arrest at specific stages of differentiation. Despite recent and extensive insights into the molecular and cellular mechanisms responsible for T-ALL onset and progression, this knowledge has not been translated into efficient targeted therapies. Current clinical treatments include chemotherapy associated or not with hematopoietic stem cell transplantation with survival rates remaining around 50 and 70% in adult and pediatric cases, respectively. Both in pediatric and adult cases, relapses show very poor prognosis, reinforcing the need of the discovery of novel therapeutic options (Passaro et al., *Immunol. Rev.* 2016 May; 271(1):156-72). It has been shown that dual Bcl-2/Bcl-xL inhibitors, like ABT-263 and ABT-737, have promising activity in T-ALL patient derived xenograft models (Van Delft et al. *Cancer Cell* 2006; 10:389-99; Suryani et al., *Clin. Cancer Res.* 2014, 20:4520-31). Other studies have reported a differential requirement for Bcl-xL or Bcl-2 for survival of mature versus very immature (ETP subgroup) T-ALL (Chonghaile et al., *Cancer Discov.* 2014; 4:1074-87). The selective Bcl-xL inhibitor A-1331852 described previously have also shown to have in vitro and in vivo activity in the mature T-ALL cell line xenograft model MOLT-4 (Leverson et al., *Sci. Transl. Med.* 2015 Mar. 18; 7(279):279ra40). In a particular embodiment, tumor growth inhibition was also observed in MOLT-4 xenograft model upon treatment with the Bcl-xL inhibitors of the invention. These data support the use of the present compounds in the treatment of T-ALL.

Among the treatments of autoimmune diseases envisaged there may be mentioned, without implying any limitation, the treatment of rheumatoid arthritis (RA) and systemic lupus erythematosus (SLE).

The present invention relates also to pharmaceutical compositions comprising at least one compound of formula (I), as the active ingredient, in combination with one or more pharmaceutically acceptable excipients. In particular, these pharmaceutical compositions are interesting for use as pro-apoptotic and/or anti-proliferative agents, particularly, in the treatment of cancers and of auto-immune and immune system diseases.

Suitable excipients according to the invention include diluents, lubricants, binders, disintegration agents, stabilisers, preservatives, absorbents, colorants, sweeteners and flavourings.

By way of non-limiting example there may be mentioned:

as diluents: lactose, dextrose, sucrose, mannitol, sorbitol, cellulose, glycerol, as lubricants: silica, talc stearic acid and its magnesium and calcium salts, polyethylene glycol, as binders: magnesium aluminium silicate, starch, gelatin, tragacanth, methylcellulose, sodium carboxymethylcellulose and polyvinylpyrrolidone, as disintegrants: agar, alginic acid and its sodium salt, effervescent mixtures.

Among the pharmaceutical compositions according to the invention there may be mentioned more especially those that are suitable for oral, parenteral, nasal, per- or trans-cutaneous, rectal, perlingual, ocular or respiratory administration, especially tablets, drages, sublingual tablets, capsules, glossettes, capsules, lozenges, injectable or drinkable preparations, aerosols, eye or nose drops, suppositories, creams, ointments, dermal gels.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compound of the present invention employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A suitable daily dose of a compound of the invention will depend upon the factors described above and may range from 0.01 mg to 2.5 g per day in one or more administration(s).

In another aspect, the present invention relates also to the combination of a compound of formula (I) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

In another aspect, the compounds of the invention can be used in combination with radiotherapy in the treatment of cancer.

Alternatively, the compounds of the invention may be linked to monoclonal antibodies. Antibody Drug Conjugates (ADCs) represent a new class of therapeutics that is formed by chemically linking a cytotoxic drug to a monoclonal antibody through a linker. The monoclonal antibody of an ADC selectively binds to a target antigen of a cell (e.g. cancer cell) and releases the drug into the cell. ADCs have therapeutic potential because they combine the specificity of the antibody and the cytotoxic potential of the drug. Nonetheless, developing ADCs as therapeutic agents has thus far met with limited success owing to a variety of factors such as unfavorable toxicity profiles, low efficacies and poor pharmacological parameters. Accordingly, there is still a need for new ADCs that overcome these problems and can selectively deliver Bcl-xL to target cancer cells.

In another aspect, the compounds of the invention may be linked to fragments of monoclonal antibodies or linked to scaffold proteins that can be related or not to monoclonal antibodies. Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra, *J. Mol. Recogn.* 2000, 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra, *J. Biotechnol.* 2001, 74, 257-75), the protein Z derivative from the domain B of staphylococcal protein A, thioredoxin A or any protein with a repeated domain such as an "ankyrin repeat" (Kohl et al. *PNAS* 2003, 100, 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Examples illustrate the invention but do not limit it in any way. All intermediates for preparing Examples are either commercially available or can be obtained by the person skilled in the art using conventional chemical reactions described in the literature.

GENERAL PROCEDURES

All reagents obtained from commercial sources were used without further purification. Anhydrous solvents were obtained from commercial sources and used without further drying.

Column Chromatography

Automated flash column chromatography was performed on ISCO CombiFlash® Rf 200 or CombiFlash® Rf+ Lumen™ using RediSep® Rf Normal-phase Silica Flash Columns (35-70 μm, 60 Å), RediSep Rf Gold® Normal-phase Silica High Performance Columns (20-40 μm, 60 Å), RediSep® Rf Reversed-phase C18 Columns (40-63 μm, 60 Å), or RediSep Rf Gold® Reversed-phase C18 High Performance Columns (20-40 μm, 100 Å).

TLC

Thin layer chromatography was conducted with 5×10 cm plates coated with Merck Type 60 $F_{254}$ silica-gel.

Microwave Reactions

Microwave heating was performed with a CEM Discover® SP, or with an Anton Paar Monowave Microwave Reactor.

NMR $^1$H-NMR measurements were performed on a Bruker Avance III 500 MHz spectrometer, a Bruker Avance III 400 MHz spectrometer, or a Bruker DPX-400 spectrometer using DMSO-$d_6$ or $CDCl_3$ as solvent. 1H NMR data is in the form of delta values, given in part per million (ppm), using the residual peak of the solvent (2.50 ppm for DMSO-$d_6$ and 7.26 ppm for $CDCl_3$) as internal standard. Splitting patterns are designated as: s (singlet), d (doublet), t (triplet), q (quartet), quint (quintet), sept (septet), m (multiplet), br s (broad singlet), dd (doublet of doublets), td (triplet of doublets), dt (doublet of triplets), ddd (doublet of doublet of doublets).

Analytical LC-MS

Certain compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/$H_2O$ (1:1) with 5 μL loop injection. LCMS analyses were performed on two instruments, one of which was operated with basic, and the other with acidic eluents.

Basic LCMS: Gemini-NX, 3 μm, C18, 50 mm×3.00 mm i.d. column at 23° C., at a flow rate of 1 mL min-1 using 5 mM ammonium bicarbonate (Solvent A) and acetonitrile (Solvent B) with a gradient starting from 100% Solvent A and finishing at 100% Solvent B over various/certain duration of time.

Acidic LCMS: KINATEX XB-C18-100A, 2.6 μm, 50 mm*2.1 mm column at 40° C., at a flow rate of 1 mL min-1 using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

Certain other compounds of the present invention were characterized HPLC-MS under specific named methods as follows. For all of these methods UV detection was by diode array detector at 230, 254, and 270 nm. Sample injection volume was 1 μL. Gradient elutions were run by defining flow rates and percentage mixtures of the following mobile phases, using HPLC-grade solvents:

Solvent A: 10 mM aqueous ammonium formate+0.04% (v/v) formic acid

Solvent B: Acetonitrile+5.3% (v/v) Solvent A+0.04% (v/v) formic acid.

Retention times (RT) for these named methods are reported in minutes. Ionisation is recorded in positive mode, negative mode, or positive-negative switching mode. Specific details for individual methods follow.

LCMS-V-B Methods

Using an Agilent 1200 SL series instrument linked to an Agilent MSD 6140 single quadrupole with an ESI-APCI multimode source (Methods LCMS-V-B1 and LCMS-V-B2) or using an Agilent 1290 Infinity II series instrument connected to an Agilent TOF 6230 with an ESI-jet stream source (Method LCMS-V-B1); column: Thermo Accucore 2.6 μm, C18, 50 mm×2.1 mm at 55° C. Gradient details for methods LCMS-V-B1 and LCMS-V-B2:

| | LCMS-V-B1 | | LCMS-V-B2 | | |
|---|---|---|---|---|---|
| Time (min) | Solvent A (%) | Solvent B (%) | Solvent A (%) | Solvent B (%) | Flow (mLmin) |
| 0 | 95 | 5 | 60 | 40 | 1.1 |
| 0.12 | 95 | 5 | 60 | 40 | 1.3 |
| 1.30 | 5 | 95 | 2 | 98 | 1.3 |
| 1.35 | 5 | 95 | 2 | 98 | 1.6 |
| 1.85 | 5 | 95 | 2 | 98 | 1.6 |
| 1.90 | 5 | 95 | 2 | 98 | 1.3 |
| 1.95 | 95 | 5 | 95 | 5 | 1.3 |

LCMS-V-C Method

Using an Agilent 1200 SL series instrument linked to an Agilent MSD 6140 single quadrupole with an ESI-APCI multimode source; column: Agilent Zorbax Eclipse plus 3.5 μm, C18(2), 30 mm×2.1 mm at 35° C. Gradient details for method LCMS-V-C:

| Time (min) | Solvent A (%) | Solvent B (%) | Flow (mL/min) |
|---|---|---|---|
| 0 | 95 | 5 | 1 |
| 0.25 | 95 | 5 | 1 |
| 2.50 | 95 | 5 | 1 |
| 2.55 | 5 | 95 | 1.7 |
| 3.60 | 5 | 95 | 1.7 |
| 3.65 | 5 | 95 | 1 |
| 3.70 | 95 | 5 | 1 |
| 3.75 | 95 | 5 | 1 |

Preparative HPLC

Certain compounds of the present invention were purified by high performance liquid chromatography (HPLC) on an Armen Spot Liquid Chromatography or Teledyne EZ system with a Gemini-NX® 10 μM C18, 250 mm×50 mm i.d. column running at a flow rate of 118 mL min-1 with UV diode array detection (210-400 nm) using 25 mM aqueous $NH_4HCO_3$ solution and MeCN or 0.1% TFA in water and MeCN as eluents.

Certain other compounds of the present invention were purified by HPLC under specific named methods as follows:

HPLC-V-A Methods

These were performed on a Waters FractionLynx MS autopurification system, with a Gemini® 5 μm C18(2), 100 mm×20 mm i.d. column from Phenomenex, running at a flow rate or 20 $cm^3$ $min^{-1}$ with UV diode array detection (210-400 nm) and mass-directed collection. The mass spectrometer was a Waters Micromass ZQ2000 spectrometer, operating in positive or negative ion electrospray ionisation modes, with a molecular weight scan range of 150 to 1000.

Method HPLC-V-A1 (pH 4):

Solvent A: 10 mM aqueous ammonium acetate+0.08% (v/v) formic acid: Solvent B: acetonitrile+5% (v/v) Solvent A+0.08% (v/v) formic acid Method HPLC-V-A2 (pH 9):

Solvent A: 10 mM aqueous ammonium acetate+0.08% (v/v) conc. ammonia: Solvent B: acetonitrile+5% (v/v) Solvent A+0.08% (v/v) conc. ammonia HPLC-V-B Methods Performed on an AccQPrep HP125 (Teledyne ISCO) system, with a Gemini® NX 5 μm C18(2), 150 mm×21.2 mm i.d. column from Phenomenex, running at a flow rate of 20 $cm^3$ $min^{-1}$ with UV (214 and 254 nm) and ELS detection.

Method HPLC-V-B1 (pH 4):

Solvent A: water+0.08% (v/v) formic acid; solvent B: acetonitrile+0.08% (v/v) formic acid.

Method HPLC-V-B2 (pH 9):

Solvent A: water+0.08% (v/v) conc. ammonia; solvent B: acetonitrile+0.08% (v/v) conc. ammonia.

Method HPLC-V-B3 (Neutral):

Solvent A: water; Solvent B: acetonitrile.

Analytical GC-MS

Combination gas chromatography and low resolution mass spectrometry (GC-MS) was performed on Agilent 6850 gas chromatograph and Agilent 5975C mass spectrometer using 15 m×0.25 mm column with 0.25 μm HP-5MS coating and helium as carrier gas. Ion source: EI+, 70 eV, 230° C. quadrupole: 150° C. interface: 300° C.

High-Resolution MS

High-resolution mass spectra were acquired on an Agilent 6230 time-of-flight mass spectrometer equipped with a Jet Stream electrospray ion source in positive ion mode. Injections of 0.5 μl were directed to the mass spectrometer at a flow rate 1.5 ml/min (5 mM ammonium-formate in water and acetonitrile gradient program), using an Agilent 1290 Infinity HPLC system. Jet Stream parameters: drying gas (N2) flow and temperature: 8.0 l/min and 325° C., respectively; nebulizer gas (N2) pressure: 30 psi; capillary voltage: 3000 V; sheath gas flow and temperature: 325° C. and 10.0 l/min; TOFMS parameters: fragmentor voltage: 100 V; skimmer potential: 60 V; OCT 1 RF Vpp: 750 V. Full-scan mass spectra were acquired over the m/z range 105-1700 at an acquisition rate of 995.6 ms/spectrum and processed by Agilent MassHunter B.04.00 software.

Chemical Naming

IUPAC-preferred names were generated using ChemAxon's 'Structure to Name' (s2n) functionality within MarvinSketch or JChem for Excel (JChem versions 16.6.13-

18.22.3), or with the chemical naming functionality provided by Biovia® Draw 4.2.

Abbreviations

Ahx 6-hexanoic acid monomer
Boc tert-butyloxycarbonyl
$Boc_2O$ di-tert-butyl dicarbonate
$^tBuOH$ tert-butanol
cc. or conc. concentrated
CyOH cyclohexanol
dba (1E,4E)-1,5-diphenylpenta-1,4-dien-3-one, dibenzylideneacetone
DCM dichloromethane
DEA diethanolamine
DIAD diisopropylazodicarboxylate
DIBAL-H diisobutylaluminium hydride
DIPA N-isopropylpropan-2-amine, diisopropylamine
DIPEA N-ethyl-N-isopropyl-propan-2-amine, diisopropylethylamine
$EtO_2$ diethyl ether
EtOAc ethyl acetate
eq. equivalent
HF×Pyr Hydrogen fluoride pyridine
hs *Homo sapiens*
LDA lithium diisopropylamide
MeCN acetonitrile
MeOH methanol
MTBE methyl tert-butyl ether
on overnight
Pd\C palladium on carbon
$PPh_3$ triphenylphosphine
rt room temperature
RT retention time (in minutes)
TBAF tetrabutylammonium fluoride
TBAOH tetrabutylammonium hydroxide
TBSCl tert-butyl-chloro-dimethyl-silane
TEA N,N-diethylethanamine
TFA 2,2,2-trifluoroacetic acid
pTSA 4-methylbenzenesulfonic acid
THF tetrahydrofuran
TIPSCl chloro(triisopropyl)silane
Xantphos 4,5-Bis(diphenylphosphino)-9,9-dimethylxanthene
Xantphos Pd G3 [(4,5-Bis(diphenylphosphino)-9,9-dimethylxanthene)-2-(2'-amino-1,1'-biphenyl)]palladium (II) methanesulfonate
BINAP 2,2'-Bis(diphenylphosphino)-1,1'-binaphthyl
rac-BINAP Pd G3 [(2,2'-Bis(diphenylphosphino)-1,1'-binaphthyl)-2-(2'-amino-1,1'-biphenyl)]palladium(II) methanesulfonate
$Pd(dppf)Cl_2 \cdot CH_2Cl_2$ [1,1'-Bis(diphenylphosphino)ferrocene]dichloropalladium(II)
$Pd_2(dba)_3$ Tris(dibenzylideneacetone)dipalladium(0)
$Pd(PPh_3)_2Cl_2$ Bis(triphenylphosphine)palladium chloride
$Pd(AtaPhos)_2Cl_2$ bis(di-tert-butyl(4-dimethylaminophenyl)phosphine)dichloropalladium(II)

Named General Procedures

The following are representative experimental procedures that are referred to by name in subsequent Preparations.

Sonogashira General Procedure

The mixture of 1 eq. of aryl halogenide, 2 eq. of acetylene, 0.05 eq. of $Pd(PPh_3)_2Cl_2$, 0.05 eq. of CuI, and DIPA (1 mL/mmol) in THF (5 mL/mmol) was kept at 60° C. After reaching an appropriate conversion the volatiles were removed under reduced pressure, the crude intermediate was purified via flash column chromatography.

Deprotection with HFIP General Procedure

Substrate in 1,1,1,3,3,3-hexafluoropropan-2-ol (10 mL/mmol) was kept at 100-120° C. in a pressure bottle. After reaching an appropriate conversion the volatiles were removed under reduced pressure, the crude intermediate was purified via flash column chromatography.

Alkylation General Procedure

The mixture of 1 eq. of phenol/carbamate, 1-2 eq. of alkyl iodide or bromide, and 2-3 eq. of $C_2CO_3$ in acetone (5 mL/mmol) was stirred at rt for phenols and at 55° C. for carbamates. After reaching an appropriate conversion the volatiles were removed under reduced pressure, the crude intermediate was purified via flash column chromatography or reverse phase flash column chromatography.

Mitsunobu General Procedure

To the mixture of 1.0-1.5 eq. of aliphatic alcohol, 1 eq. of carbamate/phenol, and 1-2 eq. triphenylphosphine in THF or toluene (5 mL/mmol) was added 1-3 eq. of ditertbutyl azodicarboxylate/diisopropyl azodicarboxylate in one portion. The mixture was stirred at rt or 50° C., if necessary, for the carbamate and at rt for the phenol. After reaching an appropriate conversion the volatiles were removed under reduced pressure, the crude intermediate was purified via flash column chromatography.

Buchwald General Procedure I

The mixture of 1 eq. of chloro-substrate, 2 eq. of 1,3-benzothiazol-2-amine, 0.1 eq. of $Pd_2(dba)_3$, 0.2 eq. of XantPhos and 3 eq. of DIPEA in CyOH (5 mL/mmol) was kept at 140° C. After reaching an appropriate conversion, the reaction mixture was diluted with DCM (10 mL/mmol), injected onto a preconditioned silica gel column and was purified via flash column chromatography.

Buchwald General Procedure II

The mixture of 1 eq. of thiazol amine, 1.2-1.5 eq. of (Z)—N-(6-chloro-4-methyl-pyridazin-3-yl)-3-(2-trimethylsilylethoxymethyl)-1,3-benzothiazol-2-imine, 3 eq. of $C_2CO_3$, 0.1 eq. of $Pd_2(dba)_3$, 0.2 eq. of XantPhos and 3 eq. of DIPEA in 1,4-dioxane (5 mL/mmol) was kept at reflux. After reaching an appropriate conversion the volatiles were removed under reduced pressure, the crude intermediate was purified via flash column chromatography.

Finkelstein General Procedure

The mixture of 1 eq. of alkyl chloride and 2 eq. of NaI in acetone (5 mL/mmol) was kept at reflux. After reaching an appropriate conversion the volatiles were removed under reduced pressure, the crude intermediate was purified via flash column chromatography.

Nucleophile Substitution General Procedure

The mixture of 1 eq of thiazol amine, 1 eq. of 3,6-dichloro-4-methylpyridazine, and 1.5 eq. of $C_2CO_3$ in toluene (4 mL/mmol) was kept at 150° C. After reaching an appropriate conversion the volatiles were removed under reduced pressure, the crude intermediate was purified via flash column chromatography.

Alkylation with Tosylate General Procedure

An oven-dried vial was equipped with a PTFE-coated magnetic stirring bar, and was charged with 1 eq. tosylate and 5 eq. as the appropriate amine were suspended in MeCN (5 mL/mmol). The reaction mixture was then warmed up to 50° C. and stirred at that temperature until no further conversion was observed. The reaction mixture was diluted with DCM then it was injected onto a DCM preconditioned silica gel column. Then it was purified via flash column chromatography using DCM and MeOH (1.2% $NH_3$) as eluents.

Alkylation With In Situ Generated Tosylate General Procedure

An oven-dried vial was equipped with a PTFE-coated magnetic stirring bar, and was charged with 1 eq. of hydroxy derivative, 3 eq. of N,N-diethylethanamine, catalytic amount of N,N-dimethylpyridin-4-amine and DCM (5 mL/mmol) then 2 eq. of 4-methylbenzenesulfonyl chloride was added in one portion and stirred at rt until no further conversion was observed (typically >90%, 1-5 h). After the evaporation of the volatiles with $N_2$ at 40° C., 30 eq. of the appropriate primary, secondary, or tertiary amine in acetonitrile (3 mL/mmol) were added and the mixture was stirred at 50° C. until full conversion was observed regarding the tosyl derivative (typically 1-3 h). Reaction mixture was concentrated onto celite and purified via flash column chromatography using EtOAc and MeOH (1.2% $NH_3$) as eluents or reverse phase flash column chromatography (0.1% TFA in water:MeCN).

Alkylation With In Situ Generated Iodine General Procedure

An oven-dried vial was equipped with a PTFE-coated magnetic stirring bar, it was charged with 2 eq. $PPh_3$ and 2 eq. imidazole then DCM (5 mL/mmol) was added. To the resulting mixture 2 eq. iodine was added portionwise then stirred for 15 min at rt. To the resulting mixture 1 eq. of the appropriate alcohol was added dissolved in DCM and stirred at rt until no further conversion was observed. To the generated iodo compound 5 eq. of the appropriate amine was added and then stirred for 30 min at rt, while full conversion was observed. Celite was added to the reaction mixture and the volatiles were removed under reduced pressure. Then it was purified via flash chromatography using DCM and MeOH (1.2% $NH_3$) eluents.

Alkylation of Silyl-Protected Phenols General Procedure

The mixture of 1 eq. of silyl-protected phenol, 1 eq. of alkyl iodide, and 1.15 eq. of TBAF (1 M in THF) in THF (2 mL/mmol) was stirred at rt. After reaching an appropriate conversion the volatiles were removed under reduced pressure, the crude intermediate was purified via flash column chromatography.

Deprotection and Hydrolysis General Procedure

The mixture of 1 eq. of substrate and 100 eq. of HF×Pyr in MeCN (15 mL/mmol) was stirred at 60° C. After reaching an appropriate conversion, the volatiles were removed under reduced pressure and the residue was suspended in a 1:1 mixture of 1,4-dioxane-water (30 mL/mmol), treated with 150 eq. of LiOH×$H_2O$, and stirred at 60° C. After reaching an appropriate conversion, the volatiles were removed under reduced pressure and the crude product was purified via flash column chromatography using DCM and MeOH (containing 1.2% $NH_3$) as eluents.

Quaternary Salt Formation General Procedure

An oven-dried vial was equipped with a PTFE-coated magnetic stirring bar, and was charged with 1 eq. tosylate and 20 eq. as the appropriate amine were suspended in CyOH (5 mL/mmol). The reaction mixture was then warmed up to 140° C. and stirred at that temperature until no further conversion was observed. The reaction mixture was diluted with DCM then it was injected onto a DCM preconditioned silica gel column. Then it was purified via flash column chromatography using DCM and MeOH (1.2% $NH_3$) as eluents.

Quaternary Salt Deprotection General Procedure

To a THF (5 mL/mmol) solution of the appropriate quaternary salt 3 eq. TBAF was added, and then it was stirred at rt until no further conversion was observed. The reaction mixture was the evaporated to dry under reduced pressure. To a suspension of 1 eq. desilylated quaternary salt in dry MeCN (15 mL/mmol), 100 eq. of HF×Pyr added, and then was stirred at 60° C. After reaching an appropriate conversion, the volatiles were removed under reduced pressure, the residue was suspended in a 1:1 mixture of THF-water (30 mL/mmol), 150 eq. of LiOH×H2O was added, and the mixture was stirred at rt. After reaching an appropriate conversion, the volatiles were removed under reduced pressure. The crude product was purified via flash column chromatography using DCM and MeOH (containing 1.2% $NH_3$) as eluents.

Alkylation, Deprotection and Hydrolysis General Procedure

A mixture of tertiary amine (1 eq.) and alkylating agent (10 eq.) in acetonitrile (3 mL/mmol) was stirred at rt. After reaching appropriate conversion, the volatiles were removed under reduced pressure and purified via reverse phase flash column chromatography, if it was necessary, otherwise the residue was directly dissolved in acetonitrile (3 mL/mmol), HF×Pyr (100 eq.) was added and the mixture was stirred at 60° C. After reaching appropriate conversion, the volatiles were removed under reduced pressure, the residue was suspended in a 1:1 mixture of 1,4-dioxane-water (10 mL/mmol), LiOH×$H_2O$ (150 eq.) was added and the mixture was stirred at 60° C. After reaching appropriate conversion to the desired product, the volatiles were removed under reduced pressure and the crude product was purified via reverse phase flash column chromatography.

Deprotection of Tert-Butyl-Dimethyl-Silyl Protecting Group General Procedure

The appropriate TBS protected compound and [(1S,4R)-7,7-dimethyl-2-oxo-norbornan-1-yl]methanesulfonic (0.25 eq. in general, 1.25 eq. if N,N-dimethyl-amine was presented in the molecule) acid were mixed in the mixture of methanol (2.5 mL/mmol) and dichloromethane (2.5 mL/mmol) in a sealed tube and stirred at 50° C. until full conversion was observed (typically 1-5 h). After the reaction time the mixture was poured into a separation funnel, diluted with DCM and washed with cc. $NaHCO_3$ and water. Dried over $MgSO_4$, filtered and onto celite then purified via flash column chromatography.

Deprotection and Hydrolysis of Phosphonic Acid Derivatives General Procedure

The solution of the diethyl phosphonate derivative in DCM (5 mL/mmol) and MeCN (5 mL/mmol) was flushed with nitrogen then 40 eq. TEA was added and then cooled to 0° C. 20 eq. bromo(trimethyl)silane was added in one portion then stirred for further 30 mM at 0° C. Left to warm up to rt and stirred until the full conversion regarding the ethyl ester (typically 1-5 h). Boc protecting group(s) were generally but only partially eliminated, resulted in the mixture of products. After full conversion, the mixture was quenched with few mL MeOH at 0° C., concentrated to Celite then purified via flash column chromatography using EtOAc and MeOH (containing 1.2% $NH_3$) as eluents. The two products (with Boc, without Boc) were combined and continued with Deprotection and Hydrolysis General Procedure.

Amine Substitution and Hydrolysis General Procedure

To the product from Preparation 14 in a 1:1 mixture of acetonitrile and N-methyl-2-pyrrolidone (10 ml/mmol), was added the appropriate amine (3-10 eq), and the mixture was stirred at 50° C. for 2-24 h. After the addition of 70% HF in pyridine (50-100 eq) at rt, the mixture was stirred for 4-18 h. After the purification of the substitution product by column chromatography (silica gel, using DCM and MeOH as eluents), the product was dissolved in THF (8 ml/mmol), and water (2 ml/mmol) and LiOH×$H_2O$ (5 eq) was added, and stirred at 20-40° C. for 1-4 h. The hydrolysed product was purified by preparative HPLC (using acetonitrile and 5 mM aqueous $NH_4HCO_3$ solution as eluents) to give the desired product.

Preparations

The following experimental details describe the preparation of synthetic intermediates.

Preparation 1a: Methyl 2-{[(tert-butoxy)carbonyl]amino}-5-[3-(2-fluoro-4-iodophenoxy)propyl]-1,3-thiazole-4-carboxylate Step A: methyl 2-(tert-butoxycarbonylamino)-5-iodo-thiazole-4-carboxylate 50.00 g of methyl 2-(tert-butoxycarbonylamino)thiazole-4-carboxylate (193.55 mmol, 1 eq.) was suspended in 600 mL dry MeCN. 52.25 g of N-iodo succinimide (232.30 mmol, 1.2 eq.) was added and the resulting mixture was stirred overnight at room temperature. The reaction mixture was diluted with saturated brine, then it was extracted with EtOAc. The combined organic layers were extracted with 1 M $Na_2S_2O_3$, then with brine again. Then dried over $Na_2SO_4$, filtered and the filtrate was concentrated under reduced pressure. The crude product was purified via flash column chromatography using heptane as eluent to obtain 60 g (156 mmol, 80%) of the desired product.

$^1$H NMR (400 MHz, DMSO-$d_6$) δ ppm 12.03/11.06 (br s), 3.78 (s, 3H), 1.47 (s, 9H); $^{13}$C NMR (400 MHz, DMSO-$d_6$) δ ppm 153.8, 82.5, 77.7, 52.3, 28.3; HRMS-ESI (m/z): $[M+H]^+$ calcd for $C_{10}H_{14}IN_2O_4S$: 384.9713, found 384.9708.

Step B: methyl 2-(tert-butoxycarbonylamino)-5-(3-hydroxyprop-1-ynyl)thiazole-4-carboxylate A 500 mL oven-dried, one-necked, round-bottom flask was equipped with a PTFE-coated magnetic stirring bar and fitted with a reflux condenser. It was charged with 9.6 g of the product from Step A (25 mmol, 1 eq.), 2.80 g of prop-2-yn-1-ol (2.91 mL, 50 mmol, 2 eq.) and 36.10 g of DIPA (50 mL, 356.8 mmol, 14.27 eq.) then 125 mL of dry THF was added and the system was flushed with argon. After 5 minutes stirring under inert atmosphere 549 mg of $Pd(PPh_3)_2Cl_2$ (1.25 mmol, 0.05 eq.) and 238 mg of CuI (1.25 mmol, 0.05 eq.) was added. The resulting mixture was then warmed up to 60° C. and stirred at that temperature until no further conversion was observed. Celite was added to the reaction mixture and the volatiles were removed under reduced pressure. Then it was purified via flash column chromatography using heptane and EtOAc as eluents to give 7.30 g (23 mmol, 93%) of the desired product as a yellow solid.

$^1$H NMR (400 MHz, DMSO-$d_6$) δ ppm 12.10 (br s, 1H), 5.45 (t, 1H), 4.36 (d, 2H), 3.79 (s, 3H), 1.48 (s, 9H); $^{13}$C NMR (125 MHz, DMSO-$d_6$) δ ppm 161.3, 142.4, 118.1, 101.4, 73.9, 52.4, 50.2, 28.3; HRMS-ESI (m/z): $[M+H]^+$ calcd for $C_{13}H_{17}N_2O_5S$: 313.0853, found 313.0866.

Step C: methyl 2-(tert-butoxycarbonylamino)-5-(3-hydroxypropyl)thiazole-4-carboxylate An 1 L oven-dried pressure bottle equipped with a PTFE-coated magnetic stirring bar was charged with 44.75 g of the product from Step B (1433 mmol, 1 eq.), 7.62 g of Pd/C (7.17 mmol, 0.05 eq.) in 340 mL of ethanol, and then placed under a nitrogen atmosphere using hydrogenation system. After that it was filled with 4 bar $H_2$ gas and stirred at rt overnight. Full conversion was observed, but only the olefin product was formed. After filtration of the catalyst through a pad of Celite the whole procedure was repeated with 5 mol % new catalyst. The resulting mixture was stirred overnight to get full conversion. Celite was added to the reaction mixtures and the volatiles were removed under reduced pressure. Then it was purified via flash column chromatography using heptane and EtOAc as eluents to give 31.9 g (101 mmol, 70%) of the desired product as light-yellow crystals $^1$H NMR (500 MHz, DMSO-$d_6$) δ ppm 11.61 (br s, 1H), 4.54 (t, 1H), 3.76 (s, 3H), 3.43 (m, 2H), 3.09 (t, 2H), 1.74 (m, 2H), 1.46 (s, 9H); $^{13}$C NMR (125 MHz, DMSO-$d_6$) δ ppm 162.8, 143.1, 135.4, 60.3, 51.9, 34.5, 28.3, 23.4; HRMS-ESI (m/z): $[M+H]^+$ calcd for $C_{13}H_{21}N_2O_5S$: 317.1166, found 317.1164.

Step D: methyl 2-{[(tert-butoxy)carbonyl]amino}-5-[3-(2-fluoro-4-iodophenoxy)propyl]-1,3-thiazole-4-carboxylate A 250 mL oven-dried, one-necked, round-bottomed flask equipped with a PTFE-coated magnetic stirring bar, was charged with 3.40 g or 2-fluoro-4-iodo-phenol (14 mmol, 1 eq.), 5.00 g of the product from Step C (16 mmol, 1.1 equiv) and 4.10 g of $PPh_3$ (16 mmol, 1.1 eq.) and 71 mL of dry toluene. After 5 min stirring under nitrogen atmosphere, 3.10 mL of DIAD (3.20 g, 16 mmol, 1.1 eq.) was added in one portion while the reaction mixture warmed up. Then the reaction mixture was heated up to 50° C. and stirred at that temperature for 30 min, when the reaction reached complete conversion. The reaction mixture was directly injected onto a preconditioned silica gel column, and then it was purified via flash column chromatography using heptane and EtOAc as eluents. The crude product was crystallized from MeOH to give 4.64 g (9.24 mmol, 66%) of the desired product.

$^1$H NMR (500 MHz, DMSO-$d_6$) δ ppm 11.64 (br s, 1H), 7.59 (dd, 1H), 7.45 (dd, 1H), 6.98 (t, 1H), 4.06 (t, 2H), 3.73 (s, 3H), 3.22 (t, 2H), 2.06 (m, 2H), 1.46 (s, 9H); $^{13}$C NMR (125 MHz, DMSO-$d_6$) δ ppm 134.0, 124.9, 117.6, 68.2, 51.9, 30.5, 28.3, 23.2; HRMS-ESI (m/z): $[M+H]^+$ calcd for $C_{19}H_{23}N_2O_5FSI$: 537.0351, found 537.0348.

Preparation 1b: Methyl 2-(tert-butoxycarbonylamino)-5-[3-[4-[3-[tert-butoxycarbonyl(methyl)amino]prop-1-ynyl]-2-fluoro-phenoxy]propyl]thiazole-4-carboxylate A 500 mL oven-dried, one-necked, round-bottom flask was equipped with a PTFE-coated magnetic stirring bar and fitted with a reflux condenser. It was charged with 13.41 g of Preparation 1a (25 mmol, 1 eq.), 8.46 g of tert-butyl N-methyl-N-prop-2-ynyl-carbamate (50 mmol, 2 eq.) and 50 mL of DIPA (36.1.0 g, 50 mL, 356.8 mmol, 14.27 eq.) then 125 mL of dry THF was added and the system was flushed with argon. After 5 minutes stirring under inert atmosphere 549 mg of $Pd(PPh_3)_2Cl_2$ (1.25 mmol, 0.05 eq.) and 238 mg of CuI (1.25 mmol, 0.05 eq.) were added. The resulting mixture was then warmed up to 60° C. and stirred at that temperature until no further conversion was observed. Celite was added to the reaction mixture and the volatiles were removed under reduced pressure. Then it was purified via flash column chromatography using heptane and EtOAc as eluents to give 10.5 g (18.2 mmol, 73%) of the desired product.

$^1$H NMR (500 MHz, DMSO-$d_6$) δ ppm 11.65 (br s, 1H), 7.31 (br d, 1H), 7.21 (br d, 1H), 7.14 (t, 1H), 4.23 (s, 2H), 4.10 (t, 2H), 3.73 (s, 3H), 3.23 (t, 2H), 2.86 (s, 3H), 2.07 (m, 2H), 1.46/1.41 (s, 18H); $^{13}$C NMR (125 MHz, DMSO-$d_6$) δ ppm 129.1, 119.2, 115.4, 68.1, 51.9, 38.6, 33.8, 30.5, 23.2; HRMS-ESI (m/z): $[M+H]^+$ calcd for $C_{28}H_{37}FN_3O_7S$: 578.2331, found 578.2331.

Preparation 1c: Methyl 2-(tert-butoxycarbonylamino)-5-[3-[4-[3-(dimethylamino)prop-1-ynyl]-2-fluoro-phenoxy]propyl]thiazole-4-carboxylate A 250 mL oven-dried, one-necked, round-bottom flask was equipped with a PTFE-coated magnetic stirring bar and fitted with a reflux condenser. It was charged with 5.36 g of Preparation 1a (10 mmol, 1 eq.), 1.66 g of N,N-dimethy-prop-2-yn-1-amine (20 mmol, 2 eq.) and 20 mL of DIPA (142.7 mmol, 14.27 eq.) then 50 mL of dry THF was added and the system was flushed with argon. After 5 minutes stirring under inert atmosphere 220 mg of $Pd(PPh_3)_2Cl_2$ (0.5 mmol, 0.05 eq.) and 95 mg of CuI (0.5 mmol, 0.05 eq.) were added. The resulting mixture was then warmed up to 60° C. and stirred at that temperature until no further conversion was observed. Celite was added to the reaction mixture and the volatiles were removed under reduced pressure. Then it was purified via flash column chromatography using DCM and MeOH (1.2% $NH_3$) as eluents to give 4.5 g (7.8 mmol, 78%) of the desired product.

$^1$H NMR (500 MHz, DMSO-$d_6$) δ ppm 11.66 (s, 1H), 7.29 (dd, 1H), 7.19 (m, 1H), 7.12 (t, 1H), 4.09 (t, 2H), 3.73 (s, 3H), 3.44 (s, 2H), 3.23 (t, 2H), 2.24 (s, 6H), 2.07 (m, 2H), 1.45 (s, 9H); $^{13}$C NMR (125 MHz, DMSO-$d_6$) δ ppm 162.8, 147.3, 129.0, 119.2, 115.4, 84.3, 68.0, 51.9, 48.1, 44.2, 30.6, 28.3, 23.2; HRMS-ESI (m/z): $[M+H]^+$ calcd for $C_{24}H_{31}FN_3O_5S$: 492.1963, found 492.1956.

Preparation 2a: 5-[tert-Butyl(dimethyl)silyl]oxy-4-[tert-butyl(diphenyl)silyl]oxy-pentan-1-ol Step A: pent-4-enyl benzoate 30.00 g of pent-4-en-1-ol (0.35 mol, 1 eq.) and 58.5 mL of N,N-diethylethanamine (0.42 mol, 1.2 eq.) were mixed in 200 mL of DCM then cooled to 0° C. 48.5 mL of benzoyl chloride (0.42 mol, 1.2 eq.) was added to the mixture at 0° C. via dropping funnel under inert atmosphere. After the addition the mixture was further stirred at 0° C. for 30 min then at rt for on. The mixture was diluted with 100 mL of DCM then the organic phase was washed with water, 1 M NaOH, 1 M HCl, brine, respectively. The organic phase was dried over $MgSO_4$, filtered, concentrated and purified via flash column chromatography using heptane and EtOAc as eluents to give 63.19 g (95%) of the desired product as colorless liquid.

$^1$H NMR (500 MHz, DMSO-$d_6$) δ ppm 7.97 (dd, 2H), 7.66 (t, 1H), 7.53 (t, 2H), 5.91-5.81 (m, 1H), 5.09-4.97 (m, 2H), 4.27 (t, 2H), 2.17 (q, 2H), 1.81 (qv, 2H); $^{13}$C NMR (125 MHz, DMSO-$d_6$) δ ppm 166.2, 138.2, 133.8, 130.3, 129.6, 129.2, 115.8, 64.5, 30.1, 27.8; GC-MS-EI (m/z): $[M]^+$ calcd for $C_{12}H_{14}O_2$: 190.1, found 190.

Step B: 4,5-dihydroxypentyl benzoate 42.22 g of the product from Step A (0.26 mol, 1.0 eq.). 50.40 g of 4-methyl-4-oxido-morpholin-4-ium; hydrate (0.37 mol, 1.7 eq) were mixed in 360 mL of 2-methylpropan-2-ol and 40 mL of water then 6.57 g of tetraoxoosmium (2.5 w % in 2-methylpropan-2-ol, 0.64 mmol, 0.002 eq.) was added and the mixture was stirred at 60° C. for 24 h. Full conversion was observed. The mixture was cooled down to rt and 1 M $Na_2S_2O_3$ was added then stirred for further 10 min at rt. DCM was added and the organic phase was separated, washed with water, brine, respectively. The solution was dried over over $MgSO_4$, filtered, concentrated and purified via flash column chromatography using heptane and EtOAc as eluents to give 36.9 g (63%) of the desired product as white solid.

$^1$H NMR (500 MHz, DMSO-$d_6$) δ ppm 7.99-7.50 (m, 5H), 4.50 (m, 2H), 4.28 (m, 2H), 3.45 (m, 1H), 3.30-3.24 (m+m, 2H), 1.85-1.72 (m+m, 2H), 1.59-1.33 (m+m, 2H); $^{13}$C NMR (125 MHz, DMSO-$d_6$) δ ppm 166.2, 133.8-129.1, 71.2, 66.3, 65.5, 30.3, 25.2; HRMS-ESI (m/z): $[M+Na]^+$ calcd for $C_{12}H_{16}NaO_4$: 247.0941, found 247.0941.

Step C: 5-[tert-butyl(dimethyl)silyl]oxy-4-hydroxy-pentyl]benzoate 24.86 g of the product from Step B (0.11 mol, 1 eq) and 15.09 g of imidazole (0.22 mol, 2 eq.) were mixed in 120 mL of N,N-dimethylformamide then cooled to −20° C. under inert atmosphere. 16.71 g of tert-butyl-chloro-dimethyl-silane (0.11 mol, 1 eq.) in 40 mL of N,N-dimethylformamide was added in slow rate over a period of 30 min, supported with 10 mL of DCM then left to warm up to rt and further stirred for on. Full conversion was observed. Quenched with cc. $NH_4Cl$ then evaporated most of the volatiles. EtOAc and water were added to the residue, the organic phase was separated then washed with water and brine, dried over $MgSO_4$, filtered, concentrated and purified via flash column chromatography using heptane and EtOAc as eluents to give 33.71 g (90%) or the desired product as colorless oil.

$^1$H NMR (500 MHz, DMSO-$d_6$) δ ppm 7.95 (m, 2H), 7.66 (m, 1H), 7.52 (m, 2H), 4.58 (d, 1H), 4.29 (m, 2H), 3.51-3.35 (dd+dd, 2H), 3.48 (m, 1H), 1.86-1.74 (m+m, 2H), 1.67-1.34 (m+m, 2H), 0.83 (s, 9H), 0.01 (s, 6H); $^{13}$C NMR (125 MHz, DMSO-$d_6$) δ ppm 166.2, 133.7, 130.4, 129.5, 129.2, 70.6, 67.7, 65.3, 30.2, 26.3, 24.9, −4.9.

Step D: [5-[tert-butyl(dimethyl)silyl]oxy-4-[tert-butyl(diphenyl)silyl]oxy-pentyl]benzoate 33.51 g of the product from Step C (0.10 mol, 1 eq), 16.85 g of imidazole (0.25 mol, 2.5 eq.) and 1.21 g of N,N-dimethylpyridin-4-amine (0.01, 0.1 eq.) were mixed in 230 mL of N,N-dimethylformamide then 38 mL of tert-butyl-chloro-diphenyl-silane (0.15 mol, 1.5 eq.) was added in slow rate, supported with 20 mL of N,N-dimethylformamide then stirred at 50° C. for overnight. Full conversion was observed. The mixture was cooled to rt, quenched with cc. $NH_4Cl$ then evaporated most of the volatiles. EtOAc and water were added to the residue, the organic phase was separated then washed with water and brine, dried over $MgSO_4$, filtered, concentrated and purified via flash column chromatography using heptane and EtOAc as eluents to give 56.43 g (99%) of the desired product as colorless thick oil.

$^1$H NMR (500 MHz, DMSO-$d_6$) δ ppm 7.91-7.37 (m, 15H), 4.17 (m, 2H), 3.76 (m, 1H), 3.45 (m, 2H), 1.72 (m, 2H), 1.66-1.57 (m+m, 2H), 0.99 (s, 9H), 0.74 (s, 9H), −0.12/−0.16 (s+s, 6H); $^{13}$C NMR (125 MHz, DMSO-$d_6$) δ ppm 166.1, 136.0-128.0, 73.3, 66.0, 65.1, 30.3, 27.3, 26.1, 24.0, −5.1; HRMS-ESI (m/z): $[M+Na]^+$ calcd for $C_{34}H_{48}NaO_4Si_2$: 599.2983, found 599.2981.

Step E: 5-[tert-butyl(dimethyl)silyl]oxy-4-[tert-butyl (diphenyl)silyl]oxy-pentan-1-ol 46.10 g of the product from Step D (0.08 mol, 1 eq) was dissolved in 227 mL of MeOH and 117 mL of THF then 12.79 g of NaOH (0.32 mol, 4.0 eq.) in 85 mL of water was added slowly while the mixture was cooled with ice. After the addition the mixture left to stir at rt until full conversion was observed (ca. 4 h). EtOAc and water were added then separated and the organic phase was washed with brine, dried over $MgSO_4$, filtered, concentrated and purified via flash column chromatography using heptane and EtOAc as eluents to give 29.32 g (78%) of the desired product as colorless oil.

$^1$H NMR (500 MHz, DMSO-$d_6$) δ ppm 7.65-7.37 (m, 10H), 4.34 (t, 1H), 3.71 (m, 1H), 3.42 (m, 2H), 3.26 (m, 2H), 1.52 (m, 2H), 1.42 (m, 2H), 0.99 (s, 9H), 0.77 (s, 9H), −0.13 (s, 6H); $^{13}$C NMR (125 MHz, DMSO-$d_6$) δ ppm 135.8, 135.8, 134.3, 134.0, 130.3, 130.2, 128.2, 128.0, 74.0, 66.4, 61.4, 30.4, 28.3, 27.3, 26.2, −5.1; HRMS-ESI (m/z): $[M+Na]^+$ calcd for $C_{27}H_{44}NaO_3Si_2$: 495.2721, found 495.2706.

Preparation 2b: 5-[tert-Butyl(dimethyl)silyl]oxy-4-methoxy-pentan-1-ol

Step A: [5-[tert-butyl(dimethyl)silyl]oxy-4-methoxy-pentyl]benzoate 3.66 g of Preparation 2a, Step C (10.8 mmol, 1 eq), 6.95 g of N1,N1,N8,N8-tetramethylnaphthalene-1,8-diamine (32.4 mmol, 3 eq.) and a small portion 4 Å molecular sieves were mixed in 210 mL of DCM then 4.00 g of trimethyloxonium; tetrafluoroborate (27.0 mmol, 2.5 eq.) was added in one portion and the mixture was stirred at rt for 5 h. Full conversion was observed. The mixture was filtered through a pad of Celite, washed with DCM then concentrated. The leftover was redissolved in DCM and washed with water, 1 M $CuSO_4$, brine, respectively. The solution was dried over $MgSO_4$, filtered, concentrated onto Celite and purified via flash column chromatography using heptane and EtOAc as eluents to give 2.58 g (68%) of the desired product as colorless oil.

$^1$H NMR (400 MHz, DMSO-$d_6$) δ ppm 7.95 (d, 2H), 7.65 (t, 1H), 7.51 (t, 2H), 4.27 (t, 2H), 3.56 (ddd, 2H), 3.30 (s, 3H), 3.23-3.18 (m, 1H), 1.84-1.44 (m, 4H), 0.83 (s, 9H), 0.02 (s, 6H); $^{13}$C NMR (100 MHz, DMSO-$d_6$) δ ppm 165.7, 133.2, 129.9, 129.0, 128.7, 80.5, 64.7, 63.9, 57.0, 27.2, 25.7, 24.2, 17.9, −5.5, −5.5.

Step B: 5-[tert-butyl(dimethyl)silyl]oxy-4-methoxy-pentan-1-ol 2.54 g of the product from Step A (7.20 mol, 1 eq) was dissolved in 54 mL of MeOH then 1.44 g of NaOH (36 mmol, 5.0 eq.) in 18 mL of water was added slowly to the mixture. After the addition the mixture was stirred at rt until full conversion was observed (ca. 1.5 h). EtOAc and water were added then separated and the organic phase was washed with brine, dried over $MgSO_4$, filtered and concentrated to give 1.76 g (98%) of the desired product as light yellow oil.

$^1$H NMR (400 MHz, DMSO-$d_6$) δ ppm 4.37 (t, 1H), 3.58-3.50 (m, 2H), 3.39-3.32 (m, 2H), 3.29 (s, 3H), 3.17-3.10 (m, 1H), 1.51-1.32 (m, 4H), 0.86 (s, 9H), 0.03 (s, 6H); $^{13}$C NMR (100 MHz, DMSO-$d_6$) δ ppm 81.0, 64.4, 60.9, 57.0, 28.4, 27.2, 25.8, 18.0, −5.4, −5.4; LC-MS-ESI (m/z): $[M+H]^+$ calcd for $C_{12}H_{29}O_3Si$: 249.2, found 249.2.

Preparation 2c: 5-Methoxy-4-triisopropylsilyloxy-pentan-1-ol

Step A: [5-[tert-butyl(dimethyl)silyl]oxy-4-triisopropylsilyloxy-pentyl]benzoate 2.0 g of Preparation 2a, Step C (5.91 mmol, 1 eq) and 1.21 g of imidazole (17.73 mmol, 3 eq.) were mixed in 6 mL of N,N-dimethylformamide then 1.71 g of chloro(triisopropyl) silane (8.86 mol, 1.5 eq.) was added in one portion then stirred at 60° C. for 3.5 h. Additional chloro(triisopropyl) silane (0.5 eq.) and imidazole (1 eq.) were added and stirred further 3 h. Full conversion was observed. The mixture was cooled to rt then EtOAc and water were added, the organic phase was separated, washed with brine, dried over $MgSO_4$, filtered, concentrated onto Celite and purified via flash column chromatography using heptane and EtOAc as eluents to give 2.27 g (99%) of the desired product as colorless thick oil.

$^1$H NMR (400 MHz, DMSO-$d_6$) δ ppm 7.94 (d, 2H), 7.66 (t, 1H), 7.52 (t, 2H), 4.29 (t, 2H), 3.86 (qv, 1H), 3.53 (ddd, 2H) 1.83-1.56 (m, 4H), 1.02 (m, 21H), 0.84 (s, 9H), 0.02 (s, 6H).

Step B: (5-hydroxy-4-triisopropylsilyloxy-pentyl)benzoate

Using Deprotection of tert-butyl-dimethyl-silyl protecting group General Procedure starting from 2.25 g of the product from Step A (4.54 mmol, 1 eq.) followed by purification via flash column chromatography using heptane and EtOAc as eluents, 1.13 g (65%) of the desired product was obtained.

$^1$H NMR (400 MHz, DMSO-$d_6$) δ ppm 7.95 (d, 2H), 7.65 (t, 1H), 7.52 (t, 2H), 4.63 (t, 1H), 4.29 (qv, 2H), 3.85-3.78 (m, 1H), 3.45-3.26 (m, 2H), 1.83-1.54 (m, 4H), 1.01 (s, 21H); LC-MS-ESI (m/z): $[M+H]^+$ calcd for $C_{21}H_{37}O_4Si$: 381.2, found 381.3.

Step C: (5-methoxy-4-triisopropylsilyloxy-pentyl)benzoate 1.11 g of the product from Step B (2.91 mmol, 1 eq) and 1.87 g of N1,N1,N8,N8-tetramethylnaphthalene-1,8-diamine (8.7 mmol, 3 eq.) were mixed in 45 mL of DCM then 1.87 g of trimethyloxonium; tetrafluoroborate (8.7 mmol, 3 eq.) was added in one portion and the mixture was stirred at rt for 4 h. Full conversion was observed. The mixture was filtered through a pad of Celite, washed with DCM then the organic phase was washed with water, 1 M $CuSO_4$, brine, respectively. The solution was dried over $MgSO_4$, filtered, concentrated onto Celite and purified via flash column chromatography using heptane and EtOAc as eluents to give 963 mg (84%) of the desired product as colorless oil.

$^1$H NMR (400 MHz, DMSO-$d_6$) δ ppm 7.95 (d, 2H), 7.66 (t, 1H), 7.52 (t, 2H), 4.28 (t, 2H), 3.96 (qv, 1H), 3.31 (d, 2H), 3.25 (s, 3H), 1.82-1.54 (m, 4H), 1.01 (m, 21H); $^{13}$C NMR (100 MHz, DMSO-$d_6$) δ ppm 165.7, 133.3, 129.8, 129.0, 128.7, 75.9, 70.4, 64.7, 58.4, 30.7, 23.5, 18.0, 17.9, 12.0.

Step D: 5-methoxy-4-triisopropylsilyloxy-pentan-1-ol 953 mg of the product from Step C (2.41 mmol, 1 eq) was dissolved in 12 mL of MeOH and 6 mL of THF then 487 mg of NaOH (12.1 mmol, 5.0 eq.) in 6 mL of water was added slowly. After the addition the mixture left to stir at rt until full conversion was observed (ca. 2 h). EtOAc and water was added then separated and the organic phase was washed with brine, dried over $MgSO_4$, filtered, concentrated onto Celite and purified via flash column chromatography using heptane and EtOAc as eluents to give 687 mg (78%) of the desired product as colorless oil.

$^1H$ NMR (500 MHz, DMSO-$d_6$) δ ppm 4.39 (t, 1H), 3.89 (m, 1H), 3.37 (m, 2H), 3.27 (d, 2H), 3.24 (s, 3H), 1.47 (m, 2H), 1.47 (m, 2H), 1.03 (m, 21H); $^{13}C$ NMR (125 MHz, DMSO-$d_6$) δ ppm 76.8, 71.4, 61.4, 58.8, 31.4, 28.3, 18.5, 12.5; HRMS-ESI (m/z): $[M+H]^+$ calcd for $C_{15}H_{35}O_3Si$: 291.2350, found 291.2349.

Preparation 2d: 4-[tert-Butyl(dimethyl)silyl]oxy-5-(dimethylamino)pentan-1-ol

Step A: 3-(oxiran-2-yl)propyl benzoate 19.01 g of 3-chlorobenzenecarboperoxoic acid (77 w %, 85.83 mmol, 1.3 eq.) was dissolved in DCM (3 mL/mmol) in a separation funnel then the organic phase (3-4 mL water was excluded) was added directly to the solution of 12.41 g of Preparation 2a, Step A (65.25 mmol, 1 eq.) in DCM (3 mL/mmol) and stirred at rt for 4 h. Full conversion was observed. 100 mL of DCM was added then washed with 2×100 mL cc. $NaHCO_3$ and 1×100 mL brine, dried over $MgSO_4$, filtered, concentrated and purified via flash column chromatography using heptane and EtOAc as eluents to give 13.92 g (quant.) of the desired product as colorless oil.

$^1H$ NMR (400 MHz, DMSO-$d_6$) δ ppm 7.97 (dm, 2H), 7.66 (tm, 1H), 7.53 (m, 2H), 4.31 (m, 2H), 2.97 (m, 1H), 2.68-2.48 (dd+dd, 2H), 1.84 (m, 2H), 1.67-1.56 (m+m, 2H); $^{13}C$ NMR (100 MHz, DMSO-$d_6$) δ ppm 166.2, 133.8, 129.6, 129.3, 64.8, 51.7, 46.6, 29.1, 25.4; HRMS-EI (m/z): $[M]^+$ calcd for $C_{12}H_{14}O_3$: 206.0943, found 206.0941.

Step B: [4-[tert-butyl(dimethyl)silyl]oxy-5-(dimethylamino)pentyl]benzoate 7.01 g of the product from Step A (34 mmol, 1 eq.) and 51 mL of dimethylamine solution (2 M in MeOH, 102 mml, 3 eq.) were mixed in a sealed tube and stirred at 60° C. for 1 h. Full conversion was observed. The reaction mixture was concentrated and [5-(dimethylamino)-4-hydroxy-pentyl] benzoate was obtained as a thick light yellow oil. HRMS-ESI (m/z): $[M+H]^+$ calcd for $C_{14}H_{22}NO_3$: 252.1594, round 252.1597.

The crude product was redissolved in N,N-dimethylformamide (2 mL/mmol) then 6.95 g of imidazole (102 mmol, 3 eq.), 208 mg of N,N-dimethylpyridin-4-amine (1.70 mmol, 0.05 eq.) were added and after getting clear solution 12.8 g of tert-butyl-chloro-dimethyl-silane (85.0 mmol, 2.5 eq.) was added in one portion. The mixture was stirred at 60° C. for 3 h (>95% conversion was observed). Cooled down to rt then 3-4 mL cc. $NH_4Cl$ was added, stirred for 5 mins then the volatiles were evaporated. 300 mL of EtOAc, 50 mL of water and 50 mL cc. $NaHCO_3$ were added then the organic layer was separated. Organic phase was washed with 1×50 mL $H_2O$, 1×50 mL brine then dried over $MgSO_4$, filtered then concentrated. The crude product was purified via flash column chromatography using DCM and MeOH as eluents to give 8.37 g (67%) of the desired product as colorless oil.

$^1H$ NMR (400 MHz, DMSO-$d_6$) δ ppm 7.99-7.49 (m, 5H), 4.29-4.27 (m+m, 2H), 3.78 (m, 1H), 2.20-2.17 (dd+dd, 2H), 2.13 (s, 6H), 1.80-1.73 (m+m, 2H), 1.67-1.46 (m+m, 2H), 0.84 (s, 9H), 0.05 (s, 3H), 0.04 (s, 3H); $^{13}C$ NMR (100 MHz, DMSO-$d_6$) δ ppm 166.2, 130.3, 70.0, 66.0, 65.3, 46.6, 32.0, 26.3, 24.5, −3.8, −4.4; HRMS-ESI (m/z): $[M+H]^+$ calcd for $C_{20}H_{36}NO_3Si$: 366.2459, found 366.2463.

Step C: 4-[tert-butyl(dimethyl)silyl]oxy-5-(dimethylamino)pentan-1-ol 3.12 g of the product from Step B (8.53 mmol, 1 eq) was dissolved in 34 mL of MeOH and 17 mL of THF then 1.36 g of NaOH (34 mmol, 4.0 eq.) in 17 mL of water was added slowly. After the addition the mixture left to stir at rt until full conversion was observed (ca. 1.5 h). EtOAc and water was added then separated and the organic phase was washed with brine, dried over $MgSO_4$, filtered, concentrated onto Celite and purified via flash column chromatography using DCM and MeOH as eluents to give 1.60 g (72%) of the desired product as colorless oil.

$^1H$ NMR (400 MHz, $CDCl_3$) 3.83-3.76 (m, 1H), 3.65-3.55 (m, 3H), 2.31 (ddd, 2H), 2.22 (s, 6H), 1.72-1.54 (m, 4H), 0.87 (s, 9H), 0.05 (s, 3H), 0.05 (s, 3H); $^{13}C$ NMR (100 MHz, $CDCl_3$) δ ppm: 70.1, 65.2, 62.9, 46.4, 31.9, 27.9, 26.0, 18.2, −4.36, −4.62; HRMS-ESI (m/z): $[M+H]^+$ calcd for $C_{13}H_{32}NO_2Si$: 262.2197, found 262.2197.

Preparation 2e: 4-[tert-Butyl(dimethyl)silyl]oxy-5-morpholino-pentan-1-ol

Step A: [4-[tert-butyl(dimethyl)silyl]oxy-5-morpholino-pentyl]benzoate 1.50 g of Preparation 2d, Step A (7.27 mmol, 1 eq.) and 1.91 g of morpholine (21.87 mmol, 3 eq.) were stirred in 15 mL of MeCN at 82° C. for 24 h. The reaction mixture was concentrated and (4-hydroxy-5-morpholino-pentyl)benzoate was obtained as a thick light yellow oil. LC-MS-ESI (m/z): $[M+H]^+$ calcd for $C_{16}H_{24}NO_4$: 294.2, found 294.2.

The crude product was redissolved in 7 mL of N,N-dimethylformamide then 1.19 g of imidazole (17.52 mmol, 3 eq.) were added and after getting clear solution 1.76 g of tert-butyl-chloro-dimethyl-silane (11.68 mmol, 2 eq.) was added in one portion. The mixture was stirred at 60° C. for 2 h. Cooled down to rt then EtOAc was added then the organic layer was washed with $H_2O$, brine then dried over $MgSO_4$, filtered then concentrated onto Celite. The crude product was purified via flash column chromatography using heptane and EtOAc as eluents to give 2.18 g (92%) of the desired product as colorless oil.

$^1H$ NMR (400 MHz, DMSO-$d_6$) δ ppm 7.96 (dd, 2H), 7.66 (t, 1H), 7.53 (t, 2H), 4.29 (t, 2H), 3.85 (m, 1H), 3.52 (t, 4H), 2.42-2.30 (m, 4H), 2.26 (t, 2H), 1.85-1.44 (m, 4H), 0.85 (s, 9H), 0.07 (s, 3H), 0.04 (s, 3H); $^{13}C$ NMR (100 MHz, $CDCl_3$) δ ppm 165.7, 133.3, 129.9, 129.0, 128.7, 68.7, 66.2, 64.8, 64.7, 54.2, 31.6, 25.8 24.1, 17.8, −4.2, −4.8; LC-MS-ESI (m/z): $[M+H]^+$ calcd for $C_{22}H_{38}NO_4Si$: 408.3, found 408.3.

Step B: 4-[tert-butyl(dimethyl)silyl]oxy-5-morpholino-pentan-1-ol 2.18 g of the product from Step A (8.53 mmol, 1 eq) was dissolved in 20 mL of MeOH and 20 mL of THF then 2.22 g of $K_2CO_3$ (16.06 mmol, 3.0 eq.) was added in one portion. After the addition the mixture left to stir at rt until full conversion was observed. Most of the volatiles was evaporated then EtOAc and water were added, separated and the organic phase was washed with brine, dried over $MgSO_4$, filtered, concentrated. 1.49 g (72%) of the desired product as colorless oil was obtained.

$^1$H NMR (400 MHz, DMSO-$d_6$) δ ppm 7.97 (d, 2H), 7.66 (t, 1H), 7.53 (t, 2H), 4.37 (t, 1H), 3.80-3.72 (m, 1H), 3.55 (t, 4H), 3.37 (q, 2H), 2.44-2.29 (m, 4H), 2.22 (ddd, 2H), 1.56-1.29 (m, 4H), 0.85 (s, 9H), 0.06 (s, 3H), 0.04 (s, 3H); $^{13}$C NMR (100 MHz, DMSO-$d_6$) δ ppm 69.3, 66.2, 65.3, 61.0, 54.3, 32.1, 28.5, 25.8, 17.9, −4.2, −4.7; LC-MS-ESI (m/z): $[M+H]^+$ calcd for $C_{15}H_{34}NO_3Si$: 304.2, found 304.3.

Preparation 2f: 4-[tert-Butyl(dimethyl)silyl]oxy-5-[2-(dimethylamino)ethyl-methyl-amino]pentan-1-ol

Step A: [4-[tert-butyl(dimethyl)silyl]oxy-5-[2-(dimethylamino)ethyl-methyl-amino]pentyl]benzoate 908 mg of Preparation 2d, Step A (4.40 mmol, 1 eq.) and 1.35 g of N,N',N'-trimethylethane-1,2-diamine (13.2 mmol, 3 eq.) were stirred in 12 mL of MeCN at 82° C. for on. The reaction mixture was concentrated and [5-[2-(dimethylamino)ethyl-methyl-amino]-4-hydroxy-pentyl]benzoate was obtained as a thick light yellow oil. LC-MS-ESI (m/z): $[M+H]^+$ calcd for $C_{17}H_{29}N_2O_3$: 309.2, found 309.3.

The crude product was redissolved in 4 mL N,N-dimethylformamide then 609 mg of imidazole (8.95 mmol, 3 eq.) were added and after getting clear solution 898 mg of tert-butyl-chloro-dimethyl-silane (5.96 mmol, 2 eq.) was added in one portion. The mixture was stirred at 60° C. for 2 h. Cooled down to rt then EtOAc was added then the organic layer was washed with $H_2O$, brine then dried over $MgSO_4$, filtered then concentrated onto Celite. The crude product was purified via flash column chromatography using DCM and MeOH as eluents to give 1.11 g (88%) of the desired product as colorless oil.

$^1$H NMR (400 MHz, DMSO-$d_6$) δ ppm 7.95 (d, 2H), 7.66 (t, 1H), 7.52 (t, 2H), 4.28 (t, 2H), 3.81-3.74 (m, 1H), 2.42-2.36 (m, 2H), 2.32-2.26 (m, 4H), 2.16 (s, 3H), 2.10 (s, 6H), 1.83-1.40 (m, 4H), 0.84 (s, 9H), 0.05 (s, 3H), 0.04 (s, 3H); $^{13}$C NMR (100 MHz, DMSO-$d_6$) δ ppm 165.7, 133.3, 129.9, 129.0, 128.7, 69.8, 64.8, 63.9, 57.0, 56.1, 45.4, 43.4, 31.5, 25.8, 24.0, 17.8, −4.3, −4.8; LC-MS-ESI (m/z): $[M+H]^+$ calcd for $C_{23}H_{43}N_2O_3Si$: 423.3, found 423.3.

Step B: 4-[tert-butyl(dimethyl)silyl]oxy-5-[2-(dimethylamino)ethyl-methyl-amino]pentan-1-ol 3.42 g of the product from Step A (8.09 mmol, 1 eq) was dissolved in 40 mL of MeOH and 20 mL of THF then 1.62 g of NaOH (40.5 mmol, 5.0 eq.) in 20 mL of water was added in one portion. After the addition the mixture was stirred at rt until full conversion was observed. EtOAc and water were added, separated and the organic phase was washed with brine, dried over $MgSO_4$, filtered, concentrated. 2.60 g (quant.) of the desired product as light yellow oil was obtained.

$^1$H NMR (500 MHz, DMSO-$d_6$) δ ppm 3.69 (m, 1H), 3.36 (t, 2H), 2.39 (m, 2H), 2.30 (m, 2H), 2.25 (m, 2H), 2.16 (s, 3H), 2.13 (s, 6H), 1.56-1.30 (m+m, 2H), 1.50-1.40 (m+m, 2H), 0.85 (s, 9H), 0.04 (s, 3H), 0.03 (s, 3H); $^{13}$C NMR (125 MHz, DMSO-$d_6$) δ ppm 70.7, 64.8, 61.5, 57.5, 56.7, 46.0, 43.8, 32.3, 29.0, 26.3, −3.8, −4.3; HRMS-ESI (m/z): $[M+H]^+$ calcd for $C_{16}H_{39}N_2O_2Si$: 319.2775, found 319.2788.

Preparation 2g: 3-[tert-Butyl(dimethyl)silyl]oxy-4-morpholino-butan-1-ol

Step A: 2-(oxiran-2-yl)ethyl benzoate 4.063 g of but-3-enyl benzoate (23.06 mmol, 1 eq.) was dissolved in 50 mL of $CHCl_3$ then 4.97 g of 3-chlorobenzenecarboperoxoic acid (77 w %, 28.80 mmol, 1.25 eq.) was added and stirred at rt for on. 60 mL of DCM was added then washed with cc. $NaHCO_3$ and brine, dried over $MgSO_4$, filtered, concentrated and purified via flash column chromatography using heptane and EtOAc as eluents to give 3.81 g (86%) of the desired product as colorless oil.

$^1$H NMR (400 MHz, DMSO-$d_6$) δ ppm 7.98 (d, 2H), 7.66 (t, 1H), 7.53 (t, 2H), 4.39 (t, 2H), 3.11-3.05 (m, 1H), 2.73 (t, 1H), 2.53 (dd, 1H), 2.03-1.82 (m, 2H); $^{13}$C NMR (100 MHz, DMSO-$d_6$) δ ppm 165.7, 133.4, 129.7, 129.2, 128.8, 62.0, 49.2, 45.9, 31.4; LC-MS-ESI (m/z): $[M+H]^+$ calcd for $C_{11}H_{13}O_3$: 193.1, found 193.1.

Step B: [3-[tert-butyl(dimethyl)silyl]oxy-4-morpholino-butyl]benzoate 723 mg of the product from Step A (3.76 mmol, 1 eq.) and 983 mg of morpholine (11.28 mmol, 3 eq.) were stirred in 10 mL MeCN at 82° C. for 24 h. The reaction mixture was concentrated and (3-hydroxy-4-morpholino-butyl)benzoate was obtained as a thick light yellow oil. LC-MS-ESI (m/): $[M+H]^+$ calcd for $C_{15}H_{22}NO_4$: 280.2, found 280.2.

The crude product was redissolved in 5 mL of N,N-dimethylformamide then 487 mg of imidazole (7.15 mmol, 3 eq.) were added and after getting clear solution 719 mg of tert-butyl-chloro-dimethyl-silane (4.77 mmol, 2 eq.) was added in one portion. The mixture was stirred at 60° C. for 2 h. Cooled down to rt then EtOAc was added then the organic layer was washed with $H_2O$, brine then dried over $MgSO_4$, filtered then concentrated onto Celite. The crude product was purified via flash column chromatography using heptane and EtOAc as eluents to give 669 mg (71%) of the desired product as colorless oil.

$^1$H NMR (400 MHz, DMSO-$d_6$) δ ppm 7.96 (d, 2H), 7.66 (t, 1H), 7.53 (t, 2H), 4.42-4.26 (m, 2H), 4.04-3.97 (m, 1H), 3.54 (t, 4H), 2.45-2.27 (m, 6H), 2.08-1.98 (m, 1H), 1.82-1.73 (m, 1H), 0.85 (s, 9H), 0.07 (s, 3H), 0.02 (s, 3H); $^{13}$C NMR (100 MHz, DMSO-$d_6$) δ ppm 165.7, 133.3, 129.8, 129.0, 128.8, 66.3, 66.2, 65.1, 61.7, 54.2, 34.3, 25.8, 17.8, −4.2, −5.1; LC-MS-ESI (m/z): $[M+H]^-$ calcd for $C_{21}H_{36}NO_4Si$: 394.2, found 394.3.

Step C: 3-[tert-butyl(dimethyl)silyl]oxy-4-morpholino-butan-1-ol 366 mg of the product from Step B (0.93 mmol, 1 eq) was dissolved in 2 mL of MeOH and 6.75 mL of THF then 186 mg of NaOH (4.65 mmol, 5.0 eq.) in 2.25 mL of water was added in one portion. After the addition the mixture left to stir at rt until full conversion was observed. EtOAc and water were added, separated and the organic phase was washed with brine, dried over $MgSO_4$, filtered, concentrated. 262 mg (97%) of the desired product as colorless oil was obtained.

$^1$H NMR (400 MHz, DMSO-$d_6$) δ ppm 4.42 (br., 1H), 3.93-3.87 (m, 1H), 3.55 (t, 4H), 3.52-3.41 (m, 2H), 2.37 (dm, 4H), 2.29-2.20 (m, 2H), 1.73-1.66 (m, 1H), 1.52-1.44 (m, 1H), 0.85 (s, 9H), 0.06 (s, 3H), 0.04 (s, 3H); $^{13}$C NMR (100 MHz, DMSO-$d_6$) δ ppm 66.2, 65.4, 57.4, 54.2, 39.0, 25.8, 17.8, −4.3, −4.8; LC-MS-ESI (m/z): $[M+H]^+$ calcd for $C_{14}H_{32}NO_3Si$: 290.2, found 290.3.

Preparation 2h: 3-[tert-Butyl(dimethyl)silyl]oxy-4-methoxy-butan-1-ol

Step A: methyl 3-hydroxy-4-methoxy-butanoate

To 1.00 g of methyl 4-methoxy-3-oxo-butanoate (6.84 mmol, 1 eq.) in 30 mL of MeOH was added 264 mg of $NaBH_4$ (6.98 mmol 1 eq.) in portions at 0° C. and the mixture was stirred at 0° C. for 10 h. After concentration, the residue was diluted with water and extracted with EtOAc. The combined organic phases were dried and concentrated to give 0.72 g (71%) of the desired product.

$^1H$ NMR (400 MHz, DMSO-$d_6$) δ ppm 4.97 (d, 1H), 3.97 (m, 1H), 3.58 (s, 3H), 3.27 (dd, 1H), 3.24 (s, 3H), 3.20 (dd, 1H), 2.46 (dd, 1H), 2.27 (dd, 1H).

Step B: methyl 3-[tert-butyl(dimethyl)silyl]oxy-4-methoxy-butanoate

To 8.89 g of the product from Step A (60 mmol, 1 eq.) and 4.3 g of imidazole (63.2 mmol, 1.05 eq.) in 100 mL of DMF was added 10 g of tert-butyl-chloro-dimethyl-silane (66.3 mmol, 1.1 eq.) in one portion and the mixture was stirred for 18 h. After dilution with 300 mL of brine and extraction with EtOAc, the combined organic phases were dried, concentrated, and purified by flash column chromatography using heptane and EtOAc as eluents to give 11.77 g (75%) of the desired product.

$^1H$ NMR (400 MHz, DMSO-$d_6$) δ ppm 4.17 (sx, 1H), 3.58 (s, 3H), 3.27 (m, 2H), 3.26 (s, 3H), 2.54 (dd, 1H), 2.32 (dd, 1H), 0.82 (s, 9H), 0.03 (d, 6H).

Step C: 3-[tert-butyl(dimethyl)silyl]oxy-4-methoxy-butan-1-ol

To 10.77 g of the product from Step B (41 mmol, 1 eq.) in 288 mL of DCM was slowly added 124 mL of DIBAL-H (1 M in THF, 124 mmol, 3 eq.) at 0° C. After stirred for 2.5 h at 0° C., 5 mL or water, 5 mL of a 15 w % solution of NaOH, 0.5 mL of water and anhydrous $MgSO_4$ were added consecutively. After 15 min of stirring, the mixture was filtered and concentrated to give 6.73 g (70%) of the desired product.

$^1H$ NMR (500 MHz, DMSO-$d_6$) δ ppm 4.34 (t, 1H), 3.89 (m, 1H), 3.48/3.44 (m+m, 2H), 3.24 (s, 3H), 3.24/3.21 (dd+dd, 2H), 1.59/1.46 (m+m, 2H), 0.85 (s, 9H), 0.04/0.03 (s+s, 6H); HRMS-ESI (m/z): $[M+H]^+$ calcd for $C_{11}H_{27}O_3Si$: 235.1729, found: 235.1725.

Preparation 2i: 4-[tert-Butyl(dimethyl)silyl]oxy-3-methoxy-butan-1-ol

Step A: 3,4-dihydroxybutyl benzoate

The mixture of 20.1 g of but-3-enyl benzoate (113.5 mmol, 1 eq.), 21.8 g of 4-methyl-4-oxido-morpholin-4-ium; hydrate (161.3 mmol, 1.42 eq.), and 2.83 g of tetraoxoosmium (2.5 w % in 2-methylpropan-2-ol, 0.28 mmol, 0.0025 eq.) in 227 mL of 2-methylpropan-2-ol and 27 mL of water was stirred at 60° C. for 18 h. After the reaction was quenched with the addition of 270 mL of a 1 M solution of $Na_2S_2O_3$ at rt, the mixture was diluted with DCM and the organic phase was washed with water and brine, dried, and concentrated to give 22.22 g (93%) of 3,4-dihydroxybutyl benzoate.

$^1H$ NMR (500 MHz, DMSO-$d_6$) δ ppm 7.97 (m, 2H), 7.65 (m, 1H), 7.53 (m, 2H), 4.68 (d, 1H), 4.59 (t, 1H), 4.39/4.34 (m+m, 2H), 3.63 (m, 1H), 3.37/3.30 (m+m, 2H), 1.93/1.64 (m+m, 2H); $^{13}C$ NMR (125 MHz, DMSO-$d_6$) δ ppm 166.2, 133.7, 129.5, 129.2, 68.5, 66.4, 62.5, 33.0; HRMS-ESI (m/z): $[M+H]^+$ calcd for $C_{11}H_{15}O_4$: 211.0970, found: 211.0971.

Step B: [4-[tert-butyl(dimethyl)silyl]oxy-3-hydroxy-butyl]benzoate

To 10 g of the product from Step A (47.6 mmol, 1 eq.) and 6.52 g of imidazole (0.096 mol, 2 eq.) in 100 mL of DMF was added 7.17 g of tert-butyl-chloro-dimethyl-silane (47.6 mmol, 1 eq.) in one portion and the mixture was stirred for 1 h. After the mixture was diluted with EtOAc, the organic phase was washed with cc. $NaHCO_3$, water and brine, dried over $MgSO_4$, filtered, concentrated to give 14.1 g (91%) of the desired product.

$^1H$ NMR (400 MHz, DMSO-$d_6$) δ ppm 7.95 (m, 2H), 7.64 (m, 1H), 7.51 (t, 2H), 4.76 (s, 1H), 4.38 (m, 2H), 3.65 (m, 1H), 3.56 (dd, 1H), 3.43 (dd, 1H), 1.96 (m, 1H), 1.65 (m, 1H), 0.84 (s, 9H), 0.02 (s, 6H).

Step C: [4-[tert-butyl(dimethyl)silyl]oxy-3-methoxy-butyl]benzoate 7.03 g of the product from Step B (21.7 mmol, 1 eq) and 13.9 g of N1,N1,N8,N8-tetramethylnaphthalene-1,8-diamine (64.9 mmol, 3 eq.) were mixed in 420 mL of DCM then 8.0 g of trimethyloxonium; tetrafluoroborate (54.1 mmol, 2.5 eq.) was added in one portion and the mixture was stirred at rt for 18 h. Full conversion was observed. The mixture was filtered through a pad of Celite, washed with DCM then the organic phase was washed with water, brine, respectively. The solution was dried over $MgSO_4$, filtered, concentrated onto Celite and purified via flash column chromatography using heptane and EtOAc as eluents to give 4.03 g (55%) of the desired product.

$^1H$ NMR (400 MHz, DMSO-$d_6$) δ ppm 7.97 (m, 2H), 7.67 (tt, 1H), 7.52 (t, 2H), 4.35 (m, 2H), 3.63 (m, 2H), 3.35 (m, 1H), 3.33 (s, 3H), 1.94 (m, 1H), 1.80 (m, 1H), 0.85 (s, 9H), 0.03 (s, 6H).

Step D: 4-[tert-butyl(dimethyl)silyl]oxy-3-methoxy-butan-1-ol

To 4.0 g of the product from Step C (11.83 mmol, 1 eq.) in 100 mL of a 1:1 mixture of THF and MeOH was added 5.1 g of $K_2CO_3$ (36.96 mmol, 3 eq.) at 0° C. and the mixture was stirred for 3 h at 0° C. and for 2 h at rt. After the addition of cc. $NH_4Cl$ and DCM at 0° C., the organic phase was washed with cc. $NaHCO_3$, water and brine, dried over $MgSO_4$, filtered, and concentrated to give 4.14 g (94%) of a 1:1 mixture of the desired product and methyl benzoate.

$^1H$ NMR (400 MHz, DMSO-$d_6$) δ ppm 4.38 (t, 1H), 3.57 (dd, 2H), 3.45 (q, 2H), 3.29 (s, 3H), 3.28 (m, 1H), 1.53 (m, 2H), 0.87 (s, 9H), 0.04 (s, 6H).

Preparation 2j: 3-[tert-Butyl(dimethyl)silyl]oxy-2-methoxy-propan-1-ol

Step A: (2,2-dimethyl-1,3-dioxolan-4-yl)methyl benzoate

To 20 g of (2,2-dimethyl-1,3-dioxolan-4-yl)methanol (151 mmol, 1 eq.) and 25 mL of N,N-diethylethanamine (182 mmol, 1.2 eq.) in 92 mL of DCM was added 21 mL of benzoyl chloride (182 mmol, 1.2 eq.) at 0° C. and the mixture was stirred at rt for 18 h. The reaction was quenched with cc. $NaHCO_3$ and the organic phase was washed with brine, dried, and concentrated to give 37.0 g (98%) of the desired product.

$^1H$ NMR (400 MHz, DMSO-$d_6$) δ ppm 7.98 (dd, 2H), 7.67 (m, 1H), 7.54 (t, 2H), 4.42 (m, 1H), 4.37 (dd, 1H), 4.27 (dd, 1H), 4.09 (dd, 1H), 3.82 (dd, 1H), 1.33 (s, 3H), 1.29 (s, 3H).

Step B: 2,3-dihydroxypropyl benzoate

The mixture of 20 g of the product from Step A (80 mmol, 1 eq.), 220 mL of a 1 N solution of HCl, and 220 mL of EtOH was stirred at rt for 18 h. After the reaction was quenched with cc. $Na_2CO_3$ and concentrated, the residue was extracted with EtOAc. The combined organic phases were washed with brine and dried to give 15.48 g (98.7%) of the desired product.

$^1H$ NMR (400 MHz, DMSO-$d_6$) δ ppm 8.00 (dd, 2H), 7.67 (tt, 1H), 7.54 (tt, 2H), 5.03 (d, 1H), 4.71 (t, 1H), 4.30 (dd, 1H), 4.17 (dd, 1H), 3.79 (sx, 1H), 3.45 (m, 2H).

Step C: [3-[tert-butyl(dimethyl)silyl]oxy-2-hydroxy-propyl]benzoate

To 5.62 g of the product from Step B (28.7 mmol, 1 eq.) and 3.47 g of imidazole (51.0 mol, 2 eq.) in 50 mL of DMF was added 4.04 g of tert-butyl-chloro-dimethyl-silane (26.8 mmol, 1 eq.) in one portion and the mixture was stirred for 1 h. After the mixture was diluted with EtOAc, the organic phase was washed with cc. $NaHCO_3$, water and brine, dried over $MgSO_4$, filtered, concentrated and purified by flash column chromatography using heptane and EtOAc as eluents to give 3.23 g (36%) of the desired product.

$^1H$ NMR (400 MHz, DMSO-$d_6$) δ ppm 7.99 (dd, 2H), 7.66 (tt, 1H), 7.53 (t, 2H), 5.13 (d, 1H), 4.31 (dd, 1H), 4.19 (dd, 1H), 3.83 (sx, 1H), 3.63 (m, 2H), 0.85 (s, 9H), 0.03 (s, 6H).

Step D: [3-[tert-butyl(dimethyl)silyl]oxy-2-methoxy-propyl]benzoate 3.0 g of the product from Step C (9.6 mmol, 1 eq) and 6.2 g of N1,N1,N8,N8-tetramethylnaphthalene-1,8-diamine (28.9 mmol, 3 eq.) were mixed in 160 mL of DCM then 3.54 g of trimethyloxonium; tetrafluoroborate (23.9 mmol, 2.5 eq.) was added in one portion and the mixture was stirred at rt for 18 h. The mixture was filtered through a pad of Celite, washed with DCM then the organic phase was washed with water, brine, respectively. The solution was dried over $MgSO_4$, filtered, concentrated onto Celite and purified via flash column chromatography using heptane and EtOAc as eluents to give 1.7 g (55%) of the desired product.

$^1H$ NMR (400 MHz, DMSO-$d_6$) δ ppm 7.97 (dd, 2H), 7.67 (tt, 1H), 7.54 (t, 2H), 4.44 (dd, 1H), 4.26 (dd, 1H), 3.72 (d, 2H), 3.57 (m, 1H), 3.38 (s, 3H), 0.86 (s, 9H), 0.05 (s, 3H), 0.04 (s, 3H).

Step E: 3-[tert-butyl(dimethyl)silyl]oxy-2-methoxy-propan-1-ol

To 1.68 g of the product from Step D (5.17 mmol, 1 eq.) in 40 mL of a 1:1 mixture of THF and MeOH was added 2.19 g of $K_2CO_3$ (15.85 mmol, 3 eq.) at 0° C. and the mixture was stirred for 3 h at 0° C. and for 2 h at rt. After the addition of cc. $NH_4Cl$ and DCM at 0° C., the organic phase was washed with cc. $NaHCO_3$, water and brine, dried over $MgSO_4$, filtered, and concentrated to give 1.26 g (quant.) of a 1:0.25 mixture of the desired product and methyl benzoate.

$^1H$ NMR (400 MHz, DMSO-$d_6$) δ ppm 4.54 (t, 1H), 3.63 (dd, 1H), 3.55 (dd, 1H), 3.39 (m, 2H), 3.32 (s, 3H), 3.15 (m, 1H), 0.86 (s, 9H), 0.03 (s, 6H).

Preparation 2k: 3-[tert-Butyl(dimethyl)silyl]oxy-2-morpholino-propan-1-ol

Step A: diethyl 2-morpholinopropanedioate

To 16 g of morpholine (184 mmol, 1.6 eq.), 30 g of $K_2CO_3$ (217 mmol, 1.9 eq.) in 50 mL of MeCN was added 27 g of diethyl bromomalonate (113 mmol, 1 eq.) and the exotermic reaction was stirred for 0.5 h. After cooling the mixture to rt, it was filtered and concentrated and the crude product was purified via flash column chromatography using heptane and EtOAc as eluents to give 26.2 g (94%) of the desired product.

$^1H$ NMR (400 MHz, DMSO-$d_6$) δ ppm 4.27 (s, 1H), 4.16 (q, 4H), 3.57 (dd, 4H), 2.68 (dd, 4H), 1.20 (s, 6H).

Step B: 2-morpholinopropane-1,3-diol

To 3.0 g of $LiAlH_4$ (79 mmol, 4.8 eq.) in 60 mL of THF was added 4.0 g of the product from Step A (16.3 mmol, 1 eq.) in 25 mL of THF at 0° C. and the mixture was stirred at 60° C. for 4 h. After cooling to rt, the mixture was treated with a 10 N solution of NaOH and the precipitation formed was filtered off and washed with DCM. After the phases were separated, the aqueous phase was extracted with DCM and the combined organic phases were washed with brine, dried over $MgSO_4$, filtered, and concentrated to give 1.4 g (53%) of the desired product.

$^1H$ NMR (500 MHz, DMSO-$d_6$) δ ppm 4.28 (dd, 2H), 3.52 (m, 4H), 3.49/3.44 (m+m, 4H), 2.59 (m, 4H), 2.40 (qui, 1H); $^{13}C$ NMR (125 MHz, DMSO-$d_6$) δ ppm 67.5, 67.3, 59.1, 50.5; IR: 3373, 2856; HRMS-EI (m/z): $[M]^+$ calcd for $C_7H_{15}NO_3$: 161.1052, found: 161.1053.

Step C: 3-[tert-Butyl(dimethyl)silyl]oxy-2-morpholino-propan-1-ol

To 1.32 g of the product from Step B (8.22 mmol, 1 eq.) and 0.56 g of imidazole (8.24 mmol, 1 eq.) in 60 mL of DCM was added 1.24 g of tert-butyl-chloro-dimethyl-silane (8.23 mmo, 1 eq.) in 10 mL of DCM dropwise and the mixture was stirred at rt for 0.5 h. After the addition of DCM, the solution was washed with water and brine, dried, concentrated, and purified by flash column chromatography using heptane and EtOAc as eluents to give 0.79 g (35%) of the desired product.

$^1H$ NMR (500 MHz, DMSO-$d_6$) δ ppm 4.30 (brt, 1H), 3.69/3.65 (dd+dd, 2H), 3.51 (m, 4H), 3.48/3.43 (m+m, 2H), 2.64/2.59 (m+m, 4H), 2.44 (m, 1H), 0.87 (s, 9H), 0.04/0.03 (s, 6H); $^{13}C$ NMR (125 MHz, DMSO-$d_6$) δ ppm 67.4, 67.4, 61.2, 59.2, 50.8, 26.3, 18.3, —5.0; IR: 2855; HRMS-EI (m/z): $[M-C_4H_9]^+$ calcd for $C_9H_{20}NO_3Si$: 218.1217, found: 218.1202.

Preparation 3a: Methyl 5-[3-[4-[3-[tert-butoxycarbonyl(methyl)amino]prop-1-ynyl]-2-fluoro-phenoxy]propyl]-2-[[5-[tert-butyl(dimethyl)silyl]oxy-4-[tert-butyl(diphenyl)silyl]oxy-pentyl]amino]thiazole-4-carboxylate Step A: methyl 2-[tert-butoxycarbonyl-[5-[tert-butyl(dimethyl)silyl]oxy-4-[tert-butyl(diphenyl)silyl]oxy-pentyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from Preparation 1b as the appropriate carbamate and Preparation 2a as the appropriate alcohol, 2.5 g (61%) of the desired product was obtained.

$^1$H NMR (500 MHz, DMSO-$d_6$) δ ppm 7.60-7.33 (m, 10H), 7.28 (dd, 1H), 7.17 (m, 1H), 7.1 (t, 1H), 4.22 (s, 2H), 4.09 (t, 2H), 3.94 (m, 2H), 3.71 (s, 3H), 3.67 (m, 1H), 3.38 (m, 2H), 3.22 (t, 2H), 2.85 (s, 3H), 2.07 (m, 2H), 1.65 (m, 2H), 1.48 (m, 2H), 1.45/1.40 (s+s, 18H), 0.93 (s, 9H), 0.71 (s, 9H), −0.17/−0.22 (s+s, 6H); $^{13}$C NMR (125 MHz, DMSO-$d_6$) δ ppm 147.4, 129, 119.3, 115.4, 85.1, 82.3, 73.3, 68.1, 65.6, 51.9, 46.5, 38.4, 33.8, 30.5, 30.5, 28.5/28, 27.2, 26.0, 23.1, 23.0, −5.3; HRMS-ESI (m/z): $[M+H]^+$ calcd for $C_{55}H_{79}FN_3O_9SSi_2$: 1032.5054, found 1032.5060.

Step B: methyl 5-[3-[4-[3-[tert-butoxycarbonyl(methyl)amino]prop-1-ynyl]-2-fluoro-phenoxy]propyl]-2-[[5-[tert-butyl(dimethyl)silyl]oxy-4-[tert-butyl(diphenyl)silyl]oxy-pentyl]amino]thiazole-4-carboxylate Using Deprotection with HFIP General Procedure starting from the product from Step A as the appropriate carbamate, 1.2 g (53%) of the desired product was obtained.

$^1$H NMR (500 MHz, DMSO-$d_6$) δ ppm 7.68-7.35 (m, 10H), 7.56 (t, 1H), 7.30 (d, 1H), 7.20 (d, 1H), 7.11 (t, 1H), 4.22 (br., 2H), 4.07 (t, 2H), 3.70 (m, 1H), 3.68 (s, 3H), 3.42/3.38 (dd+dd, 2H), 3.11 (t, 2H), 3.04 (brq., 2H), 2.86 (br., 3H), 1.99 (quint., 2H), 134 (m, 2H), 1.53/1.45 (m+m, 2H), 1.41 (s, 9H), 0.97 (s, 9H), 0.74 (s, 9H), −0.14/−0.18 (s+s, 6H); 13C NMR (125 MHz, DMSO-$d_6$) δ ppm 164.6, 163.0, 154.9, 151.4, 147.5, 136.9, 136.0, 129.1, 119.3, 115.4, 114.8, 85.2, 82.3, 79.8, 73.6, 68.0, 66.2, 51.7, 44.7, 38.5, 33.8, 31.1, 30.6, 28.5, 27.2, 26.2, 24.3, 23.3, 19.4, 18.3, −5.2; HRMS-ESI (m/z): $[M+H]^+$ calcd for $C_{50}H_{71}FN_3O_7SSi_2$: 932.4530, found 932.4526.

Preparation 3b: Methyl 2-[[5-[tert-butyl(dimethyl)silyl]oxy-4-[tert-butyl(diphenyl)silyl]oxy-pentyl]amino]-5-[3-[4-[3-(dimethylamino)prop-1-ynyl]-2-fluoro-phenoxy]propyl]thiazole-4-carboxylate Step A: methyl 2-[tert-butoxycarbonyl-[5-[tert-butyl(dimethyl)silyl]oxy-4-[tert-butyl(diphenyl)silyl]oxy-pentyl]amino]-5-[3-[4-[3-(dimethylamino)prop-1-ynyl]-2-fluoro-phenoxy]propyl]thiazole-4-carboxylate Using Mitsunobu General Procedure starting from Preparation 1c as the appropriate carbamate and Preparation 2a as the appropriate alcohol, 3.2 g (65%) of the desired product was obtained.

$^1$H NMR (500 MHz, DMSO-$d_6$) δ ppm 7.60-7.35 (m, 10H), 7.28 (dd, 1H), 7.18 (m, 1H), 7.10 (t, 1H), 4.10 (t, 2H), 3.95 (m, 2H), 3.72 (s, 3H), 3.68 (m, 1H), 3.41 (s, 2H), 3.38 (m, 2H), 3.22 (t, 2H), 2.21 (s, 6H), 2.07 (m, 2H), 1.66 (m, 2H), 1.45 (s, 9H), 1.45 (m, 2H), 0.94 (s, 9H), 0.72 (s, 9H), −0.16/−0.21 (s+s, 6H); $^{13}$C NMR (125 MHz, DMSO-$d_6$) δ ppm 162.8, 147.2, 128.9, 119.2, 115.4, 84.2, 73.3, 68.1, 65.6, 52.0, 48.2, 46.7, 44.3, 30.7, 30.5, 28.0, 27.2, 26.1, 23.1, 23.0, −5.3; HRMS-ESI (m/z): $[M+H]^+$ calcd for $C_{51}H_{73}FN_3O_7SSi_2$: 946.4686, found 946.4684.

Step B: methyl 2-[[5-[tert-butyl(dimethyl)silyl]oxy-4-[tert-butyl(diphenyl)silyl]oxy-pentyl]amino]-5-[3-[4-[3-(dimethylamino)prop-1-ynyl]-2-fluoro-phenoxy]propyl]thiazole-4-carboxylate Using Deprotection with HFIP General Procedure starting from the product from Step A as the appropriate carbamate, 2.2 g (55%) of the desired product was obtained.

$^1$H NMR (500 MHz, DMSO-$d_6$) δ ppm 7.64-7.37 (m, 10H), 7.56 (t, 1H), 7.28 (dd, 1H), 7.18 (m, 1H), 7.10 (t, 1H), 4.07 (t, 2H), 3.69 (q, 1H), 3.69 (s, 3H), 3.41 (s, 2H), 3.41 (m, 2H), 3.11 (t, 2H), 3.04 (q, 2H), 2.21 (s, 6H), 2.00 (m, 2H), 1.55 (m, 2H), 1.54/1.45 (m+m, 2H), 0.97 (s, 9H), 0.74 (s, 9H), −0.14/−0.17 (s+s, 6H); $^{13}$C NMR (125 MHz, DMSO-$d_6$) δ ppm 164.6, 147.2, 129.0, 119.2, 115.4, 73.6, 68.0, 66.2, 51.7, 48.2, 44.8, 44.3, 31.1, 30.7, 27.2, 26.2, 24.4, 23.3, −5.2; HRMS-ESI (m/z); $[M+H]^+$ calcd for $C_{46}H_{66}FN_3O_5SSi_2$: 846.4162, found 1346.4160.

Preparation 3c: Methyl 5-[3-[4-[3-[tert-butoxycarbonyl(methyl)amino]prop-1-ynyl]-2-fluoro-phenoxy]propyl]-2-[4-[tert-butyl(dimethyl)silyl]oxy-butylamino]thiazole-4-carboxylate Step A: methyl 2-[tert-butoxycarbonyl-[4-[tert-butyl(dimethyl)silyl]oxybutyl]amino]-5-[3-(2-fluoro-4-iodo-phenoxy)propyl]thiazole-4-carboxylate Using Alkylation General Procedure starting from 536 g of Preparation 1a (10 mmol, 1 eq.) and 3.77 g of tert-butyl-(4-iodobutoxy)-dimethyl-silane (3.10 mL, 12 mmol, 1.2 eq.) as the appropriate halide, 6.1 g (84%) of the desired product was obtained.

$^1$H NMR (500 MHz, DMSO-$d_6$) δ ppm 7.58 (dd, 1H), 7.45 (m, 1H), 6.97 (t, 1H), 4.06 (t, 2H), 4.01 (t, 2H), 3.75 (s, 3H), 3.58 (t, 2H), 3.21 (t, 2H), 2.06 (m, 2H), 1.68 (m, 2H), 1.50 (s, 9H), 1.43 (m, 2H), 0.82 (s, 9H), −0.01 (s, 6H); $^{13}$C NMR (125 MHz, DMSO-$d_6$) δ ppm 147.0, 134.0, 124.9, 117.6, 68.2, 62.6, 52.1, 46.4, 30.5, 30.0, 28.1, 26.2, 24.5, 23.2, −4.9; HRMS-ESI (m/z): $[M+H]^+$ calcd for $C_{29}H_{45}N_2O_6FSiSI$: 723.1791, found 723.1775.

Step B: methyl 2-[4-[tert-butyl(dimethyl)silyl]oxy-butylamino]-5-[3-(2-fluoro-4-iodo-phenoxy)propyl]thiazole-4-carboxylate Using Deprotection with HFIP General Procedure starting from 6.0 g of the product from Step A (8.30 mmol) as the appropriate carbamate, 3.0 g (58%) of the desired product was obtained.

$^1$H NMR (500 MHz, DMSO-$d_6$) δ ppm 7.59 (dd, 1H), 7.58 (t, 1H), 7.45 (dm, 1H), 6.97 (t, 1H), 4.03 (t, 2H), 3.69 (s, 3H), 3.58 (t, 2H), 3.16 (q, 2H), 3.11 (t, 2H), 1.98 (m, 2H), 1.59-1.44 (m, 4H), 0.84 (s, 9H), 0.01 (s, 6H); $^{13}$C NMR (125 MHz, DMSO-$d_6$) δ ppm 164.7, 163.0, 152.1, 147.0, 136.9, 136.1, 134.0, 124.9, 117.6, 82.4, 68.0, 62.7, 51.7, 44.3, 30.6, 30.6, 26.3, 25.6, 23.3, −4.8; HRMS-ESI (m/z); $[M+H]^+$ calcd for $C_{24}H_{37}FIN_2O_4SSi$: 623.1266, found 623.1272.

Step C: methyl 5-[3-[4-[3-[tert-butoxycarbonyl (methyl)amino]prop-1-ynyl]-2-fluoro-phenoxy]propyl]-2-[4-[tert-butyl(dimethyl)silyl]oxybutylamino] thiazole-4-carboxylate Using Sonogashira General Procedure starting from 3.00 g of the product from Step B (4.82 mmol, 1 eq.) and 1.63 g of tert-butyl N-methyl-N-prop-2-ynyl-carbamate (9.63 mmol, 2 eq.) as the appropriate acetylene, 2.50 g (65%) of the desired product was obtained.

$^{1}$H NMR (500 MHz, DMSO-$d_6$) δ ppm 7.58 (t, 1H), 7.31 (brd., 1H), 7.21 (d, 1H), 7.13 (t, 1H), 4.23 (br., 2H), 4.07 (t, 2H), 3.69 (s, 3H), 3.58 (t, 2H), 3.16 (q, 2H), 3.11 (t, 2H), 2.86 (br., 3H), 2 (quint., 2H), 1.54 (m, 2H), 1.49 (m, 2H), 1.41 (s, 9H), 0.84 (s, 9H), 0.01 (s, 6H); $^{13}$C NMR (125 MHz, DMSO-$d_6$) δ ppm 129.1, 119.3, 115.4, 68.0, 62.7, 51.7, 44.3, 38.6, 33.8, 30.6, 30.1, 28.5, 26.3, 25.6, 23.3, −4.8; HRMS-ESI (m/z): $[M+H]^+$ calcd for $C_{33}H_{51}FN_3O_6SSi$: 664.3246, found 664.3245.

Preparation 3d: Methyl 2-[4-[tert-butyl(dimethyl) silyl]oxybutylamino]-5-[3-[4-[3-(dimethylamino) prop-1-ynyl]-2-fluoro-phenoxy]propyl]thiazole-4-carboxylate Using Sonogashira General Procedure starting from 100 g of Preparation 3c, Step B (4.82 mmol, 1 eq.) and 801 mg of N,N-dimethyl-N-prop-2-yn-1-amine (9.63 mmol, 2 eq.) as the appropriate acetylene, 2.20 g (79%) of the desired product was obtained.

$^{1}$H NMR (500 MHz, DMSO-$d_6$) δ ppm 7.58 (t, 1H), 7.30 (dd, 1H), 7.20 (dm, 1H), 7.12 (t, 1H), 4.07 (t, 2H), 3.69 (s, 3H), 3.58 (t, 2H), 3.44 (s, 2H), 3.16 (q, 2H), 3.12 (t, 2H), 2.24 (s, 6H), 2.00 (m, 2H), 1.60-1.44 (m, 4H), 0.84 (s, 9H), 0.01 (s, 6H); $^{13}$C NMR (125 MHz, DMSO-$d_6$) δ ppm 129.0, 119.2, 115.4, 84.9, 84.3, 68.0, 62.7, 51.7, 48.1, 44.3, 44.2, 30.6, 30.2, 26.3, 25.6, 23.3, −4.8; HRMS-ESI (m/z): $[M+H]^+$ calcd for $C_{29}H_{45}FN_3O_4SSi$: 578.2878, found 578.2865.

Preparation 3e: Ethyl 5(3-chloropropyl)-2-(methylamino)thiazole-4-carboxylate

A suspension of 2.25 g or methylthiourea (25.0 mmol, 1 eq.) in 100 mL of ethanol was cooled to 0° C., and then 7.46 g of ethyl 3-bromo-6-chloro-2-oxo-hexanoate (27.5 mmol, 1.1 eq.) was added dropwise at this temperature. After 15 min stirring at 0° C., 7 mL of TEA (5.06 g, 50 mmol, 2 eq.) was added. The resulting mixture was stirred overnight at rt. Full conversion was observed. The volatiles were removed in vacuo, then the resultant residue was portioned between EtOAc and water. The layers were separated then the organic layer was washed with water then followed with brine. The combined organic layers were dried over $Na_2SO_4$, filtered and the filtrate was concentrated under reduced pressure. Then it was purified via flash column chromatography using heptane and EtOAc as eluents to give 5 g (76%) of the desired product.

$^{1}$H NMR (400 MHz, DMSO-$d_6$) δ ppm 7.55 (q, 1H), 4.21 (q, 2H), 3.65 (t, 2H), 3.09 (m, 2H), 2.78 (d, 3H), 1.98 (m, 2H), 1.26 (t, 3H); $^{13}$C NMR (125 MHz, DMSO-$d_6$) δ ppm 165.6, 162.5, 137.4, 135.5, 60.5, 450, 34.1, 31.2, 24.4, 14.7; HRMS-ESI (m/z): $[M+H]^+$ calcd for $C_{10}H_{16}ClN_2O_2S$: 263.0616, found 263.0615.

Preparation 3f: Methyl 5-[3-[4-[3-[tert-butoxycarbonyl(methyl)amino]prop-1-ynyl]-2-fluoro-phenoxy] propyl]-2-[[5-[tert-butyl(dimethyl)silyl]oxy-4-methoxy-pentyl]amino]thiazole-4-carboxylate Step A: methyl 2-[tert-butoxycarbonyl-[5-[tert-butyl (dimethyl)silyl]oxy-4-[tert-butyl(diphenyl)silyl]oxy-pentyl]amino]-5-[3-[4-[3-[tert-butoxycarbonyl (methyl)amino]prop-1-ynyl]-2-fluoro-phenoxy] propyl]thiazole-4-carboxylate Using Mitsunobu General Procedure starting from 577 mg of Preparation 1b (1 mmol) as the appropriate carbamate and 496 mg of Preparation 2b (2 mmol) as the appropriate alcohol 790 mg (96%) of the desired product was obtained.

Step B: methyl 5-[3-[4-[3-[tert-butoxycarbonyl (methyl)amino]prop-1-ynyl]-2-fluoro-phenoxy]propyl]-2-[[5-[tert-butyl(dimethyl)silyl]oxy-4-methoxy-pentyl]amino]thiazole-4-carboxylate Using Deprotection with HFIP General Procedure starting from 790 mg of the product from Step A (0.95 mmol) as the appropriate carbamate, 270 mg (38%) of the desired product was obtained.

$^{1}$H NMR (500 MHz, DMSO-$d_6$) δ ppm 7.58 (t, 1H), 7.31 (brd, 1H), 7.21 (dm, 1H), 7.13 (t, 1H), 4.23 (brs, 2H), 4.07 (t, 2H), 3.69 (s, 3H), 3.56/3.53 (dd+dd, 2H), 3.29 (s, 3H), 3.16 (m, 1H), 3.15 (m, 2H), 3.11 (t, 2H), 2.86 (brs, 3H), 2.00 (m, 2H), 1.63-1.43 (m, 4H), 1.42 (s, 9H), 0.84 (s, 9H), 0.02 (s, 6H); HRMS-ESI (m/z): $[M+H]^+$ calcd for $C_{35}H_{55}FN_3O_7SSi$: 708.3508, found 708.3502.

Preparation 3g: Methyl 5-[3-[4-[3-(tert-butoxycarbonylamino)prop-1-ynyl]-2-fluoro-phenoxy]propyl]-2-[4-[tert-butyl(dimethyl)silyl]oxybutylamino]thiazole-4-carboxylate Using Sonogashira General Procedure starting from 880 mg of Preparation 3c, Step B (1.41 mmol, 1 eq.) and 438 mg of tert-butyl N-prop-2-ynylcarbamate (2.82 mmol, 2 eq.) as the appropriate acetylene, 918 mg (85%) of the desired product was obtained.

$^{1}$H NMR (500 MHz, DMSO-$d_6$) δ ppm 7.58 (t, 1H), 7.34 (t, 1H), 7.26 (ff, 1H), 7.17 (m, 1H), 7.12 (t, 1H), 4.06 (t, 2H), 3.95 (d, 2H), 3.69 (s, 3H), 3.58 (t, 2H), 3.17 (q, 2H), 3.11 (t, 2H), 2.00 (m, 2H), 1.54 (m, 2H), 1.50 (m, 2H), 1.39 (s, 9H), 0.85 (s, 9H), 0.01 (s, 6H); $^{13}$C NMR (125 MHz, DMSO-$d_6$) δ ppm 164.7, 163.0, 147.4, 136.9, 136.1, 129.0, 119.1, 115.4, 68.0, 62.7, 51.7, 44.3, 30.6, 30.5, 30.2, 28.7, 26.3, 25.6, 23.3, 18.4, −4.8 HRMS-ESI (m/z): $[M+H]^+$ calcd for $C_{32}H_{49}FN_3O_6SSi$: 650.3090, found 650.3093.

Preparation 3h: Methyl 5-[3-[4-[3-[tert-butoxycarbonyl(methyl)amino]prop-1-ynyl]-2-fluoro-phenoxy]propyl]-2-[2-(2,2-dimethyl-1,3-dioxolan-4-yl) ethylamino]thiazole-4-carboxylate Step A: methyl 2-[tert-butoxycarbonyl-[2-(2,2-dimethyl-1,3-dioxolan-4-yl)ethyl]amino]-5-[3-(2-fluoro-4-iodo-phenoxy)propyl]thiazole-4-carboxylate Using Mitsunobu General Procedure starting from 2.68 g of Preparation 1a (5 mmol, 1 eq.) and 1.46 g of 2-(2,2-dimethyl-1,3-dioxolan-4-yl)ethanol (1.42 mL, 10 mmol, 2 eq.) as the appropriate alcohol, 2.8 g (84%) of the desired product was obtained.

$^1H$ NMR (500 MHz, DMSO-$d_6$) δ ppm 7.57 (dd, 1H), 7.44 (dm, 1H), 6.96 (t, 1H), 4.12/4.02 (m+m, 2H), 4.07 (m, 1H), 4.05 (t, 2H), 4.02/3.54 (dd+dd, 2H), 3.75 (s, 3H), 3.21 (t, 2H), 2.06 (m, 2H), 1.86/1.82 (m+m, 2H), 1.51 (s, 9H), 1.29 (s, 3H), 1.22 (s, 3H); $^{13}C$ NMR (125 MHz, DMSO-$d_6$) δ ppm 134.0, 124.9, 117.6, 73.8, 68.9, 68.1, 52.0, 44.0, 32.2, 30.5, 28.1, 27.3, 25.9, 23.1; HRMS-ESI (m/z): $[M+H]^+$ calcd for $C_{26}H_{35}FIN_2O_7S$: 665.1188, found 665.1175.

Step B: methyl 2-[2-(2,2-dimethyl-1,3-dioxolan-4-yl)ethylamino]-5-[3-(2-fluoro-4-iodo-phenoxy)propyl]thiazole-4-carboxylate Using Deprotection with HFIP General Procedure starting from 2.5 g of the product from Step A (3.80 mmol) as the appropriate carbamate, 1.6 g (75%) of the desired product was obtained.

$^1H$ NMR (500 MHz, DMSO-$d_6$) δ ppm 7.6 (t, 1H), 7.59 (dd, 1H), 7.45 (dm, 1H), 6.97 (dd, 1H), 4.10 (m, 1H), 4.03 (t, 2H), 4.01/3.48 (dd+dd, 2H), 3.69 (s, 3H), 3.27/3.19 (m+m, 2H), 3.11 (t, 2H), 1.99 (m, 2H), 1.76/1.72 (m+m, 2H), 1.31 (s, 3H), 1.25 (s, 3H); HRMS-ESI (m/z): $[M+H]^+$ calcd for $C_{21}H_{27}FIN_2O_5S$: 565.0663, found 565.0642.

Step C: methyl 5-[3-[4-[3-[tert-butoxycarbonyl(methyl)amino]prop-1-ynyl]-2-fluoro-phenoxy]propyl]-2-[2-(2,2-dimethyl-1,3-dioxolan-4-yl)ethylamino]thiazole-4-carboxylate Using Sonogashira General Procedure starting from 400 mg of the product from Step B (0.71 mmol, 1 eq.) and 240 mg of tert-butyl N-methyl-N-prop-2-ynyl-carbamate (1.42 mmol, 2 eq.) as the appropriate acetylene, 300 mg (70%) of the desired product was obtained.

$^1H$ NMR (500 MHz, DMSO-$d_6$) δ ppm 7.60 (t, 1H), 7.31 (brd, 1H), 7.21 (dd, 1H), 7.13 (t, 1H), 4.23 (brs, 2H), 4.09 (m, 1H), 4.07 (t, 2H), 4.00/3.48 (dd+dd, 2H), 3.69 (s, 3H), 3.27/3.19 (m+m, 2H), 3.12 (t, 2H), 2.86 (brs, 3H), 2.00 (m, 2H), 1.74 (m, 2H), 1.41 (s, 9H), 1.31 (s, 3H), 1.25 (s, 3H); $^{13}C$ NMR (125 MHz, DMSO-$d_6$) δ ppm 164.5, 136.9, 136.4, 129.1, 119.3, 115.4, 85.2, 82.3, 73.8, 69.0, 68.0, 51.7, 41.4, 38.4, 33.8, 33.2, 30.6, 28.5, 27.3, 26.1, 23.3; HRMS-ESI (m/z): $[M+H]^+$ calcd for $C_{30}H_{41}FN_3O_7S$: 606.2644, found 606.2650.

Preparation 3i: Methyl 5-[3-[4-[3-(dimethyl)amino]prop-1-ynyl]-2-fluoro-phenoxy]propyl]-2-[2-(2,2-dimethyl-1,3-dioxolan-4-yl)ethylamino]thiazole-4-carboxylate Using Sonogashira General Procedure starting from 400 mg of Preparation 3h, Step B (0.71 mmol, 1 eq.) and 117 mg of N,N-dimethylprop-2-yn-1-amine (1.42 mmol, 2 eq.) as the appropriate acetylene, 250 mg (58%) of the desired product was obtained.

$^1H$ NMR (500 MHz, DMSO-$d_6$) δ ppm 7.61 (t, 1H), 7.29 (dd, 1H), 7.2 (dd, 1H), 7.12 (t, 1H), 4.1 (m, 1H), 4.07 (t, 2H), 4/3.48 (dd+dd, 2H), 3.69 (s, 3H), 3.41 (s, 2H), 3.28/3.19 (m+m, 2H), 3.12 (t, 2H), 2.22 (s, 6H), 2 (qn, 2H), 1.75/1.72 (m+m, 2H), 1.31 (s, 3H), 1.25 (s, 3H); $^{13}C$ NMR (125 MHz, DMSO-$d_6$) δ ppm 164.5, 163, 151.5, 147.3, 136.9, 136.4, 128.9, 119.2, 115.4, 115.3, 108.4, 85.2, 84.2, 73.8, 69.0, 68.0, 51.8, 48.1, 44.3, 41.4, 33.3, 30.6, 27.4, 26.1, 23.4; HRMS-ESI (m/z): $[M+H]^+$ calcd for $C_{26}H_{35}FN_3O_5S$: 520.2281, found 520.2272.

Preparation 3j: Methyl 2-[2-(2,2-dimethyl-1,3-dioxolan-4-yl)ethylamino]-5-[3-[2-fluoro-4-[3-[(4-methoxyphenyl)methyl-methyl-amino]prop-1-ynyl]phenoxy]propyl]thiazole-4-carboxylate Using Sonogashira General Procedure starting from 400 mg of the product from Preparation 3h, Step B (0.71 mmol, 1 eq.) and 268 mg of N-[(4-methoxyphenyl)methyl]-N-methyl-prop-2-yn-1-amine (1.42 mmol, 2 eq.) as the appropriate acetylene, 280 mg (63%) of the desired product was obtained.

$^1H$ NMR (500 MHz, DMSO-$d_6$) δ ppm 7.61 (t, 1H), 7.33 (dd, 1H), 7.24 (dd, 1H), 7.23 (d, 2H), 7.13 (t, 1H), 6.89 (d, 2H), 4.10 (qn, 1H), 4.07 (t, 2H), 4/3.48 (dd+dd, 2H), 3.73 (s, 3H), 3.7 (s, 3H), 3.49 (s, 2H), 3.44 (s, 2H), 3.28/3.19 (m+m, 2H), 3.13 (t, 2H), 2.24 (s, 3H), 2.01 (qn, 2H), 1.75/1.73 (m+m, 2H), 1.31 (s, 3H), 1.25 (s, 3H); $^{13}C$ NMR (125 MHz, DMSO-$d_6$) δ ppm 164.5, 163.0, 158.8, 151.5, 147.3, 136.6, 136.5, 130.8, 130.5, 129.0, 119.3, 115.4, 115.3, 114.1, 108.4, 84.9, 84.5, 73.8, 69.0, 68.0, 59.4, 55.5, 51.8, 45.8, 41.7, 41.4, 33.3, 30.6, 27.3, 26.1, 23.4; HRMS-ESI (m/z): $[M+H]^+$ calcd for $C_{33}H_{41}FN_3O_6S$: 626.2694, found 626.2697.

Preparation 3k: Methyl 2-[2-(2,2-dimethyl-1,3-dioxolan-4-yl)ethylamino]-5-[3-[2-fluoro-4-[3-[methyl(p-tolylsulfonyl)amino]prop-1-ynyl]phenoxy]propyl]thiazole-4-carboxylate Using Sonogashira General Procedure starting from 400 mg of Preparation 3h, Step B (0.71 mmol, 1 eq.) and 316 mg of N, 4-dimethyl-N-prop-2-ynyl-benzenesulfonamide (1.42 mmol, 2 eq.) as the appropriate acetylene, 260 mg (55%) of the desired product was obtained.

$^1H$ NMR (500 MHz, DMSO-$d_6$) δ ppm 7.72 (d, 2H), 7.61 (t, 1H), 7.4 (d, 2H), 7.07 (t, 1H), 6.88 (dd, 1H), 6.86 (dd, 1H), 4.25 (s, 2H), 4.1 (qn, 1H), 4.05 (t, 2H), 4/3.48 (dd+dd, 2H), 3.69 (s, 3H), 3.27/3.19 (m+m, 2H), 3.11 (t, 2H), 2.79 (s, 3H), 2.33 (s, 3H), 1.99 (qn, 2H), 1.75/1.73 (m+m, 2H), 1.31 (s, 3H), 1.25 (s, 3H); $^{13}C$ NMR (125 MHz, DMSO-$d_6$) δ ppm 164.5, 163.0, 151.2, 147.5, 144.0, 136.9, 136.4, 134.4, 130.2, 128.9, 128.2, 119.1, 115.2, 114.2, 108.4, 84.6, 81.9, 73.9, 69.0, 68.1, 51.8, 41.5, 40.4, 34.9, 33.3, 30.6, 27.4, 26.1, 23.4, 21.4; HRMS-ESI (m/z): $[M+H]^+$ calcd for $C_{32}H_{39}FN_3O_7S_2$: 660.22079, found 660.2231.

Preparation 3l: Methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-4-methoxy-butyl]amino]thiazole-4-carboxylate Step A: methyl 2-[tert-butoxycarbonyl-[3-[tert-butyl(dimethyl)silyl]oxy-4-methoxy-butyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from 577 mg of Preparation 1b (1 mmol, 1 eq.) as the appropriate carbamate and 469 mg of Preparation 2h (2 mmol, 2 eq.) as the appropriate alcohol 794 mg (99%) of the desired product was obtained.

Step B: methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-4-methoxy-butyl]amino]thiazole-4-carboxylate Using Deprotection with HFIP General Procedure starting from 794 mg of the product from Step A (1 mmol) as the appropriate carbamate, 320 mg (46%) of the desired product was obtained.

$^1H$ NMR (400 MHz, DMSO-$d_6$) δ ppm 7.54 (t, 1H), 7.28 (d, 1H), 7.18 (d, 1H), 7.09 (t, 1H), 4.04 (t, 2H), 4.20 (bs, 2H), 3.89-3.81 (m, 1H), 3.67 (s, 3H), 3.23-3.14 (m, 4H), 3.22 (s, 3H), 3.10 (t, 2H), 2.83 (brs, 3H), 2.03-1.93 (m, 2H), 1.74-1.50 (m, 2H), 1.39 (s, 9H), 0.81 (s, 9H), 0.00 (s, 3H), −0.01 (s, 3H).

Preparation 3m: Methyl 5-[3-[4-[3-[tert-butoxycarbonyl(methyl)amino]prop-1-ynyl]-2-fluoro-phenoxy]propyl]-2-[5-[tert-butyl(dimethyl)silyl]oxypentylamino]thiazole-4-carboxylate Step A: methyl 2-[tert-butoxycarbonyl-[5-[tert-butyl(dimethyl)silyl]oxypentyl]amino]-5-[3-(2-fluoro-4-iodo-phenoxy)propyl]thiazole-4-carboxylate Using Alkylation General Procedure starting from 5.00 g of Preparation 1a (7.55 mmol, 1 eq.) and 2.97 g of tert-butyl-(5-iodopentoxy)-dimethyl-silane (9.06 mmol, 1.2 eq.) as the appropriate halide, 4.72 g (85%) of the desired product was obtained.

$^1H$ NMR (500 MHz, DMSO-$d_6$) δ ppm 7.59 (dm, 1H), 7.46 (dm, 1H), 6.99 (t, 1H), 4.07 (t, 2H), 4.01 (t, 2H), 3.76 (s, 3H), 3.56 (t, 2H), 3.21 (t, 2H), 2.07 (m, 2H), 1.64 (m, 2H), 1.52 (s, 9H), 1.48 (m, 2H), 1.30 (m, 2H), 0.82 (s, 9H), −0.02 (s, 6H); $^{13}C$ NMR (125 MHz, DMSO-$d_6$) δ ppm 163.1, 156.3/153.2, 151.8, 147.0, 143.2, 135.6, 133.9, 124.9, 117.6, 83.5, 82.3, 67.3, 62.5, 52.0, 46.5, 32.3, 30.5, 28.1, 27.6, 26.3, 22.9, 22.6, 18.1, −4.9; HRMS-ESI (m/z): $[M+H]^+$ calcd for $C_{30}H_{47}FIN_2O_6SSi$: 737.1947, found 737.1948.

Step B: methyl 2-[[5-[tert-butyl(dimethyl)silyl]oxypentyl]amino]-5-[3-(2-fluoro-4-iodo-phenoxy)propyl]thiazole-4-carboxylate Using Deprotection with HFIP General Procedure starting from 2.36 g of the product from Step A (3.20 mmol) as the appropriate carbamate. After completion of the reaction the reaction mixture was evaporated to dryness under reduced pressure which resulted in the crude desired product.

$^1H$ NMR (400 MHz, DMSO-$d_6$) δ ppm 7.60-7.54 (m, 2H), 7.44 (d, 1H), 6.96 (t, 1H), 4.03 (t, 2H), 3.69 (s, 3H), 3.56 (t, 2H), 3.18-3.08 (m, 4H), 1.98 (qv., 2H), 1.55-1.42 (m, 4H), 1.37-1.29 (m, 2H), 0.84 (s, 9H), 0.00 (s, 6H).

Step C: methyl 5-[3-[4-[3-[tert-butoxycarbonyl(methyl)amino]prop-1-ynyl]-2-fluoro-phenoxy]propyl]-2-[5-[tert-butyl(dimethyl)silyl]oxypentylamino]thiazole-4-carboxylate Using Sonogashira General Procedure starting from crude product from Step B and tert-butyl N-methyl-N-prop-2-ynyl-carbamate as the appropriate acetylene, 1.92 g (89% for 2 steps) of the desired product was obtained.

$^1H$ NMR (500 MHz, DMSO-$d_6$) δ ppm 7.57 (br., 1H), 7.31 (d, 1H), 7.21 (d, 1H), 7.12 (t, 1H), 4.23 (br., 2H), 4.07 (t, 2H), 3.69 (s, 3H), 3.56 (t, 2H), 3.14 (m, 2H), 3.11 (t, 2H), 2.86 (br., 3H), 2.00 (quint., 2H), 1.51 (m, 2H), 1.45 (m, 2H), 1.41 (s, 9H), 1.33 (m, 2H), 0.84 (s, 9H), 0.00 (s, 6H); $^{13}C$ NMR (125 MHz, DMSO-$d_6$) δ ppm 129.1, 119.3, 115.4, 68.0, 62.8, 51.7, 44.5, 38.6, 33.8, 32.4, 30.6, 28.9, 28.5, 26.3, 23.3, 23.2, −4.9; HRMS-ESI (m/z): $[M+H]^+$ calcd for $C_{34}H_{53}FN_3O_6SSi$: 678.3403, found 678.3393.

Preparation 3n: Methyl 5-[3-[4-[3-[tert-butoxycarbonyl(methyl)amino]prop-1-ynyl]-2-fluoro-phenoxy]propyl]-2-[3-[tert-butyl(dimethyl)silyl]oxypropylamino]thiazole-4-carboxylate Step A: methyl 2-[tert-butoxycarbonyl-[3-[tert-butyl(dimethyl)silyl]oxypropyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from 577 mg of Preparation 1b (1 mmol, 1 eq.) as the appropriate carbamate and 380 mg of 3-[tert-butyl(dimethyl)silyl]oxypropan-1-ol (2 mmol, 2 eq.) as the appropriate alcohol, 600 mg (80%) of the desired product was obtained.

Step B: methyl 5-[3-[4-[3-[tert-butoxycarbonyl(methyl)amino]prop-1-ynyl]-2-fluoro-phenoxy]propyl]-2-[3-[tert-butyl(dimethyl)silyl]oxypropylamino9 thiazole-4-carboxylate Using Deprotection with HFIP General Procedure starting from the product from Step A as the appropriate carbamate, 310 mg (47%) of the desired product was obtained.

$^1H$ NMR (400 MHz, DMSO-$d_6$) δ ppm 7.50 (t, 1H), 7.30 (d, 1H), 7.20 (d, 1H), 7.11 (t, 1H), 4.21 (bs, 2H), 4.05 (t, 2H), 3.62 (t, 2H), 3.67 (s, 3H), 3.19 (q, 2H), 3.10 (t, 2H), 2.84 (brs, 3H), 2.04-1.94 (m, 2H), 1.74-1.63 (m, 2H), 1.40 (s, 9H), 0.84 (s, 9H), 0.00 (s, 6H).

Preparation 3o: Methyl 5-[3-[4-[3-[tert-butoxycarbonyl(methyl)amino]prop-1-ynyl]-2-fluoro-phenoxy]propyl]-2-[(2,2-dimethyl-1,3-dioxolan-4-yl)methylamino]thiazole-4-carboxylate Step A: methyl 2-[tert-butoxycarbonyl-[(2,2-dimethyl-1,3-dioxolan-4-yl)methyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from 577 mg of Preparation 1b (1 mmol, 1 eq.) as the appropriate carbamate and 264 mg of (2,2-dimethyl-1,3-dioxolan-4-yl)methanol (2 mmol, 2 eq.) as the appropriate alcohol, 640 mg (92%) of the desired product was obtained.

Step B: methyl 5-[3-[4-[3-[tert-butoxycarbonyl(methyl)amino]prop-1-ynyl]-2-fluoro-phenoxy]propyl]-2-[(2,2-dimethyl-1,3-dioxolan-4-yl)methylamino]thiazole-4-carboxylate Using Deprotection with HFIP General Procedure starting from the product from Step A as the appropriate carbamate, 282 mg (51%) of the desired product was obtained.

$^1H$ NMR (400 MHz, DMSO-$d_6$) δ ppm 7.73 (t, 1H), 7.31 (d, 1H), 7.21 (d, 1H), 7.13 (t, 1H), 4.23 (bs, 2H), 4.19 (q, 1H), 4.07 (t, 2H), 4.05-3.96 (m, 2H), 3.64 (dd, 1H), 3.69 (s, 3H), 3.31-3.24 (m, 1H), 3.11 (t, 2H), 2.86 (brs, 3H), 2.05-1.95 (m, 2H), 1.41 (s, 9H) 1.33 (s, 3H), 1.26 (s, 3H).

Preparation 3p: Methyl 5-[3-[4-[3-(dimethylamino)prop-1-ynyl]-2-fluoro-phenoxy]propyl]-2-[(2,2-dimethyl-1,3-dioxolan-4-yl)methylamino]thiazole-4-carboxylate Step A: methyl 2-[tert-butoxycarbonyl-[(2,2-dimethyl-1,3-dioxolan-4-yl)methyl]amino]-5-[3-[4-[3-(dimethylamino)prop-1-ynyl]-2-fluoro-phenoxy]propyl]thiazole-4-carboxylate Using Mitsunobu General Procedure starting from 491 mg of Preparation 1c (1 mmol, 1 eq.) as the appropriate carbamate and 292 mg of (2,2-dimethyl-1,3-diaxolan-4-yl) methanol (2 mmol, 2 eq.) as the appropriate alcohol, 573 mg (92%) of the desired product was obtained.

Step B: Methyl 5-[3-[4-[3-(dimethylamino)prop-1-ynyl]-2-fluoro-phenoxy]propyl]-2-[(2,2-dimethyl-1,3-dioxolan-4-yl)methylamino]thiazole-4-carboxylate Using Deprotection with HFIP General Procedure starting from the product from Step A as the appropriate carbamate, 378 mg (74%) of Preparation 3p was obtained.

$^1$H NMR (400 MHz, DMSO-$d_6$) δ ppm 7.74 (t, 1H), 7.30 (dd, 1H), 7.21 (d, 1H), 7.13 (t, 1H), 4.21 (qui, 1H), 4.07 (t, 2H), 4.02-3.96 (m, 2H), 3.70 (s, 3H), 3.65 (dd, 1H), 3.42 (s, 2H), 3.33-3.26 (m, 1H), 3.12 (t, 2H), 2.23 (s, 6H), 2.05-1.96 (m, 2H), 1.34 (s, 3H), 1.26 (s, 3H).

Preparation 3g: Methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-2-methoxy-propyl]amino]thiazole-4-carboxylate Step A: methyl 2-[tert-butoxycarbonyl-[3-[tert-butyl(dimethyl)silyl]oxy-2-methoxy-propyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from 577 mg of Preparation 1b (1 mmol, 1 eq.) as the appropriate carbamate and 440 mg of Preparation 2j (2 mmol, 2 eq.) as the appropriate alcohol, 780 mg (quant.) of the desired product was obtained.

Step B: methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-2-methoxy-propyl]amino]thiazole-4-carboxylate Using Deprotection with HFIP General Procedure starting from the product from Step A as the appropriate carbamate, 400 mg (58%) of the desired product was obtained.

$^1$H NMR (400 MHz, DMSO-$d_6$) δ ppm 7.60 (t, 1H), 7.31 (d, 1H), 7.21 (d, 1H), 7.13 (t, 1H), 4.23 (bs, 2H), 4.07 (t, 2H), 3.69 (s, 3H), 3.67-3.57 (m, 2H), 3.40-3.31 (m, 2H), 3.33 (s, 3H), 3.26-3.18 (m, 1H), 3.12 (t, 2H), 2.87 (brs, 3H), 2.01 (qui, 2H), 1.42 (s, 9H), 0.86 (s, 9H), 0.03 (s, 3H), 0.02 (s, 3H).

Preparation 3r: Methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-2-morpholino-propyl]amino]thiazole-4-carboxylate Step A: methyl 2-[tert-butoxycarbonyl-[3-[tert-butyl(dimethyl)silyl]oxy-2-morpholino-propyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from 577 mg of Preparation 1b (1 mmol, 1 eq.) as the appropriate carbamate and 413 mg of Preparation 2k (1.5 mmol, 1.5 eq.) as the appropriate alcohol, 473 mg (56%) of the desired product was obtained.

Step B: methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-2-morpholino-propyl]amino]thiazole-4-carboxylate Using Deprotection with HFIP General Procedure starting from the product from Step A as the appropriate carbamate, 390 mg (93%) of the desired product was obtained.

$^1$H NMR (400 MHz, DMSO-$d_6$) δ ppm 7.38 (t, 1H), 7.32 (d, 1H), 7.21 (d, 1H), 7.12 (t, 1H), 4.23 (bs, 2H), 4.07 (t, 2H), 3.73 (dd, 1H), 3.69 (s, 3H), 3.64 (dd, 1H), 3.58-3.46 (m, 4H), 3.25 (t, 2H), 3.13 (t, 2H), 2.87 (brs, 3H) 2.72-2.63 (m, 3H), 2.59-2.53 (m, 2H), 2.01 (qui, 2H), 1.42 (s, 9H), 0.86 (s, 9H), 0.03 (s, 6H).

Preparation 3s: Methyl 5-[3-(2-fluoro-4-iodo-phenoxy)propyl]-2-(methylamino)thiazole-4-carboxylate Step A: methyl 2-[tert-butoxycarbonyl(methyl)amino]-5-[3-(2-fluoro-4-iodo-phenoxy)propyl]thiazole-4-carboxylate Using Alkylation General Procedure starting from 2.68 g of Preparation 1a (10 mmol, 1 eq.) and 1.70 g of iodomethane (12 mmol, 1.2 eq.) as the appropriate alkyl halide, 2.8 g (77%) of the desired product was obtained.

Step B: methyl 5-[3-(2-fluoro-4-iodo-phenoxy)propyl]-2-(methylamino)thiazole-4-carboxylate Using Deprotection with HFIP General Procedure starting from 2.0 g of the product from Step A (4.44 mmol) as the appropriate carbamate, 1.2 g (73%) of the desired product was obtained.

$^1$H NMR (500 MHz, DMSO-$d_6$) ppm 7.59 (dd, 1H), 7.50 (q, 1H), 7.45 (m, 1H), 6.97 (t, 1H), 4.03 (t, 2H), 3.70 (s, 3H), 3.12 (t, 2H), 2.77 (d, 3H), 1.99 (m, 2H); $^{13}$C NMR (125 MHz, DMSO-$d_6$) δ ppm 165.4, 163.0, 147.0, 134.0, 124.9, 117.6, 68.0, 51.8, 31.1, 30.6, 23.3; HRMS-ESI (m/z): $[M+H]^+$ calcd for $C_{15}H_{17}FIN_2O_3S$: 450.9983, found 450.9971.

Preparation 3t: Methyl 2-[5-[tert-butyl(dimethyl)silyl]oxypentylamino]-5-[3-[4-[3-(dimethylamino)prop-1-ynyl]-2-fluoro-phenoxy]propyl]thiazole-4-carboxylate Using Sonogashira General Procedure starting from crude Preparation 3m, Step B and N,N-dimethylprop-2-yn-1-amine as the appropriate acetylene, 3.73 g (quant. for 2 steps) of the desired product was obtained.

HRMS-ESI (m/z): $[M+H]^+$ calcd for $C_{30}H_{47}FN_3O_4SSi$: 592.3035, found 592.3033.

Preparation 3u: Ethyl 2-amino-5-(3-{4-[3-(dimethylamino)prop-1-yn-1-yl]-2-fluorophenoxy}propyl)-1,3-thiazole-4-carboxylate Step A: ethyl 3-bromo-6-chloro-2-oxohexanoate Bromine (1.6 mL, 31.2 mmol, 1.2 eq) was added to a stirred solution of ethyl 6-chloro-2-oxohexanoate (5 g, 26.0 mmol, 1 eq) in chloroform (70 mL). The reaction was stirred at ambient temperature for 6.5 h then diluted with dichloromethane and washed with 10% aqueous sodium thiosulphate followed by water then brine. The organic extract was dried (magnesium sulfate) and the solvent removed in vacuo to afford the desired compound (7 g, 25.8 mmol, 99%) as a colourless oil.

$^1$H NMR (400 MHz, DMSO-$d_6$) δ 5.25 (dd, J=9.0, 4.7 Hz, 1H), 4.30 (q, J=7.1 Hz, 2H), 3.72 (t, J=6.3 Hz, 2H), 2.24-2.10 (m, 1H), 2.07-1.89 (m, 2H), 1.92-1.76 (m, 1H), 1.30 (t, J=7.1 Hz, 3H).

Step B: ethyl 5-(3-chloropropyl)-2-acetamido-1,3-thiazole-4-carboxylate

N-Acetylthiourea, (3.05 g, 25.78 mmol, 1 eq) was added to a stirred solution of the product from Step A (7 g, 25.8 mmol, 1 eq) in ethanol (150 mL). The reaction was heated at reflux for 6 h, then allowed to cool to ambient temperature and the solvent was removed in vacuo. The residue was dissolved in dichloromethane (150 mL) then acetic anhydride (4.74 mL, 50.21 mmol, 2 eq) and 4-dimethylamino-pyridine (6.13 g, 50.21 mmol, 2 eq) were added. After stirring at ambient temperature for 2 h the mixture was diluted with dichloromethane then washed with water (×2) followed by brine. The organic extract was dried (magnesium sulfate) then the solvent removed in vacuo. The crude material was triturated with diethyl ether and the solid was collected by filtration and washed with diethyl ether to yield the desired product (1, 1 g, 3.78 mmol, 13.9%). Two cycles of filtrate evaporation, re-trituration, and filtration afforded further product batches (142 g, 11.76 g, 43%). Finally, evaporation of the final filtrate and purification by automated flash column (CombiFlash Rf, 12 g RediSep™ silica cartridge) eluting in a gradient of 0-100% ethyl acetate in iso-heptane afforded further desired product (1.46 g, 5.02 mmol, 18.5%) [overall yield: 76%].

LC/MS ($C_{11}H_{15}ClN_2O_3S$) 291 [M+H]$^+$; RT 1.08 (LCMS-V-B1);

$^1$H NMR (400 MHz, DMSO-$d_6$) δ 12.43 (s, 1H), 4.26 (q, J=7.1 Hz, 2H), 3.68 (t, J=6.4 Hz, 2H), 3.27-3.18 (m, 2H), 2.13 (s, 3H), 2.19-2.00 (m, 2H), 1.29 (t, J=7.1 Hz, 3H).

Step C: ethyl 2-acetamido-5-(3-iodopropyl)-1,3-thiazole-4-carboxylate

A solution of the product from Step B (5.84 g, 20.1 mmol, 1 eq) and sodium iodide (18.1 g, 0.12 mol, 6 eq) in acetonitrile (130 mL) was heated at reflux for 6 h. The mixture was cooled to ambient temperature and the solvent removed in vacuo. The mixture was diluted with ethyl acetate and washed with water and brine. The organic extract was dried (magnesium sulfate) and concentrated in vacuo. The resultant solid was triturated in diethyl ether then collected by filtration affording the desired product as a cream solid (6.28 g, 16.4 mmol, 82%).

LC/MS ($C_{11}H_{15}IN_2O_3S$) 383 [M+H]$^+$; RT 0.96 (LCMS-V-B1)

$^1$H NMR (400 MHz, DMSO-$d_6$) δ 12.43 (s, 1H), 4.26 (q, J=7.1 Hz, 2H), 3.29 (t, J=6.7 Hz, 2H), 3.18 (t, J=7.4 Hz, 2H), 2.12 (s, 3H), 2.16-2.04 (m, 2H), 1.30 (t, J=7.1 Hz, 3H).

Step D: ethyl 5-(3-{4-[3-(dimethylamino)prop-1-yn-1-yl]-2-fluorophenoxy}propyl)-2-acetamido-1,3-thiazole-4-carboxylate Sodium hydride (60% in mineral oil)(0.56 g, 14.1 mmol, 2 eq) was added to a stirred solution of the product from Step C (1.64 g, 8.46 mmol, 1.2 eq) in dimethylformamide (20 mL). The reaction was stirred at ambient temperature for 30 min then cooled in an ice bath and a solution of the product from Preparation 6b (2.7 g, 7.05 mmol, 1 eq) in dimethylformamide (20 mL) was added slowly. After 40 min the reaction was allowed to warm to ambient temperature and stirred for 5 h. The solvent was removed in vacuo, and the crude material was partitioned between ethyl acetate and water, washed with brine, and dried (magnesium sulfate). The solvent was removed in vacuo and purification by automated flash column chromatography (CombiFlash Rf, 80 g RediSep™ silica cartridge) eluting in a gradient of 0-10% methanol in dichloromethane afforded the desired product as a cream solid (1.48 g, 3.32 mmol, 47%).

LC/MS ($C_{22}H_{26}FN_3O_4S$) 448 [M+H]$^+$; RT 0.76 (LCMS-V-B1)

$^1$H NMR (400 MHz, DMSO-$d_6$) δ 12.41 (s, 1H), 7.30 (dd, J=11.9, 2.3 Hz, 1H), 7.25-7.18 (m, 1H), 7.17-7.10 (m, 1H), 4.22 (q, J=7.1 Hz, 2H), 4.11 (t, J=6.1 Hz, 2H), 3.42 (s, 2H), 3.24 (dt, J=14.7, 7.5 Hz, 2H), 2.23 (s, 6H), 2.10 (s, 3H), 2.12-2.01 (m, 2H), 1.27 (t, J=7.1 Hz, 3H).

Step E: ethyl 2-amino-5-(3-{4-[3-(dimethylamino)prop-1-yn-1-yl]-2-fluorophenoxy}propyl)-1,3-thiazole-4-carboxylate A solution of the product from Step D (1.49 g, 3.32 mmol, 1 eq) and hydrochloric acid (4 M in 1,4-dioxane)(8.3 mL, 0.03 mol, 10 eq) in ethanol (40 mL) was healed at 60° C. for 18 h. The reaction was allowed to cool to ambient temperature then the solvent removed in vacuo. The resultant oil was dissolved in a small amount of methanol then loaded onto an SCX-2 cartridge (50 g, methanol-washed). The cartridge was washed with methanol then eluted with 3.5 N methanolic ammonia. The solvent was removed in vacuo and the resultant oil was purified by automated flash column chromatography (CombiFlash Rf, 80 g RediSep™ silica cartridge) eluting in a gradient of 0-10% methanol in dichloromethane to afford the desired product as a cream solid (0.78 g, 1.93 mmol, 58%).

LC/MS ($C_{20}H_{24}FN_3O_3S$) 406 [M+H]$^+$; RT 0.706 (LCMS-V-B1)

$^1$H NMR (400 MHz, DMSO-$d_6$) δ 7.30 (dd, J=12.0, 2.0 Hz, 1H), 7.25-7.17 (m, 1H), 7.13 (t, J=8.7 Hz, 1H), 7.02 (s, 2H), 4.16 (q, 2H), 4.07 (t, 2H), 3.42 (s, 2H), 3.12 (t, J=7.5 Hz, 2H), 2.23 (s, 6H), 2.09-1.94 (m, 2H), 1.23 (t, J=7.1 Hz, 3H).

Preparation 3v: Ethyl 2-amino-5-(3-phenoxypropyl)-1,3-thiazole-4-carboxylate

Step A: ethyl 5-bromo-2-acetamido-1,3-thiazole-4-carboxylate

A solution of ethyl 2-amino-5-bromo-1,3-thiazole-4-carboxylate (2 g, 7.96 mmol, 1 eq), acetic anhydride (0.83 mL, 8.76 mmol, 1.1 eq) and 4-dimethylaminopyridine (1.12 g, 9.16 mmol, 1.15 eq) in dichloromethane (30 mL) was stirred at ambient temperature for 3 days. The reaction was diluted with dichloromethane, washed successively with water and brine, then dried (magnesium sulfate) and the solvent removed in vacuo. The resultant solid was triturated with diethyl ether, filtered, and dried under vacuum to afford the desired product as an off-white solid (1.8 g, 6.14 mmol, 77%).

LC/MS ($C_8H_9BrN_2O_3S$) 293 [M+H]$^+$; RT 1.01 (LCMS-V-B1)

$^1$H NMR (400 MHz, DMSO-$d_6$) δ 12.80 (s, 1H), 4.28 (q, J=7.1 Hz, 2H), 2.16 (s, 3H), 1.30 (t, J=7.1 Hz, 3H).

Step B: ethyl 2-acetamido-5-(3-phenoxyprop-1-yn-1-yl)-1,3-thiazole-4-carboxylate The product from Step A (200 mg, 0.68 mmol, 1 eq), phenyl propargyl ether (0.18 mL, 1.36 mmol, 2 eq), triethylamine (0.28 mL, 2.05 mmol, 3 eq), copper (I) iodide (13 mg, 0.07 mmol, 0.1 eq) and tetrakis(triphenylphosphine) palladium(0)(39.4 mg, 0.03 mmol, 0.05 eq) were combined. The mixture was sparged with nitrogen (10 min) then heated at 100° C. for 1 h under microwave irradiation. The reaction mixture was partitioned between ethyl acetate and water, and the organics were washed with water followed by brine, and dried (magnesium sulfate). The solvent was removed in vacuo and purification by automated flash column chromatography (CombiFlash Rf, 12 g RediSep™ silica cartridge) eluting with a gradient of 0-100% ethyl acetate in iso-heptane afforded the desired product as an off-white solid (122 mg, 0.35 mmol, 52%).

LC/MS ($C_{17}H_{16}N_2O_4S$) 345 $[M+H]^+$; RT 1.21 (LCMS-V-B1)

$^1H$ NMR (400 MHz, DMSO-$d_6$) δ 12.85 (s, 1H), 7.34 (t, J=7.8 Hz, 2H), 7.09-7.03 (m, 2H), 7.02-6.96 (m, 1H), 5.13 (s, 2H), 4.24 (q, J=7.0 Hz, 2H), 2.16 (s, 3H), 1.27 (t, J=7.1 Hz, 3H).

Step C: ethyl 2-acetamido-5-(3-phenoxypropyl)-1,3-thiazole-4-carboxylate

Ethyl acetate (10 mL) was added to a flask containing the product from Step B (122 mg, 0.35 mmol, 1 eq) and platinum(IV) oxide (8.04 mg, 0.04 mmol, 0.1 eq) under a nitrogen atmosphere. The mixture was shaken at ambient temperature under an atmosphere of hydrogen for 6.5 h. Further platinum(IV) oxide (spatula tip) was added and the reaction was shaken under a hydrogen atmosphere for a further 18 h. The mixture was filtered through a methanol-wet pad of celite, eluted with methanol, and the solvent removed in vacuo. Purification by automated flash column chromatography (CombiFlash Rf, 12 g RediSep™ silica cartridge) eluting with a gradient of 0-100% ethyl acetate in iso-heptane afforded the desired product as a cream solid (77.2 mg, 0.22 mmol, 63%).

LC/MS ($C_{17}H_{20}N_2O_4S$) 349 $[M+H]^+$; RT 1.22 (LCMS-V-B1)

$^1H$ NMR (400 MHz, DMSO-$d_6$) δ 12.41 (s, 1H), 7.36-7.24 (m, 2H), 7.03-6.88 (m, 3H), 4.23 (q, J=7.1 Hz, 2H), 4.00 (t, J=6.2 Hz, 2H), 3.26 (dd J=8.3, 6.8 Hz, 2H), 2.12 (s, 3H), 2.11-2.01 (m, 2H), 1.28 (t, 1 Hz, 3H).

Step D: ethyl 2-amino-5-(3-phenoxypropyl)-1,3-thiazole-4-carboxylate

Hydrochloric acid (4M in 1,4-dioxane; 0.55 mL, 2.22 mmol, 10 eq) was added to a stirred solution of the product from Step C (77.2 mg, 0.22 mmol, 1 eq) in ethanol (5 mL). The reaction was heated at 60° C. for 5 h. The solvent was removed in vacuo then the residue was dissolved in methanol and loaded onto a methanol-wet SCX-2 cartridge (5 g). The cartridge was washed with methanol, then eluted with 3.5N methanolic ammonia, and the solvent was removed in vacuo. Purification by automated flash column chromatography (CombiFlash Rf, 12 g RediSep™ silica cartridge) eluting with a gradient of 0-10% methanol in dichloromethane afforded the desired product as a yellow gum (48.2 mg, 0.16 mmol, 71%).

LC/MS ($C_{15}H_{18}N_2O_3S$) 307 $[M+H]^+$; RT 1.16 (LCMS-V-B1)

$^1H$ NMR (400 MHz, DMSO-$d_6$) δ 7.33-7.24 (m, 2H), 7.02 (s, 2H), 6.95-6.90 (m, 3H), 4.16 (q, J=7.1 Hz, 2H), 3.97 (t, J=6.2 Hz, 2H), 3.13 (t, 2H), 2.03-1.94 (m, 2H), 1.24 (t, J=7.1 Hz, 3H).

Preparation 3w: Ethyl 2-amino-5-(3-methoxypropyl)-1,3-thiazole-4-carboxylate

Step A: ethyl 2-acetamido-5-(3-methoxyprop-1-yn-1-yl)-1,3-thiazole-4-carboxylate Dimethylformamide (10 mL) was added to the product from Preparation 3v, Step A (400 mg, 1.36 mmol, 1 eq), methyl propargyl ether (0.23 mL, 2.73 mmol, 2 eq), triethylamine (0.57 mL, 4.09 mmol, 3 eq) and copper (I) iodide (26 mg, 0.14 mmol, 0.1 eq) then tetrakis(triphenylphosphine)palladium(0)(78.8 mg, 0.07 mmol, 0.05 eq) was added. The vessel was sparged with nitrogen (10 min) then heated at 100° C. for 1 h under microwave irradiation. The solvent was removed in vacuo and purification by automated flash column chromatography (CombiFlash Rf, 12 g RediSep™ silica cartridge) eluting with a gradient of 0-5% methanol in dichloromethane afforded a solid that was triturated with diethyl ether to afford the desired product as a cream solid (213.7 mg, 0.76 mmol, 55%). The filtrate was evaporated to afford a second batch of desired product as an orange gum (94.6 mg, 0.34 mmol, 24%) [overall yield 79%].

LC/MS ($C_{12}H_{14}N_2O_4S$) 283 $[M+H]^+$; RT 1.00 (LCMS-V-B1)

$^1H$ NMR (400 MHz, DMSO-$d_6$) δ 12.84 (s, 1H), 4.41 (s, 2H), 4.28 (q, J=7.1 Hz, 2H), 3.36 (s, 3H), 2.16 (s, 3H), 1.30 (t, J=7.1 Hz, 3H).

Step B: ethyl 2-acetamido-5-(3-methoxypropyl)-1,3-thiazole-4-carboxylate

A solution of the product from Step A (308 mg, 1.09 mmol, 1 eq) in 2:1 ethyl acetate/methanol (15 mL) was added to a flask containing catalytic platinum(IV) oxide under a nitrogen atmosphere. The vessel was evacuated and back-filled with nitrogen (×3), then evacuated and placed under an atmosphere of hydrogen. After shaking at ambient temperature for 18 h, the reaction was filtered through celite, eluted with methanol, and the solvent removed in vacuo. Purification by automated flash column chromatography (CombiFlash Rf, 12 g RediSep™ silica cartridge) eluting with a gradient of 0-100% ethyl acetate in iso-heptane afforded the desired product as a cream solid (207 mg, 0.72 mmol, 66%).

LC/MS ($C_{12}H_{18}N_2O_4S$) 287 $[M+H]^+$; RT 0.99 (LCMS-V-B1)

$^1H$ NMR (400 MHz, DMSO-$d_6$) δ 12.40 (s, 1H), 4.25 (q, J=7.1 Hz, 2H), 3.39-3.31 (m, 2H), 3.24 (s, 3H), 3.17-3.08 (m, 2H), 2.12 (s, 3H), 1.89-1.77 (m, 2H), 1.29 (t, J=7.1 Hz, 3H).

Step C: ethyl 2-amino-5-(3-methoxypropyl)-1,3-thiazole-4-carboxylate

Hydrochloric acid (4M in 1,4-dioxane; 2.1 mL, 8.38 mmol, 10 eq) was added to a stirred solution of the product from Step B (240 mg, 0.84 mmol, 1 eq) in ethanol (10 mL). The mixture was heated to 60° C. for 7 h then allowed to cool to ambient temperature and concentrated in vacuo. Purification by automated flash column chromatography (CombiFlash Rf, 12 g RediSep™ silica cartridge) eluting with a gradient of 0-10% methanol in dichloromethane afforded the desired product as a brown gum (219 mg, 0.81 mmol, 97%).

LC/MS ($C_{10}H_{16}N_2O_3S$) 245 $[M+H]^+$; RT 0.88 (LCMS-V-B1)

$^1H$ NMR (400 MHz, DMSO-$d_6$) δ 8.00 (br s, 2H), 4.25 (q, J=7.1 Hz, 2H), 3.34 (t, J=6.3 Hz, 2H), 3.23 (s, 3H), 3.05-2.96 (m, 2H), 1.84-1.72 (m, 2H), 1.28 (t, J=7.1 Hz, 3H).

Preparation 3x: Ethyl 2-amino-5-[3-(2-fluorophenoxy)propyl]-1,3-thiazole-4-carboxylate Step A: ethyl 2-acetamido-5-(3-hydroxyprop-1-yn-1-yl)-1,3-thiazole-4-carboxylate To a mixture of the product from Preparation 3v, Step A (1 g, 3.41 mmol, 1 eq), propargyl alcohol (0.4 mL, 6.82 mmol, 2 eq), triethylamine (1.42 mL, 10.2 mmol, 3 eq) and copper (I) iodide (65 mg, 0.34 mmol, 0.1 eq) in dimethylformamide (20 mL) was added tetrakis(triphenylphosphine) palladium(0)(197 mg, 0.17 mmol, 0.05 eq). The mixture was sparged with nitrogen (10 min) then heated at 100° C. for 1 h under microwave irradiation. The solvent was removed in vacuo then purification by automated flash column chromatography (CombiFlash Rf, 40 g RediSep™ silica cartridge) eluting with a gradient of 0-10% methanol in dichloromethane afforded the desired product as a brown solid (1.01 g, 3.75 mmol, >100%).

LC/MS ($C_1H_{12}N_2O_4$) 269 $[M+H]^+$; RT 0.82 (LCMS-V-B1)

$^1H$ NMR (400 MHz, DMSO-$d_6$) δ 12.80 (s, 1H), 5.45 (t, J=6.0 Hz, 1H), 4.37 (d, J=6.1 Hz, 2H), 4.27 (q, J=7.1 Hz, 2H), 2.16 (s, 3H), 1.30 (t, J=7.1 Hz, 3H).

Step B: ethyl 2-acetamido-5-(3-hydroxypropyl)-1,3-thiazole-4-carboxylate

A solution of the product from Step A (1.01 g, 3.75 mmol, 1 eq) in 4:1 ethyl acetate/methanol (25 mL) was added to a flask containing platinum(IV) oxide hydrate (spatula tip) under a nitrogen atmosphere. The reaction was evacuated and back-filled with nitrogen (×3), then evacuated and placed under an atmosphere of hydrogen. The reaction was shaken at ambient temperature for 30 h, then filtered through celite, eluted with methanol, and the solvent removed in vacuo. Purification by automated flash column chromatography (CombiFlash Rf, 24 g RediSep™ silica cartridge) eluting with a gradient of 0-10% methanol in dichloromethane afforded the desired product as a brown gum (582 mg, 2.14 mmol, 57%).

LC/MS ($C_{11}H_{16}N_2O_4S$) 273 $[M+H]^+$; RT 0.81 (LCMS-V-B1)

$^1H$ NMR (400 MHz, DMSO-$d_6$) δ 12.39 (s, 1H), 4.54 (t, J=5.1 Hz, 1H), 4.25 (q, J=7.1 Hz, 2H), 3.44 (td, J=6.4, 5.1 Hz, 2H), 3.15-3.09 (m, 2H), 2.12 (s, 3H), 1.81-1.69 (m, 2H), 1.29 (t, J=7.1 Hz, 3H).

Step C: ethyl 2-acetamido-5-[3-(2-fluorophenoxy)propyl]-1,3-thiazole-4-carboxylate A solution of 2-fluorophenol (0.1 mL, 1.1 mmol, 1.5 eq), the product from Step B (200 mg, 0.73 mmol, 1 eq) and triphenylphosphine (289 mg, 1.1 mmol, 1.5 eq) in tetrahydrofuran (10 mL) was cooled in an ice bath then diisopropyl azobicarboxylate (0.22 mL, 1.1 mmol, 1.5 eq) was added dropwise. The reaction was allowed to warm gradually to ambient temperature and then stirred for 18 h. The mixture was diluted with ethyl acetate, washed with brine, and the organic phase was dried (magnesium sulfate) and concentrated in vacuo. Purification by automated flash column chromatography (CombiFlash Rf, 24 g RediSep™ silica cartridge) eluting with a gradient of 0-100% ethyl acetate in heptane afforded the desired product as a white solid (162 mg, 0.44 mmol, 60%).

LC/MS ($C_{17}H_{19}FN_2O_4S$) 367 $[M+H]^+$; RT 1.22 (LCMS-V-B1)

$^1H$ NMR (400 MHz, DMSO-$d_6$) δ 12.41 (s, 1H), 7.29-7.07 (m, 3H), 7.00-6.89 (m, 1H), 4.23 (q, J=7.1 Hz, 2H), 4.08 (t, J=6.2 Hz, 2H), 3.27 (dd, J=8.2, 6.9 Hz, 2H), 2.12 (s, 3H), 2.18-2.03 (m, 2H), 1.27 (t, J=7.1 Hz, 3H).

Step D: ethyl 2-amino-5-[3-(2-fluorophenoxy)propyl]-1,3-thiazole-4-carboxylate

A solution of the product from Step C (217 mg, 0.59 mmol, 1 eq) and hydrochloric acid (4M in dioxane; 1.48 mL, 5.92 mmol, 10 eq) in ethanol (8 mL) was heated at 60° C. overnight. The mixture was allowed to cool to ambient temperature then the solvent removed in vacuo. Purification by automated flash column chromatography (CombiFlash Rf, 12 g RediSep™ silica cartridge) eluting with a gradient of 0-10% methanol in dichloromethane afforded the desired product as a yellow foam (181 mg, 0.56 mmol, 94%).

LC/MS ($C_{15}H_{17}FN_2O_3S$) 325 $[M+H]^+$; RT 1.16 (LCMS-V-B1)

$^1H$ NMR (400 MHz, DMSO-$d_6$) δ 7.62 (br s, 2H), 7.26-7.07 (m, 3H), 6.99-6.89 (m, 1H), 4.20 (q, J=7.1 Hz, 2H), 4.07 (t, J=6.1 Hz, 2H), 3.15 (t, J=7.5 Hz, 2H), 2.08-1.99 (m, 1.25 (t, J=7.1 Hz, 3H).

Preparation 3y: Ethyl 2-amino-5-[3-(4-bromo-2-fluorophenoxy)propyl]-1,3-thiazole-4-carboxylate Step A: ethyl 5-[3-(4-bromo-2-fluorophenoxy)propyl]-2-acetamido-1,3-thiazole-4-carboxylate A solution of the product from Preparation 3x, Step B (248 mg, 0.91 mmol, 1 eq), 4-bromo-2-fluorophenol (0.15 mL, 1.37 mmol, 1.5 eq) and triphenylphosphine (358 mg, 1.37 mmol, 1.5 eq) in tetrahydrofuran (10 mL) was cooled in an ice bath then diisopropylazodicarboxylate (0.27 mL, 1.37 mmol, 1.5 eq) was added dropwise. The reaction was stirred in the ice-bath for 30 min then stirred at ambient temperature for 3 h. The reaction was diluted with ethyl acetate and washed with water then brine. The organics were dried (magnesium sulfate) and the solvent removed in vacuo. Purification by automated flash column chromatography (CombiFlash Rf, 24 g RediSep™ silica cartridge) eluting with a gradient of 0-100% ethyl acetate in heptane afforded the desired product as a white solid (229 mg, 0.51 mmol, 56%).

LC/MS ($C_{17}H_{18}BrFN_2O_4S$) 445 $[M+H]^+$; RT 1.36 (LCMS-V-B1)

$^1H$ NMR (400 MHz, DMSO-$d_6$) δ 12.42 (s, 1H) 7.53 (dd, J=10.9, 2.4 Hz, 1H), 7.32 (ddd, J=8.8, 2.4, 1.5 Hz, 1H), 7.13 (t, J=9.0 Hz, 1H), 4.22 (q, J=7.1 Hz, 2H), 4.08 (t, J=6.1 Hz, 2H), 3.25 (dd, J=8.4, 6.7 Hz, 2H), 2.12 (s, 3H), 2.18-2.02 (m, 2H), 1.27 (t, J=7.1 Hz, 3H).

Step B: ethyl 2-amino-5-[3-(4-bromo-2-fluorophenoxy)propyl]-1,3-thiazole-4-carboxylate A solution of the product from Step A (229 mg, 0.51 mmol, 1 eq) and hydrochloric acid (4M in dioxane; 1.29 mL, 5.14 mmol, 10 eq) in ethanol (8 mL) was heated at 60° C. for 18 h. The reaction was allowed to cool to ambient temperature then the solvent was removed in vacuo. Purification by automated flash column chromatography (CombiFlash Rf, 12 g RediSep™ silica cartridge) eluting with a gradient of 0-10% methanol in dichloromethane afforded the desired product as a yellow gum (199 mg, (1.49 mmol, 96%).

LC/MS ($C_{15}H_{16}BrFN_2O_3S$) 405 $[M+H]^+$; RT 1.30 (LCMS-V-B1)

$^1$H NMR (400 MHz, DMSO-$d_6$) δ 7.54 (dd, J=11.0, 2.4 Hz, 1H), 7.33 (ddd, J=8.8, 2.4, 1.5 Hz, 1H), 7.13 (t, J=9.0 Hz, 1H), 4.19 (q, J=7.1 Hz, 2H), 4.07 (t, J=6.1 Hz, 2H), 3.16-3.10 (m, 2H), 2.11-1.96 (m, 2H), 1.24 (t, J=7.1 Hz, 3H).

Preparation 3z: Ethyl 2-[(2-methoxyethyl)amino]-1, 3-thiazole-4-carboxylate

Ethyl bromopyruvate (2.5 mL, 17.9 mmol, 1.07 eq) was added to a suspension of 2-methoxyethylthiourea (2.25 g, 16.8 mmol, 1 eq) in ethanol (40 mL) at 0° C. under a nitrogen atmosphere and the mixture stirred for 1 h at ambient temperature. Triethylamine (4.7 mL, 33.5 mmol, 2 eq) was added and the mixture heated at 75° C. for 18 h. The solution was allowed to cool to ambient temperature and was partitioned between ethyl acetate (300 mL) and water (200 mL). The organic phase was washed with water (200 mL) and brine, dried (magnesium sulfate) and concentrated in vacuo. Purification by flash column chromatography (100 g silica) eluting with 1:1 ethyl acetate/heptane gave a solid that was triturated with heptane (20 mL), filtered, washed with heptane (2×15 mL) and dried under vacuum to afford the desired product as a pale brown solid (3.15 g, 13.7 mmol, 82%).

LC/MS ($C_9H_{14}N_2O_3S$) 231 $[M+H]^+$; RT 0.88 (LCMS-V-B1)

$^1$H NMR (400 MHz, $CDCl_3$) δ 7.40 (s, 1H), 5.78 (t, 1H), 4.34 (q, J=7.1 Hz, 2H), 3.60-3.54 (m, 2H), 3.48 (td, J=5.5, 4.4 Hz, 2H), 3.36 (s, 3H), 1.36 (t, J=7.1 Hz, 3H).

Preparation 3za: Ethyl 5-[4-(benzyloxy)piperidin-1-yl]-2-(methylamino)-1,3-thiazole-4-carboxylate Step A: ethyl 5-[4-(benzyloxy)piperidin-1-yl]-1,3-thiazole-4-carboxylate A solution of ethyl 5-bromothiazole-4-carboxylate (500 mg, 2.12 mmol, 1 eq), 4-benzyloxy-piperidine hydrochloride (579 mg, 2.54 mmol, 1.2 eq) and 1,8-diazabicyclo [5.4.0]undec-7-ene (0.64 mL, 4.24 mmol 2 eq) in acetonitrile (10 mL) was heated at 100° C. for 2 h under microwave irradiation. The reaction was allowed to cool to ambient temperature then concentrated in vacuo, partitioned between dichloromethane and water, and the organic phase washed with brine, dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a yellow oil (499 mg, 1.44 mmol, 68%).

LC/MS ($C_{18}H_{22}N_2O_3S$) 347 $[M+H]^+$; RT 1.08 (LCMS-V-B1)

$^1$H NMR (400 MHz, DMSO-$d_6$) δ 8.46 (s, 1H), 7.41-7.33 (m, 4H), 7.32-7.26 (m, 1H), 4.55 (s, 2H), 4.25 (q, J=7.1 Hz, 2H), 3.62 (tt, J=7.7, 3.6 Hz, 1H), 3.42-3.30 (m, 2H), 3.08-2.97 (m, 2H), 2.05-1.95 (m, 2H), 1.81-1.66 (m, 2H), 1.28 (t, J=7.1 Hz, 3H).

Step B: ethyl 5-[4-(benzyloxy)piperidin-1yl]-2-bromo-1,3-thiazole-4-carboxylate

N-Bromosuccinimide (308 mg, 1.73 mmol, 1.2 eq) was added to a stirred solution of the product from Step A (499 mg, 1.44 mmol, 1 eq) in acetonitrile (20 mL) and the mixture was stirred at ambient temperature overnight. The reaction was diluted with ethyl acetate, washed with water followed by brine, dried (magnesium sulfate), and concentrated in vacuo. Purification by automated flash column chromatography (CombiFlash Rf, 24 g RediSep™ silica cartridge) eluting with a gradient of 0-60% ethyl acetate in iso-heptane afforded the desired product as a yellow solid (454 mg, 1.07 mmol, 74%).

LC/MS ($C_{18}H_{21}BrN_2O_3S$) 427 $[M+H]^+$; RT 1.26 (LCMS-V-B1)

$^1$H NMR (400 MHz, DMSO-$d_6$) δ 7.41-7.33 (m, 4H), 7.32-7.26 (m, 1H), 4.54 (s, 2H), 4.24 (q, J=7.1 Hz, 2H), 3.62 (tt, J=7.5, 3.5 Hz, 1H), 3.43-3.28 (m, 2H), 3.07 (ddd, J=11.8, 8.5, 3.4 Hz, 2H), 2.06-1.88 (m, 2H), 1.79-1.65 (m, 2H), 1.28 (t, J=7.1 Hz, 3H).

Step C: ethyl 5-[4-(benzyloxy)piperidin-4-yl]-2-{[(tert-butoxy)carbonyl](methyl)amino}-1,3-thiazole-4-carboxylate The product from Step B (454 mg, 1.07 mmol, 1 eq) and tert-butyl methylcarbamate (0.19 mL, 1.28 mmol, 1.2 eq) were added to a solution of tris(dibenzylideneacetone)dipalladium(0)(48.9 mg, 0.05 mmol, 0.05 eq) and Xantphos (61.8 mg, 0.11 mmol, 0.1 eq) in 1,4-dioxane (10 mL) under a nitrogen atmosphere. Cesium carbonate (522 mg, 1.6 mmol, 1.5 eq) was added and the mixture heated at 100° C. overnight. The reaction was allowed to cool to ambient temperature and concentrated in vacuo. The residue was dissolved in ethyl acetate, then washed with water followed by brine, dried (magnesium sulfate) and concentrated in vacuo. Purification by automated flash column chromatography (CombiFlash Rf, 50 g RediSep™ silica cartridge) eluting with a gradient of 0-50% ethyl acetate in iso-heptane afforded the desired product as a cream solid (339 mg, 0.71 mmol, 67%).

LC/MS ($C_{24}H_{33}N_3O_5S$) 476 $[M+H]^+$; RT 1.37 (LCMS-V-B1)

$^1$H NMR (400 MHz, DMSO-$d_6$) δ 7.41-7.33 (m, 4H), 7.32-7.26 (m, 1H), 4.55 (s, 2H), 4.23 (q, J=7.1 Hz, 2H), 3.59 (tt, J=8.0, 3.7 Hz, 1H), 3.38 (s, 3H), 3.37-3.29 (m, 2H), 2.97 (ddd, J=11.6, 8.8, 3.1 Hz, 2H), 2.06-1.91 (m, 2H), 1.76-1.62 (m, 2H), 1.52 (s, 9H), 1.28 (t, J=7.1 Hz, 3H).

Step D: ethyl 5-[4-(benzyloxy)piperidin-1-yl]-2-(methylamino)-1,3-thiazole-4-carboxylate Trifluoroacetic acid (0.53 mL, 7.11 mmol, 10 eq) was added to a stirred solution of the product from Step C (339 mg, 0.71 mmol, 1 eq) in dichloromethane (10 mL) at 0° C. and the mixture was allowed to warm to ambient temperature and stir overnight. The reaction was partitioned between dichloromethane and saturated aqueous sodium bicarbonate, and the organic phase washed with brine, dried (magnesium sulfate), and concentrated in vacuo. The material was triturated with diethyl ether, filtered, and dried under vacuum to afford the desired product as a white solid (213 mg, 0.57 mmol, 80%).

LC/MS ($C_{19}H_{25}N_3O_3S$) 376 $[M+H]^+$; RT 1.07 (LCMS-V-B1)

$^1$H NMR (400 MHz, DMSO-$d_6$) δ 7.38-7.33 (m, 3H), 7.32-7.23 (m, 2H), 4.53 (s, 2H), 4.18 (q, J=7.1 Hz, 2H), 3.54 (dt, J=8.2, 4.3 Hz, 1H), 3.19-3.08 (m, 2H), 2.83-2.72 (m, 5H), 2.02-1.89 (m, 2H), 1.76-1.60 (m, 2H), 1.26 (t, J=7.1 Hz, 3H).

Preparation 3zb: Ethyl 5-{1-[(tert-butoxy)carbonyl] azetidin-3-yl}-2-(methylamino)-1,3-thiazole-4-carboxylate Step A: ({1-[(tert-butoxy)carbonyl]azetidin-3-yl}methyl)(iodo)zinc To an oven-dried Schlenk flask was added zinc (3.3 g, 50.5 mmol, 1.5 eq) and the vessel was heated at 160° C. for 20 min under vacuum then allowed to cool to ambient temperature and placed under a nitrogen atmosphere. Dimethylacetamide (25 mL) was added followed by slow addition of a mixture of trimethylchlorosilane (0.69 mL, 5.42 mmol, 0.16 eq) and 1,2-dibromoethane (0.49 mL, 5.69 mmol, 0.17 eq). The resultant mixture was allowed to cool to ambient temperature then a solution of 1-boc-3-(iodomethyl)azetidine (10 g, 33.65 mmol, 1 eq) in dimethylacetamide (7 mL) was added slowly and the mixture was stirred overnight. Cannulation through a filter (cotton-wool/celite/cotton-wool) into a dry 25 mL Schlenk tube afforded the desired product as a 0.62M solution (as determined by titration with a 0.5M solution of iodine) that was used without further characterisation.

Step A: tert-butyl 3-(3-ethoxy-2,3-dioxopropyl)azetidine-1-carboxylate

A solution of copper(I) iodide (154 g, 18.6 mmol, 2 eq) in tetrahydrofuran (20 mL) was cooled to −20° C. then the product from Step A (0.62M in dimethylacetamide; 30 mL, 18.6 mmol, 2 eq) was added slowly and the mixture was stirred at −20° C. for 10 min then at 0° C. for 20 min. The mixture was cooled to −20° C. then ethyl chloroglyoxylate (1.04 mL, 9.3 mmol, 1 eq) was added slowly and the mixture was allowed to warm to ambient temperature and stir for 1 h. The reaction was quenched by addition of saturated aqueous ammonium chloride, extracted with ethyl acetate (×2), and the combined organic extracts were washed with brine, dried (magnesium sulfate), and concentrated in vacuo. Purification by automated flash column chromatography (CombiFlash Rf, 40 g RediSep™ silica cartridge) eluting with a gradient of 0-30% ethyl acetate in iso-heptane afforded the desired product as a colourless oil (0.57 g, 2.1 mmol, 23%).

$^1$H NMR (400 MHz, Chloroform-d) δ 4.33 (q, J=72 Hz, 2H), 4.13 (t, J=8.5 Hz, 2H), 3.57 (dd, J=8.9, 5.4 Hz, 2H), 3.20 (d, J=7.5 Hz, 2H), 2.99-2.84 (m, 1H), 1.43 (s, 9H), 1.37 (t, J=7.1 Hz, 3H).

Step C: tert-butyl 3-[(1Z)-3-ethoxy-3-oxo-2-[(trimethylsilyl)oxy]prop-1-en-1-yl]azetidine-1-carboxylate To a solution of the product from Step B (570 mg, 2.1 mmol, 1 eq) and chlorotrimethylsilane (0.3 mL, 2.35 mmol, 1.12 eq) in tetrahydrofuran (10 mL) was slowly added triethylamine (0.38 mL, 2.73 mmol, 1.3 eq) and the mixture was stirred at ambient temperature for 3.5 h. The reaction was partitioned between ethyl acetate and water, and the organic phase was washed with brine, dried (magnesium sulfate) and concentrated in vacuo to afford the desired product as a colourless oil (643 mg, 1.87 mmol, 89%).

$^1$H NMR (400 MHz, Chloroform-d) δ 6.23 (d, J=8.9 Hz, 1H), 4.22 (q, J=7.1 Hz, 2H), 4.14 (t, J=8.5 Hz, 2H), 3.74 (dd, J=8.4, 6.0 Hz, 2H), 3.61-3.46 (m, 1H), 1.44 (s, 9H), 1.32 (t, J=7.1 Hz, 3H), 0.20 (s, 9H).

Step D: tert-butyl 3-(1-bromo-3-ethoxy-2,3-dioxopropyl)azetidine-1-carboxylate

A solution of the product from Step C (643 mg, 1.87 mmol, 1 eq) and N-bromosuccinimide (367 mg, 2.06 mmol, 1.1 eq) in tetrahydrofuran (15 mL) was heated at reflux for 2.5 h then allowed to cool to ambient temperature. The reaction was partitioned between ethyl acetate and saturated aqueous sodium bicarbonate and the organic phase was washed with brine, dried (magnesium sulfate), and concentrated in vacuo. Purification by automated flash column chromatography (CombiFlash Rf, 24 g RediSep™ silica cartridge) eluting with a gradient of 0-40% ethyl acetate in iso-heptane afforded the desired product as a yellow gum (507 mg, 1.45 mmol, 77%).

$^1$H NMR (400 MHz, Chloroform-d) δ 5.25 (d, J=9.3 Hz, 1H), 4.40 (q, 2H), 4.14 (t, 1H), 4.08 (t, J=8.8 Hz, 1H), 3.85 (dd, J=9.1, 5.5 Hz, 1H), 3.58 (dd, J=9.3, 5.2 Hz, 1H), 3.25-3.10 (m, 1H), 1.44 (s, 9H), 1.40 (t, J=7.2 Hz, 3H).

Step E: ethyl 5-(azetidin-3-yl)-2-(methylamino)-1,3-thiazole-4-carboxylate

A solution of the product from Step D (452 mg, 1.29 mmol, 1 eq) and N-methylthiourea (140 mg, 1.55 mmol, 1.2 eq) in ethanol (8 mL) was heated at reflux for 4.5 h then allowed to cool to ambient temperature. The resultant precipitate was collected by filtration, washed with ethanol (2 mL), and dried under vacuum to afford the desired product as a white solid (161 mg, 0.5 mmol, 39%). The filtrate was transferred to a microwave vial and hydrochloric acid (4M in 1,4-dioxane, 0.2 mL, 0.8 mmol) was added and the mixture was heated at 60° C. for 40 min under microwave irradiation. The reaction mixture was loaded onto a methanol-conditioned SCX-2 cartridge (10 g), then washed with methanol, and eluted with 3.5N methanolic ammonia. The solvent was removed in vacuo and purification by automated flash column chromatography (CombiFlash Rf, 24 g RediSep™ silica cartridge) eluting with a gradient of 0-15% 2.33N methanolic ammonia in dichloromethane afforded the desired product as a colourless gum (115 mg, 0.48 mmol, 37%). The two product batches were combined and used in the subsequent steps.

LC/MS ($C_{10}H_{15}N_3O_2S$) 242 $[M+H]^+$; RT 0.34 (LCMS-V-B1)

$^1$H NMR (400 MHz, DMSO-$d_6$) δ 8.84 (s, 1H), 8.57 (s, 1H), 7.83 (q, J=4.8 Hz, 1H), 4.76 (p, J=8.8 Hz, 1H), 4.32-4.17 (m, 4H), 3.95 (q, J=8.0 Hz, 2H), 2.82 (d, J=4.7 Hz, 3H), 1.28 (t, J=7.1 Hz, 3H).

Step F: ethyl 2-{[(tert-butoxy)carbonyl](methyl) amino}-5-{1-[(tert-butoxy)carbonyl]azetidin-3-yl}-1,3-thiazole-4-carboxylate To a solution of the product of Step E (298 mg, 1.23 mmol, 1 eq) in dichloromethane (10 mL) was added di-tert-butyl dicarbonate (809 mg, 3.7 mmol, 3 eq), 4-(dimethylamino)pyridine (45.3 mg, 0.37 mmol, 0.3 eq) and triethylamine (0.51 mL, 3.7 mmol, 3 eq) and the mixture was stirred at ambient temperature overnight. The reaction was partitioned between dichloromethane and water, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-40% ethyl acetate in iso-heptane afforded the desired product as a white foam (390 mg, 0.88 mmol, 72%).

LC/MS ($C_{20}H_{31}N_3O_6S$) 442 $[M+H]^+$; RT 1.47 (LCMS-V-B1)

$^1H$ NMR (400 MHz, DMSO-$d_6$) δ 4.53 (tt, J=8.6, 5.8 Hz, 1H), 4.38-4.30 (m, 2H), 4.27 (q, 4H), 3.85-3.76 (m, 2H), 3.45 (s, 3H), 1.54 (s, 9H), 1.40 (s, 9H), 1.30 (t, J=7.1 Hz, 3H).

Step G: ethyl 5-{1-[(tert-butoxy)carbonyl]azetidin-3-yl}-2-(methylamino)-1,3-thiazole-4-carboxylate A solution of the product from Step F (390 mg, 0.88 mmol, 1 eq) in 1,1,1,3,3,3-hexafluoro-2-propanol (3 mL) was heated at 100° C. for 55 min under microwave irradiation. The mixture was concentrated in vacuo and purification by automated flash column chromatography (CombiFlash Rf, 12 g RediSep™ silica cartridge) eluting with a gradient of 0-100% ethyl acetate in iso-heptane afforded the desired product as a white solid (199 mg, 0.58 mmol, 66%).

LC/MS ($C_{15}H_{23}N_3O_4S$) 342 $[M+H]^+$; RT 0.98 (LCMS-V-B1)

$^1H$ NMR (400 MHz, DMSO-$d_6$) δ 7.70 (q, J=4.7 Hz, 1H), 4.49 (tt, J=8.6, 5.9 Hz, 1H), 4.28 (t, J=8.6 Hz, 2H), 4.21 (q, J=7.1 Hz, 2H), 3.73-3.65 (m, 2H), 2.81 (d, J=4.7 Hz, 3H), 1.39 (s, 9H), 1.26 (t, J=7.1 Hz, 3H).

Preparation 3zc: Methyl 5-(3-{4-[3-(dimethylamino)prop-1-yn-1-yl]-2-fluorophenoxy}-2,2-dimethylpropyl)-2-(methylamino)-1,3-thiazole-4-carboxylate Step A: 4-methoxy-2,2-dimethyl-4-oxobutanoic acid To a solution of 2,2-dimethylsuccinic acid (20 g, 137 mmol, 1 eq) in methanol (200 mL), cooled to 0° C., was added sulfuric acid (2 mL) and the mixture was stirred at ambient temperature overnight. The reaction was concentrated in vacuo then quenched by portionwise addition or saturated aqueous sodium bicarbonate (200 mL) and washed with iso-heptane (×2). The aqueous phase was cooled to 0° C., acidified with 6N aqueous hydrochloric acid, and extracted with diethyl ether (×2). The combined organic extracts were dried (magnesium sulfate), and concentrated in vacuo to afford the desired product as a clear oil (13.7 g, 85.4 mmol, 62%).

$^1H$ NMR (400 MHz, Chloroform-d) δ 3.67 (s, 3H), 2.62 (s, 2H), 1.30 (s, 6H).

Step B: methyl 4-hydroxy-3,3-dimethylbutanoate

A solution of the product from Step A (13.7 g, 85.4 mmol, 1 eq) in tetrahydrofuran (140 mL) was cooled to −30° C. and borane dimethyl sulfide complex (13 g, 16.2 mL, 171 mmol, 2 eq) was added dropwise. The mixture was stirred at −30° C. for 1.5 h, then warmed to 0° C. and stirred at this temperature for 45 min. The reaction was quenched by the slow addition of methanol (50 mL), then concentrated in vacuo. Purification by automated flash column chromatography (CombiFlash Rf, 220 g RediSep™ silica cartridge) eluting with a gradient of 0-50% ethyl acetate in iso-heptane afforded the desired product as a clear oil (8.14 g, 55.7 mmol, 65%).

$^1H$ NMR (400 MHz, DMSO-$d_6$) δ 4.65 (t, J=5.4 Hz, 1H), 3.57 (s, 3H), 3.15 (d, J=5.4 Hz, 2H), 2.19 (s, 2H), 0.89 (s, 6H).

Step C: methyl 4-[(tert-butyldiphenylsilyl)oxy]-3-3,3-dimethylbutonoate

To a solution of the product from Step B (8.14 g, 55.7 mmol, 1 eq) in dimethylformamide (200 mL) was added tert-butyl(chloro)diphenylsilane (17.4 mL, 66.8 mmol, 1.2 eq) and imidazole (7.36 mL, 111 mmol, 2 eq) and the mixture was stirred at ambient temperature overnight. The reaction was partitioned between heptane (500 mL) and 2:1 water/saturated aqueous ammonium chloride (500 mL), and the aqueous phase was extracted with heptane (500 mL). The combined organic extracts were dried (magnesium sulfate) and purification by automated flash column chromatography (CombiFlash Rf, 330 g RediSep™ silica cartridge) eluting with a gradient of 0-10% ethyl acetate in iso-heptane afforded the desired product as a clear oil (14.4 g, 37.4 mmol, 67%).

$^1H$ NMR (400 MHz, DMSO-$d_6$) δ 7.65-7.58 (m, 4H), 7.53-7.40 (m, 6H), 3.56 (s, 3H), 3.41 (s, 2H), 2.33 (s, 2H), 1.01 (s, 9H), 0.97 (s, 6H).

Step D: 4-[(tert-butyldiphenylsilyl)oxy]-3,3-dimethylbutan-1-ol

A solution of the product from Step C (14.4 g, 37.4 mmol, 1 eq) in tetrahydrofuran (70 mL) was cooled to −78° C. and diisobutyl aluminum hydride (1M in tetrahydrofuran; 112 mL, 112 mmol, 3 eq) was added and the mixture was stirred at −78° C. for 2 h. Saturated aqueous ammonium chloride was added and the mixture stirred at −78° C. for 10 min, then allowed to warm to ambient temperature. The mixture was filtered through a pad of celite eluting with ethyl acetate, and the organics were dried (magnesium sulfate) and concentrated in vacuo. Purification by automated flash column chromatography (CombiFlash Rf, 220 g RediSep™ silica cartridge) eluting with a gradient of 0-15% ethyl acetate in iso-heptane afforded the desired product as a clear oil (12.5 g, 35 mmol, 94%).

LC/MS ($C_{22}H_{32}O_2Si$) 357 $[M+H]^+$; RT 2.68 (LCMS-V-C)

$^1H$ NMR (400 MHz, DMSO-$d_6$) δ 7.65-7.56 (m, 4H), 7.53-7.40 (m, 6H), 4.28 (t, J=5.0 Hz, 1H), 3.50-3.41 (m, 2H), 3.30 (s, 2H), 1.48 (dd, J=8.1, 7.1 Hz, 2H), 1.02 (s, 9H), 0.88 (s, 6H).

Step E: 4-[(tert-butyldiphenylsilyl)oxy]-3,3-dimethylbutyl methanesulfonate

To a stirred solution of the product from Step D (12.5 g, 35 mmol, 1 eq) in dichloromethane (200 mL), cooled to 0° C., was added triethylamine (7.31 mL, 52.5 mmol, 1.5 eq) and methanesulfonyl chloride (3.25 mL, 42 mmol, 1.2 eq) and the mixture was stirred at ambient temperature overnight. The reaction was diluted with dichloromethane, washed with saturated aqueous sodium bicarbonate, dried (PTFE phase separator), and concentrated in vacuo to afford the desired product as a yellow oil (15.1 g, 34.8 mmol, 99%).

$^1H$ NMR (400 MHz, DMSO-$d_6$) δ 7.66-7.58 (m, 4H), 7.53-7.40 (m, 6H), 4.27 (t, J=7.4 Hz, 2H), 3.33 (s, 2H), 3.15 (s, 3H), 1.74 (t, J=7.4 Hz, 2H), 1.02 (s, 9H), 0.92 (s, 6H).

Step F: (4-bromo-2,2-dimethylbutoxy)(tert-butyl)diphenylsilane

To a solution of the product from Step E (15.1 g, 34.8 mmol, 1 eq) in tetrahydrofuran (400 mL) was added lithium bromide (9.07 g, 105 mmol, 3 eq) portionwise and the mixture stirred at 70° C. for 4 h, then allowed to cool to ambient temperature. The reaction was concentrated in vacuo then partitioned between dichloromethane and brine, and the organic phase was washed with 10% aqueous sodium thiosulfate, dried (PTFE phase separator), and concentrated in vacuo. Purification by automated flash column chromatography (CombiFlash Rf, 220 g RediSep™ silica cartridge) eluting with a gradient of 0-2% ethyl acetate in iso-heptane afforded the desired product as a clear oil (12.8 g, 30.5 mmol, 88%).

$^1H$ NMR (400 MHz, DMSO-$d_6$) δ 7.65-7.55 (m, 4H), 7.53-7.40 (m, 6H), 3.52-3.42 (m, 2H), 3.34 (s, 2H), 1.96-1.86 (m, 2H), 1.03 (s, 9H), 0.88 (s, 6H).

Step G: ethyl 6-[(tert-butyldiphenylsilyl)oxy]-5,5-dimethyl-2-oxohexanoate

To an oven-dried flask was added magnesium (496 mg, 20.4 mmol, 1.2 eq) and this was stirred vigorously under nitrogen for 20 min. A solution of the product from Step F (7.13 g, 17 mmol, 1 eq) in tetrahydrofuran (12 mL) was sparged with nitrogen (10 min) and a portion of this solution was added to the magnesium (without stirring). The mixture was briefly heated to reflux (heat-gun) and a crystal of iodine was added. Stirring was initiated, and the remaining solution was added to the magnesium suspension at such a rate as to maintain gentle reflux. After complete addition the mixture was heated at reflux for 2 h, then allowed to cool to ambient temperature. A stirred solution of diethyl oxalate (2.31 mL, 17 mmol, 1 eq) in tetrahydrofuran (6 mL) was sparged with nitrogen (10 min) then cooled to −78° C. To this was added the above Grignard reagent solution portionwise, then the mixture was allowed to gradually warm to ambient temperature over 2 h. The reaction partitioned between ethyl acetate and saturated aqueous ammonium chloride, and the organic phase was dried (magnesium sulfate) and concentrated in vacuo. Purification by automated flash column chromatography (CombiFlash Rf, 220 g RediSep™ silica cartridge) eluting with a gradient of 0-8% ethyl acetate in iso-heptane afforded the desired product as a clear oil (3.06 g, 6.95 mmol, 41%).

$^1H$ NMR (400 MHz, Chloroform-d) δ 7.67-7.61 (m, 4H), 7.45-7.34 (m, 6H), 4.31 (q, J=7.0 Hz, 2H), 3.31 (s, 2H), 2.80-2.71 (m, 2H), 1.67-1.58 (m, 2H), 1.36 (s, 3H), 1.05 (s, 9H), 0.88 (s, 6H).

Step GH: ethyl 3-bromo-6-[(tert-butyldiphenylsilyl)oxy]-5,5-dimethyl-2-oxohexanoate To a stirred mixture of copper(II) bromide (3.1 g, 13.9 mmol, 2 eq) in ethyl acetate (80 mL) was added portionwise a solution of the product from Step G (3.06 g, 6.94 mmol, 1 eq) in chloroform (40 mL) and the reaction was heated at reflux for 16 h. The reaction mixture was allowed to cool to ambient temperature then filtered through a pad of celite, eluted with dichloromethane, and evaporated. Purification by automated flash column chromatography (CombiFlash Rf, 80 g RediSep™ silica cartridge) eluting with a gradient of 0-10% ethyl acetate in iso-heptane afforded the desired product as a clear oil (2.62 g, 5.04 mmol, 72%).

LC/MS ($C_{26}H_{35}BrO_4Si$) 441 $[M-Ph]^+$; RT 1.36 (LCMS-V-B2)

$^1H$ NMR (400 MHz, Chloroform-d) δ 7.69-7.61 (m, 4H), 7.50-7.34 (m, 6H), 5.28 (dd, J=8.4, 4.5 Hz, 1H), 4.36 (qd, J=7.1, 1.4 Hz, 2H), 3.33 (d, J=1.5 Hz, 2H), 2.56 (dd, J=14.9, 8.5 Hz, 1H), 2.11 (dd, J=14.9, 4.5 Hz, 1H), 1.38 (t, J=7.1 Hz, 3H), 1.07 (s, 9H), 0.88 (d, J=3.7 Hz, 6H).

Step H: ethyl 5-{3-[(tert-butyldiphenylsilyl)oxy]-2,2-dimethylpropyl}-2-(methylamino)-1,3-thiazole-4-carboxylate To a solution of the product from Step GH (2.62 g, 5.04 mmol, 1 eq) in ethanol (35 mL) was added N-methylthiourea (455 mg, 5.04 mmol, 1 eq) and triethylamine (1.4 mL, 10.1 mmol, 2 eq) and the mixture was heated at 85° C. for 4 h, then allowed to cool to ambient temperature. The reaction was partitioned between dichloromethane and brine, and the organic phase was dried (PTFE phase separator) and concentrated in vacuo. Purification by automated flash column chromatography (CombiFlash Rf, 80 g RediSep™ silica cartridge) eluting with a gradient of 0-50% ethyl acetate in iso-heptane afforded the desired product as a yellow solid (1.45 g, 2.84 mmol, 56%).

LC/MS ($C_{28}H_{38}N_2O_3SiS$) 511 $[M+H]^+$; RT 1.28 (LCMS-V-B2)

$^1H$ NMR (400 MHz, DMSO-$d_6$) δ 7.66-7.58 (m, 4H), 7.52-7.40 (m, 6H), 4.15 (q, J=7.1 Hz, 2H), 3.37 (s, 2H), 3.08 (s, 2H), 2.77 (d, J=4.8 Hz, 3H), 1.20 (t, 3H), 1.04 (s, 9H), 0.86 (s, 6H).

Step I: ethyl 2-{[(tert-butoxy)carbonyl](methyl)amino}-5-{3-[(tert-butyldiphenylsilyl)oxy]-2,2-dimethylpropyl}-1,3-thiazole-4-carboxylate To a solution of the product from Step H (1 g 1.96 mmol, 1 eq) in tetrahydrofuran (20 mL) was added 4-(dimethylamino)pyridine (23.9 mg, 0.2 mmol, 0.1 eq), triethylamine (0.82 mL, 5.87 mmol, 3 eq) and di-tert-butyl dicarbonate (0.84 mL, 3.92 mmol, 2 eq) and the mixture was stirred at ambient temperature for 3 h. The reaction was partitioned between ethyl acetate and water, and the organic phase was dried (magnesium sulfate), and concentrated in vacuo. Purification by automated flash column chromatography (CombiFlash Rf, 24 g RediSep™ silica cartridge) eluting with a gradient of 0-15% ethyl acetate in iso-heptane afforded the desired product as a yellow oil (1.19 g, 1.95 mmol, 100%).

LC/MS ($C_{33}H_{46}N_2O_5SiS$) 611 $[M+H]^+$; RT 1.48 (LCMS-V-B2)

$^1H$ NMR (400 MHz, DMSO-$d_6$) δ 7.68-7.60 (m, 4H), 7.52-7.39 (m, 6H), 4.22 (q, J=7.1 Hz, 2H), 3.44 (s, 3H), 3.37 (s, 2H), 3.20 (s, 2H), 1.54 (s, 9H), 1.23 (t, 3H), 1.04 (s, 9H), 0.87 (s, 6H).

Step J: 2-{[(tert-butoxy)carbonyl](methyl)amino}-5-(3-hydroxy-2,2-dimethylpropyl)-1,3-thiazole-4-carboxylic acid To a solution of the product from Step I (600 mg, 0.98 mmol, 1 eq) in tetrahydrofuran (12 mL) was added TBAF (1M in tetrahydrofuran; 2.95 mL, 2.95 mmol, 3 eq) and the mixture was stirred at ambient temperature for 2 h. The reaction was partitioned between ethyl acetate and water, and the organic phase was dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as a white solid (178 mg, 0.52 mmol, 53%).

LC/MS ($C_{15}H_{24}N_2O_5S$) 345 $[M+H]^+$; RT 1.87 (LCMS-V-C)

$^1H$ NMR (400 MHz, DMSO-$d_6$) δ 12.69 (br s, 1H), 4.72 (br s, 1H), 3.34 (s, 3H), 3.16 (s, 2H), 3.10 (s, 2H), 1.53 (s, 9H), 0.83 (s, 6H).

Step K: methyl 2-{[(tert-butoxy)carbonyl](methyl)amino}-5-(3-hydroxy-2,2-dimethylpropyl)-1,3-thiazole-4-carboxylate To a solution of the product from Step J (178 mg, 0.52 mmol, 1 eq) in 1:1 dichloromethane/methanol (4 mL), cooled to 0° C., was added (trimethylsilyl)diazomethane (2M in hexanes; 0.31 mL, 0.62 mmol, 1.2 eq) and the mixture was stirred at ambient temperature overnight. The reaction was partitioned between dichloromethane and water, and the organic phase was dried (PTFE phase separator) and concentrated in vacuo. Purification by automated flash column chromatography (CombiFlash Rf, 4 g RediSep™ silica cartridge) eluting with a gradient of 0-50% ethyl acetate in iso-heptane afforded the desired product as a white solid (119 mg, 0.33 mmol, 64%).

LC/MS ($C_{16}H_{26}N_2O_5S$) 359 $[M+H]^+$; RT 2.10 (LCMS-V-C)

$^1H$ NMR (400 MHz, DMSO-$d_6$) δ 4.74 (t, J=5.1 Hz, 1H), 3.78 (s, 3H), 3.43 (s, 3H), 3.16 (d, J=5.2 Hz, 2H), 3.10 (s, 2H), 1.53 (s, 9H), 0.82 (s, 6H).

Step L: methyl 2-{[(tert-butoxy)carbonyl](methyl)amino}-5-[3-(2-fluoro-4-iodophenoxy)-2,2-dimethylpropyl]-1,3-thiazole-4-carboxylate To a solution of the product from Step K (119 mg, 0.33 mmol, 1 eq) in toluene (2 mL) was added 2-fluoro-4-iodophenol (158 mg, 0.66 mmol, 2 eq), triphenylphosphine (174 mg, 0.66 mmol, 2 eq) and diisopropylazodicarboxylate (131 µL, 0.66 mmol, 2 eq) and the mixture was heated at 120° C. for 24 h. The reaction was partitioned between dichloromethane and water, and the organic phase was dried (PTFE phase separator) and concentrated in vacuo. Purification by automated flash column chromatography (CombiFlash Rf, 4 g RediSep™ silica cartridge) eluting with a gradient of 0-20% ethyl acetate in iso-heptane afforded the desired product as a clear gum (136 mg, 0.24 mmol, 71%).

LC/MS ($C_{22}H_{28}FIN_2O_5S$) 579 $[M+H]^+$; RT 2.76 (LCMS-V-C)

$^1H$ NMR (400 MHz, DMSO-$d_6$) δ 7.60 (dd, J=10.7, 2.1 Hz, 1H), 7.49-7.42 (m, 1H), 3.75 (s, 5H), 3.42 (s, 3H), 3.26 (s, 2H), 1.49 (s, 9H), 1.01 (s, 6H).

Step M: methyl 2-{[(tert-butoxy)carbonyl](methyl)amino}-5-(3-{4-[3-(dimethylamino)prop-1-yn-1-yl]-2-fluorophenoxy}-2,2-dimethylpropyl)-1,3-thiazole-4-carboxylate To a solution of the product from Step L (136 mg, 0.24 mmol, 1 eq) in tetrahydrofuran (6 mL) was added 3-dimethylamino-1-propyne (38.1 µL, 0.35 mmol, 1.5 eq), copper (I) iodide (4.48 mg, 0.02 mmol, 0.1 eq) and N,N-diisopropylethylamine (81.9 µL, 0.47 mmol, 2 eq). The mixture was sparged with nitrogen (10 min) then bis(triphenylphosphine) palladium(II) dichloride (16.5 mg, 0.02 mmol, 0.1 eq) was added and the mixture was heated at 70° C. overnight. The reaction was partitioned between ethyl acetate and brine, and the organic phase was dried (magnesium sulfate) and concentrated in vacuo. Purification by automated flash column chromatography (CombiFlash Rf, 4 g RediSep™ silica cartridge) eluting with a gradient of 0-4% methanol in dichloromethane afforded the desired product as a brown gum (27 mg, 0.05 mmol, 22%).

LC/MS ($C_{27}H_{36}FN_3O_5S$) 534 $[M+H]^+$; RT 2.053 (LCMS-V-C)

$^1H$ NMR (400 MHz, DMSO-$d_6$) δ 7.31 (dd, J=11.9, 2.0 Hz, 1H), 7.25-7.18 (m, 1H), 7.13 (t, J=8.7 Hz, 1H), 3.78 (s, 2H), 3.75 (s, 3H), 3.43 (s, 2H), 3.42 (s, 3H), 3.27 (s, 2H), 2.24 (s, 6H), (s, 9H), 1.02 (s, 6H).

Step N: methyl 5-(3-{4-[3-(dimethylamino)prop-1-yn-1-yl]-2-fluorophenoxy}-2,2-dimethylpropyl)-2-(methylamino)-1,3-thiazole-4-carboxylate To a solution of the product from Step M (27 mg, 0.05 mmol, 1 eq) in dichloromethane (5 mL) was added trifluoroacetic acid (1 mL) and the mixture was stirred at ambient temperature for 2 h. The reaction was diluted with dichloromethane, then cooled to 0° C. and neutralised by the addition of 2N aqueous sodium hydroxide. The layers were separated and dried (PTFE phase separator) and concentrated in vacuo. Purification by automated flash column chromatography (CombiFlash Rf, 4 g RediSep™ silica cartridge) eluting with a gradient of 0-7% methanol in dichloromethane afforded the desired product as a brown solid (8 mg, 0.02 mmol, 37%).

LC/MS ($C_{22}H_{28}FN_3O_3S$) 434 $[M+H]^+$; RT 1.62 (LCMS-V-C)

$^1H$ NMR (400 MHz, DMSO-$d_6$) δ 7.52-7.46 (m, 1H), 7.32 (dd, J=11.8, 2.0 Hz, 1H), 7.24-7.19 (m, 1H), 7.13 (t, J=8.7 Hz, 1H), 3.76 (s, 2H), 3.71 (s, 3H), 3.42 (s, 2H), 3.16 (s, 2H), 2.76 (d, J=4.8 Hz, 3H), 2.23 (s, 6H), 1.00 (s, 6H).

Preparation 3zd: Methyl 5-{[1-({4-[3-(dimethylamino)prop-1-yn-1-yl]-2-fluorophenoxy}methyl)cyclopropyl]methyl}-2-(methylamino)-1,3-thiazole-4-carboxylate Step A: 2-(1-{[(tert-butyldiphenylsilyl)oxy]methyl}cyclopropyl)acetonitrile To a solution of 2-[1-(hydroxymethyl)cyclopropyl]acetonitrile (8 g, 72 mmol, 1 eq) in dimethylformamide (200 mL) was added tert-butyl(chloro)diphenylsilane (22.5 mL, 86.4 mmol, 1.2 eq) and imidazole (9.51 mL, 144 mmol, 2 eq) and the mixture was stirred at ambient temperature overnight. The reaction was partitioned between iso-heptane (600 mL) and 2:1 water/saturated aqueous ammonium chloride (600 mL) and the aqueous phase was extracted with iso-heptane (600 mL). The combined organic extracts were dried (magnesium sulfate) and concentrated in vacuo. Purification by automated flash column chromatography (CombiFlash Rf, 330 g RediSep™ silica cartridge) eluting with a gradient of 0-6% ethyl acetate in iso-heptane afforded the desired product as a clear oil (23 g, 65.7 mmol, 91%).

$^1H$ NMR (400 MHz, DMSO-d6) δ 7.67-737 (m, 4H), 7.53-7.36 (m, 6H), 334 (s, 2H), 2.71 (s, 2H), 1.02 (s, 9H), 0.57-0.50 (m, 2H), 0.50-0.43 (m, 2H).

Step B: 2-(1-{[(tert-butyldiphenylsilyl)oxy]methyl}cyclopropyl)acetaldehyde

To a solution of the product from Step A (23 g, 65.7 mmol, 1 eq) in dichloromethane (300 mL), cooled to 0° C., was added diisobutyl aluminum hydride (1M in hexanes; 72.3 mL, 72.3 mmol, 1.1 eq) portionwise and the mixture was stirred at 0° C. for 1.5 h. The reaction was quenched by the addition of water, then 2N aqueous hydrochloric acid (100 mL) was added, followed by saturated aqueous potassium sodium tartrate (500 mL). The mixture was extracted with dichloromethane (2×400 mL), and the combined organic extracts were dried (magnesium sulfate) and concentrated in vacuo. Purification by automated flash column chromatography (CombiFlash Rf, 330 g RediSep™ silica cartridge) eluting with a gradient of 0-10% ethyl acetate in iso-heptane afforded the desired product as a clear oil (19.6 g, 55.5 mmol, 85%).

LC/MS ($C_{22}H_{28}O_2Si$) 353 $[M+H]^+$; RT 1.19 (LCMS-V-B2)

$^1H$ NMR (400 MHz, DMSO-$d_6$) δ 9.77 (t, J=2.5 Hz, 1H), 7.61-7.56 (m, 4H), 7.50-7.38 (m, 6H), 3.33 (s, 2H), 2.41 (d, J=23 Hz, 2H), 0.97 (s, 9H), 0.57-0.50 (m, 2H), 0.47-0.40 (m, 2H).

Step C: 2-(1-{[(tert-butyldiphenylsilyl)oxy]methyl}cyclopropyl)ethan-1-ol

To a solution of the product of Step B (19.6 g, 55.5 mmol, 1 eq) in methanol (200 mL), cooled to 0° C., was added sodium borohydride (2.31 g, 61.1 mmol, 1.1 eq) portionwise and the mixture was stirred at ambient temperature for 3 h. The reaction was concentrated in vacuo, then partitioned between ethyl acetate and water, and the organic phase was dried (magnesium sulfate) and concentrated in vacuo to afford the desired product as a clear oil (18.8 g, 53 mmol, 96%).

$^1H$ NMR (400 MHz, DMSO-$d_6$) δ 7.66-7.57 (m, 4H), 7.52-7.37 (m, 6H), 4.32 (t, J=5.1 Hz, 1H), 3.57-3.47 (m, 2H), 3.46 (s, 2H), 1.59 (t, J=7.3 Hz, 2H), 1.00 (s, 9H), 0.35-0.26 (m, 4H).

Step D: 2-(1-{[(tert-butyldiphenylsilyl)oxy]methyl}cyclopropyl)ethyl methanesulfonate To a solution of the product from Step C (18.8 g, 53 mmol, 1 eq) in dichloromethane (300 mL), cooled to 0° C., was added triethylamine (22.1 mL, 159 mmol, 3 eq) and methanesulfonyl chloride (4.92 mL, 63.6 mmol, 1.2 eq) and the mixture was stirred at ambient temperature overnight. The reaction was partitioned between dichloromethane and saturated aqueous sodium bicarbonate, and the organic phase was separated and dried (PTFE phase separator) and concentrated in vacuo to afford the desired product as a brown oil (23.3 g, 53 mmol, 100%).

$^1H$ NMR (400 MHz, DMSO-$d_6$) δ 7.67-7.56 (m, 4H), 7.53-7.37 (m, 6H), 4.31 (t, J=7.1 Hz, 2H), 3.48 (s, 2H), 3.13 (s, 3H), 1.84 (t, J=7.1 Hz, 2H), 1.01 (s, 9H), 0.49-0.38 (m, 2H), 0.36-0.29 (m, 2H).

Step E: {[1-(2-bromoethyl)cyclopropyl]methoxy}(tert-butyl)diphenylsilane

To a solution of the product from Step D (23.3 g, 53.9 mmol, 1 eq) in tetrahydrofuran (600 mL) was added lithium bromide (14 g, 162 mmol, 3 eq) and the mixture was heated at 70° C. for 5 h then allowed to cool to ambient temperature and the solvent removed in vacuo. The residue was partitioned between dichloromethane and brine, and the organic phase was washed with 10% aqueous sodium thiosulfate, dried (magnesium sulfate), and concentrated in vacuo. Purification by automated flash column chromatography (CombiFlash Rf, 330 g RediSep™ silica cartridge) eluting with a gradient of 0-2% diethyl ether in iso-heptane afforded the desired product as a clear oil (17.4 g, 41.6 mmol, 77%).

$^1H$ NMR (400 MHz, DMSO-$d_6$) δ 7.65-7.58 (m, 4H), 7.53-7.39 (m, 6H), 3.54 (dd, J=7.4 Hz, 2H), 3.47 (s, 2H), 1.98 (dd, J=8.6, 7.3 Hz, 2H), 1.02 (s, 9H), 0.46-0.38 (m, 2H), 0.35-0.28 (m, 2H).

Step F: ethyl 4-(1-{[(tert-butyldiphenylsilyl)oxy]methyl}cyclopropyl)-2-oxobutanoate To an oven-dried flask was added magnesium (1.21 g, 49.9 mmol, 1.2 eq) and this was vigorously stirred under nitrogen for 20 min. A solution of the product from Step E (17.4 g, 41.6 mmol, 1 eq) in tetrahydrofuran (30 mL) was sparged with nitrogen (10 min) then an aliquot of this solution was added to the magnesium (without stirring), the mixture was briefly heated at reflux and a crystal of iodine was added. Stirring was initiated and the remaining solution was added to the magnesium at such a rate as to maintain gentle reflux. After complete addition the mixture was heated at reflux for 2 h, then allowed to cool to ambient temperature. A solution of diethyl oxalate (5.64 mL, 41.6 mmol, 1 eq) in tetrahydrofuran (15 mL) was sparged with nitrogen (10 min) then cooled to −78° C. The above Grignard reagent solution was slowly added then the mixture was allowed to warm to ambient temperature over 2 h. The reaction was partitioned between ethyl acetate and saturated aqueous ammonium chloride, and the organic phase was dried (magnesium sulfate) and concentrated in vacuo. Purification by automated flash column chromatography (CombiFlash Rf, 330 g RediSep™ silica cartridge) eluting with a gradient of 0-8% ethyl acetate in iso-heptane afforded the desired product as a clear oil (10 g, 22.8 mmol, 55%).

$^1H$ NMR (400 MHz, DMSO-$d_6$) δ 7.65-7.57 (m, 4H), 7.53-7.36 (m, 6H), 4.19 (q, J=24.7, 7.1 Hz, 2H), 3.45 (s, 2H), 2.89-2.80 (m, 2H), 1.67-1.59 (m, 2H), 1.33-1.17 (m, 5H), 1.05-0.96 (s, 11H).

Step G: ethyl 3-bromo-4-(1-{[(tert-butyldiphenylsilyl)oxy]methyl}cyclopropyl)-2-oxobutanoate A solution of the product from Step F (10 g, 22.8 mmol, 1 eq) in chloroform (125 mL) was added to copper(II) bromide (10.2 g, 45.6 mmol, 2 eq) in ethyl acetate (250 mL) and the mixture was heated at 85° C. overnight. The reaction was filtered through celite, eluted with dichloromethane, and concentrated in vacuo. Purification by automated flash column chromatography (CombiFlash Rf, 220 g RediSep™ silica cartridge) eluting with a gradient of 0-8% ethyl acetate in iso-heptane afforded the desired product as a yellow oil (2.09 g, 4.04 mmol, 18%).

$^1H$ NMR (400 MHz, DMSO-$d_6$) δ 7.68-7.59 (m, 4H), 7.53-7.40 (m, 6H), 5.52 (dd, J=8.9, 5.2 Hz, 1H) 4.28 (q, 2H), 3.68 (d, 1H), 3.37 (s, 1H), 2.44 (dd, J=15.2, 5.2 Hz, 1H), 2.02-1.88 (m, 1H), 1.26 (t, 3H), 1.03 (s, 9H), 0.62-0.53 (m, 1H), 0.48-0.39 (m, 1H), 0.39-0.32 (m, 1H), 0.32-0.23 (m, 1H).

Step H: ethyl 5-[(1-{[(tert-butyldiphenylsilyl)oxy]methyl}cyclopropyl)methyl]-2-(methylamino)-1,3-thiazole-4-carboxylate To a solution of the product from Step G (2.09 g, 4.04 mmol, 1 eq) in ethanol (30 mL) was added N-methylthiourea (364 mg, 4.04 mmol, 1 eq) and triethylamine (1.12 mL, 8.08 mmol, 2 eq) and the mixture was heated at 85° C. overnight. The reaction was partitioned between dichloromethane and brine, and the organic phase was dried (PTFE phase separator), and concentrated in vacuo. Purification by automated flash column chromatography (CombiFlash Rf, 40 g RediSep™ silica cartridge) eluting with a gradient of 0-50% ethyl acetate in iso-heptane afforded the desired product as an orange solid (1.8 g, 3.53 mmol, 88%).

LC/MS ($C_{28}H_{36}N_2O_3SiS$) 509 $[M+H]^+$; RT 2.69 (LCMS-V-C)

$^1H$ NMR (400 MHz, DMSO-$d_6$) δ 7.59-7.31 (m, 4H), 7.46-7.36 (m, 6H), 4.16 (q, J=7.1 Hz, 2H), 3.44 (s, 2H), 3.22 (s, 2H), 2.79 (d, J=4.8 Hz, 3H), 1.20 (t, 3H), 0.96 (s, 9H), 0.55-0.48 (m, 2H), 0.48-0.41 (m, 2H).

Step I: ethyl 2-{[(tert-butoxy)carbonyl](methyl)amino}-5-[(1-{[(tert-butyldiphenylsilyl)oxy]methyl}cyclopropyl)methyl]-1,3-thiazole-4-carboxylate To a solution of the product from Step H (1.8 g, 3.54 mmol, 1 eq) in tetrahydrofuran (40 mL) was added 4-(dimethylamino)pyridine (43.2 mg, 0.35 mmol, 0.1 eq), triethylamine (1.48 mL, 10.6 mmol, 3 eq) and di-tert-butyl dicarbonate (1.51 mL, 7.08 mmol, 2 eq) and the mixture was stirred at ambient temperature overnight. The reaction was partitioned between ethyl acetate and water, and the organic phase was dried (magnesium sulfate) and concentrated in vacuo. Purification by automated flash column chromatography (CombiFlash Rf, 40 g RediSep™ silica cartridge) eluting with a gradient of 0-15% ethyl acetate in iso-heptane afforded the desired product as a yellow oil (2.03 g, 3.33 mmol, 94%).

LC/MS ($C_{33}H_{44}N_2O_5SiS$) 609 $[M+H]^+$; RT 1.98 (LCMS-V-C)

$^1H$ NMR (400 MHz, DMSO-$d_6$) δ 7.56-7.48 (m, 4H), 7.46-7.34 (m, 6H), 4.23 (q, J=7.1 Hz, 2H), 3.48-3.42 (m, 5H), 3.32 (s, 2H), 1.53 (s, 9H), 1.24 (t, 3H), 0.94 (s, 9H), 0.62-0.55 (m, 1H), 0.55-0.46 (m, 1H).

Step J: 2-{[(tert-butoxy)carbonyl](methyl)amino}-5-{[1-(hydroxymethyl)cyclopropyl]methyl}-1,3-thiazole-4-carboxylic acid To a solution of the product from Step I (2.03 g, 3.33 mmol, 1 eq) in tetrahydrofuran (35 mL) was added tetrabutylammonium fluoride (1M in tetrahydrofuran; 10 mL, 10 mmol, 3 eq) and the mixture was stirred at 70° C. for 2.5 h. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a yellow solid (460 mg, 1.34 mmol, 40%).

LC/MS ($C_{15}H_{22}N_2O_5S$) 343 $[M+H]^+$; RT 1.77 (LCMS-V-C)

$^1H$ NMR (400 MHz, DMSO-$d_6$) δ 4.54 (br s, 1H), 3.44 (s, 3H), 3.22 (s, 2H), 3.19 (s, 2H), 1.53 (s, 9H), 0.50-0.42 (m, 4H).

Step K: methyl 2-{[(tert-butoxy)carbonyl](methyl)amino}-5-{[1-(hydroxymethyl)cyclopropyl]methyl}-1,3-thiazole-4-carboxylate To a solution of the product from Step J (460 mg, 1.34 mmol, 1 eq) in 1:1 dichloromethane/methanol (12 mL), cooled to 0° C., was added (trimethylsilyl)diazomethane (2M in hexanes; 0.87 mL 1.75 mmol, 1.3 eq) and the mixture was stirred at ambient temperature overnight. The reaction was partitioned between dichloromethane and water, and the organic phase was dried (PTFE phase separator) and concentrated in vacuo. Purification by automated flash column chromatography (CombiFlash Rf, 4 g RediSep™ silica cartridge) eluting with a gradient of 0-50% ethyl acetate in iso-heptane afforded the desired product as a white solid (418 mg, 1.17 mmol, 87%).

LC/MS ($C_{16}H_{24}N_2O_5S$) 357 $[M+H]^+$; RT 1.98 (LCMS-V-C)

$^1H$ NMR (400 MHz, DMSO-$d_6$) δ 4.54 (t, J=5.5 Hz, 1H), 3.78 (s, 3H), 3.44 (s, 3H), 3.22 (d, 2H), 3.20 (s, 2H), 1.53 (s, 9H), 0.51-0.44 (m, 4H).

Step L: methyl 2-{[(tert-butoxy)carbonyl](methyl)amino}-5-({1-[(2-fluoro-4-iodophenoxy)methyl]cyclopropyl}methyl)-1,3-thiazole-4-carboxylate To a solution of the product from Step K (418 mg, 1.17 mmol, 1 eq) in toluene (10 mL) was added 2-fluoro-4-iodophenol (558 mg, 2.35 mmol, 2 eq), triphenylphosphine (615 mg, 2.35 mmol, 2 eq) and diisopropylazodicarboxylate (0.46 mL, 2.35 mmol, 2 eq) and the mixture was heated at 120° C. overnight, then allowed to cool to ambient temperature. The reaction was partitioned between dichloromethane and water, and the organic phase was separated and dried (PTFE phase separator) and concentrated in vacuo. Purification by automated flash column chromatography (CombiFlash Rf, 12 g RediSep™ silica cartridge) eluting with a gradient of 0-20% ethyl acetate in iso-heptane afforded the desired product as a yellow oil (649 mg 1.13 mmol, 96%).

LC/MS ($C_{22}H_{26}FIN_2O_5S$) 577 $[M+H]^+$; RT 2.65 (LCMS-V-C)

$^1H$ NMR (400 MHz, DMSO-$d_6$) δ 7.56 (dd, J=10.8, 2.1 Hz, 1H), 7.39 (dt, J=8.6, 1.7 Hz, 1H), 6.84 (t, J=8.8 Hz, 1H), 3.75 (s, 3H), 3.42 (s, 3H), 3.34 (s, 2H), 3.31 (s, 2H), 1.52 (s, 9H), 0.77-0.64 (m, 4H).

Step M: methyl 2-{[(tert-butoxy)carbonyl](methyl)amino}-5-{[1-({4-[3-(dimethylamino)prop-1-yn-1-yl]-2-fluorophenoxy}methyl)cyclopropyl]methyl}-1,3-thiazole-4-carboxylate To a solution of the product from Step L (649 mg, 1.13 mmol, 1 eq) in tetrahydrofuran (12 mL) was added 3-dimethylamino-1-propyne (182 μL, 1.69 mmol, 1.5 eq), copper (I) iodide (21.4 mg, 0.11 mmol, 0.1 eq) and N,N-diisopropylethylamine (392 μL, 2.25 mmol, 2 eq). The mixture was sparged with nitrogen (10 min) then bis(triphenylphosphine)palladium(II) dichloride (79 mg, 0.11 mmol, 0.1 eq) was added and the mixture was heated at 80° C. for 24 h. The reaction was partitioned between ethyl acetate and brine, and the organic phase was dried (magnesium sulfate) and concentrated in vacuo. Purification by automated flash column chromatography (CombiFlash Rf, 24 g RediSep™ silica cartridge) eluting with a gradient of 0-7% methanol in dichloromethane afforded the desired product as a brown solid (173 mg, (1.33 mmol, 29%).

LC/MS ($C_{27}H_{34}FN_3O_5S$) 532 $[M+H]^+$; RT 2.004 (LCMS-V-C)

$^1H$ NMR (400 MHz, DMSO-d6) δ 7.27 (dd, J=11.9, 2.0 Hz, 1H), 7.18-7.10 (m, 1H), 6.99 (t, J=8.7 Hz, 1H), 3.79 (s, 2H), 3.65 (s, 3H), 3.42 (s, 5H), 3.32 (s, 2H), 2.23 (s, 6H), 1.52 (s, 9H), 0.77-0.65 (m, 4H).

Step N: methyl 5-{[1-({4-[3-(dimethylamino)prop-1-yn-1-yl]-2-fluorophenoxy}methyl)cyclopropyl]methyl}-2-(methylamino)-1,3-thiazole-4-carboxylate To a solution of the product from Step M (173 mg, 0.33 mmol, 1 eq) in dichloromethane (10 mL) was added trifluoroacetic acid (2 mL) and the mixture was stirred at ambient temperature for 2 h. The reaction was diluted with dichloromethane, then cooled to 0° C. and neutralised by the addition of 2N aqueous sodium hydroxide. The organic phase was separated and dried (PTFE phase separator) and concentrated in vacuo. Purification by automated flash column chromatography (CombiFlash Rf, 4 g RediSep™ silica cartridge) eluting with a gradient of 0-7% methanol in dichloromethane afforded the desired product as a yellow solid (84 mg, 19 mmol, 60%).

LC/MS ($C_{22}H_{26}FN_3O_3S$) 432 $[M+H]^+$; RT 1.55 (LCMS-V-C)

$^1$H NMR (400 MHz, DMSO-$d_6$) δ 7.51 (q, J=4.7 Hz, 1H), 7.28 (dd, J=11.9, 2.0 Hz, 1H), 7.19-7.12 (m, 1H), 7.01 (t, J=8.7 Hz, 1H), 3.78 (s, 2H), 3.60 (s, 3H), 3.42 (s, 2H), 3.20 (s, 2H), 2.78 (d, J=4.7 Hz, 3H), 2.23 (s, 6H), 0.69-0.60 (m, 4H).

Preparation 3ze: Ethyl 2-{[4-(tert-butoxy)-4-oxobutyl]amino}-1,3-thiazole-4-carboxylate Step A: ethyl 2-{[4-(tert-butoxy)-4-oxobutyl][(tert-butoxy)carbonyl]amino}-1,3-thiazole-4-carboxylate To a solution of ethyl 2-[(tert-butoxycarbonyl)amino]-1,3-thiazole-4-carboxylate (5.2 g, 19.1 mmol, 1 eq) and tert-butyl 4-hydroxybutanoate (4.59 g, 28.6 mmol, 1.5 eq) in tetrahydrofuran (150 mL) was added triphenylphosphine (7.51 g, 28.6 mmol, 1.5 eq), followed by dropwise addition of diisopropylazodicarboxylate (5.64 mL, 28.6 mmol, 1.5 eq) and the mixture was stirred at ambient temperature for 1 h. The reaction was partitioned between ethyl acetate and water, the aqueous phase was extracted with ethyl acetate (3×60 mL), and the combined organic extracts were washed with brine (100 mL), dried (magnesium sulfate), and concentrated in vacuo. Purification by automated flash column chromatography (CombiFlash Rf, 120 g RediSep™ silica cartridge) eluting with a gradient of 0-20% ethyl acetate in iso-heptane afforded the desired product as a colourless oil (7.7 g, 18.6 mmol, 97%).

LC/MS ($C_{19}H_{30}N_2O_6S$) 415 $[M+H]^+$; RT 1.49 (LCMS-V-B1)

$^1$H NMR (400 MHz, DMSO-$d_6$) δ 8.07 (s, 1H), 4.27 (q, J=7.1 Hz, 2H), 4.12-4.02 (m, 2H), 2.26 (t, J=7.2 Hz, 2H), 1.90 (p, J=7.1 Hz, 2H), 1.54 (s, 9H), 1.37 (s, 9H), 1.30 (t, J=7.1 Hz, 3H).

Step B: ethyl 2-{[4-(tert-butoxy)-4-oxobutyl]amino}-1,3-thiazole-4-carboxylate

A solution of the product from Step A (7.7 g, 18.6 mmol, 1 eq) in 1,1,1,3,3,3-hexafluoro-2-propanol (40 mL) was heated in a sealed flask at 80° C. for 7 h. The reaction was concentrated is vacuo and purification by automated flash column chromatography (CombiFlash Rf, 80 g RediSep™ silica cartridge) eluting with a gradient of 0-35% ethyl acetate in iso-heptane afforded the desired product as a white solid (3.61 g, 11.5 mmol, 62%).

LC/MS ($C_{14}H_{22}N_2O_4S$) 315 $[M+H]^+$; RT 1.20 (LCMS-V-B1)

$^1$H NMR (400 MHz, DMSO-$d_6$) δ 7.82 (t, J=5.4 Hz, 1H), 7.50 (s, 1H), 4.21 (q, J=7.1 Hz, 2H), 3.22 (td, J=7.0, 5.4 Hz, 2H), 2.29 (t, J=7.4 Hz, 2H), 1.76 (p, J=7.2 Hz, 2H), 1.40 (s, 9H) 1.26 (t, J=7.1 Hz, 3H).

Preparation 3zf: Ethyl 5-[(2S)-3-{4-[3-(dimethylamino)prop-1-yn-1-yl]-2-fluorophenoxy}-2-methylpropyl]-2-(methylamino)-1,3-thiazole-4-carboxylate Step A: [(2R)-3-bromo-2-methylpropoxy](tert-butyl)diphenylsilane To a solution of (R)-(−)-3-bromo-2-methyl-1-propanol (5 g, 32.68 mmol, 1 eq) in dimethylformamide (120 mL) was added imidazole (4.32 mL, 65.4 mmol, 2 eq) and tert-butyl(chloro)diphenylsilane (11.1 mL, 42.5 mmol, 1.3 eq) and the mixture was stirred at ambient temperature overnight. The reaction was partitioned between iso-heptane (300 mL) and 2:1 water/saturated aqueous ammonium chloride (200 mL), the aqueous phase was extracted with iso-heptane (200 mL), and the combined organic extracts were dried (magnesium sulfate) and concentrated in vacuo. Purification by automated flash column chromatography (CombiFlash Rf, 220 g RediSep™ silica cartridge) eluting with a gradient of 0-2% diethyl ether in iso-heptane afforded the desired product as a clear oil (12.1 g, 309 mmol, 95%).

$^1$H NMR (400 MHz, DMSO-d6) δ 7.67-7.59 (m, 4H), 7.53-7.40 (m, 6H), 3.63 (d, 2H), 3.61-3.54 (m, 2H), 2.10-1.98 (m, 1H), 1.01 (s, 9H), 0.96 (d, 3H).

Step B: (3S)-4-[(tert-butyldiphenylsilyl)oxy]-3-methylbutanenitrile

To a solution of the product from Step A (12.1 g, 30.9 mmol, 1 eq) in dimethylsulfoxide (120 mL) was added sodium cyanide (4.54 g, 92.7 mmol, 3 eq) and the mixture was heated at 120° C. for 5 h. The reaction was partitioned between diethyl ether and water and the organic phase was dried (magnesium sulfate) and concentrated in vacuo. Purification by automated flash column chromatography (CombiFlash Rf, 220 g RediSep™ silica cartridge) eluting with a gradient of 0-3% ethyl acetate in iso-heptane afforded the desired product as a clear oil (7.17 g, 21.2 mmol, 69%).

$^1$H NMR (400 MHz, DMSO-d6) δ 7.67-7.57 (m, 4H), 7.55-7.40 (m, 6H), 3.62-3.46 (m, 2H), 2.68-2.53 (m, 2H), 2.12-1.96 (m, 1H), 1.02 (m, 9H), 0.98 (d, 3H).

Step C: (3S)-4-[(tert-butyldiphenylsilyl)oxy]-3-methylbutanal

To a solution of the product from Step B (7.17 g, 21.2 mmol, 1 eq) in dichloromethane (100 mL), cooled to 0° C., was added diisobutylaluminum hydride (23.4 mL, 23.4 mmol, 1.1 eq) and the mixture was stirred overnight. Water was added, followed by 2N aqueous hydrochloric acid (36 mL) and saturated aqueous potassium sodium tartrate (180 mL). The mixture was diluted with further water and dichloromethane and the organic phase washed successively with water and brine, dried (PTFE phase separator), and concentrated in vacuo. Purification by automated flash column chromatography (CombiFlash Rf, 220 g RediSep™ silica cartridge) eluting with a gradient of 0-6% ethyl acetate in iso-heptane afforded the desired product as a clear oil (6.21 g, 18.2 mmol, 86%).

$^1$H NMR (400 MHz, DMSO-d6) δ 9.70 (t, J=1.9 Hz, 1H), 7.66-7.57 (m, 4H), 7.53-7.40 (m, 6H), 3.56-3.42 (m, 2H), 2.57-2.44 (m, 1H), 2.37-2.20 (m, 2H), 0.99 (s, 9H), 0.90 (d, J=6.0 Hz, 3H).

Step D: (3S)-4-[(tert-butyldiphenylsilyl)oxy]-3-methylbutan-1-ol

To a solution of the product of Step C (6.21 g, 18.24 mmol, 1 eq) in methanol (80 mL), cooled in an ice-water bath, was added sodium borohydride (759 mg, 20.1 mmol, 1.1 eq) and the mixture was allowed to warm to ambient temperature and stir for 3 h. The reaction was concentrated in vacuo, then partitioned between ethyl acetate and water, and the organic phase was dried (magnesium sulfate) and concentrated in vacuo to afford the desired product as a clear oil (6.36 g, 18.6 mmol, >100%).

$^1$H NMR (400 MHz, DMSO-d6) δ 7.66-7.56 (m, 4H), 7.52-7.39 (m, 6H), 4.35 (t, J=5.1 Hz, 1H), 3.56-3.34 (m, 4H), 1.85-1.70 (m, 1H), 1.65-1.51 (m, 1H), 1.31-1.21 (m, 1H), 1.01 (s, 9H), 0.91 (d, J=6.7 Hz, 3H).

Step E: (3S)-4-[(tert-butyldiphenylsilyl)oxy]-3-methylbutyl methanesulfonate

To a cooled solution of the product of Step D (6.36 g, 18.6 mmol, 1 eq) in dichloromethane (100 mL) was added triethylamine (7.75 mL, 55.7 mmol, 3 eq) and methanesulfonyl chloride (1.72 mL, 22.3 mmol, 1.2 eq) and the mixture was stirred at ambient temperature overnight. The reaction was partitioned between dichloromethane and saturated aqueous sodium bicarbonate, and the organic phase was separated and dried (PTFE phase separator) and concentrated in vacuo to afford the desired product as a brown oil (8.28 g, 19.7 mmol, >100%).

$^1$H NMR (400 MHz, DMSO-d6) δ 7.66-7.58 (m, 4H), 7.53-7.40 (m, 6H), 4.25 (t, J=6.6 Hz, 2H), 3.56-3.46 (m, 2H), 3.15 (s, 3H), 1.95-1.76 (m, 2H), 1.59-1.46 (m, 1H), 1.01 (s, 9H), 0.93 (d, J=6.7 Hz, 3H).

Step F: [(2S)-4-bromo-2-methylbutoxy](tert-butyl)diphenylsilane

To a solution of the product from Step E (8.28 g, 19.7 mmol, 1 eq) in tetrahydrofuran (180 mL) was added lithium bromide (5.13 g, 59.1 mmol, 3 eq) and the mixture was heated at 70° C. for 5 h. The reaction was concentrated in vacuo, the residue was partitioned between dichloromethane and brine, and the organic phase was separated and dried (PTFE phase separator) and concentrated in vacuo. Purification by automated flash column chromatography (CombiFlash Rf, 120 g RediSep™ silica cartridge) eluting with a gradient of 0-2% diethyl ether in iso-heptane afforded the desired product as a clear oil (6.3 g, 15.5 mmol, 79%).

$^1$H NMR (400 MHz, DMSO-d6) δ 7.66-7.58 (m, 4H), 7.53-7.40 (m, 6H), 164-3.47 (m, 414), 2.08-1.93 (m, 1H), 1.92-1.79 (m, 1H), 1.74-1.60 (m, 1H), 1.01 (s, 9H), 0.90 (d, J=6.8 Hz, 3H).

Step G: ethyl (5S)-6-[(tert-butyldiphenylsilyl)oxy]-5-methyl-2-oxohexanoate

To an oven-dried flask under nitrogen was added magnesium (453 mg, 18.7 mmol, 1.2 eq) and the solid was vigorously stirred for 20 min then stirring was stopped. A solution of the product from Step F (6.3 g, 15.5 mmol, 1 eq) in tetrahydrofuran (12 mL) was prepared and an aliquot was added to the magnesium followed by iodine (39.4 mg, 0.16 mmol, 0.01 eq) and the mixture was briefly heated at reflux. The remaining solution was added at such a rate as to maintain a gentle reflux, and upon complete addition the mixture was heated for 2 h at reflux then allowed to cool to ambient temperature. To a stirred solution of diethyl oxalate (2.11 mL, 15.5 mmol, 1 eq) in tetrahydrofuran (6 mL), cooled to −78° C., was added the Grignard solution via cannula, and the mixture was allowed to warm to ambient temperature and stir for 5 h. The reaction was partitioned between ethyl acetate and saturated aqueous ammonium chloride, and the organic phase was dried (magnesium sulfate), and concentrated in vacuo. Purification by automated flash column chromatography (CombiFlash Rf, 80 g RediSep™ silica cartridge) eluting with a gradient of 0-8% ethyl acetate in iso-heptane afforded the desired product as a clear oil (4.13 g. 9.68 mmol, 62%).

$^1$H NMR (400 MHz, DMSO-d6) δ 7.65-7.57 (m, 4H), 7.53-7.38 (m, 6H), 4.32-4.18 (m, 2H), 3.53-3.45 (m, 2H), 2.86-2.74 (m, 1H), 1.74-1.61 (m, 1H), 1.32-1.1.4 (m, 6H), 1.01 (s, 9H), 0.88 (d, 3H).

Step H: ethyl (5S)-3-bromo-6-[(tert-butyldiphenylsilyl)oxy]-5-methyl-2-oxohexanoate To a mixture of copper(II) bromide (4.14 g, 18.5 mmol, 2 eq) in ethyl acetate (120 mL) was added a solution of the product from Step G (3.95 g, 9.26 mmol, 1 eq) in chloroform (60 mL) and the mixture was heated at 85° C. overnight. The reaction was filtered through celite, eluting with dichloromethane, then concentrated in vacuo. Purification by automated flash column chromatography (CombiFlash Rf, 80 g RediSep™ silica cartridge) eluting with a gradient of 0-8% ethyl acetate in iso-heptane afforded the desired product as a yellow oil (1.92 g, 3.8 mmol, 41%) that was used directly in the subsequent step without characterisation.

Step I: ethyl 5-[(2S)-3-[(tert-butyldiphenylsilyl)oxy]-2-methylpropyl]-2-(methylamino)-1,3-thiazole-4-carboxylate To a solution of the product from Step H (1.67 g, 3.3 mmol, 1 eq) in ethanol (30 mL) was added N-methylthiourea (298 mg, 3.3 mmol, 1 eq) followed by triethylamine (0.92 mL, 6.61 mmol, 2 eq) and the mixture was heated at 80° C. for 4 h. The reaction was allowed to cool to ambient temperature and the solvent was removed by rotary evaporation. The crude material was partitioned between dichloromethane and water, the aqueous phase was extracted with dichloromethane, and the combined organics were washed with brine, dried (magnesium sulfate), and concentrated in vacuo. Purification by automated flash column chromatography (CombiFlash Rf, 40 g RediSep™ silica cartridge) eluting with a gradient of 0-50% ethyl acetate in iso-heptane afforded the desired product as a brown gum (914 mg, 1.84 mmol, 56%).

LC/MS ($C_{27}H_{36}N_2O_3SiS$) 497 $[M+H]^+$; RT 1.46 (LCMS-V-B1)

$^1$H NMR (400 MHz, DMSO-d6) δ 7.64-7.56 (m, 4H), 7.55-7.36 (m, 6H), 4.16 (q, J=7.1 Hz, 2H), 3.60-3.47 (m, 2H), 3.08 (dd, J=14.4, 6.6 Hz, 1H), 2.92 (dd, J=14.4, 7.7 Hz, 1H), 2.78 (d, J=4.8 Hz, 3H), 1.96-1.84 (m, 1H), 1.21 (t, J=7.1 Hz, 3H), 1.01 (s, 9H), 0.92 (d, J=6.7 Hz, 3H).

Step J: ethyl 2-{[(tert-butoxy)carbonyl](methyl)amino}-5-[(2S)-3-[(tert-butyldiphenylsilyl)oxy]-2-methylpropyl]-1,3-thiazole-4-carboxylate To a solution of the product from Step 1 (914 mg, 1.84 mmol, 1 eq) in tetrahydrofuran (20 mL) was added di-tertbutyl dicarbonate (803 mg, 3.68 mmol, 2 eq) followed by triethylamine (0.77 mL, 5.52 mmol, 3 eq) and 4-(dimethylamino)pyridine (22.5 mg, 0.18 mmol, 0.1 eq) and the mixture was stirred at ambient temperature for 2 h. The reaction was partitioned between ethyl acetate and water, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-20% ethyl acetate in iso-heptane afforded the desired product as a brown gum (961 mg, 1.61 mmol, 88%).

LC/MS ($C_{32}H_{44}N_2O_5SiS$) 597 $[M+H]^+$; RT 1.67 (LCMS-V-B1)

$^1$H NMR (400 MHz, DMSO-d6) δ 7.64-7.56 (m, 4H), 7.51-7.37 (m, 6H), 4.23 (q, J=7.1 Hz, 2H), 3.60-3.47 (m, 2H), 3.44 (s, 3H), 3.19 (dd, J=14.4, 6.8 Hz, 1H), 3.00 (dd, J=14.3, 7.5 Hz, 1H), 2.06-1.94 (m, 1H), 1.54 (s, 9H), 1.24 (t, J=7.1 Hz, 3H), 1.00 (s, 9H) 0.94 (d, J=6.7 Hz, 3H).

Step K: ethyl 2-{[(tert-butoxy)carbonyl](methyl)amino}-5-[(2S)-3-hydroxy-2-methylpropyl]-1,3-thiazole-4-carboxylate To a solution of the product from Step J (961 mg, 1.61 mmol, 1 eq) in tetrahydrofuran (20 mL) was added tetrabutylammonium fluoride (1M in tetrahydrofuran, 4.83 mL, 4.83 mmol, 3 eq) and the mixture was heated at reflux for 1.5 h. The reaction was allowed to cool to ambient temperature, then partitioned between ethyl acetate and water, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-80% ethyl acetate in iso-heptane afforded the desired product as a colourless gum (204 mg, 0.57 mmol, 35%).

LC/MS ($C_{16}H_{26}N_2O_5S$) 359 $[M+H]^+$; RT 1.07 (LCMS-V-B1)

$^1$H NMR (400 MHz, DMSO-d6) δ 4.59 (t, J=5.2 Hz, 1H), 4.26 (q, J=7.1 Hz, 2H), 3.43 (s, 3H), 3.37-3.22 (m, 2H), 3.12 (dd, J=14.3, 6.0 Hz, 1H), 2.91 (dd, J=14.3, 8.2 Hz, 1H), 1.89-1.75 (m, 1H), 1.53 (s, 9H), 1.29 (t, J=7.1 Hz, 3H), 0.85 (d, J=6.7 Hz, 3H).

Step L: ethyl 2-{[(tert-butoxy)carbonyl](methyl)amino}-5-[(2S)-3-(2-fluoro-4-iodophenoxy)-2-methylpropyl]-1,3-thiazole-4-carboxylate To a solution of the product from Step K (159 mg, 0.44 mmol, 1 eq) in toluene (6 mL) was added 2-fluoro-4-iodophenol (211 mg, 0.89 mmol, 2 eq) followed by triphenylphosphine (233 mg, 0.89 mmol, 2 eq) and diisopropylazodicarboxylate (0.17 mL, 0.89 mmol, 2 eq) and the mixture was heated at 120° C. overnight. The reaction was allowed to cool to ambient temperature and the solvent removed by rotary evaporation. The resultant oil was partitioned between dichloromethane and water, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-20% ethyl acetate in isoheptane afforded the desired product as a colourless gum (203 mg, 0.35 mmol, 79%).

$^1$H NMR (400 MHz, DMSO-d6) δ 7.59 (dd, J=10.8, 2.1 Hz, 1H), 7.48-7.42 (m, 1H), 6.97 (t, J=8.8 Hz, 1H), 4.24 (q, 2H), 3.99-3.87 (m, 2H), 3.43 (s, 3H), 3.24 (dd, J=14.2, 6.5 Hz, 1H), 3.08 (dd, J=14.3, 7.9 Hz, 1H), 2.33-2.20 (m, 1H), 1.51 (s, 9H), 1.27 (t, J=7.1 Hz, 3H), 1.01 (d, J=6.7 Hz, 3H).

Step M: ethyl 2-{[(tert-butoxy)carbonyl](methyl)amino}-5-[(2S)-3-{4-[3-(dimethylamino)prop-1-yn-1-yl]-2-fluorophenoxy}-2-methylpropyl]-1,3-thiazole-4-carboxylate To a solution of the product in Step L (226 mg, 0.39 mmol, 1 eq) in tetrahydrofuran (5 mL) was added 3-dimethylamino-1-propyne (0.08 mL, 0.78 mmol, 2 eq), N,N-diisopropylethylamine (0.19 mL, 1.17 mmol, 3 eq) and copper(I) iodide (7.44 mg, 0.04 mmol, 0.1 eq) followed by tetrakis(triphenylphosphine)palladium(0)(45.2 mg, 0.04 mmol, 0.1 eq) and the mixture was heated at reflux for 24 h. The reaction was partitioned between ethyl acetate and water, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-5% methanol in dichloromethane afforded the desired product as a brown gum (68 mg, 0.13 mmol, 33%).

LC/MS ($C_{27}H_{36}FN_3O_5S$) 534 $[M+H]^+$; RT 1.07 (LCMS-V-B1)

$^1$H NMR (400 MHz, DMSO-d6) δ 7.30 (dd, J=11.9, 2.0 Hz, 1H), 7.25-7.17 (m, 1H), 7.12 (t, J=8.7 Hz, 1H), 4.24 (q, 2H), 4.02-3.90 (m, 2H), 3.43 (s, 3H), 3.42 (s, 2H), 3.25 (dd, J=14.2, 6.5 Hz, 1H), 3.09 (dd, J=14.3, 8.0 Hz, 1H), 2.31-2.24 (m, 1H), 2.23 (s, 6H), 1.51 (s, 9H), 1.28 (t, J=7.1 Hz, 3H), 1.02 (d, J=6.7 Hz, 3H).

Step N: ethyl 5-[(2S)-3-{4-[3-(dimethylamino)prop-1-yn-1-yl]-2-fluorophenoxy}-2-methylpropyl]-2-(methylamino)-1,3-thiazole-4-carboxylate To a solution of the product from Step M (68 mg, 0.13 mmol, 1 eq) in dichloromethane (3 mL) was added trifluoroacetic acid (0.3 mL, 4.03 mmol, 31.6 eq) and the mixture was stirred at ambient temperature overnight. The reaction was diluted with dichloromethane, cooled in an ice-bath, and quenched by the addition of saturated aqueous sodium bicarbonate. The organic phase was washed with brine, dried (magnesium sulfate) and concentrated in vacuo. Purification by automated flash column chromatography (CombiFlash Rf, 4 g RediSep™ silica cartridge) eluting with a gradient or 0-7% methanol in dichloromethane afforded the desired product as a brown gum (40 mg, 0.09 mmol, 72%).

LC/MS ($C_{22}H_{28}FN_3O_3S$) 434 $[M+H]^+$; RT 0.82 (LCMS-V-B1)

$^1$H NMR (400 MHz, DMSO-d6) δ 7.52 (q, J=4.8 Hz, 1H), 7.30 (dd, J=11.9, 2.0 Hz, 1H), 7.25-7.17 (m, 1H), 7.12 (t, J=8.7 Hz, 1H), 4.19 (q, J=7.1 Hz, 2H), 4.00-3.88 (m, 2H), 3.42 (s, 2H), 3.13 (dd, J=14.5, 6.6 Hz, 1H), 3.02 (dd, J=14.4, 7.8 Hz, 1H), 2.78 (d, J=4.7 Hz, 3H), 2.23 (s, 6H), 2.21-2.12 (m, 1H), 1.25 (t, J=7.1 Hz, 3H), 1.01 (d, J=6.8 Hz, 3H).

Preparation 3zg: Ethyl 5-(3-{4-[3-(dimethylamino)prop-1-yn-1-yl]-2-fluorophenoxy}-2-(oxan-2-yloxy)propyl)-2-(methylamino)-1,3-thiazole-4-carboxylate

Step A: ethyl 2-{[(tert-butoxy)carbonyl](methyl)amino}-5-(prop-2-en-1-yl)-1,3-thiazole-4-carboxylate Isopropylmagnesium chloride (2M in tetrahydrofuran; 6 mL, 12 mmol 1.2 eq) was added dropwise to a solution of ethyl 5-bromo-2-[(tert-butoxycarbonyl)(methyl)amino]-1,3- thiazole-4-carboxylate (3.65 g, 9.99 mmol, 1 eq) in dichloromethane (30 mL) at −78° C. and the mixture was stirred for 30 min. Zinc chloride solution (1.9 M in 2-methyltetrahydrofuran; 8 mL, 15.2 mmol, 1.52 eq) was added dropwise and the mixture was stirred for 60 min at −78° C. then for 3 h at ambient temperature. The solution was cooled in ice-water and copper(I) cyanide di(lithium chloride) complex (1M in tetrahydrofuran; 2 mL, 2 mmol, 0.2 eq) and allyl bromide (2 mL, 23.11 mmol, 2.31 eq) were added slowly. The mixture was stirred for 60 min at 0° C. and then at ambient temperature for 18 h. Dichloromethane (125 mL) was added and the mixture was successively washed with saturated aqueous ammonium chloride solution (75 mL), water (2×75 mL) and brine (75 mL), dried (magnesium sulfate), and concentrated in vacuo. Purification by flash column chromatography (50 g silica) eluting with a gradient of 0-10% ethyl acetate in iso-heptane afforded the desired product as a colourless gum (1.64 g, 5.02 mmol, 50%).

LC/MS ($C_{15}H_{22}N_2O_4S$) 327 $[M+H]^+$; RT 1.43 (LCMS-V-B1)

$^1H$ NMR (400 MHz, DMSO-d6) δ 6.04-5.90 (m, 1H), 5.20-5.06 (m, 2H), 4.37 (q, J=7.1 Hz, 2H), 3.86 (dt, J=6.6, 1.4 Hz, 2H), 3.55 (s, 3H), 1.56 (s, 9H), 1.39 (t, J=7.1 Hz, 3H).

Step B: ethyl 5-(3-bromo-2-hydroxypropyl)-2-{[(tert-butoxy)carbonyl](methyl)amino}-1,3-thiazole-4-carboxylate To a solution of the product from Step A (1.29 g, 3.95 mmol, 1 eq) in acetone (16 mL), cooled in ice-water, was added N-bromosuccinimide (774 mg, 4.35 mmol, 1.1 eq), ammonium acetate (30.5 mg, 0.4 mmol, 0.1 eq) and water (4 mL) and the resulting solution was stirred for 45 min at ambient temperature. Ethyl acetate (150 mL) was added and the mixture was successively washed with water (2×75 mL) and brine (75 mL), dried (magnesium sulfate), and concentrated in vacuo. Purification by flash column chromatography (100 g silica) eluting with a gradient of 0-25% ethyl acetate in iso-heptane afforded the desired product as a colourless gum (960 mg, 2.27 mmol, 57%).

LC/MS ($C_{15}H_{23}BrN_2O_5S$) 425 $[M+H]^+$; RT 1.29 (LCMS-V-B1)

$^1H$ NMR (400 MHz, DMSO-d6) δ 5.59 (d, J=5.4 Hz, 1H), 4.27 (q, 2H), 3.95-3.80 (m, 1H), 3.54-3.45 (m, 3H), 3.44 (s, 3H), 3.08 (dd, J=14.7, 8.3 Hz, 1H), 1.53 (s, 9H), 1.30 (t, J=7.1 Hz, 3H).

Step C: ethyl 5-[3-bromo-2-(oxan-2-yloxy)propyl]-2-{[(tert-butoxy)carbonyl](methyl)amino}-1,3-thiazole-4-carboxylate To a solution of the product from Step B (1.15 g, 2.72 mmol, 1 eq) in dichloromethane (30 mL), cooled to 0° C., was added 3,4-dihydro-2H-pyran (1 mL, 11 mmol, 4 eq), followed by pyridinium para-toluenesulphonate (75 mg, 0.3 mmol, 0.11 eq) and the mixture was stirred for 30 min at 0° C. and then for 5 h at ambient temperature. Dichloromethane (30 mL) was added and the mixture was successively washed with water (2×25 mL) and brine (25 mL), dried (magnesium sulfate), and concentrated in vacuo to afford the desired product as a yellow gum (1.52 g, 2.7 mmol, 99%) that was used directly in the next step without further characterisation.

Step D: ethyl 5-[3-(4-bromo-2-fluorophenoxy)-2-(oxan-2-yloxy)propyl]-2-{[(tert-butoxy)carbonyl](methyl)amino}-1,3-thiazole-4-carboxylate 4-Bromo-2-fluorophenol (0.4 mL, 3.65 mmol, 1.35 eq) was added to a suspension of potassium tert-butoxide (400 mg, 3.56 mmol, 1.32 eq) in dimethylsulfoxide (5 mL) and the mixture was stirred. A solution of the product from Step C (1.52 g, 2.7 mmol, 1 eq) in dimethylsulfoxide (10 mL) was added and the mixture was stirred for 60 min at ambient temperature then at 60° C. for 3 h. The reaction was allowed to cool to ambient temperature and was partitioned between ethyl acetate (150 mL) and water (75 mL), and the organic phase was successively washed with water (2×75 mL) and brine (75 mL), dried (magnesium sulfate), and concentrated in vacuo. Purification by flash column chromatography (100 g silica) eluting with a gradient of 0-25% ethyl acetate in iso-heptane afforded the desired product as a pale yellow gum (1.05 g, 1.7 mmol, 63%).

LC/MS ($C_{26}H_{34}BrFN_2O_7S$) 617 $[M+H]^+$; RT 1.61 (LCMS-V-B1)

$^1H$ NMR (400 MHz, DMSO-d6) δ 7.54 (dd, J=10.8, 2.4, 0.8 Hz, 1H), 7.35-7.28 (m, 1H), 7.12 (td, J=9.0, 1.1 Hz, 1H), 4.25 (q, 3H), 4.19-4.08 (m, 2H), 3.56-3.37 (m, 7H), 1.77-1.55 (m, 4H), 1.52 (d, J=2.2 Hz, 9H), 1.49-1.38 (m, 4H), 1.27 (t, J=7.1 Hz, 3H).

Step E: ethyl 2-{[(tert-butoxy)carbonyl](methyl)amino}-5-(3-{4-[3-(dimethylamino)prop-1-yn-1-yl]-2-fluorophenoxy}-2-(oxan-2-yloxy)propyl)-1,3-thiazole-4-carboxylate To a solution of the product from Step D (1.05 g, 1.7 mmol, 1 eq) in dimethylformamide (10 mL) was added dimethyl(prop-2-yn-1-yl)amine (0.25 mL, 2.32 mmol, 1.37 eq), copper(I) iodide (32.4 mg, 0.17 mmol, 0.1 eq) and bis(triphenylphosphine)palladium(II) dichloride (119 mg, 0.17 mmol, 0.1 eq). N,N-Diisopropylethylamine (0.9 mL, 5.1 mmol, 3 eq) was added and the mixture was heated at 75° C. for 24 h. The reaction was allowed to cool to ambient temperature and was partitioned between ethyl acetate (150 mL) and water (75 mL), and the organic phase was successively washed with water (75 mL) and brine (75 mL), dried (magnesium sulfate), and concentrated in vacuo. Purification by flash column chromatography (50 g silica) eluting with a gradient of 0-100% ethyl acetate in iso-heptane afforded the desired product as a brown gum (395 mg, 0.64 mmol, 38%).

LC/MS ($C_{31}H_{42}FN_3O_7S$) 620 $[M+H]^+$; RT 1.31 (LCMS-V-B1)

Step F: ethyl 5-(3-{4-[3-(dimethylamino)prop-1-yn-1-yl]-2-fluorophenoxy}-2-(oxan-2-yloxy)propyl)-2-(methylamino)-1,3-thiazole-1-carboxylate To a solution of the product in Step E (390 mg, 0.63 mmol, 1 eq) in 1,1,1,3,3,3-hexafluoropropan-2-ol (7 mL) was heated in a sealed tube at 100° C. for 60 min then allowed to cool to ambient temperature and concentrated in vacuo. Purification by flash column chromatography (20 g silica) eluting with a gradient of 0-2.5% methanol in dichloromethane afforded the desired product as a brown gum (170 mg, 0.33 mmol, 52%).

LC/MS ($C_{26}H_{34}FN_3O_5S$) 520 $[M+H]^+$; RT 1.05 (LCMS-V-B1)

Preparation 3zh: Ethyl 5-(2-methoxy-3-{[tris(propan-2-yl)silyl]oxy}propyl)-2-(methylamino)-1,3-thiazole-4-carboxylate Step A: ethyl 2-{[(tert-butoxy)carbonyl](methyl)amino}-5-(2,3-dihydroxypropyl)-1,3-thiazole-4-carboxylate To a solution of the product from Preparation 3zg, Step A (8.39 g, 25.7 mmol, 1 eq) in 9:1 acetone/water (250 mL) was added 4-methylmorpholine-N-oxide (4.75 g, 40.6 mmol, 1.58 eq), followed by osmium tetroxide (3.5 mL, 0.28 mmol 0.01 eq) and the resulting mixture was stirred for 18 h at ambient temperature. Water (300 mL) was added and the mixture was extracted with ethyl acetate (4×200 mL), and the combined organics were washed with brine (150 mL), dried (magnesium sulfate), and concentrated in vacuo. Purification by flash column chromatography (100 g silica) eluting with a gradient of 0-5% methanol in dichloromethane afforded the desired product as a brown gum (8.66 g, 24 mmol, 94%).

LC/MS ($C_{15}H_{24}N_2O_6S$) 361 $[M+H]^+$; RT 1.07 (LCMS-V-B1)

$^1H$ NMR (400 MHz, DMSO-d6) δ 4.95 (d, J=5.4 Hz, 1H), 4.66 (t, J=5.6 Hz, 1H), 4.26 (q, J=7.1 Hz, 2H), 3.69-3.58 (m, 1H), 3.49-3.40 (m, 1H), 3.38-3.26 (m, 2H), 2.89 (dd, J=14.9, 8.7 Hz, 1H), 1.53 (s, 9H), 1.29 (t, J=7.1 Hz, 3H).

Step B: ethyl 2-{[(tert-butoxy)carbonyl](methyl)amino}-5-(2-hydroxy-3-{[tris(propan-2-yl)silyl]oxy}propyl)-1,3-thiazole-4-carboxylate To a solution of the product from Step A (8.65 g 24 mmol, 1 eq) in dichloromethane (100 mL), cooled in ice-water, was added imidazole (3.5 g, 51.4 mmol, 2.14 eq), followed by triisopropylsilyl chloride (6 mL, 28 mmol, 1.17 eq) dropwise and the mixture was stirred for 60 min at 0° C. then for 18 h at ambient temperature. The reaction was concentrated in vacuo and purification by flash column chromatography (100 g silica) eluting with a gradient of 0-25% ethyl acetate in iso-heptane afforded the desired product as a colourless oil (12.2 g, 23.5 mmol, 98%).

LC/MS ($C_{24}H_{44}N_2O_6SiS$) 517 $[M+H]^+$; RT 1.69 (LCMS-V-B1)

$^1H$ NMR (400 MHz, DMSO-d6) δ 5.07 (d, J=5.2 Hz, 1H), 4.24 (q, J=7.1 Hz, 2H), 3.75-3.61 (m, 2H), 3.55-3.48 (m, 2H), 3.42 (s, 3H), 2.98 (dd, J=15.0, 8.3 Hz, 1H), 1.53 (s, 9H), 1.28 (t, J=7.1 Hz, 3H), 1.09-0.97 (m, 21H).

Step C: ethyl 2-{[(tert-butoxy)carbonyl](methyl)amino}-5-(2-methoxy-3-{[tris(propan-2-yl)silyl]oxy}propyl)-1,3-thiazole-4-carboxylate Trimethyloxonium tetrafluoroborate (1.5 g, 10.1 mmol, 2.02 eq) was added to a cooled solution of the product from Step B (2.6 g, 5.03 mmol, 1 eq) and N,N,N',N'-tetramethylnaphthalene-1,8-diamine (2.2 g, 10.3 mmol, 2.04 eq) in dichloromethane (75 mL) and the mixture was stirred at 0° C. for 60 min then for 24 h at ambient temperature. The mixture was diluted with dichloromethane (75 mL) and washed successively with 1M aqueous copper(II) sulphate (2×75 mL), water (75 mL) and brine (75 mL), dried (magnesium sulfate), and concentrated in vacuo. Purification by flash column chromatography (50 g silica) eluting with a gradient of 0-5% ethyl acetate in iso-heptane afforded the desired product as a colourless gum (2.54 g, 4.79 mmol, 95%).

LC/MS ($C_{25}H_{46}N_2O_6SiS$) 531 $[M+H]^+$; RT 1.80 (LCMS-V-B1)

$^1H$ NMR (400 MHz, DMSO-d6) δ 4.37 (q, J=7.1 Hz, 2H), 3.75 (dd, J=5.0, 2.6 Hz, 2H), 3.55 (s, 3H), 3.52-3.44 (m, 2H), 3.41 (s, 3H), 3.26-3.14 (m, 1H), 1.39 (t, J=7.1 Hz, 3H), 1.09-1.01 (m, 21H).

Step D: ethyl 5-(2-methoxy-3-{[tris(propan-2-yl)silyl]oxy}propyl)-2-(methylamino)-1,3-thiazole-4-carboxylate A solution of the product from Step C (2.54 g, 4.79 mmol, 1 eq) in 1,1,1,3,3,3-hexafluoropropan-2-ol (20 mL) was heated in a sealed tube at 100° C. for 5 h. The solution was allowed to cool to ambient temperature, concentrated in vacuo and dried under vacuum to afford the desired product as a white solid (1.75 g, 4.06 mmol, 85%).

$^1H$ NMR (400 MHz, DMSO-d6) δ 5.44 (q, J=5.1 Hz, 1H), 4.35 (q, J=7.1 Hz, 2H), 3.79-3.69 (m, 2H), 3.52 (dd, J=15.0, 4.1 Hz, 1H), 3.48-3.39 (m, 4H), 3.13 (dd, J=15.0, 7.8 Hz, 1H), 2.95 (d, J=5.0 Hz, 3H), 1.37 (t, J=7.1 Hz, 3H), 1.09-1.01 (m, 21H).

Preparation 4a: N-(6-Chloro-4-methyl-pyridazin-3-yl)-3-(2-trimethylsilylethoxymethyl)-1,3-benzothiazol-2-imine Step A: N-(6-chloro-4-methyl-pyridazin-3-yl)-1,3-benzothiazol-2-amine A 2 L oven-dried, one-necked, round-bottom flask was equipped with a PTFE-coated magnetic stirring bar and fitted with a reflux condenser. It was charged with 34.0 g of 6-chloro-4-methyl-pyridazin-3-amine (237 mmol, 1 eq.), 34 mL or 2-chloro-1,3-benzothiazole (44.2 g, 260 mmol, 1.1 eq.). 124 mL or DIPEA (91.8 g, 710 mmol, 3 eq.) and 137 g of $Cs_2CO_3$ (710 mmol, 3 eq.), then 1 L of DMF were added and the system was flushed with argon. After 5 minutes stirring under inert atmosphere 2.01 g of $Pd_2(dba)_3$ (5.9 mmol, 0.025 eq.) and 6.85 g of XantPhos (11.8 mmol, 0.05 eq.) were added. The resulting mixture was then warmed up to 75° C. and stirred at that temperature for 4 hours to reach complete conversion. Reaction mixture was left to cool down to rt, then poured into 3 L of water while it was intensively stirred. After 30 min the precipitated product was removed by filtration, and then it was washed with water for 2 times (2×2 L). The product was dried overnight on high vacuum. The dried crude product was stirred in 1 L of heptane:$Et_2O$ (3:2) for 30 min then filtered off to give 64.5 g (98%) of the desired product as green powder.

$^1H$ NMR (500 MHz, DMSO-$d_6$) δ ppm 11.96 (brs, 1H), 7.86 (d, 1H), 7.65 (s, 1H), 7.51 (d, 1H), 7.38 (t, 1H), 7.21 (t, 1H), 2.37 (s, 3H); $^{13}C$ NMR (125 MHz, DMSO-$d_6$) δ ppm 130.3, 129.5, 126.6, 122.8, 122.3, 17.2; HRMS-ESI (m/z): $[M+H]^+$ calcd for $C_{12}H_{10}ClN_4S$: 277.0309, found 277.0305.

Step B: N-(6-chloro-4-methyl-pyridazin-3-yl)-3-(2-trimethylsilylethoxymethyl)-1,3-benzothiazol-2-imine A 2 L oven-dried, one-necked, round-bottomed flask equipped with a PTFE-coated magnetic stirring bar was charged with 64.5 g of the product from Step A (236 mmol, 1 eq.), 123 mL of DIPEA (9.16 g, 708 mmol, 3 eq.), 14.43 g of N,N-dimethylpyridin-4-amine (11.81 mmol, 0.05 eq.) in 1 L of dry DCM were cooled down to 0° C. under $N_2$. And during intensive mechanical stirring 46.00 mL of 2-(chloromethoxy)ethyl-trimethyl-silane (43.32 g, 259 mmol, 1.1 eq.) was added to the mixture dropwise over 5 min period of time. It was stirred at 0° C. for 30 min when the reaction reached complete conversion. 24.5 mL of water was added to the reaction mixture then Celite was added to the reaction mixture and the volatiles were removed under reduced pressure. It was purified via flash column chromatography using heptane and EtOAc as eluents to obtain 46.62 g (48%) of the desired product.

$^1H$ NMR (500 MHz, DMSO-$d_6$) δ ppm 7.85 (dm, 1H), 7.72 (q, 1H), 7.53 (dm, 1H), 7.47 (m, 1H), 7.29 (m, 1H), 5.89 (s, 2H), 3.70 (m, 2H), 2.39 (d, 3H), 0.90 (m, 2H), −0.12 (s, 9H); $^{13}C$ NMR (125 MHz, DMSO-d6) δ ppm 159.5, 158.5, 150.0, 138.1, 137.4, 129.5, 127.4, 125.5, 123.8, 123.2, 112.4, 73.0, 66.8, 17.7, 17.1, −1.0; HRMS-ESI (m/z): $[M+H]^+$ calcd for $C_{18}H_{24}ClN_4OSSi$: 407.1123, found 407.1120.

Preparation 4b: (2Z)—N-(6-Chloropyridazin-3-yl)-3-{[2-(trimethylsilyl)ethoxy]methyl}-2,3-dihydro-1,3-benzothiazol-2-imine N,N-Diisopropylethylamine (3 mL, 16.6 mmol, 3 eq) was added to a suspension of the product from Preparation 9b (1.45 g, 5.52 mmol, 1 eq) in dichloromethane (75 mL) at 0° C. under a nitrogen atmosphere. [2-(chloromethoxy)ethyl] trimethylsilane (1.2 mL, 6.78 mmol, 1.23 eq) and 4-dimethylaminopyridine (33.7 mg, 0.28 mmol, 0.05 eq) were added and the mixture was stirred at room temperature for 3 h. Dichloromethane (75 mL) was added and the mixture washed with water (2×75 mL) and brine (75 mL). The solution was dried (magnesium sulfate) and concentrated in vacuo. Trituration with methanol (20 mL) gave a solid that was filtered, washed with methanol (2×10 mL) and dried under vacuum to afford the desired product as a pale brown solid (1.85 g, 4.71 mmol, 85%).

LC/MS ($C_{17}H_{21}ClN_4OSiS$) 393 $[M+H^+$; RT 1.56 (LCMS-V-B1).

Preparation 5a: Methyl 5-[3-[4-[3-[tert-butoxycarbonyl(methyl)amino]prop-1-ynyl]-2-fluoro-phenoxy]propyl]-2-[[4-[tert-butyl(diphenyl)silyl]oxy-5-(p-tolylsulfonyloxy)pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Step A: methyl 5-[3-[4-[3-[tert-butoxycarbonyl (methyl)amino]prop-1-ynyl]-2-fluoro-phenoxy]propyl]-2-[[5-[tert-butyl(dimethyl)silyl]oxy-4-[tert-butyl (diphenylsilyl]oxy-pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 12 g of Preparation 3a (13 mmol) and 6.30 g of Preparation 4a (15.6 mmol) as the appropriate halide, 14 g (83%) of the desired product was obtained.

$^1H$ NMR (500 MHz, DMSO-$d_6$) δ ppm 7.85-7.23 (m, 14H), 7.58 (s, 1H), 7.31 (t, 1H), 7.19 (m, 1H), 7.14 (t, 1H), 5.86 (s, 2H), 4.37 (t, 2H), 4.20 (s, 2H), 4.15 (t, 2H), 3.73 (s, 3H), 3.71 (t, 2H), 3.67 (m, 1H), 3.39 (m, 2H), 3.27 (t, 2H), 2.83 (s, 3H), 2.41 (s, 3H), 2.12 (m, 2H), 1.72 (m, 2H), 1.52 (m, 2H), 1.40 (s, 9H), 0.90 (t, 2H), 0.89 (s, 9H), 0.69 (s, 9H), −0.14 (s, 9H), −0.19/−0.23 (s+s, 6H); $^{13}C$ NMR (125 MHz, DMSO-$d_6$) δ ppm 147.5, 129.1, 119.3, 117.5, 115.4, 73.4, 72.3, 68.4, 66.8, 65.8, 51.8, 46.6, 38.5, 33.8, 31.0, 30.5, 28.5, 27.1, 26.1, 23.0, 22.6, 17.9, 17.8, −1.0, −5.3; HRMS-ESI (m/z): $[M+H]^+$ calcd for $C_{68}H_{93}FN_7O_8S_2Si_3$: 1302.5813, found 1302.5819.

Step B: methyl 5-[3-[4-[3-[tert-butoxycarbonyl (methyl)amino]prop-1-ynyl]-2-fluoro-phenoxy]propyl]-2-[[4-[tert-butyl(diphenyl)silyl]oxy-5-hydroxy-pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate A 100 mL oven-dried, one-necked, round-bottom flask was equipped with a PTFE-coated magnetic stirring bar and fitted with a reflux condenser. It was charged with 1.40 g of the product from Step A (1.1 mmol, 1 eq.) and 12 mg of camphor sulfonic acid (0.054 mmol, 0.05 eq.), 5 mL of DCM and 1 mL of MeOH. The resulting mixture was stirred overnight at rt to reach complete conversion. Reaction mixture was concentrated directly to Celite then purified by flash column chromatography using heptane and EtOAc as eluents to give 700 mg (55%) of the desired product as yellow solid.

$^1H$ NMR (500 MHz, DMSO-$d_6$) δ ppm 7.85-7.14 (m, 14H), 7.56 (s, 1H), 7.32 (dd, 1H), 7.20 (m, 1H), 7.15 (t, 1H), 5.86 (s, 2H), 4.56 (t, 1H), 4.33 (m, 2H), 4.20 (s, 2H), 4.15 (t, 2H), 3.74 (s, 3H), 3.72 (t, 2H), 3.65 (m, 1H), 3.27 (t, 2H), 3.27 (t, 2H), 2.83 (s, 3H), 2.41 (s, 3H), 2.13 (m, 2H), 1.73/1.64 (m+m, 2H), 1.52 (m, 2H), 1.40 (s, 9H), 0.90 (t, 2H), 0.86 (s, 9H), −0.13 (s, 9H); $^{13}C$ NMR (125 MHz, DMSO-$d_6$) δ ppm 154.9, 147.6, 129.1, 119.4, 117.5, 115.4, 82.4, 73.7, 72.9, 68.4, 66.8, 64.5, 51.9, 46.8, 38.5, 33.8, 31.0, 30.6, 28.5, 27.2, 23.1, 22.5, 17.9, 17.8, −1.0; HRMS-ESI (m/z): $[M+H]^+$ calcd for $C_{62}H_{79}FN_7O_8S_2Si_2$: 1188.4949, found 1188.4938.

Step C: methyl 5-[3-[4-[3-[tert-butoxycarbonyl (methyl)amino]prop-1-ynyl]-2-fluoro-phenoxy]propyl]-2-[[4-[tert-butyl(diphenyl)silyl]oxy-5-(p-tolylsulfonyloxy)pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate A 100 mL oven-dried, one-necked, round-bottom flask was equipped with a PTFE-coated magnetic stirring bar was charged with 700 mg of the product from Step B (0.58 mmol, 1 eq.) and 907 mg of N,N-dimethyl-1 (p-tolylsulfonyl)pyridin-1-ium-4-amine chloride (2.9 mmol, 5 eq., *Tetrahedron Lett* 2016, 57, 4620) were dissolved in 35 mL of DCM and stirred overnight at rt. Reaction reached complete conversion. Reaction mixture directly was concentrated onto Celite, and then purified by flash column chromatography using heptane and EtOAc as eluents to give 450 mg (56%) of the desired product.

$^1H$ NMR (500 MHz, DMSO-$d_6$) δ ppm 7.88-7.23 (m, 14H), 7.58 (m, 2H), 7.53 (s, 1H), 7.31 (m, 2H), 7.31 (dd, 1H), 7.19 (m, 1H), 7.15 (t, 1H), 5.86 (s, 2H), 4.20 (s, 2H), 4.16 (t, 2H), 4.15 (t, 2H), 3.92 (m, 2H), 3.84 (m, 1H), 3.72 (t, 2H), 3.70 (s, 3H), 3.27 (t, 2H), 2.83 (s, 3H), 2.41 (s, 3H), 2.33 (s, 3H), 2.13 (m, 2H), 1.47 (m, 2H), 1.47 (m, 2H), 1.40 (s, 9H), 0.91 (t, 2H), 0.86 (s, 9H), −0.13 (s, 9H); $^{13}C$ NMR (125 MHz, DMSO-$d_6$) δ ppm 147.5, 145.3, 130.4, 129.1, 128.0, 119.3, 117.4, 115.5, 72.9, 72.6, 70.4, 68.4, 66.8, 51.8, 46.2, 38.6, 33.8, 31.0, 30.1, 28.5, 27.0, 23.1, 22.4, 21.5, 17.8, 17.8, −1.0; HRMS-ESI (m/z): $[M+H]^+$ calcd for $C_{69}H_{85}FN_7O_{10}S_3Si_2$: 1342.5037, found 1342.5039.

Preparation 5b: Methyl 2-[[4-[tert-butyl(diphenyl) silyl]oxy-5-(p-tolylsulfonyloxy)pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy] propyl]thiazole-4-carboxylate Step A: methyl 2-[[5-[tert-butyl(dimethyl)silyl]oxy-4-[tert-butyl(diphenyl)silyl]oxy-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy] propyl]thiazole-4-carboxylate Using Buchwald General Procedure II starting from 6.0 g of Preparation 3b (7.1 mmol, 1 eq.) and 3.46 g of Preparation 4a (8.51 mmol, 1.2 eq.) as the appropriate halide, 7.0 g (81%) of the desired product was obtained.

$^1$H NMR (500 MHz, DMSO-$d_6$) δ ppm 7.84-7.25 (m, 4H), 7.60-7.11 (m, 10H), 7.58 (s, 1H), 7.29 (t, 1H), 7.19 (dd, 1H), 7.14 (m, 1H), 5.86 (s, 2H), 4.37 (t, 2H), 4.15 (t, 2H), 3.74 (s, 3H), 3.71 (t, 2H), 3.67 (m, 1H), 3.39 (d, 2H), 3.38 (s, 2H), 3.27 (t, 2H), 2.41 (s, 3H), 2.19 (s, 6H), 213 (m, 2H), 1.73 (m, 2H), 1.51 (m, 2H), 0.91 (t, 2H), 0.89 (s, 9H), 0.69 (s, 9H), −0.13 (s, 9H), −0.19/−0.23 (s+s, 6H); $^{13}$C NMR (125 MHz, DMSO-$d_6$) δ ppm 135.9-111.3, 127.2-112.0, 128.9, 119.2, 117.6, 115.5, 73.4, 72.9, 68.4, 66.8, 65.9, 51.9, 48.1, 46.6, 44.2, 31.0, 30.9, 27.3, 26.0, 23.1, 22.6, 17.9, 17.8, −1.0, −5.3; HRMS-ESI (m/z): $[M+H]^+$ calcd for $C_{64}H_{87}FN_7O_6S_2Si_3$: 1216.5446, found 1216.5425.

Step B: methyl 2-[[4-[tert-butyl(diphenyl)silyl]oxy-5-hydroxy-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate A 100 mL oven-dried, one-necked, round-bottom flask was equipped with a PTFE-coated magnetic stirring bar and fitted with a reflux condenser. It was charged with 7.0 g of the product from Step A (5.75 mmol, 1 eq.) and 1.60 g of camphor sulfonic acid (6.90 mmol, 1.2 eq.) dissolved in 25 mL of DCM and 5 mL of MeOH. The resulting mixture was stirred overnight at rt to reach complete conversion. Reaction mixture was concentrated directly to Celite, and purified by flash column chromatography using DCM and MeOH (1.2% $NH_3$) as eluents to give 3.0 g (47%) of the desired product as yellow solid.

Step C: methyl 2-[[4-[tert-butyl(diphenyl)silyl]oxy-5 (p-tolylsulfonyloxy)pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate A 100 mL oven-dried, one-necked, round-bottom flask was equipped with a PTFE-coated magnetic stirring bar was charged with 3.80 g of the product from Step B (3.40 mmol, 1 eq.), 5.40 g of N,N-dimethyl-1-(p-tolylsulfonyl)pyridin-1-ium-4-amine chloride (17.0 mmol, 5 eq., Tetrahedron Lett. 2016, 57, 4620) and 20 mL of DCM then stirred overnight at rt. Reaction reached complete conversion. Reaction mixture was concentrated directly to Celite then purified by flash column chromatography using DCM and MeOH (1.2% $NH_3$) as eluents to give 3.58 g (83%) of the desired product.

$^1$H NMR (500 MHz, DMSO-$d_6$) δ ppm (m, 10H), 7.85 (d, 1H), 7.59 (d, 2H), 7.53 (m, 1H), 7.47 (d, 1H), 7.44 (t, 1H), 7.32 (d, 2H), 7.3 (dd, 1H), 7.26 (t, 1H), 7.20 (d, 1H), 7.15 (t, 1H), 5.87 (s, 2H), 4.16 (t, 2H), 4.16 (br., 2H), 3.92 (m, 2H), 3.84 (m, 1H), 3.72 (t, 2H), 3.70 (s, 3H), 3.38 (s, 2H), 3.27 (t, 2H), 2.42 (s, 3H), 2.33 (s, 3H), 2.19 (s, 6H), 2.13 (m, 2H), 1.47 (br., 2H), 1.47 (br., 2H), 0.91 (1.2H), 0.87 (s, 9H), −0.13 (s, 9H); $^{13}$C NMR (125 MHz, DMSO-d6) δ ppm 130.5, 128.9, 128.0, 127.2, 123.5, 123.2, 119.2, 117.4, 115.5, 112.0, 72.9, 72.6, 70.4, 68.4, 66.8, 51.8, 48.1, 46.1, 44.2, 31.0, 30.1, 27.0, 23.1, 22.4, 21.5, 17.8, 17.8, −1.0; HRMS-ESI (m/z): $[M+H]^+$ calcd for $C_{65}H_{79}FN_7O_8S_3Si_2$: 1256.4669, found 1256.4677.

Preparation 5c: Methyl 5-[3-[4-[3-[tert-butoxycarbonyl(methyl)amino]prop-1-ynyl]-2-fluoro-phenoxy]propyl]-2-[4-hydroxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Step A: methyl 5-[3-[4-[3-[tert-butoxycarbonyl(methyl)amino]prop-1-ynyl]-2-fluoro-phenoxy]propyl]-2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 250 mg of Preparation 3c (0.38 mmol, 1 eq.) and 250 mg of Preparation 4a (0.38 mmol, 1 eq.) as the appropriate halide, 295 mg (75%) of the desired product was obtained.

$^1$H NMR (500 MHz, DMSO-$d_6$) δ ppm 7.83-7.25 (m, 4H), 7.64 (s, 1H), 7.31 (dd, 1H), 7.21 (m, 1H), 7.15 (t, 1H), 5.85 (s, 2H), 4.41 (t, 2H), 4.20 (s, 2H), 4.14 (t, 2H), 3.77 (s, 3H), 3.71 (t, 2H), 3.61 (t, 2H), 3.26 (t, 2H), 2.84 (s, 3H), 2.44 (s, 3H), 2.12 (m, 2H), 1.74 (m, 2H), 1.51 (m, 2H), 1.40 (s, 9H), 0.91 (t, 2H), 0.79 (s, 9H), −0.03 (s, 6H), −0.12 (s, 9H); $^{13}$C NMR (125 MHz, DMSO-$d_6$) δ ppm 147.5, 137.6, 129.1, 127.2-112, 119.3, 117.7, 115.5, 72.8, 68.4, 66.8, 62.5, 51.9, 46.7, 38.3, 33.8, 31.0, 29.8, 28.5, 26.2, 23.8, 23.1, 17.9, 17.8, −1.0, −4.9; HRMS-ESI (m/z): $[M+H]^+$ calcd for $C_{51}H_{73}FN_7O_7S_2Si_2$: 1034.4530 found 1034.4517.

Step B: methyl 5-[3-[4-[3-[tert-butoxycarbonyl(methyl)amino]prop-1-ynyl]-2-fluoro-phenoxy]propyl]-2-[4-hydroxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Deprotection of tert-butyl-dimethyl-silyl protecting group General Procedure starting from 650 mg of the product from Step A (0.63 mmol, 1 eq.) and 36 mg of [(1S,4R)-7,7-dimethyl-2-oxo-norbornan-1-yl]methanesulfonic (0.16 mmol, 0.25 eq.), 178 mg (31%) of the desired product was obtained.

$^1$H NMR (500 MHz, DMSO-$d_6$) δ ppm 7.84 (d, 1H), 7.68 (s, 1H), 7.46 (d, 1H), 7.43 (td, 1H), 7.32 (brd., 1H), 7.25 (td, 1H), 7.22 (d, 1H), 7.17 (t, 1H), 5.86 (s, 2H), 4.39 (t, 2H), 4.20 (br., 2H), 4.15 (t, 2H), 3.76 (s, 3H), 3.72 (t, 2H), 3.45 (q, 2H), 3.26 (t, 2H), 2.84 (br., 3H), 2.45 (s, 3H), 2.12 (m, 2H), 1.72 (m, 2H), 1.50 (m, 2H), 1.40 (s, 9H), 0.92 (t, 2H), −0.11 (s, 9H); $^{13}$C NMR (125 MHz, DMSO-$d_6$) δ ppm 129.1, 127.2, 1214, 123.2, 119.3, 117.6, 115.5, 111.9, 72.9, 68.4, 66.7, 60.9, 52.0, 46.8, 38.5, 33.8, 31.0, 29.9, 28.5, 24.1, 23.2, 17.9, 17.8, −1.0; HRMS-ESI (m/z); $[M+H]^+$ calcd for $C_{45}H_{59}FN_7O_7S_2Si$: 920.3665, found 920.3650.

Preparation 5d: Methyl 5-[3-[4-[3-(dimethylamino)prop-1-ynyl]-2-fluoro-phenoxy]propyl]-2-[4-hydroxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Step A: methyl 2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Buchwald General Procedure II starting from 1800 mg of Preparation 3d (3.11 mmol, 1 eq.) and 1267 mg of Preparation 4a (3.11 mmol, 1 eq.) as the appropriate halide, 2035 mg (69%) of the desired product was obtained.

$^{1}$H NMR (500 MHz, DMSO-d$_{6}$) δ ppm 7.82 (dm, 1H), 7.61 (s, 1H), 7.44 (dm, 1H), 7.42 (m, 1H), 7.29 (dd, 1H), 7.23 (m, 1H), 7.19 (dm, 1H), 7.13 (t, 1H), 5.83 (s, 2H), 4.40 (t, 2H), 4.13 (t, 2H), 3.77 (s, 3H), 3.70 (m, 2H), 3.60 (t, 2H), 3.38 (s, 2H), 3.25 (m, 2H), 2.42 (s, 3H), 2.19 (s, 6H), 2.11 (m, 2H), 1.73 (m, 2H), 1.51 (m, 2H), 0.90 (m, 2H), 0.78 (s, 9H), −0.03 (s, 6H), −0.13 (s, 9H); $^{13}$C NMR (125 MHz, DMSO-d$_{6}$) δ ppm 128.9, 127.1, 123.4, 123.2, 119.2, 117.5, 115.4, 111.9, 72.8, 68.4, 66.7, 62.5, 51.9, 45.1, 46.5, 44.2, 30.9, 29.7, 26.2, 23.7, 23.1, 17.9, 17.8, −1.0, −4.9; HRMS-ESI (m/z): [M+H]$^{+}$ calcd for $C_{47}H_{67}FN_{7}O_{5}S_{2}Si_{2}$: 948.4162, found 948.4161.

Step B: methyl 5-[3-[4-[3-(dimethylamino)prop-1-ynyl]-2-fluoro-phenoxy]propyl]-2-[4-hydroxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Deprotection of tert-butyl-dimethyl-silyl protecting group General Procedure starting from 7.23 g of the product from Step A (7.63 mmol, 1 eq.) and 2.22 g of [(1S,4R)-7,7-dimethyl-2-oxo-norbornan-1-yl]methanesulfonic (9.54 mmol, 1.25 eq.), 5.23 g (82%) of the desired product was obtained.

$^{1}$H NMR (500 MHz, DMSO-d$_{6}$) δ ppm 7.84 (d, 1H), 7.69 (s, 1H), 7.47 (d, 1H), 7.44 (td, 1H), 7.35 (dd, 1H), 7.25 (td, 1H), 7.25 (dm, 1H), 7.18 (t, 1H), 5.86 (s, 2H), 4.46 (t, 1H), 4.39 (t, 2H), 4.15 (t, 2H), 3.78 (s, 3H), 3.72 (m, 2H), 3.65 (s, 2H), 3.45 (q, 2H), 3.27 (t, 2H), 2.46 (s, 3H), 2.39 (s, 6H), 2.13 (m, 2H), 1.72 (m, 2H), 1.50 (m, 2H), 0.92 (m, 2H), −0.11 (s, 9H); $^{13}$C NMR (125 MHz, DMSO-d$_{6}$) δ ppm 163.2, 129.2, 127.2, 123.4, 123.2, 119.3, 117.6, 115.5, 112.0, 72.9, 68.4, 66.8, 60.9, 52.0, 47.8, 46.8, 43.6, 31.0, 29.9, 24.1, 23.1, 17.9, 17.8, −0.9; HRMS-ESI (m/z): [M+H]$^{+}$ calcd for $C_{41}H_{53}FN_{7}O_{5}S_{2}Si$: 834.3297, found 834.3296.

Preparation 5e: Methyl 5-[3-[4-[3-[tert-butoxycarbonyl(methyl)amino]prop-1-ynyl]-2-fluoro-phenoxy]propyl]-2-[5-hydroxypentyl-[5-methyl-6-[(Z)-[3-(2-trimethylsilylethoxymethyl)-1,3-benzothiazol-2-ylidene]amino]pyridazin-3-yl]amino]thiazole-4-carboxylate Step A: methyl 5-[3-[4-[3-[tert-butoxycarbonyl(methyl)amino]prop-1-ynyl]-2-fluoro-phenoxy]propyl]-2-[5-[tert-butyl(dimethyl)silyl]oxypentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 350 mg of Preparation 3m (0.52 mmol, 1 eq.) and 210 mg of Preparation 4a (0.52 mmol, 1 eq.) as the appropriate halide, 481 mg (88%) of the desired product was obtained.

$^{1}$H NMR (500 MHz, DMSO-d$_{6}$) δ ppm 7.81 (dd, 1H), 7.62 (s, 1H), 7.45 (dd, 1H), 7.42 (m, 1H), 7.28 (dd, 1H), 7.24 (m, 1H), 7.19 (m, 1H), 7.15 (t, 1H), 5.84 (s, 2H), 4.38 (t, 2H), 4.20 (s, 2H), 4.16 (t, 2H), 3.78 (s, 3H), 3.73 (t, 2H), 3.55 (t, 2H), 3.26 (t, 2H), 2.85 (s, 3H), 2.44 (s, 3H), 2.13 (m, 2H), 1.71 (m, 2H), 1.51 (m, 2H), 1.41 (s, 9H), 1.40 (m, 2H), 0.92 (t, 2H), 0.80 (s, 9H), 0.04 (s, 6H), −0.10 (s, 9H); $^{13}$C NMR (125 MHz, DMSO-d$_{6}$) δ ppm 163.2, 147.5, 137.6, 129.0, 127.1, 123.5, 123.1, 119.3, 117.7, 115.7, 111.9, 73.0, 68.6, 66.8, 62.7, 51.8, 47.0, 38.6, 33.8, 32.4, 31.0, 28.5, 27.1, 26.2, 23.1, 23.0, 17.9, 17.8, −1.0, −5.0; HRMS-ESI (m/z): [M+H]$^{+}$ calcd for $C_{52}H_{75}FN_{7}O_{7}S_{2}Si_{2}$: 1048.4686, found 1048.4692.

Step B: methyl 5-[3-[4-[3-[tert-butoxycarbonyl(methyl)amino]prop-1-ynyl]-2-fluoro-phenoxy]propyl]-2-[5-hydroxypentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Deprotection of tert-butyl-dimethyl-silyl protecting group General Procedure starting from 2.52 g of the product from Step A (2.40 mmol, 1 eq.) and 0.70 g of [(1S,4R)-7,7-dimethyl-2-oxo-norbornan-1-yl]methanesulfonic (3.00 mmol, 1.25 eq.), 1.19 g (53%) of the desired product was obtained.

$^{1}$H NMR (500 MHz, DMSO-d$_{6}$) δ ppm 7.84 (d, 1H), 7.66 (s, 1H), 7.46 (d, 1H), 7.43 (t, 1H), 7.32 (d, 1H), 7.25 (t, 1H), 7.22 (d, 1H), 7.16 (t, 1H), 5.86 (s, 2H), 4.36 (t, 2H), 4.20 (s, 2H), 4.15 (t, 2H), 3.78 (s, 3H), 3.72 (t, 2H), 3.4 (t, 2H), 3.26 (t, 2H), 2.84 (s, 3H), 2.46 (s, 3H), 2.12 (qn, 2H), 1.69 (qn, 2H), 1.49 (m, 2H), 1.40 (s, 9H), 1.40 (qn, 2H), 0.92 (t, 2H), −0.11 (s, 9H); $^{13}$C NMR (125 MHz, DMSO-d$_{6}$) δ ppm 129.1, 127.2, 123.4, 123.2, 119.3, 117.6, 115.5, 112.0, 72.9, 68.4, 66.7, 61.0, 52.0, 47.0, 38.5, 33.9, 32.5, 31.0, 28.5, 27.1, 23.2, 23.1, 17.9, 17.8, −1.0; HRMS-ESI (m/z): [M+Na]$^{+}$ calcd for $C_{46}H_{60}FN_{7}NaO_{7}S_{2}Si$: 956.3641, found 956.3646.

Preparation 5f: Methyl 5-[3-[4-[3-(dimethylamino)prop-1-ynyl]-2-fluoro-phenoxy]propyl]-2-[5-hydroxypentyl-[5-methyl-6-[(Z)-[3-(2-trimethylsilylethoxymethyl)-1,3-benzothiazol-2-ylidene]amino]pyridazin-3-yl]amino]thiazole-4-carboxylate Step A: methyl 2-[5-[tert-butyl(dimethyl)silyl]oxypentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Buchwald General Procedure II starting from 3.68 g of Preparation 3t (6.22 mmol, 1 eq.) and 3.29 g of Preparation 4a (8.08 mmol, 1.3 eq.) as the appropriate halide, 3.92 g (65%) of the desired product was obtained.

$^{1}$H NMR (500 MHz, DMSO-d$_{6}$) δ ppm 7.133 (dm, 1H), 7.66 (s, 1H), 7.46 (dm, 1H), 7.43 (m, 1H), 7.30 (dd, 1H), 7.25 (m, 1H), 7.15 (dm, 1H), 5.85 (s, 2H), 4.40 (t, 2H), 4.14 (t, 2H), 4.14 (t, 1H), 3.77 (s, 3H), 3.71 (m, 2H), 3.54 (t, 2H), 3.38 (s, 2H), 3.26 (t, 2H), 2.44 (s, 3H), 2.19 (s, 6H), 2.12 (m, 2H), 1.70 (m, 2H), 1.49 (m, 2H), 1.37 (m, 2H), 0.91 (m, 2H), 0.79 (s, 9H), −0.06 (s, 6H), −0.12 (s, 9H); HRMS-ESI (m/z): [M+H]$^{+}$ calcd for $C_{48}H_{69}FN_{7}O_{5}S_{2}Si_{2}$: 962.4319, found 962.4301.

Step B: methyl 5-[3-[4-[3-(dimethylamino)prop-1-ynyl]-2-fluoro-phenoxy]propyl]-2-[5-hydroxypentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Deprotection of tert-butyl-dimethyl-silyl protecting group General Procedure starting from 3.91 g of the product from Step A (4.06 mmol, 1 eq.) and 1.18 g of [(1S,4R)-7, 7-dimethyl-2-oxo-norbornan-1-yl]methanesulfonic (5.08 mmol, 1.25 eq.), 2.61 g (76%) of the desired product was obtained.

$^{1}H$ NMR (500 MHz, DMSO-$d_6$) δ ppm 7.84 (dm, 1H), 7.67 (s, 1H), 7.47 (dm, 1H), 7.42 (td, 1H), 7.31 (dd, 1H), 7.25 (td, 1H), 7.21 (dd, 1H), 7.16 (t, 1H), 5.86 (s, 2H), 4.37 (m, 1H), 4.37 (m, 2H), 4.14 (t, 2H), 3.78 (s, 3H), 3.72 (t, 2H), 3.40 (m, 2H), 3.38 (s, 2H), 3.27 (m, 2H), 2.46 (s, 3H), 2.20 (s, 6H), 2.12 (m, 2H), 1.69 (m, 2H), 1.49 (m, 2H), 1.39 (m, 2H), 0.92 (t, 2H), −0.11 (s, 9H); $^{13}C$ NMR (125 MHz, DMSO-$d_6$) δ ppm 129.0, 127.2, 123.5, 123.2, 119.2, 117.6, 115.5, 111.9, 72.9, 68.4, 66.7, 61.0, 52.0, 48.1, 47.0, 44.2, 32.5, 31.0, 27.1, 23.1, 23.1, 17.8, 17.8, −0.9; HRMS-ESI (m/z): $[M+2H]^{2+}$ calcd for $C_{42}H_{56}FN_7O_5S_2Si$: 424.6764, found 424.6755.

Preparation 5g: Ethyl 5-(3-iodopropyl)-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Step A: ethyl 5-(3-chloropropyl)-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 3.15 g of Preparation 3e (12 mmol, 1.2 eq.) and 4.07 g of Preparation 4a (10 mmol, 1 eq.) as the appropriate halide, 2.6 g (41%) of the desired product was obtained.

$^{1}H$ NMR (500 MHz, DMSO-$d_6$) δ ppm 7.84 (d, 1H), 7.65 (s, 1H), 7.45 (d, 1H), 7.43 (tm, 1H), 7.25 (tm, 1H), 5.85 (s, 2H), 4.30 (q, 2H), 3.77 (s, 3H), 3.71 (t, 2H), 3.71 (t, 2H), 3.22 (t, 2H), 2.48 (s, 3H), 2.10 (quin, 2H), 1.31 (t, 3H), 0.92 (t, 2H), −0.11 (s, 9H); $^{13}C$ NMR (125 MHz, DMSO-$d_6$) δ ppm 162.6, 157.4, 156.8, 155.1, 151.7, 140.5, 137.6, 137.1, 135.3, 125.6, 123.5, 123.2, 123.1, 117.6, 111.9, 72.9, 66.7, 60.7, 45.3, 35.4, 34.4, 24.3, 18.0, 17.8, 14.7, −1.0; HRMS-ESI (m/z): $[M+H]^{+}$ calcd for $C_{28}H_{38}ClN_6O_3S_2Si$: 633.1899, found 633.1891.

Step B: ethyl 5-(3-iodopropyl)-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate A 100 mL one-necked, round-bottomed flask was equipped with a PTFE-coated magnetic stirring bar and fitted with a reflux condenser. It was charged with 2.6 g of the product from Step A (4.10 mmol, 1 eq.), 1.23 g of NaI (8.2 mmol, 2 eq.) and 20 mL of dry acetone. The reaction mixture was warmed up to 60° C. and stirred at that temperature for 3 days, when the reaction reached complete conversion. The reaction mixture was diluted with the addition of water then the precipitated product was collected by filtration, washed with water, and then dried on high vacuum to obtain 2.5 (84%) of the desired product.

$^{1}H$ NMR (500 MHz, DMSO-$d_6$) δ 7.82 (d, 1H), 7.61 (s, 1H), 7.47-7.39 (m, 1H), 7.47-7.39 (m, 1H), 7.23 (t, 1H), 5.83 (s, 2H), 4.29 (q, 2H), 3.75 (s, 3H), 3.71 (t, 2H), 3.33 (t, 2H), 3.16 (t, 2H), 2.42 (s, 3H), 2.13 (quint., 2H), 1.33 (t, 3H), 0.91 (t, 2H), −0.12 (s, 9H); $^{13}C$ NMR (125 MHz, DMSO-$d_6$) δ ppm 162.6, 157.3, 156.7, 155.1, 151.6, 140.2, 137.6, 137.1, 135.2, 127.1, 125.4, 123.4, 123.2, 117.5, 111.9, 72.8, 66.7, 60.7, 35.2, 35.2, 27.6, 17.8, 17.8, 14.8, 7.8, −1.0; HRMS-ESI (m/z): $[M+H]^{+}$ calcd for $C_{28}H_{38}IN_6O_3S_2Si$: 725.1255, found 725.1248.

Preparation 5h: Ethyl 5-[3-[4-[3-[tert-butoxycarbonyl-[2-(dimethylamino)ethyl]amino]prop-1-ynyl]-2-fluoro-phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Step A: tert-butyl N-[2-(dimethylamino)ethyl]-N-prop-2-ynyl-carbamate 365 mg of N',N'-dimethyl-N-prop-2-ynyl-ethane-1,2-diamine (1.83 mmol, 1 eq.) and 22 mg of N,N-dimethylpyridin-4-amine (0.18 mmol, 0.1 eq.) were mixed in dichloromethane (2.2 mL/mmol) then 600 mg of tert-butoxycarbonyl tert-butyl carbonate (2.75 mmol, 1.5 eq.) was added in one portion at rt and the mixture was and stirred at ambient temperature for 3 h. After the reaction time ca. 10 mL of DCM and ca. 10 mL of cc. $NaHCO_3$ were added, separated and the organic layer was dried over $MgSO_4$, filtered and concentrated. Yellowish oil was obtained as crude product: 332 mg (77%) of the desired product.

$^{1}H$ NMR (400 MHz, DMSO-$d_6$) δ ppm 4.02 (s, 2H), 3.29 (t, 2H), 3.18 (t, 1H), 2.37 (t, 2H), 2.15 (s, 6H), 1.40 (s, 9H); $^{13}C$ NMR (100 MHz, DMSO-$d_6$) δ ppm 149.3, 106.7, 79.2, 57.0, 45.3, 43.7, 38.6, 28.0.

Step B: (2-fluoro-4-iodo-phenoxy)-triisopropyl-silane

A 100 mL oven-dried, one-necked, round-bottomed flask was equipped with a PTFE-coated magnetic stirring bar. It was charged with 2.38 g of 2-fluoro-4-iodo-phenol (10.00 mmol), 1.98 g of $K_2CO_3$ (20.00 mmol, 2 eq.) and acetonitrile (4 mL/mmol). To the resulting mixture 2.31 g of chloro(triisopropyl)silane (12.00 mmol, 1.2 eq) was added dropwise near intensive stirring at rt. The resulting mixture was stirred at rt for 30 min, while the reaction reached complete conversion. The reaction mixture was filtered through a pad of Celite then concentrated onto Celite and purified via flash column chromatography using heptane and EtOAc as eluents to give 3.70 g (94%) of the desired product (94%) as a colorless oil.

$^{1}H$ NMR (500 MHz, DMSO-$d_6$) δ ppm 7.60 (dd, 1H), 7.40 (dm, 1H), 6.82 (dd, 1H), 1.24 (sp, 3H), 1.04 (d, 18H); $^{13}C$ NMR (125 MHz, DMSO-$d_6$) δ ppm 153.9, 143.8, 134.2, 125.5, 124.1, 83.6, 18.0, 12.5; HRMS-EI (m/z): $[M]^{+}$ calcd for $C_{15}H_{24}FIOSi$: 394.0625, found 394.0616.

Step C: tert-butyl N-[2-(dimethylamino)ethyl]-N-[3-(3-fluoro-4-triisopropylsilyloxy-phenyl)prop-2-ynyl]carbamate Using Sonogashira General Procedure starting from 99 mg of the product from Step B (0.25 mmol, 1 eq.) and 73 mg of the product from Step A to give 90 mg (75%) of the desired product as yellow oil.

$^{1}H$ NMR (400 MHz, DMSO-$d_6$) δ ppm 7.09 (dd, 1H), 7.03 (d, 1H), 6.83 (t, 1H), 4.40-4.15 (br., 2H), 3.46 (brt., 2H), 2.50 (t, 2H), 2.26 (s, 6H), 1.47 (s, 9H), 1.25 (m, 3H), 1.07 (d, 18H); $^{13}C$ NMR (100 MHz, DMSO-$d_6$) δ ppm 128.1, 121.6, 119.7, 57.5, 45.7, 44.2, 37.8, 36.8, 28.4, 17.7, 12.7; HRMS-ESI (m/z): $[M+H]^{+}$ calcd for $C_{27}H_{46}FN_2O_3Si$: 493.3256, found 493.3264.

Step D: ethyl 5-[3-[4-[3-[tert-butoxycarbonyl-[2-(dimethylamino)ethyl]amino]prop-1-ynyl]-2-fluoro-phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation of Silyl-Protected Phenols General Procedure starting from 147 mg of Preparation 5g, Step B (0.20 mmol, 1 eq.) and 100 mg of the product from Step C (0.20 mmol, 1 eq.) to give 164 mg (87%) of the desired product as brown solid.

$^1$H NMR (500 MHz, DMSO-$d_6$) δ ppm 7.84 (d, 1H), 7.66 (s, 1H), 7.45 (m, 1H), 7.44 (td, 1H), 7.30 (br, 1H), 7.25 (td, 1H), 7.20 (m, 1H), 7.17 (t, 1H), 5.86 (s, 2H), 4.26 (q, 2H), 4.22 (br, 2H), 4.15 (t, 2H), 3.77 (s, 3H), 3.72 (t, 2H), 3.37 (m, 2H), 3.27 (t, 2H), 2.48 (m, 2H), 2.45 (s, 3H), 2.22 (br, 6H), 2.12 (quin, 2H), 1.41 (s, 9H), 1.28 (t, 3H), 0.92 (t, 2H), −0.10 (s, 9H); $^{13}$C NMR (125 MHz, DMSO-$d_6$) δ ppm 171.0, 157.6, 156.7, 155.3, 154.7, 151.7, 151.5, 147.6, 141.2, 137.6, 137.1, 135.3, 129.0, 127.2, 125.4, 123.5, 123.1, 119.2, 117.8, 115.5, 114.7, 111.9, 85.6, 82.1, 79.9, 72.8, 68.7, 66.7, 60.3, 57.0, 45.8, 44.0, 36.9, 35.2, 31.2, 28.5, 23.3, 17.8, 17.5, 14.7, −1.0; HRMS-ESI (m/z): [M+H]$^+$ calcd for $C_{46}H_{62}FN_8O_6S_2Si$: 933.3982, found 933.3977.

Preparation 5i: Methyl 5-[3-[4-[3-(tert-butoxycarbonylamino)prop-1-ynyl]-2-fluoro-phenoxy]propyl]-2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 780 mg of Preparation 3g (1.20 mmol, 1 eq.) and 489 mg of Preparation 4a (1.20 mmol, 1 eq.) as the appropriate halide, 570 mg (47%) of the desired product was obtained.

$^1$H NMR (500 MHz, DMSO-$d_6$) δ ppm 7.83 (dd, 1H), 7.64 (s, 1H), 7.45 (dd, 1H), 7.43 (m, 1H), 7.33 (t, 1H), 7.27 (dd, 1H), 7.26 (m, 1H), 7.18 (m, 1H), 7.15 (t, 1H), 5.85 (s, 2H), 4.41 (t, 2H), 4.14 (t, 2H), 3.93 (d, 2H), 3.76 (s, 3H), 3.71 (t, 2H), 3.61 (t, 2H), 3.25 (t, 2H), 2.44 (s, 3H), 2.12 (m, 2H), 1.74 (m, 2H), 1.51 (nt, 2H), 1.39 (s, 9H), 0.91 (t, 2H), 0.79 (s, 9H), −0.03 (s, 6H), −0.12 (s, 9H); $^{13}$C NMR (125 MHz, DMSO-$d_6$) δ ppm 162.2, 147.4, 137.6, 129.0, 127.2, 123.4, 123.2, 119.2, 117.6, 115.4, 111.9, 80.8, 72.8, 68.4, 66.7, 62.5, 51.9, 46.5, 31.1, 30.5, 29.7, 28.7, 26.1, 23.8, 23.1, 17.9, 17.8, −1.0, −4.9; HRMS-ESI (m/z): [M+H]$^+$ calcd for $C_{50}H_{71}FN_7O_7S_2Si_2$: 1020.4373, found 1020.4373.

Preparation 5j: Ethyl 5-(3-{2-fluoro-4-[3-(methylamino)prop-1-yn-1-yl]phenoxy}propyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Step A: ethyl 5-{3-[4-(3-{[(tert-butoxy)carbonyl](methyl)amino}prop-1-yn-1-yl)-2-fluorophenoxy]propyl}-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To the product from Preparation 5g (1.75 g, 2.41 mmol, 1 eq) in dimethylformamide (50 mL) was added the product from Preparation 6a (877 mg, 3.14 mmol, 1.3 eq) in dimethylformamide (10 mL) and cesium carbonate (2.36 g, 7.24 mmol, 3 eq) and the mixture was heated at 80° C. for 16 h. The reaction was concentrated in vacuo then partitioned between ethyl acetate and brine, and the organic phase was dried (magnesium sulfate) and concentrated it vacuo. Purification by automated flash column chromatography (CombiFlash Rf, 40 g RediSep™ silica cartridge) eluting with a gradient of 0-50% ethyl acetate in iso-heptane afforded the desired product as a yellow oil (1.75 g, 2 mmol, 83%).

LC/MS ($C_{43}H_{54}FN_7O_6SiS_2$) 876 [M+H]$^+$; RT 1.46 (LCMS-V-B2)

$^1$H NMR (400 MHz, DMSO-d6) δ 7.83 (dd, 1H), 7.65 (d, J=1.1 Hz, 1H), 7.49-7.39 (m, 214), 7.35-7.28 (m, 1H), 7.27-7.12 (m, 3H), 5.86 (s, 2H), 4.25 (q, J=7.1 Hz, 2H), 4.19 (s, 2H), 4.14 (t, J=6.1 Hz, 2H) 3.77 (s, 3H), 3.76-3.68 (m, 2H), 3.26 (t, J=7.7 Hz, 2H), 2.84 (s, 3H), 2.45 (s, 3H), 2.19-2.05 (m, 1H), 1.41 (s, 9H), 1.30 (t, 3H), 0.97-0.88 (m, 2H), −0.12 (s, 9H).

Step B: ethyl 5-(3-{2-fluoro-4-[3-(methylamino)prop-1-yn-1-yl]phenoxy}propyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Trifluoroacetic acid (20 mL) was added to a stirred solution of the product from Step A (1.5 g, 1.71 mmol, 1 eq) in dichloromethane (60 mL) and the mixture was stirred at ambient temperature for 5 h. The reaction was diluted with dichloromethane, cooled to 0° C. and basified by the addition of 2N aqueous sodium hydroxide. The organic phase was dried (magnesium sulfate) and concentrated in vacuo. Purification by automated flash column chromatography (CombiFlash Rf, 40 g RediSep™ silica cartridge) eluting with a gradient of 0-10% methanol in dichloromethane afforded the desired product as a yellow gum (329 mg, 0.42 mmol, 25%).

LC/MS ($C_{38}H_{46}FN_7O_4SiS_2$) 776 [M+H]$^+$; RT 2.58 (LCMS-V-C)

$^1$H NMR (400 MHz, DMSO-d6) δ 7.84 (dd, 1H), 7.67 (d, J=1.0 Hz, 1H), 7.49-7.40 (m, 2H), 7.31-7.22 (m, 2H), 7.21-7.11 (m, 2H), 5.86 (s, 2H), 4.26 (q, J=7.1 Hz, 2H), 4.15 (t, J=6.1 Hz, 2H), 3.76 (s, 3H), 3.76-3.67 (m, 2H), 3.45 (s, 2H), 3.33-3.22 (m, 2H), 2.46 (d, J=1.0 Hz, 3H), 2.30 (s, 3H), 2.18-2.06 (m, 2H), 1.29 (t, J=7.1 Hz, 3H), 0.97-0.88 (m, 2H), 0.11 (s, 9H).

Preparation 5k: Ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(piperidin-4-yl)-1,3-thiazole-4-carboxylate Step A: bromo({1-[(tert-butoxy)carbonyl]piperidin-4-yl})zinc To a 50 mL Schlenk flask equipped with a magnetic stirrer bar was added zinc (1.96 g, 30 mmol, 1.5 eq) and lithium chloride (1.27 g, 30 mmol, 1.5 eq) and the mixture was heated with a heat gun under high vacuum (<1 mbar) for 10 min with gentle stirring. While still under high vacuum the mixture was allowed to cool to ambient temperature, and was then swapped to the Schlenk line and back-filled with nitrogen. Tetrahydrofuran (15 mL) was added followed by 1,2-dibromoethane (0.06 mL, 0.75 mmol, 0.04 eq) and the mixture was heated to 60° C. over 10 min. The reaction was then removed from the heat and trimethylchlorosilane (0.02 mL, 0.15 mmol, 0.01 eq) was added, followed by iodine (0.5M in tetrahydrofuran; 0.15 mL, 0.175 mmol, 0.05 eq). The mixture was then heated at 60° C. for 10 min before cooling to <35° C. A solution of tert-butyl 4-bromopiperidine-1-carboxylate (5.28 g, 20 mmol, 1 eq) in tetrahydrofuran (10 mL) was added over 3 min and the mixture was then stirred at 50° C. for 6 h, then at ambient temperature overnight. The reaction was allowed to cool to ambient temperature then cannulation through a filter (cotton-wool/celite/cotton-wool) under slight vacuum into a dry 25 mL Schlenk tube afforded the desired product as a 0.5M solution (as determined by titration with a 0.5M solution of iodine) that was used without further characterisation.

Step B: tert-butyl 4-[4-(ethoxycarbonyl)-2-[methyl (5-methyl-6-{[(2Z)-3-{[2-(trimethylsilyl)ethoxy] methyl}-2,3-dihydro-1,3-benzothiazol-2-ylidene] amino}pyridazin-3-yl)amino]-1,3-thiazol-5-yl] piperidine-1-carboxylate To an oven dried flask was added the product from Preparation 11b (500 mg, 0.79 mmol, 1 eq) and Copper(I) Iodide (300 mg, 1.57 mmol, 2 eq) and the mixture was evacuated and purged with nitrogen (×3). Dimethylacetamide (15 mL) was added, resulting in a brown suspension that was allowed to stir for 5 mins. The product from Step A (0.5M in tetrahydrofuran; 9.44 mL, 4.72 mmol, 6 eq) was added and the mixture was stirred at ambient temperature overnight. The reaction was quenched by the addition of saturated aqueous ammonium chloride (25 mL), then further diluted with 1:1 water/saturated aqueous ammonium chloride (150 mL). The organics were extracted with dichloromethane (×3) and the combined organic extracts were washed with brine, dried (magnesium sulfate), and concentrated in vacuo. Purification by automated flash column chromatography (CombiFlash Rf, 40 g RediSep™ silica cartridge) eluting with a gradient of 0-40% ethyl acetate in iso-heptane afforded the desired product as a pale yellow foam (429 mg, 0.58 mmol, 74%).

LC/MS ($C_{35}H_{49}N_7O_5SiS_2$) 740 $[M+H]^+$; RT 1.40 (LCMS-V-B2)

$^1$H NMR (400 MHz, $CDCl_3$) δ 7.63 (dt, J=7.7, 1.0 Hz, 1H), 7.46-7.34 (m, 2H), 7.31 (d, J=1.2 Hz, 1H), 7.22 (ddd, J=7.7, 5.8, 2.6 Hz, 1H), 5.85 (s, 2H), 4.40 (q, J=7.1 Hz, 2H), 4.26 (s, 2H), 3.90 (ddd, J=12.1, 8.5, 3.7 Hz, 1H), 3.85 (s, 3H), 3.80-3.69 (m, 2H), 2.85 (s, 2H), 2.47 (d, J=1.0 Hz, 3H), 2.04 (d, J=12.8 Hz, 2H), 1.71 (q, J=12.1 Hz, 2H), 1.50 (s, 9H), 1.47 (s, 0H), 1.44 (t, J=7.1 Hz, 3H), 1.02-0.93 (m, 2H), −0.07 (s, 9H).

Step C: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-3-(piperidin-4-yl)-1,3-thiazole-4-carboxylate Trifluoroacetic acid (0.5 mL, 6.71 mmol, 49.7 eq) was added slowly to a cooled solution of the product from Step B (100 mg, 0.14 mmol, 1 eq) in dichloromethane (6 mL) and the mixture was stirred at 0° C. for 1.5 h. The reaction was quenched by the addition of saturated aqueous sodium bicarbonate, extracted with dichloromethane, and the organic extract washed with brine, dried (magnesium sulfate), and concentrated in vacuo. Purification by automated flash column chromatography (CombiFlash Rf, 12 g RediSep™ silica cartridge) eluting with a gradient of 0-10% methanol in dichloromethane afforded the desired product as an off-white glass (59 mg, 0.09 mmol, 68%).

LC/MS ($C_{30}H_{41}N_7O_3SiS_2$) 640 $[M+H]^+$; RT 1.23 (LCMS-V-B1)

$^1$H NMR (400 MHz, DMSO-d6) δ 7.85 (dd, J=7.6, 1.1 Hz, 1H), 7.67 (d, J=1.1 Hz, 1H), 7.51-7.40 (m, 2H), 7.25 (ddd, J=8.3, 6.9, 1.5 Hz, 1H), 5.87 (s, 2H), 4.29 (q, J=7.1 Hz, 2H), 3.90-3.61 (m, 6H), 3.12 (d, J=12.2 Hz, 2H), 2.68 (td, J=12.5, 2.3 Hz, 3H), 2.46 (d, J=1.0 Hz, 3H), 2.00-1.89 (m, 2H), 1.71-1.54 (m, 2H), 1.32 (t, J=7.1 Hz, 3H), 0.92 (dd, J=8.6, 7.4 Hz, 2H), −0.11 (s, 9H).

Preparation 51: Ethyl 5-(azetidin-3-yl)-2-[methyl(5-methyl-6-{[(2Z)-3-{[2-(trimethylsilyl)ethoxy] methyl}-2,3-dihydro-1,3-benzothiazol-2-ylidene] amino}pyridazin-3-yl)amino]-1,3-thiazole-4-carboxylate Step A: ethyl 5-{1-[(tert-butoxy)carbonyl]azetidin-3-yl}-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 4a (401 mg, 0.98 mmol, 2 eq) in 1,4-dioxane (5 mL) was added the product from Preparation 3zb (168 mg, 0.49 mmol, 1 eq), N,N-diisopropylethylamine (0.24 mL, 1.48 mmol, 3 eq), cesium carbonate (481 mg, 1.48 mmol, 3 eq) and Xantphos (56.9 mg, 0.1 mmol, 0.2 eq) and the mixture was sparged with nitrogen (10 min). Tris(dibenzylideneacetone)dipalladium(0)(45.1 mg, 0.05 mmol, 0.1 eq) was added and the mixture was heated at 120° C. for 2 h under microwave irradiation. The reaction was diluted with dichloromethane then washed with water followed by brine, dried (magnesium sulfate), and concentrated in vacuo. Purification by automated flash column chromatography (CombiFlash Rf, 24 g RediSep™ silica cartridge) eluting with a gradient of 0-100% ethyl acetate in iso-heptane afforded the desired product as a brown solid (99 mg, 0.14 mmol, 28%).

LC/MS ($C_{33}H_{45}N_7O_5SiS_2$) 712 $[M+H]^+$; RT 1.52 (LCMS-V-B1)

$^1$H NMR (400 MHz, DMSO-d6) δ 7.90-7.81 (m, 1H), 7.70 (d, J=1.1 Hz, 1H), 7.52-7.39 (m, 2H), 7.29-7.21 (m, 1H), 5.87 (s, 2H), 4.59 (tt, J=8.6, 6.0 Hz, 1H), 4.37 (t, J=8.6 Hz, 2H), 4.29 (q, J=7.1 Hz, 2H), 3.89 (t, J=7.3 Hz, 2H), 3.79 (s, 3H), 3.76-3.68 (m, 2H), 2.46 (d, J=1.0 Hz, 3H), 1.43 (s, 9H), 1.32 (t, J=7.1 Hz, 3H), 0.99-0.83 (m, 2H), −0.11 (s, 9H).

Step B: ethyl 5-(azetidin-3-yl)-2-[methyl(5-methyl-6-{[(2Z)-3-{[2-(trimethylsilyl)ethoxy]methyl}-2,3-dihydro-1,3-benzothiazol-2-ylidene] amino}pyridazin-3-yl)amino]-1,3-thiazole-4-carboxylate To a solution of the product from Step A (78 mg, 0.11 mmol, 1 eq) in dichloromethane (6 mL), cooled in an ice-bath, was slowly added trifluoroacetic acid (0.5 mL, 6.71 mmol, 61.2 eq) slowly and the mixture was stirred at 0° C. for 5 h. The reaction was quenched by the addition of saturated aqueous sodium bicarbonate, then extracted with dichloromethane, washed with brine, dried (magnesium sulfate), and concentrated in vacuo. Purification by automated flash column chromatography (CombiFlash Rf, 12 g RediSep™ silica cartridge) eluting with a gradient of 0-10% methanol in dichloromethane afforded the desired product as a cream solid (29.6 mg, 0.05 mmol, 44%).

LC/MS ($C_{28}H_{37}N_7O_3SiS_2$) 612 $[M+H]^+$; RT 1.18 (LCMS-V-B1)

$^1H$ NMR (400 MHz, DMSO-d6) δ 7.83 (d, J=7.7 Hz, 1H), 7.71 (s, 1H), 7.52-7.40 (m, 2H), 7.30-7.23 (m, 1H), 5.87 (s, 2H), 4.76 (p, J=8.2 Hz, 1H), 4.29 (q, J=7.1 Hz, 2H), 4.17 (t, J=9.0 Hz, 2H), 3.91 (r, J=8.5 Hz, 2H), 3.79 (s, 3H), 3.75-3.66 (m, 2H), 2.47 (s, 3H), 1.32 (t, J=7.1 Hz, 3H), 0.98-0.87 (m, 2H), −0.11 (s, 9H).

Preparation 5m: Ethyl 5-[(1E)-3-hydroxy-2-methyl-prop-1-en-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate

Step A: tert-butyldimethyl(prop-2-yn-1-yloxy)silane

To a cooled solution of propargyl alcohol (5.21 mL, 89.2 mmol, 1 eq) in dichloromethane (250 mL) was added imidazole (8.84 mL, 134 mmol, 1.5 eq) and tert-butyldimethylsilyl chloride (20.2 g, 134 mmol, 1.5 eq) and the mixture was stirred at 0° C. for 90 min. The reaction was partitioned between dichloromethane and saturated aqueous ammonium chloride, separated (PTFE phase separator), and the organic phase concentrated in vacuo. Purification by automated flash column chromatography (CombiFlash Rf, 220 g RediSep™ silica cartridge) eluting with a gradient of 0-10% ethyl acetate in iso-heptane afforded the desired product as a clear oil (4.07 g, 23.9 mmol, 27%).

$^1H$ NMR (400 MHz, DMSO-d6) δ 4.28 (d, J=2.4 Hz, 2H), 3.37 (t, J=2.4 Hz, 1H), 0.86 (s, 9H), 0.08 (s, 6H).

Step B: tert-butyldimethyl{[(2E)-2-methyl-3-(4,4,5,5-tetramethyl-1,3,2-dioxaborolan-2-yl)prop-2-en-1-yl]oxy}silane To an oven-dried flask was added copper(I) chloride (237 mg, 2.39 mmol, 0.1 eq), Xantphos (1.38 g, 2.39 mmol, 0.1 eq), bis(pinacolato)diboron (6.67 g, 26.3 mmol, 1.1 eq) and tetrahydrofuran (17 mL) and the mixture was sparged with nitrogen (10 min). A solution of sodium 2-methylpropan-2-olate (2.53 g, 26.3 mmol, 1.1 eq) in tetrahydrofuran (14 mL) was added and the mixture was stirred for 5 min. A solution of the product from Step A (4.07 g, 23.9 mmol, 1 eq) in tetrahydrofuran (14 mL) was added followed by methyl iodide (5.95 mL, 95.6 mmol, 4 eq) and the mixture was stirred at ambient temperature overnight. The reaction was partitioned between ethyl acetate and water, and the organic phase was dried (magnesium sulfate), and concentrated in vacuo. Purification by automated flash column chromatography (CombiFlash Rf, 80 g RediSep™ silica cartridge) eluting with a gradient of 0-5% ethyl acetate in iso-heptane afforded the desired product as a clear oil (616 mg, 1.97 mmol, 8%).

$^1H$ NMR (400 MHz, DMSO-d6) δ 5.34-5.30 (m, 1H), 4.04-3.97 (m, 2H), 1.83 (s, 3H), 1.23-1.16 (m, 12H), 0.88 (s, 9H), 0.03 (s, 6H).

Step C: ethyl 5-[(1E)-3-[(tert-butyldimethylsilyl)oxy]-2-methylprop-1-en-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 11e (224 mg, 0.33 mmol, 1 eq) in tetrahydrofuran (7.5 mL) was added the product from Step B (123 mg, 0.39 mmol, 1.2 eq), followed by water (2.5 mL) and potassium carbonate (136 mg, 0.98 mmol, 3 eq). The mixture was sparged with nitrogen (10 min) before adding [1,1'-bis(diphenylphosphino)ferrocene]dichloropalladium(II) (24 mg, 0.03 mmol, 0.1 eq) and the mixture was heated at 100° C. for 1 h under microwave irradiation. The reaction was partitioned between ethyl acetate and brine, and the organic phase was dried (magnesium sulfate) and concentrated in vacuo. Purification by automated flash column chromatography (CombiFlash Rf, 12 g RediSep™ silica cartridge) eluting with a gradient of 0-40% ethyl acetate in iso-heptane afforded the desired product as a white solid (192 mg, 0.26 mmol, 79%).

LC/MS ($C_{35}H_{52}N_6O_4Si_2S_2$) 741 $[M+H]^+$; RT 1.58 (LCMS-V-B2)

$^1H$ NMR (400 MHz, DMSO-$d_6$) δ 7.86-7.79 (m, 1H), 7.70 (d, J=1.1 Hz, 1H), 7.51-7.40 (m, 2H), 7.29-7.20 (m, 2H), 5.86 (s, 2H), 4.28 (q, 2H), 4.22 (s, 2H), 3.79 (s, 3H), 3.76-3.67 (m, 2H), 2.46 (s, 3H), 1.93 (s, 3H), 1.30 (t, 3H), 0.93 (s, 9H), 0.91-0.83 (m, 2H), 0.11 (s, 6H), −0.12 (s, 9H).

Step D: ethyl 5-[(1E)-3-hydroxy-2-methylprop-1-en-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Step C (192 mg, 0.26 mmol, 1 eq) in tetrahydrofuran (6 mL) was added tetrabutylammonium fluoride (1M in tetrahydrofuran; 0.39 mL, 0.39 mmol, 1.5 eq) and the mixture was stirred at ambient temperature for 2 h. The reaction was partitioned between ethyl acetate and water, and the organic phase was dried (magnesium sulfate) and concentrated in vacuo. Purification by automated flash column chromatography (CombiFlash Rf, 4 g RediSep™ silica cartridge) eluting with a gradient of 0-60% ethyl acetate in iso-heptane afforded the desired product as a yellow solid (160 mg, 0.26 mmol, 99%).

LC/MS ($C_{29}H_{38}N_6O_4SiS_2$) 627 $[M+H]^+$; RT 2.71 (LCMS-V-C)

$^1H$ NMR (400 MHz, DMSO-d6) δ 7.86-7.80 (m, 1H), 7.70 (d, J=1.1 Hz, 1H), 7.49-7.39 (m, 2H), 7.28-7.21 (m, 2H), 5.86 (s, 2H), 5.12 (t, J=5.7 Hz, 1H), 4.29 (q, J=7.1 Hz, 2H), 4.09-3.98 (m, 2H), 3.81 (s, 3H), 3.77-3.67 (m, 2H), 2.46 (d, J=6.8 Hz, 3H), 1.94 (s, 3H), 1.31 (t, J=7.1 Hz, 3H), 0.97-0.89 (m, 2H), −0.12 (s, 9H).

Preparation 6a: tert-Butyl N-[3-(3-fluoro-4-hydroxy-phenyl)prop-2-ynyl]-N-methylcarbamate Using Sonogashira General Procedure starting from 10.00 g of 2-fluoro-4-iodo-phenol (42.0 mmol, 1 eq.) as the appropriate phenol and 10.67 g of tert-butyl N-methyl-N-prop-2-ynyl-carbamate (63.1 mmol, 1.5 eq.) as alkyne reactant, 10.8 g (92%) of the desired product was obtained.

$^1H$ NMR (500 MHz, DMSO-$d_6$) δ ppm 10.32 (s, 1H), 7.22 (brd, 1H), 7.08 (dm, 1H), 6.92 (dd, 1H), 4.21 (s, 2H), 2.85 (s, 3H), 1.41 (s, 9H); $^{13}C$ NMR (125 MHz, DMSO-$d_6$) δ ppm 150.8, 146.4, 129.0, 119.6, 118.4, 113.2, 84.4, 82.7, 38.5, 33.8, 28.5; HRMS-ESI (m/z): $[M-C_4H_8+H]^+$ calcd for $C_{11}H_{11}FNO_3$: 224.0717, found 224.0720.

Preparation 6b: 4-[3-(Dimethylamino)prop-1-ynyl]-2-fluoro-phenol

Using Sonogashira General Procedure starting from 10.00 g of 2-fluoro-4-iodo-phenol (42.0 mmol, 1 eq.) as the appropriate phenol and 5.24 g of N,N-dimethylprop-2-yn-1-amine (63 mmol, 1.5 eq.) as alkyne reactant, 7.30 g (90%) of the desired product was obtained.

$^1$H NMR (500 MHz, DMSO-$d_6$) δ ppm 7.20 (dd, 1H), 7.07 (dm, 1H), 6.91 (m, 1H), 3.39 (m, 2H), 2.21 (m, 3H); $^{13}$C NMR (125 MHz, DMSO-$d_6$) δ ppm 150.9, 146.2, 128.9, 119.5, 118.4, 113.6, 84.5, 84.2, 48.2, 44.3; HRMS-ESI (m/z): $[M+H]^+$ calcd for $C_{11}H_{13}FNO$: 194.0976, found 194.0981.

Preparation 6c: 2-Fluoro-4-(3-pyrrolidin-1-ylprop-1-ynyl)phenol

Step A: 3-(3-fluoro-4-triisopropylsilyloxy-phenyl) prop-2-yn-1-ol

A 500 mL oven-dried, one-necked, round-bottomed flask equipped with a PTFE-coated magnetic stirring bar was charged with 4.76 g of 2-fluoro-4-iodophenol (20 mmol, 1 eq.) and 3.96 g of $K_2CO_3$ (40 mmol, 2 eq.) then 100 mL of dry MeCN was added. To the resulting mixture 5.13 mL of TIPSCl (4.62 g, 24 mmol, 1.2 eq.) was added dropwise near intensive stirring at rt. The resulting mixture was stirred at room temperature for 30 min, while the reaction reached complete conversion. The reaction mixture was filtered through a pad of Celite to remove the solid particles then to the filtrate 2.33 mL of prop-2-yn-1-ol (2.24 g, 40 mmol, 2 eq.) and 20 mL of DCPA were added and placed under a nitrogen atmosphere through a gas inlet. After addition of 702 mg of $Pd(PPh_3)_2Cl_2$ (1 mmol, 0.05 eq.) and 190 mg of CuI (1 mmol, 0.05 eq.) the resulting mixture was stirred at room temperature for 30 min, while the reaction reached complete conversion. Celite was added to the reaction mixture and the volatiles were removed under reduced pressure. Then it was purified via flash column chromatography using heptane and EtOAc as eluents to give 5.2 g (81%) of the desired product as brown oil.

$^1$H NMR (500 MHz, DMSO-$d_6$) δ ppm 7.26 (dd, 1H), 7.14 (dm, 1H), 6.96 (t, 1H), 4.27 (d, 2H), 1.23 (m, 3H), 1.03 (d, 18H); $^{13}$C NMR (125 MHz, DMSO-$d_6$) δ ppm 153.3, 144.1, 128.8, 122.3, 119.6, 116.5, 89.8, 82.8, 49.8, 17.9, 12.5; HRMS-ESI (m/z): $[M+H]^+$ calcd for $C_{18}H_{28}FO_2Si$: 323.1837, found 323.1832.

Step B: [2-fluoro-4-(3-pyrrolidin-1-ylprop-1-ynyl) phenoxy]-triisopropyl-silane Using Alkylation with in situ generated iodine General Procedure starting from 322 mg of the product from Step A (1 mmol, 1 eq.) as the appropriate alcohol and 355 mg of pyrrolidine (5 mmol, 5 eq.), 130 mg (34%) of the desired product was obtained.

$^1$H NMR (500 MHz, DMSO-$d_6$) δ ppm 7.29 (dd, 1H), 7.14 (dm, 1H), 6.97 (t, 1H), 3.56 (s, 2H), 2.55 (m, 4H), 1.71 (m, 4H), 1.25 (m, 3H), 1.05 (d, 18H); $^{13}$C NMR (125 MHz, DMSO-$d_6$) δ ppm 153.2, 144.0, 129.0, 122.3, 119.8, 116.6, 86.2, 83.2, 52.3, 43.3, 23.8, 18.0, 12.5; HRMS-ESI (m/z): $[M+H]^+$ calcd for $C_{22}H_{35}FNOSi$: 376.2466, found 376.2456.

Step C: 2-fluoro-4-(3-pyrrolidin-1-ylprop-1-ynyl)phenol

A 4 mL oven-dried vial equipped with a PTFE-coated magnetic stirring bar was charged with 83 mg of the product from Step B (0.221 mmol, 1 eq.) and 1.1 mL of dry THF then 265 uL of TBAF (1 M in THF, 225.9 mg, 0.2652 mmol, 1.2 eq.) was added dropwise at rt. The resulting mixture was stirred at rt for 15 min, when the reaction reached complete conversion. The reaction mixture was quenched with the addition of 200 uL of cc. $NH_4Cl$ then Celite was added to the reaction mixture and the volatiles were removed under reduced pressure. Then it was purified via flash column chromatography using DCM and MeOH (1.2% $NH_3$) as eluents to give 43 mg (88%) of the desired product.

$^1$H NMR (500 MHz, DMSO-$d_6$) δ ppm 10.30 (brs, 1H), 7.17 (dd, 1H), 7.04 (dm, 1H), 6.88 (t, 1H), 3.53 (s, 2H), 2.54 (m, 4H), 1.70 (m, 4H); $^{13}$C NMR (125 MHz, DMSO-$d_6$) δ ppm 151.1, 146.8, 128.9, 119.4, 118.5, 113.1, 84.8, 83.8, 52.3, 43.4, 23.8; HRMS-ESI (m/z): $[M+H]^+$ calcd for $C_{13}H_{15}FNO$: 220.1132, found 220.1129.

Preparation 6d: 2-Fluoro-4-[3-(1-piperidyl)prop-1-ynyl]phenol

Step A: [2-fluoro-4-[3-(1-piperidyl)prop-1-ynyl] phenoxy]-triisopropyl-silane Using Alkylation with in situ generated iodine General Procedure starting from 322 mg of Preparation 6c, Step A (1 mmol, 1 eq.) as the appropriate alcohol and 425 mg of piperidine (5 mmol, 5 eq.), 250 mg (64%) of the desired product was obtained.

$^1$H NMR (500 MHz, DMSO-$d_6$) δ ppm 7.3 (dd, 1H), 7.15 (dm, 1H), 6.98 (t, 1H), 3.42 (s, 2H), 2.46 (br., 4H), 1.51 (m, 4H), 1.37 (br., 2H), 1.26 (m, 3H), 1.05 (d, 18H); $^{13}$C NMR (125 MHz, DMSO-$d_6$) δ ppm 153.2, 144.0, 129.0, 122.3, 119.8, 116.6, 85.9, 83.8, 53.1, 48.0, 25.9, 24.0, 18.0, 12.5; HRMS-ESI (m/z): $[M+H]^+$ calcd for $C_{23}H_{37}FNOSi$: 390.2622, found 390.2608.

Step B: 2-fluoro-4-[3-(1-piperidyl)prop-1-ynyl]phenol

A 4 mL oven-dried vial equipped with a PTFE-coated magnetic stirring bar was charged with 272 mg of the product from Step A (0.69 mmol, 1 eq.) dissolved in 3.5 mL of dry THF and then 698 uL of TBAF (1 M in THF, 0.69 mmol, 1 eq.) was added dropwise at rt. The resulting mixture was stirred at rt for 15 min, when the reaction reached complete conversion. The reaction mixture was quenched with the addition of 200 uL of cc. $NH_4Cl$ then Celite was added to the reaction mixture and the volatiles were removed under reduced pressure. Then it was purified via flash column chromatography using DCM and MeOH (1.2% $NH_3$) as eluents to give 143 mg (87%) of the desired product.

$^1$H NMR (500 MHz, DMSO-$d_6$) δ ppm 10.27 (s, 1H), 7.20 (dd, 1H), 7.07 (dm, 1H), 6.90 (t, 1H), 3.40 (s, 2H), 2.44 (br, 4H), 1.51 (m, 4H), 1.37 (br, 2H); $^{13}$C NMR (125 MHz, DMSO-$d_6$) δ ppm 150.9, 146.1, 128.9, 119.5, 118.4, 113.7, 84.7, 84.2, 53.1, 48.0, 25.9, 24.1; HRMS-ESI (m/z): $[M+H]^+$ calcd for $C_{14}H_{17}FNO$: 234.1289, found 234.1292.

Preparation 6e: 2-Fluoro-4-(3-morpholinoprop-1-ynyl)phenol

Step A: [2-fluoro-4-(3-morpholinoprop-1-ynyl)phenoxy]-triisopropyl-silane

Using Alkylation with in situ generated iodine General Procedure starting from 322 mg of Preparation 6c, Step A (1 mmol, 1 eq.) as the appropriate alcohol and 435 mg of morpholine (5 mmol, 5 eq.), 160 mg (41%) of the desired product was obtained.

$^1$H NMR (500 MHz, DMSO-$d_6$) δ ppm 7.32 (dd, 1H), 7.16 (dd, 1H), 6.98 (t, 1H), 3.6 (t, 4H), 3.47 (s, 2H), 2.49 (t, 4H), 1.25 (m, 3H), 1.05 (d, 18H); $^{13}$C NMR (125 MHz, DMSO-$d_6$) δ ppm 153.3, 144.1, 129.0, 122.3, 119.8, 116.4, 85.3, 84.1, 66.6, 52.3, 47.5, 18.0, 12.5; HRMS-ESI (m/z): $[M+H]^+$ calcd for $C_{22}H_{35}FNO_2Si$: 392.2415, found 392.2408.

Step B: 2-fluoro-4-(3-morpholinoprop-1-ynyl)phenol

A 4 mL oven-dried vial equipped with a PTFE-coated magnetic stirring bar was charged with 220 mg of the product from Step A (0.56 mmol, 1 eq.) dissolved in 3.0 mL of dry THF then 525 uL of TBAF (1 M in THF, 0.52 mmol, 1 eq.) was added dropwise at rt. The resulting mixture was stirred at rt for 15 min, when the reaction reached complete conversion. The reaction mixture was quenched with the addition of 200 uL of cc. $NH_4Cl$, then Celite was added to the reaction mixture and the volatiles were removed under reduced pressure. It was purified via flash column chromatography using DCM and MeOH (1.2% $NH_3$) as eluents to give 120 mg (91%) of the desired product.

$^1$H NMR (400 MHz, DMSO-$d_6$) δ ppm 10.28 (s, 1H), 7.22 (dd, 1H), 7.08 (dm, 1H), 6.91 (dd, 1H), 3.60 (m, 4H), 3.45 (s, 2H), 2.48 (m, 4H); $^{13}$C NMR (125 MHz, DMSO-$d_6$) δ ppm 150.8, 146.2, 128.9, 119.5, 118.4, 113.6, 84.6, 84.1, 66.5, 52.2, 47.5; HRMS-ESI (m/z): $[M+H]^+$ calcd for $C_{13}H_{15}FNO_2$: 236.1081, found 236.1082.

Preparation 6f: 4-[3-(Dimethylamino)but-1-ynyl]-2-fluoro-phenol

Step A: 4-(3-fluoro-4-triisopropylsilyloxy-phenyl)but-3-yn-2-ol

A 500 mL oven-dried, one-necked, round-bottomed flask equipped with a PTFE-coated magnetic stirring bar. It was charged with 4.76 g of 2-fluoro-4-iodo-phenol (20 mmol, 1 eq.) and 3.96 g of $K_2CO_3$ (40 mmol, 2 eq.) then 100 mL of dry MeCN was added. To the resulting mixture 5.13 mL of TIPSCl (4.62 g, 24 mmol, 1.2 eq.) was added dropwise near intensive stirring at rt. The resulting mixture was stirred at room temperature for 30 min, while the reaction reached complete conversion. The reaction mixture was filtered through a pad of Celite to remove the solid particles then to the filtrate 3.10 mL of but-3-yn-2-ol (2.81 g, 40 mmol, 2 eq.) and 20 mL of DIPA were added and placed under a nitrogen atmosphere through a gas inlet. After addition of 702 mg of $Pd(PPh_3)_2Cl_2$ (1 mmol, 0.05 eq.) and 190 mg of CuI (1 mmol, 0.05 eq.) the resulting mixture was stirred at room temperature for 30 min, while the reaction reached complete conversion. Celite was added to the reaction mixture and the volatiles were removed under reduced pressure. Then it was purified via flash column chromatography using heptane and EtOAc as eluents to give 6.2 g (92%) of the desired product as yellow oil.

$^1$H NMR (400 MHz, DMSO-$d_6$) δ ppm 7.26 (dd, 1H), 7.12 (dm, 1H), 6.98 (t, 1H), 5.44 (d, 1H), 4.55 (m, 1H), 1.36 (d, 3H), 1.24 (sp, 1H), 1.05 (d, 18H); $^{13}$C NMR (100 MHz, DMSO-$d_6$) δ ppm 153.2, 144.1, 128.8, 122.3, 119.6, 116.5, 93.4, 81.4, 57.1, 25.0, 18.0, 12.5; HRMS-ESI (m/z): $[M+H]^+$ calcd for $C_{19}H_{30}FO_2Si$: 337.1994, found 337.1994.

Step B: 4-(3-fluoro-4-triisopropylsilyloxy-phenyl)-N,N-dimethyl-but-3-yn-2-amine Using Alkylation with in situ generated iodine General Procedure starting from 644 mg of the product from Step A (2 mmol, 1 eq.) as the appropriate alcohol and 5 mL of N-methylmethanamine (10 mmol, 5 eq., 2 M solution in MeOH), 360 mg (50%) of the desired product was obtained.

$^1$H NMR (500 MHz, DMSO-$d_6$) δ ppm 7.28 (dd, 1H), 7.14 (dm, 1H), 6.97 (t, 1H), 3.67 (q, 1H), 2.19 (s, 6H), 1.27 (d, 3H), 1.25 (m, 3H), 1.05 (d, 18H); $^{13}$C NMR (500 MHz, dmso-d6) δ ppm 153.1, 144.0, 129.0, 122.3, 119.8, 116.6, 88.2, 84.1, 52.3, 41.3, 20.1, 18.0, 12.5; HRMS-ESI (m/z): $[M+H]^+$ calcd for $C_{21}H_{35}FNOSi$: 364.2466, found 364.2470.

Step C: 4-[3-(dimethylamino)but-1-ynyl]-2-fluoro-phenol

A 4 mL oven-dried vial equipped with a PTFE-coated magnetic stirring bar was charged with 200 mg of the product from Step B (0.55 mmol, 1 eq.) dissolved in 3.0 mL of dry THF, and then 660 uL of TBAF (1 M in THF, 0.66 mmol, 1.1 eq.) was added dropwise at rt. The resulting mixture was stirred at rt for 15 min, when the reaction reached complete conversion. The reaction mixture was quenched with the addition of 200 uL of cc. $NH_4Cl$, then Celite was added to the reaction mixture and the volatiles were removed under reduced pressure. Then it was purified via flash column chromatography using DCM and MeOH (1.2% $NH_3$) as eluents to give 80 mg (70%) of the desired product.

Preparation 6g and 6h: 2-Fluoro-4-(3-morpholinobut-1-ynyl)phenol (Enantiomers 1 and 2)

Step A: [2-fluoro-4-(3-morpholinobut-1-ynyl)phenoxy]-triisopropyl-silane

Using Alkylation with in situ generated iodine General Procedure starting from 644 mg of Preparation 6f, Step A (2 mmol, 1 eq.) as the appropriate alcohol and 5 mL of morpholine (10 mmol, 5 eq., 2 M solution in MeOH), 370 mg (45%) of the desired product was obtained.

$^1$H NMR (500 MHz DMSO-$d_6$) δ ppm 7.29 (dd, 1H), 7.15 (dm, 1H), 6.98 (t, 1H), 3.69 (q, 1H), 3.60 (m, 4H), 2.6/2.45 (m+m, 4H), 1.30 (d, 3H), 1.25 (m, 3H), 1.05 (d, 18H); $^{13}$C NMR (500 MHz, dmso-d6) δ ppm 153.2, 144.0, 129.0, 122.3, 119.8, 116.5, 88.5, 84.1, 66.7, 52.1, 49.5, 19.3, 18.0, 12.5; HRMS-ESI (m/z): $[M+H]^+$ calcd for $C_{23}H_{37}FNO_2Si$: 406.2572, found 406.2579.

Step B: 2-fluoro-4-(3-morpholinobut-1-ynyl)phenol

A 4 mL oven-dried vial equipped with a PTFE-coated magnetic stirring bar was charged with 370 mg of the product from Step A (0.90 mmol, 1 eq.) dissolved in 3.0 mL of dry THF, and then 990 uL of TBAF (1 M in THF, 0.99 mmol, 1.1 eq.) was added dropwise at rt. The resulting mixture was stirred at rt for 15 min, when the reaction reached complete conversion. The reaction mixture was quenched with the addition of 200 uL of cc. $NH_4Cl$, then Celite was added to the reaction mixture and the volatiles were removed under reduced pressure. Then it was purified via flash column chromatography using DCM and MeOH (1.2% $NH_3$) as eluents to give 150 mg (60%) of the desired product.

Enantiomers were separated via chiral chromatography. Column: AD-H, Eluents: heptane/EtOH+0.1% DEA; the enantiomer eluting earlier was collected as Preparation 6g with 99.8% ee and the enantiomer eluting later was collected as Preparation 6h with 99.4% ee.

Preparation 6i: 4-[1-[(Dimethylamino)methyl]-bicyclo[1.1.1]pentanyl]phenol

Step A: 1-(4-methoxyphenyl)-N,N-dimethyl-bicyclo[1.1.1]pentane-3-carboxamide 300 mg of 1-(4-methoxyphenyl)-bicyclo[1.1.1]pentane-3-carboxylic acid (1.38 mmol, 1 eq.) and 278 mg of N,N-diethylethanamine (2.75 mmol, 2 eq.) were mixed in EtOAc (3 mL/mmol) then 1312 mg of 2,4,6-tripropyl-1,3,5,2λ^{5},4λ^{5},6λ^{5}-trioxatriphosphinane 2,4,6-trioxide (50 w % in EtOAc, 2.06 mmol, 1.5 eq.) was added in one portion then stirred at rt for 40 min. After the reaction time 1.03 mL of N-methylmethanamine (2 M in MeOH, 2.06 mmol, 1.5 eq.) was added and stirred at rt until full conversion was observed (30 min). Reaction mixture was diluted with DCM then washed with cc. $NaHCO_3$ then the organic phase was washed with cc. NaCl, dried over $MgSO_4$, filtered, concentrated, dried in vacuo to give 346 mg (quant.) of the desired product as a solid with peach color.

$^{1}H$ NMR (500 MHz, DMSO-$d_6$) δ ppm 7.14 (m, 2H), 6.86 (m, 2H), 3.72 (s, 3H), 3.08 (s, 3H), 2.81 (s, 3H), 2.26 (s, 6H); $^{13}C$ NMR (125 MHz, DMSO-$d_6$) δ ppm 168.9, 158.6, 132.5, 127.6, 114.1, 55.5, 54.2, 42.0, 39.0, 37.4, 35.9; HRMS-ESI (m/z): $[M+H]^+$ calcd for $C_{15}H_{20}NO_2$: 246.1488, found 246.1495.

Step B: 1-[3-(4-methoxyphenyl)-1-bicyclo[1.1.1]pentanyl]-N,N-dimethyl-methanamine 289 mg of the product from Step A (1.18 mmol, 1 eq.) was dissolved in THF (5 mL/mmol) then 2.36 mL of $LiAlH_4$ (1 M in THF, 2.36 mmol, 2 eq.) was added under nitrogen atmosphere at ambient temperature then stirred until full conversion was achieved (ca. 1 h). The mixture was cooled to 0° C. then quenched with cc. $NH_4Cl$. After quenching ~5 mL water and ~10 mL EtOAc were added and shaked well. 2 M HCl was added and the (acidic) water phase was separated then the organic phase was extracted with further 2 M HCl. The combined water phases were made basic with 2 M NaOH and extracted with DCM. The combined organic phases were washed with brine, dried over $MgSO_4$ and concentrated, dried in vacuo. 219 mg (80%) of the desired product was obtained as viscous oil.

$^{1}H$ NMR (500 MHz, DMSO-$d_6$) δ ppm 7.10 (m, 2H), 6.84 (m, 2H), 3.71 (s, 3H), 2.35 (s, 2H), 2.16 (s, 6H), 1.89 (s, 6H); $^{13}C$ NMR (125 MHz, DMSO-$d_6$) δ ppm 158.4, 133.4, 127.4, 114, 60.8, 55.5, 52.9, 46.6, 41.9, 38.0; HRMS-ESI (m/z): $[M+H]^+$ calcd for $C_{15}H_{22}NO$: 232.1696, found 232.1700.

Step C: 4-[1-[(dimethylamino)methyl]-3-bicyclo[1.1.1]pentanyl]phenol 50 mg of the product from Step B (0.22 mmol, 1 eq.) was dissolved in DCM (5 mL/mmol) then 0.65 mL of $BBr_3$ (1 M in DCM, 0.65 mmol, 3 eq.) was added under nitrogen atmosphere at 0° C. then stirred for 30 min at 0° C. and at rt until full conversion was achieved (ca. 45 min). DCM was added then poured into $NaHCO_3$ solution, stirred for a few minutes then made it neutral with cc. $NH_4Cl$. The organic phase was separated and washed with brine, dried over $MgSO_4$ and concentrated, dried in vacuo. 47 mg (quant.) of the crude desired product was obtained as viscous oil.

$^{1}H$ NMR (400 MHz, $CDCl_3$) δ ppm 7.07 (d, 2H), 6.81 (d, 2H), 5.18 (br. s, 1H), 3.83 (s, 2H), 3.17/3.16 (s+s, 6H), 2.23 (s, 6H); $^{13}C$ NMR (100 MHz, $CDCl_3$) δ ppm 155.0, 131.3, 127.3, 115.4, 59.6, 54.7, 53.4, 46.0, 44.1; LC-MS-ESI (m/z): $[M+H]^+$ calcd for $C_{14}H_{20}NO$: 218.2, found 218.2.

Preparation 6j: N,N-Dimethyl-3-(4-triisopropylsilyloxyphenyl)prop-2-yn-1-amine 500 mg of 4-iodophenol (2.27 mmol, 1 eq.) and 628 mg of $K_2CO_3$ (4.55 mmol, 2 eq.) were mixed in acetonitrile (5 mL/mmol) then 526 mg of chloro(triisopropyl)silane (2.73 mmol, 1.2 eq.) was added at rt and stirred for 1 h. The reaction mixture was filtered through a pad of celite then 236 mg of N,N-dimethylprop-2-yn-1-amine (2.84 mmol, 1.25 eq.), 50 mg of $Pd(PPh_3)_2Cl_2$ (0.11 mmol, 0.05 eq.), 22 mg of CuI (0.11 mmol, 0.05 eq.) and 2.27 mL of N-isopropyl-propan-2-amine (1 mL/mmol) were added then stirred at 50° C. for 3 h. The reaction mixture was concentrated to Celite and purified via flash column chromatography using heptane and EtOAc as eluents to give 449 mg (60%) of the desired product as a yellow oil.

$^{1}H$ NMR (500 MHz, DMSO-$d_6$) δ ppm 7.32 (dm, 2H), 6.84 (dm, 2H), 3.41 (s, 2H), 2.22 (s, 6H), 1.24 (m, 3H), 1.06 (d, 18H); $^{13}C$ NMR (125 MHz, DMSO-$d_6$) 156, 133.5, 120.3, 116, 85.1/84.5, 44.3, 18.3, 12.4; HRMS-ESI (m/z): $[M+H]^+$ calcd for $C_{20}H_{34}NOSi$: 332.2404, found 332.2405.

Preparation 6k: 2-Fluoro-4-{3-[(4-methoxyphenyl)methoxy]prop-1-yn-1-yl}phenol

Step A: 4-bromo-2-fluorophenyl acetate

To a solution of 4-bromo-2-fluorophenol (2.29 mL, 20.9 mmol, 1 eq) in dichloromethane (60 mL) was added 4-(dimethylamino)pyridine (5.12 g, 41.9 mmol, 2 eq) and acetic anhydride (4.94 mL, 52.4 mmol, 2.5 eq) and the mixture was stirred at ambient temperature for 18 h. The reaction was concentrated, then partitioned between dichloromethane and water, washed with brine, separated (phase separator) and concentrated in vacuo. Purification by automated flash column chromatography (CombiFlash Rf, 80 g RediSep™ silica cartridge) eluting with a gradient of 0-10% ethyl acetate in iso-heptane afforded the desired product as a clear oil (5.1 g, 21.9 mmol, >100%).

$^{1}H$ NMR (400 MHz, DMSO-d6) 7.75 (dd, J=10.0, 2.3 Hz, 1H), 7.48 (ddd, J=8.6, 2.3, 1.3 Hz, 1H), 7.30 (t, J=8.5 Hz, 1H), 2.41 (s, 3H).

Step B: 1-methoxy-4-[(prop-2-yn-1-yloxy)methyl]benzene

To a stirred suspension of sodium hydride (60% dispersion; 856 mg, 21.4 mmol, 1.2 eq) in tetrahydrofuran (25 mL), cooled to 0° C., was added a solution of propargyl alcohol (1.04 mL, 17.8 mmol, 1 eq) in tetrahydrofuran (10 mL), followed by 1-(bromomethyl)-4-methoxybenzene (3.09 mL, 21.4 mmol, 1.2 eq) and the mixture was stirred at ambient temperature for 18 h. The reaction was partitioned between ethyl acetate and saturated aqueous ammonium chloride, and the organic phase was dried (magnesium sulfate), filtered and concentrated in vacuo. Purification by automated flash column chromatography (CombiFlash Rf, 80 g RediSep™ silica cartridge) eluting with a gradient of 0-10% ethyl acetate in iso-heptane afforded the desired product as a clear oil (2.44 g, 13.9 mmol, 78%).

$^1$H NMR (400 MHz, DMSO-d6) δ 7.31-7.18 (m, 2H), 6.97-6.86 (m, 2H), 4.44 (s, 2H), 4.13 (d, J=2.4 Hz, 2H), 3.75 (s, 3H), 3.48 (t, J=2.4 Hz, 1H).

Step C: 2-fluoro-4-{3-[(4-methoxyphenyl)methoxy]prop-1-yn-1-yl}phenyl acetate

To an oven-dried pressure tube was added the product from Step A (1.68 g, 7.23 mmol, 1 eq), triethylamine (18 mL), the product from Step B (1.91 g, 10.8 mmol, 1.5 eq), copper (I) iodide (275 mg, 1.45 mmol, 0.2 eq) and tetrakis (triphenylphosphine)palladium(0)(835 mg, 0.72 mmol, 0.1 eq) and the mixture was sparged with nitrogen (10 mins) before sealing and heating at 90° C. for 4 h. The reaction was allowed to cool to ambient temperature, then partitioned between dichloromethane and brine, and the organic phase was separated and dried (PTFE phase separator) and concentrated in vacuo. Purification by automated flash column chromatography (CombiFlash Rf, 40 g RediSep™ silica cartridge) eluting with a gradient of 0-30% ethyl acetate in iso-heptane afforded the desired product as an orange solid (2.11 g, 6.43 mmol, 89%).

$^1$H NMR (400 MHz, DMSO-d6) δ 7.55 (dd, J=11.1, 1.7 Hz, 1H), 7.44-7.28 (m, 4H), 6.96-6.91 (m, 2H), 4.53 (s, 2H), 4.39 (s, 2H), 3.76 (s, 3H), 2.34 (s, 3H).

Step D: 2-fluoro-4-{3-[(4-methoxyphenyl)methoxy]prop-1-yn-1-yl}phenol

To a solution of the product from Step C (200 mg, 0.61 mmol, 1 eq) in methanol (15 mL) was added potassium carbonate (253 mg, 1.83 mmol, 3 eq) and the mixture was stirred at ambient temperature for 3 h. The reaction was concentrated in vacuo, partitioned between dichloromethane and dilute aqueous hydrochloric acid, and the organic phase was separated (PTFE phase separator) and concentrated in vacuo. Purification by automated flash column chromatography (CombiFlash Rf, 12 g RediSep™ silica cartridge) eluting with a gradient of 0-40% ethyl acetate in iso-heptane afforded the desired product as a yellow gum (128 mg, 0.45 mmol, 73%).

LC/MS ($C_{17}H_{15}FO_3$) 285 $[M-H]^-$; RT 2.09 (LCMS-V-C)

$^1$H NMR (400 MHz, DMSO-d6) δ 10.37 (s, 1H), 7.32-7.24 (m, 3H), 7.16-7.10 (m, 1H), 6.98-6.90 (m, 3H), 4.50 (s, 2H), 4.34 (s, 2H), 3.75 (s, 3H).

Preparation 7c: 3,6-Dichloro-4-(propan-2-yl)pyridazine 3,6-Dichloropyridazine (5 g, 33.6 mmol, 1 eq), silver nitrate (5.7 g, 33.6 mmol, 1 eq) and isobutyric acid (2.96 g, 33.6 mmol, 1 eq) were suspended in water (100 mL). The mixture was heated to 50° C. and sulfuric acid (9.88 g, 101 mmol, 3 eq) was added. The mixture was heated to 60° C. and 1.6M aqueous ammonium persulfate (62.9 mL, 101 mmol, 3 eq) was added dropwise and the reaction was heated at 70° C. for 30 mins. The mixture was allowed to cool to ambient temperature, then cooled to 0° C. and neutralised with concentrated ammonium hydroxide solution slowly to pH 7 then adjusted to pH 8-9. A yellow precipitate formed which was filtered and washed with water and ethyl acetate to afford a white solid. The filtrates were combined, the layers separated, and the aqueous phase extracted with ethyl acetate (100 mL). The combined organics were washed with brine (100 mL), dried (magnesium sulfate) and concentrated in vacuo to obtain a yellow oil. Purification by automated flash column chromatography (CombiFlash Rf, 80 g RediSep™ silica cartridge) eluting with a gradient of 0-5% ethyl acetate in heptane afforded the desired product as a colourless oil (4.61 g, 24.1 mmol, 72%).

LC/MS ($C_7H_8Cl_2N_2$) 191 $[M+H]^+$; RT 1.11 (LCMS-V-B1)

$^1$H NMR (400 MHz, DMSO-d6) δ 8.00 (d, J=0.6 Hz, 1H), 3.16 (h, 1H), 1.26 (d, J=6.8 Hz, 6H).

Preparation 7e: 3,6-Dichloro-4-methyl-5-(propan-2-yl)pyridazine

A suspension of 3,6-dichloro-4-methyl-pyridazine (0.5 g, 3.07 mmol, 1 eq), isobutyric acid (0.28 mL, 3.07 mmol, 1 eq) and silver nitrate (0.52 g, 3.07 mmol, 1 eq) in water (10 mL) was heated to 50° C. Sulfuric acid (0.49 mL, 9.2 mmol, 3 eq) was added and the mixture was heated to 60° C. 1.6M aqueous ammonium persulfate (5.75 mL, 9.2 mmol, 3 eq) was added dropwise and the mixture was stirred for 30 min, then allowed to cool to ambient temperature. Neutralisation with ammonium hydroxide, filtration through celite, and elution with ethyl acetate afforded a biphasic mixture. The layers were separated, the aqueous phase was extracted with ethyl acetate, and the combined organics were dried (magnesium sulfate) and concentrated in vacuo. Purification by automated flash column chromatography (CombiFlash Rf, 40 g RediSep™ silica cartridge) eluting with a gradient of 0-15% ethyl acetate in iso-heptane afforded the desired product as a white solid (476 mg, 2.32 mmol, 76%).

LC/MS ($C_8H_{10}Cl_2N_2$) 205 $[M+H]^+$; RT 1.15 (LCMS-V-B1)

$^1$H NMR (400 MHz, DMSO-d6) δ 3.57 (hept, J=7.2 Hz, 1H), 2.49 (s, 3H), 1.35 (d, J=7.2 Hz, 6H).

Preparation 7f: 3,6-Dichloro-4-ethyl-5-methylpyridazine

To a stirred suspension of 3,6-dichloro-4-methylpyridazine (5 g, 30.7 mmol, 1 eq) and propionic acid (2.75 mL, 36.8 mmol, 1.2 eq) in water (100 mL) was added silver nitrate (5.21 g, 30.7 mmol, 1 eq) and the mixture was heated to 50° C. Sulfuric acid (4.91 mL, 92 mmol, 3 eq) was added dropwise and the reaction was heated to 60° C. 1.6M aqueous ammonium persulfate (57.5 mL, 92 mmol, 3 eq) was then added dropwise over 20 min. The reaction was heated to 70° C. for 30 min and then left cool to ambient temperature. The mixture was basified to pH 8 using conc. ammonium hydroxide and the product extracted with ethyl acetate (100 mL×2). The combined organic extracts were dried (magnesium sulfate) and concentrated in vacuo. Purification by automated flash column chromatography (CombiFlash Rf, 120 g RediSep™ silica cartridge) eluting with a gradient of 0-25% ethyl acetate in iso-heptane afforded the desired product as a white solid (4.11 g, 21.5 mmol, 70%).

LC/MS ($C_7H_8Cl_2N_2$) 191 $[M+H]^+$; RT 2.17 (LCMS-V-C)

$^1$H NMR (400 MHz, DMSO-d6) δ 2.82 (q, 7.6 Hz, 2H), 2.44 (s, 3H), 1.13 (t, J=7.6 Hz, 3H).

Preparation 7g: 4-[(Benzyloxy)methyl]-3,6-dichloro-5-methylpyridazine

To a suspension of 3,6-dichloro-4-methylpyridazine (5.1 g, 30.7 mmol, 1 eq) and benzyloxyacetic acid (5.61 g, 33.7 mmol, 1.1 eq) in water (100 mL) was added silver nitrate (5.21 g, 30.7 mmol, 1 eq) and the mixture was heated to 50° C. Sulfuric acid (4.91 mL, 92 mmol, 3 eq) was added and the mixture was heated to 60° C. 1.6M aqueous ammonium persulfate (57.5 mL, 92 mmol, 3 eq) was added dropwise and the reaction was heated at 70° C. for 30 min. The mixture was allowed to cool to ambient temperature and basified to pH 8 with conc. aqueous ammonium hydroxide. The mixture was extracted with ethyl acetate (2×150 mL) and the combined organics were washed with brine (200 mL), dried (magnesium sulfate), and concentrated in vacuo. Purification by automated flash column chromatography (CombiFlash Rf, 120 g RediSep™ silica cartridge) eluting with a gradient of 0-25% ethyl acetate in iso-heptane afforded the desired product as a yellow oil (4.67 g, 16.5 mmol, 54%).

LC/MS ($C_{13}H_{12}Cl_2N_2O$) 283 $[M+H]^+$; RT 1.26 (LCMS-V-B1)

$^1H$ NMR (400 MHz, DMSO-d6) δ 7.42-7.27 (m, 5H), 4.71 (s, 2H) 4.60 (s, 2H), 2.46 (s, 3H).

Preparation 7h: 3,6-Dichloro-4-cyclopropyl-5-methylpyridazine

To a suspension of 3,6-dichloro-4-methylpyridazine (4.88 g, 29.9 mmol, 1 eq) and cyclopropanecarboxylic acid (2.63 mL, 32.9 mmol, 1.1 eq) in water (100 mL) was added silver nitrate (5.09 g, 29.9 mmol, 1 eq) and the mixture was heated to 50° C. To this was added sulfuric acid (4.79 mL, 89.8 mmol, 3 eq) and the mixture was heated to 60° C. 1.6M aqueous ammonium persulfate (56.1 mL, 89.8 mmol, 3 eq) was added dropwise over 20 min then the mixture was heated to 70° C. and stirred for 30 min. The mixture was allowed to cool to ambient temperature and basified to pH 8 with conc. ammonium hydroxide. The product was extracted into the organic phase using ethyl acetate (2×200 mL) and the combined organic extracts were washed with brine, dried (magnesium sulfate) and concentrated in vacuo. Purification by automated flash column chromatography (CombiFlash Rf, 120 g RediSep™ silica cartridge) eluting with a gradient of 0-30% ethyl acetate in iso-heptane afforded the desired product as a white solid (3.99 g, 19.7 mmol, 66%).

LC/MS ($C_8H_8Cl_2N_2$) 203 $[M+H]^+$; RT 1.09 (LCMS-V-B1)

$^1H$ NMR (400 MHz, DMSO-d6) δ 2.49 (d, J=0.9 Hz, 3H), 1.98-1.88 (m, 1H), 1.26-1.11 (m, 2H), 0.78-0.67 (m, 2H).

Preparation 7l: 3,6-Dichloro-4-cyclopropylpyridazine

To a suspension of 3,6-dichloropyridazine (2 g, 13.4 mmol, 1 eq) and cyclopropanecarboxylic acid (1.07 mL, 13.4 mmol, 1 eq) in water (85 mL) was added silver nitrate (2.28 g, 13.4 mmol, 1 eq) and the mixture was heated to 50° C. Sulfuric acid (2.15 mL, 40.3 mmol, 3 eq) was added and the mixture was heated to 60° C. 1.6M aqueous ammonium persulfate (25.2 mL, 40.3 mmol, 3 eq) was added dropwise over 15 mins and the reaction was then heated at 70° C. for 30 min. The mixture was allowed to cool to ambient temperature and basified to pH 10 with conc. ammonium hydroxide. The product was extracted into ethyl acetate (2×150 mL) and the extracts were washed with brine, dried (magnesium sulfate) and concentrated in vacuo. Purification by automated flash column chromatography (CombiFlash Rf, 80 g RediSep™ silica cartridge) eluting with a gradient of 0-20% ethyl acetate in iso-heptane afforded the desired product as a white solid (985 mg, 5.21 mmol, 39%).

LC/MS ($C_7H_6Cl_2N_2$) 189 $[M+H]^+$; RT 1.00 (LCMS-V-B1)

$^1H$ NMR (400 MHz, DMSO-$d_6$) δ 7.61 (d, J=0.6 Hz, 1H), 2.19-2.09 (m, 1H), 1.25-1.19 (m, 2H), 1.08-1.03 (m, 2H).

Preparation 7m: 4-[3-(Benzyloxy)propyl]-3,6-dichloro-5-methylpyridazine

Step A: [(pent-4-yn-1-yloxy)methyl]benzene

To an oven-dried flask was added 4-Pentyn-1-ol (5.53 mL, 59.4 mmol, 1 eq) and tetrahydrofuran (50 mL) and the solution was cooled to 0° C. Sodium hydride (60%; 2.85 g, 119 mmol, 2 eq) was added portionwise and the reaction was allowed to stir for 30 min at 0° C. Benzyl bromide (7.42 mL, 62.4 mmol, 1.05 eq) was added dropwise and the reaction was allowed to warm to ambient temperature and stirred for 16 h. The reaction was cooled to 0° C. and quenched by the addition of saturated aqueous ammonium chloride (20 mL). Water (20 mL) was added and the layers separated. The aqueous layer was extracted with ethyl acetate (2×50 mL) and the combined organics were washed with brine (50 mL), dried (magnesium sulfate), and concentrated in vacuo. Purification by automated flash column chromatography (CombiFlash Rf, 120 g RediSep™ silica cartridge) eluting with a gradient of 0-10% ethyl acetate in iso-heptane afforded the desired product as a yellow oil (8.93 g, 51.3 mmol, 86%).

LC/MS ($C_{12}H_{14}O$) 175 $[M+H]^+$; RT 1.25 (LCMS-V-B1)

$^1H$ NMR (400 MHz, $CDCl_3$) δ 7.42-7.21 (m, 5H), 4.52 (s, 2H), 3.57 (t, J=6.2 Hz, 2H), 2.32 (td, J=7.1, 2.7 Hz, 2H), 1.94 (t, J=2.7 Hz, 1H), 1.84 (tt, J=7.1, 6.2 Hz, 2H).

Step B: [(hex-4-yn-1-yloxy)methyl]benzene

To an oven-dried flask was added a solution of the product from Step A (3.9 g, 22.4 mmol, 1 eq) in tetrahydrofuran (30 mL) under nitrogen. The reaction was cooled to −78° C. and n-butyllithium (2.2M in hexane; 12.2 mL, 26.9 mmol, 1.2 eq) was added over 30 min and the mixture was stirred at −78° C. for 1 h. Iodomethane (2.09 mL, 33.6 mmol, 1.5 eq) was added dropwise and the resultant mixture was allowed to warm to 0° C. over 2 h. The reaction was quenched by the addition of saturated aqueous saturated ammonium chloride (20 mL), then diluted with water (20 mL), and extracted with ethyl acetate (3×20 mL). The combined organic extracts were washed successively with 2M aqueous sodium thiosulfate (50 mL) and brine (50 mL), dried (magnesium sulfate) and concentrated in vacuo. Purification by automated flash column chromatography (CombiFlash Rf, 80 g RediSep™ silica cartridge) eluting with a gradient of 0-10% ethyl acetate in iso-heptane afforded the desired product as a straw-coloured liquid (3.61 g, 19.2 mmol, 86%).

LC/MS ($C_{13}H_{16}O$) no ionisation; RT 1.15 (LCMS-V-B1)

$^1H$ NMR (400 MHz, DMSO-d6) δ 7.43-7.19 (m, 5H), 4.46 (s, 2H), 3.48 (t, J=6.3 Hz, 2H), 2.23-2.14 (m, 2H), 1.72 (t, 3H), 1.71-1.62 (m, 2H).

Step C: 4-[3-(Benzyloxy)propyl]-3,6-dichloro-5-methylpyridazine

A solution of dichloro-1,2,4,5-tetrazine (2.5 g, 16.6 mmol, 1 eq) and the product from Step B (3.74 g, 19.9 mmol, 1.2 eq) in toluene (15 mL) was heated in a sealed tube at 160° C. for 20 h. The mixture was allowed to cool to ambient temperature and concentrated in vacuo. Purification by automated flash column chromatography (CombiFlash Rf, 80 g RediSep™ silica cartridge) eluting with a gradient of 0-35% ethyl acetate in iso-heptane afforded the desired product as an orange oil (3.06 g, 9.83 mmol, 62%).

LC/MS ($C_{15}H_{16}Cl_2N_2O$) 311 $[M+H]^+$; RT 1.35 (LCMS-V-B1)

$^1$H NMR (400 MHz, DMSO-d6) δ 7.47-7.14 (m, 5H), 4.48 (s, 2H), 3.53 (t, J=5.9 Hz, 2H), 2.96-2.81 (m, 2H), 2.42 (s, 3H), 1.87-1.72 (m, 2H).

Preparation 8ca and 8cb: 6-Chloro-5-(propan-2-yl) pyridazin-3-amine and 6-Chloro-4-(propan-2-yl) pyridazin-3-amine The product from Preparation 7c (3.61 g, 18.9 mmol, 1 eq) was suspended in ammonium hydroxide (20 mL) and heated at 150° C. for 4 h under microwave irradiation. The solids were collected by filtration, washed with water and dried to afford 6-chloro-5-(propan-2-yl)pyridazin-3-amine (2.06 g, 12 mmol, 64%) as an off-white solid [~9:1 mix with other regioisomer] (Preparation 8ca).

LC/MS ($C_7H_{10}ClN_3$) 172 $[M+H]^+$; RT 0.81 (LCMS-V-B1)

$^1$H NMR (400 MHz, DMSO-d6) δ 6.76 (d, J=0.7 Hz, 1H), 6.51 (s, 2H), 3.06-2.82 (m, 1H), 1.18 (d, 6H).

The filtrate was concentrated in vacuo and the crude solid residue was extracted with dichloromethane, filtered, and evaporated to afford 6-Chloro-4-isopropylpyridazine-3-amine (447 mg, 2.6 mmol, 14%) as a yellow oil [~7:3 mix with other regioisomer] (Preparation 8cb).

LC/MS ($C_7H_{10}ClN_3$) 172 $[M+H]^+$; RT 0.79 (LCMS-V-B1)

$^1$H NMR (400 MHz, DMSO-d6) δ 7.23 (s, 1H), 6.53 (s, 2H), 2.95-2.80 (m, 1H), 1.15 (d, 6H).

Preparation 8d: 6-Chloro-5-methylpyridazin-3-amine and 6-Chloro-4-methylpyridazin-3-amine A suspension of 3,6-dichloro-4-methyl-pyridazine (2 g, 12.3 mmol, 1 eq) in ammonium hydroxide (40 mL) was heated in a pressure reactor at 150° C. for 6 h, then allowed to cool to ambient temperature. The resultant precipitate was filtered, washed with water (10 mL) and dried to afford the desired product as fine brown needles (1.31 g, 0.01 mol, 74%) [~6:4 ratio of regioisomers]. The mixture of isomers was used in the next step without further purification.

LC/MS ($C_5H_6ClN_3$) no ionisation; RT 0.28 (LCMS-V-B1)

Preparation 8e: 6-Chloro-4-methyl-5-(propan-2yl) pyridazin-3-amine and 6-Chloro-5-methyl-4-(propan-2-yl)pyridazin-3-amine The product from Preparation 7e (480 mg, 2.34 mmol, 1 eq) was introduced into the 'bomb' apparatus. Ammonium hydroxide (15 mL) was added, the vessel sealed and the mixture was stirred at 160° C. for 6 h. After allowing to cool to ambient temperature, the vessel was opened and the reaction mixture was concentrated in vacuo and the mixture of isomers was used in the next step without purification.

LC/MS ($C_8H_{12}ClN_3$) 186 $[M+H]^+$; RT 0.88 (LCMS-V-B1)

Preparation 8f: 6-Chloro-5-ethyl-4-methylpyridazin-3-amine and 6-Chloro-4-ethyl-5-methylpyridazin-3-amine A suspension of the product from Preparation 7f (4 g, 21 mmol, 1 eq) in ammonium hydroxide (15 mL) was stirred at 160° C. in a sealed flask for 24 h. The mixture was allowed to cool to ambient temperature and a brown solid precipitated. The solid was collected by filtration, washed with water, and dried under vacuum to afford the desired products as a brown solid (1.4 g, 8.16 mmol, 39%) [2:1 mixture of regioisomers]. The mixture of isomers was used in the next step without purification.

LC/MS ($C_7H_{10}ClN_3$) 172 $[M+H]^+$; RT 1.53 (LCMS-V-C)

Preparation 8g: 5-[(Benzyloxy)methyl]-6-chloro-4-methylpyridazin-3-amine and 4-[(Benzyloxy) methyl]-6-chloro-5-methylpyridazin-3-amine The product from Preparation 7g (600 mg, 2.12 mmol, 1 eq) was suspended as an oil in ammonium hydroxide (7 mL) and heated at 160° C. for 5 h in a sealed tube. The mixture was allowed to cool to ambient temperature and a brown solid precipitated. The solid was collected by filtration, washed with water and dried under vacuum to afford the desired product (455 mg, 1.73 mmol, 81%) as a mixture of two regioisomers that was used directly in the next step.

LC/MS ($C_{13}H_{14}ClN_3O$) 264 $[M+H]^+$; RT 1.02 (LCMS-V-B1)

Preparation 8ba and 8hb: 6-Chloro-5-cyclopropyl-4-methylpyridazin-3-amine and 6-Chloro-4-cyclopropyl-5-methylpyridazin-3-amine The product from Preparation 7h (3.99 g, 19.7 mmol, 1 eq) was suspended in ammonium hydroxide (10 mL) and heated in a sealed tube for 20 h. The mixture was allowed to cool to ambient temperature and the precipitated solid was collected by filtration and dried to afford 6-chloro-5-cyclopropyl-4-methylpyridazin-3-amine (2.44 g, 13.3 mmol, 68%) [Preparation 8ha], which was used directly in the next step without further purification.

LC/MS ($C_8H_{10}ClN_3$) 184 $[M+H]^+$; RT 0.80 (LCMS-V-B1)

The filtrate was concentrated under reduced pressure, then evaporated from toluene (×3) to remove residual water, to afford crude material (2.00 g, 10.89 mmol, 55%) containing 6-chloro-4-cyclopropyl-5-methylpyridazin-3-amine that was used directly in subsequent steps without further purification [Preparation 8hb].

LC/MS ($C_8H_{10}ClN_3$) 184 $[M+H]^+$; RT 0.79 (LCMS-V-B1)

Preparation 8ia and 8ib: (6-Amino-3-chloro-5-methylpyridazin-4-yl)methanol and (3-Amino-6-chloro-5-methylpyridazin-4-yl)methanol To a cooled solution of the product from Preparation 8g (3.1 g, 11.8 mmol, 1 eq) in dichloromethane (100 mL) was added boron trichloride solution (58.8 mL, 1 M, 0.06 mol, 5 eq) dropwise and the mixture was stirred at ambient temperature for 2 h. The reaction was cooled to 0-5° C. and cautiously quenched by the addition of methanol (30 mL). Further methanol (30 mL) was added and the mixture was heated at reflux for 30 min. The solvent was removed in vacuo and purification by automated flash column chromatography (CombiFlash Rf, 120 g RediSep™ silica cartridge) eluting with a gradient of 0-17.5% methanol in dichloromethane afforded the desired regioisomeric products:

(3-Amino-6-chloro-5-methylpyridazin-4-yl)methanol as a beige solid (0.87 g, 5.0 mmol, 42%) [Preparation 8ib].

LC/MS ($C_6H_8ClN_3O$) 174 $[M+H]^+$; RT 0.26 (LCMS-V-B1)

$^1$H NMR (400 MHz, DMSO-d6) δ 8.13 (s, 2H), 4.57 (s, 2H), 2.40 (s, 3H).

(6-Amino-3-chloro-5-methylpyridazin-4-yl)methanol as a beige solid (1.38 g, 7.9 mmol, 67%) [Preparation 8ia].

LC/MS ($C_6H_8ClN_3O$) 174 [M+H]$^+$; RT 0.18 (LCMS-V-B1)

$^1$H NMR (400 MHz, DMSO-d6) δ 8.18 (s, 2H), 4.56 (s, 2H), 2.31 (s, 3H).

Preparation 8ja: 6-Chloro-5-(methoxymethyl)-4-methylpyridazin-3-amine

Step A: 5-(bromomethyl)-6-chloro-4-methylpyridazin-3-amine

To a suspension of the product from Preparation 8ia (960 mg, 5.53 mmol, 1 eq) in dichloromethane (50 mL) was added phosphorus tribromide (0.62 mL, 6.34 mmol, 1.2 eq) and the mixture was stirred for 1 h at ambient temperature. The reaction was quenched by addition of methanol (20 mL) and concentrated in vacuo to afford a solid (3.2 g). The material was used directly in the next step without further purification.

LC/MS ($C_6H_7BrCl_3$) 238 [M+H]$^+$; RT 0.81 (LCMS-V-B1)

Step B: 6-chloro-5-(methoxymethyl)-4-methylpyridazin-3-amine

A solution of the crude product from Step A (780 mg) in methanol (10 mL) was heated at 120° C. for 1 h under microwave irradiation. The mixture was concentrated in vacuo and purification by automated flash column chromatography (CombiFlash Rf, 12 g RediSep™ silica cartridge) eluting with a gradient of 0-10% methanol in dichloromethane afforded the desired product as a brown oil (323 mg, 0.90 mmol, 66% over both steps).

LC/MS ($C_7H_{10}ClN_3O$) 188 [M+H]$^+$; RT 0.61 (LCMS-V-B1)

Preparation 8jb: 6-Chloro-4-(methoxymethyl)-5-methylpyridazin-3-amine

Step A: 4-(bromomethyl)-6-chloro-5-methylpyridazin-3-amine

To a suspension of the product from Preparation 8ib (500 mg, 2.88 mmol, 1 eq) in dichloromethane (50 mL) was added phosphorus tribromide (0.32 mL, 3.46 mmol, 1.2 eq) and the mixture was stirred for 1 h at ambient temperature. The reaction was quenched by the addition of methanol (20 mL) and then the volatile organics were removed in vacuo. Purification by automated flash column chromatography (CombiFlash Rf, 24 g RediSep™ silica cartridge) eluting with a gradient of 0-5% methanol in dichloromethane afforded the desired product as an orange solid (695 mg, 2.94 mmol, 100%).

LC/MS ($C_6H_7BrClN_3$) 238 [M+H]$^+$; RT 0.82 (LCMS-V-B1)

$^1$H NMR (400 MHz, DMSO-$d_6$) δ 7.84 (br s including water peak), 4.76 (s, 2H), 2.38 (s, 3H).

Step B: 6-chloro-4-(methoxymethyl)-5-methylpyridazin-3-amine

A solution of the product from Step A (430 mg, 1.82 mmol, 1 eq) in methanol (10 mL) was heated at 120° C. for 30 min under microwave irradiation. The mixture was concentrated in vacuo and purification by automated flash column chromatography (CombiFlash Rf, 24 g RediSep™ silica cartridge) eluting with a gradient of 0-5% methanol in dichloromethane afforded the desired product as a purple crystalline solid (91 mg, 0.49 mmol, 27%).

LC/MS ($C_7H_{10}ClN_3O$) 188 [M+H]$^+$; RT 0.70 (LCMS-V-B1)

$^1$H NMR (400 MHz, DMSO-d6) δ 7.66 (s, 2H), 4.50 (s, 2H), 3.32 (s, 3H), 2.38 (s, 3H).

Preparation 8ka: 6-Chloro-5-(ethoxymethyl)-4-methylpyridazin-3-amine

A solution of the product from Preparation 8ja Step A (500 mg, 2.11 mmol, 1 eq) in ethanol (15 mL) was heated at 120° C. for 1 h under microwave irradiation. The mixture was concentrated in vacuo and purification by automated flash column chromatography (CombiFlash Rf, 24 g RediSep™ silica cartridge) eluting with a gradient of 0-10% methanol in dichloromethane afforded the desired product as a thick oil that crystallised on scratching (136 mg, 0.67 mmol, 32%).

LC/MS ($C_8H_{12}ClN_3O$) 202 [M+H]$^+$; RT 0.63 (LCMS-V-B1)

$^1$H NMR (400 MHz, DMSO-d6) δ 4.56 (s, 2H), 3.55 (q, J=7.0 Hz, 2H), 2.28 (s, 3H), 1.14 (t, J=7.0 Hz, 3H).

Preparation 8ma and 8mb: 5-[3-(Benzyloxy)propyl]-6-chloro-4-methylpyridazin-3-amine and 4-[3-Benzyloxy)propyl]-6-chloro-5-methylpyridazin-3-amine The product from Preparation 7m (3.06 g, 9.83 mmol, 1 eq) and ammonium hydroxide (15 mL) were heated in a sealed flask for 48 h at 160° C. The mixture was allowed to cool to ambient temperature and extracted with dichloromethane (2×100 mL). The organics were washed with brine (50 mL) and concentrated in vacuo. Purification by automated flash column chromatography (CombiFlash Rf, 80 g RediSep™ silica cartridge) eluting with a gradient of 0-100% ethyl acetate in iso-heptane afforded the desired regioisomeric products:

5-[3-(Benzyloxy)propyl]-6-chloro-4-methylpyridazin-3-amine as a beige solid (1.3 g, 4.46 mmol, 45%) [Preparation 8ma].

LC/MS ($C_{18}H_{18}ClN_3O$) 292 [M+H]$^+$; RT 1.12 (LCMS-V-B1)

$^1$H NMR (400 MHz, DMSO-$d_6$) δ 7.47-7.20 (m, 5H), 6.33 (s, 2H), 4.48 (s, 2H), 3.49 (t, J=6.0 Hz, 2H), 2.79-2.66 (m, 2H), 2.08 (s, 3H), 1.84-1.65 (m, 2H).

4-[3-(Benzyloxy)propyl]-6-chloro-5-methylpyridazin-3-amine as a beige solid (500 mg, 1.71 mmol, 17%) [Preparation 8mb].

LC/MS ($C_{15}H_{18}ClN_3O$) 292 [M+H]$^+$; RT 1.15 (LCMS-V-B1)

$^1$H NMR (400 MHz, DMSO-d6) δ 7.49-7.15 (m, 5H), 6.34 (s, 2H), 4.48 (s, 2H), 3.47 (t, J=6.2 Hz, 2H), 2.72-2.54 (m, 2H), 2.22 (s, 3H), 1.83-1.61 (m, 2H).

Preparation 9a: N-(6-Chloro-4,5-dimethylpyridazin-3-yl)-1,3-benzothiazol-2-amine To a solution of 3-amino-6-chloro-4,5-dimethylpyridazine (450 mg, 2.86 mmol, 1 eq) and 2-bromo-1,3-benzothiazole (672 mg, 3.14 mmol, 1.1 eq) in 1,4-dioxane (20 mL) was added sodium hydride (60% dispersion; 457 mg, 11.42 mmol, 4 eq) portionwise and the mixture was refluxed for 16 h. The reaction mixture was allowed to cool to ambient temperature and then quenched with acetic acid. The mixture was diluted with ethyl acetate (200 mL) and washed with aqueous saturated sodium bicarbonate (100 mL), and brine (100 mL). The organic extract was dried (magnesium sulfate) and concentrated in vacuo. Purification by automated flash column chromatography (CombiFlash Rf, 40 g RediSep™ silica cartridge) eluting with a gradient of 0-3% methanol in dichloromethane afforded the desired product as a yellow solid (673 mg, 2.32 mmol, 81%).

LC/MS ($C_{13}H_{11}ClN_4S$) 291 $[M+H]^+$; RT 1.22 (LCMS-V-B1)

$^1H$ NMR (400 MHz, DMSO-d6) δ 11.80 (br s, 1H), 7.86 (d, J=7.75 Hz, 1H), 7.50 (s, 1H), 7.40 (td, J=1.28, 7.69 Hz, 1H), 7.22 (t, J=7.67 Hz, 1H), 2.37 (s, 3H), 2.33 (s, 3H).

Preparation 9b: N-(6-Chloropyridazin-3-yl)-1,3-benzothiazol-2-amine

To a solution of 3-amino-6-chloropyridazine (2 g, 15.4 mmol, 1 eq) and 2-bromo-1,3-benzothiazole (3.64 g, 17.0 mmol, 1.1 eq) in 1,4-dioxane (120 mL) was added sodium hydride (60% dispersion; 2.47 g, 61.8 mmol, 4 eq) portionwise and the mixture was refluxed for 30 mins. The reaction mixture was allowed to cool to ambient temperature, and was then cooled in an ice-water bath and quenched with methanol. Removal of the methanol by rotary evaporation caused a solid to precipitate. The mixture was cooled in ice-water and the solid was collected by filtration, washed with ice-cold 1,4-dioxane (100 mL), then diethyl ether (100 mL). Finally the solid was suspended in water, the pH was adjusted to 7, and the solid was collected by filtration and dried in vacuo to afford the desired product (1.94 g, 7.38 mmol, 48%).

LC/MS ($C_{11}H_7ClN_4S$) 263 $[M+H]^+$; RT 1.1 (LCMS-V-B1)

$^1H$ NMR (400 MHz, DMSO-d6) δ 12.03 (s, 1H), 8.00-7.93 (m, 1H), 7.82 (d, J=9.3 Hz, 1H), 7.69 (d, J=8.0 Hz, 1H), 7.59 (d, J=9.3 Hz, 1H), 7.46-7.37 (m, 1H), 7.30-7.23 (m, 1H).

Preparation 9ca: N-[6-Chloro-5-(propan-2-yl)pyridazin-3-yl]-1,3-benzothiazol-2-amine To a suspension of the product from Preparation 8ca (2.06 g, 12 mmol, 1 eq) in 1,4-dioxane (70 mL) was added 2-bromo-1,3-benzothiazole (2.83 g, 13.2 mmol, 1.1 eq) followed by sodium hydride (60% dispersion; 0.96 g, 24.01 mmol, 2 eq) portionwise and the mixture was heated at 90° C. for 30 min. After allowing to cool to ambient temperature the reaction was cooled in ice-water, quenched by the addition of acetic acid, and concentrated in vacuo. The resultant solid was triturated with water, filtered, and dried under vacuum. Purification by automated flash column chromatography (CombiFlash Rf, 120 g RediSep™ silica cartridge) eluting with a gradient 0-50% ethyl acetate in iso-heptane afforded a solid that was triturated with ethyl acetate, filtered, and dried under vacuum to afford the desired product as an off-white solid (1.54 g, 5.05 mmol, 42%).

LC/MS ($C_{14}H_{13}ClN_4S$) 305 $[M+H]^+$; RT 1.31 (LCMS-V-B1)

$^1H$ NMR (400 MHz, DMSO-d6) δ 11.87 (s, 1H), 7.99-7.91 (m, 1H), 7.69 (d, J=8.1 Hz, 1H), 7.51 (s, 1H), 7.42 (ddd, J=8.3, 7.2, 1.3 Hz, 1H), 7.26 (ddd, J=8.2, 7.3, 1.2 Hz, 1H), 3.25-3.06 (m, 1H), 1.26 (d, J=6.8 Hz, 6H).

Preparation 9cb: N-[6-Chloro-4-(propan-2-yl)pyridazin-3-yl]-1,3-benzothiazol-2-amine To a solution of the product from Preparation 8cb (47 mg, 2.6 mmol, 1 eq) and 2-bromo-1,3-benzothiazole (669 mg, 3.13 mmol, 1.2 eq) in 1,4-dioxane (10 mL) was added sodium hydride (60% dispersion; 208 mg, 5.21 mmol, 2 eq) portionwise and the mixture was refluxed for 1 h. The mixture was allowed to cool to ambient temperature then cooled to 0° C. and quenched by addition of acetic acid. After evaporation the residue was partitioned between ethyl acetate and water and the organic phase was washed with brine, dried (magnesium sulfate) and concentrated in vacuo. Purification by automated flash column chromatography (CombiFlash Rf, 24 g RediSep™ silica cartridge) eluting with a gradient of 0-20% ethyl acetate in iso-heptane afforded the desired product as a bright yellow solid (367 mg, 1.2 mmol, 46%).

LC/MS ($C_{14}H_{13}ClN_4S$) 305 $[M+H]^+$; RT 1.35 (LCMS-V-B1)

$^1H$ NMR (400 MHz, DMSO-d6) δ 12.64 (s, 1H), 7.82 (br s, 1H), 7.61 (s, 1H), 7.40 (br s+t, J=7.3 Hz, 2H), 7.22 (t, J=6.8 Hz, 1H), 3.49 (p, J=6.8 Hz, 1H), 1.25 (d, J=6.9 Hz, 6H).

Preparation 9da and 9db: N-(6-Chloro-5-methylpyridazin-3-yl)-1,3-benzothiazol-2-amine and N-(6-Chloro-4-methylpyridazin-3-yl)-1,3-benzothiazol-2-amine To a suspension of the product from Preparation 8d (1.31 g, 9.1 mmol, 1 eq) and 2-bromo-1,3-benzothiazole (2.14 g, 10.01 mmol, 1.1 eq) in 1,4-dioxane (50 mL) was added sodium hydride (60% dispersion; 0.73 g, 18.2 mmol, 2 eq) portionwise and the mixture was refluxed for 1 h. The reaction mixture was allowed to cool to ambient temperature, quenched with acetic acid, then neutralised with aqueous sodium bicarbonate. The mixture was extracted with ethyl acetate (100 mL×3) and the combined organic extracts were washed with brine, dried (magnesium sulfate), and concentrated in vacuo. Purification by automated flash column chromatography (CombiFlash Rf, 120 g RediSep™ silica cartridge) eluting with a gradient of 0-80% ethyl acetate in iso-heptane afforded the desired products:

N-(6-Chloro-4-methylpyridazin-3-yl)-1,3-benzothiazol-2-amine as a yellow solid (140 mg, 0.51 mmol, 5.6%) [Preparation 9db].

LC/MS ($C_{12}H_9ClN_4S$) 277 $[M+H]^+$; RT 1.18 (LCMS-V-B1)

$^1H$ NMR (400 MHz, DMSO-d6) δ 7.90 (s, 1H), 7.71 (s, 1H), 7.57 (br s, 1H), 7.41 (t, J=7.5 Hz, 1H), 7.24 (t, J=7.5 Hz, 1H), 2.39 (s, 3H).

N-(6-Chloro-5-methylpyridazin-3-yl)-1,3-benzothiazol-2-amine as a yellow solid (69 mg, 0.25 mmol, 2.7%) [Preparation 9da].

LC/MS ($C_{12}H_9ClN_4S$) 277 $[M+H]^+$; RT 1.15 (LCMS-V-B1)

$^1H$ NMR (400 MHz, DMSO-d6) δ 11.92 (s, 1H), 7.96 (d, J=7.7 Hz, 1H), 7.69 (d, J=8.5 Hz, 1H), 7.48 (d, J=1.2 Hz, 1H), 7.42 (ddd, J=8.2, 7.2, 1.3 Hz, 1H), 7.26 (ddd, J=8.2, 7.3, 1.2 Hz, 1H), 2.38 (d, J=1.0 Hz, 3H).

Preparation 8ea and 9eb: N-[6-Chloro-4-methyl-5-(propan-2-yl)pyridazin-3-yl]-1,3-benzothiazol-2-amine and N-[6-Chloro-5-methyl-4-(propan-2-yl)pyridazin-3-yl]-1,3-benzothiazol-2-amine To a suspension of the product from Preparation 8e (434 mg, 2.34 mmol, 1 eq) and 2-bromo-1,3-benzothiazole (551 mg, 2.57 mmol, 1.1 eq) in 1,4-dioxane (10 mL) was added sodium hydride (60% dispersion; 187 mg, 4.68 mmol, 2 eq) portionwise and the mixture was refluxed for 1 h. The reaction mixture was allowed to cool to ambient temperature and then quenched with acetic acid. The mixture was then diluted with aqueous sodium bicarbonate and the product extracted with dichloromethane. The organics were washed with brine, dried (magnesium sulfate) and concentrated in vacuo. Purification by automated flash column chromatography (CombiFlash Rf, 40 g RediSep™ silica cartridge) eluting with a gradient of 0-30% ethyl acetate in iso-heptane afforded the desired product regioisomers:

N-[6-Chloro-5-methyl-4-(propan-2-yl)pyridazin-3-yl]-1,3-benzothiazol-2-amine as a yellow solid (114 mg, 0.36 mmol, 15%) [Preparation 9eb].

LC/MS ($C_{15}H_{15}ClN_4S$) 319 $[M+H]^+$; RT 1.39 (LCMS-V-B1)

$^1H$ NMR (400 MHz, DMSO-d6) δ 12.48 (s, 1H), 7.73 (d, J=7.8 Hz, 1H), 7.41-7.32 (m, 1H), 732-7.26 (m, 1H), 7.18 (t, J=7.5 Hz, 1H), 3.76-3.58 (m, 1H), 2.41 (s, 3H), 1.41 (d, J=7.0 Hz, 6H).

N-[6-Chloro-4-methyl-5-(propan-2-yl)pyridazin-3-yl]-1,3-benzothiazol-2-amine as an orange solid (300 mg, 0.94 mmol, 40%) [Preparation 9ea].

LC/MS ($C_{15}H_{15}ClN_4S$) 319 $[M+H]^+$; RT 1.36 (LCMS-V-B1)

$^1H$ NMR (400 MHz, DMSO-$d_6$) δ 12.64 (br s, 1H), 7.91-7.78 (m, 1H), 7.46 (br s, 1H), 7.40 (t, 1H), 7.22 (t, 1H), 3.56 (h, 1H), 2.47 (s, 3H), 1.37 (d, J=7.2 Hz, 6H).

Preparation 9fa and 9fb: N-(6-Chloro-5-ethyl-4-methylpyridazin-3-yl)-1,3-benzothiazol-2-amine and N-(6-Chloro-4-ethyl-5-methylpyridazin-3-yl)-1,3-benzothiazol-2-amine To a suspension of the product from Preparation 8f (1.4 g, 8.16 mmol, 1 eq) and 2-bromo-1,3-benzothiazole (2.1 g, 9.79 mmol, 1.2 eq) in 1,4-dioxane (50 mL) was added sodium hydride (60% dispersion; 1.31 g, 32.6 mmol, 4 eq) portionwise. The mixture was heated at reflux for 1.5 h then allowed to cool to ambient temperature. The reaction was quenched with acetic acid and neutralised with sodium bicarbonate. The mixture was extracted with ethyl acetate (×2), and the combined organic extracts were washed with brine, dried (magnesium sulfate) and concentrated in metro. Purification by automated flash column chromatography (CombiFlash Rf, 120 g RediSep™ silica cartridge) eluting with a gradient of 0-35% ethyl acetate in iso-heptane afforded the desired regioisomeric products:

N-(6-Chloro-4-ethyl-5-methylpyridazin-3-yl)-1,3-benzothiazol-2-amine as a yellow solid (330 mg, 1.08 mmol, 13%) [Preparation 9fb].

LC/MS ($C_{14}H_{13}ClN_4S$) 305 $[M+H]^+$; RT 1.31 (LCMS-V-B1)

$^1H$ NMR (400 MHz, DMSO-d6) δ 7.82 (br s, 1H), 7.38 (br s+t, 2H), 7.21 (t, 1H) 2.91 (q, J=7.4 Hz, 2H), 2.38 (s, 3H), 1.12 (t, J=7.5 Hz, 3H).

N-(6-Chloro-5-ethyl-4methylpyridazin-3-yl)-1,3-benzothiazol-2-amine as a yellow solid (750 mg, 2.46 mmol, 30%) [Preparation 9fa].

LC/MS ($C_{14}H_{13}ClN_4S$) 305 $[M+H]^+$; RT 1.30 (LCMS-V-B1)

$^1H$ NMR (400 MHz, DMSO-d6) δ 7.86 (s, 1H), 7.49 (br s, 1H), 7.40 (t, 1H), 7.22 (t, 1H), 2.79 (q, J=7.5 Hz, 2H), 2.41 (s, 3H), 1.14 (t, J=7.5 Hz, 3H).

Preparation 9ga and 9gb: N-{5-[(Benzyloxy)methyl]-6-chloro-4-methylpyridazin-3-yl}-1,3-benzothiazol-2-amine and N-{4-[(Benzyloxy)methyl]-6-chloro-5-methylpyridazin-3-yl}-1,3-benzothiazol-2-amine To a solution of the product from Preparation 8g (1.16 g, 4.4 mmol, 1 eq) and 2-bromo-1,3-benzothiazole (1.22 g, 5.72 mmol, 1.3 eq) in 1,4-dioxane (30 mL) was added sodium hydride (60% dispersion; 352 mg, 8.8 mmol, 2 eq) portionwise and the reaction was heated at reflux for 2 h. The mixture was allowed to cool to ambient temperature, quenched with acetic acid and neutralised with sodium bicarbonate. The product was extracted using ethyl acetate (200 mL×2) and washed with brine (100 mL). The organic extract was dried (magnesium sulfate) and concentrated in vacuo. Purification by automated flash column chromatography (CombiFlash Rf, 120 g RediSep™ silica cartridge) eluting with a gradient of 0-30% ethyl acetate in iso-heptane afforded the desired regioisomeric products:

N-{4-[(Benzyloxy)methyl]-6-chloro-5-methylpyridazin-3-yl}-1,3-benzothiazol-2-amine as a yellow solid (250 mg, 0.63 mmol, 14%) [Preparation 9gb].

LC/MS ($C_{20}H_{17}ClN_4OS$) 398 $[M+H]^+$; RT 1.43 (LCMS-V-B1)

$^1H$ NMR (400 MHz, DMSO-d6) δ 12.53 (br s, 1H), 7.84 (d, J=7.6 Hz, 1H), 7.55-7.27 (m, 7H), 7.23 (t, 1H), 4.89 (s, 2H), 4.61 (s, 2H), 2.38 (s, 3H).

N-{5-[(Benzyloxy)methyl]-6-chloro-4-methylpyridazin-3-yl}-1,3-benzothiazol-2-amine as a yellow solid (253 mg, 0.64 mmol, 14%) [Preparation 9ga].

LC/MS ($C_{20}H_{17}ClN_4OS$) 398 $[M+H]^+$; RT 1.39 (LCMS-V-B1)

$^1H$ NMR (400 MHz, DMSO-d6) δ 12.71 (br s, 1H), 7.85 (s, 1H), 7.45-7.27 (m, 7H), 7.26-7.15 (m, 1H), 4.67 (s, 2H), 4.60 (s, 2H), 2.44 (s, 3H).

Preparation 9ha: N-(6-Chloro-5-cyclopropyl-4-methylpyridazin-3-yl)-1,3-benzothiazol-2-amine To a solution of the product from Preparation 8ha (2.44 g, 13.3 mmol, 1 eq) and 2-bromo-1,3-benzothiazole (3.7 g, 17.3 mmol, 1.3 eq) in 1,4-dioxane (50 mL) was added sodium hydride (60% dispersion; 1.06 g, 26.6 mmol, 2 eq) portionwise and the mixture was heated at reflux for 1 h. The reaction was allowed to cool to ambient temperature, then quenched with acetic acid and neutralised by the addition of sodium bicarbonate. The resultant precipitate was collected by filtration and dried under vacuum to afford the desired product (0.98 g, 3.09 mmol, 23%).

LC/MS ($C_{15}H_{13}ClN_4S$) 317 $[M+H]^+$; RT 1.30 (LCMS-V-B1)

$^1H$ NMR (400 MHz, DMSO-d6) δ 11.88 (br s, 1H), 7.82 (d, 1H), 7.47 (d, J=8.0 Hz, 1H), 7.39-7.32 (m, 1H), 7.21-7.13 (m, 1H), 2.47 (d, J=1.0 Hz, 3H), 1.93-1.79 (m, 1H), 1.23-1.08 (m, 2H), 0.69 (td, J=6.2, 4.4 Hz, 2H).

Preparation 9hb: N-(6-Chloro-4-cyclopropyl-5-methylpyridazin-3-yl)-1,3-benzothiazol-2-amine To a solution of 2-bromo-1,3-benzothiazole (2.8 g, 13.1 mmol, 1.2 eq) and the product from Preparation 8hb (2 g, 10.9 mmol, 1 eq) in 1,4-dioxane (50 mL) was added sodium hydride (60% dispersion; 0.52 g, 21.8 mmol, 2 eq) portionwise and the reaction was heated at reflux for 1 h. The mixture was allowed to cool to ambient temperature and concentrated in vacuo. The residue was taken-up in ethyl acetate, filtered, and the solid residue extracted with ethyl acetate. The combined organic extracts were washed with brine, dried (magnesium sulfate) and concentrated in vacuo. Purification by automated flash column chromatography (CombiFlash Rf, 40 g RediSep™ silica cartridge) eluting with a gradient of 0-40% ethyl acetate in iso-heptane afforded the desired product as a yellow solid (219 mg, 0.69 mmol, 6%).

LC/MS ($C_{15}H_{13}ClN_4S$) 317 $[M+H]^+$; RT 1.28 (LCMS-V-B1)

$^1H$ NMR (400 MHz, DMSO-d6) δ 10.74 (br s, 1H), 8.05-7.85 (m, 1H), 7.78-7.55 (m, 1H), 7.42 (t, 1H), 7.25 (t, 1H), 2.47 (d, J=0.9 Hz, 4H), 2.01-1.89 (m, 1H), 1.14-1.02 (m, 2H), 0.72-0.60 (m, 2H).

Preparation 9ja: N-[6-Chloro-5-(methoxymethyl)-4-methylpyridazin-3-yl]-1,3-benzothiazol-2-amine To a solution of the product from Preparation 8ja (323 mg, 1 eq) and 2-bromo-1,3-benzothiazole (442 mg 2.07 mmol, 1.2 eq) in 1,4-dioxane (10 mL) was added sodium hydride (60% dispersion; 138 mg, 3.44 mmol, 2 eq) portionwise and the mixture was heated at reflux for 1.5 h. The mixture was cooled to ambient temperature, neutralised with acetic acid and concentrated in vacuo. The crude material was partitioned between dichloromethane and water, and the organic phase was dried (magnesium sulfate) and concentrated in vacuo. Purification by automated flash column chromatography (CombiFlash Rf, 40 g RediSep™ silica cartridge) eluting with a gradient of 0-50% ethyl acetate in iso-heptane afforded the desired product as a bright yellow solid (85 mg, 0.26 mmol, 15%).

LC/MS ($C_{14}H_{13}ClN_4OS$) 321 $[M+H]^+$; RT 1.19 (LCMS-V-B1)

$^1H$ NMR (400 MHz, DMSO-d6) δ 8.18-6.98 (m, 5H), 4.58 (s, 2H), 3.35 (s, 3H), 2.46 (s, 3H).

Preparation 9jb: N-[6-Chloro-4-(methoxymethyl)-5-methylpyridazin-3-yl]-1,3-benzothiazol-2-amine To a solution of the product from Preparation 8jb (140 mg, 0.81 mmol, 1 eq) and 2-bromo-1,3-benzothiazole (224 mg, 1.05 mmol, 1.3 eq) in 1,4-dioxane (7 mL) was added sodium hydride (60% dispersion; 58.1 mg, 2.42 mmol, 3 eq) portionwise and the mixture was heated at reflux for 30 min. The reaction was cooled to 0° C. and slowly quenched with water, diluted with ethyl acetate and washed with sodium bicarbonate and brine. The organic phase was dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a yellow solid (169 mg, 0.53 mmol, 58%).

LC/MS ($C_{14}H_{13}ClN_4OS$) 321 $[M+H]^+$; RT 1.23 (LCMS-V-B1)

$^1H$ NMR (400 MHz, DMSO-d6) δ 12.63 (s, 1H), 7.79 (s, 1H), 7.54-7.26 (m, 2H), 7.22 (s, 1H), 4.77 (s, 2H), 3.36 (s, 3H), 2.41 (s, 3H).

Preparation 9ka: N-[6-Chloro-5-(ethoxymethyl)-4-methylpyridazin-3-yl]-1,3-benzothiazol-2-amine To a solution of the product from Preparation 8ka (136 mg, 0.67 mmol, 1 eq) and 2-bromo-1,3-benzothiazole (173 mg, 0.81 mmol, 1.2 eq) in 1,4-dioxane mL) was added sodium hydride (60% dispersion; 53.9 mg, 1.35 mmol, 2 eq) portionwise and the mixture was heated at reflux for 1 h. The reaction was allowed to cool to ambient temperature and quenched with water. The mixture was partitioned between ethyl acetate and saturated aqueous sodium bicarbonate, and the organic phase was washed with brine then dried (magnesium sulfate) and concentrated in vacuo. Purification by automated flash column chromatography (CombiFlash Rf, 24 g RediSep™ silica cartridge) eluting with a gradient of 0-40% ethyl acetate in iso-heptane afforded the desired product as a yellow solid (113 mg, 0.34 mmol, 50%).

LC/MS ($C_{15}H_{15}ClN_4OS$) 335 $[M+H]^+$; RT 1.28 (LCMS-V-B1)

$^1H$ NMR (400 MHz, DMSO-d6) δ 7.86 (s, 1H), 7.46 (br s, 1H), 7.41 (t, 1H), 7.23 (t, J=7.7 Hz, 1H), 4.61 (s, 2H), 3.56 (q, J=7.0 Hz, 2H), 2.47 (s, 3H), 1.16 (t, J=7.0 Hz, 3H).

Preparation 9ma: N-{5-[3-(Benzyloxy)propyl]-6-chloro-4-methylpyridazin-3-yl}-1,3-benzothiazol-2-amine To a solution of the product from Preparation 8ma (1.3 g, 4.46 mmol, 1 eq) and 2-bromo-1,3-benzothiazole (1.14 g, 5.35 mmol, 1.2 eq) in 1,4-dioxane (50 mL) was added sodium hydride (60% dispersion; 356 mg, 8.91 mmol, 2 eq) portionwise and the mixture was heated at reflux for 1 h. The reaction was allowed to cool to ambient temperature then quenched by the addition of water and partitioned between ethyl acetate (100 mL) and sodium bicarbonate (50 mL). The organic phase was washed with brine (50 mL), dried (magnesium sulfate), and concentrated in vacuo. Purification by automated flash column chromatography (CombiFlash Rf, 80 g RediSep™ silica cartridge) eluting with a gradient of 0-55% ethyl acetate in iso-heptane afforded the desired product as a cream solid (1.59 g, 3.74 mmol, 84%).

LC/MS ($C_{22}H_{21}ClN_4OS$) 425 $[M+H]^+$; RT 1.25 (LCMS-V-B1)

$^1H$ NMR (400 MHz, DMSO-d6) δ 7.86 (s, 1H), 7.67-7.11 (m, 8H), 4.50 (s, 2H), 3.53 (t, J=6.0 Hz, 2H), 2.94-2.81 (m, 2H), 2.41 (s, 3H), 1.89-1.72 (m, 2H).

Preparation 10a: 1-(1-Adamantylmethyl)-5-methyl-4-(4,4,5,5-tetramethyl-1,3,2-dioxaborolan-2-yl)pyrazole

Step A: 1-(1-adamantylmethyl)-4-iodo-pyrazole

The mixture of 35.9 g of 1-adamantylmethanol (216 mmol), 73.48 g of triphenylphosphine (280 mmol, 1.3 eq.), 54.25 g of 4-iodo-1H-pyrazole (280 mmol, 1.3 eq.) and 64.4 g of tert-butyl N-(tert-butoxycarbonyliminomethylene)carbamate (266 mmol, 1.3 eq.) in 1078 mL of THF was stirred at rt for 48 h. After the addition of extra 10.94 g of 4-iodo-1H-pyrazole (56 mmol, 0.26 eq.), 12.81 g of tert-butyl N-(tert-butoxycarbonyliminomethylene)carbamate (53 mmol, 0.26 eq.) and 14.69 g of triphenylphosphine (56 mmol, 0.26 eq.), the reaction was stirred at rt for 24 h then concentrated, purified via flash column chromatography using DCM as eluent, triturated in cold MeOH, and filtered off to give 53.6 g (73%) of the desired product.

Step B: 1-(1-adamantylmethyl)-4-iodo-5-methyl-pyrazole

To 9.8 mL of diisopropylamine (69.5 mmol, 1.1 eq.) in 180 mL of THF was added dropwise 33.4 mL of a 2.5 M solution of butyl lithium (84 mmol, 1.3 eq.) at −78° C. and the mixture was stirred at −78° C. for 0.5 h, treated with 22.0 g of the product from Step A (64.28 mmol, 1 eq.) in 90 mL of THF, stirred at −78° C. for 1 h, treated with 4.67 mL of methyliodide (73.3 mmol, 1.14 eq.), and stirred at −78° C. for 18 h. After quenching with cc. $NH_4Cl$, the reaction was extracted with EtOAc and the combined organic phases were washed with brine, dried, concentrated, triturated in MeOH, and filtered off to give 21 g (92%) of the desired product.

$^1$H NMR (400 MHz, $CDCl_3$) δ ppm 7.44 (s, 1H), 3.77 (s, 2H), 2.30 (s, 3H), 1.99 (bs, 3H), 1.74/1.52 (m, 12H).

Step C: 1-(1-adamantylmethyl)-5-methyl-4-(4,4,5,5-tetramethyl-1,3,2-dioxaborolan-2-yl)pyrazole To 21 g of the product from Step B (58.95 mmol, 1 eq.) in 300 mL of THF was added 28.3 mL of a 2.5 M solution of butyllithium (70.8 mmol, 1.2 eq) at −78° C. and the mixture was stirred at −78° C. for 0.5 h, treated with 16.4 g of 2-isopropoxy-4,4,5,5-tetramethyl-1,3,2-dioxaborolane (88.1 mmol, 1.5 eq.)(addition in portions over 40 min), and kept at −78° C. for 24 h. After quenching with cc. $NH_4Cl$ at rt, the reaction was extracted with EtOAc and the combined organic phases were washed with brine, dried, concentrated, triturated in MeOH, and filtered off to give 19.7 g (94%) of the desired product.

$^1$H NMR (500 MHz, DMSO-$d_6$) δ ppm 7.45 (s, 1H), 3.69 (s, 2H), 2.36 (s, 3H), 1.91 (m, 1H), 1.64/1.54 (m, 6H), 1.50 (m, 6H), 1.24 (s, 12H); $^{13}$C NMR (500 MHz, DMSO-$d_6$) δ ppm 146.9, 144.1, 104.6, 59.7, 40.6, 36.8, 35.4, 28.1, 25.1, 12.1; HRMS-ESI (m/z): [M+H]+ calcd for $C_{21}H_{34}BN_2O_2$: 357.2713, found 357.2704.

Preparation 10b: 1-{[1-(3-Methoxypropyl)cyclooctyl]methyl}-5-methyl-4-(4,4,5,5-tetramethyl-1,3,2-dioxaborolan-2-yl)-1H-pyrazole Step A: methyl 1-(3-methoxypropyl)cyclooctanecarboxylate To 4.74 g (1.14 eq.) of diisopropylamine in 90 mL of tetrahydrofuran was added 18.8 mL (1.14 eq.) of a 2.5 M solution of butyl lithium at −78° C. and after 0.5 h at −78° C., 7.0 g (41.1 mmol) of methyl cyclooctanecarboxylate in 40 mL of tetrahydrofuran was added over 1 h. After 1 h at −78° C., 7.2 g (1.14 eq.) of 1-bromo-3-methoxy-propane was added and the mixture was stirred for 18 h. After quenching the reaction with the addition of saturated $NH_4Cl$ solution, the mixture was extracted with EtOAc and the organic phases were dried over $MgSO_4$ and concentrated to give 8.0 g (80%) of the desired product.

$^1$H NMR (400 MHz, $CDCl_3$) δ ppm 3.66 (s, 3H), 3.33 (t, 2H), 3.31 (s, 3H), 2.03-1.94 (m, 2H), 1.64-1.38 (m, 16H).

Step B: [1-(3-methoxypropyl)cyclooctyl]methanol

To 9.0 g (37.13 mmol) of the product from Step A in 93 mL of diethyl ether was added 1.76 g (1.25 eq.) of lithium aluminum hydride portion wise at 0° C. After stirring at rt for 2 h, the reaction was quenched by the addition of icy water and EtOAc and a 10% solution of NaOH were added. The mixture was extracted with EtOAc, dried, and concentrated to give 7.4 g (93%) of the desired product.

$^1$H NMR (400 MHz, $CDCl_3$) δ ppm 3.37 (t, 2H), 3.34 (s, 3H), 3.30 (s, 2H), 1.61-1.23 (m, 18H).

Step C: 4-iodo-1-[[1-(3-methoxypropyl)cyclooctyl]methyl]pyrazole

To 1.39 g (6.5 mmol) of the product from Step B and 1.64 g (1.3 eq.) of 4-iodo-1H-pyrazole in 33 mL of tetrahydrofuran was added 2.22 g (1.3 eq.) of triphenylphosphine and 1.95 g (1.3 eq.) of ditertbutyl azodicarboxylate and the mixture was stirred at rt for 67 h. To the mixture was added 278 mg of 4-iodo-1H-pyrazole, 444 mg of triphenylphosphine, and 390 mg of ditertbutyl azodicarboxylate and was stirred at rt for 24 h. After the addition of reagents and stirring at rt for 24 h was repeated (115 h stirring in total), the mixture was concentrated and purified via flash column chromatography (silica gel) using heptane and EtOAc as eluents to give 1.24 g (49%) of the desired product.

$^1$H NMR (400 MHz, $CDCl_3$) δ ppm 7.47 (s, 1H), 7.42 (s, 1H), 3.93 (s, 2H), 3.37 (t, 2H), 3.36 (s, 3H), 1.68-1.18 (m, 18H).

Step D: 4-iodo-1-[[1-(3-methoxypropyl)cyclooctyl]methyl]-5-methyl-pyrazole

To 1.2 g (3.07 mmol) of the product from Step C in 5 mL of tetrahydrofuran was added 3.7 mL (1.2 eq.) of a 1 M solution of LDA at −78° C. After 0.6 h at −78° C., 0.5 mL (1.14 eq.) of methyl iodide was added dropwise to the mixture and it was let to warm up to rt over 20 h. Reaction was quenched with a saturated solution of $NH_4Cl$ and extracted with EtOAc. The combined organic phases were dried, concentrated, and purified via flash column chromatography (silica gel) using heptane and EtOAc as eluents to give 0.79 g (64%) of the desired product.

$^1$H NMR (400 MHz, $CDCl_3$) δ ppm 7.43 (s, 1H), 3.85 (s, 2H), 3.38 (t, 2H), 3.35 (s, 3H), 2.29 (s, 3H), 1.69-1.24 (m, 18H).

Step E: 1-[[1-(3-methoxypropyl)cyclooctyl]methyl]-5-methyl-4-(4,4,5,5-tetramethyl-1,3,2-diaxaborolan-2-yl)pyrazole To the solution of 0.81 g (2 mmol) of the product from Step D in 15 mL of tetrahydrofuran was added 0.96 mL (1.2 eq.) of a 2.5 M solution of butyl lithium dropwise at −78° C. After 0.5 h, 0.5 mL (1.2 eq.) of 2-isopropoxy-4,4,5,5-tetramethyl-1,3,2-dioxaborolane was added over 20 min and the mixture was kept at −78° C. for 6 h and at rt for 6 h. After quenching the reaction with saturated solution of $NH_4Cl$ and extracting with EtOAc, the combined organic phases were washed with brine, dried, and purified via flash column chromatography (silica gel) using heptane and EtOAc as eluents to give 0.33 g (34%) of the desired product.

$^1$H NMR (500 MHz, dmso-d6) δ ppm 7.46 (s, 1H), 3.75 (s, 2H), 3.27 (t, 2H), 3.21 (s, 3H), 2.36 (s, 3H), 1.66-1.1 (m, 14H), 1.57 (m, 2H), 1.24 (s, 12H), 1.24 (m, 2H). $^{13}$C NMR (500 MHz, dmso-d6) δ ppm 147.3, 144.5, 104.5, 73.2, 58.2, 54.4, 40.5, 33.2, 25.1, 23.6, 11.8. IR: 2922, 1556, 1246, 1144, 1055. HRMS-ESI (m/z): [M+H+ calcd for $C_{23}H_{42}N_2O_3B$: 405.3289, found 404.3334.

Preparation 10c: 1-{[1-(3-Methoxypropyl)cyclohexyl]methyl}-5-methyl-4-(4,4,5,5-tetramethyl-1,3,2-dioxaborolan-2-yl)-1H-pyrazole Step A: methyl 1-(3-methoxypropyl)cyclohexanecarboxylate To 6.84 g (1.09 eq.) of diisopropylamine in 130 mL of tetrahydrofuran was added 27 mL (1.09 eq.) of a 2.5 M solution of butyl lithium at −78° C. and after 0.5 h at −78° C., 8.8 g of methyl cyclohexanecarboxylate in 50 mL of tetrahydrofuran was added over 1 h. After 1 h at −78° C., 10.7 g (1.13 eq.) of 1-bromo-3-methoxy-propane was added and the mixture was stirred for 18 h. After quenching the reaction with the addition of saturated $NH_4Cl$ solution, the mixture was extracted with EtOAc and the organic phases were dried over $MgSO_4$ and concentrated to give 12 g (92%) of the desired product.

$^1H$ NMR (400 MHz, $CDCl_3$) δ ppm 3.67 (s, 3H), 3.35 (d, 1H), 3.32 (d, 1H), 3.31 (s, 3H), 2.11-2.03 (m, 2H), 1.60-1.16 (m, 12H).

Step B: [1-(3-methoxypropyl)cyclohexyl]methanol

To 12 g (56.41 mmol) of the product from Step A in 140 mL of diethyl ether was added 2.68 g (1.25 eq.) of lithium aluminum hydride portion wise at 0° C. After stirring at rt for 2 h, the reaction was quenched by the addition of icy water and EtOAc and a 10% solution of NaOH were added. The mixture was extracted with EtOAc, dried, and concentrated to give 9.37 g (89%) of the desired product.

$^1H$ NMR (400 MHz, $CDCl_3$) δ ppm 3.41 (s, 2H), 3.38 (t, 2H), 3.35 (s, 3H), 1.56-1.27 (m, 14H).

Step C: 4-iodo-1-[[1-(3-methoxypropyl)cyclohexyl]methyl]pyrazole

To 1.21 g (6.5 mmol) of the product from Step B and 2.58 g (2.05 eq.) of 4-iodo-1H-pyrazole in 33 mL of tetrahydrofuran was added 3.5 g (2.05 eq.) of triphenylphosphine and 3.07 g (2.05 eq.) of ditertbutyl azodicarboxylate and the mixture was stirred at rt for 2 h. To the mixture was added 140 mg of 4-iodo-1H-pyrazole, 230 mg of triphenylphosphine, and 200 mg of ditertbutyl azodicarboxylate and was stirred at rt for 24 h. After the addition of reagents and stirring at rt for 24 h was repeated twice (96 h stirring in total), the mixture was concentrated and purified via flash column chromatography (silica gel) using heptane and EtOAc as eluents to give 1.4 g (59.5%) of the desired product.

$^1H$ NMR (400 MHz, $CDCl_3$) δ ppm 7.47 (s, 1H), 7.41 (s, 1H), 4.00 (s, 2H), 3.36 (t, 2H), 3.35 (s, 3H), 1.62-1.21 (m, 14H).

Step D: 4-iodo-1-[[1-(3-methoxypropyl)cyclohexyl]methyl]-5-methyl-pyrazole

To 3.7 g (10.21 mmol) of the product from Step C in 15 mL of tetrahydrofuran was added 12.3 mL (1.2 eq.) of a 1 M solution of LDA in tetrahydrofuran at −78° C. After 0.6 h at −78° C., 0.73 mL (1.14 eq.) of methyl iodide was added dropwise to the mixture and it was let to warm up to it over 20 h. Reaction was quenched with a saturated solution of $NH_4Cl$ and extracted with EtOAc. The combined organic phases were dried, concentrated, and purified via flash column chromatography (silica gel) using heptane and EtOAc as eluents to give 2.85 g (74%) of the desired product.

$^1H$ NMR (400 MHz, $CDCl_3$) δ ppm 7.44 (s, 1H), 3.92 (s, 2H), 3.38 (t, 2H), 3.35 (s, 3H), 2.29 (s, 3H), 1.58-1.13 (m, 14H).

Step E: 1-[[1-(3-methoxypropyl)cyclohexyl]methyl]-5-methyl-4-(4,4,5,5-tetramethyl-1,3,2-dioxaborolan-2-yl)pyrazole To the solution of 5.0 g (13.3 mmol) of the product from Step D in 71 mL of tetrahydrofuran was added 6.38 mL (1.2 eq.) of a 2.5 M solution of butyl lithium dropwise at −78° C. After 0.5 h, 4.1 mL (1.5 eq.) of 2-isopropoxy-4,4,5,5-tetramethyl-1,3,2-dioxaborolane was added over 40 min and the mixture was kept at −78° C. for 6 h and at rt for 6 h. After quenching the reaction with saturated solution of $NH_4Cl$ and extracting with EtOAc, the combined organic phases were washed with brine, dried, and purified via flash column chromatography (silica gel) using heptane and EtOAc as eluents to give 2.3 g (46%) of the desired product.

$^1H$ NMR (500 MHz, dmso-d6) δ ppm 7.47 (s, 1H), 3.84 (s, 2H), 3.27 (t, 2H), 3.2 (s, 3H), 2.37 (s, 3H), 1.54-1.07 (m, 10H), 1.46 (m, 2H), 1.32 (m, 2H), 1.24 (s, 12H). $^{13}C$ NMR (500 MHz, dmso-d6) δ ppm 147.3, 144.4, 104.6, 73.1, 58.2, 55.7, 37.9, 30.6, 25.1, 23.1, 12.0. IR: 2927, 1556, 1257, 1144, 1053. HRMS-ESI (m/z): [M+H+ calcd for $C_{21}H_{38}N_2O_3B$: 376.2897, found 376.3019.

Preparation 11a: Ethyl 5-bromo-2-[(4,5-dimethyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Step A: (2Z)—N-(6-chloro-4,5-dimethylpyridazin-3-yl)-3-{[2-(trimethylsilyl)ethoxy]methyl}-2,3-dihydro-1,3-benzothiazol-2-imine N,N-Diisopropylethylamine (3.6 mL, 20.6 mmol, 2 eq) was added to a suspension of the product from. Preparation 9a (3 g, 10.3 mmol, 1 eq) in dichloromethane (75 mL) at 0° C. under a nitrogen atmosphere. [2-(chloromethoxy)ethyl]trimethylsilane (2 mL, 11.3 mmol, 1.1 eq) and 4-dimethylaminopyridine (63.0 mg, 0.52 mmol, 0.05 eq) were added and the mixture was stirred at room temperature for 3 h. Dichloromethane (75 mL) was added and the mixture washed with water (2×75 mL) and brine (75 mL). The solution was dried (magnesium sulfate) and concentrated in vacuo. Purification by column chromatography, isolute flash silica (20 g) eluting with dichloromethane afforded the desired product as a pale brown solid (3.95 g, 8.44 mmol, 82%) that was used directly in the next step without further characterisation.

Step B: ethyl 2-[(4,5-dimethyl-6-{[(2Z)-3-{[(2-(trimethylsilyl)ethoxy]methyl}-2,3-dihydro-1,3-benzothiazol-2-ylidene]amino}pyridazin-3-yl)amino]-1,3-thiazole-4-carboxylate The product from Step A (500 mg, 1.19 mmol, 1 eq) and ethyl 2-amino-1,3-thiazole-4-carboxylate (245.4 mg, 1.43 mmol, 1.2 eq) were added to a solution of cesium carbonate (1.16 g. 3.56 mmol, 3 eq), tris(dibenzylideneacetone)dipalladium(0)(54.4 mg, 0.06 mmol, 0.05 eq) and Xantphos (68.7 mg, 0.12 mmol, 0.1 eq) in alpha,alpha,alpha-trifluorotoluene (10 mL) under a nitrogen atmosphere. The mixture was sparged with nitrogen (10 min) then heated at 170° C. for 1 h under microwave irradiation. The solution was allowed to cool to ambient temperature and concentrated in vacuo. The mixture was partitioned between ethyl acetate and water and the organic phase was washed with brine, dried (magnesium sulfate) and solvent removed in vacuo. Purification by automated flash column chromatography (CombiFlash Rf, 24 g RediSep™ silica cartridge) eluting with a gradient of 0-50% ethyl acetate in iso-heptane afforded the desired product as an orange foam (301 mg, 0.54 mmol, 46%).

LC/MS ($C_{25}H_{32}N_6O_3SiS_2$) 557 $[M+H]^+$; RT 1.49 (LCMS-V-B1)

$^1$H NMR (400 MHz, DMSO-d6) δ 10.98 (s, 1H), 7.93 (s, 1H), 7.81 (dd, J=7.6, 1.1 Hz, 1H), 7.48-7.37 (m, 2H), 7.27-7.20 (m, 1H), 5.84 (s, 2H), 4.29 (q, J=7.1 Hz, 2H), 3.71 (dd, J=8.4, 7.5 Hz, 2H), 2.41 (s, 3H), 2.35 (s, 3H), 1.31 (t, J=7.1 Hz, 3H), 0.97-0.86 (m, 2H), −0.12 (s, 9H).

Step C: ethyl 5-bromo-2-[(4,5-dimethyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate N-Bromosuccinimide (125 mg, 0.7 mmol, 1.3 eq) was added to a stirred solution of the product from Step B (301 mg, 0.54 mmol, 1 eq) in dichloromethane (15 mL). The reaction was stirred at ambient temperature for 1.5 h then the solvent was removed in vacuo. Purification by automated flash column chromatography (CombiFlash Rf, 24 g RediSep™ silica cartridge) eluting with a gradient of 0-60% ethyl acetate in iso-heptane afforded the desired product as a brown gum (198 mg, 0.31 mmol, 58%).

LC/MS ($C_{25}H_{31}BrN_6O_3SiS_2$) 637 $[M+H]^+$; RT 1.57 (LCMS-V-B1)

$^1$H NMR (400 MHz, DMSO-d6) δ 11.31 (s, 1H), 7.82 (d, 1H), 7.48-7.38 (m, 2H), 7.28-7.20 (m, 1H), 5.84 (s, 2H), 4.30 (q, J=7.1 Hz, 2H), 3.70 (dd, J=8.5, 7.4 Hz, 2H), 2.41 (s, 3H), 2.34 (s, 3H), 1.32 (t, J=7.1 Hz, 3H), 0.97-0.86 (m, 2H), −0.12 (s, 9H).

Preparation 11b: Ethyl 5-bromo-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Step A: ethyl 2-[(6-chloro-5-methylpyridazin-3-yl(methyl)amino]-1,3-thiazole-4-carboxylate A solution of 3,6-dichloro-4-methyl-pyridazine (662 mg, 4.06 mmol, 1.02 eq) and ethyl 2-(methylamino)-1,3-thiazole-4-carboxylate (742 mg, 3.98 mmol, 1 eq) in tetrahydrofuran (20 mL) was cooled in an ice bath then sodium hydride (60% in mineral oil; 188 mg, 4.7 mmol, 1.18 eq) was added slowly. The mixture was maintained in the ice bath for 1 h then stirred at ambient temperature for 3 h. Saturated aqueous ammonium chloride solution was added and the solution was extracted with dichloromethane (×2). The combined organic extracts were washed with water (×2) followed by brine then dried (magnesium sulfate) and the solvent removed in vacuo. The residue was triturated in a mix of dichloromethane and methanol and the solids collected by filtration and dried under vacuum to afford the desired product as a cream solid (324 mg, 1.04 mmol, 26%).

LC/MS ($C_{12}H_{13}ClN_4O_2S$) 313 $[M+H]^+$; RT 1.15 (LCMS-V-B1)

$^1$H NMR (400 MHz, DMSO-d6) δ 8.04 (s, 1H), 7.87 (d, J=1.2 Hz, 1H), 4.30 (q, J=7.1 Hz, 2H), 3.83 (s, 3H), 2.44 (d, J=1.0 Hz, 3H), 1.32 (t, J=7.1 Hz, 3H).

Step B: ethyl 2-({6-[(1,3-benzothiazol-2-yl)amino]-5-methylpyridazin-3-yl}(methyl)amino)-1,3-thiazole-4-carboxylate The product from Step A (467 mg, 1.49 mmol, 1 eq) and 2-aminobenzothiazole (269 mg, 1.79 mmol, 1.2 eq) were added to a mixture of cesium carbonate (1.46 g, 4.47 mmol, 3 eq), tris(dibenzylideneacetone)dipalladium(0)(68.3 mg, 0.07 mmol, 0.05 eq) and Xantphos (86.3 mg, 0.15 mmol, 0.1 eq) in alpha,alpha,alpha-trifluorotoluene (10 mL) under a nitrogen atmosphere. The mixture was sparged with nitrogen (10 min) then heated at 170° C. for 1 h under microwave irradiation. The solution was allowed to cool to ambient temperature, filtered, eluting with dichloromethane, and the filtrate concentrated in vacuo. Purification by automated flash column chromatography (CombiFlash Rf, 24 g RediSep™ silica cartridge) eluting with a gradient of 0-5% methanol in dichloromethane afforded the desired product as a yellow solid (133 mg, 0.31 mmol, 21%).

LC/MS ($C_{19}H_{18}N_6O_2S_2$) 427 $[M+H]^+$; RT 1.30 (LCMS-V-B1)

$^1$H NMR (400 MHz, DMSO-d6) δ 11.10 (s, 1H), 7.99 (d, J=6.9 Hz, 1H), 7.76-7.67 (m, 1H), 7.54-7.34 (m, 2H), 7.28-7.17 (m, 1H), 4.30 (q, J=7.2 Hz, 2H), 3.83 (s, 3H), 2.48 (s, 3H), 1.31 (t, 3H).

Step C: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A solution of the product from Step B (133 mg, 0.31 mmol, 1 eq) in dichloromethane (5 mL) was cooled in an ice bath then N,N-diisopropylethylamine (0.1 mL, 0.62 mmol, 2 eq) was added. After 5 min 4-dimethylaminopyridine (1.9 mg, 0.02 mmol, 0.05 eq) was added, followed by 2-(trimethylsilyl)ethoxymethyl chloride (0.06 mL, 0.34 mmol, 1.1 eq). The mixture was allowed to slowly warm to ambient temperature and was stirred overnight. The reaction was diluted with dichloromethane, washed successively with water (×2) and brine, dried (magnesium sulfate), and the solvent removed in vacuo. Purification by automated flash column chromatography (CombiFlash Rf, 12 g RediSep™ silica cartridge) eluting with a gradient of 0-50% ethyl acetate in iso-heptane afforded the desired product as a yellow glass (56.3 mg, 0.1 mmol, 32%).

LC/MS ($C_{25}H_{32}N_6O_3SiS_2$) 557 $[M+H]^+$; RT 1.64 (LCMS-V-B1)

$^1$H NMR (400 MHz, DMSO-d6) δ 7.97 (s, 1H), 7.85 (dd, J=7.6, 1.0 Hz, 1H), 7.71 (d, J=1.1 Hz, 1H), 7.50-7.40 (m, 2H), 7.29-7.22 (m, 1H), 5.87 (s, 2H), 4.29 (q, J=7.1 Hz, 2H), 3.83 (s, 3H), 3.78-3.67 (m, 2H), 2.46 (d, J=1.0 Hz, 3H), 1.31 (t, J=7.1 Hz, 3H), 0.98-0.87 (m, 2H), −0.12 (s, 9H).

Step D: ethyl 5-bromo-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate N-Bromosuccinimide (23.4 mg, 0.13 mmol, 1.3 eq) was added to a stirred solution of the product from Step C (56.3 mg, 0.1 mmol, 1 eq) in dichloromethane (5 mL). The reaction was stirred at ambient temperature for 1.5 h then the solvent removed in vacuo. Purification by automated flash column chromatography (CombiFlash Rf, 24 g RediSep™ silica cartridge) eluting with a gradient of 0-60% ethyl acetate in iso-heptane afforded the desired product as a white solid (54.7 mg, 0.09 mmol, 85%)

LC/MS ($C_{25}H_{31}BrN_6O_3SiS_2$) 635 $[M+H]^+$; RT 1.73 (LCMS-V-B1)

$^1$H NMR (400 MHz, DMSO-d6) δ 7.86 (dd, J=7.7, 1.0 Hz, 1H), 7.73 (d, J=1.1 Hz, 1H), 7.52-7.38 (m, 2H), 7.25 (ddd, J=8.3, 7.0, 1.5 Hz, 1H), 5.87 (s, 2H), 4.31 (q, J=7.1 Hz, 2H), 3.78 (s, 3H), 3.76-3.66 (m, 2H), 2.46 (d, J=1.0 Hz, 3H), 1.32 (t, J=7.1 Hz, 3H), 0.98-0.85 (m, 2H), −0.11 (s, 9H).

Preparation 11c: Ethyl 5-bromo-2-[(3-methoxypropyl)(5-methyl-6-{[(2Z)-3-{[2-(trimethylsilyl)ethoxy] methyl}-2,3-dihydro-1,3-benzothiazol-2-ylidene] amino}pyridazin-3-yl)amino]-1,3-thiazole-4-carboxylate Step A: ethyl 2-[(3-methoxypropyl)amino]-1,3-thiazole-4-carboxylate Ammonia (2M in isopropanol; 60 mL, 0.12 mol, 3.45 eq) was added to a solution of 3-methoxypropylisothiocyanate (4.5 g, 34.3 mmol, 1 eq) in isopropanol (15 mL) at 0° C. and the mixture was stirred for 1 h at 0° C. then for 18 h at ambient temperature. The suspension was concentrated in vacuo to afford a pale yellow gum. Ethanol (60 mL) and ethyl bromopyruvate (5 mL, 35.9 mmol, 1.05 eq) were added and the mixture was stirred for 1 h under a nitrogen atmosphere. Triethylamine (10 mL, 68.6 mmol, 2 eq) was added and the mixture was stirred at ambient temperature for 18 h. The reaction mixture was partitioned between ethyl acetate (300 mL) and water, and the organic phase was successively washed with water (150 mL) and brine (100 mL), dried (magnesium sulfate) and concentrated in vacuo. Purification by flash column chromatography (100 g silica) eluting with 99:1 dichloromethane/methanol gave a dark yellow oil that was triturated heptane (30 mL), filtered, washed with heptane (20 mL) and dried under vacuum afford the desired product as a pale brown powder (5.75 g, 23.5 mmol, 69%).

LC/MS ($C_{10}H_{16}N_2O_3S$) 245 $[M+H]^+$; RT 0.99 (LCMS-V-B1)

$^1H$ NMR (400 MHz, $CDCl_3$) δ 7.38 (d, J=0.7 Hz, 1H), 6.03 (t, J=5.6 Hz, 1H), 4.34 (q, J=7.1 Hz, 2H), 3.54-3.42 (m, 2H), 3.40-3.33 (m, 2H), 3.32 (s, 3H), 1.97-1.83 (m, 2H), 1.36 (t, J=7.1 Hz, 3H).

Step B: ethyl 2-[(6-chloro-5-methylpyridazin-3-yl)(3-methoxypropyl)amino]-1,3-thiazole-4-carboxylate Sodium hydride (60% dispersion; 350 mg, 8.75 mmol, 1.22 eq) was added to a solution of the product from Step A (1.75 g, 7.16 mmol, 1 eq) and 3,6-dichloro-4-methylpyridazine (1.3 g, 7.98 mmol, 1.11 eq) in 1,4-dioxane (30 mL) at 0° C. under a nitrogen atmosphere and the mixture was stirred for 1 h at 0° C. then heated at 60° C. for 6 h. The reaction mixture was allowed to cool to ambient temperature then partitioned between ethyl acetate (300 mL) and saturated aqueous ammonium chloride (150 mL). The organic phase was successively washed with water (2×150 mL) and brine (100 mL), dried (magnesium sulfate), and concentrated in vacuo. Purification by flash column chromatography (50 g silica) eluting with 39:1 dichloromethane/methanol gave a brown oil that was triturated with diethyl ether (10 mL), filtered, washed with diethyl ether (10 mL) and dried under vacuum afford the desired product as a pale brown powder (1.3 g, 3.51 mmol, 49%).

LC/MS ($C_{15}H_{19}ClN_4O_3S$) 371 $[M+H]^+$; RT 1.28 (LCMS-V-B1)

$^1H$ NMR (400 MHz, $CDCl_3$) δ 7.81 (s, 1H), 7.55 (d, J=1.1 Hz, 1H), 4.57-4.44 (m, 2H), 4.37 (q, J=7.1 Hz, 2H), 3.45 (t, J=5.5 Hz, 2H), 3.34 (s, 3H), 2.45 (d, J=0.9 Hz 3H), 2.20-2.06 (m, 2H), 1.39 (t, J=7.1 Hz, 3H).

Step C: ethyl 2-({6-[(1,3-benzothiazol-2-yl)amino]-5-methylpyridazin-3-yl}(3-methoxypropyl)amino)-1,3-thiazole-4-carboxylate The product from Step B (1.3 g, 3.51 mmol, 1 eq) and 2-aminobenzothiazole (600 mg, 3.99 mmol, 1.14 eq) were added to a solution of tris(dibenzylideneacetone)dipalladium(0)(161 mg, 0.18 mmol, 0.05 eq) and Xantphos (203 mg, 0.35 mmol, 0.1 eq) in 1,4-dioxane (20 mL) under a nitrogen atmosphere and the mixture was stirred. N,N-Diisopropylethylamine (1.9 mL, 10.5 mmol, 3 eq) was added and the mixture was heated in a sealed tube at 150° C. for 24 h. The solution was allowed to cool to ambient temperature and concentrated in vacuo. Purification by flash column chromatography (50 g silica) eluting with 99:1 dichloromethane/methanol gave a red gum that was triturated with methanol (15 mL), filtered, washed with methanol (10 mL) and dried under vacuum to afford the desired product as a yellow solid (1.35 g, 2.79 mmol, 80%).

LC/MS ($C_{22}H_{24}N_6O_3S_2$) 485 $[M+H]^+$; RT 1.41 (LCMS-V-B1)

$^1H$ NMR (400 MHz, DMSO-d6) δ 11.15 (br s, 1H), 7.97 (s, 1H), 7.92 (br s, 1H), 7.69 (s, 1H), 7.56 (br s, 1H), 7.40 (t, J=7.4 Hz, 1H), 7.22 (t, J=7.5 Hz, 1H), 4.44 (t, J=7.2 Hz, 2H), 4.29 (q, J=7.1 Hz, 2H), 3.43 (t, J=6.0 Hz, 2H), 3.25 (s, 3H), 2.48 (s, 3H), 2.05-1.93 (m, 2H), 1.32 (t, J=7.1 Hz, 3H).

Step D: ethyl 2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A solution of the product from Step C (860 mg, 1.77 mmol, 1 eq) in dichloromethane (30 mL) was cooled in an ice bath then N,N-diisopropylethylamine (0.59 mL, 3.55 mmol, 2 eq) was added. After stirring for 10 min, 2-(trimethylsilyl)ethoxymethyl chloride (0.37 mL, 2.13 mmol, 1.2 eq) was added followed by 4-(dimethylamino)pyridine (10.8 mg, 0.09 mmol, 0.05 eq). The reaction was allowed to warm to ambient temperature and stirred for 5 h. The mixture was diluted with dichloromethane then washed with water followed by brine, dried (magnesium sulfate), and concentrated in vacuo. Purification by automated flash column chromatography (CombiFlash Rf, 24 g RediSep™ silica cartridge) eluting with a gradient of 0-50% ethyl acetate in iso-heptane afforded the desired product as a cream foam (0.83 g, 1.35 mmol, 76%).

LC/MS ($C_{28}H_{38}N_6O_4SiS_2$) 615 $[M+H]^+$; RT 1.51 (LCMS-V-B1)

$^1H$ NMR (400 MHz, DMSO-d6) δ 7.96 (s, 1H), 7.85 (d, 1H), 7.69 (s, 1H), 7.50-7.40 (m, 2H), 7.30-7.22 (m, 1H), 5.86 (s, 2H), 4.43 (t, J=7.2 Hz, 2H), 4.28 (q, J=7.1 Hz, 2H), 3.78-3.67 (m, 2H), 3.42 (t, J=6.0 Hz, 2H), 3.24 (s, 3H), 2.46 (d, J=0.9 Hz, 3H), 2.06-1.92 (m, 2H), 1.31 (t, J=7.1 Hz, 3H), 0.98-0.86 (m, 2H), −0.12 (s, 9H).

Step E: ethyl 5-bromo-2-[(3-methoxypropyl)(5-methyl-6-{[(2Z)-3-{[2-(trimethylsilyl)ethoxy] methyl}-2,3-dihydro-1,3-benzothiazol-2-ylidene] amino}pyridazin-3-yl)amino]-1,3-thiazole-4-carboxylate N-Bromosuccinimide (63.7 mg, 0.36 mmol, 1.1 eq) was added to a stirred solution of the product of Step A (200 mg, 0.33 mmol, 1 eq) in dichloromethane (10 mL) and the mixture was stirred for 4 h. The solvent was removed in vacuo and purification by automated flash column chromatography (CombiFlash Rf, 12 g RediSep™ silica cartridge) eluting with a gradient of 0-60% ethyl acetate in iso-heptane afforded the desired product as a cream foam (193 mg, 0.28 mmol, 85%).

LC/MS ($C_{28}H_{37}BrN_6O_4SiS_2$) 695 $[M+H]^+$; RT 1.60 (LCMS-V-B1)

$^1$H NMR (400 MHz, DMSO-d6) δ 7.87 (dd, J=7.6, 1.1 Hz, 1H), 7.72 (d, J=1.2 Hz, 1H), 7.53-7.39 (m, 2H), 7.26 (ddd, J=8.3, 7.0, 1.4 Hz, 1H), 5.87 (s, 2H), 4.43 (t, J=7.1 Hz, 2H), 4.31 (q, J=7.1 Hz, 2H), 3.77-3.67 (m, 2H), 3.41 (t, J=6.0 Hz, 2H), 3.23 (s, 3H), 2.47 (s, 3H), 2.04-1.90 (m, 2H), 1.32 (t, J=7.1 Hz, 3H), 0.97-0.86 (m, 2H), −0.11 (s, 9H).

Preparation 11d: Ethyl 5-bromo-2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-1,3-thiazole-4-carboxylate Step A: ethyl 2-[(6-chloro-5-cyclopropylpyridazin-3-yl)(methyl)amino]-1,3-thiazole-4-carboxylate To a solution of the product from Preparation 7l (495 mg, 2.62 mmol, 1 eq) and ethyl 2-(methylamino)-1,3-thiazole-4-carboxylate (488 mg, 2.62 mmol, 1 eq) in tetrahydrofuran (25 mL) at 0° C. was added slowly sodium hydride (60% in mineral oil; 124 mg, 3.09 mmol, 1.18 eq) under a nitrogen atmosphere. The mixture was stirred for 1 h at 0° C., then allowed to warm to ambient temperature and stirred for 18 h. Saturated aqueous ammonium chloride solution (75 mL) was added and the mixture extracted with dichloromethane (250 mL). The organics were successively washed with water (2×75 mL) and brine (75 mL), dried (magnesium sulfate) and concentrated in vacuo. Purification by automated flash column chromatography (CombiFlash Rf, 40 g RediSep™ silica cartridge) eluting with a gradient of 0-60% ethyl acetate in iso-heptane afforded the desired product as a white crystalline solid (398 mg, 1.17 mmol, 45%).

LC/MS ($C_{14}H_{15}ClN_4O_2S$) 339 [M+H]$^+$; RT 1.25 (LCMS-V-B1)

$^1$H NMR (400 MHz, DMSO-d6) δ 8.03 (s, 1H), 7.24 (s, 1H), 4.30 (q, J=7.1 Hz, 2H) 3.83 (s, 3H), 2.23-2.12 (m, 1H), 1.32 (t, J=7.1 Hz, 3H), 1.24-1.16 (m, 2H), 1.13-1.06 (m, 2H).

Step B: ethyl 2-({6-[(1,3-benzothiazol-2-yl)amino]-5-cyclopropylpyridazin-3-yl}(methyl)amino)-1,3-thiazole-4-carboxylate 2-Aminobenzothiazole (0.21 g, 1.41 mmol, 1.2 eq) and the product from Step A (398 mg, 1.17 mmol, 1 eq) were added to a solution of Xantphos (68 mg, 0.12 mmol, 0.1 eq) and tris(dibenzylideneacetone)dipalladium(0)(53.8 mg, 0.06 mmol, 0.05 eq) in 1,4-dioxane (20 mL) under a nitrogen atmosphere. N,N-diisopropylethylamine (0.61 mL, 3.52 mmol, 3 eq) was added and the mixture was heated in a sealed tube at 150° C. for 24 h. The solution was allowed to cool to ambient temperature and concentrated in vacuo. Purification by automated flash column chromatography (CombiFlash Rf, 40 g RediSep™ silica cartridge) eluting with a gradient of 0-90% ethyl acetate in iso-heptane afforded the desired product as a yellow solid (249 mg, 0.55 mmol, 47%).

LC/MS ($C_{21}H_{20}N_6O_2S_2$) 453 [M+H]$^+$; RT 1.38 (LCMS-V-B1)

$^1$H NMR (400 MHz, DMSO-d6) δ 7.96 (s, 1H), 7.90 (s, 1H), 7.50 (br s, 1H), 7.39 (t, J=7.6 Hz, 1H), 7.29-7.08 (m, 2H), 4.30 (q, 3H), 3.82 (s, 3H), 1.32 (t, 3H), 1.21-1.07 (m, 2H), 1.06-0.95 (m, 2H).

Step C: ethyl 2-[(5-cyclopropyl-6-{[(2Z)-3-{[2-(trimethylsilyl)ethoxy]methyl}-2,3-dihydro-1,3-benzothiazol-2-yildene]amino}pyridazin-3-yl)(methyl)amino]-1,3-thiazole-4-carboxylate A solution of the product from Step B (221 mg, 0.49 mmol, 1 eq) in dichloromethane (10 mL) was cooled in an ice bath then N,N-diisopropylethylamine (0.16 mL, 0.98 mmol, 2 eq) was added and the mixture was stirred for 10 min. 2-(Trimethylsilyl)ethoxymethyl chloride (0.1 mL, 0.59 mmol, 1.2 eq) was added followed by 4-(dimethylamino)pyridine (2.98 mg, 0.02 mmol, 0.05 eq) and the mixture was stirred at ambient temperature for 7 h. The reaction was partitioned between dichloromethane and water and the organic phase was washed with water followed by brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a cream foam (185 mg, 0.32 mmol, 65%).

LC/MS ($C_{27}H_{34}N_6O_3SiS_2$) 583 [M+H]$^+$; RT 1.45 (LCMS-V-B1)

$^1$H NMR (400 MHz, DMSO-d6) δ 7.95 (s, 1H), 7.84 (dd, J=7.9, 1.1 Hz, 11.1), 7.51-7.40 (m, 2H), 7.29-7.21 (m, 1H), 7.11 (s, 1H), 5.88 (s, 2H), 4.29 (q, J=7.1 Hz, 2H), 3.82 (s, 3H), 3.77-3.65 (m, 2H), 2.73-2.61 (m, 1H), 1.31 (t, J=7.1 Hz, 3H), 1.24-1.12 (m, 2H), 1.11-1.03 (m, 2H), 0.96-0.86 (m, 2H), −0.13 (s, 9H).

Step D: ethyl 5-bromo-2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-1,3-thiazole-4-carboxylate N-Bromosuccinimide (62.2 mg, 0.35 mmol, 1.1 eq) was added to a stirred solution of the product from Step C (185 mg, 0.32 mmol, 1 eq) in dichloromethane (10 mL). After 2.5 h the solvent was removed in vacuo and purification by automated flash column chromatography (CombiFlash Rf, 12 g RediSep™ silica cartridge) eluting with a gradient of 0-60% ethyl acetate in iso-heptane afforded the desired product as a cream solid (149 mg, 0.23 mmol, 71%).

LC/MS ($C_{27}H_{33}BrN_6O_3SiS_2$) 663 [M+H]$^+$; RT 1.52 (LCMS-V-B1)

$^1$H NMR (400 MHz, DMSO-d6) δ 7.86 (dd, J=7.8, 1.1 Hz, 1H), 7.52-7.39 (m, 2H) 7.30-7.22 (m, 1H), 7.09 (s, 1H), 5.88 (s, 2H), 4.31 (q, J=7.1 Hz, 2H), 3.79 (s, 3H), 3.75-3.66 (m, 2H), 2.74-2.61 (m, 1H), 1.33 (t, J=7.1 Hz, 3H), 1.22-1.13 (m, 2H), 1.13-1.05 (m, 2H), 0.95-0.84 (m, 2H), −0.13 (s, 9H).

Preparation 11e: Ethyl 5-iodo-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Step A: ethyl 2-(methylamino)-1,3-thiazole-4-carboxylate To a suspension of N-methylthiourea (5 g, 55.5 mmol, 1 eq) in ethanol (80 mL), cooled in ice-water, was added ethyl bromopyruvate (7.45 mL, 59.4 mmol, 1.07 eq) slowly. After 10 min the mixture was allowed to warm to ambient temperature and stirred for 1.5 h. Triethylamine (15.4 mL, 111 mmol, 2 eq) was added and the mixture stirred at ambient temperature for 18 h. The reaction was concentrated in vacuo, the residue partioned between ethyl acetate and water, the aqueous phase was extracted with ethyl acetate (×2), and the combined organic extracts were dried (magnesium sulphate) and concentrated in vacuo. Purification by automated flash column chromatography (CombiFlash Rf, 80 g RediSep™ silica cartridge) eluting with a gradient of 0-100% ethyl acetate in iso-heptane afforded the desired product as a beige solid (5.26 g, 28.2 mmol, 51%).

LC/MS ($C_7H_{10}N_2O_2S$) 187 $[M+H]^+$; RT 0.85 (LCMS-V-B1)

$^1H$ NMR (400 MHz, DMSO-d6) δ 7.73 (q, J=4.7 Hz, 1H), 7.51 (d, J=0.5 Hz, 1H), 4.22 (q, J=7.1 Hz, 2H), 2.83 (d, J=4.8 Hz, 3H), 1.27 (t, J=7.1 Hz, 3H).

Step B: ethyl 2-[(6-chloro-5-methylpyridazin-3-yl)(methyl)amino]-1,3-thiazole-4-carboxylate A solution of 3,6-dichloro-4-methylpyridazine (4.6 g, 28.2 mmol, 1 eq) and the product from Step A (5.26 g, 28.2 mmol, 1 eq) in tetrahydrofuran (100 mL) was cooled in an ice bath and sodium hydride (60% in mineral oil; 1.24 g, 31.1 mmol, 1.1 eq) was added portionwise. The mixture was allowed to gradually warm to ambient temperature and was stirred for 18 h. Dichloromethane and saturated aqueous ammonium chloride were added forming a precipitate. The solid was collected by filtration, washed with water then dried under vacuum at 40° C. for 12 h to afford the desired product as a cream solid (4.24 g, 13.6 mmol, 48%).

LC/MS ($C_{12}H_{13}ClN_4O_2S$) 313 $[M+H]^+$; RT 1.19 (LCMS-V-B1)

$^1H$ NMR (400 MHz, DMSO-d6) δ 8.04 (s, 1H), 7.87 (d, J=1.1 Hz, 1H), 4.30 (q, J=7.1 Hz, 2H), 3.83 (s, 3H), 2.44 (d, J=1.0 Hz, 3H), 1.32 (t, J=7.1 Hz, 3H).

Step C: ethyl 2-({6-[(1,3-benzothiazol-2-yl)amino]-5-methylpyridazin-3-yl}(methyl)amino)-1,3-thiazole-4-carboxylate Tris(dibenzylideneacetone)dipalladium(0)(0.62 g, 0.68 mmol, 0.05 eq) followed by N,N-diisopropylethylamine (6.74 mL, 40.7 mmol, 3 eq) were added to a sealed flask containing the product from Step B (4.24 g 13.6 mmol, 1 eq), 2-aminobenzothiazole (2.44 g, 16.3 mmol, 1.2 eq) and Xantphos (0.78 g, 1.36 mmol, 0.1 eq) in 1,4-dioxane (250 mL) under a nitrogen atmosphere and the vessel was sealed and heated at 150° C. for 24 h. The reaction was allowed to cool to ambient temperature and purification by automated flash column chromatography (CombiFlash Rf, 120 g RediSep™ silica cartridge) eluting with a gradient of 0-100% ethyl acetate in iso-heptane afforded the desired product as a beige solid (3.05 g, 7.14 mmol, 53%).

LC/MS ($C_{19}H_{18}N_6O_2S_2$) 427 $[M+H]^+$; RT 1.16 (LCMS-V-B1)

$^1H$ NMR (400 MHz, DMSO-d6) δ 7.97 (s, 1H), 7.95-7.82 (m, 1H), 7.71 (s, 1H), 7.55 (br s, 1H), 7.39 (t, J=7.5 Hz, 1H), 7.22 (t, J=7.5 Hz, 1H), 4.31 (q, 3H), 3.83 (s, 3H), 2.48 (s, 3H), 1.33 (t, 3H).

Step D: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a suspension of the product from Step C (3.05 g, 7.15 mmol, 1 eq) in dichloromethane (100 mL), cooled to 0° C. was added N,N-diisopropylethylamine (2.37 mL, 14.3 mmol, 2 eq). After 10 min 2-(trimethylsilyl)ethoxymethyl chloride (1.51 mL, 8.58 mmol, 1.2 eq) was added followed by 4-(dimethylamino)pyridine (43.7 mg, 0.36 mmol, 0.05 eq) and the mixture was allowed to warm to ambient temperature and stir for 6 h. The reaction mixture was washed with water, followed by brine then dried (magnesium sulphate) and concentrated in vacuo. Purification by automated flash column chromatography (CombiFlash Rf, 80 g RediSep™ silica cartridge) eluting with a gradient of 0-50% ethyl acetate in iso-heptane afforded the desired product as a white solid (1.38 g, 2.47 mmol, 35%).

LC/MS ($C_{23}H_{32}N_6O_3SiS_2$) 557 $[M+H]^+$; RT 1.65 (LCMS-V-B1)

$^1H$ NMR (400 MHz, DMSO-d6) δ 7.96 (s, 1H), 7.84 (dd, 1H), 7.70 (d, J=0.9 Hz, 1H), 7.51-7.39 (m, 2H), 7.25 (ddd, J=8.3, 6.9, 1.6 Hz, 1H), 5.86 (s, 2H), 4.28 (q, J=7.1 Hz, 2H), 3.83 (s, 3H), 3.77-3.66 (m, 2H), 2.46 (d, J=1.0 Hz, 3H), 1.32 (t, J=7.1 Hz, 3H), 0.99-0.879 (m, 2H), −0.10 (s, 9H).

Step E: ethyl 5-iodo-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate N-Iodosuccinimide (0.05 mL, 2.25 g/mL, 0.54 mmol, 1.5 eq) was added to a stirred solution of the product from Step D (200 mg, 0.36 mmol, 1 eq) in dichloromethane (6 mL) and the mixture was stirred at ambient temperature for 18 h. The reaction was successively washed with water and brine, dried (magnesium sulphate) and concentrated in vacuo. Purification by automated flash column chromatography (CombiFlash Rf, 12 g RediSep™ silica cartridge) eluting with a gradient of 0-60% ethyl acetate in iso-heptane afforded the desired product as a cream solid (180 mg, 0.26 mmol, 73%).

LC/MS ($C_{25}H_{31}IN_6O_3SiS_2$) 683 $[M+H]^+$; RT 1.73 (LCMS-V-B1)

$^1H$ NMR (400 MHz, DMSO-d6) δ 7.88 (dd, J=7.5, 1.0 Hz, 1H), 7.71 (s, 1H), 7.53-7.40 (m, 2H), 7.31-7.22 (m, 1H), 5.86 (s, 2H), 4.32 (q, J=7.1 Hz, 2H), 3.82 (s, 3H), 3.78-3.69 (m, 2H), 2.48 (d, J=1.0 Hz, 3H), 1.34 (t, J=7.1 Hz, 3H), 0.99-0.89 (m, 2H), −0.13 (s, 9H).

Preparation 11f: Ethyl 5-bromo-2-[(6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Step A: ethyl 2-[(6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate The product from Preparation 4b (1 g, 2.54 mmol, 1 eq) and ethyl 2-amino-1,3-thiazole-4-carboxylate (500 mg, 2.9 mmol, 1.14 eq) were added to a solution of tris(dibenzylideneacetone)dipalladium(0)(116.5 mg, 0.13 mmol, 0.05 eq) and Xantphos (147.2 mg, 0.25 mmol, 0.1 eq) in 1,4-dioxane (20 mL) under a nitrogen atmosphere. N,N-diisopropylethylamine (1.5 mL, 7.63 mmol, 3 eq) was added and the mixture heated at 100° C. for 18 h. The solution was allowed to cool to ambient temperature and concentrated in vacuo. Purification by column chromatography (50 g silica) eluting with 50% ethyl acetate in heptane gave a dark yellow solid. Trituration with heptane (20 mL) gave a solid that was collected by filtration, washed with heptane (2×10 mL) and dried under vacuum to afford the desired product as a yellow solid (995 mg, 1.88 mmol, 74%) [mixture of isomers].

LC/MS ($C_{23}H_{28}N_6O_3SiS_2$) 529 $[M+H]^+$; RT 1.54 (LCMS-V-B1)

$^1H$ NMR (400 MHz, Chloroform-d) δ 10.83 (s, 1H), 7.90-7.29 (m, 6H), 7.26-7.13 (m, 1H), 5.95-5.68 (m, 2H), 4.53-4.19 (m, 2H), 3.85-3.68 (m, 2H), 1.39-1.19 (m, 3H), 1.06-0.77 (m, 2H), 0.21--0.31 (m, 9H).

Step B: ethyl 5-bromo-2-[(6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate N-Bromosuccinimide (45.2 mg, 0.25 mmol, 1.3 eq) was added to a stirred solution of the product from Step A (100 mg, 0.19 mmol, 1 eq) in dichloromethane (10 mL) and the mixture was stirred at ambient temperature for 1 h. The solvent was removed in vacuo and purification by automated flash column chromatography (CombiFlash Rf, 12 g RediSep™ silica cartridge) eluting with a gradient of 0-80% ethyl acetate in iso-heptane afforded the desired product as a cream solid (64.1 mg, 0.11 mmol, 56%) [mixture of isomers].

LC/MS ($C_{23}H_{27}BrN_6O_3SiS_2$) 609 $[M+H]^+$; RT 1.47 (LCMS-V-B1)

$^1$H NMR (400 MHz, DMSO-d6) δ 12.45 (s, 1H), 12.31 (s, 1H), 8.13-8.04 (m, 1H), 8.04-7.90 (m, 2H), 7.84-7.71 (m, 1H), 7.69-7.48 (m, 5H), 7.46-7.32 (m, 3H), 5.98 (s, 2H), 5.92 (s, 2H), 4.41 (qd, J=7.1, 2.4 Hz, 4H), 3.87-3.74 (m, 4H), 1.43 (td, J=7.1, 1.1 Hz, 6H), 1.03 (s, 2H), 1.08-0.98 (m, 2H), 0.26--0.36 (m, 18H).

Preparation 12: tert-butyl-diphenyl-[2-[[3,5-dimethyl-7-[[5-methyl-4-(4,4,5,5-tetramethyl-1,3,2-dioxaborolan-2-yl)pyrazol-1-yl]methyl]-1-adamantyl]oxy]ethoxy]silane Step A: 3-bromo-5,7-dimethyladamantane-1-carboxylic acid After stirring iron (6.7 g, 120 mmol) in bromine (30.7 mL, 600 mmol, 5 eq) at 0° C. for 1 h, 3,5-dimethyladamantane-1-carboxylic acid (25 g, 1 eq) was added and the reaction mixture was stirred at rt for 2 days. After the addition of EtOAc, the reaction mixture was treated carefully with a saturated solution of sodium-thiosulfate at 0° C. and stirred for 15 min. After filtration through a pad of Celite and rinsing with EtOAc, the organic phase was separated, washed with a saturated solution of sodium-thiosulfate and brine, dried, concentrated to give the desired product (34.28 g, 74.6%), which was used without further purification.

$^1$H NMR (400 MHz, DMSO-$d_6$): δ ppm 12.33 (br., 1H), 2.21 (s, 2H), 1.96/1.91 (d+d, 4H), 1.50/1.43 (d+d, 4H), 1.21/1.14 (dm+dm, 2H), 0.86 (s, 6H); $^{13}$C NMR (100 MHz, DMSO-$d_6$) δ ppm 176.8, 66.8, 54.0, 48.7, 48.5, 45.7, 43.3, 35.5, 29.4; HRMS-ESI (m/z): [M−H]− calcd for $C_{13}H_{18}BrO_2$: 285.0496; found 285.0498.

Step B: 3-bromo-5,7-dimethyl-1-adamantyl-methanol

To the product from Step A (34.3 g, 119 mmol) in THF (77.6 mL) was added slowly a 1 M solution of $BH_3$-THF in THF (358 mL, 3 eq) and the reaction mixture was stirred for 18 h. After the addition of methanol and stirring for 30 min, purification by column chromatography (silica gel, heptane and MTBE as eluents) afforded the desired product (16.19 g, 49.6%).

$^1$H NMR (400 MHz, DMSO-$d_6$): δ ppm 4.51 (t, 1H), 3.05 (d, 2H), 1.91 (s, 2H), 1.91 (s, 4H), 1.19/1.09 (d+d, 2H), 1.19/1.05 (d+d, 4H), 0.85 (s, 6H) $^{13}$C NMR (100 MHz, DMSO-$d_6$) δ ppm 70.4, 68.9, 54.9, 49.8, 49.3, 43.8, 41.4, 35.7, 29.7; HRMS-ESI (m/z): [M−Br]− calcd for $C_{13}H_{21}O$: 193.1598 found: 193.1589.

Step C: 1-[3-bromo-5,7-dimethyl-1-adamantyl]methyl]pyrazole

To the product from Step B (16.19 g, 59.26 mmol) and 1H-pyrazole (4.841 g, 1.2 eq) in toluene (178 mL) was added (cyanomethylene)tributylphosphorane (18.64 mL, 1.2 eq) in one portion and the reaction mixture was stirred at 90° C. for 2 h. Purification by column chromatography (silica gel, heptane and MTBE as eluents) afforded the desired product (17.88 g, 93%).

$^1$H NMR (400 MHz, DMSO-$d_6$): δ ppm 7.63 (d, 1H), 7.43 (d, 1H), 6.23 (t, 1H), 3.90 (s, 2H), 1.92-1.02 (m, 12H), 0.83 (s, 6H); $^{13}$C NMR (100 MHz, DMSO-$d_6$) δ ppm 139.0, 131.8, 105.2, 67.7, 61.4, 54.4/48.8/44.6, 50.4, 35.7, 29.6; HRMS-ESI (m/z): [M]+ calcd for $C_{16}H_{23}BrN_2$: 322.1045 found: 322.1014.

Step D: 5-methyl-1-[[3-bromo-5,7-dimethyl-1-adamantyl]methyl]pyrazole

To the solution of the product from Step C (17.88 g, 55.3 mmol) in THF (277 mL) was added butyllithium (2.5 M in THF, 66 mL, 3 eq) at −78° C., then after 1 h, iodomethane (17.2 mL, 5 eq) was added. After 10 min, the motion mixture was quenched with a saturated solution of $NH_4Cl$, extracted with EtOAc and the combined organic layers were dried and concentrated to give the desired product (18.7 g, 100%), which was used in the next step without further purification.

$^1$H NMR (400 MHz, DMSO-$d_6$): δ ppm 7.31 (d, 1H), 6.00 (d, 1H), 3.79 (s, 2H), 2.23 (s, 3H), 2.01 (s, 2H), 1.89/1.85 (d+d, 4H), 1.23/1.15 (d+d, 4H), 1.16/1.05 (d+d, 2H), 0.83 (s, 6H); $^{13}$C NMR (100 MHz, DMSO-$d_6$) δ ppm 139.2, 138.0, 105.2, 67.8, 57.8, 54.4, 50.6, 48.8, 44.8, 41.5, 35.7, 29.6, 11.8; HRMS-ESI (m/z): [M+H]+ calcd for $C_{17}H_{26}BrN_2$: 337.1279 found: 337.1289.

Step E: 2-[[3,5-dimethyl-7-[(5-methylpyrazol-1-yl)methyl]-1-adamantyl]oxy]ethanol The mixture of the product from Step D (18.7 g, 55.3 mmol), ethylene glycol (123 mL, 40 eq), and DIPEA (48.2 mL, 5 eq) was stirred at 120° C. for 6 h. After the reaction mixture was diluted with water and extracted with EtOAc, the combined organic layers were dried and concentrated to give the desired product (18.5 g, 105%), which was used in the next step without further purification.

$^1$H NMR (400 MHz, DMSO-$d_6$): δ ppm 7.29 (d, 1H), 5.99 (d, 1H), 4.45 (t, 1H), 3.78 (s, 3.39 (q, 2H), 3.32 (t, 2H), 2.23 (s, 3H) 1.34 (s, 2H), 1.27/1.21 (d+d, 4H), 1.13/1.07 (d+d, 4H), 1.04/0.97 (d+d, 2H), 0.84 (s, 6H); $^{13}$C NMR (100 MHz, DMSO-$d_6$) δ ppm 139.0, 137.8, 105.1, 74.0, 62.1, 61.5, 58.5, 50.1, 47.0, 46.1, 43.3, 39.7, 33.5, 30.2, 11.9; HRMS-ESI (m/z): [M+H]+ calcd for $C_{19}H_{31}N_2O_2$: 319.2386 found: 319.2387.

Step F: tert-butyl-diphenyl-[2-[[3,5-dimethyl-7-[(5-methylpyrazol-1-yl)methyl]-1-adamantyl]oxy]ethoxy]silane To the mixture of the product from Step E (17.6 g, 55.3 mmol) and imidazole (5.65 g, 1.5 eq) in DCM (150 mL) was added tert-butyl-chloro-diphenyl-silane (18.6 g, 1.2 eq) and the reaction mixture was stirred for 1 h. Purification by column chromatography (silica gel, heptane and MTBE as eluents) afforded the desired product (27.0 g, 87.8%).

$^1H$ NMR (400 MHz, DMSO-$d_6$): δ ppm 7.72-7.34 (m, 10H), 7.29 (d, 1H), 5.99 (br., 1H), 3.78 (s, 2H), 3.67 (t, 2H), 3.44 (t, 2H), 2.21 (s, 3H), 1.33 (s, 2H), 1.26/1.18 (d+d, 4H), 1.12/1.06 (d+d, 4H), 1.03/0.96 (d+d, 2H), 0.98 (s, 9H), 0.82 (s, 6H); $^{13}C$ NMR (100 MHz, DMSO-$d_6$) δ ppm 139.0, 137.8, 105.1, 74.2, 64.4, 61.7, 58.5, 50.0, 46.9, 46.0, 43.4, 39.6, 33.5, 30.1, 27.1, 19.3, 11.9; HRMS-ESI (m/z): [M+H]+ calcd for $C_{35}H_{49}N_2O_2Si$: 557.3563 found: 557.3564.

Step G: tert-butyl-diphenyl-[2-[[3-[(4-iodo-5-methyl-pyrazol-1-yl)methyl]-5,7-dimethyl-1-adamantyl]oxy]ethoxy]silane To the solution of the product from Step F (27.0 g, 48.56 mmol) in DMF (243 mL) was added N-iodosuccinimide (13.6 g, 1.25 eq) and the reaction mixture was stirred for 2 h. After dilution with water, the mixture was extracted with DCM. The combined organic layers were washed with saturated solution of sodium-thiosulphate and brine, dried, and concentrated to afford the desired product (30.1 g, 90%).

$^1H$ NMR (400 MHz, DMSO-$d_6$): δ ppm 7.68-7.37 (m, 10H), 7.45 (s, 1H), 3.89 (s, 2H), 3.67 (t, 2H), 3.44 (t, 2H), 2.23 (s, 3H), 1.30 (s, 2H), 1.26/1.17 (d+d, 4H), 1.12/1.05 (d+d, 4H), 1.00/0.96 (d+d, 2H), 0.98 (s, 9H), 0.82 (s, 6H); $^{13}C$ NMR (100 MHz, DMSO-$d_6$) δ ppm 142.5, 140.8, 133.7, 64.4, 61.7, 60.3, 59.9, 49.9, 46.8, 45.9, 43.2, 39.7, 33.5, 30.1, 27.1, 19.3, 12.2; HRMS-ESI (m/z): [M+H]+ calcd for $C_{35}H_{48}IN_2O_2Si$: 683.2530 found: 683.2533.

Step H: tert-butyl-diphenyl-[2-[[3,5-dimethyl-7-[[5-methyl-4-(4,4,5,5-tetramethyl-1,3,2-dioxaborolan-2-yl)pyrazol-1-yl]methyl]-1-adamantyl]oxy]ethoxy] silane To the product from Step G (17.5 g, 25.6 mmol) in THF (128 mL) was added chloro(isopropyl)magnesium-LiCl (1.3 M in THF, 24 mL, 1.2 eq) at 0° C., stirred for 40 min, treated with 2-isopropoxy-4,4,5,5-tetramethyl-1,3,2-dioxaborolane (15.7 mL, 3 eq), and the reaction mixture was stirred for 10 min. After dilution with a saturated solution $NH_4Cl$ and extraction with EtOAc, the combined organic phases were concentrated and purified by column chromatography (silica gel, heptane and MTBE as eluents) to give the desired product (15.2 g, 86.9%).

$^1H$ NMR (400 MHz, DMSO-$d_6$): δ ppm 7.65 (dm, 4H), 7.47 (s, 1H), 7.45 (tm, 2H), 7.40 (tm, 4H), 3.80 (s, 2H), 3.66 (t, 2H), 3.44 (t, 2H), 2.35 (s, 3H), 1.35-0.94 (m, 12H), 1.24 (s, 12H), 0.97 (s, 9H), 0.83 (s, 6H); $^{13}C$ NMR (100 MHz, DMSO-$d_6$) δ ppm 146.9, 144.3, 135.6, 130.2, 128.2, 104.7, 83.0, 74.2, 64.4, 61.7, 58.4, 30.1, 27.1, 25.2, 19.3, 12.0; HRMS-ESI (m/z): [M+H]+ calcd for $C_{41}H_{60}BN_2O_4Si$: 683.4415 found: 683.4423.

Preparation 13: methyl 3-bromo-6-(methylamino)pyridine-2-carboxylate

Step A: methyl 6-[bis(tert-butoxycarbonyl)amino]-3-bromo-pyridine-2-carboxylate

To methyl 6-amino-3-bromo-pyridine-2-carboxylate (25.0 g, 108.2 mmol) and DMAP (1.3 g, 0.1 eq) in DCM (541 mL) was added $Boc_2O$ (59.0 g, 2.5 eq) at 0° C. and the reaction mixture was stirred for 2.5 h. After the addition of a saturated solution of $NaHCO_3$ and the extraction with DCM, the combined organic phases were dried and concentrated to get the desired product (45.0 g, 72.3%).

LC/MS ($C_{17}H_{23}BrN_2O_6Na$) 453 $[M+H]^+$.

Step B: methyl 3-bromo-6-(tert-butoxycarbonylamino)pyridine-2-carboxylate

To the product from Step A (42.7 g, 74.34 mmol) in DCM (370 mL) was added TFA (17.1 mL, 3 eq) at 0° C. and the reaction mixture was stirred for 18 h. After washing with a saturated solution of $NaHCO_3$ and brine, the combined organic phases were dried, concentrated, and purified by column chromatography (silica gel, heptane and EtOAc as eluents) to give the desired product (28.3 g, 115.2%).

$^1H$ NMR (400 MHz, DMSO-$d_6$): δ ppm 10.29 (s, 1H), 8.11 (d, 1H), 7.88 (d, 1H), 3.87 (s, 3H), 1.46 (s, 9H) $^{13}C$ NMR (100 MHz, DMSO-$d_6$) δ ppm 165.6, 153.1, 151.8/148.3, 143.5, 116.3, 109.2, 53.2, 28.4. LC/MS ($C_{12}H_{15}BrN_2O_4Na$) 353 $[M+H]^+$.

Step C: methyl 3-bromo-6-[tert-butoxycarbonyl(methyl)amino]pyridine-2-carboxylate To the product from Step B (2.96 g, 8.93 mmol) in acetone (45 mL) was added $C_2CO_3$ (8.7 g, 3 eq) and iodomethane (0.67 mL, 1.2 eq) and the reaction mixture was stirred for 3 h. After dilution with water and extraction with EtOAc, the combined organic phases were washed with brine, dried and concentrated to give the desired product (3.5 g, 112%).

$^1H$ NMR (400 MHz, DMSO-$d_6$): δ ppm 8.13 (d, 1H), 7.78 (d, 1H), 190 (s, 3H), 3.27 (s, 3H), 1.47 (s, 9H); $^{13}C$ NMR (100 MHz, DMSO-$d_6$) δ ppm 165.5, 153.6, 153.6, 147.5, 142.8, 122.5, 111.3, 82.0, 53.3, 34.3, 28.2; HRMS-ESI (m/z): [M+H]+ calcd for $C_{13}H_{18}BrN_2O_4$: 345.0450 found: 345.0429.

Step D: methyl 3-bromo-6-(methylamino)pyridine-2-carboxylate

The product from Step C (3.0 g, 88.9 mmol) in 1,1,1,3,3,3-hexafluoroisopropanol (90 mL) was stirred at 100° C. for 18 h. Purification by column chromatography (silica gel, heptane and EtOAc as eluents) afforded the desired product (2.1 g, 96%).

$^1H$ NMR (400 MHz, DMSO-$d_6$): δ ppm 7.63 (d, 1H), 7.04 (q, 1H), 6.53 (d, 1H), 3.83 (s, 3H), 2.73 (d, 3H); $^{13}C$ NMR (100 MHz, DMSO-$d_6$) δ ppm 166.6, 158.2, 148.2, 141.3, 112.1, 101.3, 52.9, 28.3; HRMS-ESI (m/z): [M]+ calcd for $C_8H_9BrN_2O_2$: 243.9847 found: 243.9843.

Preparation 14: methyl 3-[1-[[3,5-dimethyl-7-[2-(p-tolylsulfonyloxy)ethoxy]-1-adamantyl]methyl]-5-methyl-pyrazol-4-yl]-6-[methyl-[5-methyl-6-[(Z)-[3-(2-trimethylsilylethoxymethyl)-1,3-benzothiazol-2-ylidene]amino]pyridazin-3-yl]amino]pyridine-2-carboxylate Step A: methyl 3-[1-[[3-[2-[tert-butyl(diphenyl)silyl]oxyethoxy]-5,7-dimethyl-1-adamantyl]methyl]-5-methyl-pyrazol-4-yl]-6-(methylamino)pyridine-2-carboxylate The mixture of the product from Preparation 13 (2.07 g, 8.45 mmol), the product from Preparation 12 (6.9 g, 1.2 eq), $Cs_2CO_3$ (8.26 g, 3 eq), and $Pd(AtaPhos)_2Cl_2$ (374 mg, 0.1 eq) in 1,4-dioxane (51 mL) and water (8.5 mL) was stirred at 80° C. for 1 h. Purification by column chromatography (silica gel, heptane and EtOAc as eluents) afforded the desired product (4.5 g, 74%).

$^{1}$H NMR (400 MHz, DMSO-$d_6$): δ ppm 7.66 (dm, 4H), 7.47-7.38 (m, 6H), 7.31 (d, 1H), 7.23 (s, 1H), 6.78 (q, 1H), 6.59 (d, 1H), 3.82 (s, 2H), 3.67 (t, 2H), 3.58 (s, 3H), 3.46 (t, 2H) 2.77 (d, 3H), 2.06 (s, 3H), 1.35 (s, 2H), 1.27/1.20 (d+d, 4H), 1.14/1.09 (d+d, 4H), 1.05/0.97 (d+d, 2H), 0.98 (s, 9H), 0.84 (s, 6H); $^{13}$C NMR (100 MHz, DMSO-$d_6$) δ ppm 140.1, 137.4, 135.6, 130.2/128.3, 109.8, 74.2, 64.4, 61.7, 58.9, 52.2, 50.0, 46.9, 46.0, 43.4, 39.8, 33.5, 30.1, 28.4, 27.1, 10.8; HRMS-ESI (m/z): [M+H+ calcd for $C_{41}H_{57}N_4O_4Si$: 721.4149 found: 721.4148.

Step B: methyl 3-[1-[[3-[2-[tert-butyl(diphenyl) silyl]oxyethoxy]-5,7-dimethyl-1-adamantyl]methyl]-5-methyl-pyrazol-4-yl]-6-[methyl-[5-methyl-6-[(Z)-[3-(2-trimethylsilylethoxymethyl)-1,3-benzothiazol-2-ylidene]amino]pyridazin-3-yl]amino]pyridine-2-carboxylate Using Buchwald General Procedure II starting from the product from Step A at reflux for 18 h, 4.7 g (86%) of the desired product was obtained.

$^{1}$H NMR (400 MHz, DMSO-$d_6$): δ ppm 7.78 (dm, 1H), 7.69-7.36 (m, 10H), 7.63 (q, 1H), 7.63 (d, 1H), 7.47 (dm, 1H) 7.44 (m, 1H), 7.35 (s, 1H), 7.31 (d, 1H), 7.24 (m, 1H), 5.86 (s, 2H), 3.86 (s, 2H), 3.72 (m, 2H), 3.67 (t, 2H), 3.64 (s, 3H), 3.61 (s, 3H), 3.46 (t, 2H), 2.36 (d, 3H), 2.13 (s, 3H), 1.40-0.94 (m, 12H), 0.97 (s, 9H), 0.92 (m, 2H), 0.85 (s, 6H), −0.11 (s, 9H); HRMS-ESI (m/z): [M+H]+ calcd for $C_{61}H_{79}N_8O_5SSi_2$: 1091.5433 found: 1091.5426.

Step C: methyl 3-[1-[[3-(2-hydroxyethoxy)-5,7-dimethyl-1-adamantyl]methyl]-5-methyl-pyrazol-4-yl]-6-[methyl-[5-methyl-6-[(Z)-[3-(2-trimethylsilylethoxymethyl)-1,3-benzothiazol-2-ylidene]amino] pyridazin-3-yl]amino]pyridine-2-carboxylate To the product from Step B (1.0 g, 0.916 mmol) in THF (9 mL) was added a 1 M solution of TBAF in THF (1.0 mL, 1.1 eq) at 0° C. and the reaction mixture was stirred for 1 h. After quenching with a saturated solution of $NH_4Cl$ and extraction with EtOAc, the combined organic phases were dried, concentrated, and purified by column chromatography (silica gel, DCM and MeOH as eluents) to give the desired product (752 mg, 96%).

$^{1}$H NMR (500 MHz, dmso-d6) δ ppm 7.79 (dm, 1H), 7.66 (d, 1H), 7.64 (s, 1H), 7.47 (dm, 1H), 7.43 (m, 1H), 7.36 (s, 1H), 7.33 (d, 1H), 7.25 (m, 1H), 5.87 (s, 2H), 4.46 (t, 1H), 3.86 (s, 2H), 3.73 (m, 2H), 3.68 (s, 3H), 3.62 (s, 3H), 3.40 (m, 2H), 3.35 (t, 2H), 2.37 (s, 3H), 2.14 (s, 3H), 1.42-0.96 (m, 12H), 0.92 (m, 2H), 0.86 (s, 6H), −0.10 (s, 9H); HRMS-ESI (m/z): [M+H]+ calcd for $C_{45}H_{61}N_8O_5SSi$: 853.4255 found: 853.4256.

Step D: methyl 3-[1-[[3,5-dimethyl-7-[2-(p-tolylsulfonyloxy)ethoxy]-1-adamantyl]methyl]-5-methyl-pyrazol-4-yl]-6-[methyl-[5-methyl-6-[(Z)-[3-(2-trimethylsilylethoxymethyl)-1,3-benzothiazol-2-ylidene]amino]pyridazin-3-yl]amino]pyridine-2-carboxylate To the product from Step C (752 mg, 0.88 mmol) and triethylamine (0.5 mL, 4 eq) in DCM (4.4 mL) was added p-tolylsulfonyl-4-methylbenzenesulfonate (575.4 mg, 1.76 mmol, 2 eq) and the reaction mixture was stirred for 1 h. Purification by column chromatography (silica gel, heptane and EtOAc as eluents) afforded the desired product (722 mg, 81%).

$^{1}$H NMR (400 MHz, DMSO-$d_6$): δ ppm 7.79 (dm, 1H), 7.76 (dm, 2H), 7.68 (d, 1H), 7.64 (s, 1H), 7.47 (m, 1H), 7.46 (dm, 2H), 7.43 (td, 1H), 7.36 (s, 1H), 7.33 (d, 1H), 7.25 (td, 1H), 5.87 (s, 2H), 4.06 (m, 2H), 3.84 (s, 2H), 3.73 (t, 2H), 3.66 (s, 3H), 3.62 (s, 3H), 3.48 (m, 2H), 2.40 (s, 3H), 2.37 (s, 3H), 2.13 (s, 3H), 1.31-0.94 (m, 12H), 0.92 (t, 2H), 0.83 (s, 6H), −0.10 (s, 9H); $^{13}$C NMR (100 MHz, DMSO-$d_6$) δ ppm 141.2, 137.5, 130.6, 128.1, 127.2, 123.4, 123.4, 123.1, 114.7, 112.0, 72.9, 71.5, 66.7, 58.8, 58.4, 52.6, 36.6, 30.1, 21.6, 17.8, 17.4, 10.8, −0.9; HRMS-ESI (m/z): [M+H+ calcd for $C_{52}H_{67}N_8O_7S_2Si$: 1007.4343 found: 1007.4344.

Example 1: 2-({6-[(1,3-Benzothiazol-2-yl)amino]-4,5-dimethylpyridazin-3-yl}amino)-1,3-thiazole-1-carboxylic acid

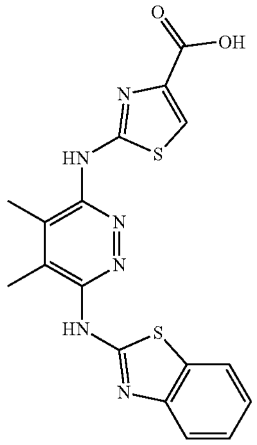 [SMILES: Cc1c(Nc2nc(C(=O)O)cs2)nnc(Nc2nc3ccccc3s2)c1C]

Step A: ethyl 2-({6-[(1,3-benzothiazol-2-yl)amino]-4,5-dimethylpyridazin-3-yl}amino)-1,3-thiazole-4-carboxylate To an oven-dried microwave vial was added ethyl 2-aminothiazole-4-carboxylate (71 mg, 0.41 mmol, 1.2 eq), the product from Preparation 9a (100 mg, 0.34 mmol, 1 eq), Xantphos (19.9 mg, 0.03 mmol, 0.1 eq), tris(dibenzylideneacetone)dipalladium(0)(15.8 mg, 0.02 mmol, 0.05 eq) and cesium carbonate (134.5 mg, 0.41 mmol, 1.2 eq). The vessel was evacuated and flushed with nitrogen (×3), and then toluene (6 mL) was added. The mixture was sparged with nitrogen (10 mins) then heated at 180° C. for 1.5 h under microwave irradiation. The mixture was partitioned between ethyl acetate (100 mL) and brine (50 mL), and the organic phase was dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product (63 mg, 0.15 mmol, 43%).

LC/MS ($C_{19}H_{18}N_6O_2S_2$) 427 $[M+H]^+$; RT 1.32 (LCMS-V-B1)

$^{1}$H NMR (400 MHz, DMSO-$d_6$) δ 10.99 (s, 1H), 10.87 (br s, 1H), 7.95 (s, 1H), 7.89 (br s, 1H), 7.57 (br s, 1H), 7.37 (t, J=7.59 Hz, 1H), 7.20 (t, 1H), 4.30 (q, J=7.10 Hz, 2H), 2.38 (s, 3H), 2.36 (s, 3H), 1.32 (t, J=7.11 Hz, 3H).

Step B: 2-({6-[(1,3-benzothiazol-2-yl)amino]-4,5-dimethylpyridazin-3-yl}amino-1,3-thiazole-4-carboxylic acid To a solution of the product from Step A (38 mg, 0.09 mmol, 1 eq) in 1,4-dioxane (5 mL) was added 2M aqueous lithium hydroxide (90 µL, 0.18 mmol, 2 eq) and the mixture was stirred at ambient temperature for 30 min, then heated at 40° C. for 1 h, and finally at 80° C. for 1 h. After allowing to cool to ambient temperature the reaction was partitioned between ethyl acetate (10 mL) and water (10 mL) adjusting to pH 6. The aqueous phase was concentrated in vacuo and the residue was triturated with water and collected by filtration. Washing with water, diethyl ether, then dichloromethane, and drying under vacuum afforded the desired product as an orange solid (14 mg, 0.04 mmol, 39%).

HRMS-ESI (m/z) [M+H]+ calcd for $C_{17}H_{15}N_6O_2S_2$: 399.0692, found 399.0729.

Example 2: 6-({6-[(1,3-Benzothiazol-2-yl)amino]-4,5-dimethylpyridazin-3-yl}amino)pyridine-2-carboxylic acid

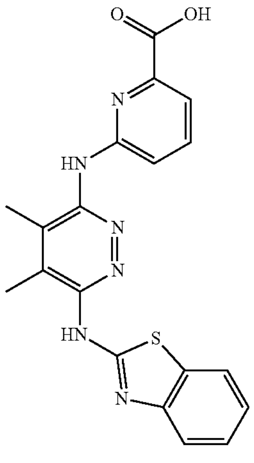 [SMILES: Cc1c(Nc2cccc(C(=O)O)n2)nnc(Nc2nc3ccccc3s2)c1C]

Step A: ethyl 6-({6-[(1,3-benzothiazol-2-yl)amino]-4,5-dimethylpyridazin-3-yl}amino)pyridine-2-carboxylate To an oven-dried microwave vial was added ethyl 6-aminopyridine-2-carboxylate (171 mg, 1.03 mmol, 1.5 eq), the product from Preparation 9a (200 mg, 0.69 mmol, 1 eq), Xantphos (39.8 mg, 0.07 mmol, 0.1 eq), tris(dibenzylideneacetone)dipalladium(0)(31.5 mg, 0.03 mmol, 0.05 eq) and cesium carbonate (336 mg, 1.03 mmol, 1.5 eq). The vessel was evacuated and flushed with nitrogen (×3), and then toluene (5 mL) was added. The mixture was sparged with nitrogen (10 mins) then heated at 180° C. for 3 h under microwave irradiation. The mixture was diluted with ethyl acetate and water and filtered through a small silica pad. The organic layer was washed with brine, dried (magnesium sulfate), filtered and concentrated in vacuo Purification by automated flash column chromatography (CombiFlash Rf, 24 g RediSep™ silica cartridge) eluting with a gradient of 0-100% ethyl acetate in hexane afforded the desired compound as a yellow, glassy solid (55 mg, 0.13 mmol, 19%).

LC/MS ($C_{21}H_{20}N_6O_2S$) 421 $[M+H]^+$; RT 1.17 (LCMS-V-B1)

$^1$H NMR (400 MHz, DMSO-$d_6$) δ 10.91 (br s, 1H), 9.17 (s, 1H), 7.85 (br s, 1H), 7.84 (dd, J=7.32, 8.47 Hz, 1H), 7.66 (d, J=8.47 Hz, 1H), 7.55 (d, J=7.20 Hz, 1H), 7.37 (t, J=7.73 Hz, 1H), 7.19 (s, 1H), 4.32 (q, J=7.13 Hz, 2H), 2.38 (s, 3H), 2.27 (s, 3H), 1.32 (t, J=7.10 Hz, 3H).

Step B: 6-({6-[1,3-benzothiazol-2-yl)amino]-4,5-dimethylpyridazin-3-yl}amino)pyridine-2-carboxylic acid To a solution of the product from Step A (50 mg, (1.12 mmol, 1 eq) in 1,4-dioxane (5 mL) was added 2M aqueous lithium hydroxide (0.12 mL, 0.24 mmol, 2 eq) and the mixture was heated at 90° C. for 1 h. The mixture was cooled to ambient temperature, the solvent evaporated in vacuo and the residue was triturated with water and collected by filtration to afford the desired product as an orange solid (9 mg, 0.02 mmol, 19%).

HRMS-ESI (m/z) [M+H+ calcd for $C_{19}H_{17}N_6O_2S$: 393.1128, found 393.1163.

Example 3: 2-({6-[(1,3-Benzothiazol-2-yl)amino]-4,5-dimethylpyridazin-3-yl}amine)-5-(3-{4-[3-(dimethylamino)prop-1-yn-1-yl]-2-fluorophenoxy}propyl)-1,3-thiazole-4-carboxylic acid

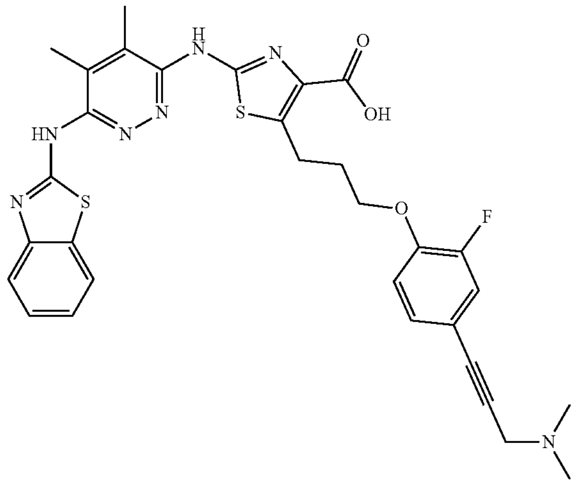 [SMILES: Cc1c(Nc2nc(C(=O)O)c(CCCOc3ccc(C#CCN(C)C)cc3F)s2)nnc(Nc2nc3ccccc3s2)c1C]

Step A: ethyl 2-({6-[(1,3-benzothiazol-2-yl)amino]-4,5-dimethylpyridazin-3-yl}amino)-5-(3-{4-[3-(dimethylamino)prop-1-yn-1-yl]-2-fluorophenoxy}propyl)-1,3-thiazole-4-carboxylate To an oven-dried microwave vial was added the product from Preparation 9a (376 mg, 1.29 mmol, 1.5 eq), the product from Preparation 3u (350 mg, 0.86 mmol, 1 eq), cesium carbonate (394 mg, 1.21 mmol, 1.4 eq), Xantphos (49.9 mg, 0.09 mmol, 0.1 eq) and tris(dibenzylideneacetone)dipalladium(0)(39.5 mg, 0.04 mmol, 0.05 eq). The vessel was evacuated and flushed with nitrogen (×3), and then trifluorotoluene (10 mL) was added. The mixture was sparged with nitrogen (10 mins) then heated at 180° C. for 1 h under microwave irradiation. Purification by reverse phase automated flash chromatography (CombiFlash Rf, C18 43 g RediSep column) eluting with 5-95% acetonitrile in water afforded the desired product as a bright yellow glass (266 mg, 0.4 mmol, 47%).

LC/MS ($C_{33}H_{34}FN_7O_3S_2$) 660 $[M+H]^+$; RT 1.18 (LCMS-V-B1)

$^1H$ NMR (400 MHz DMSO-$d_6$) δ 11.31 (br s, 1H), 10.81 (br s, 1H), 7.88 (d, J=7.8 Hz, 1H), 7.50 (d, J=7.8 Hz, 1H), 7.37 (ddd, J=8.2, 7.3, 1.3 Hz, 1H), 7.31 (dd, J=11.9, 2.0 Hz, 1H), 7.25-7.11 (m, 3H), 4.26 (q, J=7.1 Hz, 2H), 4.16 (t, J=6.2 Hz, 2H), 3.39 (s, 2H), 3.30 (t, J=7.6 Hz, 2H), 2.37 (s, 3H), 2.35 (s, 3H), 2.21 (s, 6H), 2.14 (q, J=7.2, 6.5 Hz, 2H), 1.29 (t, J=7.1 Hz, 3H).

Step B: 2-({6-[(1,3-benzothiazol-2-yl)amino]-4,5-dimethylpyridazin-3-yl}amino)-5-(3-{4-[3-(dimethylamino)prop-1-yn-1-yl]-2-fluorophenoxy}propyl)-1,3-thiazole-4-carboxylic acid To a solution of the product from Step A (266 mg, 0.4 mmol, 1 eq) in 1,4-dioxane (10 mL) was added 2M aqueous lithium hydroxide (0.4 mL, 0.81 mmol, 2 eq) and the mixture was stirred at reflux for 3 h. After allowing to cool to ambient temperature, the reaction was concentrated in vacuo and triturated with water (10 mL). The solids were collected by filtration, washed with water, and dried under vacuum to afford the desired product as a bright yellow solid (209 mg, 0.33 mmol, 82%) [as a lithium salt].

HRMS-ESI [M+H]+ calcd for $C_{31}H_{31}FN_7O_3S_2$: 632.1908, found 632.1914.

Example 4: 2-({6-[(1,3-Benzothiazol-2-yl)amino]pyridazin-3-yl}amino)-1,3-thiazole-4-carboxylic acid

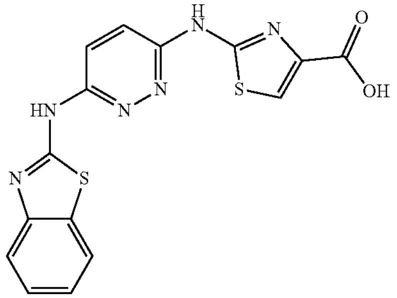 [SMILES: O=C(O)c1csc(Nc2ccc(Nc3nc4ccccc4s3)nn2)n1]

Step A: ethyl 2-({6-[(1,3-benzothiazol-2-amino]pyridazin-3-yl}amino)-1,3-thiazole-4-carboxylate To an oven-dried flask was added the product from Preparation 9b (500 mg, 1.9 mmol, 1 eq), ethyl 2-amino-1,3-thiazole-4-carboxylate (393 mg, 2.28 mmol, 1.2 eq), cesium carbonate (930 mg, 2.85 mmol, 1.5 eq), Xantphos (110 mg, 0.19 mmol, 0.1 eq) and tris(dibenzylideneacetone)dipalladium(0)(87.1 mg, 0.1 mmol, 0.05 eq). The flask was evacuated and flushed with nitrogen (×3) and then toluene (20 mL) was added. The mixture was then sparged with nitrogen (15 mins) then heated at 180° C. for 1.5 h under microwave irradiation. The mixture was partitioned between dichloromethane (200 mL) and water (200 mL) and the organic phase was concentrated in vacuo. The crude material was triturated with dichloromethane and filtered, washed with dichloromethane and dried to afford the desired product as a yellow solid (417 mg, 1.05 mmol, 55%).

LC/MS ($C_{17}H_{14}N_6O_2S_2$) 397 $[M+H]^+$; RT 1.20 (LCMS-V-B1)

$^1H$ NMR (400 MHz, DMSO-d6) δ 11.86 (s, 2H), 7.97 (s, 1H), 7.95 (s, 1H), 7.65 (d, J=8.1 Hz, 1H), 7.52 (d, J=9.3 Hz, 1H), 7.46-7.32 (m, 2H), 7.23 (t, 1H), 4.29 (q, J=7.1 Hz, 2H), 1.32 (t, J=7.1 Hz, 3H).

Step B: 2-({6-[(1,3-benzothiazol-2-yl)amino]pyridazin-3-yl}amino)-1,3-thiazole-4-carboxylic acid To a solution of the product from Step A (417 mg, 1.05 mmol, 1 eq) in 1,4-dioxane (20 mL) was added 2M aqueous lithium hydroxide (1.05 mL, 2.09 mmol, 2 eq) and the reaction was heated at reflux for 1 h. The mixture was allowed to cool to ambient temperature, then the solvent was removed in vacuo and the residue was triturated with acetone, followed by a 1:1 mix of iso-propanol/water. The solid was collected by filtration and dried in vacuo to afford the desired product as a brown solid (161 mg, 0.43 mmol, 42%).

HRMS-ESI (m/z) [M+H]+ calcd for $C_{15}H_{11}N_6O_2S_2$: 371.0379, found 371.0404.

Example 5: 2-({6-[(1,3-Benzothiazol-2-yl)amino]-5-(propan-2-yl)pyridazin-3-yl}amino)-1,3-thiazole-4-carboxylic acid

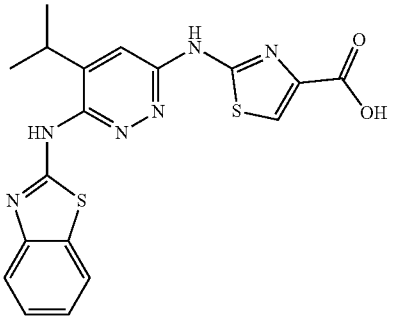

Step A: ethyl 2-({6-[(1,3-benzothiazol-2-yl)amino]-5-(propan-2-yl)pyridazin-3-yl}amino)-1,3-thiazole-4-carboxylate To an oven-dried microwave vial was added the product from Preparation 9cb (367 mg, 1.2 mmol, 1 eq), ethyl 2-amino-1,3-thiazole-4-carboxylate (249 mg, 1.44 mmol, 1.2 eq), cesium carbonate (589 mg, 1.81 mmol, 1.5 eq), Xantphos (69.7 mg, 0.12 mmol, 0.1 eq) and tris(dibenzylideneacetone)dipalladium(0)(55.1 mg, 0.06 mmol, 0.05 eq). The vial was evacuated and flushed with nitrogen (×3) and then toluene (10 mL) was added. The mixture was sparged with nitrogen (15 min) then heated at 180° C. for 1 h under microwave irradiation. The mixture was partitioned between ethyl acetate and water, and the aqueous phase was extracted with ethyl acetate. The combined organics were washed with brine, dried (magnesium sulfate), and concentrated in vacuo. Purification by automated flash column chromatography (CombiFlash Rf, 40 g RediSep™ silica cartridge) eluting with a gradient of 0-50% ethyl acetate in iso-heptane afforded the desired product as a bright yellow solid (303 mg, 0.69 mmol, 57%).

LC/MS ($C_{20}H_{20}N_6O_2S_2$) 441 [M+H]$^+$; RT 1.39 (LCMS-V-B1)

$^1$H NMR (400 MHz, DMSO-d6) δ 12.03 (d, J=233.3 Hz, 1H), 11.72 (s, 1H), 7.94 (s, 1H), 7.85-7.09 (m, 5H), 4.29 (q, J=7.1 Hz, 2H), 3.33 (s, 1H), 1.32 (t, J=7.1 Hz, 3H), 1.25 (d, J=6.8 Hz, 6H).

Step B: 2-({6-[(1,3-benzothiazol-2-yl)amino]-5-(propan-2-yl)pyridazin-3-yl}amino)-1,3-thiazole-4-carboxylic acid To a solution of the product from Step A (300 mg, 0.68 mmol, 1 eq) in 1,4-dioxane (10 mL) was added 2M aqueous lithium hydroxide (0.68 mL, 1.36 mmol, 2 eq) and the reaction heated at 60° C. for 18 h. The mixture was allowed to cool to ambient temperature and concentrated in vacuo. The residue was diluted with water and acidified with 2M aqueous hydrochloric acid. The resultant solid was collected by filtration, washed with water and dried under vacuum to afford a brown solid (130 mg, 0.32 mmol, 46%) [as a hydrochloric acid salt].

HRMS-ESI (m/z) [M+H]+ calcd for $C_{18}H_{17}N_6O_2S_2$: 413.0849, found 413.0885.

Example 6: 2-({6-[(1,3-Benzothiazol-2-yl)amino]-4-(propan-2-yl)pyridazin-3-yl}amino)-1,3-thiazole-4-carboxylic acid

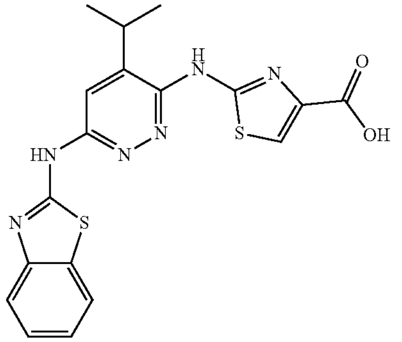 [SMILES: CC(C)c1cc(Nc2nc3ccccc3s2)nnc1Nc1nc(C(=O)O)cs1]

Step A: ethyl 2-({6-[(1,3-benzothiazol-2-yl)amino]-4-(propan-2-yl)pyridazin-3-yl}amino)-1,3-thiazole-4-carboxylate To an oven-dried flask was added the product from Preparation 9ca (500 mg, 1.64 mmol, 1 eq), ethyl 2-amino-1,3-thiazole-4-carboxylate (339 mg, 1.97 mmol, 1.2 eq), Xantphos (94.9 mg, 0.16 mmol, 0.1 eq), cesium carbonate (802 mg, 2.46 mmol, 1.5 eq) and tris(dibenzylideneacetone) dipalladium(0)(75.1 mg, 0.08 mmol, 0.05 eq). The vial was evacuated and flushed with nitrogen (×3) and then toluene (20 mL) was added. The mixture was sparged with nitrogen (10 min) then heated at 200° C. for 1.5 h under microwave irradiation. Further Xantphos (94.9 mg, 0.16 mmol, 0.1 eq) and tris(dibenzylideneacetone)dipalladium(0) (75.1 mg, 0.08 mmol, 0.05 eq) were added, the mixture was sparged with nitrogen (10 min) then heated at 180° C. for 3 h under microwave irradiation. The reaction was partitioned between ethyl acetate and water, the aqueous phase extracted with ethyl acetate, and the combined organics washed with brine, dried (magnesium sulfate) and concentrated in vacuo. Purification by automated flash column chromatography (CombiFlash Rf, 40 g RediSep™ silica cartridge) eluting with a gradient of 0-55% ethyl acetate in iso-heptane afforded the desired product as an orange solid (147 mg, 0.33 mmol, 20%).

LC/MS ($C_{20}H_{20}N_6O_2S_2$) 441 [M+H]$^+$; RT 1.35 (LCMS-V-B1)

Step B: 2-({6-[(1,3-benzothiazol-2-yl)amino]-4-(propan-2-yl)pyridazin-3-yl}amino)-1,3-thiazole-4-carboxylic acid To a solution of the product from Step A (147 mg, 0.33 mmol, 1 eq) in 1,4-dioxane (5 mL) was added 2M aqueous lithium hydroxide (0.33 mL, 0.67 mmol, 2 eq) and mixture was heated at reflux for 1 h. The mixture was cooled to ambient temperature and concentrated in vacuo. The residue was taken up in water and acidified to pH 6. The aqueous phase was extracted with ethyl acetate, and the organics were dried (magnesium sulfate) and concentrated in vacuo. Purification by reverse phase automated flash chromatography (CombiFlash Rf, C18 4.3 g RediSep column) eluting with a gradient of 5-95% acetonitrile in water afforded the desired product as a yellow solid (7 mg, 0.02 mmol, 5%).

HRMS-ESI (m/z) [M+H]+ calcd for $C_{18}H_{17}N_6O_2S_2$: 413.0849, found 413.0886.

Example 7: 2-({6-[(1,3-Benzothiazol-2-yl)amino]-5-methylpyridazin-3-yl}amino)-1,3-thiazole-4-carboxylic acid

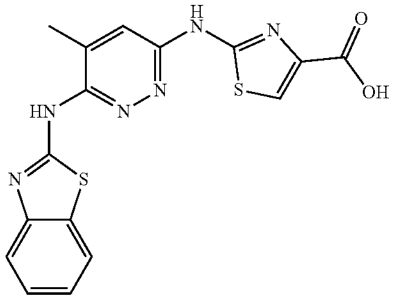 [SMILES: Cc1cc(Nc2nc(C(=O)O)cs2)nnc1Nc1nc2ccccc2s1]

Step A: ethyl 2-({6-[(1,3-benzothiazol-2-yl)amino]-5-methylpyridazin-3-yl}amino)-1,3-thiazole-4-carboxylate To an oven-dried microwave vial was added the product from Preparation 9db (400 mg, 1.45 mmol, 1 eq), ethyl 2-amino-1,3-thiazole-4-carboxylate (373 mg, 2.17 mmol, 1.5 eq), cesium carbonate (706 mg, 2.17 mmol, 1.5 eq), tris(dibenzylideneacetone)dipalladium(0)(66.2 mg, 0.07 mmol, 0.05 eq) and Xantphos (83.6 mg, 0.14 mmol, 0.1 eq). The vessel was evacuated and flushed with nitrogen (×3), and then toluene (15 mL) was added. The mixture was sparged with nitrogen (5 min) then heated at 150° C. for 2 h under microwave irradiation. Further ethyl 2-amino-1,3-thiazole-4-carboxylate (375 mg, 2.17 mmol, 1.5 eq), Xantphos (83.6 mg, 0.14 mmol, 0.1 eq), and tris(dibenzylideneacetone)dipalladium(0)(66.2 mg, (1.07 mmol, 0.05 eq) were added, the mixture was sparged with nitrogen (5 min)

then heated at 180° C. for 1 h under microwave irradiation. The mixture was concentrated in vacuo and purification by reverse phase automated flash chromatography (CombiFlash Rf, C18 4.3 g RediSep column) eluting with a gradient of 5-95% acetonitrile in water afforded the desired product (169 mg, 0.41 mmol, 28%).

LC/MS ($C_{18}H_{16}N_6O_2S_2$) 413 $[M+H]^+$; RT 1.27 (LCMS-V-B1)

$^1H$ NMR (400 MHz, DMSO-d6) δ 11.81 (s, 1H), 11.04 (br s, 1H), 7.94 (s, 1H), 7.90 (br s, 1H), 7.55 (br s, 1H), 7.39 (t, J=7.6 Hz, 1H), 7.21 (t, J=7.5 Hz, 1H), 7.14 (s, 1H) 4.29 (q, J=7.1 Hz, 2H), 2.40 (s, 3H), 1.32 (t, J=7.1 Hz, 3H).

Step B: 2-({6-[(1,3-benzothiazol-2-yl)amino]-5-methylpyridazin-3-yl}amino)-1,3-thiazole-4-carboxylic acid To a stirred suspension of the product from Step A (169 mg, (1.41 mmol, 1 eq) in 1,4-dioxane (5 mL) was added 2M aqueous lithium hydroxide (0.49 mL, 0.49 mmol, 1.2 eq) and the mixture was stirred at 100° C. for 4.5 h. The reaction mixture was allowed to cool to ambient temperature and concentrated in vacuo. The crude product was suspended in a 2:1 mixture of isopropanol/water and stirred for 30 min. The solids were collected by filtration and dried under vacuum to afford the desired product as a bright yellow solid (17 mg, 0.04 mmol, 11%) [as a lithium salt].

HRMS-ESI (m/z) [M+H+ calcd for $C_{16}H_{13}N_6O_2S_2$: 385.0536, found 385.0567.

Example 8: 2-({6-[(1,3-Benzothiazol-2-yl)amino]-5-methyl-4-(propan-2-yl)pyridazin-3-yl}amino)-1,3-thiazole-4-carboxylic acid

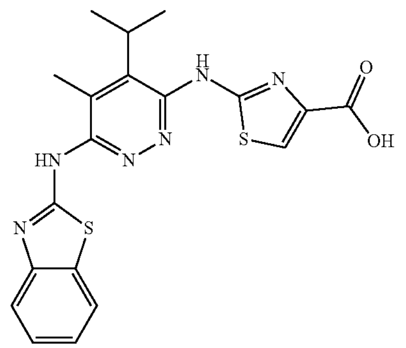 [SMILES: Cc1c(Nc2nc3ccccc3s2)nnc(Nc2nc(C(=O)O)cs2)c1C(C)C]

Step A: ethyl 2-({6-[(1,3-benzothiazol-2-yl)amino]-5-methyl-4-(propan-2-yl)pyridazin-3-yl}amino)-1,3-thiazole-4-carboxylate To an oven-dried microwave vial was added the product from Preparation 9ea (300 mg, 0.94 mmol, 1 eq), ethyl 2-amino-1,3-thiazole-4-carboxylate (243 mg, 1.41 mmol, 1.5 eq), cesium carbonate (460 mg, 1.41 mmol, 1.5 eq), Xantphos (218 mg, 0.38 mmol, 0.4 eq), and tris(dibenzylideneacetone)dipalladium(0)(172.4 mg, 0.18 mmol, 0.2 eq). The vessel was evacuated and flushed with nitrogen (×3), and then toluene (4 mL) was added. The mixture was sparged with nitrogen (15 mins) then heated at 180° C. for 2 h under microwave irradiation. The mixture was concentrated in vacuo and the residue was adsorbed onto isolute. Purification by reverse phase automated flash chromatography (CombiFlash Rf, C18 4.3 g RediSep column) eluting with a gradient of 5-95% acetonitrile in water afforded the desired product (22 mg, 0.05 mmol, 5%).

LC/MS ($C_{21}H_{22}N_6O_2S_2$) 455 $[M+H]^+$; RT 1.42 (LCMS-V-B1)

$^1H$ NMR (400 MHz, DMSO-d6) δ 10.96 (s, 1H), 7.92 (s, 1H), 7.87 (br s, 1H), 7.53 (br s, 1H), 7.38 (t, J=7.5 Hz, 1H), 7.20 (t, J=7.6 Hz, 1H), 4.30 (q, J=7.1 Hz, 2H), 3.66 (p, J=7.0 Hz, 1H), 2.48 (s, 3H), 1.35 (d, 6H), 1.32 (t, 3H).

Step B: 2-({6-[(1,3-benzothiazol-2-yl)amino]-5-methyl-4-(propan-2-yl)pyridazin-3-yl}amino)-1,3-thiazole-4-carboxylic acid To a solution of the product from Step A (22 mg, 0.05 mmol, 1 eq) in tetrahydrofuran mL) and methanol (0.5 mL) was added 2M aqueous lithium hydroxide (50 μL, 0.1 mmol, 2 eq) and the mixture was heated at 75° C. for 1 h. The reaction mixture was allowed to cool to ambient temperature and concentrated in vacuo. The resultant solid was taken back up in water (2 mL) and the pH was adjusted to 6. The organics were extracted with ethyl acetate (20 mL), dried (magnesium sulfate), concentrated in vacuo and dried under vacuum to afford the desired product as a light orange solid (19 mg, 0.04 mmol, 92%).

HRMS-ESI (m/z) [M+H+ calcd for $C_{19}H_{19}N_6O_2S_2$: 427.1005, found 427.1043.

Example 9: 2-({6-[(1,3-Benzothiazol-2-yl)amino]-4,5-dimethylpyridazin-3-yl}amino)-5-(3-phenoxypropyl)-1,3-thiazole-4-carboxylic acid

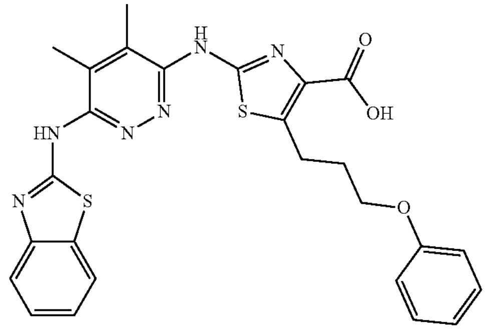 [SMILES: Cc1c(Nc2nc(C(=O)O)c(CCCOc3ccccc3)s2)nnc(Nc2nc3ccccc3s2)c1C]

Step A: ethyl 2-({6-[(1,3-benzothiazol-2-yl)amino]-4,5-dimethylpyridazin-3-yl}amino)-5-(3-phenoxypropyl)-1,3-thiazole-4-carboxylate To an oven-dried microwave vial was added the product from Preparation 9a (45.7 mg, 0.16 mmol, 1 eq), the product from Preparation 3v (48.2 mg, 0.16 mmol, 1 eq), Xantphos (9.1 mg, 0.02 mmol, 0.1 eq), tris(dibenzylideneacetone) dipalladium(0)(7.2 mg, 0.01 mmol, 0.05 eq) and cesium carbonate (61.5 mg, 0.19 mmol, 1.2 eq). The vessel was evacuated and flushed with nitrogen (×3) and then toluene (2 mL) was added. The mixture was sparged with nitrogen (10 mins) then heated at 180° C. for 2 h under microwave irradiation. The reaction was partitioned between ethyl acetate and water, then successively washed with water and brine. The organic phase was dried (magnesium sulfate) and the solvent removed in vacuo. Purification by automated flash column chromatography (CombiFlash Rf, 12 g RediSep™ silica cartridge) eluting with a gradient of 0-10% methanol in afforded the desired product as a brown glass (19.2 mg, 0.03 mmol, 22%).

LC/MS ($C_{28}H_{28}N_6O_3S_2$) 561 $[M+H]^+$; RT 1.51 (LCMS-V-B1)

$^1$H NMR (400 MHz, DMSO-d6) δ 10.81 (br s, 2H), 7.65 (s, 1H), 7.38 (s, 1H), 7.31 (t, 2H), 7.21 (s, 2H), 7.00-6.89 (m, 3H), 4.27 (q, J=7.2 Hz, 2H), 4.06 (t, J=6.2 Hz, 2H), 3.30 (d, J=8.3 Hz, 2H), 2.37 (s, 3H) 2.35 (s, 3H), 2.13 (q, 2H), 1.30 (t, J=7.1 Hz, 3H).

Step B: 2-({6-[(1,3-benzothiazol-2-yl)amino]-4,5-dimethylpyridazin-3-yl}amino)-5-(3-phenoxypropyl)-1,3-thiazole-1-carboxylic acid To a solution of the product from Step A (19 mg, 0.03 mmol, 1 eq) in 1,4-dioxane (2 mL) was added a 2M aqueous lithium hydroxide (14.2mg, 0.34 mmol, 10 eq) and the mixture was heated at reflux for 10 h. After allowing to cool to ambient temperature the solvent was removed in vacuo and the residue was triturated with water and the crude product collected by filtration. Purification by reverse-phase preparative HPLC (method HPLC-V-A2) afforded the desired product as a beige solid (3.5 mg, 6.6 µmol, 19%).

HRMS-ESI (m/z) [M+H]+ calcd for $C_{26}H_{25}N_6O_3S_2$: 533.1424, found 533.1460.

Example 10: 2-({6-[(1,3-Benzothiazol-2-yl)amino]-4-methyl-5-(propan-2-yl)pyridazin-3-yl}amino)-1,3-thiazole-4-carboxylic add

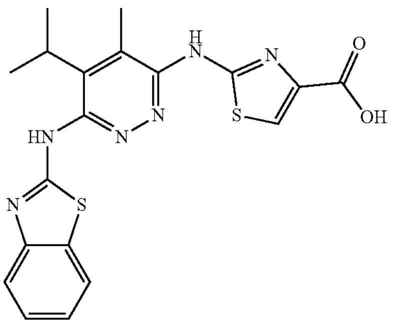

Step A: ethyl 2-({6-[(1,3-benzothiazol-2-yl)amino]-4-methyl-5-(propan-2-yl)pyridazin-3-yl}amino)-1,3-thiazole-4-carboxylate To an oven-dried microwave vial was added the product from Preparation 9eb (114 mg, 0.36 mmol, 1 eq), ethyl 2-amino-1,3-thiazole-4-carboxylate (92.4 mg, 0.54 mmol, 1.5 eq), cesium carbonate (175 mg, 0.54 mmol, 1.5 eq), Xantphos (41.4 mg, 0.7 mmol, 0.2 eq), and tris(dibenzylideneacetone)dipalladium(0)(32.7 mg, 0.04 mmol, 0.1 eq). The vessel was evacuated and flushed with nitrogen (×3), and then toluene (4 mL) was added. The mixture was sparged with nitrogen (15 mins) then heated at 180° C. for 1 h under microwave irradiation. The mixture was concentrated in vacuo and purification by reverse phase automated flash chromatography (CombiFlash Rf, C18 4.3 g RediSep column) eluting with a gradient of 5-70% acetonitrile in water afforded the desired product as a yellow solid (20 mg, 0.04 mmol, 12%).

LC/MS ($C_{21}H_{22}N_6O_2S_2$) 455 $[M+H]^+$; RT 1.45 (LCMS-V-B1).

Step B: 2-({6-[(1,3-benzothiazol-2-yl)amino]-4-methyl-5-(propan-2-yl)pyridazin-3-yl}amino)-1,3-thiazole-4-carboxylic acid To a solution of the product from Step A (20 mg, 0.04 mmol, 1 eq) in tetrahydrofuran (2 mL) and methanol (0.5 mL) was added lithium hydroxide monohydrate (3.69 mg, 0.09 mmol, 2 eq) and the reaction was heated at reflux for 1 h. The mixture was allowed to cool to ambient temperature and concentrated in vacuo. The product was taken up in water (3 mL), acidified to pH 6 with 1M aqueous hydrochloric acid and extracted with 19:1 dichloromethane/isopropanol. The organic extract was dried (magnesium sulfate) and concentrated in vacuo to afford the desired product as a crisp yellow solid (13.5 mg, 0.03 mmol, 72%).

HRMS-ESI (m/z) [M+H]+ calcd for $C_{19}H_{19}N_6O_2S_2$: 427.1005, found 427.1043.

Example 11: 2-({6-[(1,3-Benzothiazol-2-yl)amino]-4-methylpyridazin-3-yl}amino)-1,3-thiazole-4-carboxylic acid

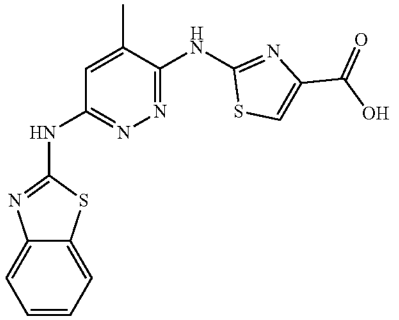 [SMILES: Cc1cc(Nc2nc3ccccc3s2)nnc1Nc1nc(C(=O)O)cs1]

Step A: ethyl 2-({6-[(1,3-benzothiazol-2-yl)amino]-4-methylpyridazin-3-yl}amino)-1,3-thiazole-4-carboxylate To an oven-dried microwave vial was added the product from Preparation 9da (240 mg, 0.87 mmol, 1 eq), ethyl 2-amino-1,3-thiazole-4-carboxylate (224 mg, 1.3 mmol, 1.5 eq), cesium carbonate (424 mg, 1.3 mmol, 1.5 eq), tris (dibenzylideneacetone)dipalladium(0)(39.7 mg, 0.04 mmol, 0.05 eq) and Xantphos (50.2 mg, 0.09 mmol, 0.1 eq). The vessel was evacuated and flushed with nitrogen (×3), and then toluene (15 mL) was added. The mixture was sparged with nitrogen (5 min) then heated at 180° C. for 3 h under microwave irradiation. The mixture was concentrated in vacuo and purification by reverse phase automated flash chromatography (CombiFlash Rf, C18 26 g RediSep column) eluting with a gradient of 5-95% acetonitrile in water to afford the desired product as a brown solid (44 mg, 0.11 mmol, 12%).

LC/MS ($C_{18}H_{16}N_6O_2S_2$) 413 $[M+H]^+$; RT 1.24 (LCMS-V-B1)

$^1$H NMR (400 MHz, DMSO-d6) δ 11.61 (br s, 1H), 11.17 (s, 1H), 7.97 (s, 1H), 7.95 (br s, 7.64 (d, J=8.0 Hz, 1H), 7.39

(ddd, J=8.2, 7.2, 1.3 Hz, 1H), 7.31 (d, J=1.2 Hz, 1), 7.22 (ddd, J=8.2, 7.3, 1.2 Hz 1H), 4.30 (q, J=7.1 Hz, 2H), 2.42 (s, 3H) 1.32 (t, J=7.1 Hz, 3H).

Step B: 2-({6-[(1,3-benzothiazol-2-yl)amino]-4-methylpyridazin-3-yl}amino)-1,3-thiazole-4-carboxylic acid To a solution of the product from Step A (44 mg, 0.11 mmol, 1 eq) in 1,4-dioxane (5 mL) was added 2M aqueous lithium hydroxide (0.21 mL, 0.21 mmol, 2 eq) and the reaction was heated at reflux for 1 h. The mixture was allowed to cool to ambient temperature then concentrated in vacuo. The solid was triturated with 4:1 isopropanol/water (4 mL) and stirred for 30 min. The solid was collected by filtration, washed with further cold isopropanol (3 mL) and dried under vacuum to afford the desired product as a brown solid (33 mg, 0.09 mmol, 80%).

HRMS-ESI (m/z) [M+H]+ calcd for $C_{16}H_{13}N_6O_2S_2$: 385.0536, found 385.0572.

Example 12: 2-({6-[(1,3-Benzothiazol-2-yl)amino]-4,5-dimethylpyridazin-3-yl}amino)-5-(3-methoxypropyl)-1,3-thiazole-1-carboxylic acid

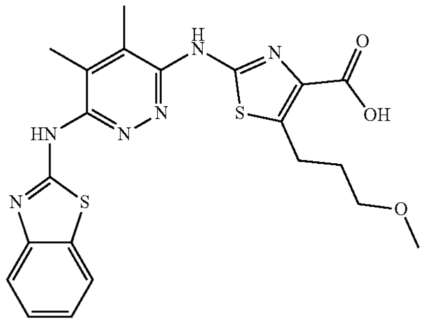 [SMILES: COCCCc1sc(Nc2nnc(Nc3nc4ccccc4s3)c(C)c2C)nc1C(=O)O]

Step A: ethyl 2-({6-[(1,3-benzothiazol-2-yl)amino]-4,5-dimethylpyridazin-3-yl}amino)-5-(3-methoxypropyl)-1,3-thiazole-4-carboxylate To an oven-dried microwave vial was added the product from Preparation 9a (260 mg, 0.89 mmol, 1 eq), the product from Preparation 3w (219 mg, 0.89 mmol, 1 eq), Xantphos (51.8 mg, 0.09 mmol, 0.1 eq), tris(dibenzylideneacetone) dipalladium(0)(41 mg, 0.04 mmol, 0.05 eq) and cesium carbonate (350 mg, 1.07 mmol, 1.2 eq). The vessel was evacuated and flushed with nitrogen (×3), and then toluene (5 mL) was added. The mixture was sparged with nitrogen (10 min) then heated at 180° C. for 1 h under microwave irradiation. The reaction was diluted with ethyl acetate, successively washed with water and brine, then dried (magnesium sulfate) and the solvent removed in vacuo. Purification by reverse phase automated flash chromatography (CombiFlash Rf, C18 13 g RediSep column) eluting with 5-95% acetonitrile in water afforded the desired product as a yellow glass (72.5 mg, 0.15 mmol, 16%).

LC/MS ($C_{23}H_{26}N_6O_3S_2$) 499 $[M+H]^+$; RT 1.38 (LCMS-V-B1)

$^1$H NMR (400 MHz, DMSO-d6) δ 10.76 (br s, 1H), 7.88 (d, J=7.7 Hz, 1H), 7.50 (br s, 1H), 7.37 (td, J=8.1, 7.7, 1.3 Hz, 1H), 7.20 (t, J=7.7 Hz, 1H), 4.29 (q, J=7.1 Hz, 2H), 3.41 (t, J=6.3 Hz, 1H), 3.27 (s, 3H), 3.21-3.12 (m, 2H), 2.37 (s, 3H), 2.35 (s, 3H), 1.96-1.84 (m, 2H), 1.32 (t, J=7.1 Hz, 3H).

Step B: 2-({6-[(1,3-benzothiazol-2-yl)amino]-4,5-dimethylpyridazin-3-yl}amino)-5-(3-methoxypropyl)-1,3-thiazole-4-carboxylic acid To a solution of the product from Step A (72.5 mg, 0.15 mmol, 1 eq) in 1,4-dioxane (5 mL) was added lithium hydroxide monohydrate (12.2 mg, 0.29 mmol, 2 eq) and the mixture was heated at reflux for 10 h. The reaction was allowed to cool to ambient temperature and the solvent removed in vacuo. The resultant residue was triturated with water then collected by filtration, washed with water, and dried under vacuum to afford the desired product as a brown solid (40.9 mg, 0.09 mmol, 60%) [as a lithium salt].

HRMS-ESI (m/z) [M+H]+ calcd for $C_{21}H_{23}N_6O_3S_2$: 471.1268, found 471.1306.

Example 13: 2-({6-[(1,3-Benzothiazol-2-yl)amino]-4,5-dimethylpyridazin-3-yl}amino)-5-[3-(2-fluorophenoxy)propyl]-1,3-thiazole-4-carboxylic acid

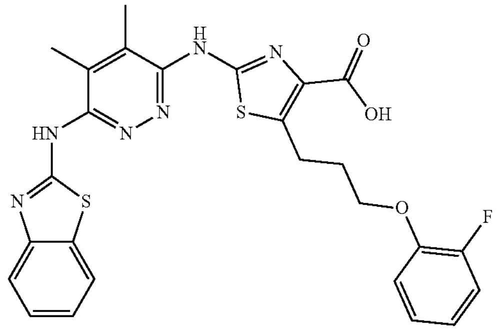 [SMILES: Cc1c(Nc2nc(C(=O)O)c(CCCOc3ccccc3F)s2)nnc(Nc2nc3ccccc3s2)c1C]

Step A: ethyl 2-({6-[(1,3-benzothiazol-2-yl)amino]-4,5-dimethylpyridazin-3-yl}amino)-5-[3-(2-fluorophenoxy)propyl]-1,3-thiazole-4-carboxylate To an oven-dried microwave vial was added the product from Preparation 9a (162 mg, 0.56 mmol, 1 eq), the product from Preparation 3x (181 mg, 0.56 mmol, 1 eq), Xantphos (36.0 mg, 0.06 mmol, 0.11 eq), tris(dibenzylideneacetone) dipalladium(0)(25.6 mg, 0.03 mmol, 0.05 eq) and cesium carbonate (243 mg, 0.75 mmol, 1.34 eq). The vessel was evacuated and flushed with nitrogen (×3), and then toluene (4 mL) and dimethylformamide (1 mL) were added. The mixture was sparged with nitrogen (10 min) then heated at 180° C. for 1 h under microwave irradiation. The reaction was diluted with ethyl acetate, successively washed with water and brine, dried (magnesium sulfate), and concentrated in vacuo. Purification by reverse phase automated flash chromatography (CombiFlash Rf, C18 13 g RediSep column) eluting with a gradient of 5-95% acetonitrile in water afforded the desired product as a brown glass (76.1 mg, 0.13 mmol, 24%).

LC/MS ($C_{28}H_{27}FN_6O_3S_2$) 579 $[M+H]^+$; RT 1.49 (LCMS-V-B1)

$^1$H NMR (400 MHz, DMSO-d6) δ 10.78 (br s, 1H), 7.89 (brs, 1H), 7.42-7.28 (m, 2H), 7.28-7.08 (m, 4H), 7.00-6.86

(m, 1H), 4.26 (q, J=7.1 Hz, 2H), 4.14 (t, J=6.2 Hz, 2H), 3.30 (d, J=6.8 Hz, 2H), 2.37 (s, 3H), 2.35 (s, 3H), 2.21-2.11 (m, 2H), 1.30 (t, J=7.1 Hz, 3H).

Step B: 2-({6-[(1,3-benzothiazol-2-yl)amino]-4,5-dimethylpyridazin-3-yl}amino)-5-[3-(2-fluorophenoxy)propyl]-1,3-thiazole-4-carboxylic acid To a solution of the product from Step A (76 mg, 0.13 mmol, 1 eq) in 1,4-dioxane (5 mL) was added lithium hydroxide monohydrate (11.02 mg, 0.26 mmol, 2 eq) and the mixture was heated at reflux for 8 h. The mixture was allowed to cool to ambient temperature and the solvent was removed in vacuo. Purification by reverse phase automated flash chromatography (CombiFlash Rf, C18 13 g RediSep column) eluting with a gradient of 5-95% acetonitrile in water afforded material that was further purified by reverse phase preparative HPLC (method HPLC-V-A2) to afford the desired product as a beige solid (7.2 mg, 0.01 mmol, 10%).

HRMS-ESI (m/z) [M+H]+ calcd for $C_{26}H_{24}FN_6O_3S_2$: 551.1330, found 551.1368.

Example 14: 2-({6-[(1,3-Benzothiazol-2-yl)amino]-4,5-dimethylpyridazin-3-yl}amino)-5-{3-[4-(dimethylcarbamoyl)-2-fluorophenoxy]propyl}-1,3-thiazole-4-carboxylic acid

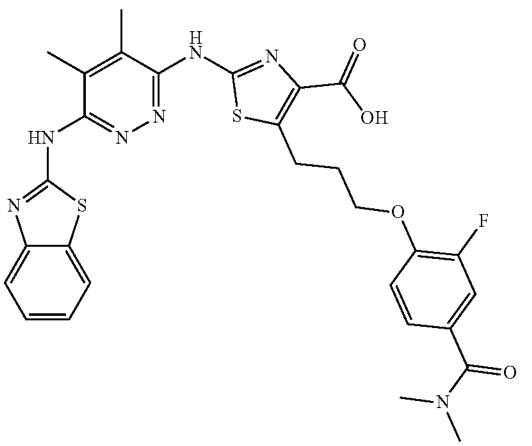 [SMILES: Cc1c(Nc2nc(C(=O)O)c(CCCOc3ccc(C(=O)N(C)C)cc3F)s2)nnc(Nc2nc3ccccc3s2)c1C]

Step A: ethyl 2-({6-[(1,3-benzothiazol-2-yl)amino]-4,5-dimethylpyridazin-3-yl}amino)-5-{3-[4-(dimethylcarbamoyl)-2-fluorophenoxy]propyl}-1,3-thiazole-4-carboxylate To an oven-dried microwave vial was added the product from Preparation 9a (143 mg, 0.49 mmol, 1 eq), the product from Preparation 3y (199 mg, 0.49 mmol, 1 eq), Xantphos (28.5 mg, 0.05 mmol, 0.1 eq), tris(dibenzylideneacetone) dipalladium(0)(22.5 mg, 0.02 mmol, 0.05 eq) and cesium carbonate (192 mg, 0.59 mmol, 1.2 eq). The vessel was evacuated and flushed with nitrogen (×3), and then toluene (4 mL) and dimethylformamide (1 mL) were added. The mixture was sparged with nitrogen (10 min) then heated at 180° C. for 1 h under microwave irradiation. The reaction was diluted with ethyl acetate then washed with water followed by brine. The organic extract was dried (magnesium sulfate) and the solvent removed in vacuo. Purification by automated flash column chromatography (CombiFlash Rf, 12 g RediSep™ silica cartridge) eluting with a gradient or 0-10% methanol in dichloromethane afforded the desired product as a brown glass (60 mg, 0.09 mmol, 19%).

LC/MS ($C_{31}H_{32}FN_7O_4S_2$) 650 $[M+H]^+$; RT 1.36 (LCMS-V-B1)

$^1H$ NMR (400 MHz, DMSO-d6) δ 10.77 (br s, 1H), 7.87 (s, 1H), 7.42-7.28 (m, 2H), 7.26-7.17 (m, 4H), 4.26 (q, J=7.1 Hz, 2H), 4.19 (t, J=6.2 Hz, 2H), 2.97-2.94 (m, 2H), 2.93 (s, 6H), 2.37 (s, 3H), 2.35 (s, 3H), 2.18 (q, J=7.3, 6.9 Hz, 2H), 1.29 (t, 3H).

Step B: 2-({6-[(1,3-benzothiazol-2-yl)amino]-4,5-dimethylpyridazin-3-yl}amino)-5-{3-[4-(dimethylcarbamoyl)-2-fluorophenoxy]propyl}-1,3-thiazole-4-carboxylic acid To a solution of the product from Step A (60 mg, 0.09 mmol, 1 eq) in 1,4-dioxane was added lithium hydroxide monohydrate (19.4 mg, 0.46 mmol, 5 eq) and the mixture was heated at reflux for 14 h. The reaction was allowed to cool to ambient temperature and the solvent removed in vacuo. The residue was triturated with water, followed by ethanol, then purified by reverse phase preparative HPLC (method HPLC-V-A2) to afford the desired product as a brown solid (11.6 mg, 0.02 mmol, 20%).

HRMS-ESI (m/z) [M+H]+ calcd for $C_{29}H_{29}FN_7O_4S_2$: 622.1701, found 622.1740.

Example 15: 2-({6-[(1,3-Benzothiazol-2-yl)amino]-4-ethyl-5-methylpyridazin-3-yl}amino)-1,3-thiazole-4-carboxylic acid

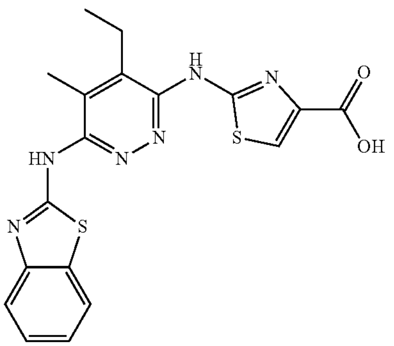 [SMILES: CCc1c(Nc2nc(C(=O)O)cs2)nnc(Nc2nc3ccccc3s2)c1C]

Step A: ethyl 2-({6-[(1,3-benzothiazol-2-yl)amino]-4-ethyl-5-methylpyridazin-3-yl}amino)-1,3-thiazole-1-carboxylate To an oven-dried microwave vial was added the product from Preparation 9fa (400 mg, 1.31 mmol, 1 eq), ethyl 2-amino-1,3-thiazole-4-carboxylate (316 mg, 1.84 mmol, 1.4 eq), cesium carbonate (599 mg, 1.84 mmol, 1.4 eq), Xantphos (75.9 mg, 0.13 mmol, 0.1 eq) and tris(dibenzylideneacetone)dipalladium(0)(60.1 mg, 0.07 mmol, 0.05 eq). The vial was evacuated and flushed with nitrogen (×3), and then toluene (15 mL) was added. The mixture was sparged with nitrogen (10 mins) then heated at 200° C. for 2 h under microwave irradiation. The reaction was concentrated in vacuo and purification by reverse phase automated flash chromatography (CombiFlash Rf, C18 13 g RediSep column) eluting with a gradient of 5-95% acetonitrile in water afforded the desired product (70 mg, 0.16 mmol, 12%).

LC/MS ($C_{20}H_{20}N_6O_2S_2$) 441 $[M+H]^+$; RT 1.37 (LCMS-V-B1)

$^1H$ NMR (400 DMSO-d6) δ 11.08 (s, 1H), 10.88 (br s, 1H), 7.94 (s, 1H), 7.89 (br s, 1H), 7.53 (br s, 1H), 7.38 (t, 1H), 7.20 (t, 1H), 4.30 (q, J=7.1 Hz, 2H), 2.93 (q, J=7.4 Hz, 2H), 2.40 (s, 3H), 1.32 (t, J=7.1 Hz, 3H), 1.09 (t, J=7.4 Hz, 3H).

Step B: 2-({6-[(1,3-benzothiazol-2-yl)amino]-4-ethyl-5-methylpyridazin-3-yl}amino)-1,3-thiazole-4-carboxylic acid To a solution of the product from Step A (70 mg, 0.16 mmol, 1 eq) in 1,4-dioxane (4 mL) was added lithium hydroxide monohydrate (0.32 mL, 0.32 mmol, 2 eq) and the mixture was heated at reflux for 1 h. The reaction was allowed to cool to ambient temperature and concentrated in vacuo. The residue was then suspended in water and the pH adjusted to 6 then re-concentrated. The solid was triturated with isopropanol plus a few drops of water, then collected by filtration, washed with isopropanol, and dried under vacuum to afford the desired product as a brown solid (38.8 mg, 0.09 mmol, 59%).

HRMS-ESI (m/z) [M−H]− called for $C_{18}H_{15}N_6O_2S_2$: 411.0703, found 411.0707.

Example 16: 2-({6-[(1,3-Benzothiazol-2-yl)amino]-5-ethyl-4-methylpyridazin-3-yl}amino)-1,3-thiazole-4-carboxylic acid

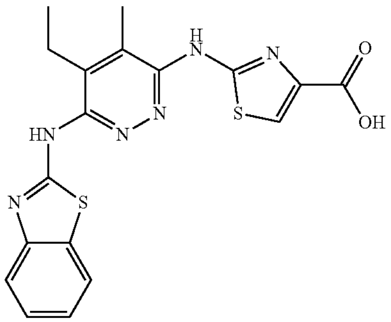 [SMILES: CCc1c(Nc2nc3ccccc3s2)nnc(Nc2nc(C(=O)O)cs2)c1C]

Step A: ethyl 2-({6-[(1,3-benzothiazol-2-yl)amino]-5-ethyl-4-methylpyridazin-3-yl}amino)-1,3-thiazole-4-carboxylate To an oven-dried microwave vial was added the product from Preparation 9fb (300 mg, 0.98 mmol, 1 eq), ethyl 2-amino-1,3-thiazole-4-carboxylate (220 mg, 1.28 mmol, 1.3 eq), cesium carbonate (449 mg, 1.38 mmol, 1.4 eq), Xantphos (57 mg, 0.1 mmol, 0.1 eq) and tris(dibenzylideneacetone)dipalladium(0)(45.1 mg, 0.05 mmol, 0.05 eq). The vial was evacuated and flushed with nitrogen (×3), and then toluene (15 mL) was added. The mixture was sparged with nitrogen (10 mins) then heated at 200° C. for 2 h under microwave irradiation. The reaction was concentrated in vacuo and purification by reverse phase automated flash chromatography (CombiFlash Rf, C18 13 g RediSep column) eluting with 5-95% acetonitrile in water to afford the desired product as a yellow solid (54 mg, 0.12 mmol, 12%).

LC/MS ($C_{20}H_{20}N_6O_2S_2$) 441 $[M+H]^+$; RT 1.38 (LCMS-V-B1)

$^1H$ NMR (400 MHz, DMSO-d6) δ 10.98 (s, 1H), 7.95 (s, 1H), 7.84 (s, 1H), 7.43 (br s, 1H), 7.36 (t, J=7.5 Hz, 1H), 7.18 (t, J=7.5 Hz, 1H), 4.30 (q, J=7.1 Hz, 2H), 2.92 (q, J=7.5, 7.1 Hz, 2H), 2.38 (s, 3H), 1.32 (t, J=7.1 Hz, 3H), 1.11 (t, J=7.4 Hz, 3H).

Step B: 2-({6-[(1,3-benzothiazol-2-yl)amino]-5-ethyl-4-methylpyridazin-3-yl}amino)-1,3-thiazole-4-carboxylic acid To a solution of the product from Step A (54 mg, 0.12 mmol, 1 eq) in 1,4-dioxane (4 mL) was added 2M aqueous lithium hydroxide (0.12 mL, 0.25 mmol, 2 eq) and the reaction was heated at reflux for 2 h. The mixture was concentrated in vacuo and then suspended in water and the pH adjusted to 5-6 before re-concentrating in vacuo. The crude solid was triturated with water, stirred for 30 min, then collected by filtration, washed with cold water and dried under vacuum to afford the desired product as a yellow solid (28.9 mg, 0.07 mmol, 57%).

HRMS-ESI (m/z) [M+H]+ calcd for $C_{18}H_{17}N_6O_2S_2$: 413.0849, found 413.0848.

Example 17: 2-[[4-(1,3-Benzothiazol-2-ylamino)-5,6,7,8-tetrahydrophthalazin-1-yl]amino]thiazole-4-carboxylic acid

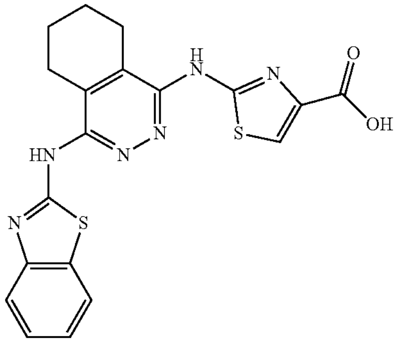 [SMILES: O=C(O)c1csc(Nc2nnc(Nc3nc4ccccc4s3)c3c2CCCC3)n1]

Step A: 4-bromo-5,6,7,8-tetrahydrophthalazin-1-amine

The mixture of 4.0 g of 1,4-dibromo-5,6,7,8-tetrahydrophthalazine (13.7 mmol) in 50 mL of a 25% solution of $NH_3$ in water was kept at 100° C. for 18 h. After concentration, the residue was taken up in methanol, treated with charcoal, stirred, filtered, concentrated, taken up in EtOAc, washed with a 10% solution of NaOH, dried on $MgSO_4$, filtered, and concentrated to give 1.28 g (41%) of the desired product.

LC-MS-ESI (m/z): [M+H]+ calcd for $C_8H_{11}BrN_3$: 228, 230, found: 228, 230.

Step B: N-(4-bromo-5,6,7,8-tetrahydrophthalazin-1-yl)-1,3-benzothiazol-2-amine

The mixture of 1.05 g of the product from Step A (4.6 mmol, 1 eq.), 1.8 g of 2-bromo-1,3-benzothiazole (8.4 mmol, 1.8 eq.), 736 mg of sodium hydride (60% suspension, 18.4 mmol, 3.6 eq.) in 80 mL of 1,4-dioxane was kept at reflux for 0.5 h. Alter cooling and quenching with methanol, the mixture was concentrated, treated with water, filtered off and dried. The solid was triturated in EtOAc, filtered off and dried to give 1.56 g (94%) of the desired product.

$^1$H NMR (500 MHz, DMSO-$d_6$) δ ppm 11.51 (br., 1H), 7.83 (d, 1H), 7.53 (brd., 1H), 7.38 (td, 1H), 7.22 (td, 1H), 2.75/2.62 (m+m, 4H), 1.79 (m, 4H); $^{13}$C NMR (125 MHz, dmso-d6) δ ppm 126.6, 122.9, 122.2, 28.8/24, 21.4/21.1; HRMS-ESI $[M+H]^+$ calcd for $C_{15}H_{14}BrN_4S$: 361.0117, found: 361.0107.

Step C: ethyl 2-[[4-(1,3-benzothiazol-2-ylamino)-5,6,7,8-tetrahydrophthalazin-1-yl]amino]thiazole-4-carboxylate The mixture of 120 mg of the product from Step B (0.33 mmol, 1 eq.), 57 mg of ethyl 2-aminothiazole-4-carboxylate (0.33 mmol, 1 eq.), 12 mg of $Pd_2(dba)_3$ (0.013 mmol, 0.04 eq.), 19 mg of Xantphos (0.033 mmol, 0.1 eq.), and 217 mg of $Cs_2CO_3$ (0.66 mmol, 2 eq.) in 10 mL of trifluoromethylbenzene was kept at 200° C. for 0.5 h. The reaction mixture was concentrated and purified by preparative HPLC to give 31 mg (21%) of the desired product.

$^1$H NMR (500 MHz, DMSO-$d_6$) δ ppm 7.90 (s, 1H), 7.86 (br., 1H), 7.55 (br., 1H), 7.36 (t, 1H), 7.19 (t, 1H), 4.31 (q, 2H), 2.75 (br., 4H), 1.81 (br., 4H), 1.33 (t, 3H); $^{13}$C NMR (125 MHz, DMSO-$d_6$) δ ppm 126.3, 122.5, 121.5; HRMS-ESI (m/z): $[M+H]^+$ calcd for $C_{21}H_{21}N_6O_2S_2$: 453.1162, found: 453.1151.

Step D: 2-[[4-(1,3-benzothiazol-2-ylamino)-5,6,7,8-tetrahydrophthalazin-1-yl]amino]thiazole-4-carboxylic acid The mixture of 31 mg of the product from Step C (0.069 mmol, 1 eq.), 5.8 mg of LiOH×$H_2O$ (2 eq.), and 8 drops of water in 10 mL of 1,4-dioxane was kept at reflux for 2 h. The reaction mixture was concentrated and purified by preparative HPLC to give 24 mg (83%) of the desired product.

HRMS-ESI (m/z): $[M+H]^+$ calcd for $C_{19}H_{17}N_6O_2S_2$: 425.0849, found: 425.0854.

Example 18: 2-({6-[(1,3-Benzothiazol-2-yl)amino]-4-(hydroxymethyl)-5-methylpyridazin-3-yl}amino)-1,3-thiazole-4-carboxylic acid

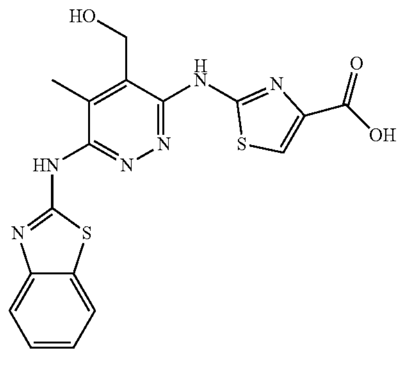 [SMILES: Cc1c(Nc2nc3ccccc3s2)nnc(Nc2nc(C(=O)O)cs2)c1CO]

Step A: ethyl 2-({6-[(1,3-benzothiazol-2-yl)amino]-4-[(benzyloxy)methyl]-5-methylpyridin-3-yl}amino)-1,3-thiazole-4-carboxylate To an oven-dried microwave vial was added the product from Preparation 9ga (176 mg, 0.44 mmol, 1 eq), ethyl 2-amino-1,3-thiazole-4-carboxylate (115 mg, 0.67 mmol, 1.5 eq), cesium carbonate (202 mg, 0.62 mmol, 1.4 eq), tris(dibenzylideneacetone)dipalladium(0)(40.6 mg, 0.04 mmol, 0.1 eq) and Xantphos (12.8 mg, 0.02 mmol, 0.05 eq). The vial was evacuated and flushed with nitrogen (×3), and then toluene (15 mL) was added. The mixture was sparged with nitrogen (5 mins) then heated at 180° C. for 1 h under microwave irradiation. The mixture was concentrated in vacuo and purification by reverse phase automated flash chromatography (CombiFlash Rf, C18 24 g RediSep column) eluting with a gradient of 5-95% acetonitrile in water to afford the desired product (82 mg, 0.15 mmol, 35%).

LC/MS ($C_{26}H_{24}N_6O_3S_2$) 533 $[M+H]^+$; RT 1.44 (LCMS-V-B1)

$^1$H NMR (400 MHz, DMSO-d6) δ 10.91 (br s, 1H), 7.96 (s, 1H), 7.88 (br s, 1H), 7.56 (br s, 1H), 7.43-7.26 (m, 6H), 7.23-7.18 (m, 1H), 4.87 (s, 2H), 4.65 (s, 2H), 4.31 (q, J=7.1 Hz, 2H), 2.40 (s, 3H), 1.33 (t, J=7.1 Hz, 3H).

Step B: ethyl 2-({6-[(1,3-benzothiazol-2-yl)amino]-4-(hydroxymethyl)-5-methylpyridin-3-yl}amino)-1,3-thiazole-4-carboxylate A solution of the product from Step A (72 mg, 0.14 mmol, 1 eq) in dichloromethane (5 mL) was cooled to 0° C. and a 1M boron trichloride solution (0.68 mL, 0.68 mmol, 5 eq) was added dropwise. The mixture was then allowed to warm to ambient temperature over 2 h. The reaction mixture was quenched by addition of methanol and concentrated in vacuo. The resultant solid was triturated with dichloromethane, filtered, washed with dichloromethane and dried under vacuum to afford the desired product as a cream solid (54 mg, 0.12 mmol, 90%).

LC/MS ($C_{19}H_{18}N_6O_3S_2$) 443 $[M+H]^+$; RT 1.23 (LCMS-V-B1)

$^1$H NMR (400 MHz, DMSO-d6) δ 7.97 (s, 1H), 7.89 (d, J=7.7 Hz, 1H), 7.51 (d, J=8.0 Hz, 1H), 7.39 (ddd, J=8.2, 7.3, 1.3 Hz, 1H), 7.22 (td, J=7.5, 1.2 Hz, 1H), 4.83 (s, 2H), 4.30 (q, J=7.1 Hz, 2H), 2.43 (s, 3H), 1.32 (t, J=7.1 Hz, 3H).

Step C: 2-({6-[(1,3-benzothiazol-2-yl)amino]-4-(hydroxymethyl)-5-methylpyridin-3-yl}amino)-1,3-thiazole-4-carboxylic acid To a solution of the product from Step B (50 mg, 0.11 mmol, 1 eq) in 1,4-dioxane (5 mL) was added 2M aqueous lithium hydroxide (0.56 mL, 0.56 mmol, 5 eq) and the mixture was heated at reflux for 30 min. The mixture was cooled to ambient temperature and concentrated in vacuo. The solid was taken up in water (5 mL) and neutralised to pH 6 with 1M HCl and then concentrated in vacuo. The solid was then triturated with 4:1 isopropanol/water and stirred for 30 min. The solids were collected by filtration and dried under vacuum to afford the desired product as an orange solid (30 mg, 0.07 mmol, 64%).

HRMS-ESI (m/z) [M+H]+ calcd for $C_{17}H_{15}N_6O_3S_2$: 415.0642, found 415.0638.

Example 19: 2-({6-[(1,3-Benzothiazol-2-yl)amino]-4-cyclopropyl-5-methylpyridazin-3-yl}amino)-1,3-thiazole-4-carboxylic acid

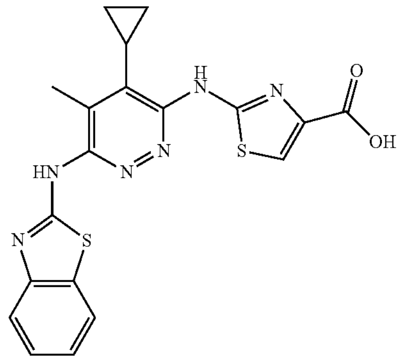 [SMILES: Cc1c(Nc2nc3ccccc3s2)nnc(Nc2nc(C(=O)O)cs2)c1C1CC1]

Step A: ethyl 2-({6-[(1,3-benzothiazol-2-yl)amino]-4-cyclopropyl-5-methylpyridazin-3-yl}amino)-1,3-thiazole-4-carboxylate To an oven-dried microwave vial was added the product from Preparation 9ha (300 mg, 0.95 mmol, 1 eq), ethyl 2-amino-1,3-thiazole-4-carboxylate (245 mg, 1.42 mmol, 1.5 eq), cesium carbonate (463 mg, 1.42 mmol, 1.5 eq), Xantphos (54.8 mg, 0.09 mmol, 0.1 eq) and tris(dibenzylideneacetone)dipalladium(0)(43.4 mg, 0.05 mmol, 0.05 eq). The vial was evacuated and flushed with nitrogen (×3), and then alpha,alpha,alpha-trifluorotoluene (10 mL) was added. The mixture was sparged with nitrogen (5 mins) then heated at 180° C. for 1 h under microwave irradiation. The reaction mixture was concentrated in vacuo and purification by reverse phase automated flash chromatography (CombiFlash Rf, C18 26 g RediSep column) eluting with a gradient of 5-95% acetonitrile (with 0.08% formic acid modifier) in water (with 0.08% formic acid modifier) afforded the desired product as a bright yellow solid (67 mg, 0.15 mmol, 16%).

LC/MS ($C_{21}H_{20}N_6O_2S_2$) 453 $[M+H]^+$; RT 1.34 (LCMS-V-B1)

$^1H$ NMR (400 MHz, DMSO-d6) δ 11.37 (br s, 1H), 10.56 (s, 1H), 7.96 (s, 1H), 7.89 (d, J=7.7 Hz, 1H), 7.51 (s, 1H), 7.38 (td, J=7.7, 1.3 Hz, 1H), 7.20 (t, 1H), 4.30 (q, J=7.1 Hz, 2H), 2.49 (s, 3H), 1.90 (q, 1H), 1.31 (t, 3H), 1.27-1.21 (m, 2H), 0.59 (dt, J=5.9, 3.1 Hz, 2H).

Step B: 2-({6-[(1,3-benzothiazol-2-yl)amino]-4-cyclopropyl-5-methylpyridazin-3-yl}amino)-1,3-thiazole-4-carboxylic acid To a solution of the product from Step A (67 mg, 0.15 mmol, 1 eq) in 1,4-dioxane (5 mL) was added a 2M aqueous lithium hydroxide (0.15 mL, 0.3 mmol, 2 eq) and the mixture was heated at reflux for 1 h. The reaction was concentrated in vacuo, then taken-up in water and the pH was adjusted to 6 with 1N aqueous hydrochloric acid, before re-concentrating in vacuo. Trituration with 5:1 isopropanol/water (5 mL) gave a solid that was collected by filtration, washed with isopropanol and dried under vacuum to afford the desired product as a yellow solid (28 mg, 0.07 mmol, 45%).

HRMS-ESI (m/z) [M+H]+ calcd for $C_{19}H_{17}N_6O_2S_2$: 425.0849, found 425.0857.

Example 20: 2-({6-[(1,3-Benzothiazol-2-yl)amino]-5-cyclopropyl-4-methylpyridazin-3-yl}amino)-1,3-thiazole-4-carboxylic acid

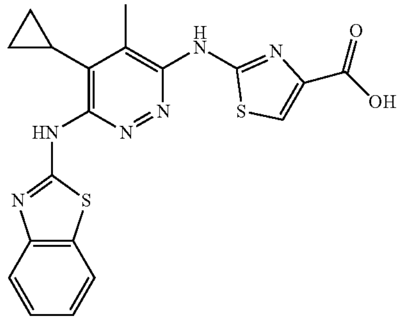 [SMILES: Cc1c(Nc2nc(C(=O)O)cs2)nnc(Nc2nc3ccccc3s2)c1C1CC1]

Step A: ethyl 2-({6-[(1,3-benzothiazol-2-yl)amino]-5-cyclopropyl-4-methylpyridazin-3-yl}amino)-1,3-thiazole-4-carboxylate To an oven-dried microwave vial was added the product from Preparation 9hb (219 mg, 0.69 mmol, 1 eq), ethyl 2-amino-1,3-thiazole-4-carboxylate (179 mg, 1.04 mmol, 1.5 eq), cesium carbonate (338 mg, 1.04 mmol, 1.5 eq), Xantphos (40 mg, 0.07 mmol, 0.1 eq) and tris(dibenzylideneacetone)dipalladium(0)(31.7 mg, 0.03 mmol, 0.05 eq). The vial was evacuated and flushed with nitrogen (×3), and then alpha,alpha,alpha-trifluorotoluene (15 mL) was added. The mixture was sparged with nitrogen (5 mins) then heated at 170° C. for 1 h under microwave irradiation. The reaction mixture was concentrated in vacuo and purification by reverse phase automated flash chromatography (CombiFlash Rf, C18 24 g RediSep column) eluting with a gradient of 5-95% acetonitrile (containing 0.08% formic acid) in water (containing 0.08% formic acid) afforded the desired product (54 mg, 0.12 mmol, 17%).

LC/MS ($C_{21}H_{20}N_6O_2S_2$) 453 $[M+H]^+$; RT 1.16 (LCMS-V-B1)

$^1H$ NMR (400 MHz, DMSO-d6) δ 10.86 (br s, 1H), 10.56 (s, 1H), 7.96 (s, 1H), 7.87 (s, 1H), 7.55 (br s, 1H), 7.38 (t, J=7.5 Hz, 1H), 7.20 (t, J=7.5 Hz, 1H), 4.30 (q, J=7.1 Hz, 2H), 2.49 (s, 3H), 1.91 (p, J=7.7 Hz, 1H), 1.33 (t, 3H), 1.27-1.21 (m, 2H), 0.59 (dt, J=5.9, 3.1 Hz, 2H).

Step B: 2-({6-[(1,3-benzothiazol-2-yl)amino]-5-cyclopropyl-4-methylpyridazin-3-yl}amino)-1,3-thiazole-4-carboxylic acid To a solution of the product from Step A (54 mg, 0.12 mmol, 1 eq) in 1,4-dioxane (5 mL) was added 2M aqueous lithium hydroxide (0.24 mL, 0.24 mmol, 2 eq) and the mixture was heated at reflux for 1 h. The reaction was allowed to cool to ambient temperature and concentrated in vacuo. The residue was taken up in water and neutralised to pH 6 with 1M aqueous hydrochloric acid and then concentrated in vacuo. The solid was triturated in 4:1 isopropanol/water and stirred for 30 min. The solids were collected by filtration, washed with cold isopropanol and dried under vacuum to afford the desired product as an orange solid (30 mg, 0.07 mmol, 59%).

HRMS-ESI (m/z) [M+H]+ calcd for $C_{19}H_{17}N_6O_2S_2$: 425.0849, found 425.0853.

Example 21: 2-({6-[(1,3-Benzothiazol-2-yl)amino]-5-methylpyridazin-3-yl}(methyl)amino)-1,3-thiazole-4-carboxylic acid

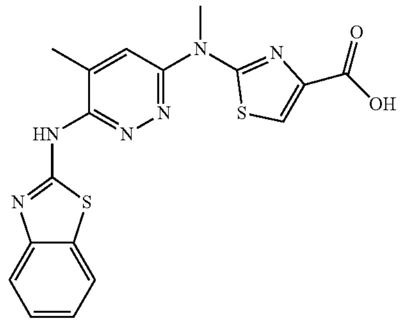 [SMILES: Cc1cc(N(C)c2nc(C(=O)O)cs2)nnc1Nc1nc2ccccc2s1]

Step A: ethyl 2-[(6-chloro-5-methylpyridazin-3-yl)(methyl)amino]-1,3-thiazole-4-carboxylate Sodium hydride (60% dispersion, 240 mg, 6 mmol, 1.18 eq) was added slowly to a solution of 3,6-dichloro-4-methylpyridazine (850 mg, 5.21 mmol, 1.02 eq) and ethyl 2-(methylamino)-1,3-thiazole-4-carboxylate (950 mg 5.1 mmol, 1 eq) in tetrahydrofuran (25 mL) at 0° C. under a nitrogen atmosphere. The mixture was stirred for 1 h at 0° C. and for 18 h at ambient temperature to give a dark brown suspension. Saturated aqueous ammonium chloride solution (75 mL) was added and the mixture extracted with dichloromethane (250 mL). The extracts were washed with water (2×75 mL) and brine (75 mL). The solution was dried (magnesium sulfate) and concentrated in vacuo. Purification by flash column chromatography (100 g silica) eluting with 1% methanol in dichloromethane gave a solid that was triturated with diethyl ether (15 mL), filtered, washed with diethyl ether (2×10 mL) and dried in vacuo to afford the desired product as a pale brown solid (960 mg, 3.07 mmol, 60%).

LC/MS ($C_{12}H_{13}ClN_4O_2S$) 313 $[M+H]^+$; RT 1.17 (LCMS-V-B1)

$^1H$ NMR (400 MHz, DMSO-d6) δ 8.04 (s, 1H), 7.86 (s, 1H), 4.30 (q, J=7.1 Hz, 2H) 3.83 (s, 3H), 2.43 (s, 3H), 1.32 (t, J=7.1 Hz, 3H).

Step B: ethyl 2-({6-[(1,3-benzothiazol-2-yl)amino]-5-methylpyridazin-3-yl}(methyl)amino)-1,3-thiazole-4-carboxylate 2-Aminobenzothiazole (245 mg, 1.63 mmol, 1.16 eq) and the product from Step A (440 mg, 1.41 mmol, 1 eq) were added to a solution of tris(dibenzylideneacetone)dipalladium(0)(64.4 mg, 0.07 mmol, 0.05 eq) and Xantphos (81.4 mg, 0.14 mmol, 0.1 eq) in 1,4-dioxane (20 mL) under a nitrogen atmosphere and the mixture was stirred. N,N-diisopropylethylamine (0.75 mL, 4.22 mmol, 3 eq) was added and the mixture was heated in a sealed tube at 150° C. for 24 h. The solution was allowed to cool to ambient temperature and concentrated in vacuo. Purification by flash column chromatography (50 g silica), eluting with ethyl acetate gave a yellow solid that was triturated with methanol (10 mL), filtered, washed with methanol (15 mL) and dried under vacuum to afford the desired product as a yellow solid (315 mg, 0.74 mmol, 53%).

LC/MS ($C_{19}H_{18}N_6O_2S_2$) 427 $[M+H]^+$; RT 1.32 (LCMS-V-B1)

$^1H$ NMR (400 MHz, DMSO-d6) δ 11.23 (br s, 1H), 7.97 (s, 1H), 7.91 (br s, 1H), 7.70 (s, 1H), 7.54 (br s, 1H), 7.39 (td, J=7.7, 1.2 Hz, 1H), 7.22 (t, 1H), 4.30 (q, J=7.1 Hz, 2H), 3.82 (s, 3H), 2.46 (s, 3H), 1.32 (t, J=7.1 Hz, 3H).

Step C: 2-({6-[(1,3-benzothiazol-2-yl)amino]-5-methylpyridazin-3-yl}(methyl)amino)-1,3-thiazole-4-carboxylic acid To a solution of the product from Step B (200 mg, 0.47 mmol, 1 eq) in 1,4-dioxane (3 mL) was added lithium hydroxide monohydrate (98.4 mg, 2.34 mmol, 5 eq) and the mixture was stirred at ambient temperature for 3 hr. Water (10 mL) was added and the solution filtered through celite, the solids were washed with water (5 mL) and the combined filtrate acidified with acetic acid to give a pale yellow suspension. The solids were collected by filtration, washed with water (20 mL) and dried under vacuum to afford the desired product as a pale yellow solid (150 mg, 0.34 mmol, 72%).

LC/MS ($C_{17}H_{14}N_6O_2S_2$) 399 $[M+H]^+$; RT 1.1 (LCMS-V-B1)

$^1H$ NMR (400 MHz, DMSO-d6) δ 12.21 (br s, 2H), 7.95-7.84 (m, 2H), 7.71 (s, 1H), 7.54 (d, J=8.0 Hz, 1H), 7.39 (ddd, J=8.2, 7.3, 1.3 Hz, 1H), 7.22 (td, J=7.6, 1.2 Hz, 1H), 3.82 (s, 3H), 2.47 (s, 3H).

Example 22: 2-({6-[(1,3-Benzothiazol-2-yl)amino]-4,5-dimethylpyridazin-3-yl}amino)-5-(3-{4-[3-(dimethylamino)propyl]-2-fluorophenoxy}propyl)-1,3-thiazole-4-carboxylic acid

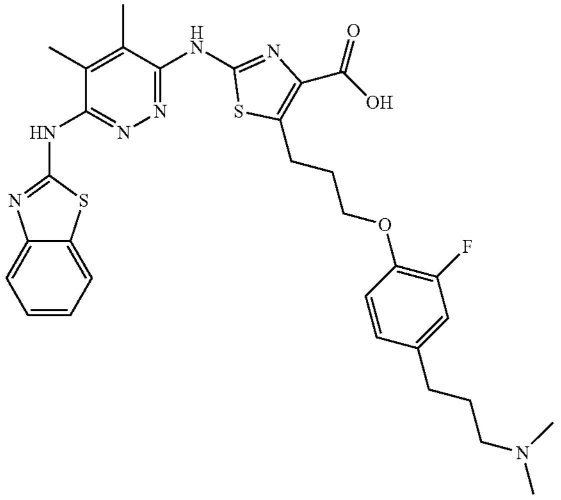 [SMILES: Cc1c(Nc2nc(C(=O)O)c(CCCOc3ccc(CCCN(C)C)cc3F)s2)nnc(Nc2nc3ccccc3s2)c1C]

Step A: ethyl 5-(3-{4-[(1E)-3-(dimethylamino)prop-1-en-1-yl]-2-fluorophenoxy}propyl)-2-acetamido-1,3-thiazole-4-carboxylate Sodium hydride (60% in mineral oil)(1.61 g, 40.3 mmol, 2.34 eq) was added to a stirred solution of the product from Preparation 6b (4.65 g, 24.1 mmol, 1.4 eq) in dimethylformamide (70 mL). The reaction was stirred at ambient temperature for 30 min then cooled in an ice bath and a solution of the product from Preparation 3u, Step C (6.57 g, 17.2 mmol, 1 eq) in dimethylformamide (30 mL) was added slowly. After 40 min the reaction was allowed to warm to ambient temperature and stirred for 5 h. The mixture was cooled, acidified with 2N aqueous HCl and the organics extracted with ethyl acetate, then 3:1 dichloromethane/isopropanol. The combined organics were dried (magnesium sulfate) and the solvent removed in vacuo. Purification by automated flash column chromatography (CombiFlash Rf, 80 g RediSep™ silica cartridge) eluting with a gradient of 0-10% methanol in dichloromethane afforded the desired product as a brown foam (2.26 g, 5.69 mmol, 33%) that was used in subsequent steps without further purification. A sample of the material was further purified by preparative HPLC (method HPLC-V-A1) to generate analytical data.

LC/MS ($C_{22}H_{28}FN_3O_4S$) 450 $[M+H]^+$; RT 0.75 (LCMS-V-B1)

$^1$H NMR (400 MHz, DMSO-d6) δ 7.25-7.08 (m, 2H), 7.05 (dd, J=8.5, 2.0 Hz, 1H), 6.45 (dt, J=12.0, 1.9 Hz, 1H), 5.69 (dt, J=12.4, 6.4 Hz, 1H), 4.23 (qd, J=7.1, 2.2 Hz, 2H), 4.09 (t, 2H), 3.27 (t, J=7.5 Hz, 2H), 3.11 (dd, J=6.4, 1.9 Hz, 2H), 2.16 (s, 6H), 2.12 (s, 3H), 2.11-2.06 (m, 2H), 1.27 (t, J=7.1 Hz, 3H).

Step B: ethyl 2-amino-5-(3-{4-[(1E)-3-(dimethylamino)prop-1-en-1-yl]-2-fluorophenoxy}propyl)-1,3-thiazole-4-carboxylate To a solution of the product from Step A (2.25 g, 4.99 mmol, 1 eq) in ethanol (40 mL) was added hydrochloric acid (4M in 1,4-dioxane; 12.5 mL, 49.9 mmol, 10 eq) and the mixture was heated at 60° C. for 18 h. The reaction was allowed to cool to ambient temperature and the solvent removed in vacuo. Purification by automated flash column chromatography (CombiFlash Rf, 40 g RediSep™ silica cartridge) eluting with a gradient of 0-20% methanol in dichloromethane afforded a crude product. This was dissolved in methanol and loaded onto a methanol-wet SCX-2 cartridge (10 g). Elution with methanol followed by 3.5N methanolic ammonia, then evaporation afforded the desired product as a brown gum (2.07 g, 5.07 mmol, 100%).

LC/MS ($C_{20}H_{26}FN_3O_3S$) 408 $[M+H]^+$; RT 0.71 (LCMS-V-B1)

$^1$H NMR (400 MHz, DMSO-d6) δ 7.34 (br s, 2H), 7.26-7.15 (m, 3H), 6.74 (d, J=11.9 Hz, 1H), 5.80 (dt, J=12.5, 6.5 Hz, 1H), 4.16 (q, 2H), 4.09 (t, 2H), 4.03 (dd, 2H), 3.14 (t, J=7.5 Hz, 2H), 2.73 (s, 6H), 2.02 (p, J=6.3 Hz, 2H), 1.24 (t, 3H).

Step C: ethyl 2-amino-5-(3-{4-[3-(dimethylamino)propyl]-2-fluorophenoxy}propyl)-1,3-thiazole-4-carboxylate A solution of the product from Step B (0.84 g, 2.06 mmol, 1 eq) in 1:1 ethyl acetate/methanol (40 mL) was added to a flask containing platinum(IV) oxide hydrate, (spatula tip) under a nitrogen atmosphere. The vessel was evacuated and back-filled with nitrogen (×3), then evacuated, placed under an atmosphere of hydrogen, and shaken at ambient temperature for 72 h. The mixture was filtered through celite (10 g pre-packed cartridge), eluted with methanol, and the solvent was removed in vacuo. Purification by automated flash column chromatography (CombiFlash Rf, 40 g RediSep™ silica cartridge) eluting with a gradient of 0-20% methanol (containing 20% ammonia) in dichloromethane afforded the desired product as a yellow gum (519 mg, 1.27 mmol, 53%).

LC/MS ($C_{20}H_{28}FN_3O_3S$) 410 $[M+H]^+$; RT 0.70 (LCMS-V-B1)

$^1$H NMR (400 MHz, DMSO-d6) δ 7.15-7.03 (m, 2H), 7.02 (s, 2H), 6.95 (dt, J=8.3, 1.3 Hz, 1H), 4.16 (q, J=7.1 Hz, 2H), 4.02 (t, J=6.2 Hz, 2H), 3.12 (dd, J=8.2, 6.8 Hz, 2H), 2.63-2.57 (m, 2H), 2.54 (t, 2H), 2.44 (s, 6H), 2.0.5-1.93 (m, 2H), 1.79 (p, J=7.9 Hz, 2H), 1.24 (t, J=7.1 Hz, 3H).

Step D: ethyl 2-({6-[(1,3-benzothiazol-2-yl)amino]-4,5-dimethylpyridazin-3-yl}amino)-5-(3-{4-[3-(dimethylamine)propyl]-2-fluorophenoxy}propyl)-1,3-thiazole-4-carboxylate To an oven-dried microwave vial was added the product from Preparation 9a (118 mg, 0.41 mmol, 1 eq), the product from Step C (200 mg, 0.49 mmol, 1.2 eq), cesium carbonate (265 mg, 0.81 mmol, 2 eq), Xantphos (23.6 mg, 0.04 mmol, 0.1 eq) and tris(dibenzylideneacetone)dipalladium(0)(18.6 mg, 0.02 mmol, 0.05 eq). The vial was evacuated and flushed with nitrogen (×3), and then alpha,alpha,alpha-trifluorotoluene (4 mL) was added. The mixture was sparged with nitrogen (5 mins) then heated at 170° C. for 1 h under microwave irradiation. The mixture was partitioned between ethyl acetate and water, and the organic phase dried (magnesium sulfate) and concentrated in vacuo. Purification by reverse phase automated flash chromatography (CombiFlash Rf, C18 13 g RediSep column) eluting with 5-95% acetonitrile in water afforded the desired product as a yellow foam (36 mg, 0.05 mmol, 13%).

LC/MS ($C_{33}H_{38}FN_7O_3S_2$) 664 $[M+H]^+$; RT 1.01 (LCMS-V-B1)

$^1$H NMR (400 MHz, DMSO-d6) δ 10.71 (br s, 1H), 7.81 (d, J=7.8 Hz, 1H), 7.44 (d, J=8.0 Hz, 1H), 7.30 (td, 1H), 7.13 (td, J=7.5, 1.1 Hz, 1H), 7.05-6.95 (m, 2H), 6.91-6.82 (m, 1H), 4.20 (q, J=7.1 Hz, 2H), 4.03 (t, J=6.2 Hz, 2H), 3.28-3.19 (m, 4H), 2.30 (s, 3H), 2.28 (s, 3H), 2.15-2.02 (m, 4H), 2.04 (s, 6H), 1.57 (p, J=7.4 Hz, 2H), 1.23 (t, J=7.1 Hz, 3H).

Step E: 2-({6-[(1,3-benzothiazol-2-yl)amino]-4,5-dimethylpyridazin-3-yl}amino)-5-(3-{4-[3-(dimethylamino)propyl]-2-fluorophenoxy}propyl)-1,3-thiazole-4-carboxylic acid To a solution of the product from Step D (57.1 mg, 0.09 mmol, 1 eq) in 1,4-dioxane (5 mL) was added lithium hydroxide monohydrate (14.4 mg, 0.34 mmol, 4 eq) and the mixture was heated at reflux for 5.5 h. The mixture was allowed to cool to ambient temperature and the solvent removed in vacuo. The residue was triturated in water and solids were collected by filtration. The solids were further triturated with diethyl ether, then collected by filtration and dried under vacuum to afford the desired product as a brown solid (19.1 mg, 0.03 mmol, 35%).

HRMS-ESI (m/z) [M+H]+ calcd for $C_{31}H_{35}FN_7O_3S_2$: 636.2221, found 636.2224.

Example 23: 2-[[1-(1,3-Benzothiazol-2-ylamino)-6,7-dihydro-5H-cyclopenta[d]pyridazin-4-yl]amino]thiazole-4-carboxylic acid

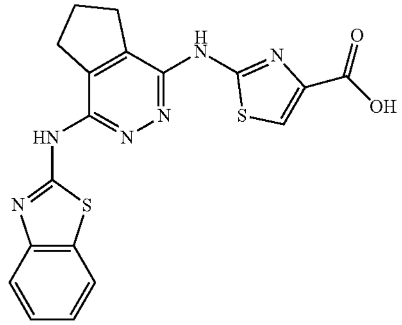 [SMILES: O=C(O)c1csc(Nc2nnc(Nc3nc4ccccc4s3)c3c2CCC3)n1]

Step A: 1,4-dibromo-6,7-dihydro-5H-cyclopenta[d]pyridazine

The mixture of 1.86 g of 2,3,6,7-tetrahydro-1H-cyclopenta[d]pyridazine-1,4(5H)-dione (12.3 mmol, 1 eq.) and 10.55 g (36.8 mmol, 3 eq.) of $POBr_3$ in 50 mL of 1,2-dichloroethane was kept at reflux for 3 h. After cooling to rt and concentration, the residue was treated with 100 g of ice, the pH was set to 7 by the addition of cc. $NaHCO_3$, and the solid precipitation was filtered off to give 1.88 g (55%) of the desired product.

Step B: 4-bromo-6,7-dihydro-5H-cyclopenta[d]pyridazin-1-amine

The mixture of 1.88 g of the product from Step A (6.8 mmol) in 25 mL of a 30% solution of $NH_3$ in water was kept at 130° C. for 18 h. After concentration, the residue was taken up in EtOAc, washed with a 10% solution of NaOH, dried on $MgSO_4$, filtered, and concentrated to give 1.28 g (88%) of the desired product.

LC-MS-ESI (m/z): $[M+H]^+$ calcd for $C_7H_9BrN_3$: 214, 216, found: 214, 216.

Step C: N-(4-bromo-6,7-dihydro-5H-cyclopenta[d]pyridazin-1-yl)-1,3-benzothiazol-2-amine The mixture of 214 mg of the product from Step B (1 mmol, 1 eq.), 321 mg of 2-bromo-1,3-benzothiazole (1.50 mmol, 1.5 eq.), 160 mg of sodium hydride (60% suspension)(4 mmol, 4 eq.) in 25 mL of 1,4-dioxane was kept at reflux for 1 h. After cooling and quenching with methanol, the mixture was concentrated, treated with water, filtered off and dried. The solid was triturated with EtOAc and dried to give 275 mg (79%) of the desired product.

LC-MS-ESI (m/z): $[M+H]^+$ calcd for $C_{14}H_{12}BrN_4S$: 347, 349, found: 347, 349.

Step D: ethyl 2-[[1-(1,3-benzothiazol-2-ylamino)-6,7-dihydro-5H-cyclopenta[d]pyridazin-4-yl]amino]thiazole-4-carboxylate The mixture of 270 mg of the product from Step C (0.778 mmol, 1 eq.), 134 mg of ethyl 2-aminothiazole-4-carboxylate (0.78 mmol, 1 eq.), 29 mg of $Pd_2(dba)_3$ (0.032 mmol, 0.04 eq.), 45 mg of Xantphos (0.078 mmol, 0.1 eq.), and 507 mg of $C_2CO_3$ (1.56 mmol, 2 eq.) in 10 mL of trifluoromethylbenzene was kept at 200° C. for 0.5 h. The reaction mixture was concentrated and purified by preparative HPLC to give 97 mg (28%) of the desired product.

LC-MS-ESI (m/z): $[M+H]^+$ calcd for $C_{20}H_{19}N_6O_2S_2$: 439.5, found: 439.

Step E: 2-[[1-(1,3-benzothiazol-2-ylamino)-6,7-dihydro-5H-cyclopenta[d]pyridazin-4-yl]amino]thiazole-4-carboxylic acid The mixture of 90 mg of the product from Step D (0.22 mmol, 1 eq.), 18 mg $LiOH \times H_2O$ (0.43 mmol, 2 eq.) of, and 13 drops of water in 5 mL of 1,4-dioxane was kept at reflux for 2 h. The reaction mixture was concentrated and purified by preparative HPLC to give 54 mg (64%) of the desired product.

HRMS-ESI (m/z): [M+H]+ calcd for $C_{18}H_{15}N_6O_2S_2$: 411.0697, found: 411.0685.

Example 24: 6-[[4-(1,3-Benzothiazol-2-ylamino)-5,6,7,8-tetrahydrophthalazin-1-yl]amino]pyridine-2-carboxylic acid

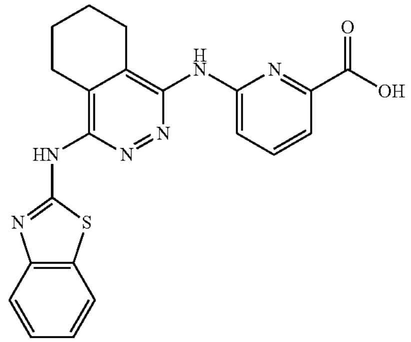 [SMILES: O=C(O)c1cccc(Nc2nnc(Nc3nc4ccccc4s3)c3c2CCCC3)n1]

Step A: ethyl 6-[[4-(1,3-benzothiazol-2-ylamino)-5,6,7,8-tetrahydrophthalazin-1-yl]amino]pyridine-2-carboxylate The mixture of 245 mg of Example 17, Step B (0.68 mmol, 1 eq.), 113 mg of ethyl 6-aminopyridine-2-carboxylate (0.68 mmol, 1 eq.), 25 mg of $Pd_2(dba)_3$ (0.027 mmol, 0.04 eq.), 40 mg of Xantphos (0.069 mmol, 0.1 eq.), and 443 mg of $Cs_2CO_3$ (1.36 mmol, 2 eq.) in 10 mL of trifluoromethylbenzene was kept at 200° C. for 1.5 h. The reaction mixture was concentrated and purified by preparative HPLC to give 45 mg (15%) of the desired product.

LC-MS-ESI (m/z): $[M+H]^+$ calcd for $C_{23}H_{23}N_6O_2S$: 447, found: 447.

Step B: 6-[[4-(1,3-benzothiazol-2-ylamino)-5,6,7,8-tetrahydrophthalazin-1-yl]amino]pyridine-2-carboxylic acid The mixture of 45 mg of the product from Step A (0.11 mmol, 1 eq.), 8.5 mg or $LiOH \times H_2O$ (0.20 mmol, 2 eq.), and 10 drops of water in 10 mL of 1,4-dioxane was kept at reflux for 2 h. The reaction mixture was concentrated and purified by preparative HPLC to give 21 mg (50%) of the desired product.

HRMS-ESI (m/z): [M+H]+ calcd for $C_{21}H_{19}N_6O_2S$: 419.1290, found: 419.1294.

Example 25: 6-[[4-(1,3-Benzothiazol-2-ylamino)-6,7-dihydro-5H-cyclopenta[d]pyridazin-1-yl]amino]pyridine-2-carboxylic add

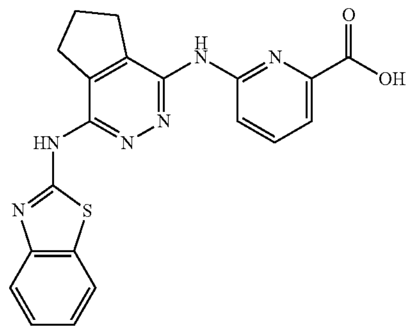 [SMILES: O=C(O)c1cccc(Nc2nnc(Nc3nc4ccccc4s3)c3c2CCC3)n1]

Step A: 6-[[4-(1,3-benzothiazol-2-ylamino)-6,7-dihydro-5H-cyclopenta[d]pyridazin-1-yl]amino]pyridine-2-carboxylate The mixture of 290 mg of Example 23, Step C (0.84 mmol, 1 eq.), 139 mg of ethyl 6-aminopyridine-2-carboxylate (0.84 mmol, 1 eq.), 31 mg of $Pd_2(dba)_3$ (0.034 mmol, 0.04 eq.), 48 mg (0.083 mmol, 0.1 eq.) of Xantphos, and 545 mg of $Cs_2CO_3$ (1.67 mmol, 2 eq.) in 10 mL of trifluoromethylbenzene was kept at 200° C. for 1.5 h. The reaction mixture was concentrated and purified by preparative HPLC to give 70 mg (19.4%) of the desired product.

LC-MS-ESI (m/z): $[M+H]^+$ calcd for $C_{22}H_{21}N_6O_2S$: 433.5, found: 433 and 431 $[M-H]^-$.

Step B: 6-[[4-(1,3-benzothiazol-2-ylamino)-6,7-dihydro-5H-cyclopenta[d]pyridazin-1-yl]amino]pyridine-2-carboxylic acid The mixture of 70 mg of the product from Step A (0.16 mmol, 1 eq.), 14 mg of $LiOH \times H_2O$ (0.33 mmol, 2 eq.), and 10 drops of water in 10 mL of 1,4-dioxane was kept at reflux for 2 h. The reaction mixture was concentrated and purified by preparative HPLC to give 24 mg (31%) of the desired product.

HRMS-ESI (m/z): [M+H]+ calcd for $C_{20}H_{17}N_6O_2S$: 405.1134, found: 405.1123.

Example 26: 2-({6-[(1,3-Benzothiazol-2-yl)amino]-4,5-dimethylpyridazin-3-yl}(methyl)amino)-1,3-thiazole-4-carboxylic acid

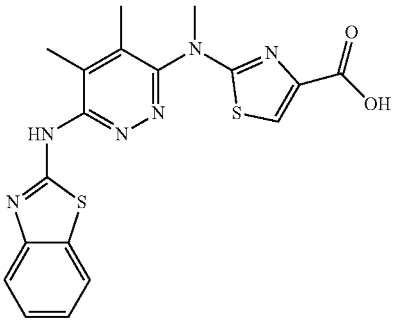 [SMILES: Cc1c(Nc2nc3ccccc3s2)nnc(N(C)c2nc(C(=O)O)cs2)c1C]

Step A: ethyl 2-[(6-chloro-4,5-dimethylpyridazin-3-yl)(methyl)amino]-1,3-thiazole-4-carboxylate Sodium hydride (60% dispersion, 250 mg, 6.25 mmol, 1.16 eq) was added slowly to a solution of 3,6-dichloro-4,5-dimethylpyridazine (950 mg, 5.37 mmol, 1 eq) and ethyl 2-(methylamino)-1,3-thiazole-4-carboxylate (1.2 g, 6.44 mmol, 1.2 eq) in 1,4-dioxane (20 mL) at 0° C. under a nitrogen atmosphere. The mixture was stirred for 1 h at ambient temperature, then at 60° C. for 2 h. Saturated aqueous ammonium chloride solution (75 mL) was added and the mixture extracted with ethyl acetate (150 mL). The organic extract was washed with water (2×75 mL), brine (75 mL), dried (magnesium sulfate) and concentrated in vacuo. Purification by column chromatography (100 g silica) eluting with ethyl acetate afforded the desired product as a brown gum (715 mg, 2.19 mmol, 41%).

LC/MS ($C_{13}H_{15}ClN_4O_2S$) 327 $[M+H]^+$; RT 1.09 (LCMS-V-B1)

$^1H$ NMR (400 MHz, $CDCl_3$) δ 7.56 (s, 1H), 4.34 (q, J=7.2 Hz, 2H), 3.66 (s, 3H), 2.43 (s, 3H), 2.23 (s, 3H), 1.36 (t, J=7.2 Hz, 3H).

Step B: ethyl 2-({6-[(1,3-benzothiazol-2-yl)amino]-4,5-dimethylpyridazin-3-yl}(methyl)amino)-1,3-thiazole-1-carboxylate 2-Aminobenzothiazole (250 mg, 1.66 mmol, 1.21 eq) and the product from Step A (500 mg, 1.38 mmol, 1 eq) were added to a solution of tris(dibenzylideneacetone)dipalladium(0)(63.1 mg, 0.07 mmol, 0.05 eq) and Xantphos (79.7 mg, 0.14 mmol, 0.1 eq) in 1,4-dioxane (20 mL) under a nitrogen atmosphere and the mixture stirred. N,N-diisopropylethylamine (0.75 mL, 4.13 mmol, 3 eq) was added and the mixture was heated in a sealed tube at 150° C. for 24 h. The solution was allowed to cool to ambient temperature and concentrated in vacuo. Purification by flash column chromatography (50 g silica) eluting with 1% methanol in dichloromethane gave a dark yellow gum that was triturated with diethyl ether (15 mL), filtered, washed with diethyl ether (15 mL) and dried under vacuum to afford the desired product as a pale yellow solid (365 mg, 0.83 mmol, 60%).

LC/MS ($C_{20}H_{20}N_6O_2S_2$) 441 $[M+H]^+$; RT 1.26 (LCMS-V-B1)

$^1H$ NMR (400 MHz, DMSO-d6) δ 11.22 (br s, 1H), 7.87 (br s, 1H), 7.76 (s, 1H), 7.56 (br s, 1H), 7.40 (t, J=7.5 Hz,

1H), 7.23 (t, J=7.7 Hz, 1H), 4.25 (q, J=7.1 Hz, 2H), 3.49 (s, 3H), 2.41 (s, 3H), 2.19 (s, 3H), 1.28 (t, J=7.1 Hz, 3H).

Step C: 2-({6-[(1,3-benzothiazol-2-yl)amino]-4,5-dimethylpyridazin-3-yl}(methyl)amino)-1,3-thiazole-4-carboxylic acid To a solution of the product from Step B (200 mg, 0.45 mmol, 1 eq) in 1:3 water/1,4-dioxane (4 mL) was added lithium hydroxide monohydrate (95.3 mg, 2.27 mmol, 5 eq) and the mixture was stirred at ambient temperature for 18 h. Water (10 mL) was added and the solution filtered through celite, the solids were washed with water (5 mL) and the combined filtrate acidified with acetic acid to give a pale yellow suspension. Solids were collected by filtration, washed with water (20 mL) and dried under vacuum to afford the desired product as a pale yellow solid (150 mg, 0.36 mmol, 80%).

HRMS-ESI (m/z) [M−H]− calcd for $C_{18}H_{15}N_6O_2S_2$: 411.0703, found 411.0689.

Example 27: 2-({6-[(1,3-Benzothiazol-2-yl)amino]-5-(hydroxymethyl)-4-methylpyridazin-3-yl}amino)-1,3-thiazole-4-carboxylic acid

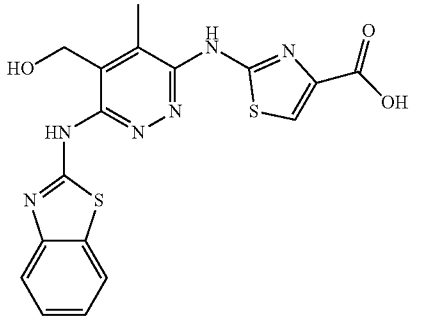 [SMILES: Cc1c(Nc2nc(C(=O)O)cs2)nnc(Nc2nc3ccccc3s2)c1CO]

Step A: ethyl 2-({6-[(1,3-benzothiazol-2yl)amino]-5-(methoxymethyl)-4-methylpyridazin-3-yl}amino)-1,3-thiazole-4-carboxylate To an oven-dried microwave vial was added the product from Preparation 9jb (169 mg, 0.53 mmol, 1 eq), ethyl 2-amino-1,3-thiazole-4-carboxylate (109 mg, 0.63 mmol, 1.2 eq), cesium carbonate (240 mg, 11.74 mmol, 1.4 eq), Xantphos (30.5 mg, 0.05 mmol, 0.1 eq) and tris(dibenzylideneacetone)dipalladium(0)(24.1 mg, 0.03 mmol, 0.05 eq). The vessel was evacuated and flushed with nitrogen (×3), and then alpha,alpha,alpha-trifluorotoluene (10 mL) was added. The mixture was sparged with nitrogen (10 mins) then heated at 180° C. for 1 h under microwave irradiation. The mixture was concentrated in vacuo and purification by automated flash column chromatography (CombiFlash Rf, 12 g RediSep™ silica cartridge) eluting with a gradient of 0-5% methanol in dichloromethane afforded the desired product (138 mg, 0.30 mmol, 57%).

LC/MS ($C_{20}H_{20}N_6O_3S_2$) 457 [M+H]$^+$; RT 1.17 (LCMS-V-B1)

$^1$H NMR (400 MHz, DMSO-d6) δ 12.25 (br s, 1H), 11.07 (br s, 1H), 10.63 (br s, 1H), 7.96 (s, 1H), 7.87 (s, 1H), 7.49 (br s, 1H), 7.38 (t, J=7.5 Hz, 1H), 7.20 (t, 1H), 4.78 (s, 2H), 4.30 (q, J=7.1 Hz, 2H), 3.38 (s, 3H), 2.43 (s, 3H), 1.33 (t, J=7.1 Hz, 3H).

Step B: ethyl 2-({6-[(1,3-benzothiazol-2-yl)amino]-5-(hydroxymethyl)-4-methylpyridazin-3-yl}amino)-1,3-thiazole-4-carboxylate To a solution of the product from Step A (55 mg, 0.12 mmol, 1 eq) in dichloromethane (2 mL) was added boron tribromide (0.6 mL, 1 M, 0.6 mmol, 5 eq) at 0° C. and the mixture was stirred at ambient temperature for 1 h. The reaction was quenched with methanol and concentrated in vacuo. The solid was taken-up in methanol and refluxed for 30 min then allowed to cool to ambient temperature. Purification by reverse phase automated flash column chromatography (CombiFlash Rf, C18 4.3 g RediSep column) eluting with a gradient of 5-95% acetonitrile afforded a crude product (53 mg) that was taken through to the next step without further purification.

Step C: 2-({6-[(1,3-benzothiazol-2-yl)amino]-5-(hydroxymethyl)-4-methylpyridazin-3-yl}amino)-1,3-thiazole-4-carboxylic acid To a solution of the product from Step B (53.3 mg, 0.12 mmol, 1 eq) in 1,4-dioxane (5 mL) was added 2M aqueous lithium hydroxide (0.24 mL, 0.24 mmol, 2 eq) and the mixture was heated at reflux for 1 h. The reaction was allowed to cool to ambient temperature and concentrated in vacuo. The residue was taken up in minimal water, acidified to pH 6 with 1M aqueous hydrochloric acid and allowed to stir for 10 mins. Solvent was removed in vacuo and the residue was triturated with 5:1 isopropanol/water. The suspension was stirred for 30 min then the solid was collected by filtration, washed with isopropanol and dried under vacuum to afford the desired product as a brown solid (16 mg, 0.04 mmol, 32%).

HRMS-ESI (m/z) [M−H]− calcd for $C_{17}H_{13}N_6O_3S_2$: 413.0496, found 413.0499.

Example 28: 2-({6-[(1,3-Benzothiazol-2-yl)amino]-5-(methoxymethyl)-4-methylpyridazin-3-yl}amino)-1,3-thiazole-4-carboxylic acid

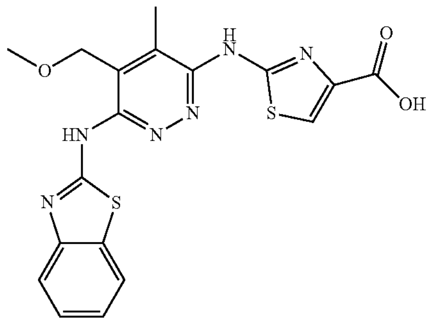 [SMILES: COCc1c(Nc2nc3ccccc3s2)nnc(Nc2nc(C(=O)O)cs2)c1C]

To a solution of the product from Example 27, Step A (59 mg, 0.13 mmol, 1 eq) in 1,4-dioxane (5 mL) was added 2M aqueous lithium hydroxide (0.26 mL, 0.26 mmol, 2 eq) and the mixture was heated at reflux for 1 h. The mixture was allowed to cool to ambient temperature and concentrated in vacuo. The residue was taken up in minimal water, acidified to pH 6 with 1M aqueous hydrochloric acid and allowed to stir for 10 mins. Solvent was removed in mom and the residue was triturated with 5:1 isopropanol/water. The suspension was stirred for 30 min then solids were collected by filtration, washed with isopropanol and dried under vacuum to afford the desired product as an orange solid (18.5 mg, 0.04 mmol, 33%).

HRMS-ESI (m/z) [M–H]– calcd for $C_{18}H_{15}N_6O_3S_2$: 427.0653, found 427.0650.

Example 29: 2-({6-[(1,3-Benzothiazol-2-yl)amino]-4-(methoxymethyl)-5-methylpyridazin-3-yl}amino)-1,3-thiazole-4-carboxylic acid

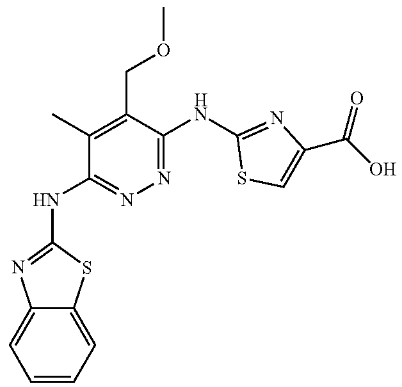 [SMILES: COCc1c(Nc2nc(C(=O)O)cs2)nnc(Nc2nc3ccccc3s2)c1C]

Step A: methyl 2-({6-[(1,3-benzothiazol-2-yl)amino]-4-(methoxymethyl)-5-methylpyridazin-3-yl}amino)-1,3-thiazole-1-carboxylate To an oven-dried microwave vial was added the product from Preparation 9ja (85 mg, 0.26 mmol, 1 eq), ethyl 2-amino-1,3-thiazole-4-carboxylate (59.3 mg, 0.34 mmol, 1.3 eq), cesium carbonate (121 mg, 0.37 mmol, 1.4 eq), Xantphos (7.67 mg, 0.01 mmol, 0.05 eq) and tris(dibenzylideneacetone)dipalladium(0)(24.3 mg, 0.03 mmol, 0.1 eq). The vessel was evacuated and flushed with nitrogen (×3), and then alpha,alpha,alpha-trifluorotoluene (10 mL) was added. The mixture was sparged with nitrogen (10 mins) then heated at 180° C. for 1 h under microwave irradiation. The mixture was concentrated in vacuo and purification by automated flash column chromatography (CombiFlash Rf, 12 g RediSep™ silica cartridge) eluting with a gradient of 0-5% methanol in dichloromethane afforded the desired product as an orange glassy solid (82.5 mg, 0.18 mmol, 68%).

LC/MS ($C_{19}H_{18}N_6O_3S_2$) 443 $[M+H]^+$; RT 1.26 (LCMS-V-B1)

$^1$H NMR (400 MHz, DMSO-d6) δ 10.78 (br s, 1H), 7.98 (s, 1H), 7.42-7.34 (m, 2H), 7.25-7.14 (m, 2H), 4.77 (s, 2H), 3.83 (s, 3H), 3.39 (s, 3H), 2.44 (s, 3H).

Step B: 2-({6-[(1,3-benzothiazol-2-yl)amino]-4-(methoxymethyl)-5-methylpyridazin-3-yl}amino)-1,3-thiazole-4-carboxylic acid To a solution of the product from Step A (82.5 mg, 0.18 mmol, 1 eq) in 1,4-dioxane (5 mL) was added 2M aqueous lithium hydroxide (0.18 mL, 0.36 mmol, 2 eq) and the mixture was heated at reflux for 1 h. The reaction was allowed to cool to ambient temperature and concentrated in vacuo. The residue was taken up in minimal water, acidified to pH 6 with 1M aqueous hydrochloric acid and allowed to stir for 10 mins. The solvent was removed in vacuo and the residue was triturated with 5:1 isopropanol/water. The solids were collected by filtration, washed with isopropanol (2×4 mL) and dried in vacuo. Purification by reverse phase HPLC (method HPLC-V-A2) afforded the desired product as a yellow solid (22 mg, 0.05 mmol, 28%).

HRMS-ESI (m/z) [M+H]+ calcd for $C_{18}H_{17}N_6O_3S_2$: 429.0798, found 429.0800.

Example 30: 2-({6-[(1,3-Benzothiazol-2-yl)amino]-4-(ethoxymethyl)-5-methylpyridazin-3-yl}amino)-1,3-thiazole-4-carboxylic acid

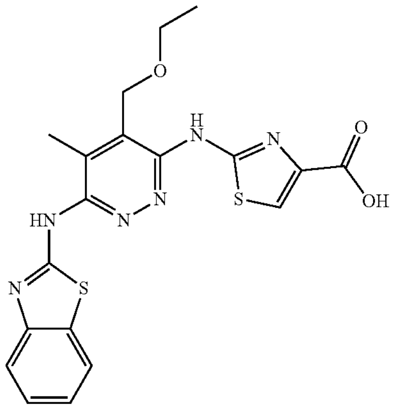 [SMILES: CCOCc1c(Nc2nc(C(=O)O)cs2)nnc(Nc2nc3ccccc3s2)c1C]

Step A: ethyl 2-({6-[(1,3-benzothiazol-2-yl)amino]-4-(ethoxymethyl)-5-methylpyridazin-3-yl}amino)-1,3-thiazole-4-carboxylate To an oven-dried microwave vial was added the product from Preparation 9ka (113 mg, 0.34 mmol, 1 eq), ethyl 2-amino-1,3-thiazole-4-carboxylate (69.7 mg, 0.4 mmol, 1.2 eq), cesium carbonate (154 mg, 0.47 mmol, 1.4 eq), Xantphos (19.5 mg, (1.03 mmol, 0.1 eq) and tris(dibenzylideneacetone)dipalladium(0)(15.5 mg, 0.02 mmol, 0.05 eq). The vessel was evacuated and flushed with nitrogen (×3), and then alpha,alpha,alpha-trifluorotoluene (7 mL) was added. The mixture was sparged with nitrogen (10 mins) then heated at 180° C. for 1 h under microwave irradiation. The mixture was concentrated in vacuo and purification by automated flash column chromatography (CombiFlash Rf, 24 g RediSep™ silica cartridge) eluting with a gradient of 0-100% ethyl acetate in iso-heptane to afford the desired product as (47 mg, 0.1 mmol, 30%).

LC/MS ($C_{21}H_{22}N_6O_3S_2$) 471 $[M+H]^+$; RT 1.36 (LCMS-V-B1)

$^1$H NMR (400 MHz, $CDCl_3$) δ 7.82 (s, 1H), 7.73 (d, J=35.3 Hz, 3H), 7.43 (t, 1H), 7.28-7.23 (m, 1H), 4.72 (s, 2H), 4.45 (q, J=7.1 Hz, 2H), 3.68 (q, J=7.0 Hz, 2H), 2.47 (s, 3H), 1.45 (t, J=7.1 Hz, 3H), 1.35 (t, J=7.0 Hz, 3H).

Step B: 2-({6-[(1,3-benzothiazol-2-yl)amino]-4-(ethoxymethyl)-5-methylpyridazin-3-yl}amino)-1,3-thiazole-4-carboxylic acid To a solution of the product from Step A (49 mg, 0.1 mmol, 1 eq) in 1,4-dioxane (5 mL) was added 2M aqueous lithium hydroxide (0.1 mL 0.21 mmol, 2 eq) and the mixture was heated at reflux for 2 h. The mixture was allowed to cool to ambient temperature and concentrated in vacuo. The residue was taken up in minimal water, acidified to pH 6 with 1M aqueous hydrochloric acid and allowed to stir for 10 mins. The sample was triturated with 5:1 isopropanol/water and the solids collected by filtration, washed with isopropanol and dried under vacuum to afford the desired product as a brown solid (23.9 mg, 0.05 mmol, 52%).

HRMS-ESI (m/z) [M−H]− calcd for $C_{19}H_{17}N_6O_3S_2$: 441.0809, found 441.0803.

Example 31: 2-({6-[(1,3-Benzothiazol-2-yl)amino]-5-cyclopropylpyridazin-3-yl}(methyl)amino)-1,3-thiazole-4-carboxylic acid

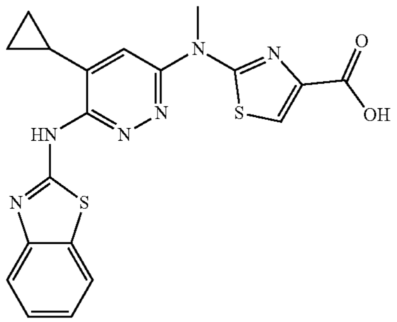 [SMILES: CN(c1cc(C2CC2)c(Nc2nc3ccccc3s2)nn1)c1nc(C(=O)O)cs1]

To a solution of the product from Preparation 11d, Step B (249 mg, 0.55 mmol, 1 eq) in 1,4-dioxane (10 mL) was added 2M aqueous lithium hydroxide (0.55 mL, 1.1 mmol, 2 eq) and the mixture was heated at reflux for 3 h. The reaction was allowed to cool to ambient temperature and concentrated in vacuo. Purification by reverse phase automated flash chromatography (CombiFlash Rf, C18 43 g RediSep column) eluting with a gradient of 5-95% acetonitrile in water afforded the desired product as a yellow powder (33 mg, 0.08 mmol, 14%) [as a lithium salt].

HRMS-ESI (m/z) [M+H]+ calcd for $C_{19}H_{17}N_6O_2S_2$: 425.0849, found 425.0851.

Example 32: 5-{1-[(Adamantan-1-yl)methyl]-5-methyl-1H-pyrazol-4-yl}-2-({6-[(1,3-benzothiazol-2-yl)amino]pyridazin-3-yl}amino)-1,3-thiazole-4-carboxylic acid

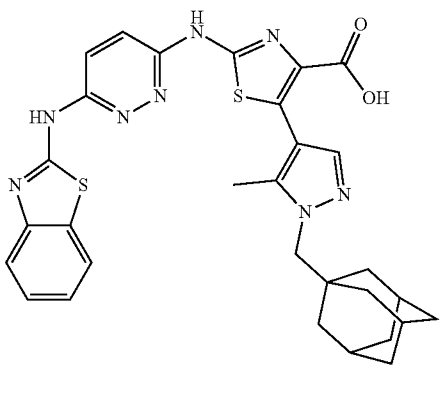 [SMILES: Cc1c(-c2sc(Nc3ccc(Nc4nc5ccccc5s4)nn3)nc2C(=O)O)cnn1CC12CC3CC(CC(C3)C1)C2]

Step A: ethyl 5-[1-[(adamantan-1-yl)methyl]-5-methyl-1H-pyrazol-4-yl]-2-[(6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 11f (64 mg, 0.11 mmol, 1 eq), Preparation 10a (45.0 mg, 0.13 mmol, 1.2 eq) and potassium carbonate (43.7 mg, 0.32 mmol, 3 eq) in a 3:1 mixture of tetrahydrofuran/water (4 mL) was added [1,1'-bis(diphenylphosphino)ferrocene]dichloropalladium (II)(7.71 mg, 0.01 mmol, 0.1 eq). The mixture was sparged with nitrogen (10 min) then heated at 120° C. for 1 h under microwave irradiation. The mixture was diluted with ethyl acetate then successively washed with water and brine. The organic extract was dried (magnesium sulfate) and the solvent removed in vacuo. Purification by automated flash column chromatography (CombiFlash Rf, 12 g RediSep™ silica cartridge) eluting with a gradient of 0-50% ethyl acetate in iso-heptane afforded the desired product as a cream solid (39.2 mg, 0.05 mmol, 49%).

LC/MS ($C_{38}H_{48}N_8O_3SiS_2$) 757 $[M+H]^+$; RT 1.64 (LCMS-V-B1)

Step B: ethyl 5-{1-[(adamantan-1-yl)methyl]-5-methyl-1H-pyrazol-4-yl}-2-({6-[(1,3-benzothiazol-2-yl)amino]pyridazin-3-yl}amino)-1,3-thiazole-4-carboxylate A solution of the product from Step A (39 mg, 0.05 mmol, 1 eq) in dichloromethane (2 mL) was cooled to 0° C. then trifluoroacetic acid (0.3 mL, 4.03 mmol, 78.1 eq) was added. The mixture was allowed to warm to ambient temperature and stirred for 18 h. The mixture was diluted with dichloromethane and washed successively with saturated aqueous sodium bicarbonate, water, and brine. The organic phase was dried (magnesium sulfate) then the solvent removed in vacuo. Purification by automated flash column chromatography (CombiFlash Rf, 12 g RediSep™ silica cartridge) eluting with a gradient of 0-7% methanol in dichloromethane afforded the desired product as a cream solid (10.5 mg, 0.02 mmol, 33%).

LC/MS ($C_{32}H_{34}N_8O_2S_2$) 627 $[M+H]^+$; RT 1.38 (LCMS-V-B1)

$^1$H NMR (400 MHz, DMSO-d6) δ 11.87 (br s, 1H), 11.67 (br s, 1H), 7.93 (d, J=7.8 Hz, 1H), 7.64 (d, 1H), 7.57 (s, 1H), 7.51 (d, J=27.8 Hz, 1H), 7.44-7.33 (m, 2H), 7.21 (t, J=7.6 Hz, 1H), 4.17 (q, J=7.1 Hz, 2H), 3.80 (s, 2H), 2.23 (s, 3H), 1.98 (s, 3H), 1.72-1.56 (m, 12H), 1.20 (t, J=7.1 Hz, 3H).

Step C: 5-{1-[(adamantan-1-yl)methyl]-5-methyl-1H-pyrazol-4-yl}-2-({6-[(1,3-benzothiazol-2-yl)amino]pyridazin-3-yl}amino)-1,3-thiazole-4-carboxylic acid To a solution of the product from Step B (10.5 mg, 0.02 mmol, 1 eq) in 1,4-dioxane (2 mL) was added lithium hydroxide monohydrate (3.51 mg, 0.08 mmol, 5 eq) and the mixture was heated at reflux overnight. The reaction was allowed to cool to ambient temperature and the solvent removed in vacuo. The residue was triturated with water and the solids were collected by filtration and dried tinder vacuum to afford the desired product as a beige solid (7.2 mg, 0.01 mmol, 71%).

HRMS-ESI (m/z) [M+H]+ calcd for $C_{30}H_{31}N_8O_2S_2$: 599.2006, found 599.2037.

Example 33: 5-{1-[(Adamantan-1-yl)methyl]-5-methyl-1H-pyrazol-4-yl}-2-({6-[(1,3-benzothiazol-2-yl)amino]-4,5-dimethylpyridazin-3-yl}amino)-1,3-thiazole-4-carboxylic acid

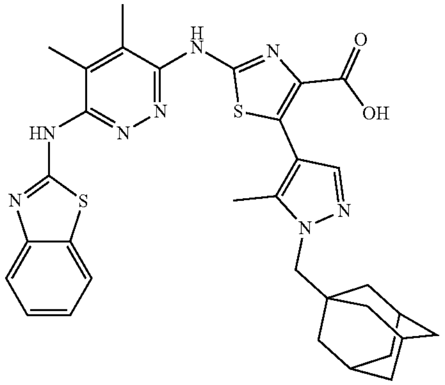 [SMILES: Cc1c(Nc2nc(C(=O)O)c(-c3cnn(CC45CC6CC(CC(C6)C4)C5)c3C)s2)nnc(Nc2nc3ccccc3s2)c1C]

Step A: ethyl 5-{1-[(adamantan-1-yl)methyl]-5-methyl-1H-pyrazol-4-yl}-2-[(4,5-dimethyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a mixture of the product from Preparation 11a (99 mg, 0.16 mmol, 1 eq), the product from Preparation 10a (66.6 mg, 0.19 mmol, 1.2 eq) and potassium carbonate (64.6 mg, 0 mol, 3 eq) in 3:1 tetrahydrofuran/water (4 mL) was added [1,1'-bis(diphenylphosphino)ferrocene]dichloropalladium (II)(11.4 mg, 0.02 mmol, 0.1 eq). The mixture was sparged with nitrogen (10 min) then heated at 120° C. for 1 h under microwave irradiation. The reaction was diluted with ethyl acetate then successively washed with water and brine. The organic extract was dried (magnesium sulfate) then the solvent removed in vacuo. Purification by automated flash column chromatography (CombiFlash Rf, 12 g RediSep™ silica cartridge) eluting with a gradient of 0-50% ethyl acetate in iso-heptane afforded the desired product as a yellow glass (65.5 mg, 0.08 mmol, 54%).

LC/MS ($C_{40}H_{52}N_8O_3SiS_2$) 785 $[M+H]^+$; RT 1.82 (LCMS-V-B1)

$^1H$ NMR (400 MHz, DMSO-d6) δ 10.93 (br s, 1H), 7.78 (d, J=7.6 Hz, 1H), 7.54 (s, 1H), 7.46-7.38 (m, 2H), 7.21 (dt, 1H), 5.84 (s, 2H) 4.17 (q, J=7.1 Hz, 2H), 3.78 (s, 2H), 3.71 (t, 2H), 2.40 (s, 3H), 2.36 (s, 3H), 2.20 (s, 3H), 1.96 (s, 3H), 1.71-1.55 (m, 12H), 1.17 (t, 3H), 0.91 (t, 2H), 0.00 (s, 9H).

Step B: ethyl 5-{1-[(adamantan-1-yl)methyl]-5-methyl-1H-pyrazol-4-yl}-2-({6-[(1,3-benzothiazol-2-yl)amino]-4,5-dimethylpyridazin-3-yl}amino)-1,3-thiazole-4-carboxylate A solution of the product from Step A (65.5 mg, 0.08 mmol, 1 eq) in dichloromethane (4 mL) was cooled in an ice bath then trifluoroacetic acid (0.4 mL, 5.37 mmol, 64 eq) was added. The mixture was allowed to warm to ambient temperature and stirred for 18 h. The reaction was diluted with dichloromethane and washed successively with saturated aqueous sodium bicarbonate, water, and brine. The organics were dried (magnesium sulfate) and the solvent removed in vacuo. Purification by automated flash column chromatography (CombiFlash Rf, 12 g RediSep™ silica cartridge) eluting with a gradient of 0-5% methanol in dichloromethane afforded the desired product as a yellow glass (34.2 mg, 0.05 mmol, 63%).

LC/MS ($C_{34}H_{38}N_8O_2S_2$) 655 $[M+H]^+$; RT 1.47 (LCMS-V-B1)

$^1H$ NMR (400 MHz, DMSO-d6) δ 10.94 (br s, 1H), 7.88 (br s, 1H), 7.64 (br s, 1H), 7.55 (s, 1H), 7.36 (t, 1H) 7.22-7.13 (m, 1H), 4.18 (q, J=7.1 Hz, 2H), 3.80 (s, 2H), 2.38 (s+s, 6H), 2.21 (s, 3H), 1.99 (d, J=8.2 Hz, 3H), 1.73-1.54 (m, 12H), 1.18 (t, J=7.1 Hz, 3H).

Step C: 5-{1-[(adamantan-1-yl)methyl]-5-methyl-1H-pyrazol-4-yl}-2-({6-[(1,3-benzothiazol-2yl)amino]-4,5-dimethylpyridazin-3-yl}amino)-1,3-thiazole-4-carboxylic acid To a solution of the product from Step B (34.2 mg, 0.05 mmol, 1 eq) in 1,4-dioxane (5 mL) was added lithium hydroxide monohydrate (22 mg, 0.52 mmol, 10 eq) and the mixture was heated at reflux for 18 h. The reaction was allowed to cool to ambient temperature then the solvent removed in vacuo. The residue was triturated with water, and the solids collected by filtration and dried under vacuum to afford the desired product as a yellow solid (28 mg, 0.04 mmol, 86%) [as a lithium salt].

HRMS-ESI (m/z) [M+H]+ calcd for $C_{32}H_{35}N_8O_2S_2$: 627.2319, found 627.2357.

Example 34: 2-({6-[(1,3-Benzothiazol-2-yl)amino]-5-(propan-2-yl)pyridazin-3-yl}(methyl)amino)-1,3-thiazole-4-carboxylic acid

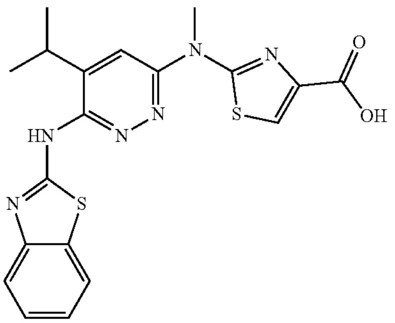 [SMILES: CC(C)c1cc(N(C)c2nc(C(=O)O)cs2)nnc1Nc1nc2ccccc2s1]

Step A: ethyl 2-{[6-chloro-5-(propan-2-yl)pyridazin-3-yl](methyl)amino}-1,3-thiazole-4-carboxylate To a solution of the product from Preparation 7c (300 mg, 1.57 mmol, 1 eq) and ethyl 2-(methylamino)-1,3-thiazole-4-carboxylate (292 mg, 1.57 mmol, 1 eq) in tetrahydrofuran (25 mL) at 0° C. was added slowly sodium hydride (60% in mineral oil; 75.4 mg, 1.88 mmol, 1.2 eq) under a nitrogen atmosphere and the mixture was stirred at 0° C. for 1 h, then at ambient temperature for 18 h. Saturated aqueous ammonium chloride solution (20 mL) was added and the mixture extracted with dichloromethane (75 mL). The organic extracts were washed successively with water (2×50 mL) and brine (50 mL), then dried (magnesium sulfate) and concentrated in vacuo. Purification by automated flash column chromatography (CombiFlash Rf, 24 g RediSep™ silica cartridge) eluting with a gradient of 0-50% ethyl acetate in iso-heptane afforded the desired product as a white crystalline solid (340 mg, 1 mmol, 64%).

LC/MS ($C_{14}H_{17}ClN_4O_2S$) 341 $[M+H]^+$; RT 1.31 (LCMS-V-B1)

$^1H$ NMR (400 MHz, DMSO-d6) δ 8.05 (s, 1H), 7.67 (s, 1H), 4.30 (q, J=7.1 Hz, 2H), 3.88 (s, 3H), 3.20 (hept, J=6.9 Hz, 1H), 1.32 (dt, J=7.1, 3.7 Hz, 9H).

Step B: ethyl 2-({6-[(1,3-benzothiazol-2-yl)amino]-5-(propan-2-yl)pyridazin-3-yl}(methyl)amino)-1,3-thiazole-4-carboxylate To a solution of the product from Step A (340 mg, 1 mmol, 1 eq) and 2-aminobenzothiazole (180 mg, 1.2 mmol, 1.2 eq) in 1,4 dioxane (15 mL) was added Xantphos (115 mg, 0.2 mmol, 0.2 eq) and tris(dibenzylideneacetone)dipalladium(0) (91.4 mg, 0.1 mmol, 0.1 eq) under a nitrogen atmosphere. N,N-Diisopropylethylamine (0.52 mL, 2.99 mmol, 3 eq) was added and the mixture was heated in a sealed tube at 150° C. for 18 h. The mixture was allowed to cool to ambient temperature and the solvent removed in vacuo. Purification by automated flash column chromatography (CombiFlash Rf, 24 g RediSep™ silica cartridge) eluting with a gradient or 0-3% methanol in dichloromethane afforded the desired product as a yellow solid (110 mg, 0.24 mmol, 24%).

LC/MS ($C_{21}H_{22}N_6O_2S_2$) 455 $[M+H]^+$; RT 1.44 (LCMS-V-B1)

$^1H$ NMR (400 MHz, DMSO-d6) δ 12.40 (br s, 1H), 7.97 (s, 1H), 7.79 (br s, 1H), 7.55 (s, 1H), 7.37 (br s+t, 2H), 7.19 (br s, 1H), 4.30 (q, J=7.1 Hz, 2H), 3.87 (s, 3H), 3.57 (p, J=6.8 Hz, 1H), 1.40-1.27 (m, 9H).

Step C: 2-({6-[(1,3-benzothiazol-2-yl)amino]-5-(propan-2-yl)pyridazin-3-yl}(methyl)amino)-1,3-thiazole-4-carboxylic acid To a stirred solution of the product from Step B (111 mg, 0.24 mmol, 1 eq) in 1,4-dioxane (5 mL) was added 2M aqueous lithium hydroxide (0.24 mL, 0.49 mmol, 2 eq) and the mixture was heated at reflux for 2 h. The reaction was allowed to cool to ambient temperature and concentrated in vacuo. The crude material was triturated with diethyl ether (10 mL) and the solids collected by filtration, washed with diethyl ether and dried under vacuum. The resultant material was dissolved in water and acidified to pH 5-6 with 1M aqueous hydrochloric acid then concentrated in vacuo. The solids were triturated with 4:1 isopropanol/water (5 mL), collected by filtration and dried under vacuum to afford the desired product as a yellow solid (66.7 mg, 0.16 mmol, 64%).

HRMS-ESI (m/z) [M+H]+ calcd for $C_{19}H_{19}N_6O_2S_2$: 427.1005, found 427.1042.

Example 35: 2-({6-[(1,3-Benzothiazol-2-yl)amino]-4,5-dimethylpyridazin-3-yl}amino)-5-(1-{[1-(3-methoxypropyl)cyclooctyl]methyl}-5-methyl-1H-pyrazol-4-yl)-1,3-thiazole-4-carboxylic acid

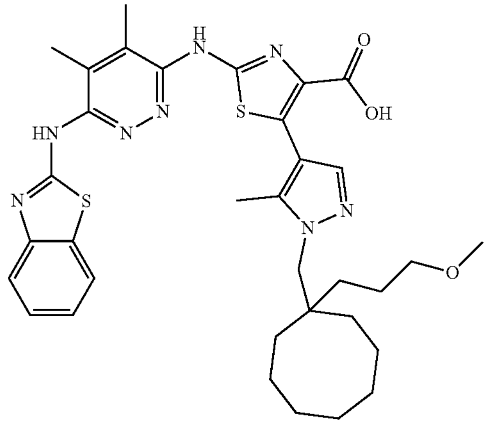 [SMILES: COCCCC1(Cn2ncc(-c3sc(Nc4nnc(Nc5nc6ccccc6s5)c(C)c4C)nc3C(=O)O)c2C)CCCCCCC1]

Step A: ethyl 2-[(4,5-dimethyl-6-{[(2Z)-3-{[2-(trimethylsilyl)ethoxy]methyl}-2,3-dihydro-1,3-benzothiazol-2-ylidene]amino}pyridazin-3-yl)amino]-5-(1-{[1-(3-methoxypropyl)cyclooctyl]methyl}-5-methyl-1H-pyrazol-4yl)-1,3-thiazole-4-carboxylate To a mixture of the product from Preparation 11a (99 mg, 0.16 mmol, 1 eq), the product from Preparation 10b (75.6 mg, 0.19 mmol, 1.2 eq) and potassium carbonate (64.6 mg, 0 mol, 3 eq) in 3:1 tetrahydrofuran/water (4 mL) was added [1,1'-bis(diphenylphosphino)ferrocene]dichloropalladium (II)(11.4 mg, 0.02 mmol, 0.1 eq). The mixture was sparged with nitrogen (10 min) then heated at 120° C. for 2 h under microwave irradiation. The reaction was diluted with ethyl acetate then washed with water followed by brine. The organic extract was dried (magnesium sulfate) and the solvent removed in vacuo. Purification by automated flash column chromatography (CombiFlash Rf, 12 g RediSep™ silica cartridge) eluting with a gradient of 0-50% ethyl acetate in iso-heptane afforded the desired product as an orange glass (43.4 mg, 0.05 mmol, 33%).

LC/MS ($C_{42}H_{60}N_8O_4SiS_2$) 834 $[M+H]^+$; RT 1.88 (LCMS-V-B1)

$^1H$ NMR (400 MHz, DMSO-d6) δ 10.92 (br s, 1H), 7.77 (d, J=7.8 Hz, 1H), 7.56 (s, 1H), 7.45-7.37 (m, 2H), 7.21 (t, J=7.0 Hz, 1H), 5.84 (s, 2H), 4.17 (q, J=7.1 Hz, 2H), 3.85 (s, 2H), 3.71 (t, J=8.0 Hz, 2H), 2.67 (q, 3H), 2.41 (s, 3H), 2.36 (s, 3H), 2.33 (q, 2H), 2.19 (s, 3H), 1.65-1.52 (m, 6H), 1.49-1.36 (m, 6H), 1.34-1.22 (m, 8H), 1.18 (t, J=7.1 Hz, 3H), 1.07 (s, 2H), 0.91 (t, 3H), −0.11 (s, 9H).

Step B: ethyl 2-({6-[(1,3-benzothiazol-2-yl)amino]-4,5dimethylpyridazin-3-yl}amino)-5-(1-{[1-(3-methoxypropyl)cyclooctyl]methyl}-5-methyl-1H-pyrazol-4-yl)-1,3-thiazole-4-carboxylate A solution of the product from Step A (43.4 mg. 0.05 mmol, 1 eq) in dichloromethane (4 mL) was cooled in an ice bath then trifluoroacetic acid (0.4 mL, 5.37 mmol 103 eq) was added. The mixture was allowed to warm to ambient temperature where it was stirred for 18 h. The reaction was diluted with dichloromethane then successively washed with saturated aqueous sodium bicarbonate, water, and brine. The organics were dried (magnesium sulfate) and the solvent was removed in vacuo. Purification by automated flash column chromatography (CombiFlash Rf, 12 g RediSep™ silica cartridge) eluting with a gradient of 0-5% methanol in dichloromethane afforded the desired product as a yellow glass (21.3 mg, 003 mmol, 58%).

LC/MS ($C_{36}H_{46}N_8O_3S_2$) 703 [M+H]$^+$; RT 1.33 (LCMS-V-B1)

$^1$H NMR (400 MHz, DMSO-d6) δ 10.94 (br s, 1H), 7.88 (br s, 1H), 7.63 (br s, 1H), 7.57 (s, 1H), 7.40-7.32 (m, 1H), 7.22-7.14 (m, 1H), 4.18 (q, J=7.1 Hz, 2H), 3.86 (s, 2H), 3.25 (s, 3H), 2.38 (s+s, 6H), 2.21 (s, 3H), 1.70-1.51 (m, 9H), 1.50-1.35 (m, 6H), 1.34-1.23 (m, 95), 1.18 (t, 3H).

Step C: 2-({6-[(1,3-benzothiazol-2-yl)amino]-4,5-dimethylpyridazin-3-yl}amino)-5-(1-{[1-(3-methoxypropyl)cyclooctyl]methyl}-5-methyl-1H-pyrazol-4-yl)-1,3-thiazole-4-carboxylic acid To a solution of the product from Step B (21.3 mg, 0.03 mmol, 1 eq) in 1,4-dioxane (4 mL) was added lithium hydroxide monohydrate (12.7 mg, 0.3 mmol, 10 eq) and the mixture was heated at reflux for 18 h. The reaction was allowed to cool to ambient temperature and the solvent removed in vacuo. The residue was triturated with water and solids were collected by filtration and dried under vacuum afforded the desired product as a beige solid (13.9 mg, 0.02 mmol, 68%) [as a lithium salt].

HRMS-ESI (m/z) [M+H]+ calcd for $C_{34}H_{43}N_8O_3S_2$: 675.2894, found 675.2933.

Example 36: 2-({6-[(1,3-Benzothiazol-2-yl)amino]-4,5-dimethylpyridazin-3-yl}amino)-5-(1-{[1-(3-methoxypropyl)cyclooctyl]methyl}-5-methyl-1H-pyrazol-4-yl)-1,3-thiazole-4-carboxylic acid

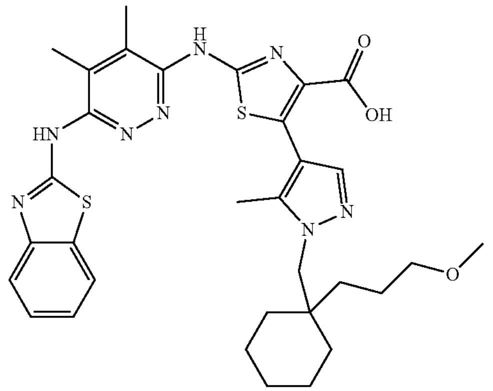 [SMILES: COCCCC1(Cn2ncc(-c3sc(Nc4nnc(Nc5nc6ccccc6s5)c(C)c4C)nc3C(=O)O)c2C)CCCCC1]

Step A: ethyl 2-[(4,5-dimethyl-6-{[(2Z)-3-{[3-(trimethylsilyl)propoxy]methyl}-2,3-dihydro-1,3-benzothiazol-2-ylidene]amino}pyridazin-3-yl)amino]-5-(1-{[1-(3-methoxypropyl)cyclohexyl]methyl}-5-methyl-1H-pyrazol-4-yl)-1,3-thiazole-4-carboxylate To a mixture of the product from Preparation 11a (110 mg, 0.17 mmol, 1 eq), the product from Preparation 10c (81 mg, 0.22 mmol, 1.25 eq) and potassium carbonate (71.4 mg, 0.52 mmol, 3 eq) in 3:1 tetrahydrofuran/water (4 mL) was added [1,1'-bis(diphenylphosphino)ferrocene]dichloropalladium (II)(12.6 mg, 0.02 mmol, 0.1 eq). The mixture was sparged with nitrogen (10 min) then heated at 120° C. for 1 h under microwave irradiation. The reaction was diluted with ethyl acetate and successively washed with water and brine. The organics were dried (magnesium sulfate) and the solvent removed in vacuo. Purification by automated flash column chromatography (CombiFlash Rf, 12 g RediSep™ silica cartridge) eluting with a gradient of 0-50% ethyl acetate in iso-heptane afforded the desired product as an orange gum (81.2 mg, 0.1 mmol, 59%).

LC/MS ($C_{40}H_{56}N_8O_4SiS_2$) 805 [M+H]$^+$; RT 1.85 (LCMS-V-B1)

$^1$H NMR (400 MHz, DMSO-d6) δ 10.94 (s, 1H), 7.77 (d, J=7.7 Hz, 1H), 7.56 (s, 1H), 7.47-7.37 (m, 2H), 7.24-7.19 (m, 1H), 5.84 (s, 2H), 4.17 (q, J=7.1 Hz, 2H), 3.93 (s, 2H), 3.71 (t, 2H), 3.24 (s, 3H), 2.41 (s, 3H), 2.37 (s, 3H), 2.21 (s, 3H), 1.56-1.47 (m, 5H), 1.42-1.31 (m, 8H), 1.24-1.14 (m, 6H), 0.91 (t, 2H), −0.11 (s, 9H).

Step B: ethyl 2-({6-[(1,3-benzothiazol-2-yl)amino]-4,5-dimethylpyridazin-3-yl}amino)-5-(1-{[1-(3-methoxypropyl)cyclohexyl]methyl}-5-methyl-1H-pyrazol-4-yl)-1,3-thiazole-4-carboxylate A solution of the product from Step A (81.2 mg, 0.1 mmol, 1 eq) in dichloromethane (5 mL) was cooled in an ice bath and trifluoroacetic acid (0.5 mL, 6.71 mmol, 67 eq) was added. The mixture was allowed to warm to ambient temperature and stirred for 18 h. The reaction was diluted with dichloromethane then successively washed with saturated aqueous sodium bicarbonate, water, and brine. The organics were dried (magnesium sulfate) and the solvent removed in vacuo. Purification by automated flash column chromatography (CombiFlash Rf, 12 g RediSep™ silica cartridge) eluting with a gradient of 0-5% methanol in dichloromethane afforded the desired product as a yellow glass (49.6 mg, 0.07 mmol, 73%).

LC/MS ($C_{34}H_{42}N_8O_3S_2$) 675 [M+H]$^+$; RT 1.54 (LCMS-V-B1)

$^1$H NMR (400 MHz, DMSO-d6) δ 10.94 (br s, 1H), 7.88 (br s, 1H), 7.57 (s, 1H), 7.40-7.32 (m, 1H), 7.22-7.13 (m, 1H), 4.18 (q, 2H), 3.95 (s, 2H), 3.25 (s, 3H), 2.37 (s, 61.1), 2.22 (s, 3H), 1.60-1.45 (m, 6H), 1.44-1.34 (m, 8H), 1.28-1.22 (m, 2H), 1.19 (t, J=7.1 Hz, 3H).

Step C: 2-({6-[(1,3-benzothiazol-2-yl)amino]-4,5-dimethylpyridazin-3-yl}amino)-5-(1-{[1-(3-methoxypropyl)cyclohexyl]methyl}-5-methyl-1H-pyrazol-4-yl)-1,3-thiazole-4-carboxylic acid To a solution of the product from Step B (49.6 mg, 0.07 mmol, 1 eq) in 1,4-dioxane was added lithium hydroxide monohydrate (14.7 mg, 0.37 mmol, 5 eq) and the mixture was heated at reflux for 2 h. The reaction was allowed to cool to ambient temperature and the solvent removed in vacuo. The residue was triturated with water and the solids were collected by filtration, successively washed with 2M aqueous hydrochloric acid, then dichloromethane, and dried under vacuum to afford the desired product as a pale yellow solid (10.8 mg, 0.02 mmol, 23%).

HRMS-ESI (m/z) [M+H]+ calcd for $C_{32}H_{39}N_8O_3S_2$: 647.2581, found 647.2620.

Example 37: 2-({6-[(1,3-Benzothiazol-2-yl)amino]-5-methylpyridazin-3-yl}(ethyl)amino)-1,3-thiazole-4-carboxylic acid

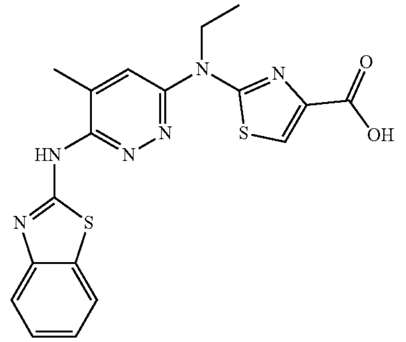 [SMILES: CCN(c1cc(C)c(Nc2nc3ccccc3s2)nn1)c1nc(C(=O)O)cs1]

Step A: ethyl 2-[(6-chloro-5-methylpyridazin-3-yl)(ethyl)amino]-1,3-thiazole-4-carboxylate Sodium hydride (60% dispersion; 150 mg, 3.75 mmol, 1.25 eq) was added to a solution of 3,6-dichloro-4-methylpyridazine (530 mg, 3.25 mmol, 1.09 eq) and ethyl 2-(ethylamino)-1,3-thiazole-4-carboxylate (600 mg, 3 mmol, 1 eq) in 1,4-dioxane (20 mL) at 0° C. under a nitrogen atmosphere. The mixture was stirred for 1 h at 0° C. and for 18 h at ambient temperature. Ethyl acetate (150 mL) was added and the mixture was successively washed with saturated aqueous ammonium chloride solution (75 mL), water (2×75 mL), and brine (75 mL), dried (magnesium sulfate) and concentrated in vacuo. Purification by flash column chromatography (50 g silica) eluting with dichloromethane gave a pale yellow solid. Trituration with diethyl ether (10 mL) gave a solid that was collected by filtration, washed with diethyl ether (2×5 mL) and dried under vacuum to afford the desired product as an off-white solid (475 mg, 1.45 mmol, 49%).

LC/MS ($C_{13}H_{15}ClN_4O_2S$) 327 $[M+H]^+$; RT 1.25 (LCMS-V-B1)

$^1H$ NMR (400 MHz, DMSO-d6) δ 8.03 (s, 1H), 7.89 (s, 1H), 4.46 (q, 2H), 4.30 (q, 2H), 2.44 (s, 3H), 1.35-1.26 (m, 6H).

Step B: ethyl 2-({6-[(1,3-benzothiazol-2-yl)amino]-5-methylpyridazin-3-yl}(ethyl)amino)-1,3-thiazole-4-carboxylate 2-Aminobenzothiazole (250 mg, 1.66 mmol, 1.2 eq) and the product from Step A (450 mg, 1.38 mmol, 1 eq) were added to a solution of tris(dibenzylideneacetone)dipalladium(0)(63.1 mg, 0.07 mmol, 0.05 eq) and Xantphos (79.7 mg, 0.14 mmol, 0.1 eq) in 1,4-dioxane (10 mL) under a nitrogen atmosphere. N,N-Diisopropylethylamine (0.75 mL, 4.13 mmol, 3 eq) was added and the mixture was healed in a sealed tube at 150° C. for 7 h. The solution was allowed to cool to ambient temperature and concentrated in vacuo. Purification by flash column chromatography (50 g silica) eluting with ethyl acetate gave a yellow solid. Trituration with methanol (10 mL) gave a solid that was collected by filtration, washed with methanol (2×5 mL) and dried under vacuum to afford the desired product as a yellow solid (265 mg, 0.6 mmol, 44%).

LC/MS ($C_{20}H_{20}N_6O_2S_2$) 441 $[M+H]^+$; RT 1.37 (LCMS-V-B1)

$^1H$ NMR (400 MHz, DMSO-d6) δ 11.12 (br s, 1H), 7.97 (s, 1H), 7.92 (s, 1H), 7.74 (s, 1H), 7.57 (br s, 1H), 7.39 (t, J=7.5 Hz, 1H), 7.22 (t, J=7.5 Hz, 1H), 4.46 (q, J=6.9 Hz, 2H), 4.30 (q, J=7.1 Hz, 2H), 2.49 (s, 3H), 1.31 (t+t, 6H).

Step C: 2-({6-[(1,3-benzothiazol-2-yl)amino]-5-methylpyridazin-3-yl}(ethyl)amino)-1,3-thiazole-4-carboxylic acid To a solution of the product from Step B (210 mg, 0.48 mmol, 1 eq) in 1:3 water/1,4-dioxane (4 mL) was added lithium hydroxide monohydrate (80.0 mg, 1.91 mmol, 4 eq) and the mixture was stirred at ambient temperature overnight. Water (5 mL) was added, the mixture was filtered through elite, and the solider were washed with water (10 mL). The combined filtrate was acidified with acetic acid to give a yellow suspension and the solids were collected by filtration, washed with water (30 mL) and dried under vacuum to afford the desired product as a yellow solid (170 mg, 0.41 mmol, 86%).

HRMS-ESI (m/z) [M+H]+ calcd for $C_{18}H_{17}N_6O_2S_2$: 413.0849, found 413.0882.

Example 38: 6-({6-[(1,3-Benzothiazol-2-yl)amino]pyridazin-3-yl}(methyl)amino)pyridine-2-carboxylic acid

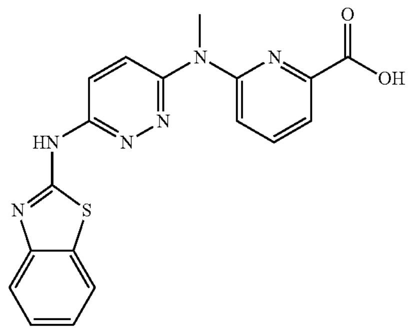 [SMILES: CN(c1ccc(Nc2nc3ccccc3s2)nn1)c1cccc(C(=O)O)n1]

Step A: tert-butyl N-[(tert-butoxy)carbonyl]-N-(6-chloropyridazin-3-yl)carbamate 4-dimethylaminopyridine (122 mg, 1 mmol, 0.02 eq) was added to a suspension of 3-amino-6-chloropyridazine (6.5 g, 50.2 mmol, 1 eq) and di-tert-butyl dicarbonate (25.2 g, 115 mmol, 2.3 eq) in dimethylformamide (45 mL) under a nitrogen atmosphere. The suspension was heated at 50° C. for 3 h then allowed to cool to ambient temperature and water (350 mL) was added. The solids were collected by filtration, washed with water (250 mL) then dissolved in dichloromethane (250 mL) and the solution filtered through silica (25 g), eluting with dichloromethane. The filtrate was concentrated in vacuo and trituration with heptane (50 mL) gave a solid that was collected by filtration, washed with heptane (50 mL) and dried under vacuum to afford the desired product as a white solid (9.85 g, 29.9 mmol, 60%).

LC/MS ($C_{14}H_{20}ClN_3O_4$) 174 $[M-Boc-tBu+3H]^+$; RT 1.28 (LCMS-V-B1)

$^1H$ NMR (400 MHz, DMSO-d6) δ 7.53 (d, 2H), 1.46 (s, 18H).

Step B: methyl 6-[(6-{bis[(tert-butoxy)carbonyl]amino}pyridazin-3-yl)amino]pyridine-2-carboxylate Methyl 6-aminopyridine-2-carboxylate (1.65 g, 10.8 mmol, 1.1 eq) and the product from Step A (3.25 g, 9.86 mmol, 1 eq) were added to a solution of tris(dibenzylideneacetone)dipalladium(0)(451 mg, 0.49 mmol, 0.05 eq) and Xantphos (570 mg, 0.99 mmol, 0.1 eq) in 1,4-dioxane (60 mL) under a nitrogen atmosphere. N,N-Diisopropylethylamine (5.2 mL, 29.6 mmol, 3 eq) was added and the mixture was heated at 100° C. for 3 h. The solution was allowed to cool to ambient temperature and concentrated in vacuo. The residue was partitioned between dichloromethane (300 mL) and water (200 mL) and the organic phase was washed successively with water (200 mL) and brine (150 mL), then dried (magnesium sulfate) and concentrated in vacuo. Purification by flash column chromatography (100 g silica) eluting with 2:3 ethyl acetate/heptane gave a yellow solid. Trituration with diethyl ether (20 mL) gave a solid that was collected by filtration, washed with diethyl ether (20 mL) and dried under vacuum to afford the desired product as a pale yellow solid (3.35 g, 7.52 mmol, 76%).

LC/MS ($C_{21}H_{27}N_5O_6$) 446 [M+H]$^+$; RT 1.27 (LCMS-V-B1)

$^1$H NMR (400 MHz, DMSO-d6) δ 10.41 (s, 1H), 9.02 (d, 1H), 7.97 (dd, 1H), 7.83-7.73 (m, 2H), 7.45 (d, 1H), 4.01 (s, 3H), 1.46 (s, 9H).

Step C: methyl 6-[(6-{bis[(tert-butoxy)carbonyl]amino}pyridazin-3-yl)(methyl)amino]pyridine-2-carboxylate Potassium tert-butoxide (750 mg, 6.68 mmol, 1.32 eq) was added to a suspension of the product from Step B (2.25 g, 5.05 mmol, 1 eq) in dimethylsulfoxide (25 mL) under a nitrogen atmosphere and the mixture was stirred for 30 min. Methyl iodide (0.5 mL, 8.03 mmol, 1.59 eq) was added and the suspension was stirred for 3 h. The mixture was partitioned between ethyl acetate (250 mL) and saturated aqueous ammonium chloride solution (150 mL), washed with water (2×150 mL) and brine (100 mL), dried (magnesium sulfate) and concentrated in vacuo. Purification by flash column chromatography (100 g silica) eluting with 2:3 ethyl acetate/heptane afforded the desired product as a yellow solid (1.4 g, 2.59 mmol, 51%) that was used directly in the next step without further purification.

LC/MS ($C_{22}H_{29}N_5O_6$) 460 [M+H]$^+$; RT 1.29 (LCMS-V-B1).

Step D: methyl 6-[(6-aminopyridazin-3-yl)(methyl)amino]pyridine-2-carboxylate

Trifluoroacetic acid (5 mL, 64.7 mmol, 25 eq) was added to the product from Step C (1.4 g, 2.59 mmol, 1 eq) in dichloromethane (35 mL) at 0° C. and the solution was stirred for 1 h at 0° C. then 18 h at ambient temperature. The solution was concentrated in vacuo and water (25 mL) was added to give a pale yellow suspension that was neutralised with sodium bicarbonate carbonate and the solids were collected by filtration, washed with water (75 mL) and dried under vacuum to afford the desired product as a yellow solid (650 mg, 2.51 mmol, 97%) that was used directly in the next step without further purification or characterisation.

Step E: methyl 6-({6-[(1,3-benzothiazol-2-yl)amino]pyridazin-3-yl}(methyl)amino)pyridine-2-carboxylate The product from Step D (650 mg, 2.51 mmol, 1 eq) and 2-bromo-1,3-benzothiazole (600 mg, 2.8 mmol, 1.12 eq) were added to a solution of tris(dibenzylideneacetone)dipalladium(0)(115 mg, 0.13 mmol, 0.05 eq) and Xantphos (145 mg, 0.25 mmol, 0.1 eq) in 1,4-dioxane (10 mL) under a nitrogen atmosphere. N,N-Diisopropylethylamine (1.4 mL, 7.52 mmol, 3 eq) was added and the mixture was heated at 100° C. for 24 h. The reaction was allowed to cool to ambient temperature and concentrated in vacuo. Water (20 mL) was added to give a brown suspension and the solids were collected by filtration, washed with water (40 mL) and dried under vacuum. Purification by flash column chromatography (50 g silica) eluting with 39:1 dichloromethane/methanol gave a solid that was triturated with methanol (10 mL), filtered, washed with methanol (10 mL) and dried under vacuum to afford the desired product as a pale brown solid (225 mg, 0.57 mmol, 23%).

LC/MS ($C_{19}H_{16}N_6O_2S$) 393 [M+H]$^+$; RT 1.14 (LCMS-V-B1)

$^1$H NMR (400 MHz, DMSO-d6) δ 11.73 (br s, 1H), 7.94 (d, 1H), 7.91-7.85 (m, 1H), 7.80 (d, J=9.5 Hz, 1H), 7.70-7.59 (m, 2H), 7.46 (d, 1H), 7.43-7.35 (m, 2H), 7.28-7.19 (m, 1H), 3.86 (s, 3H), 3.64 (s, 3H).

Step F: 6-({6-[(1,3-benzothiazol-2-yl)amino]pyridazin-3-yl}(methyl)amino]pyridine-2-carboxylic acid To a solution of the product from Step E (200 mg, 0.51 mmol, 1 eq) in 1:3 water/1,4-dioxane (4 mL) was added lithium hydroxide monohydrate (85.5 mg, 2.04 mmol, 4 eq) and the mixture was stirred at ambient temperature for 2 h. Water (5 mL) was added, the solution was filtered through celite, and the solids washed with water (10 mL). The combined filtrate was acidified with acetic acid to give a solid, that was collected by filtration, washed with water (20 mL) and dried under vacuum to afford the desired product as a yellow solid (160 mg, 0.42 mmol, 83%).

HRMS-ESI (m/z) [M+H]+ calcd for $C_{18}H_{15}N_6O_2S$: 379.0972, found 379.0993.

Example 39: 2-({6-[(1,3-Benzothiazol-2-yl)amino]-5-methylpyridazin-3-yl}(2-methoxyethyl)amino)-1,3-thiazole-4-carboxylic acid

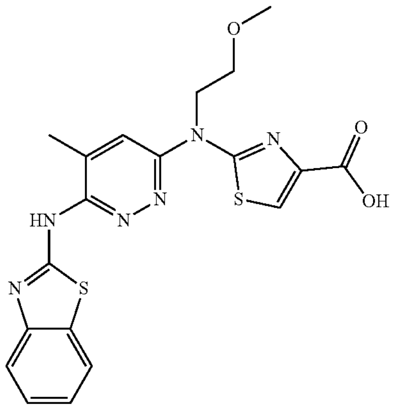 [SMILES: COCCN(c1cc(C)c(Nc2nc3ccccc3s2)nn1)c1nc(C(=O)O)cs1]

Step A: ethyl 2-[(6-chloro-5-methylpyridazin-3-yl)(2-methoxyethyl)amino]-1,3-thiazole-4-carboxylate Sodium hydride (60% dispersion; 650 mg, 16.3 mmol, 1.2 eq) was added to a solution of the product from Preparation 3z (3.15 g, 13.7 mmol, 1 eq) and 3,6-dichloro-4-methylpyridazine (2.5 g, 15.3 mmol, 1.12 eq) in 1,4-dioxane (50 mL) at 0° C. under a nitrogen atmosphere. The mixture was stirred for 1 h at 0° C. then heated at 60° C. for 24 h. The mixture was allowed to cool to ambient temperature then partitioned between ethyl acetate (300 mL) and saturated aqueous ammonium chloride solution (150 mL), and the organic phase was successively washed with water (2×150 mL) and brine (100 mL), dried (magnesium sulfate) and concentrated in vacuo. Trituration with diethyl ether (25 mL) gave a solid that was collected by filtration, washed with diethyl ether (15 mL) and dried under vacuum to afford the desired product as a pale pink solid (2.55 g, 7.15 mmol, 52%).

LC/MS ($C_{14}H_{17}ClN_4O_3S$) 357 $[M+H]^+$; RT 1.22 (LCMS-V-B1)

$^1H$ NMR (400 MHz, $CDCl_3$) δ 7.83 (s, 1H), 7.65 (s, 1H), 4.60 (t, 2H), 4.39 (q, 2H), 3.91 (t, 2H), 3.32 (s, 3H), 2.46 (s, 3H), 1.41 (t, 3H).

Step B: ethyl 2-({6-[(1,3-benzothiazol-2-yl)amino]-5-methylpyridazin-3-yl}(2-methoxyethyl)amino)-1,3-thiazole-4-carboxylate 2-aminobenzothiazole (1.15 g, 746 mmol, 1.09 eq) and the product from Step A (2.5 g, 7.01 mmol, 1 eq) were added to a solution of tris(dibenzylideneacetone)dipalladium(0) (321 mg, 0.35 mmol, 0.05 eq) and Xantphos (405 mg, 0.7 mmol, 0.1 eq) in 1,4-dioxane (45 mL) under a nitrogen atmosphere. N,N-Diisopropylethylamine (3.8 mL, 21.0 mmol, 3 eq) was added and the mixture was heated in a sealed flask at 150° C. for 18 h. The solution was allowed to cool to ambient temperature, filtered through celite, and the solids were washed with dichloromethane. The combined filtrate was concentrated in vacuo and triturated with methanol (25 mL) to give a solid that was collected by filtration, washed with methanol (3×15 mL) and dried under vacuum to afford the desired product as an orange solid (2.55 g, 5.42 mmol, 77%).

LC/MS ($C_{21}H_{22}N_6O_3S_2$) 471 $[M+H]^+$; RT 1.35 (LCMS-V-B1)

$^1H$ NMR (400 MHz, $CDCl_3$) δ 7.85-7.80 (m, 1H), 7.79 (s, 1H), 7.77-7.69 (m, 1H), 7.66 (d, J=1.3 Hz, 1H), 7.48-7.36 (m, 1H), 7.31-7.21 (m, 1H), 4.64-4.48 (m, 2H), 4.41 (q, J=7.1 Hz, 2H), 3.94-3.85 (m, 2H), 3.40-3.31 (m, 3H), 2.44 (s, 3H), 1.43 (t, J=7.1 Hz, 3H).

Step C: 2-({6-[(1,3-benzothiazol-2-yl)amino]-5-methylpyridazin-3-yl}(2-methoxyethyl)amino)-1,3-thiazole-4-carboxylic acid To a solution of the product from Step B (250 mg, 0.53 mmol, 1 eq) in 1:3 water/1,4-dioxane (4 mL) was added lithium hydroxide monohydrate (89.2 mg, 2.13 mmol, 4 eq) and the mixture was stirred at ambient temperature for 18 h. Water (10 mL) was added and the suspension acidified with acetic acid. The solids were collected by filtration, washed with water (3×25 mL) and dried in vacuum to afford the desired product as a yellow solid (175 mg, 0.4 mmol, 74%).

HRMS-ESI (m/z) [M+H]+ calcd for $C_{19}H_{19}N_6O_3S_2$: 443.0955, found 443.0983.

Example 40: 5-{1-[(Adamantan-1-yl)methyl]-5-methyl-1H-pyrazol-4-yl}-2-({6-[(1,3-benzothiazol-2-yl)amino]-5-methylpyridazin-3-yl}(methyl)amino)-1,3-thiazole-4-carboxylic acid

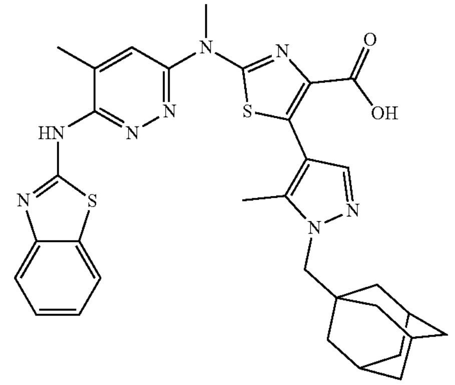 [SMILES: Cc1cc(N(C)c2nc(C(=O)O)c(-c3cnn(CC45CC6CC(CC(C6)C4)C5)c3C)s2)nnc1Nc1nc2ccccc2s1]

Step A: ethyl 5-{1-[(adamantan-1-yl)methyl]-5-methyl-1H-pyrazol-4-yl}-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-1-carboxylate To a mixture of the product from Preparation 11b (54.7 mg, 0.09 mmol, 1 eq), Preparation 10a (36.8 mg, 0.1 mmol, 1.2 eq) and potassium carbonate (35.7 mg, 0.26 mmol, 3 eq) in 3:1 tetrahydrofuran/water (4 mL) was added [1,1'-bis(diphenylphosphino)ferrocene]dichloropalladium(II)(6.3 mg, 0.01 mural, 0.1 eq). The mixture was sparged with nitrogen (10 min) then heated at 120° C. for 1 h under microwave irradiation. The reaction was partitioned between ethyl acetate and water, and the organic phase was washed with brine, dried (magnesium sulfate), and concentrated in vacuo Purification by automated flash column chromatography (CombiFlash Rf, 12 g RediSep™ silica cartridge) eluting with a gradient 0-50% ethyl acetate in iso-heptane afforded the desired product as a brown glass (46.7 mg, 0.06 mmol, 69%).

LC/MS ($C_{40}H_{52}N_8O_3SiS_2$) 785 $[M+H]^+$; RT 1.91 (LCMS-V-B1)

$^1H$ NMR (400 MHz, DMSO-d6) δ 7.82 (dd, J=7.7, 1.1 Hz, 1H), 7.71 (d, J=1.1 Hz, 1H), 7.53 (s, 1H), 7.48-7.39 (m, 2H), 7.23 (ddd, J=8.3, 7.0, 1.5 Hz, 1H), 5.86 (s, 2H), 4.16 (q, J=7.1 Hz, 2H), 3.82 (s, 3H), 3.78 (s, 2H), 3.71 (t, 2H), 2.46 (s, 3H), 2.18 (s, 3H), 1.95 (s, 3H), 1.72-1.54 (m, 12H), 1.16 (t, J=7.1 Hz, 3H), 0.92 (t, 3H), −0.11 (s, 9H).

Step B: ethyl 5-{1-[(adamantan-1-yl)methyl]-5-methyl-1H-pyrazol-4-yl}-2-({6-[(1,3-benzothiazol-2-yl)amino]-5-methylpyridazin-3-yl}(methyl)amino)-1,3-thiazole-1-carboxylate A solution of the product from Step A (46.7 mg, 0.06 mmol, 1 eq) in dichloromethane (3 mL) was cooled in an ice bath then trifluoroacetic acid (0.3 mL, 4.03 mmol, 67.7 eq) was added then the mixture was allowed to warm to ambient temperature and stirred for 18 h. The reaction was partitioned between dichloromethane and saturated aqueous sodium bicarbonate and the organic phase was successively washed with water and brine, then dried (magnesium sulfate) and the solvent removed in vacuo. Purification by automated flash column chromatography (CombiFlash Rf, 12 g RediSep™ silica cartridge) eluting with a gradient of 0-5% methanol in dichloromethane afforded the desired product as a yellow glass (24.2 mg, 0.04 mmol, 62%).

LC/MS ($C_{34}H_{38}N_8O_2S_2$) 655 $[M+H]^+$; RT 1.53 (LCMS-V-B2)

$^1$H NMR (400 MHz, DMSO-d6) δ 7.90 (br s, 1H) 7.73 (s, 1H), 7.54 (s, 1H), 7.37 (t, J=7.7 Hz, 1H), 7.24-7.15 (m, 1H), 4.17 (q, J=7.1 Hz, 2H), 3.81 (s, 3H), 3.79 (s, 2H), 2.47 (s, 3H), 2.20 (s, 3H), 1.97 (s, 3H), 1.72-1.55 (m, 12H), 1.17 (t, J=7.1 Hz, 3H).

Step C: 5-{1-[(adamantan-1-yl)methyl]-5-methyl-1H-pyrazol-4-yl}-2-({6-[(1,3-benzothiazol-2-yl)amino]-5-methylpyridazin-3-yl}(methyl)amino)-1,3-thiazole-4-carboxylic acid To a solution of the product from Step B (24.2 mg, 0.04 mmol, 1 eq) in 1,4-dioxane (3 mL) was added lithium hydroxide monohydrate (7.8 mg, (1.18 mmol, 5 eq) and the mixture was heated at reflux for 18 h. The reaction was allowed to cool to ambient temperature then the solvent removed in vacuo. The residue was triturated with water, filtered and dried under vacuum to afford the desired product as a yellow solid (16.3 mg, 0.03 mmol, 70%) [as a lithium salt].

HRMS-ESI (m/z) [M+H]+ calcd for $C_{32}H_{35}N_8O_2S_2$: 627.2319, found 627.2358.

Example 41: 2-({6-[(1,3-Benzothiazol-2-yl)amino]-5-methylpyridazin-3-yl}[2-(morpholin-4-yl)ethyl]amino)-1,3-thiazole-4-carboxylic acid

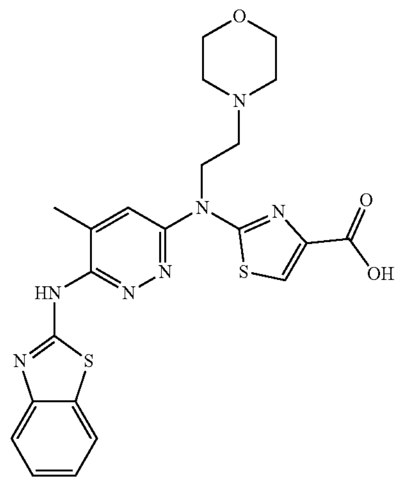 [SMILES: Cc1cc(N(CCN2CCOCC2)c2nc(C(=O)O)cs2)nnc1Nc1nc2ccccc2s1]

Step A: ethyl 2-[(2,2-dimethoxyethyl)amino]-1,3-thiazole-4-carboxylate

Ammonia (2M in isopropanol; 25 mL, 50 mmol, 2.1 eq) was added to a solution of 1,1-dimethoxy-2-isothiocyanatoethane (3.5 g, 20 mmol, 1 eq) in isopropanol (15 mL) at 0° C. under a nitrogen atmosphere and the mixture stirred for 1 h at 0° C. then 18 h at ambient temperature. The solvent was removed in vacuo and the residue was dissolved in ethanol (60 mL) and cooled to 0° C. To this was added ethyl bromopyruvate (16 mL 25.8 mmol, 1.09 eq) under a nitrogen atmosphere and the mixture was allowed to warm to ambient temperature and stirred for 1.5 h. Triethylamine (5.6 mL, 39.9 mmol, 2 eq) was added and the mixture was stirred for 2 h then concentrated in vacuo. The residue was partitioned between ethyl acetate (250 mL) and water (150 mL) and the organic phase was successively washed with water (150 mL) and brine (150 mL), dried (magnesium sulfate), and concentrated in vacuo. Purification by flash column chromatography (100 g silica) eluting with 2:3 ethyl acetate/heptane gave a pale yellow solid that was triturated with heptane (40 mL), filtered, washed with heptane (40 mL) and dried under vacuum to afford the desired product as an off-white solid (2.95 g, 11.33 mmol, 48%).

LC/MS ($C_{10}H_{16}N_2O_4S$) 261 $[M+H]^+$; RT 0.92 (LCMS-V-B1)

$^1$H NMR (400 MHz, $CDCl_3$) δ 7.41 (s, 1H), 5.59 (t, J=5.5 Hz, 1H), 4.52 (t, J=5.4 Hz, 1H), 4.35 (q, J=7.1 Hz, 2H), 3.41 (dd+s, 8H), 1.36 (t, J=7.1 Hz, 3H).

Step B: ethyl 2-[(6-chloro-5-methylpyridazin-3-yl)(2,2-dimethoxyethyl)amino]-1,3-thiazole-4-carboxylate Sodium hydride (60% dispersion; 500 mg, 12.5 mmol, 1.25 eq) was added to a solution of the product from Step A (2.6 g, 9.99 mmol, 1 eq) and 3,6-dichloro-4-methylpyridazine (1.85 g, 11.4 mmol, 1.14 eq) in 1,4-dioxane (40 mL) at 0° C. under a nitrogen atmosphere and the mixture was stirred for 1 h at 0° C. then for 5 h at 60° C. The solution was allowed to cool to ambient temperature then partitioned between ethyl acetate (300 mL) and saturated aqueous ammonium chloride (150 mL). The organic phase was successively washed with water (2×150 mL) and brine (150 mL), dried (magnesium sulfate), and concentrated in vacuo. Purification by flash column chromatography (100 g silica) eluting with 99:1 dichloromethane/methanol gave an orange gum that was triturated with diethyl ether (15 mL) to give a solid that was collected by filtration, washed with diethyl ether (20 mL) and dried under vacuum to afford the desired product as a pale pink powder (1.95 g, 5.04 mmol, 50%).

LC/MS ($C_{15}H_{19}ClN_4O_4S$) 387 $[M+H]^+$; RT 1.26 (LCMS-V-B1)

$^1$H NMR (400 MHz, DMSO-d6) δ 8.06 (s, 1H), 7.95 (d, J=1.1 Hz, 1H), 4.78 (t, J=5.2 Hz, 1H), 4.51 (d, J=5.2 Hz, 2H), 4.29 (q, J=7.1 Hz, 2H), 3.34 (s, 6H), 2.42 (d, J=0.9 Hz, 3H), 1.31 (t, J=7.1 Hz, 3H).

Step C: ethyl 2-({6-[(1,3-benzothiazol-2-yl)amino]-5-methylpyridazin-3-yl}(2,2-dimethoxyethyl)amino)-1,3-thiazole-4-carboxylate The product from Step B (1.6 g, 4.14 mmol, 1 eq) and 2-aminobenzothiazole (700 mg, 4.66 mmol, 1.13 eq) were added to a solution of tris(dibenzylideneacetone)dipalladium(0)(189 mg, 0.21 mmol, 0.05 eq) and Xantphos (239 mg, 0.41 mmol, 0.1 eq) in 1,4-dioxane (20 mL) under a nitrogen atmosphere and the mixture stirred. N,N-Diisopropylethylamine (2.2 mL, 12.4 mmol, 3 eq) was added and the mixture was heated in a sealed tube at 150° C. for 18 h. The solution was allowed to cool to ambient temperature and concentrated in vacuo. Trituration with diethyl ether (20 mL) gave a solid that was collected by filtration, washed with diethyl ether (2×10 mL) and dried under vacuum to afford the desired product as a yellow/green solid (1.9 g, 3.42 mmol, 83%) that was used in the next step without further purification.

LC/MS ($C_{22}H_{24}N_6O_4S_2$) 501 $[M+H]^+$; RT 1.37 (LCMS-V-B1)

$^1$H NMR (400 MHz, DMSO-d6) δ 11.11 (br s, 1H), 7.99 (s, 1H), 7.92 (br s, 7.78 (s, 1H), 7.57 (br s, 2H), 7.40 (t, J=7.6 Hz, 1H), 7.22 (t, J=7.6 Hz, 1H), 4.78 (t, J=5.2 Hz, 1H), 4.48 (d, J=5.2 Hz, 2H), 429 (q, J=7.1 Hz, 2H), 3.35 (s, 6H), 2.46 (s, 3H), 1.31 (t, J=7.1 Hz, 3H).

Step D: ethyl 2-({6-[(1,3-benzothiazol-2-yl)amino]-5-methylpyridazin-3-yl}[2-(morpholin-4-yl)ethyl]amino)-1,3-thiazole-4-carboxylate Formic acid (10 mL, 0.27 mol, 177 eq) was added to a suspension of the product from Step C (750 mg, 1.5 mmol, 1 eq) in water (5 mL) and the mixture was heated at 85° C. for 3 h. The solution was allowed to cool to ambient temperature and concentrated in vacuo. Dichloromethane (20 mL) was added followed by morpholine (0.5 mL, 5.78 mmol, 3.86 eq) and sodium triacetoxyborohydride (1.59 g, 7.49 mmol, 5 eq) and the mixture was stirred for 18 h. The reaction was partitioned between dichloromethane (125 mL) and 10% aqueous potassium carbonate (75 mL) and the organic phase was successively washed with water (2×75 mL) and brine (75 mL), dried (magnesium sulfate), and concentrated in vacuo. Purification by flash column chromatography (20 g silica) eluting with 19:1 dichloromethane/methanol gave a yellow solid that was triturated with diethyl ether (15 mL), filtered, washed with diethyl ether (15 mL), and dried under vacuum to afford the desired product as a pale orange solid (375 mg, 0.71 mmol, 48%).

LC/MS ($C_{24}H_{27}N_7O_3S_2$) 526 $[M+H]^+$; RT 1.08 (LCMS-V-B1)

$^1$H NMR (400 MHz, DMSO-d6) δ 11.18 (br s, 1H), 7.97 (s, 1H), 7.91 (br s, 1H), 7.75 (s, 1H), 7.55 (br s, 1H), 7.39 (t, 1H), 7.22 (t, J=7.6 Hz, 1H), 4.53 (t, J=6.5 Hz, 2H), 4.29 (q, J=7.1 Hz, 2H), 3.48 (t, J=4.5 Hz, 4H), 2.65 (t, J=6.5 Hz, 2H), 2.47 (s, 3H), 1.31 (t, J=7.1 Hz, 3H).

Step E: 2-({6-[(1,3-benzothiazol-2-yl)amino]-5-methylpyridazin-3-yl}[2-(morpholin-4-yl)ethyl]amino)-1,3-thiazole-4-carboxylic acid To a solution of the product from Step D (275 mg, 0.52 mmol, 1 eq) in 2:3 water/1,4-dioxane (5 mL) was added lithium hydroxide monohydrate (87.8 mg, 2.09 mmol, 4 eq) and the mixture was stirred at ambient temperature for 18 h. Water (10 mL) was added and the mixture was acidified with acetic acid. The solids were collected by filtration, washed with water and dried under vacuum to afford the desired product as a pale orange solid (215 mg, 0.43 mmol, 83%).

HRMS-ESI (m/z) [M−H]− calcd for $C_{22}H_{22}N_7O_3S_2$: 496.1231, found 496.1232.

Example 42: 2-({6-[(1,3-Benzothiazol-2-yl)amino]-5-methylpyridazin-3-yl}(methyl)amino)-5-(1-{[1-(3-methoxypropyl)cyclohexyl]methyl}-5-methyl-1H-pyrazol-4-yl)-1,3-thiazole-4-carboxylic acid

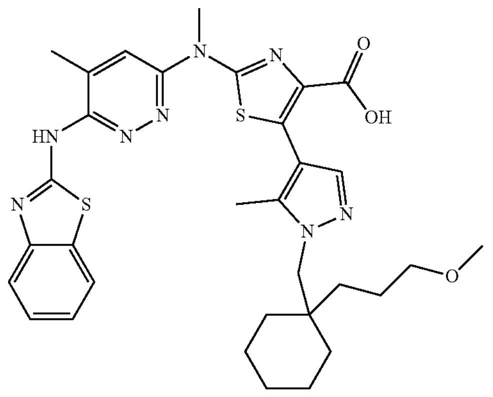 [SMILES: COCCCC1(Cn2ncc(-c3sc(N(C)c4cc(C)c(Nc5nc6ccccc6s5)nn4)nc3C(=O)O)c2C)CCCCC1]

Step A: ethyl 5-(1-{[1-(3-methoxypropyl)cyclohexyl]methyl}-5-methyl-1H-pyrazol-4-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a mixture of the product from Preparation 11b (110 mg, 0.17 mmol, 1 eq), the product from Preparation 10c (78.2 mg, 0.21 mmol, 1.2 eq) and potassium carbonate (71.8 mg, 0.52 mmol, eq) in 10:1 tetrahydrofuran (4 mL)/water (0.4 was added [1,1'-bis(diphenylphosphino)ferrocene]dichloropalladium(II)(12.7 mg, 0.02 mmol, 0.1 eq). The mixture was sparged with nitrogen (10 min) then heated at 120° C. for 1 h under microwave irradiation. The reaction was partitioned between ethyl acetate and water and the organic phase was washed with brine, dried (magnesium sulfate), and the solvent removed in vacuo. Purification by automated flash column chromatography (CombiFlash Rf, 12 g RediSep™ silica cartridge) eluting with a gradient of 0-50% ethyl acetate in iso-heptane afforded the desired product as a yellow foam (56.1 mg, 0.07 mmol, 40%).

LC/MS ($C_{40}H_{56}N_8O_4SiS_2$) 805 $[M+H]^+$; RT 1.74 (LCMS-V-B2)

$^1$H NMR (400 MHz, DMSO-d6) δ 7.92 (dd, J=7.6, 1.0 Hz, 1H), 7.82 (d, J=1.1 Hz, 1H), 7.66 (s, 1H), 7.61-7.47 (m, 2H), 7.35 (ddd, J=8.3, 7.0, 1.5 Hz, 1H), 5.96 (d, J=9.8 Hz, 2H), 4.28 (q, J=7.1 Hz, 2H), 4.05 (s, 2H), 3.93 (s, 3H), 3.83 (t, 2H), 3.35 (s, 3H), 2.58 (d, J=1.0 Hz, 3H), 2.31 (s, 3H), 1.69-1.58 (m, 5H), 1.52-1.44 (m, 7H), 1.38-1.32 (s, 4H), 1.28 (t, J=7.1 Hz, 3H), 1.03 (t, 2H), 0.00 (s, 9H).

Step B: ethyl 2-({6-[(1,3-benzothiazol-2-yl)amino]-5-methylpyridazin-3-yl}(methyl)amino)-5-(1-{[1-(3-methoxypropyl)cyclohexyl]methyl}-5-methyl-1H-pyrazol-4-yl)-1,3-thiazole-4-carboxylate A solution of the product from Step A (56.1 mg, 0.07 mmol, 1 eq) in dichloromethane (3 mL) was cooled in an ice bath and trifluoroacetic acid (0.5 mL, 6.71 mmol, 96 eq) was added. The mixture was allowed to warm to ambient temperature where it was stirred overnight. The solvent was removed in vacuo and purification by reverse phase automated flash chromatography (CombiFlash Rf, C18 13 g RediSep column) eluting with a gradient of 5-95% acetonitrile (pH 4; formic acid) in water water (pH 4; formic acid) afforded the desired product as a yellow glass (34.2 mg, 0.05 mmol, 73%).

LC/MS ($C_{34}H_{42}N_8O_3S_2$) 675 $[M+H]^+$; RT 1.47 (LCMS-V-B2)

$^1$H NMR (400 MHz, DMSO-d6) δ 7.88 (br s, 1H), 7.73 (s, 1H), 7.55 (s, 1H), 7.52 (br s, 1H), 7.37 (t, 1H), 7.19 (t, 1H), 4.17 (q, J=7.1 Hz, 2H), 3.94 (s, 2H), 3.82 (s, 3H), 3.24 (s, 3H), 2.48 (s, 3H), 2.20 (s, 3H), 1.60-1.45 (m, 6H), 1.45-1.31 (m, 8H), 1.29-1.21 (m, 2H), 1.17 (t, 3H).

Step C: 2-({6-[(1,3-benzothiazol-2-yl)amino]-5-methylpyridazin-3-yl}(methyl)amino)-5-(1-{[1-(3-methoxypropyl)cyclohexyl]methyl}-5-methyl-1H-pyrazol-4-yl)-1,3-thiazole-4-carboxylic acid To a solution of the product from Step B (34 mg, 0.05 mmol, 1 eq) in 1,4-dioxane (3 mL) was added lithium hydroxide monohydrate (10.6 mg, 0.25 mmol, 5 eq) and the mixture was heated at reflux overnight. The reaction was allowed to cool to ambient temperature then the solvent removed in vacuo. The residue was diluted with water, acidified with 2N aqueous hydrochloric acid, and extracted with 3:1 dichloromethane/isopropanol. The organic extracts were dried (magnesium sulfate), concentrated in vacuo, and dried under vacuum afford the desired product as a cream solid (16.7 mg, 0.03 mmol, 51%).

HRMS-ESI (m/z) [M+H]+ calcd for $C_{32}H_{39}N_8O_3S_2$: 647.2581, found 647.2591.

Example 43: 2-({6-[(1,3-Benzothiazol-2-yl)amino]-5-methylpyridazin-3-yl}(methyl)amino)-5-(1-{[1-(3-methoxypropyl)cyclooctyl]methyl}-5-methyl-1H-pyrazol-4-yl)-1,3-thiazole-4-carboxylic acid

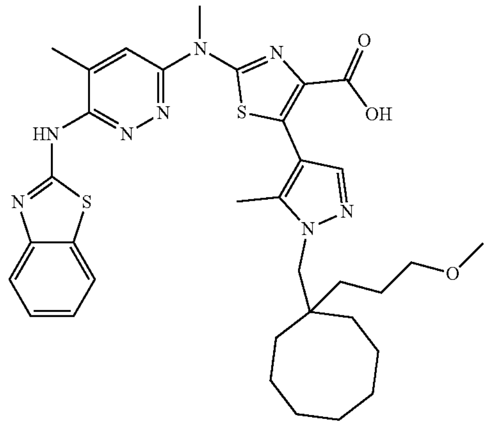 [SMILES: COCCCC1(Cn2ncc(-c3sc(N(C)c4cc(C)c(Nc5nc6ccccc6s5)nn4)nc3C(=O)O)c2C)CCCCCCC1]

Step A: ethyl 5-(1-{[1-(3-methoxypropyl)cyclooctyl]methyl}-5-methyl-1H-pyrazol-4yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a mixture of the product from Preparation 11b (106 mg, 0.17 mmol, 1 eq), the product from Preparation 10b (80.9 mg, 0.2 mmol, 1.2 eq) and potassium carbonate (69.1 mg, 0.5 mmol, 3 eq) in 3:1 tetrahydrofuran/water (4 mL) was added [1,1'-bis(diphenylphosphino)ferrocene]dichloropalladium(II)(12.2 mg, 0.02 mmol, 0.1 eq). The mixture was sparged with nitrogen (10 min) then heated at 120° C. for 1 h under microwave irradiation. The reaction was partitioned between ethyl acetate and water and the organic phase was washed with brine, dried (magnesium sulfate), and the solvent removed in vacuo. Purification by automated flash column chromatography (CombiFlash Rf, 12 g RediSep™ silica cartridge) eluting with a gradient of 0-50% ethyl acetate in iso-heptane afforded the desired product as a colourless gum (81.3 mg, 0.1 mmol, 59%).

LC/MS ($C_{42}H_{60}N_8O_4SiS_2$) 833 $[M+H]^+$; RT 1.81 (LCMS-V-B2)

$^1$H NMR (400 MHz, DMSO-d6) δ 7.92 (d, J=7.6 Hz, 1H), 7.82 (s, 1H), 7.66 (s, 1H), 7.61-7.50 (m, 2H), 7.37-7.28 (m, 1H), 5.98 (s, 2H), 4.28 (q, J=7.1 Hz, 2H), 3.96 (s, 2H), 3.93 (s, 3H), 3.83 (t, J=8.0 Hz, 2H), 3.35 (s, 3H), 2.58 (s, 3H), 2.29 (s, 3H), 1.76-1.64 (m, 9H), 1.60-1.45 (m, 5H), 1.46-1.33 (m, 6H), 1.28 (t, J=7.1 Hz, 3H), 1.03 (t, 3H), 0.00 (s, 9H).

Step B: ethyl 2-({6-[(1,3-benzothiazol-2-yl)amino]-5-methylpyridazin-3-yl}(methyl)amino)-5-(1-{[1-(3-methoxypropyl)cyclooctyl]methyl}-5-methyl-1H-pyrazol-4-yl)-1,3-thiazole-4-carboxylate A solution of the product from Step A (81.3 mg, 0.1 mmol, 1 eq) in dichloromethane (3 mL) was cooled in an ice bath then trifluoroacetic acid (0.3 mL, 4.03 mmol, 41 eq) was added and the mixture was stirred at ambient temperature for 18 h. The solvent was removed in vacuo and purification by automated flash column chromatography (CombiFlash Rf, 12 g RediSep™ silica cartridge) eluting with a gradient of 0-5% methanol in dichloromethane afforded the desired product as a white solid (81.5 mg, 0.12 mmol, >100%).

LC/MS ($C_{36}H_{46}N_8O_3S_2$) 703 $[M+H]^+$; RT 1.56 (LCMS-V-B2)

$^1$H NMR (400 MHz, DMSO-d6) 7.88 (br s, 1H), 7.73 (s, 1H), 7.56 (s, 1H), 7.50 (br s, 1H), 7.38 (t, J=7.5 Hz, 1H), 7.20 (t, J=7.6 Hz, 1H), 4.17 (q, J=7.1 Hz, 2H), 3.85 (s, 2H), 3.81 (s, 3H), 3.33 (t, J=6.5 Hz, 2H), 3.25 (s, 3H), 2.48 (s, 3H), 2.19 (s, 3H), 1.66-1.54 (m, 9H), 1.49-1.36 (m, 4H), 1.33-1.22 (m, 5H), 1.18 (t, J=7.1 Hz, 3H).

Step C: 2-({6-[(1,3-benzothiazol-2-yl)amino]-5-methylpyridazin-3-yl}(methyl)amino)-5-(1-{[1-(3-methoxypropyl)cyclooctyl]methyl}-5-methyl-1H-pyrazol-4-yl)-1,3-thiazole-4-carboxylic acid To a solution of the product from Step B (81.5 mg, 0.12 mmol, 1 eq) in 1,4-dioxane (5 mL) was added lithium hydroxide monohydrate (24.3 mg, 0.58 mmol, 5 eq) and the mixture was heated at reflux overnight. The reaction was allowed to cool to ambient temperature and the solvent removed in vacuo. The residue was diluted with water, acidified with 2N aqueous hydrochloric acid, and extracted with 3:1 dichloromethane/isopropanol. The organic extracts were dried (magnesium sulfate) and concentrated under reduced pressure to afford the desired product as a cream solid (53.6 mg, 0.08 mmol, 69%).

HRMS-ESI (m/z) [M+H]+ calcd for $C_{34}H_{43}N_8O_3S_2$: 675.2894, found 675.2890.

Example 44: 2-({6-[(1,3-Benzothiazol-2-yl)amino]-5-methylpyridazin-3-yl}[3-(morpholin-4-yl)propyl]amino)-1,3-thiazole-4-carboxylic acid

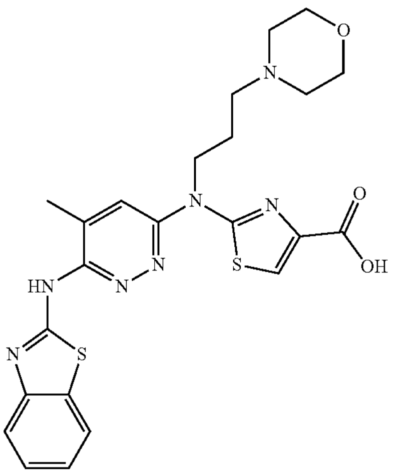 [SMILES: Cc1cc(N(CCCN2CCOCC2)c2nc(C(=O)O)cs2)nnc1Nc1nc2ccccc2s1]

Step A: ethyl 2-{[3-(morpholin-4-yl)propyl]amino}-1,3-thiazole-4-carboxylate

Ethyl bromopyruvate (2.5 mL, 17.9 mmol, 1.18 eq) was added to a suspension of 3-(morpholin-4-yl)propylthiourea (3.1 g, 15.3 mmol, 1 eq) in ethanol (50 mL) at 0° C. under a nitrogen atmosphere and the mixture was stirred for 1 h at ambient temperature. Triethylamine (4.5 mL, 30.5 mmol, 2 eq) was added the mixture was heated at 85° C. for 4 h. The solution was allowed to cool to ambient temperature and concentrated in vacuo. 10% aqueous potassium carbonate (150 mL) was added and the mixture extracted with ethyl acetate (5×100 mL). The combined organic extracts were washed with water (2×150 mL) and brine (100 mL), then dried (magnesium sulfate) and concentrated in vacuo. Purification by flash column chromatography (100 g silica) eluting with 19:1 dichloromethane/methanol (19:1) gave a solid that was triturated with heptane (50 mL), filtered, washed with heptane (50 mL) and dried under vacuum to afford the desired product as a pale brown solid (4 g, 13.4 mmol, 88%).

LC/MS ($C_{13}H_{21}N_3O_3S$) 300 $[M+H]^+$; RT 0.58 (LCMS-V-B1)

$^1H$ NMR (400 MHz, $CDCl_3$) δ 7.41 (s, 1H), 6.48 (t, 1H), 4.37 (q, J=7.1 Hz, 2H), 3.75 (t, J=4.7 Hz, 4H), 3.42 (q, J=6.0 Hz, 2H), 2.54-2.43 (m, 6H), 1.83 (p, J=6.4 Hz, 2H), 1.39 (t, J=7.1 Hz, 3H).

Step B: ethyl 2-[(6-chloro-5-methylpyridazin-3-yl)[3-(morpholin-4-yl)propyl]amino]-1,3-thiazole-4-carboxylate Sodium hydride (60% dispersion; 350 mg, 8.75 mmol, 1.31 eq) was added to a solution of the product from Step A (2 g, 6.68 mmol, 1 eq) and 3,6-dichloro-4-methylpyridazine (1.25 g, 7.67 mmol, 1.15 eq) in 1,4-dioxane (30 mL) at 0° C. under a nitrogen atmosphere and the mixture stirred for 1 h at 0° C. then for 3 h at 60° C. The solution was allowed to cool to ambient temperature then partitioned between ethyl acetate (300 mL) and saturated aqueous ammonium chloride solution (100 mL). The organic phase was successively washed with water (150 mL) and brine (100 mL), dried (magnesium sulfate), and concentrated in vacuo. Purification by flash column chromatography (50 g silica) eluting with ethyl acetate gave a brown oil. Trituration with heptane (15 mL) gave a solid that was collected by filtration, washed with heptane (20 mL) and dried under vacuum to afford the desired product as a pale brown solid (1.5 g, 3.52 mmol, 53%).

LC/MS ($C_{18}H_{24}ClN_5O_3S$) 426 $[M+H]^+$; RT 0.96 (LCMS-V-B1)

$^1H$ NMR (400 MHz, $CDCl_3$) δ 7.83 (s, 1H), 7.56 (d, J=1.1 Hz, 1H), 4.51 (t, 2H), 4.40 (q, J=7.1 Hz, 2H), 3.75 (t, J=4.6 Hz, 4H), 2.52-2.42 (m, 9H), 2.06 (p, 2H), 1.41 (t, J=7.1 Hz, 3H).

Step C: ethyl 2-({6-[(1,3-benzothiazol-2-yl)amino]-5-methylpyridazin-3-yl}[3-(morpholin-4-yl)propyl]amino)-1,3-thiazole-4-carboxylate The product from Step B (900 mg, 2.11 mmol, 1 eq) and 2-aminobenzothiazole (350 mg, 2.33 mmol, 1.1 eq) were added to a solution of tris(dibenzylideneacetone)dipalladium(0)(96.8 mg, 0.11 mmol, 0.05 eq) and Xantphos (122 mg, 0.21 mmol, 0.1 eq) in 1,4-dioxane (20 mL) under a nitrogen atmosphere and the mixture stirred. N,N-Diisopropylethylamine (1.1 mL, 6.34 mmol, 3 eq) was added and the mixture was heated in a sealed tube at 150° C. for 24 h. The solution was allowed to cool to ambient temperature and concentrated in vacuo. Purification by flash column chromatography (50 g silica) eluting with 10:1 dichloromethane/methanol gave a red/brown gum. Trituration with diethyl ether (20 mL) gave a solid that was collected by filtration, washed with diethyl ether (2×10 mL) and dried under vacuum to afford the desired product as a pale brown solid (875 mg, 1.62 mmol, 77%).

LC/MS ($C_{25}H_{29}N_7O_3S_2$) 540 $[M+H]^+$; RT 1.12 (LCMS-V-B1)

$^1H$ NMR (400 MHz, DMSO-d6) δ 11.16 (br s, 1H), 7.96 (s, 1H), 7.92 (s, 1H), 7.76 (s, 1H), 7.63-7.47 (m, 1H), 7.39 (t, 1H), 7.22 (t, J=7.5 Hz, 1H), 4.43 (t, J=7.4 Hz, 2H), 4.29 (q, J=7.1 Hz, 2H), 3.59 (t, J=5.0 Hz, 4H), 2.48 (s, 3H), 2.43-2.33 (m, 6H), 1.99-1.85 (m, 2H), 1.32 (t, J=7.1 Hz, 3H).

Step D: 2-({6-[(1,3-benzothiazol-2yl)amino]-5-methylpyridazin-3-yl}[3-(morpholin-4-yl)propyl]amino)-1,3-thiazole-4-carboxylic acid To a solution of the product from Step C (300 mg, 0.56 mmol, 1 eq) in 3:1 1,4-dioxane/water (4 mL) was added lithium hydroxide monohydrate (93.3 mg, 2.22 mmol, 4 eq) and the mixture was stirred at ambient temperature overnight. Water (5 mL) was added and the mixture was filtered through celite and washed through with further water (10 mL). The filtrate was acidified with acetic acid and stirred for 15 min, then the solids were collected by filtration, washed with water (10 mL) and drying under vacuum to afford the desired product as a yellow solid (180 mg, 0.35 mmol, 63%).

HRMS-ESI (m/z) [M−H]− calcd for $C_{23}H_{24}N_7O_3S_2$: 510.1388, found 510.1406.

Example 45: 2-({6-[(1,3-Benzothiazol-2-yl)amino]-5-methylpyridazin-3-yl}(propyl)amino)-1,3-thiazole-4-carboxylic acid

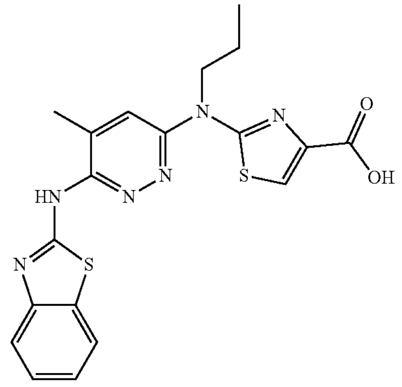 [SMILES: CCCN(c1cc(C)c(Nc2nc3ccccc3s2)nn1)c1nc(C(=O)O)cs1]

Step A: ethyl 2-(propylamino)-1,3-thiazole-4-carboxylate

Ethyl bromopyruvate (4 mL, 28.7 mmol, 1.13 eq) was added to a solution of propylthiourea (3 g, 25.4 mmol, 1 eq) in ethanol (50 mL) at 0° C. under a nitrogen atmosphere and the mixture was stirred for 1 h at ambient temperature. Triethylamine (7 mL, 50.8 mmol, 2 eq) was added the mixture was stirred for 18 h. The reaction mixture was partitioned between ethyl acetate (300 mL) and water (150 mL) and the organic phase was successively washed with water (150 mL) and brine (100 mL), dried (magnesium sulfate), and concentrated in vacuo. Purification by flash column chromatography (50 g silica) eluting with dichloromethane afforded the desired product as a pale brown oil that solidified upon standing (3.4 g, 15.9 mmol, 63%).

LC/MS ($C_9H_{14}N_2O_2S$) 215 $[M+H]^+$; RT 1.04 (LCMS-V-B1)

$^1$H NMR (400 MHz, $CDCl_3$) δ 7.42 (s, 1H), 5.63 (s, 1H), 4.37 (q, 2H), 4.40 (q, J=7.1 Hz, 2H), 3.24 (q, 2H), 1.75-1.64 (m, 2H), 1.39 (t, 3H), 1.00 (t, J=7.1 Hz, 3H).

Step B: ethyl 2-[(6-chloro-5-methylpyridazin-3-yl)(propyl)amino]-1,3-thiazole-4-carboxylate Sodium hydride (60% dispersion; 500 mg, 12.5 mmol, 1.25 eq) was added to a solution or the product from Step A (2.15 g, 10.0 mmol, 1 eq) and 3,6-dichloro-4-methylpyridazine (1.75 g, 10.7 mmol, 1.07 eq) in 1,4-dioxane (30 mL) at 0° C. under a nitrogen atmosphere and the mixture was stirred for 1 h at 0° C. then for 18 h at ambient temperature. The reaction mixture was partitioned between ethyl acetate (300 mL) and saturated aqueous ammonium chloride (150 mL) and the organic phase was successively washed with water (2×150 mL) and brine (100 mL), dried (magnesium sulfate), and concentrated in vacuo. Purification by flash column chromatography (100 g silica) eluting with dichloromethane gave a solid that was triturated with heptane (30 mL), filtered, washed with heptane (15 mL) and dried under vacuum to afford the desired product as a white solid (1.3 g, 3.81 mmol, 38%).

LC/MS ($C_{14}H_{17}ClN_4O_2S$) 341 $[M+H]^+$; RT 1.32 (LCMS-V-B1)

$^1$H NMR (400 MHz, $CDCl_3$) δ 7.82 (s, 1H), 7.39 (d, 1H), 4.47-4.35 (m, 4H), 2.48 (d, J=1.0 Hz, 3H), 1.93-1.78 (m, 2H), 1.42 (t, J=7.1 Hz, 3H), 1.05 (t, J=7.4 Hz, 3H).

Step C: ethyl 2-({6-[(1,3-benzothiazol-2-yl)amino]-5-methylpyridazin-3-yl}(propyl)amino)-1,3-thiazole-4-carboxylate The product from Step B (850 mg, 2.49 mmol, 1 eq) and 2-aminobenzothiazole (425 mg, 2.83 mmol, 1.13 eq) were added to a solution of tris(dibenzylideneacetone)dipalladium(0)(114 mg, 0.12 mmol, 0.05 eq) and Xantphos (144 mg, 0.25 mmol, 0.1 eq) in 1,4-dioxane (10 mL) under a nitrogen atmosphere and the mixture stirred. N,N-Diisopropylethylamine (1.3 mL, 7.48 mmol, 3 eq) was added and the mixture was heated in a sealed tube at 150° C. for 24 h. The solution was allowed to cool to ambient temperature and concentrated in vacuo. Purification by flash column chromatography (50 g silica) eluting with 39:1 dichloromethane/methanol gave a dark yellow solid that was triturated with methanol (15 mL), filtered, washed with methanol (15 mL) and dried under vacuum to afford the desired product as a yellow solid (915 mg, 2.01 mmol, 81%).

LC/MS ($C_{21}H_{22}N_6O_2S_2$) 455 $[M+H]^+$; RT 1.44 (LCMS-V-B1)

$^1$H NMR (400 MHz, DMSO-d6) δ 11.12 (br s, 1H), 7.96 (s, 1H), 7.92 (br s, 1H), 7.73 (s, 1H), 7.59 (br s, 1H), 7.39 (t, J=7.5 Hz, 1H), 7.22 (t, J=7.3 Hz, 1H), 4.37 (dd, J=9.0, 6.3 Hz, 2H), 4.29 (q, J=7.1 Hz, 2H), 2.48 (s, 3H), 1.74 (q, J=7.5 Hz, 2H), 1.32 (t, J=7.1 Hz, 3H), 0.96 (t, J=7.4 Hz, 3H).

Step D: 2-({6-[(1,3-benzothiazol-2-yl)amino]-5-methylpyridazin-3-yl}(propyl)amino)-1,3-thiazole-4-carboxylic acid To a solution of the product from Step C (250 mg, 0.55 mmol, 1 eq) in 3:1 1,4-dioxane/water (4 mL) was added lithium hydroxide monohydrate (92.3 mg, 2.2 mmol, 4 eq) and the mixture was stirred at ambient temperature for 18 h. Water (5 mL) was added and the solution was filtered through celite and washed through with water (10 mL). The filtrate was acidified with acetic acid to give a suspension, that was collected by filtration, washed with water (10 mL) and dried under vacuum to afford the desired product as a pale yellow solid (185 mg, 0.43 mmol, 79%).

HRMS-ESI (m/z) [M−H]− calcd for $C_{19}H_{17}N_6O_2S_2$: 425.0860, found 425.0867.

Example 46: 2-({6-[(1,3-Benzothiazol-2-yl)amino]-5-methylpyridazin-3-yl}[3-(diethylamino)propyl]amino)-1,3-thiazole-4-carboxylic acid

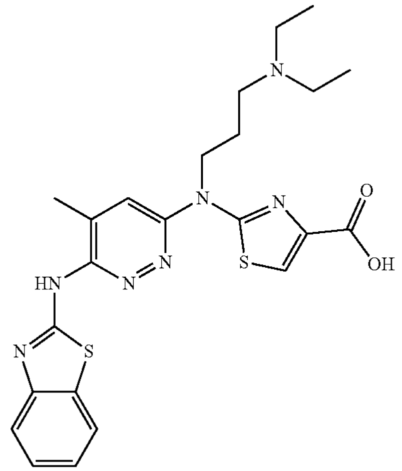 [SMILES: CCN(CC)CCCN(c1cc(C)c(Nc2nc3ccccc3s2)nn1)c1nc(C(=O)O)cs1]

Step A: ethyl 2-[[3-(diethylamino)propyl]amino]-1,3-thiazole-4-carboxylate

Ammonia (2M in isopropanol; 60 mL, 0.12 mol, 3.45 eq) was added to a solution of 3-(diethylamino)propyl isothiocyanate (6 g, 34.8 mmol, 1 eq) in isopropanol (15 mL) at 0° C. and the mixture stirred for 1 h at 0° C. and then 18 h at ambient temperature. The suspension was concentrated in vacuo then triturated with heptane (50 mL), filtered, and washed with heptane (2×25 mL). Ethanol (150 mL) and ethyl bromopyruvate (5 mL, 39.8 mmol, 1.14 eq) were added and the mixture was stirred under a nitrogen atmosphere for 1 h. Triethylamine (10 mL, 69.7 mmol, 2 eq) was added and the mixture was heated at 85° C. for 4 h. The solution was allowed to cool to ambient temperature and concentrated in vacuo. Purification by flash column chromatography (100 g silica) eluting with 19:1 dichloromethane/methanol afforded the desired product as a dark brown gum (3.95 g, 13.8 mmol, 40%).

LC/MS ($C_{13}H_{23}N_3O_2S$) 286 $[M+H]^+$; RT 0.78 (LCMS-V-B1)

$^1$H NMR (400 MHz, $CDCl_3$) δ 7.39 (s, 1H) 7.05 (s, 1H), 4.37 (q, J=7.1 Hz, 2H), 3.42 (td, J=6.2, 3.1 Hz, 2H), 2.64-2.51 (m, 6H), 1.84-1.76 (m, 2H), 1.39 (t, J=7.1 Hz, 3H), 1.06 (t, J=7.1 Hz, 6H).

Step B: ethyl 2-[(6-chloro-5-methylpyridazin-3-yl)[3-(diethylamino)propyl]amino]-1,3-thiazole-4-carboxylate Sodium hydride (60% dispersion; 700 mg, 17.5 mmol, 1.26 eq) was added to a solution of the product from Step A (3.95 g, 13.8 mmol, 1 eq) and 3,6-dichloro-4-methylpyridazine (2.5 g, 15.3 mmol, 1.11 eq) in 1,4-dioxane (50 mL) at 0° C. under a nitrogen atmosphere and the mixture stirred for 1 h at 0° C. then for 18 h at ambient temperature. The reaction was partitioned between ethyl acetate (300 mL) and water (150 mL) and the organic phase was successively washed with water (150 mL) and brine (100 mL), dried (magnesium sulfate), and concentrated in vacuo. Purification by flash column chromatography (100 g silica) eluting with 19:1 dichloromethane/methanol afforded the desired product as a brown gum (2.3 g, 5.58 mmol, 40%).

LC/MS ($C_{18}H_{26}ClN_5O_2S$) 412 $[M+H]^+$; RT 1.00 (LCMS-V-B1)

$^1$H NMR (400 MHz, $CDCl_3$) δ 7.80 (s, 1H), 7.63 (d, J=1.1 Hz, 1H), 4.47 (q, 2H), 4.37 (q, J=7.1 Hz, 2H), 2.64-2.54 (m, 6H), 2.45 (d, J=0.9 Hz, 3H), 1.98 (q, 2H), 1.39 (t, J=7.1 Hz, 3H), 1.06 (t, J=7.1 Hz, 6H).

Step C: ethyl 2-({6-[(1,3-benzothiazol-2-yl)amino]-5-methylpyridazin-3-yl}[3-(diethylamino)propyl]amino)-1,3-thiazole-4-carboxylate The product from Step B (2.1 g, 5.1 mmol, 1 eq) and 2-aminobenzothiazole (850 mg, 5.66 mmol, 1.11 eq) were added to a solution or tris(dibenzylideneacetone)dipalladium(0)(233 mg, 0.25 mmol, 0.05 eq) and Xantphos (295 mg, 0.51 mmol, 0.1 eq) in 1,4-dioxane (20 mL) under a nitrogen atmosphere and the mixture stirred. N,N-Diisopropylethylamine (2.7 mL, 15.3 mmol, 3 eq) was added and the mixture was heated in a sealed tube at 150° C. for 24 h. The solution was allowed to cool to ambient temperature and concentrated in vacuo. Purification by flash column chromatography (100 g silica) eluting with a gradient of 5-10% methanol in dichloromethane gave a dark yellow gum that was triturated with diethyl ether (10 mL), filtered, washed with diethyl ether (10 mL) and dried under vacuum to afford the desired product as a yellow solid (240 mg, 0.46 mmol, 9%).

LC/MS ($C_{25}H_{31}N_7O_2S_2$) 526 $[M+H]^+$; RT 1.18 (LCMS-V-B1)

$^1$H NMR (400 MHz, DMSO-d6) δ 11.78 (br s, 1H), 7.88-7.67 (m, 4H), 7.44-7.34 (m, 1H), 7.26-7.18 (m, 1H), 4.49 (s, 2H), 4.36 (q, J=7.1 Hz, 2H), 3.31-3.22 (m, 2H), 3.22-3.12 (m, 4H), 2.52-2.39 (m, 5H), 1.39 (t, J=7.1 Hz, 9H).

Step D: 2-({6-[(1,3-benzothiazol-2-yl)amino]-5-methylpyridazin-3-yl}[3-(diethylamino)propyl]amino)-1,3-thiazole-4-carboxylic acid To a solution of the product from Step C (218) mg, 0.38 mmol, 1 eq) in 3:1 1,4-dioxane/water (4 mL) was added lithium hydroxide monohydrate (63.9 mg, 1.52 mmol, 4 eq) and the mixture was stirred at ambient temperature for 18 h. Water (5 mL) was added and the mixture was filtered through celite, washing through with water (10 mL). The filtrate was acidified with acetic acid to give a solid that was collected by filtration, washed with water (10 mL) and dried under vacuum to afford the desired product as a pale yellow solid (105 mg, 0.21 mmol, 55%).

HRMS-ESI (m/z) [M−H]− calcd for $C_{23}H_{26}N_7O_2S_2$: 496.1595, found 496.1614.

Example 47: 2-({6-[(1,3-Benzothiazol-2-yl)amino]-5-methylpyridazin-3-yl}(3-methoxypropyl)amino)-1,3-thiazole-4-carboxylic acid

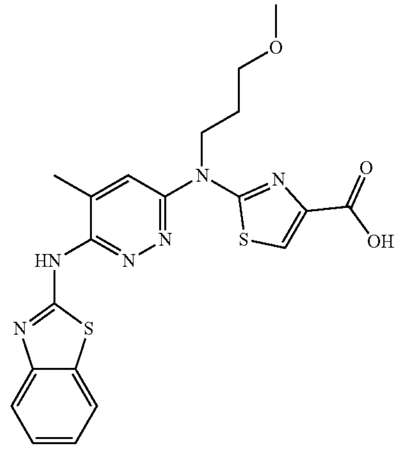 [SMILES: COCCCN(c1cc(C)c(Nc2nc3ccccc3s2)nn1)c1nc(C(=O)O)cs1]

To a solution of the product from Preparation 11c, Step C (300 mg, 0.62 mmol, 1 eq) in 3:1 1,4-dioxane/water (4 mL) was added lithium hydroxide monohydrate (104 mg, 2.48 mmol, 4 eq) and the mixture was stirred at ambient temperature overnight. Water (15 mL) was added and the mixture was acidified with acetic acid to give a solid that was collected by filtration, washed wall water (25 mL) and dried under vacuum to afford the desired product as an orange solid (245 mg, 0.54 nmol, 87%).

HRMS-ESI (m/z) [M+H]+ calcd for $C_{20}H_{21}N_6O_3S_2$: 457.1111, found 457.1119.

Example 48: 2-[[4,5-Dimethyl-6-[(4-methyl-1,3-benzothiazol-2-yl)amino]pyridazin-3-yl]amino]thiazole-4-carboxylic acid

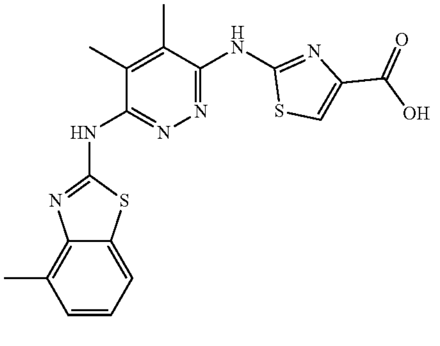 [SMILES: Cc1c(Nc2nc(C(=O)O)cs2)nnc(Nc2nc3c(C)cccc3s2)c1C]

Step A: N-(6-chloro-4,5-dimethyl-pyridazin-3-yl)-4-methyl-1,3-benzothiazol-2-amine To 611 mg of 6-chloro-4,5-dimethylpyridazin-3-amine (3.9 mmol, 1 eq.) and 884 mg of 2-bromo-4-methyl-1,3-benzothiazole (3.9 mmol, 1 eq.) in 13 mL of 1,4-dioxane was added 1.5 g of sodium hydride (60 w %, 37.5 mmol, 9.6 eq.) and the mixture was stirred at reflux for 1 h. After cooling, the reaction was poured onto ice-water and acidified with 2 N HCl. The precipitation was filtered off and washed with $NaHCO_3$ solution and dried to give 810 mg (67%) of the desired product.

LC-MS-ESI (m/z): $[M+H]^+$ calcd for $C_{14}H_{14}ClN_4S$: 305, found 305.

Step B: ethyl 2-[[4,5-dimethyl-6-[(4-methyl-1,3-benzothiazol-2-yl)amino]pyridazin-3-yl]amino]thiazole-4-carboxylate The mixture of 600 mg of the product from Step A (1.96 mmol, 1 eq.), 730 mg of ethyl 2-aminothiazole-4-carboxylate (4.24 mmol, 2.1 eq.), 78 mg of $Pd_2(dba)_3$ (0.085 mmol, 0.04 eq.), 124 mg of 4,5-bis(diphenylphosphino)-9,9-dimethylxanthene (0.21 mmol, 0.1 eq.) and 2.8 mL of DIPEA (8 eq.) in 16 mL of 1,4-dioxane was stirred at 185° C. in a microwave reactor for 1.5 h. After cooling, the volatiles were removed and the crude intermediate was purified via flash column chromatography using heptane and EtOAc as eluents to give 328 mg (38%) of the desired product.

$^1H$ NMR (500 MHz, DMSO-$d_6$) δ ppm 11.00/10.81 (s+brs, 2H), 7.94 (s, 1H), 7.72 (brs, 1H), 7.19 (d, 1H), 7.10 (t, 1H), 4.29 (q, 2H), 2.57 (brs, 3H), 2.39/2.36 (s+s, 6H), 1.31 (t, 3H); $^{13}C$ NMR (125 MHz, DMSO-$d_6$) δ ppm 126.9, 122.4, 121.7, 119.4, 60.8, 18.4, 14.7; HRMS-ESI (m/z): $[M+H]^+$ calcd for $C_{20}H_{20}N_6O_2S_2$: 441.1167, found: 441.1165.

Step C: 2-[[4,5-dimethyl-6-[(4-methyl-1,3-benzothiazol-2-yl)amino]pyridazin-3-yl]amino]thiazole-4-carboxylic acid The mixture of the product from Step B, $LiOH{\times}H_2O$, water and 1,4-dioxane was stirred at reflux for 1 h. After cooling and concantration, 1 N HCl was added and the precipitation was filtered off, purified further by reverse phase preparative chromatography to give the desired product.

HRMS-ESI (m/z): $[M+H]^+$ calcd for $C_{18}H_{17}N_6O_2S_2$: 413.0854, found: 413.0855.

Example 49: 2-({6-[(1,3-Benzothiazol-2-yl)amino]-5-methylpyridazin-3-yl}(3-hydroxypropyl)amino)-1,3-thiazole-4-carboxylic acid

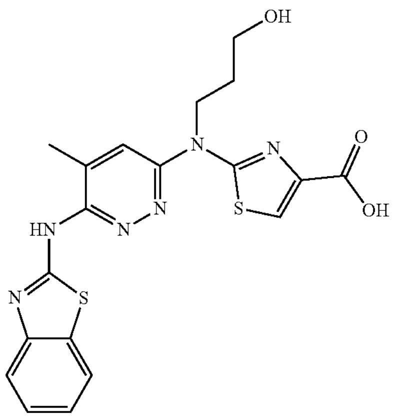 [SMILES: Cc1cc(N(CCCO)c2nc(C(=O)O)cs2)nnc1Nc1nc2ccccc2s1]

Step A: ethyl 2-[(6-chloro-5-methylpyridazin-3-yl)(3-hydroxypropyl)amino]-1,3-thiazole-4-carboxylate Boron tribromide (1M in dichloromethane; 16 mL, 16.2 mmol, 2 eq) was added to a solution of the product from Preparation 11c, Step B (3 g, 8.09 mmol, 1 eq) in dichloromethane (50 mL) at −78° C. under a nitrogen atmosphere. The mixture was stirred for 1 h at −78° C. then heated at 50° C. for 1 h. The suspension was allowed to cool to ambient temperature then partitioned between dichloromethane (250 mL) and saturated aqueous sodium hydrogen carbonate (150 mL). The organic phase was washed sequentially with water (2×150 mL) and brine (100 mL), dried (magnesium sulfate), and concentrated in vacuo. Purification by flash column chromatography (50 g silica) eluting with 39:1 dichloromethane/methanol gave a solid that was triturated with diethyl ether (15 mL), filtered, washed with diethyl ether (20 mL) and dried under vacuum afford the desired product as an orange solid (900 mg, 2.52 mmol, 31%).

LC/MS ($C_{14}H_{17}ClN_4O_3S$) 357 $[M+H]^+$; RT 1.15 (LCMS-V-B1)

$^1$H NMR (400 MHz, DMSO-d6) δ 8.04 (s, 1H), 7.87 (dd, J=18.1, 1.1 Hz, 1H), 4.71 (td, J=5.4, 1.1 Hz, 1H), 4.46 (t, 2H), 4.29 (q, J=7.1 Hz, 2H), 3.50 (q, J=5.9 Hz, 2H), 2.43 (dd, J=2.6, 0.9 Hz, 3H), 1.89 (p, J=6.5 Hz, 2H), 1.31 (t, J=7.1 Hz, 3H).

Step B: ethyl 2-({6-[(1,3-benzothiazol-2-yl)amino]-5-methylpyridazin-3-yl}(3-hydroxypropyl)amino)-1,3-thiazole-4-carboxylate The product from Step A (500 mg, 1.4 mmol, 1 eq) and 2-aminobenzothiazole (240 mg, 1.6 mmol, 1.14 eq) were added to a solution of tris(dibenzylideneacetone)dipalladium(0)(64.2 mg, 0.07 mmol, 0.05 eq) and Xantphos (81.1 mg, 0.14 mmol, 0.1 eq) in 1,4-dioxane (10 mL) under a nitrogen atmosphere and the mixture stirred. N,N-Diisopropylethylamine (0.75 mL, 4.2 mmol, 3 eq) was added and the mixture was heated in a sealed tube at 150° C. for 24 h. The solution was allowed to cool to ambient temperature and concentrated in vacuo. Purification by flash column chromatography (50 g silica) eluting with 19:1 dichloromethane/methanol gave a red/orange gum that was triturated with diethyl ether (15 mL), filtered, washed with diethyl ether (2×10 mL) and dried under vacuum to afford the desired product as an orange solid (490 mg, 0.94 mmol, 67%).

LC/MS ($C_{21}H_{22}N_6O_3S_2$) 471 $[M+H]^+$; RT 1.31 (LCMS-V-B1)

$^1$H NMR (400 MHz, DMSO-d6) δ 11.12 (br s, 1H), 7.98 (s, 1H), 7.92 (br s, 1H), 7.72 (s, 1H), 7.63 (br s, 1H), 7.40 (t, J=7.6 Hz, 1H), 7.23 (t, 1H), 4.74 (t, J=5.4 Hz, 1H), 4.46 (t, J=7.1 Hz, 2H), 4.30 (q, J=7.1 Hz, 2H), 3.54-3.46 (m, 2H), 2.48 (s, 3H), 1.90 (p, J=6.5 Hz, 2H), 1.32 (t, J=7.1 Hz, 3H).

Step C: 2-({6-[(1,3-benzothiazol-2-yl)amino]-5-methylpyridazin-3-yl}(3-hydroxypropyl)amino)-1,3-thiazole-4-carboxylic acid To a solution of the product from Step B (275 mg, 0.53 mmol, 1 eq) in a 3:1 mixture of 1,4-dioxane/water (4 mL) was added lithium hydroxide monohydrate (88.3 mg, 2.1 mmol, 4 eq) and the mixture was stirred at ambient temperature for 18 h. Water (15 mL) was added and the mixture was filtered through celite. The filtrate was acidified with acetic acid to give a solid that was collected by filtration, washed with water (30 mL) and dried under vacuum to afford the desired product as a yellow solid (190 mg, 0.43 mmol, 82%).

HRMS-ESI (m/z) [M+H]+ calcd for $C_{19}H_{19}N_6O_3S_2$: 443.0955, found 443.0996.

Example 50: 2-[[6-(1,3-Benzothiazol-2-ylamino)-5-methyl-pyridazin-3-yl]-methyl-amino]-5-[3-[4-[3-(dimethylamino)prop-1-ynyl]-2-fluoro-phenoxy]propyl]thiazole-4-carboxylic acid

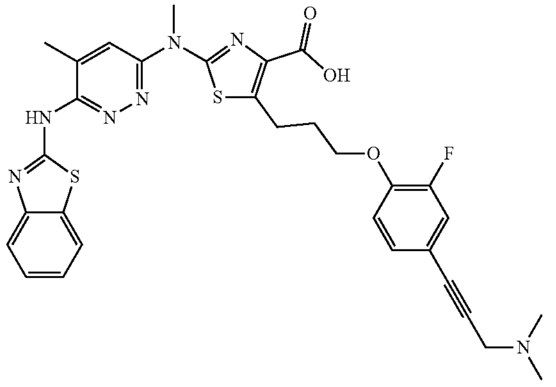 [SMILES: Cc1cc(N(C)c2nc(C(=O)O)c(CCCOc3ccc(C#CCN(C)C)cc3F)s2)nnc1Nc1nc2ccccc2s1]

Step A: ethyl 5-[3-[4-[3-(dimethylamino)prop-1-ynyl]-2-fluoro-phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation General Procedure starting from Preparation 5g and Preparation 6b as the appropriate phenol, the desired product was obtained.

$^1$H NMR (500 MHz, DMSO-$d_6$) δ ppm 7.84 (d, 1H), 7.67 (s, 1H), 7.47 (d, 1H), 7.44 (t, 1H), 7.33 (dd, 1H), 7.25 (t, 1H), 7.22 (dd, 1H), 7.16 (t, 1H), 5.86 (s, 2H), 4.26 (q, 2H), 4.15 (t, 2H), 3.77 (s, 3H), 3.72 (t, 2H), 3.49 (brs, 2H), 3.27 (t, 2H), 2.46 (s, 3H), 2.27 (s, 6H), 2.13 (qn, 2H), 1.29 (t, 3H), 0.92 (t, 2H), −0.11 (s, 9H); $^{13}$C NMR (125 MHz, DMSO-$d_6$) δ ppm 129.0, 127.2, 123.5, 123.2, 119.2, 117.7, 115.5, 111.9, 72.8, 68.5, 66.7, 60.7, 48.2, 44.0, 35.3, 31.1, 23.2, 17.9, 17.8, 14.6, −0.9; HRMS-ESI (m/z): $[M+H]^+$ calcd for $C_{39}H_{49}FN_7O_4S_2Si$: 790.3035, found 790.3023.

Step B: 2-[[6-(1,3-benzothiazol-2-ylamino)-5-methyl-pyridazin-3-yl]-methyl-amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate ethyl ester, the desired product was obtained.

HRMS-ESI (m/z): $[M+H]^+$ calcd for $C_{31}H_{31}FN_7O_3S_2$: 632.1908, found 632.1913.

Example 51: 2-({6-[(1,3-Benzothiazol-2-yl)amino]-5-methyl-4-[3-(4-methylpiperazin-1-yl)propyl]pyridazin-3-yl}amino)-1,3-thiazole-4-carboxylic acid

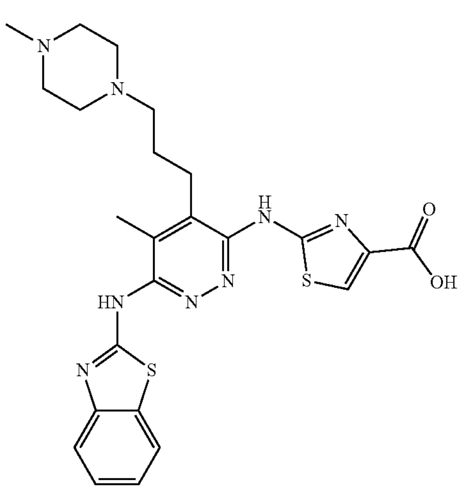 [SMILES: Cc1c(Nc2nc3ccccc3s2)nnc(Nc2nc(C(=O)O)cs2)c1CCCN1CCN(C)CC1]

Step A: ethyl 2-({6-[(1,3-benzothiazol-2-yl)amino]-4-[3-(benzyloxy)propyl]-5-methylpyridazin-3-yl}amino)-1,3-thiazole-4-carboxylate To an oven-dried microwave vial was added the product from Preparation 9ma (500 mg, 1.18 mmol, 1 eq), ethyl 2-amino-1,3-thiazole-4-carboxylate (284 mg, 1.65 mmol, 1.4 eq), cesium carbonate (575 mg, 1.76 mmol, 1.5 eq), Xantphos (68.1 mg, 0.12 mmol, 0.1 eq) and tris(dibenzylideneacetone)dipalladium(0)(53.9 mg, 0.06 mmol 0.05 eq). The vessel was evacuated and flushed with nitrogen (×3), and then alpha,alpha,alpha-trifluorotoluene (20 mL) was added. The mixture was sparged with nitrogen (10 min) then heated at 180° C. for 1 h under microwave irradiation. The reaction was concentrated in vacuo and purification by automated flash column chromatography (CombiFlash Rf, 40 g RediSep™ silica cartridge) eluting with a gradient of 0-70% ethyl acetate in iso-heptane afforded the desired product as a yellow solid (336 mg, 0.6 mmol, 51%).

LC/MS ($C_{28}H_{28}N_6O_3S_2$) 561 $[M+H]^+$; RT 1.53 (LCMS-V-B1)

$^1H$ NMR (400 MHz, DMSO-d6) δ 11.08 (br s, 1H), 7.95 (d, 1H), 7.88 (br s, 1H), 7.40-7.33 (m, 6H), 7.32-7.26 (m, 1H), 7.20 (t, 1H), 4.51 (s, 2H), 4.30 (q, J=7.1 Hz, 2H), 3.54 (t, J=6.2 Hz, 2H), 2.96 (t, J=7.8 Hz, 2H), 2.39 (s, 3H), 1.76 (p, 2H), 1.32 (t, J=7.1 Hz, 3H).

Step B: ethyl 2-({6-[(1,3-benzothiazol-2-yl)amino]-4-(3-hydroxypropyl)-5-methylpyridazin-3-yl}amino)-1,3-thiazole-4-carboxylate To a cooled solution of the product from Step A (330 mg, 0.59 mmol, 1 eq) in anhydrous dichloromethane (15 mL) was added boron trichloride (1M in dichloromethane; 1.18 mL, 1.18 mmol, 2 eq) dropwise and the mixture was stirred for 3 h. The reaction was cooled to 0° C. and quenched by the addition of saturated aqueous sodium bicarbonate. The mixture was diluted with dichloromethane and the layers were separated. The organic phase was washed successively with water and brine, dried (magnesium sulfate), and concentrated in vacuo to afford the desired product (301 mg, 0.64 mmol, >100%) as a mixture with the corresponding methyl ester that was used directly in the next step without further purification.

LC/MS ($C_{21}H_{21}N_6O_3S_2$) 471 $[M+H]^+$; RT 1.295 (LCMS-V-B1).

Step C: ethyl 2-{[4-(3-hydroxypropyl)-5-methyl-6-{[(2Z)-3-{[2-(trimethylsilyl)ethoxy]methyl}-2,3-dihydro-1,3-benzothiazol-2-ylidene]amino}pyridazin-3-yl]amino}-1,3-thiazole-4-carboxylate To a cooled solution of the product from Step B (300 mg, 0.64 mmol, 1 eq) in dichloromethane (15 mL) was added 2-(trimethylsilyl)ethoxymethyl chloride (0.12 mL, 0.7 mmol, 1.1 eq), diisopropylethylamine (0.22 mL, 1.28 mmol, 2 eq) and DMAP (3.89 mg, 0.03 mmol, 0.05 eq). The mixture was stirred for 2 h at ambient temperature then cooled to 0° C. and quenched by the addition of aqueous sodium bicarbonate. The layers were separated and the organic phase was washed with water followed by brine, dried (magnesium sulfate), and concentrated in vacuo. Purification by automated flash column chromatography (CombiFlash Rf, 24 g RediSep™ silica cartridge) eluting with a gradient of 0-70% ethyl acetate in iso-heptane afforded the desired product as an orange solid (105 mg, 0.17 mmol, 27%) that was found to be a mixture with the corresponding methyl ester. The mixture was used directly in the next step without further purification.

LC/MS ($C_{27}H_{36}N_6O_4SiS_2$) 601 $[M+H]^+$; RT 1.59 (LCMS-V-B1)

Step D: ethyl 2-{[5-methyl-1-(3-oxopropyl)-6-{[(2Z)-3-{[2-(trimethylsilyl)ethoxy]methyl}-2,3-dihydro-1,3-benzothiazol-2-ylidene]amino}pyridazin-3-yl]amino}-1,3-thiazole-4-carboxylate To an oven-dried flask was added dimethyl sulfoxide (29.6 μL, 0.42 mmol, 2.5 eq) in dichloromethane (5 mL) and the stirred solution was cooled to −78° C. Oxalyl chloride solution (2M; 91.5 μL, 0.18 mmol, 1.1 eq) was added dropwise and the mixture was stirred for 1 h. A solution of the product from Step C (100 mg, 0.17 mmol, 1 eq) in dichloromethane (5 mL) was added dropwise and the resultant mixture was stirred at −78° C. for 1 h. Triethylamine (0.14 mL, 1 mmol, 6 eq) was added and the mixture was allowed to warm to 0° C. over 1 h. The reaction was quenched with water (10 mL), diluted with sodium bicarbonate (10 mL) and extracted with dichloromethane (2×50 mL). The combined organic extracts were washed with brine (50 mL), dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the desired product as an orange glass (68 mg, 0.11 mmol, 68%) that was found to be a mixture with the corresponding methyl ester and was used directly in the next step without further purification.

LC/MS ($C_{27}H_{34}N_6O_4SiS_2$) 599 [M+H]$^+$; RT 1.62 (LCMS-V-B1).

Step E: ethyl 2-({6-[(1,3-benzothiazol-2-yl)amino]-5-methyl-4-[3-(4-methylpiperazin-1-yl)propyl]pyridazin-3-yl}amino)-1,3-thiazole-4-carboxylate To a solution of the product from Step D (68 mg, 0.11 mmol, 1 eq) in 3:1 methanol/acetic acid (8 mL) was added 1-methylpiperazine (25.2 μL, 0.23 mmol, 2 eq) followed by sodium cyanoborohydride (14.3 mg, 0.23 mmol, 2 eq) and the mixture was stirred at ambient temperature for 40 min. The reaction was quenched with by the addition of 1M aqueous sodium hydroxide and the mixture was extracted with dichloromethane (3×50 mL). The combined organic extracts were washed with water followed by brine (50 mL), dried (magnesium sulfate) and concentrated in vacuo. The residue was dissolved in dichloromethane (5 mL), trifluoroacetic acid (1 mL) was added, and the mixture was stirred for 1 h. The mixture was diluted with dichloromethane (20 mL) and washed with 1M aqueous sodium hydroxide (20 mL). The organic phase was washed with brine, dried (magnesium sulfate) and concentrated in vacuo. Purification by automated flash column chromatography (CombiFlash Rf, 12 g RediSep™ silica cartridge) eluting with a gradient of 0-20% 7N methanolic ammonia in dichloromethane afforded the desired product as an orange glass (40 mg, 0.07 mmol 64%) that was found to be a mixture with the corresponding methyl ester and was used directly in the next step without further purification.

LC/MS ($C_{26}H_{32}N_8O_2S_2$) 553 [M+H]$^+$; RT 1.17 (LCMS-V-B1).

Step F: 2-({6-[(1,3-benzothiazol-2-yl)amino]-5-methyl-4-[3-(4-methylpiperazin-1-yl)propyl]pyridazin-3-yl}amino)-1,3-thiazole-4-carboxylic acid To a solution of the product of Step E (40 mg, 0.07 mmol, 1 eq) in 1,4-dioxane (5 mL) was added 2M aqueous lithium hydroxide (0.14 mL, 0.14 mmol, 2 eq) and the mixture was heated at reflux for 1 h. The reaction was concentrated in vacuo then hydrochloric acid (4M in 1,4-dioxane) was added and the mixture was stirred for 1 h. The mixture was concentrated in vacuo and triturated with diethyl ether, filtered, washed with diethyl ether and dried under vacuum to afford the desired product as a dark yellow solid (14.4 mg, 0.03 mmol, 38%) [as a bis-hydrochloric acid salt].

HRMS-ESI (m/z) [M+H]+ calcd for $C_{24}H_{29}N_8O_2S_2$: 525.1849, found 525.1888.

Example 52: 5-{1-[(Adamantan-1-yl)methyl]-5-methyl-1H-pyrazol-4-yl}-2-({6-[(1,3-benzothiazol-2-yl)amino]-5-methylpyridazin-3-yl}(3-methoxypropyl)amino)-1,3-thiazole-4-carboxylic acid

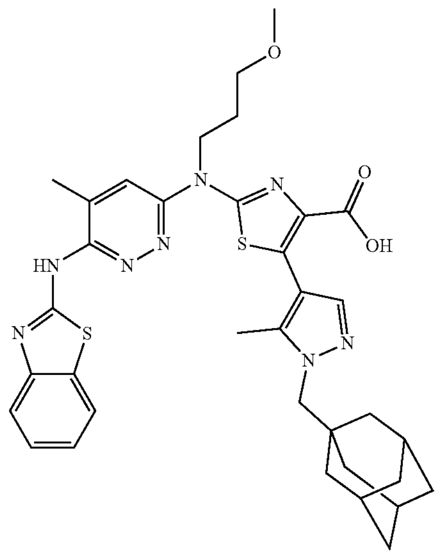 [SMILES: COCCCN(c1cc(C)c(Nc2nc3ccccc3s2)nn1)c1nc(C(=O)O)c(-c2cnn(CC34CC5CC(CC(C5)C3)C4)c2C)s1]

Step A: ethyl 5-{1-[(adamantan-1-yl)methyl]-5-methyl-1H-pyrazol-4-yl}-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a mixture of the product from Preparation 11c (100 mg, 0.14 mmol, 1 eq), the product from Preparation 10a (61.6 mg, 0.17 mmol, 1.2 eq) and potassium carbonate (59.8 mg, 0.43 mmol, 3 eq) in 4:1 tetrahydrofuran/water (5 mL) was added [1,1'-bis(diphenylphosphino)ferrocene]dichloropalladium(II)(10.6 mg, 0.01 mmol, 0.1 eq). The mixture was sparged with nitrogen (10 min) then heated at 120° C. for 1 h under microwave irradiation. The reaction was diluted with ethyl acetate, washed with water followed by brine, dried (magnesium sulfate), and concentrated in vacuo. Purification by automated flash column chromatography (CombiFlash Rf, 12 g RediSep™ silica cartridge) eluting with a gradient or 0-50% ethyl acetate in iso-heptane afforded the desired product as a cream foam (89.2 mg, 0.11 mmol, 73%).

LC/MS ($C_{43}H_{58}N_8O_4SiS_2$) 843 [M+H]$^+$; RT 1.88 (LCMS-V-B2)

$^1$H NMR (400 MHz, DMSO-d6) δ 7.82 (dd, J=7.7, 1.0 Hz, 1H), 7.70 (d, J=1.1 Hz, 1H), 7.52 (s, 1H), 7.48-7.40 (m, 2H), 7.23 (ddd, J=8.3, 7.0, 1.5 Hz, 1H), 5.87 (s, 2H), 4.44 (t, J=7.2 Hz, 2H), 4.14 (q, J=7.1 Hz, 2H), 3.78 (s, 2H), 3.72 (t, 2H), 3.44 (t, J=6.0 Hz, 2H), 3.25 (s, 3H), 2.45 (s, 3H), 2.19 (s, 3H), 2.06-1.91 (m, 5H), 1.72-1.54 (m, 12H), 1.14 (t, J=7.1 Hz, 3H), 0.91 (t, 2H), −0.13 (s, 9H).

Step B: ethyl 5-{1-[(adamantan-1-yl)methyl]-5-methyl-1H-pyrazol-4-yl}-2-({6-[(1,3-benzothiazol-2-yl)amino]-5-methylpyridazin-3-yl}(3-methoxypropyl)amino)-1,3-thiazole-4-carboxylate A solution of the product from Step A (89 mg, 0.11 mmol, 1 eq) in dichloromethane (5 mL) was cooled in an ice bath and trifluoroacetic acid (0.5 mL, 6.71 mmol, 64 eq) was added. The mixture was allowed to warm to ambient temperature and stirred overnight. The reaction was diluted with diluted with dichloromethane, washed with saturated aqueous sodium bicarbonate, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (63.2 mg, 0.09 mmol, 84%).

LC/MS ($C_{34}H_{44}N_8O_3S_2$) 713 $[M+H]^+$; RT 1.48 (LCMS-V-B1)

$^1H$ NMR (400 MHz, DMSO-d6) δ 11.10 (br s, 1H), 7.93 (br s, 1H), 7.71 (br s+s, 2H), 7.54 (s, 1H), 7.38 (t, 1H), 7.25-7.16 (m, 1H), 4.44 (t, J=7.2 Hz, 2H), 4.16 (q, J=7.1 Hz, 2H), 3.79 (s, 2H), 3.46 (t, J=6.0 Hz, 2H), 3.26 (s, 3H), 2.48 (s, 3H), 2.20 (s, 3H), 2.07-1.97 (m, 5H), 1.72-1.56 (m, 12H), 1.16 (t, J=7.1 Hz, 3H).

Step C: 5-{1-[(adamantan-1yl)methyl]-5-methyl-1H-pyrazol-4-yl}-2-({6-[(1,3-benzothiazol-2-yl)amino]-5-methylpyridazin-3-yl}(3-methoxypropyl)amino)-1,3-thiazole-4-carboxylic acid To a solution of the product from Step B (63 mg, 0.09 mmol, 1 eq) in 1,4-dioxane (5 mL) was added lithium hydroxide monohydrate (18.5 mg, 0.44 mmol, 5 eq) and the mixture was heated at reflux overnight. The reaction was allowed to cool to ambient temperature then concentrated in vacuo. The residue was triturated with water and the solids collected by filtration, washed with water and dried under vacuum afford the desired product as a yellow solid (11.5 mg, 0.02 mmol, 19%) [as a lithium salt].

HRMS-ESI (m/z) [M+H]+ calcd for $C_{35}H_{41}N_8O_3S_2$: 685.2738, found 685.2753.

Example 53: 5-{1-[(Adamantan-1-yl)methyl]-5-methyl-1H-pyrazol-4-yl}-2-({6-[(1,3-benzothiazol-2-yl)amino]-5-cyclopropylpyridazin-3-yl}(methyl)amino)-1,3-thiazole-4-carboxylic acid

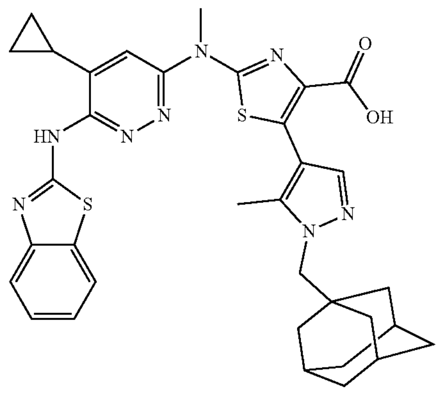 [SMILES: Cc1c(-c2sc(N(C)c3cc(C4CC4)c(Nc4nc5ccccc5s4)nn3)nc2C(=O)O)cnn1CC12CC3CC(CC(C3)C1)C2]

Step A: ethyl 5-{1-[(adamantan-1-yl)methyl]-5-methyl-1H-pyrazol-4-yl}-2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-1,3-thiazole-4-carboxylate To a mixture of the product from Preparation 11d (149 mg, 0.23 mmol, 1 eq), the product from Preparation 10a (96.3 mg, 0.27 mmol, 1.2 eq) and potassium carbonate (93.4 mg, 0.68 mmol, 3 eq) in 5:2 tetrahydrofuran/water (7 mL) was added [1,1'-bis(diphenylphosphino)ferrocene]dichloropalladium(II)(16.5 mg, 0.02 mmol, 0.1 eq). The mixture was sparged with nitrogen (10 min) then heated at 120° C. for 1 h under microwave irradiation. The reaction mixture was partitioned between ethyl acetate and water and the organic phase was washed with brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a white foam (130 mg, 0.16 mmol, 71%).

LC/MS ($C_{42}H_{54}N_8O_3SiS_2$) 811 $[M+H]^+$; RT 1.64 (LCMS-V-B1)

$^1H$ NMR (400 MHz, DMSO-d6) δ 7.81 (dd, J=7.6, 1.0 Hz, 1H), 7.52 (s, 1H), 7.49-7.40 (m, 2H), 7.23 (ddd, J=8.3, 7.0, 1.4 Hz, 1H), 7.10 (s, 1H), 5.88 (s, 2H), 4.15 (q, J=7.1 Hz, 2H), 3.80 (s, 3H), 3.79 (s, 2H), 3.70 (t, 2H), 2.72-2.62 (m, 1H), 2.18 (s, 3H), 2.01-1.92 (m, 3H), 1.71-1.54 (m, 12H), 1.21-1.13 (m, 5H), 1.12-1.07 (m, 2H), 0.90 (t, 3H), −0.13 (s, 9H).

Step B: ethyl 5-{1-[(adamantan-1yl)methyl]-5-methyl-1H-pyrazol-4-yl}-2-({6-[(1,3-benzothiazol-2-yl)amino]-5-cyclopropylpyridazin-3-yl}(methyl)amino]-1,3-thiazole-4-carboxylate Trifluoroacetic acid (1 mL, 13.4 mmol, 78.9 eq) was added to a stirred solution of the product from Step A (138 mg, 0.17 mmol, 1 eq) in dichloromethane (3 mL) and the mixture was stirred for 18 h. The reaction was partitioned between dichloromethane and saturated aqueous sodium bicarbonate, washed successively with water and brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (104 mg, 0.15 mmol, 90%).

LC/MS ($C_{36}H_{40}N_8O_2S_2$) 681 $[M+H]^+$; RT 1.45 (LCMS-V-B1)

$^1H$ NMR (400 MHz, DMSO-d6) δ 11.16 (br s, 1H), 7.76 (br s, 2H), 7.51 (s, 1H), 7.41-7.33 (m, 1H), 7.24-7.14 (m, 2H), 4.16 (q, J=7.1 Hz, 2H), 3.81 (s, 3H), 3.78 (s, 2H), 2.18 (s, 3H), 2.00-1.92 (m, 3H), 1.72-1.53 (m, 12H), 1.20-1.12 (m, 5H), 1.07-1.00 (m, 2H).

Step C: 5-{1-[(adamantan-1-yl)methyl]-5-methyl-1H-pyrazol-4-yl}-2-({6-[(1,3-benzothiazol-2-yl)amino]-5-cyclopropylpyridazin-3-yl}(methyl)amino)-1,3-thiazole-4-carboxylic acid To a solution of the product from Step B (104 mg, 0.15 mmol, 1 eq) in 1,4-dioxane (5 mL) was added lithium hydroxide monohydrate (32 mg, 0.76 mmol, 5 eq) and the mixture was heated at reflux overnight. The reaction was allowed to cool to ambient temperature and concentrated in vacuo. The resultant solid was triturated with water, filtered, and dried under vacuum to afford the desired product as a yellow solid (83.5 mg, 0.13 mmol, 84%) [as a lithium salt].

HRMS-ESI (m/z) [M+H]+ calcd for $C_{34}H_{37}N_8O_2S$: 653.2475, found 653.2475.

Example 54: 2-({6-[(1,3-Benzothiazol-2-yl)amino]-5-methylpyridazin-3-yl}(3-methoxypropyl)amino)-5-(3-{4-[3-(dimethylamino)prop-1-yn-1-yl]-2-fluorophenoxy}propyl)-1,3-thiazole-4-carboxylic acid

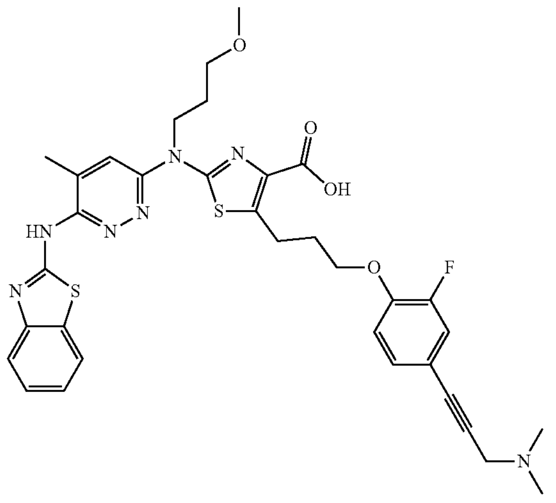 [SMILES: COCCCN(c1cc(C)c(Nc2nc3ccccc3s2)nn1)c1nc(C(=O)O)c(CCCOc2ccc(C#CCN(C)C)cc2F)s1]

Step A: ethyl 5-(3-hydroxyprop-1-yn-1-yl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Tetrakis(triphenylphosphine)palladium(0)(140.6 mg, 0.12 mmol, 0.1 eq) was added to a stirred solution of the product from Preparation 11c (844 mg, 1.22 mmol, 1 eq), propargyl alcohol (0.28 mL, 4.86 mmol, 4 eq), triethylamine (1.02 mL, 7.3 mmol, 6 eq) and copper(I) iodide (46.4 mg, 0.24 mmol, 0.2 eq) in dimethylformamide (20 mL) under a nitrogen atmosphere and the mixture was heated at 100° C. overnight. The reaction was allowed to cool to ambient temperature then concentrated in vacuo. Purification by automated flash column chromatography (CombiFlash Rf, 40 g RediSep™ silica cartridge) eluting with a gradient or 0-100% ethyl acetate in iso-heptane afforded the desired product as a brown gum (671 mg, 1 mmol, 83%).

LC/MS ($C_{31}H_{40}N_6O_5SiS_2$) 669 $[M+H]^+$; RT 1.43 (LCMS-V-B1)

$^1H$ NMR (400 MHz, DMSO-d6) δ 7.88 (d, 1H), 7.73 (s, 1H), 7.50-7.41 (m, 2H), 7.26 (ddd, J=8.3, 7.0, 1.5 Hz, 1H), 5.88 (s, 2H), 4.45 (t, 2H), 4.29 (q, J=7.1 Hz, 2H), 4.17 (d, J=6.1 Hz, 2H), 3.72 (t, 2H), 3.42 (t, J=5.9 Hz, 2H), 3.22 (s, 3H), 2.47 (s, 3H), 1.98 (p, J=6.7 Hz, 2H), 1.33 (t, J=7.1 Hz, 3H), 0.92 (t, 2H), −0.11 (s, 9H).

Step B: ethyl 5-(3-hydroxypropyl)-2-[(3-methoxypropyl)(3-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A suspension of the product from Step A (671 mg, 1 mmol, 1 eq) in 1:1 ethyl acetate/methanol (30 mL) was added to a flask containing platinum (IV) oxide (0.02 g, 0.1 mmol, 0.1 eq) under a nitrogen atmosphere. The mixture was evacuated and backfilled with nitrogen (×3) then evacuated and placed under an atmosphere of hydrogen. The mixture was shaken for 3.5 h then filtered through celite (10 g) and washed through with methanol. The solvent was removed in vacuo and purification by automated flash column chromatography (CombiFlash Rf, 12 g RediSep™ silica cartridge) eluting with a gradient of 0-60% ethyl acetate in iso-heptane afforded the desired product as a yellow foam (431 mg, 0.64 mmol, 64%).

LC/MS ($C_{31}H_{44}N_6O_5SiS_2$) 673 $[M+H]^+$; RT 1.43 (LCMS-V-B1)

$^1H$ NMR (400 MHz, DMSO-d6) δ 7.86 (d, 1H), 7.66 (s, 1H), 7.49-7.40 (m, 2H), 7.28-7.22 (m, 1H), 5.87 (s, 2H), 4.39 (t, J=7.2 Hz, 2H), 4.27 (q, J=7.1 Hz, 2H), 3.72 (t, 2H), 3.48 (q, 2H), 3.42 (t, 2H) 3.24 (s, 3H), 3.12 (t, 2H), 2.46 (s, 3H), 1.96 (p, J=6.2 Hz, 2H), 1.80 (p, 2H), 1.30 (t, J=7.1 Hz, 3H), 0.92 (t, 2H), −0.11 (s, 9H).

Step C: ethyl 5-(3-iodopropyl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Step B (431 mg, 0.64 mmol, 1 eq) in 4:1 diethyl ether/acetonitrile (25 mL) was added imidazole (65.4 mg, 0.96 mmol, 1.5 eq), triphenylphosphine (252 mg, 0.96 mmol, 1.5 eq), and iodine (244 mg, 0.96 mmol, 1.5 eq) and the mixture was stirred for 18 h. The reaction mixture was diluted with ethyl acetate and successively washed with 10% aqueous sodium thiosulfate, water, and brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as a yellow gum (378 mg, 0.48 mmol, 75%).

LC/MS ($C_{31}H_{43}IN_6O_4SiS_2$) 783 $[M+H]^+$; RT 1.78 (LCMS-V-B1)

$^1H$ NMR (400 MHz, DMSO-d6) δ 7.85 (d, 1H), 7.67 (s, 1H), 7.49-7.40 (m, 2H), 7.25 (ddd, J=8.2, 6.9, 1.6 Hz, 1H), 5.87 (s, 2H), 4.38 (t, J=7.2 Hz, 2H), 4.29 (q, J=7.1 Hz, 2H), 3.72 (t, 2H), 3.42 (t, J=6.0 Hz, 2H), 3.33 (t, 2H), 3.23 (s, 3H), 3.21-3.14 (m, 2H), 2.46 (s, 3H), 2.14 (p, J=6.9 Hz, 2H), 1.97 (p, J=6.2 Hz, 2H), 1.32 (t, J=7.1 Hz, 3H), 0.92 (t, 2H), −0.11 (s, 9H).

Step D: ethyl 5-(3-{4-[3-(dimethylamino)prop-1-yn-1-yl]-2-fluorophenoxy}propyl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Sodium Hydride (60% in mineral oil; 38.6 mg, 0.96 mmol, 2 eq) was added to a solution of the product from Preparation 6b (103 mg, 0.53 mmol, 1.1 eq) in dimethylformamide (8 mL). After 10 min the reaction was cooled to 0° C. and a solution of the product from Step C (378 mg, 0.48 mmol, 1 eq) in dimethylformamide (8 mL) was added. The mixture was allowed to warm to ambient temperature and stirred for 5 h. The reaction was quenched with water, acidified with 2N aqueous hydrochloric acid and extracted with ethyl acetate (×2). The combined organic extracts were washed with brine, dried (magnesium sulfate) and concentrated in vacuo. Purification by automated flash column chromatography (CombiFlash Rf, 24 g RediSep™ silica cartridge) eluting with a gradient of 0-10% methanol in dichloromethane afforded the desired product as a brown foam (115 mg, 0.14 mmol, 28%).

LC/MS ($C_{42}H_{54}FN_7O_5SiS_2$) 848 $[M+H]^+$; RT 1.43 (LCMS-V-B1)

$^1H$ NMR (400 MHz, DMSO-d6) δ 7.84 (dd, J=7.5, 1.1 Hz, 1H), 7.67 (s, 1H), 7.49-7.41 (m, 2H), 7.39-7.34 (m, 1H), 7.28-7.23 (m, 2H), 7.19 (t, J=8.6 Hz, 1H), 5.86 (s, 2H), 4.38 (t, J=7.3 Hz, 2H), 4.24 (q, J=7.1 Hz, 2H), 4.16 (t, J=6.1 Hz, 2H), 3.72 (t, J=8.0 Hz, 2H), 3.41 (t, J=5.9 Hz, 2H), 3.33 (s, 2H), 3.31-3.25 (m, 2H), 3.24 (s, 3H), 2.35 (s, 2H), 2.48-2.41 (m, 9H), 2.13 (p, 2H), 1.97 (p, 2H), 1.29 (t, J=7.1 Hz, 3H), 0.92 (t, 2H), −0.12 (s, 9H).

Step E: ethyl 2-({6-[(1,3-benzothiazol-2-yl)amino]-5-methylpyridazin-3-yl}(3-methoxypropyl)amino)-5-(3-{4-[3-(dimethylamino)prop-1-yn-1-yl]-2-fluorophenoxy}propyl)-1,3-thiazole-4-carboxylate Trifluoroacetic acid (1 mL, 13.4 mmol, 99 eq) was added to a stirred solution of the product from Step D (115 mg, 0.14 mmol, 1 eq) in dichloromethane (3 mL) and the mixture was stirred for 18 h. The reaction was diluted with dichloromethane, washed with saturated aqueous sodium bicarbonate, dried (magnesium sulfate), and concentrated in vacuo. Purification by automated flash column chromatography (CombiFlash Rf, 12 g RediSep™ silica cartridge) eluting with a gradient of 0-10% methanol in dichloromethane afforded the desired product as a yellow glass (32.2 mg, 0.04 mmol, 33%).

LC/MS ($C_{36}H_{40}FN_7O_4S_2$) 718 $[M+H]^+$; RT 1.32 (LCMS-V-B1)

$^1H$ NMR (400 MHz, DMSO-d6) δ 7.91 (d, J=7.6 Hz, 1H), 7.67 (s, 1H), 7.54 (d, J=8.2 Hz, 1H), 7.44-7.37 (m, 1H), 7.31 (dd, 1H), 7.26-7.12 (m, 3H), 4.39 (t, J=7.2 Hz, 2H), 4.26 (q, J=7.0 Hz, 2H), 4.16 (t, J=6.1 Hz, 2H), 3.43 (t, J=6.0 Hz, 2H), 3.40 (s, 2H), 3.31-3.26 (m, 2H), 3.25 (s, 3H), 2.47 (s, 3H), 2.21 (s, 6H), 2.17-2.10 (m, 2H), 1.97 (p, 2H), 1.30 (t, J=7.1 Hz, 3H).

Step F: 2-({6-[(1,3-benzothiazol-2-yl)amino]-5-methylpyridazin-3-yl}(3-methoxypropyl)amino)-5-(3-{4-[3-(dimethylamino)prop-1-yn-1-yl]-2-fluorophenoxy}propyl)-1,3-thiazole-4-carboxylic acid To a solution of the product from Step E (32.2 mg, 0.04 mmol, 1 eq) in 1,4-dioxane (3 mL) was added lithium hydroxide monohydrate (9.41 mg, 0.22 mmol, 5 eq) and the mixture was heated at reflux overnight. The reaction was allowed to cool to ambient temperature and concentrated in vacuo. The residue was triturated with water then centrifuged and the solvent decanted. Toluene was added to the residual solid and the mixture was sonicated, centrifuged, and the solvent decanted. Drying under vacuum afforded the desired product as a yellow solid (29.6 mg, 0.04 mmol, 96%) [as a lithium salt].

HRMS-ESI (m/z) [M+H]+ calcd for $C_{34}H_{37}FN_7O_4S_2$: 690.2327, found 690.2318.

Example 55: 2-[[6-[(4-Fluoro-1,3-benzothiazol-2-yl)amino]-4,5-dimethyl-pyridazin-3-yl]amino]thiazole-4-carboxylic acid

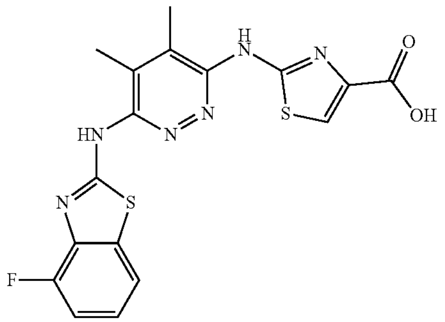 [SMILES: Cc1c(Nc2nc(C(=O)O)cs2)nnc(Nc2nc3c(F)cccc3s2)c1C]

Step A: N-(6-chloro-1,5-dimethyl-pyridazin-3-yl)-4-fluoro-1,3-benzothiazol-2-amine To 158 mg of 6-chloro-4,5-dimethyl-pyridazin-3-amine (1 mmol, 1 eq.) and 232 mg of 2-bromo-4-fluoro-1,3-benzothiazole (1 mmol, 1 eq.) in 8 mL of 1,4-dioxane was added 160 mg of sodium hydride (60 w %, 4 mmol, 4 eq.) and the mixture was stirred at reflux for 1 h. After cooling, the reaction was quenched with water and the mixture was extracted with EtOAc. The combined and dried organic phases were concentrated to give 311 mg (101%) of the desired product.

LC-MS-ESI (m/z): $[M+H]^+$ calcd for $C_{13}H_{11}ClFN_4S$: 309, found 309.

Step B: ethyl 2-[[6-[(4-fluoro-1,3-benzothiazol-2-yl)amino]-4,5-dimethyl-pyridazin-3-yl]amino]thiazole-4-carboxylate The mixture of 300 mg of the product from Step A (0.97 mmol, 1 eq.), 167 mg of ethyl 2-aminothiazole-4-carboxylate (0.97 mmol, 1 eq.), 33 mg of $Pd_2(dba)_3$ (0.036 mmol, 0.04 eq.), 53 mg of 4,5-bis(diphenylphosphino)-9,9-dimethylxanthene (0.092 mmol, 0.1 eq.) and 0.23 mL of DIPEA (2 eq.) in 8 mL of 1,4-dioxane was stirred at 160° C. in a microwave reactor for 0.75 h. After cooling, the crude product was purified by reverse phase preparative chromatography to give 110 mg (26%) of the desired product.

$^1H$ NMR (400 MHz, DMSO-$d_6$) δ ppm 11.17 (s, 1H), 11.05 (s, 1H), 7.96 (s, 1H), 7.81 (m, 1H), 7.24 (m, 1H), 7.22 (m, 1H), 4.29 (q, 2H), 2.39/2.37 (s+s, 6H), 1.31 (t, 3H).

Step C: 2-[[6-[(4-fluoro-1,3-benzothiazol-2-yl)amino]-4,5-dimethylpyridazin-3-yl]amino]thiazole-4-carboxylic acid The mixture of the product from Step B, LiOH×$H_2O$, water and 1,4-dioxane was stirred at reflux for 9 h. After cooling and concentration, 1 N HCl was added and the precipitation was filtered off to give the desired product.

HRMS-ESI (m/z): $[M+H]^+$ calcd for $C_{17}H_{14}FN_6O_2S_2$: 417.0604, found: 417.0595.

Example 56: 5-({6-[(1,3-Benzothiazol-2-yl)amino]-5-methylpyridazin-3-yl}(methyl)amino)thiophene-2-carboxylic acid

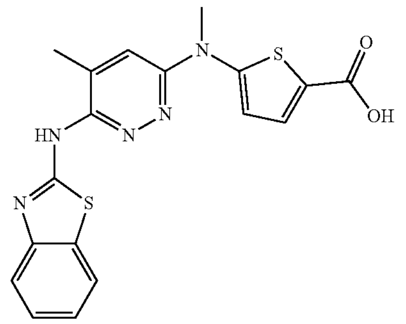 [SMILES: Cc1cc(N(C)c2ccc(C(=O)O)s2)nnc1Nc1nc2ccccc2s1]

Step A: tert-butyl N-[(tert-butoxy)carbonyl]-N-(6-chloro-4-methylpyridazin-3-yl)carboxylate To a solution of di-tert-butyl dicarbonate (5.7 g, 26.1 mmol, 3 eq) in dichloromethane (40 mL) was added 6-chloro-4-methylpyridazin-3-amine (1.25 g, 8.71 mmol, 1 eq) followed by 4-dimethylaminopyridine (53.2 mg, 0.44 mmol, 0.05 eq) and the mixture was stirred overnight. The reaction mixture was concentrated in vacuo and purification by flash column chromatography (50 g silica) eluting with 2:3 ethyl acetate/heptane gave a yellow solid. Trituration with heptane (15 mL) gave a solid that was collected by filtration, washed with heptane (2×15 mL) and dried under vacuum to afford the desired product as a pale yellow solid (1.85 g, 5.38 mmol, 62%).

LC/MS ($C_{15}H_{22}ClN_3O_4$) 188 [M-Boc-tBu+3H]$^+$; RT 1.28 (LCMS-V-B1)

$^1$H NMR (400 MHz, $CDCl_3$) δ 7.43 (d, 1H), 2.27 (d, 3H), 1.40 (s, 9H).

Step B: methyl 5-[(6-{bis[(tert-butoxy)carbonyl]amino}-5-methylpyridazin-3-yl)amino]thiophene-2-carboxylate Tris(dibenzylideneacetone)dipalladium(0)(107 mg, 0.12 mmol, 0.05 eq) was added to a stirred solution of the product from Step A (800 mg, 2.33 mmol, 1 eq), methyl 5-aminothiophene-2-carboxylate (439 mg, 2.79 mmol, 1.2 eq), N,N-diisopropylethylamine (1.16 mL, 6.98 mmol, 3 eq) and Xantphos (135 mg, 0.23 mmol, 0.1 eq) in 1,4-dioxane (20 mL) under a nitrogen atmosphere and the mixture was heated at 100° C. overnight. The reaction was allowed to cool to ambient temperature and concentrated in vacuo. Purification by automated flash column chromatography (CombiFlash Rf, 24 g RediSep™ silica cartridge) eluting with a gradient of 0-10% methanol in dichloromethane gave material that was triturated in diethyl ether and the solids collected by filtration to afford the desired product as a beige solid (442 mg, 0.95 mmol, 41%).

LC/MS ($C_{21}H_{28}N_4O_6S$) 465 [M+H]$^+$; RT 1.10 (LCMS-V-B1)

$^1$H NMR (400 MHz, DMSO-d6) δ 11.22 (s, 1H), 7.64 (d, J=4.2 Hz, 1H), 7.17 (s, 1H), 6.74 (d, J=4.3 Hz, 1H), 3.78 (s, 3H), 2.17 (s, 3H), 1.39 (s, 18H).

Step C: methyl 5-[(6-{bis[(tert-butoxy)carbonyl]amino}-5-methylpyridazin-3-yl)(methyl)amino]thiophene-2-carboxylate Sodium hydride (60% dispersion; 60.9 mg, 1.52 mmol, 1.6 eq) was added to a stirred solution of the product from Step B (442 mg, 0.95 mmol, 1 eq) in dimethylformamide (10 mL). After 15 min, iodomethane (0.12 mL, 1.9 mmol, 2 eq) was added and the mixture was stirred at ambient temperature for 5 h. The reaction was diluted with ethyl acetate then washed with water (×2) followed by brine, dried (magnesium sulfate), and concentrated in vacuo. Purification by automated flash column chromatography (CombiFlash Rf, 24 g RediSep™ silica cartridge) eluting with a gradient of 0-100% ethyl acetate in iso-heptane afforded the desired product as a cream solid (295 mg, 0.62 mmol, 65%).

LC/MS ($C_{22}H_{30}N_4O_6S$) 479 [M+H]$^+$; RT 1.23 (LCMS-V-B1)

$^1$H NMR (400 MHz, DMSO-d6) δ 7.73 (s, 1H), 7.69 (d, 1H), 6.92 (d, J=4.4 Hz, 1H), 3.79 (s, 3H), 3.66 (s, 3H), 2.22 (d, J=0.9 Hz, 3H), 1.40 (s, 18H).

Step D: methyl 5-[(6-amino-5-methylpyridazin-3-yl)(methyl)amino]thiophene-2-carboxylate A solution of the product from Step C (343 mg, 0.72 mmol, 1 eq) in dichloromethane (8 mL) was cooled in an ice bath then trifluoroacetic acid (2 mL, 26.8 mmol, 37 eq) was added. The mixture was allowed to warm to ambient temperature and stirred for 18 h. The solvent was removed in vacuo then the residue was dissolved in methanol and loaded onto a methanol-conditioned SCX-2 cartridge (5 g). The cartridge was washed with methanol, then eluted with 3.5N methanolic ammonia. The solvent was removed in vacuo and the resultant solid triturated with diethyl ether and filtered to afford the desired product as a cream solid (142 mg, 0.51 mmol, 71%).

LC/MS ($C_{12}H_{14}N_4O_2S$) 279 [M+H]$^+$; RT 0.67 (LCMS-V-B1)

$^1$H NMR (400 MHz, DMSO-d6) δ 7.59 (d, J=4.4 Hz, 1H), 7.35 (s, 1H), 6.58 (d, J=4.4 Hz, 1H), 6.00 (s, 2H), 3.75 (s, 3H), 3.50 (s, 3H), 2.16 (s, 3H).

Step E: methyl 5-({6-[(1,3benzothiazol-2-yl)amino]-5-methylpyridazin-3-yl}(methyl)amino)thiophene-2-carboxylate Tris(dibenzylideneacetone)dipalladium(0)(23.4 mg, 0.03 mmol, 0.05 eq) was added to a stirred solution of the product from Step D (142 mg, 0.51 mmol, 1 eq), 2-bromo-1,3-benzothiazole (131 mg, 0.61 mmol, 1.2 eq), N,N-diisopropylethylamine (0.25 mL, 1.53 mmol, 3 eq) and Xantphos (29.5 mg, 0.05 mmol, 0.1 eq) in 1,4-dioxane (5 mL) under a nitrogen atmosphere and the mixture was heated at 100° C. for 18 h. The reaction was allowed to cool to ambient temperature and concentrated in vacuo. Purification by automated flash column chromatography (CombiFlash Rf, 12 g RediSep™ silica cartridge) eluting with a gradient 0-6% methanol in dichloromethane afforded the desired product as a brown solid (158 mg, 0.38 mmol, 75%).

LC/MS ($C_{19}H_{17}N_5O_2S_2$) 412 [M+H]$^+$; RT 1.18 (LCMS-V-B1)

$^1$H NMR (400 MHz, DMSO-d6) δ 11.04 (br s, 1H), 8.01 (br s, 1H), 7.70-7.63 (m, 3H), 7.43-7.35 (m, 1H), 7.27-7.17 (m, 1H), 6.80 (d, J=4.4 Hz, 1H), 3.81 (s, 3H), 3.63 (s, 3H), 2.46 (s, 3H).

Step F: 5-({6-[(1,3-benzothiazol-2-yl)amino]-5-methylpyridazin-3-yl}(methyl)amino)thiophene-2-carboxylic acid To a suspension of the product from Step E (158 mg, 0.38 mmol, 1 eq) in 1,4-dioxane (10 mL) was added lithium hydroxide monohydrate (161 mg, 3.84 mmol, 10 eq) and the mixture was heated at reflux overnight. The reaction was allowed to cool to ambient temperature and the resulting suspension was centrifuged, decanted, and dried under vacuum to afford the desired product as a yellow solid (90.5 mg, 0.23 mmol, 59%).

HRMS-ESI (m/z) [M–H]– calcd for $C_{18}H_{14}N_5O_2S_2$: 396.0594, found 396.0576.

Example 57: 2-[[6-[(5,6-Difluoro-1,3-benzothiazol-2-yl)amino]-4,5-dimethyl-pyridazin-3-yl]amino]thiazole-4-carboxylic acid

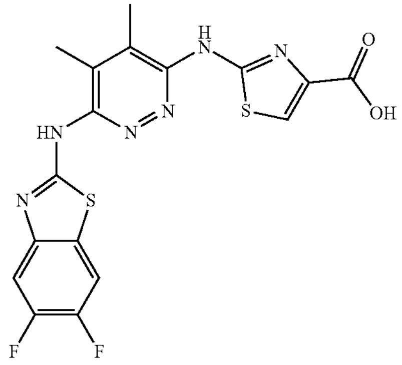 [SMILES: Cc1c(Nc2nc(C(=O)O)cs2)nnc(Nc2nc3cc(F)c(F)cc3s2)c1C]

Step A: N-(6-chloro-4,5-dimethyl-pyridazin-3-yl)-5,6-difluoro-1,3-benzothiazol-2-amine To 158 mg of 6-chloro-4,5-dimethyl-pyridazin-3-amine (1 mmol, 1 eq.) and 250 mg of 2-bromo-5,6-difluoro-1,3-benzothiazole (1 mmol, 1 eq.) in 8 mL of 1,4-dioxane was added 160 mg of sodium hydride (60 w %, 4 mmol, 4 eq.) and the mixture was stirred at reflux for 1 h. After cooling, the reaction was quenched with water and the mixture was extracted with EtOAc. The combined and dried organic phases were concentrated to give 300 mg (92%) of the desired product.

LC-MS-ESI (m/z): $[M+H]^+$ calcd for $C_{13}H_{10}ClF_2N_4S$: 327, found 327.

Step B: ethyl 2-[[6-[(5,6-difluoro-1,3-benzothiazol-2-yl)amino]-4,5-dimethyl-pyridazin-3-yl]amino]thiazole-4-carboxylate The mixture of 300 mg of the product from Step A (0.9 mmol, 1 eq.), 155 mg of ethyl 2-aminothiazole-4-carboxylate (0.9 mmol, 1 eq.), 33 mg of $Pd_2(dba)_3$ (0.036 mmol, 0.04 eq.), 53 mg of 4,5-bis(diphenylphosphino)-9,9-dimethylxanthene (0.092 mmol, 0.1 eq.) and 0.23 mL of DIPEA (2 eq.) in 8 mL of 1,4-dioxane was stirred at 200° C. in a microwave reactor for 1 h. After cooling, the crude product was purified by reverse phase preparative chromatography to give 110 mg (26%) of the desired product.

LC-MS-ESI (m/z): $[M+H]^+$ calcd for $C_{19}H_{17}F_2N_6O_2S_2$: 463, found 463.

Step C: 2-[[6-[(5,6-difluoro-1,3-benzothiazol-2-yl)amino]-4,5-dimethyl-pyridazin-3-yl]amino]thiazole-4-carboxylic acid The mixture of the product from Step B, LiOH×$H_2O$, water and 1,4-dioxane was stirred at reflux for 9 h. After cooling, the crude product was purified by reverse phase preparative chromatography to give the desired product.

HRMS-ESI (m/z): $[M+H]^+$ calcd for $C_{17}H_{13}F_2N_6O_2S_2$: 435.0509, found: 435.0506.

Example 58: 2-[[6-[(5-Fluoro-1,3-benzothiazol-2-yl)amino]-4,5-dimethyl-pyridazin-3-yl]amino]thiazole-4-carboxylic acid

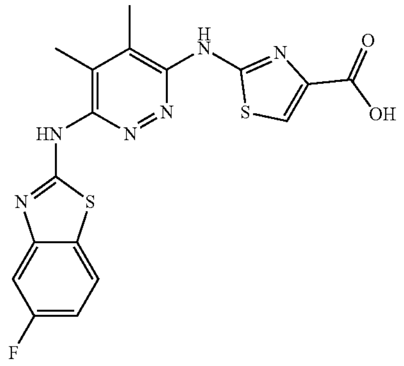 [SMILES: Cc1c(Nc2nc(C(=O)O)cs2)nnc(Nc2nc3cc(F)ccc3s2)c1C]

Step A: N-(6-chloro-4,5-dimethyl-pyridazin-3-yl)-5-fluoro-1,3-benzothiazol-2-amine To 158 mg of 6-chloro-4,5-dimethyl-pyridazin-3-amine (1 mmol, 1 eq.) and 348 mg of 2-bromo-5-fluoro-1,3-benzothiazole (1.5 mmol, 1.5 eq.) in 20 mL or 1,4-dioxane was added 160 mg of sodium hydride (60 w %, 4 mmol, 4 eq.) and the mixture was stirred at reflux for 1 h. After cooling, the reaction was quenched with 2 mL of EtOH, concentrated, and treated with 20 mL of water. The precipitated solid was filtered off to give 300 mg (97%) of the desired product.

$^1H$ NMR (500 MHz, DMSO-$d_6$) δ ppm 7.81 (dd, 1H), 7.29 (dd, 1H), 7.00 (dd, 1H), 2.34 (s, 3H), 2.29 (s, 3H); $^{13}C$ NMR (125 MHz, DMSO-$d_6$) δ ppm 162.2, 161.9, 154.1, 152.0, 145.5, 137.4, 131.1, 125.8, 123.3, 110.6, 103.5, 15.7, 13.3; LC-MS-ESI (m/z): calcd for $C_{13}H_{11}ClFN_4S$: 309.8, found: 309 and 307 $[M-H]^-$.

Step B: ethyl 2-[[6-[(5-fluoro-1,3-benzothiazol-2-yl)amino]-1,5-dimethyl-pyridazin-3-yl]amino]thiazole-4-carboxylate The mixture of 300 mg of the product from Step A (0.97 mmol, 1 eq.), 167 mg of ethyl 2-aminothiazole-4-carboxylate (0.97 mmol, 1 eq.), 36 mg of $Pd_2(dba)_3$ (0.039 mmol, 0.04 eq.), 56 mg of 4,5-bis(diphenylphosphino)-9,9-dimethylxanthene (0.097 mmol, 0.1 eq) and 0.34 mL of DIPEA (2 eq.) in 10 mL of 1,4-dioxane was stirred at 200° C. in a microwave reactor for 1 h. After cooling, the crude product was purified by reverse phase preparative chromatography to give 150 mg (35%) of the desired product.

LC-MS-ESI (m/z): $[M+H]^+$ calcd for $C_{19}H_{18}FN_6O_2S_2$: 445.5, found: 445 and 443 $[M-H]^-$.

Step C: 2-[[6-[(5-fluoro-1,3-benzothiazol-2-yl)amino]-4,5-dimethyl-pyridazin-3-yl]amino]thiazole-4-carboxylic acid The mixture of 150 mg of the product from Step B (0.338 mmol, 1 eq.), 28 mg of LiOH×$H_2O$ (0.67 mmol, 2 eq.), and 10 drops of water in 10 mL of 1,4-dioxane was stirred at reflux for 3 h. After cooling and concentration, the crude product was purified by reverse phase preparative chromatography to give 112 mg (79%) of the desired product.

HRMS-ESI (m/z): [M+H]+ calcd for $C_{17}H_{14}FN_6O_2S_2$: 417.0604, found: 417.0598.

Example 59: 2-({6-[(1,3-Benzothiazol-2-yl)amino]-5-methylpyridazin-3-yl}(methyl)amino)-5-[3-(2-fluorophenoxy)propyl]-1,3-thiazole-4-carboxylic acid

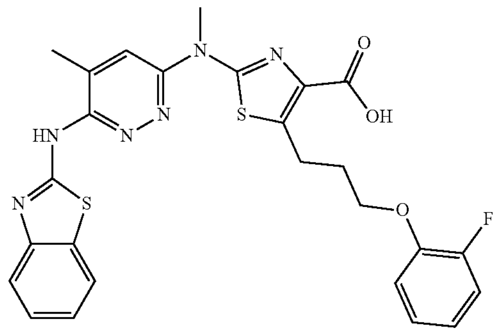 [SMILES: Cc1cc(N(C)c2nc(C(=O)O)c(CCCOc3ccccc3F)s2)nnc1Nc1nc2ccccc2s1]

Step A: ethyl 5-[3-(2-fluorophenoxy)propyl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Sodium Hydride (60% in mineral oil; 19.5 mg, 0.49 mmol, 2 eq) was added to a solution of 2-fluorophenol (0.03 mL, 0.29 mmol, 1.2 eq) in dimethylformamide (4 mL). After 15 min the reaction was cooled to 0° C. and a solution of the product from Preparation 5g (177 mg, 0.24 mmol, 1 eq) in dimethylformamide (3 mL) was added. The mixture was allowed to warm to ambient temperature and stirred for 18 h. The reaction was quenched by the addition of water, acidified with 2N aqueous hydrochloric acid and extracted with ethyl acetate (×2). The combined organic extracts were washed with brine, dried (magnesium sulfate) and concentrated vacuo. Purification by automated flash column chromatography (CombiFlash Rf, 12 g RediSep™ silica cartridge) eluting with a gradient of 0-10% methanol in dichloromethane afforded the desired product as a beige foam (144 mg, 0.2 mmol, 83%).

LC/MS ($C_{34}H_{41}FN_6O_4SiS_2$) 709 $[M+H]^+$; RT 1.62 (LCMS-V-B1)

$^1H$ NMR (400 MHz, DMSO-d6) δ 7.84 (dd, J=7.6, 1.0 Hz, 1H), 7.67 (d, J=1.1 Hz, 1H), 7.49-7.40 (m, 2H), 7.28-7.08 (m, 4H), 6.96-6.89 (m, 1H), 5.86 (s, 2H), 4.26 (q, J=7.1 Hz, 2H), 4.13 (t, J=6.2 Hz, 2H), 3.77 (s, 3H), 3.72 (t, 2H), 3.31-3.25 (m, 2H), 2.45 (d, J=1.0 Hz, 3H), 2.17-2.08 (m, 2H), 1.29 (t, J=7.1 Hz, 3H), 0.92 (t, 2H), −0.12 (s, 9H).

Step B: ethyl 2-({6-[(1,3-benzothiazol-2-yl)amino]-5-methylpyridazin-3-yl}(methyl)amino)-5-[3-(2-fluorophenoxy)propyl]-1,3-thiazole-4-carboxylate Trifluoroacetic acid (1 mL, 13.4 mmol, 66 eq) was added to a stirred solution of the product from Step A (144 mg, 0.2 mmol, 1 eq) in dichloromethane (3 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow solid (71 mg, 0.12 mmol, 61%).

LC/MS ($C_{28}H_{27}FN_6O_3S_2$) 579 $[M+H]^+$; RT 1.37 (LCMS-V-B1)

$^1H$ NMR (400 MHz, DMSO-d6) δ 11.07 (br s, 1H), 7.92 (s, 1H), 7.69 (s, 1H), 7.61 (br s, 1H), 7.40 (t, J=7.6 Hz, 1H), 7.32-7.08 (m, 4H), 6.98-6.90 (m, 1H), 4.27 (q, J=7.1 Hz, 2H), 4.13 (t, J=6.2 Hz, 2H), 3.77 (s, 3H), 3.34-3.24 (m, 2H), 2.47 (s, 3H), 2.14 (p, J=6.2 Hz, 2H), 1.30 (t, J=7.1 Hz, 3H).

Step C: 2-({6-[(1,3-benzothiazol-2-yl)amino]-5-methylpyridazin-3-yl}(methyl)amino)-5-[3-(2-fluorophenoxy)propyl]-1,3-thiazole-4-carboxylic acid To a solution of the product from Step B (71 mg, 0.12 mmol, 1 eq) in 1,4-dioxane (4 mL) was added lithium hydroxide monohydrate (25.7 mg, 0.61 mmol, 5 eq) and the mixture was heated at reflux overnight. The reaction was allowed to cool to ambient temperature and concentrated in vacuo. The residue was triturated in water and the solids collected by filtration. The solid was further triturated in diethyl ether, filtered, and dried under vacuum to afford the desired product as a yellow solid (49 mg, 0.09 mmol, 73%) [as a lithium salt].

HRMS-ESI (m/z) [M+H]+ calcd for $C_{26}H_{24}FN_6O_3S_2$: 551.1330, found 551.1335.

Example 60: 2-({6-[(1,3-Benzothiazol-2-yl)amino]-5-methylpyridazin-3-yl}(methyl)amino)-5-(3-methoxypropyl)-1,3-thiazole-4-carboxylic acid

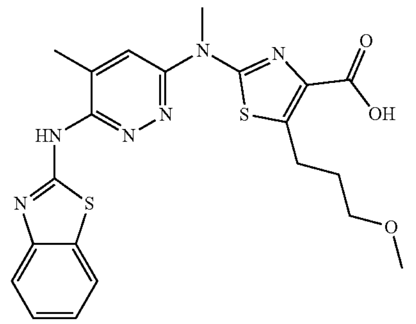 [SMILES: COCCCc1sc(N(C)c2cc(C)c(Nc3nc4ccccc4s3)nn2)nc1C(=O)O]

Step A: ethyl 5-(3-methoxyprop-1-yn-1-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Tetrakis(triphenylphosphine)palladium(0)(36.4 mg, 0.04 mmol, 0.1 eq) was added to a stirred solution of the product from Preparation 11b (200 mg, 0.31 mmol, 1 eq), methyl propargyl ether (0.06 mL, 0.76 mmol, 2.4 eq), triethylamine (0.26 mL, 1.88 mmol, 6 eq) and copper(I) iodide (12 mg, 0.06 mmol, 0.2 eq) in dimethylformamide (5 mL) under a nitrogen atmosphere and the mixture was heated at 100° C. overnight. The reaction was allowed to cool to ambient temperature then concentrated in vacuo. Purification by automated flash column chromatography (CombiFlash Rf, 12 g RediSep™ silica cartridge) eluting with a gradient of 0-100% ethyl acetate in iso-heptane afforded the desired product as a cream solid (78 mg, 0.12 mmol, 40%).

LC/MS ($C_{29}H_{36}N_6O_4SiS_2$) 625 $[M+H]^+$; RT 1.56 (LCMS-V-B1)

$^1H$ NMR (400 MHz, DMSO-d6) δ 7.86 (d, J=7.7 Hz, 1H), 7.74 (s, 1H), 7.51-7.41 (m, 2H), 7.26 (td, J=7.6, 1.5 Hz, 1H), 5.87 (s, 2H), 4.43 (s, 2H), 4.31 (q, J=7.1 Hz, 2H), 3.82 (s, 3H), 3.72 (t, J=8.0 Hz, 2H), 3.38 (s, 3H), 2.47 (s, 3H), 1.32 (t, J=7.1 Hz, 3H), 0.91 (dd, J=10.7, 5.4 Hz, 2H), 0.00 (s, 9H).

Step B: ethyl 5-(3-methoxypropyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A suspension of the product from Step A (78 mg, 0.12 mmol, 1 eq) in 1:1 ethyl acetate/methanol (8 mL) was added to a flask containing platinum (IV) oxide (2.83 mg, 0.01 mmol, 0.1 eq) under a nitrogen atmosphere. The vessel was evacuated and back-filled with nitrogen (×3) then evacuated and placed under an atmosphere of hydrogen and shaken overnight. The mixture was filtered through celite eluted with methanol, and the solvent removed in vacuo. Purification by automated flash column chromatography (CombiFlash Rf, 12 g RediSep™ silica cartridge) eluting with a gradient of 0-10% methanol in dichloromethane afforded the desired product as a white foam (56.1 mg, 0.09 mmol, 71%).

LC/MS ($C_{29}H_{40}N_6O_4SiS_2$) 629 $[M+H]^+$; RT 1.54 (LCMS-V-B1)

$^1H$ NMR (400 MHz, DMSO-d6) δ 7.84 (dd, J=7.7, 1.0 Hz, 1H), 7.66 (d, J=1.1 Hz, 1H), 7.49-7.41 (m, 2H), 7.25 (ddd, J=8.4, 6.9, 1.6 Hz, 1H), 5.86 (s, 2H), 4.28 (q, J=7.1 Hz, 2H), 3.77 (s, 3H), 3.72 (t, 2H), 3.38 (t, J=6.3 Hz, 2H), 3.26 (s, 3H), 3.189-3.09 (m, 2H), 2.46 (d, J=1.1 Hz, 3H), 1.86 (p, 1H), 1.31 (t, J=7.1 Hz, 3H), 0.97-0.87 (m, 2H), 0.00 (s, 9H).

Step C: ethyl 2-({6-[(1,3-benzothiazol-2-yl)amino]-5-methylpyridazin-3-yl}(methyl)amino)-5-(3-methoxypropyl)-1,3-thiazole-4-carboxylate Trifluoroacetic acid (1 mL, 13.4 mmol, 150 eq) was added to a stirred solution of the product from Step B (56 mg, 0.09 mmol, 1 eq) in dichloromethane (3 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-6% methanol in dichloromethane afforded the desired product as a yellow glass (40 mg, 0.08 mmol, 90%).

LC/MS ($C_{23}H_{26}N_6O_3S_2$) 499 $[M+H]^+$; RT 1.25 (LCMS-V-B1)

$^1H$ NMR (400 MHz, DMSO-d6) δ 11.11 (br s, 1H), 7.93 (br s, 1H), 7.69 (s, 1H), 7.58 (br s, 1H), 7.39 (t, J=7.5 Hz, 1H), 7.22 (t, 1H), 4.29 (q, J=7.1 Hz, 2H), 3.77 (s, 3H), 3.39 (t, J=6.3 Hz, 2H), 3.27 (s, 3H), 3.18-3.10 (m, 2H), 2.47 (s, 3H), 1.94-1.82 (m, 2H), 1.33 (t, J=7.1 Hz, 3H).

Step D: 2-({6-[(1,3-benzothiazol-2-yl)amino]-5-methylpyridazin-3-yl}(methyl)amino)-5-(3-methoxypropyl)-1,3-thiazole-4-carboxylic acid To a solution of the product from Step C (40 mg, 0.08 mmol, 1 eq) in 1,4-dioxane (3 mL) was added lithium hydroxide monohydrate (16.8 mg, 0.4 mmol, 5 eq) and the mixture was heated at reflux for 5 h. The reaction was allowed to cool to ambient temperature, concentrated in vacuo, triturated with water and the solids collected by filtration. The solid was suspended in 1,4-dioxane (4 mL) then hydrochloric acid (4M in 1,4-dioxane; 0.5 mL) was added. The suspension was stirred at ambient temperature for 2 h then centrifuged and the solvent removed by decanting. The solid was washed with 1,4-dioxane (2×2 mL) then again centrifuged and the solvent removed by decanting. The solid was finally triturated with water, filtered, and dried under vacuum to afford the desired product as an off-white solid (28.4 mg, 0.06 mmol, 75%) [as a hydrochloric acid salt].

HRMS-ESI (m/z) [M+H]+ calcd for $C_{21}H_{23}N_6O_3S_2$: 471.1268, found 471.1271.

Example 61: 2-({6-[(1,3-Benzothiazol-2-yl)amino]-5-methylpyridazin-3-yl}(methyl)amino)-5-[3-(cyclohexyloxy)propyl]-1,3-thiazole-4-carboxylic acid

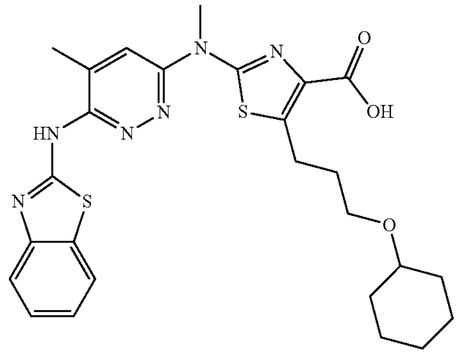 [SMILES: Cc1cc(N(C)c2nc(C(=O)O)c(CCCOC3CCCCC3)s2)nnc1Nc1nc2ccccc2s1]

Step A: ethyl 5-[3-(cyclohexyloxy)prop-1-yn-1-yl]-2-[methyl(5-methyl-6-{[(2Z)-3-{[2-(trimethylsilyl)ethoxy]methyl}-2,3-dihydro-1,3-benzothiazol-2-yliden]amino}pyridazin-3-yl)amino]-1,3-thiazole-4-carboxylate Tetrakis(triphenylphosphine)palladium(0)(36.4 mg, 0.04 mmol, 0.1 eq) was added to a stirred solution of the product from Preparation 11b (200 mg, 0.31 mmol, 1 eq), (prop-2-yn-1-yloxy)cyclohexane (120 mg, 0.86 mmol, 2.76 eq), triethylamine (0.26 mL, 1.88 mmol, 6 eq) and copper(I) iodide (12 mg, 0.06 mmol, 0.2 eq) in dimethylformamide (6 mL) under a nitrogen atmosphere and the mixture was heated at 100° C. overnight. The reaction was allowed to cool to ambient temperature, then diluted with ethyl acetate, washed with water (×2) followed by brine, dried (magnesium sulfate) and concentrated in vacuo. Purification by automated flash column chromatography (CombiFlash Rf, 12 g RediSep™ silica cartridge) eluting with a gradient of 0-70% ethyl acetate in iso-heptane afforded the desired product as a cream solid (50 mg, 0.07 mmol, 23%).

LC/MS ($C_{34}H_{44}N_6O_4SiS_2$) 693 $[M+H]^+$; RT 1.66 (LCMS-V-B1)

$^1$H NMR (400 MHz, DMSO-d6) δ 7.85 (d, J=7.7 Hz, 1H), 7.75 (d, J=1.1 Hz, 1H), 7.52-7.39 (m, 2H), 7.25 (td, J=7.5, 1.4 Hz, 1H), 5.88 (s, 2H), 4.48 (s, 2H), 4.30 (q, J=7.1 Hz, 2H), 3.82 (s, 3H), 3.72 (t, 2H), 3.57-3.49 (m, 1H), 2.48 (d, J=1.0 Hz, 3H), 1.95-1.86 (m, 2H), 1.73-1.65 (m, 2H), 1.55-1.46 (m, 2H), 1.32 (t, 3H), 1.32-1.22 (m, 4H), 0.92 (dd, J=8.5, 7.5 Hz, 2H), 0.00 (s, 9H).

Step B: ethyl 5-[3-(cyclohexyloxy)propyl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A suspension of the product from Step A (50 mg, 0.07 mmol, 1 eq) in 1:1 ethyl acetate/methanol (6 mL) was added to a flask containing platinum (IV) oxide (21.6 mg, 0.01 mmol, 0.1 eq) under a nitrogen atmosphere. The vessel was evacuated and back-filled with nitrogen (×3), then evacuated and placed under an atmosphere of hydrogen and shaken for 18 h. The reaction was filtered through celite (2.5 g), eluted with ethyl acetate and methanol, and the solvent removed in vacuo. Purification by automated flash column chromatography (CombiFlash Rf, 12 g RediSep™ silica cartridge) eluting with a gradient of 0-60% ethyl acetate in iso-heptane afforded the desired product as a colourless glass (42.2 mg, 0.06 mmol, 84%).

LC/MS ($C_{34}H_{48}N_6O_4SiS_2$) 697 $[M+H]^+$; RT 1.71 (LCMS-V-B1)

$^1$H NMR (400 MHz, DMSO-d6) δ 7.82 (d, J=7.5 Hz, 1H), 7.67 (d, J=1.1 Hz, 1H), 7.50-7.41 (m, 2H), 7.28-7.23 (m, 1H), 5.87 (s, 2H), 4.28 (q, J=7.1 Hz, 2H), 3.77 (s, 3H), 3.72 (t, 2H), 3.45 (t, J=6.1 Hz, 2H), 3.27-3.20 (m, 1H), 3.18-3.11 (m, 2H), 2.46 (d, J=1.0 Hz, 3H), 1.90-1.79 (m, 4H), 1.72-1.62 (m, 2H), 1.51-1.42 (m, 2H), 1.31 (t, J=7.1 Hz, 3H), 1.28-1.17 (m, 5H), 0.96-0.89 (m, 2H), 0.00 (s, 9H).

Step C: ethyl 2-({6-[(1,3-benzothiazol-2-yl)amino]-5-methylpyridazin-3-yl}(methyl)amino)-5-[3-(cyclohexyloxy)propyl]-1,3-thiazole-4-carboxylate Trifluoroacetic acid (0.6 mL, 8.06 mmol, 134 eq) was added to a stirred solution of the product from Step B (42 mg, 0.06 mmol, 1 eq) in dichloromethane (3 mL) and the mixture was stirred at ambient temperature overnight. The reaction was partitioned between dichloromethane and saturated aqueous sodium bicarbonate, and the organic phase washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow glass (19.6 mg, 0.03 mmol, 57%).

LC/MS ($C_{28}H_{34}N_6O_3S_2$) 567 $[M+H]^+$; RT 1.43 (LCMS-V-B1)

$^1$H NMR (400 MHz, DMSO-d6) δ 11.085 (br s, 1H), 7.90 (s, 1H), 7.68 (s, 1H), 7.60 (br s, 1H), 7.38 (t, 1H), 7.22 (t, 1H), 4.29 (q, J=7.1 Hz, 2H), 3.77 (s, 3H), 3.46 (t, J=6.2 Hz, 2H), 3.28-3.20 (m, 1H) 3.15 (t, 2H), 2.47 (s, 3H), 1.92-1.81 (m, 4H), 1.73-1.62 (m, 2H), 1.52-1.43 (m, 2H), 1.32 (t, 3H), 1.29-1.15 (m, 4H).

Step D: 2-({6-[(1,3-benzothiazol-2-yl)amino]-5-methylpyridazin-3-yl}(methyl)amino)-5-[3-(cyclohexyloxy)propyl]-1,3-thiazole-4-carboxylic acid To a solution of the product from Step C (19.6 mg, 0.03 mmol, 1 eq) in 1,4-dioxane (4 mL) was added lithium hydroxide monohydrate (7.26 mg, 0.17 mmol, 5 eq) and the mixture was heated at 100° C. for 6.5 h then allowed to cool to ambient temperature and concentrated in vacuo. The residue was triturated with water, filtered, and dried under vacuum to afford the desired product as a yellow solid (11 mg, 0.02 mmol, 59%) [as a lithium salt].

HRMS-ESI (m/z) [M+H]+ calcd for $C_{26}H_{31}N_6O_3S_2$: 539.1894, found 539.1895.

Example 62: 2-({6-[(1,3-Benzothiazol-2-yl)amino]-5-cyclopropylpyridazin-3-yl}(methyl)amino)-5-(3-{4-[3-(dimethylamino)prop-1-yn-1-yl]-2-fluorophenoxy}propyl)-1,3-thiazole-4-carboxylic acid

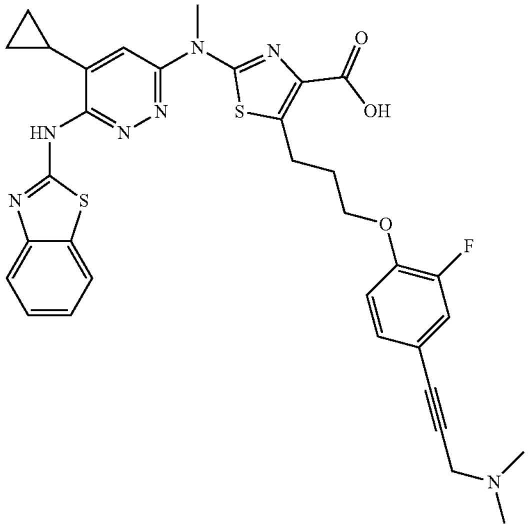 [SMILES: CN(C)CC#Cc1ccc(OCCCc2sc(N(C)c3cc(C4CC4)c(Nc4nc5ccccc5s4)nn3)nc2C(=O)O)c(F)c1]

Step A: ethyl 2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-5-(3-hydroxyprop-1-yn-1-yl)-1,3-thiazole-4-carboxylate Tetrakis(triphenylphosphine)palladium(0)(422 mg, 0.36 mmol, 0.1 eq) was added to a stirred solution of the product from Preparation 11d (2.42 g, 3.65 mmol, 1 eq), propargyl alcohol (0.86 mL, 14.6 mmol, 4 eq), triethylamine (3.04 mL, 21.9 mmol, 6 eq) and copper(I) iodide (139 mg, 0.72 mmol, 0.2 eq) in dimethylformamide (50 mL) under a nitrogen atmosphere and the mixture was heated at 100° C. overnight. The reaction was allowed to cool to ambient temperature then concentrated in vacuo. Purification by automated flash column chromatography (CombiFlash Rf, 80 g RediSep™ silica cartridge) eluting with a gradient of 0-100% ethyl acetate in iso-heptane afforded the desired product as a cream solid (0.91 g, 1.43 mmol, 39%).

LC/MS ($C_{30}H_{36}N_6O_4SiS_2$) 637 $[M+H]^+$; RT 1.44 (LCMS-V-B1)

$^1$H NMR (400 MHz, DMSO-d6) δ 11.18 (br s, 1H), 7.87 (d, 1H), 7.50-7.40 (m, 2H), 7.26 (td, 1H), 7.11 (s, 1H), 6.00 (d, J=10.2 Hz, 2H), 5.88 (s, 2H), 5.43 (t, 1H), 4.39 (d, J=5.9, 0.8 Hz, 2H), 4.30 (q, J=7.1 Hz, 2H), 3.82 (s, 3H), 3.75-3.67 (m, 2H), 2.72-2.62 (m, 1H), 1.32 (t, J=7.1 Hz, 3H), 1.22-1.12 (m, 2H), 1.12-1.06 (m, 2H), 0.94-0.85 (m, 2H), 0.00 (s, 9H).

Step B: ethyl 2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-5-(3-hydroxypropyl)-1,3-thiazole-4-carboxylate A suspension of the product from Step A (913 mg, 1.43 mmol, 1 eq) in 1:1 ethyl acetate/methanol (40 mL) was added to a flask containing platinum (IV) oxide (32.6 mg, 0.14 mmol, 0.1 eq) under a nitrogen atmosphere. The vessel was evacuated and back-filled with nitrogen (×3) then evacuated and placed under an atmosphere of hydrogen and shaken for 3.5 h. The reaction was filtered through celite (10 g), eluted with methanol, and the solvent removed in vacuo. Purification by automated flash column chromatography (CombiFlash Rf, 12 g RediSep™ silica cartridge) eluting with a gradient of 0-70% ethyl acetate in iso-heptane afforded the desired product as a cream foam (762 mg, 1.19 mmol, 83%).

LC/MS ($C_{30}H_{40}N_6O_4SiS_2$) 641 [M+H]$^+$; RT 1.44 (LCMS-V-B1)

$^1$H NMR (400 MHz, DMSO-d6) δ 7.85 (dd, J=7.5, 1.0 Hz, 1H), 7.49-7.39 (m, 2H), 7.28-7.22 (m, 1H), 7.07 (s, 1H), 5.87 (s, 2H), 4.56 (t, J=5.1, 3.1 Hz, 1H), 4.28 (q, J=7.1 Hz, 3H), 3.76 (s, 3H), 3.75-3.66 (m, 2H), 3.48 (q, 2H), 3.17-3.07 (m, 2H), 2.71-2.62 (m, 1H), 1.79 (p, 2H), 1.31 (t, J=7.1 Hz, 3H), 1.19-1.12 (m, 2H), 1.11-1.04 (m, 2H), 0.94-0.86 (m, 2H), 0.00 (s, 9H).

Step C: ethyl 2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-5-(3-iodopropyl)-1,3-thiazole-4-carboxylate To a stirred solution of the product from Step B (762 mg, 1.19 mmol, 1 eq) in 10:3 diethyl ether/acetonitrile (26 mL) was added imidazole (122 mg, 1.78 mmol, 1.5 eq), triphenylphosphine (468 mg, 1.78 mmol, 1.5 eq) and iodine (453 mg, 1.78 mmol, 1.5 eq) and the mixture was stirred at ambient temperature overnight. The reaction was diluted with ethyl acetate, washed with 10% aqueous sodium thiosulfate solution followed by water then brine, dried (magnesium sulfate), and concentrated in vacuo. Purification by automated flash column chromatography (CombiFlash Rf, 40 g RediSep™ silica cartridge) eluting with a gradient of 0-60% ethyl acetate in iso-heptane afforded the desired product as a cream foam (613 mg, 0.82 mmol, 69%).

LC/MS ($C_{30}H_{39}IN_6O_3SiS_2$) 751 [M+H]$^+$; RT 1.62 (LCMS-V-B1)

$^1$H NMR (400 MHz, DMSO-d6) δ 7.84 (dd, J=7.7, 1.0 Hz, 1H), 7.49-7.38 (m, 2H), 7.25 (ddd, J=8.2, 7.0, 1.5 Hz, 1H), 7.07 (s, 1H), 5.88 (s, 2H), 4.30 (q, J=7.1 Hz, 2H), 3.75 (s, 3H), 3.74-3.65 (m, 2H), 3.38-3.29 (m, 2H), 3.17 (t, J=6.8 Hz, 2H), 2.70-2.60 (m, 1H), 2.14 (p, 2H), 1.32 (t, J=7.1 Hz, 3H), 1.20-1.11 (m, 2H), 1.10-1.04 (m, 2H), 0.95-0.85 (m, 2H), 0.00 (s, 9H).

Step D: ethyl 2-[(5-cyclopropyl-6-{[(2Z)-3-{[2-(trimethylsilyl)ethoxy]methyl}-2,3-dihydro-1,3-benzothiazol-2-ylidene]amino}pyridazin-3-yl)(methyl)amino]-5-(3-{4-[3-(dimethylamino)prop-1-yn-1-yl]-2-fluorophenoxy}propyl)-1,3-thiazole-4-carboxylate Sodium Hydride (60% in mineral oil; 65.3 mg, 1.63 mmol, 2 eq) was added to a solution of the product from Preparation 6b (189 mg, 0.98 mmol, 1.2 eq) in dimethylformamide (10 mL). After 10 min the reaction was cooled to 0° C. and a solution of the product from Step C (613 mg, 0.82 mmol, 1 eq) in dimethylformamide (10 mL) was added. The mixture was allowed to warm to ambient temperature and stirred for 3.5 h. The reaction was quenched by the addition of water, acidified with 2N aqueous hydrochloric acid and extracted with dichloromethane (×2). The combined organic extracts were washed with brine, dried (magnesium sulfate) and concentrated in vacuo. Purification by automated flash column chromatography (CombiFlash Rf, 24 g RediSep™ silica cartridge) eluting with a gradient of 0-10% methanol in dichloromethane gave a solid that was further purified by preparative HPLC (method HPLC-V-A1) to afford the desired product as an off-white solid (283 mg, 0.35 mmol, 43%).

LC/MS ($C_{41}H_{50}FN_7O_4SiS_2$) 816 [M+H]$^+$; RT 1.41 (LCMS-V-B1)

$^1$H NMR (400 MHz, DMSO-d6) δ 8.35 (s, 1H), 7.82 (d, 1H), 7.48-7.39 (m, 2H), 7.33-7.11 (m, 3H), 7.06 (s, 1H), 5.86 (s, 2H), 4.25 (q, J=7.1 Hz, 2H), 4.13 (t, J=6.2 Hz, 21), 3.75 (s, 3H), 3.70 (t, 2H), 3.37 (s, 2H), 3.25 (t, J=7.6 Hz, 2H), 2.69-2.59 (m, 1H), 2.19 (s, 6H), 2.10 (p, J=6.3 Hz, 2H), 1.28 (t, J=7.1 Hz, 3H), 1.19-1.11 (m, 2H), 1.10-1.02 (m, 2H), 0.89 (dd, J=8.7, 7.4 Hz, 2H), 0.00 (s, 9H).

Step E: ethyl 2-({6-[(1,3-benzothiazol-2-yl)amino]-5-cyclopropylpyridazin-3-yl}(methyl)amino)-5-(3-{4-[3-(dimethylamino)prop-1-yn-1-yl]-2-fluorophenoxy}propyl)-1,3-thiazole-4-carboxylate Trifluoroacetic acid (4 mL, 53.7 mmol, 155 eq) was added to a stirred solution of the product from Step D (283 mg, 0.35 mmol, 1 eq) in dichloromethane (10 mL) and the mixture was stirred at ambient temperature overnight. The reaction was partitioned between dichloromethane and saturated aqueous sodium bicarbonate, washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow glass (56.5 mg, 0.08 mmol, 24%).

LC/MS ($C_{35}H_{36}FN_7O_3S_2$) 686 [M+H]$^+$; RT 1.12 (LCMS-V-B1)

$^1$H NMR (400 MHz, DMSO-d6) δ 11.71 (br s, 1H), 7.89 (d, 1H), 7.50 (d, J=8.0 Hz, 1H), 7.39 (ddd, J=8.2, 7.3, 1.3 Hz, 1H), 7.31 (dd, J=12.0, 2.0 Hz, 1H), 7.27-7.10 (m, 4H), 4.26 (q, J=7.1 Hz, 2H), 4.15 (t, J=6.2 Hz, 2H), 3.77 (s, 3H), 3.40 (s, 2H), 3.30-3.24 (m, 2H), 2.49-2.45 (m, 1H), 2.21 (s, 6H), 2.13 (p, J=6.3 Hz, 2H), 1.30 (t, J=7.1 Hz, 2H), 1.20-1.10 (m, 2H), 1.06-0.99 (m, 2H).

Step F: 2-({6-[(1,3-benzothiazol-2-yl)amino]-5-cyclopropylpyridazin-3-yl}(methyl)amino)-5-(3-{4-[3-(dimethylamino)prop-1-yn-1-yl]-2-fluorophenoxy}propyl)-1,3-thiazole-4-carboxylic acid To a solution of the product from Step E (56.5 mg, 0.08 mmol, 1 eq) in 1,4-dioxane (4 mL) was added lithium hydroxide monohydrate (17.3 mg, 0.41 mmol, 5 eq) and the mixture was heated at 100° C. for 6.5 h. The reaction was allowed to cool to ambient temperature and concentrated in vacuo. The residue was triturated with water, filtered, and dried under vacuum to afford the desired product as a yellow solid (46.5 mg, 0.07 mmol, 86%) [as a lithium salt].

HRMS-ESI (m/z) [M+H]+ calcd for $C_{33}H_{33}FN_7O_3S_2$: 658.2065, found 658.2070.

Example 63: 2-({6-[(1,3-Benzothiazol-2-yl)amino]-5-methylpyridazin-3-yl}(methyl)amino)-5-(3-phenoxypropyl)-1,3-thiazole-4-carboxylic acid

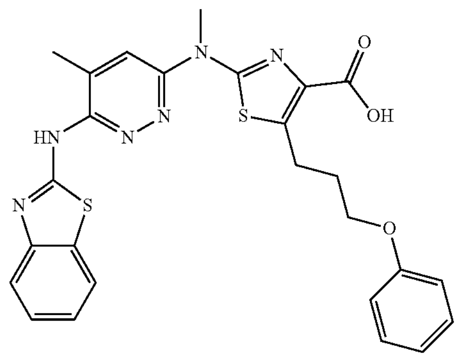 [SMILES: Cc1cc(N(C)c2nc(C(=O)O)c(CCCOc3ccccc3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(3-phenoxyprop-1-yn-1-yl)-1,3-thiazole-4-carboxylate Tetrakis(triphenylphosphine)palladium(0)(85.2 mg, 0.08 mmol, 0.1 eq) was added to a stirred solution of the product from Preparation 11b (469 mg, 0.74 mmol, 1 eq), phenyl propargyl ether (0.38 mL, 2.96 mmol, 4 eq), triethylamine (0.62 mL, 4.42 mmol, 6 eq) and copper(I) iodide (28.1 mg, 0.14 mmol, 0.2 eq) in dimethylformamide (12 mL) under a nitrogen atmosphere and the mixture was heated at 100° C. overnight. The reaction was allowed to cool to ambient temperature and concentrated in vacuo. Purification by automated flash column chromatography (CombiFlash Rf, 40 g RediSep™ silica cartridge) eluting with a gradient of 0-100% ethyl acetate in iso-heptane afforded the desired product as a brown foam (296 mg, 0.43 mmol, 58%).

LC/MS ($C_{34}H_{38}N_6O_4SiS_2$) 687 $[M+H]^+$; RT 1.57 (LCMS-V-B1)

$^1$H NMR (400 MHz, DMSO-d6) δ 7.87 (dd, J=7.8, 1.0 Hz, 1H), 7.74 (d, J=1.1 Hz, 1H), 7.51-7.42 (m, 2H), 7.38-7.33 (m, 2H), 7.26 (ddd, J=9.2, 5.5, 1.5 Hz, 1H), 7.10-7.06 (m, 2H), 7.00 (tt, J=7.4, 1.1 Hz, 1H), 5.87 (s, 2H), 5.15 (s, 2H), 4.26 (q, J=7.1 Hz, 2H), 3.83 (s, 3H), 3.76-3.70 (m, 2H), 2.47 (d, J=1.0 Hz, 3H), 1.28 (t, J=7.1 Hz, 3H), 0.97-0.88 (m, 2H), 0.00 (s, 9H).

Step B: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(3-phenoxypropyl)-1,3-thiazole-4-carboxylate A suspension of the product from Step A (296 mg, 0.43 mmol, 1 eq) in 1:1 ethyl acetate/methanol (10 mL) was added to a flask containing platinum (IV) oxide (978 mg, 0.04 mmol, 0.1 eq) under a nitrogen atmosphere. The vessel was evacuated and back-filled with nitrogen (×3) then evacuated and placed under an atmosphere of hydrogen and shaken overnight. The reaction was littered through celite (2.5 g), eluted with methanol, and the solvent was removed in vacuo. Purification by automated flash column chromatography (CombiFlash Rf, 12 g RediSep™ silica cartridge) eluting with a gradient of 0-40% ethyl acetate in iso-heptane afforded the desired product as a brown gum (148 mg, 0.21 mmol, 50%).

LC/MS ($C_{34}H_{42}N_6O_4SiS_2$) 691 $[M+H]^+$; RT 1.59 (LCMS-V-B1)

$^1$H NMR (400 MHz, DMSO-d6) δ 7.84 (d, J=7.7 Hz, 1H), 7.67 (d, 1.2 Hz, 1H), 7.51-7.40 (m, 2H), 7.33-7.22 (m, 3H), 7.05-6.88 (m, 3H), 5.76 (s, 2H), 4.26 (q, 2H), 4.04 (t, J=6.2 Hz, 2H), 3.78 (s, H), 3.73 (t, 2H), 3.33-3.22 (m, 2H), 2.46 (s, 3H), 2.11 (p, 1H), 1.30 (t, J=7.1 Hz, 3H), 0.93 (t, J=8.0 Hz, 2H), 0.00 (s, 9H).

Step C: ethyl 2-({6-[(1,3-benzothiazol-2-yl)amino]-5-methylpyridazin-3-yl}(methyl)amino)-5-(3-phenoxypropyl)-1,3-thiazole-4-carboxylate Hydrochloric acid (4M in 1,4-dioxane; 3 mL) was added slowly to a solution of the product from Step B (148 mg, 0.21 mmol, 1 eq) in tetrahydrofuran (5 mL) and the mixture was stirred at ambient temperature overnight. The reaction was partitioned between ethyl acetate and saturated aqueous sodium bicarbonate, washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow glass (46.7 mg, 0.08 mmol, 39%).

LC/MS ($C_{28}H_{28}N_6O_3S_2$) 561 $[M+H]^+$; RT 1.37 (LCMS-V-B1)

$^1$H NMR (400 MHz, DMSO-d6) δ 11.07 (br s, 1H), 8.01-7.81 (m, 2H), 7.69 (s, 1H), 7.39 (t, 1H), 7.35-7.26 (m, 2H), 7.25-7.19 (m, 1H), 7.00-6.88 (m, 3H), 4.28 (q, J=7.1 Hz, 2H), 4.05 (t, J=6.2 Hz, 2H), 3.78 (s, 3H), 3.34-3.24 (m, 2H), 2.47 (s, 3H), 2.21-1.99 (m, 2H), 1.31 (t, J=7.1 Hz, 3H).

Step D: 2-({6-[(1,3-benzothiazol-2-yl)amino]-5-methylpyridazin-3-yl}(methyl)amino)-5-(3-phenoxypropyl)-1,3-thiazole-4-carboxylic acid To a solution of the product from Step C (46.7 mg, 0.08 mmol, 1 eq) in 1,4-dioxane (4 mL) was added lithium hydroxide monohydrate (17.5 mg, 0.42 mmol, 5 eq) and the mixture was heated at 100° C. for 6 h. The reaction was allowed to cool to ambient temperature and concentrated in vacuo. The residue was triturated in water, filtered, and dried under vacuum to afford the desired product as a yellow solid (28.7 mg, 0.05 mmol, 65%) [as a lithium salt].

HRMS-ESI (m/z) [M−H]− calcd for $C_{26}H_{23}N_6O_3S_2$: 531.1279, found 531.1285.

Example 64: 2-({6-[(1,3-Benzothiazol-2-yl)amino]-5-methylpyridazin-3-yl}(3-methoxypropyl)amino)-5-(3-methoxypropyl)-1,3-thiazole-4-carboxylic acid

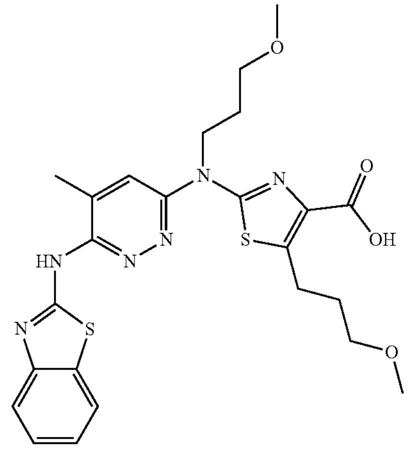 [SMILES: COCCCc1sc(N(CCCOC)c2cc(C)c(Nc3nc4ccccc4s3)nn2)nc1C(=O)O]

Step A: ethyl 5-(3-methoxyprop-1-yn-1-yl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Tetrakis(triphenylphosphine)palladium(0)(83.3 mg, 0.08 mmol, 0.1 eq) was added to a stirred solution of the product from Preparation 11c (500 mg, 0.72 mmol, 1 eq), methyl propargyl ether (0.24 mL, 2.88 mmol, 4 eq), triethylamine (0.6 mL, 4.32 mmol, 6 eq) and copper(I) iodide (27.5 mg, 0.14 mmol, 0.2 eq) in dimethylformamide (10 mL) under a nitrogen atmosphere and the mixture was heated at 100° C. overnight. The reaction was allowed to cool to ambient temperature then concentrated in vacuo. Purification by automated flash column chromatography (CombiFlash Rf, 40 g RediSep™ silica cartridge) eluting with a gradient or 0-80% ethyl acetate in iso-heptane afforded the desired product as a brown gum (337 mg, 0.49 mmol, 68%).

LC/MS ($C_{32}H_{42}N_6O_5SiS_2$)683 $[M+H]^+$; RT 1.57 (LCMS-V-B1)

$^1$H NMR (400 MHz, DMSO-d6) δ 7.87 (dd, J=7.4, 1.1 Hz, 1H), 7.73 (d, J=1.1 Hz, 1H), 7.51-7.42 (m, 2H), 7.26 (dt, 1H), 5.87 (s, 2H), 4.51-4.44 (m, 2H), 4.43 (s, 2H), 4.30 (q, J=7.1 Hz, 2H), 3.72 (t, 2H), 3.42 (J=5.9 Hz, 2H), 3.37 (s, 3H), 3.23 (s, 3H), 2.48 (d, J=0.9 Hz, 3H), 1.99 (p, J=6.6 Hz, 2H), 1.32 (t, J=7.1 Hz, 3H), 0.92 (t, J=8.6, 7.4 Hz, 2H), 0.00 (s, 9H).

Step B: ethyl 5-(3-methoxypropyl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A suspension of the product from Step A (337 mg, 0.49 mmol, 1 eq) in 1:1 ethyl acetate/methanol (10 mL) was added to a flask containing platinum (IV) oxide (11.2 mg, 0.05 mmol, 0.1 eq) under a nitrogen atmosphere. The vessel was evacuated and back-filled with nitrogen (×3) then evacuated and placed under an atmosphere of hydrogen and shaken overnight. The reaction was filtered through celite (2.5 g), eluted with ethyl acetate then methanol, and the solvent removed in vacuo. Purification by automated flash column chromatography (CombiFlash Rf, 12 g RediSep™ silica cartridge) eluting with a gradient of 0-3% methanol in dichloromethane afforded the desired product as a yellow gum (286 mg, 0.42 mmol, 84%).

LC/MS ($C_{32}H_{46}N_6O_5SiS_2$) 687 $[M+H]^+$; RT 1.58 (LCMS-V-B1)

$^1$H NMR (400 MHz, DMSO-d6) δ 7.85 (d, 1H), 7.66 (s, 1H), 7.49-7.41 (m, 2H), 7.29-7.22 (m, 1H), 5.86 (s, 2H), 4.39 (t, J=7.2 Hz, 2H), 4.28 (q, J=7.1 Hz, 2H), 3.77-3.68 (m, 2H), 3.48-3.36 (m, 4H), 3.27 (s, 3H), 3.24 (s, 3H), 3.16-3.09 (m, 2H), 2.46 (s, 3H), 2.02-1.93 (m, 2H), 1.92-1.82 (m, 2H), 1.31 (t, J=7.1 Hz, 3H), 0.97-0.88 (m, 2H), 0.00 (s, 9H).

Step C: ethyl 2-({6-[(1,3-benzothiazol-2-yl)amino]-5-methylpyridazin-3-yl}(3-methoxypropyl)amino)-5-(3-methoxypropyl)-1,3-thiazole-4-carboxylate Hydrochloric acid (4M in 1,4-dioxane; 5 mL, 20 mmol, 48 eq) was added to a stirred solution of the product from Step B (286 mg, 0.42 mmol, 1 eq) in 1,4-dioxane (2 mL) and the mixture was stirred at ambient temperature overnight. The reaction was partitioned between ethyl acetate and saturated aqueous sodium bicarbonate, washed with brine, dried (magnesium sulfate) and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow foam (162 mg, 0.29 mmol, 70%).

LC/MS ($C_{26}H_{32}N_6O_4S_2$) 557 $[M+H]^+$; RT 1.28 (LCMS-V-B1)

$^1$H NMR (400 MHz, DMSO-d6) δ 11.06 (br s, 1H), 7.94 (s, 1H), 7.67 (br s+s, 2H), 7.40 (t, J=7.5 Hz, 1H), 7.22 (s, 1H), 4.39 (t, J=7.2 Hz, 2H), 4.29 (q, J=7.1 Hz, 2H), 3.49-3.37 (m, 4H), 3.28 (s, 3H), 3.25 (s, 3H), 3.14 (dd, J=8.7, 6.7 Hz, 2H), 2.47 (s, 3H), 2.03-1.93 (m, 2H), 1.96-1.82 (m, 2H), 1.32 (t, J=7.1 Hz, 3H).

Step D: 2-({6-[(1,3-benzothiazol-2-yl)amino]-5-methylpyridazin-3-yl}(3-methoxypropyl)amino)-5-(3-methoxypropyl)-1,3-thiazole-4-carboxylic acid To a solution of the product from Step C (162 mg, 0.29 mmol, 1 eq) in 1,4-dioxane (4 mL) was added lithium hydroxide monohydrate (60.9 mg, 1.45 mmol, 5 eq) and the mixture was heated at reflux for 7 h. The reaction was allowed to cool to ambient temperature and concentrated in vacuo then dissolved in water, acidified with 2N aqueous hydrochloric acid and re-evaporated. The residue was triturated with water, filtered, and dried under vacuum to afford the desired product as a beige solid (87.8 mg, 0.17 mmol, 57%) [as a hydrochloric acid salt].

HRMS-ESI (m/z) [M+H]+ calcd for $C_{24}H_{29}N_6O_4S_2$: 529.1686, found 529.1685.

Example 65: 2-{[6-[(1,3-Benzothiazol-2-yl)amino]-5-methylpyridazin-3-yl}(3-methoxypropyl)amino)-5-(3-phenoxypropyl)-1,3-thiazole-4-carboxylic acid

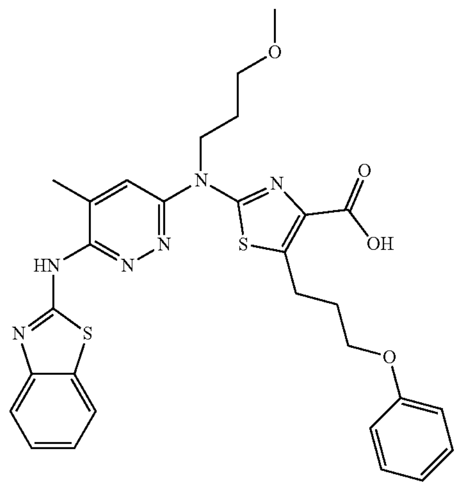 [SMILES: COCCCN(c1cc(C)c(Nc2nc3ccccc3s2)nn1)c1nc(C(=O)O)c(CCCOc2ccccc2)s1]

Step A: ethyl 2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(3-phenoxyprop-1-yn-1-yl)-1,3-thiazole-4-carboxylate Tetrakis(triphenylphosphine)palladium(0)(83.3 mg, 0.08 mmol, 0.1 eq) was added to a stirred solution of the product from Preparation 11c (500 mg, 0.72 mmol, 1 eq), phenyl propargyl ether (0.36 mL, 2.88 mmol, 4 eq), triethylamine (0.6 mL, 4.32 mmol, 6 eq) and copper(I) iodide (27.5 mg, 0.14 mmol, 0.2 eq) in dimethylformamide (10 mL) under a nitrogen atmosphere and the mixture was heated at 100° C. overnight. The reaction was allowed to cool to ambient temperature and concentrated in vacuo. Purification by automated flash column chromatography (CombiFlash Rf, 24 g RediSep™ silica cartridge) eluting with a gradient of 0-100% ethyl acetate in iso-heptane afforded the desired product as a brown foam (356 mg, 0.48 mmol, 66%).

LC/MS ($C_{37}H_{44}N_6O_5SiS_2$) 745 $[M+H]^+$; RT 1.67 (LCMS-V-B1)

$^1$H NMR (400 MHz, DMSO-d6) δ 7.87 (dd, J=7.9, 1.1 Hz, 1H), 7.73 (s, 1H), 7.52-7.42 (m, 2H), 7.38-7.32 (m, 2H), 7.30-7.24 (m, 1H), 7.10-7.05 (m, 2H), 7.00 (t, J=7.4, 1.1 Hz, 1H), 5.88 (s, 2H), 5.15 (s, 2H), 4.45 (t, J=7.1 Hz, 2H), 4.25 (q, J=7.1 Hz, 2H), 3.77-3.67 (m, 2H), 3.41 (t, J=5.9 Hz, 2H), 3.21 (s, 2H), 2.47 (s, 3H), 1.98 (p, 2H), 1.28 (t, J=7.1 Hz, 3H), 0.92 (dd, J=8.5, 7.5 Hz, 2H), 0.00 (s, 9H).

Step B: ethyl 2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(3-phenoxypropyl)-1,3-thiazole-4-carboxylate A suspension of the product from Step A (356 mg, 0.48 mmol, 1 eq) in ethyl acetate (5 mL) was added to a flask containing platinum (IV) oxide (10.8 mg, 0.05 mmol, 0.1 eq) under a nitrogen atmosphere. The vessel was evacuated and back-filled with nitrogen (×3) then evacuated and placed under an atmosphere of hydrogen and shaken overnight. The reaction was filtered through celite (2.5 g), eluted with ethyl acetate and methanol, and the solvent was removed in maw and purification by automated flash column chromatography (CombiFlash Rf, 12 g RediSep™ silica cartridge) eluting with a gradient of 0-40% ethyl acetate in iso-heptane afforded the desired product as a yellow gum (286 mg, 0.38 mmol, 80%).

LC/MS ($C_{37}H_{48}N_6O_5SiS_2$) 749 $[M+H]^+$; RT 1.66 (LCMS-V-B1)

$^1$H NMR (400 MHz, DMSO-d6) δ 7.84 (dd, J=7.7, 1.0 Hz, 1H), 7.66 (s, 1H), 7.50-7.40 (m, 2H), 7.32-7.23 (m, 3H), 6.98-6.88 (m, 3H), 5.88 (s, 2H), 4.40 (t, J=7.3 Hz, 2H), 4.26 (q, 2H), 4.05 (t, J=6.1 Hz, 2H), 3.78-3.68 (m, 2H), 3.42 (t, J=6.0 Hz, 2H), 3.31-3.26 (m, 2H), 3.23 (s, 3H), 2.46 (s, 3H), 2.17-2.06 (m, 2H), 2.03-1.92 (m, 2H), 1.30 (t, J=7.1, 5.2 Hz, 3H), 0.97-0.88 (m, 2H), 0.00 (s, 9H).

Step C: ethyl 2-({6-[(1,3-benzothiazol-2-yl)amino]-5-methylpyridazin-3-yl}(3-methoxypropyl)amino)-5-(3-phenoxypropyl)-1,3-thiazole-4-carboxylate Hydrochloric acid (4 M in 1,4-dioxane; 5 mL, 20 mmol, 52 eq) was added slowly to a solution of the product from Step B (286 mg, 0.38 mmol, 1 eq) in 1,4-dioxane (2 mL) and the mixture was stirred at ambient temperature overnight. The reaction was partitioned between ethyl acetate and saturated aqueous sodium bicarbonate, and the organic phase washed with brine, dried (magnesium sulfate) and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow foam (145 mg, 0.23 mmol, 62%).

LC/MS ($C_{31}H_{34}N_6O_4S_2$) 619 $[M+H]^+$; RT 1.40 (LCMS-V-B1)

$^1$H NMR (400 MHz, DMSO-d6) δ 11.07 (br s, 1H), 7.95 (br s, 1H), 7.68 (br s+s, 2H), 7.40 (t, 1H), 7.29 (dd, J=8.8, 7.3 Hz, 2H), 7.26-7.19 (m, 1H), 7.00-6.89 (m, 3H), 4.39 (t, J=7.2 Hz, 2H), 4.27 (q, J=7.1 Hz, 2H), 4.05 (t, J=6.2 Hz, 2H), 3.44 (t, J=6.0 Hz, 2H), 3.33-3.27 (m, 2H), 3.25 (s, 3H), 2.47 (s, 3H), 2.18-2.06 (m, 2H), 2.03-1.93 (m, 2H), 1.31 (t, J=7.1 Hz, 3H).

Step D: 2-({6-[(1,3-benzothiazol-2-yl)amino]-5-methylpyridazin-3-yl}(3-methoxypropyl)amino)-5-(3-phenoxypropyl)-1,3-thiazole-4-carboxylic acid To a solution of the product from Step C (145 mg, 0.23 mmol, 1 eq) in 1,4-dioxane (4 mL) was added lithium hydroxide monohydrate (49.3 mg, 1.17 mmol, 5 eq) and the mixture was heated at 100° C. for 7 h. The reaction was allowed to cool to ambient temperature and concentrated in vacuo, triturated with water, filtered, and dried under vacuum to afford the desired product as a brown solid (90.6 mg, 0.15 mmol, 65%) [as a lithium salt].

HRMS-ESI (m/z) [M+H]+ calcd for $C_{29}H_{31}N_6O_4S_2$: 591.1843, found 591.1843.

Example 66: 2-({6-[(1,3-Benzothiazol-2-yl)amino]-5-methylpyridazin-3-yl}(3-methoxypropyl)amino)-5-[3-(cyclohexyloxy)propyl]-1,3-thiazole-4-carboxylic acid

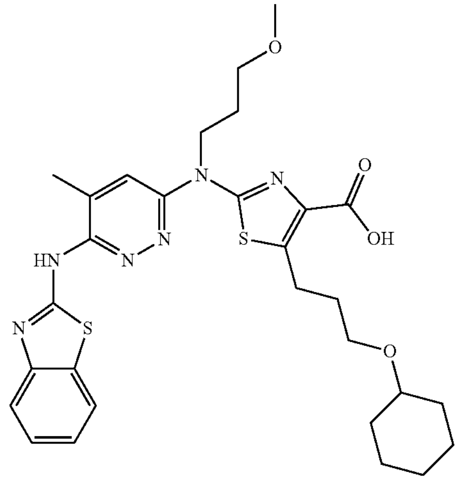 [SMILES: COCCCN(c1cc(C)c(Nc2nc3ccccc3s2)nn1)c1nc(C(=O)O)c(CCCOC2CCCCC2)s1]

Step A: ethyl 5-[3-(cyclohexyloxy)prop-1-yn-1-yl]-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Tetrakis(triphenylphosphine)palladium(0)(83.3 mg, 0.08 mmol, 0.1 eq) was added to a stirred solution of the product from Preparation 11c (500 mg, 0.72 mmol, 1 eq), (prop-2-yn-1-yloxy)cyclohexane (400 mg, 2.88 mmol, 4 eq), triethylamine (0.60 mL, 4.32 mmol, 6 eq) and copper(I) iodide (27.5 mg, 0.14 mmol, 0.2 eq) in dimethylformamide (10 mL) under a nitrogen atmosphere and the mixture was heated at 100° C. overnight. The reaction was allowed to cool to ambient temperature and concentrated in vacuo. Purification by automated flash column chromatography (CombiFlash Rf, 40 g RediSep™ silica cartridge) eluting with a gradient of 0-70% ethyl acetate in iso-heptane afforded the desired product as a brown gum (330 mg, 0.44 mmol, 61%).

LC/MS ($C_{37}H_{50}N_6O_5SiS_2$) 751 [M+H]$^+$; RT 1.81 (LCMS-V-B1)

$^1$H NMR (400 MHz, DMSO-d6) δ 7.86 (d, 1H), 7.73 (s, 1H), 7.51-7.39 (m, 2H), 7.27 (ddd, J=8.3, 7.1, 1.4 Hz, 1H), 5.88 (s, 2H), 4.50 (s, 2H), 4.46 (t, 2H), 4.30 (q, J=7.1 Hz, 2H), 3.73 (t, 2H), 3.60-3.50 (m, 1H), 3.42 (t, J=6.0 Hz, 2H), 3.23 (s, 3H), 2.48 (s, 3H), 1.98 (p, J=6.3 Hz, 2H), 1.94-1.86 (m, 2H), 1.75-1.63 (m, 2H), 1.54-1.45 (m, 2H), 1.36-1.17 (m, 7H), 0.92 (dd, J=8.4, 7.6 Hz, 2H), 0.00 (s, 9H).

Step B: ethyl 5-[3-(cyclohexyloxy)propyl]-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate A suspension of the product from Step A (330 mg, 0.44 mmol, 1 eq) in 1:1 ethyl acetate/methanol (10 mL) was added to a flask containing platinum (IV) oxide (9.98 mg, 0.04 mmol, 0.1 eq) under a nitrogen atmosphere. The vessel was evacuated and back-filled with nitrogen (×3) then evacuated and placed under an atmosphere of hydrogen and shaken overnight. The reaction was filtered through celite (2.5 g), eluted with ethyl acetate and methanol, and the solvent removed in vacuo. Purification by automated flash column chromatography (CombiFlash Rf, 12 g RediSep™ silica cartridge) eluting with a gradient of 0-40% ethyl acetate in iso-heptane afforded the desired product as a yellow gum (272 mg, 0.36 mmol, 82%).

LC/MS ($C_{37}H_{54}N_6O_5SiS_2$) 755 [M+H]$^+$; RT 1.79 (LCMS-V-B1)

$^1$H NMR (400 MHz, DMSO-d6) δ 7.82 (d, J=7.7 Hz, 1H), 7.66 (s, 1H), 7.51-7.40 (m, 2H), 7.26 (ddd, J=8.2, 6.9, 1.6 Hz 1H), 4.38 (t, 2H), 4.27 (q, J=7.0 Hz, 2H), 3.71 (t, 2H), 3.50-3.38 (m, 4H), 3.24 (s, 3H), 3.23-3.19 (m, 1H), 3.14 (t, J=7.6 Hz, 2H), 2.45 (s, 3H), 1.97 (p, 2H), 1.91-1.79 (m, 5H), 1.72-1.58 (m, 2H), 1.52-1.39 (m, 2H), 1.31 (t, J=7.1 Hz, 3H), 1.28-1.14 (m, 4H), 0.92 (t, 2H), 0.00 (s, 9H).

Step C: ethyl 2-({6-[(1,3-benzothiazol-2-yl)amino]-5-methylpyridazin-3-yl}(3-methoxypropyl)amino)-5-[3-(cyclohexyloxy)propyl]-1,3-thiazole-4-carboxylate Hydrochloric acid (4 M in 1,4-dioxane; 4 mL, 16 mmol, 45 eq) was added to a stirred solution of the product from Step B (272 mg, 0.36 mmol, 1 eq) in 1,4-dioxane (4 mL) and the mixture was stirred at ambient temperature overnight. The reaction was partitioned between ethyl acetate and saturated aqueous sodium bicarbonate, and the organic phase washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow foam (120 mg, 0.19 mmol, 53%).

LC/MS ($C_{31}H_{40}N_6O_4S_2$) 625 [M+H]$^+$; RT 1.45 (LCMS-V-B1)

$^1$H NMR (400 MHz, DMSO-d6) δ 11.09 (br s, 1H), 7.93 (s, 1H), 7.67 (br s+s, 2H), 7.39 (t, 1H), 7.23 (t, 1H), 4.39 (t, J=7.2 Hz, 2H), 4.28 (q, J=7.1 Hz, 2H), 3.45 (dt, J=9.9, 6.1 Hz, 4H), 3.25 (s, 3H), 3.24-3.20 (m, 1H), 3.15 (t, J=7.6 Hz, 2H), 2.47 (s, 3H), 1.97 (p, J=6.3 Hz, 2H), 1.94-1.78 (m, 4H), 1.74-1.62 (m, 2H), 1.54-1.41 (m, 2H), 1.32 (t, J=7.1 Hz, 3H), 129-1.16 (m, 4H).

Step D: 2-({6-[(1,3-benzothiazol-2-yl)amino]-5-methylpyridazin-3-yl}(3-methoxypropyl)amino)-5-[3-(cyclohexyloxy)propyl]-1,3-thiazole-4-carboxylic acid To a solution of the product from Step C (120 mg, 0.19 mmol, 1 eq) in 1,4-dioxane (4 mL) was added lithium hydroxide monohydrate (40.3 mg, 0.96 mmol, 5 eq) and the mixture was heated at 100° C. overnight. The reaction was allowed to cool to ambient temperature and concentrated in mow, triturated with water, filtered, and dried under vacuum to afford the desired product as a yellow solid (98 mg, 0.16 mmol, 86%) [as a lithium salt].

HRMS-ESI (m/z) [M+H]+ calcd for $C_{29}H_{37}N_6O_4S_2$: 597.2312, found 597.2314.

Example 67: 2-({6-[(1,3-Benzothiazol-2-yl)amino]-5-methylpyridazin-3-yl}(3-methoxypropyl)amino)-5-[3-(2-fluorophenoxy)propyl]-1,3-thiazole-4-carboxylic acid

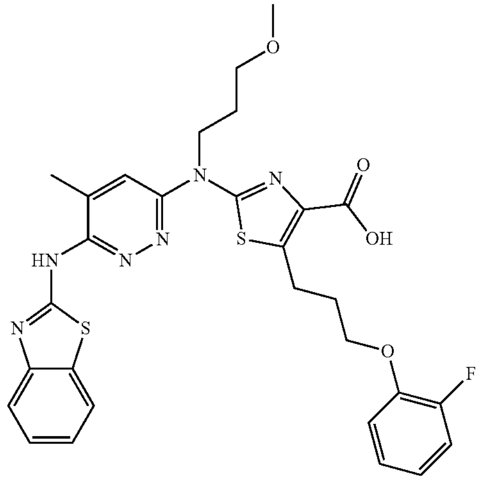 [SMILES: COCCCN(c1cc(C)c(Nc2nc3ccccc3s2)nn1)c1nc(C(=O)O)c(CCCOc2ccccc2F)s1]

Step A: ethyl 5-(3-hydroxyprop-1-yn-1-yl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Tetrakis(triphenylphosphine)palladium(0)(83.3 mg, 0.08 mmol, 0.1 eq) was added to a stirred solution of the product from Preparation 11c (500 mg, 0.72 mmol, 1 eq), propargyl alcohol (0.16 mL, 2.88 mmol, 4 eq), triethylamine (0.60 mL, 4.32 mmol, 6 eq) and copper(I) iodide (27.5 mg, 0.14 mmol, 0.2 eq) in dimethylformamide (10 mL) under a nitrogen atmosphere and the mixture was heated at 100° C. overnight. The reaction was allowed to cool to ambient temperature then concentrated in vacuo. Purification by automated flash column chromatography (CombiFlash Rf, 40 g RediSep™ silica cartridge) eluting with a gradient of 0-100% ethyl acetate in iso-heptane afforded the desired product as a brown solid (362 mg, 0.54 mmol, 75%).

LC/MS ($C_{31}H_{40}N_6O_5SiS_2$) 669 $[M+H]^+$; RT 1.45 (LCMS-V-B1)

$^1$H NMR (400 MHz, DMSO-d6) δ 7.88 (dd, J=7.4, 1.1 Hz, 1H), 7.72 (s, 1H), 7.51-7.41 (m, 2H), 7.27 (ddd, J=8.3, 7.1, 1.4 Hz, 1H), 5.89 (s, 2H), 5.44 (t, J=6.0 Hz, 1H), 4.45 (t, J=7.2 Hz, 2H), 4.40 (d, J=5.9 Hz, 2H), 4.29 (q, J=7.1 Hz, 2H), 3.77-3.68 (m, 2H), 3.42 (t, J=6.0 Hz, 2H), 3.24 (s, 3H), 2.48 (s, 3H), 1.99 (p, J=6.3 Hz, 2H), 1.33 (t, J=7.1 Hz, 3H), 0.99-0.88 (m, 2H), 0.00 (s, 9H).

Step B: ethyl 5-(3-hydroxypropy)-2-[(3-methoxypropyl)(5-methyl-6-{[(2Z)-3-{[2-(trimethylsilyl)ethoxy]methyl}-2,3-dihydro-1,3-benzothiazol-4-ylidene]amino}pyridazin-yl)amino]-1,3-thiazole-4-carboxylate A suspension of the product from Step A (362 mg, 0.54 mmol, 1 eq) in 1:1 ethyl acetate/methanol (10 mL) was added to a flask containing platinum (IV) oxide (12.3 mg, 0.05 mmol, 0.1 eq) under a nitrogen atmosphere. The vessel was evacuated and back-filled with nitrogen (×3) then evacuated and placed under an atmosphere of hydrogen and shaken overnight. The mixture was filtered through celite (2.5 g), eluted with methanol, and the solvent removed in vacuo. Purification by automated flash column chromatography (CombiFlash Rf, 24 g RediSep™ silica cartridge) eluting with a gradient of 0-80% ethyl acetate in iso-heptane afforded the desired product as a cream foam (230 mg, 0.34 mmol, 63%).

LC/MS ($C_{31}H_{44}N_6O_5SiS_2$) 673 $[M+H]^+$; RT 1.47 (LCMS-V-B1)

$^1$H NMR (400 MHz, DMSO-d6) δ 7.86 (dd, J=7.5, 1.1 Hz, 1H), 7.66 (s, 1H), 7.51-7.40 (m, 2H), 7.25 (ddd, J=8.3, 6.9, 1.6 Hz, 1H), 5.87 (s, 2H), 4.57 (t, J=5.1 Hz, 1H), 4.39 (t, J=7.2 Hz, 2H), 4.28 (q, J=7.1 Hz, 2H), 3.72 (dd, J=8.5, 7.5 Hz, 2H), 3.52-3.44 (m, 2H) 3.43 (t, 2H), 3.23 (s, 3H), 3.16-3.08 (m, 2H), 2.46 (s, 3H), 1.96 (p, J=6.4 Hz, 2H), 1.86-1.75 (m, 2H), 1.31 (t, J=7.1 Hz, 3H), 0.92 (dd, J=8.6, 7.4 Hz, 2H) 0.00 (s, 9H).

Step C: ethyl 5-(3-iodopropyl)-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Step B (230 mg, 0.34 mmol, 1 eq) in 3:1 diethyl ether/acetonitrile (16 mL) was added imidazole (34.9 mg, 0.51 mmol, 1.5 eq), triphenylphosphine (135 mg, 0.51 mmol, 1.5 eq) and iodine (130 mg, 0.51 mmol, 1.5 eq) and the mixture was stirred at ambient temperature overnight. The reaction was diluted with ethyl acetate, washed with 10% aqueous sodium thiosulfate solution followed by water then brine, dried (magnesium sulfate), and concentrated in vacuo. Purification by automated flash column chromatography (CombiFlash Rf, 12 g RediSep silica cartridge) eluting with a gradient of 0-50% ethyl acetate in iso-heptane afforded the desired product as a yellow gum (129 mg, 0.16 mmol, 48%).

LC/MS ($C_{31}H_{43}IN_6O_4SiS_2$) 783 $[M+H]^+$; RT 1.63 (LCIS-V-B1)

$^1$H NMR (400 MHz, DMSO-d6) δ 7.85 (dd, J=7.5, 1.1 Hz, 1H), 7.67 (s, 1H), 7.49-7.41 (m, 2H), 7.26 (ddd, J=8.3, 6.9, 1.6 Hz, 1H), 5.87 (s, 2H), 4.40 (t, J=7.3 Hz, 2H), 4.29 (q, J=7.1 Hz, 2H), 3.73 (dd, J=8.6, 7.4 Hz, 2H), 3.42 (t, J=6.0 Hz, 2H), 3.40-3.28 (m, 2H), 3.24 (s, 3H), 3.21-3.14 (m, 2H), 2.45 (s, 3H), 2.14 (p, J=7.0 Hz, 2H), 2.02-1.95 (m, 2H), 1.34 (t, J=7.1 Hz, 3H), 0.92 (dd, J=8.6, 7.4 Hz, 2H), 0.00 (s, 9H).

Step D: ethyl 5-[3-(2-fluorophenoxy)propyl]-2-[(3-methoxypropyl)(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Sodium Hydride (60% in mineral oil; 13.2 mg, 0.33 mmol, 2 eq) was added to a solution of 2-fluorophenol (0.02 mL, 0.2 mmol, 1.2 eq) in dimethylformamide (3 mL). After 15 min the mixture was cooled to 0° C. and a solution of the product from Step C (129 mg, 0.16 mmol, 1 eq) in dimethylformamide (3 mL) was added. The mixture was allowed to warm to ambient temperature and stirred overnight. The reaction was quenched by the addition of water, acidified with 2N aqueous hydrochloric acid, and extracted with ethyl acetate (×2). The combined organic extracts were washed with brine, dried (magnesium sulfate) and concentrated in vacuo. Purification by automated flash column chromatography (CombiFlash Rf, 12 g RediSep™ silica cartridge) eluting with a gradient of 0-6% methanol in dichloromethane afforded the desired product as a cream gum (75.6 mg, 0.1 mmol, 60%).

LC/MS ($C_{37}H_{47}FN_6O_5SiS_2$) 767 $[M+H]^+$; RT 1.61 (LCMS-V-B1)

$^1H$ NMR (400 MHz, DMSO-d6) δ 7.84 (d, 1H), 7.67 (s, 1H), 7.51-7.40 (m, 2H), 7.30-7.07 (m, 4H), 6.97-6.89 (m, 1H), 5.87 (s, 2H), 4.40 (t, J=7.2 Hz, 2H), 4.26 (q, J=7.0 Hz, 2H), 4.13 (t, J=6.1 Hz, 2H), 3.78-3.69 (m, 2H), 3.42 (t, J=6.0 Hz, 2H), 3.31-3.25 (m, 2H), 3.24 (s, 3H), 2.46 (s, 3H), 2.25-2.05 (m, 2H), 1.97 (p, J=6.2 Hz, 2H), 1.29 (t, J=7.1 Hz, 3H), 0.98-0.89 (m, 2H), 0.00 (s, 9H).

Step E: ethyl 2-({6-[(1,3-benzothiazol-2-yl)amino]-5-methylpyridazin-3-yl}(3-methoxypropyl)amino)-5-[3-(2-fluorophenoxy)propyl]-1,3-thiazole-4-carboxylate Hydrochloric acid (4M in 1,4-dioxane; 1 mL, 4 mmol, 40.6 eq) was added to a stirred solution of the product from Step D (75.6 mg, 0.1 mmol, 1 eq) in 1,4-dioxane (2 mL) and the mixture was stirred at ambient temperature overnight. The reaction was partitioned between ethyl acetate and saturated aqueous sodium bicarbonate and the organic phase was washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow glass (36.2 mg, 0.06 mmol, 58%).

LC/MS ($C_{31}H_{33}FN_6O_4S_2$) 637 $[M+H]^+$; RT 1.39 (LCMS-V-B1)

$^1H$ NMR (400 MHz, DMSO-d6) 7.92 (br s, 1H), 7.67 (br s+s, 2H), 7.39 (t, J=7.5 Hz, 1H), 7.27-7.08 (m, 4H), 6.99-6.89 (m, 1H), 4.39 (t, J=7.3 Hz, 2H), 4.26 (q, J=7.1 Hz, 2H), 4.14 (t, J=6.1 Hz, 2H), 3.44 (t, J=6.0 Hz, 2H), 3.34-3.24 (m, 2H), 3.25 (s, 3H), 2.47 (s, 2H), 2.22-2.06 (m, 2H), 1.97 (p, 2H), 1.30 (t, J=7.1 Hz, 3H).

Step F: 2-({6-[(1,3-benzothiazol-2-yl)amino]-5-methylpyridazin-3-yl}(3-methoxypropyl)amino)-5-[3-(2-fluorophenoxy)propyl]-1,3-thiazole-4-carboxylic acid To a solution of the product from Step E (36.2 mg, 0.06 mmol, 1 eq) in 1,4-dioxane (3 mL) was added lithium hydroxide monohydrate (11.9 mg, 0.28 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a beige solid (19.5 mg, 0.03 mmol, 56%).

HRMS-ESI (m/z) [M+H]+ calcd for $C_{29}H_{30}FN_6O_4S_2$: 609.1749, found 609.1753.

Example 68: 2-({6-[(1,3-Benzothiazol-2-yl)amino]-5-methylpyridazin-3-yl}(methyl)amino)-5-[3-(benzyloxy)azetidin-1-yl]-1,3-thiazole-4-carboxylic acid

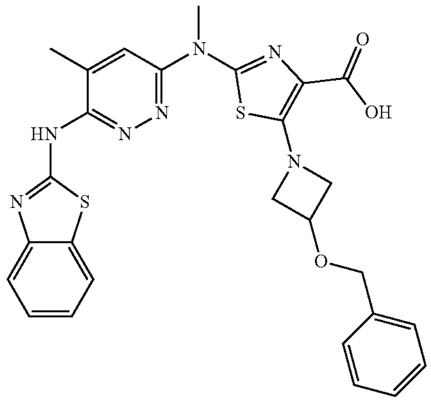 [SMILES: Cc1cc(N(C)c2nc(C(=O)O)c(N3CC(OCc4ccccc4)C3)s2)nnc1Nc1nc2ccccc2s1]

Step A: ethyl 5-[3-(benzyloxy)azetidin-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To an oven dried microwave vial was added the product from Preparation 11b (500 mg, 0.79 mmol, 1 eq), 3-(benzyloxy)azetidine hydrochloride (314 mg, 1.57 mmol, 2 eq), cesium carbonate (769 mg, 2.36 mmol, 3 eq), and 1,4-dioxane (10 mL). The mixture was sparged with nitrogen (10 min) before adding Xantphos Pd G3 (74.7 mg, 0.08 mmol, 0.1 eq) and the mixture heated at 140° C. for 2 h under microwave irradiation. The reaction was diluted with ethyl acetate then washed with water followed by brine, and the organic phase was dried (magnesium sulfate) and concentrated in vacuo. Purification by automated flash column chromatography (CombiFlash Rf, 24 g RediSep™ silica cartridge) eluting with a gradient of 0-50% ethyl acetate in iso-heptane afforded the desired product as a yellow foam (380 mg, 0.53 mmol, 67%).

LC/MS ($C_{35}H_{43}N_7O_4SiS_2$) 718 $[M+H]^+$; RT 1.53 (LCMS-V-B1)

$^1H$ NMR (400 MHz, DMSO-d6) δ 7.82 (d, 1H), 7.57 (d, J=1.0 Hz, 1H), 7.50-7.42 (m, 2H), 7.40-7.35 (m, 4H), 7.34-7.28 (m, 1H), 7.27-7.21 (m, 1H), 5.84 (s, 2H), 4.52 (s, 2H), 4.52-4.44 (m, 1H), 4.32 (ddd, J=8.9, 6.3, 1.2 Hz, 2H), 4.19 (q, J=7.1 Hz, 2H), 4.03-3.94 (m, 2H), 3.76-3.70 (m, 2H), 3.66 (s, 3H), 2.44 (d, J=1.0 Hz, 3H), 1.26 (t, J=7.1 Hz, 3H), 0.97-0.88 (m, 2H), 0.00 (s, 9H).

Step B: ethyl 2-({6-[(1,3-Benzothiazol-2-yl)amino]-5-methylpyridazin-3-yl}(methyl)amino)-5-[3-(benzyloxy)azetidin-1-yl]-1,3-thiazole-4-carboxylate Trifluoroacetic acid (1 mL, 13.4 mmol, 96.3 eq) was added to a stirred solution of the product from Step A (100 mg, 0.14 mmol, 1 eq) in dichloromethane (3 mL) and the mixture was stirred at ambient temperature overnight. The reaction was diluted with dichloromethane and washed with saturated aqueous sodium bicarbonate then brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH4; formic acid) afforded the desired product as a yellow glass (48 mg, 0.08 mmol, 59%).

LC/MS ($C_{29}H_{29}N_7O_3S_2$) 588 $[M+H]^+$; RT 1.31 (LCMS-V-B1)

$^1H$ NMR (400 MHz, DMSO-d6) δ 11.02 (br s, 1H), 7.90 (br s, 1H), 7.59 (br s+s, 2H), 7.44-7.28 (m, 6H), 7.21 (t, J=7.5 Hz, 1H), 4.52 (s, 2H), 4.51-4.46 (m, 1H), 4.37-4.28 (m, 2H), 4.20 (q, J=7.1 Hz, 2H), 4.01-3.96 (m, 2H), 3.66 (s, 3H), 2.45 (s, 3H), 1.27 (t, J=7.1 Hz, 3H).

Step C: 2-({6-[(1,3-benzothiazol-2-yl)amino]-5-methylpyridazin-3-yl}(methyl)amino)-5-[3-(benzyloxy)azetidin-1-yl]-1,3-thiazole-4-carboxylic acid To a solution of the product from Step B (48 mg, 0.08 mmol, 1 eq) in 1,4-dioxane (4 mL) was added lithium hydroxide monohydrate (17.1 mg, 0.41 mmol, 5 eq) and the mixture was heated at 100° C. overnight. The reaction was allowed to cool to ambient temperature and concentrated in vacuo. The residue was triturated in water, filtered, and dried under vacuum to afford the desired product as a beige solid (33.2 mg, 0.06 mmol, 73%) [as a lithium salt].

HRMS-ESI (m/z) [M+H]+ calcd for $C_{27}H_{26}N_7O_3S_2$: 560.1533, found 560.1531.

Example 69: 2-({6-[(1,3-Benzothiazol-2-yl)amino]-5-methylpyridazin-3-yl}(methyl)amino)-5-(3-phenoxyazetidin-1-yl)-1,3-thiazole-4-carboxylic acid

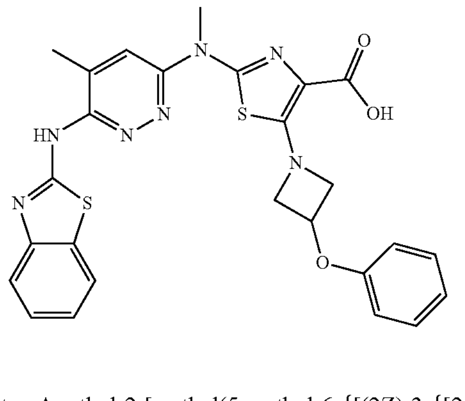

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(3-phenoxyazetidin-1-yl)-1,3-thiazole-4-carboxylate To an oven-dried vial was added the product from Preparation 11b (100 mg, 0.16 mmol, 1 eq), 3-phenoxy-azetidine hydrochloride (58.4 mg, 0.31 mmol, 2 eq), cesium carbonate (154 mg, 0.47 mmol, 3 eq), and 1,4-dioxane (4 mL). The mixture was sparged with nitrogen (10 min) and rac-BINAP Pd G3 (15.6 mg, 0.02 mmol, 0.1 eq) was added and the mixture was heated at 100° C. for 24 h. The reaction was diluted with ethyl acetate, washed with water followed by brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow glass (55.7 mg, 0.08 mmol, 50%).

LC/MS ($C_{34}H_{41}N_7O_4SiS_2$) 704 $[M+H]^+$; RT 1.60 (LCMS-V-B1)

$^1H$ NMR (400 MHz, DMSO-d6) δ 7.82 (d, 1H), 7.59 (d, J=1.1 Hz, 1H), 7.51-7.39 (m, 2H), 7.39-7.30 (m, 2H), 7.29-7.20 (m, 1H), 7.00 (tt, J=7.4, 1.1 Hz, 1H), 6.91 (dt, J=7.7, 1.1 Hz, 2H), 5.85 (s, 2H), 5.16 (tt, J=6.6, 3.8 Hz, 1H), 4.62-4.53 (m, 2H), 4.22 (q, J=7.1 Hz, 2H), 4.18-4.09 (m, 2H), 3.73 (dd, J=8.5, 7.5 Hz, 2H), 3.69 (s, 3H), 2.45 (d, J=1.0 Hz, 3H), 1.28 (t, J=7.1 Hz, 3H), 0.97-0.88 (m, 2H), 0.00 (s, 9H).

Step B: ethyl 2-({6-[(1,3-benzothiazol-2-yl)amino]-5-methylpyridazin-3-yl}(methyl)amino)-5-(3-phenoxyazetidin-1-yl)-1,3-thiazole-4-carboxylate Trifluoroacetic acid (1 mL, 13.4 mmol, 170 eq) was added to a stirred solution of the product from Step A (55.7 mg, 0.08 mmol, 1 eq) in dichloromethane (3 mL) and the mixture was stirred at ambient temperature overnight. The reaction was diluted with dichloromethane, washed with saturated aqueous sodium bicarbonate then brine, dried (magnesium sulfate), and concentrated in vacuo. Purification by reverse phase automated flash chromatography (CombiFlash Rf, C18 13 g RediSep column) eluting with a gradient of 5-95% acetonitrile (pH4; formic acid) in water (pH 4; formic acid) afforded the desired product as a yellow glass (20.4 mg, 0.04 mmol, 45%).

LC/MS ($C_{28}H_{27}N_7O_3S_2$) 574 $[M+H]^+$; RT 1.31 (LCMS-V-B1)

$^1H$ NMR (400 MHz, DMSO-d6) δ 7.92 (br s, 1H), 7.60 (br s+s, 2H), 7.41-7.30 (m, 3H), 7.21 (s, 1H), 7.01 (tt, J=7.4, 1.1 Hz, 1H), 6.91 (dt, J=7.8, 1.1 Hz, 2H), 5.16 (tt, J=6.5, 3.7 Hz, 1H), 4.62-4.53 (m, 2H), 4.22 (q, J=7.1 Hz, 2H), 4.17-4.10 (m, 2H), 3.68 (s, 3H), 2.45 (s, 2H), 1.28 (t, J=7.1 Hz, 3H).

Step C: 2-({6-[(1,3-benzothiazol-2-yl)amino]-5-methylpyridazin-3-yl}(methyl)amino)-5-(3-phenoxyazetidin-1-yl)-1,3-thiazole-4-carboxylic acid To a solution attic product from Step B (20 mg, 003 mmol, 1 eq) in 1,4-dioxane (3 mL) was added lithium hydroxide monohydrate (7.31 mg, 0.17 mmol, 5 eq) and the mixture was heated at 100° C. overnight. The reaction was allowed to cool to ambient temperature, concentrated in vacuo, triturated with water, filtered, and dried under vacuum to afford the desired product as a beige solid (11.2 mg, 0.02 mmol, 59%) [as a lithium salt].

HRMS-ESI (m/z) [M+H]+ calcd for $C_{26}H_{24}N_7O_3S_2$: 546.1377, found 546.1381.

Example 70: 2-({6-[(1,3-Benzothiazol-2-yl)amino]-5-methylpyridazin-3-yl}(methyl)amino)-5-[(3S)-3-(benzyloxy)pyrrolidin-1-yl]-1,3-thiazole-4-carboxylic acid

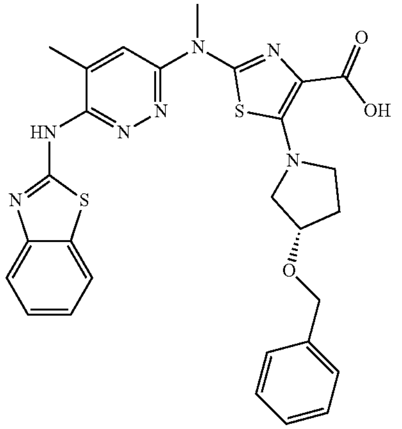 [SMILES: Cc1cc(N(C)c2nc(C(=O)O)c(N3CC[C@H](OCc4ccccc4)C3)s2)nnc1Nc1nc2ccccc2s1]

Step A: ethyl 5-[(3S)-3-(benzyloxypyrrolidin-1-yl]-2-[methyl(5-methyl-6-{[(2Z-3-{[2-(trimethylsilyl)ethoxy]methyl}-2,3-dihydro-1,3-benzothiazol-2-ylidene]amino}pyridazin-3-yl)amino]-1,3-thiazole-1-carboxylate To an oven dried vial was added the product from Preparation 11b (200 mg, 0.31 mmol, 1 eq), (S)-3-benzyloxy-pyrrolidine hydrochloride (135 mg, 0.63 mmol, 2 eq), cesium carbonate (308 mg, 0.94 mmol, 3 eq), and 1,4-dioxane (8 mL). The mixture was sparged with nitrogen (10 min) before the addition of rac-BINAP Pd G3 (15.6 mg, 0.02 mmol, 0.05 eq) and the mixture heated at 100° C. for 24 h. The reaction was diluted with ethyl acetate, then washed with water followed by brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow foam (113 mg, 0.15 mmol, 49%).

LC/MS ($C_{36}H_{45}N_7O_4SiS_2$) 732 $[M+H]^+$; RT 1.54 (LCMS-V-B1)

$^1H$ NMR (400 MHz, DMSO-d6) δ 7.82 (d, 1H), 7.57 (d, 1H), 7.49-7.40 (m, 2H), 7.36-7.31 (m, 4H), 7.31-7.22 (m, 2H), 5.84 (s, 2H), 4.60-4.48 (m, 2H), 4.30-4.26 (m, 1H), 4.25-4.17 (m, 2H), 3.71 (t, 2H), 3.68 (s, 3H), 3.64-3.52 (m, 2H), 3.48-3.36 (m, 2H), 2.44 (d, J=1.0 Hz, 3H), 2.14 (s, 2H), 1.29 (t, J=7.1 Hz, 3H), 0.97-0.88 (m, 2H), 0.00 (s, 9H).

Step B: ethyl 2-({6-[(1,3-benzothiazol-2-yl)amino]-5-methylpyridazin-3-yl}(methyl)amino)-5-[(3S)-3-(benzyloxy)pyrrolidin-1-yl]-1,3-thiazole-4-carboxylate Hydrochloric acid (4M in 1,4-dioxane; 4 mL, 16 mmol, 104 eq) was added to a stirred solution of the product from Step A (113 mg, 0.15 mmol, 1 eq) in 1,4-dioxane (5 mL) and the mixture was stirred at 40° C. overnight. The reaction was diluted with ethyl acetate, washed with saturated aqueous sodium bicarbonate then brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (83 mg, 0.14 mmol, 89%).

LC/MS ($C_{30}H_{31}N_7O_3S_2$) 602 $[M+H]^+$; RT 1.32 (LCMS-V-B1)

$^1H$ NMR (400 MHz, DMSO-d6) δ 10.96 (br s, 1H), 7.96 (br s, 1H), 7.60 (br s+s, 2H), 7.42-7.23 (m, 5H), 7.21 (s, 2H), 4.61-4.48 (m, 2H), 4.33-4.26 (m, 1H), 4.25-4.16 (m, 2H), 3.73 (dd, J=11.4, 4.6 Hz, 1H), 3.67 (s, 3H), 3.64-3.53 (m, 1H), 3.45-3.36 (m, 2H), 2.45 (s, 3H), 2.26-2.05 (m, 2H), 1.29 (t, J=7.1 Hz, 3H).

Step C: 2-({6-[(1,3-benzothiazol-2-yl)amino]-5-methylpyridazin-3-yl}(methyl)amino)-5-[(3S)-3-(benzyloxy)pyrrolidin-1-yl]-1,3-thiazole-4-carboxylic acid To a solution of the product from Step B (83 mg, 0.14 mmol, 1 eq) in 1,4-dioxane (8 mL) was added lithium hydroxide monohydrate (28.9 mg, 0.69 mmol, 5 eq) and the mixture was heated at 100+ C overnight. The reaction was allowed to cool to ambient temperature and concentrated in vacuo, triturated with water, filtered, and dried under vacuum to afford the desired product as a yellow solid ((5.6 mg, 0.11 mmol, 83%).

HRMS-ESI (m/z) [M+H]+ calcd for $C_{28}H_{28}N_7O_3S_2$: 574.1690, found 574.1687.

Example 71: 2-({6-[(1,3-Benzothiazol-2-yl)amino]-5-methylpyridazin-3-yl}(methyl)amino)-5-[(3R)-3-(benzyloxy)pyrrolidin-1-yl]-1,3-thiazole-4-carboxylic acid

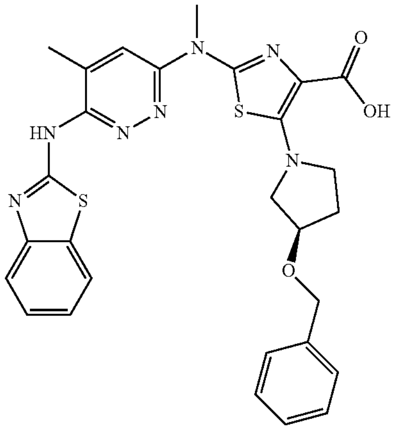 [SMILES: Cc1cc(N(C)c2nc(C(=O)O)c(N3CC[C@@H](OCc4ccccc4)C3)s2)nnc1Nc1nc2ccccc2s1]

Step A: ethyl 5-[(3R)-3-(benzyloxy)pyrrolidin-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To an oven-dried vial was added the product from Preparation 11b (200 mg, 0.31 mmol, 1 eq), (R)-3-benzyloxy-pyrrolidine hydrochloride (135 mg, 0.63 mmol, 2 eq), cesium carbonate (308 mg, 0.94 mmol, 3 eq), and 1,4-dioxane (8 mL). The mixture was sparged with nitrogen (10 min) before the addition of rac-BINAP Pd G3 (31.2 mg, 0.03 mmol, 0.1 eq) and the mixture heated at 100° C. for 24 h. The reaction was diluted with ethyl acetate, washed with water followed by brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow glass (101 mg, 0.14 mmol, 44%).

LC/MS ($C_{36}H_{45}N_7O_4SiS_2$) 732 $[M+H]^+$; RT 1.55 (LCMS-V-B1)

$^1$H NMR (400 MHz, DMSO-d6) δ 7.82 (d, 1H), 7.57 (d, J=1.1 Hz, 1H), 7.49-7.38 (m, 2H), 7.36-7.31 (m, 4H), 7.30-7.21 (m, 2H), 5.84 (s, 2H), 4.60-4.47 (m, 2H), 4.32-4.25 (m, 1H), 4.25-4.16 (m, 2H), 3.77-3.68 (m, 2H), 3.67 (s, 3H), 3.62-3.52 (m, 2H), 3.45-3.36 (m, 2H), 2.43 (s, 3H), 2.22-2.09 (m, 2H), 1.29 (t, J=7.1 Hz, 3H) 0.91 (dd, J=8.4, 7.5 Hz, 2H), 0.00 (s, 9H).

Step B: ethyl 2-({6-[(1,3-benzothiazol-2yl)amino]-5-methylpyridazin-3-yl}(methyl)amino)-5-[(3R)-3-(benzyloxy)pyrrolidin-1-yl]-1,3-thiazole-4-carboxylate Hydrochloric acid (4M in 1,4-dioxane; 4 mL, 16 mmol, 117 eq) was added to a stirred solution of the product from Step A (101 mg, 0.14 mmol, 1 eq) in 1,4-dioxane (5 mL) and the mixture was stirred at 40° C. overnight. The reaction was diluted with dichloromethane, washed with saturated aqueous sodium bicarbonate then brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow gum (80 mg, 0.13 mmol, 97%).

LC/MS ($C_{30}H_{31}N_7O_3S_2$) 602 $[M+H]^+$; RT 1.32 (LCMS-V-B1)

$^1$H NMR (400 MHz, DMSO-d6) δ 10.98 (br s, 1H), 7.91 (s, 1H), 7.60 (br s+s, 2H), 7.42-7.11 (m, 7H), 4.60-4.48 (m, 2H), 4.33-4.27 (m, 1H), 4.27-4.13 (m, 2H), 3.67 (s, 3H), 3.63-3.55 (m, 2H), 3.42 (td, J=9.3, 8.7, 3.4 Hz, 2H), 2.46 (s, 3H), 2.25-2.06 (m, 2H), 1.30 (t, J=7.1 Hz, 3H).

Step C: 2-({6-[(1,3-benzothiazol-2-yl)amino]-5-methylpyridazin-3-yl}(methyl)amino)-5-[(3R)-3-(benzyloxy)pyrrolidin-1-yl]-1,3-thiazole-4-carboxylic acid To a solution of the product from Step B (80 mg, 0.13 mmol, 1 eq) in 1,4-dioxane (5 mL) was added lithium hydroxide monohydrate (28 mg, 0.67 mmol, 5 eq) and the mixture was heated at 100° C. overnight. The reaction was allowed to cool to ambient temperature and concentrated in vacuo, triturated with water, filtered, and dried under vacuum to afford the desired product as a yellow solid (50.1 mg, 0.09 mmol, 65%) [as a lithium salt].

HRMS-ESI (m/z) [M+H]+ calcd for $C_{28}H_{28}N_7O_3S_2$: 574.1690, found 574.1723.

Example 72: 2-({6-[(1,3-Benzothiazol-2-yl)amino]-5-methylpyridazin-3-yl}(methyl)amino)-5-(3-hydroxyazetidin-1-yl)-1,3-thiazole-4-carboxylic acid

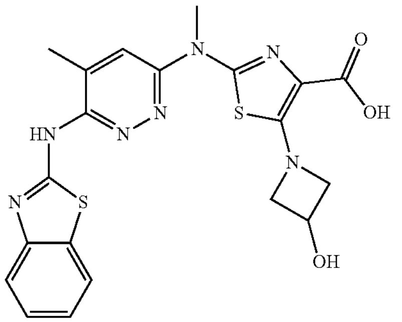 [SMILES: Cc1cc(N(C)c2nc(C(=O)O)c(N3CC(O)C3)s2)nnc1Nc1nc2ccccc2s1]

Step A: ethyl 2-({6-[(1,3-benzothiazol-2-yl)amino]-5-methylpyridazin-3-yl}(methyl)amino)-5-(3-hydroxyazetidin-1-yl)-1,3-thiazole-4-carboxylate A solution of the product from Example 68, Step B (94.2 mg, 0.16 mmol, 1 eq) in dichloromethane (5 mL) was cooled to −78° C. and boron trichloride (1M in dichloromethane; 0.48 mL, 0.48 mmol, 3 eq) was added slowly. The mixture was maintained at −78° C. for 1 h, then allowed to warm to ambient temperature over 2 h. The reaction was quenched by the addition of saturated aqueous sodium bicarbonate then extracted with dichloromethane (×2) followed by 3:1 dichloromethane/isopropanol, and the combined organic extracts were dried (magnesium sulfate) and concentrated in vacuo. Purification by automated flash column chromatography (CombiFlash Rf, 12 g RediSep™ silica cartridge) eluting with a gradient of 0-6% methanol in dichloromethane afforded the desired product as a yellow solid (13.4 mg, 0.03 mmol, 17%).

LC/MS ($C_{22}H_{23}N_7O_3S_2$) 498 $[M+H]^+$; RT 1.00 (LCMS-V-B1)

$^1$H NMR (400 MHz, DMSO-d6) δ 7.87 (d, J=7.7 Hz, 1H), 7.56 (s, 1H), 7.51 (br s, 1H), 7.41-7.32 (m, 1H), 7.18 (t, J=7.6 Hz, 1H), 5.75 (d, 1H), 4.55 (h, J=6.0 Hz, 1H), 4.40-4.31 (m, 2H), 4.21 (q, J=7.1 Hz, 2H), 3.88-3.80 (m, 2H), 3.65 (s, 3H), 2.43 (s, 3H), 1.28 (t, 7.1 Hz, 3H).

Step B: 2-({6-[(1,3-benzothiazol-2-yl)amino]-5-methylpyridazin-3-yl}(methyl)amino)-5-(3-hydroxyazetidin-1-yl)-1,3-thiazole-4-carboxylic acid To a solution of the product from Step C (13.4 mg, 0.03 mmol, 1 eq) in 1,4-dioxane (5 mL) was added lithium hydroxide monohydrate (5.65 mg, 0.13 mmol, 5 eq) and the mixture was heated at 100° C. overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a beige solid (8.1 mg, 0.02 mmol, 64%).

HRMS-ESI (m/z) [M+H]+ calcd for $C_{20}H_{20}N_7O_3S_2$: 470.1064, found 470.1072.

Example 73: 2-({6-[(1,3-Benzothiazol-2-yl)amino]-5-methylpyridazin-3-yl}(methyl)amino)-5-(3-{2-fluoro-4-[3-(methylamino)prop-1-yn-1-yl]phenoxy]propyl)-1,3-thiazole-4-carboxylic acid

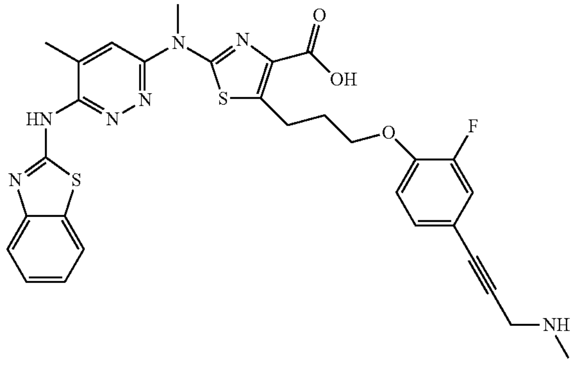 [SMILES: CNCC#Cc1ccc(OCCCc2sc(N(C)c3cc(C)c(Nc4nc5ccccc5s4)nn3)nc2C(=O)O)c(F)c1]

Step A: ethyl 2-({6-[(1,3-benzothiazol-2-yl)amino]-5-methylpyridazin-3-yl}(methyl)amino)-5-(3-{2-fluoro-4-[3-(methylamino)prop-1-yn-1-yl]phenoxy}propyl)-1,3-thiazole-4-carboxylate Trifluoroacetic acid (20 mL) was added to a stirred solution of the product from Preparation 5j, Step A (1.5 g, 1.71 mmol, 1 eq) in dichloromethane (60 mL) and the mixture was stirred at ambient temperature overnight. The reaction was diluted with dichloromethane, cooled to 0° C. then basified by the addition of 2N aqueous sodium hydroxide, and the organic phase was dried (magnesium sulfate) and concentrated in vacuo. Purification by automated flash column chromatography (CombiFlash Rf, 40 g RediSep™ silica cartridge) eluting with a gradient of 0-10% methanol in dichloromethane afforded the desired product as a yellow solid (361 mg, 0.56 mmol, 33%).

LC/MS ($C_{32}H_{32}FN_7O_3S_2$) 646 $[M+H]^+$; RT 1.98 (LCMS-V-C)

$^1$H NMR (400 MHz, DMSO-d6) δ 7.91 (d, 1H), 7.68 (d, J=1.2 Hz, 1H), 7.53 (d, J=7.9 Hz, 1H), 7.39 (ddd, J=8.2, 7.2, 1.3 Hz, 1H), 7.32-7.11 (m, 4H), 4.25 (q, J=7.1 Hz, 2H), 4.15 (t, J=6.2 Hz, 2H), 3.77 (s, 3H), 3.46 (s, 2H), 3.27 (t, J=7.7 Hz, 2H), 2.47 (d, J=1.0 Hz, 3H), 2.31 (s, 3H), 2.19-2.07 (m, 2H), 2.23 (s, 1H), 1.30 (t, J=7.1 Hz, 3H).

Step B: 2-({6-[(1,3-benzothiazol-2-yl)amino]-5-methylpyridazin-3-yl}(methyl)amino)-5-(3-{2-fluoro-4-[3-(methylamino)prop-1-yn-1-yl]phenoxy}propyl)-1,3-thiazole-4-carboxylic acid To a solution of the product from Step B (361 mg, 0.56 mmol, 1 eq) in 1,4-dioxane (15 mL) was added lithium hydroxide monohydrate (352 mg, 8.39 mmol, 15 eq) and the mixture was heated at 100° C. overnight. The reaction was allowed to cool to ambient temperature and concentrated in vacuo. The residue was triturated with water, filtered, washed with water then diethyl ether, and dried under vacuum to afford the desired product as a yellow solid (286 mg, 0.46 mmol, 83%) [as a lithium salt].

HRMS-ESI (m/z) [M+H]+ calcd for $C_{30}H_{29}FN_7O_3S_2$: 618.1752, found 618.1767.

Example 74: 2-({6-[(1,3-Benzothiazol-2-yl)amino]-5-methylpyridazin-3-yl}(methyl)amino)-5-{3-[2-fluoro-4-(3-{methyl[2-(methylamino)ethyl]amino}prop-1-yn-1-yl)phenoxy]propyl}-1,3-thiazole-4-carboxylic acid

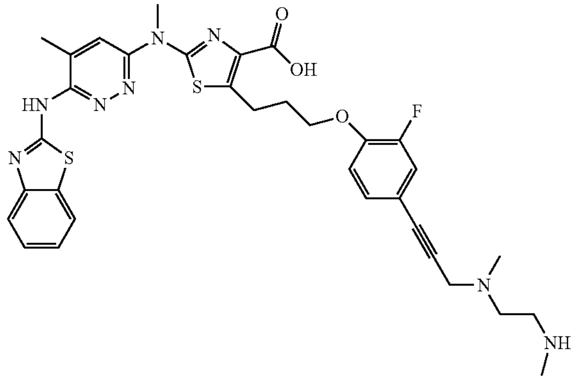 [SMILES: CNCCN(C)CC#Cc1ccc(OCCCc2sc(N(C)c3cc(C)c(Nc4nc5ccccc5s4)nn3)nc2C(=O)O)c(F)c1]

Step A: ethyl 5-[3-(4-{3-[(2-{[(tert-butoxy)carbonyl](methyl)amino}ethyl)(methyl)amino]prop-1-yn-1-yl}-2-fluorophenoxy)propyl]-2-[methyl(5-methyl-6-{[(2Z)-3-{[2-(trimethylsilyl)ethoxy[methyl}-2,3-dihydro-1,3-benzothiazol-2-ylidene]amino}pyridazin-3-yl)amino]-1,3-thiazole-4-carboxylate To a solution of the product from Preparation 5j (523 mg, 0.67 mmol, 1 eq) in acetonitrile (30 mL) was added N-Boc-(methylamino)acetaldehyde (234 mg, 1.35 mmol, 2 eq), sodium triacetoxyborohydride (343 mg, 1.62 mmol, 2.4 eq) and glacial acetic acid (50 μL) and the mixture was stirred at ambient temperature for 6 h. The reaction was partitioned between ethyl acetate and saturated aqueous sodium bicarbonate and the organic phase was dried (magnesium sulfate) and concentrated in vacuo. Purification by automated flash column chromatography (CombiFlash Rf, 40 g RediSep™ silica cartridge) eluting with a gradient of 0-50% ethyl acetate in iso-heptane afforded the desired product as a yellow gum (705 mg, 0.76 mmol, >100%).

LC/MS ($C_{46}H_{61}N_8O_6FSiS_2$) 933 $[M+H]^+$; RT 1.39 (LCMS-V-B2)

$^1$H NMR (400 MHz, DMSO-d6) δ 7.84 (d, 1H), 7.67 (d, 1H), 7.51-7.40 (m, 2H), 7.33-7.12 (m, 4H), 5.87 (s, 2H), 4.25 (q, J=7.1 Hz, 2H), 4.15 (t, J=6.1 Hz, 2H), 3.77 (s, 3H), 3.76-3.68 (m, 2H), 3.49 (s, 2H), 3.31-3.20 (m, 6H), 2.76 (s, 3H), 2.47 (d, J=1.0 Hz, 3H), 2.26 (s, 3H), 2.18-2.07 (m, 2H), 1.37 (s, 9H), 1.28 (t, J=7.1 Hz, 3H), 0.98-0.87 (m, 2H), 0.00 (s, 9H).

Step B: ethyl 2-({6-[(1,3-benzothiazol-2-yl)amino]-5-methylpyridazin-3-yl}(methyl)amino)-5-{3-[2-fluoro-4-(3-{methyl[2-(methylamino)ethyl]amino}prop-1-yn-1-yl)phenoxy]propyl}-1,3-thiazole-4-carboxylate Trifluoroacetic acid (5 mL) was added to a stirred solution of the product from Step A (705 mg, 0.76 mmol, 1 eq) in dichloromethane (20 mL) and the mixture was stirred at ambient temperature for 12 h. The reaction was diluted with dichloromethane, cooled to 0° C. and basified by the addition of 2N aqueous sodium hydroxide, and the organic phase was dried (magnesium sulfate) and concentrated in vacuo. Purification by automated flash column chromatography (CombiFlash Rf, 12 g RediSep™ silica cartridge) eluting with a gradient of dichloromethane to 20% methanol in dichloromethane afforded the desired product as a yellow gum (123 mg, 0.17 mmol, 22%).

LC/MS ($C_{35}H_{39}FN_8O_3S_2$) 703 $[M+H]^+$; RT 2.07 (LCMS-V-C)

$^1$H NMR (400 MHz, DMSO-d6) δ 7.90 (d, 1H), 7.67 (d, J=1.2 Hz, 1H), 7.53 (d, 1H), 7.42-7.36 (m, 1H), 7.34-7.26 (dd, 1H), 7.25-7.12 (m, 3H), 4.27 (q, J=7.1 Hz, 2H), 4.15 (t, J=6.1 Hz, 2H), 3.76 (s, 3H), 3.48 (s, 2H), 3.30-3.20 (m, 2H), 2.60 (dd, J=6.7, 5.2 Hz, 2H), 2.51-2.46 (m, 2H), 2.46 (s, 3H), 2.30 (s, 3H), 2.23 (s, 3H), 2.19-2.08 (m, 2H), 1.30 (t, J=7.1 Hz, 3H).

Step C: 2-({6-[(1,3-benzothiazol-2-yl)amino]-5-methylpyridazin-3-yl}(methyl)amino)-5-{3-[2-fluoro-4-(3-{methyl[2-(methylamino)ethyl]amino}prop-1-yn-1-yl)phenoxy]propyl}-1,3-thiazole-4-carboxylic acid To a solution of the product from Step B (123 mg, 0.17 mmol, 1 eq) in 1,4-dioxane (15 mL) was added lithium hydroxide monohydrate (110 mg, 2.62 mmol, 15 eq) and the mixture was heated at 100° C. overnight. The reaction was allowed to cool to ambient temperature and concentrated in vacuo. Purification by reverse phase automated flash chromatography (CombiFlash Rf, C18 3 g RediSep column) eluting with a gradient of 5-95% acetonitrile (pH 9; ammonium formate) in water (pH 9; ammonium formate) afforded the desired product as a yellow solid (75.8 mg, 0.11 mmol, 64%) [as a lithium salt].

HRMS-ESI (m/z) [M+H]+ calcd for $C_{33}H_{36}FN_8O_3S_2$: 675.2330, found 675.2331.

Example 75: 2-({6-[(1,3-Benzothiazol-2-yl)amino]-5-methylpyridazin-3-yl}(methyl)amino)-5-[4-(benzyloxy)piperidin-1-yl]-1,3-thiazole-4-carboxylic acid

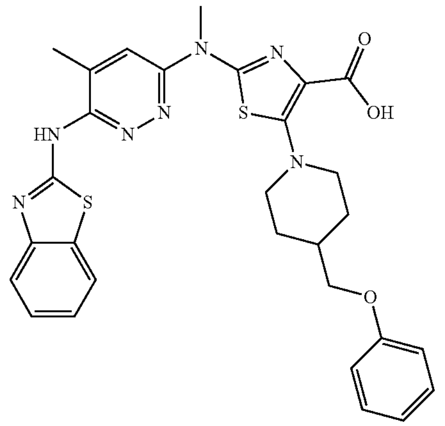 [SMILES: Cc1cc(N(C)c2nc(C(=O)O)c(N3CCC(COc4ccccc4)CC3)s2)nnc1Nc1nc2ccccc2s1]

Step A: ethyl 5-[4-(benzyloxy)piperidin-1-yl]-2-[(6-chloro-5-methylpyridazin-3-yl)(methyl)amino]-1,3-thiazole-4-carboxylate Sodium Hydride (60% in mineral oil; 27.2 mg, 0.68 mmol, 1.2 eq) was added to a cooled solution of the product from Preparation 3za (213 mg, 0.57 mmol, 1 eq) and 3,6-dichloro-4-methylpyridazine (92.5 mg, 057 mmol, 1 eq) in tetrahydrofuran (6 mL) and the mixture was allowed to warm to ambient temperature and stir overnight. The reaction was diluted with dichloromethane, washed with saturated aqueous ammonium chloride then brine, dried (magnesium sulfate), and concentrated in vacuo. Purification by automated flash column chromatography (CombiFlash Rf, 24 g RediSep™ silica cartridge) eluting with a gradient of 0-60% ethyl acetate/iso-heptane afforded the desired product as a yellow solid (101 mg, 0.2 mmol, 35%).

LC/MS ($C_{24}H_{28}ClN_5O_3S$) 502 $[M+H]^+$; RT 1.29 (LCMS-V-B1)

$^1$H NMR (400 MHz, DMSO-d6) δ 7.77 (d, J=1.2 Hz, 1H), 7.40-7.33 (m, 4H), 7.32-7.26 (m, 1H), 4.56 (s, 2H), 4.25 (q, J=7.1 Hz, 2H), 3.70 (s, 3H), 3.66-3.56 (m, 1H), 3.45-3.33 (m, 2H), 3.02 (td, J=10.1, 11.7, 3.0 Hz, 2H), 2.41 (d, J=1.0 Hz, 3H), 2.07-1.93 (m, 2H), 1.79-1.63 (m, 2H), 1.30 (t, J=7.1 Hz, 3H).

Step B: ethyl 2-({6-[(1,3-benzothiazol-2-yl)amino]-5-methylpyridazin-3-yl}(methyl)amino)-5-[4-(benzyloxy)piperidin-1-yl]-1,3-thiazole-4-carboxylate A solution of the product from Step A (101 mg, 0.2 mmol, 1 eq), 2-aminobenzothiazole (36.2 mg, 0.24 mmol, 1.2 eq), N,N-diisopropylethylamine (0.1 mL, 0.6 mmol, 3 eq) and Xantphos (11.6 mg, 0.02 mmol, 0.1 eq) in 1,4-dioxane (4 mL) was sparged with nitrogen (10 min) then tris(dibenzylideneacetone)dipalladium(0)(9.19 mg, 0.01 mmol, 0.05 eq) was added and the mixture was heated in a sealed flask at 150° C. overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile (pH4; formic acid) in water (pH 4; formic acid) afforded the desired product as a yellow glass (31.2 mg, 0.05 mmol, 25%).

LC/MS ($C_{31}H_{33}N_7O_3S_2$) 616 $[M+H]^+$; RT 1.36 (LCMS-V-B1)

$^1$H NMR (400 MHz, DMSO-d6) δ 7.90 (s, 1H), 7.63 (br s+s, 2H), 7.43-7.32 (m, 5H), 7.32-7.25 (m, 1H), 7.24-7.16 (m, 1H), 4.56 (s, 2H), 4.26 (q, J=7.1 Hz, 2H), 3.70 (s, 3H), 3.68-3.57 (m, 1H), 3.46-3.35 (m, 2H), 3.08-2.97 (m, 2H), 2.46 (s, 3H), 2.08-1.97 (m, 2H), 1.80-1.69 (m, 2H), 1.32 (t, 3H).

Step C: 2-({6-[(1,3-benzothiazol-2-yl)amino]-5-methylpyridazin-3-yl}(methyl)amino)-5-[4-(benzyloxy)piperidin-1-yl]-1,3-thiazole-4-carboxylic acid To a solution of the product from Step B (31.2 mg, 0.05 mmol, 1 eq) in 1,4-dioxane (3 mL) was added lithium hydroxide monohydrate (10.6 mg, 0.25 mmol, 5 eq) and the mixture was heated at 100° C. overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a cream solid (12.2 mg, 0.02 mmol, 41%) [as a lithium salt].

HRMS-ESI (m/z) [M+H]+ calcd for $C_{29}H_{30}N_7O_3S_2$: 588.1846, found 588.1854.

Example 76: 2-({6-[(1,3-Benzothiazol-2-yl)amino]-5-methylpyridazin-3-yl}(methyl)amino)-5-[3-(2-fluoro-4-{3-[(2-hydroxyethyl)(methyl)amino]prop-1-yn-1-yl}phenoxy)propyl]-1,3-thiazole-4-carboxylic acid

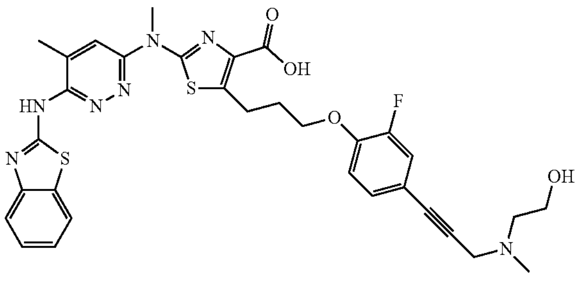 [SMILES: Cc1cc(N(C)c2nc(C(=O)O)c(CCCOc3ccc(C#CCN(C)CCO)cc3F)s2)nnc1Nc1nc2ccccc2s1]

Step A: ethyl 5-(3-{4-[3-({2-[(tert-butyldimethylsilyl)oxy]ethyl}(methyl)amino)prop-1-yn-1-yl]-2-fluorophenoxy}propyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 5j (747 mg, 0.96 mmol, 1 eq) in acetonitrile (50 mL) was added (tert-butyldimethylsiloxy)acetaldehyde (367 μL, 1.93 mmol, 2 eq), followed by sodium triacetoxyborohydride (612 mg, 2.89 mmol, 3 eq) and glacial acetic acid (50 μL) and the mixture was stirred at ambient temperature overnight. The reaction was partitioned between ethyl acetate and saturated aqueous sodium bicarbonate, and the organic phase was dried (magnesium sulfate), and concentrated in vacuo. Purification by automated flash column chromatography (CombiFlash Rf, 24 g RediSep™ silica cartridge) eluting with a gradient of 0-60% ethyl acetate in iso-heptane afforded the desired product as a clear oil (907 mg, 0.96 mmol, 100%).

LC/MS ($C_{46}H_{64}FN_7O_5Si_2S_2$) 934 $[M+H]^+$; RT 1.47 (LCMS-V-B2)

$^1$H NMR (400 MHz, DMSO-d6) δ 7.84 (d, 1H), 7.67 (d, 1H), 7.50-7.40 (m, 2H), 7.31-7.22 (m, 2H), 7.21-7.12 (m, 2H), 5.87 (s, 1H), 4.26 (q, J=7.1 Hz, 2H), 4.14 (t, J=6.1 Hz 2H), 3.77 (s, 3H), 3.75-3.62 (m, 4H), 3.50 (s, 2H), 2.46 (s, 3H), 2.24 (s, 3H), 2.19-2.06 (m, 1.29 (t, 3H), 1.24 (s, 6H), 0.96-0.89 (m, 2H), 0.04 (s, 9H), −0.11 (s, 9H).

Step B: ethyl 2-({6-[(1,3-benzothiazol-2-yl)amino]-5-methylpyridazin-3-yl}(methyl)amino)-5-[3-(2-fluoro-4-{3-[(2-hydroxyethyl)(methyl)amino]prop-1-yn-1-yl}phenoxy)propyl]-1,3-thiazole-4-carboxylate Trifluoroacetic acid (13 mL) was added to a stirred solution of the product from Step A (907 mg, 0.97 mmol, 1 eq) in dichloromethane (40 mL) and the mixture was stirred at ambient temperature for 9 h. The reaction was diluted with dichloromethane, cooled to 0° C. and basified by the addition of 2N aqueous sodium hydroxide, and the organic phase was dried (magnesium sulfate) and concentrated in vacuo. Purification by automated flash column chromatography (CombiFlash Rf, 12 g RediSep™ silica cartridge) eluting with a gradient of 0-20% methanol in dichloromethane afforded the desired product as a yellow solid (95 mg, 0.14 mmol, 14%).

LC/MS ($C_{34}H_{36}FN_7O_4S_2$) 690 $[M+H]^+$; RT 1.98 (LCMS-V-C)

$^1$H NMR (400 MHz, DMSO-d6) δ 7.91 (d, J=7.9 Hz, 1H), 7.67 (s, 1H), 7.56-7.48 (m, 1H), 7.39 (dt, 1H), 7.29 (dd, J=11.9, 1.9 Hz, 1H), 7.26-7.11 (m, 3H), 4.41 (t, J=5.5 Hz, 1H), 4.26 (q, J=7.1 Hz, 2H), 4.14 (t, J=6.1 Hz, 2H), 3.76 (s, 3H), 3.48 (s, 3H), 3.47-3.43 (m, 2H), 3.31-3.25 (m, 2H), 2.46 (s, 3H), 2.24 (s, 3H), 2.21-2.09 (m, 2H), 1.29 (t, J=7.1 Hz, 3H).

Step C: 2-({6-[(1,3-benzothiazol-2-yl)amino]-5-methylpyridazin-3-yl}(methyl)amino)-5-[3-(2-fluoro-4-{3-[(2-hydroxyethyl)(methyl)amino]prop-1-yn-1-yl}phenoxy)propyl]-1,3-thiazole-4-carboxylic acid To a solution of the product from Step B (95 mg, 0.14 mmol, 1 eq) in 1,4-dioxane (15 mL) was added lithium hydroxide monohydrate (57.8 mg, 1.38 mmol, 10 eq) and the mixture was heated at 100° C. for 6 h. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile (pH 9; ammonium acetate) in water (pH 9; ammonium acetate) afforded the desired product as a yellow solid (61.8 mg, 0.09 mmol, 67%).

HRMS-ESI (m/z) [M+H]+ calcd for $C_{32}H_{33}FN_7O_4S_2$: 662.2014, found 662.2035.

Example 77: 2-({6-[(1,3-Benzothiazol-2-yl)amino]-5-methylpyridazin-3-yl}(methyl)amino)-5-[(3S)-3-phenoxypyrrolidin-1-yl]-1,3-thiazole-4-carboxylic acid

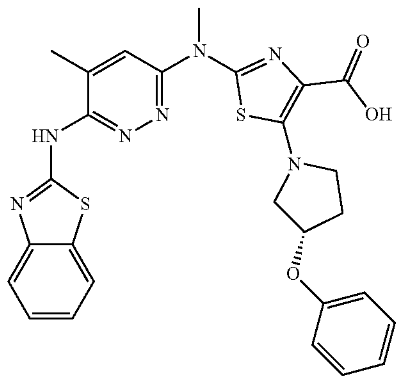 [SMILES: Cc1cc(N(C)c2nc(C(=O)O)c(N3CC[C@H](Oc4ccccc4)C3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[(3S)-3-phenoxypyrrolidin-1-yl]-1,3-thiazole-4-carboxylate To an oven-dried vial was added the product from Preparation 11b (200 mg, 0.31 mmol, 1 eq), (3S)-3-phenoxypyrrolidine hydrochloride (0.09 mL, 0.63 mmol, 2 eq), cesium carbonate (308 mg, 0.94 mmol, 3 eq) and 1,4-dioxane (8 mL). The mixture was sparged with nitrogen (10 min) then rac-BINAP Pd G3 (31.2 mg, 0.03 mmol, 0.1 eq) was added and the mixture heated at 100° C. for 6 h. The reaction was diluted with ethyl acetate then washed with water followed by brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow foam (184 mg, 0.26 mmol, 81%).

LC/MS ($C_{35}H_{43}N_7O_4SiS_2$) 718 $[M+H]^+$; RT 1.54 (LCMS-V-B1)

$^1$H NMR (400 MHz, DMSO-d6) δ 7.82 (d, 1H), 7.58 (d, 1H), 7.48-7.37 (m, 2H), 7.35-7.20 (m, 4H), 7.01-6.91 (m, 3H), 5.86 (s, 2H), 5.18-5.13 (m, 1H), 4.21 (qd, J=7.1, 2.3 Hz, 2H), 3.96 (dd, J=11.8, 4.5 Hz, 1H), 3.77-3.60 (m, 2H), 3.68 (s, 3H), 3.67-3.61 (m, 1H), 3.49 (td, J=8.7, 2.9 Hz, 1H), 3.37-3.32 (m, 1H), 2.45 (d, J=1.0 Hz, 3H), 2.37-2.26 (m, 1H), 2.25-2.15 (m, 1H), 1.27 (t, J=7.1 Hz, 3H), 0.92 (dd, J=8.4, 7.6 Hz, 2H), 0.00 (s, 9H).

Step B: ethyl 2-({6-[(1,3-benzothiazol-2-yl)amino]-5-methylpyridazin-3-yl}(methyl)amino)-5-[(3S)-3-phenoxypyrrolidin-1-yl]-1,3-thiazole-4-carboxylate Hydrochloric acid (4M in 1,4-dioxane; 3 mL, 12 mmol, 47 eq) was added to a stirred solution of the product from Step A (184 mg, 0.26 mmol, 1 eq) in 1,4-dioxane (7 mL) and the mixture was stirred at 50° C. overnight. The reaction was diluted with dichloromethane, washed with saturated aqueous sodium bicarbonate then brine, dried (magnesium sulfate) and concentrated in vacuo. Purification by reverse phase automated flash chromatography (CombiFlash Rf, C18 13 g RediSep column) eluting with 5-95% acetonitrile (pH4; formic acid) in water (pH 4; formic acid) afforded the desired product as a yellow gum (55.8 mg, 0.09 mmol, 37%).

LC/MS ($C_{29}H_{29}N_7O_3S_2$) 588 $[M+H]^+$; RT 1.32 (LCMS-V-B1)

$^1$H NMR (400 MHz, DMSO-d6) δ 7.89 (br s, 1H), 7.59 (br s+s, 2H), 7.38 (t, J=7.5 Hz, 1H), 7.33-7.26 (m, 2H), 7.19 (t, J=7.6 Hz, 1H), 7.01-6.91 (m, 3H), 5.18-5.13 (m, 1H), 4.21 (qd, J=7.1, 2.3 Hz, 2H), 3.96 (dd, J=11.8, 4.5 Hz, 1H), 3.66 (s, 3H), 3.66-3.59 (m, 1H), 3.48 (td, J=9.2, 8.8, 2.8 Hz, 1H), 3.38-3.28 (m, 1H), 2.44 (s, 3H), 2.40-2.26 (m, 1H), 2.24-2.15 (m, 2H), 1.26 (t, J=7.1 Hz, 3H).

Step C: 2-({6-[(1,3-benzothiazol-2-yl)amino]-5-methylpyridazin-3-yl}(methyl)amino)-5-[(3S)-3-phenoxypyrrolidin-1-yl]-1,3-thiazole-4-carboxylic acid To a solution of the product from Step B (55.8 mg, 0.09 mmol, 1 eq) in 1,4-dioxane (5 mL) was added lithium hydroxide monohydrate (19.9 mg, 0.47 mmol, 5 eq) and the mixture was heated at 100° C. overnight. The reaction was allowed to cool to ambient temperature, concentrated in vacuo, and the residue was triturated with water, filtered, and dried under vacuum to afford the desired product as a yellow solid (38.5 mg, 0.07 mmol, 72%) [as a lithium salt].

HRMS-ESI (m/z) [M+H]+ calcd for $C_{27}H_{26}N_7O_3S_2$: 560.1533, found 560.1541.

Example 78: 2-({6-[(1,3-Benzothiazol-2-yl)amino]-5-methylpyridazin-3-yl}(methyl)amino)-5-cyclobutyl-1,3-thiazole-4-carboxylic acid

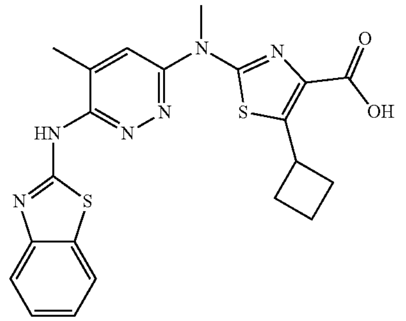 [SMILES: Cc1cc(N(C)c2nc(C(=O)O)c(C3CCC3)s2)nnc1Nc1nc2ccccc2s1]

Step A: ethyl 5-cyclobutyl-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To an oven-dried flask was added the product from Preparation 11b (500 mg, 0.79 mmol, 1 eq) and copper(I) iodide (300 mg, 1.57 mmol, 2 eq) and the flask was evacuated and flushed with nitrogen (×3) and then dimethylacetamide (15 mL) was added. Cyclobutylzinc bromide (0.5M in tetrahydrofuran; 9.44 mL, 4.72 mmol, 6 eq) was added in one portion and reaction stirred overnight at ambient temperature. The mixture was diluted with dichloromethane, then quenched with saturated aqueous sodium bicarbonate causing precipitation. The mixture was stirred vigorously stirred for 5 min, then filtered through a dichloromethane-wet celite pad, and eluted through with dichloromethane and saturated aqueous sodium bicarbonate. The layers were separated and the aqueous phase was extracted with dichloromethane (×2). The combined organic extracts were washed with brine, dried (magnesium sulfate) and concentrated in vacuo. Purification by automated flash column chromatography (CombiFlash Rf, 24 g RediSep™ silica cartridge) eluting with a gradient of 0-30% ethyl acetate in iso-heptane afforded the desired product as a pale yellow glass/foam (313 mg, 0.51 mmol, 65%).

LC/MS ($C_{29}H_{38}N_6O_3SiS_2$) 611 $[M+H]^+$; RT 1.38 (LCMS-V-B2)

$^1$H NMR (400 MHz, $CDCl_3$) δ 7.60 (dt, J=7.5, 0.9 Hz, 1H), 7.45-7.32 (m, 3H), 7.21 (ddd, J=7.6, 5.9, 2.5 Hz, 1H), 5.85 (s, 2H) 4.51-4.28 (m, 3H), 3.84 (s, 3H), 3.81-3.67 (m, 2H), 2.62-2.47 (m, 2H), 2.46 (s, 3H), 2.38-2.16 (m, 2H) 2.15-1.83 (m, 2H), 1.42 (t, J=7.1 Hz, 3H), 1.05-0.93 (m, 2H), −0.07 (s, 9H).

Step B: 2-({6-[(1,3-benzothiazol-2-yl)amino]-5-methylpyridazin-3-yl}(methyl)amino)-5-cyclobutyl-1,3-thiazole-4-carboxylic acid Trifluoroacetic acid (5.04 mL, 65.8 mmol, 130 eq) was added to a stirred solution of the product from Step A (309 mg, 0.51 mmol, 1 eq) in dichloromethane (10 mL) and the mixture was stirred at ambient temperature overnight. The reaction was concentrated in vacuo. 1,4-dioxane (10 mL) was added with stirring to afford a thick off-white suspension, to which was added 1N aqueous sodium hydroxide (5 mL) and the mixture was heated at reflux for 20 min. The mixture was allowed to cool to ambient temperature, then filtered through a pad of celite, eluting through with water then dioxane and concentrated in vacuo. The residue was partitioned between chloroform and saturated aqueous sodium bicarbonate, and the organic phase was dried (magnesium sulfate) and concentrated in vacuo. The solid material was triturated in diethyl ether, filtered, and dried under vacuum to afford the desired product as a yellow powder (98.5 mg, 0.22 mmol, 43%).

HRMS-ESI (m/z) [M+H]+ calcd for $C_{21}H_{21}N_6O_2S_2$: 453.1162, found 453.1172.

Example 79: 2-({6-[(1,3-Benzothiazol-2-yl)amino]-5-methylpyridazin-3-yl}(methyl)amino)-5-[(3R)-3-phenoxypyrrolidin-1-yl]-1,3-thiazole-4-carboxylic acid

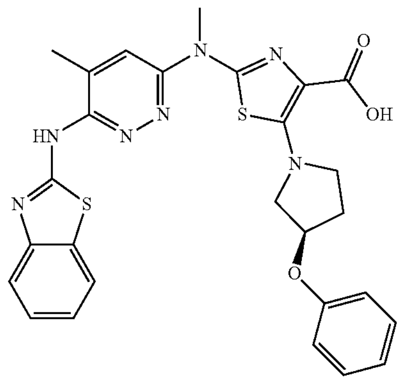 [SMILES: Cc1cc(N(C)c2nc(C(=O)O)c(N3CC[C@@H](Oc4ccccc4)C3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[(3R)-3-phenoxypyrrolidin-1-yl]-1,3-thiazole-4-carboxylate To an oven-dried flask was added the product from Preparation 11b (300 mg, 0.44 mmol, 1 eq), (R)-3-phenoxypyrrolidine (0.13 mL, 0.88 mmol, 2 eq), cesium carbonate (430 mg, 1.32 mmol, 3 eq) and 1,4-dioxane (12 mL). The mixture was sparged with nitrogen (10 min) and rac-BINAP Pd G3 (43.6 mg, 0.04 mmol, 0.1 eq) was added and the mixture heated at 100° C. overnight. The reaction was diluted with ethyl acetate then washed with water followed by brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow foam (253 mg, 0.35 mmol, 80%).

LC/MS ($C_{35}H_{43}N_7O_4SiS_2$) 718 [M+H]$^+$; RT 1.54 (LCMS-V-B1)

$^1$H NMR (400 MHz, DMSO-d6) δ 7.85-7.78 (m, 1H), 7.57 (d, J=1.1 Hz, 1H), 7.47-7.38 (m, 2H), 7.35-7.19 (m, 3H), 7.01-6.80 (m, 3H), 5.85 (s, 2H), 5.22-5.10 (m, 1H), 4.21 (qd, J=7.1, 2.4 Hz, 2H), 3.96 (dd, J=11.8, 4.5 Hz, 1H), 3.76-3.59 (m, 3H), 3.49 (td, J=8.6, 2.8 Hz, 1H), 3.33 (s, 4H), 3.36-3.28 (m, 1H), 2.44 (d, J=1.0 Hz, 3H), 2.39-2.28 (m, 1H), 2.26-2.16 (m, 1H), 1.27 (t, J=7.1 Hz, 3H), 0.96-0.83 (m, 2H), −0.11 (s, 9H).

Step B: ethyl 2-({6-[(1,3-benzothiazol-2-yl)amino]-5-methylpyridazin-3-yl}(methyl)amino)-5-[(3R)-3-phenoxypyrrolidin-1-yl]-1,3-thiazole-4-carboxylate Hydrochloric acid (4M in 1,4-dioxane; 4 mL, 16 mmol, 45 eq) was added to a stirred solution of the product from Step A (253 mg, 0.35 mmol, 1 eq) in 1,4-dioxane (8 mL) and the mixture was stirred at 50° C. overnight. The reaction was diluted with dichloromethane, washed with saturated aqueous sodium bicarbonate then brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow foam (189 mg, 0.32 mmol, 91%).

LC/MS ($C_{29}H_{29}N_7O_3S_2$) 588 [M+H]$^+$; RT 1.32 (LCMS-V-B1)

$^1$H NMR (400 MHz, DMSO-d6) δ 10.98 (br s, 1H), 7.94-7.87 (m, 1H), 7.60 (br s+s, 2H), 7.39 (t, J=7.7 Hz, 1H), 7.34-7.27 (m, 2H), 7.25-7.16 (s, 1H), 7.02-6.87 (m, 3H), 5.20-5.13 (m, 1H), 4.21 (qd, J=7.1, 2.2 Hz, 2H), 3.97 (dd, J=11.8, 4.5 Hz, 1H), 3.67 (s, 3H), 3.74-3.60 (m, 1H), 3.55-3.43 (m, 1H), 3.38-3.30 (m, 1H), 2.45 (s, 3H), 2.41-2.27 (m, 1H), 2.26-2.17 (m, 1H), 1.27 (t, J=7.1 Hz, 3H).

Step C: 2-({6-[(1,3-benzothiazol-2-yl)amino]-5-methylpyridazin-3-yl}(methyl)amino)-5-[(3R)-3-phenoxypyrrolidin-1-yl]-1,3-thiazole-4-carboxylic acid To a solution of the product from Step B (189 mg, 0.32 mmol, 1 eq) in 1,4-dioxane (10 mL) was added lithium hydroxide monohydrate (67.4 mg, 1.61 mmol, 5 eq) and the mixture was heated at reflux overnight. The reaction was allowed to cool to ambient temperature then concentrated in vacuo, triturated with water, filtered, and dried under vacuum to afford the desired product as a beige solid (118 mg, 0.21 mmol, 65%) [as a lithium salt].

HRMS-ESI (m/z) [M+H]+ calcd for $C_{27}H_{26}N_7O_3S_2$: 560.1533, found 560.1535.

Example 80: 2-({6-[(1,3-Benzothiazol-2-yl)amino]-5-methylpyridazin-3-yl}(methyl)amino)-5-(piperidin-1-yl)-1,3-thiazole-4-carboxylic acid

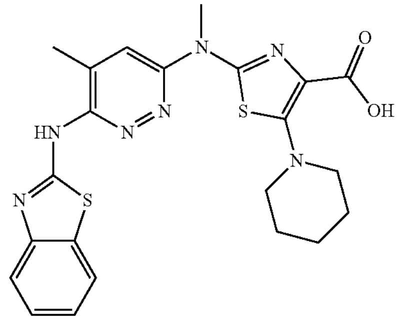 [SMILES: Cc1cc(N(C)c2nc(C(=O)O)c(N3CCCCC3)s2)nnc1Nc1nc2ccccc2s1]

Step A: ethyl 5-(piperidin-1-yl)-1,3-thiazole-4-carboxylate

A solution of ethyl 5-bromothiazole-4-carboxylate (500 mg, 2.12 mmol, 1 eq), piperidine (0.25 mL, 2.54 mmol, 1.2 eq) and 1,8-diazabicyclo[5.4.0]undec-7-ene (0.64 mL, 4.24 mmol, 2 eq) in acetonitrile (15 mL) was heated at 80° C. overnight. The reaction was allowed to cool to ambient temperature then concentrated in vacuo and purification by automated flash column chromatography (CombiFlash Rf, 24 g RediSep™ silica cartridge) eluting with a gradient of 0-60% ethyl acetate in iso-heptane afforded the desired product as a brown oil (376 mg, 1.57 mmol, 74%).

LC/MS ($C_{11}H_{16}N_2O_2S$) 241 $[M+H]^+$; RT 1.12 (LCMS-V-B1)

$^1$H NMR (400 MHz, DMSO-d6) δ 8.45 (s, 1H), 4.24 (q, J=7.1 Hz, 2H), 3.15-3.07 (m, 4H), 1.67 (p, J=5.6 Hz, 4H), 1.58-1.49 (m, 2H), 1.28 (t, J=7.1 Hz, 3H).

Step B: ethyl 2-bromo-5-(piperidin-1-yl)-1,3-thiazole-4-carboxylate

N-Bromosuccinimide (453 mg, 2.55 mmol, 1.2 eq) was added to a stirred solution of the product from Step A (510 mg, 2.12 mmol, 1 eq) in acetonitrile (20 mL) and the mixture was stirred at ambient temperature for 7 h. The reaction was partitioned between 10% aqueous sodium thiosulfate and ethyl acetate, and the organic phase was washed with water followed by brine, dried (magnesium sulfate), and concentrated in vacuo. Purification by automated flash column chromatography (CombiFlash Rf, 24 g RediSep™ silica cartridge) eluting with a gradient of 0-40% ethyl acetate in iso-heptane afforded the desired product as a colourless oil (482 mg, 1.51 mmol, 71%).

LC/MS ($C_{11}H_{15}BrN_2O_2S$) 273 $[M+H]^+$; RT 1.14 (LCMS-V-B1)

$^1$H NMR (400 MHz, DMSO-d6) δ 4.23 (q, J=7.1 Hz, 2H), 3.18-3.10 (m, 4H), 1.70-1.60 (m, 4H), 1.59-1.49 (m, 2H), 1.28 (t, J=7.1 Hz, 3H).

Step C: ethyl 2-{[(tert-butoxy)carbonyl](methyl)amino}-5-(piperidin-1-yl)-1,3-thiazole-4-carboxylate The product from Step B (482 mg, 1.51 mmol, 1 eq) and tert-butyl methylcarbamate (0.26 mL, 1.81 mmol, 1.2 eq) were added to a solution of tris(dibenzylideneacetone)dipalladium(0)(69.1 mg, 0.08 mmol, 0.05 eq) and Xantphos (87.4 mg, 0.15 mmol, 0.1 eq) in 1,4-dioxane (10 mL) under a nitrogen atmosphere. Cesium carbonate (738 mg, 2.26 mmol, 1.5 eq) was added and the mixture heated at 100° C. for 7.5 h. The solution was allowed to cool to ambient temperature and concentrated in vacuo. The mixture was diluted with ethyl acetate and washed with water followed by brine, dried (magnesium sulfate), and concentrated in vacuo. Purification by automated flash column chromatography (CombiFlash Rf, 50 g RediSep™ silica cartridge) eluting with a gradient of 0-50% ethyl acetate in iso-heptane afforded the desired product as a yellow gum (434 mg, 1.17 mmol, 78%).

LC/MS ($C_{17}H_{27}N_3O_4S$) 370 $[M+H]^+$; RT 1.304 (LCMS-V-B1)

$^1$H NMR (400 MHz, DMSO-d6) δ 4.21 (q, J=7.1 Hz, 2H), 3.37 (s, 3H), 3.11-3.03 (m, 4H), 1.64 (p, J=5.6 Hz, 4H), 1.55-1.51 (m, 2H), 1.51 (s, 9H), 1.26 (t, J=7.1 Hz, 3H).

Step D: ethyl 2-(methylamino)-5-(piperidin-1-yl)-1,3-thiazole-4-carboxylate

Trifluoroacetic acid (1.32 mL, 17.6 mmol, 15 eq) was added to a stirred solution of the product from Step C (434 mg, 1.17 mmol, 1 eq) in dichloromethane (15 mL) at 0° C. and the mixture was allowed to warm to ambient temperature and stir overnight. The reaction was partitioned between saturated aqueous sodium bicarbonate and dichloromethane, and the organic phase was washed with brine, dried (magnesium sulfate), and concentrated in vacuo. The resultant solid was triturated with diethyl ether, collected by filtration and dried under vacuum to afford the desired product as a white solid (197 mg, 0.73 mmol, 62%).

LC/MS ($C_{12}H_{19}N_3O_2S$) 270 $[M+H]^+$; RT 0.91 (LCMS-V-B1)

$^1$H NMR (400 MHz, DMSO-d6) δ 7.26 (q, J=4.8 Hz, 1H), 4.17 (q, J=7.1 Hz, 2H), 2.91-2.84 (m, 4H), 2.75 (d, J=4.8 Hz, 3H), 1.61 (p, J=5.6 Hz, 4H), 1.52-1.42 (m, 2H), 1.25 (t, J=7.1 Hz, 3H).

Step E: ethyl 2-[(6-chloro-5-methylpyridazin-3-yl)(methyl)amino]-5-(piperidin-1yl)-1,3-thiazole-4-carboxylate Sodium Hydride (60% in mineral oil; 35.2 mg, 0.88 mmol, 1.2 eq) was added to a cooled solution of the product from Step D (197 mg, 0.73 mmol, 1 eq) and 3,6-dichloro-4-methylpyridazine (119 mg, 0.73 mmol, 1 eq) in tetrahydrofuran (8 mL) and the mixture was allowed to warm to ambient temperature and stirred for 3.5 h. The reaction was diluted with dichloromethane, washed with saturated aqueous ammonium chloride followed by brine, dried (magnesium sulfate), and concentrated in vacuo. Purification by automated flash column chromatography (CombiFlash Rf, 24 g RediSep™ silica cartridge) eluting with a gradient of 0-60% ethyl acetate in iso-heptane afforded the desired product as a yellow solid (131 mg, 0.33 mmol, 45%).

LC/MS ($C_{17}H_{22}ClN_5O_2S$) 396 $[M+H]^+$; RT 1.20 (LCMS-V-B1)

$^1$H NMR (400 MHz, DMSO-d6) δ 7.76 (d, J=1.0 Hz, 1H), 4.25 (q, J=7.1 Hz, 2H), 3.70 (s, 3H), 3.16-3.08 (m, 4H), 2.41 (d, J=1.0 Hz, 3H), 1.66 (q, J=5.8 Hz, 4H), 1.60-1.46 (m, 2H), 1.30 (t, J=7.1 Hz, 3H).

Step F: ethyl 2-({6-[(1,3-benzothiazol-2-yl)amino]-5-methylpyridazin-3-yl}(methyl)amino)-5-(piperidin-1-yl)-1,3-thiazole-4-carboxylate A solution of the product from Step E (131 mg, 0.33 mmol, 1 eq), 2-aminobenzothiazole (74.7 mg, 0.5 mmol, 1.5 eq), N,N-diisopropylethylamine (0.16 mL, 0.99 mmol, 3 eq) and Xantphos (19.2 mg, 0.03 mmol, 0.1 eq) in 1,4-dioxane (7 mL) was sparged with nitrogen (10 min) then tris(dibenzylideneacetone)dipalladium(0)(15.2 mg, 0.02 mmol, 0.05 eq) was added and the mixture was heated in a sealed flask at 150° C. overnight. The reaction was allowed to cool to ambient temperature then partitioned between ethyl acetate and water, and the organic phase was washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH4; formic acid) in water (pH 4; formic acid) afforded the desired product as a yellow foam (64.8 mg, 0.13 mmol, 38%).

LC/MS ($C_{24}H_{27}N_7O_2S_2$) 510 $[M+H]^+$; RT 1.32 (LCMS-V-B1)

$^1$H NMR (400 MHz, DMSO-d6) δ 7.91 (br s, 1H), 7.63 (br s+s, 2H), 7.39 (t, J=7.6 Hz, 1H), 7.22 (t, J=7.5 Hz, 1H), 4.26 (q, 2H), 3.70 (s, 3H), 3.18-3.08 (m, 4H), 2.46 (s, 3H), 1.72-1.61 (m, 4H), 1.59-1.47 (m, 2H), 1.31 (t, J=7.1, 2.7 Hz, 3H).

Step G: 2-({6-[(1,3-benzothiazol-2-yl)amino]-5-methylpyridazin-3-yl}(methyl)amino)-5-(piperidin-1-yl)-1,3-thiazole-4-carboxylic acid To a solution of the product from Step F (64.8 mg, 0.13 mmol, 1 eq) in 1,4-dioxane (3 mL) was added lithium hydroxide monohydrate (26.7 mg, 0.64 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (23 mg, 0.05 mmol, 18%).

HRMS-ESI (m/z) [M+H]+ calcd for $C_{22}H_{24}N_7O_2S_2$: 482.1427, found 482.1435.

Example 81: 2-({6-[(1,3-Benzothiazol-2-yl)amino]-5-methylpyridazin-3-yl}(methyl)amino)-5-(4-phenoxypiperidin-1-yl)-1,3-thiazole-4-carboxylic acid

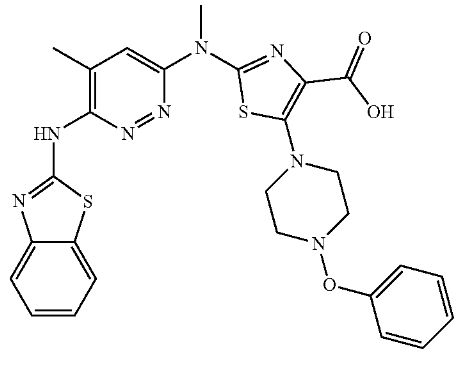 [SMILES: Cc1cc(N(C)c2nc(C(=O)O)c(N3CCN(Oc4ccccc4)CC3)s2)nnc1Nc1nc2ccccc2s1]

Step A: ethyl 5-(4-phenoxypiperidin-1-yl)-1,3-thiazole-4-carboxylate

A solution of ethyl 5-bromothiazole-4-carboxylate (500 mg, 2.12 mmol, 1 eq), 4-phenoxypiperidine (451 mg, 2.54 mmol, 1.2 eq) and 1,8-diazabicyclo[5.4.0]undec-7-ene (0.64 mL, 4.24 mmol, 2 eq) in acetonitrile (15 mL) was heated at 80° C. overnight then allowed to cool to ambient temperature and concentrated in vacuo. Purification by automated flash column chromatography (CombiFlash Rf, 40 g RediSep™ silica cartridge) eluting with a gradient of 0-60% ethyl acetate in iso-heptane afforded the desired product as a brown oil (424 mg, 1.27 mmol, 60%).

LC/MS ($C_{17}H_{20}N_2O_3S$) 333 $[M+H]^+$; RT 1.2 (LCMS-V-B1)

$^1$H NMR (400 MHz, DMSO-d6) δ 8.49 (s, 1H), 7.35-7.25 (m, 2H), 7.05-6.96 (m, 2H), 6.94 (tt, J=7.3, 1.0 Hz, 1H), 4.61 (tt, J=3.6 Hz, 1H), 4.25 (q, J=7.1 Hz, 2H), 3.45-3.35 (m, 2H), 3.20-3.08 (m, 2H), 2.15-2.02 (m, 2H), 1.88-1.75 (m, 2H), 1.29 (t, J=7.1 Hz, 3H).

Step B: ethyl 2-bromo-5-(4-phenoxypiperidin-1-yl)-1,3-thiazole-4-carboxylate

N-Bromosuccinimide (272 mg, 1.53 mmol, 1.2 eq) was added to a stirred solution of the product from Step A (424 mg, 1.27 mmol, 1 eq) in acetonitrile (20 mL) and the mixture was stirred at ambient temperature for 5.5 h. The reaction was quenched by the addition of 10% aqueous sodium thiosulfate, then extracted with ethyl acetate, washed with water followed by brine, dried (magnesium sulfate), and concentrated in vacuo. Purification by automated flash column chromatography (CombiFlash Rf, 12 g RediSep™ silica cartridge) eluting with a gradient of 0-40% ethyl acetate in iso-heptane afforded the desired product as a white solid (404 mg, 0.98 mmol, 77%).

LC/MS ($C_{17}H_{19}BrN_2O_3S$) 413 $[M+H]^+$; RT 1.26 (LCMS-V-B1)

$^1$H NMR (400 MHz, DMSO-d6) δ 7.35-7.25 (m, 2H), 7.04-6.89 (m, 3H), 4.62 (dt, J=7.6, 3.9 Hz, 1H), 4.25 (q, 2H), 3.46-3.36 (m, 2H), 3.24-3.13 (m, 2H), 2.12-2.01 (m, 2H), 1.87-1.74 (m, 2H), 1.28 (t, 3H).

Step C: ethyl 2-{[(tert-butoxy)carbonyl](methyl)amin}-5-(4-phenoxypiperidin-1-yl)-1,3-thiazole-4-carboxylate The product from Step B (404 mg, 0.98 mmol, 1 eq) and rent-butyl methylcarbamate (0.17 mL, 1.18 mmol, 1.2 eq) were added to a solution of tris(dibenzylideneacetone)dipalladium(0)(45 mg, 0.05 mmol, 0.05 eq) and Xantphos (56.8 mg, 0.1 mmol, 0.1 eq) in 1,4-dioxane (10 mL) under a nitrogen atmosphere. Cesium carbonate (480 mg, 1.47 mmol, 1.5 eq) was added and the mixture was heated at 100° C. overnight. The reaction was allowed to cool to ambient temperature then concentrated in vacuo. The residue was partitioned between ethyl acetate and water, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-50% ethyl acetate in iso-heptane afforded the desired product as a yellow gum (285 mg, 0.62 mmol, 63%).

LC/MS ($C_{23}H_{31}N_3O_5S$) 462 $[M+H]^+$; RT 1.37 (LCMS-V-B1)

$^1$H NMR (400 MHz, DMSO-d6) δ 7.34-7.24 (m, 2H), 7.02-6.97 (m, 2H), 6.93 (tt, J=7.2, 1.1 Hz, 1H) 4.58 (dt, J=7.9, 4.1 Hz, 1H), 4.23 (q, J=7.1 Hz, 2H), 3.38 (s, 3H), 3.37-3.33 (m, 2H), 3.09 (ddd, J=11.8, 8.5, 3.2 Hz, 2H), 215-1.99 (m, 2H), 1.79 (dtd, J=2.3, 8.2, 3.6 Hz, 2H), 1.52 (s, 9H), 1.27 (t, J=7.1 Hz, 3H).

Step D: ethyl 2-(methylamino)-5-(4-phenoxypiperidin-1-yl)-1,3-thiazole-4-carboxylate Trifluoroacetic acid (0.46 mL, 6.17 mmol, 10 eq) was added to a stirred solution of the product from Step C (285 mg, 0.62 mmol, 1 eq) in dichloromethane (8 mL) at 0° C. and the mixture was allowed to warm to ambient temperature and stir overnight. The reaction was quenched by the addition of saturated aqueous sodium bicarbonate, extracted with dichloromethane, and the organic extract washed with brine, dried (magnesium sulfate), and concentrated in vacuo. The resultant solid was triturated with diethyl ether/heptane, filtered, and dried under vacuum to afford the desired product as a cream solid (161 mg, 0.45 mmol, 72%).

LC/MS ($C_{18}H_{23}N_3O_3S$) 362 $[M+H]^+$; RT 1.08 (LCMS-V-B1)

$^1$H NMR (400 MHz, DMSO-d6) δ 7.35-7.24 (m, 3H), 7.02-6.97 (m, 2H), 6.93 (tt, J=7.3, 1.1 Hz, 1H), 4.53 (dt, J=7.9, 4.1 Hz, 1H), 4.19 (q, J=7.1 Hz, 2H), 3.22-3.12 (m, 2H), 2.90 (ddd, J=11.6, 8.6, 3.2 Hz, 2H), 2.76 (d, J=4.7 Hz, 3H), 2.10-1.95 (m, 2H), 1.77 (dtd, J=12.3, 8.2, 3.6 Hz, 2H), 1.26 (t, J=7.1 Hz, 3H).

Step E: ethyl 2-[(6-chloro-5-methylpyridazin-3-yl)(methyl)amino]-5-(4-phenoxypiperidin-1-yl)-1,3-thiazole-4-carboxylate Sodium Hydride (60% in mineral oil; 21.4 mg, 0.53 mmol, 1.2 eq) was added to a cooled solution of the product from Step D (161 mg, 0.45 mmol, 1 eq) and 3,6-dichloro-4-methylpyridazine (72.6 mg, 0.45 mmol, 1 eq) in tetrahydrofuran (5 mL) and the mixture was allowed to warm to ambient temperature and stir overnight. The reaction was diluted with dichloromethane, then washed with saturated aqueous ammonium chloride followed by brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as a yellow foam (63.3 mg, 0.13 mmol, 29%).

LC/MS ($C_{23}H_{26}ClN_5O_3S$) 488 $[M+H]^+$; RT 1.289 (LCMS-V-B1)

$^1$H NMR (400 MHz, DMSO-d6) δ 7.77 (d, J=1.0 Hz, 1H), 7.34-7.25 (m, 2H), 7.04-6.98 (m, 2H), 6.93 (tt, J=7.4, 1.1 Hz, 1H), 4.59 (dt, J=8.1, 4.1 Hz, 1H), 4.25 (q, J=7.1 Hz, 2H), 3.70 (s, 3H), 3.45-3.35 (m, 2H), 3.13 (ddd, J=11.5, 8.5, 3.2 Hz, 2H), 2.41 (d, J=1.0 Hz, 3H), 2.14-2.01 (m, 2H), 1.81 (dtd, J=12.2, 8.3, 3.5 Hz, 2H), 1.30 (t, J=7.1 Hz, 3H).

Step F: ethyl 2-({6-[(1,3-benzothiazol-2-yl)amino]-5-methylpyridazin-3-yl}(methyl)amino)-5-(4-phenoxypiperidin-1-yl)-1,3-thiazole-4-carboxylate A solution of the product from Step E (63.3 mg, 0.13 mmol, 1 eq), 2-aminobenzothiazole (29.2 mg, 0.19 mmol, 1.5 eq), N,N-diisopropylethylamine (0.06 mL, 0.39 mmol, 3 eq) and Xantphos (7.51 mg, 0.01 mmol, 0.1 eq) in 1,4-dioxane (4 mL) was sparged with nitrogen (10 min) then tris(dibenzylideneacetone)dipalladium(0)(5.94 mg, 0.01 mmol, 0.05 eq) was added and the mixture was heated in a sealed flask at 150° C. overnight. The reaction was allowed to cool to ambient temperature then partitioned between ethyl acetate and water, and the organic phase washed with brine, dried (magnesium sulfate), and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow foam (23 mg, 0.04 mmol, 30%).

LC/MS ($C_{30}H_{31}N_7O_3S_2$) 602 $[M+H]^+$; RT 1.37 (LCMS-V-B1)

$^1$H NMR (400 MHz, DMSO-d6) δ 7.92 (br s, 1H), 7.64 (br s+s, 2H), 7.36 (dd, J=31.4, 7.1 Hz, 1H), 7.29 (dd, J=8.6, 7.3 Hz, 2H), 7.25-7.17 (m, 1H), 7.07-6.98 (m, 2H), 6.97-6.89 (m, 1H), 4.61 (dt, 1H), 4.27 (q, 2H), 3.71 (s, 3H), 3.49-3.36 (m, 2H), 3.22-3.09 (m, 3H), 2.46 (s, 3H), 2.18-2.02 (m, 2H), 1.91-1.73 (m, 2H), 1.32 (t, 3H).

Step G: 2-({6-[(1,3-benzothiazol-2-yl)amino]-5-methylpyridazin-3-yl}(methyl)amino)-5-(4-phenoxypiperidin-1-yl)-1,3-thiazole-4-carboxylic acid To a solution of the product from Step F (23 mg, 0.04 mmol, 1 eq) in 1,4-dioxane (3 mL) was added lithium hydroxide monohydrate (8.02 mg, 0.19 mmol, 5 eq) and the mixture was heated at reflux overnight, then allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (3.7 mg, 0.01 mmol, 17%).

HRMS-ESI (m/z) [M+H]+ calcd for $C_{28}H_{28}N_7O_3S_2$: 574.1690, found 574.1697.

Example 82: 2-({6-[(1,3-Benzothiazol-2-yl)amino]-5-methylpyridazin-3-yl}(methyl)amino)-5-{3-[4-(3-{[(tert-butoxy)carbonyl](methyl)amino}prop-1-yn-1-yl)-2-fluorophenoxy]propyl}-1,3-thiazole-4-carboxylic acid

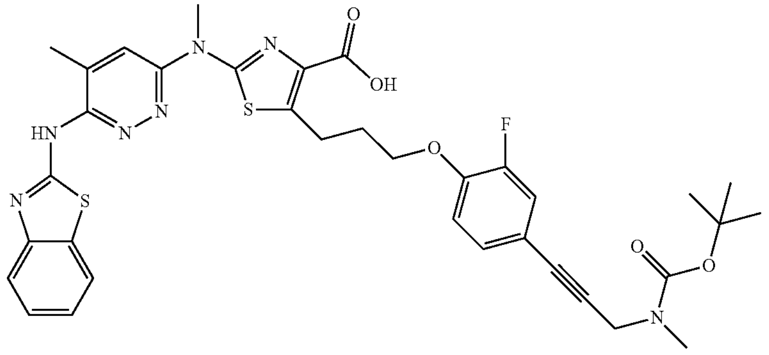 [SMILES: Cc1cc(N(C)c2nc(C(=O)O)c(CCCOc3ccc(C#CCN(C)C(=O)OC(C)(C)C)cc3F)s2)nnc1Nc1nc2ccccc2s1]

Step A: ethyl 2-({6-[(1,3-benzothiazol-2-yl)amino]-5-methylpyridazin-3-yl}(methyl)amino)-5-(3-iodopropyl)-1,3-thiazole-4-carboxylate To a solution of the product from Preparation 5g (176 mg, 024 mmol, 1 eq) in dichloromethane (5 mL) was added trifluoroacetic acid (5 mL) and the mixture was stirred at ambient temperature for 4 h. The reaction was diluted with dichloromethane, washed with 2N aqueous sodium hydroxide, dried (magnesium sulfate) and concentrated in vacuo. The residue was triturated with acetonitrile, filtered, and dried under vacuum to afford the desired product as a white solid (93 mg, 0.16 mmol, 64%).

LC/MS ($C_{22}H_{23}IN_6O_2S_2$) 595 $[M+H]^+$; RT 2.63 (LCMS-V-C)

$^1$H NMR (400 MHz, DMSO-d6) δ 7.92 (s, 1H), 7.69 (s, 1H), 7.54 (br s, 1H), 7.40 (t, J=7.8 Hz, 1H), 7.22 (t, J=7.5

Hz, 1H), 4.31 (q, J=7.1 Hz, 2H), 3.77 (s, 3H), 3.35 (t, J=6.8 Hz, 2H), 3.24-3.16 (m, 2H), 2.47 (s, 3H) 2.20-2.11 (m, 2H), 1.34 (t, J=7.1 Hz, 3H).

Step B: ethyl 2-({6-[(1,3-benzothiazol-2-yl)amino]-5-methylpyridazin-3-yl}(methyl)amino)-5-{3-[4-(3-{[(tert-butoxy)carbonyl](methyl)amino}prop-1-yn-1-yl)-2-fluorophenoxy]propyl}-1,3-thiazole-4-carboxylate To a solution of the product from Step A (93 mg, 0.16 mmol, 1 eq) in dimethylformamide (5 mL) was added the product from Preparation 6a (56.8 mg, 0.2 mmol, 1.3 eq) and cesium carbonate (153 mg, 0.47 mmol, 3 eq) and the mixture was heated at 80° C. overnight, then allowed to cool to ambient temperature and concentrated in vacuo. The residue was partitioned between ethyl acetate and brine, and the organic phase was dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as a yellow gum (45 mg, 0.06 mmol, 39%).

LC/MS ($C_{47}H_{40}FN_7O_5S_2$) 747 $[M+H]^+$; RT 2.77 (LCMS-V-C)

$^1$NMR (400 MHz, DMSO-d6) δ 7.91 (d, J=19.8 Hz, 1H), 7.68 (s, 1H), 7.54 (br s, 1H), 7.39 (t, 1H), 7.33 (d, 1H), 7.26-7.12 (m, 3H), 4.26 (q, 2H), 4.21 (s, 2H), 4.15 (t, J=6.1 Hz, 2H), 3.77 (s, 2H), 3.31-3.22 (m, 2H), 2.85 (s, 3H), 2.47 (s, 3H), 2.20-2.09 (m, 2H), 1.41 (s, 9H), 1.30 (t, 3H).

Step C: 2-({6-[(1,3-benzothiazol-2-yl)amino]-5-methylpyridazin-3-yl}(methyl)amino)-5-{3-[4-(3-{[(tert-butoxy)carbonyl](methyl)amino}prop-1-yn-1-yl)-2-fluorophenoxy]propyl}-1,3-thiazole-4-carboxylic acid To a solution of the product from Step B (45 mg, 0.06 mmol, 1 eq) in 1,4-dioxane (5 mL) was added lithium hydroxide monohydrate (25.3 mg, 0.6 mmol, 10 eq) and the mixture was heated at reflux overnight. The reaction was allowed to cool to ambient temperature and concentrated in vacuo. Purification by automated flash column chromatography (CombiFlash Rf, 4 g RediSep™ silica cartridge) eluting with a gradient of 0-10% methanol in dichloromethane afforded the desired product as a yellow solid (5.1 mg, 0.01 mmol, 12%).

HRMS-ESI (m/z) calcd for $C_{35}H_{37}FN_7O_5S_2$: 718.2276, found 718.2284.

Example 83: 2-({6-[(1,3-Benzothiazol-2-yl)amino]-5-methylpyridazin-3-yl}(methyl)amino)-5-(piperidin-4-yl)-1,3-thiazole-4-carboxylic acid

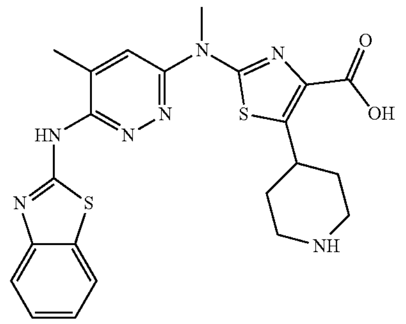 [SMILES: Cc1cc(N(C)c2nc(C(=O)O)c(C3CCNCC3)s2)nnc1Nc1nc2ccccc2s1]

Step A: ethyl 2-({6-[(1,3-benzothiazol-2-yl)amino]-5-methylpyridazin-3-yl}(methyl)amino)-5-(piperidin-4-yl)-1,3-thiazole-1-carboxylate Trifluoroacetic acid (1 mL, 13.4 mmol, 166 eq) was added to a stirred solution of the product from Preparation 5k, Step B (60 mg, 0.08 mmol, 1 eq) in dichloromethane (4 mL) and the mixture was stirred at ambient temperature overnight. The reaction mixture was loaded onto an SCX-2 cartridge (5 g, preconditioned with dichloromethane, then methanol), then washed with dichloromethane followed by methanol. Elution with 3.5N methanolic ammonia and concentration in vacuo afforded the desired product as a yellow solid (40.9 mg, 0.08 mmol, 99%).

LC/MS ($C_{24}H_{27}N_7O_2S_2$) 510 $[M+H]^+$; RT 0.857 (LCMS-V-B1)

$^1$H NMR (400 MHz, DMSO-d6) δ 7.91 (d, J=7.9, 1.2 Hz, 1H), 7.68 (d, J=1.2 Hz, 1H), 7.53 (d, J=8.0 Hz, 1H), 7.39 (ddd, J=8.2, 7.3, 1.3 Hz, 1H), 7.21 (td, J=7.6, 1.2 Hz, 1H), 4.29 (q, J=7.1 Hz, 2H), 3.90-3.67 (m, 4H), 3.18-3.09 (m, 2H), 2.75-2.63 (m, 2H), 2.46 (d, J=1.0 Hz, 3H), 2.00-1.92 (m, 2H), 1.63 (qd, J=12.4, 3.9 Hz, 2H), 1.32 (t, J=7.1 Hz, 3H).

Step B: 2-({6-[(1,3-benzothiazol-2-yl)amino]-5-methylpyridazin-3-yl}(methyl)amino)-5-(piperidin-4-yl)-1,3-thiazole-4-carboxylic acid To a solution of the product from Step A (40.9 mg, 0.08 mmol, 1 eq) in 1,4-dioxane (3 mL) was added lithium hydroxide monohydrate (16.8 mg, 0.4 mmol, 5 eq) and the mixture was heated at reflux overnight. The reaction was allowed to cool to ambient temperature then concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded a solid that was triturated with chloroform, filtered, and dried under vacuum to afford the desired product as a yellow solid (27.4 mg, 0.06 mmol, 71%).

LC/MS ($C_{22}H_{23}N_7O_2S_2$) 482 $[M+H]^+$; RT 0.772 (LCMS-V-B1)

$^1$H NMR (400 MHz, DMSO-d6) δ 7.83 (d, J=7.7 Hz, 1H), 7.55 (s, 1H), 7.46 (d, J=7.9 Hz, 1H), 7.35-7.27 (m, 1H), 7.16-7.05 (m, 1H), 4.21 (tt, J=12.0, 3.8 Hz, 1H), 3.65 (s, 3H), 3.09-2.95 (m, 2H), 2.62-2.53 (m, 2H), 2.43 (d, J=1.1 Hz, 3H), 1.83 (dd, J=12.9, 9.4 Hz, 2H), 1.47 (qd, J=12.1, 3.9 Hz, 2H)

HRMS-ESI (m/z) [M+H]+ calcd for $C_{22}H_{23}N_7O_2S_2$: 482.1427, found 482.1430.

Example 84: 2-({6-[(1,3-Benzothiazol-2-yl)amino]-5-methylpyridazin-3-yl}(methyl)amino)-5-{1-[(tert-butoxy)carbonyl]piperidin-4-yl}-1,3-thiazole-4-carboxylic acid

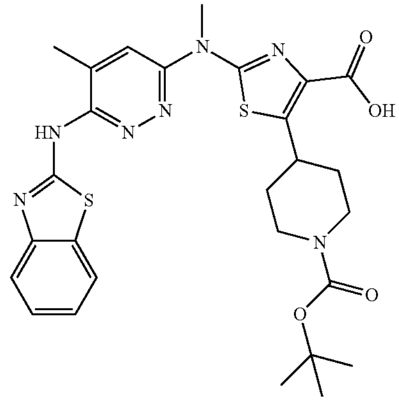 [SMILES: Cc1cc(N(C)c2nc(C(=O)O)c(C3CCN(C(=O)OC(C)(C)C)CC3)s2)nnc1Nc1nc2ccccc2s1]

Step A: tert-butyl 4-[2-({6-[(1,3-benzothiazol-2-yl)amino]-5-methylpyridazin-3-yl}(methyl)amino)-4-(ethoxycarbonyl)-1,3-thiazol-5-yl]piperidine-1-carboxylate Tetrabutylammonium fluoride (1 M in tetrahydrofuran, 0.48 mL, 0.48 mmol, 6 eq) was added to a stirred solution of the product from Preparation 5k, Step B (60 mg, 0.08 mmol, 1 eq) in tetrahydrofuran (3 mL) and the mixture was heated at 55° C. overnight. The mixture was allowed to cool to ambient temperature, partitioned between ethyl acetate and saturated aqueous sodium bicarbonate, and the organic phase was dried (magnesium sulfate) and concentrated in vacuo. Purification by automated flash column chromatography (CombiFlash Rf, 12 g RediSep™ silica cartridge) eluting with a gradient of 0-10% methanol in dichloromethane afforded the desired product as a yellow glass (37.7 mg, 0.06 mmol, 76%).

LC/MS ($C_{29}H_{35}N_7O_4S_2$) 610 $[M+H]^+$; RT 1.356 (LCMS-V-B1)

$^1H$ NMR (400 MHz, DMSO-d6) δ 8.00 (br s, 1H), 7.68 (br s+s, 2H), 7.52-7.351 (m, 1H), 7.31-7.14 (m, 1H), 4.31 (q, J=7.1 Hz, 2H), 4.22 (d, J=12.8 Hz, 2H), 3.86-3.70 (m, 4H), 2.97-2.71 (m, 2H), 2.46 (s, 3H), 2.05-1.94 (m, 2H), 1.59-1.46 (m, 2H), 1.44 (s, 9H), 1.35 (t, 3H).

Step B: 2-({6-[(1,3-benzothiazol-2-yl)amino]-5-methylpyridazin-3-yl}(methyl)amino)-5-{1-[(tert-butoxy)carbonyl]piperidin-4-yl}-1,3-thiazole-4-carboxylic acid To a solution of the product from Step A (47 mg, 0.08 mmol, 1 eq) in 1,4-dioxane (3 mL) was added lithium hydroxide monohydrate (16.2 mg, 0.39 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile (pH 4; formic acid) in water (pH 4; formic acid) afforded the desired product as a yellow solid (23 mg, 0.04 mmol, 51%).

HRMS-ESI (m/z) [M+H]+ calcd for $C_{27}H_{31}N_7O_4S_2$: 582.1952, found 582.1956.

Example 85: 2-[[6-(1,3-Benzothiazol-2-ylamino)-5-methyl-pyridazin-3-yl]-(3,4-dihydroxybutyl)amino]thiazole-4-carboxylic acid

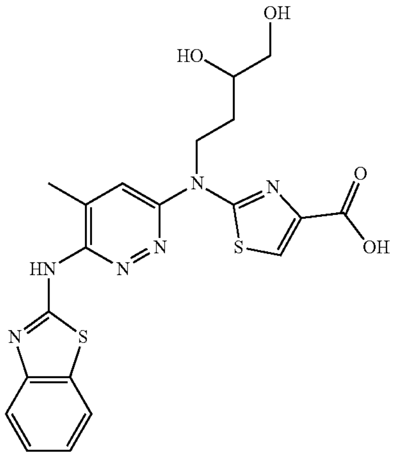 [SMILES: Cc1cc(N(CCC(O)CO)c2nc(C(=O)O)cs2)nnc1Nc1nc2ccccc2s1]

Step A: methyl 2-[tert-butoxycarbonyl-[2-(2,2-dimethyl-1,3-dioxolan-4-yl)ethyl]amino]thiazole-4-carboxylate Using Mitsunobu General Procedure starting from methyl 2-(tert-butoxycarbonylamino)thiazole-4-carboxylate and 2-(2,2-dimethyl-1,3-dioxolan-4-yl)ethanol as starting materials, 3.07 g (99%) of the desired product was obtained.

$^1H$ NMR (500 MHz, DMSO-$d_6$) δ ppm 8.08 (s, 1H), 4.17/4.07 (m+m, 2H), 4.08 (m, 1H), 4.03/3.54 (dd+dd, 2H), 3.80 (s, 3H), 1.88/1.84 (m+m, 2H), 1.53 (s, 9H), 1.28 (s, 3H), 1.22 (s, 3H); HRMS-ESI (m/z): $[M+H]^+$ calcd for $C_{17}H_{26}N_2O_6S$: 387.1589, found: 387.1585.

Step B: methyl 2-[2-(2,2-dimethyl-1,3-dioxolan-4-yl)ethylamino]thiazole-4-carboxylate Using Deprotection with HFIP General Procedure starting from the product from Step A as the appropriate carbamate, 1.21 g (60%) of the desired product was obtained.

$^1H$ NMR (500 MHz, DMSO-$d_6$) δ ppm 7.82 (t, 1H), 7.53 (s, 1H), 4.11 (m, 1H), 4.02/3.49 (dd+dd, 2H), 3.74 (s, 3H), 3.33/3.24 (m+m, 2H), 1.78/1.75 (m+m, 2H), 1.32 (s, 3H), 1.26 (s, 3H); HRMS-ESI (m/z): $[M+H]^+$ calcd for $C_{12}H_{18}N_2O_4S$: 287.1065, found: 287.1055.

Step C: methyl 2-[(6-chloro-5-methyl-pyridazin-3-yl)-[2-(2,2-dimethyl-1,3-diaxolan-4-yl)ethyl]amino]thiazole-4-carboxylate Using Nucleophile Substitution General Procedure starting from the product from Step B as starting material, 178 mg (35%) of the desired product was obtained.

$^1H$ NMR (500 MHz, DMSO-$d_6$) δ ppm 8.07 (s, 1H), 7.85 (d, 1H), 4.57/4.37 (m+m, 2H), 4.17 (m, 1H), 4.03/3.62 (dd+dd, 2H), 3.82 (s, 3H), 2.43 (d, 3H), 1.96 (m, 2H), 1.35/1.23 (s+s, 6H); HRMS-ESI (m/z): $[M+H]^+$ calcd for $C_{17}H_{22}ClN_4O_4S$: 413.1045, found: 413.1048.

Step D: methyl 2-[[6-(1,3-benzothiazol-2-ylamino)-5-methyl-pyridazin-3-yl]-[2-(2,2-dimethyl-1,3-dioxolan-4-yl)ethyl]amino]thiazole-4-carboxylate Using Buchwald General Procedure II starting from the product from Step C as starting material in toluene at 150° C. for 4 h, 184 mg (81%) of the desired product was obtained.

HRMS-ESI (m/z): $[M+H]^+$ calcd for $C_{24}H_{27}N_6O_4S_2$: 527.1530, found 527.1512.

Step E: 2-[[6-(1,3-benzothiazol-2-ylamino)-5-methyl-pyridazin-3-yl]-(3,4-dihydroxybutyl)amino]thiazole-4-carboxylic acid To the solution of the product from Step D in 1,4-dioxane was added 2 M solution of NaOH and the mixture was stirred at 80° C. for 1 h. After acidifying the mixture with a 1 N solution of HCl, the reaction was stirred at 80° C. for 0.5 h, then the precipitate was filtered off and purified by flash column chromatography to give the desired product.

HRMS-ESI (m/z): $[M+H]^+$ calcd for $C_{20}H_{21}N_6O_4S_2$: 473.1066, found: 473.1055.

Example 86: 2-({6-[(1,3-Benzothiazol-2-yl)amino]-5-methylpyridazin-3-yl}(methyl)amino)-5-(1-benzylpiperidin-4-yl)-1,3-thiazole-4-carboxylic acid

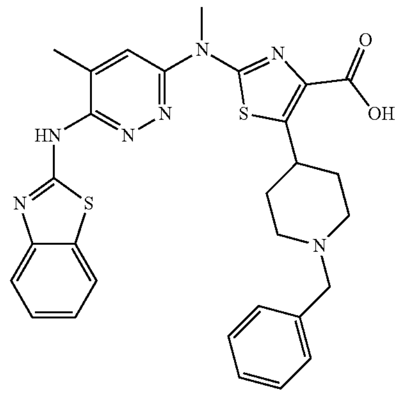 [SMILES: Cc1cc(N(C)c2nc(C(=O)O)c(C3CCN(Cc4ccccc4)CC3)s2)nnc1Nc1nc2ccccc2s1]

Step A: ethyl 5-(1-benzylpiperidin-4-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Preparation 5k (65 mg, 0.1 mmol, 1 eq) in acetonitrile (5 mL) was added benzaldehyde (0.02 mL, 0.2 mmol, 2 eq), sodium triacetoxyborohydride (64.6 mg, 0.3 mmol, 3 eq), and glacial acetic acid (5 μL) and the mixture was stirred at ambient temperature overnight. The reaction was partitioned between ethyl acetate and saturated aqueous sodium bicarbonate and the organic phase was washed with brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as a colourless gum (44.7 mg, 0.0) mmol, 60%).

LC/MS ($C_{37}H_{47}N_7O_3SiS_2$) 730 $[M+H]^+$; RT 1.32 (LCMS-V-B1)

$^1H$ NMR (400 MHz, DMSO-d6) δ 7.89 (d, 1H), 7.66 (d, J=1.1 Hz, 1H), 7.51-7.41 (m, 2H), 7.40-7.31 (m, 4H), 7.30-7.22 (m, 2H), 5.86 (s, 2H), 4.29 (q, J=7.1 Hz, 2H), 3.76 (s, 3H), 3.76-3.69 (m, 2H), 3.63 (tt, J=12.3, 3.8 Hz, 1H), 3.51 (s, 2H), 2.94 (d, J=1.1 Hz, 2H), 2.46 (d, J=1.0 Hz, 3H), 2.15-1.89 (m, 4H), 1.67 (qd, J=12.2, 3.6 Hz, 2H), 1.32 (t, J=7.1 Hz, 3H), 0.92 (dd, J=8.6, 7.4 Hz, 2H), −0.11 (s, 9H).

Step B: ethyl 2-({6-[(1,3-benzothiazol-2-yl)amino]-5-methylpyridazin-3-yl}(methyl)amino)-5-(1-benzylpiperidin-4-yl)-1,3-thiazole-4-carboxylate Hydrochloric acid (4M in 1,4-dioxane; 3 mL, 12 mmol, 196 eq) was added to a stirred solution of the product from Step A (44.7 mg, 0.06 mmol, 1 eq) in 1,4-dioxane (3 mL) and the mixture was stirred at 60° C. overnight. The reaction was allowed to cool to ambient temperature, partitioned between dichloromethane and saturated aqueous sodium bicarbonate, and the organic phase was washed with brine, dried (magnesium sulfate) and concentrated in vacuo. Purification by automated flash column chromatography (CombiFlash Rf, 12 g RediSep™ silica cartridge) eluting with a gradient of 0-5% methanol in dichloromethane afforded the desired product as a yellow gum (22 mg, 0.04 mmol, 60%).

LC/MS ($C_{31}H_{33}N_7O_2S_2$) 600 $[M+H]^+$; RT 0.99 (LCMS-V-B1)

$^1H$ NMR (400 MHz, DMSO-d6) δ 11.05 (br s, 1H), 7.98 (br s, 1H), 7.68 (br s+s, 2H), 7.43-7.31 (m, 5H), 7.30-7.19 (m, 2H), 4.29 (q, J=7.1 Hz, 2H), 3.76 (s, 3H), 3.63 (tt, J=12.0, 3.8 Hz, 1H), 3.52 (s, 2H), 2.98-2.91 (m, 2H), 2.46 (s, 3H), 2.05 (t, 2H), 2.01-1.94 (m, 2H), 1.67 (qd, J=12.2, 3.6 Hz, 2H), 1.32 (t, J=7.1 Hz, 3H).

Step C: 2-({6-[(1,3-benzothiazol-2-yl)amino]-5-methylpyridazin-3-yl}(methyl)amino)-5-(1-benzylpiperidin-4-yl)-1,3-thiazole-4-carboxylic acid To a solution of the product from Step B (22 mg, 0.04 mmol, 1 eq) in 1,4-dioxane (3 mL) was added lithium hydroxide monohydrate (7.7 mg, 0.18 mmol, 5 eq) and the mixture was heated at reflux overnight, then allowed to cool to ambient temperature and concentrated in vacuo. The resultant solid was triturated with water then diethyl ether, filtered, and dried under vacuum to afford the desired product as a yellow solid (9.6 mg, 0.02 mmol, 46%).

HRMS-ESI (m/z) [M+H]+ calcd for $C_{29}H_{30}N_7O_2S_2$: 572.1897, found 572.1903.

Example 87: 2-({6-[(1,3-Benzothiazol-2-yl)amino]-5-methylpyridazin-3-yl}(methyl)amino)-5-[1-(2-methylpropyl)piperidin-4-yl]-1,3-thiazole-4-carboxylic acid

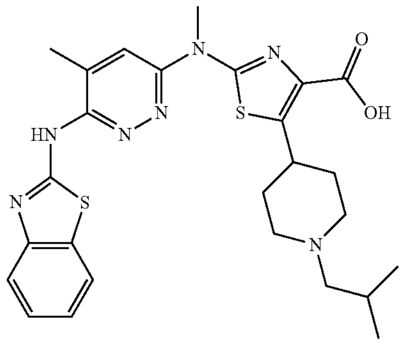 [SMILES: Cc1cc(N(C)c2nc(C(=O)O)c(C3CCN(CC(C)C)CC3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[1-(2-methylpropyl)piperidin-4-yl]-1,3-thiazole-4-carboxylate To a stirred solution of the product from Preparation 5k (134 mg, 0.21 mmol, 1 eq) in 2:1 acetonitrile/dichloromethane (6 mL) was added isobutyraldehyde (0.04 mL, 0.42 mmol, 2 eq), sodium triacetoxyborohydride (133 mg, 0.63 mmol, 3 eq), and glacial acetic acid (10 μL) and the mixture was stirred at ambient temperature overnight. The reaction mixture was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as an off-white solid (114 mg, 0.16 mmol, 79%).

LC/MS ($C_{34}H_{49}N_7O_3SiS_2$) 696 $[M+H]^+$; RT 1.30 (LCMS-V-B1)

$^1$H NMR (400 MHz, DMSO-d6) δ 7.92-7.85 (m, 1H), 7.66 (d, J=1.1 Hz, 1H), 7.50-7.38 (m, 2H), 7.29-7.20 (m, 1H), 5.86 (s, 2H), 4.29 (q, J=7.1 Hz, 2H) 3.76 (s, 3H), 3.75-3.68 (m, 2H), 3.66-3.53 (m, 1H), 2.99-2.90 (m, 2H), 2.46 (d, J=1.0 Hz, 3H), 2.07 (d, J=7.4 Hz, 2H), 2.00-1.88 (m, 4H), 1.79 (hept, J=6.7 Hz, 1H), 1.73-1.59 (m, 2H), 1.32 (t, J=7.1 Hz, 3H), 0.97-0.85 (m, 8H), −0.11 (s, 9H).

Step B: ethyl 2-({6-[(1,3-benzothiazol-2-yl)amino]-5-methylpyridazin-3-yl}(methyl)amino)-5-[1-(2-methylpropyl)piperidin-4-yl]-1,3-thiazole-4-carboxylate Trifluoroacetic acid (1.2 mL, 16.1 mmol, 98 eq) was added to a stirred solution of the product from Step A (114 mg, 0.16 mmol, 1 eq) in dichloromethane (4 mL) and the mixture was stirred at ambient temperature overnight. The reaction was allowed to cool to ambient temperature then partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow solid (76.8 mg, 0.14 mmol, 83%).

LC/MS ($C_{28}H_{35}N_7O_2S_2$) 566 $[M+H]^+$; RT 0.96 (LCMS-V-B1)

$^1$H NMR (400 MHz, DMSO-d6) δ 7.96 (br s, 1H), 7.68 (s, 1H), 7.56 (br s, 1H), 7.39 (t, J=7.6 Hz, 1H), 7.21 (t, J=7.4 Hz, 1H), 4.30 (q, J=7.1 Hz, 2H), 3.76 (s, 3H), 3.67-3.55 (m, 1H), 2.96 (d, J=11.5 Hz, 2H), 2.47 (s, 3H), 2.08 (d, J=7.4 Hz, 2H), 2.02-1.89 (m, 4H), 1.80 (hept, J=6.7 Hz, 1H), 1.66 (td, J=14.3, 13.7, 10.3 Hz, 2H), 1.33 (t, J=7.1 Hz, 3H), 0.90 (d, J=6.5 Hz, 6H).

Step C: 2-({6-[(1,3-benzothiazol-2-yl)amino]-5-methylpyridazin-3-yl}(methyl)amino)-5-[1-(2-methylpropyl)piperidin-4-yl]-1,3-thiazole-4-carboxylic acid To a solution of the product from Step B (76.8 mg, 0.14 mmol, 1 eq) in 1,4-dioxane (5 mL) was added lithium hydroxide monohydrate (28.5 mg, 0.68 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (50 mg, 0.09 mmol, 69%).

HRMS-ESI (m/z) [M+H]+ calcd for $C_{26}H_{32}N_7O_2S_2$: 538.2053, found 538.2060.

Example 88: 2-({6-[(1,3-Benzothiazol-2-yl)amino]-5-methylpyridazin-3-yl}(methyl)amino)-5-[4-(phenoxymethyl)piperidin-1-yl]-1,3-thiazole-4-carboxylic acid

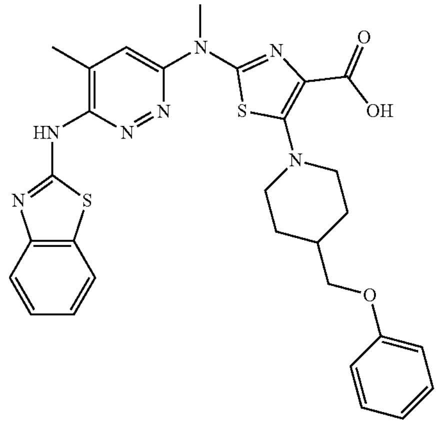 [SMILES: Cc1cc(N(C)c2nc(C(=O)O)c(N3CCC(COc4ccccc4)CC3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[4-(phenoxymethyl)piperidin-1-yl]-1,3-thiazole-4-carboxylate To a stirred solution of the product from Preparation 11b (200 mg, 0.31 mmol, 1 eq), 4-(phenoxymethyl)piperidine hydrochloride (143 mg, 0.63 mmol, 2 eq) and cesium carbonate (308 mg, 0.94 mmol, 3 eq) in 1,4-dioxane (8 mL) was added rac-BINAP-Pd-G3, (31.2 mg, 0.03 mmol, 0.1 eq)

under a nitrogen atmosphere and the mixture was heated at 100° C. overnight. The reaction was allowed to cool to ambient temperature, then diluted with ethyl acetate, washed with water then brine, dried (magnesium sulfate), and concentrated in vacuo to afford the desired product as a yellow foam (153 mg, 0.2 mmol, 65%).

LC/MS ($C_{37}H_{47}N_7O_4SiS_2$) 746 $[M+H]^+$: RT 1.60 (LCMS-V-B1)

$^1$H NMR (400 MHz, DMSO-d6) δ 7.82 (d, 1H), 7.61 (d, J=1.1 Hz, 1H), 7.50-7.39 (m, 2H), 7.33-7.20 (m, 3H), 6.99-6.90 (m, 3H), 5.85 (s, 2H), 4.25 (q, J=7.1 Hz, 2H), 3.91 (d, J=6.1 Hz, 2H), 3.79-3.68 (m, 5H), 3.55 (d, J=11.2 Hz, 2H), 2.88 (td, J=11.6, 2.3 Hz, 2H), 2.44 (d, J=0.9 Hz, 3H), 2.00-1.82 (m, 3H), 1.54 (qd, J=12.0, 3.9 Hz, 2H), 1.31 (t, J=7.1 Hz, 3H), 0.95-0.89 (m, 2H), −0.11 (s, 9H).

Step B: ethyl 2-({6-[(1,3-benzothiazol-2-yl)amino]-5-methylpyridazin-3-yl}(methyl)amino)-5-[4-(phenoxymethyl)piperidin-1-yl]-1,3-thiazole-1-carboxylate Hydrochloric acid (4M in 1,4-dioxane; 3 mL, 12 mmol, 58.7 eq) was added to a stirred solution of the product from Step A (153 mg, 0.2 mmol, 1 eq) in dichloromethane (10 mL) and the mixture was stirred at 50° C. overnight. The reaction was allowed to cool to ambient temperature, then partitioned between dichloromethane and saturated aqueous sodium bicarbonate, and the organic phase was washed with brine, dried (magnesium sulfate) and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (83.8 mg, 0.14 mmol, 67%).

LC/MS ($C_{31}H_{33}N_7O_3S_2$) 616 $[M+H]^+$; RT 1.39 (LCMS-V-B1)

$^1$H NMR (400 MHz, DMSO-d6) δ 11.01 (br s, 1H), 7.94 (br s, 1H), 7.63 (br s+s, 2H), 7.42-7.35 (m, 1H), 7.34-7.26 (m, 2H), 7.23-7.15 (m, 1H), 7.00-6.88 (m, 3H), 4.25 (q, J=7.1 Hz, 2H), 3.91 (d, J=6.1 Hz, 2H), 3.70 (s, 3H), 3.55 (d, J=14.2 Hz, 2H), 2.88 (dd, J=12.2, 9.8 Hz, 2H), 2.45 (s, 3H), 2.02-1.81 (m, 3H), 1.62-1.47 (m, 2H), 1.30 (t, J=7.1 Hz, 3H).

Step C: 2-({6-[(1,3-benzothiazol-2-yl)amino]-5-methylpyridazin-3-yl}(methyl)amino)-5-[4-(phenoxymethyl)piperidin-1-yl]-1,3-thiazole-4-carboxylic acid To a solution of the product from Step B (83.8 mg, 0.14 mmol, 1 eq) in 1,4-dioxane (3 mL) was added lithium hydroxide monohydrate (28.6 mg, 0.68 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (59.7 mg, 0.1 mmol, 75%).

HRMS-ESI (m/z) [M+H+ calcd for $C_{29}H_{30}N_7O_3S_2$: 588.1846, found 588.1853.

Example 89: 5-(1-Benzoylpiperidin-4-yl)-2-({6-[(1,3-benzothiazol-2-yl)amino]-5-methylpyridazin-3-yl}(methyl)amino)-1,3-thiazole-4-carboxylic acid

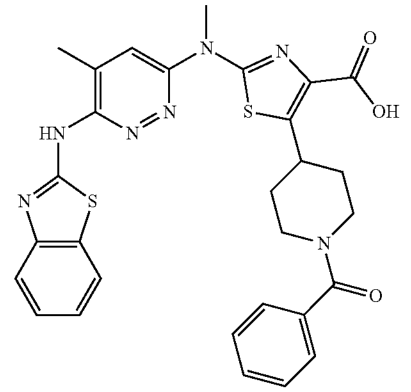 [SMILES: Cc1cc(N(C)c2nc(C(=O)O)c(C3CCN(C(=O)c4ccccc4)CC3)s2)nnc1Nc1nc2ccccc2s1]

Step A: ethyl 5-(1-benzoylpiperidin-4-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Preparation 5k (88 mg, 0.14 mmol, 1 eq) and triethylamine (0.04 mL, 0.28 mmol, 2 eq) in dichloromethane (3 mL) was added benzoyl chloride (0.02 mL, 0.17 mmol, 1.2 eq) and the mixture was stirred at ambient temperature for 4.5 h, then concentrated in vacuo. Purification by automated flash column chromatography (CombiFlash Rf, 12 g RediSep™ silica cartridge) eluting with a gradient of 0-100% ethyl acetate in iso-heptane afforded the desired product as an off-white foam (89.6 mg, 0.12 mmol, 88%).

LC/MS ($C_{37}H_{45}N_7O_4SiS_2$) 744 $[M+H]^+$; RT 1.49 (LCMS-V-B1)

$^1$H NMR (400 MHz, DMSO-d6) δ 7.88 (d, J=7.7 Hz, 1H), 7.67 (d, J=1.2 Hz, 1H), 7.51-7.40 (m, 7H), 7.25 (ddd, J=8.1, 7.0, 1.5 Hz, 1H), 5.86 (s, 2H), 4.66 (br s, 1H), 4.30 (q, J=7.1 Hz, 2H), 3.97-3.85 (m, 1H), 3.77 (s, 3H), 3.75-3.67 (m, 2H), 3.19 (br s, 1H), 2.88 (br s, 1H), 2.47 (d, J=0.9 Hz, 3H), 2.10-1.87 (m, 2H), 1.77-1.55 (m, 2H), 1.35 (t, J=7.1 Hz, 3H), 0.98-0.88 (m, 2H), −0.07 (s, 9H).

Step B: ethyl 5-(1-benzoylpiperidin-4-yl)-2-({6-[(1,3-benzothiazol-2-yl)amino]-5-methylpyridazin-3-yl}(methyl)amino)-1,3-thiazole-4-carboxylate Trifluoroacetic acid (1.2 mL, 16.1 mmol 134 eq) was added to a stirred solution of the product from Step A (89.6 mg, 0.12 mmol, 1 eq) in dichloromethane (4 mL) and the mixture was stirred at ambient temperature overnight. The reaction was partitioned between dichloromethane and saturated aqueous sodium bicarbonate, and the organic phase was washed with brine, dried (magnesium sulfate) and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (55 mg, 0.09 mmol, 74%).

LC/MS ($C_{31}H_{13}N_7O_3S_2$) 614 $[M+H]^+$; RT 1.41 (LCMS-V-B1)

$^1$H NMR (400 MHz, DMSO-d6) δ 11.08 (br s, 1H), 7.96 (br s, 1H), 7.69 (br s+s, 2H), 7.64-7.43 (m, 5H), 7.40 (t, J=7.5 Hz, 1H), 7.23 (t, 1H), 4.69 (br s, 1H), 4.31 (q, J=7.1 Hz, 2H), 4.00-3.80 (m, 1H), 3.82-3.66 (m, 4H), 3.30-2.74 (m, 2H), 2.47 (s, 3H), 2.21-1.84 (m, 2H), 1.76-1.57 (m, 2H), 1.33 (t, J=7.1 Hz, 3H).

Step C: 5-(1-benzoylpiperidin-4-yl)-2-({6-[(1,3-benzothiazol-2-yl)amino]-5-methylpyridazin-3-yl}(methyl)amino)-1,3-thiazole-4-carboxylic acid To a solution of the product from Step B (55 mg, 0.09 mmol, 1 eq) in 1,4-dioxane (4 mL) was added lithium hydroxide monohydrate (18.8 mg, 0.45 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (35.8 mg, 0.06 mmol, 68%).

HRMS-ESI (m/z) [M+H]+ calcd for $C_{29}H_{28}N_7O_3S_2$: 586.1690, found 586.1702.

Example 90: 3-{1-[(Adamantan-1-yl)methyl]-5-methyl-1H-pyrazol-4-yl}-6-({6-[(1,3-benzothiazol-2-yl)amino]-5-methylpyridazin-3-yl}(methyl)amino)pyridine-2-carboxylic acid

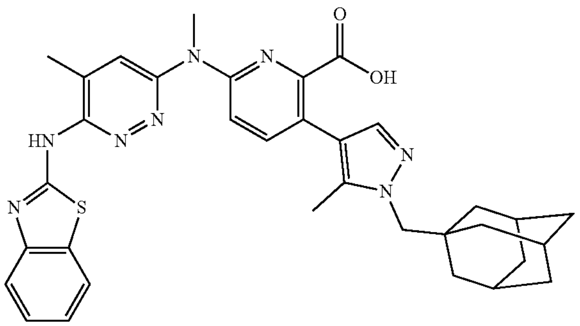 [SMILES: Cc1cc(N(C)c2ccc(-c3cnn(CC45CC6CC(CC(C6)C4)C5)c3C)c(C(=O)O)n2)nnc1Nc1nc2ccccc2s1]

Step A: ethyl 3-bromo-6-{[(tert-butoxy)carbonyl](methyl)amino}pyridine-2-carboxylate Cesium carbonate (4.9 g, 15.1 mmol, 1.5 eq) was added to a solution of ethyl 3,6-dibromopyridine-2-carboxylate (3.1 g, 10.03 mmol, 1 eq), tert-butyl N-methylcarbamate (1.65 g, 12.6 mmol, 1.25 eq), tris(dibenzylideneacetone)dipalladium(0)(91.9 mg, 0.1 mmol, 0.01 eq) and Xantphos (116 mg, 0.2 mmol, 0.02 eq) in 1,4-dioxane (40 mL) under a nitrogen atmosphere and the mixture was heated at 100° C. overnight. The reaction was allowed to cool to ambient temperature and ethyl acetate (250 mL) was added. The mixture was washed with water (2×100 mL), brine (100 mL), dried (magnesium sulfate) and concentrated in vacuo. Purification by flash column chromatography (100 g silica) eluting with dichloromethane afforded the desired product as a pale green oil (1.78 g, 4.96 mmol, 49%).

LC/MS ($C_{14}H_{19}BrN_2O_4$) 303 [M-tBu+H]$^+$; RT 1.43 (LCMS-V-B1)

$^1$H NMR (400 MHz, $CDCl_3$) δ 7.85-7.74 (m, 2H), 4.45 (q, J=7.1 Hz, 2H), 3.40 (s, 3H), 1.52 (s, 9H), 1.42 (t, J=7.1 Hz, 3H).

Step B: ethyl 3-bromo-6-(methylamino)pyridine-2-carboxylate

Trifluoroacetic acid (1.9 mL, 24.8 mmol, 5 eq) was added to a solution of the product from Step A (1.78 g, 4.96 mmol, 1 eq) in dichloromethane (15 mL) at 0° C. and the mixture was allowed to warm to ambient temperature and stir overnight. The reaction was partitioned between dichloromethane (50 mL) and saturated aqueous sodium bicarbonate, and the organic phase was washed with water (2×50 mL) and brine (50 mL), dried (magnesium sulfate), and concentrated in vacuo to afford the desired product as a yellow oil (1.2 g, 4.63 mmol, 94%).

LC/MS ($C_9H_{11}BrN_2O_2$) 260 [M+H]$^+$; RT 1.11 (LCMS-V-B1)

$^1$H NMR (400 MHz, $CDCl_3$) δ 7.61 (d, J=8.9 Hz, 1H), 6.36 (d, J=8.9 Hz, 1H), 4.82 (s, 1H), 4.43 (q, J=7.1 Hz, 2H), 2.90 (d, J=4.3 Hz, 3H), 1.41 (t, J=7.1 Hz, 3H).

Step C: ethyl 3-bromo-6-[(6-chloro-1,2,4,5-tetrazin-3-yl)(methyl)amino]pyridine-2-carboxylate A solution of 3,6-dichloro-1,2,4,5-tetrazine (664 mg, 4.4 mmol, 0.95 eq) and the product from Step B (1.2 g, 4.63 mmol 1 eq) in acetonitrile (20 mL) was heated in a sealed flask for 18 h. The reaction was allowed to cool to ambient temperature and concentrated in vacuo. Purification by automated flash column chromatography (CombiFlash Rf, 40 g RediSep™ silica cartridge) eluting with a gradient of 0-15% ethyl acetate in iso-heptane afforded the desired product as a red solid (898 mg, 2.4 mmol, 55%).

LC/MS ($C_{11}H_{10}BrClN_6O_2$) 373 [M+H]$^+$; RT 1.31 (LCMS-V-B1)

$^1$H NMR (400 MHz, $CDCl_3$) δ 7.99 (d, J=8.7 Hz, 1H), 7.69 (d, J=8.7 Hz, 1H), 4.49 (q, J=7.1 Hz, 2H), 3.87 (s, 3H), 1.44 (t, J=7.1 Hz, 3H).

Step D: ethyl 3-bromo-6-[(6-chloro-5-methylpyridazin-3-yl)(methyl)amino]pyridine-2-carboxylate Ethyl-1-propenyl ether (2.64 mL, 23.8 mmol 10 eq) was added to a solution of the product from Step C (890 mg, 2.38 mmol, 1 eq) in 1,4-dioxane (15 mL) and the mixture was heated in a sealed tube at 100° C. for 24 h. The reaction was allowed to cool to ambient temperature and concentrated in vacuo. Purification by automated flash column chromatography (CombiFlash Rf, 80 g RediSep™ silica cartridge) eluting with a gradient of 0-50% ethyl acetate in iso-heptane afforded the desired product as an orange solid (776 mg, 2.01 mmol, 85%).

LC/MS ($C_{14}H_{14}BrClN_4O_2$) 385 [M+H]$^+$; RT 1.29 (LCMS-V-B1)

$^1$H NMR (400 MHz, $CDCl_3$) δ 7.86 (d, J=8.9 Hz, 1H), 7.65 (q, J=1.0 Hz, 1H), 7.15 (d, J=8.8 Hz, 1H), 4.44 (q, J=7.1 Hz, 2H), 3.70 (s, 3H), 2.35 (d, J=1.0 Hz, 3H), 1.42 (t, J=7.1 Hz, 3H).

Step E: ethyl 3-{1-[(adamantan-1-yl)methyl]-5-methyl-1H-pyrazol-4-yl}-6-[(6-chloro-5-methylpyridazin-3-yl)(methyl)amino]pyridine-2-carboxylate To a suspension of the product from Step D (770 mg, 2 mmol, 1 eq) and the product from Preparation 10a (783 mg, 2.2 mmol, 1.1 eq) in tetrahydrofuran (12 mL) was added a solution of potassium carbonate (552 mg, 3.99 mmol, 2 eq) in water (2 mL) and the mixture was sparged with nitrogen (10 mins). Pd(dppf)$Cl_2$·$CH_2Cl_2$ (163 mg, 0.2 mmol, 0.1 eq) was added and the mixture was heated at reflux overnight. The reaction was allowed to cool to ambient temperature, then partitioned between ethyl acetate and brine and the organic phase was dried (magnesium sulfate) and concentrated in vacuo. Purification by automated flash column chromatography (CombiFlash Rf, 40 g RediSep™ silica cartridge) eluting with a gradient of 0-60% ethyl acetate in iso-heptane afforded the desired product as a cream solid (680 mg, 1.27 mmol, 64%).

LC/MS ($C_{29}H_{35}ClN_6O_2$) 535 $[M+H]^+$; RT 135 (LCMS-V-B1)

$^1H$ NMR (400 MHz, DMSO-d6) δ 7.82-7.73 (m, 2H), 7.50 (d, J=8.6 Hz, 1H), 7.35 (s, 1H), 4.14 (q, J=7.1 Hz, 2H), 3.77 (s, 2H), 3.63 (s, 3H), 2.32 (d, J=1.0 Hz, 3H), 2.18 (s, 3H), 2.01-1.88 (m, 3H), 1.72-1.62 (m, 3H), 1.61-1.52 (m, 9H), 1.13 (t, J=7.1 Hz, 3H).

Step F: ethyl 3-{1-[(adamantan-1-yl)methyl]-5-methyl-1H-pyrazol-4-yl}-6-({6-[(1,3-benzothiazol-2-yl)amino]-5-methylpyridazin-3-yl}(methyl)amino) pyridine-2-carboxylate To a solution of the product from Step E (600 mg, 1.12 mmol, 1 eq) and 2-aminobenzothiazole (253 mg, 1.68 mmol, 1.5 eq) in 1,4-dioxane (20 mL) was added N,N-diisopropylethylamine (0.59 mL, 3.36 mmol, 3 eq), Xantphos (64.9 mg, 0.11 mmol, 0.1 eq) and tris(dibenzylideneacetone)dipalladium(0)(51.3 mg, 0.06 mmol, 0.05 eq) and the mixture was heated in a sealed tube for 64 h. The reaction was allowed to cool to ambient temperature then diluted with ethyl acetate, washed with brine, and concentrated in vacuo. Purification by reverse phase automated flash chromatography (CombiFlash Rf, C18 130 g RediSep column) eluting with a gradient of 30-95% acetonitrile in water afforded the desired product as a yellow glass (513 mg, 0.79 mmol, 71%).

LC/MS ($C_{36}H_{40}N_8O_2S$) 649 $[M+H]^+$; RT 1.62 (LCMS-V-B1)

$^1H$ NMR (400 MHz, DMSO-d6) δ 11.09 (br s, 1H), 7.89 (br s, 1H), 7.74-7.51 (m, 3H), 7.40 (t, 1H), 7.33 (s, 1H), 7.30 (d, 1H), 7.22 (t, 1H), 4.13 (q, J=7.1 Hz, 2H), 3.76 (s, 2H), 3.61 (s, 3H), 2.39 (s, 3H), 2.17 (s, 3H), 1.95 (s, 3H), 1.74-1.62 (m, 3H), 1.62-1.46 (m, 9H), 1.12 (t, J=7.1 Hz, 3H).

Step G: 3-{1-[(adamantan-1-yl)methyl]-5-methyl-1H-pyrazol-4-yl}-6-({6-[(1,3-benzothiazol-2-yl) amino]-5-methylpyridazin-3-yl}(methyl)amino)pyridine-2-carboxylic acid To a solution of the product from Step F (510 mg, 0.79 mmol, 1 eq) in 1,4-dioxane (10 mL) was added lithium hydroxide monohydrate (82.5 mg, 1.97 mmol, 2.5 eq) and the mixture was heated at reflux for 1 h. The reaction was allowed to cool to ambient temperature and concentrated in vacuo then water (5 mL) was added and the pH was adjusted to 3 by the addition of 2M aqueous hydrochloric acid. The mixture was extracted into dichloromethane and the organic extract was washed with brine, dried (magnesium sulfate), and concentrated in vacuo. The resultant solid was triturated with methanol, filtered, washed with methanol, and dried under vacuum to afford the desired product as an off-white solid (362 mg, 0.58 mmol, 74%).

HRMS-ESI (m/z) [M+H]+ calcd for $C_{34}H_{37}N_8O_2S$: 621.2755, found 621.2765.

Example 91: 2-({6-[(1,3-Benzothiazol-2-yl)amino]-5-methylpyridazin-3-yl}(methyl)amino)-5-(1-phenylpiperidin-4-yl)-1,3-thiazole-4-carboxylic acid

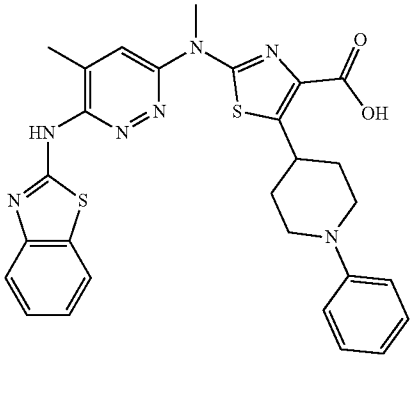 [SMILES: Cc1cc(N(C)c2nc(C(=O)O)c(C3CCN(c4ccccc4)CC3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(1-phenylpiperidin-4-yl)-1,3-thiazole-4-carboxylate Tris(dibenzylideneacetone)dipalladium(0)(10.7 mg, 0.01 mmol, 0.05 eq) was added to a stirred solution of the product from Preparation 5k (150 mg, 0.23 mmol, 1 eq), bromobenzene (0.04 mL, 0.35 mmol, 1.5 eq), cesium carbonate (229 mg, 0.7 mmol, 3 eq) and Xantphos (13.6 mg, 0.02 mmol, 0.1 eq) in 1,4-dioxane (5 mL) under a nitrogen atmosphere and the mixture was heated at 100° C. overnight. The reaction was allowed to cool to ambient temperature then partitioned between dichloromethane and water, and the organic phase was washed with water then brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a brown foam (156 mg, 0.22 mmol, 93%).

LC/MS ($C_{36}H_{45}N_7O_3SiS_2$) 716 $[M+H]^+$; RT 1.68 (LCMS-V-B1)

$^1H$ NMR (400 MHz, DMSO-d6) δ 7.84 (d, 1H), 7.67 (d, J=1.1 Hz, 1H), 7.50-739 (m, 2H), 7.30-7.18 (m, 3H), 7.04-6.96 (m, 2H), 6.79 (t, 1H), 5.86 (s, 2H), 4.31 (q, J=7.1 Hz, 2H), 3.94-3.64 (m, 8H), 2.83-2.68 (m, 2H), 2.46 (d, J=1.0 Hz, 3H), 2.10 (d, J=12.1 Hz, 2H), 1.88-1.71 (m, 2H), 1.34 (t, J=7.1 Hz, 3H), 1.00-0.86 (m, 2H), −0.11 (s, 9H).

Step B: ethyl 2-({6-[(1,3-benzothiazol-2-yl)amino]-5-methylpyridazin-3-yl}(methyl)amino)-5-(1-phenylpiperidin-4-yl)-1,3-thiazole-4-carboxylate Trifluoroacetic acid (1.2 mL, 16.1 mmol, 74 eq) was added to a stirred solution of the product from Step A (156 mg, 0.22 mmol, 1 eq) in dichloromethane (6 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. The resultant solid was triturated with 1:1 dichloromethane/heptane, filtered, and dried under vacuum to afford the desired product as a yellow solid (92 mg, 0.16 mmol, 72%).

LC/MS ($C_{30}H_{31}N_7O_2S_2$) 586 $[M+H]^+$; RT 1.40 (LCIS-V-B1)

$^1H$ NMR (400 MHz, DMSO-d6) δ 12.44 (br s, 1H), 11.02 (br s, 1H), 7.98 (br s, 1H), 7.81-7.54 (m, 2H), 7.38 (br s, 1H), 7.30-7.12 (m, 3H), 7.05-6.97 (m, 2H), 6.80 (t, 1H), 4.31 (q, J=7.1 Hz, 2H), 3.91-3.69 (m, 6H), 2.82-2.70 (m, 2H), 2.47 (s, 3H), 2.11 (d, J=12.4 Hz, 2H), 1.88-1.69 (m, 2H), 1.33 (t, J=7.1 Hz, 3H).

Step C: 2-({6-[(1,3-benzothiazol-2-yl)amino]-5-methylpyridazin-3-yl}(methyl)amino)-5-(1-phenylpiperidin-4-yl)-1,3-thiazole-4-carboxylic acid To a solution of the product from Step B (92 mg, 0.16 mmol, 1 eq) in 1,4-dioxane (3 mL) was added lithium hydroxide monohydrate (33 mg, 0.79 mmol, 5 eq) and the mixture was heated at reflux overnight. The reaction was allowed to cool to ambient temperature, and the solids collected by filtration, washed with 1,4-dioxane, then triturated in water, filtered and dried under vacuum to afford the desired product as a yellow solid (50.3 mg, 0.09 mmol, 57%) [as a lithium salt].

HRMS-ESI (m/z) [M+H]+ calcd for $C_{28}H_{28}N_7O_2S_2$: 558.1740, found 558.1749.

Example 92: 5-[1-(Benzenesulfonyl)piperidin-4-yl]-2-({6-[(1,3-benzothiazol-2-yl)amino]-5-methylpyridazin-3-yl}(methyl)amino)-1,3-thiazole-4-carboxylic acid

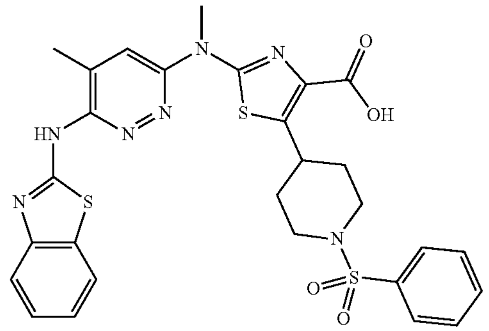 [SMILES: Cc1cc(N(C)c2nc(C(=O)O)c(C3CCN(S(=O)(=O)c4ccccc4)CC3)s2)nnc1Nc1nc2ccccc2s1]

Step A: ethyl 5-[1-(benzenesulfonyl)piperidin-4-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Preparation 5k (200 mg, 0.31 mmol, 1 eq) and triethylamine (0.09 mL, 0.63 mmol, 2 eq) in dichloromethane (5 mL) was added benzenesulfonyl chloride (0.05 mL, 0.38 mmol, 1.2 eq) and a catalytic amount of 4-(dimethylamino)pyridine and the mixture was stirred at ambient temperature overnight. The reaction was partitioned between dichloromethane and water, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as a cream solid (204 mg, 0.26 mmol, 84%).

LC/MS ($C_{36}H_{45}N_7O_5SiS_3$) 780 $[M+H]^+$; RT 1.53 (LCMS-V-B1)

$^1H$ NMR (400 MHz, DMSO-d6) δ 7.94-7.87 (m, 1H), 7.85-7.64 (m, 6H), 7.51-7.40 (m, 2H), 7.31-7.22 (m, 1H), 5.87 (s, 2H), 4.24 (q, J=7.1 Hz, 2H), 3.84 (d, J=11.8 Hz, 2H), 3.78-3.68 (m, 5H), 3.61-3.49 (m, 1H), 2.46 (d, J=0.9 Hz, 3H), 2.39-2.29 (m, 2H), 2.05 (d, J=11.2 Hz, 2H), 1.77-1.61 (m, 2H), 1.25 (t, J=7.1 Hz, 3H), 0.97-0.88 (m, 2H), −0.11 (s, 9H).

Step B: ethyl 5-[1-(benzenesulfonyl)piperidin-4-yl]-2-({6-[(1,3-benzothiazol-2-yl)amino]-5-methylpyridazin-3-yl}(methyl)amino)-1,3-thiazole-4-carboxylate Trifluoroacetic acid (1 mL, 13.4 mmol, 51 eq) was added to a stirred solution of the product from Step A (204 mg, 0.26 mmol, 1 eq) in dichloromethane (6 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (121 mg, 0.19 mmol, 71%).

LC/MS ($C_{30}H_{31}N_7O_4S_3$) 650 $[M+H]^+$; RT 1.28 (LCMS-V-B1)

$^1H$ NMR (400 MHz, DMSO-d6) δ 12.44 (br s, 1H), 11.06 (br s, 1H), 8.14-7.86 (m, 2H), 7.86-7.63 (m, 6H), 7.45-7.34 (m, 1H), 7.28-7.16 (m, 1H), 4.23 (q, J=7.1 Hz, 2H), 3.88-3.80 (m, 2H), 3.75 (s, 3H), 3.62-3.47 (m, 1H), 2.46 (s, 3H), 2.40-2.29 (m, 2H), 2.04 (d, J=12.5 Hz, 2H), 1.75-1.58 (m, 2H), 1.25 (t, J=7.1 Hz, 3H).

Step C: 5-[1-(benzenesulfonyl)piperidin-4-yl]-2-({6-[(1,3-benzothiazol-2-yl)amino]-5-methylpyridazin-3-yl}(methyl)amino)-1,3-thiazole-4-carboxylic acid To a solution of the product from Step B (121 mg, 0.19 mmol, 1 eq) in 1,4-dioxane (3 mL) was added lithium hydroxide monohydrate (39.1 mg, 0.93 mmol, 5 eq) and the mixture was heated at reflux overnight. The reaction was allowed to cool to ambient temperature and the solids collected by filtration and washed with 1,4 dioxane. The material was triturated with water, filtered, and dried under vacuum to afford the desired product as a yellow solid (102 mg, 0.16 mmol, 88%) [as a lithium salt].

HRMS-ESI (m/z) [M+H]+ calcd for $C_{28}H_{28}N_7O_4S_3$: 622.1359, found 622.1367.

Example 93: 2-[[6-(1,3-Benzothiazol-2-ylamino)-5-methyl-pyridazin-3-yl]-(3-hydroxy-4-methoxy-butyl)amino]thiazole-4-carboxylic acid

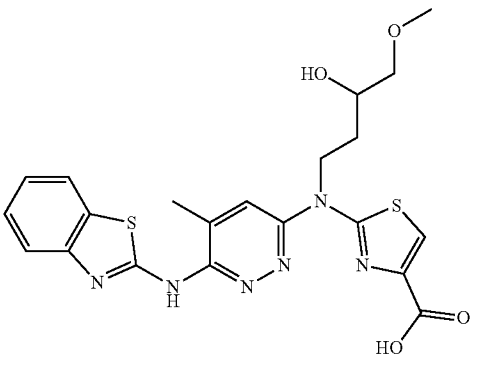 [SMILES: COCC(O)CCN(c1cc(C)c(Nc2nc3ccccc3s2)nn1)c1nc(C(=O)O)cs1]

Step A: methyl 2-[tert-butoxycarbonyl-[3-[tert-butyl(dimethyl)silyl]oxy-4-methoxy-butyl]amino]thiazole-4-carboxylate Using Mitsunobu General Procedure starting from methyl 2-(tert-butoxycarbonylamino)thiazole-4-carboxylate and Preparation 2h as starting materials in THF at rt for 1 h, 4.16 g (81%) of the desired product was obtained.

$^{1}$H NMR (500 MHz, DMSO-$d_6$) δ ppm 8.08 (s, 1H), 4.14/4.07 (m+m, 2H), 3.86 (m, 1H), 3.79 (s, 3H), 3.35/3.29 (dd+dd, 2H), 3.26 (s, 3H), 1.83/1.74 (m+m, 2H), 1.53 (s, 9H), 0.85 (s, 9H), 0.04/0.03 (s+s, 6H). $^{13}$C NMR (125 MHz, DMSO-$d_6$) δ ppm 161.9, 160.7, 153.0, 141.0, 124.8, 83.8, 76.6, 69.8, 58.9, 52.3, 44.4, 32.7, 28.1, 26.2, 18.3, −4.1/−4.5.

Step B: methyl 2-[[3-[tert-butyl(dimethyl)silyl]oxy-4-methoxy-butyl]amino]thiazole-4-carboxylate Using Deprotection with HFIP General Procedure starting from the product from Step A as the appropriate carbamate, 3.1 g (55%) of the desired product was obtained.

$^{1}$H NMR (400 MHz, DMSO-$d_6$) δ ppm 7.79 (t, 1H), 7.52 (s, 1H), 3.91 (m, 1H), 3.74 (s, 3H), 3.29-3.21 (m, 7H), 1.75 (m, 1H), 1.63 (m, 1H), 0.86 (s, 9H), 0.04 (s, 6H).

Step C: methyl 2-[[3-[tert-butyl(dimethyl)silyl]oxy-4-methoxy-butyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a as the appropriate halide, 118 mg (61%) of the desired product was obtained.

$^{1}$H NMR (500 MHz, DMSO-$d_6$) δ ppm 7.99 (s, 1H), 7.84 (d, 1H), 7.58 (s, 1H), 7.47 (d, 1H), 7.44 (td, 1H), 7.25 (td, 1H), 5.87 (s, 2H), 4.52/4.44 (m+m, 2H), 4.02 (m, 1H), 3.81 (s, 3H), 3.72 (t, 2H), 3.37 (m, 2H), 3.29 (s, 3H), 2.46 (s, 3H), 1.93/1.81 (m+m, 2H), 0.92 (t, 2H), 0.89 (s, 9H), 0.09/0.07 (s+s, 6H), −0.12 (s, 9H); $^{13}$C NMR (125 MHz, DMSO-$d_6$) δ ppm 162.3, 160.4, 157.7, 155.3, 150.9, 140.5, 137.5, 137.2, 127.2, 125.4, 123.5, 123.2, 123.2, 117.5, 112.0, 76.7, 72.9, 69.6, 66.7, 58.9, 52.2, 44.8, 31.8, 26.3, 17.9, 17.8, −1.0, −4.1/−4.5; LC-MS-ESI (m/z): $[M+H]^+$ calcd for $C_{34}H_{53}N_4O_5S_2Si_2$: 745, found: 745.

Step D: 2-[[6-(1,3-benzothiazol-2-ylamino)-5-methyl-pyridazin-3-yl]-(3-hydroxy-4-methoxy-butyl)amino]thiazole-4-carboxylic acid Using Deprotection and Hydrolysis General Procedure followed by repurification via reverse phase preparative chromatography (C18, 0.1% TFA in water:MeCN) starting from the product from Step C, TFA-salt of the desired product was obtained.

HRMS-ESI (m/z): $[M+H]^+$ calcd for $C_{21}H_{23}N_6O_4S_2$: 487.1217, found: 487.1222.

Example 94: 2-({6-[(1,3-Benzothiazol-2-yl)amino]-5-methylpyridazin-3-yl}(methyl)amino)-5-(1-methanesulfonylpiperidin-4-yl)-1,3-thiazole-4-carboxylic acid

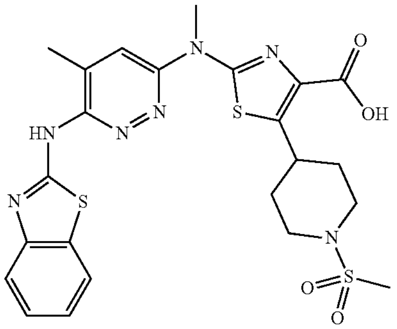 [SMILES: Cc1cc(N(C)c2nc(C(=O)O)c(C3CCN(S(C)(=O)=O)CC3)s2)nnc1Nc1nc2ccccc2s1]

Step A: ethyl 5-(1-methanesulfonylpiperidin-4-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Preparation 5k (150 mg, 0.23 mmol, 1 eq) and triethylamine (0.07 mL, 0.47 mmol, 2 eq) in dichloromethane (5 mL) was added methanesulfonyl chloride (0.02 mL, 0.28 mmol, 1.2 eq) followed by a catalytic amount of 4-(dimethylamino)pyridine and the mixture was stirred at ambient temperature overnight. The reaction was diluted with dichloromethane then washed with water followed by brine, dried (magnesium sulfate) and concentrated in vacuo. Purification by automated flash column chromatography (CombiFlash Rf, 12 g RediSep™ silica cartridge) eluting with a gradient of 0-60% ethyl acetate in iso-heptane afforded the desired product as a white foam (106 mg, 0.15 mmol, 63%).

LC/MS ($C_{31}H_{43}N_7O_5SiS_3$) 718 $[M+H]^+$; RT 1.45 (LCMS-V-B1)

$^{1}$H NMR (400 MHz, DMSO-d6) δ 7.89 (dd, J=7.9, 1.1 Hz, 1H), 7.68 (d, J=1.1 Hz, 1H), 7.51-7.39 (m, 2H), 7.29-7.21 (m, 1H), 5.87 (s, 2H), 4.31 (q, J=7.1 Hz, 2H), 3.77 (s, 3H), 3.76-3.63 (m, 5H), 2.93 (s, 3H), 2.89-2.78 (m, 2H), 2.46 (d, J=1.0 Hz, 3H), 2.12 (d, J=12.3 Hz, 2H), 1.78-1.63 (m, 2H), 1.33 (t, J=7.1 Hz, 3H), 0.97-0.88 (m, 2H), −0.11 (s, 9H).

Step B: ethyl 2-({6-[(1,3-benzothiazol-2-yl)amino]-5-methylpyridazin-3-yl}(methyl)amino)-5-(1-methanesulfonylpiperidin-4-yl)-1,3-thiazole-4-carboxylate Trifluoroacetic acid (1 mL, 13.4 mmol, 91 eq) was added to a stirred solution of the product from Step A (106 mg, 0.15 mmol, 1 eq) in dichloromethane (5 mL) and the mixture was stirred at ambient temperature overnight. The reaction was partitioned between dichloromethane and saturated aqueous sodium bicarbonate and the organic phase was washed with brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane gave a solid that was triturated with diethyl ether, filtered, and dried under vacuum to afford the desired product as a yellow solid (75 mg, 0.13 mmol, 86%).

LC/MS ($C_{25}H_{29}N_7O_4S_3$) 588 $[M+H]^+$; RT 1.36 (LCMS-V-B1)

$^1H$ NMR (400 MHz, DMSO-d6) δ 7.95 (br s, 1H), 7.68 (s, 1H), 7.53 (br s, 1H), 7.38 (t, J=7.6 Hz, 1H), 7.20 (t, J=7.5 Hz, 1H), 4.30 (q, J=7.1 Hz, 2H), 3.80-3.67 (m, 6H), 2.93 (s, 3H), 2.84 (dd, J=13.0, 10.6 Hz, 2H), 2.46 (s, 3H), 2.12 (d, J=11.9 Hz, 2H), 1.79-1.59 (m, 2H), 1.33 (t, J=7.1 Hz, 3H).

Step C: 2-({6-[(1,3-benzothiazol-2-yl)amino]-5-methylpyridazin-3-yl}(methyl)amino)-5-(1-methanesulfonylpiperidin-4-yl)-1,3-thiazole-4-carboxylic acid To a solution of the product from Step B (75 mg, 0.13 mmol, 1 eq) in 1,4-dioxane (3 mL) was added lithium hydroxide monohydrate (26.8 mg, 0.64 mmol, 5 eq) and the mixture was heated at reflux overnight. The reaction was allowed to cool to ambient temperature and the solids collected by filtration and washed with 1,4 dioxane. Purification by reverse phase automated flash chromatography (CombiFlash Rf, C18 13 g RediSep column) eluting with a gradient of 5-95% acetonitrile in water afforded the desired product as a yellow solid (37.1 mg, 0.07 mmol, 52%).

HRMS-ESI (m/z) [M+H]+ calcd for $C_{23}H_{26}N_7O_4S_3$: 560.1203, found 560.1209.

Example 95: 2-({6-[(1,3-Benzothiazol-2-yl)amino]-5-methylpyridazin-3-yl}(methyl)amino)-5-(1-phenylmethanesulfonylpiperidin-4-yl)-1,3-thiazole-4-carboxylic acid

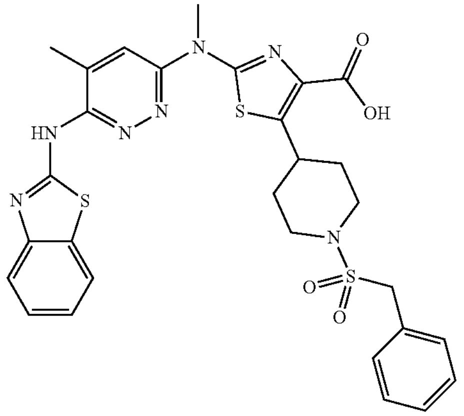 [SMILES: Cc1cc(N(C)c2nc(C(=O)O)c(C3CCN(S(=O)(=O)Cc4ccccc4)CC3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(1-phenylmethanesulfonylpiperidin-4-yl)-1,3-thiazole-4-carboxylate To a stirred solution of the product from Preparation 5k and triethylamine (0.07 mL 0.47 mmol, 2 eq) in dichloromethane (5 mL) was added alpha-toluenesulfonyl chloride (53.6 mg, 0.28 mmol, 1.2 eq) followed by a catalytic amount of 4-(dimethylamino)pyridine and the mixture was stirred at ambient temperature overnight. The reaction was diluted with dichloromethane, washed with water followed by brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as a cream foam (95 mg, 0.12 mmol, 51%).

LC/MS ($C_{37}H_{47}N_7O_5SiS_3$) 794 $[M+H]^+$; RT 1.50 (LCMS-V-B1)

$^1H$ NMR (400 MHz, DMSO-d6) δ 7.81 (dd, J=7.8, 1.1 Hz, 1H), 7.67 (d, J=1.1 Hz, 1H), 7.53-7.36 (m, 7H), 7.27-7.20 (m, 1H), 5.86 (s, 2H), 4.49 (s, 2H), 4.29 (q, J=7.1 Hz, 2H), 3.77 (s, 3H), 3.77-3.64 (m, 5H), 2.82 (td, J=12.4, 2.3 Hz, 2H), 2.46 (d, J=1.0 Hz, 3H), 2.03-1.95 (m, 2H), 1.62-1.46 (m, 2H), 1.32 (t, J=7.1 Hz, 3H), 0.92 (dd, J=8.6, 7.4 Hz, 2H), −0.11 (s, 9H).

Step B: ethyl 2-({6-[(1,3-benzothiazol-2-yl)amino]-5-methylpyridazin-3-yl}(methyl)amino)-5-(1-phenylmethanesulfonylpiperidin-4-yl)-1,3-thiazole-4-carboxylate Trifluoroacetic acid (0.5 mL, 6.71 mmol, 56 eq) was added to a stirred solution of the product from Step A (95 mg, 0.12 mmol, 1 eq) in dichloromethane (5 mL) and the mixture was stirred at ambient temperature overnight. The reaction was partitioned between dichloromethane and saturated aqueous sodium bicarbonate, and the organic phase was washed with brine, dried (magnesium sulfate) and concentrated in vacuo. The resultant solid was triturated in diethyl ether, filtered, and dried under vacuum to afford the desired product as a yellow solid (74 mg, 0.11 mmol, 93%).

LC/MS ($C_{31}H_{33}N_7O_4S_3$) 664 $[M+H]^+$; RT 1.27 (LCMS-V-B1)

$^1H$ NMR (400 MHz, DMSO-d6) δ 11.03 (br s, 1H), 7.91 (br s, 1H), 7.74-7.65 (m, 1H), 7.53-7.33 (m, 7H), 7.25-7.13 (m, 1H), 4.49 (s, 2H), 4.29 (q, J=7.1 Hz, 2H), 3.76 (s, 3H), 3.74-3.64 (m, 3H), 2.88-2.77 (m, 2H), 2.50-2.44 (m, 3H), 2.03-1.94 (m, 2H), 1.60-1.46 (m, 2H), 1.32 (t, J=7.1 Hz, 3H).

Step C: 2-({6-[(1,3-benzothiazol-2-yl)amino]-5-methylpyridazin-3-yl}(methyl)amino)-5-(1-phenylmethanesulfonylpiperidin-4-yl)-1,3-thiazole-1-carboxylic acid To a solution of the product from Step B (74 mg, 0.11 mmol, 1 eq) in 1,4-dioxane (3 mL) was added lithium hydroxide monohydrate (23.4 mg, 0.56 mmol, 5 eq) and the mixture was heated at reflux for 6.5 h. The reaction was allowed to cool to ambient temperature and purification by reverse phase automated flash chromatography (CombiFlash Rf, C18 13 g RediSep column) eluting with a gradient of 5-95% acetonitrile in water afforded the desired product as a yellow solid (43.2 mg, 0.07 mmol, 61%).

HRMS-ESI (m/z) [M+H]+ calcd for $C_{29}H_{30}N_7O_4S_3$: 636.1516, found 636.1521.

Example 96: 2-({6-[(1,3-Benzothiazol-2-yl)amino]-5-methylpyridazin-3-yl}(methyl)amino)-5-[1-(2-phenylacetyl)piperidin-4-yl]-1,3-thiazole-4-carboxylic acid

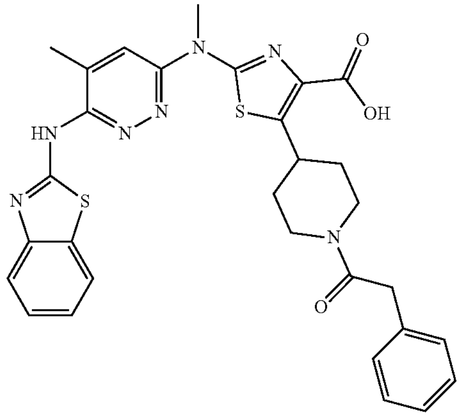 [SMILES: Cc1cc(N(C)c2nc(C(=O)O)c(C3CCN(C(=O)Cc4ccccc4)CC3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[1-(2-phenylacetyl)piperidin-4-yl]-1,3-thiazole-4-carboxylate To a stirred solution of the product from Preparation 5k (150 mg, 0.23 mmol, 1 eq) and triethylamine (0.07 mL, 0.47 mmol, 2 eq) in dichloromethane (5 mL) was added phenylacetyl chloride (0.04 mL, 0.28 mmol, 1.2 eq) and the mixture was stirred at ambient temperature overnight. The reaction was diluted with dichloromethane then washed with saturated aqueous sodium bicarbonate followed by brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as an off-white foam (122 mg, 0.16 mmol, 69%).

LC/MS ($C_{38}H_{47}N_7O_4SiS_2$) 758 $[M+H]^+$; RT 1.49 (LCMS-V-B1)

$^1$H NMR (400 MHz, DMSO-d6) δ 7.88-7.81 (m, 1H), 7.66 (d, J=1.1 Hz, 1H), 7.51-7.41 (m, 2H), 7.39-7.32 (m, 2H), 7.30-7.20 (m, 4H), 5.87 (s, 2H), 4.59 (d, J=12.7 Hz, 1H), 4.29 (q, J=7.1 Hz, 2H), 4.10 (d, J=13.6 Hz, 1H), 3.94-3.66 (m, 8H), 3.09 (t, J=12.7 Hz, 1H), 2.72-2.57 (m, 1H), 2.46 (d, J=1.0 Hz, 3H), 2.11-1.83 (m, 2H), 1.50-1.36 (m, 2H), 1.32 (t, J=7.1 Hz, 3H), 0.97-0.87 (m, 2H), −0.11 (s, 9H).

Step B: ethyl 2-({6-[(1,3-benzothiazol-2-yl)amino]-5-methylpyridazin-3-yl}(methyl)amino)-5-[1-(2-phenylacetyl)piperidin-4-yl)-1,3-thiazole-4-carboxylate Trifluoroacetic acid (0.5 mL, 6.71 mmol, 42 eq) was added to a stirred solution of the product from Step A (122 mg, 0.16 mmol, 1 eq) in dichloromethane (5 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow solid (81.8 mg, 0.13 mmol, 81%).

LC/MS ($C_{32}H_{33}N_7O_3S_2$) 628 $[M+H]^+$; RT 1.22 (LCMS-V-B1)

$^1$H NMR (400 MHz, DMSO-d6) δ 11.06 (br s, 1H), 7.98 (br s, 1H), 7.71-7.65 (m, 2H), 7.43-7.32 (m, 3H), 7.31-7.14 (m, 4H), 4.59 (d, J=13.3 Hz, 1H), 4.29 (q, J=7.1 Hz, 2H), 4.10 (d, J=13.9 Hz, 1H), 3.91-3.70 (m, 6H), 3.09 (t, J=12.4 Hz, 1H), 2.72-2.58 (m, 1H) 2.48-2.43 (m, 3H), 2.07 (d, J=12.6 Hz, 1H), 1.91 (d, J=13.0 Hz, 1H), 1.50-1.33 (m, 2H), 1.32 (t, J=7.1 Hz, 3H).

Step C: 2-({6-[(1,3-benzothiazol-2-yl)amino]-5-methylpyridazin-3-yl}(methyl)amino)-5-[1-(2-phenylacetyl)piperidin-4-yl]-1,3-thiazole-4-carboxylic acid To a solution of the product from Step B (81.8 mg, 0.13 mmol, 1 eq) in 1,4-dioxane (3 mL) was added lithium hydroxide monohydrate (27.3 mg, 0.65 mmol, 5 eq) and the mixture was heated at reflux overnight. The reaction was allowed to cool to ambient temperature and purification by reverse phase automated flash chromatography (CombiFlash Rf, C18 13 g RediSep column) eluting with a gradient of 5-95% acetonitrile in water afforded the desired product as a yellow solid (54.3 mg, 0.09 mmol, 70%).

HRMS-ESI (m/z) [M+H]+ calcd for $C_{30}H_{30}N_7O_3S_2$: 600.1846, found 600.1850.

Example 97: 5-(1-Acetylpiperidin-4-yl)-2-({6-[(1,3-benzothiazol-2-yl)amino]-5-methylpyridazin-3-yl}(methyl)amino)-1,3-thiazole-4-carboxylic acid

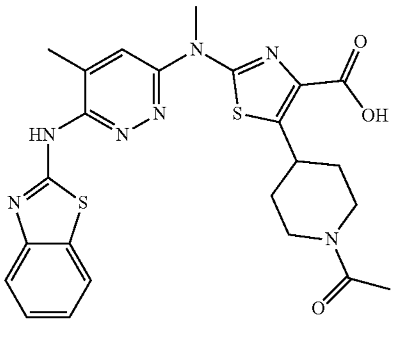 [SMILES: CC(=O)N1CCC(c2sc(N(C)c3cc(C)c(Nc4nc5ccccc5s4)nn3)nc2C(=O)O)CC1]

Step A: ethyl 5-(1-acetylpiperidin-4-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a stirred solution of the product from Preparation 5k and triethylamine (0.07 mL, 0.47 mmol, 2 eq) in dichloromethane (5 mL) was added acetyl chloride (0.02 mL, 0.28 mmol, 1.2 eq) and the mixture was stirred at ambient temperature overnight. The reaction was diluted with dichloromethane then washed with saturated aqueous sodium bicarbonate followed by brine, dried (magnesium sulfate), and concentrated in vacuo. Purification by automated flash column chromatography (CombiFlash Rf, 12 g RediSep™ silica cartridge) eluting with a gradient of 0-100% ethyl acetate in iso-heptane afforded the desired product as a colourless foam (119 mg, 0.17 mmol, 74%).

LC/MS ($C_{32}H_{43}N_7O_4SiS_2$) 682 $[M+H]^+$; RT 1.44 (LCMS-V-B1)

$^1$NMR (400 MHz, DMSO-d6) δ 7.90-7.83 (m, 1H), 7.67 (d, J=1.2 Hz, 1H), 7.50-7.39 (m, 2H), 7.29-7.21 (m, 1H), 5.86 (s, 2H), 4.57 (d, J=13.3 Hz, 1H), 4.31 (q, J=7.1 Hz, 2H), 3.96 (d, J=13.6 Hz, 1H), 3.91-3.82 (m, 1H), 3.77 (s, 3H), 3.75-3.67 (m, 2H), 3.14 (t, J=12.2 Hz, 1H), 2.69-2.54 (m, 1H), 2.45 (d, 3H), 2.06 (s, 3H), 2.06-1.95 (m, 2H), 1.72-1.56 (m, 1H), 1.54-1.38 (m, 1H), 1.33 (t, J=7.1 Hz, 3H), 0.96-0.87 (m, 2H), −0.11 (s, 9H).

Step B: ethyl 5-(1-acetylpiperidin-4-yl)-2-({6-[(1,3-benzothiazol-2-yl)amino]-5-methylpyridazin-3-yl}(methyl)amino)-1,3-thiazole-4-carboxylate To a stirred solution of the product from Step A (119 mg, 0.17 mmol, 1 eq) in tetrahydrofuran (5 mL) was added tetrabutylammonium fluoride (1M in tetrahydrofuran; 0.07 mL, 0.5 mmol, 3 eq) and ethylenediamine (0.03 mL, 0.5 mmol, 3 eq) and the mixture was heated at 60° C. overnight. The reaction was allowed to cool to ambient temperature, then partitioned between dichloromethane and saturated aqueous sodium bicarbonate, and the organic phase was washed with brine, dried (magnesium sulfate) and concentrated in vacuo. Purification by automated flash column chromatography (CombiFlash Rf, 12 g RediSep™ silica cartridge) eluting with a gradient of 0-4% methanol in dichloromethane afforded the desired product as a yellow solid (40 mg, 0.07 mmol, 42%).

LC/MS ($C_{26}H_{29}N_7O_3S_2$) 552 $[M+H]^+$; RT 1.09 (LCMS-V-B1)

$^1$H NMR (400 MHz, DMSO-d6) δ 11.08 (br s, 1H), 7.94 (br s, 1H), 7.69 (s, 1H), 7.57 (br s, 1H), 7.39 (t, J=7.5 Hz, 1H), 7.23 (t, 1H), 4.58 (d, J=13.3 Hz, 1H), 4.31 (q, J=7.1 Hz, 2H), 4.02-3.93 (m, 1H), 3.92-3.82 (m, 1H), 3.77 (s, 3H), 3.21-3.09 (m, 1H), 2.66-2.55 (m, 1H), 2.47 (s, 3H), 2.07 (s, 3H), 2.06-1.96 (m, 2H), 1.76-1.57 (m, 1H), 1.54-1.39 (m, 1H), 1.34 (t, J=7.1 Hz, 3H).

Step C: 5-(1-acetylpiperidin-4-yl)-2-({6-[(1,3-benzothiazol-2-yl)amino]-5-methylpyridazin-3-yl}(methyl)amino)-1,3-thiazole-4-carboxylic acid To a solution of the product from Step B (40 mg, 0.07 mmol, 1 eq) in 1,4-dioxane (3 mL) was added lithium hydroxide monohydrate (15.2 mg, 0.36 mmol, 5 eq) and the mixture was heated at reflux overnight. The reaction was allowed to cool to ambient temperature and purification by reverse phase automated flash chromatography (CombiFlash Rf, C18 13 g RediSep column) eluting with a gradient of 5-95% acetonitrile in water afforded the desired product as a yellow solid (32.4 mg, 0.06 mmol, 85%).

HRMS-ESI (m/z) [M+H]+ calcd for $C_{24}H_{26}N_7O_3S_2$: 524.1533, found 524.1541.

Example 98: 2-[[6-(1,3-Benzothiazol-2-ylamino)-5-methyl-pyridazin-3-yl]-(4-hydroxy-3-methoxy-butyl)amino]thiazole-4-carboxylic acid

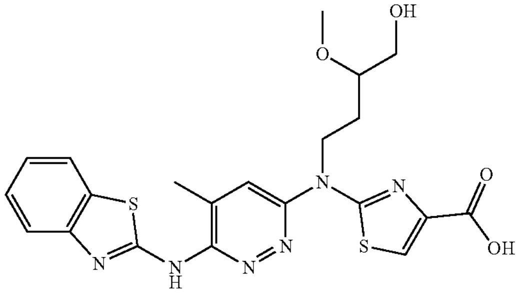 [SMILES: COC(CO)CCN(c1cc(C)c(Nc2nc3ccccc3s2)nn1)c1nc(C(=O)O)cs1]

Step A: methyl 2-[tert-butoxycarbonyl-[4-[tert-butyl(dimethyl)silyl]oxy-3-methoxy-butyl]amino]thiazole-4-carboxylate Using Mitsunobu General Procedure starting from methyl 2-(tert-butoxycarbonylamino)thiazole-4-carboxylate and Preparation 2i as starting materials in THF at rt for 3 h, 4.54 g (86%) of the desired product was obtained.

LC-MS-ESI (m/z): [M+H]+ calcd for $C_{21}H_{39}N_2O_6SSi$: 475, found: 475.

Step B: methyl 2-[[4-[tert-butyl(dimethyl)silyl]oxy-3-methoxy-butyl]amino]thiazole-4-carboxylate Using Deprotection with HFIP General Procedure starting from the product from Step A as the appropriate carbamate, 2.88 g (55%) of the desired product was obtained.

$^1$H NMR (400 MHz, DMSO-$d_6$) δ ppm 7.80 (t, 1H), 7.52 (s, 1H), 3.74 (s, 3H), 3.59 (m, 2H), 3.32 (s, 3H), 3.28 (m, 3H), 1.76 (m, 1H), 1.61 (m, 1H), 0.86 (s, 9H), 0.04 (s, 6H).

Step C: methyl 2-[[4-[tert-butyl(dimethyl)silyl]oxy-3-methoxy-butyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a as the appropriate halide, 319 mg (70%) of the desired product was obtained.

$^1$H NMR (500 MHz, DMSO-$d_6$) δ ppm 7.99 (s, 1H), 7.85 (dm, 1H), 7.66 (s, 1H), 7.48 (dm, 1H), 7.44 (m, 1H), 7.26 (m, 1H), 5.88 (s, 2H), 4.60 (m, 1H), 4.47 (m, 1H), 3.81 (s, 3H), 3.72 (m, 2H), 3.66 (dd, 1H), 3.53 (dd, 1H), 3.29 (s, 3H), 3.27 (m, 1H), 2.46 (s, 3H), 2.03 (m, 1H), 1.76 (m, 1H), 0.92 (m, 2H), 0.77 (s, 9H), 0.00 (s, 3H), −0.01 (s, 3H), −0.12 (s, 9H).

Step D: 2-[[6-(1,3-benzothiazol-2-ylamino)-5-methyl-pyridazin-3-yl]-(4-hydroxy-3methoxy-butyl)amino]thiazole-4-carboxylic acid Using Deprotection and Hydrolysis General Procedure followed by repurification via reverse phase preparative chromatography (C18, 0.1% TFA in water:MeCN) starting from the product from Step C, TFA-salt of the desired product was obtained.

HRMS-ESI (m/z): $[M+H]^+$ for $C_{21}H_{23}N_6O_4S$: 487.1217, found: 487.1222.

Example 99: 2-({6-[(1,3-Benzothiazol-2-yl)amino]-5-methylpyridazin-3-yl}(methyl)amino)-5-(1-methylpiperidin-4-yl)-1,3-thiazole-4-carboxylic acid

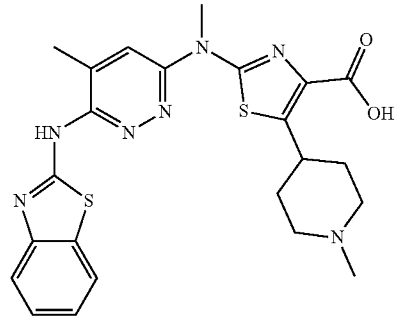 [SMILES: Cc1cc(N(C)c2nc(C(=O)O)c(C3CCN(C)CC3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(1-methylpiperidin-4-yl)-1,3-thiazole-4-carboxylate To a stirred solution of the product from Preparation 5k (150 mg, 0.23 mmol, 1 eq) in 1:1 acetonitrile/dichloromethane (10 mL) was added formaldehyde (37% in water; 0.04 mL, 0.47 mmol, 2 eq), sodium triacetoxyborohydride (149 mg, 0.7 mmol, 3 eq), and glacial acetic acid (10 μL) and the mixture was stirred at ambient temperature overnight. The reaction was partitioned between dichloromethane and saturated aqueous sodium bicarbonate and the organic phase was washed with brine, dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as an off-white foam (76.7 mg 0.12 mmol, 50%).

LC/MS ($C_{31}H_{43}N_7O_3SiS_2$) 654 $[M+H]^+$; RT 1.24 (LCMS-V-B1)

$^1H$ NMR (400 MHz, DMSO-d6) δ 7.88 (dd, J=7.7, 1.0 Hz, 1H), 7.67 (d, J=1.2 Hz, 1H), 7.51-7.39 (m, 2H), 7.28-7.22 (m, 1H), 5.87 (s, 2H), 4.29 (q, J=7.1 Hz, 2H), 3.76 (s, 3H), 3.75-3.67 (m, 2H), 3.64-3.52 (m, 1H), 2.89 (d, J=11.1 Hz, 2H), 2.46 (d, J=1.0 Hz, 3H), 2.21 (s, 3H), 2.01-1.90 (m, 4H), 1.75-1.61 (m, 2H), 1.32 (t, J=7.1 Hz, 3H), 0.99-0.88 (m, 2H), −0.11 (s, 9H).

Step B: ethyl 2-({6-[(1,3-benzothiazol-2-yl)amino]-5-methylpyridazin-3-yl}(methyl)amino)-5-(1-methylpiperidin-4-yl)-1,3-thiazole-4-carboxylate Trifluoroacetic acid (1.0 mL, 13.4 mmol, 114 eq) was added to a stirred solution of the product from Step A (76.7 mg, 0.12 mmol, 1 eq) in dichloromethane (4 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-10% methanol in dichloromethane afforded the desired product as a yellow glass (24.1 mg, 0.05 mmol, 39%).

LC/MS ($C_{25}H_{29}N_7O_2S_2$) 524 $[M+H]^+$; RT 0.87 (LCMS-V-B1)

$^1H$ NMR (400 MHz, DMSO-d6) δ 8.01-7.90 (m, 1H), 7.69 (s, 1H), 7.54 (br s, 1H), 7.44-7.35 (m, 1H), 7.22 (t, J=7.7 Hz, 1H), 4.30 (q, J=7.1 Hz, 2H), 3.76 (s, 3H), 3.64-3.53 (m, 1H), 2.97-2.86 (m, 2H), 2.47 (s, 3H), 2.22 (s, 3H) 2.04-1.89 (m, 4H), 1.77-1.60 (m, 2H), 1.33 (t, J=7.1 Hz, 3H).

Step C: 2-({6-[(1,3-benzothiazol-2-yl)amino]-5-methylpyridazin-3-yl}(methyl)amino)-5-(1-methylpiperidin-4-yl)-1,3-thiazole-4-carboxylic acid To a solution of the product from Step B (24 mg, 0.05 mmol, 1 eq) in 1,4-dioxane (3 mL) was added lithium hydroxide monohydrate (9.62 mg, 0.23 mmol, 5 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (17.2 mg, 0.03 mmol, 76%).

HRMS-ESI (m/z) [M+H]+ calcd for $C_{23}H_{26}N_7O_2S_2$: 496.1584, found 496.1602.

Example 100: 2-({6-[(1,3-Benzothiazol-2-yl)amino]-5-methylpyridazin-3-yl}(methyl)amino)-5-{3-[2-fluoro-4-(3-hydroxyprop-1-yn-1-yl)phenoxy]propyl}-1,3-thiazole-4-carboxylic acid

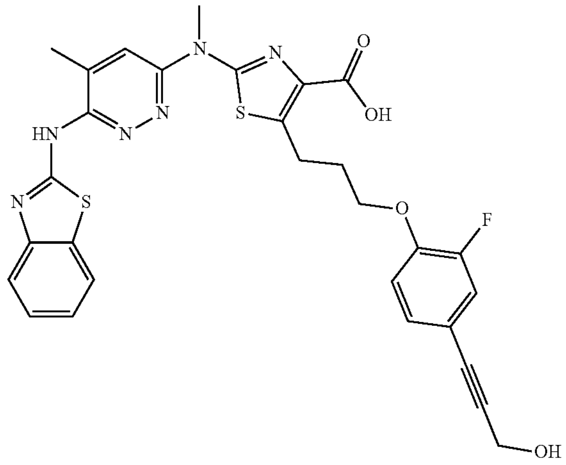 [SMILES: Cc1cc(N(C)c2nc(C(=O)O)c(CCCOc3ccc(C#CCO)cc3F)s2)nnc1Nc1nc2ccccc2s1]

Step A: ethyl 5-[3-(2-fluoro-4-{3-[(4-methoxyphenyl)methoxy]prop-1-yn-1-yl}phenoxy)propyl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 5g (249 mg, 0.34 mmol, 1 eq) in dimethylformamide (5 mL) was added the product from Preparation 6k (128 mg, 0.45 mmol, 1.3 eq) and cesium carbonate (336 mg, 1.03 mmol, 3 eq) and the mixture was heated at 80° C. overnight. The reaction was partitioned between ethyl acetate and water, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow gum (231 mg, 0.26 mmol, 76%).

LC/MS ($C_{45}H_{51}FN_6O_6SiS_2$) 883 $[M+H]^+$; RT 1.41 (LCMS-V-B2)

$^1H$ NMR (400 MHz, DMSO-d6) δ 7.84 (d, 1H), 7.67 (d, J−1.1 Hz, 1H), 7.49-7.40 (m, 2H), 7.37 (dd, J=11.9, 2.0 Hz, 1H), 7.31-7.22 (m, 4H), 7.21-7.14 (m, 1H), 6.94-6.89 (m, 2H), 5.86 (s, 2H), 5.87 (s, 2H), 4.48 (s, 2H), 4.32 (s, 2H), 4.26 (t, 2H), 4.16 (t, J=6.1 Hz, 2H), 3.78 (s, 3H), 3.75 (s, 3H), 3.75-3.68 (m, 2H), 3.34-3.22 (m, 2H), 2.46 (d, J=1.0 Hz, 3H), 2.19-2.08 (m, 2H), 1.30 (t, 3H), 0.97-0.88 (m, 2H), −0.11 (s, 9H).

Step B: ethyl 5-{3-[2-fluoro-4-(3-hydroxyprop-1-yn-1-yl)phenoxy]propyl}-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate Trifluoroacetic acid (1.8 mL) was added to a solution of the product from Step A (391 mg, 0.44 mmol, 1 eq) in dichloromethane (18 mL) and the mixture was stirred at ambient temperature for 1 h. The reaction was diluted with dichloromethane, cooled to 0° C., and neutralised by the addition of 0.5M aqueous sodium hydroxide. The layers were separated and the organic phase was dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the desired product as an off white solid (121 mg, 0.16 mmol, 36%).

LC/MS ($C_{37}H_{43}FN_6O_5SiS_2$) 763 $[M+H]^+$; RT 1.29 (LCMS-V-B2)

$^1H$ NMR (400 MHz, DMSO-d6) δ 7.87-7.81 (m, 1H), 7.67 (s, 1H), 7.50-7.40 (m, 2H), 7.33-7.13 (m, 4H), 5.86 (s, 2H), 5.30 (t, J=6.0 Hz, 1H), 4.34-4.21 (m, 4H), 4.15 (t, J=6.2 Hz, 2H), 3.77 (s, 3H), 3.76-3.67 (m, 2H), 3.32-3.22 (m, 2H), 2.46 (d, J=1.0 Hz, 3H), 2.20-2.06 (m, 2H), 1.28 (t, 3H), 0.97-0.88 (m, 2H), −0.12 (s, 9H).

Step C: ethyl 2-({6-[(1,3-benzothiazol-2-yl)amino]-5-methylpyridazin-3-yl}(methyl)amino)-5-{3-[2-fluoro-4-(3-hydroxyprop-1-yn-1-yl)phenoxy]propyl}-1,3-thiazole-4-carboxylate To a solution of the product from Step B (121 mg, 0.16 mmol, 1 eq) in tetrahydrofuran (15 mL) was added ethylenediamine (31.8 μL, 0.48 mmol, 3 eq) and TBAF (476 μL, 0.48 mmol, 3 eq) and the mixture was heated at 65° C. overnight. The reaction was allowed to cool to ambient temperature then partitioned between ethyl acetate and water, dried (magnesium sulfate), and concentrated in vacuo. Purification by automated flash column chromatography (CombiFlash Rf, 12 g RediSep™ silica cartridge) eluting with a gradient of 0-100% ethyl acetate in iso-heptane afforded the desired product as a yellow solid (43 mg, 0.07 mmol, 43%).

LC/MS ($C_{31}H_{29}FN_6O_4S_2$) 633 $[M+H]^+$; RT 2.43 (LCMS-V-C)

$^1H$ NMR (400 MHz, DMSO-d6) δ 11.08 (br s, 1H), 7.92 (br s, 1H), 7.67 (br s+s, 2H), 7.39 (t, J=7.5 Hz, 1H), 7.29 (dd, J=11.9, 1.9 Hz, 1H), 7.25-7.12 (m, 2H), 5.29 (t, J=5.9 Hz, 1H), 4.33-4.20 (m, 4H), 4.14 (t, 2H), 3.77 (s, 3H) 3.31-3.21 (m, 1H), 2.46 (s, 3H), 2.20-2.07 (m, 2H), 1.29 (t, J=7.1 Hz, 3H).

Step D: 2-({6-[(1,3-benzothiazol-2-yl)amino]-5-methylpyridazin-3-yl}(methyl)amino)-5-{3-[2-fluoro-4-(3-hydroxyprop-1-yn-1-yl)phenoxy]propyl}-1,3-thiazole-4-carboxylic acid To a solution of the product from Step C (50 mg, 0.08 mmol, 1 eq) in 1,4-dioxane (15 mL) was added lithium hydroxide monohydrate (33.2 mg, 0.79 mmol, 10 eq) and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 30-95% acetonitrile in water afforded the desired product as a yellow solid (31.9 mg, 0.05 mmol, 67%).

HRMS-ESI (m/z) [M−H]− calcd for $C_{29}H_{24}FN_6O_4S_2$: 603.1290, found 603.1294.

Example 101: 3-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynyl-dimethyl-ammonio]propane-1-sulfonate

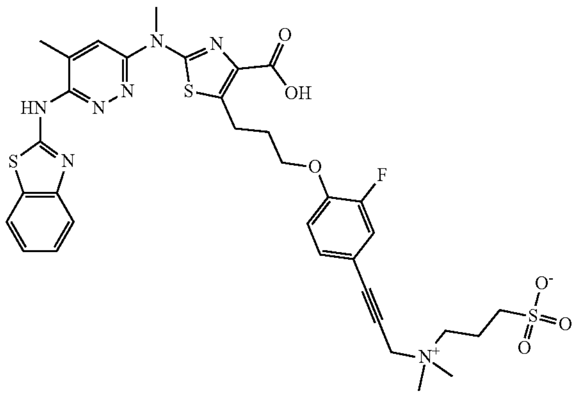 [SMILES: Cc1cc(N(C)c2nc(C(=O)O)c(CCCOc3ccc(C#CC[N+](C)(C)CCCS(=O)(=O)[O-])cc3F)s2)nnc1Nc1nc2ccccc2s1]

Using Alkylation, Deprotection and Hydrolysis General procedure starting from Example 50, Step A and oxathiolane 2,2-dioxide, the desired product was obtained.

HRMS-ESI (m/z): [M+H]+ calcd for $C_{34}H_{37}FN_7O_6S_3$: 754.1946, found: 754.1947.

Example 102: 2-({6-[(1,3-Benzothiazol-2-yl)amino]-5-methylpyridazin-3-yl}(methyl)amino)-5-cyclohexyl-1,3-thiazole-4-carboxylic acid

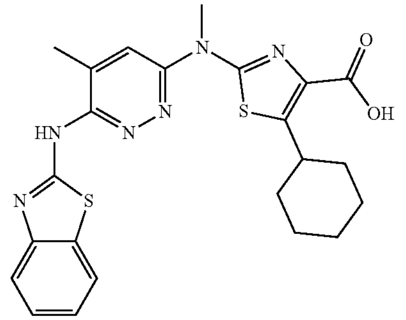 [SMILES: Cc1cc(N(C)c2nc(C(=O)O)c(C3CCCCC3)s2)nnc1Nc1nc2ccccc2s1]

Step A: cyclohexyl(iodo)zinc

Zinc (3.03 g, 46.3 mmol, 3 eq) and lithium chloride (0.98 g, 23.1 mmol, 1.5 eq) were added to a 50 mL oven-dried Schlenk flask and the mixture was heated at 160° C. for 20 min under high vacuum then allowed to cool to ambient temperature and placed under nitrogen on a Schlenk line. Dimethylacetamide (10 mL) was added followed by 1,2-dibromoethane (0.13 mL, 1.54 mmol, 0.1 eq) and the mixture was stirred for 20 min. Iodocyclohexane (2 mL, 15.4 mmol, 1 eq) was added slowly then the mixture heated at 40° C. overnight. The reaction was allowed to cool to ambient temperature and cannulation through a filter (cotton-wool/celite/cotton-wool) under slight vacuum into a dry 25 mL Schlenk tube afforded the desired product as a 1M solution (as determined by titration with a 0.5M solution of iodine) that was used without further characterisation.

Step B: ethyl 5-cyclohexyl-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To an oven-dried flask was added a solution of the product from Preparation 11b (200 mg, 0.31 mmol, 1 eq) and copper (I) iodide (112 mg, 0.63 mmol, 2 eq). Dimethylacetamide (5 mL) was added and the mixture was stirred for 5 min before the product from Step A (1M in dimethylacetamide; 1.42 mL, 1.42 mmol, 4.5 eq) was added slowly and the mixture was stirred at ambient temperature overnight. The reaction mixture was poured onto saturated aqueous ammonium chloride then extracted with dichloromethane (×2). The combined organic extracts were washed with brine, dried (magnesium sulfate), and concentrated in vacuo. Purification by automated flash column chromatography (CombiFlash Rf, 12 g RediSep™ silica cartridge) eluting with a gradient of 0-30% ethyl acetate in iso-heptane afforded the desired product as a yellow gum (135 mg, 0.21 mmol, 67%).

LC/MS ($C_{31}H_{42}N_6O_3S_2Si$) 639 $[M+H]^+$; RT 1.68 (LCMS-V-B1)

$^1H$ NMR (400 MHz, DMSO-d6) δ 7.85 (dd, J=7.6, 1.0 Hz, 1H), 7.66 (d, J=1.2 Hz, 1H), 7.50-7.40 (m, 2H), 7.29-7.22 (m, 1H) 5.86 (s, 2H), 4.28 (q, J=7.1 Hz, 2H), 3.76 (s, 3H), 3.75-3.69 (m, 2H), 3.68-3.56 (m, 1H), 2.45 (s, 3H), 2.05-1.97 (m, 2H), 1.87-1.78 (m, 2H), 1.77-1.68 (m, 2H), 1.52-1.35 (m, 4H), 1.32 (t, 3H), 0.96-0.88 (m, 2H), −0.11 (s, 9H).

Step C: 2-({6-[(1,3-benzothiazol-2-yl)amino]-5-methylpyridazin-3-yl}(methyl)amino)-5-cyclohexyl-1,3-thiazole-4-carboxylic acid Trifluoroacetic acid (1 mL, 13.4 mmol, 63.7 eq) was added to a stirred solution of the product from Step B (135 mg, 0.21 mmol, 1 eq) in dichloromethane (6 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. The resultant solid was suspended in 1,4-dioxane (4 mL) then lithium hydroxide (44.2 mg, 1.05 mmol, 5 eq) added and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a yellow solid (42 mg, 0.09 mmol, 41%).

HRMS-ESI (m/z) [M+H]+ calcd for $C_{23}H_{25}N_6O_2S_2$: 481.1475, found 481.1518.

Example 103: 2-[[6-(1,3-Benzothiazol-2-ylamino)-5-methyl-pyridazin-3-yl]-(2,3-dihydroxypropyl)amino]thiazole-4-carboxylic acid

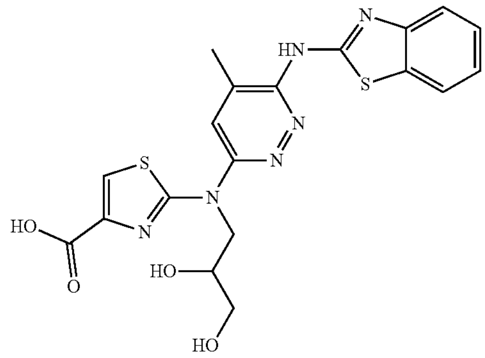 [SMILES: Cc1cc(N(CC(O)CO)c2nc(C(=O)O)cs2)nnc1Nc1nc2ccccc2s1]

Step A: methyl 2-[tert-butoxycarbonyl-[(2,2-dimethyl-1,3-dioxolan-4-yl)methyl]amino]thiazole-4-carboxylate Using Mitsunobu General Procedure starting from methyl 2-(tert-butoxycarbonylamino)thiazole-4-carboxylate and (2,2-dimethyl-1,3-dioxolan-4-yl)methanol as starting materials in THF at rt for 19 h, 5.09 g (91%) of the desired product was obtained.

$^1H$ NMR (500 MHz, DMSO-$d_6$) δ ppm 8.10 (s, 1H), 4.40 (m, 1H), 4.26/4.07 (dd+dd, 2H), 4.01/3.79 (dd+dd, 2H), 3.80 (s, 3H), 1.53 (s, 9H), 1.34 (s, 3H), 1.23 (s, 3H); $^{13}C$ NMR (125 MHz, DMSO-$d_6$) δ ppm 161.8, 161.1, 153.2, 140.9, 124.9, 73.1, 67.1, 52.4, 49.1, 28.1, 27.1, 25.8; HRMS-ESI (m/z): $[M+H]^+$ calcd for $C_{16}H_{25}N_2O_6S$: 373.1433 found: 373.1431.

Step B: methyl 2-[(2,2-dimethyl-1,3-dioxolan-4-yl)methylamino]thiazole-4-carboxylate Using Deprotection with HFIP General Procedure starting from the product from Step A as the appropriate carbamate, 1.77 g (48%) of the desired product was obtained.

$^1$H NMR (500 MHz, DMSO-$d_6$) δ ppm 7.94 (t, 1H), 7.53 (s, H), 4.23 (m, 1H), 4.00/3.66 (dd+dd, 2H), 3.74 (s, 3H), 3.39/3.35 (m+m, 2H), 1.34 (s, 3H), 1.26 (s, 3H); $^{13}$C NMR (125 MHz, DMSO-$d_6$) δ ppm 168.7, 162.0, 142.3, 117.6, 74.3, 67.0, 52.1, 47.4, 27.3, 25.8; HRMS-ESI (m/z): $[M+H]^+$ calcd for $C_{11}H_{17}N_2O_4S$: 273.0909 found: 273.0906.

Step C: methyl 2-[(2,2-dimethyl-1,3-dioxolan-4-yl) methyl-[5-methyl-6-[(Z)-[3-(2-trimethylsilylethoxymethyl)-1,3-benzothiazol-2-ylidene]amino] pyridazin-3-yl]amino]thiazole-4-carboxylate Using Buchwald General Procedure II starting from the product from Step B and Preparation 4a as the appropriate halide, 450 mg (33%) of the desired product was obtained.

$^1$H NMR (500 MHz, DMSO-$d_6$) δ ppm 8.00 (s, 1H), 7.84 (d, 1H), 7.83 (s, 1H), 7.47 (d, 1H), 7.44 (td, 1H), 7.25 (td, 1H), 5.87 (s, 2H), 4.60 (m, 2H), 4.55 (m, 1H), 4.09/3.83 (dd+dd, 2H), 3.82 (s, 3H), 3.71 (t, 2H), 2.44 (s, 3H), 1.27/1.19 (s+s, 6H), 0.92 (t, 2H), −0.12 (s, 9H); $^{13}$C NMR (125 MHz, DMSO-$d_6$) δ ppm 162.2, 161.1, 157.7, 155.4, 151.7, 140.4, 137.5, 136.4, 127.2, 125.4, 123.5, 123.4, 123.2, 119.1, 112.0, 73.9, 72.8, 66.9, 66.7, 52.3, 50.2, 26.6/25.6, 17.8, 17.7, −1.0; HRMS-ESI (m/z): $[M+H]^+$ calcd for $C_{29}H_{39}N_6O_5S_2Si$: 643.2192 found: 643.2184.

Step D: 2-[[6-(1,3-benzothiazol-1-ylamino)-5-methyl-pyridazin-3-yl]-(2,3-dihydroxypropyl)amino] thiazole-4-carboxylic acid Using Deprotection and Hydrolysis General Procedure followed by repurification reverse phase preparative chromatography (C18, 25 mM $NH_4HCO_3$ water:MeCN) starting from the product from Step C, the desired product was obtained.

HRMS-ESI (m/z): $[M+H]^+$ calcd for $C_{19}H_{19}N_6O_4S_2$: 459.0909 found: 459.0891.

Example 104: 2-[[6-(1,3-Benzothiazol-2-ylamino)-5-methyl-pyridazin-3-yl]-(4,5-dihydroxypentyl) amino]thiazole-4-carboxylic acid

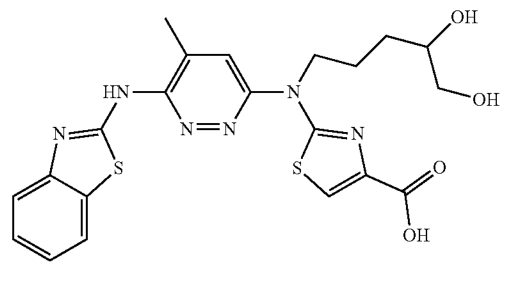 [SMILES: Cc1cc(N(CCCC(O)CO)c2nc(C(=O)O)cs2)nnc1Nc1nc2ccccc2s1]

Step A: methyl 2-[tert-butoxycarbonyl(pent-4-enyl) amino]thiazole-4-carboxylate

Using Mitsunobu General Procedure starting from methyl 2-[tert-butoxycarbonylamino)thiazole-4-carboxylate and 4-penten-1-ol as starting materials in THF at rt for 2 h, 4.36 g (89%) of the desired product was obtained.

Step B: methyl 2-[3-(2,2-dimethyl-1,3-dioxolan-4-yl)propylamino]thiazole-4-carboxylate To 4.35 g of the product from Step 4 (13.3 mmol) was added 3.6 g of 4-methyl-41-oxido-morpholin-4-ium; hydrate (26.6 mmol, 2 eq.), 135 mg of tetraoxoosmium (2.5 w % in 2-methylpropan-2-ol, 0.013 mmol, 0.001 eq.), 10 mL of water, and 100 mL of 2-methylpropan-2-ol and the mixture was stirred at rt for 18 h. After the addition of 50 mL of 1 M $Na_2S_2O_3$ and removal of the $^t$BuOH under reduced pressure, the mixture was extracted with DCM and the combined organic phases were dried and concentrated to give 6.25 g (130%) of methyl 2-[tert-butoxycarbonyl(4,5-dihydroxypentyl)amino]thiazole-4-carboxylate. The crude product was taken up in 100 mL of EtOH, treated with 20 mL of a 1 N HCl at 100° C. for 24 h, and concentrated to give 5.42 g (157%) of methyl 2-(4,5-dihydroxypentylamino) thiazole-4-carboxylate (LC-MS-ESI (m/z): $[M+H]^+$ calcd for $C_{10}H_{17}N_2O_4S$: 261, found 261). After the product was taken up in 50 mL of 2,2-dimethoxypropane and the addition of 124 mg of 4-methylbenzenesulfonic acid (0.72 mmol, 0.05 eq.), the mixture was stirred at reflux for 3 h. After concentration, the residue was taken up in DCM and washed with cc. $NaHCO_3$ to give 3.66 g (92% for three steps) of the desired product.

$^1$H NMR (500 MHz, DMSO-$d_6$) δ ppm 7.81 (t, 1H), 7.50 (s, 1H), 4.04 (m, 1H), 3.98/3.42 (dd+dd, 2H), 3.73 (s, 3H), 3.23 (q, 2H), 1.54 (m, 2H), 1.54 (m, 2H), 1.30 (s, 3H), 1.25 (s, 3H); $^{13}$C NMR (125 MHz, DMSO-$d_6$) δ ppm 117.0, 75.6, 69.0, 52.0, 44.7, 27.3, 27.3, 26.1, 25.5; HRMS-ESI (m/z): $[M+H]^+$ calcd for $C_{13}H_{21}N_2O_4S$: 301.1222 found: 301.1217.

Step C: methyl 2-[3-(2,2-dimethyl-1,3-dioxolan-4-yl)propyl-[5-methyl-6-[(Z)-[3-(2-trimethylsilylethoxymethyl)-1,3-benzothiazol-2-ylidene]amino] pyridazin-3-yl]amino]thiazole-4-carboxylate Using Buchwald General Procedure II starting from the product from Step B and Preparation 4a as the appropriate halide, 74 mg (50%) of the desired product was obtained.

$^1$H NMR (500 MHz, DMSO-$d_6$) δ ppm 7.99 (s, 1H), 7.84 (d, 1H), 7.72 (brs., 1H), 7.47 (d, 1H), 7.44 (td, 1H), 7.25 (td, 1H), 5.87 (s, 2H), 4.49/4.39 (m+m, 2H), 4.13 (m, 1H) 4.02/3.44 (dd+t, 2H), 3.82 (s, 3H), 3.72 (m, 2H), 2.47 (s, 3H), 1.79/1.73 (m+m, 2H), 1.67-1.52 (m, 2H), 1.29/1.26 (s+s, 6H), 0.92 (m, 2H), −0.11 (s, 9H); $^{13}$C NMR (125 MHz, DMSO-$d_6$) δ ppm 162.3, 157.7, 155.3, 150.9, 137.5, 137.2, 127.2, 125.4, 123.5, 123.2, 123.2, 117.7, 112.0, 75.5, 72.9, 69.1, 66.7, 52.3, 47.3, 30.3, 27.4/26.1, 23.7, 17.8, 17.8, −1.0; HRMS-ESI (m/z): $[M+H]^+$ calcd for $C_{31}H_{43}N_6O_5S_2Si$: 671.2505 found: 671.2489.

Step D: 2-[[6-(1,3-benzothiazol-2-ylamino)-5-methyl-pyridazin-3-yl]-4,5-dihydroxypentyl)amino] thiazole-4-carboxylic acid Using Deprotection and Hydrolysis General Procedure followed by repurification via reverse phase preparative chromatography (C18, 25 mM $NH_4HCO_3$ water:MeCN) starting from the product from Step C, the desired product was obtained.

HRMS-ESI (m/z): $[M+H]^+$ calcd for $C_{21}H_{23}N_6O_4S_2$: 487.1222, found: 487.1212.

Example 105: 2-({6-[(1,3-Benzothiazol-2-yl)amino]-5-methylpyridazin-3-yl}(methyl)amino)-5-cyclopentyl-1,3-thiazole-4-carboxylic acid

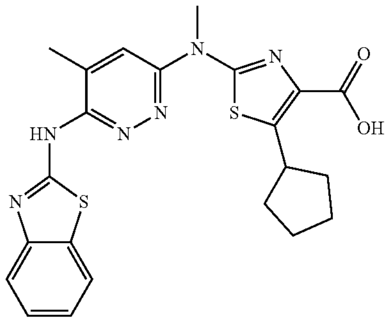 [SMILES: Cc1cc(N(C)c2nc(C(=O)O)c(C3CCCC3)s2)nnc1Nc1nc2ccccc2s1]

Step A: bromo(cyclopentyl)zinc

Zinc (1.83 g, 28 mmol, 3 eq) and lithium chloride (593 mg, 14 mmol, 1.5 eq) were added to an oven-dried Schlenk flask (50 mL). The flask was placed under vacuum and heated at 160° C. for 20 min, then allowed to cool to ambient temperature and placed under nitrogen on a Schlenk line. Dimethylacetamide (10 mL) was added followed by 1,2-dibromoethane (0.08 mL, 0.93 mmol, 0.1 eq) and the mixture was stirred for 20 min. Bromocyclopentane (1 mL, 9.33 mmol, 1 eq) was added slowly then the reaction heated at 40° C. overnight. The reaction mixture was allowed to cool to ambient temperature and cannulation through a filter (cotton-wool/celite/cotton-wool) under slight vacuum into a dry 25 mL Schlenk tube afforded the desired product as a 0.25M solution (as determined by titration with a 0.5M solution of iodine) that was used without further characterisation.

Step B: ethyl 5-cyclopentyl-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To an oven-dried flask was added the product from Preparation 11b (200 mg, 0.31 mmol, 1 eq) and copper (I) iodide (120 mg, 0.63 mmol, 2 eq) followed by dimethylacetamide (5 mL) and the mixture was stirred for 5 min before the product from Step A (0.25M in dimethylacetamide; 5.66 mL, 1.42 mmol, 4.5 eq) was added slowly and the mixture was stirred overnight. The reaction was poured onto saturated aqueous ammonium chloride and extracted with dichloromethane (×2). The organic phase was washed with brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded a solid that was triturated with iso-heptane, filtered, washed with diethyl ether, and dried under vacuum to afford the desired product as a white solid (112 mg, 0.18 mmol, 57%).

LC/MS ($C_{30}H_{40}N_6O_3S_2Si$) 625 $[M+H]^+$; RT 1.79 (LCMS-V-B1)

$^1H$ NMR (400 MHz, DMSO-d6) δ 7.88-7.80 (m, 1H), 7.66 (d, J=1.1 Hz, 1H), 7.52-7.39 (m, 2H), 7.29-7.21 (m, 1H), 5.86 (s, 2H), 4.29 (q, J=7.1 Hz, 2H), 4.06-3.88 (m, 1H), 3.75 (s, 3H), 3.74-3.68 (m, 2H), 2.45 (d, J=1.0 Hz, 3H), 2.24-2.12 (m, 2H), 1.90-1.76 (m, 2H), 1.73-1.49 (m, 2H), 1.31 (t, J=7.1 Hz, 3H), 0.96-0.81 (m, 2H), −0.11 (s, 9H).

Step C: 2-({6-[(1,3-benzothiazol-2-yl)amino]-5-methylpyridazin-3-yl}(methyl)amino)-5-cyclopentyl-1,3-thiazole-4-carboxylic acid Trifluoroacetic acid (0.8 mL, 10.73 mmol, 60 eq) was added to a stirred solution of the product from Step B (112 mg, 0.18 mmol, 1 eq) in dichloromethane (4 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. The resultant solid was suspended in 1,4-dioxane (3 mL) then lithium hydroxide (37.6 mg, 0.9 mmol, 5 eq) was added and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient of 5-95% acetonitrile in water afforded the desired product as a brown solid (34.8 mg, 0.07 mmol, 42%).

HRMS-ESI (m/z) [M−H]− calcd for $C_{22}H_{21}N_6O_2S_2$: 465.1173, found 465.1175.

Example 106: 2-({6-[(1,3-benzothiazol-2-yl)amino]-5-methylpyridazin-3-yl}(methyl)amino)-5-ethenyl-1,3-thiazole-4-carboxylic acid

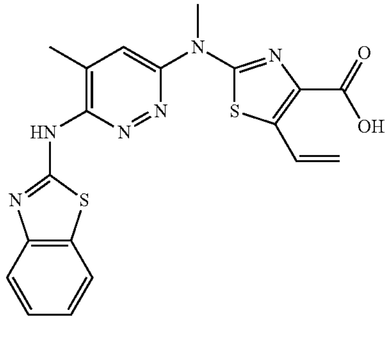 [SMILES: C=Cc1sc(N(C)c2cc(C)c(Nc3nc4ccccc4s3)nn2)nc1C(=O)O]

Step A: ethyl 5-ethenyl-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 11b (100 mg, 0.16 mmol, 1 eq) in 5:1 tetrahydrofuran/water (6 mL) was added $Pd(dppf)Cl_2{\cdot}CH_2Cl_2$ (12.9 mg, 0.02 mmol, 0.1 eq), potassium vinyltrifluoroborate (31.6 mg, 0.24 mmol, 1.5 eq) and potassium carbonate (65.2 mg, 0.47 mmol, 3 eq) and the mixture was heated at reflux for 3 days. The reaction was allowed to cool to ambient temperature, then partitioned between ethyl acetate and water, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a white solid (39.5 mg, 0.07 mmol, 43%).

LC/MS ($C_{27}H_{34}N_6O_3S_2Si$) 583 $[M+H]^+$; RT 1.52 (LCMS-V-B1)

$^1$H NMR (400 MHz, DMSO-d6) 7.88-7.80 (m, 1H), 7.71 (d, J=1.1 Hz, 1H), 7.59-7.40 (m, 3H), 7.28-7.23 (m, 1H), 5.87 (s, 2H), 5.71-5.62 (m, 1H), 5.45-5.37 (m, 1H), 4.32 (q, J=7.1 Hz, 2H), 3.80 (s, 3H), 3.78-3.68 (m, 2H), 2.46 (d, J=1.0 Hz, 3H), 1.33 (t, J=7.1 Hz, 3H), 0.97-0.87 (m, 2H), −0.11 (s, 9H).

Step B: 2-({6-[(1,3-benzothiazol-2-yl)amino]-5-methylpyridazin-3-yl}(methyl)amino)-5-ethenyl-1,3-thiazole-4-carboxylic acid Trifluoroacetic acid (0.5 mL, 6.71 mmol, 99 eq) was added to a stirred solution of the product from Step A (39.5 mg, 0.07 mmol, 1 eq) in dichloromethane (3 mL) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. The resultant solid was suspended in 1,4-dioxane (3 mL), lithium hydroxide monohydrate (14.2 mg, 0.34 mmol, 5 eq) was added, and the mixture was heated at reflux overnight. The reaction was allowed to cool to ambient temperature and concentrated in vacuo. Purification by reverse phase automated flash chromatography (CombiFlash Rf, C18 13 g RediSep column) eluting with a gradient or 5-95% acetonitrile in water afforded the desired product as a yellow solid (13.4 mg, 0.03 mmol, 47%).

HRMS-ESI (m/z) [M−H]− calcd for $C_{19}H_{15}N_6O_2S_2$: 423.0703, found 423.0711.

Example 107: 2-[[6-(1,3-Benzothiazol-2-ylamino)-5-methyl-pyridazin-3-yl]-(3-hydroxy-2-morpholino-propyl)amino]thiazole-4-carboxylic acid

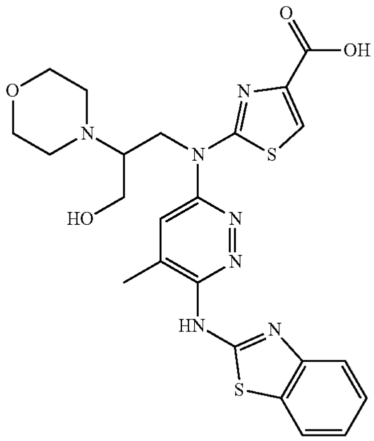 [SMILES: Cc1cc(N(CC(CO)N2CCOCC2)c2nc(C(=O)O)cs2)nnc1Nc1nc2ccccc2s1]

Step A: methyl 2-[tert-butoxycarbonyl-[3-[tert-butyl(dimethyl)silyl]oxy-2-morpholino-propyl]amino]thiazole-4-carboxylate Using Mitsunobu General Procedure starting from methyl 2-(tert-butoxycarbonylamino)thiazole-4-carboxylate and Preparation 2k as starting materials at rt for 1 h, 1.29 g (89%) of the desired product was obtained.

$^1$H NMR (500 MHz, DMSO-$d_6$) δ ppm 8.08 (s, 1H), 4.36/3.86 (dd+dd, 2H), 3.78 (s, 3H), 3.77/3.67 (dd+dd, 2H), 3.32/3.21 (m+m, 4H), 3.01 (m, 1H), 2.82/2.36 (m+m, 4H), 1.53 (s, 9H), 0.86 (s, 9H), 0.04/0.03 (s, 6H); $^{13}$C NMR (125 MHz, DMSO-$d_6$) δ ppm 161.8, 161.6, 153.3, 140.7, 124.5, 67.4, 63.8, 61.0, 52.3, 50.1, 45.8, 28.2, 26.2, 18.3, −5.1; IR: 2954, 1703; HRMS-ESI (m/z): $[M+H]^+$ calcd for $C_{23}H_{43}N_3O_6SSi$: 516.2564, found: 516.2570.

Step B: methyl 2-[[3-[tert-butyl(dimethyl)silyl]oxy-2-morpholino-propyl]amino]thiazole-4-carboxylate Using Deprotection with HFIP General Procedure starting from the product from Step A as the appropriate carbamate, 0.71 g (68%) of the desired product was obtained.

$^1$H NMR (500 MHz, DMSO-$d_6$) δ ppm 7.58 (t, 1H), 7.51 (s, 1H), 3.74/3.66 (dd+dd, 2H), 3.73 (s, 3H), 3.59-3.45 (m, 4H), 3.32/3.29 (m+m, 2H), 2.71 (m, 1H), 2.70/2.56 (m+m, 4H), 0.87 (s, 9H), 004 (s, 6H); $^{13}$C NMR (125 MHz, DMSO-$d_6$) δ ppm 168.8, 162.0, 142.5, 1 17.1, 67.3, 64.5, 61.2, 52.0, 50.1, 43.2, 26.3, 18.3, −5.0; IR: 2854, 1729; HRMS-ESI (m/z): $[M-C_4H_9]^+$ calcd for $C_{14}H_{24}N_3O_4SSi$: 358.1262, found: 358.1255.

Step C: methyl 2-[[3-[tert-butyl(dimethyl)silyl]oxy-2-morpholino-propyl]-[5-methyl-6-[(Z)-[3-(2-trimethylsilylethoxymethyl)-1,3-benzothiazol-2-ylidene]amino]pyridazin-3-yl]amino}thiazole-4-carboxylate Using Buchwald General Procedure II starting from the product from Step B and Preparation 4a as the appropriate halide followed by purification via reverse phase preparative chromatography (C18, 25 mM $NH_4HCO_3$ water:MeCN), 270 mg (70%) of the desired product was obtained.

$^1$H NMR (500 MHz, DMSO-$d_6$) δ ppm 7.97 (s, 1H), 7.84 (d, 1H), 7.74 (s, 1H), 7.48 (d, 1H), 7.44 (t, 1H), 7.26 (t, 1H), 5.89 (s, 2H), 4.71/4.26 (dd+dd, 2H), 3.84/3.79 (dd+dd, 2H), 3.80 (s, 3H), 3.71 (t, 2H), 3.27/3.16 (t+t, 4H), 2.97 (m, 1H), 2.88/2.39 (t+t, 4H), 2.45 (s, 3H), 0.92 (t, 2H), 0.88 (s, 9H), 0.06 (s, 6H), −0.12 (s, 9H); $^{13}$C NMR (125 MHz, DMSO-$d_6$) δ ppm 127.2, 123.5, 123.2, 122.9, 118.5, 112.0, 72.8, 67.3, 66.7, 64.2, 61.0, 52.3, 50.3, 46.4, 26.3, 17.8, 17.8, −1, −5.1; HRMS-ESI (m/z): $[M+H]^+$ calcd for $C_{36}H_{56}N_7O_5S_2Si_2$: 786.3322, found: 786.3312.

Step D: 2-[[6-(1,3-benzothiazol-2-ylamino)-5-methyl-pyridazin-3-yl]-(3-hydroxy-2-morpholino-propyl)amino]thiazole-4-carboxylic acid Using Deprotection and Hydrolysis General Procedure followed by repurification via reverse phase preparative chromatography (C18, 25 mM $NH_4HCO_3$ water:MeCN) starting from the product from Step C, the desired product was obtained.

HRMS-ESI (m/z): $[M+H]^+$ calcd for $C_{23}H_{26}N_7O_4S_2$: 528.1487, found: 528.1489.

Example 108: 2-[[6-(1,3-Benzothiazol-2-ylamino)-5-methyl-pyridazin-3-yl]-(3,4-dihydroxybutyl)amino]-5-[3-[2-fluoro-4-[3-(methylamino)prop-1-ynyl]phenoxy]propyl]thiazole-4-carboxylic acid

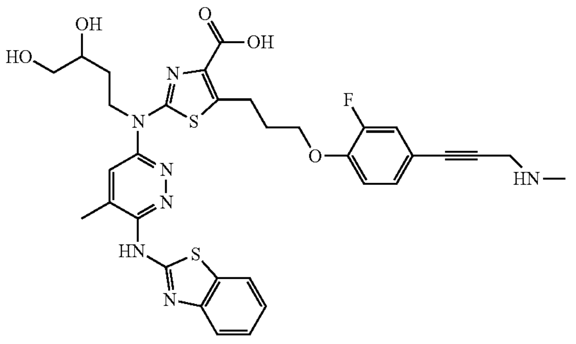 [SMILES: CNCC#Cc1ccc(OCCCc2sc(N(CCC(O)CO)c3cc(C)c(Nc4nc5ccccc5s4)nn3)nc2C(=O)O)c(F)c1]

Step A: methyl 5-[3-[4-[3-[tert-butoxycarbonyl(methyl)amino]prop-1-ynyl]-2-fluoro-phenoxy]propyl]-2-[2-(2,2-dimethyl-1,3-dioxolan-4-yl)ethyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 350 mg of Preparation 3h (0.57 mmol, 1 eq.) and 235 mg of Preparation 4a (0.57 mmol, 1 eq.) as the appropriate halide, 490 mg (87%) of the desired product was obtained.

$^1$H NMR (500 MHz, DMSO-d$_6$) δ ppm 7.84 (d, 1H), 7.68 (s, 1H), 7.47 (d, 1H), 7.44 (td, 1H), 7.32 (brd., 1H), 7.25 (td, 1H), 7.22 (d, 1H), 7.16 (t, 1H), 5.86 (s, 2H), 4.49/4.33 (m+m, 2H), 4.20 (br., 2H), 4.17 (m, 1H), 4.15 (t, 2H), 4.04/3.63 (dd+dd, 2H), 3.77 (s, 3H), 3.72 (t, 2H), 3.27 (t, 2H), 2.84 (br., 3H), 2.45 (s, 3H), 2.13 (m, 2H), 1.75 (m, 2H), 1.40 (s, 9H), 1.37/1.24 (s+s, 6H), 0.92 (t, 2H), −0.11 (s, 9H); $^{13}$C NMR (125 MHz, DMSO-d$_6$) δ ppm 129.1, 127.2, 123.5, 123.2, 119.3, 117.5, 115.5, 112.0, 108.6, 73.7, 72.8, 68.9, 68.4, 66.7, 51.9, 44.4, 38.5, 33.8, 30.9, 28.5, 27.3/26.0, 23.3, 23.1, 17.9, 17.8, −1.0; HRMS-ESI (m/z): [M+H]$^+$ calcd for $C_{48}H_{63}FN_7O_8S_2Si$: 976.3927, found 976.3916.

Step B: 2-[[6-(1,3-benzothiazol-2-ylamino)-5-methyl-pyridazin-3-yl]-(3,4-dihydroxybutyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): [M+H]$^+$ calcd for $C_{33}H_{35}FN_7O_5S_2$: 692.2120, found 692.2114.

Example 109: 2-[[6-(1,3-Benzothiazol-2-ylamino)-5-methyl-pyridazin-3-yl]-(3-hydroxy-4-methoxy-butyl)amino]-5-[3-[2-fluoro-4-[3-(methylamino)prop-1-ynyl]phenoxy]propyl]thiazole-4-carboxylic acid

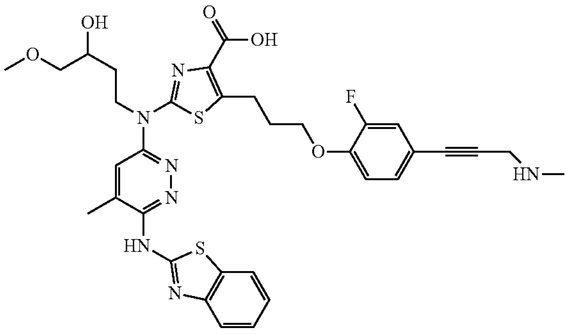

Step A: methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-4-methoxy-butyl]-[5-methyl-6-[(Z)-[3-(2-(trimethylsilylethoxymethyl)-1,3-benzothiazol-2-ylidene]amino]pyridazin-3-yl]amino]thiazole-4-carboxylate Using Buchwald General Procedure II starting from 320 mg of Preparation 31 (0.46 mmol, 1 eq.) and 188 mg of Preparation 4a (0.46 mmol, 1 eq.) as the appropriate halide, 415 mg (84%) of the desired product was obtained.

$^1$H NMR (500 MHz, DMSO-d$_6$) δ ppm 7.84 (d, 1H), 7.55 (s, 1H), 7.47 (d, 1H), 7.44 (td, 1H), 7.32 (brd., 1H), 7.25 (td, 1H), 7.21 (d, 1H), 7.16 (t, 1H), 5.86 (s, 2H), 4.49/4.37 (m+m, 2H), 4.20 (br., 2H), 4.14 (t, 2H), 4.01 (m, 1H), 3.76 (s, 3H), 3.71 (t, 2H), 3.36 (m, 2H), 3.28 (s, 3H), 3.27 (t, 2H), 2.84 (br., 3H), 2.45 (s, 3H), 2.12 (m, 2H), 1.90/1.79 (m+m, 2H), 1.40 (s, 9H), 0.92 (t, 2H), 0.88 (s, 9H), 0.08/0.06 (s/s, 6H), −0.12 (s, 9H); $^{13}$C NMR (125 MHz, DMSO-d$_6$) δ ppm 129.1, 127.2, 123.4, 123.2, 119.3, 119.3, 117.3, 115.5, 112.0, 76.6, 72.8, 69.6, 68.4, 66.7, 58.8, 51.9, 44.2, 38.5, 33.8, 31.8, 30.9, 28.5, 26.3, 23.1, 17.8, 17.8, −1.0, −4.1/−4.5; HRMS-ESI (m/z): [M+H]$^+$ calcd for $C_{52}H_{75}FN_7O_8S_2Si_2$: 1064.4636, found 1064.4629.

Step B: 2-[[6-(1,3-benzothiazol-2-ylamino)-5-methyl-pyridazin-3-yl]-(3-hydroxy-4-methoxy-butyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): [M+H]$^+$ calcd for $C_{34}H_{37}FN_7O_5S_2$: 706.2276, found 706.2285.

Example 110: 2-[[6-(1,3-Benzothiazol-2-ylamino)-5-methyl-pyridazin-3-yl]-(4-hydroxybutyl)amino]thiazole-4-carboxylic acid

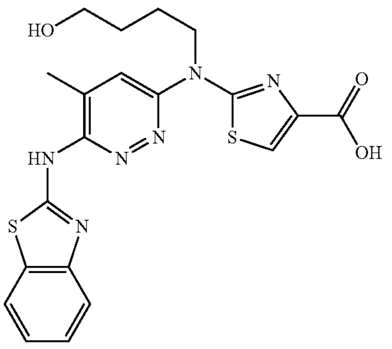 [SMILES: Cc1cc(N(CCCCO)c2nc(C(=O)O)cs2)nnc1Nc1nc2ccccc2s1]

Step A: methyl 2-[tert-butoxycarbonyl-[4-[tert-butyl(dimethyl)silyl]oxybutyl]amino]thiazole-4-carboxylate Using Mitsunobu General Procedure starting from methyl 2-(tert-butoxycarbonylamino)thiazole-4-carboxylate and 4-[tert-butyl(dimethyl)silyl]oxybutan-1-ol as starting materials in THF at rt for 1 h, 3.38 g (98%) of the desired product was obtained.

$^1$H NMR (500 MHz, DMSO-d$_6$) δ ppm 8.09 (s, 1H), 4.07 (t, 2H), 3.79 (s, 3H), 3.59 (t, 2H), 1.69 (qn, 2H), 1.53 (s, 9H), 1.45 (qn, 2H), 0.83 (s, 9H), 0.00 (s, 6H); $^{13}$C NMR (125 MHz, DMSO-d$_6$) ppm 161.9, 160.9, 153.1, 141.0, 124.8, 83.7, 62.5, 52.4, 47, 30.0, 28.1, 26.3, 24.5, 18.3, −4.9; HRMS-ESI (m/z): [M+H]$^+$ calcd for $C_{20}H_{37}N_2O_5SSi$: 445.2192 found: 445.2193.

Step B: methyl 2-[tert-butoxycarbonyl-[4-[tert-butyl(dimethyl)silyl]oxybutyl]amino]thiazole-4-carboxylate Using Deprotection with HFIP General Procedure starting from the product from Step A as the appropriate carbamate, 2.0 g (80%) of the desired product was obtained.

$^1$H NMR (500 MHz, DMSO-d$_6$) δ ppm 7.79 (t, 1H), 7.50 (s, 1H), 3.73 (s, 3H), 3.59 (t, 2H), 3.22 (q, 2H), 1.58 (m, 2H), 1.51 (m, 2H), 0.85 (s, 9H), 0.02 (s, 6H); $^{13}$C NMR (125 MHz, DMSO-d$_6$) δ ppm 168.7, 162.0, 142.6, 116.9, 62.7, 52.0, 44.7, 30.2, 26.3, 25.6, −4.8; IR: 2929, 1732; HRMS-ESI (m/z): [M+H]$^+$ calcd for $C_{15}H_{29}N_2O_3SSi$: 345.1668 found: 345.1652.

Step C: methyl 2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a as the appropriate halide, 451 mg (73%) of the desired product was obtained.

$^1$H NMR (500 MHz, DMSO-d$_6$) δ ppm 7.98 (s, 1H), 7.84 (dm, 1H), 7.69 (s, 1H), 7.47 (dm, 1H), 7.44 (m, 1H), 7.25 (m, 1H), 5.87 (s, 2H), 4.47 (t, 2H), 3.82 (s, 3H), 3.72 (m, 2H), 3.62 (t, 2H), 2.46 (s, 3H), 1.76 (m, 2H), 1.53 (m, 2H), 0.92 (m, 2H), 0.80 (s, 9H), −0.01 (s, 6H), −0.10 (s, 9H); $^{13}$C NMR (125 MHz, DMSO-d$_6$) δ ppm 127.2, 123.5, 123.2, 123.1, 117.7, 112.0, 72.9, 66.7, 62.5, 52.2, 47.2, 29.7, 26.2, 23.8, 17.8, 17.8, −1.0, −4.9; IR: 2951, 1732; HRMS-ESI (m/z): [M+H]$^+$ calcd for $C_{33}H_{51}N_6O_4S_2Si_2$: 715.2952 found: 715.2963.

Step D: 2-[[6-(1,3-benzothiazol-2-ylamino)-5-methyl-pyridazin-3-yl]-(4-hydroxybutyl)amino]thiazole-4-carboxylic acid Using Deprotection and Hydrolysis General Procedure followed by repurification via reverse phase preparative chromatography (C18, 25 mM $NH_4HCO_3$ water:MeCN) starting from the product from Step C, the desired product was obtained.

HRMS-ESI (m/z): [M+H]$^+$ calcd for $C_{20}H_{21}N_6O_3S_2$: 457.1117, found: 457.1108.

Example 111: 2-[[6-(1,3-Benzothiazol-2-ylamino)-5-methyl-pyridazin-3-yl]-(3-hydroxy-2-methoxy-propyl)amino]thiazole-4-carboxylic acid

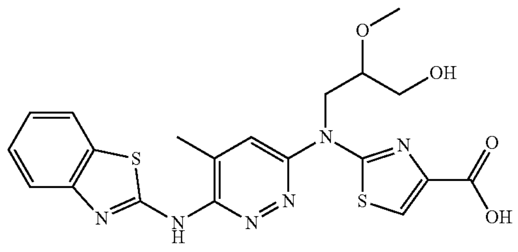 [SMILES: COC(CO)CN(c1cc(C)c(Nc2nc3ccccc3s2)nn1)c1nc(C(=O)O)cs1]

Step A: methyl 2-[tert-butoxycarbonyl-[3-[tert-butyl(dimethyl)silyl]oxy-2-methoxy-propyl]amino]thiazole-4-carboxylate Using Mitsunobu General Procedure starting from methyl 2-(tert-butoxycarbonylamino)thiazole-4-carboxylate and Preparation 2j as starting materials in THF at rt for 1 h, 683 mg (88%) of the desired product was obtained.

$^1$H NMR (400 MHz, DMSO-d$_6$) δ ppm 8.09 (s, 1H), 4.22 (dd, 1H), 4.06 (dd, 1H), 3.79 (s, 3H), 3.71-3.55 (m, 3H), 3.29 (s, 3H), 1.52 (s, 9H), 0.84 (s, 9H), 0.01 (s, 3H), 0.00 (s, 3H).

Step B: methyl 2-[[3-[tert-butyl(dimethyl)silyl]oxy-2-methoxy-propyl]amino]thiazole-4-carboxylate Using Deprotection with HFIP General Procedure starting from the product from Step A as the appropriate carbamate, 514 mg (quant.) of the desired product was obtained.

$^1$H NMR (400 MHz, DMSO-d$_6$) δ ppm 7.80 (t, 1H), 7.52 (s, 1H), 3.73 (s, 3H), 3.34 (s, 3H), 3.66 (dd, 1H), 3.62 (dd, 1H), 3.41 (m, 1H), 3.39 (m, 1H), 3.26 (m, 1H), 0.86 (s, 9H), 0.04 (s, 3H), 0.03 (s, 3H); LC-MS-ESI (m/z): [M+H]$^+$ calcd for $C_{15}H_{29}N_2O_4SSi$: 361, found: 361.

Step C: methyl 2-[[3-[tert-butyl(dimethyl)silyl]oxy-2-methoxy-propyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a as the appropriate halide, 313 mg (70%) of the desired product was obtained.

$^1H$ NMR (500 MHz, DMSO-$d_6$) δ ppm 7.98 (s, 1H), 7.84 (d, 1H), 7.75 (s, 1H), 7.51-7.41 (m, 2H), 7.26 (tm, 1H), 5.88 (s, 1H), 5.87 (s, 1H), 4.53 (dd, 1H), 4.41 (dd, 1H), 3.81 (s, 3H), 3.78 (m, 2H), 3.75-3.65 (m, 3H), 3.29 (s, 3H), 2.44 (s, 3H), 0.92 (t, 2H), 0.86 (s, 9H), 0.05 (s, 3H), 0.04 (s, 3H), −0.12 (s, 9H).

Step D: 2-[[6-(1,3-benzothiazol-2-ylamino)-5-methyl-pyridazin-3-yl]-(3-hydroxy-2-methoxy-propyl)amino]thiazole-4-carboxylic acid Using Deprotection and Hydrolysis General Procedure followed by repurification via reverse phase preparative chromatography (C18, 0.1% TFA in water:MeCN) starting from the product from Step C, TFA-salt of the desired product was obtained.

HRMS-ESI (m/z): $[M+H]^+$ calcd for $C_{20}H_{21}N_6O_4S_2$: 473.1066 found: 473.1063.

Example 112: 2-[[6-(1,3-Benzothiazol-2-ylamino)-5-methyl-pyridazin-3-yl]-(5-hydroxy-4-methoxy-pentyl)amino]-5-[3-[2-fluoro-4-[3-(methylamino)prop-1-ynyl]phenoxy]propyl]thiazole-4-carboxylic acid

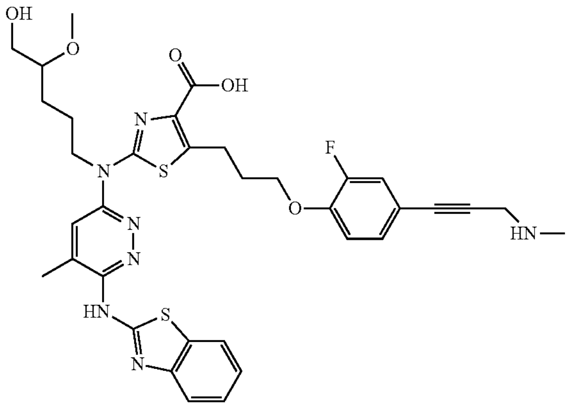 [SMILES: CNCC#Cc1ccc(OCCCc2sc(N(CCCC(CO)OC)c3cc(C)c(Nc4nc5ccccc5s4)nn3)nc2C(=O)O)c(F)c1]

Step A: methyl 5-[3-[4-[3-[tert-butoxycarbonyl(methyl)amino]prop-1-ynyl]-2-fluoro-phenoxy]propyl]-2-[[5-[tert-butyl(dimethyl)silyl]oxy-4-methoxy-pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 12 g of Preparation 3f (13 mmol) and 6.30 g of Preparation 4a (15.6 mmol) as the appropriate halide, 14 g (83%) of the desired product was obtained.

Step B: 2-[[6-(1,3-benzothiazol-2-ylamino)-5-methyl-pyridazin-3-yl]-(5-hydroxy-4-methoxy-pentyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

$^1H$ NMR (500 MHz, DMSO-$d_6$) δ ppm 7.91 (d, 1H), 7.66 (s, 1H), 7.53 (d, 1H), 7.39 (td, 1H), 7.26 (dd, 1H), 7.21 (td, 1H), 7.18 (dd, 1H), 7.15 (t, 1H), 4.38 (m, 2H), 4.14 (t, 2H), 3.47 (s, 2H), 3.41/3.36 (dd+dd, 2H), 3.28 (s, 3H), 3.26 (t, 2H), 3.20 (m, 1H), 2.46 (s, 3H), 2.31 (s, 3H), 2.13 (m, 2H), 1.72 (m, 2H), 1.57/1.49 (m+m, 2H); $^{13}C$ NMR (125 MHz, DMSO-$d_6$) δ ppm 128.9, 126.6, 122.6, 122.3, 119.1, 118.3, 116.9, 115.5, 81.4, 68.5, 62.7, 57.1, 47.0, 40.2, 35.2, 31.0, 28.2, 23.3, 23.1, 17.8 HRMS-ESI (m/z): $[M+H]^+$ calcd for $C_{35}H_{39}FN_7O_5S_2$: 720.2433, found 720.2437.

Example 113: 2-[[6-(1,3-Benzothiazol-2-ylamino)-5-methyl-pyridazin-3-yl]-(4-hydroxy-5-morpholino-pentyl)amino]-5-[3-[2-fluoro-4-[3-(methylamino)prop-1-ynyl]phenoxy]propyl]thiazole-4-carboxylic acid

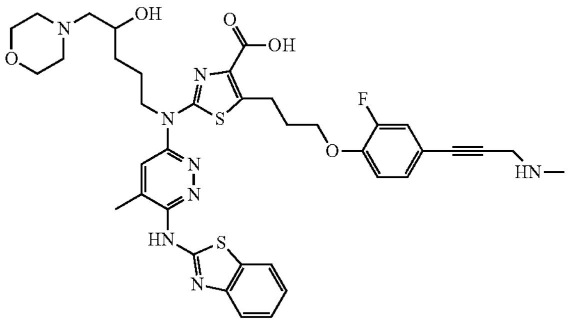 [SMILES: CNCC#Cc1ccc(OCCCc2sc(N(CCCC(O)CN3CCOCC3)c3cc(C)c(Nc4nc5ccccc5s4)nn3)nc2C(=O)O)c(F)c1]

Step A: methyl 5-[3-[4-[3-[tert-butoxycarbonyl(methyl)amino]prop-1-ynyl]-2-fluoro-phenoxy]propyl]-2-[[4-[tert-butyl(diphenyl)silyl]oxy-5-morpholino-pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with tosylate General Procedure starting from Preparation 5a and morpholine as the appropriate amine, the desired product was obtained.

Step B: 2-[[6-(1,3-benzothiazol-2-ylamino)-5-methyl-pyridazin-3-yl]-(4-hydroxy-5-morpholino-pentyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{38}H_{44}FN_8O_5S_2$: 775.2855, found 775.2851.

Example 114: 2-({6-[(1,3-Benzothiazol-2-yl)amino]-5-methylpyridazin-3-yl}(4-hydroxybutyl)amino)-5-(3-{2-fluoro-4-[3-(methylamino)prop-1-yn-1-yl]phenoxy}propyl)-1,3-thiazole-4-carboxylic acid

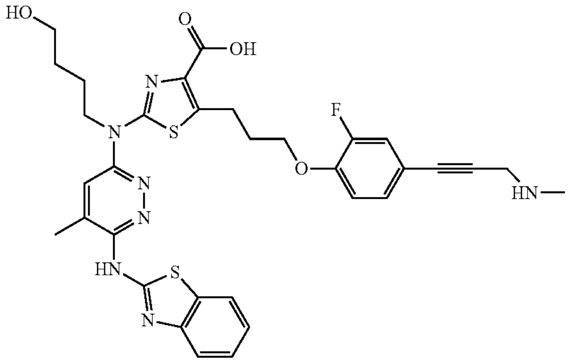 [SMILES: CNCC#Cc1ccc(OCCCc2sc(N(CCCCO)c3cc(C)c(Nc4nc5ccccc5s4)nn3)nc2C(=O)O)c(F)c1]

Using Deprotection and Hydrolysis General Procedure starting from the appropriate methyl ester Preparation 5c, Step A, the desired product was obtained.

HRMS-ESI (m/z): $[M+H]^+$ calcd for $C_{33}H_{35}FN_7O_4S_2$: 676.2170, found 676.2177.

Example 115: 2-[[6-(1,3-Benzothiazol-2-ylamino)-5-methyl-pyridazin-3-yl]-(3-hydroxy-2-morpholino-propyl)amino]-5-[3-[2-fluoro-4-[3-(methylamino)prop-1-ynyl]phenoxy]propyl]thiazole-4-carboxylic acid

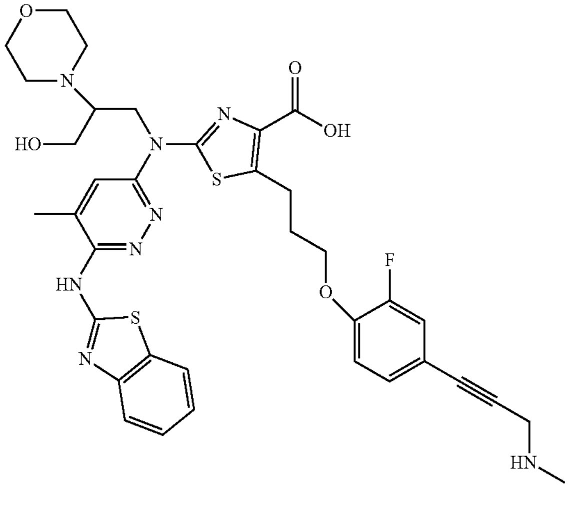 [SMILES: CNCC#Cc1ccc(OCCCc2sc(N(CC(CO)N3CCOCC3)c3cc(C)c(Nc4nc5ccccc5s4)nn3)nc2C(=O)O)c(F)c1]

Step A: methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-2-morpholino-propyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 390 mg or Preparation 3r (0.59 mmol, 1 eq.) and 216 mg of Preparation 4a (0.59 mmol, 1 eq.) as the appropriate halide, 500 mg (83%) of the desired product was obtained.

$^1H$ NMR (500 MHz, DMSO-$d_6$) δ ppm 7.84 (dm, 1H), 7.71 (s, 1H), 7.47 (dm, 1H), 7.44 (m, 1H), 7.31 (brd, 1H), 7.25 (m, 1H), 7.21 (brd, 1H), 7.14 (t, 1H), 5.88/5.85 (d+d, 2H), 4.66/4.19 (dd+dd, 2H), 4.20 (brs, 2H), 4.14 (t, 2H), 3.82/3.77 (dd+dd, 2H), 3.75 (s, 3H), 3.71 (m, 2H), 3.29/3.26 (m+m, 2H), 3.28/3.18 (m+m, 4H), 2.95 (m, 1H), 2.89/2.39 (m+m, 4H), 2.84 (brs, 3H), 2.43 (s, 3H), 2.13 (m, 2H), 1.40 (s, 9H), 0.92 (m, 2H), 0.87 (s, 9H), 0.05 (s, 6H), −0.12 (s, 9H); $^{13}C$ NMR (125 MHz, DMSO-$d_6$) δ ppm 163.1, 157.4, 156.8/151.5, 141.2, 134.6, 129.0, 127.2, 123.4, 123.1, 119.2, 118.3, 115.4, 111.9, 85.1, 82.2, 72.7, 68.3, 67.3, 66.6, 64.1, 60.9, 51.8, 50.1, 45.9, 38.5, 33.7, 30.9, 28.4, 26.2, 23.0, 17.9, 17.7, −1.1, −5.2; HRMS-ESI (m/z): $[M+H]^+$ calcd for $C_{54}H_{78}FN_8O_8S_2Si_2$: 1105.4901, found 1105.4896.

Step B: 2-[[6-(1,3-benzothiazol-2-ylamino)-5-methyl-pyridazin-3-yl]-(3-hydroxy-2-morpholino-propyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{36}H_{40}FN_8O_5S_2$: 747.2542, found 747.2531.

Example 116: 2-({6-[(1,3-Benzothiazol-2-yl)amino]-5-methylpyridazin-3-yl}(methyl)amino)-5-(3-{4-[3-(dimethylamino)prop-1-yn-1-yl]-2-fluoro-phenoxy}-2-methylpropyl)-1,3-thiazole-4-carboxylic acid

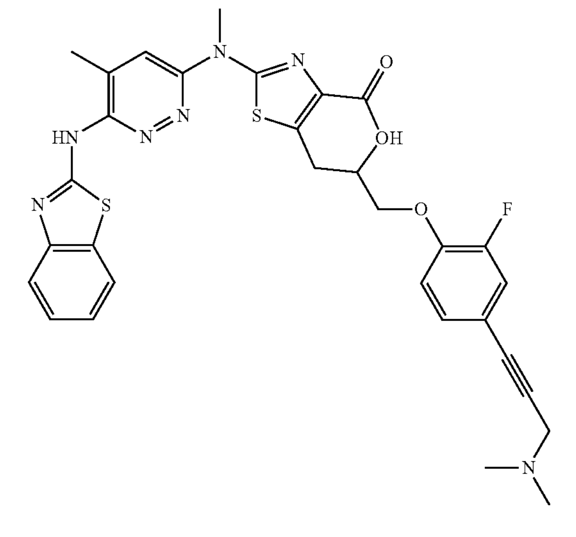 [SMILES: Cc1cc(N(C)c2nc3c(s2)CC(COc2ccc(C#CCN(C)C)cc2F)OC3=O)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(2-methyl-3-oxopropyl)-1,3-thiazole-4-carboxylate To a solution of the product from Preparation 11b (1.2 g, 1.89 mmol, 1 eq) in 1,4-dioxane (20 mL) was added 2-methyl-2-propen-1-ol (0.48 mL, 5.66 mmol, 3 eq), N,N-dicyclohexylmethylamine (0.81 ml, 3.78 mmol, 2 eq) and 2-(di-tert-butyl-phosphino)-phenyl-1H-pyrrole (54.3 mg, 0.19 mmol, 0.1 eq). The mixture was sparged with nitrogen (10 min) and tris(dibenzylideneacetone)dipalladium(0)(86.4 mg, 0.09 mmol, 0.05 eq) was added and the mixture was heated at 100° C. in a sealed flask overnight. The reaction was partitioned between ethyl acetate and water, and the organic phase was washed with brine, dried (magnesium sulfate), and concentrated in vacuo. Purification by automated flash column chromatography (CombiFlash Rf, 40 g RediSep™ silica cartridge) eluting with a gradient of 0-40% ethyl acetate in iso-heptane afforded the desired product as a yellow oil (779 mg, 1.24 mmol, 66%).

LC/MS ($C_{29}H_{38}N_6O_4SiS_2$) 627 $[M+H]^+$; RT 2.86 (LCMS-V-C)

$^1$H NMR (400 MHz, DMSO-d6) δ 9.67 (d, J=1.4 Hz, 1H), 7.88-7.81 (m, 1H), 7.68-7.63 (m, 1H), 7.51-7.40 (m, 2H), 7.29-7.21 (m, 1H), 5.85 (s, 2H), 4.28 (q, 2H), 3.77 (s, 3H), 3.75-3.66 (m, 2H), 3.49 (dd, J=14.4, 6.7 Hz, 1H), 3.16 (dd, J=14.4, 7.6 Hz, 1H), 2.86-2.74 (m, 1H), 2.44 (d, 3H), 1.31 (t, 3H), 1.08 (d, 3H), 0.95-0.88 (m, 2H), −0.12 (s, 9H).

Step B: ethyl 5-(3-hydroxy-2-methylpropyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product of Step A (779 mg, 1.24 mmol, 1 eq) in methanol (20 mL), cooled to 0° C. was added sodium borohydride (51.7 mg, 1.37 mmol, 1.1 eq) and the mixture was stirred for 20 min. The reaction was partitioned between ethyl acetate and water, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-50% ethyl acetate in iso-heptane afforded the desired product as a yellow foam (336 mg, 0.53 mmol, 43%).

LC/MS ($C_{29}H_{40}N_6O_4SiS_2$) 629 $[M+H]^+$; RT 2.74 (LCMS-V-C)

$^1$H NMR (400 MHz, DMSO-d6) δ 7.87-7.83 (m, 1H), 7.66 (d, J=1.1 Hz, 1H), 7.49-7.40 (m, 2H), 7.28-7.21 (m, 1H), 5.85 (s, 2H), 4.62 (t, J=5.2 Hz, 1H), 4.27 (q, J=7.1 Hz, 2H), 3.76 (s, 3H), 3.75-3.66 (m, 3H), 3.42-3.26 (m, 2H), 3.13 (dd, J=14.2, 6.0 Hz, 1H), 2.96 (dd, J=14.2, 8.5 Hz, 1H), 2.45 (d, J=1.0 Hz, 3H), 1.95-1.83 (m, 1H), 1.31 (t, 3H), 0.95-0.89 (m, 2H), 0.88 (d, 3H), −0.11 (s, 9H).

Step C: ethyl 5-(3-iodo-2-methylpropyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product of Step B (469 mg, 0.75 mmol, 1 eq) in 6:1 diethyl ether/acetonitrile (21 mL) was added iodine (284 mg, 1.12 mmol, 1.5 eq), triphenylphosphine (293 mg, 1.12 mmol, 1.5 eq) and imidazole (0.07 mL, 1.12 mmol, 1.5 eq) and the mixture was stirred at ambient temperature for 16 h. The reaction was partitioned between ethyl acetate and 10% aqueous sodium thiosulphate, and the organic phase was dried (magnesium sulfate) and concentrated in vacuo. Purification by automated flash column chromatography (CombiFlash Rf, 12 g RediSep™ silica cartridge) eluting with a gradient of 0-30% ethyl acetate in iso-heptane afforded the desired product as a yellow oil (523 mg, 0.71 mmol, 95%).

LC/MS ($C_{29}H_{39}IN_6O_3SiS_2$) 739 $[M+H]^+$; RT 3.23 (LCMS-V-C)

$^1$H NMR (400 MHz, DMSO-d6) δ 7.87-7.81 (m, 1H), 7.67 (d, J=1.2 Hz, 1H), 7.52-7.40 (m, 2H), 7.28-7.22 (m, 1H), 5.85 (s, 2H), 4.29 (q, J=7.1 Hz, 2H), 3.78 (s, 3H), 3.75-3.67 (m, 2H), 3.48-3.37 (m, 1H), 3.35-3.27 (m, 1H), 3.17-3.03 (m, 2H), 2.45 (d, J=1.0 Hz, 3H), 1.94-1.78 (m, 1H), 1.32 (t, J=7.1 Hz, 3H), 0.97 (d, J=6.5 Hz, 3H), 0.95-0.87 (m, 2H), −0.13 (s, 9H).

Step D: ethyl 5-(3-{4-[3-(dimethylamino)prop-1-yn-1-yl]-2-fluorophenoxy}-2-methylpropyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Step C (523 mg, 0.71 mmol, 1 eq) in dimethylformamide (20 mL) was added the product from Preparation 6b (178 mg, 0.92 mmol, 1.3 eq) and cesium carbonate (692 mg, 2.12 mmol, 3 eq) and the mixture was heated at 80° C. for 3 h. The reaction was partitioned between ethyl acetate and brine, and the organic phase was dried (magnesium sulfate) and concentrated in vacuo. Purification by automated flash column chromatography (CombiFlash Rf, 24 g RediSep™ silica cartridge) eluting with a gradient of 0-5% methanol in dichloromethane afforded the desired product as a yellow oil (257 mg, 0.32 mmol, 45%).

LC/MS ($C_{40}H_{50}FN_7O_4SiS_2$) 804 $[M+H]^+$; RT 2.66 (LCMS-V-C)

$^1$H NMR (400 MHz, DMSO-d6) δ 7.86-7.80 (m, 1H), 7.66 (d, J=1.1 Hz, 1H), 7.49-7.40 (m, 2H), 7.33-7.10 (m, 4H), 5.85 (s, 2H), 4.26 (q, 2H), 4.08-3.95 (m, 3.77 (s, 3H), 3.75-3.65 (m, 2H), 3.36 (s, 2H), 3.32-3.25 (m, 1H), 3.17-3.05 (m, 1H), 2.44 (d, J=1.0 Hz, 3H), 2.37-2.24 (m, 1H), 2.18 (s, 6H), 1.29 (t, J=7.1 Hz, 3H), 1.04 (d, J=6.7 Hz, 3H), 0.96-0.85 (m, 2H), −0.12 (s, 9H).

Step E: ethyl 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-methylpropyl)-1,3-thiazole-4-carboxylate To a solution of the product of Step D (257 mg, 0.32 mmol, 1 eq) in tetrahydrofuran (15 mL) was added ethylenediamine (64 µL, 0.96 mmol, 3 eq) followed by TBAF (1M in tetrahydrofuran; 0.96 mL, 0.96 mmol, 3 eq) and the mixture was heated at 60° C. for 18 h. The reaction was partitioned between ethyl acetate and water, and the organic phase was dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (110 mg, 0.16 mmol, 51%).

LC/MS ($C_{34}H_{36}FN_7O_3S_2$) 674 $[M+H]^+$; RT 2.11 (LCMS-V-C)

$^1$H NMR (400 MHz, DMSO-d6) δ 11.55 (br s, 1H), 7.92 (d, J=8.0 Hz, 1H), 7.69 (s, 1H), 7.54 (d, J=8.0 Hz, 1H), 7.43-7.36 (m, 1H), 7.31 (dd, J=11.9, 1.9 Hz, 1H), 7.27-7.17 (m, 2H), 7.15 (t, J=8.6 Hz, 1H), 4.26 (q, 2H), 4.08-3.95 (m, 2H), 3.78 (s, 3H), 3.38 (s, 2H), 3.33-3.27 (m, 1H), 3.18-3.07 (m, 1H), 247 (d, J=1.0 Hz, 3H), 2.40-2.27 (m, 1H), 2.20 (s, 6H), 1.31 (t, J=7.1 Hz, 3H), 1.05 (d, J=6.7 Hz, 3H).

Step F: 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-methylpropyl)-1,3-thiazole-4-carboxylic acid To a solution of the product of Step E (110 mg, 0.16 mmol, 1 eq) in 1,4-dioxane (15 mL) was added lithium hydroxide monohydrate (68.5 mg, 1.63 mmol, 10 eq) and the mixture was heated at reflux for 16 h. The reaction was concentrated in vacuo and the residue was triturated with water (5 mL), filtered, washed with water and dried under vacuum to afford the desired product as a yellow solid (91.2 mg, 0.14 mmol, 87%) [as a lithium salt].

HRMS-ESI (m/z) [M+H]+ calcd for $C_{32}H_{33}FN_7O_3S_2$: 646.2065, found 646.2091.

Example 117: 2-[[6-(1,3-Benzothiazol-2-ylamino)-5-methyl-pyridazin-3-yl]-(2,3-dihydroxypropyl)amino]-5-[3-[2-fluoro-4-[3-(methylamino)prop-1-ynyl]phenoxy]propyl]thiazole-4-carboxylic acid

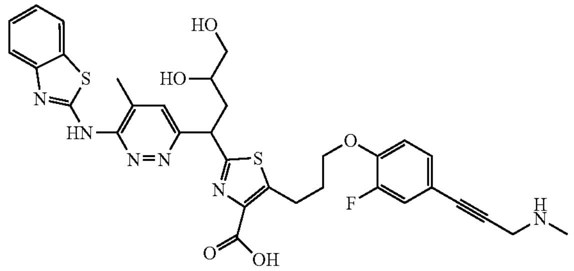 [SMILES: CNCC#Cc1ccc(OCCCc2sc(C(CC(O)CO)c3cc(C)c(Nc4nc5ccccc5s4)nn3)nc2C(=O)O)c(F)c1]

Step A: methyl 5-[3-[4-[3-[tert-butoxycarbonyl(methyl)amino]prop-1-ynyl]-2-fluoro-phenoxy]propyl]-2-[(2,2-dimethyl-1,3-dioxolan-4-yl)methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 280 mg of Preparation 3o (0.47 mmol, 1 eq.) and 193 mg of Preparation 4a (0.47 mmol, 1 eq.) as the appropriate halide, 400 mg (88%) of the desired product was obtained.

$^1$H NMR (500 MHz, DMSO-$d_6$) δ ppm 7.84 (d, 1H), 7.80 (s, 1H), 7.47 (d, 1H), 7.44 (td, 1H), 7.32 (brd., 1H), 7.26 (td, 1H), 7.22 (d, 1H), 7.16 (t, 1H), 5.87 (s, 2H), 4.55 (m, 2H), 4.53 (m, 1H), 4.20 (br., 2H), 4.15 (t, 2H), 4.07/3.83 (dd+dd, 2H), 3.77 (s, 3H), 3.71 (t, 2H), 3.27 (t, 2H), 2.84 (br., 3H), 2.43 (s, 3H), 2.13 (m, 2H), 1.40 (s, 9H), 1.27/1.20 (s+s, 6H), 0.92 (t, 2H), −0.12 (s, 9H); $^{13}$C NMR (125 MHz, DMSO-$d_6$) δ ppm 129.1, 127.2, 123.2, 123.2, 119.3, 118.9, 115.5, 112.0, 109.2, 74.0, 72.8, 68.4, 66.9, 66.7, 52.0, 49.6, 38.5, 33.8, 30.9, 28.5, 26.6/25.7, 23.1, 17.8, 17.7, −1.0; HRMS-ESI (m/z): $[M+H]^+$ calcd for $C_{47}H_{61}FN_7O_8S_2Si$: 962.3771, found 962.3767.

Step B: 2-[[6-(1,3-benzothiazol-2-ylamino)-5-methyl-pyridazin-3-yl]-(2,3-dihydroxypropyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{32}H_{33}FN_7O_5S_2$: 678.1963, found 678.1965.

Example 118: 2-[[6-(1,3-Benzothiazol-2-ylamino)-5-methyl-pyridazin-3-yl]-(3-hydroxy-2-methoxy-propyl)amino]-5-[3-[2-fluoro-4-[3-(methylamino)prop-1-ynyl]phenoxy]propyl]thiazole-4-carboxylic acid

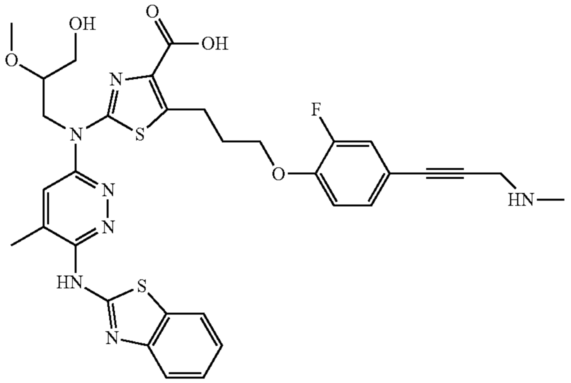

Step A: methyl 5-[3-[4-[3-[tert-butoxycarbonyl(methyl)amino]prop-1-ynyl]-2-fluoro-phenoxy]propyl]-2-[[3-[tert-butyl(dimethyl)silyl]oxy-2-methoxy-propyl]-5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 400 mg of Preparation 3q (0.59 mmol, 1 eq.) and 240 mg of Preparation 4a (0.59 mmol, 1 eq.) as the appropriate halide, 534 mg (86%) of the desired product was obtained.

$^1$H NMR (500 MHz, DMSO-$d_6$) δ ppm 7.84 (dm, 1H), 7.72 (s, 1H), 7.47 (dm, 1H), 7.44 (m, 1H), 7.31 (brd, 1H), 7.25 (m, 1H), 7.21 (dd, 1H), 7.16 (t, 1H), 5.88/5.85 (d+d, 2H), 4.48/4.35 (dd+dd, 2H), 4.20 (brs, 2H), 4.15 (t, 2H), 3.77/3.66 (dd+dd, 2H), 3.76 (m, 1H), 3.76 (s, 3H), 3.71 (m, 2H), 3.27 (m, 2H), 3.23 (s, 3H), 2.84 (brs, 3H), 2.42 (s, 3H), 2.12 (m, 2H), 1.40 (s, 9H), 0.92 (m, 2H), 0.85 (s, 9H), 0.04 (s, 3H), 0.03 (s, 3H), −0.12 (s, 9H); $^{13}$C NMR (125 MHz, DMSO-$d_6$) δ ppm 129.1, 127.2, 123.4, 123.2, 119.3, 118.6, 115.5, 112.0, 79.4, 72.8, 68.4, 66.7, 63.1, 58.2, 51.8, 48.4, 38.3, 33.7, 30.9, 28.4, 26.2, 23.0, 18.0, 17.7, −1.6, −5.1, −5.1: HRMS-ESI (m/z): $[M+H]^+$ calcd for $C_{51}H_{73}FN_7O_8S_2Si_2$: 1050.4479, found 1050.4469.

Step B: 2-[[6-(1,3-benzothiazol-2-ylamino)-5-methyl-pyridazin-3-yl]-(3-hydroxy-2-methoxy-propyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{33}H_{35}FN_7O_5S_2$: 692.2120, found 692.2117.

Example 119: 2-[[6-(1,3-Benzothiazol-2-ylamino)-5-methyl-pyridazin-3-yl]-(4,5-dihydroxypentyl)amino]-5-[3-[2-fluoro-4-[3-(methylamino)prop-1-ynyl]phenoxy]propyl]thiazole-4-carboxylic acid

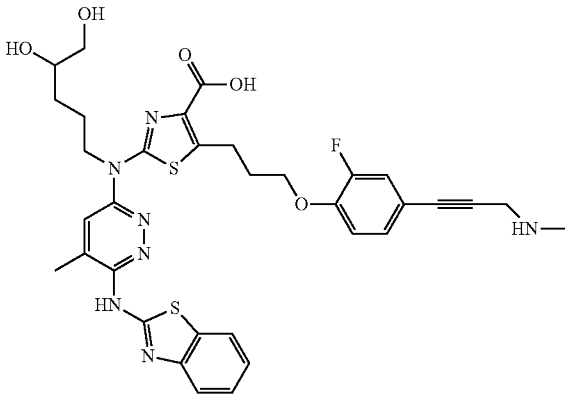 [SMILES: CNCC#Cc1ccc(OCCCc2sc(N(CCCC(O)CO)c3cc(C)c(Nc4nc5ccccc5s4)nn3)nc2C(=O)O)c(F)c1]

Using Deprotection and Hydrolysis General Procedure starting from the product from Preparation 5a, Step A as the appropriate methyl ester, the desired product was obtained. HRMS-ESI (m/z): $[M+H]^+$ calcd for $C_{34}H_{37}FN_7O_5S_2$: 706.2276, found 706.2274.

Example 120: 2-[[6-(1,3-Benzothiazol-2-ylamino)-5-methyl-pyridazin-3-yl]-(3,4-dihydroxybutyl)amino]-5-[3-[2-fluoro-4-[3-[methyl(p-tolylsulfonyl)amino]prop-1-ynyl]phenoxy]propyl]thiazole-4-carboxylic acid

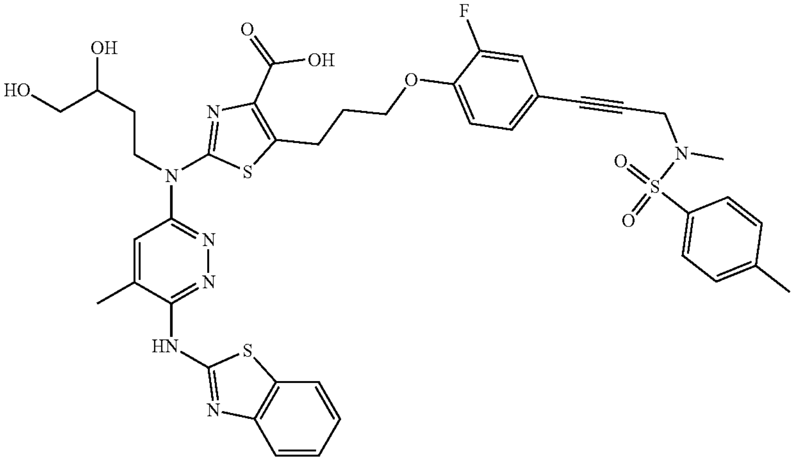 [SMILES: Cc1ccc(S(=O)(=O)N(C)CC#Cc2ccc(OCCCc3sc(N(CCC(O)CO)c4cc(C)c(Nc5nc6ccccc6s5)nn4)nc3C(=O)O)c(F)c2)cc1]

Step A: methyl 2-[2-(2,2-dimethyl-1,3-dioxolan-4-yl)ethyl-[5-methyl-6-[(Z)-[3-(2-trimethylsilylethoxymethyl)-1,3-benzothiazol-2-ylidene]amino]pyridazin-3-yl]amino]-5-[3-[2-fluoro-4-[3-[methyl(p-tolylsulfonyl)amino]prop-1-ynyl]phenoxy]propyl]thiazole-4-carboxylate Using Buchwald General Procedure II starting from 470 mg of Preparation 3k (0.71 mmol, 1 eq.) and 290 mg of Preparation 4a (0.71 mmol, 1 eq.) as the appropriate halide, 660 mg (90%) of the desired product was obtained.

Step B: 2-[[6-(1,3-benzothiazol-2-ylamino)-5-methyl-pyridazin-3-yl]-(3,4-dihydroxybutyl)amino]-5-[3-[2-fluoro-4-[3-[methyl(p-tolylsulfonyl)amino]prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{40}H_{41}FN_7O_7S_3$: 846.2208. found 846.2201.

Example 121: 2-[[6-(1,3-Benzothiazol-2-ylamino)-5-methyl-pyridazin-3-yl]-(3,4-dihydroxybutyl)amino]-5-[3-[2-fluoro-4-[3-[(4-methoxyphenyl)methyl-methyl-amino]prop-1-ynyl]phenoxy]propyl]thiazole-4-carboxylic acid

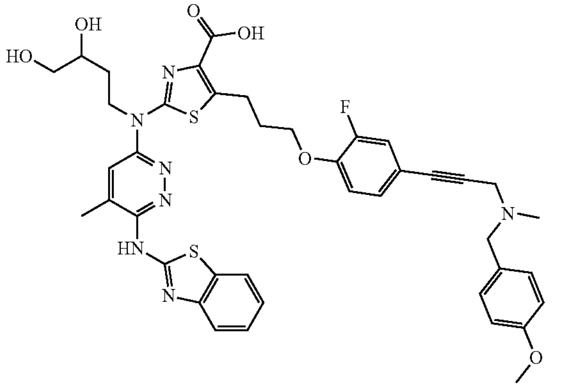 [SMILES: COc1ccc(CN(C)CC#Cc2ccc(OCCCc3sc(N(CCC(O)CO)c4cc(C)c(Nc5nc6ccccc6s5)nn4)nc3C(=O)O)c(F)c2)cc1]

Step A: methyl 2-[2-(2,2-dimethyl-1,3-dioxolan-4-yl)ethyl-[5-methyl-6-[(Z)-[3-(2-trimethylsilylethoxymethyl)-1,3-benzothiazol-2-ylidene]amino]pyridazin-3-yl]amino]-5-[3-[2-fluoro-4-[3-[(4-methoxyphenyl)methyl-methyl-amino]prop-1-ynyl]phenoxy]propyl]thiazole-4-carboxylate Using Buchwald General Procedure II starting from 625 mg of Preparation 3j (1 mmol, 1 eq.) and 407 mg of Preparation 4a (1 mmol, 1 eq.) as the appropriate halide, 550 mg (55%) of the desired product was obtained.

Step B: 2-[[6-(1,3-benzothiazol-2-ylamino)-5-methyl-pyridazin-3-yl]-(3,4-dihydroxybutyl)amino]-5-[3-[2-fluoro-4-[3-[(4-methoxyphenyl)methyl-methyl-amino]prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{41}H_{43}FN_7O_6S_2$: 812.2695, found 812.2674.

Example 122: 2-[[6-(1,3-Benzothiazol-2-ylamino)-5-methyl-pyridazin-3-yl]-(2,3-dihydroxypropyl)amino]-5-[3-[4-[3-(dimethylamino)prop-1-ynyl]-2-fluoro-phenoxy]propyl]thiazole-4-carboxylic acid

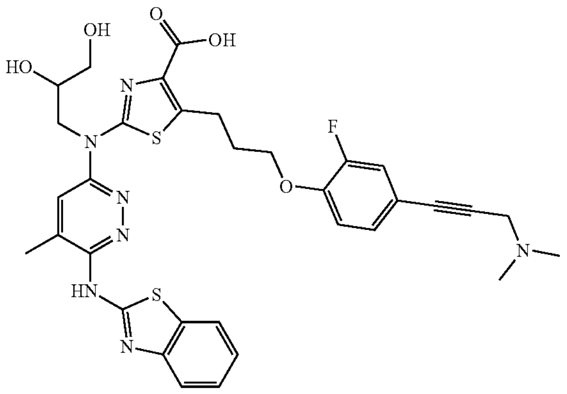

Step A: methyl 5-[3-[4-[3-(dimethylamino)prop-1-ynyl]-2-fluoro-phenoxy]propyl]-2-[(2,2-dimethyl-1,3-dioxolan-4-yl)methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 380 mg of Preparation 3p (0.75 mmol, 1 eq.) and 306 mg of Preparation 4a (0.75 mmol, 1 eq.) as the appropriate halide, 480 mg (72%) of the desired product was obtained.

$^1H$ NMR (500 MHz, DMSO-$d_6$) δ ppm 7.84 (dm, 1H), 7.78 (s, 1H), 7.47 (dm, 1H), 7.44 (m, 1H), 7.30 (dd, 1H), 7.26 (m, 1H), 7.21 (m, 1H), 7.15 (t, 1H), 5.86 (s, 2H), 4.57/4.53 (m+m, 2H), 4.52 (m, 1H), 4.15 (t, 2H), 4.07/3.83 (dd+dd, 2H) 3.77 (s, 3H), 3.71 (m, 2H), 3.38 (s, 2H), 3.27 (m, 2H), 2.43 (s, 3H), 2.20 (s, 6H), 2.13 (m, 2H), 1.27 (s, 3H), 1.20 (s, 3H), 0.92 (m, 2H), −0.12 (s, 9H); $^{13}C$ NMR (125 MHz, DMSO-$d_6$) δ ppm 163.1, 157.6, 156.8/151.7, 141.5, 137.6, 134.9, 128.9, 127.1, 123.4, 123.2, 119.2, 118.8, 115.4, 111.9, 85.1, 84.1, 73.9, 72.7, 68.3, 66.9, 66.6, 51.9, 49.6, 48.1, 44.2, 30.9, 26.6, 25.6, 23.0, 17.8, 17.7, −1.0; HRMS-ESI (m/z): $[M+H]^+$ calcd for $C_{43}H_{55}FN_7O_6S_2Si$: 876.3403, found 876.3408.

Step B: 2-[[6-(1,3-benzothiazol-2-ylamino)-5-methyl-pyridazin-3-yl]-(2,3-dihydroxypropyl)amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{33}H_{35}FN_7O_5S_2$: 692.2120, found 692.2117.

Example 123: 2-[[6-(1,3-Benzothiazol-2-ylamino)-5-methyl-pyridazin-3-yl]-(3,4-dihydroxybutyl)amino]-5-[3-[4-[3-(dimethylamino)prop-1-ynyl]-2-fluoro-phenoxy]propyl]thiazole-4-carboxylic acid

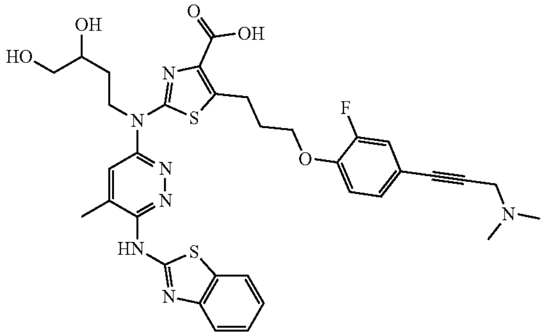 [SMILES: Cc1cc(N(CCC(O)CO)c2nc(C(=O)O)c(CCCOc3ccc(C#CCN(C)C)cc3F)s2)nnc1Nc1nc2ccccc2s1]

Step A: methyl 5-[3-[4-[3-(dimethylamino)prop-1-ynyl]-2-fluoro-phenoxy]propyl]-2-[2-(2,2-dimethyl-1,3-dioxolan-4-yl)ethyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 350 mg of Preparation 3i (0.67 mmol, 1 eq.) and 275 mg of Preparation 4a (0.67 mmol, 1 eq.) as the appropriate halide, 510 mg (85%) of the desired product was obtained.

Step B: 2-[[6-(1,3-benzothiazol-2-ylamino)-5-methylpyridazin-3-yl]-(3,4-dihydroxybutyl)amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{34}H_{37}FN_7O_5S_2$: 706.2276, found 706.2270.

Example 124: 2-[[6-(1,3-Benzothiazol-2-ylamino)-5-methyl-pyridazin-3-yl]-[5-[2-(dimethylamino)ethyl-methyl-amino]-4-hydroxy-pentyl]amino]-5-[3-[4-[3-(dimethylamino)prop-1-ynyl]-2-fluoro-phenoxy]propyl]thiazole-4-carboxylic acid

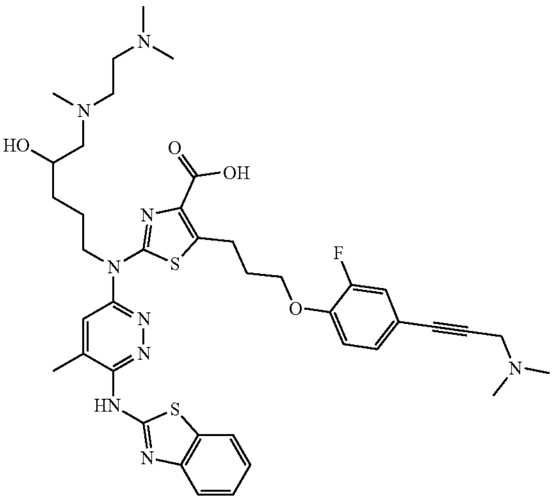 [SMILES: Cc1cc(N(CCCC(O)CN(C)CCN(C)C)c2nc(C(=O)O)c(CCCOc3ccc(C#CCN(C)C)cc3F)s2)nnc1Nc1nc2ccccc2s1]

Step A: methyl 2-[[4-[tert-butyl(diphenyl)silyl]oxy-5-[2-(dimethylamino)ethyl-methyl-amino]pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with tosylate General Procedure starting from Preparation 5b and N,N',N'-trimethylethane-1,2-diamine as the appropriate amine, the desired product was obtained.

Step B: 2-[[6-(1,3-benzothiazol-2-ylamino)-5-methyl-pyridazin-3-yl]-[5-[2-(dimethylamino)ethyl-methyl-amino]-4-hydroxy-pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{40}H_{51}FN_9O_4S_2$: 804.3484, found 804.3487.

Example 125: 2-[[6-(1,3-Benzothiazol-2-ylamino)-5-methyl-pyridazin-3-yl]-(5-hydroxypentyl)amino]thiazole-4-carboxylic acid

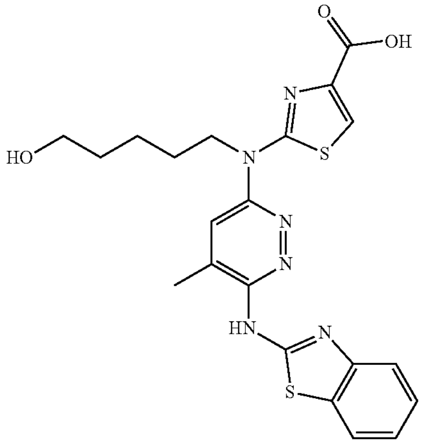 [SMILES: Cc1cc(N(CCCCCO)c2nc(C(=O)O)cs2)nnc1Nc1nc2ccccc2s1]

Step A: methyl 2-[tert-butoxycarbonyl-[5-[tert-butyl(dimethyl)silyl]oxypentyl]amino]thiazole-4-carboxylate Using Mitsunobu General Procedure starting from methyl 2-(tert-butoxycarbonylamino)thiazole-4-carboxylate and 5-[tert-butyl(dimethyl)silyl]oxypentan-1-ol as starting materials in THF at rt for 2 h, 565 mg (82%) of the desired product was obtained.

$^1H$ NMR (400 MHz, DMSO-$d_6$) δ ppm 8.08 (s, 1H), 4.05 (t, 2H), 3.79 (s, 3H), 3.56 (t, 2H), 1.65 (m, 2H), 1.52 (s, 9H), 1.48 (m, 2H), 1.31 (m, 2H), 0.83 (s, 9H), −0.02 (s, 6H).

Step B: methyl 2-[5-[tert-butyl(dimethyl)silyl]oxypentylamino]thiazole-4-carboxylate Using Deprotection with HFIP General Procedure starting from the product from Step A as the appropriate carbamate, 484 mg (113%) of the desired product was obtained.

$^1$H NMR (400 MHz, DMSO-$d_6$) δ ppm 7.78 (t, 1H), 7.50 (s, 1H), 3.57 (t, 2H), 3.73 (s, 3H), 3.20 (q, 2H), 1.59-1.42 (m, 4H), 1.40-1.29 (m, 2H), 0.85 (s, 9H), 0.02 (s, 6H).

Step C: methyl 2-[5-[tert-butyl(dimethyl)silyl]oxypentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a as the appropriate halide, 535 mg (61%) of the desired product was obtained.

$^1$H NMR (400 MHz, DMSO-$d_6$) δ ppm 7.97 (s, 1H), 7.84 (d, 1H), 7.70 (s, 1H), 7.46 (t, 1H), 7.43 (t, 1H), 7.25 (dt, 1H), 5.86 (s, 2H), 4.45 (t, 2H), 3.81 (s, 3H), 3.72 (t, 2H), 3.55 (t, 2H), 2.46 (s, 3H), 1.72 (m, 2H), 1.50 (m, 2H), 1.38 (m, 2H), 0.92 (t, 2H), 0.79 (s, 9H), −0.04 (s, 6H), −0.11 (s, 9H).

Step D: 2-[[6-(1,3-benzothiazol-2-ylamino)-5-methyl-pyridazin-3-yl]-(5-hydroxypentyl)amino]thiazole-4-carboxylic acid Using Deprotection and Hydrolysis General Procedure followed by repurification via reverse phase preparative chromatography (C18, 25 mM $NH_4HCO_3$ water:MeCN) starting from the product from Step C, the desired product was obtained.

HRMS-ESI (m/z): $[M+H]^+$ calcd for $C_{21}H_{23}N_6O_3S_2$: 471.1273, found: 471.1271.

Example 126: 2-[[6-(1,3-Benzothiazol-2-ylamino)-5-methyl-pyridazin-3-yl]-(3-hydroxypropyl)amino]-5-[3-[4-[3-(dimethylamino)prop-1-ynyl]-2-fluoro-phenoxy]propyl]thiazole-4-carboxylic acid

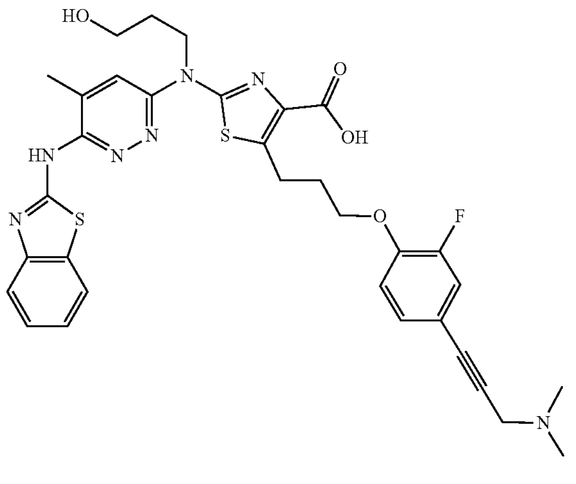 [SMILES: Cc1cc(N(CCCO)c2nc(C(=O)O)c(CCCOc3ccc(C#CCN(C)C)cc3F)s2)nnc1Nc1nc2ccccc2s1]

Step A: ethyl 3-bromo-6-chloro-2-oxo-hexanoate

To 2 g of ethyl 6-chloro-2-oxo-hexanoate (10.4 mmol, 1 eq.) in 20 mL of $CCl_4$ was added 0.6 mL of bromine (11.5 mmol, 1.1 eq.) dropwise and the mixture was stirred at rt for 1 h. After pouring the mixture into 50 mL of a 1 M aqueous solution $Na_2S_2O_3$, it was extracted with 2×50 mL of ethyl acetate and the combined organic layers were washed with brine, dried, concentrated, and purified by silica gel chromatography using petroleum ether and EtOAc as eluents to give 2.05 g (73%) of the desired product.

$^1$H NMR (400 MHz, DMSO-$d_6$) δ ppm 5.25 (dd, 1H) 4.30 (q, 2H), 3.71 (t, 2H), 2.21-1.80 (m, 4H), 1.29 (t, 3H); GC/LR-EI: $[M]^+$=270.

Step B: 3-[tert-butyl(dimethyl)silyl]oxypropan-1-amine

To 8.25 g of 3-aminopropan-1-ol (110 mmol, 1 eq.), 23 mL of N,N-diethylethanamine (170 mmol, 1.5 eq.), and 30 mg of imidazole (0.44 mmol, 0.004 eq.) in 200 mL of DCM was added 18.2 g of tert-butyldimethylsilyl chloride (150 mmol, 1.4 eq.) and the mixture was stirred at rt for 15 h. After pouring the reaction mixture onto 250 mL of water and extracting with 2×200 mL of DCM, the combined organic layers were washed with 50 mL of water and 50 mL of brine, dried, and concentrated to give 20.9 g (100%) of the desired product.

$^1$H NMR (400 MHz, DMSO-$d_6$) δ ppm 3.60 (t, 2H), 2.55 (t, 2H), 1.50 (quint, 2H), 0.80 (s, 9H), 0.10 (s, 6H); IR: 3000-2900, 1100, 830-770.

Step C: 3-[tert-butyl(dimethyl)silyl]oxypropylthiourea

To 5.3 g of 9-fluorenylmethoxycarbonyl isothiocyanate (18.9 mmol, 1 eq.) and 6.4 mL of DIPEA (37.6 mmol, 2 eq.) in 50 mL of DCM was added dropwise a solution of 3.5 g of the product from Step B (18.5 mmol, 1 eq.) in 10 mL of DCM and the mixture was stirred at rt for 2 h. After concentration, the crude product was purified by silica gel chromatography using petroleum ether and EtOAc as eluents to give 3.87 g (80%) of the desired product.

$^1$H NMR (400 MHz, DMSO-$d_6$) δ ppm 7.49 (brs, 1H), 6.83 (brs, 1H), 7.21 (s, 1H), 3.57 (t, 2H), 3.34/3.02 (m, 2H), 1.61 (m, 2H), 0.83 (s, 9H), 0.02 (s, 6H); IR: 3275, 1619.

Step D: ethyl 2-[3-[tert-butyl(dimethyl)silyl]oxypropylamino]-5-(3-chloropropyl)thiazole-4-carboxylate A solution of 7.4 g of the product from Step C (29.7 mmol, 1 eq.), 8.1 g of the product from Step A (30 mmol, 1 eq.) and 8.2 mL of N,N-diethylethanamine (59.4 mmol, 2 eq.) in 206 mL of ethanol was heated to reflux for 18 h. After concentration, the crude residue was taken up in DCM, washed with water, dried, concentrated, and purified by silica gel chromatography using petroleum ether and EtOAc as eluents to give 10.1 g (81%) of the desired product.

$^1$H NMR (400 MHz, DMSO-$d_6$) δ ppm 7.56 (t, 1H), 4.17 (q, 2H), 3.62 (2t, 4H), 3.18 (q, 2H), 3.06 (t, 2H), 1.95 (m, 2H), 1.69 (m, 2H), 1.23 (t, 3H), 0.83 (s, 9H), 0.01 (s, 6H); IR: 3197, 1716, 1586.

Step E: ethyl 2-[3-[tert-butyl(dimethyl)silyl]oxypropyl-(6-chloropyridazin-3-yl)amino]-5-(3-chloropropyl)thiazole-4-carboxylate To 10 g of the product from Step D (23.7 mmol, 1 eq.) and 5.8 g of 3,6-dichloro-4-methylpyridazine (35.6 mmol, 1.5 eq.) in 120 mL of THF was added 2.1 g of sodium hydride (52.1 mmol, 2.2 eq.) portion wise at 50° C. The chilled mixture was poured into ice and extracted with 2×200 mL of ethyl acetate. The combined organic layers were washed with brine, dried, concentrated, and purified by silica gel chromatography using petroleum ether and EtOAc as eluents to give 4.3 g (32%) of the desired product.

$^1$H NMR (400 MHz, DMSO-$d_6$) δ ppm 7.76 (s, 1H), 4.39 (t, 2H), 4.26 (q, 2H), 3.68 (m, 4H), 3.19 (t, 2H), 2.39 (s, 3H), 2.06 (m, 2H), 1.89 (m, 2H), 1.29 (t, 3H), 0.83 (s, 9H), 0.01 (s, 6H); IR: 1704, 1592, 1195, 1095+1066, 649.

Step F: ethyl 2-[3-[tert-butyl(dimethyl)silyl]oxypropyl-(6-chloro-5-methyl-pyridazin-3-yl)amino]-5-(3-iodopropyl)thiazole-4-carboxylate The mixture of 4.6 g of the product from Step E (8.42 mmol, 1 eq.) and 12.6 g of sodium iodide (84.2 mmol, 10 eq.) in 58 mL of acetone was kept at 60° C. for 18 h. After concentration, the residue was taken up in ethyl acetate, washed with water and brine, dried, and concentrated to give the desired product, which was used without further purification in the next step.

$^1$H NMR (400 MHz, DMSO-$d_6$) δ ppm 7.78 (s, 1H), 4.41 (t, 2H), 4.29 (q, 2H), 3.71 (t, 2H), 3.31 (t, 2H), 3.17 (t, 2H), 2.41 (s, 3H), 2.12 (m, 2H), 1.91 (m, 2H), 1.32 (t, 3H), 0.84 (s, 9H), 0.02 (s, 6H).

Step G: ethyl 2-[3-[tert-butyl(dimethyl)silyl]oxypropyl-(6-chloro-5-methyl-pyridazin-3-yl)amino]-5-[3-[4-[3-(dimethylamino)prop-1-ynyl]-2-fluoro-phenoxy]propyl]thiazole-4-carboxylate The mixture of 800 mg of the product from Step F (1.25 mmol, 1 eq.), 821 mg of cesium carbonate (2.5 mmol, 2 eq.) and 290 mg of Preparation 6b (1.5 mmol, 1.2 eq.) in 6 mL of MeCN was heated to reflux for 2 h. After dilution with 100 mL of ethyl acetate, the organic layer was washed with 50 mL of water and 50 mL of brine, dried, concentrated, and was purified by silica gel chromatography using DCM and MeOH (containing 7 N $NH_3$) as eluents to give 500 mg (57%) of the desired product.

$^1$H NMR (400 MHz, DMSO-$d_6$) δ ppm 7.77 (m, 1H), 7.27 (dd, 1H), 7.18 (d, 1H), 7.11 (t, 1H), 4.40 (t, 2H), 4.23 (q, 2H), 4.11 (t, 2H), 3.69 (t, 2H), 3.40 (s, 2H), 3.24 (t, 2H), 2.40 (s, 3H), 2.21 (s, 6H), 2.10 (m, 2H), 1.89 (m, 2H), 1.27 (t, 3H), 0.83 (s, 9H), 0.00 (s, 6H); IR: 3600-3100, 2237, 1716, 835, 777.

Step H: ethyl 2-[[6-(1,3-benzothiazol-2-ylamino)-5-methyl-pyridazin-3-yl]-(3-hydroxypropyl)amino]-5-[3-[4-[3-(dimethylamino)prop-1-ynyl]-2-fluoro-phenoxy]propyl]thiazole-4-carboxylate The mixture of 100 mg of the product from Step G (0.142 mmol, 1 eq.), 28 mg of 1,3-benzothiazol-2-amine (0.185 mmol, 1.3 eq.), 10 mg of 4,5-bis(diphenylphosphino)-9,9-dimethylxanthene (0.017 mmol, 0.12 eq.), 8 mg of tris(dibenzylideneacetone)dipalladium(0) (8.52 μmol, 0.06 eq.), and 72 μL of DIPEA (0.426 mmol, 3 eq.) in 0.7 mL of N-methyl-2-pyrrolidone was kept at 120° C. for 18 h. After pouring the mixture into 50 mL of DCM, the organic layer was washed with 10 mL of water and 10 mL of a saturated aqueous solution of lithium chloride, dried, concentrated, and purified by silica gel chromatography using DCM and MeOH (containing 7 N $NH_3$) as eluents to afford 40 mg (40%) of the desired product.

$^1$H NMR (400 MHz, DMSO-$d_6$) δ ppm 11.54 (brs, 1H), 7.91 (d, 1H), 7.69 (s, 1H), 7.53 (d, 1H), 7.39 (t, 1H), 7.30 (dd, 1H), 7.22 (dd, 1H), 7.21 (dd, 1H), 7.16 (t, 1H), 4.72 (t, 1H), 4.41 (t, 2H), 4.25 (q, 2H), 4.16 (t, 2H), 3.48 (q, 2H), 3.39 (s, 2H), 3.27 (t, 2H), 2.46 (s, 3H), 2.2 (s, 6H), 2.13 (m, 2H), 1.87 (m, 2H), 1.29 (t, 3H); IR: 3414, 3400-2200, 1709, 1602, 1149/1087.

Step I: 2-[[6-(1,3-benzothiazol-2-ylamino)-5-methyl-pyridazin-3-yl]-(3-hydroxypropyl)amino]-5-[3-[4-[3-(dimethylamino)prop-1-ynyl]-2-fluoro-phenoxy]propyl]thiazole-4-carboxylic acid The mixture of the product from Step H and LiOH×$H_2O$ (4 eq.) in 1,4-dioxane and water was stirred at rt for 3 h. After the addition of an extra 1 eq. of LiOH×$H_2O$ in water, the reaction was stirred at rt for 18 h. After the slow addition of 2 N solution of HCl, the reaction mixture was concentrated and purified via reverse phase preparative chromatography (0.2 M $NH_4CO_3$ in water:MeCN) to give the desired product.

HRMS-ESI (m/z): $[M+H]^+$ calcd for $C_{33}H_{35}FN_7O_4S_2$: 676.2170 found: 676.2169.

Example 127: 2-[[6-(1,3-Benzothiazol-2-ylamino)-5-methyl-pyridazin-3-yl]-(3-hydroxypropyl)amino]-5-[3-[2-fluoro-4-[3-(methylamino)prop-1-ynyl]phenoxy]propyl]thiazole-4-carboxylic acid

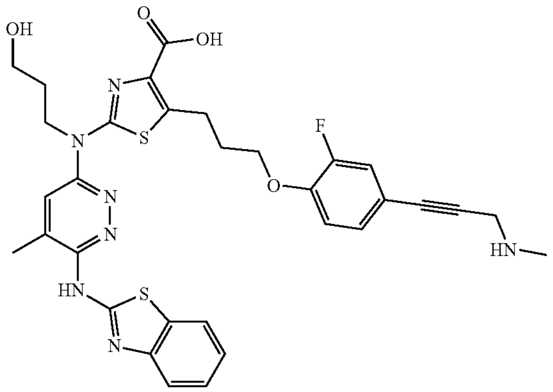 [SMILES: CNCC#Cc1ccc(OCCCc2sc(N(CCCO)c3cc(C)c(Nc4nc5ccccc5s4)nn3)nc2C(=O)O)c(F)c1]

Step A: methyl 5-[3-[4-[3-[tert-butoxycarbonyl(methyl)amino]prop-1-ynyl]-2-fluoro-phenoxy]propyl]-2-[3-[tert-butyl(dimethyl)silyl]oxypropyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 300 mg of Preparation 3n (0.46 mmol, 1 eq.) and 187 mg of Preparation 4a (0.46 mmol, 1 eq.) as the appropriate halide, 395 mg (83%) of the desired product was obtained.

$^1$H NMR (500 MHz, DMSO-$d_6$) δ ppm 7.82 (dd, 1H), 7.60 (s, 1H), 7.44 (m, 1H), 7.44 (dd, 1H), 7.31 (dd, 1H), 7.24 (m, 1H), 7.20 (m, 1H), 7.15 (t, 1H), 5.84 (s, 2H), 4.39 (t, 2H), 4.20 (s, 2H), 4.14 (t, 2H), 3.76 (s, 3H), 3.70 (t, 2H), 3.70 (t, 2H), 3.25 (t, 2H), 2.84 (s, 3H), 2.42 (s, 3H), 2.11 (m, 2H), 1.91 (m, 2H), 1.40 (s, 9H), 0.91 (t, 2H), 0.85 (s, 9H), 0.01 (s, 6H), −0.12 (s, 9H): $^{13}$C NMR (125 MHz, DMSO-$d_6$) δ ppm 162.2, 147.5, 137.6, 129.1, 127.2, 123.4, 123.2, 119.3, 117.5, 115.4, 112.0, 79.7, 72.8, 68.4, 66.7, 60.5, 51.9, 44.6, 38.1, 318, 30.9, 30.4, 28.6, 26.3, 23.1, 17.9, 17.8, −0.9, −5.0; HRMS-ESI (m/z): $[M+H]^+$ calcd for $C_{50}H_{71}FN_7O_7S_2Si_2$: 1020.4373, found 1020.4306.

Step B: 2-[[6-(1,3-benzothiazol-2-ylamino)-5-methyl-pyridazin-3-yl]-(3-hydroxypropyl)amino]-5-[3-[2-fluoro-4-[3-(methylamino)prop-1-ynyl]phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{32}H_{33}FN_7O_4S_2$: 662.2014, found 662.2016.

Example 128: 2-[[6-(1,3-Benzothiazol-2-ylamino)-5-methyl-pyridazin-3-yl]-5-hydroxypentyl)amino]-5-[3-[2-fluoro-4-[3-(methylamino)prop-1-ynyl]phenoxy]propyl]thiazole-4-carboxylic acid

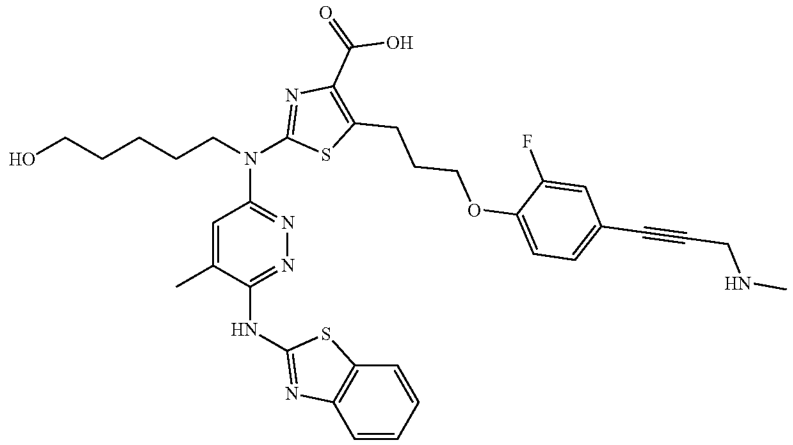 [SMILES: CNCC#Cc1ccc(OCCCc2sc(N(CCCCCO)c3cc(C)c(Nc4nc5ccccc5s4)nn3)nc2C(=O)O)c(F)c1]

Using Deprotection and Hydrolysis General Procedure starting from the appropriate methyl ester Preparation 5e, Step A, the desired product was obtained.

HRMS-ESI (m/z): $[M+H]^+$ calcd for $C_{34}H_{37}FN_7O_4S_2$: 690.2327, found 690.2318.

Example 130: 3-[3-[4-[3-[2-[[6-(1,3-Benzothiazol-2-ylamino)-5-methyl-pyridazin-3-yl]-(4-hydroxybutyl)amino]-4-carboxy-thiazol-5-yl]propoxy]-3-fluoro-phenyl]prop-2-ynyl-dimethyl-ammonio]propane-1-sulfonate

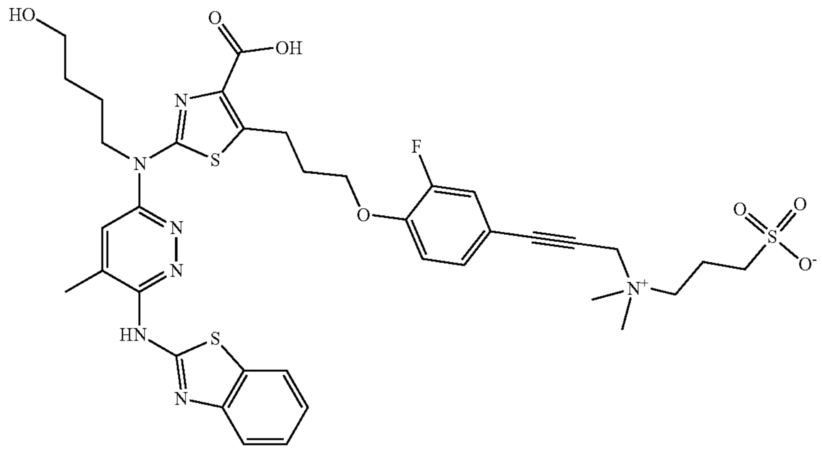 [SMILES: Cc1cc(N(CCCCO)c2nc(C(=O)O)c(CCCOc3ccc(C#CC[N+](C)(C)CCCS(=O)(=O)[O-])cc3F)s2)nnc1Nc1nc2ccccc2s1]

Step A: 3-[3-[4-[3-[2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]-4-methoxycarbonyl-thiazol-5-yl]propoxy]-3-fluoro-phenyl]prop-2-ynyl-dimethyl-ammonio]propane-1-sulfonate To a suspension of 660 mg of Preparation 5d, Step A (0.7 mmol, 1 eq.) in 5 mL dry acetonitrile 257 mg of oxathiolane 2,2-dioxide (2.1 mmol, 3 eq.) was added in one portion. The resulting mixture was stirred overnight at rt. The crude product was purified by flash column chromatography to obtain 550 mg (75%) of the desired product.

$^1$H NMR (500 MHz, DMSO-$d_6$) δ ppm 7.83-7.20 (m, 4H), 7.62 (s, 1H), 7.58 (dd, 1H), 7.41 (m, 1H), 7.22 (t, 1H), 5.83 (s, 2H), 4.55 (s, 2H), 4.40 (t, 2H), 4.17 (t, 2H), 3.77 (s, 3H), 3.70 (t, 2H), 3.60 (t, 2H), 3.57 (t, 2H), 3.25 (t, 2H), 3.12 (s, 6H), 2.52 (t, 2H), 2.42 (s, 3H), 2.12 (m, 2H), 2.12 (m, 2H), 2.05 (m, 2H), 1.73 (m, 2H), 0.90 (t, 2H), 0.78 (s, 9H), −0.03 (s, 6H), −0.13 (s, 9H); $^{13}$C NMR (125 MHz, DMSO-$d_6$) δ ppm 163.2, 148.5, 137.5, 129.8, 120.0, 117.5, 115.3, 89.6, 72.8, 68.5, 66.7, 63.1, 62.5, 54.6, 51.9, 50.3, 48.2, 46.5, 31.0, 29.7, 26.2, 23.7, 23.2, 19.6, 17.9, 17.7, −1.0, −4.9; HRMS-ESI (m/z): $[M+2H]^{2+}$ calcd for $C_{50}H_{74}FN_7O_8S_3Si_2$: 535.7136, found 535.7136.

Step B: 3-[3-[4-[3-[2-[[6-(1,3-benzothiazol-2-ylamino)-5-methyl-pyradazin-3-yl]-(4-hydroxybutyl)amino]-4-carboxy-thiazol-5-yl]propoxy]-3-fluoro-phenyl]prop-2-ynyl-dimethyl-ammonio]propane-1-sulfonate Using Deprotection and Hydrolysis General Procedure starting from the product from Step A as the appropriate methyl ester, the desired product was obtained.

HRMS-ESI (m/z): $[M+H]^+$ calcd for $C_{37}H_{43}FN_7O_7S_3$: 812.2365, found 812.2357.

Example 131: 2-[[6-(1,3-Benzothiazol-2-ylamino)-5-methyl-pyridazin-3-yl]-(4-hydroxy-5-morpholino-pentyl)amino]thiazole-4-carboxylic acid

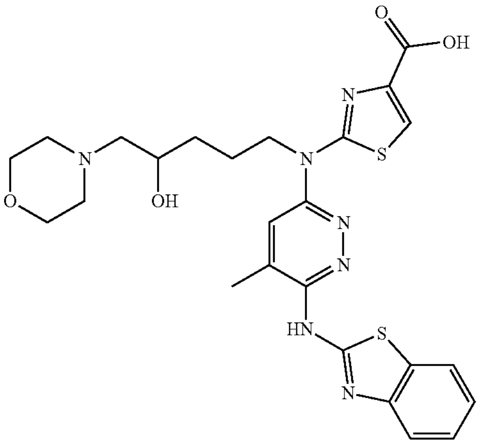 [SMILES: Cc1cc(N(CCCC(O)CN2CCOCC2)c2nc(C(=O)O)cs2)nnc1Nc1nc2ccccc2s1]

Step A: methyl 2-[tert-butoxycarbonyl-[4-[tert-butyl(dimethyl)silyl]oxy-5-morpholino-pentyl]amino]thiazole-4-carboxylate Using Mitsunobu General Procedure starting from 639 mg of methyl 2-(tert-butoxycarbonylamino)thiazole-4-carboxylate (2.47 mmol, 1.5 eq.) and 500 mg of Preparation 2e (1.65 mmol, 1 eq.) as the appropriate alcohol, 730 mg (81%) of the desired product was obtained.

$^1$H NMR (400 MHz, DMSO-$d_6$) δ ppm 8.08 (s, 1H), 4.09-4.03 (m, 2H), 3.79 (s+m, 4H), 3.51 (t, 4H), 2.39-2.28 (m, 4H), 2.21 (ddd, 2H), 1.85-1.73 (m, 1H), 1.70-1.59 (m, 1H), 1.53 (s+m, 10H), 1.39-1.28 (m, 1H), 0.79 (s, 9H), 0.02 (s, 3H), −0.01 (s, 3H); $^{13}$C NMR (100 MHz, DMSO-$d_6$) 160.3, 140.6, 124.2, 71.2, 68.9, 66.2, 64.7, 59.8, 54.2, 51.8, 46.8, 32.3, 27.6, 25.7, 23.2, 21.8, 21.5, 20.8, 17.7, 14.1, −4.3, −4.9; LC-MS-ESI (m/z): $[M+H]^+$ calcd for $C_{25}H_{46}N_3O_6SSi$: 544.3, found 544.3.

Step B: methyl 2-[[4-[tert-butyl(dimethyl)silyl]oxy-5-morpholino-pentyl]amino]thiazole-4-carboxylate Using Deprotection with HFIP General Procedure starting from 304 mg of the product from Step A (0.56 mmol) as the appropriate carbamate, 231 mg (93%) of the desired product was obtained.

$^1$H NMR (400 MHz, DMSO-$d_6$) δ ppm 7.81 (t, 1H), 7.49 (s, 1H), 3.79 (brs, 1H), 3.73 (s, 3H), 3.53 (t, 4H), 3.21 (q, 2H), 2.42-2.23 (m, 4H), 2.23 (ddd, 2H), 1.69-1.34 (m, 4H), 0.84 (s, 9H), 0.05 (s, 3H), 0.03 (s, 3H); $^{13}$C NMR (100 MHz, DMSO-$d_6$) 168.3, 161.6, 142.2, 116.3, 66.2, 65.2, 59.8, 54.3, 51.5, 44.5, 32.7, 25.8, 24.5, 17.8, 4.2, −4.8; LC-MS-ESI (m/z): $[M+H]^+$ calcd for $C_{20}H_{38}N_3O_4SSi$: 444.2, found 444.3.

Step C: methyl 2-[[4-[tert-butyl(dimethyl)silyl]oxy-5-morpholino-pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 231 mg of the product from Step B (0.52 mmol, 1 eq.) and 315 mg of Preparation 4a (0.77 mmol, 1.5 eq.) as the appropriate halide, 344 mg (81%) of the desired product was obtained.

$^1$H NMR (500 MHz, DMSO-$d_6$) δ ppm 7.97 (s, 1H), 7.85-7.23 (4H), 7.69 (s, 1H), 5.86 (d, 2H), 4.49 (t, 2H), 3.81 (m, 1H), 3.81 (s, 3H), 3.71 (t, 2H), 3.50-2.13 (8H), 2.45 (s, 3H), 2.20 (m, 2H), 1.83-1.73 (m+m, 2H), 1.56-1.41 (m+m, 2H), 0.91 (t, 2H), 0.75 (s, 9H), 0.01-(−0.05)(s+s, 6H), −0.12 (s, 9H); $^{13}$C NMR (125 MHz, DMSO-$d_6$) δ ppm 162.3, 160.8, 157.6, 155.3, 123.1, 117.9, 72.9, 69.0, 66.7, 65.4, 52.3, 47.1, 32.4, 26.2, 22.9, 17.9, 17.8, −1.0, −3.8, −4.5; HRMS-ESI (m/z): $[M+H]^+$ calcd for $C_{38}H_{60}N_7O_5S_2Si_2$: 814.3630, found 814.3629.

Step D: 2-[[6-(1,3-benzothiazol-2-ylamino)-5-methyl-pyridazin-3-yl]-(4-hydroxy-5-morpholino-pentyl)amino]thiazole-4-carboxylic acid Using Deprotection and Hydrolysis General Procedure followed by purification via reverse phase preparative chromatography (C18, 25 mM $NH_4HCO_3$ in water:MeCN) starting from the product from Step C, the desired product was obtained.

HRMS-ESI (m/z): $[M+H]^+$ calcd for $C_{25}H_{30}N_7O_4S_2$: 556.1795, found 556.1807.

Example 132: 2-[[6-(1,3-Benzothiazol-2-ylamino)-5-methyl-pyridazin-3-yl]-(4-hydroxy-5-methoxy-pentyl)amino]thiazole-4-carboxylic acid

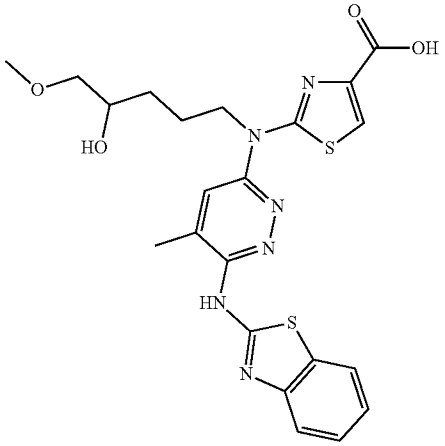 [SMILES: COCC(O)CCCN(c1cc(C)c(Nc2nc3ccccc3s2)nn1)c1nc(C(=O)O)cs1]

Step A: methyl 2-[tert-butoxycarbonyl-(5-methoxy-4-triisopropylsilyloxy-pentyl)amino]thiazole-4-carboxylate Using Mitsunobu General Procedure starting from 284 mg of methyl 2-(tert-butoxycarbonylamino)thiazole-4-carboxylate (1.10 mmol, 1.1 eq.) and 291 mg of Preparation 2c (1.00 mmol, 1 eq.) as the appropriate alcohol, 456 mg (86%) of the desired product was obtained.

$^{1}$H NMR (400 MHz, DMSO-$d_6$) δ ppm 8.08 (s, 1H), 4.07 (dt, 2H), 3.89 (qv, 1H), 3.79 (s, 3H), 3.27 (dd, 2H), 3.23 (s, 3H), 1.73 (qv, 2H), 1.52 (s, 9H) 1.50-1.38 (m, 2H), 0.96 (s, 21H); $^{13}$C NMR (100 MHz, DMSO-$d_6$) δ ppm 161.4, 160.3, 140.6, 124.2, 75.7, 70.5, 58.4, 51.9, 46.8, 31.2, 22.5, 17.89, 17.87, 11.9; LC-MS-ESI (m/z): $[M+H]^+$ calcd for $C_{25}H_{47}N_2O_6SSi$: 531.3, found 531.4.

Step B: methyl 2-[(5-methoxy-4-triisopropylsilyloxy-pentyl)amino]thiazole-4-carboxylate Using Deprotection with HFIP General Procedure starting from 444 mg of the product from Step A (0.84 mmol) as the appropriate carbamate, 334 mg (93%) of the desired product was obtained.

$^{1}$H NMR (500 MHz, DMSO-$d_6$) δ ppm 7.82 (t, 1H), 7.50 (s, 1H), 3.91 (t, 1H), 3.73 (s, 3H), 3.28 (d, 2H), 3.24 (s, 3H), 3.21 (q, 2H), 1.61 (m, 2H), 1.52 (m, 2H), 1.01 (m, 21H); $^{13}$C NMR (125 MHz, DMSO-$d_6$) δ ppm 162.0, 116.9, 76.7, 71.2, 58.9, 52.0, 45.0, 32.2, 24.4; HRMS-ESI (m/z): $[M+H]^+$ calcd for $C_{20}H_{39}N_2O_4SSi$: 431.2394, found 431.2392.

Step C: methyl 2-[(5-methoxy-4-triisopropylsilyloxy-pentyl)-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 324 mg of the product from Step B (0.75 mmol, 1 eq.) and 337 mg of Preparation 4a (0.83 mmol, 1.1 eq.) as the appropriate halide, 540 mg (90%) of the desired product was obtained.

$^{1}$H NMR (400 MHz, DMSO-$d_6$) δ ppm 7.97 (s, 1H), 7.85-7.22 (4H), 7.68 (s, 1H), 5.86 (s, 2H), 4.48 (m, 2H), 3.88 (m, 1H), 3.81 (s, 3H), 3.71 (t, 2H), 3.26 (d, 2H), 3.21 (s, 3H), 2.44 (s, 3H), 1.79 (m, 2H), 1.53 (m, 2H), 0.91 (t, 2H), 0.91 (m, 21H), −0.13 (s, 9H); $^{13}$C NMR (125 MHz, DMSO-$d_6$) δ ppm 162.3, 160.7, 123.1, 117.7, 76.4, 73.0, 71.0, 66.7, 58.8, 52.2, 47.2, 31.4, 22.5, 18.3, 12.3, 17.8, 17.8, −1.0 HRMS-ESI (m/z): $[M+H]^+$ calcd for $C_{38}H_{61}N_6O_5S_2Si_2$: 801.3678, found 801.3671.

Step D: 2-[[6-(1,3-benzothiazol-2-ylamino)-5-methyl-pyridazin-3-yl]-(4-hydroxy-5-methoxy-pentyl)amino]thiazole-4-carboxylic acid Using Deprotection and Hydrolysis General Procedure followed by purification via reverse phase preparative chromatography (C18, 25 mM $NH_4HCO_3$ in water:MeCN) starting from the product from Step C, the desired product was obtained.

HRMS-ESI (m/z): $[M+H]^+$ calcd for $C_{22}H_{25}N_6O_4S_2$: 501.1373, found 501.136.

Example 133: 2-[[6-(1,3-Benzothiazol-2-ylamino)-5-methyl-pyridazin-3-yl]-(5hydroxy-4-methoxy-pentyl)amino]thiazole-4-carboxylic acid

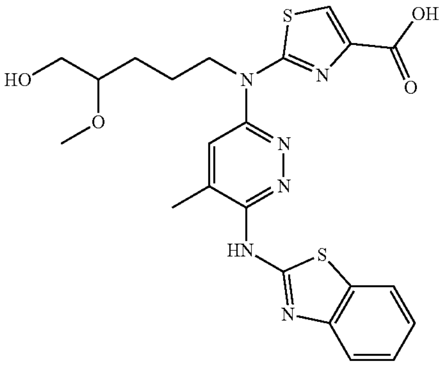 [SMILES: COC(CO)CCCN(c1cc(C)c(Nc2nc3ccccc3s2)nn1)c1nc(C(=O)O)cs1]

Step A: methyl 2-[tert-butoxycarbonyl-[5-[tert-butyl(dimethyl)silyl]oxy-4-methoxy-pentyl]amino]thiazole-4-carboxylate Using Mitsunobu General Procedure starting from 571 mg of methyl 2-(tert-butoxycarbonylamino)thiazole-4-carboxylate (2.21 mmol, 1.1 eq.) and 500 mg of Preparation 2b (2.01, 1 eq.) as the appropriate alcohol, 818 mg (83%) of the desired product was obtained.

$^{1}$H NMR (400 MHz, DMSO-$d_6$) δ ppm 8.08 (s, 1H), 4.06 (t, 2H), 3.79 (s, 3H), 3.53 (ddd, 2H), 3.28 (s, 3H), 3.20-3.14 (m, 1H), 1.77-1.63 (m, 2H), 1.53 (s, 3H), 1.49-1.33 (m, 2H), 0.82 (s, 9H), −0.01 (s, 6H); $^{13}$C NMR (100 MHz, DMSO-$d_6$) δ ppm 161.4, 160.4, 140.6, 124.3, 80.4, 63.6, 56.9, 51.9, 46.8, 27.4, 27.6, 25.7, 23.4, 17.9, −5.5; LC-MS-ESI (m/z): $[M+H]^+$ calcd for $C_{22}H_{41}N_2O_6SSi$: 489.2, found 489.3.

Step B: methyl 2-[[5-[tert-butyl(dimethyl)silyl]oxy-4-methoxy-pentyl]amino]thiazole-4-carboxylate Using Deprotection with HFIP General Procedure starting from 306 mg of the product from Step A (0.63 mmol) as the appropriate carbamate, 234 mg (96%) of the desired product was obtained.

$^1$H NMR (400 MHz, DMSO-$d_6$) δ ppm 7.80 (t, 1H), 7.50 (s, 1H), 3.73 (s, 3H), 3.60-3.51 (m, 2H), 3.30 (s, 3H), 3.24-3.15 (m, 3H), 1.64-1.34 (m, 4H), 0.85 (s, 9H), 0.03 (s, 6H); $^{13}$C NMR (100 MHz, DMSO-$d_6$) δ ppm 168.3, 161.6, 142.1, 116.4, 80.7, 64.3, 57.0, 51.6, 44.5, 25.8, 24.6, 17.9, −5.4; LC-MS-ESI (m/z): $[M+H]^+$ calcd for $C_{17}H_{33}N_2O_4SSi$: 389.2, found 389.3.

Step C: methyl 2-[[5-[tert-butyl(dimethyl)silyl]oxy-4-methoxy-pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 224 mg of the product from Step B (0.58 mmol, 1 eq.) and 349 mg of Preparation 4a (0.86 mmol, 1.5 eq.) as the appropriate halide, 357 mg (82%) of the desired product was obtained.

$^1$H NMR (500 MHz, DMSO-$d_6$) δ ppm 7.98 (s, 1H), 7.83 (d, 1H), 7.69 (s, 1H), 7.46 (d, 1H), 7.43 (td, 1H), 7.25 (td, 1H), 5.86 (s, 2H), 4.46 (t, 2H), 3.81 (s, 3H), 3.72 (t, 2H), 3.56-3.51 (dd+dd, 2H), 3.29 (s, 3H), 3.22 (m, 1H), 2.45 (s, 3H), 1.76 (m, 2H), 1.54-1.47 (m+m, 2H), 0.91 (t, 2H), 0.79 (s, 9H), −0.04 (s, 6H), −0.12 (s, 9H); $^{13}$C NMR (125 MHz, DMSO-$d_6$) δ ppm 162.3, 127.2, 123.4, 123.2, 123.1, 117.6, 112.0, 80.9, 72.9, 66.7, 64.2, 57.3, 52.2, 47.4, 28.1, 26.2, 23.3, 17.9, 17.8, −1.0, −5.1; HRMS-ESI (m/z): $[M+H]^+$ calcd for $C_{35}H_{55}N_6O_5S_2Si_2$: 759.3208, found 759.3212.

Step D: 2-[[6-(1,3-benzothiazol-2-ylamino)-5-methyl-pyridazin-3-yl]-(5-hydroxy-4-methoxy-pentyl)amino]thiazole-4-carboxylic acid Using Deprotection and Hydrolysis General Procedure followed by purification via reverse phase preparative chromatography (C18, 25 mM $NH_4HCO_3$ in water:MeCN) starting from the product from Step C, the desired product was obtained.

HRMS-ESI (m/z): $[M+H]^+$ calcd for $C_{22}H_{25}N_6O_4S_2$: 501.1373, found 501.1366.

Example 134: 2-[[6-(1,3-Benzothiazol-2-ylamino)-5-methyl-pyridazin-3-yl]-(4-hydroxybutyl)amino]-5-[3-[4-[3-(dimethylamino)prop-1-ynyl]-2-fluoro-phenoxy]propyl]thiazole-4-carboxylic acid

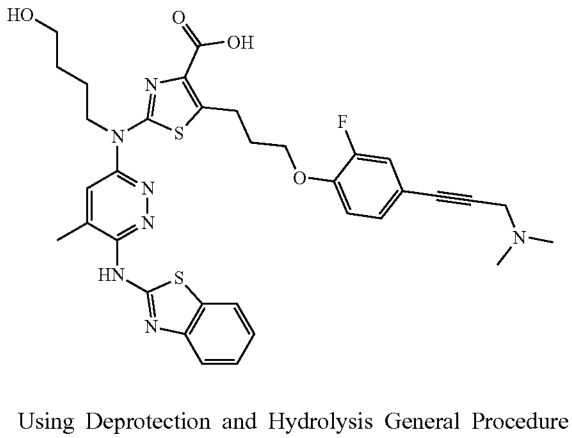

Using Deprotection and Hydrolysis General Procedure starting from the appropriate methyl ester Preparation 5d, Step A, the desired product was obtained.

HRMS-ESI (m/z): $[M+H]^+$ calcd for $C_{34}H_{37}FN_7O_4S_2$: 690.2327, found 690.2347.

Example 135: 2-({6-[(1,3-Benzothiazol-2-yl)amino]-5-methylpyridazin-3-yl}(methyl)amino)-5-{1-[(tert-butoxy)carbonyl]azetidin-3-yl}-1,3-thiazole-4-carboxylic acid

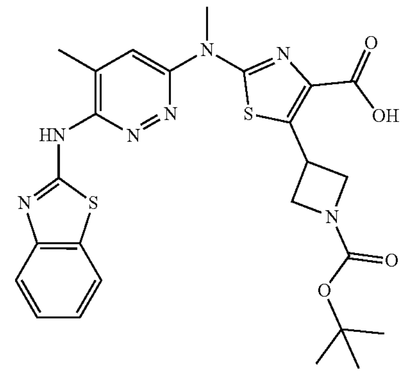 [SMILES: Cc1cc(N(C)c2nc(C(=O)O)c(C3CN(C(=O)OC(C)(C)C)C3)s2)nnc1Nc1nc2ccccc2s1]

Step A: ethyl 2-({6-[(1,3-benzothiazol-2-yl)amino]-5-methylpyridazin-3-yl}(methyl)amino)-5-{1-[(tert-butoxy)carbonyl]azetidin-3-yl}-1,3-thiazole-4-carboxylate To a solution of the product from Preparation 5l, Step A (122 mg, 0.17 mmol, 1 eq) in tetrahydrofuran (6 mL) was added tetrabutylammonium fluoride (1M in tetrahydrofuran; 0.24 mL, 1.38 mmol, 8 eq) and the mixture was heated at 50 for 13 h. The reaction was allowed to cool to ambient temperature then partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 24 g RediSep™ silica cartridge) eluting with a gradient of 0-10% methanol in dichloromethane afforded the desired product as a yellow glass (38 mg, 0.07 mmol, 38%).

LC/MS ($C_{27}H_{31}N_7O_4S_2$) 582 $[M+H]^+$; RT 1.26 (LCMS-V-B1)

$^1$H NMR (400 MHz, DMSO-d6) 11.05 (br s, 1H), 7.98 (br s, 1H), 7.81-7.61 (m, 2H), 7.50-7.33 (m, 1H), 7.31-7.16 (m, 1H), 4.65-4.53 (m, 1H), 4.37 (t, 2H) 4.29 (q, J=7.1 Hz, 2H), 3.98-3.84 (m, 2H), 3.78 (s, 3H) 2.47 (s, 3H), 1.43 (s, 9H), 1.31 (t, 3H).

Step B: 2-({6-[(1,3-benzothiazol-2-yl)amino]-5-methylpyridazin-3-yl}(methyl)amino)-5-{1-[(tert-butoxy)carbonyl]azetidin-3-yl}-1,3-thiazole-4-carboxylic acid To a solution of the product from Step A (38 mg, 0.07 mmol, 1 eq) in 1,4-dioxane (3 mL) was added 2M aqueous sodium hydroxide (0.5 mL, 1 mmol, 15 eq) and the mixture was heated at 100° C. for 30 min. The reaction was allowed to cool to ambient temperature and concentrated in vacuo. Purification by reverse phase automated flash chromatography (CombiFlash Rf, C18 13 g RediSep column) doting with a gradient of 5-95% acetonitrile in water afforded the desired product as a yellow solid (21.4 mg, 0.04 mmol, 59%).

HRMS-ESI (m/z) [M−H]− calcd for $C_{25}H_{26}N_7O_4S_2$: 552.1493, found 552.1511.

Example 136: 5-(1-Benzoylazetidin-3-yl)-2-({6-[(1,3-benzothiazol-2-yl)amino]-5-methylpyridazin-3-yl}(methyl)amino]-1,3-thiazole-4-carboxylic acid

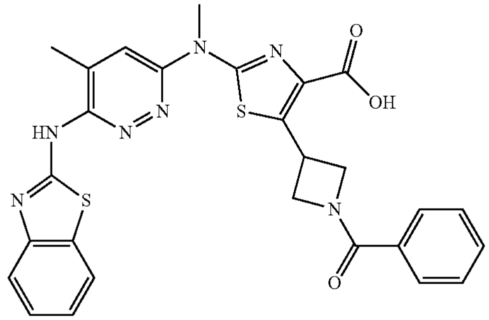 [SMILES: Cc1cc(N(C)c2nc(C(=O)O)c(C3CN(C(=O)c4ccccc4)C3)s2)nnc1Nc1nc2ccccc2s1]

Step A: ethyl 5-(1-benzoylazetidin-3-yl)-2-[methyl(5-methyl-6-{[(2Z)-3-{[2-(trimethylsilyl)ethoxy]methyl}-2,3-dihydro-1,3-benzothiazol-2-ylidene]amino]pyridazin-3-yl)amino]-1,3-thiazole-4-carboxylate To a solution of the product from Preparation 51 (29.6 mg, 0.05 mmol, 1 eq) and benzoyl chloride (6.74 μL, 0.06 mmol, 1.2 eq) in dichloromethane (3 mL) was added triethylamine (0.01 mL, 0.1 mmol, 2 eq) and the mixture was stirred at ambient temperature for 3.5 h. Purification by automated flash column chromatography (CombiFlash Rf, 12 g RediSep™ silica cartridge) eluting with a gradient of 0-85% ethyl acetate in iso-heptane afforded the desired product as a colourless glass (32 mg, 0.04 mmol, 92%).

LC/MS ($C_{35}H_{41}N_7O_4SiS_2$) 716 $[M+H]^+$; RT 1.59 (LCMS-V-B1)

$^1$H NMR (400 MHz, DMSO-d6) δ 7.86 (dd, J=7.6, 1.1 Hz, 1H), 7.75-7.67 (m, 3H), 7.58-7.39 (m, 5H), 7.29-7.22 (m, 1H), 5.87 (s, 2H), 4.88-4.77 (m, 1H), 4.75-4.66 (m, 1H), 4.65-4.54 (m, 1H) 4.46-4.34 (m, 1H), 4.29 (q, J=7.1 Hz, 2H), 4.22-4.10 (m, 1H), 3.79 (s, 3H), 3.76-3.67 (m, 2H), 2.47 (d, J=1.0 Hz, 3H), 1.31 (t, J=7.1 Hz, 3H), 0.97-0.88 (m, 2H), −0.11 (s, 9H).

Step B: ethyl 5-(1-benzoylazetidin-3-yl)-2-({6-[(1,3-benzothiazol-2-yl)amino]-5-methylpyridazin-3-yl}(methyl)amino)-1,3-thiazole-4-carboxylate To a solution of the product from Step A (32 mg, 0.04 mmol, 1 eq) in dichloromethane (3 mL) was added trifluoroacetic acid (0.45 mL, 6.05 mmol, 135 eq) and the mixture was stirred at ambient temperature for 5 h. The reaction was partitioned between dichloromethane and saturated aqueous sodium bicarbonate, and the organic phase was washed with saturated aqueous sodium bicarbonate then brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (17.5 mg, 0.03 mmol, 67%).

LC/MS ($C_{29}H_{27}N_7O_3S_2$) 586 $[M+H]^+$; RT 1.30 (LCMS-V-B1)

$^1$H NMR (400 MHz, DMSO-d6) δ 7.94 (br s, 1H), 7.76-7.68 (m, 3H), 7.60-7.44 (m, 4H), 743-7.32 (m, 1H), 7.29-7.15 (m, 1H), 4.86-4.77 (m, 1H), 4.76-4.67 (m, 1H), 4.66-4.57 (m, 1H), 4.43-4.34 (m, 1H), 4.29 (q, 2H), 4.21-4.11 (m, 1H), 3.79 (s, 3H), 2.47 (s, 3H), 1.32 (t, J=7.1 Hz, 3H).

Step C: 5-(1-benzoylazetidin-3-yl)-2-({6-[(1,3-benzothiazol-2-yl)amino]-5-methylpyridazin-3-yl}(methyl)amino)-1,3-thiazole-4-carboxylic acid To a solution of the product from Step B (17.5 mg, 0.03 mmol, 1 eq) in 1,4-dioxane (3 mL) was added 2M aqueous sodium hydroxide (0.5 mL, 1 mmol, 33.5 eq) and the mixture was heated at reflux for 2 h. The reaction was allowed to cool to ambient temperature and purification by reverse phase automated flash chromatography (CombiFlash Rf, C18 13 g RediSep column) eluting with a gradient of 5-95% acetonitrile in water afforded the desired product as a yellow solid (16 mg, 0.03 mmol, 96%) [as a sodium salt].

HRMS-ESI (m/z) [M−H]− calcd for $C_{27}H_{22}N_7O_3S_2$: 556.1231, found 556.1260.

Example 137: 2-({6-[(1,3-Benzothiazol-2-yl)amino]-5-methylpyridazin-3-yl}(methyl)amino)-5-(3-{4-[3-(dimethylamino)prop-1-yn-1-yl]-2-fluorophenoxy}-2,2-dimethylpropyl)-1,3-thiazole-4-carboxylic acid

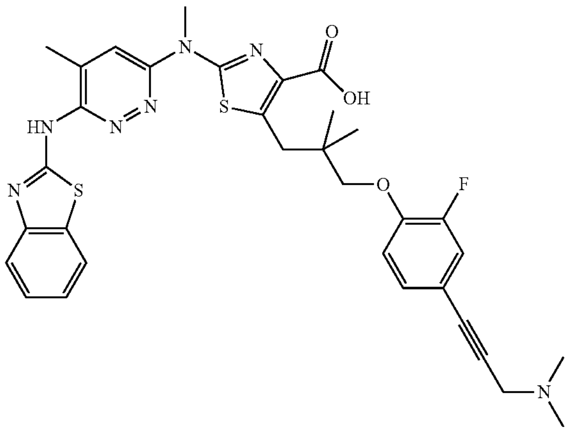 [SMILES: Cc1cc(N(C)c2nc(C(=O)O)c(CC(C)(C)COc3ccc(C#CCN(C)C)cc3F)s2)nnc1Nc1nc2ccccc2s1]

Step A: methyl 5-(3-{4-[3-(dimethylamino)prop-1-yn-1-yl]-2-fluorophenoxy}-2,2-dimethylpropyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 3zc (8 mg, 0.02 mmol, 1 eq) in 1,4-dioxane (2 mL) was added the product from Preparation 4a (9.76 mg, 0.02 mmol, 1.3 eq), Xantphos (2.14 mg, 3.69 μmol, 0.2 eq), cesium carbonate (18 mg, 0.06 mmol, 3 eq) and N,N-diisopropylethylamine (9.64 μL, 0.06 mmol, 3 eq). The mixture was sparged with nitrogen (10 min) then tris(dibenzylideneacetone)dipalladium(0)(1.69 mg, 0.1 eq) was added and the mixture was heated at 120° C. overnight. The reaction was partitioned between ethyl acetate and brine, and the organic phase was dried (magnesium sulfate) and concentrated in vacuo. Purification by automated flash column chromatography (CombiFlash Rf, 4 g RediSep™ silica cartridge) eluting with a gradient of 0-6% methanol in dichloromethane afforded the desired product as a yellow solid (15 mg, 0.02 mmol, 100%).

LC/MS ($C_{40}H_{50}FN_7O_4SiS_2$) 804 $[M+H]^+$; RT 2.65 (LCMS-V-C)

$^1$H NMR (400 MHz, DMSO-d6) δ 7.83 (d, J=7.9 Hz, 1H), 7.67 (d, J=1.2 Hz, 1H), 7.49-7.42 (m, 2H), 7.35-7.23 (m, 2H), 7.22-7.13 (m, 2H), 5.86 (s, 2H), 3.83 (s, 2H), 3.79-3.75 (m, 5H), 3.75-3.67 (m, 2H), 2.45 (s, 3H), 2.15 (s, 6H), 1.05 (s, 6H), 0.96-0.88 (m, 2H), −0.11 (s, 9H).

Step B: 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2,2-dimethylpropyl)-1,3-thiazole-4-carboxylic acid To a solution of the product from Step A (60 mg, 0.07 mmol, 1 eq) in tetrahydrofuran (6 mL) was added ethylenediamine (15 μL, 0.22 mmol, 3 eq) and tetrabutylammonium fluoride (1M in tetrahydrofuran, 224 μL, 0.22 mmol, 3 eq) and the mixture was heated at 70° C. overnight. The solvent was removed in vacuo and purification by reverse phase automated flash chromatography (CombiFlash Rf, C18 13 g RediSep column) eluting with a gradient of 5-95% acetonitrile in water afforded a solid that was triturated with diethyl ether, filtered, and dried under vacuum to afford the desired product as a yellow solid (13.1 mg, 0.02 mmol, 27%).

HRMS-ESI (m/z) [M+H]+ calcd for $C_{33}H_{35}FN_7O_3S_2$: 660.2221, found 660.2264.

Example 138: 2-({6-[(1,3-Benzothiazol-2-yl)amino]-5-methylpyridazin-3-yl}(methyl)amino)-5-[1-(2-phenylacetyl)azetidin-3-yl]-1,3-thiazole-4-carboxylic acid

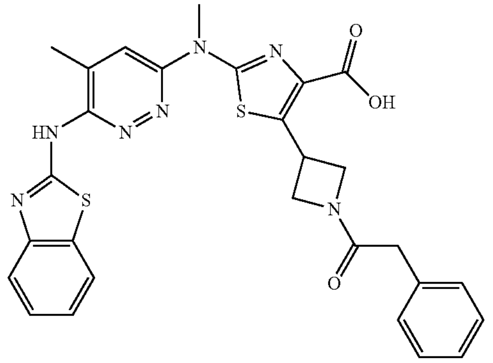 [SMILES: Cc1cc(N(C)c2nc(C(=O)O)c(C3CN(C(=O)Cc4ccccc4)C3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino]pyridazin-3-yl)amino]-5-[1-(2-phenylacetyl)azetidin-3-yl]-1,3-thiazole-4-carboxylate To a solution of the product from Preparation 51 (105 mg, 0.17 mmol, 1 eq) in dichloromethane (6 mL) was added triethylamine (0.05 mL, 0.34 mmol, 2 eq) and phenylacetyl chloride (0.03 mL, 0.21 mmol, 1.2 eq) and the mixture was stirred at ambient temperature for 3 h. The reaction was diluted with dichloromethane then washed with water and brine, dried (magnesium sulfate), and concentrated in vacuo. Purification by automated flash column chromatography (CombiFlash Rf, 12 g RediSep™ silica cartridge) eluting with a gradient of 0-100% ethyl acetate in iso-heptane afforded the desired product as a yellow foam (66 mg, 0.09 mmol, 53%).

LC/MS ($C_{36}H_{43}N_7O_4SiS_2$) 730 $[M+H]^+$; RT 1.45 (LCMS-V-B1)

$^1$H NMR (400 MHz, DMSO-d6) δ 7.85 (dd, J=7.8, 1.1 Hz, 1H), 7.70 (d, J=1.1 Hz, 1H), 7.52-7.39 (m, 2H), 7.34-7.25 (m, 5H), 7.24-7.18 (m, 1H), 5.87 (s, 2H), 4.74-4.58 (m, 2H), 4.39 (t, J=9.1 Hz, 1H), 4.29 (q, J=7.1 Hz, 2H), 4.23 (dd, J=8.1, 5.8 Hz, H), 3.96 (dd, J=9.7, 6.1 Hz, 1H), 3.79 (s, 3H), 3.77-3.68 (m, 2H), 3.51 (d, J=2.1 Hz, 2H), 2.47 (d, J=1.0 Hz, 3H), 1.32 (t, J=7.1 Hz, 3H), 0.98-0.87 (m, 2H), −0.11 (s, 9H).

Step B: ethyl 2-({6-[(1,3-benzothiazol-2-yl)amino]-5-methylpyridazin-3-yl}(methyl)amino)-5-[1(2-phenylacetyl)azetidin-3-yl]-1,3-thiazole-4-carboxylate To a solution of the product from Step A (66 mg, 0.09 mmol, 1 eq) in dichloromethane (3 mL) was added trifluoroacetic acid (1 mL, 13.4 mmol, 148 eq) and the mixture was stirred at ambient temperature overnight. The reaction was partitioned between dichloromethane and saturated aqueous sodium bicarbonate, washed with saturated aqueous sodium bicarbonate then brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (39 mg, 0.07 mmol, 72%).

LC/MS ($C_{30}H_{29}N_7O_3S_2$) 600 $[M+H]^+$; RT 1.33 (LCMS-V-B1)

$^1$H NMR (400 MHz, DMSO-d6) δ 11.07 (br s, 1H), 8.00 (br s, 1H), 7.72 (br s+s, 2H), 7.40 (br s, 1H), 7.37-7.25 (m, 4H), 7.27-7.18 (m, 1H), 4.75-4.57 (m, 2H), 4.40 (t, J=9.1 Hz, 1H), 4.30 (q, J=7.1 Hz, 2H), 4.24 (dd, J=8.1, 5.9 Hz, 1H), 3.96 (dd, J=9.7, 6.1 Hz, 1H), 3.79 (s, 3H), 3.52 (s, 2H), 1.33 (t, J=7.1 Hz, 3H).

Step C: 2-({6-[(1,3-benzothiazol-2-yl)amino]-5-methylpyridazin-3-yl}(methyl)amino)-5-[1-(2-phenylacetyl)azetidin-3-yl]-1,3-thiazole-4-carboxylic acid To a solution of the product from Step B (39 mg, 0.07 mmol, 1 eq) in 1,4-dioxane (4 mL) was added a 2M aqueous sodium hydroxide (1 mL, 2 mmol, 30.8 eq) and the mixture was heated at reflux for 1.5 h. The solvent was removed in vacuo and purification by reverse phase automated flash chromatography (CombiFlash Rf, C18 13 g RediSep column) eluting with a gradient of 5-95% acetonitrile in water afforded the desired product as a yellow solid (28.7 mg, 0.05 mmol, 77%) [as a sodium salt].

HRMS-ESI (m/z) [M−H]− calcd for $C_{28}H_{24}N_7O_3S_2$: 570.1388, found 570.1423.

Example 139: 5-(Azetidin-3-yl)-2-({6-[(1,3-benzothiazol-2-yl)amino]-5-methylpyridazin-3-yl}(methyl)amino)-1,3-thiazole-4-carboxylic acid

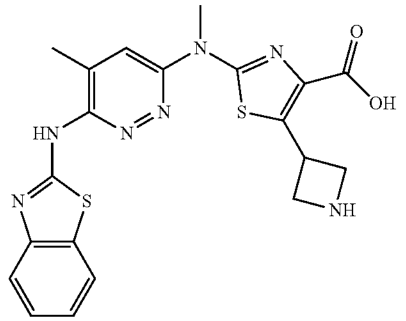 [SMILES: Cc1cc(N(C)c2nc(C(=O)O)c(C3CNC3)s2)nnc1Nc1nc2ccccc2s1]

During the preparation of Example 138, Step C, sodium 5-(azetidin-3-yl)-2-({6-[(1,3-benzothiazol-2-yl)amino]-5-methylpyridazin-3-yl}(methyl)amino)-1,3-thiazole-4-carboxylate (7.5 mg, 0.02 mmol, 25%) was isolated as a byproduct [as a sodium salt].

HRMS-ESI (m/z) [M−H]− calcd for $C_{20}H_{18}N_7O_2S_2$: 452.0969, found 452.0977.

Example 140: 2-({6-[(1,3-Benzothiazol-2-yl)amino]-5-methylpyridazin-3-yl}(methyl)amino)-5-{[1-({4-[3-(dimethylamino)prop-1-yn-1-yl]-2-fluorophenoxy}methyl)cyclopropyl]methyl}-1,3-thiazole-4-carboxylic acid

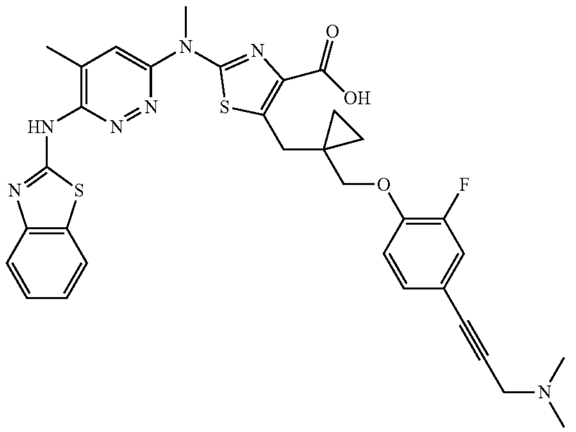 [SMILES: Cc1cc(N(C)c2nc(C(=O)O)c(CC3(COc4ccc(C#CCN(C)C)cc4F)CC3)s2)nnc1Nc1nc2ccccc2s1]

Step A: methyl 5-{[1-({4-[3-(dimethylamino)prop-1-yn-1-yl]-2-fluorophenoxy}methyl)cyclopropyl]methyl}-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 3zd (84 mg, 0.19 mmol, 1 eq) in 1,4-dioxane (6 mL) was added the product from Preparation 4a (103 mg, 0.25 mmol, 1.3 eq), Xantphos (22.5 mg, 0.04 mmol, 0.2 eq), cesium carbonate (190 mg, 0.58 mmol, 3 eq) and N,N-diisopropylethylamine (102 μL, 0.58 mmol, 3 eq). The mixture was sparged with nitrogen (10 min), then tris(dibenzylideneacetone)dipalladium(0)(17.8 mg, 0.02 mmol, 0.1 eq) was added and the mixture was heated at 120° C. overnight. The reaction was partitioned between ethyl acetate and brine, and the organic phase was dried (magnesium sulfate), and concentrated in vacuo. Purification by automated flash column chromatography (CombiFlash Rf, 4 g RediSep™ silica cartridge) eluting with a gradient of 0-5% methanol in dichloromethane afforded the desired product as a brown solid (98 mg, 0.12 mmol, 63%).

LC/MS ($C_{40}H_{48}FN_7O_4SiS_2$) 802 $[M+H]^+$; RT 2.63 (LCMS-V-C)

$^1$H NMR (400 MHz, DMSO-d6) δ 7.87-7.80 (m, 1H), 7.67 (d, 1H), 7.52-7.40 (m, 2H), 7.33-7.22 (m, 2H), 7.18-7.11 (m, 1H), 7.03 (t, J=8.7 Hz, 1H), 5.87 (s, 2H), 3.83 (s, 2H), 3.76 (s, 3H), 3.76-3.69 (m, 2H), 3.66 (s, 3H), 3.39 (s, 2H), 3.36 (s, 2H), 2.46 (d, J=1.0 Hz, 3H), 2.18 (s, 6H), 0.97-0.88 (m, 2H), 0.78-0.65 (m, 4H), −0.10 (s, 9H).

Step B: methyl 2-({6-[(1,3-benzothiazol-2-yl)amino]-5-methylpyridazin-3-yl}(methyl)amino)-5-{[1-({4-[3-(dimethylamino)prop-1-yn-1-yl]-2-fluorophenoxy}methyl)cyclopropyl]methyl}-1,3-thiazole-4-carboxylate To a solution of the product from Step A (98 mg, 0.12 mmol, 1 eq) in tetrahydrofuran (6 mL) was added ethylenediamine (24.5 μL, 0.37 mmol, 3 eq) and tetrabutylammonium fluoride (1M in tetrahydrofuran; 224 μL, 0.37 mL, 0.37 mmol, 3 eq) and the mixture was heated at 70° C. overnight. The reaction was partitioned between water and 9:1 dichloromethane/methanol, and the organic phase was separated and dried (PTFE phase separator), and concentrated in vacuo. Purification by reverse phase automated flash chromatography (CombiFlash Rf, C18 13 g RediSep column) eluting with a gradient of 5-95% acetonitrile in water afforded the desired product as a yellow solid (5.01 mg, 0.01 mmol, 6%).

LC/MS ($C_{34}H_{34}FN_7O_3S_2$) 672 $[M+H]^+$; RT 2.04 (LCMS-V-C)

$^1$H NMR (400 MHz, DMSO-d6) δ 11.52 (br s, 1H), 7.95-7.88 (m, 1H), 7.69 (d, J=1.2 Hz, 1H), 7.54 (d, J=7.9 Hz, 1H), 7.45-7.35 (m, 1H), 7.33-7.18 (m, 2H), 7.19-7.11 (m, 1H), 7.03 (t, J=8.8 Hz, 1H), 3.83 (s, 2H), 3.75 (s, 3H), 3.67 s, 3H), 3.40 (s, 2H), 3.38 (s, 2H), 2.47 (d, J=1.1 Hz, 3H), 2.19 (s, 6H), 0.78-0.65 (m, 4H).

Step C: 2-({6-[(1,3-benzothiazol-2-yl)amino]-5-methylpyridazin-3-yl}(methyl)amino)-5-{[1-({4-[3-(dimethylamino)prop-1-yn-1-yl]-2-fluorophenoxy}methyl)cyclopropyl]methyl}-1,3-thiazole-4-carboxylic acid To a solution of the product from Step B (35 mg, 0.05 mmol, 1 eq) in 1,4-dioxane (5 mL) was added lithium hydroxide monohydrate (21.9 mg, 0.52 mmol, 10 eq) and the mixture was heated at 110° C. overnight. The reaction was concentrated in vacuo and the residue was triturated with water, filtered, and dried under vacuum to afford the desired product as a yellow solid (23.8 mg, 0.04 mmol, 70%) [as a lithium salt].

HRMS-ESI (m/z) [M+H]+ calcd for $C_{33}H_{33}FN_7O_3S_2$: 658.2065, found 658.2109.

Example 141: 2-[[6-(1,3-Benzothiazol-2-ylamino)-5-methyl-pyridazin-3-yl]-(5-hydroxypentyl)amino]-5-[3-[4-[3-(dimethylamino)prop-1-ynyl]-2-fluoro-phenoxy]propyl]thiazole-4-carboxylic acid

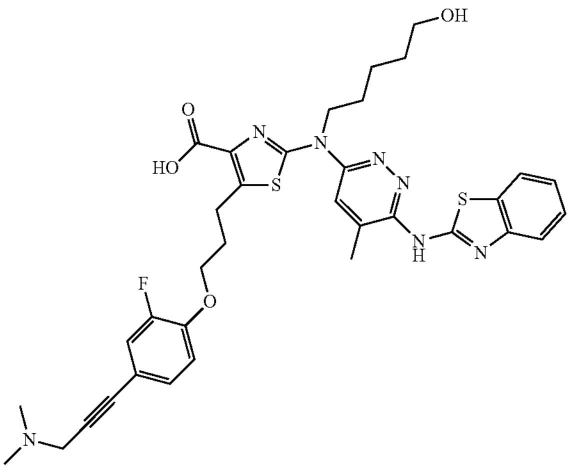 [SMILES: Cc1cc(N(CCCCCO)c2nc(C(=O)O)c(CCCOc3ccc(C#CCN(C)C)cc3F)s2)nnc1Nc1nc2ccccc2s1]

Using Deprotection and Hydrolysis General Procedure followed by repurification via reverse phase preparative chromatography (C18, 25 mM $NH_4HCO_3$ in water:MeCN), starting from Preparation 5f the desired product was obtained.

HRMS-ESI (m/z): $[M+H]^+$ calcd for $C_{35}H_{39}FN_7O_4S_2$: 714.2489 found: 704.2483.

Example 142: 2-[[6-(1,3-Benzothiazol-2-ylamino)-5-methyl-pyridazin-3-yl]-[5-[2-(dimethylamino)ethyl-methyl-amino]-4-hydroxy-pentyl]amino]thiazole-4-carboxylic acid

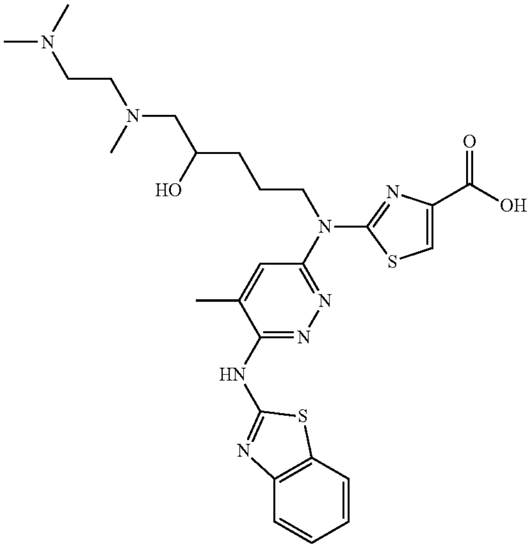 [SMILES: Cc1cc(N(CCCC(O)CN(C)CCN(C)C)c2nc(C(=O)O)cs2)nnc1Nc1nc2ccccc2s1]

Step A: methyl 2-[tert-butoxycarbonyl-[4-[tert-butyl(dimethyl)silyl]oxy-5-[2-(dimethylamino)ethyl-methyl-amino]pentyl]amino]thiazole-4-carboxylate Using Mitsunobu General Procedure starting from 426 mg of methyl 2-(tert-butoxycarbonylamino)thiazole-4-carboxylate (1.65 mmol, 1.1 eq.) and 478 mg of Preparation 2f (1.65 mmol, 1 eq.) as the appropriate alcohol, 359 mg (43%) of the desired product was obtained.

$^1H$ NMR (400 MHz, DMSO-$d_6$) δ ppm 8.08 (s, 1H), 3.79 (s, 3H), 3.72 (m, 1H), 2.44-2.20 (m, 8H), 2.18 (s, 6H), 2.14 (s, 3H), 1.85-1.56 (m, 3H), 1.53 (s, 9H), 1.39-1.25 (m, 1H), 0.79 (s, 9H), 0.01 (s, 3H), −0.02 (s, 3H); LC-MS-ESI (m/z): $[M+H]^+$ calcd for $C_{26}H_{51}N_4O_5SSi$: 559.3, found 559.4.

Step B: methyl 2-[[4-[tert-butyl(dimethyl)silyl]oxy-5-[2-(dimethylamino)ethyl-methyl-amino]pentyl]amino]thiazole-4-carboxylate Using Deprotection with HFIP General Procedure starting from 811 mg of the product from Step A (1.45 mmol) as the appropriate carbamate, 262 mg (39%) of the desired product was obtained.

$^1H$ NMR (500 MHz, DMSO-$d_6$) δ ppm 7.81 (t, 1H), 7.50 (s, 1H), 3.73 (s, 3H), 3.72 (m, 1H), 3.20 (m, 2H), 2.40 (m, 2H), 2.32 (m, 2H), 2.27 (d, 2H), 2.16 (s, 3H), 2.14 (s, 6H), 1.63-1.54 (m+m, 2H), 1.61-1.37 (m+m, 2H), 0.84 (s, 9H), 0.04 (s, 3H), 0.03 (s, 3H); $^{13}C$ NMR (125 MHz, DMSO-$d_6$) δ ppm 168.7, 162.0, 142.6, 116.8, 70.4, 64.6, 57.4, 56.5, 52.0, 45.9, 45.1, 43.8, 33.0, 26.3, 24.9, −3.8, −4.3; GC-MS-ESI (m/z): $[M+H]^+$ calcd for $C_{21}H_{43}N_4O_3SSi$: 459.3, found 459.4.

Step C: methyl 2-[[4-[tert-butyl(dimethyl)silyl]oxy-5-[2-(dimethylamino)ethyl-methyl-amino]pentyl]-[5-methyl-6-{[(Z)-[3-(2-trimethylsilylethoxymethyl)-1,3-benzothiazol-2-ylidene]amino]pyridazin-3-yl]amino]thiazole-4-carboxylate Using Buchwald General Procedure II starling from 255 mg of the product from Step B (0.56 mmol, 1 eq.) and 226 mg of Preparation 4a (0.77 mmol, 1.0 eq.) as the appropriate halide, 311 mg (67%) of the desired product was obtained.

$^1H$ NMR (500 MHz, DMSO-$d_6$) δ ppm 7.97 (s, 1H), 7.83 (dd, 1H), 7.70 (s, 1H), 7.46 (dd, 1H), 7.43 (m, 1H) 7.25 (m, 1H), 5.86 (s, 2H), 4.48 (t, 2H), 3.81 (s, 3H), 3.77 (m, 1H), 3.71 (1.2H), 2.65 (m, 2H), 2.51 (m, 2H), 2.45 (s, 3H), 2.38 (brs, 6H), 2.29 (m, 2H), 2.15 (s, 3H), 1.83-1.72 (m+m, 2H), 1.65-1.43 (m+m, 2H), 0.91 (t, 2H), 0.74 (s, 9H), −0.01 & −0.06 (s+s, 6H), −0.12 (s, 9H); $^{13}C$ NMR (125 MHz, DMSO-$d_6$) δ ppm 127.2, 123.4, 123.2, 123.1, 117.7, 112.0, 72.9, 69.9, 66.7, 64.0, 55.7, 54.9, 52.2, 47.3, 44.5, 43.2, 32.1, 26.1, 22.8, 17.9, 17.8, −0.9, −3.9, −4.5; HRMS-ESI (m/z): $[M+H]^+$ calcd for $C_{39}H_{65}N_8O_4S_2Si_2$: 829.4103, found 829.4096.

Step D: 2-[[6-(1,3-benzothiazol-2-ylamino)-5-methylpyridazin-3-yl]-[5-[2-(dimethylamino)ethyl-methyl-amino]-4-hydroxy-pentyl]amino]thiazole-4-carboxylic acid Using Deprotection and Hydrolysis General Procedure followed by purification via reverse phase preparative chromatography (C18, 25 mM $NH_4HCO_3$ in water:MeCN) starting from the product from Step C, the desired product was obtained.

HRMS-ESI (m/z): $[M+H]^+$ calcd for $C_{26}H_{34}N_8O_3S_2$: 571.2268, found 571.2270.

Example 143: 2-[[6-(1,3-Benzothiazol-2-ylamino)-5-methyl-pyridazin-3-yl]-[5-(dimethylamino)-4-hydroxy-pentyl]amino]thiazole-4-carboxylic acid

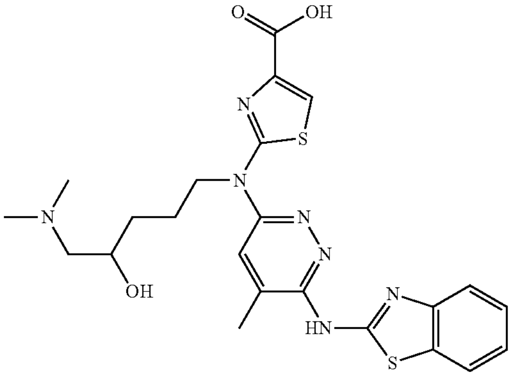 [SMILES: Cc1cc(N(CCCC(O)CN(C)C)c2nc(C(=O)O)cs2)nnc1Nc1nc2ccccc2s1]

Step A: methyl 2-[tert-butoxycarbonyl-[4-[tert-butyl(dimethyl)silyl]oxy-5-(dimethylamino)pentyl]amino]thiazole-4-carboxylate Using Mitsunobu General Procedure starting from 568 mg of methyl 2-(tert-butoxycarbonylamino)thiazole-4-carboxylate (2.2 mmol, 1.1 eq.) and 523 mg of Preparation 2d (2.0 mmol, 1 eq.) as the appropriate alcohol, 530 mg (53%) of the desired product was obtained.

$^1H$ NMR (500 MHz, DMSO-$d_6$) δ ppm 8.08 (s, 1H), 4.06 (m, 2H), 3.79 (s, 3H), 3.72 (m, 1H), 2.15 (d, 2H), 2.11 (s, 6H), 1.79-1.63 (m+m, 2H), 1.55-1.34 (m+m, 2H), 1.52 (s, 9H), 0.79 (s, 9H), 0.01 & −0.02 (s+s, 6H); $^{13}C$ NMR (125 MHz, DMSO-$d_6$) δ ppm 160.8, 153.3, 124.7, 70.1, 65.9, 52.3, 47.3, 46.6, 32.7, 28.1, 26.2, 23.7, −3.8, −4.5; HRMS-ESI (m/z): $[M+H]^+$ calcd for $C_{23}H_{44}N_3O_5SSi$: 502.2765, found 502.2762.

Step B: methyl 2-[[4-[tert-butyl(dimethyl)silyl]oxy-5-(dimethylamino)pentyl]amino]thiazole-4-carboxylate Using Deprotection with HFIP General Procedure starting from 132 mg of the product from Step A (0.26 mmol) as the appropriate carbamate, 78 mg (74%) of the desired product was obtained.

$^1H$ NMR (500 MHz, DMSO-$d_6$) δ ppm 7.81 (t, 1H), 7.50 (s, 1H), 3.73 (s, 1H), 3.73 (s, 3H), 3.21 (q, 2H), 2.17 (d, 2H), 2.13 (s, 6H), 1.63-1.55 (m+m, 2H), 1.60-1.37 (m+m, 2H), 0.84 (s, 9H), 0.04 & 0.03 (s+s, 6H); $^{13}C$ NMR (125 MHz, DMSO-$d_6$) δ ppm 168.7, 162.0, 116.9, 70.3, 66.3, 52.0, 46.6, 45.0, 33.1, 26.3, 25.0, −3.8, −4.3; HRMS-ESI (m/z): $[M+H]^+$ calcd for $C_{18}H_{36}N_3O_3SSi$: 402.2241, found 402.2249.

Step C: methyl 2-[[4-[tert-butyl(dimethyl)silyl]oxy-5-(dimethylamino)pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 72 mg of the product from Step B (0.18 mmol, 1 eq.) and 73 mg of Preparation 4a (0.18 mmol, 1.5 eq.) as the appropriate halide, 126 mg (91%) of the desired product was obtained.

$^1H$ NMR (500 MHz, DMSO-$d_6$) δ ppm 7.86-7.23 (4H), 7.97 (s, 1H), 7.69 (s, 1H), 5.87 (dd, 2H), 4.48 (m, 2H), 3.81 (s, 3H), 3.74 (m, 1H), 3.72 (t, 2H), 3.72 (t, 2H), 2.45 (s, 3H), 2.10 (brs, 6H), 1.83-1.71 (m+m, 2H), 1.59-1.41 (m+m, 2H), 0.92 (t, 2H), 0.74 (s, 9H), −0.01 & −0.06 (s+s, 6H), −0.12 (s, 9H); $^{13}C$ NMR (125 MHz, DMSO-$d_6$) δ ppm 123.1, 117.9, 72.9, 69.9, 66.8, 66.7, 52.2, 47.3, 46.6, 32.4, 26.2, 22.9, 17.8, 17.8, −1.0, −4.5; HRMS-ESI (m/z): $[M+H]^+$ calcd for $C_{36}H_{57}N_7O_4S_2Si_2$: 772.3525, found 772.3521.

Step D: 2-[[6(1,3-benzothiazol-2-ylamino)-5-methyl-pyridazin-3-yl]-[5-(dimethylamino)-4-hydroxy-pentyl]amino]thiazole-1-carboxylic acid Using Deprotection and Hydrolysis General Procedure followed by purification via reverse phase preparative chromatography (C18, 25 mM $NH_4HCO_3$ in water:MeCN) starting from the product from Step C, the desired product was obtained.

HRMS-ESI (m/z): $[M+H]^+$ calcd for $C_{23}H_{28}N_7O_3S_2$: 514.1690 found 514.1694.

Example 144: 2-[[6-(1,3-Benzothiazol-2-ylamino)-5-methyl-pyridazin-3-yl]-[4-hydroxy-5-(trimethylammonio)pentyl]amino]-5-[3-[2-fluoro-4-[3-(methylamino)prop-1-ynyl]phenoxy]propyl]thiazole-4-carboxylate

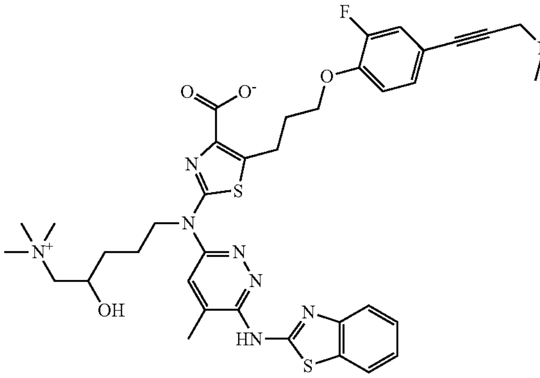

Step A: methyl 5-[3-[4-[3-[tert-butoxycarbonyl(methyl)amino]prop-1-ynyl]-2-fluoro-phenoxy]propyl]-2-[[4-[tert-butyl(diphenyl)silyl]oxy-5-(dimethylamino)pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with tosylate General Procedure starting from Preparation 5a and N-methylmethanamine as the appropriate amine, the desired product was obtained.

HRMS-ESI (m/z): $[M+H]^+$ calcd for $C_{64}H_{84}FN_8O_7S_2Si_2$: 1215.5421, found 1215.5389.

Step B: 2-[[6-(1,3-benzothiazol-2-ylamino)-5-methyl-pyridazin-3-yl]-[4-hydroxy-5-(trimethylammonio)pentyl]amino]-5-[3-[2-fluoro-4-[3-(methylamino)prop-1-ynyl]phenoxy]propyl]thiazole-4-carboxylate The product from Step A was dissolved in the mixture of acetonitrile (4 mL/mmol) and N,N-dimethylformamide (1 mL/mmol) then iodomethane (5 eq.) was added and stirred at rt until full conversion was observed (ca. 1 h). The reaction mixture was concentrated. The crude mixture which contained [5-[[5-[3-[4-[3-[tert-butoxycarbonyl(methyl) amino]prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino] pyridazin-3-yl]amino]-2-[tert-butyl(diphenyl)silyl]oxy-pentyl]-trimethyl-ammonium (LC-MS-ESI (m/z): $[M]^+$ calcd for $C_{65}H_{86}FN_8O_7S_2Si_2$: 1229.6, found 1229.4) was transferred to the next reaction using Quaternary salt deprotection General Procedure, to afford the desired product.

HRMS-ESI (m/z): $[M+H]^+$ calcd for $C_{37}H_{44}FN_8O_4S_2$: 747.2905, found 747.2900.

Example 145: 2-({6-[(1,3-Benzothiazol-2-yl) amino]-5-methylpyridazin-3-yl}(methyl)amino)-5-(1-benzylazetidin-3-yl)-1,3-thiazole-4-carboxylic acid

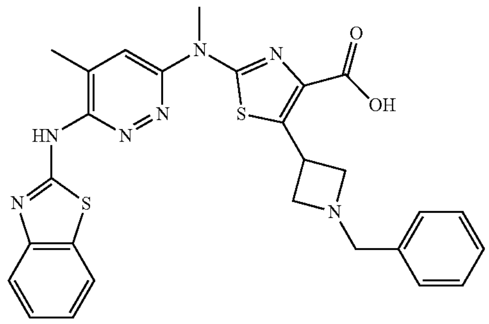 [SMILES: Cc1cc(N(C)c2nc(C(=O)O)c(C3CN(Cc4ccccc4)C3)s2)nnc1Nc1nc2ccccc2s1]

Step A: ethyl 5-(1-benzylazetidin-3-yl)-2-[methyl(5-methyl-6-{[(2Z)-3-{[2-(trimethylsilyl)ethoxy] methyl}-2,3-dihydro-1,3-benzothiazol-2-ylidene] amino}pyridazin-3-yl)amino]-1,3-thiazole-4-carboxylate To a solution of the product from Preparation 51 (36.3 mg, 0.06 mmol, 1 eq) in acetonitrile (3 mL) was added benzaldehyde (12.1 μL, 0.12 mmol, 2 eq), sodium triacetoxy borohydride (37.7 mg, 0.18 mmol, 3 eq) and glacial acetic acid (two drops) and the mixture was stirred at ambient temperature overnight. The reaction was diluted with ethyl acetate and washed with saturated aqueous sodium bicarbonate then brine, dried (magnesium sulfate), and concentrated in vacuo. Purification by automated flash column chromatography (CombiFlash Rf, 12 g RediSep™ silica cartridge) eluting with a gradient of 0-70% ethyl acetate in iso-heptane afforded the desired product as a colourless gum (28.6 mg, 0.04 mmol, 69%).

LC/MS ($C_{35}H_{43}N_7O_3SiS_2$) 702 $[M+H]^+$; RT 1.49 (LCMS-V-B1)

$^1H$ NMR (400 MHz, DMSO-d6) δ 7.78 (dd, J=7.7, 1.1 Hz, 1H), 7.69 (d, J=1.1 Hz, 1H), 7.52-7.41 (m, 2H), 7.40-7.30 (m, 4H), 7.29-7.20 (m, 2H), 5.88 (s, 2H), 4.46-4.35 (m, 1H), 4.27 (q, J=7.1 Hz, 2H), 3.78 (s, 3H), 3.77-3.65 (m, 6H), 3.18 (dd, J=7.0, 5.9 Hz, 2H), 2.47 (d, J=1.0 Hz, 3H), 1.30 (t, J=7.1 Hz, 3H), 0.93 (dd, J=8.6, 7.4 Hz, 2H), −0.10 (s, 9H).

Step B: ethyl 2-({6-[(1,3-benzothiazol-2-yl)amino]-5-methylpyridazin-3-yl}(methyl)amino)-5-(1-benzylazetidin-3-yl)-1,3-thiazole-4-carboxylate To a solution of the product from Step A (28.6 mg, 0.04 mmol, 1 eq) in dichloromethane (3 mL) was added trifluoroacetic acid (0.3 mL, 4.03 mmol, 99 eq) and the mixture was stirred at ambient temperature overnight. The reaction was partitioned between dichloromethane and saturated aqueous sodium bicarbonate, and the organic phase was washed with saturated aqueous sodium bicarbonate then brine, dried (magnesium sulfate), and concentrated in vacuo. Purification by automated flash column chromatography (CombiFlash Rf, 4 g RediSep™ silica cartridge) eluting with a gradient of 0-5% methanol in dichloromethane afforded the desired product as a yellow glass (17 mg, 0.03 mmol, 73%).

LC/MS ($C_{29}H_{29}N_7O_2S_2$) 572 $[M+H]^+$; RT 1.14 (LCMS-V-B1)

$^1H$ NMR (400 MHz, DMSO-d6) δ 7.86 (br s, 1H), 7.71 (br s+s, 2H), 7.45-7.31 (m, 5H), 7.30-7.18 (m, 2H), 4.47-4.36 (m, 1H), 4.27 (q, J=7.1 Hz, 2H), 3.78 (s, 3H), 3.73-3.61 (m, 4H), 3.19 (t, J=6.3 Hz, 2H), 2.48 (s, 3H), 1.31 (t, J=7.1 Hz, 3H).

Step C: 2-({6-[(1,3-benzothiazol-2-yl)amino]-5-methylpyridazin-3-yl}(methyl)amino)-5-(1-benzylazetidin-3-yl)-1,3-thiazole-4-carboxylic acid To a solution of the product from Step B (17 mg, 0.03 mmol, 1 eq) in 1,4-dioxane (3 mL) was added 2M aqueous sodium hydroxide (0.5 mL, 1 mmol, 33.6 eq) and the mixture was heated at reflux for 2 h. The reaction was allowed to cool to ambient temperature and the solvent was removed to vacuo. Purification by reverse phase automated flash chromatography (CombiFlash Rf, C18 13 g RediSep column) eluting with a gradient of 5-95% acetonitrile in water afforded the desired product as a yellow solid (13.9 mg, 0.03 mmol, 86%) [as a sodium salt].

HRMS-ESI (m/z) [M+H]+ calcd for $C_{27}H_{26}N_7O_2S_2$: 544.1584, found 544.1616.

Example 146: 3-[[5-[[6-(1,3-Benzothiazol-2-ylamino)-5-methyl-pyridazin-3-yl]-[4-carboxy-5-[3-[2-fluoro-4-[3-(methylamino)prop-1-ynyl]phenoxy]propyl]thiazol-2-yl]amino]-2-hydroxy-pentyl]-dimethyl-ammonio]propane-1-sulfonate

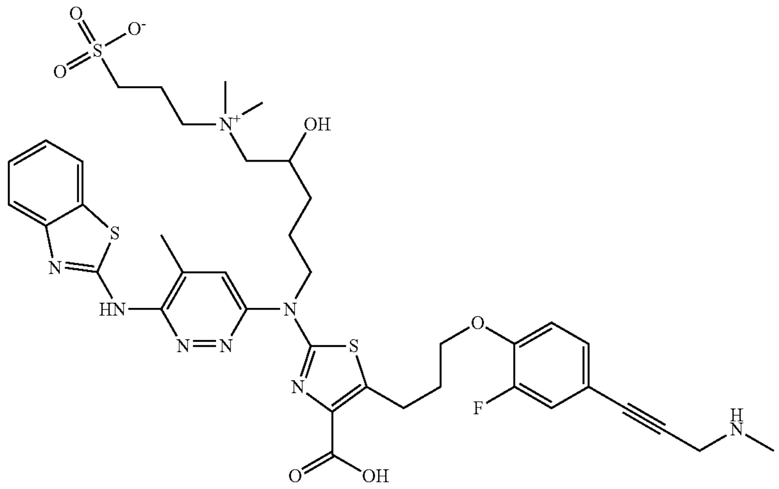 [SMILES: CNCC#Cc1ccc(OCCCc2sc(N(CCCC(O)C[N+](C)(C)CCCS(=O)(=O)[O-])c3cc(C)c(Nc4nc5ccccc5s4)nn3)nc2C(=O)O)c(F)c1]

Example 144, Step A was suspended in MeCN (5 mL/mmol) then oxathiolane 2,2-dioxide (10 eq.) was added and stirred at 60° C. for on (full conversion was observed). The reaction mixture was concentrated. The crude mixture which contained 3-[[5-[[5-[3-[4-[3-[tert-butoxycarbonyl(methyl)amino]prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]-2-[tert-butyl(diphenyl)silyl]oxy-pentyl]-dimethyl-ammonio]propane-1-sulfonate (LC-MS-ESI (m/z): $[M+H]^+$ calcd for $C_{67}H_{90}FN_8O_{10}S_3Si_2$: 1337.5, found 1337.6) was transferred directly to the next reaction using Quaternary salt deprotection General Procedure, to afford the desired product.

HRMS-ESI (m/z): $[M+H]^+$ calcd for $C_{39}H_{48}FN_8O_7S_3$: 855.2787, found 855.2786.

Example 147: 2-({6-[(1,3-Benzothiazol-2-yl)amino]-5-methylpyridazin-3-yl}(4-hydroxybutyl)amino)-5-[3-(4-{3-[bis(3-sulfopropyl)amino]prop-1-yn-1-yl}-2-fluorophenoxy)propyl]-1,3-thiazole-4-carboxylic acid

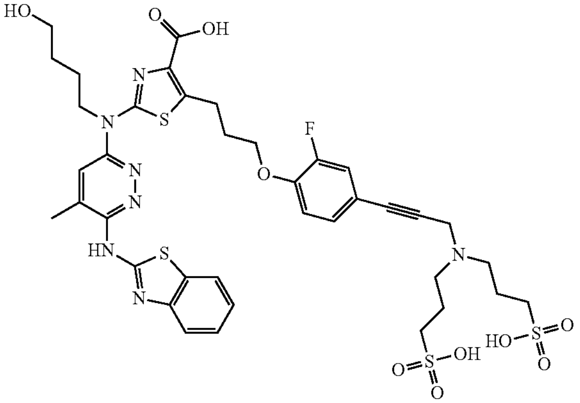 [SMILES: Cc1cc(N(CCCCO)c2nc(C(=O)O)c(CCCOc3ccc(C#CCN(CCCS(=O)(=O)O)CCCS(=O)(=O)O)cc3F)s2)nnc1Nc1nc2ccccc2s1]

Example 147 was isolated as the side product from the reaction of Example 148, Step B.

HRMS-ESI (m/z): $[M+H]^+$ calcd for $C_{38}H_{44}FN_7O_{10}S_4$: 906.2089, found 906.2098.

Example 148: 2-[[6-(1,3-Benzothiazol-2-ylamino)-5-methyl-pyridazin-3-yl]-(4-hydroxybutyl)amino]-5-[3-[2-fluoro-4-[3-(3-sulfopropylamino)prop-1-ynyl]phenoxy]propyl]thiazole-4-carboxylic acid

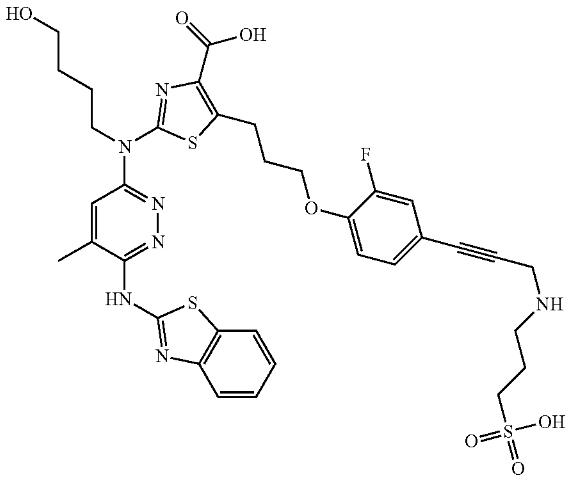 [SMILES: Cc1cc(N(CCCCO)c2nc(C(=O)O)c(CCCOc3ccc(C#CCNCCCS(=O)(=O)O)cc3F)s2)nnc1Nc1nc2ccccc2s1]

Step A: 5-[3-[4-(3-aminoprop-1-ynyl)-2-fluoro-phenoxy]propyl]-2-[[6-(1,3-benzothiazol-2-ylamino)-5-methyl-pyridazin-3yl]-(4-hydroxybutyl)amino]thiazole-4-carboxylic acid Using Deprotection and Hydrolysis General Procedure starting from 370 mg of Preparation 5i, Step A (036 mmol, 1 eq.), 150 mg (62%) of the desired product was obtained.

$^1$H NMR (500 MHz, DMSO-$d_6$) δ ppm 7.88 (d, 1H), 7.66 (s, 1H), 7.53 (d, 1H), 7.38 (t, 1H), 7.22 (dd, 1H), 7.22 (t, 1H), 7.16 (dd, 1H), 7.14 (t, 1H), 4.39 (t, 2H), 4.15 (t, 2H), 3.51 (s, 2H), 3.47 (t, 2H), 3.27 (t, 2H), 2.47 (s, 3H), 2.14 (m, 2H), 1.74 (m, 2H), 1.52 (m, 2H); $^{13}$C NMR (125 MHz, DMSO-$d_6$) δ ppm 126.7, 126.5, 122.6, 122.2, 119.1, 118.6, 116.8, 115.9, 91.0, 81.1, 68.8, 60.9, 47.2, 31.6, 31.0, 29.9, 24.2, 23.2, 17.7; HRMS-ESI (m/z): $[M+H]^+$ calcd for $C_{32}H_{33}FN_7O_4S_2$: 662.2014, found 662.2011.

Step B: 2-[[6-(1,3-benzothiazol-2-ylamino)-5-methyl-pyridazin-3-yl]-(4-hydroxybutyl)amino]-5-[3-[2-fluoro-4-[3-(3-sulfopropylamino)prop-1-ynyl]phenoxy]propyl]thiazole-4-carboxylic acid To a suspension of the product from Step A in dry acetonitrile oxathiolane 2,2-dioxide was added in one portion. The resulting mixture was stirred overnight at rt, where the disubstituted product also had formed (Example 147). The crude product was dissolved in DMSO, and then it was purified via reverse phase preparative chromatography (25 mM $NH_4HCO_3$ in water:MeCN) to obtain the desired product.

HRMS-ESI (m/z): $[M+H]^+$ calcd for $C_{35}H_{39}FN_7O_7S_3$: 784.2052, found 784.2052.

Example 149: 2-({6-[(1,3-Benzothiazol-2-yl)amino]-5-methylpyridazin-3-yl}(methyl)amino)-5-(1-methanesulfonylazetidin-3-yl)-1,3-thiazole-4-carboxylic acid

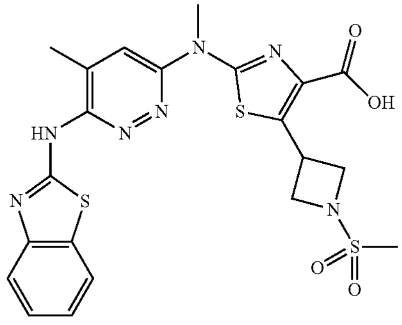 [SMILES: Cc1cc(N(C)c2nc(C(=O)O)c(C3CN(S(C)(=O)=O)C3)s2)nnc1Nc1nc2ccccc2s1]

Step A: ethyl 5-(1-methanesulfonylazetidin-3-yl)-2-[methyl(5-methyl-6-{[(Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 51 (24.6 mg, 0.04 mmol, 1 eq) in dichloromethane (3 mL) was added methanesulfonyl chloride (3.73 μL, 0.05 mmol, 1.2 eq), followed by a catalytic amount of 4-(dimethylamino)pyridine and triethylamine (0.01 mL, 0.08 mmol, 2 eq) and the mixture was stirred at ambient temperature overnight. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 4 g RediSep™ silica cartridge) eluting with a gradient of 0-100% ethyl acetate in iso-heptane afforded the desired product as an off-white solid (16.4 mg, 0.02 mmol, 59%).

LC/MS ($C_{29}H_{39}N_7O_5SiS_3$) 690 $[M+H]^+$; RT 1.41 (LCMS-V-B1)

$^1$H NMR (400 MHz, DMSO-d6) δ 7.87 (dd, J=7.6, 1.1 Hz, 1H), 7.71 (d, J=1.1 Hz, 1H), 7.51-7.39 (m, 2H), 7.29-7.22 (m, 1H), 5.87 (s, 2H), 4.61 (tt, J=8.4, 6.5 Hz, 1H), 4.39 (t, J=8.5 Hz, 2H), 4.30 (q, J=7.1 Hz, 2H), 3.93 (dd, J=8.3, 6.4 Hz, 2H), 3.80 (s, 3H), 3.76-3.67 (m, 2H), 3.10 (s, 3H), 2.47 (d, J=1.0 Hz, 3H), 1.32 (t, J=7.1 Hz, 3H), 1.00-0.88 (m, 2H), −0.11 (s, 9H).

Step B: ethyl 2-({6-[(1,3-benzothiazol-2-yl)amino]-5-methylpyridazin-3-yl}(methyl)amino)-5-(1-methanesulfonylazetidin-3-yl)-1,3-thiazole-4-carboxylate To a solution of the product from Step A (16.4 mg, 0.02 mmol, 1 eq) in dichloromethane (3 mL) was added trifluoroacetic acid (0.2 mL, 2.68 mmol, 113 eq) and the mixture was stirred at ambient temperature overnight. The reaction was diluted with dichloromethane, washed with saturated aqueous sodium bicarbonate (×2) then brine, dried (magnesium sulfate), and concentrated in vacuo. Purification by automated flash column chromatography (CombiFlash Rf, 4 g RediSep™ silica cartridge) eluting with a gradient of 0-10% methanol in dichloromethane afforded the desired product as a beige solid (10 mg, 0.02 mmol, 75%).

LC/MS ($C_{23}H_{25}N_7O_4S_3$) 560 $[M+H]^+$; RT 1.24 (LCMS-V-B1)

$^1$H NMR (400 MHz, DMSO-d6) δ 7.92 (br s, 1H), 7.72 (s, 1H), 7.51-7.42 (m, 1H), 7.40-7.34 (m, 1H), 7.27-7.15 (m, 1H), 4.68-4.54 (m, 1H), 4.49 (td, J=8.5, 2.9 Hz, 2H), 4.40 (t, 2H), 4.28 (q, 2H), 4.04 (dd, J=8.2, 6.5 Hz, 2H), 3.78 (s, 3H), 3.11 (s, 3H), 2.48 (s, 3H), 1.32 (t, J=7.1 Hz, 3H).

Step C: 2-({6-[(1,3-benzothiazol-2-yl)amino]-5-methylpyridazin-3-yl}(methyl)amino)-5-(1-methanesulfonylazetidin-3-yl)-1,3-thiazole-4-carboxylic acid To a solution of the product from Step B (10 mg, 0.02 mmol, 1 eq) in 1,4-dioxane (2 mL) was added 2M aqueous sodium hydroxide (0.2 mL, 0.4 mmol, 22.4 eq) and the mixture was heated at 60° C. for 1.5 h. Purification by reverse phase automated flash chromatography (CombiFlash Rf, C18 13 g RediSep column) eluting with a gradient of 5-95% acetonitrile in water afforded the desired product as a yellow solid (7.6 mg, 0.01 mmol, 80%) [as a sodium salt].

HRMS-ESI (m/z) [M+H]+ calcd for $C_{21}H_{22}N_7O_4S_3$: 532.0890, found 532.0894.

Example 150: 2-[[6-(1,3-Benzothiazol-2-ylamino)-5-methyl-pyridazin-3-yl]-[4-hydroxy-5-(methylamino)pentyl]amino]-5-[3-[4-[3-(dimethylamino)prop-1-ynyl]-2-fluoro-phenoxy]propyl]thiazole-4-carboxylic acid

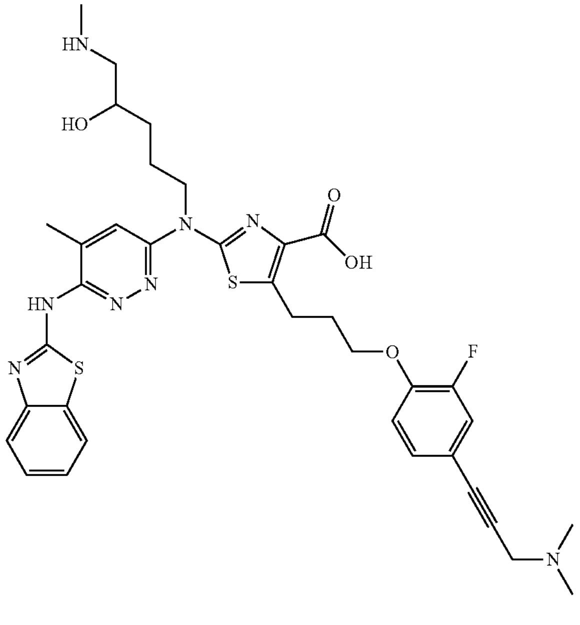 [SMILES: CNCC(O)CCCN(c1cc(C)c(Nc2nc3ccccc3s2)nn1)c1nc(C(=O)O)c(CCCOc2ccc(C#CCN(C)C)cc2F)s1]

Using Alkylation with tosylate General Procedure starting from Preparation 5b and methanamine as the appropriate amine, intermediate methyl 2-[[4-[tert-butyl(diphenyl)silyl]oxy-5-(methylamino)pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate was not isolated but after the volatiles was evaporated Deprotection and Hydrolysis General Procedure was applied to obtain the desired product.

HRMS-ESI (m/z): $[M+2H]^{2+}$ calcd for $C_{36}H_{43}FN_8O_4S_2$: 367.1411, found 367.1413.

Example 151: 2-[[6-(1,3-Benzothiazol-2-ylamino)-5-methyl-pyridazin-3-yl]-(4-hydroxybutyl)amino]-5-[3-[2-fluoro-4-[3-[methyl(3-sulfopropyl)amino]prop-1-ynyl]phenoxy]propyl]thiazole-4-carboxylic acid

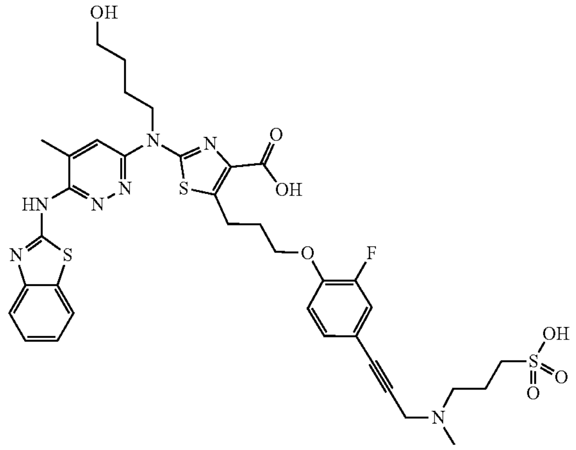 [SMILES: Cc1cc(N(CCCCO)c2nc(C(=O)O)c(CCCOc3ccc(C#CCN(C)CCCS(=O)(=O)O)cc3F)s2)nnc1Nc1nc2ccccc2s1]

Step A: 3-[methyl(prop-2-ynyl)amino]propane-1-sulfonic acid

To 0.34 mL of N-methylpropargylamine (4 mmol, 1 eq.) in 1 mL or MeCN was added 244 mg of oxathiolane 2,2-dioxide (2 mmol, 0.5 eq.) and the mixture was stirred at 60° C. for 3 h. After concentration, the residue was purified via flash column chromatography using DCM and MeOH as eluents to give 299 mg (78%) of the desired product.

$^1$H NMR (400 MHz, DMSO-$d_6$) δ ppm 10.10 (br, 1H), 4.01 (s, 2H), 3.75 (s, 1H), 3.12 (m, 2H), 2.72 (s, 3H), 2.59 (t, 2H), 1.94 (qui, 2H).

Step B: 3-[3-[4-[3-[2-[tert-butoxycarbonyl-[4-[tert-butyl(dimethyl)silyl]oxybutyl]amino]-4-methoxycarbonyl-thiazol-5-yl]propoxy]-3-fluoro-phenyl]prop-2-ynyl-methyl-amino]propane-1-sulfonic acid Using Sonogashira General Procedure starting from the product from Step A and Preparation 3c, Step A as starting materials, 303 mg (56%) of the desired product.

$^1$H NMR (400 MHz, DMSO-$d_6$) δ ppm 12.45 (vbrs, 1H), 7.45 (dd, 1H), 7.33 (dm, 1H), 7.18 (t, 1H), 4, 24 (brs, 2H), 4.16-4.06 (m, 4H), 4.02 (t, 2H), 3.75 (s, 3H), 3.58 (t, 2H), 3.22 (t, 2H), 2.80 (brs, 3H), 2.61 (brt, 2H), 2.08 (m, 2H), 1.97 (m, 2H), 1.68 (m, 2H), 1.57 (s, 9H), 1.43 (m, 2H), 0.82 (s, 9H), −0.01 (s, 6H).

Step C: 3-[3-[4-[3-[2-[4-[tert-butyl(dimethyl)silyl]oxybutylamino]-4-methoxycarbonyl-thiazol-5-yl]propoxy]-3-fluoro-phenyl]prop-2-ynyl-methyl-amino]propane-1-sulfonic acid Using Deprotection with HFIP General Procedure starting from the product from Step B as the appropriate carbamate, 200 mg (81%) of the desired product was obtained.

$^1$H NMR (500 MHz, DMSO-$d_6$) δ ppm 10.38 (s, 1H), 7.59 (t, 1H), 7.47 (dd, 1H), 7.33 (m, 1H), 7.18 (t, 1H), 4.28 (brs, 2H), 4.09 (t, 2H), 3.67 (s, 3H), 3.59 (t, 2H), 3.27 (brs, 2H), 3.17 (q, 2H), 3.12 (t, 2H), 2.82 (s, 3H), 2.62 (t, 2H), 2.00 (q, 2H), 2.00 (m, 2H), 1.54 (m, 2H), 1.49 (m, 2H), 0.84 (s, 9H), 0.02 (s, 6H); $^{13}$C NMR (125 MHz, DMSO-$d_6$) δ ppm 148.2, 129.6, 119.7, 115.4, 68.1, 62.6, 55.2, 51.7, 49.3, 45.8, 44.4, 40.0, 30.6, 30.2, 26.3, 25.6, 23.3, 21.0, −4.8.

Step D: 3-[3-[4-[3-[2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]-4-methoxycarbonyl-thiazol-5-yl]propoxy]-3-fluoro-phenyl]prop-2-ynyl-methyl-amino]propane-1-sulfonic acid Using Buchwald General Procedure II starting from the product from Step C and Preparation 4a as the appropriate halide, 270 mg (88%) of the desired product was obtained.

$^1$H NMR (500 MHz, DMSO-$d_6$) δ ppm 7.84 (d, 1H), 7.66 (s, 1H), 7.47 (dm, 1H), 7.47 (dd, 1H), 7.44 (t, 1H), 7.33 (d, 1H), 7.26 (td, 1H), 7.21 (t, 1H), 5.86 (s, 2H), 4.42 (t, 2H), 4.24 (br., 2H), 4.17 (t, 2H), 3.77 (s, 3H), 3.72 (t, 2H), 3.61 (t, 2H), 3.29 (br., 2H), 3.27 (t, 2H), 2.79 (br., 3H), 2.60 (br., 2H), 2.45 (s, 3H), 2.13 (m, 2H), 1.97 (br., 2H), 1.74 (m, 2H), 1.52 (m, 2H), 0.92 (t, 2H), 0.79 (s, 9H), −0.02 (s, 6H), −0.12 (s, 9H); $^{13}$C NMR (125 MHz, DMSO-$d_6$) δ ppm 129.5, 127.2, 123.5, 123.2, 119.7, 117.6, 115.4, 112.0, 72.9, 68.5, 66.7, 62.5, 51.9, 49.3, 46.5, 45.7, 40.0, 31.0, 29.7, 26.2, 23.8, 23.1, 21.1, 17.9, 17.8, −1.0, −4.9.

Step E: 2-[[6-(1,3-benzothiazol-2-ylamino)-5-methyl-pyridazin-3-yl]-(4-hydroxybutyl)amino]-5-[3-[2-fluoro-4-[3-[methyl(3-sulfopropyl)amino]prop-1-ynyl]phenoxy]propyl]thiazole-4-carboxylic acid The product from Step D and LiOH×$H_2O$ (10 eq.) in a 1:1 mixture of THF and water was kept at 50° C. for 18 h. After treating the reaction mixture with 2 mL of cc HCl at 0° C., the reaction was kept 50° C. for 1 h. After pouring the mixture onto cold ammonia solution, the precipitated material was filtered off and purified via reverse phase preparative chromatography (25 mM $NH_4HCO_3$ in water:MeCN) to give the desired product.

HRMS-ESI (m/z): $[M+H]^+$ calcd for $C_{36}H_{41}FN_7O_7S_3$: 798.2214 found: 798.2204.

Example 152: 5-(1-Acetylazetidin-3-yl)-2-({6-[(1,3-benzothiazol-2-yl)amino]-5-methylpyridazin-3-yl}(methyl)amino)-1,3-thiazole-4-carboxylic acid

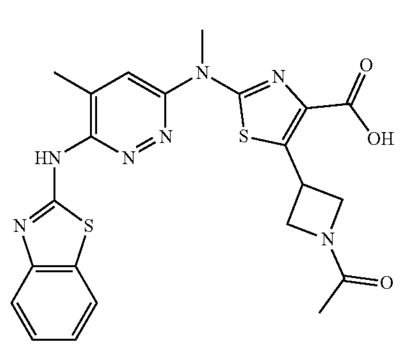 [SMILES: CC(=O)N1CC(c2sc(N(C)c3cc(C)c(Nc4nc5ccccc5s4)nn3)nc2C(=O)O)C1]

Step A: ethyl 5-(1-acetylazetidin-3-yl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 51 (100 mg, 0.16 mmol, 1 eq) in dichloromethane (5 mL) was added acetyl chloride (14 μL, 0.2 mmol, 1.2 eq) and triethylamine (0.05 mL, 0.33 mmol, 2 eq) and the mixture was stirred at ambient temperature for 4 h. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 4 g RediSep™ silica cartridge) eluting with a gradient of 0-100% ethyl acetate in iso-heptane afforded the desired product as a cream foam (67.7 mg, 0.1 mmol, 63%).

LC/MS ($C_{30}H_{39}N_7O_4SiS_2$) 654 $[M+H]^+$; RT 1.37 (LCMS-V-B1)

$^1$H NMR (400 MHz, DMSO-d6) δ 7.87 (dd, J=7.7, 1.1 Hz, 1H), 7.70 (d, J=1.2 Hz, 1H), 7.51-7.39 (m, 2H), 7.29-7.22 (m, 1H), 5.87 (s, 2H), 4.69-4.56 (m, 2H), 4.43-4.33 (m, 1H), 4.29 (q, 2H), 4.22-4.12 (m, 1H), 3.92 (dd, J=9.8, 5.3 Hz, 1H), 3.79 (s, 3H), 3.76-3.67 (m, 2H), 2.47 (d, J=1.0 Hz, 3H), 1.82 (s, 3H), 1.33 (t, J=7.1 Hz, 3H), 0.97-0.88 (m, 2H), −0.11 (s, 9H).

Step B: ethyl 5-(1-acetylazetidin-3-yl)-2-({6-[(1,3-benzothiazol-2-yl)amino]-5-methylpyridazin-3-yl}(methyl)amino)-1,3-thiazole-4-carboxylate To a solution of the product from Step A (67.7 mg, 0.1 mmol, 1 eq) in tetrahydrofuran (3 mL) was added tetrabutylammonium fluoride (1M in tetrahydrofuran; 0.04 mL, 0.31 mmol, 3 eq) and ethylenediamine (0.02 mL, 0.31 mmol, 3 eq) and the mixture was stirred at 60° C. overnight. The reaction was allowed to cool to ambient temperature, then partitioned between dichloromethane and saturated aqueous sodium bicarbonate and the organic phase was washed with brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow glass (10.5 mg, 0.02 mmol, 19%).

LC/MS ($C_{24}H_{25}N_7O_3S_2$) 524 $[M+H]^+$; RT 0.97 (LCMS-V-B1)

$^1$H NMR (400 MHz, DMSO-d6) δ 7.94 (br s, 1H), 7.72 (s, 1H), 7.55 (br s, 1H), 7.39 (t, J=7.5 Hz, 1H), 7.21 (t, J=7.6 Hz, 1H), 4.69-4.56 (m, 2H), 4.41-4.33 (m, 1H), 4.31 (q, 2H), 4.23-4.14 (m, 1H), 3.92 (dd, J=9.9, 5.3 Hz, 1H), 3.79 (s, 3H), 2.48 (s, 3H), 1.83 (s, 3H), 1.33 (t, J=7.1 Hz, 3H).

Step C: 5-(1-acetylazetidin-3-yl)-2-({6-[(1,3-benzothiazol-2-yl)amino]-5-methylpyridazin-3-yl}(methyl)amino)-1,3-thiazole-4-carboxylic acid To a solution of the product from Step B (10.5 mg, 0.02 mmol, 1 eq) in 1,4-dioxane (3 mL) was added a 1M aqueous lithium hydroxide (0.1 mL, 0.1 mmol, 5 eq) and the mixture was heated at 100° C. overnight. Purification by reverse phase automated flash chromatography (CombiFlash Rf, C18 13 g RediSep column) eluting with a gradient of 5-95% acetonitrile in water afforded the desired product as a white solid (2 mg, 4.04 μmol, 20%).

HRMS-ESI (m/z) [M+H]+ calcd for $C_{22}H_{22}N_7O_3S_2$: 496.1220, found 496.1252.

Example 153: 2-({6-[(1,3-Benzothiazol-2-yl)amino]-5-methylpyridazin-3-yl}(methyl)amino)-5-(1-phenylazetidin-3-yl)-1,3-thiazole-4-carboxylic acid

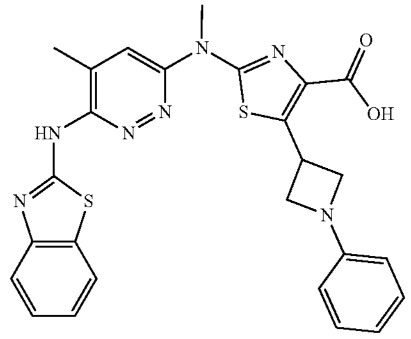 [SMILES: Cc1cc(N(C)c2nc(C(=O)O)c(C3CN(c4ccccc4)C3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(1-phenylazetidin-3-yl)-1,3-thiazole-4-carboxylate To a solution of the product from Preparation 51 (100 mg, 0.16 mmol, 1 eq) in 1,4-dioxane (3 mL) was added bromobenzene (20.6 μL, 0.2 mmol, 1.2 eq), cesium carbonate (160 mg, 0.49 mmol, 3 eq), N,N-diisopropylethylamine (0.08 mL, 0.49 mmol, 3 eq), Xantphos (18.9 mg, 0.03 mmol, 0.2 eq) and tris(dibenzylideneacetone)dipalladium(0)(15 mg, 0.02 mmol, 0.1 eq) and the mixture was heated at reflux overnight. The reaction was partitioned between dichloromethane and water, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow solid (44.2 mg, 0.06 mmol, 39%).

LC/MS ($C_{34}H_{41}N_7O_3SiS_2$) 688 $[M+H]^+$; RT 1.58 (LCMS-V-B1)

$^1$H NMR (400 MHz, DMSO-d6) δ 7.82 (dd, J=7.7, 1.1 Hz, 1H), 7.69 (d, J=1.1 Hz, 1H), 7.49-7.35 (m, 2H), 7.28-7.17 (m, 3H), 6.74 (tt, J=7.4, 1.1 Hz, 1H), 6.64-6.49 (m, 2H), 5.85 (s, 2H), 4.81-4.69 (m, 1H), 4.38-4.23 (m, 4H), 3.86 (dd, J=7.3, 5.8 Hz, 2H), 3.79 (s, 3H), 3.76-3.67 (m, 2H), 2.45 (d, J=1.0 Hz, 3H), 1.34 (t, J=7.1 Hz, 3H), 0.96-0.87 (m, 2H), −0.12 (s, 9H).

Step B: ethyl 2-({6-[(1,3-benzothiazol-2-yl)amino]-5-methylpyridazin-3-yl}(methyl)amino)-5-(1-phenylazetidin-3-yl)-1,3-thiazole-4-carboxylate To a solution of the product from Step A (44 mg, 0.06 mmol, 1 eq) in dichloromethane (5 mL) was added trifluoroacetic acid (0.5 mL, 6.71 mmol, 105 eq) and the mixture was stirred at ambient temperature overnight. The reaction was diluted with dichloromethane and washed with saturated aqueous sodium bicarbonate (×2) then brine, dried (magnesium sulfate), and concentrated in vacuo. Purification by automated flash column chromatography (CombiFlash Rf, 4 g RediSep™ silica cartridge) eluting with a gradient of 0-5% methanol in dichloromethane afforded the desired product as a yellow glass (18 mg, 0.03 mmol, 51%).

LC/MS ($C_{28}H_{27}N_7O_2S_2$) 558 $[M+H]^+$; RT 1.49 (LCMS-V-B1)

$^1$H NMR (400 MHz, DMSO-d6) δ 7.83 (br s, 1H), 7.70 (s, 1H), 7.52 (br s, 1H), 7.39-7.31 (m, 1H), 7.27-7.16 (m, 3H), 6.78-6.70 (m, 1H), 6.60-6.51 (m, 2H), 4.82-4.68 (m, 1H), 4.39-4.25 (m, 4H), 3.93-3.81 (m, 2H), 3.79 (s, 3H), 2.47 (s, 3H), 1.34 (t, J=7.1 Hz, 3H).

Step C: 2-({6-[(1,3-benzothiazol-2-yl)amino]-5-methylpyridazin-3-yl}(methyl)amine)-5-(1-phenylazetidin-3-yl)-1,3-thiazole-4-carboxylic acid To a solution of the product from Step B (18 mg, 0.03 mmol, 1 eq) in 1,4-dioxane (3 mL) was added IM aqueous lithium hydroxide (0.16 mL, 0.16 mmol, 5 eq) and the mixture was heated at reflux for 6 h. Purification by reverse phase automated flash chromatography (CombiFlash Rf, C18 13 g RediSep column) eluting with a gradient of 5-95% acetonitrile in water afforded the desired product as a yellow solid (9.5 mg, 0.02 mmol, 56%) [as a lithium salt].

HRMS-ESI (m/z) [M+H]+ calcd for $C_{26}H_{24}N_7O_2S_2$: 530.1427, found 530.1455.

Example 154: 5-[1-(Benzenesulfonyl)azetidin-3-yl]-2-({6-[(1,3-benzothiazol-2-yl)amino]-5-methylpyridazin-3-yl}(methyl)amino)-1,3-thiazole-4-carboxylic acid

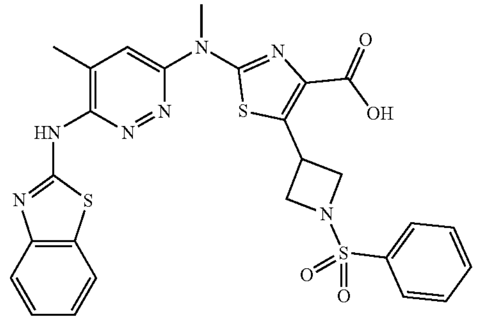 [SMILES: Cc1cc(N(C)c2nc(C(=O)O)c(C3CN(S(=O)(=O)c4ccccc4)C3)s2)nnc1Nc1nc2ccccc2s1]

Step A: ethyl 5-[1-(benzenesulfonyl)azetidin-3-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 51 (46.7 mg, 0.08 mmol, 1 eq) in dichloromethane (3 mL) was added benzenesulfonyl chloride (11.7 μL, 0.09 mmol, 1.2 eq), followed by 4-(dimethylamino)pyridine (2 mg, 0.02 mmol, 0.21 eq) and triethylamine (0.02 mL, 0.15 mmol, 2 eq) and the mixture was stirred at ambient temperature overnight. The reaction was diluted with dichloromethane and washed with saturated aqueous sodium bicarbonate then brine, then dried (magnesium sulfate) and concentrated in vacuo. Purification by automated flash column chromatography (CombiFlash Rf, 4 g RediSep™ silica cartridge) eluting with a gradient 0-67% ethyl acetate in iso-heptane afforded the desired product as a yellow glass (40.3 mg, 0.05 mmol, 70%).

LC/MS ($C_{34}H_{41}N_7O_5SiS_3$) 752 $[M+H]^+$; RT 1.47 (LCMS-V-B1)

$^1$H NMR (400 MHz, DMSO-d6) δ 7.97-7.86 (m, 3H), 7.81-7.72 (m, 2H), 7.70-7.60 (m, 2H), 7.54-7.41 (m, 2H), 7.31-7.25 (m, 1H), 5.89 (s, 2H), 4.52-4.39 (m, 1H), 4.29-4.18 (m, 4H), 3.79-3.67 (m, 7H), 2.47 (d, J=1.0 Hz, 3H), 1.27 (t, J=7.1 Hz, 3H), 0.98-0.89 (m, 2H), −0.10 (s, 9H).

Step B: ethyl 5-[1-(benzenesulfonyl)azetidin-3-yl]-2-({6-[(1,3-benzothiazol-2-yl)amino]-5-methylpyridazin-3-yl}(methyl)amino)-1,3-thiazole-4-carboxylate To a solution of the product from Step A (40.3 mg, 0.05 mmol, 1 eq) in dichloromethane (5 mL) was added trifluoroacetic acid (0.5 mL, 6.71 mmol, 125 eq) and the mixture was stirred at ambient temperature overnight. The reaction was diluted with dichloromethane and washed with saturated aqueous sodium bicarbonate (×2) then brine, dried (magnesium sulfate), and concentrated in vacuo. Purification by automated flash column chromatography (CombiFlash Rf, 4 g RediSep™ silica cartridge) eluting with a gradient of 0-6% methanol in dichloromethane afforded the desired product as a yellow solid (20 mg, 003 mmol, 60%).

LC/MS ($C_{28}H_{27}N_7O_4S_3$) 622 $[M+H]^+$; RT 1.37 (LCMS-V-B1)

$^1$H NMR (400 MHz, DMSO-d6) δ 8.00 (br s, 1H), 7.94-7.88 (m, 2H), 7.77 (t, J=7.6 Hz, 2H), 7.72-7.64 (m, 2H), 7.56 (br s, 1H), 7.40 (t, 1H), 7.24 (t, J=7.6 Hz, 1H), 4.46 (p, J=7.6 Hz, 1H), 4.30-4.18 (m, 4H), 3.81-3.66 (m, 5H), 2.45 (s, 3H), 1.26 (t, 3H).

Step C: 5-[1-(benzenesulfonyl)azetidin-3-yl]-2-({6-[(1,3-benzothiazol-2-yl)amino]-5-methylpyridazin-3-yl}(methyl)amino)-1,3-thiazole-4-carboxylic acid To a solution of the product from Step B (20 mg, 003 mmol, 1 eq) in 1,4-dioxane (3 mL) was added 1M aqueous lithium hydroxide (0.16 mL, 0.16 mmol, 5 eq) and the mixture was heated at 100° C. overnight. Purification by reverse phase automated flash chromatography (CombiFlash Rf, C18 15.5 g Gold RediSep column) eluting with a gradient of 5-95% acetonitrile in water afforded the desired product as a cream solid (4.9 mg, 0.01 mmol, 26%).

HRMS-ESI (m/z) [M+H]+ calcd for $C_{26}H_{24}N_7O_4S_3$: 594.1046, found 594.1060.

Example 155: 5-(1-Benzenesulfonamido-3-hydroxypropan-2-yl)-2-({6-[(1,3-benzothiazol-2-yl)amino]-5-methylpyridazin-3-yl}(methyl)amino)-1,3-thiazole-4-carboxylic acid

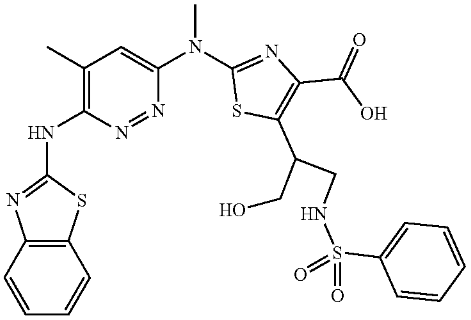 [SMILES: Cc1cc(N(C)c2nc(C(=O)O)c(C(CO)CNS(=O)(=O)c3ccccc3)s2)nnc1Nc1nc2ccccc2s1]

5-(1-Benzenesulfonamido-3-hydroxypropan-2-yl)-2-({6-[(1,3-benzothiazol-2-yl)amino]-5-methylpyridazin-3-yl}(methyl)amino)-1,3-thiazole-4-carboxylic acid (2.9 mg, 4.74 μmol, 15%) was isolated as a byproduct during the purification of Example 154, Step C.

HRMS-ESI (m/z) [M+H]+ calcd for $C_{26}H_{26}N_7O_5S_3$: 612.1152, found 612.1154

Example 156: 2-({6-[(1,3-Benzothiazol-2-yl)amino]-5-methylpyridazin-3-yl}(methyl)amino)-5-[1-(2-methylpropyl)azetidin-3-yl]-1,3-thiazole-4-carboxylic acid

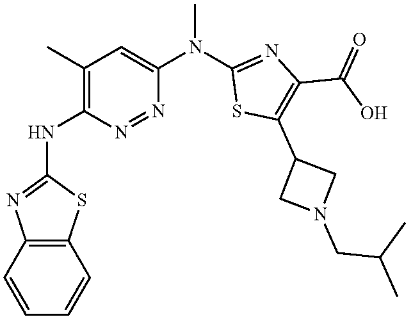 [SMILES: Cc1cc(N(C)c2nc(C(=O)O)c(C3CN(CC(C)C)C3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[1-(2-methylpropyl)azetidin-3-yl]-1,3-thiazole-4-carboxylate To a solution of the product from Preparation 51 (134 mg, 0.22 mmol, 1 eq) in 2:1 acetonitrile/dichloromethane (6 mL) was added isabutyraldehyde (0.04 mL, 0.44 mmol 2 eq) followed by sodium triacetoxyborohydride (139 mg, 0.66 mmol, 3 eq) and glacial acetic acid (10 μL) and the mixture was stirred at ambient temperature for 4.5 h. The reaction was partitioned between dichloromethane and saturated aqueous sodium bicarbonate, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-60% ethyl acetate in iso-heptane afforded the desired product as a cream foam (81.5 mg, 0.12 mmol, 56%).

LC/MS ($C_{32}H_{45}N_7O_3SiS_2$) 668 $[M+H]^+$; RT 1.25 (LCMS-V-B1)

$^1H$ NMR (400 MHz, DMSO-d6) δ 7.85-7.76 (m, 1H), 7.68 (d, 1H), 7.51-7.39 (m, 2H), 7.29-7.23 (m, 1H), 5.87 (s, 2H), 4.44-4.32 (m, 1H), 4.27 (q, J=7.1 Hz, 2H), 3.77 (s, 3H), 3.75-3.70 (m, 2H), 3.64 (t, J=7.0 Hz, 2H), 3.09 (t, J=6.4 Hz, 2H), 2.46 (d, J=1.0 Hz, 3H), 2.26 (d, J=7.1 Hz, 2H), 1.58 (hept, J=6.8 Hz, 1H), 1.31 (t, J=7.1 Hz, 3H), 0.98-0.86 (m, 8H), −0.11 (s, 9H).

Step B: ethyl 2-({6-[(1,3-benzothiazol-2-yl)amino]-5-methylpyridazin-3-yl}(methyl)amino)-5-[1-(2-methylpropyl)azetidin-3-yl]-1,3-thiazole-4-carboxylate To a cooled solution of the product from Step A (81.5 mg, 0.12 mmol, 1 eq) in dichloromethane (5 mL) was added trifluoroacetic acid (0.5 mL, 6.71 mmol, 55 eq) and the mixture was stirred at ambient temperature overnight. The reaction was quenched by the addition of saturated aqueous sodium bicarbonate, then extracted with dichloromethane and the organic extract was washed with brine, dried (magnesium sulfate), and concentrated in vacuo. Purification by automated flash column chromatography (CombiFlash Rf, 12 g RediSep™ silica cartridge) eluting with a gradient of 0-5% methanol in dichloromethane afforded the desired product as a yellow solid (50 mg, 0.09 mmol, 76%).

LC/MS ($C_{26}H_{31}N_7O_2S_2$) 538 $[M+H]^+$; RT 0.91 (LCMS-V-B1)

$^1H$ NMR (400 MHz, DMSO-d6) δ 7.87 (s, 1H), 7.70 (s, 1H), 7.52 (br s, I H), 7.40 (t, J=7.6 Hz, 1H), 7.22 (t, J=7.5 Hz, 1H), 4.44-4.33 (m, 1H), 4.28 (q, J=7.1 Hz, 2H), 3.77 (s, 3H), 3.64 (t, J=7.0 Hz, 2H), 3.10 (t, J=6.3 Hz, 2H), 2.47 (s, 3H), 2.27 (d, J=7.0 Hz, 2H), 1.66-1.51 (m, 1H), 1.32 (t, J=7.1 Hz, 3H), 0.93 (d, J=6.6 Hz, 6H).

Step C: 2-({6-[(1,3-benzothiazol-2-yl)amino]-5-methylpyridazin-3-yl}(methyl)amino)-5-[1-(2-methylpropyl)azetidin-3-yl]-1,3-thiazole-4-carboxylic acid To a solution of the product from Step B (50 mg, 0.09 mmol, 1 eq) in 1,4-dioxane (3 mL) was added 1M aqueous lithium hydroxide (0.46 mL, 0.46 mmol, 5 eq) and the mixture was heated at 100° C. overnight. Purification by reverse phase automated flash chromatography (CombiFlash Rf, C18 13 g RediSep column) eluting with a gradient of 5-95% acetonitrile in water afforded the desired product as a yellow solid (34.2 mg, 0.07 mmol, 72%).

HRMS-ESI (m/z) [M+H]+ calcd for $C_{24}H_{28}N_7O_2S_2$: 510.1740, found 510.1776.

Example 157: 2-({6-[(1,3-Benzothiazol-2-yl)amino]-5-methylpyridazin-3-yl}(methyl)amino)-5-(1-methylazetidin-3-yl)-1,3-thiazole-4-carboxylic acid

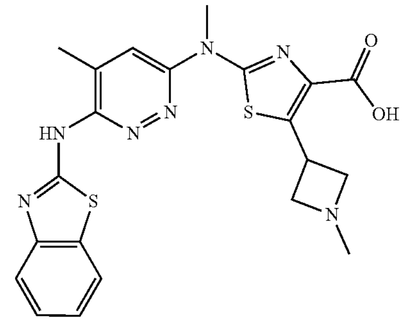 [SMILES: Cc1cc(N(C)c2nc(C(=O)O)c(C3CN(C)C3)s2)nnc1Nc1nc2ccccc2s1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-(1-methylazetidin-3-yl)-1,3-thiazole-4-carboxylate To a solution of the product from Preparation 51 (134 mg, 0.22 mmol, 1 eq) in 2:1 acetonitrile/dichloromethane (6 mL) was added formaldehyde (37% in water; 0.03 mL, 0.44 mmol, 2 eq) followed by sodium triacetoxyborohydride (139 mg, 0.66 mmol, 3 eq) and glacial acetic acid (10 μL) and the mixture was stirred at ambient temperature for 4.5 h. The reaction was diluted with dichloromethane then washed with saturated aqueous sodium bicarbonate followed by brine, dried (magnesium sulfate), and concentrated in vacuo. Purification by automated flash column chromatography (CombiFlash Rf, 12 g RediSep™ silica cartridge) eluting with a gradient of 0-100% ethyl acetate in iso-heptane afforded the desired product as a cream solid (65 mg, 0.1 mmol, 47%).

LC/MS ($C_{29}H_{39}N_7O_3SiS_2$) 626 $[M+H]^+$; RT 1.18 (LCMS-V-B1)

$^1H$ NMR (400 MHz, DMSO-d6) δ 7.89-7.82 (m, 1H), 7.68 (d, J=1.2 Hz, 1H) 7.53-7.39 (m, 2H), 7.28-7.22 (m, 1H), 5.86 (s, 2H), 4.42-430 (m, 1H), 4.27 (q, J=7.1 Hz, 2H), 3.77 (s, 3H), 3.76-3.69 (m, 2H), 3.65 (t, J=7.2 Hz, 2H), 3.18-3.10 (m, 2H), 2.46 (d, J=1.0 Hz, 3H), 2.29 (s, 3H), 1.31 (t, J=7.1 Hz, 3H), 0.97-0.86 (m, 2H), −0.11 (s, 9H).

Step B: ethyl 2-({6-[(1,3-benzothiazol-2-yl)amino]-5-methylpyridazin-3-yl}(methyl)amino)-5-(1-methylazetidin-3-yl)-1,3-thiazole-4-carboxylate To a cooled solution of the product from Step A (65 mg, 0.1 mmol, 1 eq) in dichloromethane (3 mL) was added trifluoroacetic acid (0.3 mL, 4.03 mmol, 38.8 eq) and the mixture was stirred at ambient temperature overnight. The reaction was quenched by the addition of saturated aqueous sodium bicarbonate, then extracted with dichloromethane and the organic extract was washed with brine, dried (magnesium sulfate), and concentrated in vacuo. Purification by automated flash column chromatography (CombiFlash Rf, 12 g RediSep™ silica cartridge) eluting with a gradient of 0-10% methanol in dichloromethane afforded the desired product as a yellow solid (40 mg, 0.08 mmol, 78%).

LC/MS ($C_{23}H_{25}N_7O_2S_2$) 496 $[M+H]^+$; RT 0.80 (LCMS-V-B1)

$^1H$ NMR (400 MHz, DMSO-d6) δ 7.92 (d, J=7.8 Hz, 1H), 7.69 (d, J=1.2 Hz 1H), 7.53 (s, 1H), 7.44-7.32 (m, 1H), 7.25-7.16 (m, 1H), 4.42-4.30 (m, 1H), 4.27 (q, 37.1 Hz, 2H), 3.76 (s, 3H), 3.65 (t, J=7.2 Hz, 2H), 3.15 (t, 2H), 2.47 (d, J=1.0 Hz, 3H), 2.29 (s, 3H), 1.31 (t, J=7.1 Hz, 3H).

Step C: 2-({6-[(1,3-benzothiazol-2-yl)amino]-5-methylpyridazin-3-yl}(methyl)amino)-5-(1-methylazetidin-3-yl)-1,3-thiazole-4-carboxylic acid To a solution of the product from Step B (40 mg, 0.08 mmol, 1 eq) in 1,4-dioxane (3 mL) was added 1M aqueous lithium hydroxide (0.4 mL, 0.4 mmol, 5 eq) and the mixture was heated at 100° C. overnight. Purification by reverse phase automated flash chromatography (CombiFlash Rf, C18 13 g RediSep column) eluting with a gradient of 5-95% acetonitrile in water afforded the desired product as a yellow solid (15.5 mg, 0.03 mmol, 41%).

HRMS-ESI (m/z) [M+H]+ calcd for $C_{21}H_{22}N_7O_2S_2$: 468.1271, found 468.1301.

Example 158: 2-({6-[(1,3-Benzothiazol-2-yl)amino]-5-methylpyridazin-3-yl}(3-carboxypropyl)amino)-1,3-thiazole-4-carboxylic acid

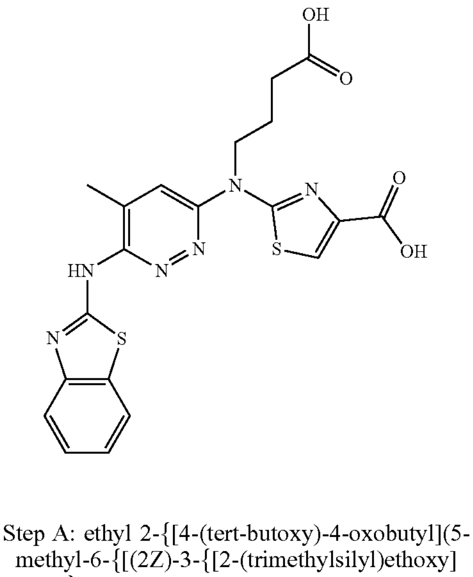

Step A: ethyl 2-{[4-(tert-butoxy)-4-oxobutyl](5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 3ze (1.74 g, 5.53 mmol, 1.5 eq) in 1,4-dioxane (60 mL) was added the product from Preparation 4a (1.5 g, 3.69 mmol, 1 eq), N,N-diisopropylethylamine (1.93 mL, 11.1 mmol, 3 eq), cesium carbonate (3.6 g, 11.1 mmol, 3 eq) and Xantphos (427 mg, 0.74 mmol, 0.2 eq) and the mixture was sparged with nitrogen (10 min). Tris(dibenzylideneacetone)dipalladium(0)(338 mg, 0.37 mmol, 0.1 eq) was added and the mixture was heated in a sealed flask at 140° C. for 2 h. The reaction was allowed to cool to ambient temperature then partitioned between water and ethyl acetate, the aqueous phase was extracted with ethyl acetate (3×80 mL), and the combined organic extracts were washed with brine, dried (magnesium sulfate), and concentrated in vacuo. Purification by automated flash column chromatography (CombiFlash Rf, 40 g RediSep™ silica cartridge) eluting with a gradient of 0-25% ethyl acetate in iso-heptane afforded the desired product as a pale yellow solid (0.93 g, 1.36 mmol, 37%).

LC/MS ($C_{32}H_{44}N_6O_5SiS_2$) 685 $[M+H]^+$; RT 1.75 (LCMS-V-B1)

$^1H$ NMR (400 MHz, DMSO-d6) δ 7.96 (s, 1H), 7.87-7.92 (m, 1H), 7.76 (d, J=1.2 Hz, 1H), 7.47-7.40 (m, 2H), 7.28-7.22 (m, 1H), 5.878 (s, 2H), 4.42 (t, J=7.4 Hz, 2H), 4.28 (q, J=7.1 Hz, 2H), 3.79-3.67 (m, 2H), 2.47 (d, J=1.0 Hz, 3H), 2.36 (t, J=7.3 Hz, 2H), 1.95 (p, J=7.4 Hz, 2H), 1.37 (s, 9H), 1.31 (t, J=7.1 Hz, 3H), 0.96-0.88 (m, 2H), −0.11 (s, 9H).

Step B: 4-({6-[(1,3-benzothiazol-2-yl)amino]-5-methylpyridazin-3-yl}[4-(ethoxycarbonyl)-1,3-thiazol-2-yl]amino)butanoic acid To a solution of the product from Step A (929 mg, 1.36 mmol, 1 eq) in dichloromethane (45 mL) was added trifluoroacetic acid (8.31 mL, 109 mmol, 80 eq) and the mixture was stirred at ambient temperature for 4 h. The reaction was quenched by the addition of saturated aqueous sodium bicarbonate then extracted with dichloromethane (3×40 mL) and the combined organic extracts were washed with brine, dried (magnesium sulfate), and concentrated in vacuo. Purification by automated flash column chromatography (CombiFlash Rf, 24 g RediSep™ silica cartridge) eluting with a gradient of 0-20% methanol in dichloromethane afforded the desired product as a yellow solid (186.8 mg, 0.37 mmol, 28%).

LC/MS ($C_{22}H_{22}N_6O_4S_2$) 499 $[M+H]^+$; RT 1.27 (LCMS-V-B1)

$^1H$ NMR (400 MHz, DMSO-d6) δ 9.23 (br s, 2H), 7.97 (s, 1H), 7.95-7.87 (m, 1H), 7.82 (s, 1H), 7.54 (br s, 1H), 7.42-7.36 (m, 1H), 7.25-7.18 (m, 1H), 4.39 (t, J=7.7 Hz, 2H), 4.29 (q, J=7.1 Hz, 2H), 2.47 (s, 3H), 2.39 (t, J=7.2 Hz, 2H), 2.01-1.98 (m, 2H), 1.31 (t, J=7.1 Hz, 2H).

Step C: 2-({6-[(1,3-benzothiazol-2-yl)amino]-5-methylpyridazin-3-yl}(3-carboxypropyl)amino)-1,3-thiazole-4-carboxylic acid To a solution of the product from Step B (80 mg, 0.16 mmol, 1 eq) in 1,4-dioxane (10 mL) was added lithium hydroxide monohydrate (13.5 mg, 0.32 mmol, 2 eq) and the mixture was heated at reflux for 2 h. The reaction was concentrated in vacuo and purification by reverse phase automated flash chromatography (CombiFlash Rf, C18 13 g RediSep column) eluting with 5-95% acetonitrile in water afforded a crude product. This was dissolved in methanol and a few drops of triethylamine then loaded onto a methanol-conditioned PE-AX cartridge, washed successively with methanol and dichloromethane, then eluted with 10% formic acid in dichloromethane, and concentrated in vacuo to afford the desired product as a yellow solid (28.9 mg, 0.06 mmol, 38%).

HRMS-ESI (m/z) [M+H]+ calcd for $C_{20}H_{19}N_6O_4S_2$: 471.0904, found 471.0915.

Example 159: 2-({6-[(1,3-Benzothiazol-2-yl)amino]-5-methylpyridazin-3-yl}(methyl)amino)-5-[1-(benzylcarbamoyl)azetidin-3-yl]-1,3-thiazole-4-carboxylic acid

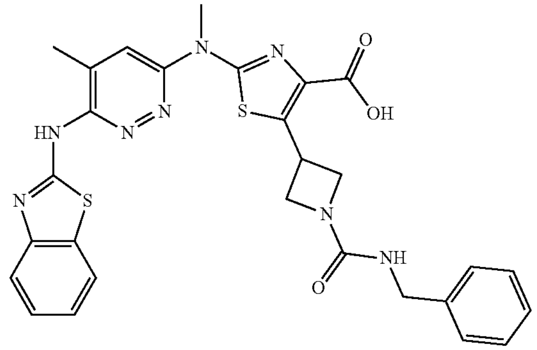 [SMILES: Cc1cc(N(C)c2nc(C(=O)O)c(C3CN(C(=O)NCc4ccccc4)C3)s2)nnc1Nc1nc2ccccc2s1]

Step A: ethyl 5-[1-(benzylcarbamoyl)azetidin-3-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 51 (150 mg, 0.25 mmol, 1 eq) in dichloromethane (5 mL) was added benzyl isocyanate (0.04 mL, 0.29 mmol, 1.2 eq) followed by triethylamine (0.07 mL, 0.49 mmol, 2 eq) and the mixture was stirred at ambient temperature overnight. The reaction was partitioned between dichloromethane and saturated aqueous ammonium chloride, and the organic phase was washed with brine, dried (magnesium sulfate), and concentrated in vacuo. Purification by automated flash column chromatography (CombiFlash Rf, 12 g RediSep™ silica cartridge) eluting with a gradient of 0-100% ethyl acetate in iso-heptane afforded the desired product as a yellow solid (125 mg, 0.17 mmol, 68%).

LC/MS ($C_{36}H_{44}N_8O_4SiS_2$) 745 $[M+H]^+$; RT 1.43 (LCMS-V-B1)

$^1H$ NMR (400 MHz, DMSO-d6) δ 7.84 (dd, J=7.5, 1.1 Hz, 1H), 7.70 (d, J=1.2 Hz, 1H), 7.51-7.39 (m, 2H), 7.35-7.20 (m, 5H), 7.19 ((d, J=6.3, 2.8 Hz, 1H), 7.08 (t, J=6.0 Hz, 1H), 5.87 (s, 2H), 4.64-4.51 (m, 1H), 4.36 (t, J=8.4 Hz, 2H), 4.29 (q, J=7.1 Hz, 2H), 4.24 (d, J=6.0 Hz, 2H), 3.88 (dd, J=8.2, 6.0 Hz, 3.79 (s, 3H), 3.76-3.69 (m, 2H), 2.47 (d, J=1.0 Hz, 3H), 1.32 (t, J=7.1 Hz, 3H), 0.97-0.88 (m, 2H), −0.11 (s, 9H).

Step B: ethyl 2-({6-[(1,3-benzothiazol-2-yl)amino]-5-methylpyridazin-3-yl}(methyl)amino)-5-[1-(benzylcarbamoyl)azetidin-3-yl]-1,3-thiazole-4-carboxylate To a solution of the product from Step A (125 mg, 0.17 mmol, 1 eq) in dichloromethane (5 mL) was added trifluoroacetic acid (0.7 mL, 9.39 mmol, 56 eq) and the mixture was stirred at ambient temperature overnight. The reaction was quenched by the addition of saturated aqueous sodium bicarbonate then extracted with dichloromethane, and the organic extract was washed with brine, dried (magnesium sulfate), and concentrated in vacuo. Purification by automated flash column chromatography (CombiFlash Rf, 12 g RediSep™ silica cartridge) eluting with a gradient of 0-9% methanol in dichloromethane afforded the desired product as a yellow glass (87.6 mg, 0.14 mmol, 85%).

LC/MS ($C_{30}H_{30}N_8O_3S_2$) 615 $[M+H]^+$; RT 1.10 (LCMS-V-B1)

$^1H$ NMR (400 MHz, DMSO-d6) δ 11.04 (br s, 1H), 7.95 (br s, 1H), 7.73-7.62 (m, 1H), 7.50-7.34 (m, 1H), 7.34-7.15 (m, 7H), 7.07 (t, J=6.0 Hz, 1H), 4.62-4.52 (m, 1H), 4.36 (t, 2H), 4.29 (q, 2H), 4.24 (d, 2H), 3.94-3.83 (m, 2H), 3.77 (s, 3H), 2.47 (d, 3H), 1.32 (t, J=7.1 Hz, 3H).

Step C: 2-({6-[(1,3-benzothiazol-2-yl)amino]-5-methylpyridazin-3-yl}(methyl)amino)-5-[1-(benzylcarbamoyl)azetidin-3-yl]-1,3-thiazole-4-carboxylic acid To a solution of the product from Step B (87.6 mg, 0.14 mmol, 1 eq) in 1,4-dioxane (5 mL) was added 1M aqueous lithium hydroxide (0.71 mL, 0.71 mmol, 5 eq) and the mixture was heated at 100° C. overnight. Purification by reverse phase automated flash chromatography (CombiFlash Rf, C18 13 g RediSep column) eluting with a gradient of 5-95% acetonitrile in water afforded the desired product as a yellow solid (25.6 mg, 0.04 mmol, 31%).

HRMS-ESI (m/z) [M+H]+ calcd for $C_{28}H_{27}N_8O_3S_2$: 587.1642, found 587.1669.

Example 160: 2-({6-[(1,3-Benzothiazol-2-yl)amino]-5-methylpyridazin-3-yl}(methyl)amino)-5-[1-(ethylcarbamoyl)azetidin-3-yl]-1,3-thiazole-4-carboxylic acid

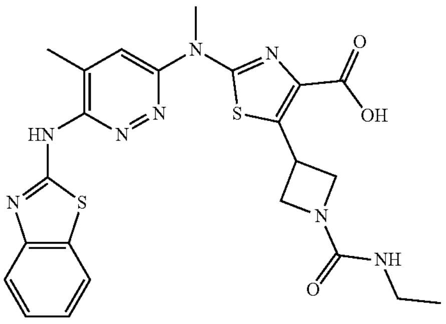 [SMILES: CCNC(=O)N1CC(c2sc(N(C)c3cc(C)c(Nc4nc5ccccc5s4)nn3)nc2C(=O)O)C1]

Step A: ethyl 5-[1-(ethylcarbamoyl)azetidin-3-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 51 (100 mg, 0.16 mmol, 1 eq) in dichloromethane (3 mL) was added ethyl isocyanate (0.02 mL, 0.2 mmol, 1.2 eq) followed by triethylamine (0.03 mL, 0.25 mmol, 1.5 eq) and the mixture was stirred at ambient temperature overnight. The reaction was partitioned between dichloromethane and saturated aqueous ammonium chloride, and the organic phase was washed with brine, dried (magnesium sulfate), and concentrated in vacuo. Purification by automated flash column chromatography (CombiFlash Rf, 4 g RediSep™ silica cartridge) eluting with a gradient of 0-100% ethyl acetate in iso-heptane afforded the desired product as a cream solid (78 mg, 0.11 mmol, 70%).

LC/MS ($C_{31}H_{42}N_8O_4SiS_2$) 683 $[M+H]^+$; RT 1.38 (LCMS-V-B1)

$^1H$ NMR (400 MHz, DMSO-d6) δ 7.86 (dd, J=7.6, 1.1 Hz, 1H), 7.69 (d, J=1.1 Hz, 1H), 7.51-7.39 (m, 2H) 7.29-7.20 (m, 1H), 6.46 (t, J=5.6 Hz, 1H), 5.87 (s, 2H), 4.61-4.49 (m, 1H), 4.35-4.23 (m, 4H), 3.82 (dd, J=8.2, 6.0 Hz, 2H), 3.79 (s, 3H), 3.77-3.68 (m, 2H), 3.09-3.01 (m, 2H), 2.47 (d, J=1.0 Hz, 3H), 1.32 (t, J=7.1 Hz, 3H), 1.03 (t, J=7.1 Hz, 3H) 1.00-0.88 (m, 2H), −0.11 (s, 9H).

Step B: ethyl 2-({6-[(1,3-benzothiazol-2-yl)amino]-5-methylpyridazin-3-yl}(methyl)amino)-5-[1-(ethylcarbamoyl)azetidin-3-yl]-1,3-thiazole-4-carboxylate To a solution of the product from Step A (78 mg, 0.11 mmol, 1 eq) in dichloromethane (3 mL) was added trifluoroacetic acid (0.4 mL, 5.37 mmol, 47 eq) and the mixture was stirred at ambient temperature overnight. The reaction was quenched by the addition of saturated aqueous sodium bicarbonate and extracted with dichloromethane, and the organic extract was washed with brine, dried (magnesium sulfate), and concentrated in vacuo. Purification by automated flash column chromatography (CombiFlash Rf, 4 g RediSep™ silica cartridge) eluting with a gradient of 0-10% methanol in dichloromethane afforded the desired product as a yellow glass (44 mg, 0.08 mmol, 70%).

LC/MS ($C_{25}H_{28}N_8O_3S_2$) 553 $[M+H]^+$; RT 1.00 (LCMS-V-B1)

$^1H$ NMR (400 MHz, DMSO-d6) δ 11.18 (br s, 1H), 7.93 (br s, 1H), 7.70 (s, 1H), 7.46 (br s, 1H), 7.43-7.34 (m, 1H), 7.27-7.14 (m, 1H), 6.46 (t, J=5.6 Hz, 1H), 4.62-4.48 (m, 1H), 4.36-4.22 (m, 4H), 3.87-3.79 (m, 2H), 3.77 (s, 3H), 3.11-2.98 (m, 2H), 2.47 (s, 3H), 1.32 (t, J=7.1 Hz, 3H), 1.02 (t, 3H).

Step C: 2-({6-[(1,3-benzothiazol-2-yl)amino]-5-methylpyridazin-3-yl}(methyl)amino)-5-[1-(ethylcarbamoyl)azetidin-3-yl]-1,3-thiazole-4-carboxylic acid To a solution of the product from Step B (44 mg, 0.08 mmol 1 eq) in 1,4-dioxane (3 mL) was added 1M aqueous lithium hydroxide (0.4 mL, 0.4 mmol, 5 eq) and the mixture was heated at 100° C. for 4.5 h. Purification by reverse phase automated flash chromatography (CombiFlash Rf, C18 13 g RediSep column) eluting with a gradient of 5-95% acetonitrile in water afforded the desired product as a yellow solid (27.4 mg, 0.05 mmol, 66%) [as a lithium salt].

HRMS-ESI (m/z) [M+H]+ calcd for $C_{23}H_{25}N_8O_3S_2$: 525.1486, found 525.1516.

Example 161: 2-({6-[(1,3-Benzothiazol-2-yl)amino]-5-methylpyridazin-3-yl}(methyl)amino)-5-[(2S)-3-{4-[3-(dimethylamino)prop-1-yn-1-yl]-2-fluorophenoxy}-2-methylpropyl]-1,3-thiazole-4-carboxylic acid

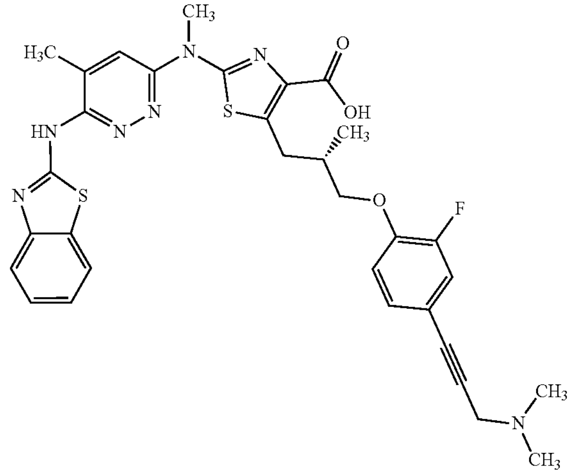 [SMILES: Cc1cc(N(C)c2nc(C(=O)O)c(C[C@H](C)COc3ccc(C#CCN(C)C)cc3F)s2)nnc1Nc1nc2ccccc2s1]

Step A: ethyl 5-[(2S)-3-{4-[3-(dimethylamino)prop-1-yn-1-yl]-2-fluorophenoxy}-2-methylpropyl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 3zf (40 mg, 0.09 mmol, 1 eq) in 1,4-dioxane (3 mL) was added Preparation 4a (37.6 mg, 0.09 mmol, 1 eq), N,N-diisopropylethylamine (0.05 mL, 0.28 mmol, 3 eq), cesium carbonate (90.2 mg, 0.28 mmol, 3 eq) and Xantphos (10.7 mg, 0.02 mmol, 0.2 eq), followed by tris(dibenzylideneacetone)dipalladium (0)(8.45 mg, 0.01 mmol, 0.1 eq) and the mixture was heated at 100° C. for 24 h then allowed to cool to ambient temperature. The reaction was partitioned between dichloromethane and water, and the organic phase was washed with brine, dried (magnesium sulfate), and concentrated in vacuo. Purification by automated flash column chromatography (CombiFlash Rf, 4 g RediSep™ silica cartridge) eluting with a gradient of 0-7% methanol in dichloromethane afforded the desired product as a brown glass (30.7 mg, 0.04 mmol, 41%).

LC/MS ($C_{40}H_{50}FN_7O_4SiS_2$) 804 $[M+H]^+$; RT 1.59 (LCMS-V-B1)

$^1H$ NMR (400 MHz, DMSO-d6) δ 7.88-7.81 (m, 1H), 7.67 (d, J=1.1 Hz, 1H), 7.51-7.39 (m, 2H), 7.34-7.23 (m, 2H), 7.22-7.11 (m, 2H), 5.86 (s, 2H), 4.26 (q, J=7.1 Hz, 2H), 4.07-3.94 (m, 2H), 3.78 (s, 2H), 3.76-3.68 (m, 2H), 3.37 (s, 3H), 3.32-3.26 (m, 1H), 3.18-3.06 (m, 1H), 2.60-2.52 (m, 1H), 2.46 (d, J=1.0 Hz, 3H), 2.19 (s, 6H), 1.30 (t, J=7.1 Hz, 3H), 1.04 (d, J=6.7 Hz, 3H), 0.97-0.88 (m, 2H), −0.11 (s, 9H).

Step B: ethyl 2-({6-[(1,3-benzothiazol-2-yl)amino]-5-methylpyridazin-3-yl}(methyl)amino)-5-[(2S)-3-{4-[3-(dimethylamino)prop-1-yn-1-yl]-2-fluorophenoxy}-2-methylpropyl]-1,3-thiazole-4-carboxylate To a solution of the product from Step A (30.7 mg, 0.04 mmol, 1 eq) in tetrahydrofuran (5 mL) was added tetrabutylammonium fluoride (1M in tetrahydrofuran, 0.22 mL, 0.22 mmol, 6 eq) and ethylenediamine (0.02 mL, 0.22 mmol, 6 eq) in tetrahydrofuran (5 mL) and the mixture was heated at reflux overnight. The reaction was partitioned between ethyl acetate and water, the aqueous phase was extracted with ethyl acetate (×2) then dichloromethane (×2), and the combined organic extracts were dried (magnesium sulfate) and concentrated in vacuo to afford the desired product that was used directly in the next step without further purification.

Step C: 2-({6-[(1,3-benzothiazol-2-yl)amino]-5-methylpyridazin-3-yl}(methyl)amino)-5-[(2S)-3-{4-[3-(dimethylamino)prop-1-yn-1-yl]-2-fluorophenoxy}-2-methylpropyl]-1,3-thiazole-4-carboxylic acid To a solution of the product from Step B (38 mg, 0.06 mmol, 1 eq) in 1,4-dioxane (3 mL) was added 1M aqueous lithium hydroxide (0.56 mL, 0.56 mmol, 10 eq) and the mixture was heated at 100+ C. for 2.5 h. The reaction was allowed to cool to ambient temperature and purification by reverse phase automated flash chromatography (CombiFlash Rf, C18 13 g RediSep column) eluting with a gradient of 5-95% acetonitrile in water afforded a brown glass. The material was dissolved in a mixture of dichloromethane and methanol, and applied to a 2 g PE-AX cartridge (preconditioned with dichloromethane then methanol). The cartridge was washed with dichloromethane followed by methanol, then elution with 10% formic acid in dichloromethane, solvent removal, and drying under vacuum afforded the desired product as a brown glass (6.4 mg, 0.01 mmol, 18%) [as a formic acid salt].

HRMS-ESI (m/z) [M+H]+ calcd for $C_{32}H_{33}FN_7O_3S_2$: 646.2065, found 646.2110.

Example 162: 2-({6-[(1,3-Benzothiazol-2-yl)amino]-5-methylpyridazin-3-yl}(methyl)amino)-5-[(1E)-2-methyl-3-phenoxyprop-1-en-1-yl]-1,3-thiazole-4-carboxylic acid

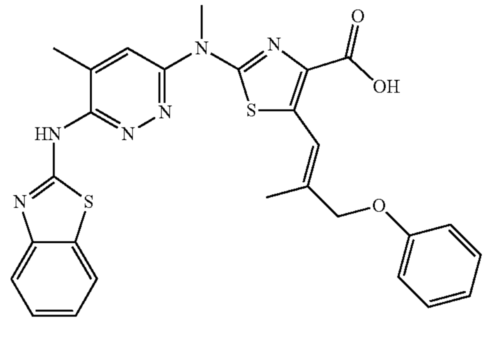 [SMILES: C/C(=C\c1sc(N(C)c2cc(C)c(Nc3nc4ccccc4s3)nn2)nc1C(=O)O)COc1ccccc1]

Step A: ethyl 2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-5-[(1E)-2-methyl-3-phenoxyprop-1-en-1-yl]-1,3-thiazole-4-carboxylate To a solution of the product from Preparation 5m (160 mg, 0.26 mmol, 1 eq) in toluene (3 mL) was added phenol (34 µL, 0.38 mmol, 1.5 eq), triphenylphosphine (100 mg, 0.38 mmol, 1.5 eq) and diisopropylazodicarboxylate (75 µL, 0.38 mmol, 1.5 eq) and the mixture was heated at 120° C. for 1 h under microwave irradiation. The reaction was partitioned between dichloromethane and water, and the organic phase was separated and dried (PTFE phase separator) and concentrated in vacuo. Purification by automated flash column chromatography (CombiFlash Rf, 4 g RediSep™ silica cartridge) eluting with a gradient of 0-60% ethyl acetate in iso-heptane afforded the desired product as a yellow gum (100 mg, 0.14 mmol, 56%).

LC/MS ($C_{35}H_{42}N_6O_4SiS_2$) 703 $[M+H]^+$; RT 3.12 (LCMS-V-C)

$^1H$ NMR (400 MHz, DMSO-d6) δ 7.86-7.81 (m, 1H), 7.72 (d, 1H), 7.51-7.40 (m, 2H), 7.36-7.21 (m, 4H), 7.06-7.00 (m, 2H), 6.99-6.93 (m, 1H), 5.87 (s, 2H), 4.68 (s, 2H), 4.26 (q, J=7.1 Hz, 1H), 3.81 (s, 3H), 3.76-3.68 (m, 2H), 2.46 (s, 3H), 2.06 (s, 3H), 1.28 (t, 3H), 0.97-0.88 (m, 2H), −0.11 (s, 9H).

Step B: ethyl 2-({6-[(1,3-benzothiazol-2-yl)amino]-5-methylpyridazin-3-yl}(methyl)amino)-5-[(1E)-2-methyl-3-phenoxyprop-1-en-1-yl]-1,3-thiazole-4-carboxylate To a solution of the product from Step A (496 mg, 0.71 mmol, 1 eq) in tetrahydrofuran (15 mL) was added ethylenediamine (141 µL, 2.12 mmol, 3 eq) and tetrabutylammonium fluoride (1M in tetrahydrofuran; 2.12 mL, 2.12 mmol, 3 eq) and the mixture was heated at 70° C. overnight. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a yellow solid (37 mg, 0.06 mmol, 9%).

LC/MS ($C_{29}H_{28}N_6O_3S_2$) 573 $[M+H]^+$; RT 2.65 (LCMS-V-C)

$^1H$ NMR (400 MHz, DMSO-d6) δ 7.91 (br s, 1H), 7.73 (s, 1H), 7.43-7.35 (m, 2H), 7.34-7.28 (m, 3H), 7.25-7.16 (m, 1H), 7.06-7.00 (m, 2H), 6.99-6.93 (m, 1H), 4.67 (s, 2H), 4.26 (q, J=7.1 Hz, 2H), 3.80 (s, 3H), 2.47 (s, 3H), 2.05 (s, 3H), 1.28 (t, J=7.1 Hz, 3H).

Step C: 2-({6-[(1,3-benzothiazol-2-yl)amino]-5-methylpyridazin-3-yl}(methyl)amino)-5-[(1E)-2-methyl-3-phenoxyprop-1-en-1-yl]-1,3-thiazole-4-carboxylic acid To a solution of the product from Step B (37 mg, 0.06 mmol, 1 eq) in 1,4-dioxane (4 mL) was added lithium hydroxide monohydrate (27.1 mg, 0.65 mmol, 10 eq) and the mixture was heated at 110° C. overnight. The reaction was allowed to cool to ambient temperature and purification by automated flash column chromatography (CombiFlash Rf, 4 g RediSep™ silica cartridge) eluting with a gradient of 0-10% 7N methanolic ammonia in dichloromethane afforded a dark yellow solid. The solid was triturated with acetonitrile, filtered, and dried under vacuum to afford the desired product as a yellow solid (12.1 mg, 0.02 mmol, 34%).

HRMS-ESI (m/z) [M+H]+ calcd for $C_{27}H_{25}N_6O_3S_2$: 545.1424, found 545.1426.

Example 163: 2-({6-[(1,3-Benzothiazol-2-yl)amino]-5-methylpyridazin-3-yl}(methyl)amino)-5-[(1E)-3-{4-[3-(dimethylamino)prop-1-yn-1-yl]-2-fluorophenoxy}-2-methylprop-1-en-1-yl]-1,3-thiazole-4-carboxylic acid

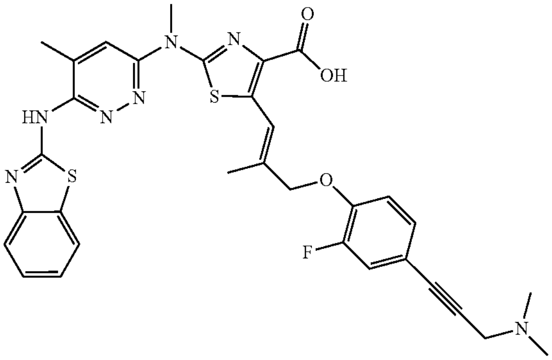 [SMILES: C/C(=C\c1sc(N(C)c2cc(C)c(Nc3nc4ccccc4s3)nn2)nc1C(=O)O)COc1ccc(C#CCN(C)C)cc1F]

Step A: ethyl 5-[(1E)-3-{4-[3-(dimethylamino)prop-1-yn-1-yl]-2-fluorophenoxy}-2-methylprop-1-en-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 5m (618 mg, 0.99 mmol, 1 eq) in toluene (18 mL) was added the product from Preparation 6b (286 mg, 1.48 mmol, 1.5 eq), triphenylphosphine (388 mg, 1.48 mmol, 1.5 eq) and diisopropylazodicarboxylate (291 μL, 1.48 mmol, 1.5 eq) and the mixture was heated at 120° C. for 1 h under microwave irradiation. The reaction was partitioned between dichloromethane and water, and the organic phase was separated and dried (PTFE phase separator) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a brown oil (406 mg, 0.51 mmol, 51%).

LC/MS ($C_{40}H_{48}FN_7O_4SiS_2$) 802 $[M+H]^+$; RT 2.68 (LCMS-V-C)

$^1$H NMR (400 MHz, DMSO-d6) δ 7.86-7.80 (m, 1H), 7.70 (s, 1H), 7.50-7.39 (m, 2H), 7.38-7.21 (m, 5H), 5.86 (s, 2H), 4.78 (s, 2H), 4.25 (q, J=7.2 Hz, 2H), 3.81 (s, 3H), 3.76-3.67 (m, 2H), 3.41 (s, 2H), 2.46 (d, J=1.0 Hz, 3H), 2.22 (s, 6H), 2.05 (s, 3H), 1.28 (t, J=7.1 Hz, 3H), 0.97-0.85 (m, 2H), −0.11 (s, 9H).

Step B: ethyl 2-({6-[(1,3-benzothiazol-2-yl)amino]-5-methylpyridazin-3-yl}(methyl)amino)-5-[(1E)-3-{4-[3-(dimethylamino)prop-1-yn-1-yl]-2-fluorophenoxy}-2-methylprop-1-en-1-yl]-1,3-thiazole-4-carboxylate To a solution of the product From Step A (406 mg, 0.51 mmol, 1 eq) in acetonitrile (5 mL) was added pyridinium poly(hydrogen fluoride)(0.88 mL, 10.1 mmol, 20 eq) and the mixture was heated at 60° C. overnight. The reaction was allowed to cool to ambient temperature then partitioned between dichloromethane and 2N aqueous sodium hydroxide (25 mL), and the organic phase was separated and dried (PTFE phase separator), and concentrated in mum. Purification by automated flash column chromatography (CombiFlash Rf, 24 g RediSep™ silica cartridge) eluting with a gradient of 0-5% methanol in dichloromethane afforded the desired product as a yellow solid (139 mg, 0.21 mmol, 41%).

LC/MS ($C_{34}H_{34}FN_7O_3S_2$) 672 $[M+H]^+$; RT 2.07 (LCMS-V-C)

$^1$H NMR (400 MHz, DMSO-d6) δ 11.56 (br s, 1H), 7.90 (d, J=7.6 Hz, 1H), 7.72 (s, 1H), 7.57-7.50 (m, 1H), 7.44-7.28 (m, 3H), 7.27-7.17 (m, 3H), 4.79 (s, 2H), 4.27 (q, J=7.2 Hz, 2H), 3.81 (s, 3H), 3.43 (s, 2H), 2.47 (s, 3H), 2.23 (s, 6H), 2.06 (s, 3H), 1.29 (t, J=7.1 Hz, 3H).

Step C: 2-({6-[(1,3-benzothiazol-2-yl)amino]-5-methylpyridazin-3-yl}(methyl)amino)-5-[(1E)-3-{4-[3-(dimethylamino)prop-1-yn-1-yl]-2-fluorophenoxy}-2-methylprop-1-en-1-yl]-1,3-thiazole-4-carboxylic acid To a solution of the product from Step B (139 mg, 0.21 mmol, 1 eq) in 1,4-dioxane (10 mL) was added lithium hydroxide monohydrate (86.8 mg, 2.07 mmol 10 eq) and the mixture was heated at 110° C. for 4 h. The reaction was allowed to cool to ambient temperature and the solvent removed by rotary evaporation. Purification by automated flash column chromatography (CombiFlash Rf, 12 g RediSep™ silica cartridge) eluting with a gradient of 0-25% 7N methanolic ammonia in dichloromethane afforded a solid. The material was triturated with acetonitrile, filtered, and dried under vacuum to afford the desired product as a yellow solid (77.9 mg, 0.12 mmol, 59%).

HRMS-ESI (m/z) [M+H]+ calcd for $C_{32}H_{31}FN_7O_3S_2$: 644.1908, found 644.1908.

Example 164: 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-hydroxypropyl)-1,3-thiazole-4-carboxylic acid

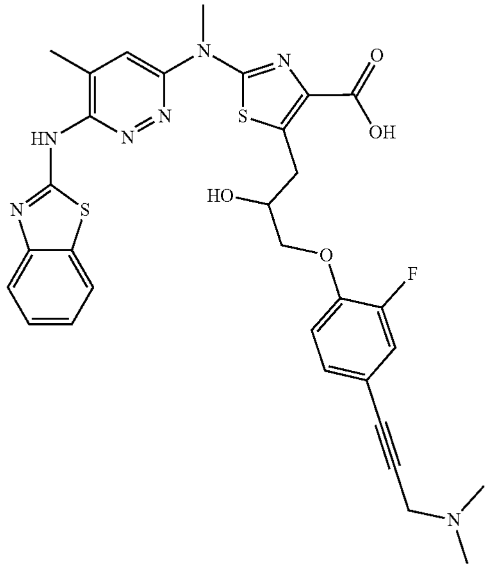 [SMILES: Cc1cc(N(C)c2nc(C(=O)O)c(CC(O)COc3ccc(C#CCN(C)C)cc3F)s2)nnc1Nc1nc2ccccc2s1]

Step A: ethyl 5-(3-{4-[3-(dimethylamino)prop-1-yn-1-yl]-2-fluorophenoxy}-2-(oxan-2-yloxy)propyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate The product from Preparation 4a (150 mg, 0.37 mmol, 1.16 eq) and the product from Preparation 3zg, (165 mg, 0.32 mmol, 1 eq) were added to a solution of tris(dibenzylideneacetone)dipalladium(0)(29.1 mg, (1.03 mmol, 0.1 eq) and Xantphos (36.8 mg, 0.06 mmol, 0.2 eq) in 1,4-dioxane (8 mL). Cesium carbonate (310 mg, 0.95 mmol, 3 eq) and N,N-diisopropylethylamine (0.2 mL, 0.95 mmol, 3 eq) were added and the mixture was heated in a sealed tube at 125° C. for 18 h. The suspension was allowed to cool and the mixture filtered through celite, the solids were washed with ethyl acetate (311 mL) and the filtrate was concentrated in vacuo. Purification by flash column chromatography (20 g silica) eluting with a gradient of 0-2.5% methanol in dichloromethane afforded the desired product as a dark brown gum (230 mg, 0.26 mmol, 81%).

LC/MS ($C_{44}H_{56}FN_7O_6SiS_2$) 890 $[M+H]^+$; RT 1.59 (LCMS-V-B1)

Step B: ethyl 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-hydroxypropyl)-1,3-thiazole-4-carboxylate To a solution of the product from Step A (225 mg, 0.25 mmol, 1 eq) in chloroform (4.5 mL), cooled in ice-water, was added trifluoroacetic acid (0.5 mL, 6.32 mmol, 25 eq) and the mixture was stirred for 1 h at 0° C. and for 18 h at ambient temperature. Dichloromethane (50 mL) was added and the mixture was washed successively with saturated aqueous sodium bicarbonate (30 mL), water (2×30 ml) and brine (30 mL), dried (magnesium sulfate), and concentrated in vacuo. Purification by flash column chromatography (20 g silica) eluting with a gradient of 0-5% methanol in dichloromethane afforded the desired product as a dark yellow solid (98 mg, 0.15 mmol, 57%).

LC/MS ($C_{33}H_{34}FN_7O_4S_2$) 676 $[M+H]^+$; RT 1.15 (LCMS-V-B1)

$^1H$ NMR (400 MHz, DMSO-d6) δ 7.86-7.63 (m, 2H), 7.48-7.31 (m, 2H), 7.30-7.21 (m, 1H), 7.20-7.11 (m, 2H), 6.96-6.85 (m, 1H), 4.46-4.31 (m, 3H), 4.16-4.01 (m, 2H), 3.92-3.76 (m, 3H), 3.64-3.53 (m, 1H), 3.51-3.44 (m, 1H), 3.42 (s, 3H), 2.44 (s, 3H), 2.34 (s, 6H), 1.43 (t, J=7.1 Hz, 3H).

Step C: 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-hydroxypropyl)-1,3-thiazole-4-carboxylic acid To a solution of the product from Step B (90 mg, 0.13 mmol, 1 eq) in a 1:3 mix of 1,4-dioxane/water (2 mL) was added lithium hydroxide monohydrate (11.2 mg, 0.27 mmol, 2 eq) and the suspension was heated at 40° C. for 7 h. The reaction was allowed to cool and the resulting solution acidified with acetic acid to pH 5 to give a yellow precipitate. The solids were collected by filtration, washed with water and dried under vacuum to afford the desired product as a yellow solid (54 mg, 0.08 mmol, 63%).

HRMS-ESI (m/z) [M+H]+ calcd for $C_{31}H_{31}FN_7O_4S_2$: 648.1857, found 648.1888.

Example 165: 2-[[6-(1,3-Benzothiazol-2-ylamino)-5-methyl-pyridazin-3-yl]-[5-[methyl(4-piperidyl)amino]pentyl]amino]-5-[3-[4-[3-(dimethylamino)prop-1-ynyl]-2-fluoro-phenoxy]propyl]thiazole-4-carboxylic acid

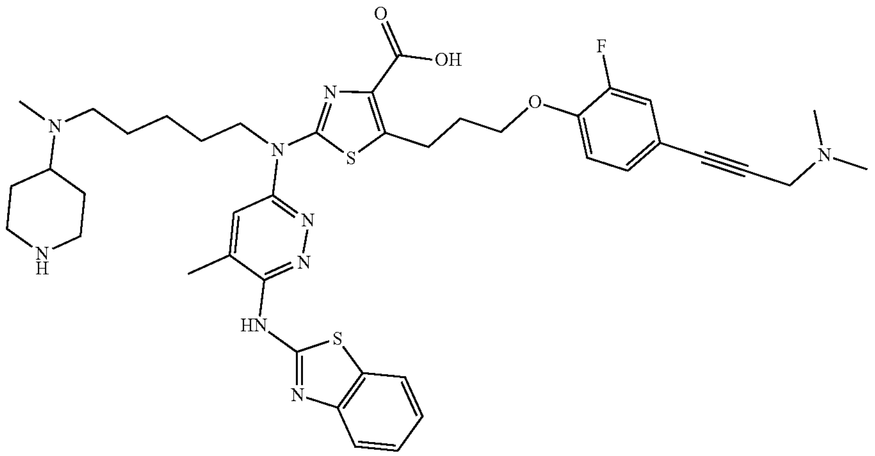 [SMILES: Cc1cc(N(CCCCCN(C)C2CCNCC2)c2nc(C(=O)O)c(CCCOc3ccc(C#CCN(C)C)cc3F)s2)nnc1Nc1nc2ccccc2s1]

Step A: methyl 2-[5-[(1-tert-butoxycarbonyl-4-piperidyl)-methyl-amino]pentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5f and tert-butyl 4-(methylamino)piperidine-1-carboxylate as the appropriate amine, the desired product was obtained.

HRMS-ESI (m/z): $[M+2H]^{2+}$ calcd for $C_{53}H_{74}FN_9O_6S_2Si$: 522.7551, found 522.7542.

Step B: 2-[[6-(1,3-benzothiazol-2-ylamino)-5-methyl-pyridazin-3-yl]-[5-[methyl(4-piperidyl)amino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{41}H_{52}FN_9O_3S_2$: 400.6804, found 400.6803.

Example 166: 2-[[6-(1,3-Benzothiazol-2-ylamino)-5-methyl-pyridazin-3-yl]-[5-(2-morpholinoethylamino)pentyl]amino]-5-[3-[4-[3-(dimethylamino)prop-1-ynyl]-2-fluoro-phenoxy]propyl]thiazole-4-carboxylic acid

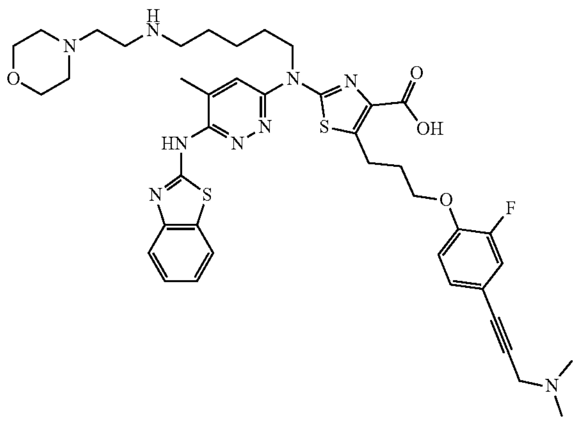 [SMILES: Cc1cc(N(CCCCCNCCN2CCOCC2)c2nc(C(=O)O)c(CCCOc3ccc(C#CCN(C)C)cc3F)s2)nnc1Nc1nc2ccccc2s1]

Step A: methyl 5-[3-[4-[3-(dimethylamino)prop-1-ynyl]-2-fluoro-phenoxy]propyl]-2-[[5-methyl-6-[(Z)-[3-(2-trimethylsilylethoxymethyl)-1,3-benzothiazol-2-ylidene]amino]pyridazin-3-yl]-[5-(2-morpholinoethylamino)pentyl]amino]thiazole-4-carboxylate Using Alkylation with in situ generated tosylate General Procedure starting from Preparation 5f and 2-morpholinoethanamine as the appropriate amine, the desired product was obtained.

$^1H$ NMR (500 MHz, DMSO-$d_6$) δ ppm 7.84 (dm, 1H), 7.66 (s, 1H), 7.47 (dm, 1H), 7.44 (m, 1H), 7.30 (dd, 1H), 7.25 (m, 1H), 7.21 (dd, 1H), 7.16 (t, 1H), 5.86 (s, 2H), 4.37 (t, 2H), 4.14 (t, 2H), 3.78 (s, 3H), 3.72 (m, 2H), 3.52 (m, 4H), 3.38 (s, 2H), 3.26 (m, 2H), 2.56 (t, 2H), 2.49 (t, 2H), 2.46 (s, 3H), 2.32 (t, 2H), 2.31 (m, 4H), 2.19 (s, 6H), 2.12 (m, 2H), 1.69 (m, 2H), 1.47 (m, 2H), 1.37 (m, 2H), 0.92 (m, 2H), −0.11 (s, 9H); HRMS-ESI (m/z): $[M+2H]^{2+}$ calcd for $C_{48}H_{68}FN_9O_5S_2Si$: 480.7269, found 480.7264.

Step B: 2-[[6-(1,3-benzothiazol-2-ylamino)-5-methyl-pyridazin-3-yl]-[5-(2-morpholinoethylamino)pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{41}H_{52}FN_9O_4S_2$: 408.6779, found 408.6769.

Example 167: 2-[[6-(1,3-Benzothiazol-2-ylamino)-5-methyl-pyridazin-3-yl]-[5-[2-(4-methylpiperazin-1-yl)ethylamino]pentyl]amino]-5-[3-[4-[3-(dimethylamino)prop-1-ynyl]-2-fluoro-phenoxy]propyl]thiazole-4-carboxylic acid

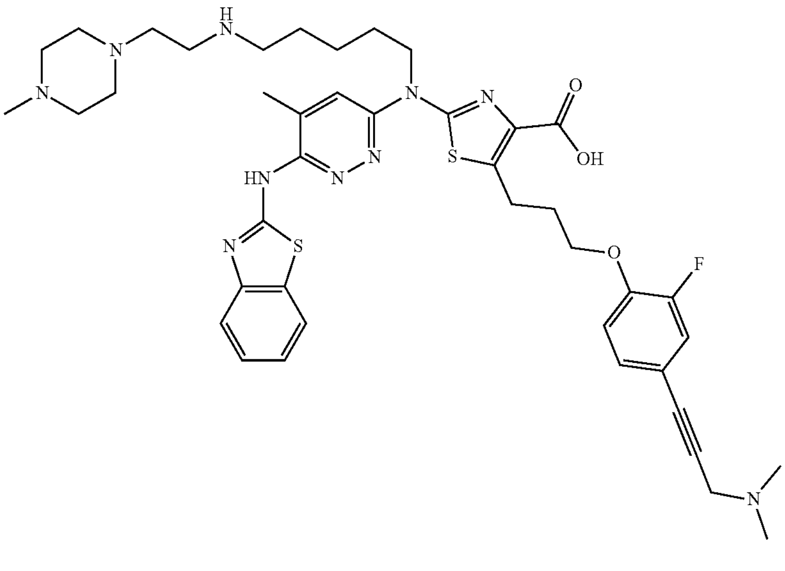

Step A: methyl 5-[3-[4-[3-(dimethylamino)prop-1-ynyl]-2-fluoro-phenoxy]propyl]-2-[5-[2-(4-methylpiperazin-1-yl)ethylamino]pentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with in situ generated tosylate General Procedure starting from Preparation 5f and 2-(4-methylpiperazin-1-yl)ethanamine as the appropriate amine, the desired product was obtained.

$^{1}$H NMR (500 MHz, DMSO-d$_6$) δ ppm 7.84 (dm, 1H), 7.67 (s, 1H), 7.47 (dm, 1H), 7.44 (m, 1H), 7.30 (dd, 1H), 7.26 (m, 1H), 7.21 (dd, 1H), 7.15 (t, 1H), 5.86 (s, 2H), 4.36 (t, 2H), 4.14 (t, 2H), 3.78 (s, 3H), 3.72 (m, 2H), 3.38 (s, 2H), 3.26 (m, 2H), 2.53 (t, 2H), 2.50-2.10 (brs, 4H), 2.50-2.10 (brs, 4H), 2.48 (t, 2H), 2.46 (s, 3H), 2.30 (t, 2H), 2.20 (s, 6H), 2.13 (m, 2H), 2.10 (s, 3H), 1.69 (m, 2H), 1.45 (m, 2H), 1.37 (m, 2H), 0.92 (m, 2H), −0.11 (s, 9H); HRMS-ESI (m/z): $[M+2H]^{2+}$ calcd for $C_{49}H_{71}FN_{10}O_4S_2Si$: 487.2422, found 487.2422.

Step B: 2-[[6-(1,3-benzothiazol-2-ylamino)-5-methyl-pyridazin-3-yl]-[5-[2-(4-methylpiperazin-1-yl)ethylamino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{42}H_{55}FN_{10}O_3S_2$: 415.19366, found 415.1939.

Example 168: 2-[[6-(1,3-Benzothiazol-2-ylamino)-5-methyl-pyridazin-3-yl]-[4-[2-(4-methylpiperazin-1-yl)ethylamino]butyl]amino]-5-[3-[4-[3-(dimethylamino)prop-1-ynyl]-2-fluoro-phenoxy]propyl]thiazole-4-carboxylic acid

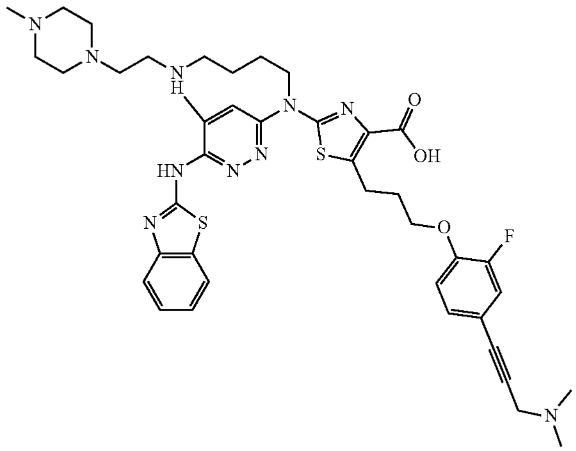

Step A: methyl 5-[3-[4-[3-(dimethylamino)prop-1-ynyl]-2-fluoro-phenoxy]propyl]-2-[4-[2-(4-methylpiperazin-1-yl)ethylamino]butyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with in situ generated tosylate General Procedure starting from Preparation 5d and 2-(4-methylpiperazin-1-yl)ethanamine as the appropriate amine, the desired product was obtained.

$^{1}$H NMR (500 MHz, DMSO-$d_6$) δ ppm 2.50-2.00 (brs, 8H), 7.84 (dm, 1H), 7.72 (s, 1H), 7.47 (dm, 1H), 7.43 (m, 1H), 7.30 (dd, 1H), 7.25 (m, 1H), 7.21 (dd, 1H), 7.16 (t, 1H), 5.86 (s, 2H), 4.38 (t, 2H), 4.15 (t, 2H), 3.78 (s, 3H), 3.72 (m, 2H), 3.39 (s, 2H), 3.27 (t, 2H), 2.56 (t, 2H), 2.54 (t, 2H), 2.46 (s, 3H), 2.31 (t, 2H), 2.20 (brs, 6H), 2.13 (m, 2H), 2.06 (s, 3H), 1.71 (m, 2H), 1.47 (m, 2H), 0.92 (m, 2H), −0.11 (s, 9H); HRMS-ESI (m/z): $[M+2H]^{2+}$ calcd for $C_{48}H_{69}FN_{10}O_4S_2Si$: 480.2344, found 480.2340.

Step B: 2-[[6-(1,3-benzothiazol-2-ylamino)-5-methyl-pyridazin-3-yl]-[4-[2-(4-methylpiperazin-1-yl)ethylamino]butyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calculated for $C_{41}H_{53}FN_{10}O_3S_2$: 408.1858, found 408.1857.

Example 169: 2-[[6-(1,3-Benzothiazol-2-ylamino)-5-methyl-pyridazin-3-yl]-[4-hydroxy-5-[methyl-[2-(methylamino)ethyl]amino]pentyl]amino]-5-[3-[4-[3-(dimethylamino)prop-1-ynyl]-2-fluoro-phenoxy]propyl]thiazole-4-carboxylic acid

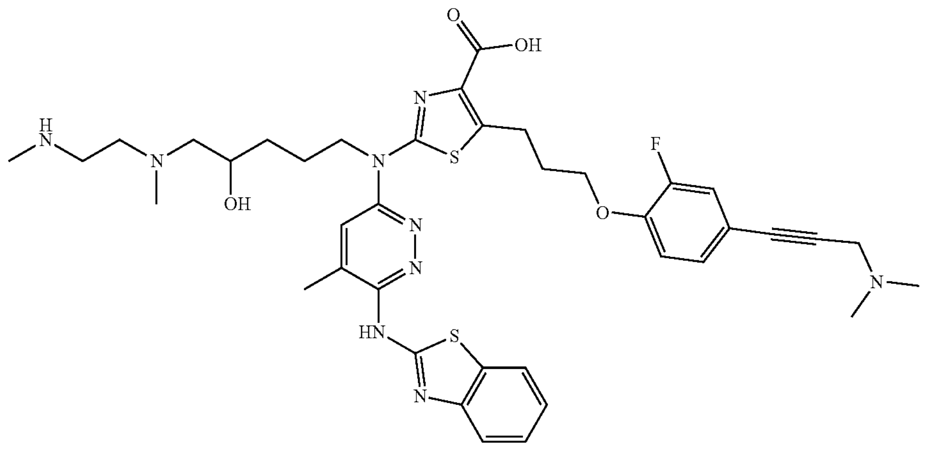

Step A: methyl 2-[[5-[2-[tert-butoxycarbonyl(methyl)amino]ethyl-methyl-amino]-4-[tert-butyl(diphenyl)silyl]oxy-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with tosylate General Procedure starting from Preparation 5b and tert-butyl N-methyl-N-[2-(methylamino)ethyl]carbamate as the appropriate amine, the desired product was obtained.

Step B: 2-[[6-(1,3-benzothiazole-2-ylamino)-5-methyl-pyridazin-3-yl]-[4-hydroxy-5-[methyl-[2-(methylamino)ethyl]amino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{39}H_{49}FN_9O_4S_2$: 790.3327, found 790.3317.

Example 170: 2-[[6-(1,3-Benzothiazol-2-ylamino)-5-methyl-pyridazin-3-yl]-[5-[2-(diethylamino)ethyl-amino]-4-hydroxy-pentyl]amino]-5-[3-[4-[3-(dimethylamino)prop-1-ynyl]-2-fluoro-phenoxy]propyl]thiazole-4-carboxylic acid

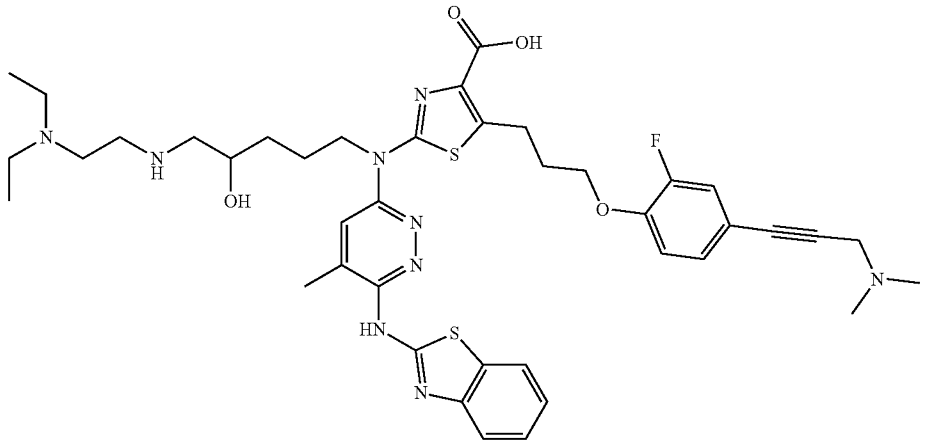 [SMILES: CCN(CC)CCNCC(O)CCCN(c1cc(C)c(Nc2nc3ccccc3s2)nn1)c1nc(C(=O)O)c(CCCOc2ccc(C#CCN(C)C)cc2F)s1]

Step A: methyl 2-[[4-[tert-butyl(diphenyl)silyl]oxy-5-[2-(diethylamino)ethylamino]pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with tosylate General Procedure starting from Preparation 5b and N',N'-diethylethane-1,2-diamine as the appropriate amine, the desired product was obtained.

Step B: 2-[[6-(1,3-benzothiazol-2-ylamino)-5-methyl-pyridazin-3-yl]-[5-[2-(diethylamino)ethyl-amino]-4-hydroxy-pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{41}H_{53}FN_9O_4S_2$: 818.3640, found 818.3613.

Example 171: 2-[[5-(4-Amino-1-piperidyl)-4-hydroxy-pentyl]-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid

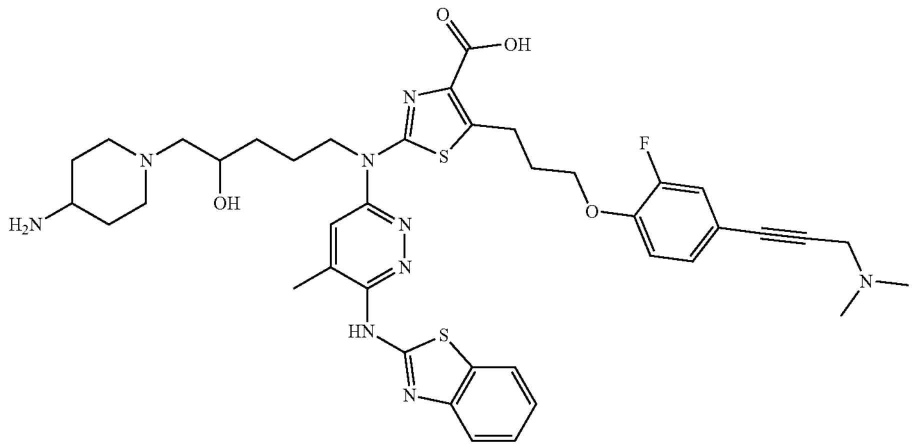 [SMILES: Cc1cc(N(CCCC(O)CN2CCC(N)CC2)c2nc(C(=O)O)c(CCCOc3ccc(C#CCN(C)C)cc3F)s2)nnc1Nc1nc2ccccc2s1]

Step A: methyl 2-[[5-[4-(tert-butoxycarbonylamino)-1-piperidyl]-4-[tert-butyl(diphenyl)silyl]oxy-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with tosylate General Procedure starting from Preparation 5b and tert-butyl N-(4-piperidyl)carbamate as the appropriate amine, the desired product was obtained.

Step B: 2-[[5-(4-amino-1-piperidyl)-4-hydroxy-pentyl]-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+H]^+$ calcd for $C_{40}H_{49}FN_9O_4S_2$: 802.3327, found 802.3324.

Example 172: 2-[[6-(1,3-Benzothiazol-2-ylamino)-5-methyl-pyridazin-3-yl]-(4-hydroxy-5-piperazin-1-yl-pentyl)amino]-5-[3-[4-[3-(dimethylamino)prop-1-ynyl]-2-fluoro-phenoxy]propyl]thiazole-4-carboxylic acid

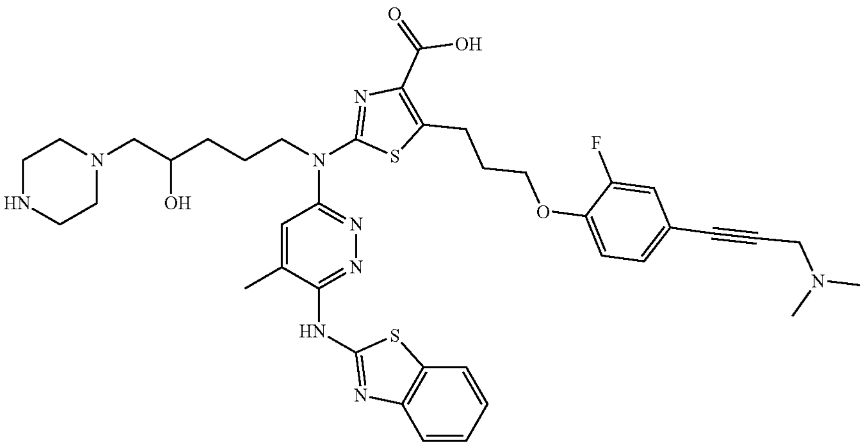 [SMILES: Cc1cc(N(CCCC(O)CN2CCNCC2)c2nc(C(=O)O)c(CCCOc3ccc(C#CCN(C)C)cc3F)s2)nnc1Nc1nc2ccccc2s1]

Step A: methyl 2-[[5-(4-tert-butoxycarbonylpiperazin-1-yl)-4-[tert-butyl(diphenyl)silyl]oxy-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with tosylate General Procedure starting from Preparation 5b and tert-butyl piperazine-1-carboxylate as the appropriate amine, the desired product was obtained.

Step B: 2-[[6-(1,3-benzothiazol-2-ylamino)-5-methyl-pyridazin-3-yl]-(4-hydroxy-5-piperazin-1-yl-pentyl)amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+2H]^{2+}$ calcd for $C_{39}H_{48}FN_9O_4S_2$: 394.6622, found 394.6614.

Example 173: 2-[[6-(1,3-Benzothiazol-2-ylamino)-5-methyl-pyridazin-3-yl]-[4-hydroxy-5-[2-(1-piperidyl)ethylamino]pentyl]amino]-5-[3-[4-[3-(dimethylamino)prop-1-ynyl]-2-fluoro-phenoxy]propyl]thiazole-4-carboxylic acid

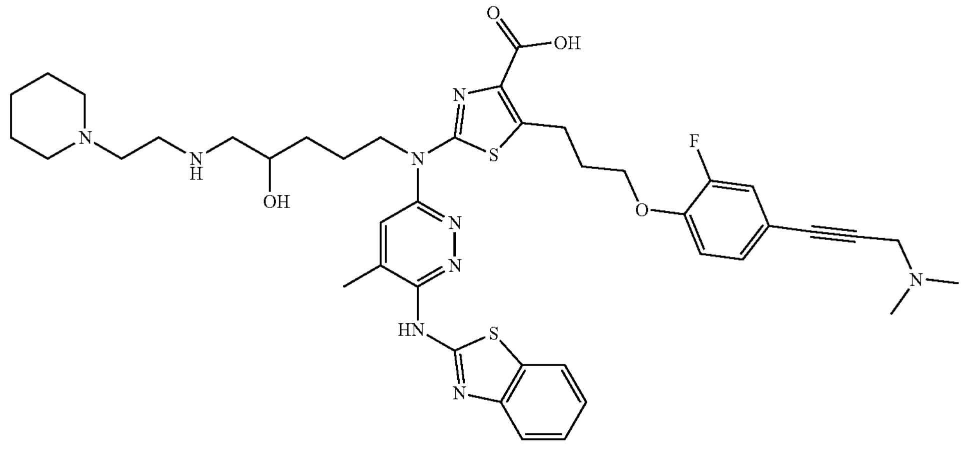 [SMILES: Cc1cc(N(CCCC(O)CNCCN2CCCCC2)c2nc(C(=O)O)c(CCCOc3ccc(C#CCN(C)C)cc3F)s2)nnc1Nc1nc2ccccc2s1]

Step A: methyl 2-[[4-[tert-butyl(diphenyl)silyl]oxy-5-[2-(1-piperidyl)ethylamino]pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with tosylate General Procedure starting from Preparation 5b and 2-(1-piperidyl)ethanamine as the appropriate amine, the desired product was obtained.

Step B: 2-[[6-(1,3-benzothiazol-2-ylamino)-5-methylpyridazin-3-yl]-[4-hydroxy-5-[2-(1-piperidyl)ethylamino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step A as the appropriate methyl ester, the desired product was obtained.

HRMS-ESI (m/z): $[M+2H]^{2+}$ calcd for $C_{42}H_{54}FN_9O_4S_2$: 415.6857, found 415.6853.

Example 174: 2-({6-[(1,3-Benzothiazol-2-yl)amino]-5-methylpyridazin-3-yl}(methyl)amino)-5-[(1E)-3-{2-fluoro-4-[3-(methylamino)prop-1-yn-1-yl]phenoxy}-2-methylprop-1-en-1-yl]-1,3-thiazole-4-carboxylic acid

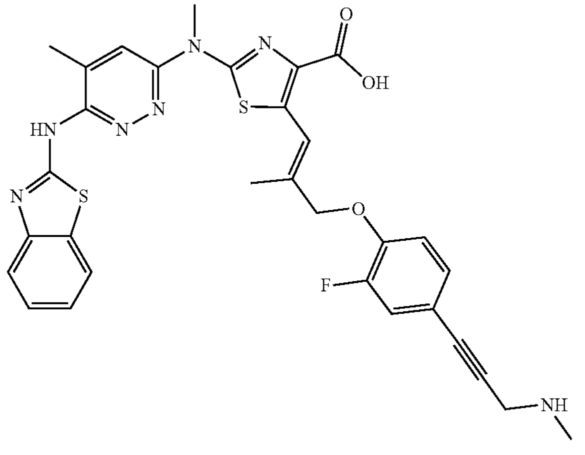 [SMILES: CNCC#Cc1ccc(OC/C(C)=C/c2sc(N(C)c3cc(C)c(Nc4nc5ccccc5s4)nn3)nc2C(=O)O)c(F)c1]

Step A: ethyl 5-[(1E)-3-[4-(3-{[(tert-butoxy)carbonyl](methyl)amino}prop-1-yn-1yl)-2-fluorophenoxy]-2-methylprop-1-en-1-yl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 5m (641 mg, 1.02 mmol, 1 eq) in toluene (18 mL) was added the product from Preparation 6a (428 mg, 1.53 mmol, 1.5 eq), triphenylphosphine (402 mg, 1.53 mmol, 1.5 eq) and diisopropylazodicarboxylate (0.3 mL, 1.53 mmol, 1.5 eq) and the mixture was heated at 120° C. for 1 h. The reaction was partitioned between dichloromethane and water, and the organic phase was separated and dried (PTFE phase separator) and concentrated in vacuo. Purification by automated flash column chromatography (CombiFlash Rf, 24 g RediSep™ silica cartridge) eluting with a gradient of 0-40% ethyl acetate in iso-heptane afforded the desired product as a yellow solid (380 mg, 0.43 mmol, 42%).

LC/MS ($C_{44}H_{54}FN_7O_6SiS_2$) 888 $[M+H]^+$; RT 1.43 (LCMS-V-B2)

$^1H$ NMR (400 MHz, DMSO-d6) δ 7.86-7.81 (m, 1H), 7.71 (d, 1H), 7.51-7.4 ((m, 2H), 7.39-7.32 (m, 1H), 7.32-7.21 (m, 4H), 5.86 (s, 2H), 4.79 (s, 2H), 4.32-4.17 (m, 4H), 3.81 (s, 3H), 3.78-3.66 (m, 2H), 2.86 (s, 3H), 2.46 (s, 3H), 2.06 (m, 3H), 1.41 (s, 9H), 1.28 (t, 3H), 0.97-0.88 (m, 2H), −0.11 (s, 9H).

Step B: ethyl 2-({6-[(1,3-benzothiazol-2-yl)amino]-5-methylpyridazin-3-yl}(methyl)amino)-5-[(1E)-3-{2-fluoro-4-[3-(methylamino)prop-1-yn-1-yl]phenoxy}-2-methylprop-1-en-1-yl]-1,3-thiazole-4-carboxylate To a solution of the product from Step A (380 mg, 0.43 mmol, 1 eq) in acetonitrile (5 mL) was added pyridinium poly(hydrogen fluoride)(744 µL, 8.56 mmol, 20 eq) and the mixture was heated at 60° C. for 3 h. The reaction was allowed to cool to ambient temperature then partitioned between dichloromethane and 2N aqueous sodium hydroxide, the aqueous phase extracted with 1:3 isopropanol/dichloromethane, and the combined organics dried (PTFE phase separator) and concentrated in vacuo. Purification by automated flash column chromatography (CombiFlash Rf, 12 g RediSep™ silica cartridge) eluting with a gradient of 0-6% methanol in dichloromethane afforded the desired product as a yellow solid (133 mg, 0.2 mmol, 47%).

LC/MS ($C_{33}H_{32}FN_7O_3S_2$) 658 $[M+H]^+$; RT 2.02 (LCMS-V-C)

$^1H$ NMR (400 MHz, DMSO-d6) δ 7.90 (d, J=7.8 Hz, 1H), 7.73 (s, 1H), 7.54 (d, J=8.0 Hz, 1H), 7.44-7.36 (m, 1H), 7.35-7.28 (m, 2H), 7.27-7.18 (m, 3H), 4.79 (s, 2H), 4.27 (q, J=7.1 Hz, 2H), 3.81 (s, 3H), 3.49 (s, 2H), 2.48 (d, J=1.0 Hz, 3H), 2.34 (s, 3H), 2.07 (s, 3H), 1.29 (t, 3H).

Step C: 2-({6-[(1,3-benzothiazol-2-yl)amino]-5-methylpyridazin-3-yl}(methyl)amino)-5-[(1E)-3-{2-fluoro-4-[3-(methylamino)prop-1-yn-1-yl]phenoxy}-2-methylprop-1-en-1-yl]-1,3-thiazole-4-carboxylic acid To a solution of the product from Step B (133 mg, 0.2 mmol, 1 eq) in 1,4-dioxane (6 mL) was added lithium hydroxide monohydrate (84.9 mg, 2.02 mmol, 10 eq) and the mixture was heated at 110° C. for 4 h. The reaction was allowed to cool to ambient temperature and purification by automated flash column chromatography (CombiFlash Rf, 12 g RediSep™ silica cartridge) eluting with a gradient of 0-25% 7N methanolic ammonia in dichloromethane afforded a solid. The solid was triturated with acetonitrile, filtered, and dried under vacuum to afford the desired product as a yellow solid (4.32 mg, 0.01 mmol, 3%).

HRMS-ESI (m/z): [M+H]+ calcd for $C_{31}H_{29}FN_7O_3S_2$: 630.1752, found 630.1781.

Example 175: 2-[4-(4-Amino-1-piperidyl)butyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid

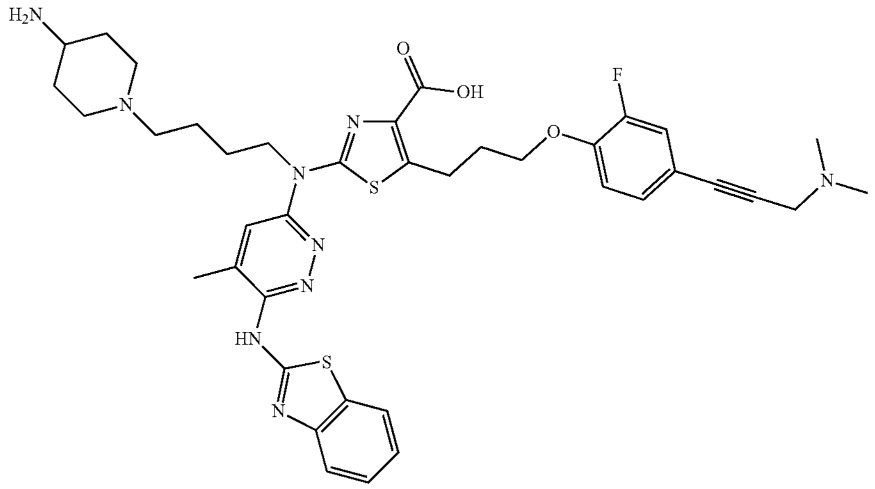 [SMILES: Cc1cc(N(CCCCN2CCC(N)CC2)c2nc(C(=O)O)c(CCCOc3ccc(C#CCN(C)C)cc3F)s2)nnc1Nc1nc2ccccc2s1]

Step A: methyl 2-[4-[4-(tert-butoxycarbonylamino)-1-piperidyl]butyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluorophenoxy]propyl]thiazole-4-carboxylate Using Alkylation with in situ generated tosylate General Procedure starting from Preparation 5d and tert-butyl N-(4-piperidyl)carbamate as the appropriate amine, the desired product was obtained.

$^1$H NMR (500 MHz, DMSO-$d_6$) δ ppm 7.65 (q, 1H), 7.33 (dd, 1H), 7.26 (dd, 1H), 7.18 (t, 1H), 6.80 (brs, 1H), 5.86 (s, 2H), 4.40 (t, 2H), 4.20 (t, 3.82 (s, 3H), 3.79 (s, 2H), 3.77 (m, 2H), 3.54 (brs, 1H), 3.36/3.00 (brs, 4H), 3.29 (t, 2H), 3.14 (t, 2H), 2.52 (brs, 6H), 2.48 (d, 3H), 2.15 (m, 2H), 1.94/1.66 (m+m, 4H), 1.79 (m, 2H), 1.76 (m, 2H), 1.40 (s, 9H), 0.94 (m, 2H), −0.07 (s, 9H); HRMS-ESI (m/z): $[M+H]^+$ calcd for $C_{51}H_{71}FN_9O_6S_2Si$: 1016.4716, found 1016.4704.

Step B: 2-[4-(4-amino-1-piperidyl)butyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{39}H_{46}FN_9O_3S_2$: 772.3222 found 772.3228.

Example 176: 2-[[6-(1,3-Benzothiazol-2-ylamino)-5-methyl-pyridazin-3-yl]-[4-[2-(diethylamino)ethylamino]butyl]amino]-5-[3-[4-[3-(dimethylamino)prop-1-ynyl]-2-fluoro-phenoxy]propyl]thiazole-4-carboxylic acid

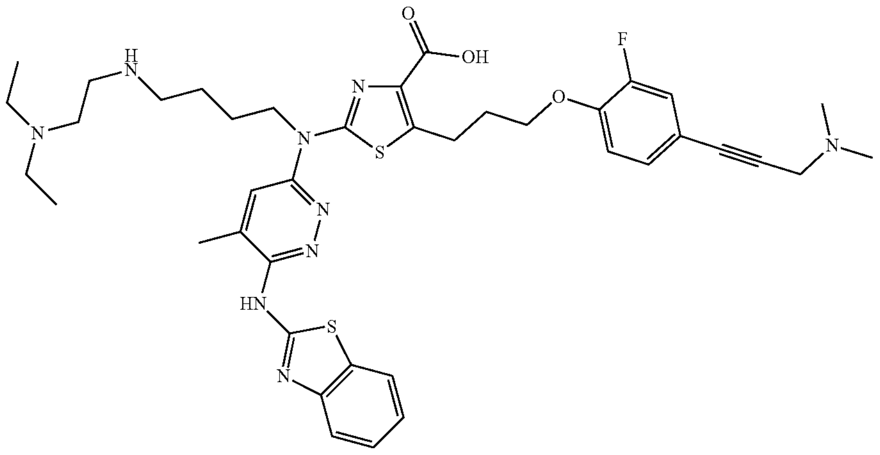 [SMILES: CCN(CC)CCNCCCCN(c1cc(C)c(Nc2nc3ccccc3s2)nn1)c1nc(C(=O)O)c(CCCOc2ccc(C#CCN(C)C)cc2F)s1]

Step A: methyl 2-[4-[2-(diethylamino)ethylamino]butyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5d and N',N'-diethylethane-1,2-diamine as the appropriate amine, the desired product was obtained.

$^1$H NMR (500 MHz, DMSO-$d_6$) δ ppm 7.84 (dm, 1H), 7.71 (s, 1H), 7.47 (dm, 1H), 7.44 (m, 1H), 7.30 (dd, 1H), 7.25 (m, 1H), 7.21 (dd, 1H), 7.16 (t, 1H), 5.86 (s, 2H) 4.39 (t, 2H), 4.15 (t, 2H), 3.78 (s, 3H), 3.72 (m, 2H), 3.38 (s, 2H), 3.27 (t, 2H), 2.57 (t, 2H), 2.51 (t, 2H), 2.46 (s, 3H), 2.41 (t, 2H), 2.40 (q, 4H), 2.19 (s, 6H), 2.12 (m, 2H), 1.71 (m, 2H), 1.48 (m, 2H), 0.92 (m, 2H), 0.89 (t, 6H), −0.11 (s, 9H); HRMS-ESI (m/z): $[M+H]^+$ calcd for $C_{47}H_{67}FN_9O_4S_2Si$: 932.4505 found 932.4489.

Step B: 2-[[6-(1,3-benzothiazol-2-ylamino)-5-methyl-pyridazin-3-yl]-[4-[2-(diethylamino)ethylamino]butyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{40}H_{52}FN_9O_3S_2$: 394.6804, found 394.6802.

Example 177: 2-[5-(4-Amino-1-piperidyl)pentyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid

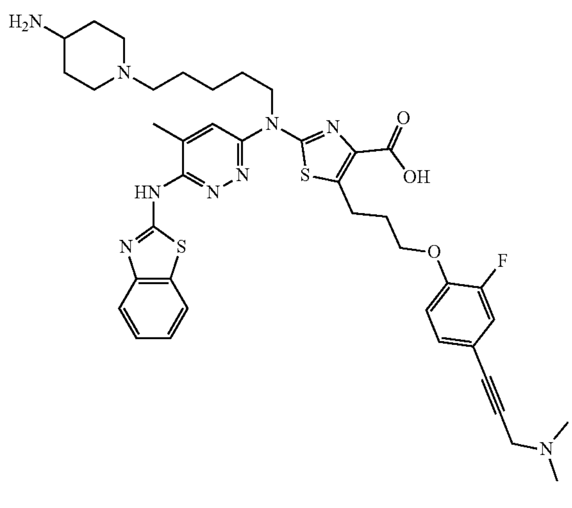 [SMILES: Cc1cc(N(CCCCCN2CCC(N)CC2)c2nc(C(=O)O)c(CCCOc3ccc(C#CCN(C)C)cc3F)s2)nnc1Nc1nc2ccccc2s1]

Step A: methyl 2-[5-[4-(tert-butoxycarbonylamino)-1-piperidyl]pentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5f and tert-butyl N-(4-piperidyl)carbamate as the appropriate amine, the desired product was obtained.

$^1$H NMR (500 MHz, DMSO-$d_6$) δ ppm 7.91-7.18 (m, 4H), 7.70 (s, 1H), 7.33 (dd, 1H), 7.24 (dd, 1H), 7.17 (t, 1H) 7.04 (d, 1H), 5.87 (s, 2H), 4.16 (t, 2H), 3.79 (s, 3H), 3.72 (t, 2H), 3.53 (s, 2H), 3.49/3.31 (m+m, 4H), 3.27 (t, 2H), 2.94 (t, 2H), 2.91 (m, 1H), 2.47 (s, 3H), 2.30 (s, 6H), 2.13 (m, 2H), 1.89/1.60 (m+m, 4H), 1.73 (m, 2H), 1.70 (m, 2H), 1.38 (m, 2H), 1.38 (m, 2H), 1.38 (s, 9H), 0.92 (t, 2H), −0.11 (s, 9H); HRMS-ESI (m/z): $[M+2H]^{2+}$ calcd for $C_{52}H_{74}FN_9O_6S_2Si$; 515.7473, found 515.74725.

Step B: 2-[5-(4-amino-1-piperidyl)pentyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{40}H_{50}FN_9O_3S_2$: 393.6726, found 393.6723.

Example 178: 2-[[6-(1,3-Benzothiazol-2-ylamino)-5-methyl-pyridazin-3-yl]-[4-[methyl-[2-(methyl-amino)ethyl]amino]butyl]amino]-5-[3-[4-[3-(dimeth-ylamino)prop-1-ynyl]-2-fluoro-phenoxy]propyl] thiazole-4-carboxylic acid

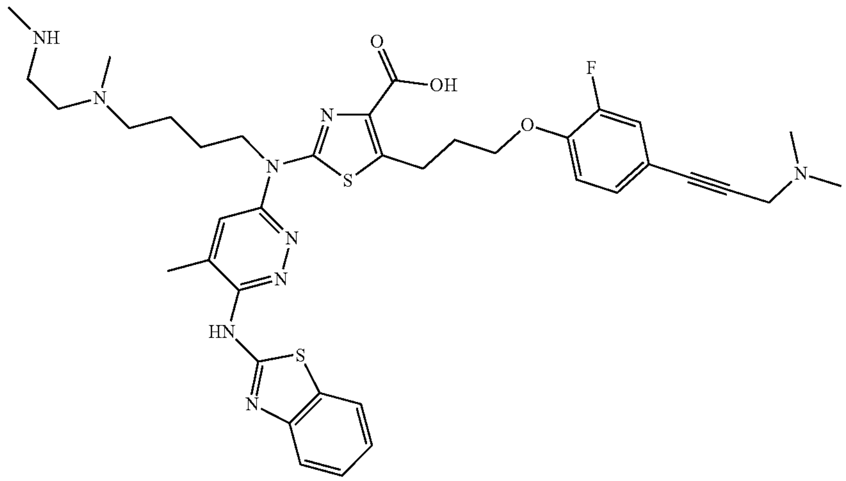

Step A: methyl 2-[4-[2-[tert-butoxycarbonyl (methyl)amino]ethyl-methyl-amino]butyl-[5-methyl-6-[(Z)-[3-(2-trimethylsilylethoxymethyl)-1,3-benzo-thiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5d and tert-butyl N-methyl-N-[2-(methylamino)ethyl]carbamate as the appropriate amine, the desired product was obtained.

$^1$H NMR (500 MHz, DMSO-$d_6$) δ ppm 7.84 (dm, 1H), 7.68 (s, 1H), 7.46 (dm, 1H), 7.44 (m, 1H), 7.30 (dd, 1H), 7.25 (m, 1H), 7.20 (dd, 1H), 7.15 (t, 1H), 5.86 (s, 2H), 4.38 (t, 2H), 4.14 (t, 2H), 3.77 (s, 3H), 3.72 (m, 2H), 3.38 (s, 2H), 3.26 (t, 2H), 3.19 (brm, 2H), 2.71 (brs, 3H), 2.46 (s, 3H), 2.37 (t, 2H), 2.36 (t, 2H), 2.19 (s, 6H), 2.15 (s, 3H), 2.12 (m, 2H), 1.69 (m, 2H), 1.48 (m, 2H), 1.31 (brs, 9H), (1.92 (m, 2H), −0.11 (s, 9H); HRMS-ESI (m/z): $[M+H]^+$ calcd for $C_{50}H_{71}FN_9O_6S_2Si$: 1004.4716, found 502.73931.

Step B: 2-[[6-(1,3-benzothiazol-2-ylamino)-5-methyl-pyridazin-3-yl]-[4-[methyl-[2-(methylamino) ethyl]amino]butyl]amino]-5-[3-[4-[3-(dimethyl-amino)prop-1-ynyl]-2-fluoro-phenoxy]propyl] thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{38}H_{48}FN_9O_3S_2$: 380.6647, found 380.6640.

Example 179: 2-[[6-(1,3-Benzothiazol-2-ylamino)-5-methyl-pyridazin-3-yl]-[4-[2-(1-piperidyl)ethylamino]butyl]amino]-5-[3-[4-[3-(dimethylamino)prop-1-ynyl]-2-fluoro-phenoxy]propyl]thiazole-4-carboxylic acid

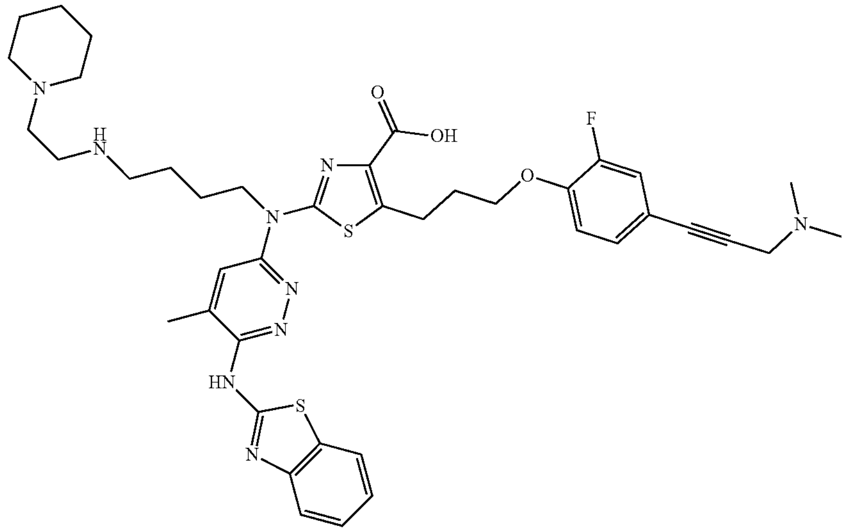 [SMILES: Cc1cc(N(CCCCNCCN2CCCCC2)c2nc(C(=O)O)c(CCCOc3ccc(C#CCN(C)C)cc3F)s2)nnc1Nc1nc2ccccc2s1]

Step A: methyl 5-[3-[4-[3-(dimethylamino)prop-1-ynyl]-2-fluoro-phenoxy]propyl]-2-[[5-methyl-6-[(Z)-[3-(2-trimethylsilylethoxymethyl)-1,3-benzothiazol-2-ylidene]amino]pyridazin-3-yl]-[4-[2-(1-piperidyl)ethylamino]butyl]amino]thiazole-4-carboxylate Using Alkylation with in situ generated tosylate General Procedure starting from Preparation 5d and 2-(1-piperidyl)ethanamine as the appropriate amine, the desired product was obtained.

$^1$H NMR (500 MHz, DMSO-$d_6$) δ ppm 7.79 (dm, 1H), 7.68 (s, 1H), 7.48 (dm, 1H), 7.44 (m, 1H), 7.30 (dd, 1H), 7.26 (m, 1H), 7.24 (dd, 1H), 7.17 (t, 1H), 5.86 (s, 2H), 4.42 (t, 2H), 4.19 (t, 2H), 3.82 (s, 3H), 3.77 (m, 2H), 3.63 (brs, 2H), 3.28 (t, 2H), 3.07 (t, 2H), 3.04 (t, 2H), 2.76 (t, 2H), 2.60 (brm, 4H), 2.48 (s, 3H), 2.41 (brs, 6H), 2.14 (m, 2H), 1.83 (m, 2H), 1.73 (m, 2H), 1.58 (m, 4H), 1.43 (m, 2H), 0.94 (m, 2H), −0.07 (s, 9H); HRMS-ESI (m/z): $[M+H]^+$ calcd for $C_{48}H_{67}FN_9O_4S_2Si$: 944.4505, found 944.44978.

Step B: 2-[[6-(1,3-benzothiazol-2-ylamino)-5-methylpyridazin-3-yl]-[4-[2-(1-piperidyl)ethylamino]butyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{41}H_{51}FN_9O_3S_2$: 800.3535, found 800.3540.

Example 180: 2-[[6-(1,3-Benzothiazol-2-ylamino)-5-methyl-pyridazin-3-yl]-[4-(2-morpholinoethyl-amino)butyl]amino]-5-[3-[4-[3-(dimethylamino)prop-1-ynyl]-2-fluoro-phenoxy]propyl]thiazole-4-carboxylic acid

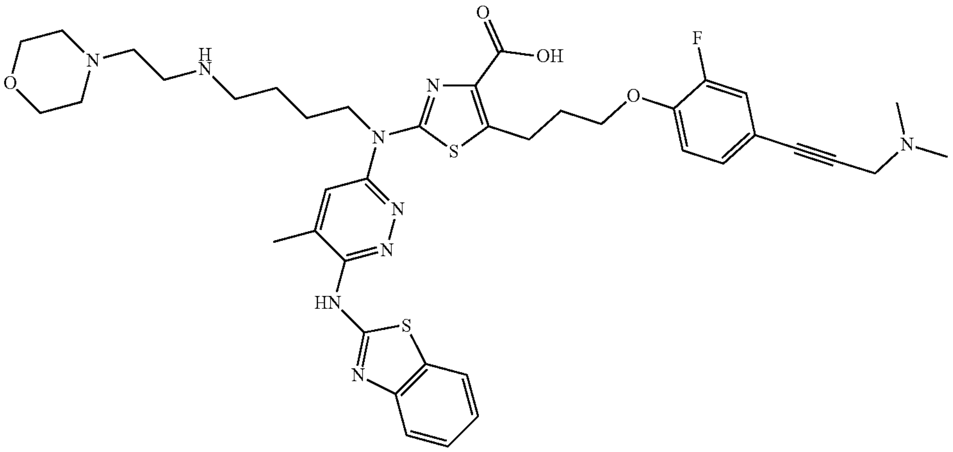 [SMILES: Cc1cc(N(CCCCNCCN2CCOCC2)c2nc(C(=O)O)c(CCCOc3ccc(C#CCN(C)C)cc3F)s2)nnc1Nc1nc2ccccc2s1]

Step A: methyl 5-[3-[4-[3-(dimethylamino)prop-1-ynyl]-2-fluoro-phenoxy]propyl]-2-[[5-methyl-6-[(Z)-[3-(2-trimethylsilylethoxymethyl)-1,3-benzothiazol-2-ylidene]amino]pyridazin-3-yl]-[4-(2-morpholinoethylamino)butyl]amino]thiazole-4-carboxylate Using Alkylation with in situ generated tosylate General Procedure starting from Preparation 5d and 2-morpholinoethanamine as the appropriate amine, the desired product was obtained.

$^{1}$H NMR (500 MHz, DMSO-d$_6$) δ ppm 7.81 (dm, 1H), 7.76 (s, 1H), 7.48 (dm, 1H), 7.44 (m, 1H), 7.40 (dd, 1H), 7.28 (dm, 1H), 7.27 (m, 1H), 7.20 (t, 1H), 5.87 (s, 2H), 4.42 (t, 2H), 4.17 (t, 2H), 3.85 (brs, 2H), 3.79 (s, 3H), 3.72 (m, 2H), 3.56 (m, 4H), 3.27 (t, 2H) 3.01 (t, 2H), 2.99 (t, 2H), 2.58 (brm, 2H), 2.51 (brs, 6H), 2.47 (s, 3H), 2.39 (brm, 4H), 2.13 (m, 2H), 1.84-1.68 (m, 4H), 0.92 (m, 2H), −0.11 (s, 9H); HRMS-ESI (m/z): $[M+2H]^{2+}$ calcd for $C_{47}H_{66}FN_9O_5S_2Si$: 473.7186, found 473.7183.

Step B: [[6-(1,3-benzothiazol-2-ylamino)-5-methyl-pyridazin-3-yl]-[4-(2-morpholinoethylamino)butyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{40}H_{50}FN_9O_4S_2$: 401.6700, found 401.6697.

Example 181: 2-[[6-(1,3-Benzothiazol-2-ylamino)-5-methyl-pyridazin-3-yl]-[4-[(1-methyl-4-piperidyl)amino]butyl]amino]-5-[3-[4-[3-(dimethylamino)prop-1-ynyl]-2-fluoro-phenoxy]propyl]thiazole-4-carboxylic acid

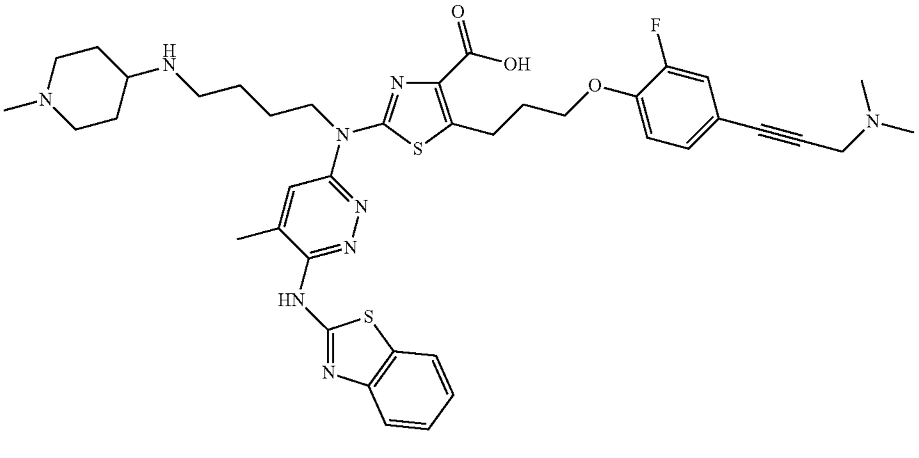

Step A: methyl 5-[3-[4-[3-(dimethylamino)prop-1-ynyl]-2-fluoro-phenoxy]propyl]-[4-[(1-methyl-4-piperidyl)amino]butyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with in situ generated tosylate General Procedure starting from Preparation 5d and 1-methylpiperidin-4-amine as the appropriate amine, the desired product was obtained.

$^1H$ NMR (500 MHz, DMSO-$d_6$) δ ppm 7.84 (dm, 1H), 7.70 (s, 1H), 7.47 (dm, 1H), 7.43 (m, 1H), 7.30 (dd, 1H), 7.25 (m, 1H), 7.21 (dm, 1H), 7.15 (t, 1H), 5.86 (s, 2H), 4.39 (t, 2H), 4.14 (t, 2H), 3.77 (s, 3H), 3.72 (m, 2H), 3.38 (s, 2H), 3.26 (t, 2H), 2.65/1.84 (m+m, 4H), 2.56 (t, 2H), 2.46 (s, 3H), 2.27 (m, 1H), 2.19 (s, 6H), 2.12 (m, 2H), 2.09 (s, 3H), 1.72 (m, 2H), 1.7/1.19 (m+m, 4H), 1.46 (m, 2H), 0.92 (m, 2H), −0.11 (s, 9H); HRMS-ESI (m/z): $[M+2H]^{2+}$ calcd for $C_{47}H_{64}FN_9O_4S_2Si$: 465.7211, found 465.7210.

Step B: 2-[[6-(1,3-benzothiazol-2-ylamino)-5-methyl-pyridazin-3-yl]-[4-[(1-methyl-4-piperidyl)amino]butyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{40}H_{48}FN_9O_3S_2$: 393.6726, found 393.6735.

Example 182: 2-[[6-(1,3-Benzothiazol-2-ylamino)-5-methyl-pyridazin-3-yl]-[5-[2-(diethylamino)ethylamino]pentyl]amino]-5-[3-[4-[3-(dimethylamino)prop-1-ynyl]-2-fluoro-phenoxy]propyl]thiazole-4-carboxylic acid

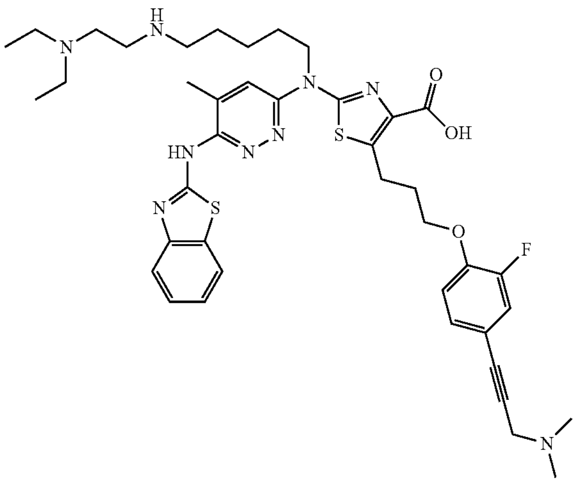 [SMILES: CCN(CC)CCNCCCCCN(c1cc(C)c(Nc2nc3ccccc3s2)nn1)c1nc(C(=O)O)c(CCCOc2ccc(C#CCN(C)C)cc2F)s1]

Step A: methyl 2-[5-[2-(diethylamino)ethylamino]pentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starling from Preparation 5f and N',N'-diethylethane-1,2-dioxamine as the appropriate amine, the desired product was obtained.

HRMS-ESI (m/z): $[M+2H]^{2+}$ calcd for $C_{48}H_{70}FN_9O_4S_2Si$: 473.7367, found 473.7360.

Step B: 2-[[6-(1,3-benzothiazol-2-ylamino)-5-methyl-pyridazin-3-yl]-[5-[2-(diethylamino)ethylamino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{41}H_{53}FN_9O_3S_2$: 802.3691, found 802.3702.

Example 183: 2-({6-[(1,3-Benzothiazol-2-yl)amino]-5-methylpyridazin-3-yl}(methyl)amino)-5-(3-{4-[3-(dimethylamino)prop-1-yn-1-yl]-2-fluorophenoxy}-2-methoxypropyl)-1,3-thiazole-4-carboxylic acid

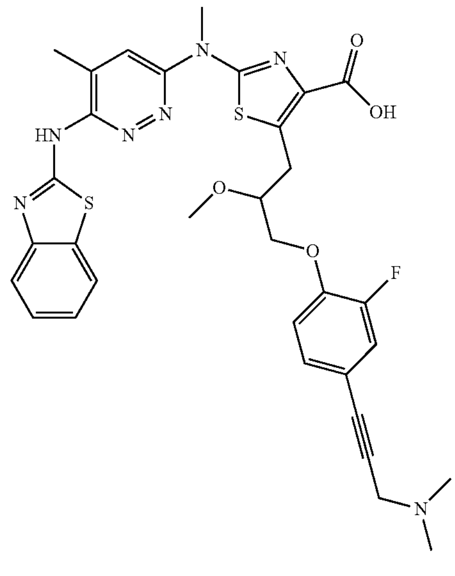 [SMILES: COC(COc1ccc(C#CCN(C)C)cc1F)Cc1sc(N(C)c2cc(C)c(Nc3nc4ccccc4s3)nn2)nc1C(=O)O]

Step A: ethyl 5-(2-methoxy-3-{[tris(propan-2-yl)silyl]oxy}propyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate The product from Preparation 4a (1.6 g, 3.93 mmol, 1 eq) and the product from Preparation 3zh (1.75 g, 4.06 mmol, 103 eq) were added to a solution of tris(dibenzylideneacetone)dipalladium(0)(180 mg, 0.2 mmol, 0.05 eq) and Xantphos (228 mg, 0.39 mmol, 0.1 eq) in 1,4-dioxane (40 mL). Cesium carbonate (3.84 g, 11.8 mmol, 3 eq) and N,N-diisopropylethylamine (2.1 mL, 11.8 mmol, 3 eq) were added and the mixture was heated in a sealed tube at 125° C. for 24 h. The suspension was allowed to cool and the mixture filtered through celite, the solids washed with 1,4-dioxane (30 mL) and the filtrate was concentrated in vacuo. Purification by flash column chromatography (100 g silica) eluting with a gradient of 0-25% ethyl acetate in iso-heptane afforded the desired product as a pale yellow solid (2.49 g, 3.11 mmol, 79%).

LC/MS ($C_{38}H_{60}N_6O_5Si_2S_2$) 801 $[M+H]^+$; RT 1.74 (LCMS-V-B2)

$^1$H NMR (400 MHz, DMSO-d6) δ 7.58 (dt, J=7.6, 0.9 Hz, 1H), 7.42 (d, J=1.2 Hz, 1H), 7.40-7.36 (m, 2H), 7.24-7.17 (m, 1H), 5.85 (s, 2H), 4.39 (q, J=7.1 Hz, 2H), 3.85 (s, 3H), 3.80 (dd, J=4.8, 2.4 Hz, 2H), 3.78-3.72 (m, 2H), 3.60-3.49 (m, 2H), 3.45 (s, 3H), 3.32-3.15 (m, 1H), 2.46 (d, J=1.0 Hz, 3H), 1.42 (t, J=7.1 Hz, 3H), 1.16-1.02 (m, 2H), 1.01-0.92 (m, 2H), −0.07 (s, 9H).

Step B: ethyl 5-(3-hydroxy-2-methoxypropyl)-2-[methyl(5-methyl-6-{[(2Z-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Step A (2.45 g, 3.06 mmol, 1 eq) in tetrahydrofuran (15 mL), cooled in ice-water, was added tetrabutylammonium fluoride (1M in tetrahydrofuran; 10 mL, 9.17 mmol, 3 eq) and the mixture was stirred for 60 min at 0° C. The reaction was partitioned between water (75 mL) and ethyl acetate (150 mL), and the organic phase was successively washed with water (2×75 mL) and brine (75 mL), dried (magnesium sulfate) and concentrated in vacuo. Purification by flash column chromatography (50 g silica) eluting with a gradient of 0-50% ethyl acetate in iso-heptane afforded the desired product as a pale yellow/green foam (1.83 g, 2.84 mmol, 93%).

LC/MS ($C_{29}H_{40}N_6O_5SiS_2$) 645 $[M+H]^+$; RT 1.56 (LCMS-V-B1)

$^1$H NMR (400 MHz, DMSO-d6) δ 7.59 (dt, J=7.6, 0.9 Hz, 1H), 7.40-7.36 (m, 2H), 7.33 (d, J=1.1 Hz, 1H), 7.24-7.18 (m, 1H), 5.84 (s, 2H), 4.41 (q, J=7.1 Hz, 2H), 3.85 (s, 3H), 3.79-3.70 (m, 2H), 3.47-3.36 (m, 2H), 2.66 (t, J=6.6 Hz 1H), 2.46 (d, J=1.0 Hz, 3H), 1.43 (t, 3H), 1.03-0.90 (m, 2H), −0.07 (s, 9H).

Step C: ethyl 5-[3-(2-fluoro-4-iodophenoxy)-2-methoxypropyl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Step B (750 mg, 1.16 mmol, 1 eq) in toluene (15 mL) was added diisopropylazodicarboxylate (0.5 mL, 2.33 mmol, 2 eq), 2-fluoro-4-iodophenol (500 mg, 2.1 mmol, 1.81 eq) and triphenylphosphine (610 mg, 2.33 mmol, 2 eq) and the mixture was heated at 100° C. for 18 h then allowed to cool to ambient temperature and concentrated in vacuo. Purification by flash column chromatography (100 g silica) eluting with a gradient of 0-35% ethyl acetate in iso-heptane afforded the desired product as an orange gum (1.2 g, 1.04 mmol, 90%).

LC/MS ($C_{35}H_{42}FIN_6O_5SiS_2$) 865 $[M+H]^+$; RT 1.78 (LCMS-V-B1)

$^1$H NMR (400 MHz, DMSO-d6) δ 7.60 (d, 1H), 7.42-7.30 (m, 5H), 7.25-7.19 (m, 1H), 6.72 (t, J=8.6 Hz, 1H), 5.85 (s, 2H), 4.40 (q, J=7.1 Hz, 2H), 4.16-4.10 (m, 1H), 4.08-4.01 (m, 1H), 3.98-3.89 (m, 1H), 3.86 (s, 3H), 3.80-3.68 (m, 2H), 3.59-3.49 (m, 4H), 3.48-3.39 (m, 1H), 2.47 (s, 3H), 1.42 (t, J=7.1 Hz, 3H), 1.01-0.92 (m, 2H), −0.07 (s, 9H).

Step D: ethyl 5-(3-{4-[3-(dimethylamino)prop-1-yn-1-yl]-2-fluorophenoxy}-2-methoxypropyl)-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Step C (1.2 g, 1.04 mmol, 1 eq) in dimethylformamide (15 mL) was added copper(I) iodide (19.8 mg, 0.1 mmol, 0.1 eq), bis(triphenylphosphine)palladium(II) dichloride (73 mg, 0.1 mmol, 0.1 eq) and dimethyl(prop-2-yn-1-yl)amine (0.25 mL, 2.32 mmol, 2.23 eq). N,N-Diisopropylethylamine (0.55 mL, 3.12 mmol, 3 eq) was added and the mixture was heated at 80° C. for 90 min. The solution was allowed to cool to ambient temperature and was partitioned between ethyl acetate (100 mL) and water (75 mL), and the organic phase was successively washed with water (2×75 mL) and brine (75 mL), dried (magnesium sulfate) and concentrated in vacuo. Purification by flash column chromatography (50 g silica) eluting with a gradient of 0-100% ethyl acetate in iso-heptane afforded the desired product as a brown gum (460 mg, 0.56 mmol, 54%).

LC/MS ($C_{40}H_{50}FN_7O_5SiS_2$) 820 $[M+H]^+$; RT 1.52 (LCIAS-V-B1)

$^1$H NMR (400 MHz, DMSO-d6) δ 7.70-7.64 (m, 1H), 7.63-7.58 (m, 1H), 7.42-7.34 (m, 2H), 7.24-7.19 (m, 1H), 7.17-7.09 (m, 2H), 6.88 (t, J=8.7 Hz, 1H), 5.85 (s, 2H), 4.40 (q, J=7.1 Hz, 2H), 4.19-4.06 (m, 2H), 4.01-3.89 (m, 1H), 3.86 (s, 3H), 3.80-3.68 (m, 2H), 3.61-3.49 (m, 4H), 3.49-3.37 (m, 3H), 2.47 (t, J=0.9 Hz, 3H), 2.34 (s, 6H), 1.43 (t, 3H), 1.01-0.92 (m, 2H), −0.07 (d, J=0.7 Hz, 9H).

Step E: ethyl 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-methoxypropyl)-1,3-thiazole-4-carboxylate To a solution of the product from Step D (460 mg, 0.56 mmol, 1 eq) in dichloromethane (4 mL) was added trifluoroacetic acid (1.1 mL, 14 mmol, 25 eq) and the mixture was stirred for 72 h at ambient temperature. Dichloromethane (150 mL) was added and the mixture was washed successively with 10% aqueous potassium carbonate (75 mL), water (2×75 mL) and brine (75 mL), dried (magnesium sulfate) and concentrated in vacuo. Trituration with diethyl ether (10 mL) gave a solid that was collected by filtration, washed with diethyl ether (2×10 mL) and dried under vacuum to afford the desired product as a green powder (250 mg, 0.33 mmol, 58%).

LC/MS ($C_{34}H_{36}FN_7O_4S_2$) 690 $[M+H]^+$; RT 1.23 (LCNIS-V-B1)

$^1$H NMR (400 MHz, DMSO-d6) δ 7.83-7.69 (m, 2H), 7.62-7.53 (m, 1H), 7.51-7.39 (m, 1H), 7.32-7.25 (m, 1H), 7.25-7.16 (m, 2H), 6.94 (t, J=8.7 Hz, 1H), 4.47 (q, J=7.1 Hz, 2H), 4.28-4.06 (m, 2H), 4.05-3.95 (m, 1H), 3.95-3.82 (m,

3H), 3.72-3.64 (m, 1H), 3.60 (s, 3H), 3.57-3.52 (m, 1H), 3.50 (s, 2H), 2.51 (s, 3H), 2.41 (s, 6H), 1.49 (t, J=7.1 Hz, 3H).

Step F: 2-({6-[(1,3-benzothiazol-2-yl)amino]-5-methylpyridazin-3-yl}(methyl)amino)-5-(3-{4-[3-(dimethylamino)prop-1-yn-1-yl]-2-fluorophenoxy}-2-methoxypropyl)-1,3-thiazole-4-carboxylic acid To a solution of the product from Step E (240 mg, 0.31 mmol, 1 eq) in a 1:2 mixture of 1,4-dioxane (6 mL) was added lithium hydroxide monohydrate (131 mg, 3.13 mmol, 10 eq) and the suspension was heated at 60° C. for 1 h. The reaction was allowed to cool and was filtered through celite and the solids washed with water (4 mL). The filtrate was acidified with acetic acid to pH 6 to give a suspension and the solids were collected by filtration, washed with water (20 mL) and dried under vacuum to afford the desired product as a green solid (110 mg, 0.17 mmol, 53%).

HRMS-ESI (m/z) [M+H]+ calcd for $C_{32}H_{33}FN_7O_4S_2$: 662.2014, found 662.2052.

Example 184: 2-[[6-(1,3-Benzothiazol-2-ylamino)-5-methyl-pyridazin-3-yl]-(4-piperazin-1-ylbutyl)amino]-5-[3-[4-[3-(dimethylamino)prop-1-ynyl]-2-fluoro-phenoxy]propyl]thiazole-4-carboxylic acid

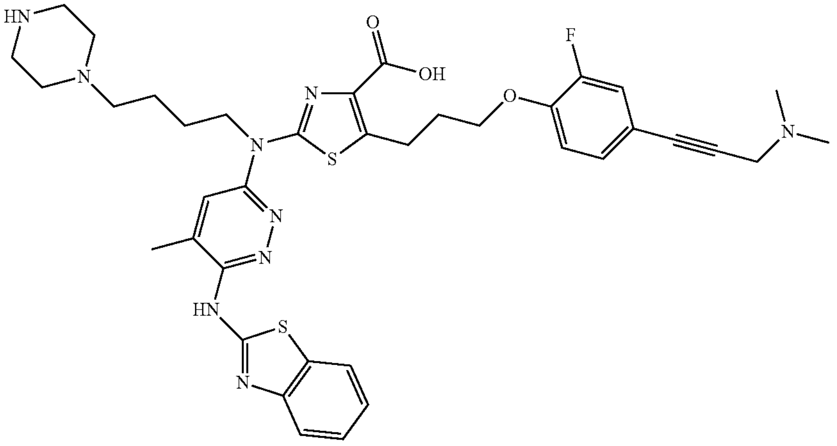 [SMILES: Cc1cc(N(CCCCN2CCNCC2)c2nc(C(=O)O)c(CCCOc3ccc(C#CCN(C)C)cc3F)s2)nnc1Nc1nc2ccccc2s1]

Step A: methyl 2-[4-(4-tert-butoxycarbonylpiperazin-1-yl)butyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5d and tert-butyl piperazine-1-carboxylate as the appropriate amine, the desired product was obtained.

HRMS-ESI (m/z): $[M+H]^+$ calcd for $C_{50}H_{69}FN_9O_6S_2Si$: 1002.4560, found 1002.4544.

Step B: 2-[[6-(1,3-benzothiazol-2-ylamino)-5-methyl-pyridazin-3-yl]-(4-piperazin-1-ylbutyl)amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{38}H_{46}FN_9O_3S_2$: 379.6569, found 379.6565.

Example 185: 2-[[6-(1,3-Benzothiazol-2-ylamino)-5-methyl-pyridazin-3-yl]-(4-hydroxybutyl)amino]-5-[3-[2-fluoro-4-[(E)-3-(methylamino)prop-1-enyl]phenoxy]propyl]thiazole-4-carboxylic acid

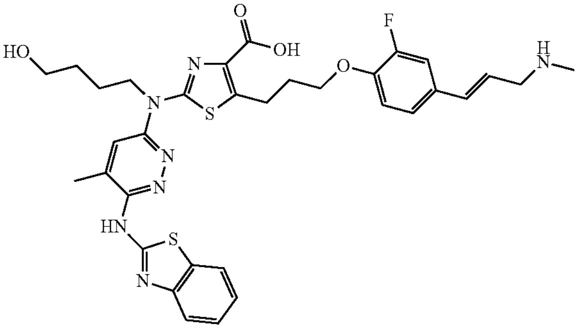 [SMILES: CNC/C=C/c1ccc(OCCCc2sc(N(CCCCO)c3cc(C)c(Nc4nc5ccccc5s4)nn3)nc2C(=O)O)c(F)c1]

Step A: tert-butyl N-methyl-N—[(E)-3-(4,4,5,5-tetramethyl-1,3,2-dioxaborolan-2-yl)allyl]carbamate The mixture of 1.50 g of tert-butyl N-methyl-N-prop-2-ynyl-carbamate (8.86 mmol, 1 eq.), 1.70 g of 4,4,5,5-tetramethyl-1,3,2-dioxaborolane (13.30 mmol, 1.5 eq.), 90 mg of N,N-diethylethanamine (0.89 mmol, 0.1 eq.) and 229 mg of chloridobis($\eta^5$-cyclopentadienyl)hydridozirconium (Schwartz's reagent)(0.89 mmol, 0.1 eq.) were stirred at 65° C. for overnight. After the reaction EtOAc and cc. $NH_4Cl$ were added the organic layer was separated and washed with cc. $NaHCO_3$, cc. NaCl, dried over $MgSO_4$, filtered then concentrated onto Celite. It was purified via flash column chromatography using heptane and EtOAc as eluents to give 1347 mg (51%) of the desired product as a colorless thick oil.

$^1H$ NMR (500 MHz, DMSO-$d_6$) δ ppm 6.38 (dt, 1H), 5.35 (dt, 1H), 3.84 (dd, 2H), 2.75 (s, 3H), 1.39 (s, 9H), 1.21 (s, 12H); $^{13}C$ NMR (125 MHz, DMSO-$d_6$) δ ppm 155.3, 148.9, 119.1, 83.4, 79.1, 52.2, 34.5, 28.5, 25.1; HRMS-EI (m/z): $[M-^tBu+H]^+$ calcd for $C_{11}H_{20}BNO_4$: 241.1480, found 241.1597.

Step B: methyl 5-[3-[4-[(E)-3-[tert-butoxycarbonyl(methyl)amino]prop-1-enyl]-2-fluoro-phenoxy]propyl]-2-[4-[tert-butyl(dimethyl)silyl]oxybutylamino]thiazole-4-carboxylate 1.00 g of Preparation 3c, Step B (1.61 mmol, 1 eq.), 716 mg of the product from Step A (2.41 mmol, 1.5 eq.), 93 mg of $Pd(PPh_3)_4$ (0.08 mmol, 0.05 eq.) and 666 mg of $K_2CO_3$ (4.82 mmol, 3 eq.) were mixed in 15 mL of 1,2-dimethoxy-ethane and 1.9 mL of water in a MW vessel and irradiated at 110° C. for 1 h. Full conversion was observed. EtOAc and water were added the organic layer was separated and washed with cc. NaCl, dried over $MgSO_4$, filtered then concentrated onto Celite. It was purified via flash column chromatography using heptane and EtOAc as eluents to give 708 mg (66%) of the desired product as a colorless thick oil.

$^1H$ NMR (500 MHz, DMSO-$d_6$) δ ppm 7.46 (t, 1H), 7.33 (dd, 1H), 7.14 (dd, 1H), 7.07 (t, 1H), 6.39 (brd, 1H), 6.13 (dt, 1H), 4.06 (t, 2H), 3.90 (brd, 2H), 3.71 (s, 3H), 3.60 (t, 2H), 3.18 (m, 2H), 3.12 (t, 2H), 2.79 (s, 3H), 2.00 (m, 2H), 1.57 (m, 2H), 1.51 (m, 2H), 1.41 (s, 9H), 0.86 (s, 9H), 0.02 (s, 6H); $^{13}C$ NMR (125 MHz, DMSO-$d_6$) δ ppm 164.8, 163.0, 155.3, 152.5, 146.3, 137.0, 136.1, 130.7, 130.5, 125.3, 123.4, 115.7, 113.8, 79.1, 68.4, 62.7, 51.6, 50.5, 44.5, 34.1, 30.9, 30.2, 28.6, 26.3, 25.7, 23.4, 18.4, −4.8; HRMS-ESI (m/z): $[M+H]^+$ calcd for $C_{33}H_{53}FN_3O_6SSi$: 666.3403, found 666.3409.

Step C: methyl 5-[3-[4-[(E)-3-[tert-butoxycarbonyl(methyl)amino]prop-1-enyl]-2-fluoro-phenoxy]propyl]-2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 138 mg of the product from Step B (0.21 mmol, 1 eq.) and 101 mg of Preparation 4a (0.25 mmol, 1.2 eq.) as the appropriate halide, 102 mg (48%) of the desired product was obtained.

$^1H$ NMR (500 MHz, DMSO-$d_d$) δ ppm 7.81 (dm, 1H), 7.62 (brs, 1H), 7.46 (dm, 1H), 7.43 (m, 1H), 7.33 (ddd, 1H), 7.25 (m, 1H), 7.15 (dm, 1H), 7.10 (t, 1H), 6.38 (d, 1H), 6.10 (dt, 1H), 5.86 (s, 2H), 4.42 (t, 2H), 4.14 (t, 2H), 3.88 (d, 2H), 3.79 (s, 3H), 3.75 (m, 2H) 3.63 (t, 2H), 3.27 (t, 2H), 2.77 (s, 3H), 2.45 (d, 3H), 2.12 (m, 2H), 1.77 (m, 2H), 1.54 (m, 2H), 1.40 (s, 9H), 0.92 (m, 2H), 0.81 (s, 3H), −0.01 (s, 6H), −0.09 (s, 9H); HRMS-ESI (m/z): $[M+H]^+$ calcd for $C_{51}H_{75}FN_7O_7S_2Si_2$: 1036.4686, found 1036.4706.

Step D: 2-[[6-(1,3-benzothiazol-2-ylamino)-5-methyl-pyridazin-3-yl]-(1-hydroxybutyl)amino]-5-[3-[2-fluoro-4-[(E)-3-(methylamino)prop-1-enyl]phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step C, the TFA-salt of the desired product was obtained in the isomeric ratio of ca. 82% E and 18% Z (based on NMR).

HRMS-ESI (m/z): $[M+H]^+$ calcd for $C_{33}H_{37}FN_7O_4S_2$: 678.2327, found 678.2326.

Example 186: 2-[[6-(1,3-Benzothiazol-2-ylamino)-5-methyl-pyridazin-3-yl]-(4-hydroxybutyl)amino]-5-[3-[2-fluoro-4-[3-(methylamino)propyl]phenoxy]propyl]thiazole-4-carboxylic acid

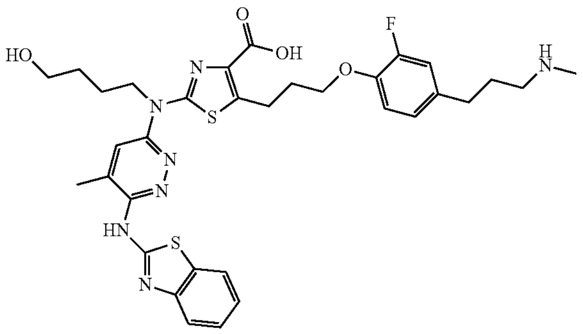 [SMILES: CNCCCc1ccc(OCCCc2sc(N(CCCCO)c3cc(C)c(Nc4nc5ccccc5s4)nn3)nc2C(=O)O)c(F)c1]

Step A: methyl 5-[3-[4-[3-[tert-butoxycarbonyl(methyl)amino]propyl]-2-fluoro-phenoxy]propyl]-2-[4-[tert-butyl(dimethyl)silyl]oxybutylamino]thiazole-4-carboxylate A 20 mL oven-dried pressure bottle equipped with a PTFE-coated magnetic stirring bar was charged with 400 mg of Example 185, Step B (0.60 mmol, 1 eq.), 64 mg of 10 w % Pd/C (0.06 mmol, 0.1 eq.) in 6 mL of methanol, and then placed under a nitrogen atmosphere using hydrogenation system. After that it was filled with 4 bar $H_2$ gas and stirred at rt for 3 h. Full conversion was observed, Celite was added to the reaction mixtures and the volatiles were removed under reduced pressure. Then it was purified via flash column chromatography using heptane and EtOAc as eluents to give 381 mg (95%) of the desired product as colorless oil.

$^1$H NMR (500 MHz, DMSO-$d_6$) δ ppm 7.57 (t, 1H), 7.07 (dd, 1H), 7.02 (t, 1H), 6.93 (d, 1H), 4.01 (t, 2H), 3.69 (s, 3H), 3.59 (t, 2H), 3.17 (q, 2H), 3.13 (m, 2H), 3.11 (t, 2H), 2.75 (brs, 3H), 2.47 (t, 2H), 1.98 (quin, 2H), 1.72 (br, 2H), 1.54 (m, 2H), 1.50 (m, 2H), 1.38/1.33 (brs+brs, 9H), 0.85 (s, 9H), 0.01 (s, 6H); $^{13}$C NMR (125 MHz, DMSO-$d_6$) δ ppm 164.6, 163.1, 155.2, 152.0, 144.7, 136.5, 135.3, 124.6, 116.2, 115.3, 79.0, 68.1, 62.7, 51.7, 47.9, 44.4, 34.1, 31.7, 30.9, 30.1, 29.3, 28.6, 26.3, 25.7, 23.4, 18.5, −4.9; HRMS-ESI (m/z): $[M+H]^+$ calcd for $C_{33}H_{55}FN_3O_6SSi$: 668.3559, found 668.3544.

Step B: methyl 5-[3-[4-[3-[tert-butoxycarbonyl (methyl)amino]propyl]-2-fluoro-phenoxy]propyl]-2-[4-[tert-butyl(dimethyl)silyl]oxybutyl-[5-methyl-6-[(Z)-[3-(2-trimethylsilylethoxymethyl)-1,3-benzothiazol-2-ylidene]amino]pyridazin-3-yl]amino] thiazole-4-carboxylate Using Buchwald General Procedure II starting from 375 mg of the product from Step A (0.56 mmol, 1 eq.) and 274 mg of Preparation 4a (0.67 mmol, 1.2 eq.) as the appropriate halide, 479 mg (82%) of the desired product was obtained.

$^1$H NMR (500 MHz, DMSO-$d_6$) δ ppm 7.80 (dm, 1H), 7.65/7.61 (s/s, 1H), 7.46 (dd, 1H), 7.43 (td, 1H), 7.24 (td, 1H), 7.05 (t, 1H), 7.04 (m, 1H), 6.93 (dm, 1H), 5.85 (s, 2H), 4.41 (t, 2H), 4.10 (t, 2H), 3.80/3.79 (s/s, 3H), 3.74 (m, 2H), 3.63/3.47 (t, 2H), 3.26 (m, 2H), 3.13 (t, 2H), 2.74 (s, 3H), 2.47 (t, 2H), 2.46/2.45 (s/s, 3H), 2.11 (m, 2H), 1.77 (m, 2H), 1.72 (m, 2H), 1.54 (m, 2H), 1.35 (br., 9H), 0.92 (m, 2H), 0.85/0.81 (s/s, 9H), −0.01/−0.03 (s, 6H), −0.09/−0.1 (s, 9H); $^{13}$C NMR (125 MHz, DMSO-$d_6$) δ ppm 155.4/155.3, 127.1, 124.6, 123.4, 123.1, 117.8, 116.2, 116.1, 111.9, 78.7, 73.1, 68.9, 66.8, 62.6/61, 51.8, 48.0, 46.9, 34.2, 31.8, 31.2, 29.8, 29.2, 28.5, 26.3/26.2, 23.9, 23.2, 17.9, 17.7, −1.0, −2.7/−4.9; HRMS-ESI (m/z): $[M+H]^+$ calcd for $C_{51}H_{77}FN_7O_7S_2Si_2$: 1038.4843, found 1038.4837.

Step C: 2-[[6-(1,3-benzothiazol-2-ylamino)-5-methyl-pyridazin-3-yl]-(4-hydroxybutyl)amino]-5-[3-[2-fluoro-4-[3-(methylamino)propyl]phenoxy] propyl]thiazole-4-carboxylic acid Using Deprotection and Hydrolysis General Procedure followed by repurification via reverse phase preparative chromatography (C18, 0.1% TFA in water:MeCN) starting from the product from Step B, the TFA-salt of the desired product was obtained.

HRMS-ESI (m/z): $[M+H]^+$ calcd for $C_{33}H_{39}FN_7O_4S_2$: 680.2483, found 680.2469.

Example 187: 2-[[6-(1,3-Benzothiazol-2-ylamino)-5-methyl-pyridazin-3-yl]-[5-[2-(1-piperidyl)ethyl-amino]pentyl]amino]-5-[3-[4-[3-(dimethylamino) prop-1-ynyl]-2-fluoro-phenoxy]propyl]thiazole-4-carboxylic acid

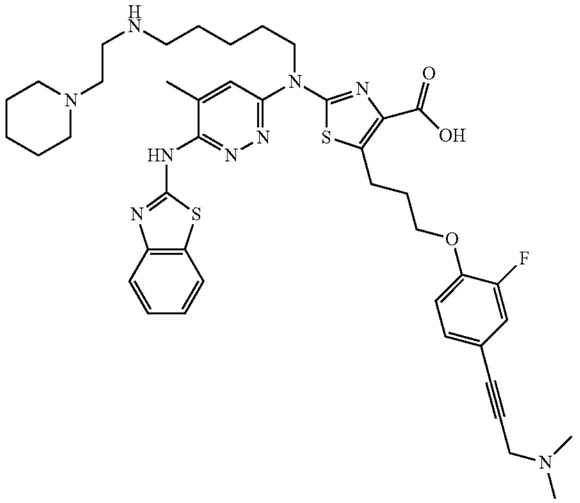 [SMILES: Cc1cc(N(CCCCCNCCN2CCCCC2)c2nc(C(=O)O)c(CCCOc3ccc(C#CCN(C)C)cc3F)s2)nnc1Nc1nc2ccccc2s1]

Step A: methyl 5-[3-[4-[3-(dimethylamino)prop-1-ynyl]-2-fluoro-phenoxy]propyl]-2-[[5-methyl-6-[(Z)-[3-(2-trimethylsilylethoxymethyl)-1,3-benzothiazol-2-ylidene]amino]pyridazin-3-yl]-[5-[2-(1-piperidyl) ethylamino]pentyl]amino]thiazole-4-carboxylate Using Alkylation with in situ generated tosylate General Procedure starting from Preparation 5f and 2-(1-piperidyl) ethanamine as the appropriate amine, the desired product was obtained.

HRMS-ESI (m/z): $[M+2H]^{2+}$ calcd for $C_{49}H_{70}FN_9O_4S_2Si$: 479.7367, found 479.7353.

Step B: 2-[[6-(1,3-benzothiazol-2-ylamino)-5-methyl-pyridazin-3-yl]-[5-[2-(1-piperidyl)ethyl-amino]pentyl]amino]-5-[3-[4-[3-(dimethylamino) prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{42}H_{53}FN_9O_3S_2$: 814.3691, found 814.3670.

Example 188: 2-[[6-(1,3-Benzothiazol-2-ylamino)-5-methyl-pyridazin-3-yl]-[4-(methylamino)butyl]amino]-5-[3-[4-[3-(dimethylamino)prop-1-ynyl]-2-fluoro-phenoxy]propyl]thiazole-4-carboxylic acid

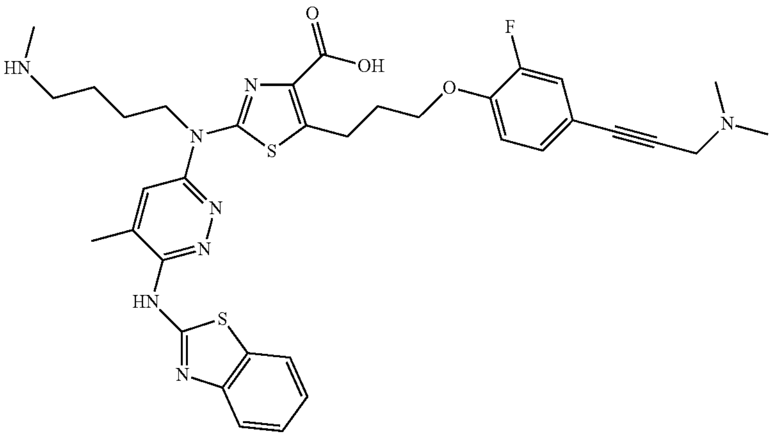 [SMILES: CNCCCCN(c1cc(C)c(Nc2nc3ccccc3s2)nn1)c1nc(C(=O)O)c(CCCOc2ccc(C#CCN(C)C)cc2F)s1]

Step A: methyl 3-[3-[4-[3-(dimethylamino)prop-1-ynyl]-2-fluoro-phenoxy]propyl]-2-[4-(methylamino)butyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with in situ generated tosylate General Procedure starting from Preparation 5d and methanamine as the appropriate amine, the desired product was obtained.

$^1$H NMR (500 MHz, DMSO-$d_6$) δ ppm 7.84 (dm, 1H), 7.72 (s, 1H), 7.47 (dm, 1H), 7.44 (m, 1H), 7.31 (dd, 1H), 7.25 (m, 1H), 7.21 (dm, 1H), 7.16 (t, 1H), 5.86 (s, 2H), 4.37 (t, 2H), 4.15 (t, 2H), 3.78 (s, 3H), 3.72 (m, 2H), 3.38 (s, 2H), 3.27 (t, 2H), 2.52 (t, 2H), 2.46 (s, 3H), 2.26 (s, 3H), 2.19 (s, 6H), 2.13 (m, 2H), 1.71 (m, 2H), 1.49 (m, 2H), 0.92 (m, 2H), −0.11 (s, 9H); HRMS-ESI (m/z): $[M+H]^+$ calcd for $C_{42}H_{56}FN_8O_4S_2Si$: 847.3614, found 847.3594.

Step B: 2-[[6-(1,3-benzothiazol-2-ylamino)-5-methyl-pyridazin-3-yl]-[4-(methylamino)butyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{35}H_{41}FN_8O_3S_2$: 352.1358, found 352.1361.

Example 189: 2-[[6-(1,3-Benzothiazol-2-ylamino)-5-methyl-pyridazin-3-yl]-(5-piperazin-1-ylpentyl)amino]-5-[3-[4-[3-(dimethylamino)prop-1-ynyl]-2-fluoro-phenoxy]propyl]thiazole-4-carboxylic acid

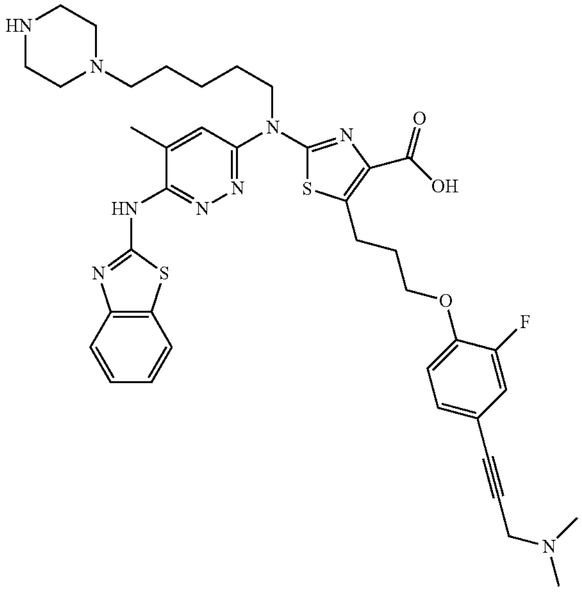 [SMILES: Cc1cc(N(CCCCCN2CCNCC2)c2nc(C(=O)O)c(CCCOc3ccc(C#CCN(C)C)cc3F)s2)nnc1Nc1nc2ccccc2s1]

Step A: methyl 2-[5-(4-tert-butoxycarbonylpiperazin-1-yl)pentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5f and tert-butyl piperazine-1-carboxylate as the appropriate amine, the desired product was obtained.

HRMS-ESI (m/z): $[M+H]^+$ calcd for $C_{51}H_{71}FN_9O_6S_2Si$: 1016.4716, found 1016.4710.

Step B: 2-[[6-(1,3-benzothiazol-2-ylamino)-5-methyl-pyridazin-3-yl]-(5-piperazin-1-ylpentyl)amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{39}H_{48}FN_9O_3S_2$: 386.6647, found 386.6642.

Example 190: 2-[[6-(1,3-Benzothiazol-2-ylamino)-5-methyl-pyridazin-3-yl]-[5-[methyl-[2-(methylamino)ethyl]amino]pentyl]amino]-5-[3-[4-[3-(dimethylamino)prop-1-ynyl]-2-fluoro-phenoxy]propyl]thiazole-4-carboxylic acid

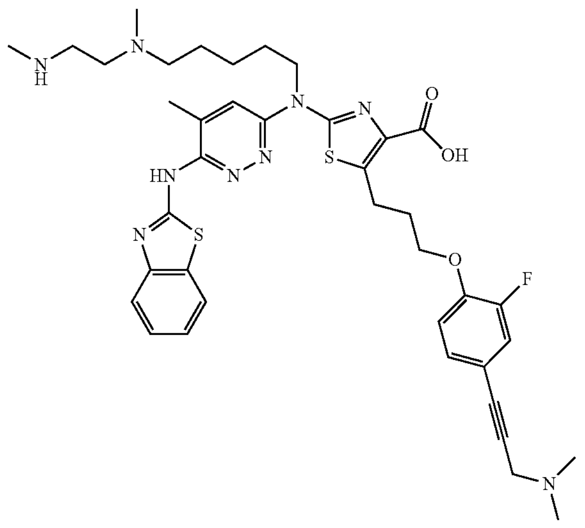

Step A: methyl 2-[5-[2-[tert-butoxycarbonyl(methyl)amino]ethyl-methyl-amino]pentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Alkylation with in situ generated tosylate General Procedure starting from Preparation 5f and tert-butyl N-methyl-N-[2-(methylamino)ethyl]carbamate as the appropriate amine, the desired product was obtained.

$^1H$ NMR (500 MHz, DMSO-$d_6$) δ ppm 7.84 (d, 1H), 7.66 (s, 1H), 7.47 (d, 1H), 7.43 (td, 1H), 7.3 (dd, 1H), 7.25 (td, 1H), 7.20 (dd, 1H), 7.15 (t, 1H), 5.86 (s, 2H), 4.37 (t, 2H), 4.14 (t, 2H), 3.77 (s, 3H), 3.72 (m, 2H), 3.38 (s, 2H), 3.26 (t, 2H), 3.16 (br., 2H), 2.73 (s, 3H), 2.45 (s, 3H), 2.35 (br., 2H), 2.28 (brt., 2H), 2.19 (s, 6H), 2.13 (s, 3H), 2.12 (m, 2H), 1.68 (m, 2H), 1.45 (m, 2H), 1.35 (m, 2H), 1.33 (s, 9H), 0.92 (m, 2H), −0.11 (s, 9H); $^{13}C$ NMR (125 MHz, DMSO-$d_6$) δ ppm 129.0, 127.2, 123.4, 123.2, 119.2, 117.6, 115.5, 112.0, 72.9, 68.4, 66.7, 57.4, 55.2, 51.9, 48.1, 46.8, 46.4, 44.2, 42.6, 34.5, 31.0, 28.5, 27.0, 26.8, 24.1, 23.1, 17.8, 17.8, −1.0; HRMS-ESI (m/z): $[M+H]^+$ calcd for $C_{51}H_{73}FN_9O_6S_2Si$: 1018.4873, found 1018.4869.

Step B: 2-[[6-(1,3-benzothiazol-2-ylamino)-5-methyl-pyridazin-3-yl]-[5-[methyl-[2-(methylamino)ethyl]amino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{39}H_{50}FN_9O_3S_2$: 387.6726, found 387.6731.

Example 191: 2-[5-Aminopentyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid

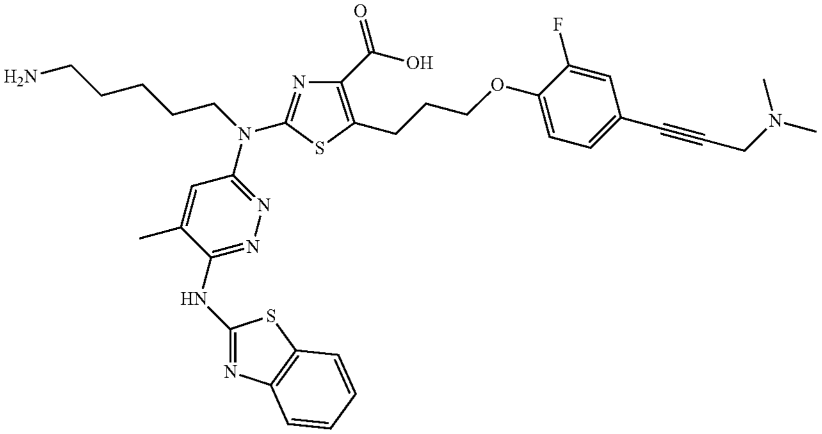 [SMILES: Cc1cc(N(CCCCCN)c2nc(C(=O)O)c(CCCOc3ccc(C#CCN(C)C)cc3F)s2)nnc1Nc1nc2ccccc2s1]

Step A: methyl 2-[tert-butoxycarbonyl-[5-(tert-butoxycarbonylamino)pentyl]amino]-5-[3-[4-[3-(dimethylamino)prop-1-ynyl]-2-fluoro-phenoxy]propyl]thiazole-4-carboxylate Using Mitsunobu General Procedure starting from 250 mg of Preparation 1c (0.51 mmol, 1 eq.) and 207 mg of tert-butyl N-(5-hydroxypentyl)carbamate (1.02 mmol, 2 eq.) as the appropriate alcohol, 189 mg (55%) of the desired product was obtained.

$^1$H NMR (400 MHz, DMSO-d$_6$) δ ppm 7.29 (dd, 1H), 7.21 (d, 1H), 7.13 (t, 1H), 6.75 (t, 1H), 4.10 (t, 2H), 3.97 (t, 2H), 3.75 (s, 31), 3.49 (br.s, 2H), 3.22 (t, 2H), 2.90 (q, 2H), 2.08 (qv, 2H), 1.99 (s, 6H), 1.66-1.56 (m, 2H), 1.50 (s, 9H), 1.44-1.36 (m, 2H), 1.35 (s, 9H), 1.28-1.20 (m, 2H); LC-MS-ESI (m/z): [M+H]$^+$ calcd for $C_{34}H_{50}FN_4O_7S$: 677.3, found 677.4.

Step B: methyl 2-[5-(tert-butoxycarbonylamino)pentylamino]-5-[3-[4-[3-(dimethylamino)prop-1-ynyl]-2-fluoro-phenoxy]propyl]thiazole-4-carboxylate Using Deprotection with HFIP General Procedure starting from 182 mg of the product from Step A (0.27 mmol, 1 eq.) as the appropriate Boc protected amine, 106 mg (68%) of the desired product was obtained.

$^1$H NMR (400 MHz, DMSO-d$_6$) δ ppm 7.56 (t, 1H), 7.30 (dd, 1H), 7.21 (d, 1H), 7.12 (t, 1H), 6.77 (t, 1H), 4.07 (t, 2H), 3.69 (s, 3H), 3.44 (s, 2H), 3.16-3.09 (m, 4H) 2.92-2.86 (m, 2H), 2.25 (s, 6H), 2.04-1.97 (m, 2H), 1.53-1.45 (m, 2H), 1.40-1.33 (m, 2H), 1.36 (s, 9H), 1.31-1.24 (m, 2H); LC-MS-ESI (m/z): [M+H]$^+$ calcd for $C_{29}H_{42}FN_4O_5S$: 577.3, found 577.4.

Step C: methyl 2-[5-(tert-butoxycarbonylamino)pentyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Buchwald General Procedure II starting from 102 mg of the product from Step B (0.18 mmol, 1 eq.) and 90 mg of Preparation 4a (0.22 mmol, 1.25 eq.) as the appropriate halide, 102 mg (61%) of the desired product was obtained.

$^1$H NMR (500 MHz, DMSO-d$_6$) δ ppm 7.84 (d, 1H), 7.67 (s, 1H), 7.47 (d, 1H), 744 (td, 1H), 7.31 (dd, 1H), 7.25 (td, 1H), 7.21 (dm, 1H), 7.16 (t, 1H), 6.77 (t, 1H), 5.86 (s, 2H), 4.34 (t, 2H), 4.15 (t, 2H), 3.78 (s, 3H), 3.72 (t, 2H), 3.39 (s, 2H), 3.27 (t, 2H), 2.92 (q, 2H), 2.47 (s, 3H), 2.21 (s, 6H), 2.13 (m, 2H), 1.69 (m, 2H), 1.44 (m, 2H), 1.35 (s, 18H), 1.34 (m, 2H), 0.92 (t, 2H), −0.11 (s, 9H); HRMS-ESI (m/z): [M+H]$^+$ calcd for $C_{47}H_{64}FN_8O_6S_2Si$: 947.4138, found 947.4133.

Step D: 2-[5-aminopentyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid Using Deprotection and Hydrolysis General Procedure starting from the product from Step C, the desired product was obtained.

HRMS-ESI (m/z): [M+2H]$^{2+}$ calcd for $C_{35}H_{41}FN_8O_3S_2$: 352.1364, found 352.1370.

Example 192: 2-[4-Aminobutyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid

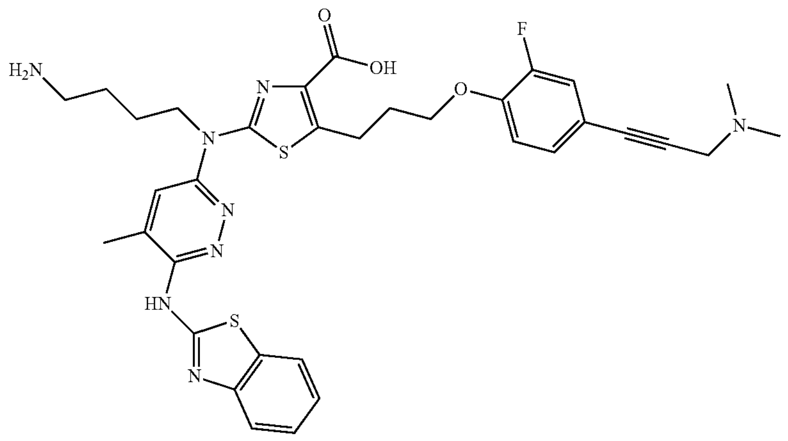 [SMILES: Cc1cc(N(CCCCN)c2nc(C(=O)O)c(CCCOc3ccc(C#CCN(C)C)cc3F)s2)nnc1Nc1nc2ccccc2s1]

Step A: methyl 2-[tert-butoxycarbonyl-[4-(tert-butoxycarbonylamino)butyl]amino]-5-[3-[4-[3-(dimethylamino)prop-1-ynyl]-2-fluoro-phenoxy]propyl]thiazole-4-carboxylate Using Mitsunobu General Procedure starting from 250 mg of Preparation 1c (0.51 mmol, 1 eq.) and 193 mg of tert-butyl N-(4-hydroxybutyl)carbamate (1.02 mmol, 2 eq.) as the appropriate alcohol, 220 mg (65%) of the desired product was obtained.

$^1$H NMR (400 MHz, DMSO-$d_6$) δ ppm 730 (dd, 1H), 7.21 (d, 1H), 7.13 (t, 1H), 6.80 (t, 1H), 4.10 (t, 2H), 4.01-3.95 (m, 2H), 3.75 (s, 3H), 3.45 (s, 2H), 3.22 (t, 2H), 2.91 (q, 2H), 2.25 (s, 6H), 2.08 (qv, 2H), 1.63-1.54 (m, 2H), 1.50 (s, 9H), 1.40-1.35 (m, 2H), 1.35 (s, 9H); LC-MS-ESI (m/z): $[M+H]^+$ calcd for $C_{33}H_{48}FN_4O_7S$: 663.3, found 663.4.

Step B: methyl 2-[4-(tert-butoxycarbonylamino)butylamino]-5-[3-[4-[3-(dimethylamino)prop-1-ynyl]-2-fluoro-phenoxy]propyl]thiazole-4-carboxylate Using Deprotection with HFIP General Procedure starting from 215 mg of the product from Step A (0.33 mmol, 1 eq.) as the appropriate Boc protected amine, 137 mg (75%) of the desired product was obtained.

$^1$H NMR (400 MHz, DMSO-$d_6$) δ ppm 7.57 (t, 1H), 7.30 (d, 1H), 7.21 (d, 1H), 7.12 (t, 1H), 6.81 (t, 1H), 4.07 (t, 2H), 3.69 (s, 3H), 3.42 (s, 2H), 3.17-3.09 (m, 4H), 2.94-2.88 (m, 2H), 2.23 (s, 6H), 2.04-2.00 (m, 2H), 1.53-1.37 (m, 4H), 1.36 (s, 9H); LC-MS-ESI (m/z): $[M+H]^+$ calcd for $C_{28}H_{40}FN_4O_5S$: 563.3, found 563.2.

Step C: methyl 2-[4-(tert-butoxycarbonylamino) butyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Buchwald General Procedure II starting from 133 mg of the product from Step B (0.24 mmol, 1 eq.) and 120 mg of Preparation 4a (0.29 mmol, 1.25 eq.) as the appropriate halide, 220 mg (98%) of the desired product was obtained.

$^1$H NMR (500 MHz, DMSO-d$_6$) δ ppm 7.84 (d, 1H), 7.69 (s, 1H), 7.47 (d, 1H), 7.44 (td, 1H), 7.31 (dd, 1H), 7.25 (td, 1H), 7.21 (dm, 1H), 7.16 (t, 1H), 6.82 (t, 1H), 5.86 (s, 2H), 4.36 (t, 2H), 4.15 (t, 2H), 3.78 (s, 3H), 3.72 (t, 2H), 3.38 (s, 2H), 3.27 (t, 2H), 2.98 (q, 2H), 2.46 (s, 3H), 2.19 (s, 6H), 2.13 (m, 2H), 1.67 (m, 2H), 1.46 (m, 2H), 1.34 (s, 9H), 0.92 (t, 2H), −0.11 (s, 9H); $^{13}$C NMR (125 MHz, DMSO-d$_6$) δ ppm 156.1, 128.9, 127.2, 123.5, 123.2, 119.2, 117.6, 115.5, 112.0, 72.9, 68.4, 66.7, 52.0, 48.1, 46.7, 44.2, 39.8, 31.0, 28.7, 27.2, 24.7, 23.1, 17.9, 17.8, −1.0; HRMS-ESI (m/z): [M+H]$^+$ calcd for $C_{46}H_{62}FN_8O_6S_2Si$: 933.3982, found 933.3995.

Step D: 2-[4-aminobutyl-[6-(1,3-benzothiazol-2-ylamino)-5-methyl-pyridazin-3-yl]amino]-5-[3-[4-[3-(dimethylamino)prop-1-ynyl]-2-fluoro-phenoxy] propyl]thiazole-4-carboxylic acid Using Deprotection and Hydrolysis General Procedure followed by repurification via reverse phase preparative chromatography (C18, 0.1% TFA in water:MeCN) starting from the product from Step C, the TFA-salt of the desired product was obtained.

HRMS-ESI (m/z): [M+2H]$^{2+}$ calcd for $C_{34}H_{39}FN_8O_3S_2$: 345.1280, found 345.1281.

Example 193: 2-[[6-(1,3-Benzothiazol-2-ylamino)-5-methyl-pyridazin-3-yl]-[5-(dimethylamino)-4-hydroxy-pentyl]amino]-5-[3-[2-fluoro-4-[3-(methylamino)prop-1-ynyl]phenoxy]propyl]thiazole-4-carboxylic acid

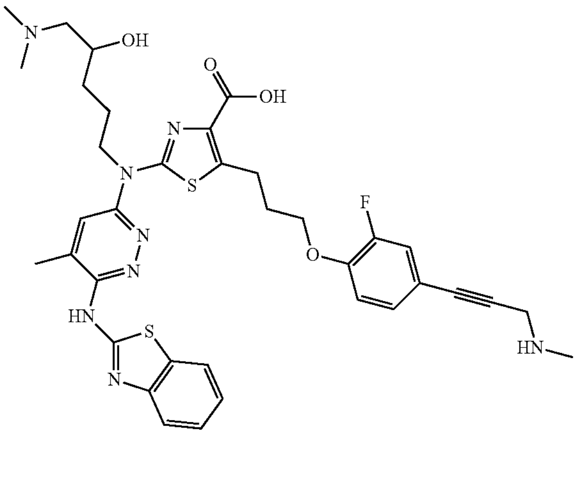

Using Quaternary salt deprotection General Procedure starting from Example 144, Step A, the desired product was obtained.

HRMS-ESI (m/z): [M+H]$^+$ calcd for $C_{36}H_{42}FN_8O_0S_2$: 733.2749, found 733.2745.

Example 194: 2-[[6-(1,3-Benzothiazol-2-ylamino)-5-methyl-pyridazin-3-yl]-[5-(methylamino)pentyl] amino]-5-[3-[4-[3-(dimethylamino)prop-1-ynyl]-2-fluoro-phenoxy]propyl]thiazole-4-carboxylic acid

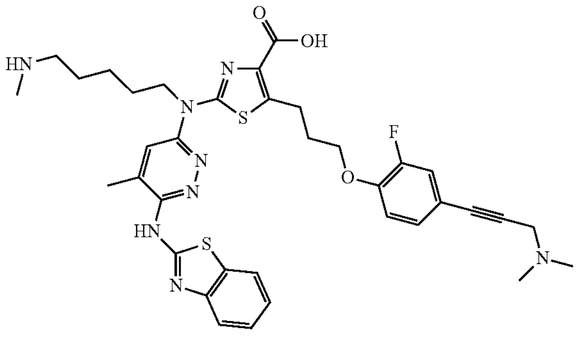

Step A: methyl 5-[3-[4-[3-(dimethylamino)prop-1-ynyl]-2-fluoro-phenoxy]propyl]-2-[5-(methylamino) pentyl-[5-methyl-6-[(Z)-[3-(2-trimethylsilylethoxymethyl)-1,3-benzothiazol-2-ylidene]amino] pyridazin-3-yl]amino]thiazole-4-carboxylate Using Alkylation with in situ generated tosylate General Procedure starting from Preparation 5f and methanamine as the appropriate amine, the desired product was obtained after concentration and transferred directly to the next step without any further purification.

Step B: 2-[[6-(1,3-benzothiazol-2-ylamino)-5-methyl-pyridazin-3-yl]-[5-(methylamino)pentyl] amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the crude product from Step A, the TFA-salt of the desired product was obtained.

HRMS-ESI (m/z): [M+H]$^+$ calcd for $C_{36}H_{42}FN_8O_3S_2$: 717.2800, found 717.2785.

Example 195: 2-[[6-(1,3-Benzothiazol-2-ylamino)-5-methyl-pyridazin-3-yl]-[5-[3-(4-methylpiperazin-1-yl)propylamino]pentyl]amino]-5-[3-[4-[3-(dimethylamino)prop-1-ynyl]-2-fluoro-phenoxy]propyl]thiazole-4-carboxylic acid

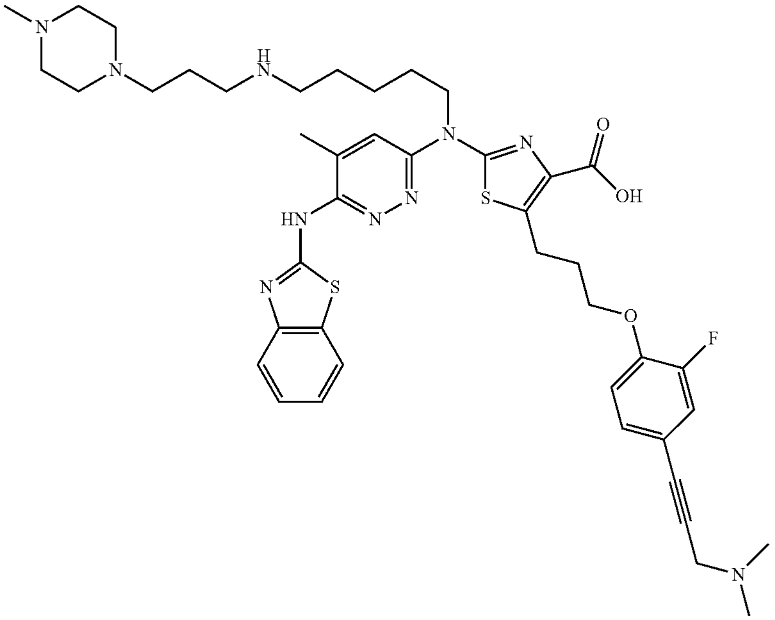

Step A: methyl 5-[3-[4-[3-(dimethylamino)prop-1-ynyl]-2-fluoro-phenoxy]propyl]-2-[5-[3-(4-methylpiperazin-1-yl)propylamino]pentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with in situ generated tosylate General Procedure starting from Preparation 5f and 3-(4-methylpiperazin-1-yl)propan-1-amine as the appropriate amine, the desired product was obtained.

$^1H$ NMR (400 MHz, DMSO-$d_6$) δ ppm 7.83 (dm, 1H), 7.65 (s, 1H), 7.42-7.46 (m, 2H), 7.36-7.08 (m, 4H), 5.85 (s, 2H), 4.36 (t, 2H), 4.14 (t, 2H), 3.78 (s, 3H), 3.72 (t, 2H), 3.26 (t, 2H), 2.70-2.00 (m, 26H), 2.45 (s, 3H), 1.80-1.30 (m, 8H), 0.91 (t, 2H), −0.12 (s, 9H); LC-MS-ESI (m/z): $[M+H]^+$ calcd for $C_{50}H_{72}FN_{10}O_4S_2Si$: 987.5, found 987.4.

Step B: 2-[[6-(1,3-benzothiazol-2-ylamino)-5-methyl-pyridazin-3-yl]-[5-[3-(4-methylpiperazin-1-yl)propylamino]pentyl]amino]-5-[3-[4-[3-(dimethylamino)prop-1-ynyl]-2-fluoro-phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{43}H_{56}FN_{10}O_3S_2$: 843.3962 found: 843.3943.

Example 196: 2-[[6-(1,3-Benzothiazol-2-ylamino)-5-methyl-pyridazin-3-yl]-[4-hydroxy-5-[methyl(2-phosphonoethyl)amino]pentyl]amino]-5-[3-[2-fluoro-4-[3-(methylamino)prop-1-ynyl]phenoxy]propyl]thiazole-4-carboxylic acid

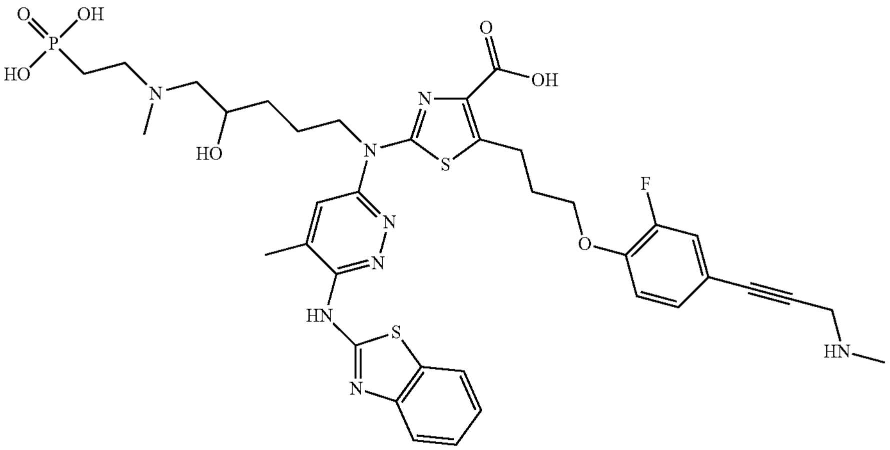 [SMILES: CNCC#Cc1ccc(OCCCc2sc(N(CCCC(O)CN(C)CCP(=O)(O)O)c3cc(C)c(Nc4nc5ccccc5s4)nn3)nc2C(=O)O)c(F)c1]

Step A: 2-diethoxyphosphoryl-N-methyl-ethanamine 3.28 g of 1-[ethoxy(vinyl)phosphoryl]oxyethane (20 mmol, 1.0 eq.) and 25 mL of methanamine (33 w % in EtOH, 200 mmol, 100 eq.) were mixed in a sealed tube and stirred at rt for 20 h. Full conversion was observed. The reaction mixture was concentrated and 3.87 g (99%) of the crude desired product was obtained.

$^{1}H$ NMR (400 MHz, DMSO-$d_6$) δ ppm 4.04-3.90 (m, 4H), 2.67-2.58 (m, 2H), 2.25 (s, 3H), 2.18-1.95 (brs, 1H), 1.93-1.82 (m, 2H), 1.22 (t, 6H); $^{13}C$ NMR (100 MHz, DMSO-$d_6$) δ ppm 60.9, 60.8, 45.03, 45.01, 35.6, 26.1, 24.7, 16.32, 16.26; GC-TOF (EI)(m/z): $[M]^+$ calcd for $C_7H_{18}NO_3P$: 195.1024, found 195.1009.

Step B: methyl 5-[3-[4-[3-[tert-butoxycarbonyl(methyl)amino]prop-1-ynyl]-2-fluoro-phenoxy]propyl]-2-[[4-[tert-butyl(diphenyl)silyl]oxy-5-[2-diethoxyphosphorylethyl(methyl)amino]pentyl]-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation with tosylate General Procedure starting from Preparation 5a and the product from Step A as the appropriate amine, the desired product was obtained.

HRMS-ESI (m/z): $[M+H]^+$ calcd for $C_{69}H_{95}FN_8O_{10}PS_2Si_2$: 1365.5867, found 1365.5916.

Step C: 2-[[6-(1,3-benzothiazol-2-ylamino)-5-methyl-pyridazin-3-yl]-[4-hydroxy-5-[methyl(2-phosphonoethyl)amino]pentyl]amino]-5-[3-[2-fluoro-4-[3-(methylamino)prop-1-ynyl]phenoxy]propyl]thiazole-4-carboxylic acid Using Deprotection and hydrolysis of phosphonic acid derivatives General Procedure starting from the product from Step B, the desired product was obtained.

HRMS-ESI (m/z): $[M+H]^+$ calcd for $C_{37}H_{45}FN_8O_7PS_2$: 827.2569, found 827.2561.

Example 197: 2-({6-[(1,3-Benzothiazol-2-yl)amino]-5-methylpyridazin-3-yl}(methyl)amino)-5-[3-({4-fluoro-6-[3-(methylamino)prop-1-yn-1-yl]pyridin-3-yl}oxy)propyl]-1,3-thiazole-4-carboxylic acid

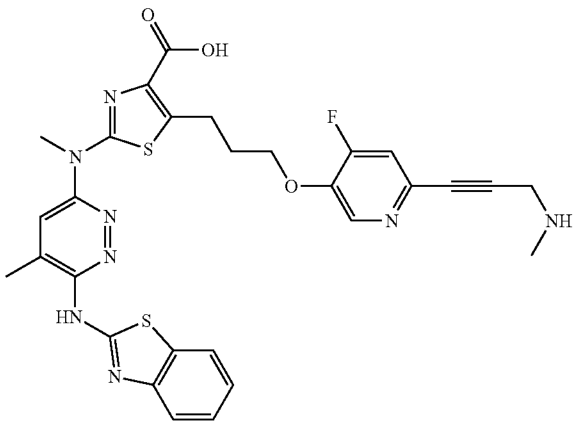 [SMILES: CNCC#Cc1cc(F)c(OCCCc2sc(N(C)c3cc(C)c(Nc4nc5ccccc5s4)nn3)nc2C(=O)O)cn1]

Step A: 2-chloro-4-fluoro-5-(4,4,5,5-tetramethyl-1,3,2-dioxaborolan-2-yl)pyridine To a solution of 2-chloro-4-fluoropyridine (2.5 g; 19.01 mmol) in tetrahydrofuran (30 mL) was successively added bis(pinacolato)diboron (2.41 g; 9.50 mmol; 0.5 eq.), 4,4'-di-tert-butyl-2,2'-dipyridyl (51.0 mg; 0.190 mmol; 0.01 eq.), and (1,5-cyclooctadiene)(methoxy)iridium(I) dimer (63.0 mg; 0.095 mmol; 0.005 eq.). The reaction mixture was flushed with Argon and was stirred at 80° C. for 16 h and then concentrated to dryness. The resulting residue was purified by column chromatography on silica gel using cyclohexane/ethyl acetate as eluent to afford the desired compound (3.64 g; 74%).

$^{1}$H NMR (DMSO-$d_6$) δ ppm 1.33 (s, 12H), 7.58 (d, 1H, J=8.8 Hz), 8.55 (d, 1H, J=9.2 Hz).

Step B: 6-chloro-4-fluoro-pyridin-3-ol

To a solution of the product from Step A (2.00 g: 7.77 mmol) in tetrahydrofuran (16 mL) was successively added at 0° C., sodium hydroxide (311 mg; 7.77 mmol; 1.0 eq.) and an aqueous solution of hydrogen peroxide 33% (2.38 mL; 23.3 mmol; 3.0 eq.). The reaction mixture was stirred at 0° C. for 3 h and at rt for 16 h. The reaction mixture was diluted with water (50 mL) and was acidified with an aqueous solution of hydrogen chloride 1N until pH=1. The aqueous layer was extracted with dichloromethane (3×100 mL) and the combined organic layers were dried over sodium sulfate, filtered, and concentrated to dryness. The resulting residue was purified by column chromatography on silica gel using cyclohexane/ethyl acetate as eluent to afford the desired compound (640 mg; 56%).

$^{1}$H NMR (DMSO-$d_6$) δ ppm 7.53 (d, 1H, J=10.4 Hz), 8.06 (d, 1H, J=10.8 Hz), 10.76 (s, 1H).

Step C: tert-butyl N-[3-(4-fluoro-5-hydroxy-2-pyridyl)prop-2-ynyl]-N-methyl-carbamate To a solution of the product from Step B (300 mg; 2.03 mmol) in acetonitrile (12 mL) was successively added tert-butyl N-methyl-N-prop-2-ynyl-carbamate (688 mg; 4.07 mmol; 2.0 eq.), cesium carbonate (1.66 g; 5.08 mmol; 2.5 eq.), Xphos (145.4 mg; 0.305 mmol; 0.15 eq.), and bis(acetonitrile)palladium(II) chloride (29.43 mg; 0.102 mmol; 0.05 eq.). The reaction mixture was flushed with argon and was stirred for 16 h at 70° C. The reaction mixture was diluted with water (50 mL) and was acidified with an aqueous solution of hydrogen chloride 1N until pH=1. The aqueous layer was extracted with dichloromethane (3×100 mL) and the combined organic layers were dried over sodium sulfate, filtered and concentrated to dryness. The resulting residue was purified by column chromatography on silica gel using cyclohexane/ethyl acetate as eluent to afford the desired compound (257 mg; 45%).

$^{1}$H NMR (DMSO): 1.41 (s, 9H), 2.86 (s, 3H), 4.25 (s, 2H), 7.45 (d, 1H, J=11.6 Hz), 8.20 (d, 1H, J=11.2 Hz), 10.87 (s, 1H); 13C NMR (DMSO): 28.01, 33.45, 37.80, 79.41, 82.10, 82.13, 83.56, 115.42, 115.53, 115.58, 133.79, 133.87, 140.96, 141.00, 142.56, 142.65, 154.13, 154.47, 156.69; LC/MS [M-tBu]+: 225.02.

Step D: ethyl 2-[[6-(1,3-benzothiazol-2-ylamino)-5-methyl-pyridazin-3-yl]-methyl-amino]-5-[3-[[6-[3-[tert-butoxycarbonyl(methyl)amino]prop-1-ynyl]-4-fluoro-3-pyridyl]oxy]propyl]thiazole-4-carboxylate Using Alkylation General Procedure starting from Preparation 5g and the product from Step C as the appropriate phenol, the desired compound was obtained.

$^{1}$H NMR (500 MHz, DMSO-$d_6$) δ ppm 8.46 (d, 1H), 7.91 (br., 1H), 7.67 (s, 1H), 7.55 (d, 1H), 7.53 (br., 1H), 7.38 (t, 1H), 7.21 (t, 1H), 4.28 (t, 2H), 4.25 (q, 2H), 4.24 (br., 2H), 3.76 (s, 3H), 3.27 (t, 2H), 2.85 (br., 3H) 2.46 (s, 3H), 2.14 (m, 2H), 1.41 (s, 9H), 1.29 (t, 3H); $^{13}$C NMR (125 MHz, DMSO-$d_6$) δ ppm 138.8, 126.6, 122.6, 122.3, 118.4, 115.7, 69.3, 60.7, 38.4, 35.3, 33.9, 31.0, 28.4, 23.1, 17.8, 14.6; HRMS-ESI (m/z): $[M+H]^+$ calcd for $C_{36}H_{40}FN_8O_5S_2$: 747.2541, found 747.2526.

Step E: 2-({6-[(1,3-Benzothiazol-2-yl)amino]-5-methylpyridazin-3-yl}(methyl)amino)-5-[3-({4-fluoro-6-[3-(methylamino)prop-1-yn-1-yl]pyridin-3-yl}oxy)propyl]-1,3-thiazole-4-carboxylic acid Using Deprotection and Hydrolysis General Procedure starting from Step D as the appropriate ethyl ester, the desired product was obtained.

$^{1}$H NMR (500 MHz, DMSO-$d_6$) δ ppm 8.41 (d, 1H), 7.91 (d, 1H), 7.67 (s, 1H), 7.53 (d, 1H), 7.48 (d, 1H), 739 (tm, 1H), 7.21 (tm, 1H), 4.27 (t, 2H), 3.76 (s, 3H), 3.48 (s, 2H), 3.27 (t, 2H), 2.46 (s, 3H), 2.31 (s, 3H), 2.14 (quin, 2H); $^{13}$C NMR (125 MHz, DMSO-$d_6$) δ ppm 164.1, 156.8, 156.7, 151.9, 151.9, 145.5, 143.8, 140.2, 138.8, 137.0, 136.0, 133.1, 130.3, 126.6, 122.6, 122.4, 118.4, 116.8, 115.4, 88.2, 82.4, 69.4, 40.0, 35.3, 35.3, 30.9, 23.1, 17.7; HRMS-ESI (m/z): $[M+H]^+$ calcd for $C_{29}H_{28}FN_8O_3S_2$: 619.1704, found 619.1698.

Example 198: 2-[[6-(1,3-Benzothiazol-2-ylamino)-5-methyl-pyridazin-3-yl]-methyl-amino]-5-[3-[2-fluoro-4-(3-morpholinoprop-1-ynyl)phenoxy]propyl]thiazole-4-carboxylic acid

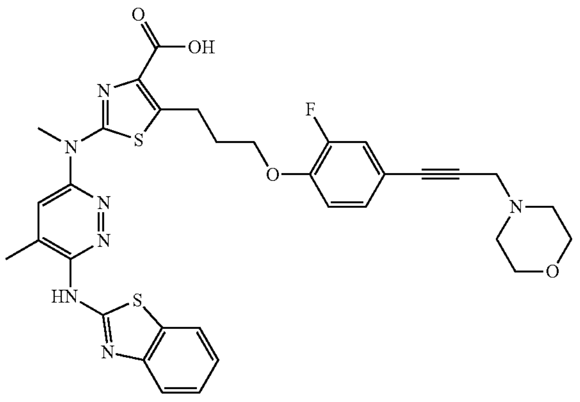 [SMILES: Cc1cc(N(C)c2nc(C(=O)O)c(CCCOc3ccc(C#CCN4CCOCC4)cc3F)s2)nnc1Nc1nc2ccccc2s1]

Step A: ethyl 5-[3-[2-fluoro-4-(3-morpholinoprop-1-ynyl)phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation General Procedure starting from Preparation 5g and Preparation 6e as the appropriate phenol, the desired product was obtained.

$^{1}$H NMR (400 MHz, DMSO-$d_6$) δ ppm 7.84 (brd, 1H), 7.64 (d, 1H), 7.45 (dm, 1H), 7.42 (tm, 1H), 7.32 (dd, 1H), 7.25 (tm, 1H), 7.21 (dm, 1H), 7.15 (t, 1H), 5.85 (s, 2H), 4.25 (q, 2H), 4.15 (t, 2H), 3.77 (s, 3H), 3.71 (t, 2H), 3.58 (t, 4H), 3.44 (s, 2H), 3.26 (t, 2H), 2.48 (br, 4H), 2.44 (s, 3H), 2.12 (quin, 2H), 1.29 (t, 3H), 0.82 (t, 2H), −0.11 (s, 9H); $^{13}$C NMR (100 MHz, DMSO-$d_6$) δ ppm 162.6, 157.4, 156.7, 155.1, 151.7, 151.6, 147.3, 141.0, 137.6, 137.0, 135.2, 129.0, 127.2, 125.6, 123.5, 123.2, 119.2, 117.6, 115.4, 115.2, 111.9, 85.0, 84.3, 72.8, 68.4, 66.7, 66.5, 60.6, 52.2, 47.4, 35.3, 31.1, 23.3, 17.8, 17.8, 14.6, −1.0; HRMS-ESI (m/z): $[M+H]^+$ calcd for $C_{41}H_{51}FN_7O_5S_2Si$: 832.3141, found 832.3146.

Step B: 2-[[6-(1,3-benzothiazol-2-ylamino)-5-methyl-pyridazin-3-yl]-methyl-amino]-5-[3-[2-fluoro-4-(3-morpholinoprop-1-ynyl)phenoxy]propyl]thiazole-4-carboxylic acid Using Deprotection and Hydrolysis General Procedure starting from the product from Step A as the appropriate ethyl ester, the desired product was obtained.

HRMS-ESI (m/z): $[M+H]^+$ calcd for $C_{33}H_{33}FN_7O_4S_2$: 674.2014, found 674.2006.

Example 199: 2-[[6-(1,3-Benzothiazol-2-ylamino)-5-methyl-pyridazin-3-yl]-[6-(dimethylamino)hexyl]amino]-5-[3-[2-fluoro-4-[3-(methylamino)prop-1-ynyl]phenoxy]propyl]thiazole-4-carboxylic acid

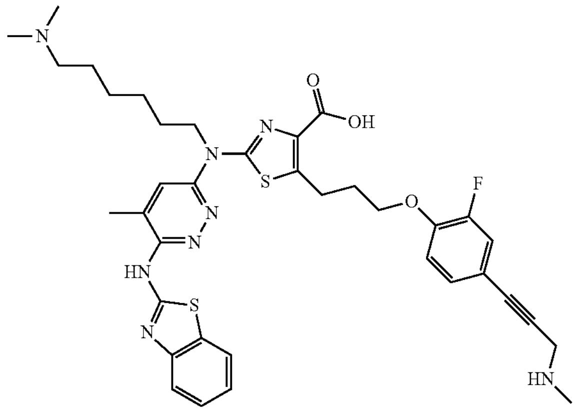

Step A: methyl 2-[tert-butoxycarbonyl-[6-(dimethylamino)hexyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from Preparation 1b and 6-(dimethylamino)hexan-1-ol, 1.51 g (quant., contained ca. 40 n/n % DIAD-2H) of the desired product was obtained.

$^1$H NMR (400 MHz, DMSO-$d_6$) δ ppm 7.30 (dd, 1H), 7.21 (dm, 1H), 7.13 (t, 1H), 4.23 (s, 2H), 4.10 (t, 2H), 3.98 (t, 2H), 3.75 (s, 3H), 3.22 (t, 2H), 2.86 (s, 3H), 2.13 (t, 2H), 2.07 (s, 6H), 1.70-1.20 (m, 8H), 1.61 (m, 2H), 1.50/1.41 (s, 18H); HRMS-ESI (m/z): $[M+H]^+$ calcd for $C_{36}H_{54}FN_4O_7S$: 705.3697, found 705.3699.

Step B: methyl 5-[3-[4-[3-[tert-butoxycarbonyl(methyl)amino]prop-1-ynyl]-2-fluoro-phenoxy]propyl]-2-[6-(dimethylamino)hexylamino]thiazole-4-carboxylate Using Deprotection with HFIP General Procedure starting from the product from Step A, 650 mg (50%) of the desired product was produced.

$^1$H NMR (500 MHz, DMSO-$d_6$) δ ppm 7.56 (t, 1H), 7.31 (d, 1H), 7.21 (d, 1H), 7.13 (t, 1H), 4.23 (br., 2H), 4.07 (t, 2H), 3.69 (s, 3H), 3.14 (m, 2H), 3.11 (t, 2H), 2.86 (br., 3H), 2.17 (m, 2H), 2.10 (s, 6H), 2.00 (quint., 2H), 1.50 (m, 2H), 1.41 (s, 9H), 1.37 (m, 2H), 1.34-1.21 (m, 2H), 1.34-1.21 (m, 2H); $^{13}$C NMR (125 MHz, DMSO-$d_6$) δ ppm 129.1, 119.3, 115.4, 68.0, 60.6, 51.7, 45.6, 44.5, 38.6, 33.9, 30.6, 29.1, 28.5, 27.4, 27.0, 26.8, 23.3; HRMS-ESI (m/z): $[M+H]^+$ calcd for $C_{31}H_{46}FN_4O_5S$: 605.3173, found 605.3160.

Step C: methyl 5-[3-[4-[3-[tert-butoxycarbonyl(methyl)amino]prop-1-ynyl]-2-fluoro-phenoxy]propyl]-2-[6-(dimethylamino)hexyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a, 1.06 g (98%) of the desired product was produced.

$^1$H NMR (500 MHz, DMSO-$d_6$) δ ppm 7.84 (d, 1H), 7.66 (s, 1H), 7.47 (d, 1H), 7.44 (td, 1H), 7.32 (d, 1H), 7.25 (td, 1H), 7.22 (d, 1H), 7.16 (t, 1H), 5.86 (s, 2H), 4.37 (t, 2H), 4.20 (m, 2H), 4.15 (t, 2H), 3.77 (s, 3H), 3.72 (t, 2H), 3.26 (t, 2H), 2.84 (s, 3H), 2.46 (s, 3H), 2.13 (m, 2H), 2.13 (m, 2H), 2.06 (s, 6H), 1.62-1.32 (m, 8H), 1.40 (s, 9H), 0.92 (t, 2H), −0.11 (s, 9H); $^{13}$C NMR (125 MHz, DMSO-$d_6$) δ ppm 163.2, 129.1, 127.2, 123.4, 123.2, 119.2, 117.6, 115.5, 112.0, 79.5, 72.8, 68.4, 66.7, 59.5, 51.9, 46.8, 45.6, 38.6, 33.8, 31.0, 28.5, 23.1, 17.8, 17.7, −0.96; HRMS-ESI (m/z): $[M+H]^+$ calcd for $C_{49}H_{68}FN_8O_6S_2Si$: 975.4457, found 975.4437.

Step D: 2-[[6-(1,3-benzothiazol-2-ylamino)-5-methyl-pyridazin-3-yl]-[6-(dimethylamino)hexyl]amino]-5-[3-[2-fluoro-4-[3-(methylamino)prop-1-ynyl]phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step C, the TFA-salt of the desired product was obtained.

HRMS-ESI (m/z): $[M+H]^+$ calcd for $C_{37}H_{44}FN_8O_3S_2$: 731.2962, found 731.2968.

Example 200: 2-[[6-(1,3-Benzothiazol-2-ylamino)-5-methyl-pyridazin-3-yl]-(dimethylamino)propyl]amino]-5-[3-[2-fluoro-4-[3-(methylamino)prop-1-ynyl]phenoxy]propyl]thiazole-4-carboxylic acid

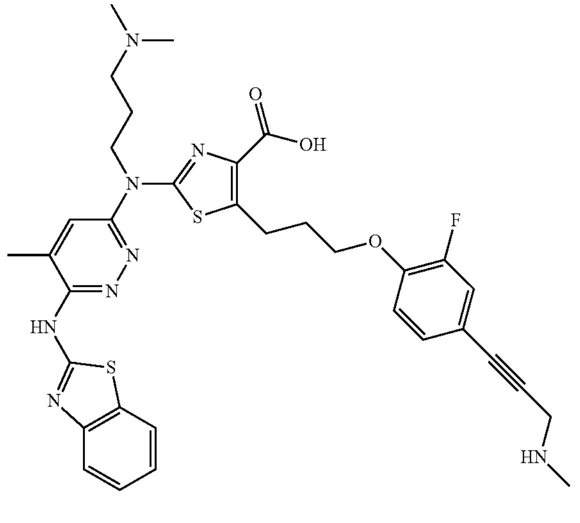

Step A: methyl 2-[tert-butoxycarbonyl-[3-(dimethylamino)propyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from Preparation 1b and 3-(dimethylamino)propan-1-ol, 1.40 g (quant., the sample contained aprox. 35 n/n % DIAD-2H) of the desired product was produced.

$^1$H NMR (400 MHz, DMSO-d$_6$) δ ppm 7.30 (dd, 1H), 7.21 (dm, 1H), 7.13 (t, 1H), 4.23 (s, 2H), 4.10 (t, 2H), 4.01 (t, 2H), 3.74 (s, 3H), 3.22 (t, 2H), 2.86 (s, 3H), 2.24 (t, 2H), 2.12 (s, 6H), 2.08 (m, 2H), 1.74 (m, 2H), 1.51/1.41 (s, 18H); HRMS-ESI (m/z): [M+H]$^+$ calcd for $C_{33}H_{48}FN_4O_7S$: 663.3228, found 663.3218.

Step B: methyl 5-[3-[4-[3-[tert-butoxycarbonyl(methyl)amino]prop-1-ynyl]-2-fluoro-phenoxy]propyl]-2-[3-(dimethylamino)propylamino]thiazole-4-carboxylate Using Deprotection with HFIP General Procedure starting from the product from Step A, 0.95 g (80%) of the desired product was produced.

$^1$H NMR (500 MHz, DMSO-d$_6$) δ ppm 7.57 (t, 1H), 7.31 (d, 1H), 7.21 (d, 1H), 7.13 (t, 1H), 4.23 (br., 2H), 4.07 (t, 2H), 3.69 (s, 3H), 3.17 (q, 2H), 3.12 (t, 2H), 2.86 (br., 3H), 2.24 (t, 2H), 2.11 (s, 6H), 2.00 (quint., 21), 1.63 (m, 2H), 1.41 (s, 9H); $^{13}$C NMR (125 MHz, DMSO-d$_6$) δ ppm 129.1, 119.3, 115.4, 68, 57.0, 51.7, 45.6, 42.8, 38.6, 33.8, 30.6, 28.5, 27.0, 23.3; HRMS-ESI (m/z): [M+H]$^+$ calcd for $C_{28}H_{40}FN_4O_5S$: 563.2703, found 563.2694.

Step C: methyl 5-[3-[4-[3-[tert-butoxycarbonyl(methyl)amino]prop-1-ynyl]-2-fluoro-phenoxy]propyl]-2-[3-(dimethylamino)propyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a, 0.79 g (51%) of the desired product was produced.

$^1$H NMR (500 MHz, DMSO-d$_6$) δ ppm 7.84 (d, 1H), 7.73 (s, 1H), 7.46 (dd, 1H), 7.43 (td, 1H), 7.31 (brd., 1H), 7.25 (td, 1H), 7.21 (d, 1H), 7.16 (t, 1H), 5.86 (s, 2H), 4.35 (t, 2H), 4.20 (br., 2H), 4.15 (t, 2H), 3.76 (s, 3H), 3.72 (t, 2H), 3.27 (t, 2H), 2.84 (br., 3H), 2.45 (s, 3H), 2.32 (t, 2H), 2.18 (s, 6H), 2.13 (m, 2H), 1.86 (m, 2H), 1.40 (s, 9H), 0.92 (t, 2H), −0.11 (s, 9H); $^{13}$C NMR (125 MHz, DMSO-d$_6$) δ ppm 129.1, 127.2, 123.4, 123.2, 119.3, 117.6, 115.4, 111.9, 72.8, 68.4, 66.7, 56.4, 51.9, 45.7, 45.5, 38.5, 33.8, 31.0, 28.5, 25.0, 23.1, 17.9, 17.8, −1.0; HRMS-ESI (m/z): [M+H]$^+$ calcd for $C_{46}H_{62}FN_8O_6S_2Si$: 933.3987, found 933.3990.

Step D: 2-[[6-(1,3-benzothiazol-2-ylamino)-5-methyl-pyridazin-3-yl]-[3-(dimethylamino)propyl]amino]-5-[3-[2-fluoro-4-[3-(methylamino)prop-1-ynyl]phenoxy]propyl]thiazole-4-carboxylate acid Using Deprotection and Hydrolysis General Procedure followed by repurification via reverse phase preparative chromatography (C18, 0.1% TFA in water:MeCN) starting from the product from Step C, the TFA-salt of the desired product was obtained.

HRMS-ESI (m/z): [M+2H]$^{2+}$ calcd for $C_{34}H_{39}FN_8O_3S_2$: 345.1280, found 345.1265.

Example 201: 2-[[6-(1,3-Benzothiazol-2-ylamino)-5-methyl-pyridazin-3-yl]-[2-(trimethylammonio)ethyl]amino]-5-[3-[2-fluoro-4-[3-(methylamino)prop-1-ynyl]phenoxy]propyl]thiazole-4-carboxylate

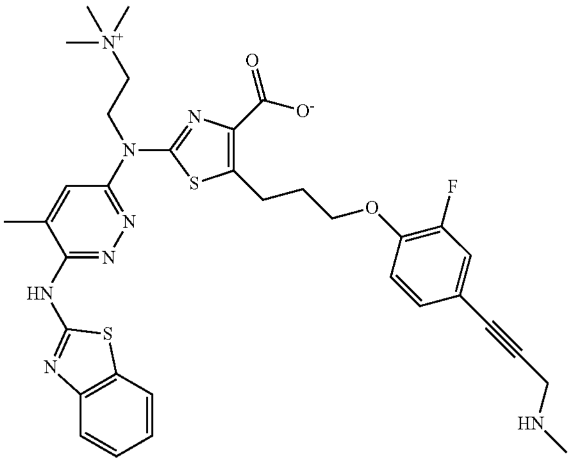

Using Alkylation, Deprotection and Hydrolysis General procedure starting from Example 207, Step C and iodomethane, the TFA-salt of the desired product was obtained.

HRMS-ESI (m/z): [M+2H]$^{2+}$ calcd for $C_{34}H_{39}FN_8O_3S_2$: 345.1280, found 345.1279.

Example 202: 2-[[6-(1,3-Benzothiazol-2-ylamino)-5-methyl-pyridazin-3-yl]-[3-(trimethylammonio)propyl]amino]-5-[3-[2-fluoro-4-[3-(methylamino)prop-1-ynyl]phenoxy]propyl]thiazole-4-carboxylate

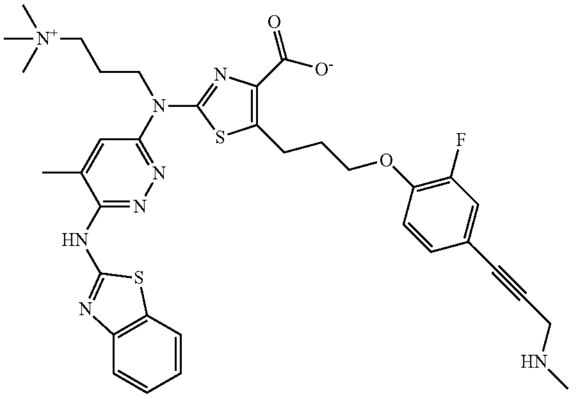

Using Alkylation, Deprotection and Hydrolysis General procedure starting from Example 200, Step C and iodomethane, the TFA-salt of the desired product was obtained.

HRMS-ESI (m/z): [M+2H]$^{2+}$ calcd for $C_{35}H_{41}FN_8O_3S_2$: 352.1358, found 352.1365.

Example 203: 2-[[6-(1,3-Benzothiazol-2-ylamino)-5-methyl-pyridazin-3-yl]-methyl-amino]-5-[3-[2-fluoro-4-(3-pyrrolidin-1-ylprop-1-ynyl)phenoxy]propyl]thiazole-4-carboxylic acid

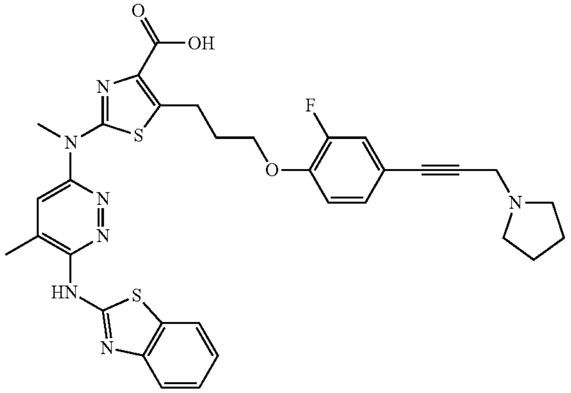 [SMILES: Cc1cc(N(C)c2nc(C(=O)O)c(CCCOc3ccc(C#CCN4CCCC4)cc3F)s2)nnc1Nc1nc2ccccc2s1]

Step A: ethyl 5-[3-[2-fluoro-4-(3-pyrrolidin-1-yl-prop-1-ynyl)phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation General Procedure starting from Preparation 5g and Preparation 6c as the appropriate phenol, the desired product was obtained.

$^1H$ NMR (400 MHz, DMSO-$d_6$) δ ppm 7.83 (dm, 1H), 7.66 (q, 16H), 7.46 (dm, 1H), 7.43 (m, 1H), 7.31 (dd, 1H), 7.25 (m, 1H), 7.21 (dm, 1H), 7.15 (t, 1H), 5.85 (s, 2H), 4.25 (q, 2H), 4.14 (t, 2H), 3.77 (s, 3H), 3.72 (m, 2H), 3.64 (s, 2H), 3.26 (t, 2H), 2.64 (brm, 4H), 2.45 (d, 3H), 2.12 (m, 2H), 1.72 (m, 4H), 1.29 (t, 3H), 0.92 (m, 2H), −0.11 (s, 9H); HRMS-ESI (m/z): $[M+H]^+$ calcd for $C_{41}H_{51}FN_7O_4S_2Si$: 816.3192, found 816.3189.

Step B: 2-[[6-(1,3-benzothiazol-2-ylamino)-5-methyl-pyridazin-3-yl]-methyl-amino]-5-[3-[2-fluoro-4-(3-pyrrolidin-1-prop-1-ynyl)phenoxy]propyl]thiazole-4-carboxylic acid Using Deprotection and Hydrolysis General Procedure starting from the product from Step A as the appropriate ethyl ester, the desired product was obtained.

HRMS-ESI (m/z): $[M+H]^+$ calcd for $C_{33}H_{33}FN_7O_3S_2$: 658.2065, found 658.2064.

Example 204: 2-[[6-(1,3-Benzothiazol-2-ylamino)-5-methyl-pyridazin-3-yl]-methyl-amino]-5-[3-[2-fluoro-4-[3-(1-piperidyl)prop-1-ynyl]phenoxy]propyl]thiazole-4-carboxylic acid

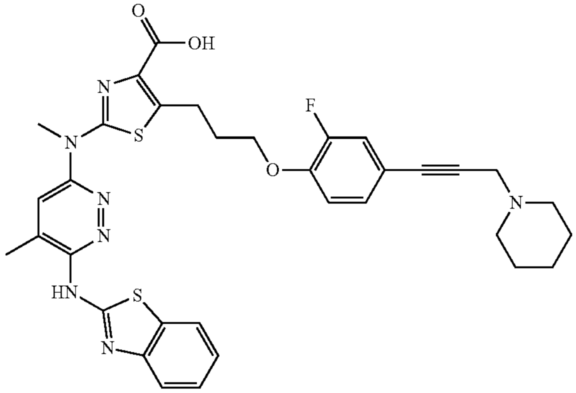 [SMILES: Cc1cc(N(C)c2nc(C(=O)O)c(CCCOc3ccc(C#CCN4CCCCC4)cc3F)s2)nnc1Nc1nc2ccccc2s1]

Step A: ethyl 5-[3-[2-fluoro-4-[3-(1-piperidyl)prop-1-ynyl]phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation General Procedure starting from Preparation 5g and Preparation 6d as the appropriate phenol, the desired product was obtained.

$^1H$ NMR (400 MHz, DMSO-$d_6$) δ ppm 7.83 (dm, 1H), 7.64 (q, 1H), 7.45 (dm, 1H), 7.43 (m, 1H), 7.30 (dd, 1H), 7.25 (m, 1H), 7.19 (dm, 1H), 7.14 (t, 1H), 5.85 (s, 2H), 4.25 (q, 2H), 4.14 (t, 2H), 3.76 (s, 3H), 3.71 (m, 2H), 3.39 (s, 2H), 3.25 (t, 2H), 2.44 (d, 3H), 2.42 (brm, 4H), 2.12 (m, 2H), 1.50 (m, 4H), 1.35 (m, 2H), 1.29 (t, 3H), 0.92 (m, 2H), −0.12 (s, 9H); HRMS-ESI (m/z): $[M+H]^+$ calcd for $C_{42}H_{53}FN_7O_4S_2Si$: 830.3348, found 830.3347.

Step B: 2-[[6-(1,3-benzothiazol-2-ylamino)-5-methyl-pyridazin-3-yl]-methyl-amino]-5-[3-[2-fluoro-4-[3-(1-piperidyl)prop-1-ynyl]phenoxy]propyl]thiazole-4-carboxylic acid Using Deprotection and Hydrolysis General Procedure starting from the product from Step A as the appropriate ethyl ester, the desired product was obtained.

HRMS-ESI (m/z): $[M+H]^+$ calcd for $C_{34}H_{35}FN_7O_3S_2$: 672.2221, found 672.2217.

Example 205: 2-[[6-(1,3-Benzothiazol-2-ylamino)-5-methyl-pyridazin-3-yl]-methyl-amino]-5-[3-[4-[3-(dimethylamino)but-1-ynyl]-2-fluoro-phenoxy]propyl]thiazole-4-carboxylic acid

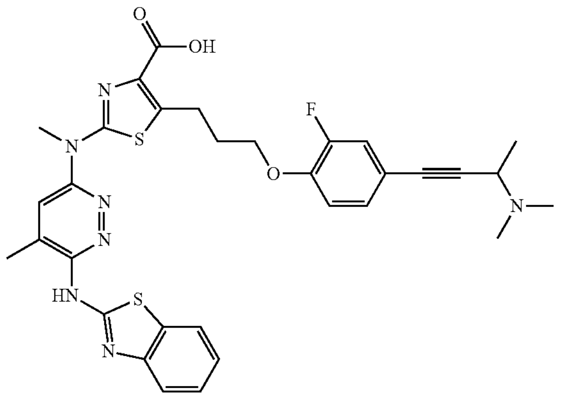

Step A: ethyl 5-[3-[4-[3-(dimethylamino)but-1-ynyl]-2-fluoro-phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation General Procedure starting from Preparation 5g and Preparation 6f as the appropriate phenol, the desired product was obtained.

Step B: 2-[[6-(1,3-benzothiazol-2-ylamino)-5-methyl-pyridazin-3-yl]-methyl-amino]-5-[3-[4-[3-(dimethylamino)but-1-ynyl]-2-fluoro-phenoxy]propyl]thiazole-4-carboxylic acid Using Deprotection and Hydrolysis General Procedure starting from the product from Step A as the appropriate ethyl ester, the desired product was obtained.

HRMS-ESI (m/z): $[M+H]^+$ calcd for $C_{32}H_{33}FN_7O_3S_2$: 646.2065, found 646.2057.

Example 206: 2-[[6-(1,3-Benzothiazol-2-ylamino)-5-methyl-pyridazin-3-yl]-methyl-amino]-5-[3-[2-fluoro-4-((3R or 3S)-morpholinobut-1-ynyl)phenoxy]propyl]thiazole-4-carboxylic acid (Enantiomer 2)

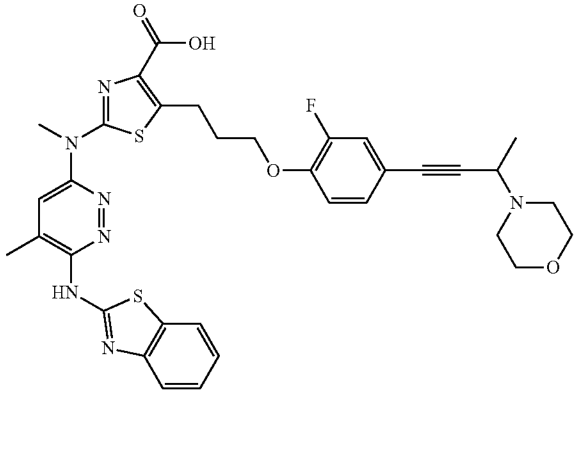 [SMILES: Cc1cc(N(C)c2nc(C(=O)O)c(CCCOc3ccc(C#CC(C)N4CCOCC4)cc3F)s2)nnc1Nc1nc2ccccc2s1]

Step A: ethyl 5-[3-[2-fluoro-4-((3R or 3S)-morpholinobut-1-ynyl)phenoxy]propyl]-2-[methyl-[5-methyl-6-[(Z)-[3-(2-trimethylsilylethoxymethyl)-1,3-benzothiazol-2-ylidene9 amino]pyridazin-3-yl]amino]thiazole-4-carboxylate (Enantiomer 2)

Using Alkylation General Procedure starting from Preparation 5g and Preparation 6h as the appropriate phenol, the desired product was obtained.

$^1H$ NMR (400 MHz, DMSO-$d_6$) δ ppm 7.84 (d, 1H), 7.66 (s, 1H), 7.46 (d, 1H), 7.43 (td, 1H), 7.29 (dd, 1H), 7.25 (td, 1H), 7.20 (dd, 1H), 7.15 (t, 1H), 5.86 (s, 2H), 4.26 (q, 2H), 4.14 (t, 2H), 3.77 (s, 3H), 3.72 (t, 2H), 3.66 (q, 1H), 3.59 (br., 4H), 3.27 (t, 2H), 2.57/2.43 (m+m, 4H), 2.45 (s, 3H), 2.13 (quint., 2H), 1.30 (t, 3H), 1.28 (d, 3H), 0.92 (t, 2H), −0.11 (s, 9H); $^{13}C$ NMR (100 MHz, DMSO-$d_6$) δ ppm 129.0, 127.2, 123.4, 123.2, 119.2, 117.6, 115.5, 111.9, 88.1, 84.2, 72.8, 68.4, 66.7, 66.7, 60.7, 52.1, 49.5, 35.3, 31.1, 23.2, 19.3, 17.8, 17.8, 14.6, −1.0; HRMS-ESI (m/z): $[M+H]^+$ calcd for $C_{42}H_{53}FN_7O_5S_2Si$: 846.3297, found 846.3283.

Step B: 2-[[6-(1,3-benzothiazol-2-ylamino)-5-methyl-pyridazin-3-yl]-methyl-amino]-5-[3-[2-fluoro-4-((3R or 3S)-morpholinobut-1-ynyl)phenoxy]propyl]thiazole-4-carboxylic acid (Enantiomer 2)

Using Deprotection and Hydrolysis General Procedure starting from the product from Step A as the appropriate ethyl ester, the desired product was obtained.

HRMS-ESI (m/z): $[M+H]^+$ calcd for $C_{34}H_{35}FN_7O_4S_2$: 688.2176, found 688.2171.

Example 207: 2-[[6-(1,3-Benzothiazol-2-ylamino)-5-methyl-pyridazin-3-yl]-[2-(dimethylamino)ethyl]amino]-5-[3-[2-fluoro-4-[3-(methylamino)prop-1-ynyl]phenoxy]propyl]thiazole-4-carboxylic acid

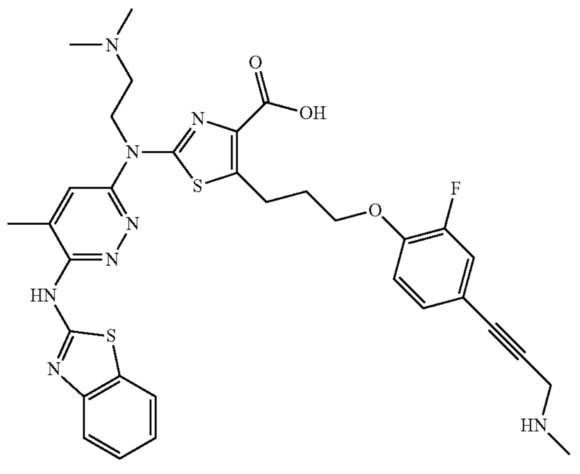

Step A: methyl 2-[tert-butoxycarbonyl-[2-(dimethylamino)ethyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from Preparation 1b, and 2-(dimethylamino)ethanol, 0.90 g (70%) of the desired product was produced.

$^1$H NMR (500 MHz, DMSO-$d_6$) δ ppm 7.30 (brd, 1H), 7.21 (dm, 1H), 7.13 (t, 4.22 (brs, 2H), 4.10 (t, 2H), 4.07 (t, 2H), 3.75 (s, 3H), 3.22 (t, 2H), 2.86 (brs, 3H), 2.46 (t, 2H), 2.17 (s, 6H), 2.08 (m, 2H), 1.50/1.41 (s, 18H); $^{13}$C NMR (125 MHz, DMSO-$d_6$) δ ppm 129.1, 119.3, 115.4, 85.2, 82.4, 68.1, 57, 52.0, 46.0, 44.3, 38.6, 33.8, 30.5, 23.2; HRMS-ESI (m/z): $[M+H]^+$ calcd for $C_{32}H_{46}FN_4O_7S$: 649.3071, found 649.3059.

Step B: methyl 5-[3-[4-[3-[tert-butoxycarbonyl (methyl)amino]prop-1-ynyl]-2-fluoro-phenoxy]propyl]-2-[2-(dimethylamino)ethylamino]thiazole-4-carboxylate Using Deprotection with HFIP General Procedure starting from the product from Step A, 0.68 g (89%) of the desired product was produced.

$^1$H NMR (500 MHz, DMSO-$d_6$) δ ppm 7.50 (t, 1H), 7.31 (d, 1H), 7.21 (d, 1H), 7.13 (t, 1H), 4.23 (br., 2H), 4.07 (t, 2H), 3.69 (s, 3H), 3.26 (q, 2H), 3.11 (t, 2H), 2.86 (br., 3H) 2.37 (t, 2H), 2.15 (s, 6H), 2.00 (quint., 2H), 1.41 (s, 9H); $^{13}$C NMR (125 MHz, DMSO-$d_6$) δ ppm 129.1, 119.3, 115.4, 68.0, 58.2, 51.7, 45.7, 42.4, 38.6, 33.8, 30.6, 28.5, 23.3; HRMS-ESI (m/z): $[M+H]^+$ calcd for $C_{27}H_{38}FN_4O_5S$: 549.2547, found 549.2543.

Step C: methyl 5-[3-[4-[3-[tert-butoxycarbonyl (methyl)amino]prop-1-ynyl]-2-fluoro-phenoxy]propyl]-2-[2-(dimethylamino)ethyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a, 0.57 g (50%) of the desired product was produced.

$^1$H NMR (500 MHz, DMSO-$d_6$) δ ppm 7.84 (d, 1H), 7.66 (s, 1H), 7.47 (dd, 1H), 7.44 (td, 1H), 7.31 (brd., 1H), 7.25 (t, 1H), 7.22 (d, 1H), 7.16 (t, 1H), 5.86 (s, 2H), 4.46 (1.2H), 4.20 (br., 2H), 4.15 (t, 2H), 3.77 (s, 3H), 172 (t, 2H), 3.26 (t, 2H), 2.84 (br., 3H), 2.56 (t, 2H), 2.45 (s, 3H), 2.23 (s, 6H), 2.12 (m, 2H), 1.40 (s, 9H), 0.92 (t, 2H), −0.11 (s, 9R); $^{13}$C NMR (125 MHz, DMSO-$d_6$) δ ppm 163.1, 129.1, 127.2, 123.5, 123.2, 119.3, 117.8, 115.4, 112.0, 72.9, 68.4, 66.7, 56.6, 51.9, 46.1, 45.3, 38.6, 33.8, 31.0, 28.5, 23.1, 17.9, 17.8, −1.0; HRMS-ESI (m/z): $[M+H]^+$ calcd for $C_{45}H_{60}FN_8O_6S_2Si$: 919.3831, found 919.3829.

Step D: 2-[[6-(1,3-benzothiazol-2-ylamino)-5-methyl-pyridazin-3-yl]-[2-(dimethylamino)ethyl] amino]-5-[3-[2-fluoro-4-[3-(methylamino)prop-1-ynyl]phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step C, the TFA-salt of the desired product was obtained.

HRMS-ESI (m/z): $[M+H]^+$ calcd for $C_{33}H_{36}FN_8O_3S_2$: 675.2336, found 675.2323.

Example 208: 2-[[6-(1,3-Benzothiazol-2-ylamino)-5-methyl-pyridazin-3-yl]-methyl-amino]-5-[3-[2-fluoro-4-((3S or 3R)-morpholinobut-1-ynyl)phenoxy]propyl]thiazole-4-carboxylic acid (Enantiomer 1)

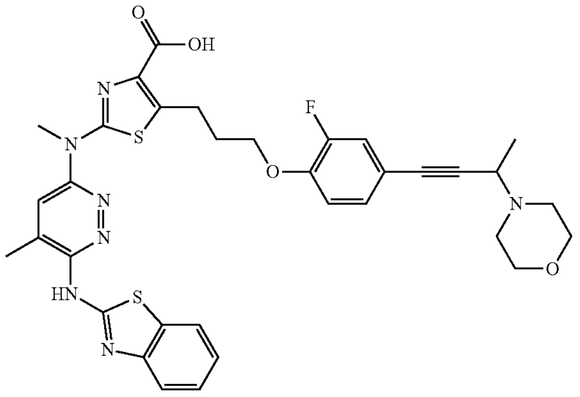 [SMILES: Cc1cc(N(C)c2nc(C(=O)O)c(CCCOc3ccc(C#CC(C)N4CCOCC4)cc3F)s2)nnc1Nc1nc2ccccc2s1]

Step A: ethyl 5-[3-[2-fluoro-4-((3S or 3R)-morpholinobut-1-ynyl)phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate (Enantiomer 1)

Using Alkylation General Procedure starting from Preparation 5g and Preparation 6g as the appropriate phenol, the desired product was obtained.

$^1$H NMR (400 MHz, DMSO-$d_6$) δ ppm 7.84 (d, 1H), 7.66 (s, 7.46 (d, 1H), 7.43 (td, 1H), 7.29 (dd, 1H), 7.25 (td, 1H), 7.20 (dd, 1H), 7.15 (t, 1H), 5.86 (s, 2H), 4.26 (q, 2H), 4.14 (t, 2H), 3.77 (s, 3H), 3.72 (t, 2H), 3.66 (q, 1H), 3.59 (br., 4H), 3.27 (t, 2H), 2.57/2.43 (m+m, 4H), 2.45 (s, 3H), 2.13 (quint., 2H), 1.30 (t, 3H), 1.28 (d, 3H), 0.92 (t, 2H), −0.11 (s, 9H); $^{13}$C NMR (100 MHz, DMSO-$d_6$) δ ppm 129.0, 127.2, 123.4, 123.2, 119.2, 117.6, 115.5, 111.9, 86.1, 84.2, 72.8, 68.4, 66.7, 66.7, 60.7, 52.1, 49.5, 35.3, 31.1, 23.2, 19.3, 17.8, 17.8, 14.6, −1.0; HRMS-ESI (m/z): $[M+H]^+$ calcd for $C_{42}H_{53}FN_7O_5S_2Si$: 846.3297, found 846.3288.

Step B: 2-[[6-(1,3-benzothiazol-2-ylamino)-5-methyl-pyridazin-3-yl]-methyl-amino]-5-[3-[2-fluoro-4-((3S or 3R)-morpholinobut-1-ynyl)phenoxy]propyl]thiazole-4-carboxylic acid (Enantiomer 1)

Using Deprotection and Hydrolysis General Procedure starting from the product from Step A as the appropriate ethyl ester, the desired product was obtained.

HRMS-ESI (m/z): $[M+H]^+$ calcd for $C_{34}H_{35}FN_7O_4S_2$: 688.2170, found 688.2166.

Example 209: 2-[[6-(1,3-Benzothiazol-2-ylamino)-5-(trifluoromethyl)pyridazin-3-yl]-methyl-amino]-5-[3-[2-fluoro-4-[3-(methylamino)prop-1-ynyl]phenoxy]propyl]thiazole-4-carboxylic acid

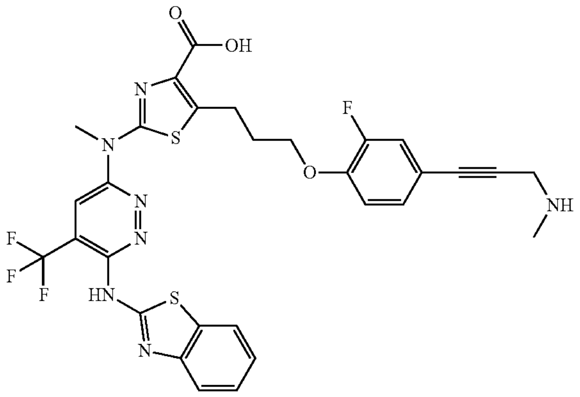 [SMILES: CNCC#Cc1ccc(OCCCc2sc(N(C)c3cc(C(F)(F)F)c(Nc4nc5ccccc5s4)nn3)nc2C(=O)O)c(F)c1]

Step A: methyl 2-[[6-chloro-5-(trifluoromethyl) pyridazin-3-yl]-methyl-amino]-5-[3-(2-fluoro-4-iodo-phenoxy)propyl]thiazole-4-carboxylate A 50 mL oven-dried, one-necked, round-bottomed flask equipped with a PTFE-coated magnetic stirring bar and fitted with a reflux condenser. It was charged with 991 mg of Preparation 3s (2.20 mmol, 1.1 eq.) dissolved in 10 mL of dry THF then it was cooled to 0° C. and 96 mg of NaH (2.40 mmol, 1.2 eq., 60% in mineral oil) was added portionwise over a period of 5 min. After stirring for 15 min at 0° C. 434 mg of 3,6-dichloro-4-(trifluoromethyl)pyridazine (2 mmol, 1 eq.) was added in one portion, and stirred at that temperature for 1 h, when the reaction reached full conversion. The reaction mixture was quenched with the addition of cc. $NH_4Cl$ solution and was extracted with EtOAc. The combined organic layers were dried over $Na_2SO_4$, filtered and concentrated under reduced pressure. The crude product was dissolved in DCM then Celite was added and the volatiles were removed under reduced pressure. It was purified via flash column chromatography using heptane and EtOAc as eluents to give 500 mg (39%) of the desired product as yellow solid.

$^1$H NMR (500 MHz, DMSO-$d_6$) δ ppm 8.16 (s, 1H), 7.58 (dd, 1H), 7.45 (m, 1H), 6.98 (t, 1H), 4.09 (t, 2H), 3.87 (s, 3H), 3.80 (s, 3H), 3.28 (t, 2H), 2.11 (quin, 2H); $^{13}$C NMR (125 MHz, DMSO-$d_6$) δ ppm 162.7, 156.2, 155.3, 152.2, 147.0, 144.2, 143.2, 135.1, 134, 128.5, 124.9, 121.4, 117.9, 117.6, 82.4, 68.2, 52.1, 35.9, 30.6, 23.5; HRMS-ESI (m/z): $[M+H]^+$ calcd for $C_{20}H_{17}ClF_4IN_4O_3S$: 630.9685, found 630.9679.

Step B: methyl 5-[3-[4-[3-[tert-butoxycarbonyl (methyl)amino]prop-1-ynyl]-2-fluoro-phenoxy]propyl]-2-[[6-chloro-5-(trifluoromethyl)pyridazin-3-yl]-methyl-amino]thiazole-4-carboxylate A 12 mL oven-dried vial equipped with a PTFE-coated magnetic stirring bar was charged with 330 mg of the product from Step A (0.52 mmol, 1 eq.), 177 mg of tert-butyl N-methyl-N-prop-2-ynyl-carbamate (1.04 mmol, 2 eq.), 2.5 mL of dry THF and 0.5 mL of DIPA then placed under an inert atmosphere through a gas inlet. After addition of 11.5 mg of $Pd(PPh_3)_2Cl_2$ (0.026 mmol, 0.05 eq.) and 4.98 mg of CuI (0.026 mmol, 0.05 eq.) the reaction mixture was warmed up to 60° C. and stirred at that temperature for 1 h. when the reaction reached full conversion. Celite was added to the reaction mixture and the volatiles were removed under reduced pressure. Then it was purified via flash column chromatography using heptane and EtOAc to give 271 mg (69%) or the desired product.

$^1$H NMR (500 MHz, DMSO-$d_6$) δ ppm 8.15 (s, 1H), 7.31 (brd, 1H), 7.21 (dm, 1H), 7.14 (t, 1H), 4.23 (brs, 2H), 4.12 (t, 2H), 3.87 (s, 3H), 3.79 (s, 3H), 3.28 (t, 2H), 2.86 (brs, 3H), 2.12 (m, 2H), 1.41 (s, 9H); $^{13}$C NMR (125 MHz, DMSO-$d_6$) δ ppm 144.2, 129.1, 121.6, 119.3, 117.8, 115.4, 85.2, 82.3, 68.2, 52.1, 38.6, 38.6, 35.8, 30.6, 28.5, 23.1; HRMS-ESI (m/z): $[M+H]^+$ calcd for $C_{29}H_{31}ClF_4N_5O_5S$: 672.1665, found 672.1651.

Step C: methyl 2-[[6-(1,3-benzothiazol-2-ylamino)-5-(trifluoromethyl)pyridazin-3-yl]-methyl-amino]-5-[3-[4-[3-[tert-butoxycarbonyl(methyl)amino]prop-1-ynyl]-2-fluoro-phenoxy]propyl]thiazole-4-carboxylate A 4 mL oven-dried vial equipped with a PTFE-coated magnetic stirring bar, was charged with 130 mg of the product from Step B (0.19 mmol, 1 eq.), 87 mg of 1,3-benzothiazol-2-amine (0.58 mmol, 3 eq.) and 168 uL of DIPEA (125 mg, 0.96 mmol, 5 eq.), suspended in 1 mL CyOH and then placed under an inert atmosphere flushed with argon. After 2 min stirring under inert atmosphere 18 mg of $Pd_2(dba)_3$ (0.019 mmol, 0.1 eq.) and 23 mg of XantPhos (0.038 mmol, 0.2 eq.) were added. The resulting mixture was then warmed up to 140° C. and stirred at that temperature for 4 h, when the reaction reached full conversion. The reaction mixture was diluted with 1 mL DCM and purified via flash column chromatography using heptane and EtOAc as eluents to give 85 mg (56%) of the desired product.

$^1$H NMR (500 MHz, DMSO-$d_6$) δ ppm 9.19 (br., 1H), 7.95 (s, 1H), 7.82 (d, 1H), 7.39 (t, 1H), 7.32 (d, 1H), 7.32 (d, 1H), 7.22 (d, 1H), 7.21 (t, 1H), 7.16 (t, 1H), 4.20 (br., 3H), 4.14 (t, 2H), 3.84 (s, 3H), 3.29 (t, 2H), 2.84 (br., 2H), 2.13 (quint., 2H), 1.40 (s, 9H); $^{13}$C NMR (125 MHz, DMSO-$d_6$) δ ppm 163.0, 160.0, 156.8, 151.7, 151.1, 141.7, 137.0, 135.1, 129.1, 127.3, 126.6, 123.2, 122.9, 122.7, 119.1, 116.4, 115.5, 112.1, 68.3, 38.5, 35.6, 33.8, 30.9, 28.5, 23.1; HRMS-ESI (m/z): $[M+H]^+$ calcd for $C_{36}H_{36}F_4N_7O_5S_2$: 786.2150, found 786.2148.

Step D: 2-[[6-(1,3-benzothiazol-2-ylamino)-5-(trifluoromethyl)pyridazin-3-yl]-methyl-amino]-5-[3-[2-fluoro-4-[3-(methylamino)prop-1-ynyl]phenoxy] propyl]thiazole-4-carboxylic acid Using Deprotection and Hydrolysis General Procedure starting from the product from Step C as the appropriate methyl ester, the desired product was obtained.

HRMS-ESI (m/z): $[M+H]^+$ calcd for $C_{30}H_{26}F_4N_7O_3S_2$: 672.1469, found 672.1458.

Example 210: 2-[[6-(1,3-Benzothiazol-2-ylamino)-5-methyl-pyridazin-3-yl]-[4-(dimethylamino)butyl]amino]-5-[3-[2-fluoro-4-[3-(methylamino)prop-1-ynyl]phenoxy]propyl]thiazole-4-carboxylic acid

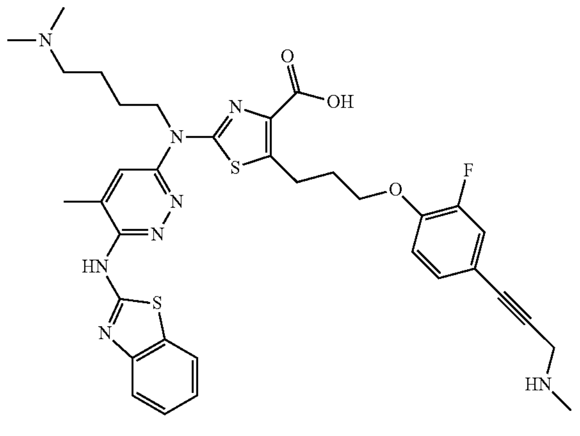

Step A: methyl 2-[tert-butoxycarbonyl-[4-(dimethylamino)butyl]amino]-5-[3-(2-fluoro-4-iodo-phenoxy)propyl]thiazole-4-carboxylate Using Mitsunobu General Procedure starting from Preparation 1a and 4-(dimethylamino)butan-1-ol, 401 mg (quant.) of the desired product was obtained.

$^1$H NMR (400 MHz, DMSO-$d_6$) δ ppm 7.60 (dd, 1H), 7.47 (dm, 1H), 6.99 (t, 1H), 4.08 (t, 2H), 4.03 (t, 2H), 3.76 (s, 3H), 3.23 (t, 2H), 3.13 (t, 2H), 2.74 (s, 6H), 2.07 (m, 2H), 1.66 (m, 2H), 1.65 (m, 2H), 1.53 (s, 9H); $^{13}$C NMR (100 MHz, DMSO-$d_6$) δ ppm 162.8, 152.7, 147.0, 143.6, 135.5, 134.1, 125.0, 117.7, 84.0, 82.4, 68.2, 56.8, 52.1, 46.0, 42.6, 30.5, 28.2, 25.2, 23.2, 21.7; HRMS-ESI (m/z): $[M+H]^+$ calcd for $C_{25}H_{36}FIN_3O_5S$: 636.1399, found 636.1400.

Step B: methyl 5-[3-[4-[3-[tert-butoxycarbonyl(methyl)amino]prop-1-ynyl]-2-fluoro-phenoxy]propyl]-2-[4-(dimethylamino)butylamino]thiazole-4-carboxylate Using Deprotection with HFIP General Procedure starting from the product from Step A, crude methyl 2-[4-(dimethylamino)butylamino]-5-[3-(2-fluoro-4-iodo-phenoxy)propyl]thiazole-4-carboxylate (LC-MS-ESI (m/z): $[M+H]^+$ calcd for $C_{20}H_{28}FIN_3O_3S$: 536.1, found 536.2) was obtained alter concentration then Sonogashira General Procedure was applied with tert-butyl N-methyl-N-prop-2-ynyl-carbamate as alkyne reactant which was resulted in 240 mg (67%) of the desired product.

$^1$H NMR (500 MHz, DMSO-$d_6$) δ ppm 7.59 (t, 1H), 7.31 (d, 1H), 7.21 (d, 1H), 7.13 (t, 1H), 4.23 (br., 2H), 4.07 (t, 2H), 3.69 (s, 3H), 3.15 (q, 2H), 3.11 (t, 2H), 2.86 (br., 3H), 2.18 (t, 2H), 2.09 (s, 6H), 2.00 (quint., 2H), 1.50 (m, 2H), 1.43 (m, 2H), 1.41 (s, 9H); $^{13}$C NMR (125 MHz, DMSO-$d_6$) δ ppm 129.1, 119.3, 115.4, 68.0, 59.2, 51.7, 45.6, 44.5, 38.6, 33.9, 30.6, 28.5, 27.0, 24.9, 23.3; HRMS-ESI (m/z): $[M+H]^+$ calcd for $C_{29}H_{42}FN_4O_5S$: 577.2854, found 577.2854.

Step C: methyl 5-[3-[4-[3-[tert-butoxycarbonyl(methyl)amino]prop-1-ynyl]-2-fluoro-phenoxy]propyl]-2-[4-(dimethylamino)butyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 235 mg of the product from Step B (0.41 mmol, 1 eq.) and 249 mg of Preparation 4a (0.61 mmol, 1.5 eq.) as the appropriate halide, 353 mg (90%) of the desired product was obtained.

$^1$H NMR (500 MHz, DMSO-$d_6$) δ ppm 7.84 (d, 1H), 7.73 (s, 1H), 7.47 (dm, 1H), 7.44 (t, 1H), 7.33 (brd, 1H), 7.26 (t, 1H), 7.22 (dm, 1H), 7.17 (t, 1), 5.86 (s, 2H), 4.39 (br, 2H), 4.21 (br, 2H), 4.14 (t, 2H), 3.80 (s, 3H), 3.72 (t, 2H), 3.28 (t, 2H), 3.13 (br, 2H), 2.85 (brs, 3H), 2.70 (s, 6H), 2.47 (s, 3H), 2.14 (quin, 2H), 1.75 (brm, 4H), 1.42 (s, 9H), 0.92 (t, 2H), −0.10 (s, 9H); $^{13}$C NMR (125 MHz, DMSO-$d_6$) δ ppm 163.1, 157.6, 155.3, 151.5, 147.6, 147.4, 141.5, 137.6, 137.5, 135.0, 129.1, 127.2, 123.5, 123.2, 119.4, 117.5, 115.5, 114.8, 112.0, 85.3, 82.3, 72.9, 68.5, 66.9, 56.5, 52.1, 46.2, 42.7, 38.4, 34.0, 31.1, 28.4, 24.5/21.5, 23.2, 17.9, 17.8, −1.1; HRMS-ESI (m/z): $[M+H]^+$ calcd for $C_{47}H_{64}FN_8O_6S_2Si$: 947.4138, found 947.4144.

Step D: 2-[[6-(1,3-benzothiazol-2-ylamino)-5-methyl-pyridazin-3-yl]-[4-(dimethylamino)butyl]amino]-5-[3-[2-fluoro-4-[3-(methylamino)prop-1-ynyl]phenoxy]propyl]thiazole-4-carboxylic acid Using Deprotection and Hydrolysis General Procedure followed by repurification via reverse phase preparative chromatography (C18, 0.1% TFA in water:MeCN), starting from the product from Step C, the TFA-salt of the desired product was obtained.

HRMS-ESI (m/z): $[M+H]^+$ calcd for $C_{35}H_{40}FN_8O_3S_2$: 703.2649, found 703.2637.

Example 211: 2-[[6-(1,3-Benzothiazol-2-ylamino)-5-methyl-pyridazin-3-yl]-[4-hydroxy-5-(trimethylammonio)pentyl]amino]-5-[3-[4-[3-(dimethylamino)prop-1-ynyl]-2-fluoro-phenoxy]propyl]thiazole-4-carboxylate

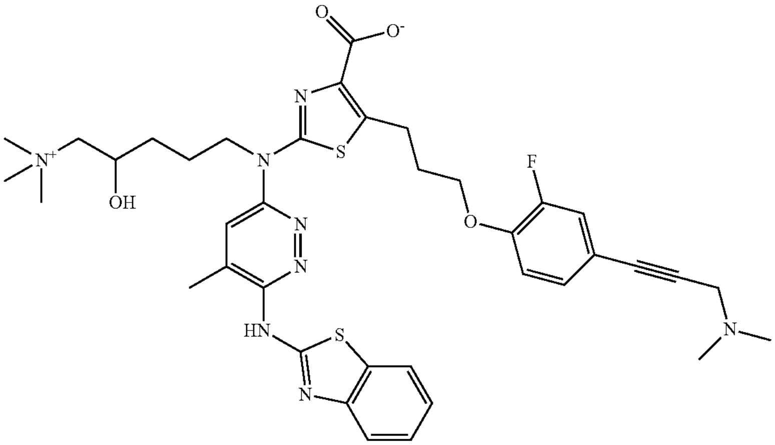

Step A: [2-[tert-butyl(diphenyl)silyl]oxy-5-[[5-[3-[4-[3-(dimethylamino)prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]pentyl]-trimethyl-ammonium Using Quaternary salt formation General Procedure starting from Preparation 5b and N,N-dimethylmethanamine as the appropriate tertiary amine, the desired product was obtained.

Step B: 2-[[6-(1,3-benzothiazol-2-ylamino)-5-methyl-pyridazin-3-yl]-[4-hydroxy-5-(trimethylammonio)pentyl]amino]-5-[3-[4-[3-(dimethylamino)prop-1-ynyl]-2-fluoro-phenoxy]propyl]thiazole-4-carboxylate Using Quaternary salt deprotection General Procedure starting from the product from Step A as the quaternary salt, the desired product was obtained.

HRMS-ESI (m/z): $[M+H]^+$ calcd for $C_{38}H_{46}FN_8O_4S_2$: 761.3062, found 761.3057.

Example 212: 3-[5-[[6-(1,3-Benzothiazol-2-ylamino)-5-methyl-pyridazin-3-yl]-[4-carboxy-5-[3-[2-fluoro-4-[3-(methylamino)prop-1-ynyl]phenoxy]propyl]thiazol-2-yl]amino]pentyl-dimethyl-ammonio]propane-1-sulfonate

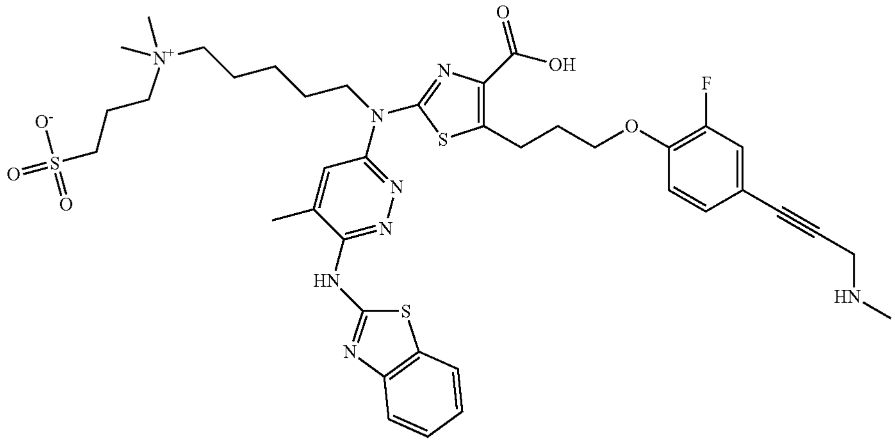 [SMILES: CNCC#Cc1ccc(OCCCc2sc(N(CCCCC[N+](C)(C)CCCS(=O)(=O)[O-])c3cc(C)c(Nc4nc5ccccc5s4)nn3)nc2C(=O)O)c(F)c1]

Using Alkylation, Deprotection and Hydrolysis General procedure starting from Example 213, Step C and oxathiolane 2,2-dioxide, the TFA-salt of the desired product was obtained.

HRMS-ESI (m/z): $[M+H]^+$ calcd for $C_{51}H_{72}FN_8O_9S_3Si$: 839.2843, found 839.2823.

Example 213: 2-[[6-(1,3-Benzothiazol-2-ylamino)-5-methyl-pyridazin-3-yl]-[5-(dimethylamino)pentyl]amino]-5-[3-[2-fluoro-4-[3-(methylamino)prop-1-ynyl]phenoxy]propyl]thiazole-4-carboxylic acid

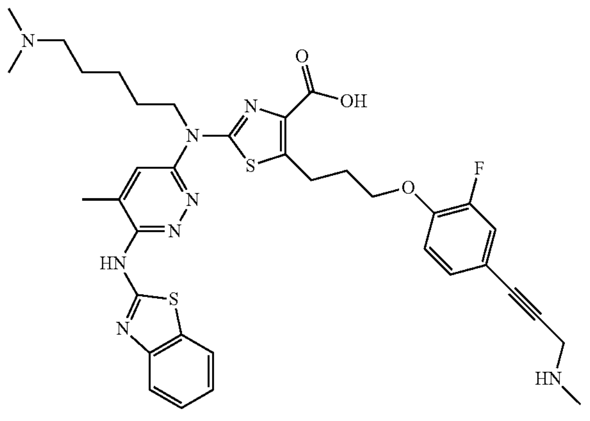

Step A: methyl 2-[tert-butoxycarbonyl-[5-(dimethylamino)pentyl]amino]-5-[3-[4-[3-[tert-butoxycarbonyl(methyl)amino]prop-1-ynyl]-2-fluoro-phenoxy]propyl]thiazole-4-carboxylate Using Mitsunobu General Procedure starting from Preparation 1b and 5-(dimethylamino)pentan-1-ol, 1.47 g (quant.) of the desired product was obtained.

$^1H$ NMR (500 MHz, DMSO-$d_6$) δ ppm 7.30 (d, 1H), 7.21 (d, 1H), 7.13 (t, 1H), 4.22 (m, 2H), 4.10 (t, 2H), 3.99 (t, 2H), 3.75 (s, 3H), 3.22 (m, 2H), 2.86 (bs, 3H), 2.35 (bs, 2H), 224 (bs, 6H), 2.08 (m, 2H), 1.62-1.13 (m, 6H), 1.51 (s, 9H), 1.42 (s, 9H); $^{13}C$ NMR (125 MHz, DMSO-$d_6$) δ ppm 129.1, 119.2, 115.4, 85.2, 79.8, 68.1, 58.8, 52.0, 46.4, 45.0, 38.3, 33.8, 30.5, 28.5, 28.1, 23.2; HRMS-ESI (m/z): $[M+H]^+$ calcd for $C_{35}H_{52}FN_4O_7S$: 691.3541, found 691.3524.

Step B: methyl 5-[3-[4-[3-[tert-butoxycarbonyl(methyl)amino]prop-1-ynyl]-2-fluoro-phenoxy]propyl]-2-[5-(dimethylamino)pentylamino]thiazole-4-carboxylate Using Deprotection with HFIP General Procedure starting from the product from Step A, 0.66 g (52%) of the desired product was produced.

$^1H$ NMR (500 MHz, DMSO-$d_6$) δ ppm 7.58 (t, 1H), 7.32 (brd., 1H), 7.21 (d, 1H), 7.13 (t, 1H), 4.23 (br., 2H), 4.07 (t, 2H), 3.69 (s, 3H), 3.15 (m, 2H), 3.11 (t, 2H), 2.87 (br., 3H), 2.35 (br., 2H), 2.24 (brs., 6H), 2.00 (quint., 2H), 1.51 (m, 2H), 1.44 (m, 2H), 1.41 (s, 9H), 1.30 (m, 2H); $^{13}C$ NMR (125 MHz, DMSO-$d_6$) δ ppm 129.1, 119.3, 115.4, 68.0, 58.9, 51.7, 45.0, 44.4, 38.6, 33.8, 30.6, 28.9, 28.5, 26.4, 24.5, 23.3; HRMS-ESI (m/z): $[M+H]^+$ calcd for $C_{30}H_{44}FN_4O_5S$: 591.3016, found 591.3005.

Step C: methyl 5-[3-[4-[3-[tert-butoxycarbonyl(methyl)amino]prop-1-ynyl]-2-fluoro-phenoxy]propyl]-2-[5-(dimethylamino)pentyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B, and Preparation 4a, 0.43 g (40%) of the desired product was produced.

$^1H$ NMR (500 MHz, DMSO-$d_6$) δ ppm 7.84 (d, 1H), 7.69 (s, 1H), 7.47 (d, 1H), 7.44 (td, 1H), 7.32 (brd., 1H), 7.25 (td, 1H), 7.22 (d, 1H), 7.15 (t, 1H), 5.86 (s, 2H), 4.38 (t, 2H), 4.20 (br., 2H), 4.15 (t, 2H), 3.78 (s, 3H), 3.72 (t, 2H), 3.26 (t, 2H), 2.84 (br., 3H), 2.57 (br., 2H), 2.46 (s, 3H), 2.39 (br., 6H), 2.12 (m, 2H), 1.71 (m, 2H), 1.58 (m, 2H), 1.40 (s, 9H), 1.37 (m, 2H), 0.92 (t, 2H), −0.11 (s, 9H); $^{13}C$ NMR (125 MHz, DMSO-$d_6$) δ ppm 129.1, 127.2, 123.5, 123.2, 119.3, 117.6, 115.5, 112, 72.9, 68.4, 66.7, 58.2, 52.0, 46.7, 44.2, 38.4, 33.8, 31.0, 28.5, 26.8, 25.4, 23.8, 23.2, 17.9, 17.8, −1.0; HRMS-ESI (m/z): $[M+H]^+$ calcd for $C_{48}H_{66}FN_8O_6S_2Si$: 961.4300, found 461.4293.

Step D: 2-[[6-(1,3-benzothiazol-2-ylamino)-5-methyl-pyridazin-3-yl]-[5-(dimethylamino)pentyl]amino]-5-[3-[2-fluoro-4-[3-(methylamino)prop-1-ynyl]phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step C, the TFA-salt of the desired product was obtained.

HRMS-ESI (m/z): $[M+H]^+$ calcd for $C_{36}H_{42}FN_8O_3S_2$: 717.2805, found 717.2779.

Example 214: 2-[[6-(1,3-Benzothiazol-2-ylamino)-5-methyl-pyridazin-3-yl]-methyl-amino]-5-[3-[4-[3-(dimethylamino)propyl]-2-fluoro-phenoxy]propyl]thiazole-4-carboxylic acid

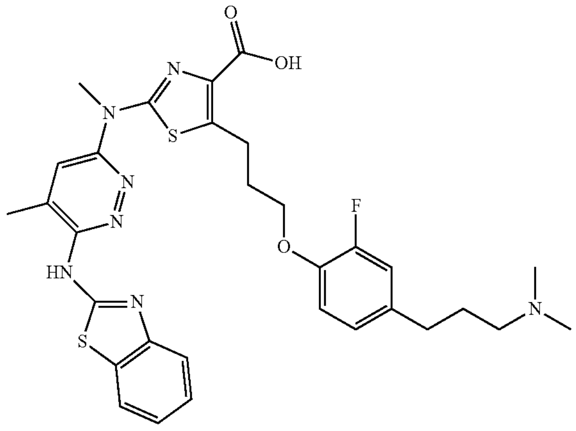

Step A: ethyl 5-[3-[4-[3-(dimethylamino)propyl]-2-fluoro-phenoxy]propyl]-2-[methyl-[5-methyl-6-[(E)-[3-(2-trimethylsilylethoxymethyl)-1,3-benzothiazol-2-ylidene]amino]pyridazin-3-yl]amino]thiazole-4-carboxylate The mixture of 59 mg of Example 50, Step A (0.075 mmol, 1 eq.) and 6 mg of 10% palladium on charcoal (0.076 eq.) in 5 mL of ethanol was kept under 4 bar of hydrogen at rt for 18 h. After filtration through Celite, the product was concentrated to give 59 mg (99%) of the desired product.

$^1$H NMR (500 MHz, DMSO-$d_6$) δ ppm 9.30 (brs, 1H), 7.84 (dm, 1H), 7.68 (q, 1H), 7.48 (dm, 1H), 7.44 (m, 1H), 7.25 (m, 1H), 7.13 (dd, 1H), 7.10 (m, 1H), 6.97 (dm, 1H), 4.27 (q, 2H), 4.10 (t, 2H), 3.78 (s, 3H), 3.72 (m, 2H), 3.27 (t, 2H) 2.99 (m, 2H), 2.75 (d, 6H), 2.55 (t, 2H), 2.46 (d, 3H), 2.12 (m, 2H), 1.88 (m, 2H), 1.30 (t, 3H), 0.92 (m, 2H), −0.11 (s, 9H); HRMS-ESI (m/z): $[M+H]^+$ calcd for $C_{39}H_{53}FN_7O_4S_2Si$: 794.3354 found: 794.3356.

Step B: 2-[[6-(1,3-benzothiazol-2-ylamino)-5-methyl-pyridazin-3-yl]-methyl-amino]-5-[3-[4-[3-(dimethylamino)propyl]-2-fluoro-phenoxy]propyl]thiazole-4-carboxylic acid To the mixture of 59 mg of the product from Step A (0.076 mmol, 1 eq.) in 5 mL of 1,4-dioxane was added 1.5 mL of a 4 N solution of HCl (6.0 mmol) and was stirred at rt for 18 h. After the addition of 510 mg of LiOH×$H_2O$ (12.14 mmol, 160 eq.) the mixture was stirred at 60° C. for 2 h. After concentration, the crude product was purified by flash column chromatography using DCM and MeOH (containing 1.2% $NH_3$) as eluents then by reverse phase preparative chromatography (C18, 25 mM $NH_4HCO_3$ in water:MeCN) to give 3 mg (6%) of the desired product.

HRMS-ESI (m/z): $[M+H]^+$ calcd for $C_{31}H_{35}FN_7O_3S$: 636.2226 found: 636.2221.

Example 215: 2-[[6-(1,3-Benzothiazol-2-ylamino)-5-methyl-pyridazin-3-yl]-(4-hydroxy-5-quinuclidin-1-ium-1-yl-pentyl)amino]-5-[3-[4-[3-(dimethylamino)prop-1-ynyl]-2-fluoro-phenoxy]propyl]thiazole-4-carboxylate

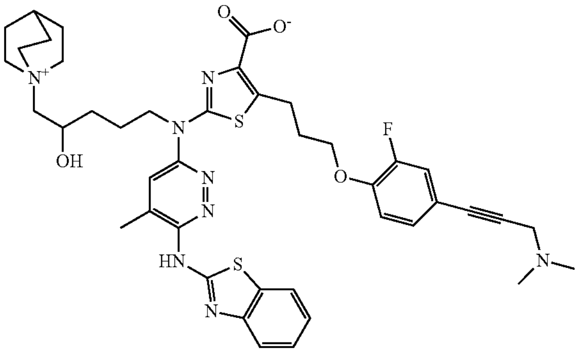 [SMILES: Cc1cc(N(CCCC(O)C[N+]23CCC(CC2)CC3)c2nc(C(=O)[O-])c(CCCOc3ccc(C#CCN(C)C)cc3F)s2)nnc1Nc1nc2ccccc2s1]

Step A: methyl 2-[[4-[tert-butyl(diphenyl)silyl]oxy-5-quinuclidin-1-ium-1-yl-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Quaternary salt formation General Procedure starting from Preparation 5b and quinuclidine as the appropriate tertiary amine, the desired product was obtained.

Step B: 2-[[6-(1,3-benzothiazol-2-ylamino)-5-methyl-pyridazin-3-yl]-(4-hydroxy-5-quinuclidin-1-ium-1-yl-pentyl)amino]-5-[3-[4-[3-(dimethylamino)prop-1-ynyl]-2-fluoro-phenoxy]propyl]thiazole-4-carboxylate Using Quaternary salt deprotection General Procedure starting from the product from Step A as the quaternary salt, the desired product was obtained.

HRMS-ESI (m/z): $[M+2H]^{2+}$ calcd for $C_{42}H_{51}FN_8O_4S_2$: 407.1724 found 407.1724.

Example 216: 2-[[5-(1-aza-4-azoniabicyclo[2.2.2]octan-4-yl)-4-hydroxy-pentyl]-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylate

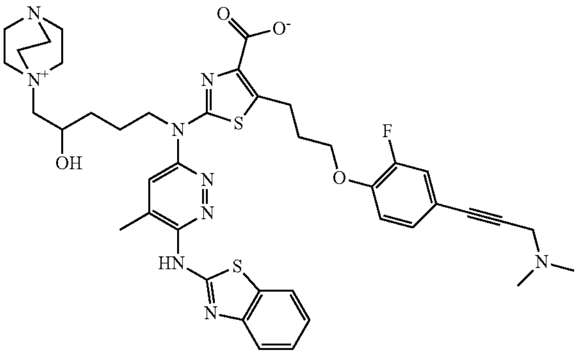 [SMILES: Cc1cc(N(CCCC(O)C[N+]23CCN(CC2)CC3)c2nc(C(=O)[O-])c(CCCOc3ccc(C#CCN(C)C)cc3F)s2)nnc1Nc1nc2ccccc2s1]

Step A: methyl 2-[[5-(1-aza-4-azoniabicyclo[2.2.2]octan-4-yl)-4-[tert-butyl(diphenyl)silyl]oxy-pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Quaternary salt formation General Procedure starting from Preparation 5b and 1,4-diazabicyclo[2.2.2]octane as the appropriate tertiary amine, the desired product was obtained.

Step B: 2-[[5-(1-aza-4-azoniabicyclo[2.2.2]octan-4-yl)-4-hydroxy-pentyl]-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylate Using Quaternary salt deprotection General Procedure starting from the product from Step A as the quaternary salt, the desired product was obtained.

HRMS-ESI (m/z): $[M+2H]^{2+}$ calcd for $C_{41}H_{50}FN_9O_4S_2$: 407.6700, found 407.6699.

Example 217: 2-[[6-(1,3-Benzothiazol-2-ylamino)-5-methyl-pyridazin-3-yl]-[4-hydroxy-5-(4-methylmorpholin-4-ium-4-yl)pentyl]amino]-5-[3-[4-[3-(dimethylamino)prop-1-ynyl]-2-fluoro-phenoxy]propyl]thiazole-4-carboxylate

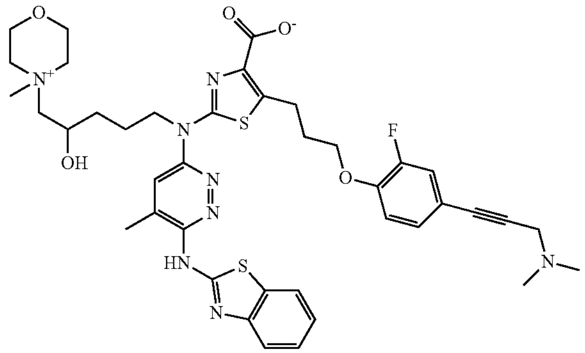 [SMILES: Cc1cc(N(CCCC(O)C[N+]2(C)CCOCC2)c2nc(C(=O)[O-])c(CCCOc3ccc(C#CCN(C)C)cc3F)s2)nnc1Nc1nc2ccccc2s1]

Step A: methyl 2-[[4-[tert-butyl(diphenyl)silyl]oxy-5-(4-methylmorpholin-4-ium-4-yl)pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Quaternary salt formation General Procedure starting from Preparation 5b and 4-methylmorpholine as the appropriate tertiary amine, the desired product was obtained.

Step B: 2-[[6-(1,3-benzothiazol-2-ylamino)-5-methyl-pyridazin-3-yl]-[4-hydroxy-5-(4-methylmorpholin-4-ium-4-yl)pentyl]amino]-5-[3-[4-[3-(dimethylamino)prop-1-ynyl]-2-fluoro-phenoxy]propyl]thiazole-4-carboxylate Using Quaternary salt deprotection General Procedure starting from the product from Step A as the quaternary salt, the desired product was obtained.

HRMS-ESI (m/z): $[M+H]^+$ calcd for $C_{40}H_{48}FN_8O_5S_2$: 803.3168, found 803.3165.

Example 218: 3-[2-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-dimethyl-ammonio]propane-1-sulfonate

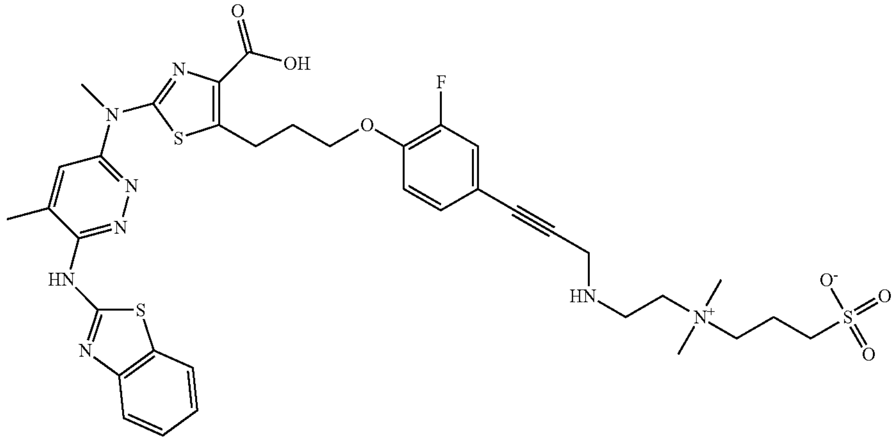 [SMILES: Cc1cc(N(C)c2nc(C(=O)O)c(CCCOc3ccc(C#CCNCC[N+](C)(C)CCCS(=O)(=O)[O-])cc3F)s2)nnc1Nc1nc2ccccc2s1]

Step A: 3-[2-[tert-butoxycarbonyl-[3-[4-[3-[4-ethoxycarbonyl-2-[methyl-[5-methyl-6-[(Z)-[3-(2-trimethylsilylethoxymethyl)-1,3-benzothiazol-2-ylidene]amino]pyridazin-3-yl]amino]thiazol-5-yl]propoxy]-3-fluoro-phenyl]prop-2-ynyl]amino]ethyl-dimethyl-ammonio]propane-1-sulfonate 159 mg of Preparation 5h (0.17 mmol, 1 eq.) and 208 mg of oxothiolane 2,2-dioxide (1.70 mmol, 10 eq.) were mixed in acetonitrile (6 mL/mmol) and the reaction mixture was stirred at 60° C. for 2.5 h when the conversion was reached >90%. The mixture was concentrated onto Celite and purified via flash column chromatography using EtOAc and MeOH (1.2% $NH_3$) as eluents to give 126 mg (70%) of the desired product as yellow solid.

$^1$H NMR (500 MHz, DMSO-$d_6$) δ ppm 7.84 (d, 1H), 7.67 (s, 1H), 7.46 (d, 1H), 7.44 (t, 1H), 7.35 (br., 1H), 7.25 (t, 1H), 7.25 (br., 1H), 7.18 (t, 1H), 5.86 (s, 2H), 4.28 (br., 2H), 4.26 (q, 2H), 4.15 (t, 2H), 3.77 (s, 3H), 3.72 (t, 2H), 3.70 (brt., 2H), 3.46 (br., 2H), 3.46 (br., 2H), 3.27 (t, 2H), 3.08 (brs., 6H), 2.46 (s, 3H), 2.46 (t, 2H), 2.13 (quint., 2H), 2.02 (br., 2H), 1.44 (brs., 9H), 1.29 (t, 3H), 0.92 (t, 2H), −0.11 (s, 9H); $^{13}$C NMR (125 MHz, DMSO-$d_6$) δ ppm 154.4, 129.2, 127.2, 123.4, 123.2, 119.3, 117.6, 115.5, 111.9, 72.8, 68.4, 66.7, 63.3, 60.7, 59.9, 50.7, 48.0, 40.7, 37.8, 35.3, 31.1, 28.3, 23.2, 19.4, 17.8, 17.8, 14.6, −1.0; HRMS-ESI (m/z): $[M+H]^+$ calcd for $C_{49}H_{68}FN_8O_9S_3Si$: 1055.4019, found 1055.4026.

Step B: 3-[2-[3-[4-[3-[2-[[6-(1,3-benzothiazol-2-ylamino)-5-methyl-pyridazin-3-yl]-methyl-amino]-4-carboxy-thiazol-5-yl]propoxy]-3-fluorophenyl]prop-2-ynylamino]ethyl-dimethyl-ammonio]propane-1-sulfonate Using Deprotection and Hydrolysis General Procedure followed by repurification via reverse phase preparative chromatography (C18, 25 mM $NH_4HCO_3$ in water:MeCN) starting from the product from Step A, the TFA-salt of the desired product was obtained.

HRMS-ESI (m/z): $[M+H]^+$ calcd for $C_{36}H_{42}FN_8O_6S_3$: 797.2368, found 797.2343.

Example 219: 2-[[6-(1,3-Benzothiazol-2-ylamino)-5-methyl-pyridazin-3-yl]-[5-(trimethylammonio)pentyl]amino]-5-[3-[2-fluoro-4-[3-(methylamino)prop-1-ynyl]phenoxy]propyl]thiazole-4-carboxylate

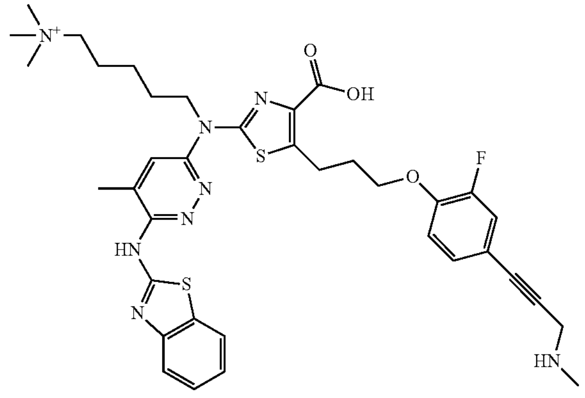

Using Alkylation, Deprotection and Hydrolysis General procedure starting from Example 213, Step C and iodomethane, the TFA-salt of the desired product was obtained.

HRMS-ESI (m/z): $[M+H]^+$ calcd for $C_{37}H_{44}FN_8O_3S_2$: 731.2956, found 731.2967.

Example 220: 2-[[6-(1,3-Benzothiazol-2-ylamino)-5-methyl-pyridazin-3-yl]-[4-hydroxy-5-(1-methylpiperidin-1-ium-1-yl)pentyl]amino]-5-[3-[4-[3-(dimethylamino)prop-1-ynyl]-2-fluoro-phenoxy]propyl]thiazole-4-carboxylate

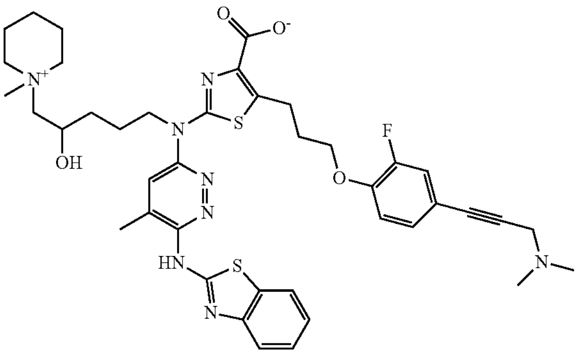 [SMILES: Cc1cc(N(CCCC(O)C[N+]2(C)CCCCC2)c2nc(C(=O)[O-])c(CCCOc3ccc(C#CCN(C)C)cc3F)s2)nnc1Nc1nc2ccccc2s1]

Step A: methyl 2-[[4-[tert-butyl(diphenyl)silyl]oxy-5-(1-methylpiperidin-1-ium-1-yl)pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Quaternary salt formation General Procedure starting from Preparation 5b and 1-methylpiperidine as the appropriate tertiary amine, the desired product was obtained.

Step B: 2-[[6-(1,3-benzothiazol-2-ylamino)-5-methyl-pyridazin-3-yl]-[4-hydroxy-5-(1-methylpiperidin-1-ium-1-yl)pentyl]amino]-5-[3-[4-[3-(dimethylamino)prop-1-ynyl]-2-fluoro-phenoxy]propyl]thiazole-4-carboxylate Using Quaternary salt deprotection General Procedure starting from the product from Step A as the quaternary salt, the desired product was obtained.

HRMS-ESI (m/z): $[M+H]^+$ calcd for $C_{41}H_{50}FN_8O_4S_2$: 801.3375, found 801.3378.

Example 221: 2-[[6-(1,3-Benzothiazol-2-ylamino)-5-methyl-pyridazin-3-yl]-[5-(1,4-dimethylpiperazin-1-ium-1-yl)-4-hydroxy-pentyl]amino]-5-[3-[4-[3-(dimethylamino)prop-1-ynyl]-2-fluoro-phenoxy]propyl]thiazole-4-carboxylate

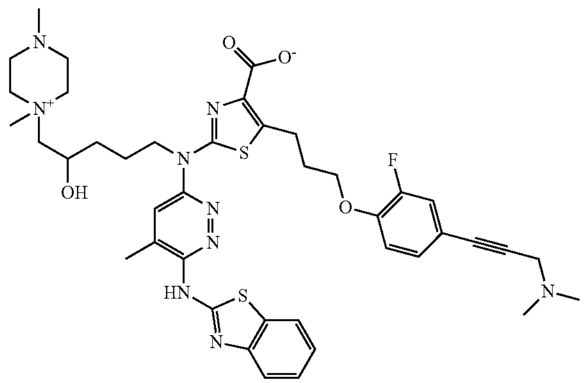 [SMILES: Cc1cc(N(CCCC(O)C[N+]2(C)CCN(C)CC2)c2nc(C(=O)[O-])c(CCCOc3ccc(C#CCN(C)C)cc3F)s2)nnc1Nc1nc2ccccc2s1]

Step A: methyl 2-[[4-[tert-butyl(diphenyl)silyl]oxy-5-(1,4-dimethylpiperazin-1-ium-1-yl)pentyl]-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Quaternary salt formation General Procedure starting from Preparation 5b and 1,4-dimethylpiperazine as the appropriate tertiary amine, the desired product was obtained.

Step B: 2-[[6-(1,3-benzothiazol-2-ylamino)-5-methyl-pyridazin-3-yl]-[5-(1,4-dimethylpiperazin-1-ium-1-yl)-4-hydroxy-pentyl]amino]-5-[3-[4-[3-(dimethylamino)prop-1-ynyl]-2-fluoro-phenoxy]propyl]thiazole-4-carboxylate Using Quaternary salt deprotection General Procedure starting from the product of Step A as the quaternary salt, the desired product was obtained.

HRMS-ESI (m/z): $[M+H]^+$ calcd for $C_{41}H_{51}FN_9O_4S_2$: 816.3484, found 816.3489.

Example 222: 2-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-trimethyl-ammonium

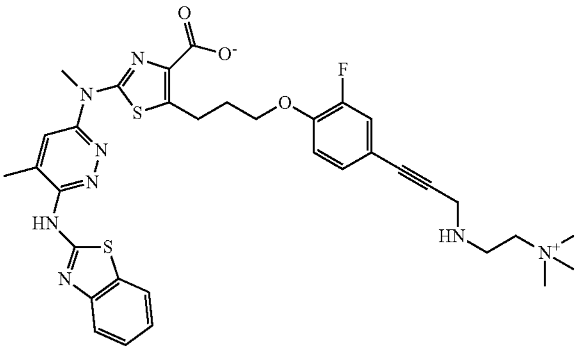

Step A: 2-[tert-butoxycarbonyl-[3-[4-[3-[4-ethoxycarbonyl-2-[methyl-[5-methyl-6-[(Z)-[3-(2-trimethylsilylethoxymethyl)-1,3-benzothiazol-2-ylidene]amino]pyridazin-3-yl]amino]thiazol-5-yl]propoxy]-3-fluoro-phenyl]prop-2-ynyl]amino]ethyl-trimethyl-ammonium 200 mg of Preparation 5h (0.21 mmol, 1 eq.) was dissolved in acetonitrile (4 mL/mmol) then 152 mg of iodomethane (1.07 mmol, 5 eq.) was added and stirred at rt for 1.5 h. The reaction did not go further therefore stopped at this point, partially conversion was observed. The volatiles were evaporated and the crude mixture (contained Preparation 5h and the desired product) was transferred directly to the next step.

LC-MS-ESI (m/z): $[M]^+$ calcd for $C_{47}H_{64}FN_8O_6S_2Si$: 947.4, found 947.4.

Step B: 2-[3-[4-[3-[2-[[6-(1,3-benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-trimethyl-ammonium Using Deprotection and Hydrolysis General Procedure followed by repurification via reverse phase preparative chromatography (C18, 25 mM $NH_4HCO_3$ in water:MeCN) starting from the product from Step A, the desired product and Example 223 were separated and isolated.

HRMS-ESI (m/z): $[M+H]^+$ calcd for $C_{34}H_{38}FN_8O_3S_2$: 689.2487, found 689.2481.

Example 223: 2-[[6-(1,3-Benzothiazol-2-ylamino)-5-methyl-pyridazin-3-yl]-methyl-amino]-5-[3-[4-[3-[2-(dimethylamino)ethylamino]prop-1-ynyl]-2-fluoro-phenoxy]propyl]thiazole-4-carboxylic acid

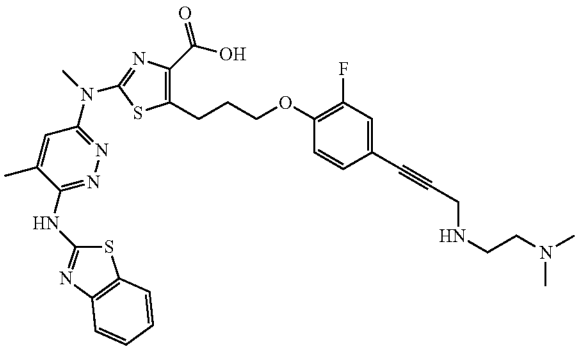

Example 223 was isolated as side product from Example 222, Step B.

HRMS-ESI (m/z): $[M+H]^+$ calcd for $C_{33}H_{36}FN_8O_3S_2$: 675.2330, found 675.2324.

Example 224: 2-[[6-(1,3-Benzothiazol-2-ylamino)-5-methyl-pyridazin-3-yl]-[6-(trimethylammonio)hexyl]amino]-5-[3-[2-fluoro-4-[3-(methylamino)prop-1-ynyl]phenoxy]propyl]thiazole-4-carboxylate

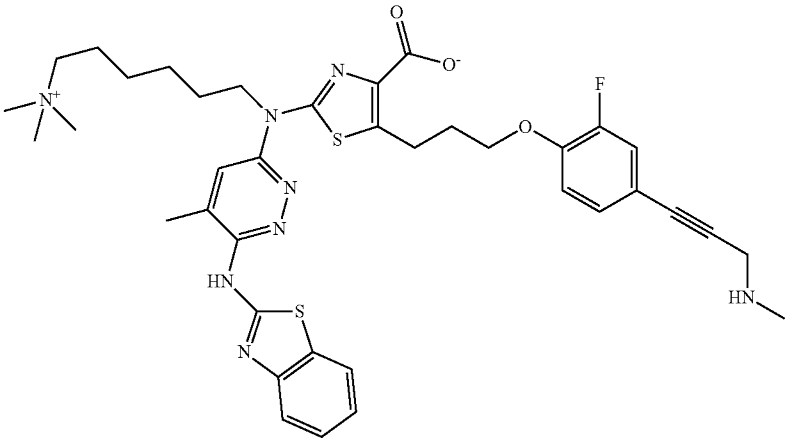

Using Alkylation, Deprotection and Hydrolysis General procedure starting from Example 199, Step C and iodomethane, TFA-salt of the desired product was obtained.

$^1$H NMR (500 MHz, DMSO-d$_6$) δ ppm 7.90 (d, 1H), 7.64 (s, 1H), 7.53 (brd, 1H), 7.39 (t, 1H), 7.26 (dd, 1H), 7.21 (t, 1H), 7.18 (m, 1H), 7.15 (t, 1H), 4.37 (t, 2H), 4.13 (t, 2H), 3.44 (brs, 2H), 3.30 (t, 2H), 3.24 (t, 2H), 3.03 (s, 9H), 2.45 (s, 3H), 2.31 (s, 3H), 2.11 (quin, 2H), 1.72-1.39 (m, 8H); $^{13}$C NMR (125 MHz, DMSO-d$_6$) δ ppm 151.5, 147.1, 128.8, 126.6, 122.6, 122.3, 119.1, 118.4, 117.0, 115.5, 88.5, 82.0, 69.0, 65.8, 52.6, 46.6, 40.3, 35.4, 31.2, 26.6-22.2, 23.2, 18.0; HRMS-ESI (m/z): $[M+H]^+$ calcd for $C_{38}H_{44}FN_8O_3S_2$: 745.3118, found 745.3110.

Example 225: 2-[[6-(1,3-Benzothiazol-2-ylamino)-5-methyl-pyridazin-3-yl]-[5-[3-hydroxypropyl(dimethyl)ammonio]pentyl]amino]-5-[3-[4-[3-(dimethylamino)prop-1-ynyl]-2-fluoro-phenoxy]propyl]thiazole-4-carboxylate

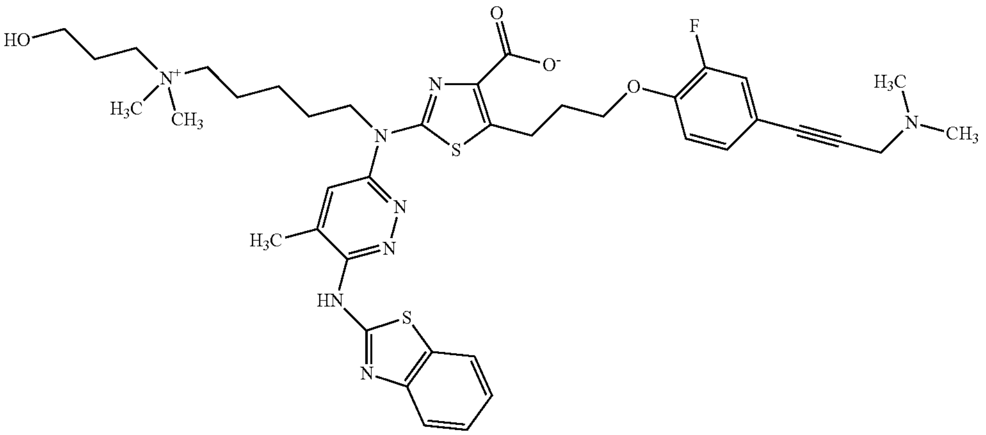 [SMILES: Cc1cc(N(CCCCC[N+](C)(C)CCCO)c2nc(C(=O)[O-])c(CCCOc3ccc(C#CCN(C)C)cc3F)s2)nnc1Nc1nc2ccccc2s1]

Step A: 5-[[5-[3-[4-[3-(dimethylamino)prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]pentyl(3-hydroxypropyl)-dimethyl-ammonium Using Alkylation with in situ generated tosylate General Procedure followed by purification via reverse phase flash column chromatography (C18, 0.1% TFA in water:MeCN) starting from Preparation 5f and 3-(dimethylamino)propan-1-ol as the appropriate amine, the desired product was obtained.

$^1$H NMR (500 MHz, DMSO-$d_6$) δ ppm 10.35 (brs, 1H), 7.84 (dm, 1H), 7.72 (s, 1H), 7.48 (dd, 1H), 7.48 (dm, 1H), 7.46 (m, 1H), 7.35 (dm, 1H), 7.26 (m, 1H), 7.24 (t, 1H), 5.87 (s, 2H), 4.79 (brs, 1H), 4.42 (t, 2H), 4.29 (s, 2H), 4.19 (t, 2H), 3.79 (s, 3H), 3.73 (m, 2H), 3.46 (m, 2H), 3.30 (m, 2H), 3.27 (t, 2H), 3.25 (t, 2H), 3.00 (s, 6H), 2.86 (s, 6H), 2.47 (s, 3H), 2.14 (m, 2H), 1.8 (m, 2H), 1.76 (m, 2H), 1.75 (m, 2H), 1.38 (m, 2H), 0.92 (m, 2H), −0.98 (s, 9H); HRMS-ESI (m/z): $[M]^+$ calcd for $C_{47}H_{66}FN_8O_5S_2Si$: 933.4346, found 933.4342.

Step B: 2-[[6-(1,3-benzothiazol-2-ylamino)-5-methyl-pyridazin-3-yl]-[5-[3-hydroxypropyl(dimethyl)ammonio]pentyl]amino]-5-[3-[4-[3-(dimethylamino)prop-1-ynyl]-2-fluoro-phenoxy]propyl]thiazole-4-carboxylate Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{40}H_{50}FN_8O_4S_2$: 789.3375, found 789.3376.

Example 226: 2-[[6-(1,3-Benzothiazol-2-ylamino)-5-methyl-pyridazin-3-yl]-[5-[2-hydroxyethyl(dimethyl)ammonio]pentyl]amino]-5-[3-[4-[3-(dimethylamino)prop-1-ynyl]-2-fluoro-phenoxy]propyl]thiazole-4-carboxylate

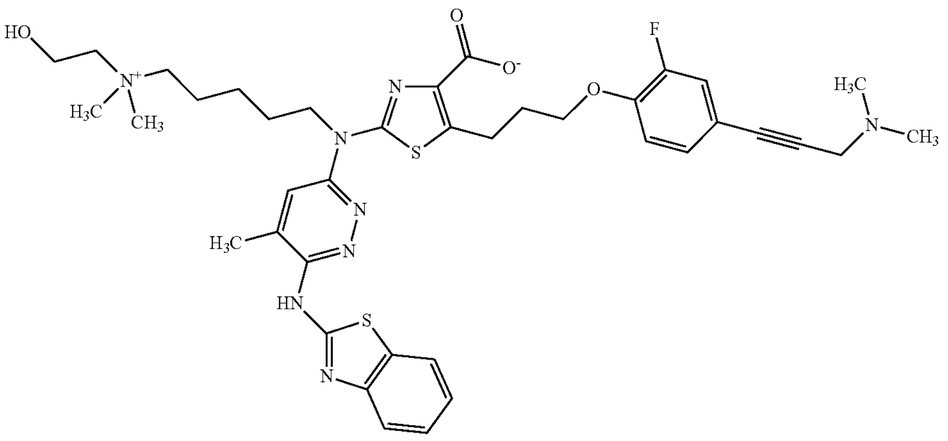 [SMILES: Cc1cc(N(CCCCC[N+](C)(C)CCO)c2nc(C(=O)[O-])c(CCCOc3ccc(C#CCN(C)C)cc3F)s2)nnc1Nc1nc2ccccc2s1]

Step A: 5-[[5-[3-[4-[3-(dimethylamino)prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]pentyl-(2-hydroxyethyl)-dimethyl-ammonium Using Alkylation with in situ generated tosylate General Procedure followed by purification via reverse phase flash column chromatography (C18, 0.1% TFA in water:MeCN) starting from Preparation 5f and 2-(dimethylamino)ethanol as the appropriate amine, the desired product was obtained. $^1$H NMR (500 MHz, DMSO-$d_6$) δ ppm 7.84 (d, 1H), 7.72 (s, 1H), 7.48 (d, 1H), 7.47 (dd, 1H), 7.45 (t, 1H), 7.35 (d, 1H), 7.26 (t, 1H), 7.24 (t, 1H), 5.87 (s, 2H), 5.29 (br., 1H), 4.42 (t, 2H), 4.28 (s, 2H), 4.19 (t, 2H), 3.81 (brt., 2H), 3.79 (s, 3H), 3.73 (t, 2H), 3.36 (m, 2H), 3.31 (m, 2H), 3.27 (t, 2H), 3.05 (s, 6H), 2.86 (s, 6H), 2.47 (s, 3H), 2.14 (m, 2H), 1.76 (m, 2H), 1.76 (m, 2H), 1.37 (m, 2H), 0.92 (t, 2H), −0.10 (s, 9H); $^{13}$C NMR (125 MHz, DMSO-$d_6$) δ ppm 129.6, 127.3, 123.5, 123.2, 119.7, 117.6, 115.5, 112.0, 72.9, 68.6, 66.8, 65.1, 64.4, 55.4, 52.0, 51.2, 46.9, 46.4, 42.2, 31.1, 26.7, 23.2, 23.2, 21.9, 17.9, 17.8, −0.9; HRMS-ESI (m/z): $[M]^+$ calcd for $C_{46}H_{64}FN_8O_5S_2Si$: 919.4189, found 919.4192.

Step B: 2-[[6-(1,3-benzothiazol-2-ylamino)-5-methyl-pyridazin-3-yl]-[5-[2-hydroxyethyl(dimethyl)ammonio]pentyl]amino]-5-[3-[4-[3-(dimethylamino)prop-1-ynyl]-2-fluoro-phenoxy]propyl]thiazole-4-carboxylate Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+2H]^{2+}$ calcd for $C_{39}H_{49}FN_8O_4S_2$: 388.16455, found 388.1639.

Example 227: 2-[[6-(1,3-Benzothiazol-2-ylamino)-5-methyl-pyridazin-3-yl]-[5-[carboxymethyl(dimethyl)ammonio]pentyl]amino]-5-[3-[4-[3-(dimethylamino)prop-1-ynyl]-2-fluoro-phenoxy]propyl]thiazole-4-carboxylate

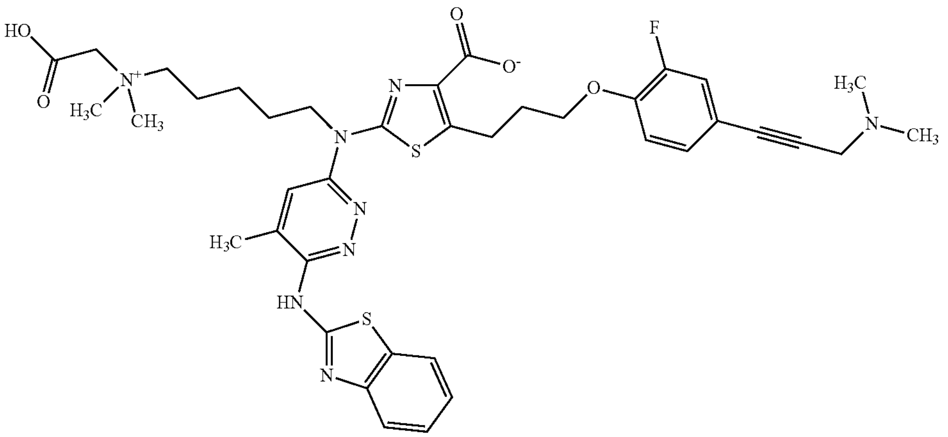 [SMILES: Cc1cc(N(CCCCC[N+](C)(C)CC(=O)O)c2nc(C(=O)[O-])c(CCCOc3ccc(C#CCN(C)C)cc3F)s2)nnc1Nc1nc2ccccc2s1]

Step A: 5-[[5-[3-[4-[3-(dimethylamino)prop-1-ynyl]-2-fluoro-phenoxy]propyl]-4-methoxycarbonyl-thiazol-2yl]-[5-methyl-6-[(Z)-[3-(2-trimethylsilylethoxymethyl)-1,3-benzothiazol-2-ylidene]amino]pyridazin-3-yl]amino]pentyl-(2-ethoxy-2-oxo-ethyl)-dimethyl-ammonium Using Alkylation with in situ generated tosylate General Procedure followed by purification via reverse phase flash column chromatography (C18, 0.1% TFA in water:MeCN) starting from Preparation 5f and ethyl 2-(dimethylamino) acetate as the appropriate amine, the desired product was obtained.

$^1H$ NMR (500 MHz, DMSO-$d_6$) δ ppm 10.33 (brs, 1H), 7.84 (dm, 1H), 7.72 (s, 1H), 7.48 (dd, 1H), 7.48 (dm, 1H), 7.46 (m, 1H), 7.35 (dm, 1H), 7.27 (m, 1H), 7.24 (t, 1H), 5.87 (s, 2H), 4.42 (t, 2H), 4.38 (s, 2H), 4.29 (s, 2H), 4.21 (q, 2H), 4.19 (t, 2H), 3.79 (s, 3H), 3.73 (m, 2H), 3.46 (m, 2H), 3.27 (t, 2H), 3.18 (s, 6H), 2.87 (s, 6H), 2.47 (s, 3H), 2.14 (m, 2H), 1.79 (m, 2H), 1.75 (m, 2H), 1.37 (m, 2H), 1.22 (t, 3H), 0.92 (m, 2H), −0.10 (s, 9H); HRMS-ESI (m/z): $[M]^+$ calcd for $C_{48}H_{66}FN_8O_6S_2Si$: 961.4294, found 961.4293.

Step B: 2-[[6-(1,3-benzothiazol-2-ylamino)-5-methyl-pyridazin-3-yl]-[5-[carboxymethyl(dimethyl)ammonio]pentyl]amino]-5-[3-[4-[3-(dimethylamino)prop-1-ynyl]-2-fluoro-phenoxy]propyl]thiazole-4-carboxylate Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{39}H_{46}FN_8O_5S_2$: 789.3011, found 789.2995.

Example 228: 3-[[5-[[6-(1,3-Benzothiazol-2-ylamino)-5-methyl-pyridazin-3-yl]-[4-carboxy-5-[3-[2-fluoro-4-[(E)-3-oxoprop-1-enyl]phenoxy]propyl]thiazol-2-yl]amino]-2-hydroxy-pentyl]-dimethyl-ammonio]propane-1-sulfonate

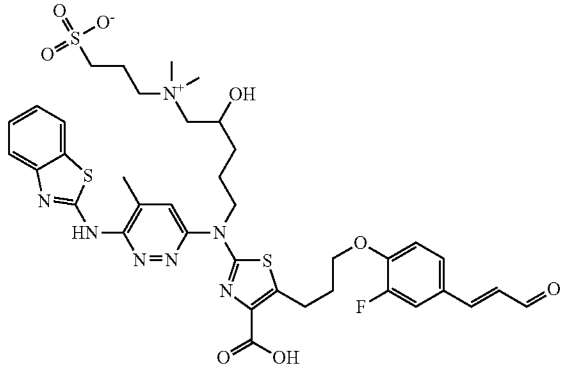 [SMILES: Cc1cc(N(CCCC(O)C[N+](C)(C)CCCS(=O)(=O)[O-])c2nc(C(=O)O)c(CCCOc3ccc(/C=C/C=O)cc3F)s2)nnc1Nc1nc2ccccc2s1]

Example 228 was isolated as side-product from the synthesis of Example-146.

HRMS-ESI (m/z): $[M+H]^+$ calcd for $C_{38}H_{45}FN_7O_8S_3$: 842.2470, found 842.2494.

Example 229: 2-[[6-(1,3-Benzothiazol-2-ylamino)-5-methyl-pyridazin-3-yl]-[5-[2-hydroxyethyl(dimethyl)ammonio]pentyl]amino]-5-[3-[2-fluoro-4-[3-(methylamino)prop-1-ynyl]phenoxy]propyl]thiazole-4-carboxylate

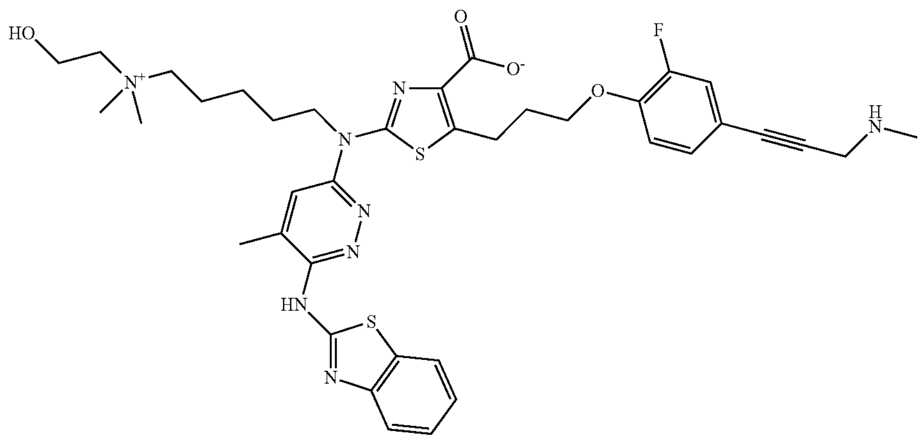 [SMILES: CNCC#Cc1ccc(OCCCc2sc(N(CCCCC[N+](C)(C)CCO)c3cc(C)c(Nc4nc5ccccc5s4)nn3)nc2C(=O)[O-])c(F)c1]

Step A: 5-[[5-[3-[4-[3-[tert-butoxycarbonyl(methyl) amino]prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]pentyl-(2-hydroxyethyl)-dimethyl-ammonium Using Alkylation with in situ generated tosylate General Procedure followed by purification via reverse phase flash column chromatography (C18, 0.1% TFA in water:MeCN) starting from Preparation 5e and 2-(dimethylamino)ethanol as the appropriate amine, the desired product was obtained. $^{1}H$ NMR (500 MHz, DMSO-$d_6$) δ ppm 7.84 (dm, 1H), 7.71 (s, 1H), 7.48 (dm, 1H), 7.45 (m, 1H), 7.33 (dd, 1H), 7.26 (m, 1H), 7.23 (dm, 1H), 7.17 (t, 1H), 5.87 (s, 2H), 5.28 (brs, 1H), 4.42 (t, 2H), 4.20 (brs, 2H), 4.16 (t, 2H), 3.81 (m, 2H), 3.78 (s, 3H), 3.73 (m, 2H), 3.36 (t, 2H), 3.31 (t, 2H), 3.27 (t, 2H), 3.04 (s, 6H), 2.84 (brs, 3H), 2.46 (s, 3H), 2.13 (m, 2H), 1.77 (m, 2H), 1.75 (m, 2H), 1.41 (s, 9H), 1.37 (m, 2H), 0.92 (m, 2H), −0.11 (s, 9H); HRMS-ESI (m/z): $[M]^+$ calcd for $C_{50}H_{70}FN_8O_7S_2Si$: 1005.4557, found 1005.4554.

Step B: 2-[[6-(1,3-benzothiazol-2-ylamino)-5-methyl-pyridazin-3-yl]-[5-[2-hydroxyethyl(dimethyl)ammonio]pentyl]amino]-5-[3-[2-fluoro-4-[3-(methylamino)prop-1-ynyl]phenoxy]propyl]thiazole-4-carboxylate Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{38}H_{46}FN_8O_4S_2$: 761.3062, found 761.3057.

Example 230: 2-[[6-(1,3-Benzothiazol-2-ylamino)-5-methyl-pyridazin-3-yl]-[5-[3-hydroxypropyl(dimethyl)ammonio]pentyl]amino]-5-[3-[2-fluoro-4-[3-(methylamino)prop-1-ynyl]phenoxy]propyl]thiazole-4-carboxylate

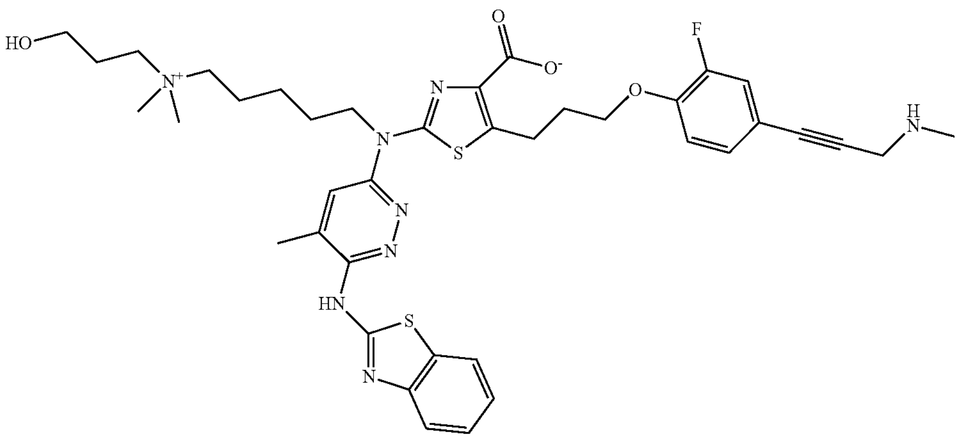 [SMILES: CNCC#Cc1ccc(OCCCc2sc(N(CCCCC[N+](C)(C)CCCO)c3cc(C)c(Nc4nc5ccccc5s4)nn3)nc2C(=O)[O-])c(F)c1]

Step A: 5-[[5-[3-[4-[3-[tert-butoxycarbonyl(methyl)amino]prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]pentyl-(3-hydroxypropyl)-dimethyl-ammonium Using Alkylation with in situ generated tosylate General Procedure followed by purification via reverse phase flash column chromatography (C18, 0.1% TFA in water:MeCN) starting from Preparation 5e and 3-(dimethylamino)propan-1-ol as the appropriate amine, the desired product was obtained.

$^1$H NMR (500 MHz, DMSO-$d_6$) δ ppm 7.84 (dm, 1H), 7.71 (s, 1H), 7.48 (dm, 1H), 7.45 (m, 1H), 7.33 (dd, 1H), 7.26 (m, 1H), 7.23 (dm, 1H), 7.18 (t, 1H), 5.87 (s, 2H), 4.78 (brs, 1H), 4.42 (t, 2H), 4.21 (s, 2H), 4.15 (t, 2H), 3.78 (s, 3H), 3.72 (m, 2H), 3.46 (m, 2H), 3.30 (t, 2H), 3.27 (t, 2H), 3.25 (t, 2H), 2.99 (s, 6H), 2.85 (brs, 3H), 2.47 (s, 3H), 2.12 (m, 2H), 1.80 (m, 2H), 1.76 (m, 2H), 1.76 (m, 2H), 1.41 (s, 9H), 1.38 (m, 2H), 0.92 (m, 2H), −0.11 (s, 9H); HRMS-ESI (m/z): $[M]^+$ calcd for $C_{51}H_{72}FN_8O_7S_2Si$: 1019.4713, found 1019.4713.

Step B: 2-[[6-(1,3-Benzothiazol-2-ylamino)-5-methyl-pyridazin-3-yl]-[5-[3-hydroxypropyl(dimethyl)ammonio]pentyl]amino]-5-[3-[2-fluoro-4-[3-(methylamino)prop-1-ynyl]phenoxy]propyl]thiazole-4-carboxylate Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{39}H_{48}FN_8O_4S_2$: 775.3218, found 775.3213.

Example 231: 2-[[6-(1,3-Benzothiazol-2-ylamino)-5-methyl-pyridazin-3-yl]-[5-[carboxymethyl(dimethyl)ammonio]pentyl]amino]-5-[3-[2-fluoro-4-[3-(methylamino)prop-1-ynyl]phenoxy]propyl]thiazole-4-carboxylate

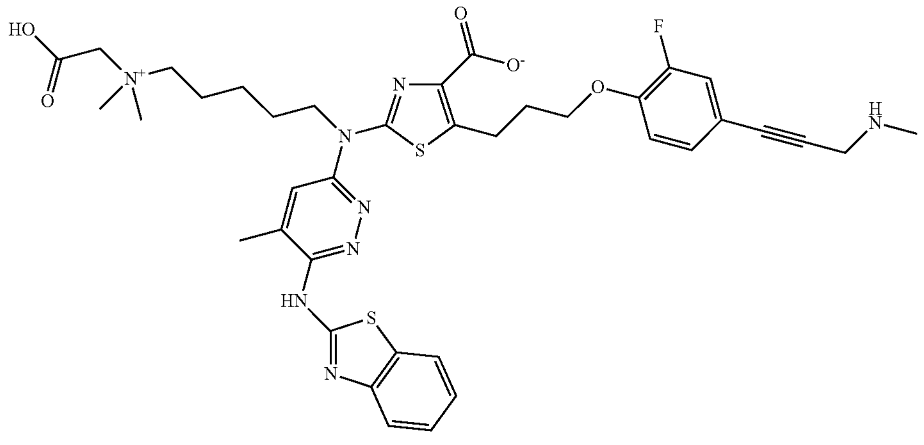 [SMILES: CNCC#Cc1ccc(OCCCc2sc(N(CCCCC[N+](C)(C)CC(=O)O)c3cc(C)c(Nc4nc5ccccc5s4)nn3)nc2C(=O)[O-])c(F)c1]

Step A: 5-[[5-[3-[4-[3-[tert-butoxycarbonyl(methyl) amino]prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]pentyl-(2-ethoxy-2-oxo-ethyl)-dimethyl-ammonium Using Alkylation with in situ generated tosylate General Procedure followed by purification via reverse phase flash column chromatography (C18, 0.1% TFA in water:MeCN) starting from Preparation 5e and ethyl 2-(dimethylamino) acetate as the appropriate amine, the desired product was obtained.

$^1$H NMR (500 MHz, DMSO-d$_6$) δ ppm 7.84 (dm, 1H), 7.71 (g, 1H), 7.48 (dm, 1H), 7.44 (m, 1H), 7.33 (dd, 1H), 7.26 (m, 1H), 7.23 (dm, 1H), 7.17 (t, 1H), 5.87 (s, 2H), 4.42 (t, 2H), 4.37 (s, 2H), 4.21 (q, 2H), 4.21 (brs, 2H), 4.16 (t, 2H), 3.78 (s, 3H), 3.72 (m, 2H), 3.46 (m, 2H), 3.27 (t, 2H), 3.18 (s, 6H), 2.84 (brs, 3H), 2.47 (d, 3H), 2.12 (m, 2H), 1.79 (m, 2H), 1.75 (m, 2H), 1.41 (s, 9H), 1.37 (m, 2H), 1.22 (t, 3H), 0.92 (m, 2H), −0.10 (s, 9H); HRMS-ESI (m/z): [M]$^+$ calcd for $C_{52}H_{72}FN_8O_8S_2Si$: 1047.4662, found 1047.468.

Step B: 2-[[6-(1,3-benzothiazol-2-ylamino)-5-methylpyridazin-3-yl]-[5-[carboxymethyl(dimethyl)ammonio]pentyl]amino]-5-[3-[2-fluoro-4-[3-(methylamino)prop-1-ynyl]phenoxy]propyl]thiazole-4-carboxylate Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): [M+H]$^+$ calcd for $C_{38}H_{44}FN_8O_5S_2$: 775.2855, found 775.2857.

Example 232: 2-[[6-(1,3-Benzothiazol-2-ylamino)-5-methyl-pyridazin-3-yl]-[4-(trimethylammonio) butyl]amino]-5-[3-[2-fluoro-4-[3-(methylamino) prop-1-ynyl]phenoxy]propyl]thiazole-4-carboxylate

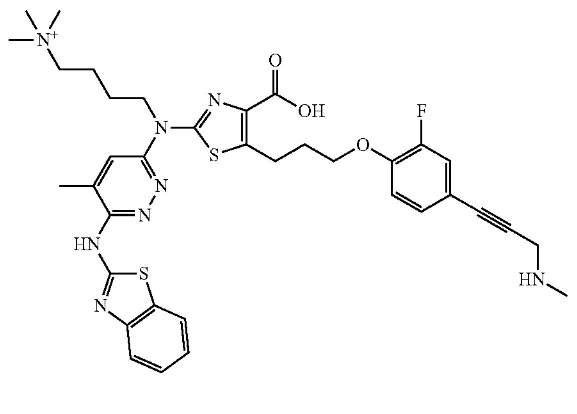

Step A: 4-[[5-[3-[4-[3-[tert-butoxycarbonyl(methyl) amino]prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]butyl-trimethyl-ammonium Using Alkylation with in situ generated tosylate General Procedure starting from Preparation 5c and N,N-dimethylmethanamine as the appropriate amine, the TFA-salt of the desired product was obtained.

$^1$H NMR (500 MHz, DMSO-d$_6$) δ ppm 7.84 (d, 1H), 7.71 (s, 1H), 7.48 (d, 1H), 7.45 (t, 1H), 7.33 (brd, 1H), 7.26 (t, 1H), 7.22 (dm, 1H), 7.17 (t, 1H), 5.87 (s, 2H), 4.40 (t, 2), 4.20 (brs, 2H) 4.15 (t, 2H), 3.79 (s, 3H), 3.73 (t, 2H), 3.46 (t, 2H), 3.27 (t, 2H), 3.06 (s, 9H), 2.84 (brs, 3H), 2.46 (s, 3H), 2.12 (m, 2H), 1.82 (m, 2H), 1.75 (m, 2H), 1.40 (s, 9H), 0.92 (t, 2H), −0.10 (s, 9H); $^{13}$C NMR (125 MHz, DMSO-d$_6$) δ ppm 129.1, 127.2, 123.6, 123.2, 119.3, 117.5, 115.5, 112.1, 72.9, 68.4, 66.7, 65.4, 52.8, 52.1, 46.3, 38.8, 33.8, 31.0, 28.5, 24.4, 23.3, 19.8, 18.0, 17.8, −1.0; HRMS-ESI (m/z): [M]$^+$ calcd for $C_{48}H_{66}FN_8O_6S_2Si$: 961.4294, found 961.4312.

Step B: 2-[[6-(1,3-benzothiazol-2-ylamino)-5-methyl-pyridazin-3-yl]-[4-(trimethylammonio)butyl] amino]-5-[3-[2-fluoro-4-[3-(methylamino)prop-1-ynyl]phenoxy]propyl]thiazole-4-carboxylate Using Deprotection and Hydrolysis General Procedure followed by repurification via reverse phase preparative chromatography (C18, 0.1% TFA in water:MeCN), starting from the product from Step A, the TFA-salt of the desired product was obtained.

HRMS-ESI (m/z): [M]$^+$ calcd for $C_{36}H_{42}FN_8O_3S_2$: 717.2800, found 717.2800.

Example 233: 2-[[6-(1,3-Benzothiazol-2-ylamino)-5-methyl-pyridazin-3-yl]-methyl-amino]-5-[3-[4-[3-(dimethylamino)prop-1-ynyl]phenoxy]propyl]thiazole-4-carboxylic acid

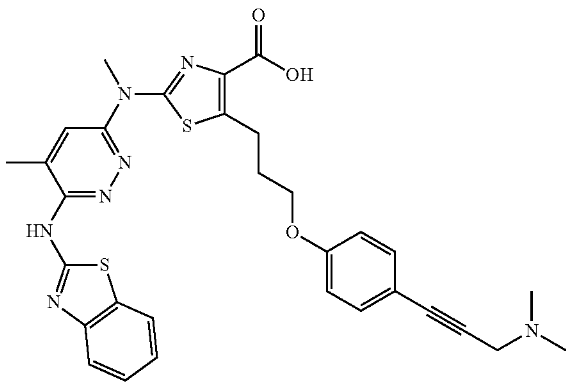

Step A: ethyl 5-[3-[4-[3-(dimethylamino)prop-1-ynyl]phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation of Silyl-Protected Phenols General Procedure starting from 219 mg of Preparation 5g (0.30 mmol, 1 eq.) and 100 mg of Preparation 6j (0.30 mmol, 1 eq.) followed by purification via flash column chromatography using EtOAc and MeOH (containing 1.2% $NH_3$) as eluents to give 37 mg (12%) of the desired product as dark yellow sticky compound.

$^1$H NMR (500 MHz, DMSO-d$_6$) δ ppm 7.83 (dm, 1H), 7.66 (q, 1H), 7.47 (dm, 1H), 7.44 (m, 1H), 7.35 (m, 2H), 7.25 (m, 1H), 6.94 (m, 2H), 5.86 (s, 4.26 (q, 2H), 4.05 (t, 2H), 3.77 (s, 3H), 3.72 (m, 2H), 3.38 (s, 2H), 126 (m, 2H), 2.45 (d, 3H), 2.19 (s, 6H), 2.10 (m, 2H), 1.30 (t, 3H), 0.92 (m, 2H), −0.11 (s, 9H); HRMS-ESI (m/z): $[M+H]^+$ calcd for $C_{39}H_{50}N_7O_4S_2Si$: 772.3129, found 772.3119.

Step B: 2-[[6-(1,3-benzothiazol-2-ylamino)-5-methyl-pyridazin-3-yl]-methyl-amino]-5-[3-[4-[3-(dimethylamino)prop-1-ynyl]phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{31}H_{32}N_7O_3S_2$: 614.2002, found 614.1998.

Example 234: 2-[[6-(1,3-Benzothiazol-2-ylamino)-5-methyl-pyridazin-3-yl]-methyl-amino]-5-[3-[4-[1-[(dimethylamino)methyl]-3-bicyclo[1.1.1]pentanyl]phenoxy]propyl]thiazole-4-carboxylic acid

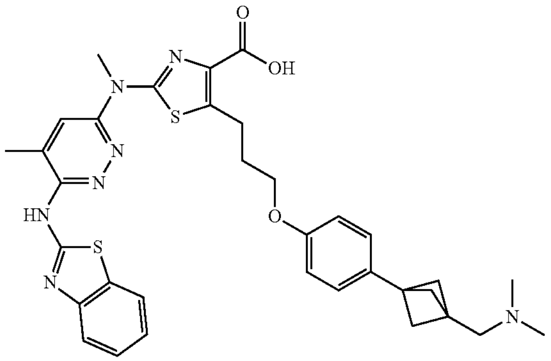

Step A: ethyl 5-[3-[4-[1-[(dimethylamino)methyl]-3-bicyclo[1.1.1]pentanyl]phenoxy]propyl]-2-[methyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Alkylation General Procedure starting from 47 mg of Preparation 6i (0.22 mmol, 1 eq.) and 157 mg of Preparation 5g (0.22 mmol, 1 eq.) followed by purification via flash column chromatography using EtOAc and MeOH (containing 1.2% $NH_3$) as eluents to give 130 mg (74%) of the desired product as yellow solid.

$^1H$ NMR (500 MHz, DMSO-$d_6$) δ ppm 10.62 (brs, 1H), 7.83 (dm, 1H), 7.65 (q, 1H), 7.46 (dm, 1H), 7.43 (m, 1H), 7.25 (m, 1H), 7.11 (m, 2H), 6.89 (m, 2H), 5.85 (s, 2H), 4.26 (q, 2H), 4.01 (t, 2H), 3.76 (s, 3H), 3.72 (m, 2H), 3.24 (s, 2H), 3.24 (t, 2H), 2.74 (s, 6H), 2.44 (d, 3H), 2.08 (m, 2H), 2.07 (s, 6H), 1.29 (t, 3H), 0.91 (m, 2H), −0.12 (s, 9H); HRMS-ESI (m/z): $[M+H]^+$ calcd for $C_{42}H_{56}N_7O_4S_2Si$: 814.3599, found 814.3592.

Step B: 2-[[6-(1,3-benzothiazol-2-ylamino)-5-methyl-pyridazin-3-yl]-methyl-amino]-5-[3-[4-[1-[(dimethylamino)methyl]-3-bicyclo[1.1.1]pentanyl]phenoxy]propyl]thiazole-4-carboxylic acid Using Deprotection and Hydrolysis General Procedure followed by repurification via reverse phase preparative chromatography (C18, 0.1% TFA in water:MeCN) starting from the product from Step A, the TFA-salt of the desired product was obtained.

HRMS-ESI (m/z): $[M+H]^+$ calcd for $C_{34}H_{38}N_7O_3S_2$: 656.2472, found 656.2467.

Example 235: 3-[3-[[6-(1,3-Benzothiazol-2-ylamino)-5-methyl-pyridazin-3-yl]-[4-carboxy-5-[3-[2-fluoro-4-[3-(methylamino)prop-1-ynyl]phenoxy]propyl]thiazol-2-yl]amino]propyl-dimethyl-ammonio]propane-1-sulfonate

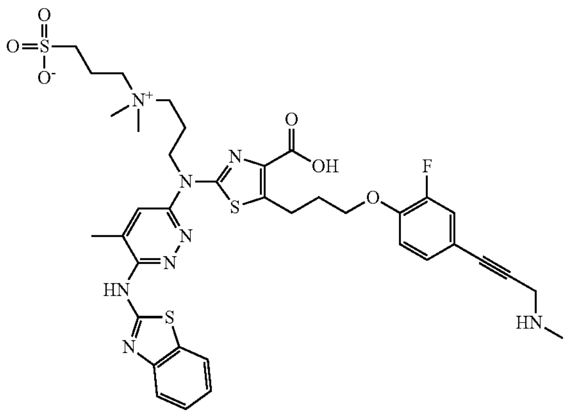 [SMILES: CNCC#Cc1ccc(OCCCc2sc(N(CCC[N+](C)(C)CCCS(=O)(=O)[O-])c3cc(C)c(Nc4nc5ccccc5s4)nn3)nc2C(=O)O)c(F)c1]

Using Alkylation, Deprotection and Hydrolysis General procedure starting from Example 200, Step C and oxathiolane 2,2-dioxide. After alkylation, the sulfonated intermediate was isolated (HRMS-ESI (m/z): $[M+H]^+$ calcd for $C_{49}H_{68}FN_8O_9S_3Si$: 1055.4025, found 1055.4028) then reacted with HFxPyridine (HRMS-ESI (m/z): $[M+H]^+$ calcd for $C_{38}H_{45}FN_8O_6S_3$: 825.2686, found 825.2675) and finally hydrolysed with $LiOH{\times}H_2O$. After purification it resulted in the TFA-salt of the desired product.

HRMS-ESI (m/z): $[M+H]^+$ calcd for $C_{37}H_{44}FN_8O_6S_3$: 811.2530, found 811.2525.

Example 236: 2-({6-[(1,3-Benzothiazol-2-yl)amino]-5-methylpyridazin-3-yl}(methyl)amino)-5-[3-(2-fluoro-4-{3-[methyl({4-[3-(trifluoromethyl)-3H-diazirin-3-yl]phenyl}methyl)amino]prop-1-yn-1-yl}phenoxy)propyl]-1,3-thiazole-4-carboxylic acid

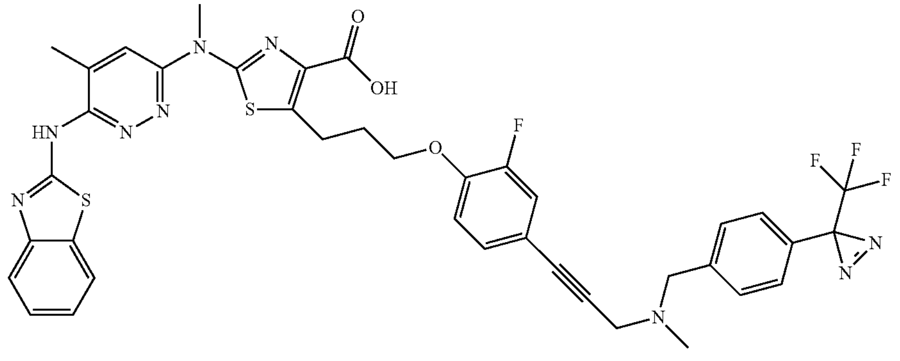 [SMILES: Cc1cc(N(C)c2nc(C(=O)O)c(CCCOc3ccc(C#CCN(C)Cc4ccc(C5(C(F)(F)F)N=N5)cc4)cc3F)s2)nnc1Nc1nc2ccccc2s1]

Step A: ethyl 5-[3-(2-fluoro-4-{3-[methyl({4-[3-(trifluoromethyl)-3H-diazirin-3-yl]phenyl}methyl)amino]prop-1-yn-1-yl}phenoxy)propyl]-2-[methyl(5-methyl-6-{[(2Z)-3-{[2-(trimethylsilyl)ethoxy]methyl}-2,3-dihydro-1,3-benzothiazol-2-ylidene]amino}pyridazin-3-yl)amino]-1,3-thiazole-4-carboxylate To a solution of the product from Preparation 5j (20 mg, 25.8 µmol, 1 eq) in dry dimethylformamide (1 mL) was added potassium carbonate (3.9 mg, 28.4 µmol, 1.1 eq) followed by 3-[4-(bromomethyl)phenyl]-3-(trifluoromethyl)diazirine (7.9 mg, 28.4 µmol, 1.1 eq) and the mixture was stirred for 16 h at ambient temperature. The reaction was diluted with 5% aqueous ammonium hydroxide (10 mL), extracted with ethyl acetate (2×10 mL), and the combined organic extracts were successively washed with 5% aqueous ammonium hydroxifluorade (10 mL) and brine (10 mL), dried (magnesium sulfate), and concentrated in vacuo. Purification by automated flash column chromatography (CombiFlash Rf, 4 g RediSep™ silica cartridge) eluting with a gradient of 0-50% ethyl acetate in iso-heptane afforded the desired product as a white solid (27.4 mg) that was used directly in the next step without further characterisation.

Step B: ethyl 2-({6-[(1,3-benzothiazol-2-yl)amino]-5-methylpyridazin-3-yl}(methyl)amino)-5-[3-(2-fluoro-4-{3-[methyl({4-[3-(trifluoromethyl)-3H-diazirin-3-yl]phenyl}methyl)amino]prop-1-yn-1-yl}phenoxy)propyl]-1,3-thiazole-4-carboxylate To a solution of the product from Step A (27.4 mg, 28 µmol, 1 eq) in acetonitrile (1 mL) was added pyridinium poly(hydrogen fluoride)(101 µL, 0.78 mmol, 28 eq) and the mixture was heated at 60° C. for 20 h. The reaction was diluted with 5% aqueous ammonium hydroxide (10 mL), extracted with ethyl acetate (2×10 mL), and the combined organic extracts were dried (magnesium sulfate) and concentrated in vacuo. Purification by reverse phase automated flash chromatography (CombiFlash Rf, C18 5.5 g RediSep aq Gold column) eluting with a gradient of 5-95% acetonitrile in water afforded the desired product as a yellow solid (6.7 mg, 0.01 mmol, 28%).

LC/MS ($C_{41}H_{37}F_4N_9O_3S_2$) 844 $[M+H]^+$; RT 1.64 (LCMS-V-B1)

Step C: 2-({6-[(1,3-benzothiazol-2-yl)amino]-5-methylpyridazin-3-yl}(methyl)amino)-5-[3-(2-fluoro-4-{3-[methyl({4-[3-(trifluoromethyl)-3H-diazirin-3-yl]phenyl}methyl)amino]prop-1-yn-1-yl}phenoxy)propyl]-1,3-thiazole-4-carboxylic acid To a solution of the product from Step B (6.7 mg, 0.01 mmol, 1 eq) in 1:1 tetrahydrofuran/methanol (0.5 mL) was added 2M aqueous sodium hydroxide (79.4 µL, 0.16 mmol, 20 eq) and the mixture was stirred at ambient temperature for 4 h then concentrated in vacuo. The residue was diluted with water (0.2 mL) and adjusted to pH 5 with 2M aqueous hydrochloric acid. Purification by reverse phase automated flash chromatography (CombiFlash Rf, C18 5.5 g RediSep aq Gold column) eluting with a gradient of 5-95% acetonitrile in water afforded the desired product as an orange brown solid (3.5 mg, 4.29 µmol, 54%).

LC/MS ($C_{39}H_{33}F_4N_9O_3S_2$) 816 $[M+H]^+$; RT 1.53 (LCMS-V-B1)

Example 237: 2-[[6-(1,3-Benzothiazol-2-ylamino)-5-methyl-pyridazin-3-yl]-(3-phosphonopropyl)amino]-5-[3-[2-fluoro-4-[3-(methylamino)prop-1-ynyl]phenoxy]propyl]thiazole-4-carboxylic acid

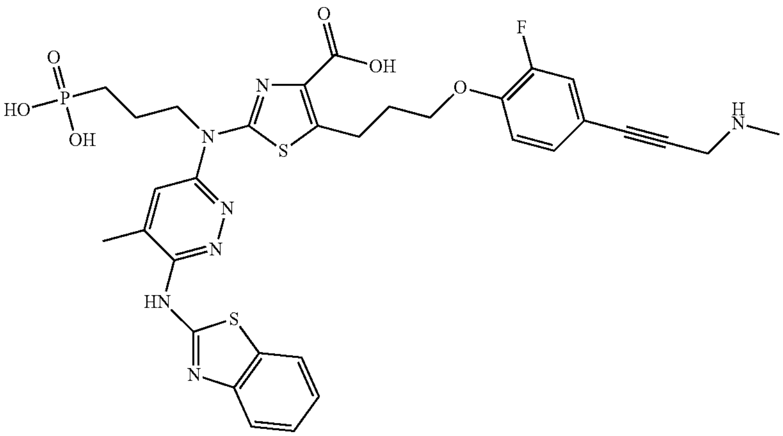 [SMILES: CNCC#Cc1ccc(OCCCc2sc(N(CCCP(=O)(O)O)c3cc(C)c(Nc4nc5ccccc5s4)nn3)nc2C(=O)O)c(F)c1]

Step A: methyl 2-[tert-butoxycarbonyl(3-diethoxyphosphorylpropyl)amino]-5-[3-[4-[3-[tert-butoxycarbonyl(methyl)amino]prop-1-ynyl]-2-fluoro-phenoxy]propyl]thiazole-4-carboxylate Using Alkylation General Procedure starting from 500 mg Preparation 1b (0.87 mmol, 1 eq.) and 336 mg of 1-bromo-3-diethoxyphosphoryl-propane (1.30 mmol, 1.5 eq.) as the appropriate halide, 517 mg (79%) of the desired product was obtained.

$^1$H NMR (500 MHz, DMSO-$d_6$) δ ppm 7.30 (dd, 1H), 7.21 (dm, 1H), 7.13 (t, 1H), 4.23 (brs, 2H), 4.10 (t, 2H), 4.04 (t, 2H), 4.03-3.90 (m, 4H), 3.75 (s, 3H), 3.22 (t, 2H), 2.86 (brs, 3H), 2.08 (m, 2H), 1.83 (m, 2H), 1.73 (m, 2H), 1.51/1.41 (s, 18H), 1.2 (t, 6H); HRMS-ESI (m/z): $[M+H]^+$ calcd for $C_{35}H_{52}FN_3O_{10}PS$; 756.3090, found 756.3095.

Step B: methyl 5-[3-[4-[3-[tert-butoxycarbonyl(methyl)amino]prop-1-ynyl]-2-fluoro-phenoxy]propyl]-2-(3-diethoxyphosphorylpropylamino)thiazole-4-carboxylate Using Deprotection with HFIP General Procedure starting from 512 mg of the product from Step A (0.68 mmol, 1 eq.), 210 mg (47%) of the desired product was obtained.

$^1$H NMR (500 MHz, DMSO-$d_6$) δ ppm 7.64 (brt, 1H), 7.31 (brd, 1H), 7.21 (dm, 1H), 7.13 (t, 1H), 4.23 (brs, 2H), 4.07 (t, 2H), 3.97 (m, 4H), 3.69 (s, 3H), 3.23 (m, 2H), 3.12 (t, 2H), 2.86 (brs, 3H), 2.00 (m, 2H), 1.84-1.63 (m, 4H), 1.41 (s, 3H), 1.21 (t, 6H); $^{13}$C NMR (125 MHz, DMSO-$d_6$) δ ppm 129.1, 119.3, 115.4, 68.0, 61.4, 51.8, 44.7, 38.6, 33.8, 30.6, 28.5, 23.3, 16.7; HRMS-ESI (m/z): $[M+H]^+$ calcd for $C_{30}H_{44}FN_3O_8PS$; 656.2565, found 656.2555.

Step C: methyl 5-[3-[4-[3-[tert-butoxycarbonyl(methyl)amino]prop-1-ynyl]-2-fluoro-phenoxy]propyl]-2-[3-diethoxyphosphorylpropyl-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from 450 mg of the product from Step B (0.69 mmol, 1 eq.) and 363 mg of Preparation 4a (0.89 mmol, 1.3 eq.) as the appropriate halide, 540 mg (77%) of the desired product was obtained.

HRMS-ESI (m/z): $[M+H]^+$ calcd for $C_{48}H_{66}FN_7O_9PS_2Si$: 1026.3849, found 1026.3849.

Step D: 2-[[6-(1,3-benzothiazol-2-ylamino)-5-methyl-pyridazin-3-yl]-(3-phosphonopropyl)amino]-5-[3-[2-fluoro-4-[3-(methylamino)prop-1-ynyl]phenoxy]propyl]thiazole-4-carboxylic acid Using Deprotection and hydrolysis of phosphoric acid derivatives General Procedure followed by repurification via reverse phase preparative chromatography (C18, 0.1% TFA in water:MeCN) starting from the product from Step C, the TFA-salt of the desired product was obtained.

HRMS-ESI (m/z): $[M+H]^+$ calcd for $C_{32}H_{34}FN_7O_6PS_2$: 726.1728, found 726.1707.

Example 238: 2-({6-[(1,3-Benzothiazol-2-yl)amino]-5-methylpyridazin-3-yl}(3-carboxypropyl)amino)-5-(3-{4-[3-(dimethylamino)prop-1-yn-1-yl]-2-fluorophenoxy}propyl)-1,3-thiazole-4-carboxylic acid

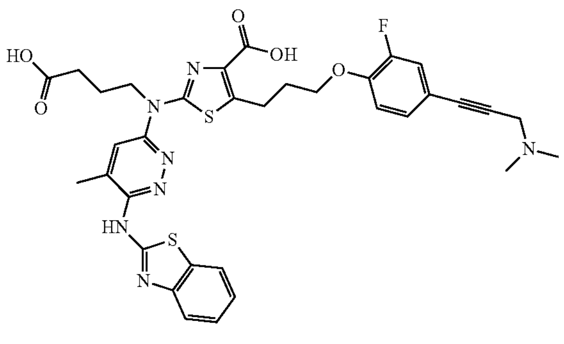 [SMILES: Cc1cc(N(CCCC(=O)O)c2nc(C(=O)O)c(CCCOc3ccc(C#CCN(C)C)cc3F)s2)nnc1Nc1nc2ccccc2s1]

Step A: methyl 2-[tert-butoxycarbonyl-(4-ethoxy-4-oxo-butyl)amino]-5-[3-[4-[3-(dimethylamino)prop-1-ynyl]-2-fluoro-phenoxy]propyl]thiazole-4-carboxylate Using Alkylation General Procedure starting from Preparation 1c and ethyl 4-bromobutanoate, 0.48 g (77%) of the desired product was obtained.

$^1$H NMR (500 MHz, DMSO-$d_6$) δ ppm 7.28 (dd, 1H), 7.20 (dm, 1H), 7.12 (t, 1H), 4.10 (t, 2H), 4.04 (t, 2H), 4.00 (q, 2H), 3.75 (s, 3H), 3.41 (s, 2H), 3.22 (t, 2H), 2.31 (t, 2H), 2.22 (s, 6H), 2.08 (m, 2H), 1.91 (m, 2H), 1.50 (s, 9H), 1.13 (t, 3H); $^{13}$C NMR (125 MHz, DMSO-$d_6$) δ ppm 128.9, 119.2, 115.4, 68.1, 60.3, 52.1, 48.2, 46.0, 44.3, 31.2, 30.5, 28.0, 23.2, 23.2, 14.5; HRMS-ESI (m/z): $[M+H]^+$ calcd for $C_{30}H_{41}FN_3O_7S$: 606.2649, found 606.2640.

Step B: methyl 5-[3-[4-[3-(dimethylamino)prop-1-ynyl]-2-fluoro-phenoxy]propyl]-2-[4-ethoxy-4-oxo-butyl)amino]thiazole-4-carboxylate Using Deprotection with HFIP General Procedure starting from the product from Step A, 0.32 g (83%) of the desired product was produced.

$^1$H NMR (400 MHz, DMSO-$d_6$) δ ppm 7.61 (t, 1H), 7.30 (dd, 1H), 7.20 (dm, 1H), 7.12 (t, 1H), 4.07 (t, 2H), 4.04 (q, 2H), 3.69 (s, 3H), 3.42 (s, 2H), 3.12 (t, 2H), 3.118 (q, 2H), 2.35 (t, 2H), 2.23 (s, 6H), 2.00 (m, 2H), 1.76 (m, 2H), 1.17 (t, 3H); $^{13}$C NMR (100 MHz, DMSO-$d_6$) δ ppm 173.1, 164.6, 163, 128.9, 119.2, 115.4, 68.0, 60.3, 51.7, 48.2, 44.3, 43.7, 31.3, 30.6, 24.5, 23.3, 14.6; HRMS-ESI (m/z): $[M+H]^+$ calcd for $C_{25}H_{33}FN_3O_5S$: 506.2125, found 506.2114.

Step C: methyl 5-[3-[4-[3-(dimethylamino)prop-1-ynyl]-2-fluoro-phenoxy]propyl]-2-[(4-ethoxy-4-oxo-butyl)-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B, and Preparation 4a, 0.26 g (48%) of the desired product was produced.

$^1$H NMR (500 MHz, DMSO-$d_6$) δ ppm 7.84 (d, 1H), 7.73 (s, 1H), 7.47 (dd, 1H), 7.44 (td, 1H), 7.30 (dd, 1H), 7.25 (td, 1H), 7.21 (dd, 1H), 7.15 (t, 1H), 5.86 (s, 2H), 4.38 (br., 2H), 4.14 (t, 2H), 4.02 (q, 2H), 3.78 (S, 3H), 3.72 (t, 2H), 3.38 (s, 2H), 3.26 (t, 2H), 2.46 (s, 3H), 2.44 (m, 2H), 2.19 (s, 6H), 2.13 (m, 2H), 1.9.7 (m, 2H), 1.14 (t, 3H), 0.92 (t, 2H), −0.11 (s, 9H); HRMS-ESI (m/z): $[M+H]^+$ calcd for $C_{42}H_{53}FN_7O_6S_2Si$: 876.3409, found 876.3403; HRMS-ESI (m/z): $[M+H]^+$ calcd for $C_{42}H_{53}FN_7O_6S_2Si$ (double Me-ester): 862.3252, found 862.3237.

Step D: 2-({6-[(1,3-Benzothiazol-2-yl)amino]-5-methylpyridazin-3-yl}(3-carboxypropyl)amino)-5-(3-{4-[3-(dimethylamino)prop-1-yn-1-yl]-2-fluorophenoxy}propyl)-1,3-thiazole-4-carboxylic acid Using Deprotection and Hydrolysis General Procedure followed by repurification via reverse phase preparative chromatography (C18, 0.1% TFA in water:MeCN) starting from the product from Step C, TFA-salt of the desired product was obtained.

HRMS-ESI (m/z): $[M+H]^+$ calcd for $C_{34}H_{35}FN_7O_5S_2$: 704.2125, found 704.2116.

Example 239: 2-({6-[(1,3-Benzothiazol-2-yl)amino]-5-methylpyridazin-3-yl}(3-phosphonopropyl)amino)-5-(3-{4-[3-(dimethylamino)prop-1-yn-1-yl]-2-fluorophenoxy}propyl)-1,3-thiazole-4-carboxylic acid

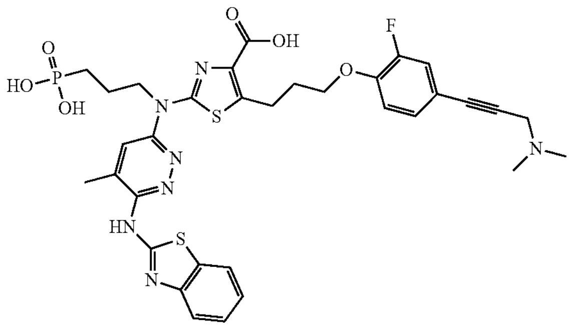 [SMILES: Cc1cc(N(CCCP(=O)(O)O)c2nc(C(=O)O)c(CCCOc3ccc(C#CCN(C)C)cc3F)s2)nnc1Nc1nc2ccccc2s1]

Step A: methyl 2-[tert-butoxycarbonyl(3-diethoxyphosphorylpropyl)amino]-5-[3-[4-[3-(dimethylamino)prop-1-ynyl]-2-fluoro-phenoxy]propyl]thiazole-4-carboxylate Using Alkylation General Procedure starting from Preparation 1c and 1-bromo-3-diethoxyphosphoryl-propane as the appropriate halide, 0.52 g (77%) of the desired product was obtained.

$^1$H NMR (500 MHz, DMSO-$d_6$) δ ppm 7.29 (dd, 1H), 7.20 (dm, 1H), 7.12 (t, 1H), 4.10 (t, 2H), 4.04 (t, 2H), 3.97 (m, 4H), 3.75 (s, 3H), 3.43 (s, 2H), 3.22 (t, 2H), 2.23 (s, 6H), 2.08 (m, 2H), 1.83 (m, 2H), 1.73 (m, 2H), 1.51 (s, 9H), 1.21 (t, 6H); $^{13}$C NMR (125 MHz, DMSO-$d_6$) δ ppm 156.5/153.0, 128.9, 119.2, 115.4, 68.1, 61.4, 52.1, 48.1, 46.9, 44.2, 30.5, 28.1, 23.2, 22.5, 21.3, 16.7; HRMS-ESI (m/z): $[M+H]^+$ calcd for $C_{31}H_{46}FN_3O_8PS$: 670.2727, found 670.2716.

Step B: methyl 2-(3-diethoxyphosphorylpropylamino)-5-[3-[4-[3-(dimethylamino)prop-1-ynyl]-2-fluoro-phenoxy]propyl]thiazole-4-carboxylate Using Deprotection with HFIP General Procedure starting from the product from Step A, 0.37 g (86%) of the desired product was obtained.

$^1$H NMR (500 MHz, DMSO-$d_6$) δ ppm 7.64 (t, 1H), 7.30 (dd, 1H), 7.21 (dm, 1H), 7.12 (t, 1H), 4.07 (t, 2H), 3.99/3.95 (m+m, 4H), 3.69 (s, 3H), 3.43 (s, 2H), 3.23 (m, 2H), 3.12 (t, 2H), 2.23 (s, 6H), 2.00 (m, 2H), 1.84-1.64 (m, 4H), 1.21 (t, 6H); HRMS-ESI (m/z): $[M+H]^+$ calcd for $C_{26}H_{38}FN_3O_6PS$: 570.2203, found 570.2183.

Step C: methyl 2-[3-diethoxyphosphorylpropyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Buchwald General Procedure II starting from the product from Step B and Preparation 4a as the appropriate halide, 0.51 g (87%) of the desired product was obtained.

$^1$H NMR (500 MHz, DMSO-$d_6$) δ ppm 7.84 (d, 1H), 7.76 (s, 1H), 7.47 (dd, 1H), 7.44 (td, 1H), 7.30 (dd, 1H), 7.25 (td, 1H), 7.21 (dd, 1H), 7.15 (t, 1H), 5.86 (s, 2H), 4.40 (brt., 2H), 4.14 (t, 2H), 3.99 (m, 4H), 3.77 (s, 3H), 3.72 (t, 2H), 3.38 (br., 2H), 3.27 (t, 2H), 2.46 (s, 3H), 2.19 (s, 6H), 2.13 (m, 2H), 1.90 (m, 2H), 1.89 (m, 2H), 1.20 (t, 6H), 0.92 (t, 2H), −0.11 (s, 9H); $^{13}$C NMR (125 MHz, DMSO-$d_6$) δ ppm 163.1, 128.9, 127.2, 123.5, 123.2, 119.2, 117.4, 115.5, 112.0, 72.9, 68.5, 66.7, 61.5, 52.0, 48.1, 48.1, 44.2, 30.9, 23.1, 22.1, 20.5, 17.8, 17.8, 16.7, 1.0; HRMS-ESI (m/z): $[M+H]^+$ calcd for $C_{44}H_{60}FN_7O_7PS_2Si$: 940.3487, found 940.3471.

Step D: 2-({6-[(1,3-Benzothiazol-2-yl)amino]-5-methylpyridazin-3-yl}(3-phosphonopropyl)amino)-5-(3-{4-[3-(dimethylamino)prop-1-yn-1-yl]-2-fluorophenoxy}propyl)-1,3-thiazole-4-carboxylic acid Using Deprotection and hydrolysis of phosphonic acid derivatives General Procedure followed by repurification via reverse phase preparative chromatography (C18, 0.1% TFA in water:MeCN) starting from the product from Step C, TFA-salt of the desired product was obtained.

HRMS-ESI (m/z): $[M+H]^+$ calcd for $C_{33}H_{36}FN_7O_6PS_2$: 740.1890, found 740.1871.

Example 240: 2-({6-[(1,3-Benzothiazol-2-yl)amino]-5-methylpyridazin-3-yl}(3-sulfopropyl)amino)-5-(3-{4-[3-(dimethylamino)prop-1-yn-1-yl]-2-fluorophenoxy}propyl)-1,3-thiazole-4-carboxylic acid

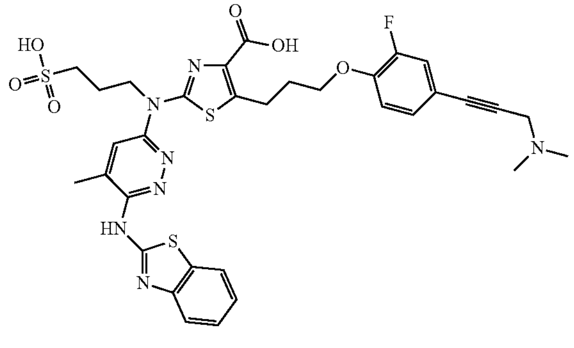 [SMILES: Cc1cc(N(CCCS(=O)(=O)O)c2nc(C(=O)O)c(CCCOc3ccc(C#CCN(C)C)cc3F)s2)nnc1Nc1nc2ccccc2s1]

Step A: 3-[tert-butoxycarbonyl-[5-[3-[4-[3-(dimethylamino)prop-1-ynyl]-2-fluoro-phenoxy]propyl]-4-methoxycarbonyl-thiazol-2-yl]amino]propane-1-sulfonic acid Using Alkylation General Procedure starting from Preparation 1c and sodium 3-bromopropane-1-sulfonate as the appropriate halide, 0.50 g (77%) of the desired product was obtained.

$^1$H NMR (500 MHz, DMSO-$d_6$) δ ppm 733 (dd, 1H), 7.23 (dm, 1H), 7.15 (t, 1H), 4.10 (t, 2H), 4.04 (t, 2H), 3.76 (s, 3H), 3.62 (s, 2H), 3.23 (t, 2H), 2.37 (s, 6H), 2.36 (m, 2H), 2.09 (m, 2H), 1.92 (m, 2H), 1.51 (s, 9H); $^{13}$C NMR (125 MHz, DMSO-$d_6$) δ ppm 129.1, 119.3, 115.4, 68.1, 52.0, 49.6, 47.9, 46.1, 43.8, 30.4, 28.1, 24.7, 23.1; HRMS-ESI (m/z): $[M+H]^+$ calcd for $C_{27}H_{37}FN_3O_8S_2$: 614.2006, found 614.1993.

Step B: 3-[[5-[3-[4-[3-(dimethylamino)prop-1-ynyl]-2-fluoro-phenoxy]propyl]-4-methoxycarbonyl-thiazol-2-yl]amino]propane-1-sulfonic acid Using Deprotection with HFIP General Procedure starting from the product from Step A, 0.26 g (63%) or the desired product was obtained.

$^1$H NMR (500 MHz, DMSO-$d_6$) δ ppm 7.61 (t, 1H), 7.33 (dd, 1H), 7.24 (dd, 1H), 7.14 (t, 1H), 4.07 (t, 2H), 3.69 (s, 3H), 3.65 (s, 2H), 3.21 (q, 2H) 3.12 (t, 2H), 2.46 (t, 2H), 2.39 (s, 6H), 2.00 (qn, 2H), 1.80 (qn, 2H); $^{13}$C NMR (125 MHz, DMSO-$d_6$) δ ppm 164.7, 163.0, 151.5, 147.6, 136.9, 136.2, 129.1, 119.3, 115.5, 114.8, 85.2, 83.4, 68.1, 51.7, 49.6, 47.9, 44.1, 43.8, 30.6, 25.5, 23.3; HRMS-ESI (m/z): $[M+Na]^+$ calcd for $C_{22}H_{28}FN_3NaO_6S_2$: 536.1301, found 536.1293.

Step C: 3-[[5-[3-[4-[3-(dimethylamino)prop-1ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]propane-1-sulfonic acid Using Buchwald General Procedure II starting from the product from Step B and Preparation 4a as the appropriate halide, 0.27 g (66%) of the desired product was obtained.

$^1$H NMR (500 MHz, DMSO-$d_6$) δ ppm 7.95 (s, 1H), 7.84 (d, 1H), 7.46 (d, 1H), 7.43 (t, 1H), 7.40 (dd, 1H), 7.28 (d, 1H), 7.25 (t, 1H), 7.19 (t, 1H), 5.86 (s, 2H), 4.48 (t, 2H), 4.16 (t, 2H), 3.90 (br., 2H), 3.78 (s, 3H), 3.72 (t, 2H), 3.27 (t, 2H), 2.57 (br., 6H), 2.53 (t, 2H), 2.45 (s, 3H), 2.14 (m, 2H), 2.00 (m, 2H), 0.92 (t, 2H), −0.11 (s, 9H); $^{13}$C NMR (125 MHz, DMSO-$d_6$) δ ppm 163.2, 156.1, 134.9, 129.4, 127.2, 123.4, 123.2, 119.4, 117.8, 115.5, 111.9, 72.9, 68.5, 66.7, 52.0, 48.7, 47.3, 46.2, 42.9, 30.9, 23.6, 23.1, 17.9, 17.9, −0.9; HRMS-ESI (m/z): $[M+H]^+$ calcd for $C_{40}H_{51}FN_7O_7S_3Si$: 884.2765, found 884.2757.

Step D: 2-({6-[(1,3-Benzothiazol-2-yl)amino]-5-methylpyridazin-3-yl}(3-sulfopropyl)amino)-5-(3-{4-[3-(dimethylamino)prop-1-yn-1-yl]-2-fluorophenoxy}propyl)-1,3-thiazole-4-carboxylic acid Using Deprotection and Hydrolysis General Procedure Followed by repurification via reverse phase preparative chromatography (C18, 0.1% TFA in water:MeCN) starting from the product from Step C, TFA-salt of the desired product was obtained.

HRMS-ESI (m/z): $[M+H]^+$ calcd for $C_{33}H_{35}FN_7O_6S_3$: 740.1795, found 740.1786.

Example 241: 2-({6-[(1,3-Benzothiazol-2-yl)amino]-5-methylpyridazin-3-yl}(4-sulfobutyl)amino)-5-(3-{4-[3-(dimethylamino)prop-1-yn-1-yl]-2-fluorophenoxy}propyl)-1,3-thiazole-4-carboxylic acid

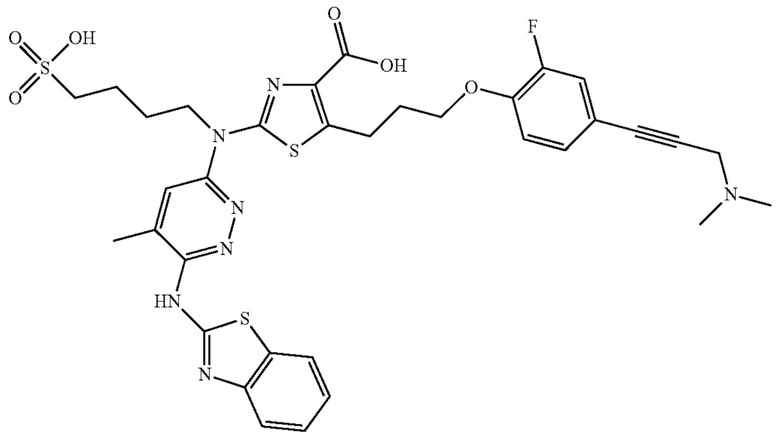 [SMILES: Cc1cc(N(CCCCS(=O)(=O)O)c2nc(C(=O)O)c(CCCOc3ccc(C#CCN(C)C)cc3F)s2)nnc1Nc1nc2ccccc2s1]

Step A: 4-[tert-butoxycarbonyl-[5-[3-[4-[3-(dimethylamino)prop-1-ynyl]-2-fluoro-phenoxy]propyl]-4-methoxycarbonyl-thiazol-2-yl]amino]butane-1-sulfonic acid Using Alkylation General Procedure starting from oxathiane 2,2-dioxide and Preparation 1c, 0.29 g of the desired product was produced.

$^{1}H$ NMR (500 MHz, DMSO-$d_6$) δ ppm 7.34 (dd, 1H), 7.24 (dd, 1H), 7.14 (t, 1H), 4.10 (t, 2H), 3.98 (t, 2H), 3.75 (s, 3H), 3.74 (s, 2H), 3.22 (t, 2H), 2.46 (s, 6H), 2.42 (t, 2H), 2.09 (qn, 2H), 1.65 (qn, 2H), 1.56 (qn, 2H), 1.51 (s, 9H); $^{13}C$ NMR (125 MHz, DMSO-$d_6$) δ ppm 129.1, 119.3, 115.5, 68.2, 52.0, 51.7, 47.7, 46.4, 43.5, 30.4, 28.2, 27.4, 23.2, 22.9; HRMS-ESI (m/z): $[M+Na]^+$ calcd for $C_{28}H_{38}FN_3NaO_8S_2$: 650.1982, found 650.1974.

Step B: 4-[[5-[3-[4-[3-(dimethylamino)prop-1-ynyl]-2-fluoro-phenoxy]propyl]-4-methoxycarbonyl-thiazol-2-yl]amino]butane-1-sulfonic acid Using Deprotection with HFIP General Procedure starting from the product from Step A, 0.12 g of the desired product was produced.

HRMS-ESI (m/z): $[M+H]^+$ calcd for $C_{23}H_{31}FN_3O_6S_2$: 528.1638, found: 528.1632.

Step C: 4-[[5-[3-[4-[3-(dimethylamino)prop-1-ynyl]-2-fluoro-phenoxy]propyl]-4-methoxycarbonyl-thiazol-2-yl]-[5-methyl-6-[(Z)-[3-(2-trimethylsilylethoxymethyl)-1,3-benzothiazol-2-ylidene]amino]pyridazin-3-yl]amino]butane-1-sulfonic acid Using Buchwald General Procedure II starting from the product from Step B and Preparation 4a, 0.16 g of the desired product was produced.

$^{1}H$ NMR (500 MHz, DMSO-$d_6$) δ ppm 7.83 (d, 1H), 7.79 (s, 1H), 7.46 (d, 1H), 7.44 (t, 1H), 7.43 (dd, 1H), 7.31 (dm, 1H), 7.25 (td, 1H), 7.18 (t, 1H), 5.86 (s, 2H), 4.34 (t, 2H), 4.28 (s, 2H), 4.17 (t, 2H), 3.76 (s, 3H), 3.73 (t, 2H), 3.28 (t, 2H), 2.86 (s, 6H), 2.51 (m, 2H), 2.46 (s, 3H), 2.15 (m, 2H), 1.73 (m, 2H), 1.67 (m, 2H), 0.92 (t, 2H), −0.11 (s, 9H); $^{13}C$ NMR (125 MHz, DMSO-$d_6$) δ ppm 129.6, 127.2, 123.4, 123.2, 119.6, 117.8, 115.4, 111.9, 72.9, 68.4, 66.8, 51.9, 51.3, 47.0, 47.0, 42.2, 30.7, 26.2, 23.1, 22.9, 17.8, 17.8, −0.9; HRMS-ESI (m/z): $[M+H]^+$ calcd for $C_{41}H_{53}FN_7O_7S_3Si$: 898.2922, found: 898.2907.

Step D: 2-({6-[(1,3-Benzothiazol-2-yl)amino]-5-methylpyridazin-3-yl}(4-sulfobutyl)amino)-5-(3-{4-[3-(dimethylamino)prop-1-yn-1-yl]-2-fluorophenoxy}propyl)-1,3-thiazole-4-carboxylic acid Using Deprotection and Hydrolysis General Procedure starting from the product from Step C, 64 mg of the desired product was produced.

HRMS-ESI (m/z): $[M+H]^+$ calcd for $C_{34}H_{37}FN_7O_6S_3$: 754.1951, found: 754.1930.

Example 242: 2-({6-[(1,3-Benzothiazol-2-yl)amino]-5-methylpyridazin-3-yl}(4-phosphonobutyl)amino)-5-(3-{4-[3-(dimethylamino)prop-1-yn-1-yl]-2-fluorophenoxy}propyl)-1,3-thiazole-4-carboxylic acid

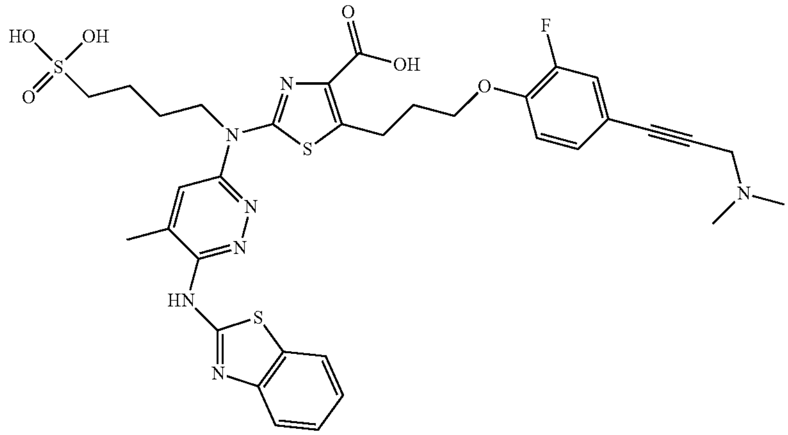

Step A: methyl 2-[tert-butoxycarbonyl(4-diethoxyphosphorylbutyl)amino]-5-[3-[4-[3-(dimethylamino)prop-1-ynyl]-2-fluoro-phenoxy]propyl]thiazole-4-carboxylate Using Alkylation General Procedure starting from 1-bromo-4-diethoxyphosphoryl-butane and Preparation 1c, 1.28 g of the desired product was produced.

$^1$H NMR (500 MHz, DMSO-$d_6$) δ ppm 7.29 (dd, 1H), 7.20 (dm, 1H), 7.13 (t, 1H), 4.10 (t, 2H), 4.01 (t, 2H), 3.93 (m, 4H), 3.75 (s, 3H), 3.42 (s, 2H), 3.22 (t, 2H), 2.23 (s, 6H), 2.08 (m, 2H), 1.78 (m, 2H), 1.71 (m, 2H), 1.51 (s, 9H), 1.45 (m, 2H), 1.18 (t, 6H); $^{13}$C NMR (125 MHz, DMSO-$d_6$) δ ppm 128.9, 119.2, 115.4, 68.1, 61.2, 52.0, 48.1, 45.9, 44.2, 30.5, 28.8, 28.0, 24.5, 23.2, 19.9, 16.7; HRMS-ESI (m/z): $[M+H]^+$ calcd for $C_{32}H_{48}FN_3O_8PS$: 684.2884, found 684.2859.

Step B: methyl 2-(4-diethoxyphosphorylbutylamino)-5-[3-[4-[3-(dimethylamino)prop-1-ynyl]-2-fluoro-phenoxy]propyl]thiazole-4-carboxylate Using Deprotection with HFIP General Procedure starting from the product from Step A, 0.92 g of the desired product was produced.

$^1$H NMR (500 MHz, DMSO-$d_6$) δ ppm 7.61 (t, 1H), 7.32 (dd, 1H), 7.22 (dm, 1H), 7.13 (t, 1H), 4.07 (t, 2H), 3.95 (m, 4H), 3.69 (s, 3H), 3.52 (brs., 2H), 3.17 (q, 213), 3.12 (t, 2H), 2.30 (s, 6H), 2.00 (m, 2H), 1.73 (m, 2H), 1.58 (m, 2H), 1.50 (m, 2H), 1.21 (t, 6H); $^{13}$C NMR (125 MHz DMSO-$d_6$) δ ppm 163.0, 129.0, 119.2, 115.4, 68.0, 61.2, 51.7, 48.0, 44.0, 43.8, 30.6, 29.8, 24.6, 23.3, 20.1, 16.8; HRMS-ESI (m/z): $[M+H]^+$ calcd for $C_{27}H_{40}FN_3O_6PS$: 584.2359, found: 584.2340.

Step C: methyl 2-[4-diethoxyphosphorylbutyl-[5-methyl-6-[(Z)-[3-(2-trimethylsilylethoxymethyl)-1,3-benzothiazol-2-ylidene]amino]pyridazin-3-yl]amino]-5-[3-[4-[3-(dimethylamino)prop-1-ynyl]-2-fluoro-phenoxy]propyl]thiazole-4-carboxylate Using Buchwald General Procedure II starting from the product from Step B and Preparation 4a, 0.69 g of the desired product was produced.

$^1$H NMR (500 MHz, DMSO-$d_6$) δ ppm 7.84 (dm, 1H), 7.72 (s, 1H), 7.47 (dm, 1H), 7.44 (m, 1H), 7.31 (dd, 1H), 7.26 (m, 1H), 7.21 (dm, 1H), 7.16 (t, 1H), 5.86 (s, 2H), 4.41 (t, 2H), 4.15 (t, 2H), 3.94/3.91 (m+m, 4H), 3.78 (s, 3H), 3.72 (m, 2H), 3.38 (s, 2H), 3.27 (t, 2H), 2.46 (s, 3H), 2.20 (s, 6H), 2.12 (m, 2H), 1.86 (m, 2H), 1.78 (m, 2H), 1.54 (m, 2H), 1.18 (t, 6H), 0.91 (m, 2H), −0.11 (s, 9H); HRMS-ESI (m/z): $[M+H]^+$ calcd for $C_{45}H_{62}FN_7O_7PS_2Si$: 954.3643, found: 954.3627.

Step D: 2-({6-[(1,3-Benzothiazol-2-yl)amino]-5-methylpyridazin-3-yl}(4-phosphonobutyl)amino)-5-(3-{4-[3-(dimethylamino)prop-1-yn-1-yl]-2-fluorophenoxy}propyl)-1,3-thiazole-4-carboxylic acid Using Deprotection and hydrolysis of phosphonic acid derivatives General Procedure starting from the product from Step C, 288 mg of the desired product was produced.

HRMS-ESI (m/z): $[M+H]^+$ calcd for $C_{34}H_{38}FN_7O_6PS_2$: 754.2047, found: 754.2036.

Example 243: 2-({6-[(1,3-Benzothiazol-2-yl)amino]-5-methylpyridazin-3-yl}(4-carboxybutyl)amino)-5-(3-{4-[3-(dimethylamino)prop-1-yn-1-yl]-2-fluorophenoxy}propyl)-1,3-thiazole-4-carboxylic acid

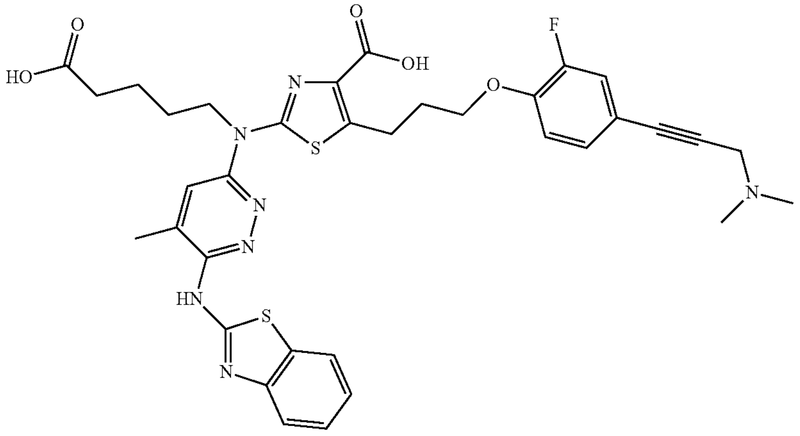 [SMILES: Cc1cc(N(CCCCC(=O)O)c2nc(C(=O)O)c(CCCOc3ccc(C#CCN(C)C)cc3F)s2)nnc1Nc1nc2ccccc2s1]

Step A: methyl 2-[tert-butoxycarbonyl-(5-methoxy-5-oxo-pentyl)amino]-5-[3-[4-[3-(dimethylamino)prop-1-ynyl]-2-fluoro-phenoxy]propyl]thiazole-4-carboxylate Using Alkylation General Procedure starting from methyl 5-bromopentanoate and Preparation 1c, 0.99 g of the desired product was produced.

$^1$H NMR (500 MHz, DMSO-d$_6$) δ ppm 7.28 (dd, 1H), 7.20 (dm, 1H), 7.13 (t, 1H), 4.10 (t, 2H), 4.00 (t, 2H), 3.75 (s, 3H), 3.56 (s, 3H), 3.41 (s, 2H), 3.22 (t, 2H), 2.37 (t, 2H), 2.22 (s, 6H), 2.08 (m, 2H), 1.63 (m, 2H), 1.51 (m, 2H), 1.51 (s, 9H); $^{13}$C NMR (125 MHz, DMSO-d$_6$) δ ppm 128.9, 119.2, 115.4, 68.1, 52.1, 51.7, 48.2, 46.0, 44.3, 33.2, 30.5, 28.1, 27.3, 23.1, 22.0; HRMS-ESI (m/z): [M+H]$^+$ calcd for $C_{30}H_{41}FN_3O_7S$: 606.2649, found 606.2644.

Step B: methyl 5-[3-[4-[3-(dimethylamino)prop-1-ynyl]-2-fluoro-phenoxy]propyl]-2-[(5-methoxy-5-oxo-pentyl)amino]thiazole-4-carboxylate Using Deprotection with HFIP General Procedure sinning from the product from Step A, 0.72 g of the desired product was produced.

$^1$H NMR (500 MHz, DMSO-d$_6$) δ ppm 7.59 (t, 1H), 7.29 (dd, 1H), 7.20 (dm, 1H), 7.12 (t, 1H), 4.07 (t, 2H), 3.69 (s, 3H), 3.58 (s, 3H), 3.41 (s, 2H), 3.16 (q, 2H), 3.12 (t, 2H), 2.33 (t, 2H), 2.22 (s, 6H), 2.00 (m, 2H), 1.56 (m, 2H), 1.51 (m, 2H); $^{13}$C NMR (125 MHz, DMSO-d$_6$) δ ppm 173.7, 164.6, 163.0, 128.9, 119.2, 115.4, 85.1, 84.1, 68.0, 51.7, 51.7, 48.2, 44.3, 44.0, 33.4, 30.6, 28.5, 23.3, 22.4; HRMS-ESI (m/z): [M+H]$^+$ calcd for $C_{25}H_{33}FN_3O_5S$: 506.2125, found 506.2123.

Step C: methyl 5-[3-[4-[3-(dimethylamino)prop-1-ynyl]-2-fluoro-phenoxy]propyl]-2-[(5-methoxy-5-oxo-pentyl)-[5-methyl-6-[(Z)-[3-(2-trimethylsilylethoxymethyl)-1,3-benzothiazol-2-ylidene]amino]pyridazin-3-yl]amino]thiazole-4-carboxylate Using Buchwald General Procedure II starting from the product from Step B and Preparation 4a, 0.79 g of the desired product was produced.

$^1$H NMR (500 MHz, DMSO-d$_6$) δ ppm 7.83 (dm, 1H), 7.65 (s, 1H), 7.45 (dm, 1H), 7.43 (m, 1H), 7.30 (dd, 1H), 7.25 (m, 1H), 7.20 (dm, 1H), 7.15 (t, 1H), 5.85 (s, 2H), 4.37 (t, 2H), 4.14 (t, 2H), 3.77 (s, 3H), 3.71 (m, 2H), 3.56 (s, 3H), 3.39 (s, 2H), 3.26 (t, 2H), 2.45 (s, 3H), 2.43 (t, 2H), 2.20 (s, 6H), 2.12 (m, 2H), 1.71 (m, 2H), 1.60 (m, 2H), 0.91 (m, 2H), −0.11 (s, 9H); HRMS-ESI (m/z): [M+H]$^+$ calcd for $C_{43}H_{55}FN_7O_6S_2Si$: 876.3409, found 876.3378.

Step D: 2-({6-[(1,3-benzothiazol-2-yl)amino]-5-methylpyridazin-3-yl}(4-carboxybutyl)amino)-5-(3-{4-[3-(dimethylamino)prop-1-yn-1-yl]-2-fluorophenoxy}propyl)-1,3-thiazole-4-carboxylic acid Using Deprotection and Hydrolysis General Procedure starting from the product from Step C, 296 mg of the desired product was produced.

HRMS-ESI (m/z): [M+H]$^+$ calcd for $C_{35}H_{37}FN_7O_5S_2$: 718.2282, found: 718.2263.

Example 244: 2-[(3-aminopropyl){6-[(1,3-benzothiazol-2-yl)amino]-5-methylpyridazin-3-yl}amino]-5-(3-{2-fluoro-4-[3-(methylamino)prop-1-yn-1-yl]phenoxy}propyl)-1,3-thiazole-4-carboxylic acid

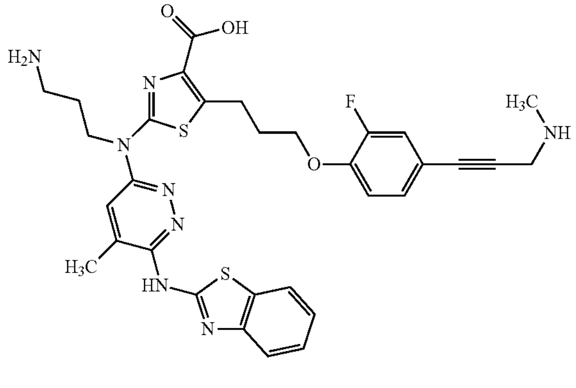 [SMILES: CNCC#Cc1ccc(OCCCc2sc(N(CCCN)c3cc(C)c(Nc4nc5ccccc5s4)nn3)nc2C(=O)O)c(F)c1]

Example 245: 2-[(3-azidopropyl){6-[(1,3-benzothiazol-2-yl)amino]-5-methylpyridazin-3-yl}amino]-5-(3-{2-fluoro-4-[3-(methylamino)prop-1-yn-1-yl]phenoxy}propyl)-1,3-thiazole-4-carboxylic acid

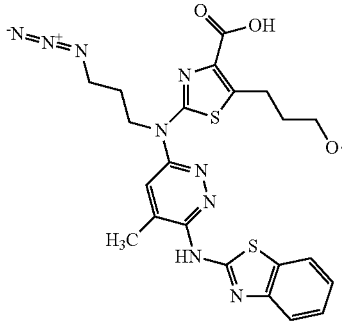

Example 246: 2-[{6-[(1,3-benzothiazol-2-yl)amino]-5-methylpyridazin-3-yl}(methyl)amino]-5-[3-(4-{3-[(dimethylamino)methyl]bicyclo[1.1.1]pentan-1-yl}-2-fluorophenoxy)propyl]-1,3-thiazole-4-carboxylic acid

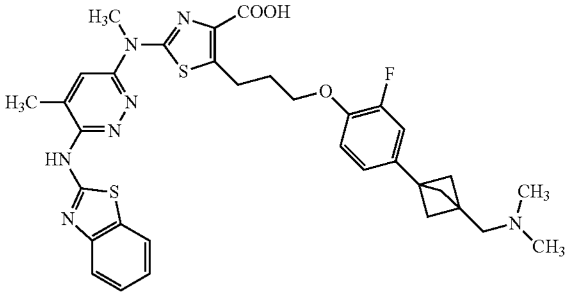

Example 247: 6-[{6-[(1,3-benzothiazol-2-yl)amino]-5-methylpyridazin-3-yl}(methyl)amino]-3-(1-{[3-(2-{[(3S)-3,4-dihydroxybutyl]amino}ethoxy)-5,7-dimethyladamantan-1-yl]methyl}-5-methyl-1H-pyrazol-4-yl)pyridine-2-carboxylic acid

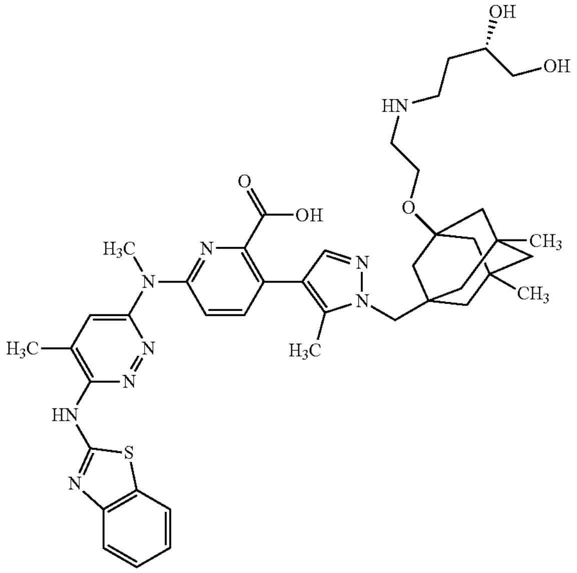 [SMILES: Cc1cc(N(C)c2ccc(-c3cnn(CC45CC6(C)CC(C)(C4)CC(OCCNCC[C@H](O)CO)(C6)C5)c3C)c(C(=O)O)n2)nnc1Nc1nc2ccccc2s1]

Using the Amine Substitution and Hydrolysis General procedure starting from Preparation 14 and 2-[(4S)-2,2-dimethyl-1,3-dioxolan-4-yl]ethanamine as the appropriate amine, the desired product was obtained.

HRMS-ESI (m/z): [M+H]+ calcd for $C_{42}H_{54}N_8O_5S$: 796.3969, found: 796.3965.

Example 248: 6-[{6-[(1,3-benzothiazol-2-yl)amino]-5-methylpyridazin-3-yl}(methyl)amino]-3-(1-{[3-(2-{[(3R)-3,4-dihydroxybutyl]amino}ethoxy)-5,7-dimethyladamantan-1-yl]methyl}-5-methyl-1H-pyrazol-4-yl)pyridine-2-carboxylic acid

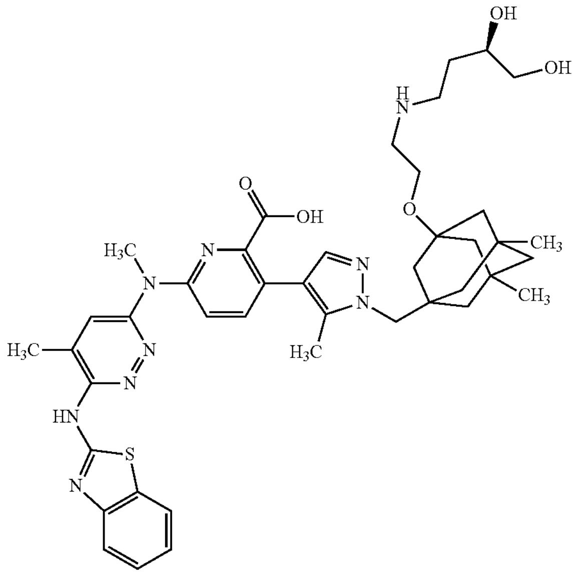 [SMILES: Cc1cc(N(C)c2ccc(-c3cnn(CC45CC6(C)CC(C)(C4)CC(OCCNCC[C@@H](O)CO)(C6)C5)c3C)c(C(=O)O)n2)nnc1Nc1nc2ccccc2s1]

Example 249: 6-[{6-[(1,3-benzothiazol-2-yl)amino]-5-methylpyridazin-3-yl}(methyl)amino]-3-[1-({3,5-dimethyl-7-[2-(methylamino)ethoxy]adamantan-1-yl}methyl)-5-methyl-1H-pyrazol-4-yl]pyridine-2-carboxylic acid

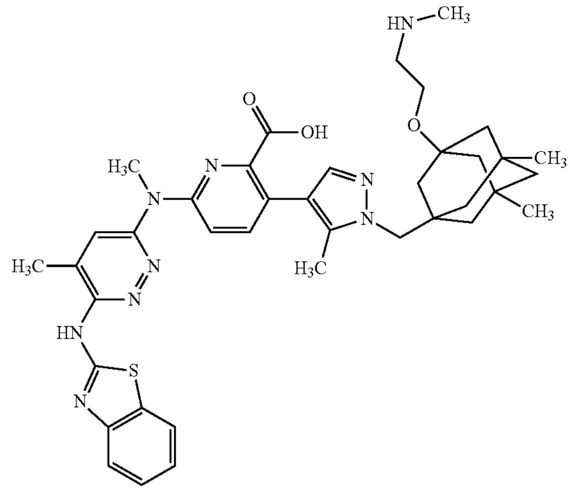

Example 250: 6-[{6-[(1,3-benzothiazol-2-yl)amino]-5-methylpyridazin-3-yl}(methyl)amino]-3-[1-{{3-[2-(dimethylamino)ethoxy]-5,7-dimethyladamantan-1-yl}methyl)-5-methyl-1H-pyrazol-4-yl]pyridine-2-carboxylic acid

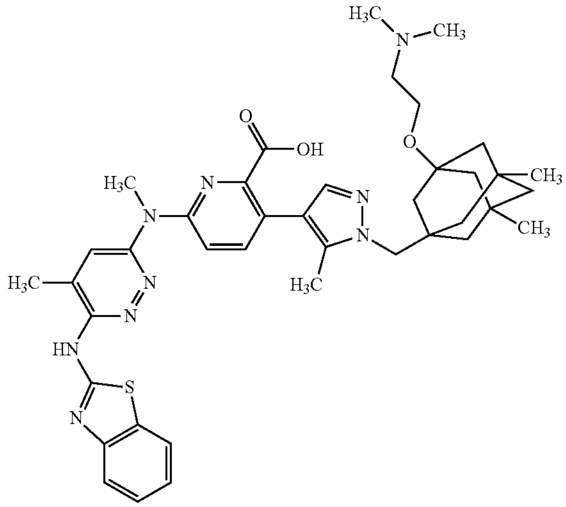

Using the Amine Substitution and Hydrolysis General procedure starting from Preparation 14 and dimethylamine as the appropriate amine, the desired product was obtained.

HRMS-ESI (m/z): [M+H]+ calcd for $C_{40}H_{50}N_9O_3S$: 736.3757, found: 736.3751.

Example 251: 6-[{6-[(1,3-benzothiazol-2-yl)amino]-5-methylpyridazin-3-yl}(methyl)amino]-3-{1-[(3,5-dimethyl-7-{2-[(2-sulfoethyl)amino]ethoxy}adamantan-1-yl)methyl]-5-methyl-1H-pyrazol-4-yl}pyridine-2-carboxylic acid

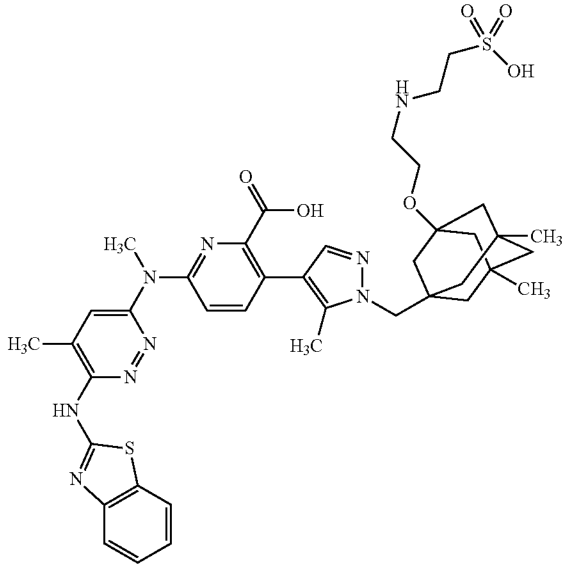

Example 252: 6-[{6-[(1,3-benzothiazol-2-yl)amino]-5-methylpyridazin-3-yl}(methyl)amino]-3-{1-[(3,5-dimethyl-7-{2-[methyl(2-sulfoethyl)amino]ethoxy}adamantan-1-yl)methyl]-5-methyl-1H-pyrazol-4-yl}pyridine-2-carboxylic acid

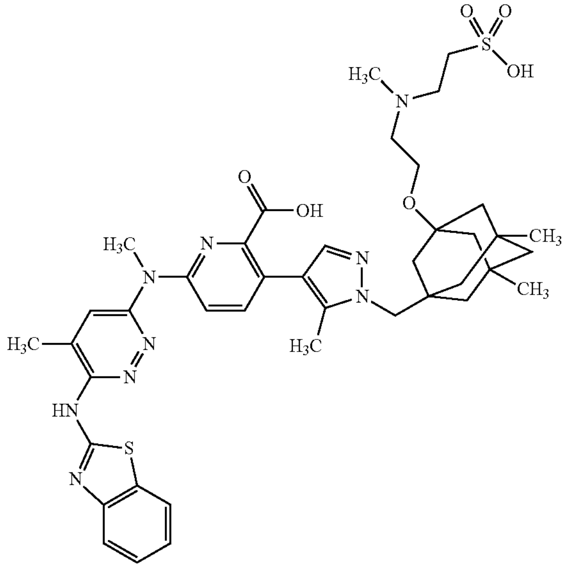

Example 253: 2-[{6-[(1,3-benzothiazol-2-yl)amino]-5-methylpyridazin-3-yl}(pent-4-yn-1-yl)amino]-5-(3-{2-fluoro-4-[3-(methylamino)prop-1-yn-1-yl]phenoxy}propyl)-1,3-thiazole-4-carboxylic acid

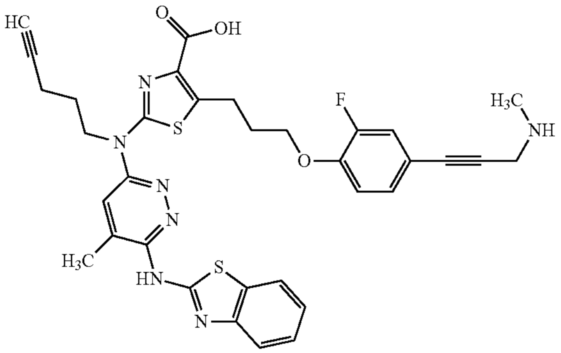 [SMILES: C#CCCCN(c1cc(C)c(Nc2nc3ccccc3s2)nn1)c1nc(C(=O)O)c(CCCOc2ccc(C#CCNC)cc2F)s1]

Step A: methyl 2-[tert-butoxycarbonyl(5-trimethylsilylpent-4-ynyl)amino]-5-[3-(2-fluoro-4-iodo-phenoxy)propyl]-1,3-thiazole-4-carboxylate Using Mitsunobu General Procedure starting from Preparation 1a (10 mmol) as the appropriate carbamate and 5-trimethylsilylpent-4-yn-1-ol (2 eq.) as the appropriate alcohol, 6.0 g (89%) of the desired product was obtained.

$^1$H NMR (500 MHz, DMSO-$d_6$) δ ppm 7.91 (dm, 1H), 7.69 (s, 1H), 7.53 (dm, 1H), 7.39 (m, 1H), 7.34 (dd, 1H), 7.25 (dm, 1H) 7.21 (m, 1H), 7.19 (t, 1H), 4.38 (t, 2H), 4.16 (t, 2H), 3.87 (s, 2H), 3.27 (t, 2H), 2.88 (t, 1H), 2.51 (s, 3H), 2.46 (s, 3H), 2.31 (m, 2H), 2.14 (m, 2H), 1.91 (m, 2H); HRMS-ESI (m/z): $[M+H]^+$ calcd for $C_{34}H_{33}FN_7O_3S_2$: 670.2070, found 670.2052.

Step B: methyl 5-[3-(2-fluoro-4-iodo-phenoxy)propyl]-2-(5-trimethylsilylpent-4-ynylamino)-1,3-thiazole-4-carboxylate Using Deprotection with HFIP General Procedure starting from the product from Step A (6.0 g, 8.9 mmol, 1 eq.) as the appropriate Boc protected amine, 4.46 g (87%) of the desired product was obtained.

$^1H$ NMR (500 MHz, DMSO-$d_6$) δ ppm 7.61 (t, 1H), 7.59 (dd, 1H), 7.45 (dm, 1H), 6.97 (t, 1H), 4.03 (t, 2H), 3.69 (s, 3H), 3.22 (m, 2H), 3.11 (t, 2H), 2.28 (t, 2H), 1.99 (rt 2H), 1.68 (m, 2H), 0.11 (s, 9H); $^{13}C$ NMR (125 MHz, DMSO-$d_6$) δ ppm 134.0, 124.9, 117.6, 107.8, 85.1, 68.1, 51.7, 43.5, 30.6, 28.0, 23.3, 17.1, 0.6; HRMS-ESI (m/z): $[M+H]^+$ calcd for $C_{22}H_{29}FIN_2O_3SSi$: 575.0697, found: 575.0695.

Step C: methyl 5-[3-[4-[3-[tert-butoxycarbonyl(methyl)amino]prop-1-ynyl]-2-fluoro-phenoxy]propyl]-2-(5-trimethylsilylpent-4-ynylamino)-1,3-thiazole-4-carboxylate Using Sonogashira General Procedure starting from the product from Step B (4.46 g, 7.76 mmol, 1 eq.) and tert-butyl N-methyl-N-prop-2-ynyl-carbamate (2.62 g, 15.53 mmol, 2 eq.) as the appropriate acetylene, 4.44 g (93%) of the desired product was obtained.

$^1H$ NMR (500 MHz, DMSO-$d_6$) δ ppm 7.61 (t, 1H), 7.30 (brd, 1H), 7.21 (dm, 1H), 7.12 (t, 1H), 4.23 (brs, 2H), 4.07 (t, 2H), 3.69 (s, 3H), 3.22 (m, 2H), 3.12 (t, 2H), 2.87 (brs, 3H), 2.28 (t, 2H), 2.00 (m, 2H), 1.68 (m, 2H), 1.41 (s, 9H), 0.11 (s, 9H); HRMS-ESI (m/z): $[M+H]^+$ calcd for $C_{31}H_{43}FN_3O_5SSi$: 616.2677, found: 616.2659.

Step D: methyl 5-[3-[4-[3-[tert-butoxycarbonyl(methyl)amino]prop-1-ynyl]-2-fluoro-phenoxy]propyl]-2-[[5-methyl-6-[(Z)-[3-(2-trimethylsilylethoxymethyl)-1,3-benzothiazol-2-ylidene]amino]pyridazin-3-yl]-(5-trimethylsilylpent-4-ynyl)amino]-1,3-thiazole-4-carboxylate Using Buchwald General Procedure I starting from the product from Step C (4.44 g, 7.2 mmol) as starting material in 1,4-dioxane at 120° C., 3.85 g (54%) of the desired product was obtained.

$^1H$ NMR (500 MHz, DMSO-$d_6$) δ ppm 7.83 (d, 1H), 7.64 (s, 1H), 7.45 (dd, 1H), 7.42 (td, 1H), 7.31 (brd., 1H), 7.24 (td, 1H), 7.21 (d, 1H), 7.15 (t, 1H), 5.85 (s, 2H), 4.37 (t, 2H), 4.20 (br., 2H), 4.14 (t, 2H), 3.77 (s, 3H), 3.71 (t, 2H), 3.25 (t, 2H), 2.84 (br., 3H), 2.44 (s, 3H), 2.37 (t, 2H), 2.12 (m, 2H), 1.91 (m, 2H), 1.4 (s, 9H), 0.91 (t, 2H), 0.09 (s, 9), −0.12 (s, 9H); $^{13}C$ NMR (125 MHz, DMSO-$d_6$) δ ppm 163.1, 157.5, 155.2, 150.9, 137.6, 129.1, 127.2, 125.4, 123.4, 123.2, 119.3, 117.4, 115.4, 111.9, 107.5, 85.2, 72.9, 68.4, 66.7, 52.0, 46.5, 38.6, 33.8, 31.0, 28.5, 26.2, 23.2, 17.9, 17.8, 17.1, 0.5, −1.0; HRMS-ESI (m/z): $[M+H]^+$ calcd for $C_{49}H_{65}FN_7O_6S_2Si_2$: 986.3960, found: 986.3932.

Step E: 2-[[6-(1,3-benzothiazol-2-ylamino)-5-methyl-pyridazin-3-yl]-pent-4-ynyl-amino]-5-[3-[2-fluoro-4-[3-(methylamino)prop-1-ynyl]phenoxy]propyl]-1,3-thiazole-4-carboxylic acid Using Deprotection and Hydrolysis General Procedure starting from the product from Step D, followed by purification via reverse phase preparative chromatography (C18, 25 mM $NH_4HCO_3$ in water:MeCN), the desired product was obtained.

HRMS-ESI (m/z): $[M+H]^+$ calcd for $C_{34}H_{33}FN_7O_3S_2$: 670.2070, found: 670.2052.

Example 254: 2-[(4-aminobutyl){6-[(1,3-benzothiazol-2-yl)amino]-5-methylpyridazin-3-yl}amino]-5-(3-{4-[3-(dimethylamino)prop-1-yn-1-yl]-2-fluorophenoxy}propyl)-1,3-thiazole-4-carboxylic acid

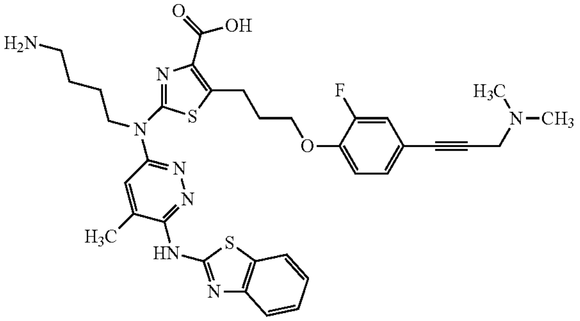 [SMILES: Cc1cc(N(CCCCN)c2nc(C(=O)O)c(CCCOc3ccc(C#CCN(C)C)cc3F)s2)nnc1Nc1nc2ccccc2s1]

Example 255: 2-[(4-azidobutyl){6-[(1,3-benzothiazol-2-yl)amino]-5-methylpyridazin-3-yl}amino]-5-(3-{4-[3-(dimethylamino)prop-1-yn-1-yl]-2-fluorophenoxy}propyl)-1,3-thiazole-4-carboxylic acid

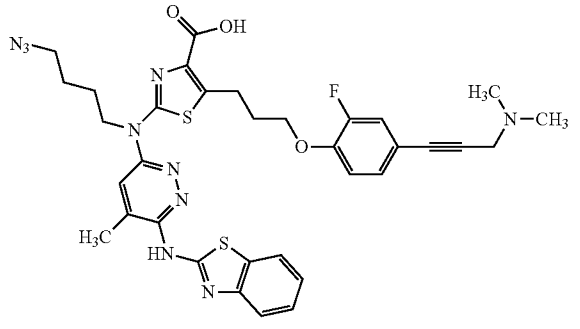 [SMILES: Cc1cc(N(CCCCN=[N+]=[N-])c2nc(C(=O)O)c(CCCOc3ccc(C#CCN(C)C)cc3F)s2)nnc1Nc1nc2ccccc2s1]

Example 256: 2-[{6-[(1,3-benzothiazol-2-yl)amino]-5-methylpyridazin-3-yl}(hex-5-yn-1-yl)amino]-5-(3-{4-[3-(dimethylamino)prop-1-yn-1-yl]-2-fluorophenoxy}propyl)-1,3-thiazole-4-carboxylic acid

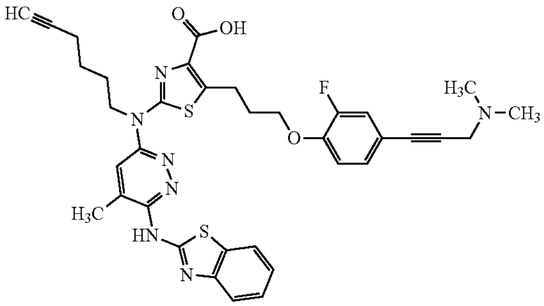 [SMILES: C#CCCCCN(c1cc(C)c(Nc2nc3ccccc3s2)nn1)c1nc(C(=O)O)c(CCCOc2ccc(C#CCN(C)C)cc2F)s1]

Example 257: 2-[{6-[(1,3-benzothiazol-2-yl)amino]-5-methylpyridazin-3-yl}(pent-4-yn-1-yl)amino]-5-(3-{4-[3-(dimethylamino)prop-1-yn-1-yl]-2-fluorophenoxy}propyl)-1,3-thiazole-4-carboxylic acid

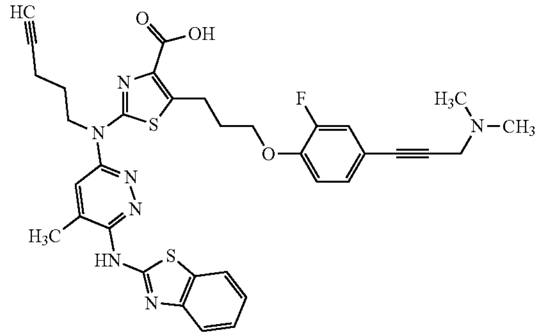 [SMILES: C#CCCCN(c1cc(C)c(Nc2nc3ccccc3s2)nn1)c1nc(C(=O)O)c(CCCOc2ccc(C#CCN(C)C)cc2F)s1]

Example 258: 2-[(3-azidopropyl){6-[(1,3-benzothiazol-2-yl)amino]-5-methylpyridazin-3-yl}amino]-5-(3-{4-[3-(dimethylamino)prop-1-yn-1-yl]-2-fluorophenoxy}propyl)-1,3-thiazole-4-carboxylic acid

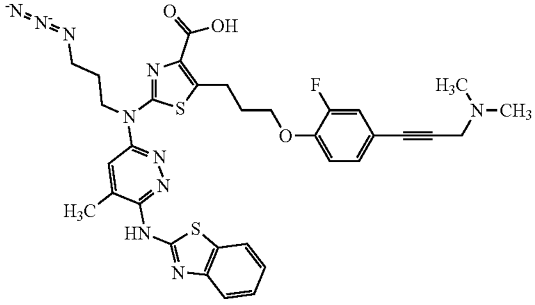

Example 259: 2-[(3-aminopropyl){6-[(1,3-benzothiazol-2-yl)amino]-5-methylpyridazin-3-yl}amino]-5-(3-{4-[3-(dimethylamino)prop-1-yn-1-yl]-2-fluorophenoxy}propyl)-1,3-thiazole-4-carboxylic acid

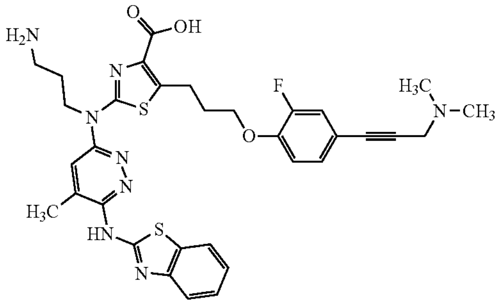 [SMILES: Cc1cc(N(CCCN)c2nc(C(=O)O)c(CCCOc3ccc(C#CCN(C)C)cc3F)s2)nnc1Nc1nc2ccccc2s1]

Example 260: 2-[(4-aminobutyl){6-[(1,3-benzothiazol-2-yl)amino]-5-methylpyridazin-3-yl}amino]-5-(3-{2-fluoro-4-[3-(methylamino)prop-1-yn-1-ylphenoxy}propyl)-1,3-thiazole-4-carboxylic acid

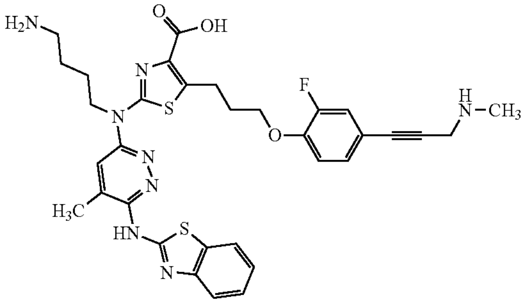 [SMILES: CNCC#Cc1ccc(OCCCc2sc(N(CCCCN)c3cc(C)c(Nc4nc5ccccc5s4)nn3)nc2C(=O)O)c(F)c1]

Example 261: 2-[(4-azidobutyl){6-[(1,3-benzothiazol-2-yl)amino]-5-methylpyridazin-3-yl}amino]-5-(3-{2-fluoro-4-[3-(methylamino)prop-1-yn-1-yl]phenoxy}propyl)-1,3-thiazole-4-carboxylic acid

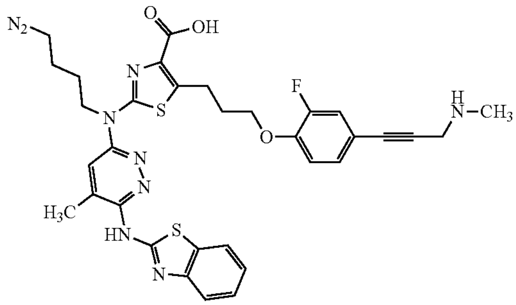

Example 262: 2-[{6-[(1,3-benzothiazol-2-yl)amino]-5-methylpyridazin-3-yl}(hex-5-yn-1-yl)amino]-5-(3-{2-fluoro-4-[3-(methylamino)prop-1-yn-1-yl]phenoxy}propyl)-1,3-thiazole-4-carboxylic acid

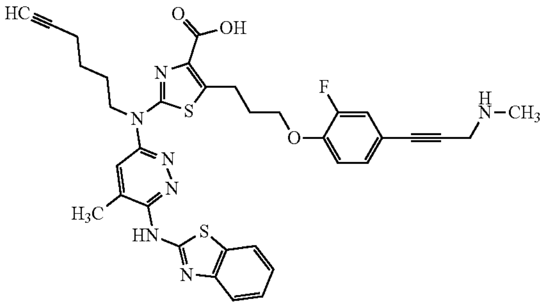 [SMILES: C#CCCCCN(c1cc(C)c(Nc2nc3ccccc3s2)nn1)c1nc(C(=O)O)c(CCCOc2ccc(C#CCNC)cc2F)s1]

Example 263: 2-[(4-aminobutyl){6-[(1,3-benzothiazol-2-yl)amino]-5-methylpyridazin-3-yl}amino]-5-(3-{2-fluoro-4-[3-(methylamino)propyl]phenoxy}propyl)-1,3-thiazole-4-carboxylic acid

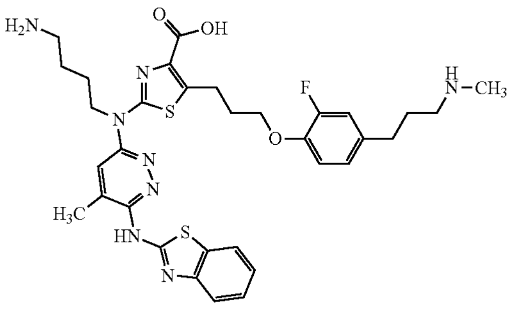 [SMILES: CNCCCc1ccc(OCCCc2sc(N(CCCCN)c3cc(C)c(Nc4nc5ccccc5s4)nn3)nc2C(=O)O)c(F)c1]

Example 264: 2-[(4-azidobutyl){6-[(1,3-benzothiazol-2-yl)amino]-5-methylpyridazin-3-yl}amino]-5-(3-{2-fluoro-4-[3-(methylamino)propyl]phenoxy}propyl)-1,3-thiazole-4-carboxylic acid

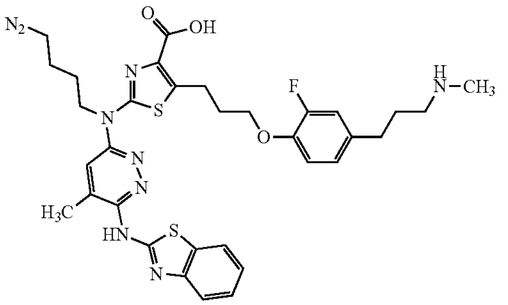

Example 265: 2-[{6-[(1,3-benzothiazol-2-yl)amino]-5-methylpyridazin-3-yl}(hex-5-yn-1-yl)amino]-5-(3-{2-fluoro-4-[3-(methylamino)propyl]phenoxy}propyl)-1,3-thiazole-4-carboxylic acid

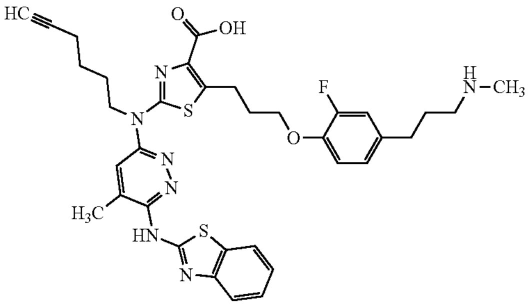 [SMILES: C#CCCCCN(c1cc(C)c(Nc2nc3ccccc3s2)nn1)c1nc(C(=O)O)c(CCCOc2ccc(CCCNC)cc2F)s1]

Example 266: 5-[3-[4-[3-[tert-butoxycarbonyl(methyl)amino]prop-1-ynyl]-2-fluoro-phenoxy]propyl]-2-[5-methyl-6-[(Z)-[3-(2-trimethylsilylethoxymethyl)-1,3-benzothiazol-2-ylidene]amino]pyridazin-3-yl]-pent-4-ynyl-amino]thiazole-4-carboxylic acid

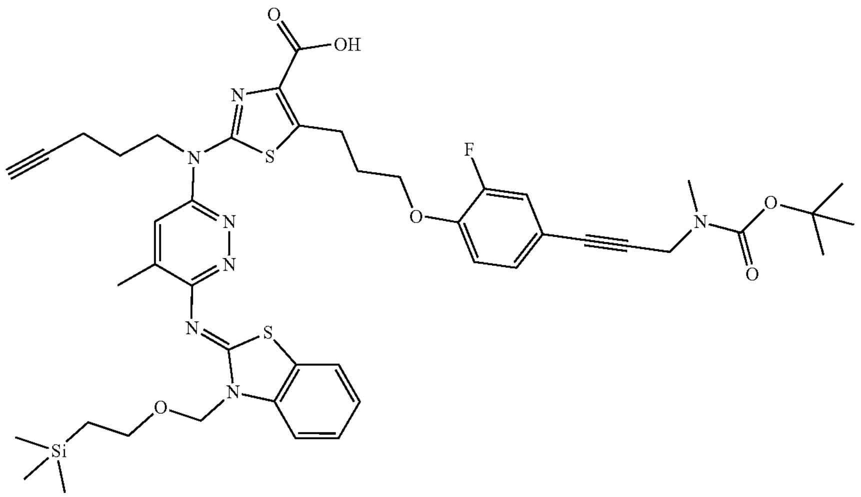 [SMILES: C#CCCCN(c1cc(C)c(/N=c2\sc3ccccc3n2COCC[Si](C)(C)C)nn1)c1nc(C(=O)O)c(CCCOc2ccc(C#CCN(C)C(=O)OC(C)(C)C)cc2F)s1]

The mixture of 500 mg of the product from Example 253, Step D and 106 mg (2.5 mmol, 5 eq.) of LiOH*$H_2O$ in the mixture of 5 mL of THF and 2 mL of water was stirred at 40° C. for 16 h, then purified by crystallization from $Et_2O$ to give 356 mg (78%) of the desired product.

HRMS-ESI (m/z): $[M+H]^+$ calcd for $C_{45}H_{55}FN_7O_6S_2Si$: 900.3409, found: 900.3383

Example 267: 2-[5-azidopentyl-[6-[(1,3-benzothiazol-2-yl)amino]-5-methyl-pyridazin-3-yl]amino]-5-[3-[2-fluoro-4-[3-(methylamino)prop-1-ynyl]phenoxy]propyl]-1,3-thiazole-4-carboxylic acid

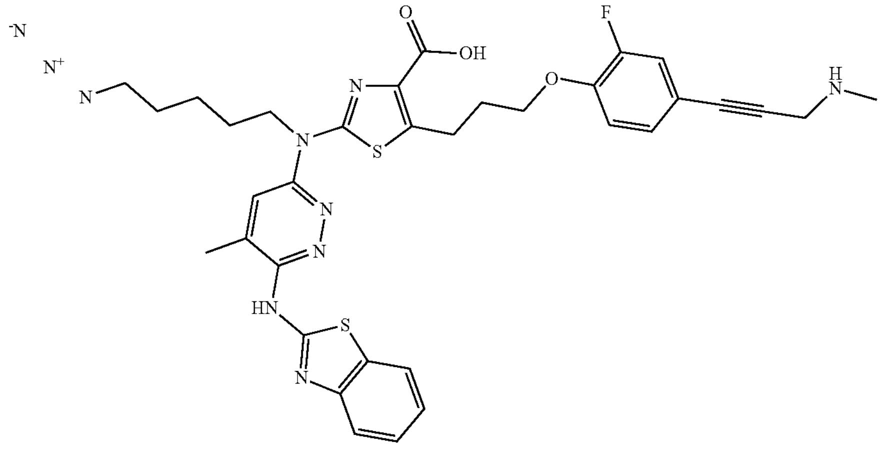

Step A: methyl 2-[tert-butoxycarbonyl-[5-[tert-butyl(dimethyl)silyl]oxypentyl]amino]-5-[3-[4-[3-[tert-butoxycarbonyl(methyl)amino]prop-1-ynyl]-2-fluoro-phenoxy]propyl]-1,3-thiazole-4-carboxylate Using Mitsunobu General Procedure starting from Preparation 1b (0.7 mmol) as the appropriate carbamate and 5-[tert-butyl(dimethyl)silyl]oxypentan-1-ol (1.5 eq.) as the appropriate alcohol, 494 mg (91%) of the desired product was obtained.

LC/MS ($C_{39}H_{60}FN_3O_8SSiNa$) 800 $[M+Na]^+$.

Step B: methyl 5-[3-[4-[3-[tert-butoxycarbonyl(methyl)amino]prop-1-ynyl]-2-fluoro-phenoxy]propyl]-2-[5-[tert-butyl(dimethyl)silyl]oxypentylamino]-1,3-thiazole-4-carboxylate Using Deprotection with HFIP General Procedure starting from the product from Step A (490 mg, 0.63 mmol, 1 eq.) as the appropriate Boc protected amine, 240 mg (56%) of the desired product was obtained.

$^1H$ NMR (500 MHz, DMSO-$d_6$) δ ppm 7.57 (br., 1H), 7.31 (d, 1H), 7.21 (d, 1H), 7.12 (t, 1H), 4.23 (br., 2H), 4.07 (t, 2H), 3.69 (s, 3H), 3.56 (t, 2H), 3.14 (m, 2H), 3.11 (t, 2H), 2.86 (br., 2.00 (quint., 2H), 1.51 (m, 2H), 1.45 (m, 2H), 1.41 (s, 9H), 1.33 (m, 2H) 0.84 (s, 9H), 0 (s, 6H); $^{13}C$ NMR (125 MHz, DMSO-$d_6$) δ ppm 129.1, 119.3, 115.4, 68.0, 62.8, 51.7, 44.5, 38.6, 33.8, 32.4, 30.6, 28.9, 28.5, 26.3, 23.3, 23.2, −4.9; HRMS-ESI (m/z): $[M+H]^+$ calcd for $C_{34}H_{53}FN_3O_6SSi$: 678.3408, found: 678.3393.

Step C: methyl 5-[3-[4-[3-[tert-butoxycarbonyl(methyl)amino]prop-1-ynyl]-2-fluoro-phenoxy]propyl]-2-[5-[tert-butyl(dimethyl)silyl]oxypentyl-[5-methyl-6-(Z)-[3-(2-trimethylsilylethoxymethyl)-1,3-benzothiazol-2-ylidene]amino]pyridazin-3-yl]amino]-1,3-thiazole-4-carboxylate Using Buchwald General Procedure I starting from the product from Step B (235 mg) as starting material in 1,4-dioxane at 120° C., 220 mg (60%) of the desired product was obtained.

$^1H$ NMR (500 MHz, DMSO-$d_6$) δ ppm 7.81 (dd, 1H), 7.62 (s, 1H), 7.45 (dd, 1H), 7.42 (m, 1H), 7.28 (dd, 1H), 7.24 (m, 1H), 7.19 (m, 1H), 7.15 (t, 1H), 5.84 (s, 2H), 4.38 (t, 2H), 4.20 (s, 2H), 4.16 (t, 2H), 3.78 (s, 3H), 3.73 (t, 2H), 3.55 (t, 2H), 3.26 (t, 2H), 2.85 (s, 3H), 2.44 (s, 3H), 2.13 (m, 2H), 1.71 (m, 2H), 1.51 (m, 2H), 1.41 (s, 9H), 1.40 (m, 2H), 0.92 (t, 2H), 0.80 (s, 9H), −0.04 (s, 6H), −0.10 (s, 9H); $^{13}C$ NMR (125 MHz, DMSO-$d_6$) δ ppm 163.2, 147.5, 137.6, 129, 127.1, 123.5, 123.1, 119.3, 117.7, 115.7, 111.9, 73.0, 68.6, 66.8, 62.7, 51.8, 47.0, 38.6, 33.8, 32.4, 31.0, 28.5, 27.1, 26.2, 23.1, 23.0, 17.9, 17.8, −1.0, −5.0; HRMS-ESI (m/z): $[M+H]^+$ calcd for $C_{52}H_{75}FN_7O_7S_2Si_2$: 1048.4692, found: 1048.4692.

Step D: methyl 5-[3-[4-[3-[tert-butoxycarbonyl(methyl)amino]prop-1-ynyl]-2-fluoro-phenoxy]propyl]-2-[5-hydroxypentyl-[5-methyl-6-[(Z)-[3-(2-trimethylsilylethoxymethyl)-1,3-benzothiazol-2-ylidene]amino]pyridazin-3-yl]amino]-1,3-thiazole-4-carboxylate The mixture of the product from Step C (0.3 mmol) and 18 mg of camphor sulfonic acid (0.07 mmol, 0.25 eq.) in 2 mL of the 1:1 mixture of DCM and MeOH was stirred at 60° C. for 1.5 h. The product was purified by flash column chromatography using heptane and EtOAc as eluents to give 195 mg (66%) of the desired product.

$^1$H NMR (500 MHz, DMSO-d$_6$) δ ppm 7.84 (d, 1H), 7.66 (s, 1H), 7.46 (d, 1H), 7.43 (t, 1H), 7.32 (d, 1H), 7.25 (t, 1H), 7.22 (d, 1H), 7.16 (t, 1H), 5.86 (s, 2H), 4.36 (t, 2H), 4.20 (s, 2H), 4.15 (t, 2H), 3.78 (s, 3H), 3.72 (t, 2H), 3.40 (t, 2H), 3.26 (t, 2H), 2.84 (s, 3H), 2.46 (s, 3H), 2.12 (qn, 2H), 1.69 (qn, 2H), 1.49 (m, 2H), 1.40 (s, 9H), 1.4 (qn, 2H), 0.92 (t, 2H), −0.11 (s, 9H); $^{13}$C NMR (125 MHz, DMSO-d$_6$) δ ppm 129.1, 127.2, 123.4, 123.2, 119.3, 117.6, 115.5, 112.0, 72.9, 68.4, 66.7, 61.0, 52.0, 47.0, 38.5, 33.9, 32.5, 31.0, 28.5, 27.1, 23.2, 23.1, 17.9, 17.8, −1.0; HRMS-ESI (m/z): $[M+Na]^+$ calcd for $C_{46}H_{60}FN_7NaO_7S_2SiNa$: 956.3641, found: 956.3646.

Step E: methyl 2-[5-azidopentyl-[5-methyl-6-[(Z)-[3-(2-trimethylsilylethoxymethyl)-1,3-benzothiazol-2-ylidene]amino]pyridazin-3-yl]amino]-5-[3-[4-[3-[tert-butoxycarbonyl(methyl)amino]prop-1-ynyl]-2-fluoro-phenoxy]propyl]-1,3-thiazole-4-carboxylate The mixture of 158 mg of the product from Step D, 70 μL of triethylamine (0.50 mmol, 3 eq.), and 83 mg of p-tolylsulfonyl 4-methylbenzenesulfonate (0.25 mmol, 1.5 eq.) in 1 mL of DCM was stirred for 5 h. After concentration, the residue was dissolved in 1 mL of acetonitrile and 133 mg of sodium azide (2.0 mmol, 12 eq.) was added and the resulting mixture was stirred at 80° C. for 0.5 h. Product was purified by flash column chromatography using heptane and EtOAc as eluents to give 120 mg (73%) of the desired product.

$^1$H NMR (500 MHz, DMSO-d$_6$) δ ppm 7.84 (dm, 1H), 7.69 (s, 1H), 7.47 (dm, 1H), 7.44 (m, 1H), 7.32 (brd, 1H), 7.26 (m, 1H), 7.22 (dm, 1H), 7.17 (t, 1H), 5.86 (s, 2H), 4.37 (t, 2H), 4.20 (brs, 2H), 4.15 (t, 2H), 3.78 (s, 3H), 3.72 (m, 2H), 3.36 (t, 2H), 3.27 (t, 2H), 2.84 (brs, 3H), 2.46 (s, 3H), 2.13 (m, 2H), 1.72 (m, 2H), 1.64 (m, 2H), 1.43 (m, 2H), 1.40 (s, 9H), 0.92 (m, 2H), −0.11 (s, 9H); HRMS-ESI (m/z): $[M+H]^+$ calcd for $C_{46}H_{60}FN_{10}O_6S_2Si$: 959.3892, found: 959.3892.

Step F: 2-[5-azidopentyl-[6-[(1,3-benzothiazol-2-yl)amino]-5-methyl-pyridazin-3-yl]amino]-5-[3-[2-fluoro-4-[3-(methylamino)prop-1-ynyl]phenoxy]propyl]-1,3-thiazole-4-carboxylic acid Using Deprotection and Hydrolysis General Procedure starting from the product from Step E, followed by purification via reverse phase preparative chromatography (C18, 0.1% TFA in water:MeCN), the desired product was obtained.

HRMS-ESI (m/z): $[M+H]^+$ calcd for $C_{34}H_{36}FN_{10}O_3S_2$: 715.2397, found: 715.2391.

Example 268: 6-[[6-(1,3-benzothiazol-2-ylamino)-5-methyl-pyridazin-3-yl]-methyl-amino]-3-[1-[[3-[2-(3-hydroxypropylamino)ethoxy]-5,7-dimethyl-1-adamantyl]methyl]-5-methyl-pyrazol-4-yl]pyridine-2-carboxylic acid

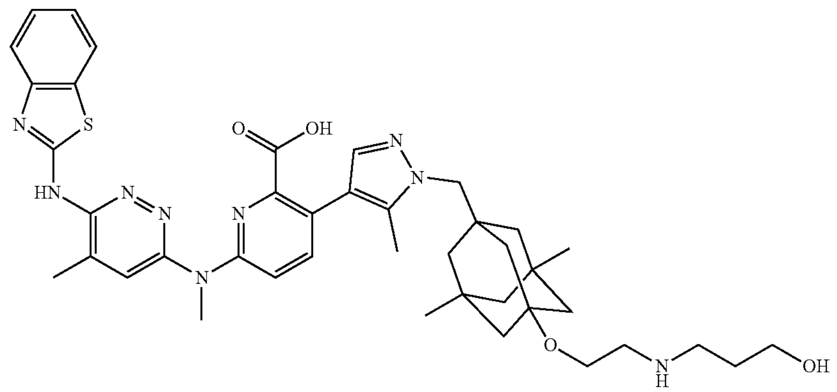 [SMILES: Cc1cc(N(C)c2ccc(-c3cnn(CC45CC6(C)CC(C)(C4)CC(OCCNCCCO)(C6)C5)c3C)c(C(=O)O)n2)nnc1Nc1nc2ccccc2s1]

Using the Amine Substitution and Hydrolysis General procedure starting from Preparation 14 and 3-aminopropane-1-ol as the appropriate amine, the desired product was obtained.

HRMS-ESI (m/z): [M+H]+ calcd for $C_{41}H_{52}N_9O_4S$: 766.3863, found: 766.3860.

Example 269: 6-[[6-(1,3-benzothiazol-2-ylamino)-5-methyl-pyridazin-3-yl]-methyl-amino]-3-[1-[[3-[2-(3-methoxypropylamino)ethoxy]-5,7-dimethyl-1-adamantyl]methyl]-5-methyl-pyrazol-4-yl]pyridine-2-carboxylic acid

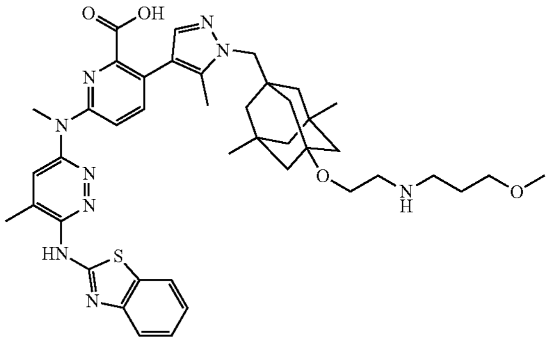

Using the Amine Substitution and Hydrolysis General procedure starting from Preparation 14 and 3-methoxypropan-1-amine as the appropriate amine, the desired product was obtained.

HRMS-ESI (m/z): [M+H]+ calcd for $C_{42}H_{54}N_9O_4S$: 780.4019, found: 780.4019.

Example 270: 6-[[6-(1,3-benzothiazol-2-ylamino)-5-methyl-pyridazin-3-yl]-methyl-amino]-3-[1-[[3,5-dimethyl-7-(2-morpholinoethoxy)-1-adamantyl]methyl]-5-methyl-pyrazol-4-yl]pyridine-2-carboxylic acid

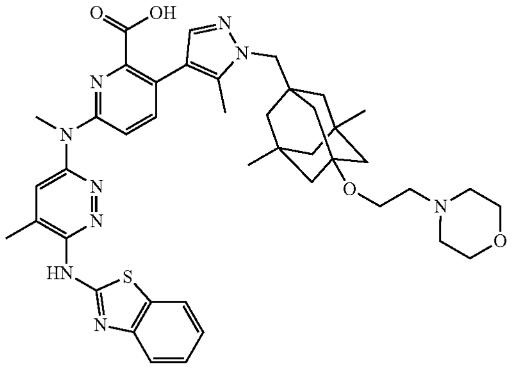 [SMILES: Cc1cc(N(C)c2ccc(-c3cnn(CC45CC6(C)CC(C)(C4)CC(OCCN4CCOCC4)(C6)C5)c3C)c(C(=O)O)n2)nnc1Nc1nc2ccccc2s1]

Using the Amine Substitution and Hydrolysis General procedure starting from Preparation 14 and morpholine as the appropriate amine, the desired product was obtained.

HRMS-ESI (m/z): [M+H]+ calcd for $C_{42}H_{52}N_9O_4S$: 778.380, found: 778.3858.

Example 271: 6-[[6-(1,3-benzothiazol-2-ylamino)-5-methyl-pyridazin-3-yl]-methyl-amino]-3-[1-[[3-[2-(2-carboxyethylamino)ethoxy]-5,7-dimethyl-1-adamantyl]methyl]-5-methyl-pyrazol-4-yl]pyridine-2-carboxylic acid

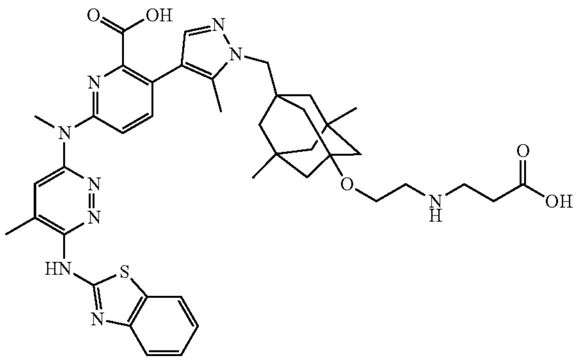 [SMILES: Cc1cc(N(C)c2ccc(-c3cnn(CC45CC6(C)CC(C)(C4)CC(OCCNCCC(=O)O)(C6)C5)c3C)c(C(=O)O)n2)nnc1Nc1nc2ccccc2s1]

Using the Amine Substitution and Hydrolysis General procedure starting from Preparation 3-aminopropanoic-acid as the appropriate amine, and 10 eq of $K_2CO_3$ as a base, the desired product was obtained.

HRMS-ESI (m/z): [M+H]+ calcd for $C_{41}H_{50}N_9O_5S$: 780.3656, found: 780.3658.

Example 272: 6-[[6-(1,3-benzothiazol-2-ylamino)-5-methyl-pyridazin-3-yl]-methyl-amino]-3-[1-[[3-[2-[(3-hydroxyphenyl)methylamino]ethoxy]-5,7-dimethyl-1-adamantyl]methyl]-5-methyl-pyrazol-4-yl]pyridine-2-carboxylic acid

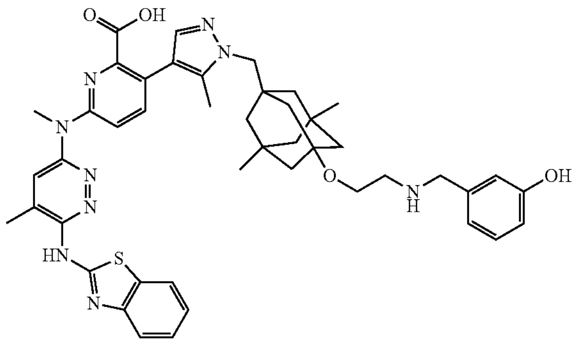 [SMILES: Cc1cc(N(C)c2ccc(-c3cnn(CC45CC6(C)CC(C)(C4)CC(OCCNCc4cccc(O)c4)(C6)C5)c3C)c(C(=O)O)n2)nnc1Nc1nc2ccccc2s1]

Using the Amine Substitution and Hydrolysis General procedure starting from Preparation 14 and 3-(aminomethyl)phenol as the appropriate amine, the desired product was obtained.

HRMS-ESI (m/z): [M+H]+ calcd for $C_{45}H_{52}N_9O_4S$: 814.3863, found: 814.3861.

The compounds of the following Examples 273-280 are synthesised using the Amine Substitution and Hydrolysis General procedure starting from the Preparation 14 and the appropriate amine.

Example 273: 6-[[6-(1,3-benzothiazol-2-ylamino)-5-methyl-pyridazin-3-yl]-methyl-amino]-3-[1-[[3,5-dimethyl-7-(2-pyrrolidin-1-ylethoxy)-1-adamantyl]methyl]-5-methyl-pyrazol-4-yl]pyridine-2-carboxylic acid

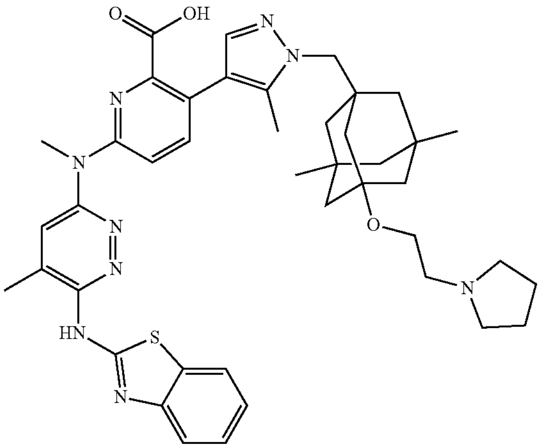 [SMILES: Cc1cc(N(C)c2ccc(-c3cnn(CC45CC6(C)CC(C)(C4)CC(OCCN4CCCC4)(C6)C5)c3C)c(C(=O)O)n2)nnc1Nc1nc2ccccc2s1]

Example 274: 6-[[6-(1,3-benzothiazol-2-ylamino)-5-methyl-pyridazin-3-yl]-methyl-amino]-3-[1-[[3,5-dimethyl-7-[2-(4-methylpiperazin-1-yl)ethoxy]-1-adamantyl]methyl]-5-methyl-pyrazol-4-yl]pyridine-2-carboxylic acid

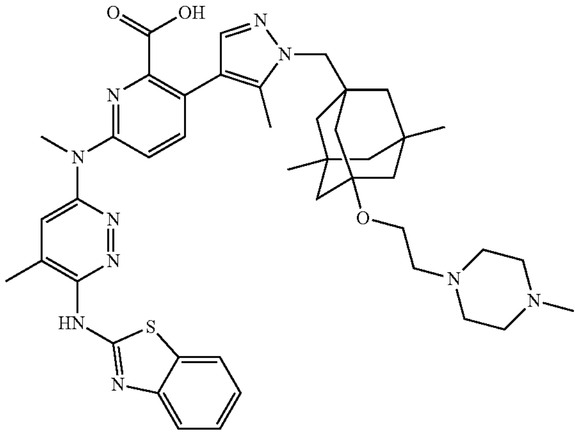

Example 275: 6-[[6-(1,3-benzothiazol-2-ylamino)-5-methyl-pyridazin-3-yl]-methyl-amino]-3-[1-[[3-[2-(4-hydroxybutylamino)ethoxy]-5,7-dimethyl-1-adamantyl]methyl]-5-methyl-pyrazol-4-yl]pyridine-2-carboxylic acid

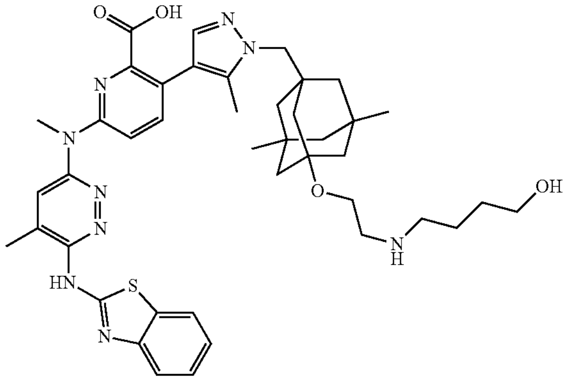 [SMILES: Cc1cc(N(C)c2ccc(-c3cnn(CC45CC6(C)CC(C)(C4)CC(OCCNCCCCO)(C6)C5)c3C)c(C(=O)O)n2)nnc1Nc1nc2ccccc2s1]

Example 276: 6-[[6-(1,3-benzothiazol-2-ylamino)-5-methyl-pyridazin-3-yl]-methyl-amino]-3-[1-[[3,5-dimethyl-7-(2-piperazin-1-ylethoxy)-1-adamantyl]methyl]-5-methyl-pyrazol-4-yl]pyridine-2-carboxylic acid

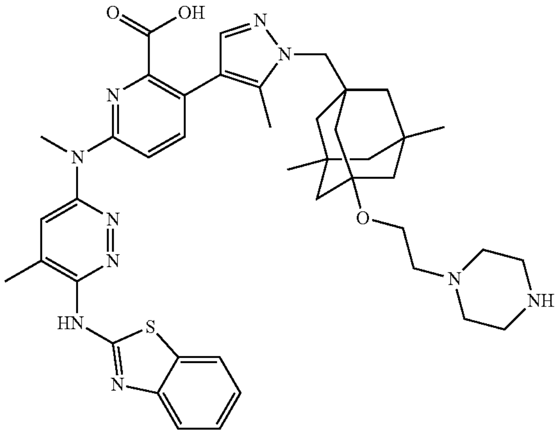 [SMILES: Cc1cc(N(C)c2ccc(-c3cnn(CC45CC6(C)CC(C)(C4)CC(OCCN4CCNCC4)(C6)C5)c3C)c(C(=O)O)n2)nnc1Nc1nc2ccccc2s1]

Example 277: 6-[[6-(1,3-benzothiazol-2-ylamino)-5-methyl-pyridazin-3-yl]-methyl-amino]-3-[1-[[3-[2-[3-hydroxypropyl(methyl)amino]ethoxy]-5,7-dimethyl-1-adamantyl]methyl]-5-methyl-pyrazol-4-yl]pyridine-2-carboxylic acid

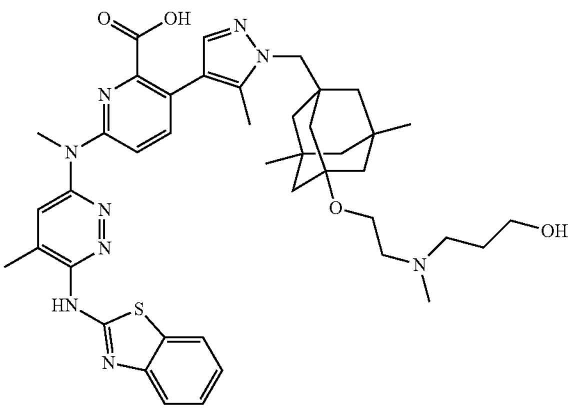 [SMILES: Cc1cc(N(C)c2ccc(-c3cnn(CC45CC6(C)CC(C)(C4)CC(OCCN(C)CCCO)(C6)C5)c3C)c(C(=O)O)n2)nnc1Nc1nc2ccccc2s1]

Example 278: 6-[[6-(1,3-benzothiazol-2-ylamino)-5-methyl-pyridazin-3-yl]-methyl-amino]-3-[1-[[3-[2-[4-hydroxybutyl(methyl)amino]ethoxy]-5,7-dimethyl-1-adamantyl]methyl]-5-methyl-pyrazol-4-yl]pyridine-2-carboxylic acid

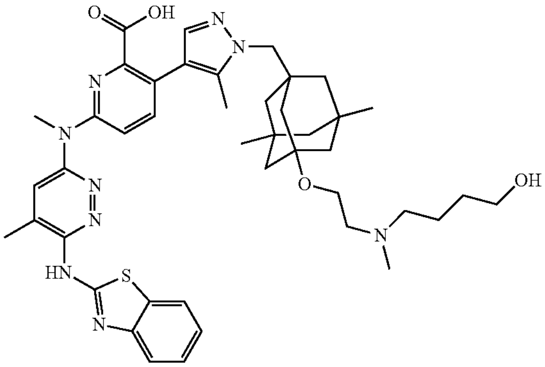 [SMILES: Cc1cc(N(C)c2ccc(-c3cnn(CC45CC6(C)CC(C)(C4)CC(OCCN(C)CCCCO)(C6)C5)c3C)c(C(=O)O)n2)nnc1Nc1nc2ccccc2s1]

Example 279: 6-[[6-(1,3-benzothiazol-2-ylamino)-5-methyl-pyridazin-3-yl]-methyl-amino]-3-[1-[[3-[2-[[3-hydroxy-2-(hydroxymethyl)propyl]amino]ethoxy]-5,7-dimethyl-1-adamantyl]methyl]-5-methyl-pyrazol-4-yl]pyridine-2-carboxylic acid

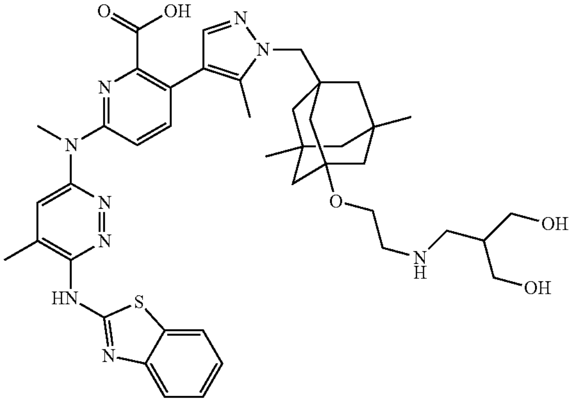 [SMILES: Cc1cc(N(C)c2ccc(-c3cnn(CC45CC6(C)CC(C)(C4)CC(OCCNCC(CO)CO)(C6)C5)c3C)c(C(=O)O)n2)nnc1Nc1nc2ccccc2s1]

Example 280: 6-[[6-(1,3-benzothiazol-2-ylamino)-5-methyl-pyridazin-3-yl]-methyl-amino]-3-[1-[[3-[2-[bis(3-hydroxypropyl)amino]ethoxy]-5,7-dimethyl-1-adamantyl]methyl]-5-methyl-pyrazol-4-yl]pyridine-2-carboxylic acid

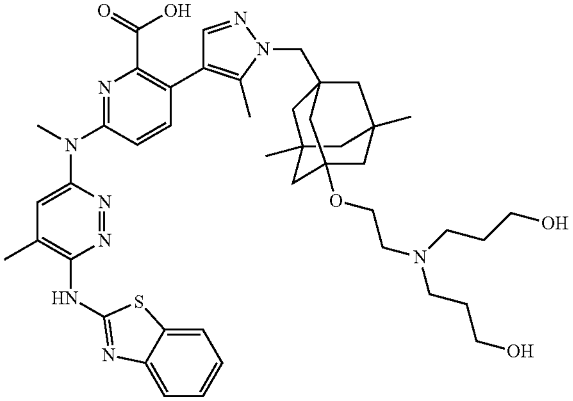 [SMILES: Cc1cc(N(C)c2ccc(-c3cnn(CC45CC6(C)CC(C)(C4)CC(OCCN(CCCO)CCCO)(C6)C5)c3C)c(C(=O)O)n2)nnc1Nc1nc2ccccc2s1]

Example 281: 2-[[6-(1,3-benzothiazol-2-ylamino)-5-methyl-pyridazin-3-yl]-methyl-amino]-5-[3-[2-fluoro-4-(3-piperazin-1-ylprop-1-ynyl)phenoxy]propyl]thiazole-4-carboxylic acid

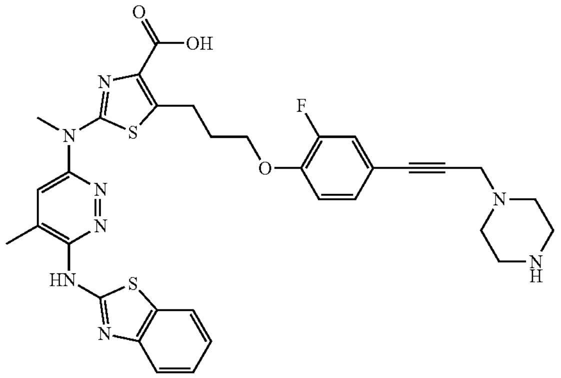 [SMILES: Cc1cc(N(C)c2nc(C(=O)O)c(CCCOc3ccc(C#CCN4CCNCC4)cc3F)s2)nnc1Nc1nc2ccccc2s1]

Example 282: 2-[[6-(1,3-benzothiazol-2-ylamino)-5-methyl-pyridazin-3-yl]-methyl-amino]-5-[3-[2-fluoro-4-[3-(4-methylpiperazin-1-yl)prop-1-ynyl]phenoxy]propyl]thiazole-4-carboxylic acid

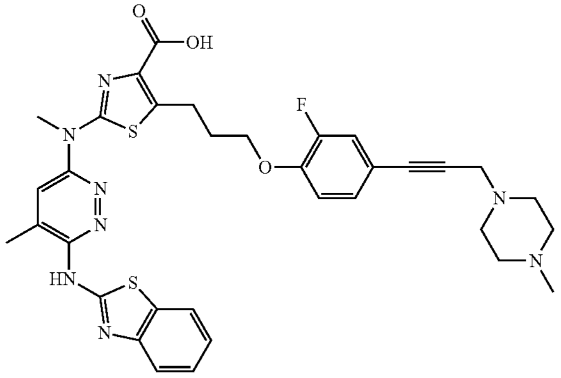

Example 283: 2-[[6-(1,3-benzothiazol-2-ylamino)-5-methyl-pyridazin-3-yl]-methyl-amino]-5-[3-[2-fluoro-4-[3-[3-hydroxypropyl(methyl)amino]prop-1-ynyl]phenoxy]propyl]thiazole-4-carboxylic acid

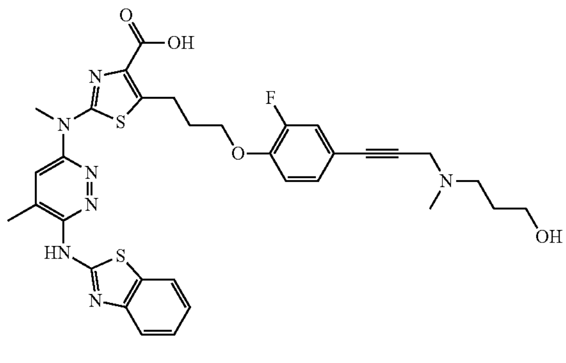 [SMILES: Cc1cc(N(C)c2nc(C(=O)O)c(CCCOc3ccc(C#CCN(C)CCCO)cc3F)s2)nnc1Nc1nc2ccccc2s1]

Example 284: 2-[[6-(1,3-benzothiazol-2-ylamino)-5-methyl-pyridazin-3-yl]-methyl-amino]-5-[3-[4-[3-[[(3S)-3,4-dihydroxybutyl]-methyl-amino]prop-1-ynyl]-2-fluoro-phenoxy]propyl]thiazole-4-carboxylic acid

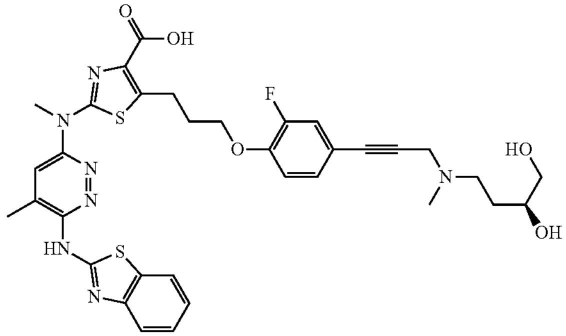 [SMILES: Cc1cc(N(C)c2nc(C(=O)O)c(CCCOc3ccc(C#CCN(C)CC[C@H](O)CO)cc3F)s2)nnc1Nc1nc2ccccc2s1]

Example 285: 2-[[6-(1,3-benzothiazol-2-ylamino)-5-methyl-pyridazin-3-yl]-methyl-amino]-5-[3-[2-fluoro-4-[3-(3-hydroxypropylamino)prop-1-ynyl]phenoxy]propyl]thiazole-4-carboxylic acid

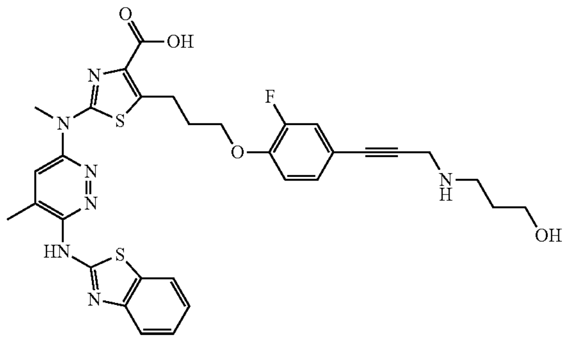 [SMILES: Cc1cc(N(C)c2nc(C(=O)O)c(CCCOc3ccc(C#CCNCCCO)cc3F)s2)nnc1Nc1nc2ccccc2s1]

Example 286: 2-[[6-(1,3-benzothiazol-2-ylamino)-5-methyl-pyridazin-3-yl]-methyl-amino]-5-[3-[4-[3-[[(3S)-3,4-dihydroxybutyl]amino]prop-1-ynyl]-2-fluoro-phenoxy]propyl]thiazole-4-carboxylic acid

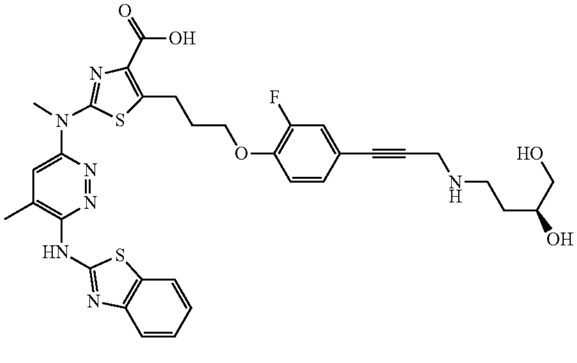 [SMILES: Cc1cc(N(C)c2nc(C(=O)O)c(CCCOc3ccc(C#CCNCC[C@H](O)CO)cc3F)s2)nnc1Nc1nc2ccccc2s1]

Example 287: 2-[[6-(1,3-benzothiazol-2-ylamino)-5-methyl-pyridazin-3-yl]-methyl-amino]-5-[3-[2-fluoro-4-[3-[4-hydroxybutyl(methyl)amino]prop-1-ynyl]phenoxy]propyl]thiazole-4-carboxylic acid
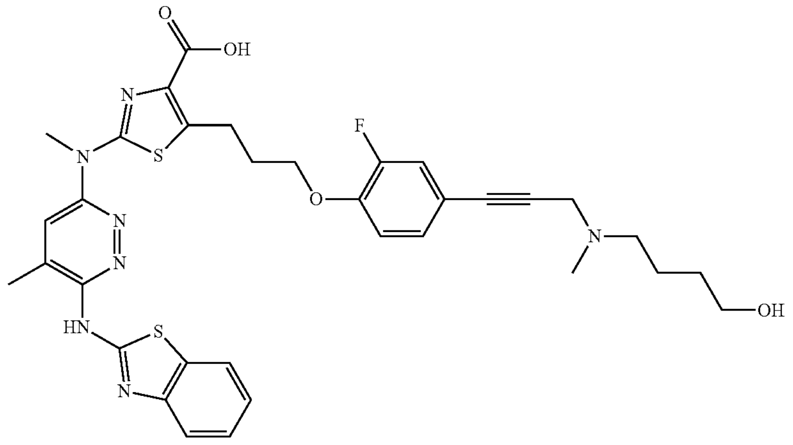 [SMILES: Cc1cc(N(C)c2nc(C(=O)O)c(CCCOc3ccc(C#CCN(C)CCCCO)cc3F)s2)nnc1Nc1nc2ccccc2s1]

Example 288: 2-[[6-(1,3-benzothiazol-2-ylamino)-5-methyl-pyridazin-3-yl]-methyl-amino]-5-[3-[4-[3-[[(3R)-3,4-dihydroxybutyl]-methyl-amino]prop-1-ynyl]-2-fluoro-phenoxy]propyl]thiazole-4-carboxylic acid
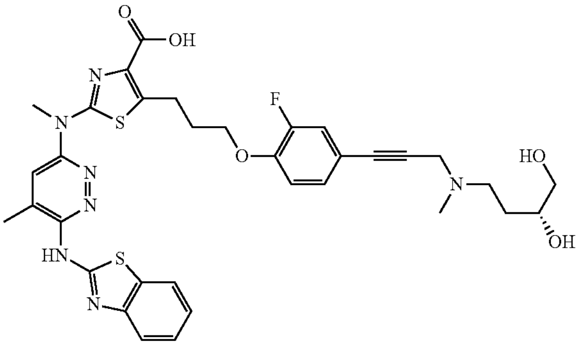 [SMILES: Cc1cc(N(C)c2nc(C(=O)O)c(CCCOc3ccc(C#CCN(C)CC[C@@H](O)CO)cc3F)s2)nnc1Nc1nc2ccccc2s1]
Example 289: 2-[[6-(1,3-benzothiazol-2-ylamino)-5-methyl-pyridazin-3-yl]-methyl-amino]-5-[3-[2-fluoro-4-[3-(4-hydroxybutylamino)prop-1-ynyl]phenoxy]propyl]thiazole-4-carboxylic acid
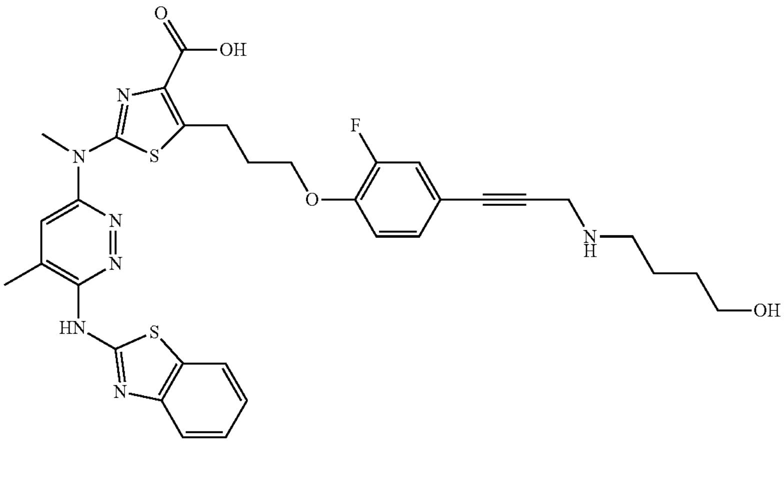 [SMILES: Cc1cc(N(C)c2nc(C(=O)O)c(CCCOc3ccc(C#CCNCCCCO)cc3F)s2)nnc1Nc1nc2ccccc2s1]

Example 290: 2-[[6-(1,3-benzothiazol-2-ylamino)-5-methyl-pyridazin-3-yl]-methyl-amino]-5-[3-[4-[3-[[(3R)-3,4-dihydroxybutyl]amino]prop-1-ynyl]-2-fluoro-phenoxy]propyl]thiazole-4-carboxylic acid

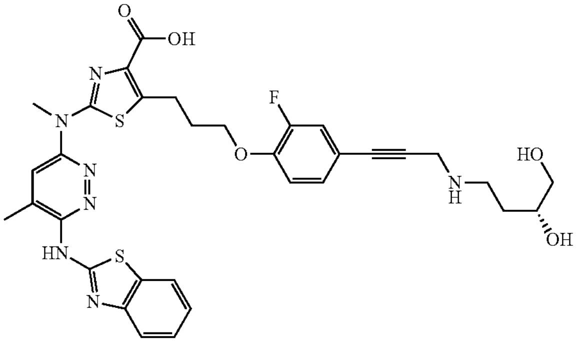 [SMILES: Cc1cc(N(C)c2nc(C(=O)O)c(CCCOc3ccc(C#CCNCC[C@@H](O)CO)cc3F)s2)nnc1Nc1nc2ccccc2s1]

PHARMACOLOGICAL STUDY

Example A: Fluorescence Polarisation Assay Data

Fluorescence polarization measures the rotation of a fluorescing species in solution, the larger the molecule the more polarized the fluorescence emission.

The fluorescent PUMA (UniProtKB® primary accession number Q9BXH1—SEQ ID:01) based probe Fluorescein-betaAla-Ahx-AREIGAQLRRMADDLNAQY-OH from Biopeptides binds to GST(1-218)-(FACTOR_XA)-hs BCLXL (2-209) having an aminoacid sequence (SEQ ID:02):

[MSPILGYWKIKGLVQPTRLLLEYLEEKYEEHLY-ERDEGDKWRNKKFELGLEFPNLPY YIDGDVKLTQS-MAIIRYIADKHNMLGGCPKERAEISMLE-GAVLDIRYGVSRIAYSKDF ETLKVDFLSKLPEMLKMFE-DRLCHKTYLNGDHVTHPDFM-LYDALDVVLYMDPMCL DAFPKLVCFKKRIEAIPQID-KYLKSSKYIAWPLQGWQATFGGGDHPPKSDLIEGRG IPE FEFSQSNRELANDFLSYKLSQKGYSWSQFSD-VEENRTEAPEGTESEMETPSAINGNPS WHLADSPAV-NGATGHSSSLDAREVIPMAAVKQALREAGDEFEL-RYRRAFSDLTSQL HITPGTAYQSFEQVVNELFRDGVNWGRIVAFFSFG-GALCVESVDKEMQVLVSRIAAW MATYLNDHLEP-WIQENGGWDTFVELYGNNAAAESRKGQER] (GST UniProtKB® primary accession number P08515 and BCLXL UniProtKB® primary accession number Q07817-1), resulting in an increase in anisotropy. If a compound is added which competitively binds to the same site as the probe, thereby releasing it, anisotropy decreases due to the increased amount of free probe.

An 11-point serial dilution of each compound was prepared in DMSO, the final buffer conditions were 10 mM 4-(2-hydroxyethyl)-1-piperazineethanesulfonic acid [HEPES], 150 mM NaCl, 0.05% Tween 20, pH 7.4 and 5% DMSO. The final protein concentration in the assay was 20 nM with the fluorescent probe present at 10 nM. The experiments were incubated for 2 hours at 23° C. before fluorescence polarization was measured on a Biotek SynergyNeo plate reader (Excitation 485 nm, emission 525 nm, parallel and perpendicular reads). The dose response curves were plotted with XL-Fit software using a 4-Parameter Logistic Model (Sigmoidal DoseResponse Model) and the inhibitory concentrations that gave a 50% increase in fluorescence intensity was determined ($IC_{50}$). The $K_I$ values were determined from the $IC_{50}$ values according to Cer et al, *Nucleic Acids Res,* 2009, Jul. 1: 37(WebServer issue): W441-W445.

The results are summarised in Table 1. They show that the compounds of the invention inhibit the interaction between the Bcl-xL protein and the fluorescent peptide described hereinbefore.

TABLE 1

| Example | Ki (M) |
|---|---|
| 1 | 3.1E−08 |
| 2 | 3.3E−07 |
| 3 | 1.9E−09 |
| 4 | 9.1E−07 |
| 5 | 1.8E−07 |
| 6 | 4.9E−07 |
| 7 | 7.2E−08 |
| 8 | 8.7E−08 |
| 9 | 4.0E−09 |
| 10 | 4.1E−07 |
| 11 | 6.0E−07 |
| 12 | 2.7E−08 |
| 13 | 3.8E−09 |
| 14 | 3.2E−09 |
| 15 | 3.7E−08 |
| 16 | 5.2E−08 |
| 17 | 2.2E−08 |
| 18 | 7.8E−08 |
| 19 | 3.0E−08 |
| 20 | 3.9E−08 |
| 21 | 7.5E−09 |
| 22 | 2.9E−09 |
| 23 | 4.0E−08 |
| 24 | 1.4E−07 |
| 25 | 9.9E−07 |
| 26 | 6.5E−06 |
| 27 | 3.1E−07 |
| 28 | 1.3E−07 |
| 29 | 3.3E−08 |
| 30 | 8.1E−08 |
| 31 | 2.6E−09 |
| 32 | 2.6E−07 |
| 33 | 6.4E−08 |
| 34 | 8.9E−09 |
| 35 | 5.9E−08 |
| 36 | 2.8E−08 |
| 37 | 1.5E−08 |
| 38 | 2.5E−04 |
| 39 | 5.4E−08 |
| 40 | 2.0E−08 |
| 41 | 3.7E−08 |
| 42 | 4.7E−09 |
| 43 | 1.9E−08 |
| 44 | 6.9E−08 |
| 45 | 1.4E−08 |
| 46 | 1.9E−07 |
| 47 | 2.3E−08 |
| 48 | 1.9E−06 |
| 49 | 8.1E−09 |
| 50 | 1.2E−09 |
| 51 | 6.4E−08 |
| 52 | 9.0E−08 |
| 53 | 1.5E−08 |
| 54 | 1.4E−09 |
| 55 | 8.2E−08 |
| 56 | >1E−05 |
| 57 | 3.5E−07 |
| 58 | 4.9E−08 |
| 59 | <1E−09 |
| 60 | 1.5E−09 |
| 61 | <1E−09 |
| 62 | <1E−09 |

TABLE 1-continued

| Example | Ki (M) |
|---|---|
| 63 | <1E−09 |
| 64 | 3.1E−08 |
| 65 | <1E−09 |
| 66 | 1.9E−09 |
| 67 | <1E−09 |
| 68 | 5.7E−09 |
| 69 | 4.2E−09 |
| 70 | 3.0E−08 |
| 71 | >1E−05 |
| 72 | 1.6E−07 |
| 73 | <1E−09 |
| 74 | 1.1E−09 |
| 75 | <1E−09 |
| 76 | <1E−09 |
| 77 | 1.1E−07 |
| 78 | 1.1E−07 |
| 79 | 9.2E−08 |
| 80 | 8.0E−08 |
| 81 | 1.6E−08 |
| 82 | <1E−09 |
| 83 | 3.2E−07 |
| 84 | 4.9E−08 |
| 85 | <1E−09 |
| 86 | 1.6E−07 |
| 87 | 5.3E−07 |
| 88 | 2.8E−09 |
| 89 | 1.6E−07 |
| 90 | <1E−09 |
| 91 | 6.4E−09 |
| 92 | 6.8E−08 |
| 93 | 6.8E−09 |
| 94 | 6.7E−08 |
| 95 | 2.4E−08 |
| 96 | 2.2E−07 |
| 97 | 1.3E−07 |
| 98 | 2.3E−09 |
| 99 | 2.4E−06 |
| 100 | 1.6E−09 |
| 101 | <1E−09 |
| 102 | 2.2E−07 |
| 103 | 1.4E−08 |
| 104 | 1.6E−08 |
| 105 | 3.8E−07 |
| 106 | 2.7E−08 |
| 107 | 1.3E−07 |
| 108 | <1E−09 |
| 109 | <1E−09 |
| 119 | <1E−09 |
| 123 | <1E−09 |
| 124 | <1E−09 |
| 127 | <1E−09 |
| 130 | <1E−09 |
| 134 | <1E−09 |
| 138 | 2.9E−08 |
| 139 | 6.4E−07 |
| 140 | <1E−09 |
| 141 | <1E−09 |
| 142 | 5.0E−08 |
| 143 | 6.2E−48 |
| 144 | <1E−09 |
| 145 | 1.8E−07 |
| 146 | <1E−09 |
| 149 | 13E−07 |
| 150 | <1E−09 |
| 151 | <1E−09 |
| 156 | 8.9E−07 |
| 157 | 1.2E−06 |
| 158 | 4.3E−08 |
| 159 | 1.8E−07 |
| 160 | 2.2E−07 |
| 161 | <1E−09 |
| 163 | <1E−09 |
| 164 | <1E−09 |
| 165 | <1E−09 |
| 166 | <1E−09 |
| 167 | <1E−09 |
| 168 | <1E−09 |
| 169 | <1E−09 |

TABLE 1-continued

| Example | Ki (M) |
|---|---|
| 170 | <1E−09 |
| 171 | <1E−09 |
| 172 | <1E−09 |

Example B: AlphaLISA Assay Data

AlphaLISA assay measures an increase in alpha signal upon binding biotinylated GST(1-218)-(FACTOR_XA)-hs BCLXL (2-209)(SEQ ID:02—GST UniProtKB® primary accession number P08515 and BCLXL UniProtKB® primary accession number Q07817-1) coupled to a Streptavidin labeled Alpha donor bead to N-terminally labeled peptide derived from BIM (Fluorescein-betaAla-Ahx-SEQID:05, wherein SEQ ID:05 is DMRPEIWIAQELRRIGDEANAYYARR) coupled to an Anti-FTIC AlphaLISA acceptor bead.

GST(1-218)(FACTOR_XA)-hs BCLXL (2-209) was biotinylated in 50 mM phosphate buffer using a 20 fold excess of EZ Link NHS-LC-Biotin (thermoFisher catalogue number 21336) overnight at 4° C.

The addition of a compound which binds competitively to the same site as the peptide will result in an decrease in the Alpha signal of the available donor bead-protein-peptide-acceptor bead complex due to displacement of the peptide.

An 11-point serial dilution of each compound was prepared in DMSO, the final buffer conditions were 10 mM 4-(2-hydroxyethyl)-1-piperazineethanesulfonic acid [HEPES], 150 mM NaCl, 0.05% Tween 20, pH 7.4 and 4% DMSO. The final protein concentration in the assay was 20 pM with the peptide present at 1 nM). Alpha beads were used at a final concentration of 5 ug/mL. The experiments were incubated for overnight at 23° C. after acceptor bead addition. Finally the donor bead is added and incubated for 2 hours at 23° C. before Alpha signal measured on a Biotek Synergy2 plate reader (Excitation 680 nm, emission 615 nm). The dose response curves were plotted with XL-Fit software using a 4-Parameter Logistic Model (Sigmoidal DoseResponse Model) and the inhibitory concentrations that gave a 50% increase in fluorescence intensity was determined ($IC_{50}$).

The results are summarised in Table 2.

TABLE 2

| Example | IC50 (M) |
|---|---|
| 3 | 9.6E−11 |
| 50 | 7.4E−12 |
| 54 | 2.5E−11 |
| 59 | 1.4E−10 |
| 60 | 9.6E−10 |
| 62 | 1.1E−10 |
| 63 | 1.0E−10 |
| 65 | 1.0E−09 |
| 73 | 7.7E−12 |
| 74 | 7.4E−11 |
| 76 | 7.7E−11 |
| 85 | 1.2E−08 |
| 89 | 1.5E−07 |
| 90 | 2.3E−11 |
| 91 | 5.3E−09 |
| 92 | 4.6E−08 |
| 93 | 6.4E−09 |
| 94 | 5.1E−08 |
| 95 | 2.2E−08 |
| 96 | 2.7E−07 |
| 97 | 2.1E−07 |

TABLE 2-continued

| Example | IC50 (M) |
|---|---|
| 98 | 1.8E−09 |
| 100 | 3.2E−11 |
| 101 | 2.2E−12 |
| 108 | 6.6E−12 |
| 109 | 1.1E−11 |
| 110 | 4.8E−10 |
| 111 | 2.7E−08 |
| 112 | 2.8E−11 |
| 113 | 2.8E−11 |
| 114 | 53E−12 |
| 115 | 8.9E−11 |
| 116 | 1.7E−11 |
| 117 | 9.9E−12 |
| 118 | 1.8E−11 |
| 119 | 6.0E−12 |
| 120 | 9.9E−11 |
| 121 | 5.8E−11 |
| 122 | 9.8E−12 |
| 123 | 4.0E−12 |
| 124 | 7.6E−12 |
| 125 | 8.6E−09 |
| 126 | 2.3E−11 |
| 127 | 6.6E−12 |
| 128 | 1.3E−11 |
| 130 | 5.4E−12 |
| 131 | 2.7E−09 |
| 132 | 7.7E−09 |
| 133 | 8.9E−09 |
| 134 | 5.3E−12 |
| 135 | 3.9E−09 |
| 136 | 7.7E−09 |
| 137 | 2.7E−10 |
| 138 | 1.1E−08 |
| 139 | 2.7E−07 |
| 140 | 2.4E−11 |
| 141 | 1.4E−11 |
| 142 | 1.0E−08 |
| 143 | 2.2E−08 |
| 144 | 1.4E−11 |
| 145 | 1.9E−07 |
| 146 | 2.2E−11 |
| 147 | 7.1E−12 |
| 148 | 5.7E−12 |
| 150 | 1.3E−11 |
| 151 | 5.0E−12 |
| 152 | 2.3E−09 |
| 153 | 8.0E−08 |
| 161 | 3.2E−11 |
| 162 | 1.9E−09 |
| 163 | 1.8E−10 |
| 164 | 7.1E−12 |
| 165 | 1.9E−11 |
| 166 | 9.2E−12 |
| 167 | 1.3E−11 |
| 168 | 1.2E−11 |
| 169 | 9.9E−12 |
| 170 | 1.4E−11 |
| 171 | 1.3E−11 |
| 172 | 7.8E−12 |
| 173 | 7.9E−12 |
| 174 | 6.0E−10 |

Example C: Quench Assay Data

Fluorescence quenching assay measures the change in fluorescence intensity of C-terminally Cy5-labeled BCL-xL protein, His-His-(EK)-hsBCLXL (2-197)[N197C] (UniProtKB® primary accession number Q07817-1) having an amino acid sequence (SEQ ID:03): [MHHHHHHHHGATG-STAGSGTAGSTGASGASTGGTGATH-HHHHHHHHDDDDKSPMGSQSN RELVVDFL-SYKLSQKGYSWSQFSDVEENRTEAPEGTESEMETPS AINGNPSWHLADSPAVN GATGHSSSLDAREVIP-MAAVKQALREAGDEFELRYR-RAFSDLTSQLHITPGTAYQSFEQVVN ELFRDGVNWGRIVAFFSFGGALCVESVD-KEMQVLVSRIAAWMATYLNDHLEPWIQENGG WDTFVELYG] which is linked in C-terminal region to the amino acid X which corresponds to a cysteine labeled on the sulfur with Sulfo-Cyanine5 from Lumiprobe GmbH catalogue number 13380, upon binding of a C-terminally labeled peptide derived from PUMA (UniProtKB® primary accession number Q9BXH1) having an aminoacid sequence (SEQ ID:04): [QWAREIGAQLRRMADDLNAQY] which is linked in C-terminal region to the amino acid X' where X' is cysteine labeled on the sulfur with TQ5WS from AAT Bioquest catalogue number 2079.

The addition of a compound which binds competitively to the same site as the peptide will result in an increase in the fluorescence intensity of the protein due to displacement of the fluorescence quencher.

An 11-point serial dilution of each compound was prepared in DMSO the final buffer conditions were 10 mM 4-(2-hydroxyethyl)-1-piperazineethanesulfonic acid [HEPES], 150 mM NaCl, 0.05% Tween 20, pH 7.4 and 5% DMSO. The final protein concentration in the assay was 1 nM with the peptide present at 400 nM. The experiments were incubated for 2 hours at 23° C. before fluorescence intensity was measured on a Biotek SynergyNeo plate reader (Excitation 620 nm, emission 680 nm). The dose response curves were plotted with XL-Fit software using a 4-Parameter Logistic Model (Sigmoidal DoseResponse Model) and the inhibitory concentrations that gave a 50% increase in fluorescence intensity was determined ($IC_{50}$). The $K_I$ values were determined from the $IC_{50}$ values according to Cer et al, *Nucleic Acids Res,* 2009, Jul. 1: 37(WebServer issue): W441-W445.

The results are summarised in Table 3.

TABLE 3

| Example | Ki (M) |
|---|---|
| 50 | 4.4E−12 |
| 62 | 6.0E−12 |
| 73 | 2.8E−12 |
| 74 | 6.1E−12 |
| 101 | 5.2E−13 |
| 108 | 5.9E−13 |
| 109 | 1.1E−12 |
| 114 | 1.1E−11 |
| 116 | 8.6E−12 |
| 117 | 6.6E−12 |
| 118 | 3.3E−11 |
| 119 | 5.5E−13 |
| 122 | 3.0E−12 |
| 123 | 8.4E−13 |
| 124 | 1.7E−12 |
| 127 | 6.8E−13 |
| 128 | 2.8E−11 |
| 130 | 3.7E−13 |
| 134 | 1.0E−12 |
| 141 | 5.5E−12 |
| 144 | 3.9E−12 |
| 146 | 1.2E−12 |
| 147 | 9.7E−12 |
| 148 | 1.2E−12 |
| 150 | 1.7E−12 |
| 151 | 8.5E−13 |
| 163 | 2.0E−11 |
| 164 | 1.9E−12 |
| 165 | 5.9E−12 |
| 166 | 2.6E−12 |
| 167 | 2.9E−12 |
| 168 | 2.6E−12 |
| 169 | 4.4E−12 |
| 170 | 5.0E−12 |

TABLE 3-continued

| Example | Ki (M) |
|---|---|
| 171 | 3.5E−12 |
| 172 | 2.6E−12 |
| 173 | 3.3E−12 |
| 174 | 4.3E−11 |
| 175 | 1.1E−12 |
| 176 | 1.1E−12 |
| 177 | 3.0E−12 |
| 178 | 7.4E−12 |
| 179 | 6.8E−12 |
| 180 | 5.2E−12 |
| 181 | 4.3E−12 |
| 182 | 7.4E−12 |
| 183 | 7.8E−12 |
| 184 | 3.6E−12 |
| 185 | 1.2E−12 |
| 186 | 1.0E−12 |
| 187 | 2.5E−12 |
| 188 | 1.8E−12 |
| 189 | 7.4E−12 |
| 190 | 3.2E−12 |
| 191 | 2.8E−12 |
| 192 | 2.9E−12 |
| 193 | 1.3E−12 |
| 194 | 3.2E−12 |
| 195 | 1.8E−12 |
| 196 | 9.0E−13 |
| 197 | 1.3E−12 |
| 198 | 7.3E−12 |
| 199 | 1.0E−12 |
| 200 | 7.7E−12 |
| 201 | 1.9E−12 |
| 202 | 8.9E−13 |
| 203 | 2.2E−12 |
| 204 | 6.0E−12 |
| 205 | 2.3E−12 |
| 206 | 9.0E−12 |
| 207 | 3.7E−12 |
| 208 | 8.8E−12 |
| 209 | 2.3E−11 |
| 210 | 8.5E−13 |
| 211 | 6.5E−12 |
| 212 | 1.0E−12 |
| 213 | 1.5E−12 |
| 214 | 4.0E−12 |
| 215 | 3.1E−12 |
| 216 | 4.0E−12 |
| 217 | 4.1E−12 |
| 218 | 1.2E−12 |
| 219 | 8.2E−13 |
| 220 | 3.5E−12 |
| 221 | 1.7E−12 |
| 222 | 1.4E−12 |
| 223 | 1.8E−12 |
| 224 | 2.0E−12 |
| 225 | 3.5E−12 |
| 226 | 5.3E−12 |
| 227 | 3.5E−12 |
| 228 | 2.2E−10 |
| 229 | 1.4E−12 |
| 230 | 1.4E−12 |
| 231 | 1.3E−12 |
| 232 | 1.7E−12 |
| 233 | 4.3E−12 |
| 234 | 1.6E−12 |
| 235 | 1.1E−12 |
| 237 | 1.8E−12 |
| 238 | 4.5E−12 |
| 239 | 2.7E−12 |
| 240 | 7.3E−12 |
| 241 | 9.4E−12 |
| 242 | 7.8E−12 |
| 243 | 5.0E−12 |
| 247 | 1.2E−12 |
| 250 | 2.2E−12 |
| 253 | 7.0E−11 |
| 267 | 1.6E−11 |
| 268 | 2.3E−12 |
| 269 | 2.7E−12 |
| 270 | 3.0E−12 |
| 271 | 3.3E−12 |
| 272 | 2.3E−12 |

The results of Tables 1-3 show that the compounds of the invention are potent inhibitors of the Bcl-xL protein.

Example D: Effect of Bcl-xL Inhibitors in MOLT-4 or H146 Cell Viability Using MTT Assay MTT colorimetric assay is based on the mitochondrial reduction of tetrazolium salt by living cells. The viable cell number is proportional to the production of formazan salts, which can be read spectrophotometrically at 540 nm.

MOLT-4 and H146 cells were purchased from ATCC and cultivated in RPMI 1640 supplemented with 10% heat inactivated fetal bovine serum, penicillin (100 IU/ml), streptomycin (100 µg/ml) and L-glutamine (2 mM). Cells were cultured at 37° C. in a humidified atmosphere containing 5% $CO_2$. Cells were seeded in 96 microwell plates (150 µL per well) and exposed to the compounds for 48 h (3.16 fold serially diluted; 9 concentrations each, triplicates). At the end of incubation time, 15 µL of MTT solution (5 mg/ml) were added per well and the cells were incubated for another 4 h. Then, 100 µL of 10% Sodium Dodecyl Sulfate (SDS)/HCl 10 mM were added per well and the plate was incubated overnight, before measurement of optical density at 540 nm. $IC_{50}$s were calculated using standard four-parametric curve fitting. $IC_{50}$ is defined as the compound concentration at which the MTT signal is reduced to 50% of that measured for the control. Results represent the mean of at least 2 independent experiments and are presented in Table 4 below.

TABLE 4

| Example | H146 IC50 (M) | MOLT-4 IC50 (M) |
|---|---|---|
| 1 | 1.5E−05 | #N/A |
| 2 | 1.25E−05 | #N/A |
| 3 | 4.2E−08 | 9E−08 |
| 5 | 8.21E−06 | #N/A |
| 6 | >4.49E−05 | #N/A |
| 7 | >1.5E−05 | #N/A |
| 8 | 1.05E−05 | #N/A |
| 9 | 2.07E−07 | 2.32E−06 |
| 10 | 8.31E−06 | #N/A |
| 12 | 9.13E−07 | 1.62E−06 |
| 13 | 2.92E−07 | 2.23E−06 |
| 14 | 2.11E−06 | #N/A |
| 15 | >1.5E−05 | #N/A |
| 16 | 8.04E−06 | #N/A |
| 17 | 1.34E−05 | 7.88E−06 |
| 18 | >1.5E−05 | #N/A |
| 19 | >=1.28E−05 | #N/A |
| 20 | 3.35E−06 | 7.21E−06 |
| 21 | 9.58E−06 | #N/A |
| 22 | 2.13E−06 | #N/A |
| 23 | >=1.27E−05 | 1.3E−05 |
| 24 | 6.93E−06 | 3.31E−06 |
| 25 | 3.18E−06 | 7.13E−06 |
| 26 | >1.5E−05 | >1.5E−05 |
| 27 | >1.5E−05 | >1.3E−05 |
| 28 | >1.5E−05 | >1.5E−05 |
| 29 | >1.5E−05 | >1.5E−05 |
| 30 | >1.5E−05 | 8.67E−06 |
| 31 | 4.19E−06 | 2.34E−06 |
| 32 | >=7.42E−06 | 1.33E−05 |
| 33 | 4.37E−06 | 6.25E−06 |
| 34 | 5.32E−06 | 3.89E−06 |

TABLE 4-continued

| Example | H146 IC50 (M) | MOLT-4 IC50 (M) |
|---|---|---|
| 35 | 2.33E−06 | 3.7E−06 |
| 36 | 1.99E−06 | 3.47E−06 |
| 37 | 1.1E−05 | 7.39E−06 |
| 38 | >1.5E−05 | >1.5E−05 |
| 39 | >1.5E−05 | >1.5E−05 |
| 40 | 3.8E−06 | 1.49E−06 |
| 41 | >=9.76E−06 | >1.3E−05 |
| 42 | 2.04E−06 | 1.02E−06 |
| 44 | >1.5E−05 | >1.5E−05 |
| 45 | >=1.18E−05 | 1.17E−05 |
| 46 | >1.5E−05 | >1.5E−05 |
| 47 | >=9.62E−06 | >1.5E−05 |
| 49 | >1.5E−05 | >1.5E−05 |
| 50 | 2.84E−09 | 4.62E−10 |
| 51 | >1.5E−05 | >1.5E−05 |
| 52 | 1.3E−05 | 8.36E−06 |
| 53 | 1.65E−06 | 7.01E−07 |
| 54 | 3.52E−08 | 5.07E−09 |
| 56 | >1.5E−05 | >1.5E−05 |
| 57 | 1.34E−05 | >1.5E−05 |
| 58 | >1.5E−05 | >1.5E−05 |
| 59 | 2.71E−07 | 7.61E−08 |
| 60 | 5.8E−06 | 2.74E−06 |
| 61 | 5.93E−07 | 1.92E−07 |
| 62 | 4.66E−09 | 4.44E−10 |
| 63 | 2.05E−07 | 8.53E−08 |
| 64 | 2.24E−08 | 3.59E−06 |
| 65 | 8.65E−07 | 2.36E−07 |
| 66 | 1.16E−06 | 5.27E−07 |
| 67 | 7.1E−07 | 7.54E−07 |
| 68 | 2.6E−06 | 2.79E−07 |
| 69 | 6.86E−07 | 4.46E−07 |
| 70 | >1.5E−05 | >4.16E−05 |
| 71 | >1.5E−05 | >1.5E−05 |
| 73 | 4.8E−09 | 1.51E−09 |
| 74 | 6.78E−09 | 6.72E−09 |
| 75 | >1.5E−05 | 2.92E−06 |
| 76 | 1.13E−08 | 2.37E−09 |
| 77 | >=1.49E−05 | 6.59E−06 |
| 78 | >1.5E−05 | >1.5E−05 |
| 82 | 9.88E−08 | 6.83E−08 |
| 83 | >1.5E−05 | >1.5E−05 |
| 84 | >1.5E−05 | 7.57E−06 |
| 85 | >1.5E−05 | >1.5E−05 |
| 86 | >=1.24E−05 | 1.46E−05 |
| 87 | >1.5E−05 | >1.5E−05 |
| 88 | 1.1E−05 | 1.61E−06 |
| 89 | >1.5E−05 | 1.31E−05 |
| 90 | 2.01E−07 | 2.33E−08 |
| 91 | 5.39E−06 | 1.13E−06 |
| 92 | >1.5E−05 | >1.5E−05 |
| 93 | >1.5E−05 | 9.4E−06 |
| 94 | 4.07E−06 | > =1E−05 |
| 95 | 9.27E−06 | 5.01E−06 |
| 98 | >1.5E−05 | >1.5E−05 |
| 100 | 3.86E−08 | 1.26E−08 |
| 101 | 1.19E−06 | 4.83E−07 |
| 102 | >1.5E−05 | >1.5E−05 |
| 105 | >1.5E−05 | >1.5E−05 |
| 106 | >1.5E−05 | >1.5E−05 |
| 108 | 2.23E−08 | 4.67E−08 |
| 109 | 6.38E−09 | 1.98E−08 |
| 112 | 3.09E−08 | 7.75E−08 |
| 113 | 1.3E−08 | 2.57E−08 |
| 114 | 1.58E−09 | 3.81E−09 |
| 115 | >1.5E−07 | >1.5E−07 |
| 116 | 1.91E−08 | 3.06E−09 |
| 117 | 4.96E−08 | 4.86E−07 |
| 118 | 3.26E−08 | 0.000000096 |
| 119 | 2.14E−08 | 9.74E−08 |
| 120 | 2.8E−07 | 5.57E−07 |
| 122 | 5.14E−08 | 0.00000028 |
| 123 | 6.25E−09 | 1.65E−08 |
| 124 | 5.06E−08 | 1.92E−08 |
| 127 | 9.04E−09 | 1.13E−08 |
| 128 | 2.08E−08 | 1.81E−08 |
| 130 | 2.01E−07 | 1.08E−07 |

TABLE 4-continued

| Example | H146 IC50 (M) | MOLT-4 IC50 (M) |
|---|---|---|
| 134 | 1.91E−09 | 7.83E−10 |
| 135 | 5.29E−06 | 3.24E−06 |
| 137 | 3.2E−07 | 6.14E−08 |
| 140 | 1.42E−07 | 2.34E−08 |
| 144 | 145E−07 | 4.3E−07 |
| 146 | 9.71E−07 | 6.68E−07 |
| 150 | 1.68E−08 | 1.36E−07 |
| 151 | #N/A | 1.94E−07 |
| 161 | 3.02E−08 | 3.23E−09 |
| 162 | 6.59E−06 | 3.17E−06 |
| 163 | 1.04E−06 | 9.62E−08 |
| 164 | 3.46E−08 | 1.29E−08 |
| 165 | 2.11E−07 | 4.3E−07 |
| 166 | 1.42E−07 | 1.72E−07 |
| 167 | 4.32E−07 | 4E−07 |
| 168 | #N/A | 1.78E−07 |
| 169 | 7.31E−08 | 1.06E−07 |
| 170 | 1.56E−07 | 1.54E−07 |
| 171 | 1.1E−07 | 4.11E−07 |
| 172 | 4.02E−08 | 1.6E−07 |
| 173 | 2.08E−07 | 1.27E−07 |
| 174 | 1.26E−05 | 1.66E−06 |
| 175 | 7.5E−08 | 2.04E−07 |
| 176 | 1.24E−07 | 7.62E−08 |
| 177 | 3.63E−08 | 0.000000225 |
| 182 | 1.99E−07 | 1.29E−07 |
| 183 | 1.87E−07 | 4.65E−08 |
| 184 | 1.07E−07 | 1.84E−07 |
| 185 | 7E−09 | 1.68E−08 |
| 186 | 1.69E−08 | 8.53E−08 |
| 187 | 234E−07 | 1.03E−07 |
| 188 | 5.44E−09 | 341E−08 |
| 189 | 9.48E−08 | 1.71E−07 |
| 190 | 7.83E−08 | 5.49E−08 |
| 191 | 8.38E−08 | 2.2E−06 |
| 192 | 1.19E−08 | 9.64E−08 |
| 193 | 6.5E−08 | 9.25E−08 |
| 194 | 2.7E−08 | 1.29E−07 |
| 195 | 5.25E−07 | 5.29E−07 |
| 196 | 1.62E−06 | 8.79E−07 |
| 197 | 4.39E−08 | #N/A |
| 198 | 142E−08 | 1.59E−09 |
| 199 | 6.41E−08 | 2.59E−08 |
| 200 | 1.15E−07 | 6.95E−07 |
| 201 | 7.53E−08 | 4.17E−07 |
| 202 | 7.48E−08 | 6.11E−07 |
| 203 | 3.9E−09 | 7.53E−10 |
| 204 | 7.3E−09 | 7.03E−10 |
| 205 | <=5.93E−09 | 3.74E−10 |
| 206 | 1.5E−08 | 1.48E−09 |
| 207 | 1.08E−06 | 3.28E−06 |
| 208 | 7.33E−09 | 7.53E−10 |
| 210 | 2.14E−08 | 2.03E−08 |
| 211 | 6.68E−08 | 4.84E−07 |
| 212 | 3.24E−06 | 2.88E−06 |
| 213 | 7.28E−08 | 9.36E−08 |
| 214 | 2.67E−08 | 2.25E−08 |
| 215 | 1.74E−07 | 4.06E−07 |
| 216 | 2.22E−07 | 1.46E−07 |
| 217 | 8.62E−08 | 1.8E−07 |
| 218 | 8.91E−07 | 2.7E−07 |
| 219 | 1.29E−07 | 1.27E−06 |
| 220 | 2.21E−07 | 9.84E−07 |
| 221 | 9.44E−08 | 2.95E−08 |
| 222 | 3.24E−08 | 6.1E−08 |
| 223 | 7.46E−09 | 3.13E−09 |
| 224 | 1.16E−06 | 2.18E−06 |
| 225 | 3.51E−07 | 1.08E−06 |
| 226 | #N/A | 7.52E−07 |
| 227 | #N/A | 8.02E−07 |
| 228 | >3E−05 | #N/A |
| 229 | 4.37E−07 | 1.64E−06 |
| 230 | 1.38E−06 | 2.18E−06 |
| 231 | 1.61E−06 | 1.19E−06 |
| 233 | 2.55E−09 | 8.79E−10 |
| 234 | 1.5E−08 | 3.8E−09 |
| 235 | 4.13E−07 | 4.13E−07 |

TABLE 4-continued

| Example | H146 IC50 (M) | MOLT-4 IC50 (M) |
|---|---|---|
| 237 | #N/A | 7.5E−07 |
| 238 | #N/A | 1.49E−07 |
| 239 | #N/A | 3.14E−07 |
| 240 | #N/A | 1.32E−06 |
| 241 | #N/A | 1.19E−06 |
| 242 | #N/A | 5.25E−07 |
| 243 | #N/A | 1.12E−07 |
| 247 | #N/A | 2.81E−09 |
| 250 | #N/A | 2.46E−10 |
| 253 | #N/A | 3.17E−08 |
| 267 | #N/A | 4.38E−08 |
| 268 | #N/A | 2.55E−10 |
| 269 | #N/A | 1.82E−10 |
| 270 | #N/A | 1.99E−10 |
| 271 | #N/A | 3.08E−08 |
| 272 | #N/A | 2.84E−10 |

These data show that the majority of these compounds are active in cells and can induce a dose dependent decrease in the viability of H146 and Molt-4 cell lines.

Example E: Pharmacodynamics and Tumor Regression Study

The in vivo therapeutic and pharmacodynamic effects of Bcl-xL-targeting small molecules were determined in MOLT-4 T-cell Acute Lymphoblastic Leukemia (T-ALL) model upon intravenous (IV) administration. The tested compounds were formulated in Hydroxypropyl-β-Cyclodextrin 20%/Hydrogen Chloride 25 mM (HPBCD/HCl).

Materials and Methods

MOLT-4 cells (ATCC No. CRL-1582) were cultured in RPMI supplemented with 10% FBS. Cells were re-suspended in 50% matrigel (BD Biosciences) and 0.1 mL containing $5\times10^6$ cells was subcutaneously inoculated into the right flank of female NOD SCID mice (Charles River). For efficacy studies, when tumors reached the appropriate volume, mice were randomized (8 animals per group) using Easy stat software. Control vehicle (HPBCD/HCl), Example 73 (3.75 or 7.5 mg/kg) or Example 100 (3.75 mg/kg) were injected IV (twice weekly for 3 weeks—Q3D6). Mice body weight was monitored three times a week and tumor size was measured using electronic calipers. Tumor volume was estimated by measuring the minimum and maximum tumor diameters using the formula: (minimum diameter)$^2$ (maximum diameter)/2. At the end of the treatment cycle (day 17), tumor growth inhibition was calculated using the formula:

$$\left(1-\frac{\text{Median}(TV \text{ at } Dx \text{ in treated group})}{\text{Median}(TV \text{ at } Dx \text{ in Control group})}\right)\times 100$$

Response was evaluated as follows: CR (Complete Response) if tumor size was ≤25 $mm^3$ for at least three consecutive measurements, PR (Partial Response) if tumor size was comprised between 25 $mm^3$ and half of the starting size for at least three consecutive measurements. Mice were sacrificed at the first measurement for which tumor volume exceeded 2000 $mm^3$ or at the first signs of animal health deterioration.

For pharmacodynamics studies, when tumors reached the appropriate volume, mice were randomized (3 animals per group) using Easy stat software. Control vehicle (HPBCD/HCl) or Bcl-xL-targeting small molecules were injected IV (once per day—QD) at 7.5 mg/kg. Tumor samples were collected 6 h after dosing and lysed (10 mM HEPES pH 7.4, 142.5 mM KCl, 5 mM $MgCl_2$, 1 mM EDTA, 1% NP40, protease and phosphatase inhibitors cocktails—Calbiochem). Cleared lysates were prepared for immunodetection of cleaved PARP and Caspase 3 by using the MSD apoptosis panel whole cell lysate kit (MSD) in 96-well plates according to manufacturer's instructions, and were analyzed on the QuickPlex SQ 120. Whole blood samples were analyzed on the Hematology Analyzer Coulter Ac·T diff (Beckman Coulter).

All experiments were conducted in accordance with the French regulations in force after approval by Servier Research Institute (IdRS) Ethical Committee. NOD SCID mice were maintained according to institutional guidelines.

Results

Efficacy of Example 73 and Example 100 on MOLT-4 xenografts is illustrated in Table 5. Treatment was started 12 days post tumor cells inoculation (average size: 214 $mm^3$). Vehicle (HPBCD/HCl), Example 73 (3.75 and 7.5 mg/kg) or Example 100 (3.75 mg/kg) were dosed IV each 3 days for a total of 6 administrations.

On day 17 after treatment start, the Tumor Growth Inhibition (% TGI) of Example 73 was 56.9% at 3.75 mg/kg and 83.3% at 7.5 mg/kg ($p<0.05$), as depicted in Table 5. At the same time-point, the % TGI induced by Example 100 at 3.75 mg/kg was 64.6% ($p<0.05$).

No clinically relevant body weight loss due to the treatment was observed.

TABLE 5

MOLT-4 tumor growth inhibition upon treatment with Example 73 (3.75 and 7.5 mg/kg, administered IV, Q3D6) or Example 100 (3.75 mg/kg, administered IV, Q3D6).

| Compound tested | Dow (mg/kg) | % TGI (day 17) |
|---|---|---|
| Example 73 | 3.75 | 56.9* |
| Example 73 | 7.5 | 83.3* |
| Example 100 | 3.75 | 64.6* |

*p value <0.05 compared to control group.

The effect of Bcl-xL-targeting small molecules on apoptosis induction in MOLT-4 tumor cells and number of circulating platelets is illustrated in Table 6. Treatment was started 18 days post tumor cells inoculation (average size: 349 $mm^3$). Vehicle (HPBCD/HCl), Example 74, Example 76 and Example 73 (7.5 mg/kg) were dosed once IV and samples were collected 6 h later. All the compounds showed an induction of apoptosis markers, namely cleaved PARP (between 14.2-26.6-fold over control) and cleaved Caspase 3 (between 4.7-5.1-fold over control) cleavage. In addition, given the well-described role of Bcl-xL in regulating platelets life-span, all tested compounds caused a significant reduction in platelet numbers (to 2-4% of control values).

TABLE 6

Cleaved PARP and Cleaved Caspase 3 in tumor cells and platelet loss in MOLT-4-grafted female NOD SCID mice 6 h after treatment with indicated compounds at 7.5 mg/kg, administered IV.

| Compound tested | Dose (mg/kg) and route | Time-point (h) | Cleaved PARP (fold increase over control) | Cleaved Caspase 3 (fold increase over control) | Platelet count ($\times 10^3/\mu l$) | % remaining platelets (vs vehicle) |
|---|---|---|---|---|---|---|
| Example 74 | 7.5, IV | 6 | 17.1 | 5.1 | 18 | 2 |
| Example 76 | 7.5, IV | 6 | 14.2 | 4.9 | 40 | 3 |
| Example 73 | 7.5, IV | 6 | 21.4 | 4.7 | 51 | 4 |

In conclusion, we show here that the Bcl-xL-targeting small molecules described in Examples 73, 74, 76 and 100 are active in vivo after intravenous administration. We observed tumor regression, apoptosis induction in tumor cells and a strong reduction in circulating platelets, in agreement with the previously described role of Bcl-xL in apoptosis control and platelets life-span regulation (Youle and Strasser, *Nat. Rev. Mol. Cell Biol.* 2008 January; 9(1): 47-59; Zhang et al., *Cell Death Differ.* 2007 May; 14(5): 943-51; Mason et al., *Cell* 2007 Mar. 23; 128(6):1173-86). In addition, no clinically relevant body weight loss was observed upon treatment with efficacious doses and platelets loss was recovered after treatment discontinuation (data not shown). Altogether, these data indicate that there is a possible therapeutic margin for the use of these Bcl-xL-targeting small molecules in cancer treatment.

Example F: In Vivo Pharmacodynamic Profile of the Compounds of Formula (I)

The pharmacokinetic profile of the compounds of formula (I) is evaluated in rodent (mouse, rat) after PO and/or IV route. The formulation is selected based on the physico-chemical properties of the tested drug as well as the route of administration. A single dose of the drug (<5 mg/kg) prepared in the adapted formulation is administered by IV (bolus or 10 min infusion) or PO (gavage) route to animals (3 animals/route). Blood samples from each animal (up to 6 samples/animal) are collected over 24 h after dosing and plasma concentrations of the tested compound are determined after extraction followed by a liquid chromatography coupled with tandem mass spectrometry detection (LC/MS-MS).

In some cases, the following experimental protocol is used to determine the pharmacokinetic profile of the compounds of the invention in the Wistar rat:

The drug is prepared in a formulation composed by a mixture of polyethylene glycol 300/anhydrous Ethanol/NaCl 0.9% (40/10/50 v/v/v). The formulation is administered by IV route to male Wistar rat (3 animals) at a dose of 0.75 mg/kg (10 min inf, 5 mL/kg). Blood samples are taken at the following time points from each animal: end of infusion (10 min), 0.5 h, 1 h, 3h, 6 h and 24 h after dosing. The plasma concentrations of the tested compound are determined after extraction followed by a liquid chromatography coupled with tandem mass spectrometry detection (LC/MS-MS).

The lower limit of quantification is 2.5 ng/mL.

The results allow to rank the compounds of the invention based on their plasma exposure, elimination rate constant, clearance and volume of distribution in order to evaluate the therapeutic range of the compounds in animal model.

The invention claimed is:

1. A compound of formula (I):

(I)

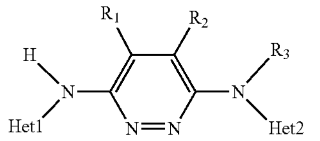

wherein:

$R_1$ and $R_2$, independently of one another, represent a group selected from: hydrogen; linear or branched C1-$C_6$alkyl optionally substituted by a hydroxyl or a $C_1$-$C_6$alkoxy group; $C_3$-$C_6$cycloalkyl; trifluoromethyl; and linear or branched $C_1$-$C_6$alkylene-heterocycloalkyl wherein the heterocycloalkyl group is optionally substituted by a linear or branched $C_1$-$C_6$alkyl group;

or $R_1$ and $R_2$, together with the carbon atoms carrying them, form a $C_3$-$C_6$cycloalkylene group, $R_3$ represents a group selected from: hydrogen; $C_3$-$C_6$cycloalkyl; linear or branched $C_1$-$C_6$alkyl; $—X_1—NR_aR_b$; $—X_1—N^+R_aR_bR_c$; $—X_1—O—R_c$; $—X_1—COOR_c$; $—X_1—PO(OH)_2$; $—X_1—SO_2(OH)$; $—X_1—N_3$ and:

$—X_1—\equiv CH$, $R_a$ and $R_b$, independently of one another, represent a group selected from: hydrogen; heterocycloalkyl; $—SO_2$-phenyl, wherein the phenyl may be substituted by a linear or branched $C_1$-$C_6$alkyl; linear or branched $C_1$-$C_6$alkyl optionally substituted by one or two hydroxyl groups; $C_1$-$C_6$alkylene-$SO_2OH$; $C_1$-$C_6$alkylene-$SO_2O$; $C_1$-$C_6$alkylene-COOH; $C_1$-$C_6$alkylene-$PO(OH)_2$; $C_1$-$C_6$alkylene-$NR_dR_e$; $C_1$-$C_6$alkylene-$N^+R_dR_eR_f$; $C_1$-$C_6$alkylene-phenyl, wherein the phenyl may be substituted by a $C_1$-$C_6$alkoxy group; and the group:

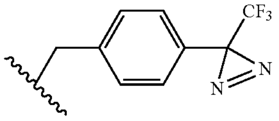

or $R_a$ and $R_b$, together with the nitrogen atom carrying them, form a cycle $B_1$;

or $R_a$, $R_b$ and $R_c$, together with the nitrogen atom carrying them, form a bridged $C_3$-$C_8$heterocycloalkyl, $R_c$, $R_d$, $R_e$, $R_f$, independently of one another, represent hydrogen or linear or branched $C_1$-$C_6$alkyl, or $R_d$ and $R_e$, together with the nitrogen atom carrying them, form a a cycle $B_2$, or $R_d$, $R_e$ and $R_f$, together with the nitrogen atom carrying them a bridged $C_3$-$C_8$heterocycloalkyl, $Het_1$ represents

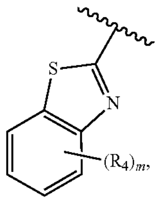

$Het_2$ represents a group selected from:

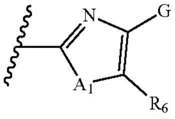

,

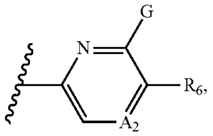

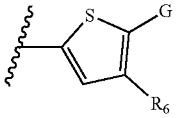

and

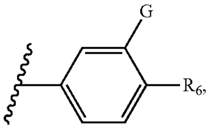

$A_1$ represents —NH—, —N($C_1$-$C_3$alkyl), O, S or Se, $A_2$ represents N, CH or C($R_5$), G is selected from:

$—C(O)OR_{G3}$, $—C(O)NR_{G1}R_{G2}$, $—C(O)R_{G2}$, $—NR_{G1}C(O)R_{G2}$, $—NR_{G1}C(O)NR_{G1}R_{G2}$, $—OC(O)NR_{G1}R_{G2}$, $—NR_{G1}C(O)OR_{G3}$, $—C({=}NOR_{G1})NR_{G1}R_{G2}$, $—NR_{G1}C({=}NCN)NR_{G1}R_{G2}$, $—NR_{G1}S(O)$ $2NR_{G1}R_{G2}$, $—S(O)_2R_{G3}$, $—S(O)_2NR_{G1}R_{G2}$, $—NR_{G1}S(O)_2R_{G2}$, $—NR_{G1}C({=}NR_{G2})NR_{G1}R_{G2}$, $—C({=}S)NR_{G1}R_{G2}$, $—C({=}NR_{G1})NR_{G1}R_{G2}$, halogen, $—NO_2$, and —CN, wherein:

$R_{G1}$ and $R_{G2}$, at each occurrence, are each independently selected from the group consisting of hydrogen, $C_1$-$C_6$alkyl optionally substituted by 1 to 3 halogen atoms, $C_2$-$C_6$alkenyl, $C_2$-$C_6$alkynyl, $C_3$-$C_6$cycloalkyl, phenyl and $—(CH_2)_{1-4}$-phenyl;

$R_{G3}$ is selected from the group consisting of $C_1$-$C_6$alkyl optionally substituted by 1 to 3 halogen atoms, $C_2$-$C_6$alkenyl, $C_2$-$C_6$alkynyl, $C_3$-$C_6$cycloalkyl, phenyl and $—(CH_2)_{1-4}$-phenyl; or $R_{G1}$ and $R_{G2}$, together with the atom to which each is attached, form a $C_3$-$C_8$heterocycloalkyl; or G is selected from:

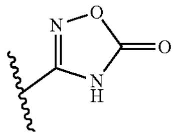, 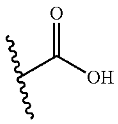, 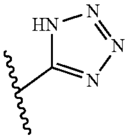,

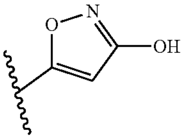, 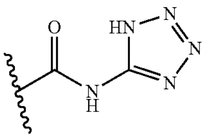,

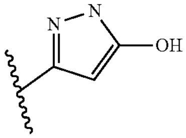, 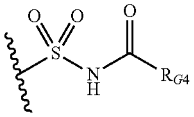,

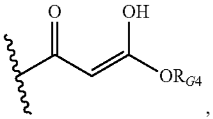, 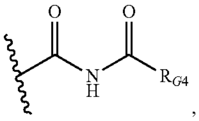,

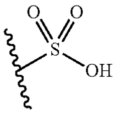, 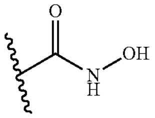, 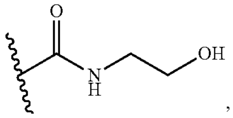,

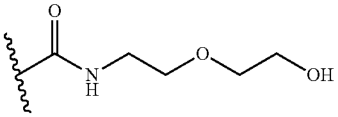, 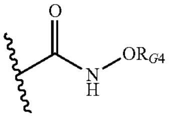,

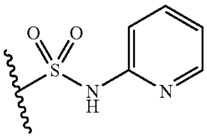, 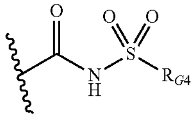 and

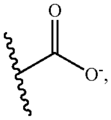

wherein $R_{G4}$ is selected from $C_1$-$C_6$alkyl optionally substituted by 1 to 3 halogen atoms, $C_2$-$C_6$alkenyl, $C_2$-$C_6$alkynyl and $C_3$-$C_6$cycloalkyl, $R_4$ represents hydrogen, fluorine, chlorine, bromine, methyl, hydroxyl or methoxy, $R_5$ represents a group selected from: $C_1$-$C_6$alkyl optionally substituted by 1 to 3 halogen atoms; $C_2$-$C_6$alkenyl; $C_2$-$C_6$alkynyl; halogen and —CN, $R_6$ represents a group selected from:

hydrogen;

—$C_2$-$C_6$alkenyl;

—$X_2$—O—$R_7$;

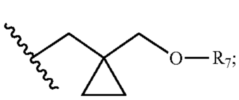

—$X_2$—$NSO_2$—$R_7$;

—C═C($R_9$)—$Y_1$—O—$R_7$;

$C_3$-$C_6$cycloalkyl;

$C_3$-$C_6$heterocycloalkyl optionally substituted by a hydroxyl group;

$C_3$-$C_6$cycloalkylene-$Y_2$—$R_7$;

$C_3$-$C_6$heterocycloalkylene-$Y_2$—$R_7$ group; and a heteroarylene-$R_7$ group optionally substituted by a linear or branched $C_1$-$C_6$alkyl group, $R_7$ represents a group selected from: linear or branched $C_1$-$C_6$alkyl group; ($C_3$-$C_6$)cycloalkylene-$R_8$; or $R_7$ represents:

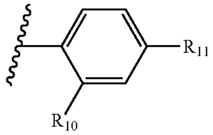, 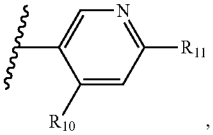,

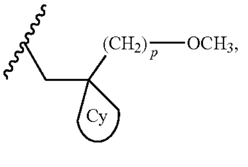

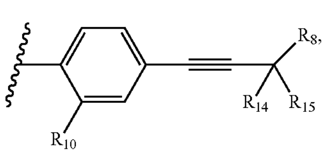

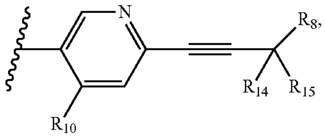

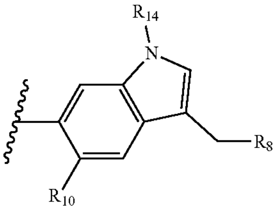, 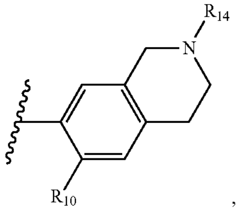,

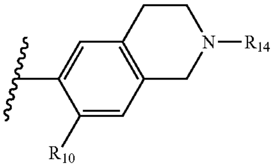, 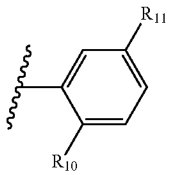,

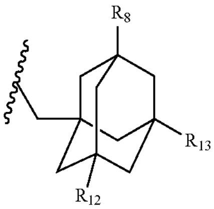, 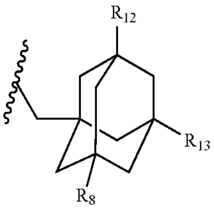,

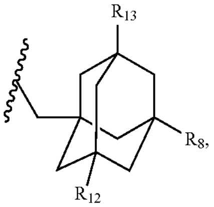

wherein Cy represents a $C_3$-$C_8$cycloalkyl, $R_8$ represents a group selected from: hydrogen; linear or branched $C_1$-$C_6$alkyl, $-NR'_aR'_b$; $-NR'_a-CO-OR'_c$; $-NR'_a-CO-R'_c$; $-N^+R'_aR'_bR'_c$; $-O-R'_c$; $-NH-X'_2-N^+R'_aR'_bR'_c$; $-O-X'_2-NR'_aR'_b$, $-X'_2-NR'_aR'_b$, $-NR'_c-X'_2-N_3$ and:

$$-NR'_c-X'_2-\equiv CH,$$

$R_9$ represents a group selected from linear or branched $C_1$-$C_6$alkyl, trifluoromethyl, hydroxyl, halogen, $C_1$-$C_6$alkoxy, $R_{10}$ represents a group selected from hydrogen, fluorine, chlorine, bromine, $-CF_3$ and methyl, $R_{11}$ represents a group selected from hydrogen, $C_1$-$C_3$alkylene-$R_8$, $-O-C_1$-$C_3$alkylene-$R_8$, $-CO-NR_hR_i$ and $-CH{=}CH-C_1$-$C_4$alkylene-$NR_hR_i$, $-CH{=}CH-CHO$, $C_3$-$C_8$cycloalkylene-$CH_2-R_8$, and $C_3$-$C_8$heterocycloalkylene-$CH_2-R_8$, $R_{12}$ and $R_{13}$, independently of one another, represent hydrogen or methyl, $R_{14}$ and $R_{15}$, independently of one another, represent a hydrogen or a methyl group, or $R_{14}$ and $R_{15}$, together with the carbon atom carrying them, form a a cyclohexyl group, $R_h$ and $R_i$, independently of one another, represent hydrogen or linear or branched $C_1$-$C_6$alkyl, $X_1$ and $X_2$, independently of one another, represent a linear or branched $C_1$-$C_6$alkylene group optionally substituted by one or two groups selected from trifluoromethyl, hydroxyl, halogen and $C_1$-$C_6$alkoxy, $X'_2$ represents linear or branched $C_1$-$C_6$alkylene, $R'_a$ and $R'_b$, independently of one another, represent a group selected from: hydrogen; heterocycloalkyl; $-SO_2$-phenyl, wherein the phenyl may be substituted by a linear or branched $C_1$-$C_6$alkyl; linear or branched $C_1$-$C_6$alkyl optionally substituted by one or two hydroxyl or $C_1$-$C_6$alkoxy groups; $C_1$-$C_6$alkylene-$SO_2OH$; $C_1$-$C_6$alkylene-$SO_2O$; $C_1$-$C_6$alkylene-COOH; $C_1$-$C_6$alkylene-$PO(OH)_2$; $C_1$-$C_6$alkylene-$NR'_aR'e$; $C_1$-$C_6$alkylene-$N^+R'_aR'_eR'_f$; $C_1$-$C_6$alkylene-O—$C_1$-$C_6$alkylene-OH; $C_1$-$C_6$alkylene-phenyl wherein the phenyl may be substituted by a hydroxyl or a $C_1$-$C_6$alkoxy group; and the group:

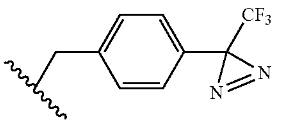 [SMILES: *Cc1ccc(C2(C(F)(F)F)N=N2)cc1]

or $R'_a$ and $R'_b$, together with the nitrogen atom carrying them, form a cycle $B_3$, or $R'_a$, $R'_b$ and $R'_c$, together with the nitrogen atom carrying them, form a bridged $C_3$-$C_8$heterocycloalkyl, $R'_c$, $R'_a$, $R'_e$, $R'_f$, independently of one another, represent a hydrogen or linear or branched $C_1$-$C_6$alkyl, or $R'_a$ and $R'_e$, together with the nitrogen atom carrying them, form a cycle $B_4$, or $R'_a$, $R'_e$ and $R'_f$, together with the nitrogen atom carrying them, form a bridged $C_3$-$C_8$heterocycloalkyl, $Y_1$ represents linear or branched $C_1$-$C_4$alkylene, $Y_2$ represents a bond, $-O-$, $-O-CH_2-$, $-O-CO-$, $-O-SO_2-$, $-CH_2-$, $-CH_2-O$, $-CH_2-CO-$, $-CH_2-SO_2-$, $-C_2H5-$, $-CO-$, $-CO-O-$, $-CO-CH_2-$, $-CO-NH-CH_2-$, $-SO_2-$, $-SO_2-CH_2-$, —NH—CO—or—NH—$SO_2-$, m represents 0, 1 or 2, p represents 1, 2, 3 or 4, $B_1$, $B_2$, $B_3$ and $B_4$, independently of one another, represent a $C_3$-$C_8$heterocycloalkyl group, which group: (i) is a mono- or bi-cyclic group, wherein bicyclic group includes fused, bridged or spiro ring system, (ii) may have, in addition to the nitrogen atom, one or two hetero atoms selected independently from oxygen, sulphur and nitrogen, and (iii) may optionally be substituted by one or two groups selected from: fluorine, bromine, chlorine, linear or branched $C_1$-$C_6$alkyl, hydroxyl, $-NH_2$, oxo and piperidinyl, its enantiomers and diastereoisomers, and addition salts thereof with a pharmaceutically acceptable acid or base.

2. The compound according to claim 1, wherein $Het_1$ represents:

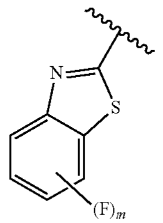

or

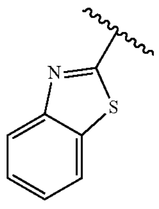

.

3. The compound according to claim 1, wherein $R_1$ represents methyl and $R_2$ represents hydrogen.

4. The compound according to claim 1, wherein $R_1$ and $R_2$ each represent methyl or hydrogen.

5. The compound according to claim 1, wherein $R_1$ or $R_2$ represents linear or branched $C_1$-$C_6$alkyl optionally substituted by a hydroxyl or a $C_1$-$C_6$alkoxy group.

6. The compound according to claim 5, wherein $R_1$ or $R_2$ represents a group selected from: methyl, methoxymethyl, hydroxymethyl, ethyl and prop-2-yl.

7. The compound according to claim 1, wherein $R_1$ or $R_2$ represents $C_3$-$C_6$cycloalkyl.

8. The compound according to claim 7, wherein $R_1$ or $R_2$ represents cyclopropyl.

9. The compound according to claim 1, wherein $R_1$ represents trifluoromethyl.

10. The compound according to claim 1, wherein $R_2$ represents linear or branched $C_1$-$C_6$alkylene-heterocycloalkyl.

11. The compound according to claim 10, wherein $R_2$ represents (4-methyl-piperazin-1-yl)propyl.

12. The compound according to claim 1, wherein $R_1$ and $R_2$, together with the carbon atoms carrying them, form a cyclohexene or a cyclopentene group.

13. The compound according to claim 1, wherein $R_3$ represents hydrogen or methyl.

14. The compound according to claim 1, wherein $R_3$ represents $-X_1-PO(OH)_2$, $-X_1-SO_2(OH)$, $-X_1-NR_aR_b$; or $-X_1-NR_aR_bR_c$, wherein $R_a$ or $R_b$, or both of them, represent a group selected from $C_1$-$C_6$alkylene-$SO_2OH$, $C_1$-$C_6$alkylene-$SO_2O-$ and $C_1$-$C_6$alkylene-$PO(OH)_2$.

15. The compound according to claim 1, wherein $R_8$ represents —$NR'_aR'_b$; —$NR'_aR'_bR'_c$; or —NH—$X'_2$—$N'R'_aR'_bR'_c$, wherein $R'_a$ and $R'_b$, or both of them, represent a group selected from $C_1$-$C_6$alkylene-$SO_2OH$ and $C_1$-$C_6$alkylene-$PO(OH)_2$.

16. The compound according to claim 1, wherein $R_3$ represents a group selected from: ethyl, propyl; 2-methoxy-ethyl, 2-(morpholin-4-yl)ethyl, 3-(morpholin-4-yl)propyl, 3-diethylamino-propyl, 3-methoxy-propyl, 3-hydroxy-propyl, 3,4-dihydroxy-butyl, 4-methoxy-3-hydroxy-butyl, 4-hydroxy-3-methoxy-butyl, 2,3-dihydroxy-propyl, 4,5-di-hydroxy-pentyl, 4-hydroxy-butyl, 3-hydroxy-2-morpholino-propyl, 5-hydroxy-4-methoxy-pentyl, 5-morpholino-4-hydroxy-pentyl, 3-hydroxy-2-methoxy-propyl, 5-[2-(dimethylamino)ethyl-methyl-amino]-4-hydroxy-pentyl, 5-hydroxy-pentyl, 5-methoxy-4-hydroxy-pentyl, 5-(dimethylamino)-4-hydroxy-pentyl, 4-hydroxy-5-(trimethylammonio)pentyl, 5-[3-sulfonate-propyl-dimethyl-ammonio]-4-hydroxy-pentyl, 4-hydroxy-5-(methylamino)pentyl, 3-carboxy-propyl, 5-[methyl(4-piperidyl)amino]pentyl, 5-(2-morpholinoethylamino)pentyl, 5-[2-(4-methyl-piperazin-1-yl)ethylamino)pentyl, 4-[2-(4-methyl-piperazin-1-yl) ethylamino)butyl, 4-hydroxy-5-[methyl-[2-(methylamino) ethyl]amino]pentyl, 5-[2-(diethylamino)ethylamino]-4-hydroxy-pentyl, 5-(4-Amino-1-piperidyl)-4-hydroxy-pentyl, 4-hydroxy-5-piperazin-1-yl-pentyl, 5-[2-(1-piperidyl)ethylamino]pentyl, 4-(4-Amino-1-piperidyl)butyl, 4-[2-(diethylamino)ethylamino]butyl, 5-(4-Amino-1-piperidyl)pentyl, 4-[methyl-[2-(methylamino)ethyl]amino] butyl, piperazin-1-yl)ethylamino)butyl, 4-(2-morpholino-ethylamino)butyl, 4-[2-(4-methyl-4-[(1-methyl-4-piperidyl) amino]butyl, 5-[2-(diethylamino)ethylamino]pentyl, 4-piperazin-1-ylbutyl, 4-(methylamino)butyl, 5-piperazin-1-ylpentyl, 5-[methyl-[2-(methylamino)ethyl, 5-aminopentyl, 4-aminobutyl, 5-(methylamino)pentyl, 5-[3-(4-methylpiperazin-1-yl)propylamino]pentyl, 4-hydroxy-5-[methyl(2-phosphonoethyl)amino]pentyl, 6-(dimethylamino)hexyl, 3-(dimethylamino)propyl, 2-(trimethylammonio)ethyl, 3-(trimethylammonio)propyl, 2-(dimethylamino)ethyl, 4-(dimethylamino)butyl, 5-[3-sulfonate-propyl-dimethyl-ammonio]pentyl, 4-(trimethylammonio)butyl, 4-hydroxy-5-quinuclidin-1-ium-1-yl-pentyl, 4-hydroxy-5-(1-aza-4-azoniabicyclo[2.2.2]octan-4-yl)pentyl, 4-hydroxy-5-(4-methylmorpholin-4-ium-4-yl)pentyl, 5-(trimethylammonio) pentyl, 4-hydroxy-5-(1-methylpiperidin-1-ium-1-yl)pentyl, 5-(1,4-dimethylpiperazin-1-ium-1-yl)-4-hydroxy-pentyl, 6-(trimethylammonio)hexyl, 5-[3-hydroxypropyl(dimethyl) ammonio]pentyl, 5-[2-hydroxyethyl(dimethyl)ammonio] pentyl, 5-[carboxymethyl(dimethyl)ammonio]pentyl, 5-[carboxymethyl(dimethyl)ammonio]pentyl, 3-phosphono-propyl, 3-[3-sulfonate-propyl-dimethyl-ammonio]propyl, 3-sulfopropyl, 4-sulfobutyl, 4-phosphonobutyl, 4-carboxy-butyl, 3-aminopropyl, 3-azidopropyl, pent-4-yn-1-yl, 4-aminobutyl, 4-azidobutyl, hex-5-yn-1-yl, and 5-azidopentyl.

17. The compound according to claim 1, wherein $Het_2$ represents:

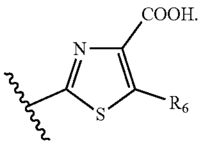

18. The compound according to claim 1, wherein $Het_2$ represents:

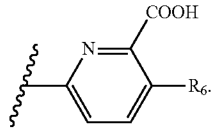

19. The compound according to claim 17, wherein $R_6$ represents hydrogen.

20. The compound according to claim 18, wherein $R_6$ represents hydrogen.

21. The compound according to claim 17, wherein $R_6$ represents a —$X_2$—O—$R_7$ group wherein $X_2$ is a propylene group.

22. The compound according to claim 21, wherein $R_7$ represents the following group:

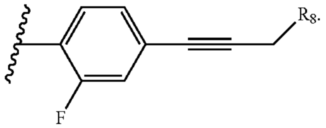

23. The compound according to claim 21, wherein $R_7$ represents the following group:

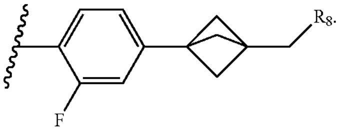

24. The compound according to claim 22, wherein $R_8$ represents a group selected from: dimethylamino, methylamino, methylethylamino, diethylamino, methyl[2-(methylamino)ethyl]amino, (2-hydroxyethyl)(methyl)amino, 4-morpholinyl, pyrrolidin-1-yl, 1-piperidyl, [(tert-butoxy) carbonyl](methyl)amino, hydroxyl, bis(3-sulfopropyl) amino, 3-sulfopropylamino, methyl(3-sulfopropyl)amino, methyl(p-tolylsulfonyl)amino, (4-methoxyphenyl)methyl-methyl-amino, and 2-(dimethylamino)ethylamino or $R_8$ represents:

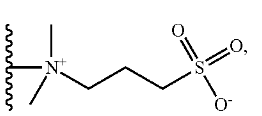,
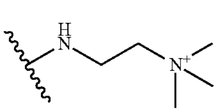
or
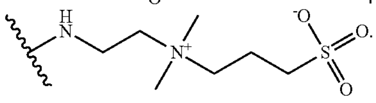

25. The compound according to claim 23, wherein $R_8$ represents a group selected from: dimethylamino, methylamino, methylethylamino, diethylamino, methyl[2-(methylamino)ethyl]amino, (2-hydroxyethyl)(methyl)amino, 4-morpholinyl, pyrrolidin-1-yl, 1-piperidyl, [(tert-butoxy) carbonyl](methyl)amino, hydroxyl, bis(3-sulfopropyl) amino, 3-sulfopropylamino, methyl(3-sulfopropyl)amino, methyl(p-tolylsulfonyl)amino, (4-methoxyphenyl)methyl-methyl-amino, and 2-(dimethylamino)ethylamino or $R_8$ represents:

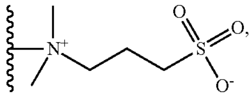

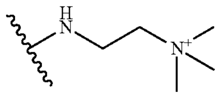

or

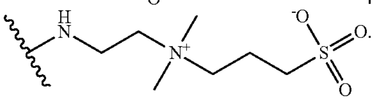

26. The compound according to claim 22, wherein $R_8$ represents a group selected from: 3-piperazin-1-yl, 4-methylpiperazin-1-yl, 3-hydroxypropyl(methyl)amino, [(3S)-3,4-dihydroxybutyl]-methyl-amino, 3-hydroxypropylamino, [(3S)-3,4-dihydroxybutyl]amino, 4-hydroxybutyl(methyl)amino, [(3R)-3,4-dihydroxybutyl]-methyl-amino, 4-hydroxybutylamino, and [(3R)-3,4-dihydroxybutyl]amino.

27. The compound according to claim 23, wherein $R_8$ represents a group selected from: 3-piperazin-1-yl, 4-methylpiperazin-1-yl, 3-hydroxypropyl(methyl)amino, [(3S)-3,4-dihydroxybutyl]-methyl-amino, 3-hydroxypropylamino, [(3S)-3,4-dihydroxybutyl]amino, 4-hydroxybutyl(methyl)amino, [(3R)-3,4-dihydroxybutyl]-methyl-amino, 4-hydroxybutylamino, and [(3R)-3,4-dihydroxybutyl]amino.

28. The compound according to claim 21, wherein $R_7$ represents:

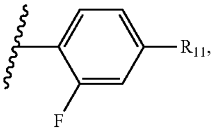

wherein $R_{11}$ is selected from dimethylcarbamoyl, 3-(dimethylamino)propyl, 3-(methylamino)propyl, and 3-(methylamino)propyl.

29. The Compound according to claim 17, wherein $R_6$ represents a $C_3$-$C_6$heterocycloalkylene-$Y_2$—$R_7$ group wherein the heterocycloalkylene group is selected from:

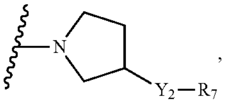

,

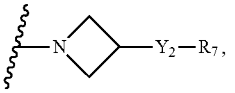

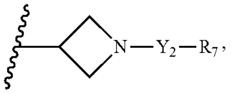

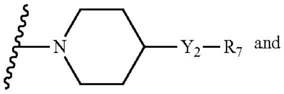

and

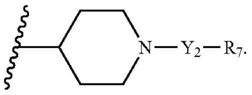

30. The compound according to claim 29, wherein $R_7$ is selected from: methyl, methylethyl, tert-butyl, 2-methylpropyl and phenyl.

31. The compound according to claim 17, wherein $R_6$ represents —C═C($R_9$)—$Y_1$—O—$R_7$ wherein $Y_1$ is a methylene group.

32. The compound according to claim 18, wherein $R_6$ represents —C═C($R_9$)—$Y_1$—O—$R_7$ wherein $Y_1$ is a methylene group.

33. The compound according to claim 17, wherein $R_6$ represents:

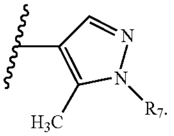

34. The compound according to claim 18, wherein $R_6$ represents:

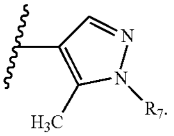

35. The compound according to claim 33, wherein $R_7$ represents a group selected from:

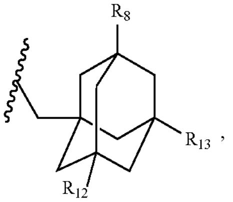

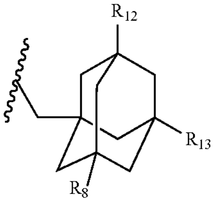

and

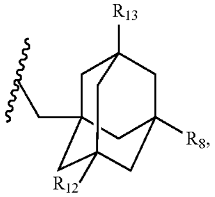

wherein $R_8$ represents a group selected from: hydrogen and 2-(methylamino)ethoxy or $R_8$ represents:

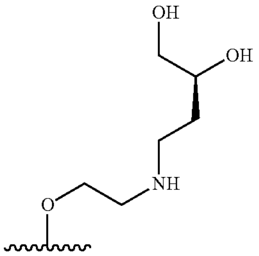

or

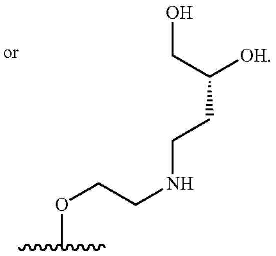

36. The compound according to claim 34, wherein $R_7$ represents a group selected from:

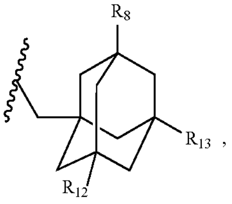

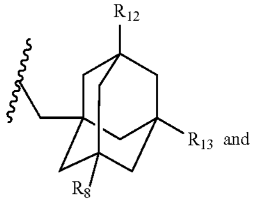

and

-continued

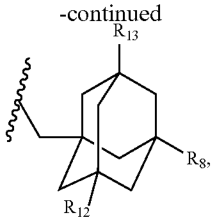

wherein $R_8$ represents a group selected from: hydrogen and 2-(methylamino)ethoxy or $R_8$ represents:

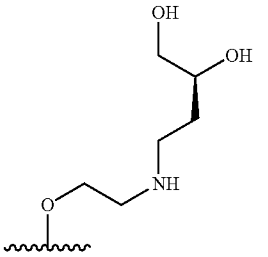

or

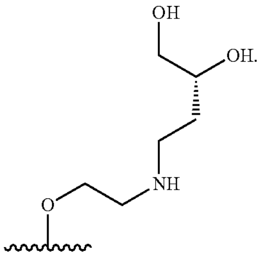

37. The compound according to claim 33, wherein $R_7$ represents a group selected from:

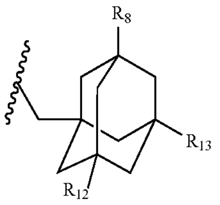

,

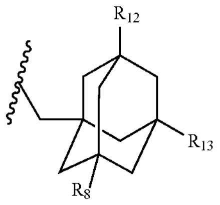

and

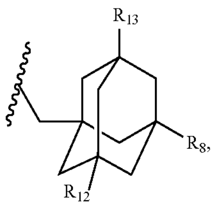

wherein $R_8$ represents a group selected from: 2-(dimethylamino)ethoxy, 2-[(2-sulfoethyl)amino]ethoxy, 2-[methyl(2-sulfoethyl)amino]ethoxy, 2-(3-hydroxypropylamino)ethoxy, 2-(3-methoxypropylamino)ethoxy, 2-morpholinoethoxy, 2-(2-carboxyethylamino)ethoxy, 2-[(3-hydroxyphenyl)methylamino]ethoxy, 2-(methylamino)ethoxy, 2-pyrrolidin-1-ylethoxy, 2-(4-methylpiperazin-1-yl)ethoxy, 2-(4-hydroxybutylamino)ethoxy, 2-piperazin-1-ylethoxy, 2-[3-hydroxypropyl(methyl)amino]ethoxy, 2-[4-hydroxy butyl (methyl)amino]ethoxy; 2-[[3-hydroxy-2-(hydroxymethyl) propyl]amino]ethoxy; and 2-[bis(3-hydroxypropyl)amino] ethoxy.

38. The compound according to claim 34, wherein $R_7$ represents a group selected from:

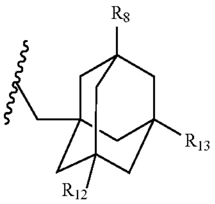

,

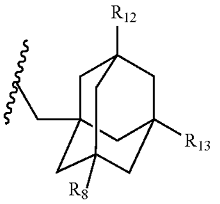

and

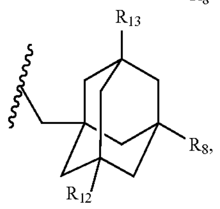

wherein $R_8$ represents a group selected from: 2-(dimethylamino)ethoxy, 2-[(2-sulfoethyl)amino]ethoxy, 2-[methyl(2-sulfoethyl)amino]ethoxy, 2-(3-hydroxypropylamino)ethoxy, 2-(3-methoxypropylamino)ethoxy, 2-morpholinoethoxy, 2-(2-carboxyethylamino)ethoxy, 2-[(3-hydroxyphenyl) methylamino]ethoxy, 2-(methylamino)ethoxy, 2-pyrrolidin-1-ylethoxy, 2-(4-methylpiperazin-1-yl)ethoxy, 2-(4-hydroxybutylamino)ethoxy, 2-piperazin-1-ylethoxy, 2-[3-hydroxypropyl(methyl)amino]ethoxy, 2-[4-hydroxybuty] (methyl)amino]ethoxy; 2-[[3-hydroxy-2-(hydroxymethyl) propyl]amino]ethoxy; and 2-[bis(3-hydroxypropyl)amino] ethoxy.

39. The compound according to claim 1, which is selected from:

2-({6-[(1,3-Benzothiazol-2-yl)amino]-5-methylpyridazin-3-yl}(4-hydroxybutyl)amino)-5-(3-{2-fluoro-4-[3-(methylamino)prop-1-yn-1-yl]phenoxy}propyl)-1,3-thiazole-4-carboxylic acid, 2-[[6-(1,3-Benzothiazol-2-ylamino)-5-methyl-pyridazin-3-yl]-methyl-amino]-5-[3-[4-[3-(dimethylamino)prop-1-ynyl]-2-fluoro-phenoxy]propyl]thiazole-4-carboxylic acid, 2-({6-[(1,3-Benzothiazol-2-yl)amino]-5-methylpyridazin-3-yl}(methyl)amino)-5-(3-{2-fluoro-4-[3-(methylamino)prop-1-yn-1-yl]phenoxy}propyl)-1,3-thiazole-4-carboxylic acid, 2-[[6-(1,3-Benzothiazol-2-ylamino)-5-methyl-pyridazin-3-yl]-(3,4-dihydroxybutyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(3-hydroxy-4-methoxy-butyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(2,3-dihydroxypropyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(4,5-dihydroxypentyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-(3,4-dihydroxybutyl)amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-(3-hydroxypropyl)amino]-5-[3-[2-fluoro-4-[3-(methylamino)prop-1-ynyl]phenoxy]propyl]thiazole-4-carboxylic acid, 2-[[6-(1,3-Benzothiazol-2-ylamino)-5-methyl-pyridazin-3-yl]-[4-hydroxy-5-(trimethylammonio)pentyl]amino]-5-[3-[2-fluoro-4-[3-(methylamino)prop-1-ynyl]phenoxy]propyl]thiazole-4-carboxylate, 3-[5-[[6-(1,3-Benzothiazol-2-ylamino)-5-methyl-pyridazin-3-yl]-[4-carboxy-5-[3-[2-fluoro-4-[3-(methylamino)prop-1-ynyl]phenoxy]propyl]thiazol-2-yl]amino]-2-hydroxy-pentyl]-dimethyl-ammonio]propane-1-sulfonate, 2-[[6-(1,3-Benzothiazol-2-ylamino)-5-methyl-pyridazin-3-yl]-(4-hydroxybutyl)amino]-5-[3-[2-fluoro-4-[3-[methyl(3-sulfopropyl)amino]prop-1-ynyl]phenoxy]propyl]thiazole-4-carboxylic acid, 5-{1-[(Adamantan-1-yl)methyl]-5-methyl-1H-pyrazol-4-yl}-2-({6-[(1,3-benzothiazol-2-yl)amino]-5-methylpyridazin-3-yl}(methyl)amino)-1,3-thiazole-4-carboxylic acid, 5-{1-[(Adamantan-1-yl)methyl]-5-methyl-1H-pyrazol-4-yl}-2-({6-[(1,3-benzothiazol-2-yl)amino]-5-cyclopropylpyridazin-3-yl}(methyl)amino)-1,3-thiazole-4-carboxylic acid, 2-[[6-(1,3-Benzothiazol-2-ylamino)-5-methyl-pyridazin-3-yl]-[5-[2-(diethylamino)ethylamino]-4-hydroxy-pentyl]amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-[5-[2-(4-methylpiperazin-1-yl)ethylamino]pentyl]amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-(4-hydroxy-5-piperazin-1-yl-pentyl)amino]-5-[3-[4-[3-(dimethylamino)prop-1-ynyl]-2-fluoro-phenoxy]propyl]thiazole-4-carboxylic acid, 2-({6-[(1,3-Benzothiazol-2-yl)amino]-5-methylpyridazin-3-yl}(methyl)amino)-5-[(2S)-3-{4-[3-(dimethylamino)prop-1-yn-1-yl]-2-fluorophenoxy}-2-methylpropyl]-1,3-thiazole-4-carboxylic acid, 2-[4-Aminobutyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid, 2-[5-Aminopentyl-[6-(1,3-benzothiazol-2-ylamino)-5-methyl-pyridazin-3-yl]amino]-5-[3-[4-[3-(dimethylamino)prop-1-ynyl]-2-fluoro-phenoxy]propyl]thiazole-4-carboxylic acid, 2-[[6-(1,3-Benzothiazol-2-ylamino)-5-methyl-pyridazin-3-yl]-[3-(dimethylamino)propyl]amino]-5-[3-[2-fluoro-4-[3-(methylamino)prop-1-ynyl]phenoxy]propyl]thiazole-4-carboxylic acid, 2-[6-(1,3-Benzothiazol-2-ylamino)-5-methyl-pyridazin-3-yl]-methyl-amino]-5-[3-[4-[3-(dimethylamino) but-1-ynyl]-2-fluoro-phenoxy]propyl]thiazole-4-carboxylic acid, 2-[[6-(1,3-Benzothiazol-2-ylamino)-5-methyl-pyridazin-3-yl]-[4-hydroxy-5-(trimethylammonio)pentyl]amino]-5-[3-[4-[3-(dimethylamino)prop-1-ynyl]-2-fluoro-phenoxy]propyl]thiazole-4-carboxylate, 3-[2-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-dimethyl-ammonio]propane-1-sulfonate, 2-[[6-(1,3-Benzothiazol-2-ylamino)-5-methyl-pyridazin-3-yl]-[4-hydroxy-5-(4-methylmorpholin-4-ium-4-yl)pentyl]amino]-5-[3-[4-[3-(dimethylamino)prop-1-ynyl]-2-fluoro-phenoxy]propyl]thiazole-4-carboxylate, 2-[3-[4-[3-[2-[[6-(1,3-Benzothiazol-2-ylamino)-5-methyl-pyridazin-3-yl]-methyl-amino]-4-carboxy-thiazol-5-yl]propoxy]-3-fluoro-phenyl]prop-2-ynylamino]ethyl-trimethyl-ammonium, 2-[[6-(1,3-Benzothiazol-2-ylamino)-5-methyl-pyridazin-3-yl]-[6-(trimethylammonio)hexyl]amino]-5-[3-[2-fluoro-4-[3-(methylamino)prop-1-ynyl]phenoxy]propyl]thiazole-4-carboxylate, 2-[[6-(1,3-Benzothiazol-2-ylamino)-5-methyl-pyridazin-3-yl]-[5-[2-hydroxyethyl(dimethyl)ammonio]pentyl]amino]-5-[3-[4-[3-(dimethylamino)prop-1-ynyl]-2-fluoro-phenoxy]propyl]thiazole-4-carboxylate, 2-[[6-(1,3-Benzothiazol-2-ylamino)-5-methyl-pyridazin-3-yl]-[5-[carboxymethyl(dimethyl)ammonio]pentyl]amino]-5-[3-[4-[3-(dimethylamino)prop-1-ynyl]-2-fluoro-phenoxy]propyl]thiazole-4-carboxylate, 3-[5-[[6-(1,3-Benzothiazol-2-ylamino)-5-methyl-pyridazin-3-yl]-[4-carboxy-5-[3-[2-fluoro-4-[(E)-3-oxoprop-1-enyl]phenoxy]propyl]thiazol-2-yl]amino]-2-hydroxy-pentyl]-dimethyl-ammonio]propane-1-sulfonate, 2-[[6-(1,3-Benzothiazol-2-ylamino)-5-methyl-pyridazin-3-yl]-methyl-amino]-5-[3-[4-[3-(dimethylamino)prop-1-ynyl]phenoxy]propyl]thiazole-4-carboxylic acid, 2-||6-(1,3-Benzothiazol-2-ylamino)-5-methyl-pyridazin-3-yl]-methyl-amino]-5-[3-[4-[1-[(dimethylamino)methyl]-3-bicyclo[1.1.1]pentanyl]phenoxy]propyl]thiazole-4-carboxylic acid, 2-[6-(1,3-Benzothiazol-2-ylamino)-5-methyl-pyridazin-3-yl]-(3-phosphonopropyl)amino]-5-[3-[2-fluoro-4-[3-(methylamino)prop-1-ynyl]phenoxy]propyl]thiazole-4-carboxylic acid, 2-({6-[(1,3-Benzothiazol-2-yl)amino]-5-methylpyridazin-3-yl}(3-carboxypropyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(3-phosphonopropyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(3-sulfopropyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(4-sulfobutyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(4-phosphonobutyl)amino)-5-(3-{4-[3-(dimethylamino)prop-1-yn-1-yl]-2-fluorophenoxy}propyl)-1,3-thiazole-4-carboxylic acid, 2-({6-[(1,3-Benzothiazol-2-yl)amino]-5-methylpyridazin-3-yl}(4-carboxybutyl)amino)-5-(3-{4-[3-(dimethylamino)prop-1-yn-1-yl]-2-fluorophenoxy}propyl)-1,3-thiazole-4-carboxylic acid, 2-[{6-[(1,3-benzothiazol-2-yl)amino]-5-methylpyridazin-3-yl}(pent-4-yn-1-yl)amino]-5-(3-{2-fluoro-4-[3-(methylamino)prop-1-yn-1-yl]phenoxy}propyl)-1,3-thiazole-4-carboxylic acid, 2-({6-[(1,3-Benzothiazol-2-yl)amino]-5-methylpyridazin-3-yl}(methyl)amino)-5-{3-[2-fluoro-4-(3-

{methyl[2-(methylamino)ethyl]amino}prop-1-yn-1-yl) phenoxy]propyl}-1,3-thiazole-4-carboxylic acid, 2-({6-[(1,3-Benzothiazol-2-yl)amino]-5-methylpyridazin-3-yl}(methyl)amino)-5-[3-(2-fluoro-4-{3-[(2-hydroxyethyl)(methyl)amino]prop-1-yn-1-yl}phenoxy)propyl]-1,3-thiazole-4-carboxylic acid, 2-({6-[(1,3-Benzothiazol-2-yl)amino]-5-methylpyridazin-3-yl}(methyl)amino)-5-{3-[2-fluoro-4-(3-hydroxyprop-1-yn-1-yl) phenoxy]propyl}-1,3-thiazole-4-carboxylic acid, 2-[5-azidopenty]-[6-[(1,3-benzothiazol-2-yl)amino]-5-methyl-pyridazin-3-yl]amino]-5-[3-[2-fluoro-4-[3-(methylamino)prop-1-ynyl]phenoxy]propyl]-1,3-thiazole-4-carboxylic acid, its enantiomers and diastereoisomers, and addition salts thereof with a pharmaceutically acceptable acid or base.

40. The compound according to claim 1, which is selected from:

6-[{6-[(1,3-benzothiazol-2-yl)amino]-5-methylpyridazin-3-yl}(methyl)amino]-3-[1-({3-[2-(dimethylamino) ethoxy]-5,7-dimethyladamantan-1-yl}methyl)-5-methyl-1H-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-(3-hydroxypropylamino)ethoxy]-5,7-dimethyl-1-adamantyl]methyl]-5-methyl-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-(3-methoxypropylamino)ethoxy]-5,7-dimethyl-1-adamantyl]methyl]-5-methyl-pyrazol-4-yl]pyridine-2-carboxylic acid, 6-[{6-[(1,3-benzothiazol-2-yl)amino]-5-methylpyridazin-3-yl}(methyl)amino]-3-(1-{[3-(2-{[(3S)-3,4-dihydroxybutyl]amino}ethoxy)-5,7-dimethyladamantan-1-yl]methyl}-5-methyl-1H-pyrazol-4-yl)pyridine-2-carboxylic acid, 6-[[6-(1,3-benzothiazol-2-ylamino)-5-methyl-pyridazin-3-yl]-methyl-amino]-3-[1-[3,5-dimethyl-7-(2-morpholinoethoxy)-1-adamantyl]methyl]-5-methyl-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-(2-carboxyethylamino)ethoxy]-5,7-dimethyl-1-adamantyl]methyl]-5-methyl-pyrazol-4-yl]pyridine-2-carboxylic acid, 6-[[6-(1,3-benzothiazol-2-ylamino)-5-methyl-pyridazin-3-yl]-methyl-amino]-3-[1-[[3-[2-[(3-hydroxyphenyl) methylamino]ethoxy]-5,7-dimethyl-1-adamantyl] methyl]-5-methyl-pyrazol-4-yl]pyridine-2-carboxylic acid, 2-[[6-(1,3-benzothiazol-2-ylamino)-5-methyl-pyridazin-3-yl]-methyl-amino]-5-[3-[4-[3-(dimethylamino)prop-1-ynyl]-2-fluoro-phenoxy]propyl]thiazole-4-carboxylic acid, 2-[[6-(1,3-benzothiazol-2-ylamino)-5-methyl-pyridazin-3-yl]-(3-hydroxypropyl)amino]-5-[3-[2-fluoro-4-[3-(methylamino)prop-1-ynyl]phenoxy]propyl]thiazole-4-carboxylic acid, 2-[[6-(1,3-benzothiazol-2-ylamino)-5-methyl-pyridazin-3-yl]-methyl-amino]-5-[3-[2-fluoro-4-(3-pyrrolidin-1-ylprop-1-ynyl) phenoxy]propyl]thiazole-4-carboxylic acid, its enantiomers and diastereoisomers, and addition salts thereof with a pharmaceutically acceptable acid or base.

41. A pharmaceutical composition comprising the compound according to claim 1, or an addition salt thereof with a pharmaceutically acceptable acid or base, in combination with one or more pharmaceutically acceptable excipients.

42. A method of treating a condition requiring a pro-apoptotic agent in a subject in need thereof, comprising administration of the compound according to claim 1, alone or in combination with one or more pharmaceutically acceptable excipients.

43. The method according to claim 42, wherein the condition is selected from cancers, auto-immune diseases and immune system diseases.

44. The method according to claim 43, wherein the cancer is a haematological malignancy or a solid tumor.

45. The method according to claim 44, wherein the haematological malignancy is myeloma, including multiple myeloma, lymphoma, including Non-Hodgkin Lymphoma (NHL), or leukemia, including Chronic Lymphocytic Leukemia (CLL), T-cell Acute Lymphoblastic Leukemia (T-ALL), B-cell Acute Lymphoblastic Leukemia (B-ALL) or Acute Myelogenous Leukemia (AML).

46. The method according to claim 44, wherein the solid tumor is selected from bladder, brain, breast, uterus, esophagus and liver cancers, colorectal cancer, renal cancer, melanoma, ovarian cancer, prostate cancer, pancreatic cancer and lung cancer.

47. A combination of the compound according to claim 1 with an anti-cancer agent selected from genotoxic agents, mitotic poisons, anti-metabolites, proteasome inhibitors, kinase inhibitors and antibodies.

48. A pharmaceutical composition comprising the combination according to claim 47 in combination with one or more pharmaceutically acceptable excipients.

49. A method of treating cancer in a subject in need thereof, comprising administration of the combination according to claim 47, alone or in combination with one or more pharmaceutically acceptable excipients.

50. A method of treating cancer requiring radiotherapy in a subject in need thereof, comprising administration of the compound according to claim 1.

51. A method of treating diseases or conditions characterized by an excess or a deregulated activity of platelets, including pro-thrombotic conditions, in a subject in need thereof, comprising administration of the compound according to claim 1, alone or in combination with one or more pharmaceutically acceptable excipients.

52. A compound which is:

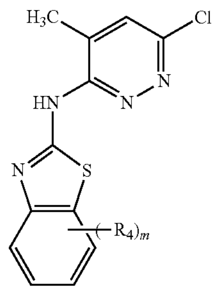

wherein $R_4$ represents hydrogen, fluorine, chlorine, bromine, methyl, hydroxyl or methoxy, and m represents 0, 1 or 2.

* * * * *